US012799140B2

(12) United States Patent
Urbano et al.

(10) Patent No.: US 12,799,140 B2
(45) Date of Patent: Nov. 17, 2026

(54) MRGPRX2 ANTAGONISTS, PHARMACEUTICAL COMPOSITION INCLUDING MRGPRX2 ANTAGONIST, AND METHOD OF TREATING MRGPRX2-MEDIATED DISEASE OR DISORDER

(71) Applicant: KYORIN PHARMACEUTICAL CO., LTD., Tokyo (JP)

(72) Inventors: Mariangela Urbano, San Diego, CA (US); Eun-Kyong Kim, San Diego, CA (US); Chixu Chen, San Diego, CA (US); Damoder R. Motati, San Diego, CA (US); Romelo Gibe, La Jolla, CA (US); Shyama Herath, San Diego, CA (US); Qiang Li, Carlsbad, CA (US); Naresh Gunaganti, San Diego, CA (US); Xiuwen Zhu, San Diego, CA (US); Mohammad B. Khaled, San Diego, CA (US); Jonathan S. Rosenblum, San Diego, CA (US); Hugh Rosen, Rancho Santa Fe, CA (US); Sean Riley, San Diego, CA (US); Emme C.K. Lin Fishburn, San Diego, CA (US); Ryosuke Namie, Nogi-machi (JP); Akihiko Kojima, Nogi-machi (JP); Yoshikazu Asahina, Nogi-machi (JP); Yosuke Nishigaya, Shiraoka (JP); Muneki Nagao, Shiraoka (JP); Akihiko Kasamatsu, Saitama (JP); Takekazu Kondo, Nogi-machi (JP)

(73) Assignee: KYORIN PHARMACEUTICAL CO., LTD., Tokyo (JP)

( * ) Notice: Subject to any disclaimer, the term of this patent is extended or adjusted under 35 U.S.C. 154(b) by 229 days.

(21) Appl. No.: 19/249,435

(22) Filed: Jun. 25, 2025

(65) Prior Publication Data

US 2025/0326773 A1 Oct. 23, 2025

Related U.S. Application Data

(63) Continuation of application No. 19/183,555, filed on Apr. 18, 2025.

(60) Provisional application No. 63/636,536, filed on Apr. 19, 2024.

(51) Int. Cl.

| | |
|---|---|
| ***C07D 471/04*** | (2006.01) |
| ***A61K 31/429*** | (2006.01) |
| ***A61K 31/437*** | (2006.01) |
| ***A61K 31/444*** | (2006.01) |
| ***A61K 31/506*** | (2006.01) |
| ***A61K 31/519*** | (2006.01) |
| ***A61K 31/5365*** | (2006.01) |
| ***A61K 31/537*** | (2006.01) |
| ***A61K 31/553*** | (2006.01) |
| ***A61P 17/00*** | (2006.01) |
| ***C07B 59/00*** | (2006.01) |
| ***C07D 487/04*** | (2006.01) |
| ***C07D 513/04*** | (2006.01) |
| ***C07D 519/00*** | (2006.01) |

(52) U.S. Cl.

CPC .......... *C07D 519/00* (2013.01); *A61K 31/429* (2013.01); *A61K 31/437* (2013.01); *A61K 31/444* (2013.01); *A61K 31/506* (2013.01); *A61K 31/519* (2013.01); *A61K 31/5365* (2013.01); *A61K 31/537* (2013.01); *A61K 31/553* (2013.01); *A61P 17/00* (2018.01); *C07B 59/002* (2013.01); *C07D 471/04* (2013.01); *C07D 487/04* (2013.01); *C07D 513/04* (2013.01)

(58) Field of Classification Search

CPC .................................................... C07D 519/00
USPC ...................................................... 514/230.5
See application file for complete search history.

(56) References Cited

U.S. PATENT DOCUMENTS

2005/0261331 A1* 11/2005 Nielsen .................. A61P 11/02 546/113

FOREIGN PATENT DOCUMENTS

WO WO-2004/016609 A1 2/2004
WO WO-2004/016610 A1 2/2004
WO WO-2005/095400 A1 10/2005

(Continued)

OTHER PUBLICATIONS

Ogasawara, "Creation of New Small Molecule Drug Discovery Target—MRGPRX2" Dissertation (Published on Nov. 18, 2020), Tohoku University.

(Continued)

*Primary Examiner* — Niloofar Rahmani
(74) *Attorney, Agent, or Firm* — Foley Hoag LLP; Brendan T. Jones; Erin M. Foley

(57) ABSTRACT

The present disclosure relates to compounds represented by structural formula (I*):

(I*)

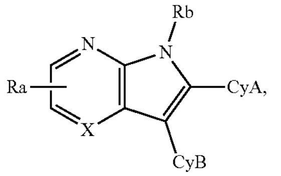

or a pharmaceutically acceptable salt thereof. Further disclosed are pharmaceutical compositions comprising the compounds and methods of treating an MRGPRX2-mediated disease or disorder using the compounds.

30 Claims, No Drawings

(56) References Cited

FOREIGN PATENT DOCUMENTS

| | | | |
|---|---|---|---|
| WO | WO-2011/075613 | A1 | 6/2011 |
| WO | WO-2016/019246 | A1 | 2/2016 |
| WO | WO-2016/118632 | A1 | 7/2016 |
| WO | WO-2020/039060 | A1 | 2/2020 |
| WO | WO-2020/229648 | A1 | 11/2020 |
| WO | WO-2021/092240 | A1 | 5/2021 |
| WO | WO-2021/092262 | A1 | 5/2021 |
| WO | WO-2021/092264 | A1 | 5/2021 |
| WO | WO-2021/165469 | A1 | 8/2021 |
| WO | WO-2022/073904 | A1 | 4/2022 |
| WO | WO-2022/073905 | A1 | 4/2022 |
| WO | WO-2022/087083 | A1 | 4/2022 |
| WO | WO-2022/111473 | A1 | 6/2022 |
| WO | WO-2022/125636 | A1 | 6/2022 |
| WO | WO-2022/140520 | A1 | 6/2022 |
| WO | WO-2023/039448 | A1 | 3/2023 |

OTHER PUBLICATIONS

Ogasawara, "Novel MRGPRX2 antagonists inhibit IgE-independent activation of human umbilical cord blood-derived mast cells," Journal of Leukocyte Biology 106 (201): 1069-1077.

Tanaka et al., "A system for detecting inflammatory responses caused by low-molecular-weight compounds" Okayama University New Technology Presentation Materials—Dec. 15, 2016.

Watanuki et al., "Analysis of G protein coupling of MRGPRX2 and evaluation of its antagonists. G proteins coupling and antagonism of MRGPRX2," The 140th Annual Meeting of the Pharmaceutical Society of Japan (Kyoto), Mar. 25-28, 2020.

Xu et al., "Alkali-amide controlled selective synthesis of 7-azaindole and 7-azaindoline through domino reactions of 2-fluoro-3-methylpyridine and aldehydes." Organic Chemistry Frontiers 9.9 (2022): 2541-2548.

International Search Report and Written Opinion for International Application No. PCT/US25/25290 dated Aug. 8, 2025.

* cited by examiner

MRGPRX2 ANTAGONISTS, PHARMACEUTICAL COMPOSITION INCLUDING MRGPRX2 ANTAGONIST, AND METHOD OF TREATING MRGPRX2-MEDIATED DISEASE OR DISORDER

CROSS-REFERENCE TO RELATED APPLICATIONS

The present application a Continuation Application of U.S. patent application Ser. No. 19/183,555, filed Apr. 18, 2025, which is based upon and claims the benefit of priority to U.S. Application No. 63/636,536, filed Apr. 19, 2024, the entire contents of each of which are incorporated herein by reference.

BACKGROUND

Technical Field

The present invention relates to MRGPRX2 antagonists, a pharmaceutical composition including a MRGPRX2 antagonist, and a method of treating an MRGPRX2-mediated disease or disorder.

Description of Background Art

Mast cells are involved in a variety of inflammatory diseases, and antigen-dependent activation of tissue mast cells with IgE bound to their surface is a major event in acute allergic reactions. In addition to the case where mast cells are activated by the combination of IgE-allergen, there is the case where the ligand directly stimulates and activates the Mas-related G protein-coupled receptor (MRGPR) on the mast cells. In particular, many new studies on MRGPRX2-mediated IgE-independent mast cell activation have been reported in recent years. International Publication No. WO 2021/092264 describes compounds as an MRGPRX2 antagonist. The entire contents of this publication are incorporated herein by reference.

BRIEF SUMMARY

In some embodiments, the present disclosure relates to a compound represented by structural formula (I*):

(I*)

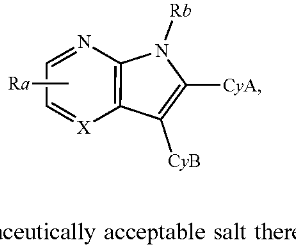

or a pharmaceutically acceptable salt thereof, wherein:

X is CH or N;

Rb is selected from H, $C_1$-$C_6$ alkyl, and C(=O)O($C_1$-$C_6$ alkyl), wherein each $C_1$-$C_6$ alkyl is optionally substituted with one or more substituents independently selected from group Q;

CyA is selected from one of the following moieties:

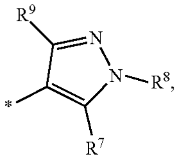

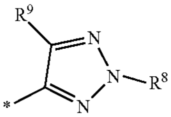

,

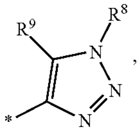

,

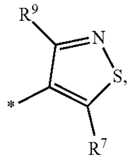

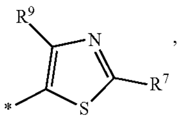

,

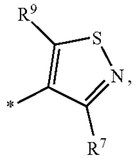

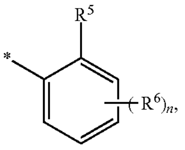

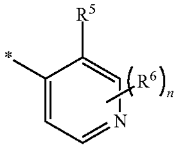

, and

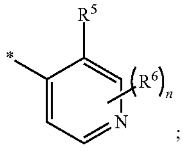

;

CyB is selected from 5- to 12-membered heteroaryl and $C_6$-$C_{12}$ aryl, wherein the 5- to 12-membered heteroaryl or $C_6$-$C_{12}$ aryl is optionally substituted with one or more substituents independently selected from group Q;

Ra is selected from H, deuterium, F, Cl, Br, CN, $NO_2$, $C_1$-$C_6$ alkyl, and $C_1$-$C_6$ alkoxy, wherein each $C_1$-$C_6$ alkyl or $C_1$-$C_6$ alkoxy is optionally substituted with one or more substituents independently selected from group Q;

$R^5$ and $R^6$ are each independently selected from deuterium, F, Cl, Br, OH, CN, $NO_2$, $NR^{10a}R^{10b}$, C(=O)$NR^{11a}R^{11b}$, $C_1$-$C_6$ alkyl, $C_1$-$C_6$ alkoxy, $C_2$-$C_6$ alkenyl, $C_2$-$C_6$ alkynyl, $C_3$-$C_{12}$ cycloalkyl, $C_6$-$C_{12}$ aryl, 5- to 12-membered heteroaryl, and 4- to 12-membered heterocyclyl, wherein each $C_1$-$C_6$ alkyl, $C_1$-$C_6$ alkoxy, $C_2$-$C_6$ alkenyl, $C_2$-$C_6$ alkynyl, $C_3$-$C_{12}$ cycloalkyl, $C_6$-$C_{12}$ aryl, 5- to 12-membered heteroaryl, or 4- to 12-membered heterocyclyl is optionally substituted with one or more substituents independently selected from group Q, or $R^5$ and $R^6$ together with the atoms to which they are attached form $C_4$-$C_{12}$ carbocyclyl, 5- to 12-membered heteroaryl, or 4- to 12-membered heterocyclyl, wherein the $C_4$-$C_{12}$ carbocyclyl, 5- to 12-membered heteroaryl, or 4- to 12-membered heterocyclyl is optionally substituted with one or more substituents independently selected from group Q;

n is 0, 1, 2, 3, or 4;

$R^7$ and $R^8$ together with the atoms to which they are attached form 4- to 12-membered heterocyclyl or 5- to 12-membered heteroaryl, wherein the 4- to 12-membered heterocyclyl or 5- to 12-membered heteroaryl is optionally substituted with one or more substituents independently selected from group Q;

$R^7$ is selected from H, deuterium, F, Cl, Br, OH, CN, $NO_2$, $NR^{10c}R^{10d}$, C(=O)$NR^{11c}R^{11c}$, $C_1$-$C_6$ alkyl, $C_1$-$C_6$ alkoxy, $C_2$-$C_6$ alkenyl, $C_2$-$C_6$ alkynyl, $C_3$-$C_{12}$ cycloalkyl, $C_6$-$C_{12}$ aryl, 5- to 12-membered heteroaryl, and 4- to 12-membered heterocyclyl, wherein each $C_1$-$C_6$ alkyl, $C_1$-$C_6$ alkoxy, $C_2$-$C_6$ alkenyl, $C_2$-$C_6$ alkynyl, $C_3$-$C_{12}$ cycloalkyl, $C_6$-$C_{12}$ aryl, 5- to 12-membered heteroaryl, or 4- to 12-membered heterocyclyl is optionally substituted with one or more substituents independently selected from a group Q;

$R^8$ is selected from H and $C_{1-6}$ alkyl optionally substituted with one or more substituents independently selected from a group Q;

$R^9$ is selected from $C_1$-$C_6$ alkyl, F, Cl, Br, OH, CN, $NO_2$, $NR^{10e}R^{10f}$, C(=O)$NR^{11e}R^{11f}$, $C_1$-$C_6$ alkoxy, $C_2$-$C_6$ alkenyl, $C_2$-$C_6$ alkynyl, $C_3$-$C_{12}$ cycloalkyl, $C_6$-$C_{12}$ aryl, 5- to 12-membered heteroaryl, and 4- to 12-membered heterocyclyl, wherein each $C_1$-$C_6$ alkyl, $C_1$-$C_6$ alkoxy, $C_2$-$C_6$ alkenyl, $C_2$-$C_6$ alkynyl, $C_3$-$C_{12}$ cycloalkyl, $C_6$-$C_{12}$ aryl, 5- to 12-membered heteroaryl, and 4- to 12-membered heterocyclyl is optionally substituted with one or more substituents independently selected from a group Q; and $R^{10a}$, $R^{10b}$, $R^{10c}$, $R^{10d}$, $R^{10c}$, $R^{10f}$, $R^{11a}$, $R^{11b}$, $R^{11c}$, $R^{11d}$, $R^{11e}$, and $R^{11f}$ are each independently selected from H and $C_1$-$C_6$ alkyl optionally substituted with one or more substituents independently selected from a group Q, or one or more of the pairs of variables selected from $R^{10a}$ and $R^{10b}$, $R^{10c}$ and $R^{10d}$, $R^{10e}$ and $R^{10f}$, $R^{11a}$ and $R^{11b}$, $R^{11e}$ and $R^{11d}$, and $R^{11e}$ and $R^{11f}$, together with the nitrogen to which they are attached, form 5- to 12-membered heteroaryl or 4- to 12-membered heterocyclyl, wherein each 5- to 12-membered heteroaryl or 4- to 12-membered heterocyclyl is optionally substituted with one or more substituents independently selected from a group Q;

wherein each of the one or more substituents of group Q is independently selected from deuterium, F, Cl, Br, OH, $NH_2$, NH(C=O)($C_1$-$C_6$ alkyl), NH(C=O)($C_3$-$C_8$ cycloalkyl), NH(C=O)(O—$C_1$-$C_6$ alkyl), $C_1$-$C_6$ alkyl optionally substituted with one or more deuterium, $C_1$-$C_6$ haloalkyl, $C_1$-$C_6$ alkoxy optionally substituted with one or more deuterium, $C_1$-$C_6$ haloalkoxy, $C_2$-$C_6$ alkenyl, $C_1$-$C_6$ hydroxyalkyl, $C_1$-$C_6$ hydroxyalkoxy, carboxy-$C_1$-$C_6$ alkyl, amino optionally having at least one $C_1$-$C_3$ alkyl, $NO_2$, CN, $CONH_2$, aminocarbonyl substituted with at least one $C_1$-$C_6$ alkyl, oxo, $C_1$-$C_6$ alkyl-carbonyl, $C_1$-$C_6$ alkoxy-carbonyl, $C_1$-$C_6$ alkyl-carbonylamino, $C_1$-$C_6$ alkoxy-carbonylamino, $C_1$-$C_6$ alkyl-carbonyl-N-methylamino, $C_1$-$C_6$ alkoxy-carbonyl-N-methylamino, $C_1$-$C_6$ alkylsulfanyl, $C_1$-$C_6$ alkylsulfinyl, $C_1$-$C_6$ alkylsulfonyl, $C_1$-$C_6$ alkylaminosulfonyl, $C_1$-$C_6$ alkylsulfinyl-$C_1$-$C_6$ alkyl, $C_1$-$C_6$ alkylsulfonyl-$C_1$-$C_6$ alkyl, $C_3$-$C_8$ cycloalkyl, $C_3$-$C_8$ cycloalkyl-$C_1$-$C_3$ alkoxy, $C_1$-$C_3$ alkoxy-$C_1$-$C_3$ alkyl, $C_1$-$C_3$ alkoxy-$C_1$-$C_3$alkoxy-$C_1$-$C_3$ alkyl, $C_1$-$C_3$ alkoxy-carbonyl-$C_1$-$C_3$ alkyl, phenyl-$C_1$-$C_6$ alkoxy, N-methylamino-carbonyl-$C_1$-$C_6$ alkyl, N,N-dimethylaminocarbonyl-$C_1$-$C_6$ alkyl, heterocyclyl, heterocyclyl-$C_1$-$C_3$ alkyl or a spiro ring.

In some embodiments, the present disclosure relates to a pharmaceutical composition comprising a compound of the disclosure (e.g., a compound represented by structural formula (I*), (Ia*) to (Ik*), (Ia) to (Ie), or (IIa) to (IIe) or a pharmaceutically acceptable salt thereof) and a pharmaceutically acceptable carrier.

In some embodiments, the present disclosure relates to a pharmaceutical composition comprising a compound of the disclosure (e.g., a compound represented by structural formula (I*), (Ia*) to (Ik*), (Ia) to (Ie), or (IIa) to (IIe) or a pharmaceutically acceptable salt thereof) and a pharmaceutically acceptable carrier, wherein the pharmaceutical composition is formulated for the treatment of MRGPRX2-mediated disease or disorder.

In some embodiments, the present disclosure relates to a method of treating an MRGPRX2-mediated disease or disorder, comprising administering to a patient in need thereof a therapeutically effective amount of a compound of the disclosure (e.g., a compound represented by structural formula (I*), (Ia*) to (Ik*), (Ia) to (Ie), or (IIa) to (IIe) or a pharmaceutically acceptable salt thereof) or a pharmaceutical composition of the disclosure.

In some embodiments, the present disclosure relates to a compound of the disclosure (e.g., a compound represented by structural formula (I*), (Ia*) to (Ik*), (Ia) to (Ie), or (IIa) to (IIe) or a pharmaceutically acceptable salt thereof) or a pharmaceutical composition of the disclosure for use in the treatment of an MRGPRX2-mediated disease or disorder.

In some embodiments, the present disclosure relates to use of a compound of the disclosure (e.g., a compound represented by structural formula (I*), (Ia*) to (Ik*), (Ia) to (Ie), or (IIa) to (IIe) or a pharmaceutically acceptable salt thereof) or a pharmaceutical composition of the disclosure in the manufacture of a medicament for use in the treatment of an MRGPRX2-mediated disease or disorder.

[1] According to one aspect of the present disclosure, a compound of Formula (Ia), (Ia)

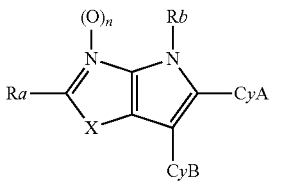

or a pharmaceutically acceptable salt thereof. In Formula (Ia), X is S, —CRd=CRe-, —CRd=N—, or —N=CRd-; Rd and Re are independently hydrogen, deuterium, halo, CN, $C_1$-$C_6$ alkyl, $C_1$-$C_6$ haloalkyl or $C_1$-$C_6$ alkoxy; Ra is hydrogen, halo, $C_1$-$C_6$ alkyl or $C_1$-$C_6$ alkoxy; Rb is hydrogen, $C_1$-$C_6$ alkyl, hydroxy-$C_1$-$C_6$ alkyl, $C_1$-$C_6$ alkoxy-$C_1$-$C_6$ alkyl, $C_1$-$C_6$ alkyl-carbonyl or $C_1$-$C_6$ alkoxy-carbonyl; CyA and CyB are independently $C_6$-$C_{10}$ aryl optionally having at least one substituent selected from a group Q, heteroaryl optionally having at least one substituent selected from the group Q, $C_3$-$C_8$ cycloalkyl optionally having at least one substituent selected from the group Q, $C_3$-$C_8$ cycloalkenyl optionally having at least one substituent selected from the group Q, heterocyclyl optionally having at least one substituent selected from the group Q, fused heterocyclic ring consisting of 9 or 10 atoms optionally having at least one substituent selected from the group Q, where the group Q is deuterium, halo, $C_1$-$C_6$ alkyl optionally substituted with one or more deuterium, $C_1$-$C_6$ haloalkyl, $C_1$-$C_6$ alkoxy optionally substituted with one or more deuterium, $C_1$-$C_6$ haloalkoxy, $C_2$-$C_6$ alkenyl, hydroxyl, $C_1$-$C_6$ hydroxyalkyl, $C_1$-$C_6$ hydroxyalkoxy, carboxy-$C_1$-$C_6$ alkyl, amino optionally having at least one $C_1$-$C_3$ alkyl, $NO_2$, CN, $CONH_2$, aminocarbonyl substituted with at least one $C_1$-$C_6$ alkyl, oxo, $C_1$-$C_6$ alkyl-carbonyl, $C_1$-$C_6$ alkoxy-carbonyl, $C_1$-$C_6$ alkyl-carbonylamino, $C_1$-$C_6$ alkoxy-carbonylamino, $C_1$-$C_6$ alkyl-carbonyl-N-methylamino, $C_1$-$C_6$ alkoxy-carbonyl-N-methylamino, $C_1$-$C_6$ alkylsulfanyl, $C_1$-$C_6$ alkylsulfinyl, $C_1$-$C_6$ alkylsulfonyl, $C_3$-$C_8$ cycloalkyl, $C_3$-$C_8$ cycloalkyl-$C_1$-$C_3$ alkoxy, $C_1$-$C_3$ alkoxy-$C_1$-$C_3$ alkyl, $C_1$-$C_3$ alkoxy-$C_1$-

$C_3$ alkoxy-$C_1$-$C_3$ alkyl, $C_1$-$C_3$ alkoxy-carbonyl-$C_1$-$C_3$ alkyl, phenyl-$C_1$-$C_6$ alkoxy, N-methylamino-carbonyl-$C_1$-$C_6$ alkyl, N,N-dimethylaminocarbonyl-$C_1$-$C_6$ alkyl, heterocyclyl, heterocyclyl-$C_1$-$C_3$ alkyl or a spiro ring; and n is 0 or 1.

[2] The compound or a pharmaceutically acceptable salt thereof according to [1], wherein the Formula (Ia) is selected from the group consisting of Formulas (Ib), (Ic), (Id) and (Ie), (Ib)

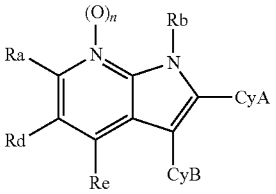

(Ic)

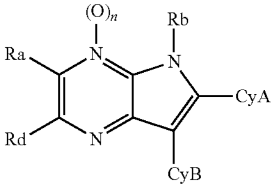

(Id)

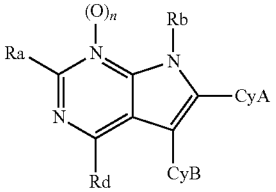

(Ie)

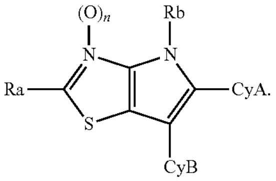

[3] The compound or a pharmaceutically acceptable salt thereof according to [1] or [2], wherein CyA is fused non-aromatic heterocyclyl-aryl optionally having at least one substituent selected from the group Q, fused non-aromatic heterocyclyl-heteroaryl optionally having at least one substituent selected from the group Q, fused arylheteroaryl optionally having at least one substituent selected from the group Q, or fused heteroarylheteroaryl optionally having at least one substituent selected from the group Q, wherein the group Q is $C_1$-$C_6$ alkyl, $C_1$-$C_6$ haloalkyl, $C_1$-$C_6$ alkoxy, $C_1$-$C_6$ haloalkoxy, hydroxyl, $C_1$-$C_6$ hydroxyalkyl, $C_1$-$C_6$ hydroxyalkoxy, carboxy-$C_{1-6}$ alkyl, amino optionally having at least one $C_{1-3}$ alkyl, $NO_2$, CN, $CONH_2$, aminocarbonyl substituted with at least one $C_1$-$C_6$ alkyl, oxo, $C_1$-$C_6$ alkyl-carbonyl, $C_1$-$C_6$ alkoxy-carbonyl, $C_1$-$C_6$ alkyl-carbonylamino, $C_1$-$C_6$ alkoxy-carbonylamino, $C_1$-$C_6$ alkyl-carbonyl-N-methylamino, $C_1$-$C_6$ alkoxy-carbonyl-N-methylamino, $C_3$-$C_8$ cyloalkyl, $C_3$-$C_8$ cyloalkyl-$C_1$-$C_3$ alkoxy, $C_1$-$C_3$ alkoxy-$C_1$-$C_3$ alkyl, $C_1$-$C_3$ alkoxy-$C_1$-$C_3$-alkoxy-$C_1$-$C_3$ alkyl, $C_1$-$C_3$ alkoxy-carbonyl-$C_1$-$C_3$ alkyl, phenyl-$C_1$-$C_6$ alkoxy, $C_1$-$C_3$ alkoxy-carbonyl-$C_1$-$C_3$ alkyl, N-methylamino-carbonyl-$C_1$-$C_6$ alkyl, N,N-dimethylaminocarbonyl-$C_1$-$C_6$ alkyl, heterocyclyl, heterocyclyl-$C_1$-$C_3$ alkyl or a spiro ring.

[4] The compound or a pharmaceutically acceptable salt thereof according to [1] or [2], wherein CyA is selected from the group consisting of

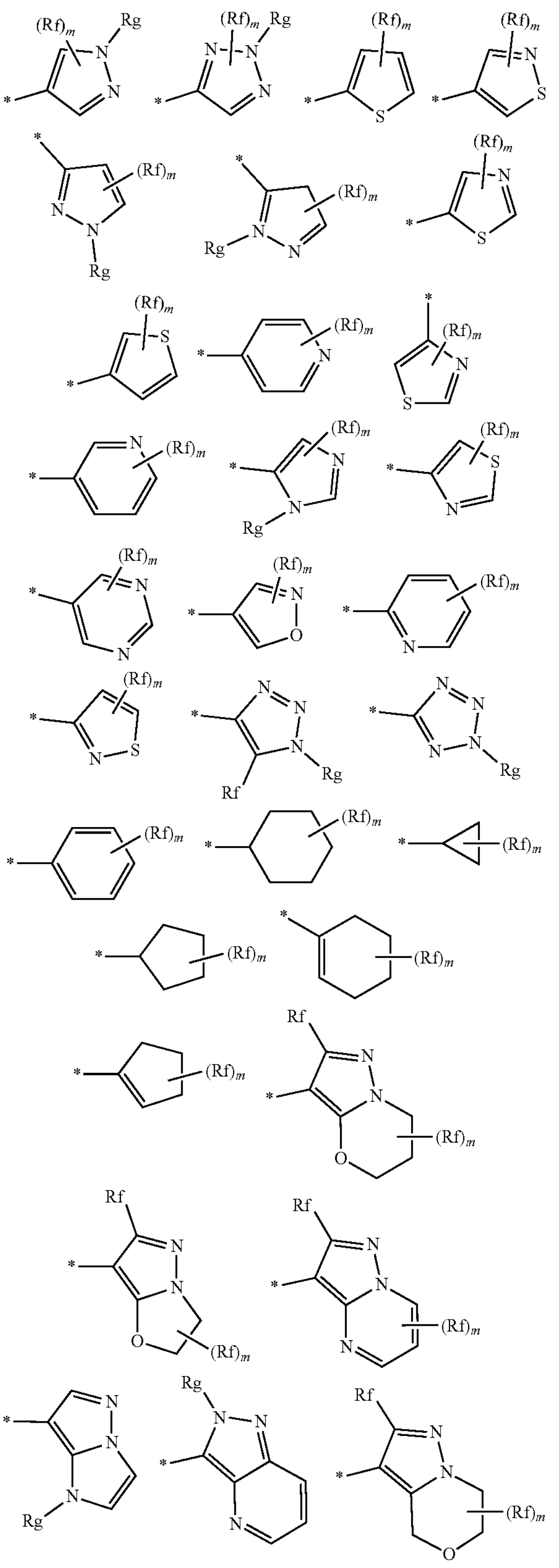

-continued

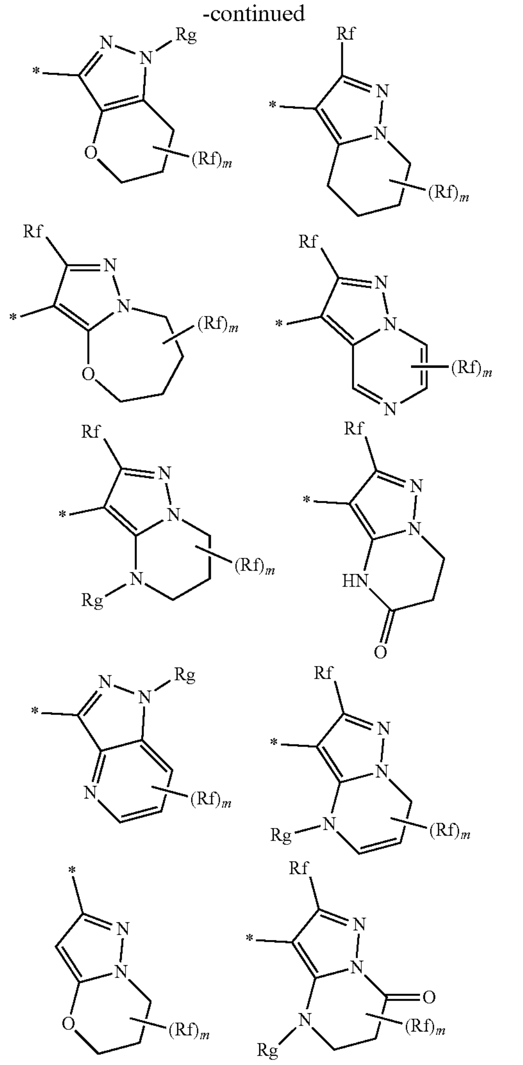

wherein each Rf is independently hydrogen, $C_1$-$C_6$ alkyl, $C_1$-$C_6$ haloalkyl, $C_1$-$C_6$ alkoxy, $C_1$-$C_6$ haloalkoxy, hydroxyl, $C_1$-$C_6$ hydroxyalkyl, $C_1$-$C_6$ hydroxyalkoxy, carboxy-$C_{1-6}$ alkyl, amino optionally having at least one $C_{1-3}$ alkyl, $NO_2$, CN, $CONH_2$, oxo, $C_1$-$C_6$ alkyl-carbonyl, $C_1$-$C_6$ alkoxy-carbonyl, $C_1$-$C_6$ alkyl-carbonylamino, $C_1$-$C_6$ alkoxy-carbonylamino, $C_1$-$C_6$ alkyl-carbonyl-N-methylamino, $C_1$-$C_6$ alkoxy-carbonyl-N-methylamino, $C_3$-$C_8$ cycloalkyl, $C_3$-$C_8$ cycloalkyl-$C_1$-$C_3$ alkoxy, $C_1$-$C_3$ alkoxy-$C_1$-$C_3$ alkyl, $C_1$-$C_3$ alkoxy-$C_1$-$C_3$-alkoxy-$C_1$-$C_3$ alkyl, $C_1$-$C_3$ alkoxy-carbonyl-$C_1$-$C_3$ alkyl, or phenyl-$C_1$-$C_6$ alkoxy or two Rf are taken together with the carbon atom to which they are attached to form a spiro ring; Rg is hydrogen, $C_1$-$C_6$ alkyl, $C_1$-$C_6$ haloalkyl, carboxy-$C_1$-$C_6$ alkyl, amino optionally having at least one $C_1$-$C_3$ alkyl, $C_1$-$C_3$ alkoxy-$C_1$-$C_3$ alkyl, $C_1$-$C_3$ alkoxy-carbonyl-$C_1$-$C_3$ alkyl, carboxy-$C_1$-$C_6$ alkyl, N-methylamino-carbonyl-$C_1$-$C_6$ alkyl, N,N-dimethylaminocarbonyl-$C_1$-$C_6$ alkyl, heterocyclyl or heterocyclyl-$C_1$-$C_3$ alkyl; m is an integer of 0 to 5; and asterisks denote the points of attachment.

[5] The compound or a pharmaceutically acceptable salt thereof according to [1] or [2], wherein CyB is $C_6$-$C_{10}$ aryl optionally having at least one substituent selected from the group Q, or heteroaryl optionally having at least one substituent selected from the group Q, and the group Q is halo, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, hydroxyl, $C_1$-$C_6$ hydroxyalkyl, amino optionally having at least one $C_1$-$C_3$ alkyl, CN, oxo, $C_1$-$C_6$ alkylsulfanyl, $C_1$-$C_6$ alkylsulfinyl, $C_1$-$C_6$ alkylsulfonyl, or $C_3$-$C_8$ cycloalkyl.

[6] The compound or a pharmaceutically acceptable salt thereof according to [1], 2] or [4], wherein CyB is selected from the group consisting of

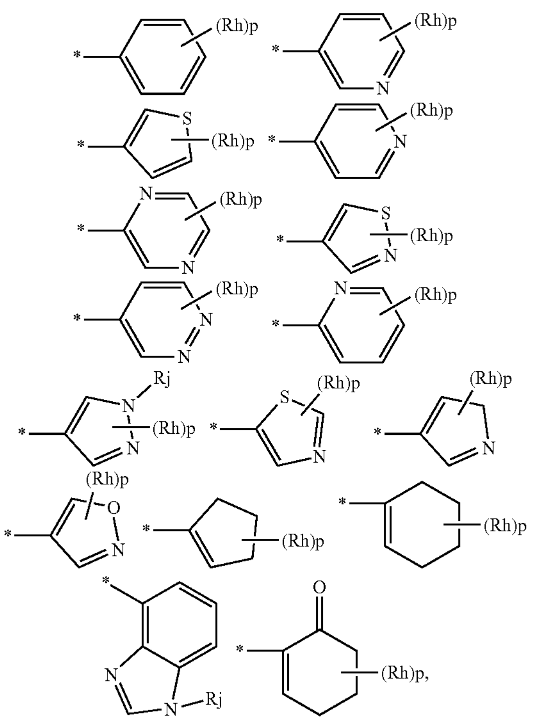

wherein each Rh is independently halo, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, hydroxyl, $C_1$-$C_6$ hydroxyalkyl, amino optionally having at least one $C_1$-$C_3$ alkyl, CN, oxo, $C_1$-$C_6$ alkylsulfonyl, or $C_3$-$C_8$ cycloalkyl; Rj is hydrogen, $C_1$-$C_6$ alkyl, or $C_1$-$C_6$ haloalkyl;

p is an integer of 0 to 5; and asterisks denote the points of attachment.

[7] The compound or a pharmaceutically acceptable salt thereof according to [1] or [6], wherein the Formula (Ia) is Formula (Ib)

(Ib)

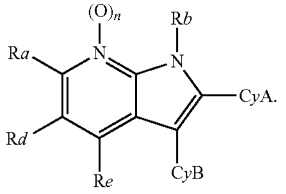

[8] The compound or a pharmaceutically acceptable salt thereof according to [7], wherein Ra, Rb, Rd and Re are hydrogens; and n is 0.

[9] The compound or a pharmaceutically acceptable salt thereof according to [8], wherein CyB is phenyl optionally having at least one substituent selected from the group Q.

[10] The compound or a pharmacologically acceptable salt thereof according to [1], wherein the compound has a structure selected from the group consisting of structures,
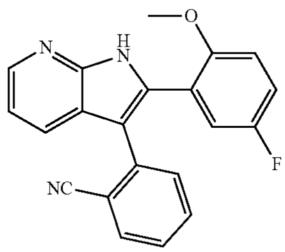
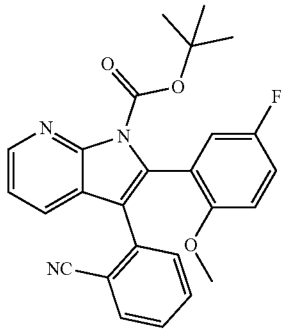
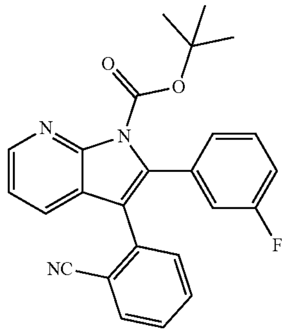
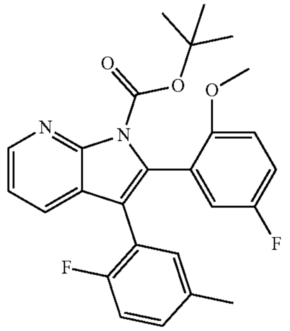
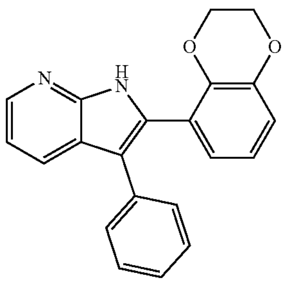
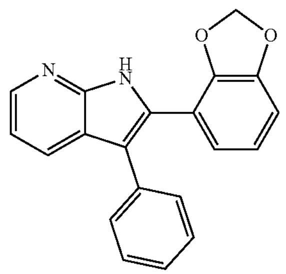
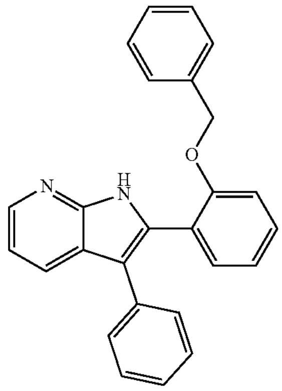
-continued
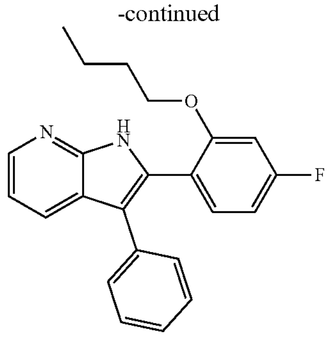
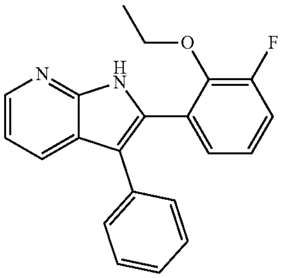
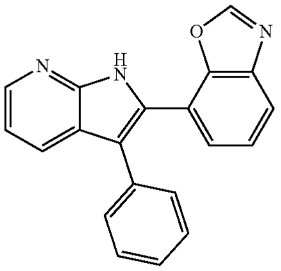
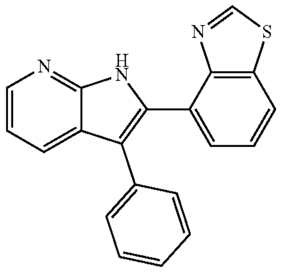
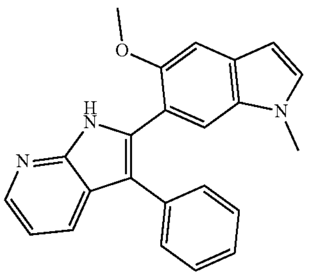
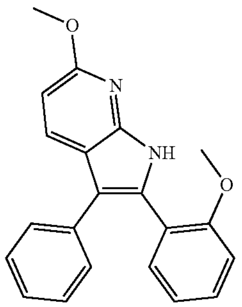
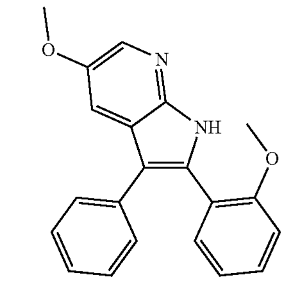
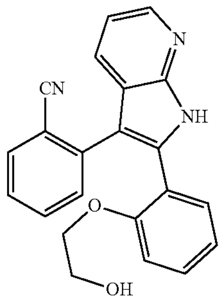

-continued
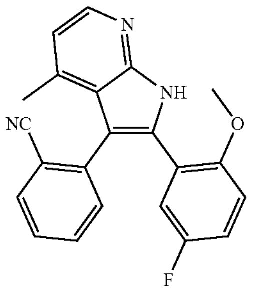
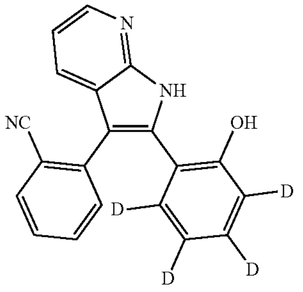
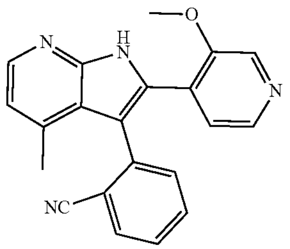
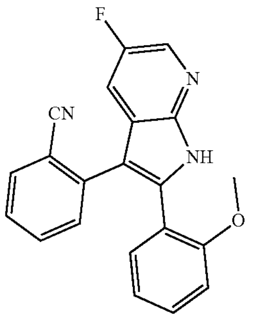
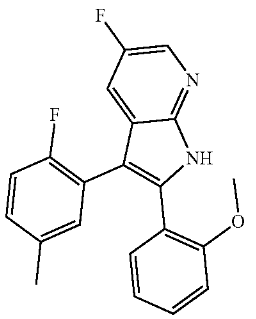
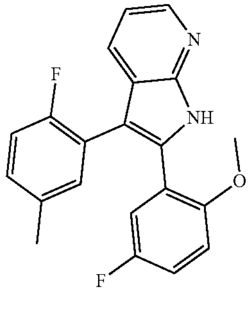
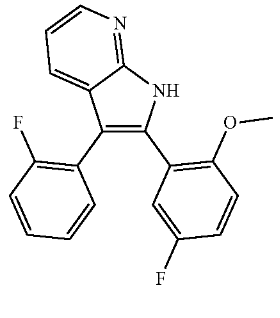
-continued
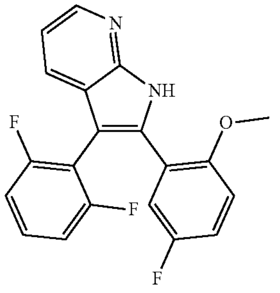
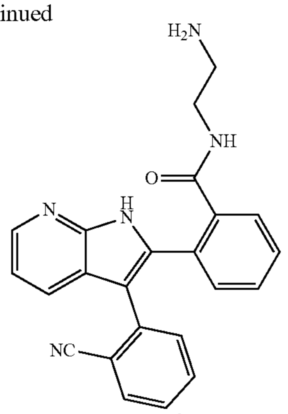
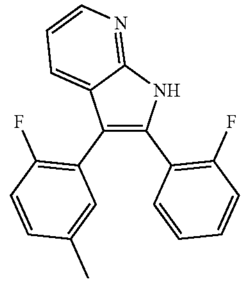
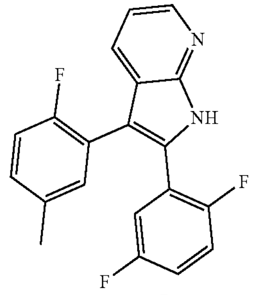
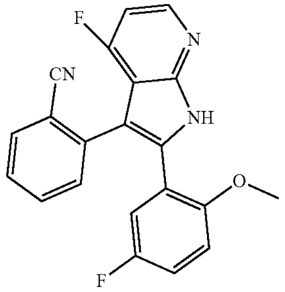
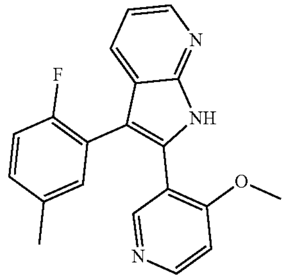
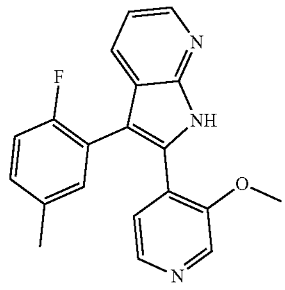
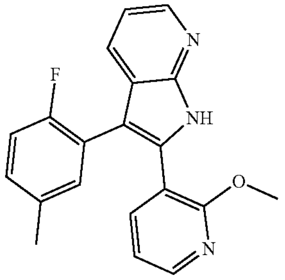
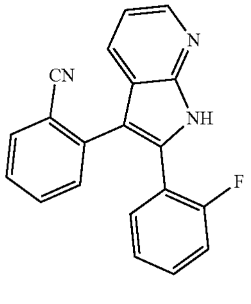
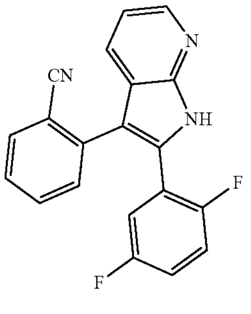

-continued
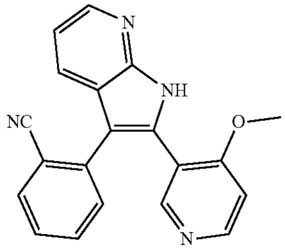
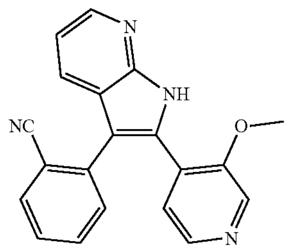
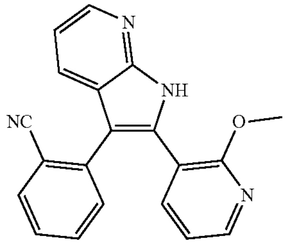
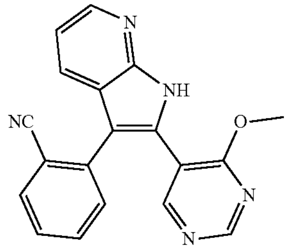
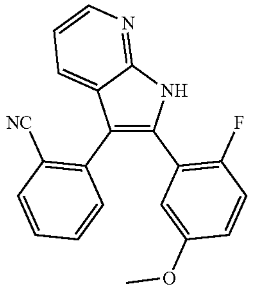
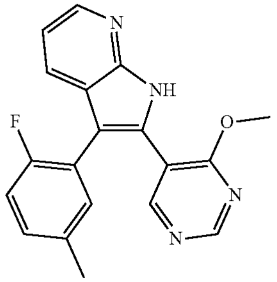
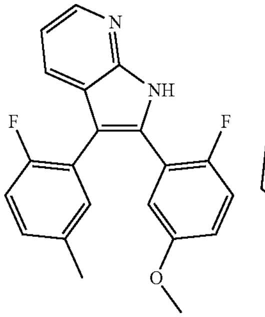
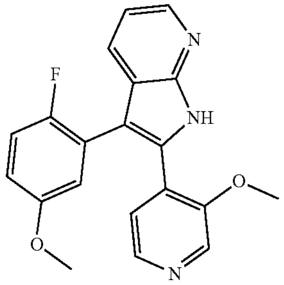
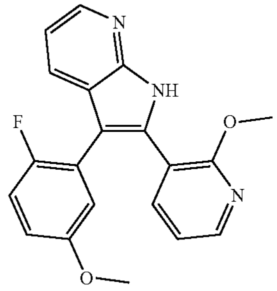
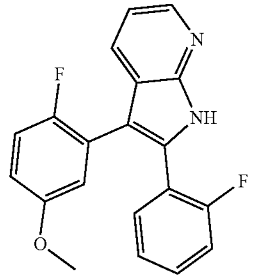
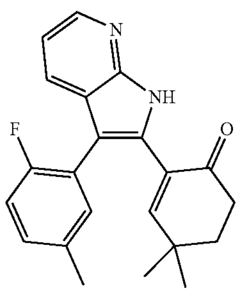
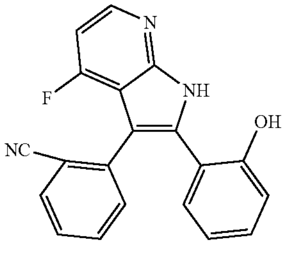
-continued
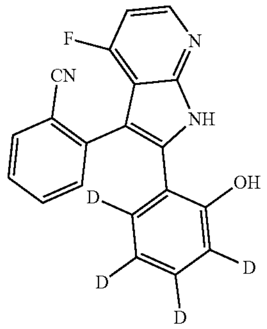
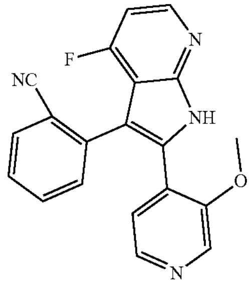
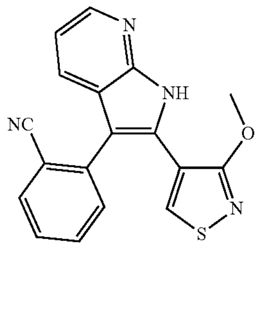
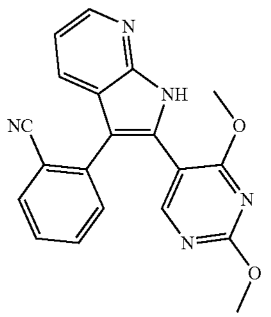
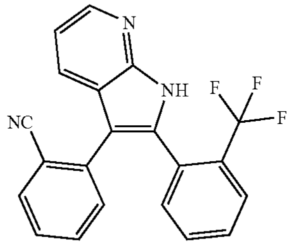
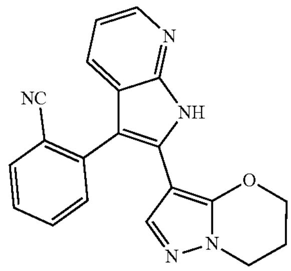
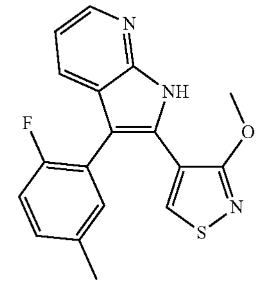
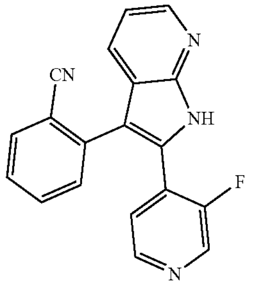
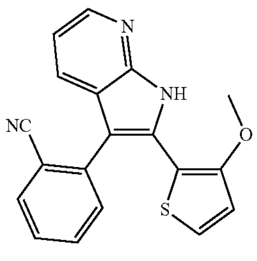
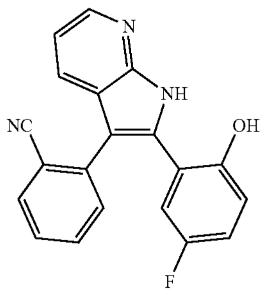

-continued
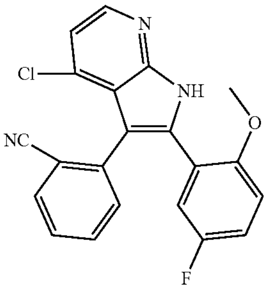
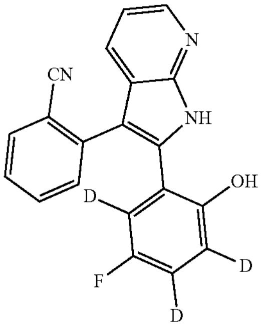
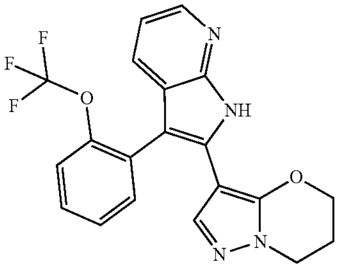
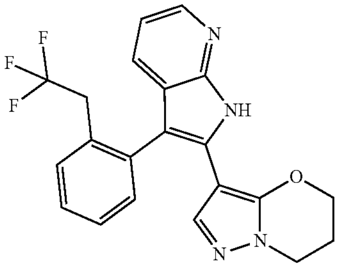
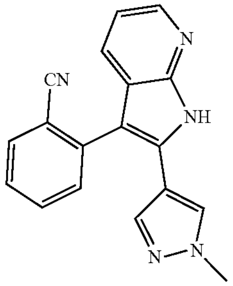
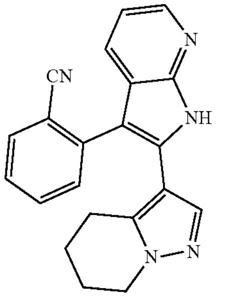
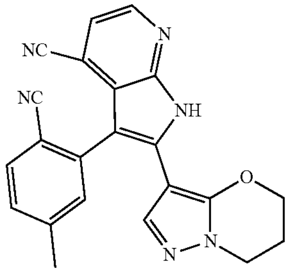
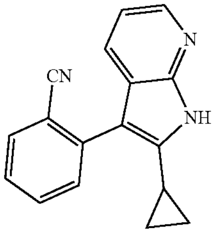
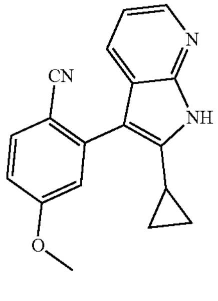
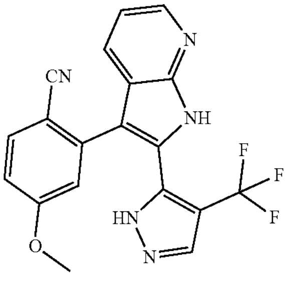
-continued
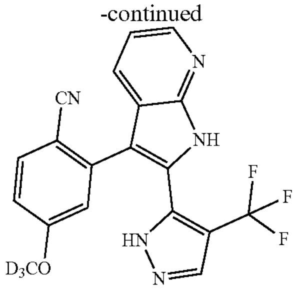
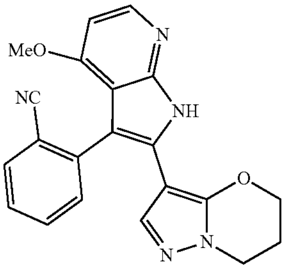
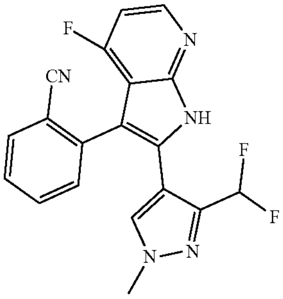
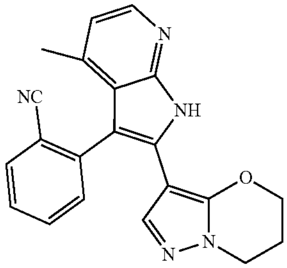
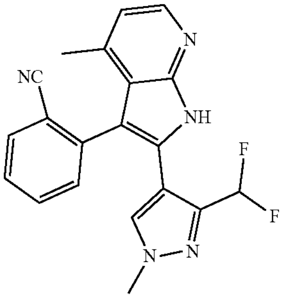
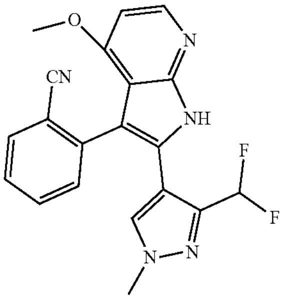
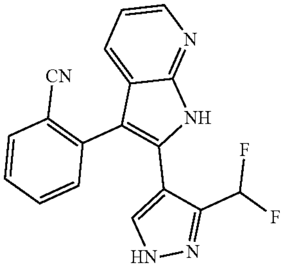
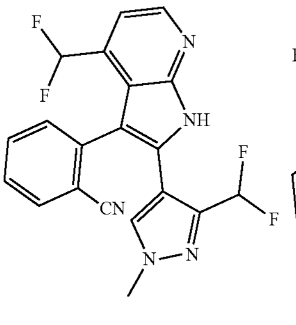
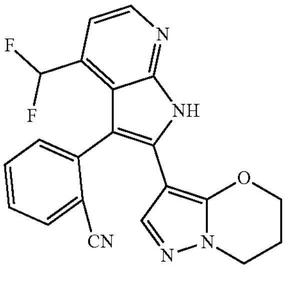

-continued
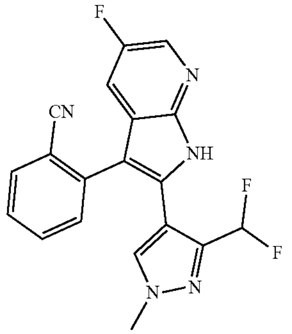
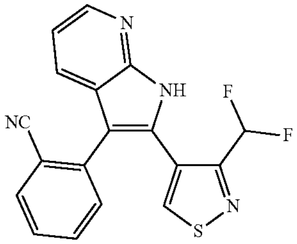
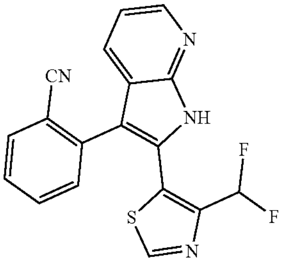
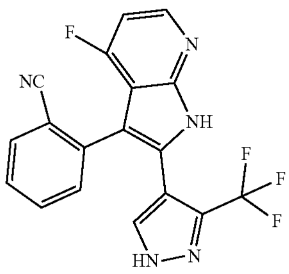
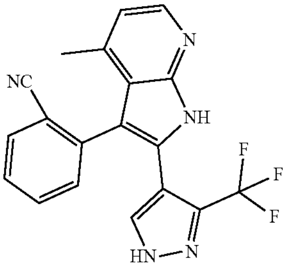
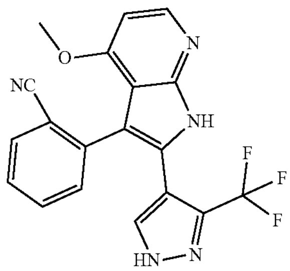
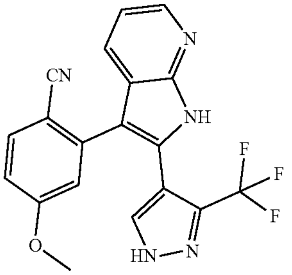
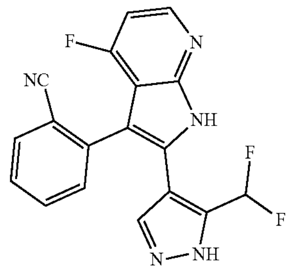
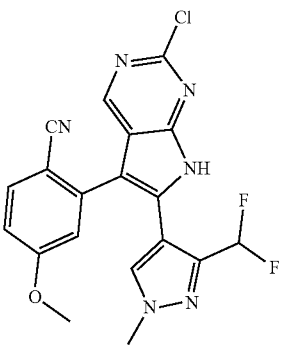
-continued
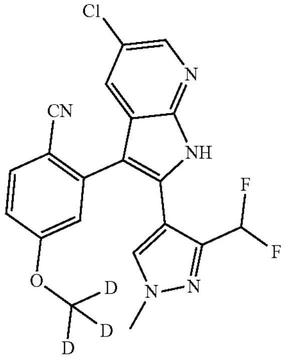
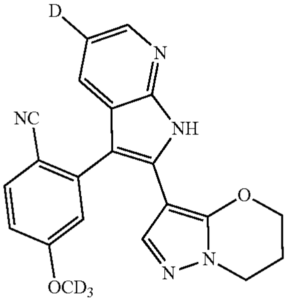
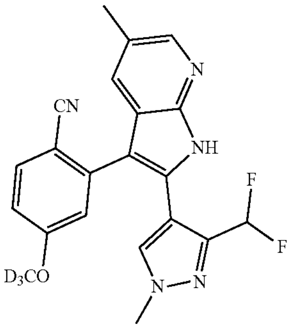
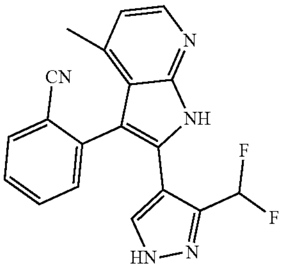
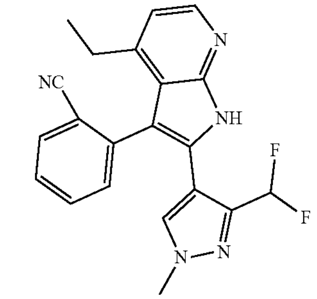
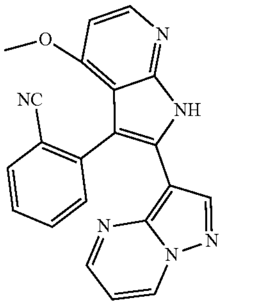
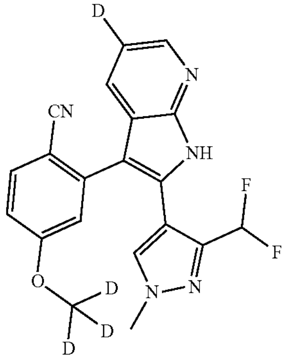
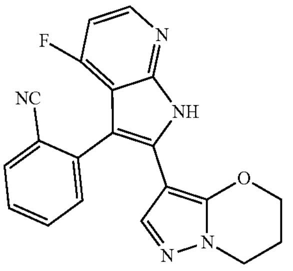
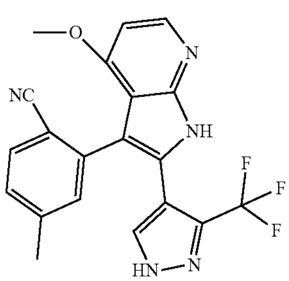
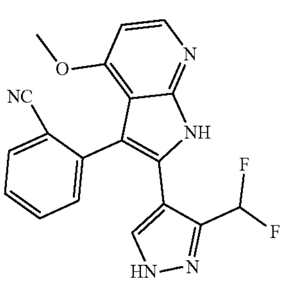

-continued
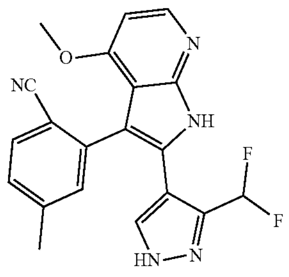
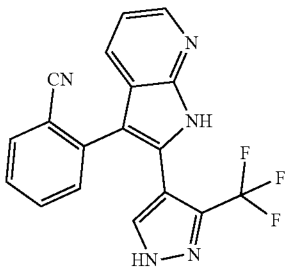
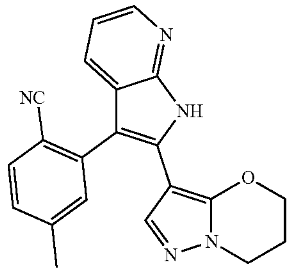
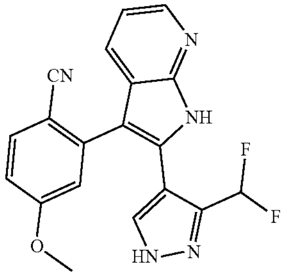
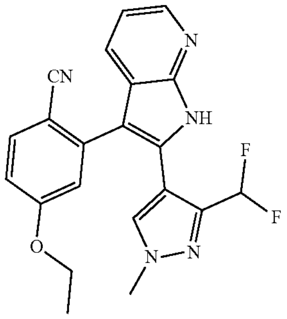
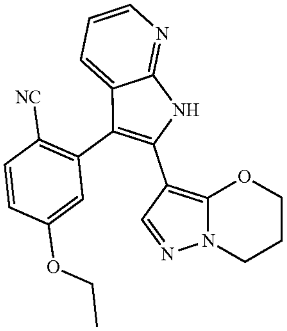
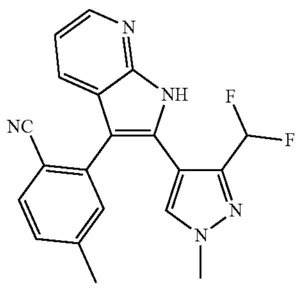
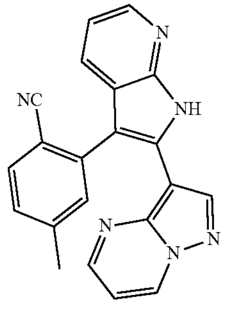
-continued
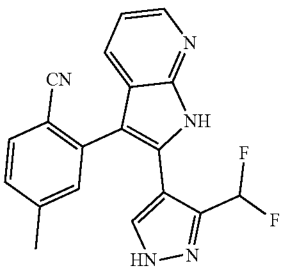
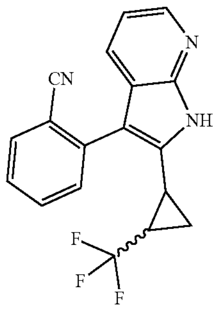
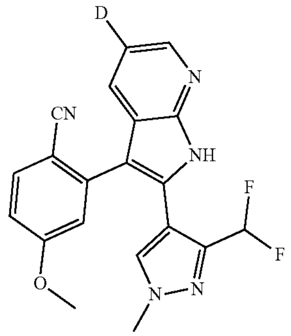
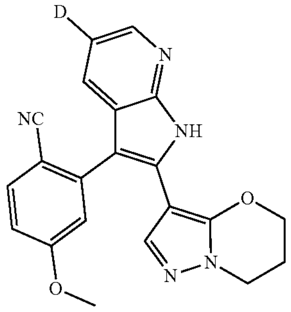
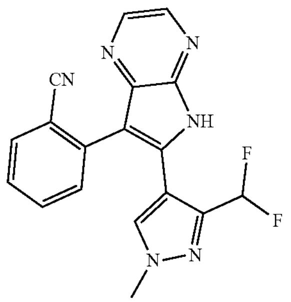
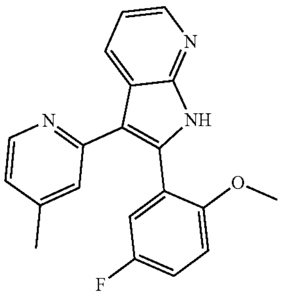
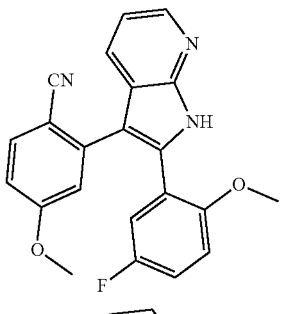
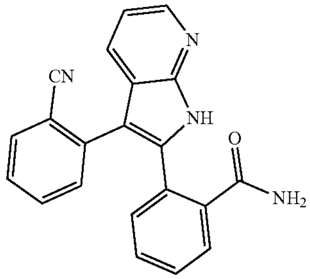

-continued
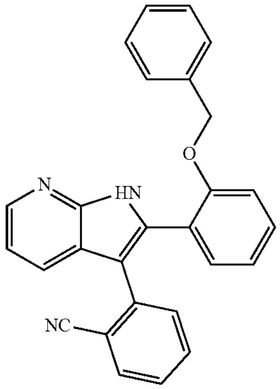
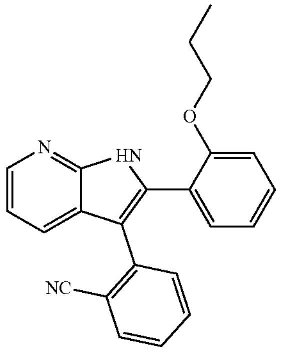
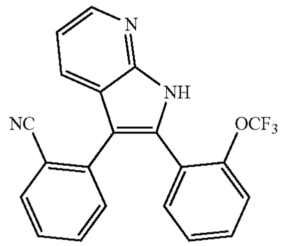
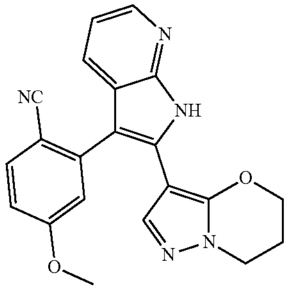
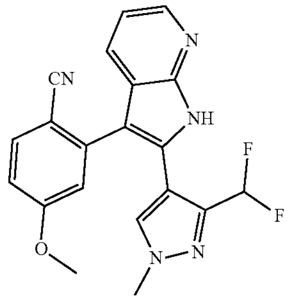
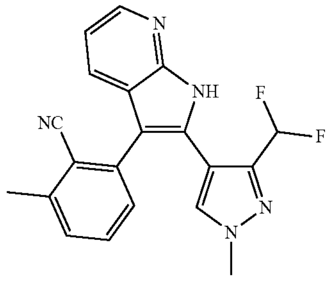
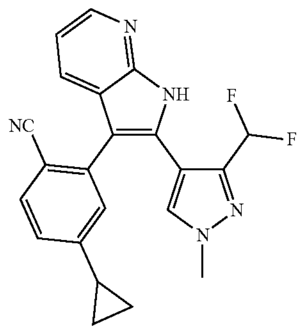
-continued
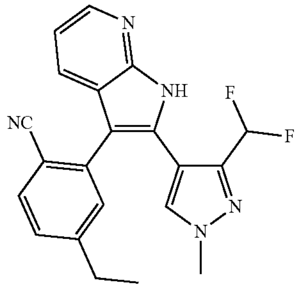
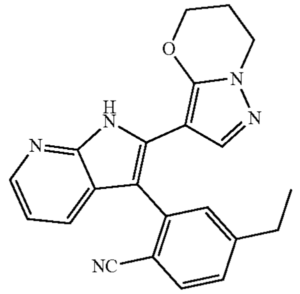
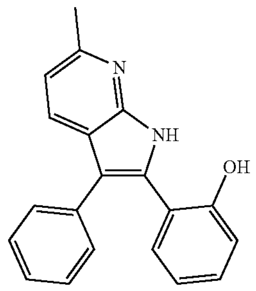
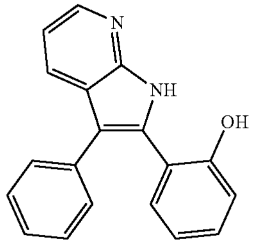
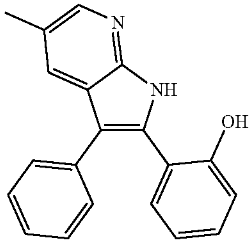
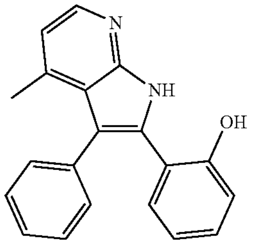
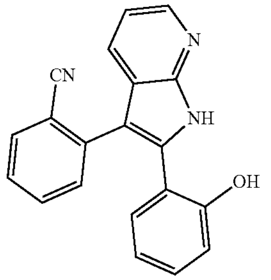
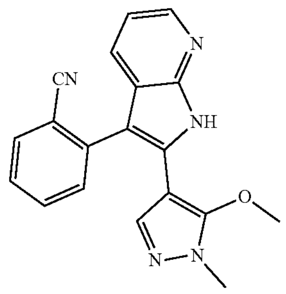
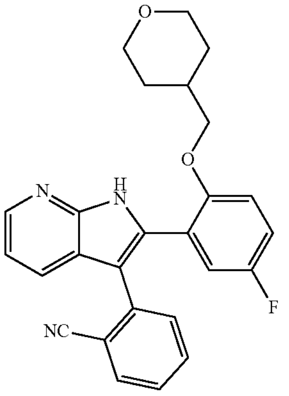

-continued
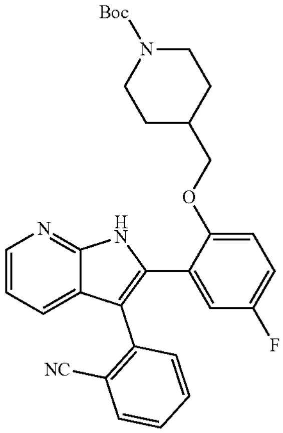
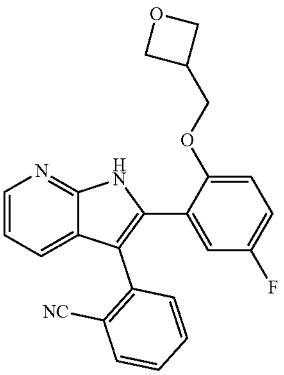
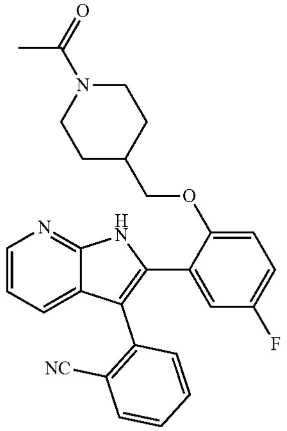
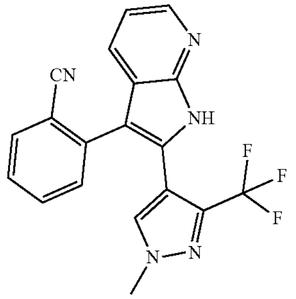
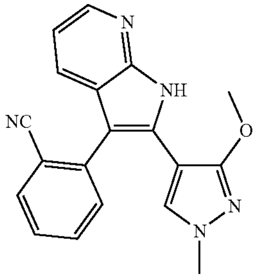
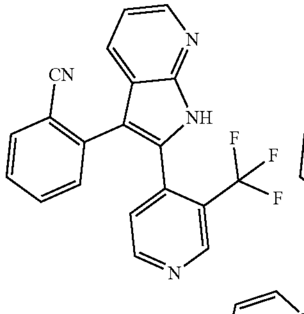
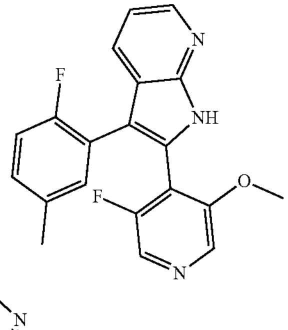
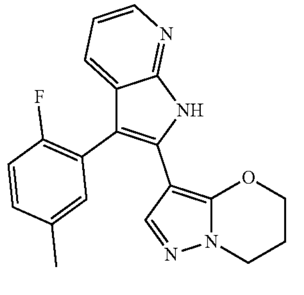
-continued
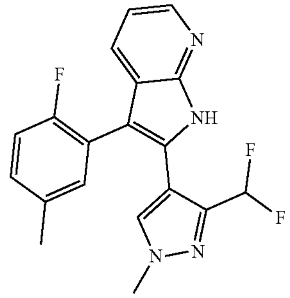
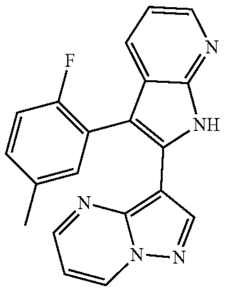
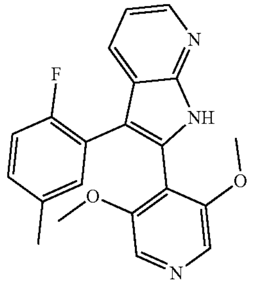
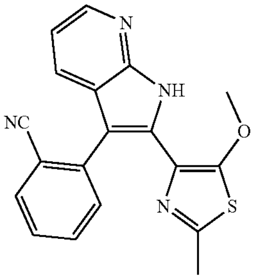
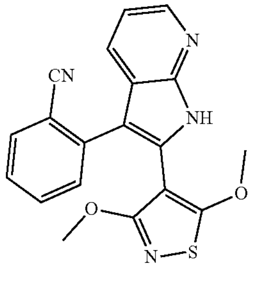
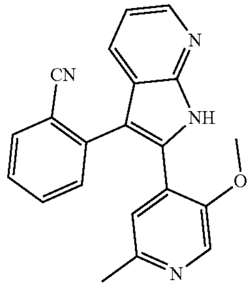
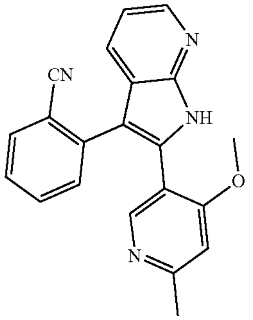
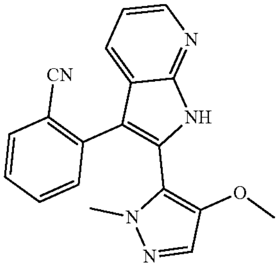
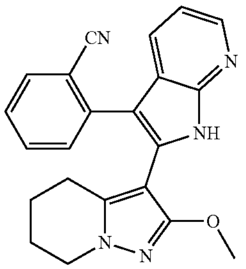
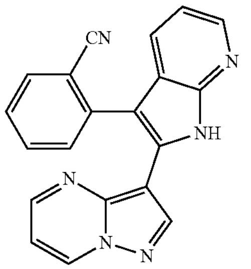

-continued
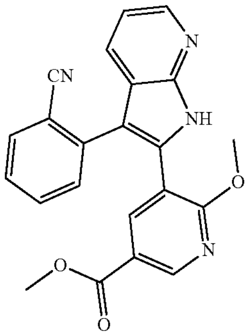
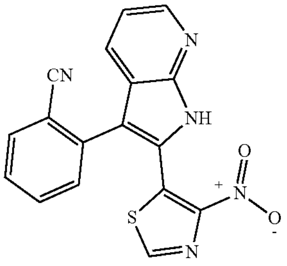
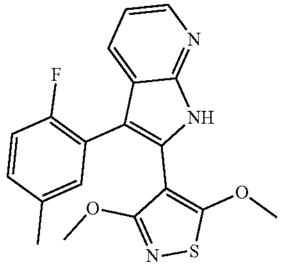
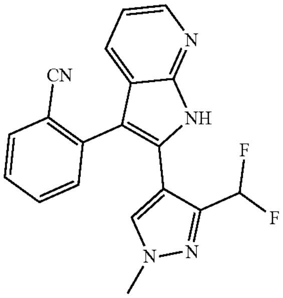
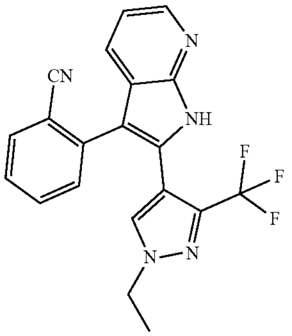
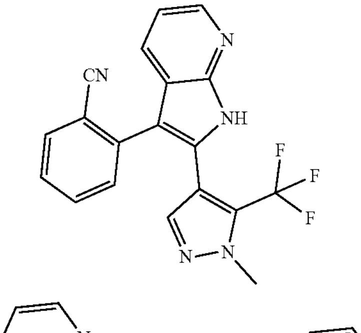
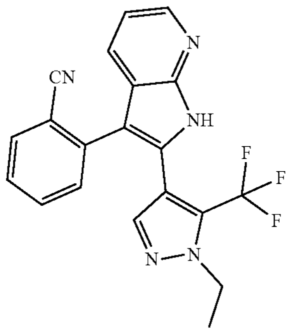
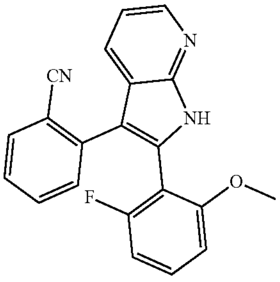
-continued
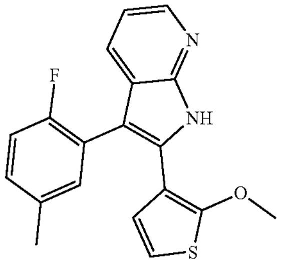
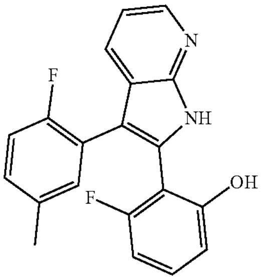
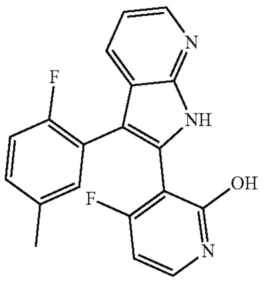
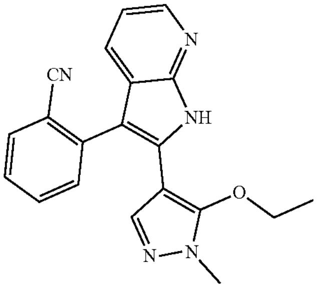
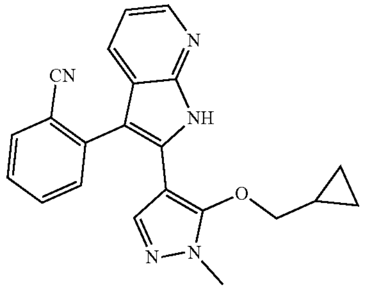
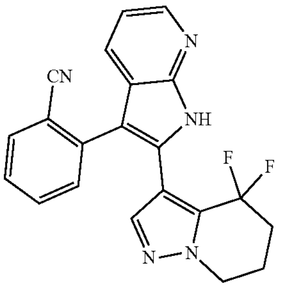
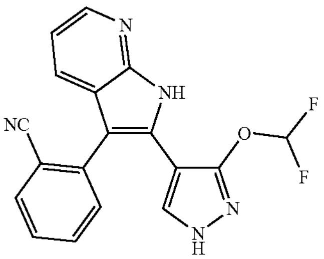

-continued
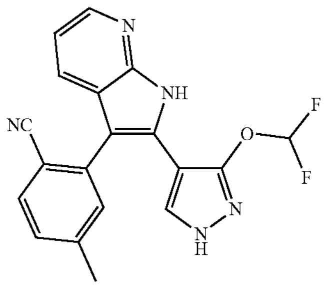
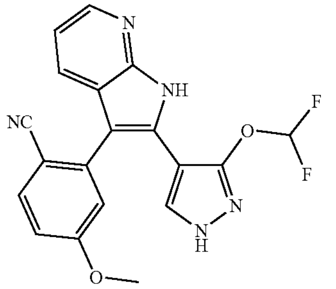
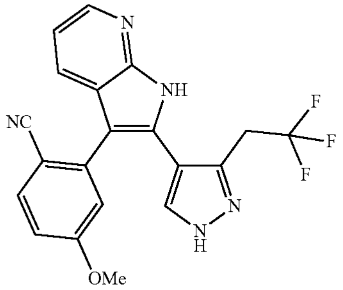
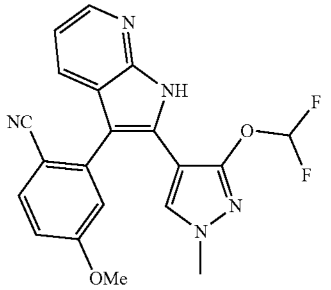
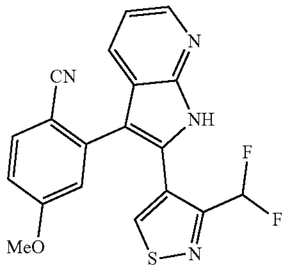
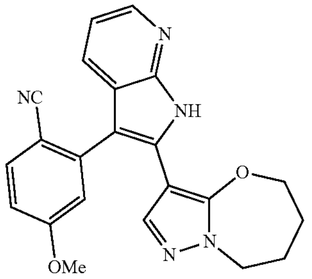
-continued
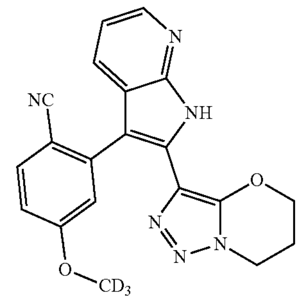
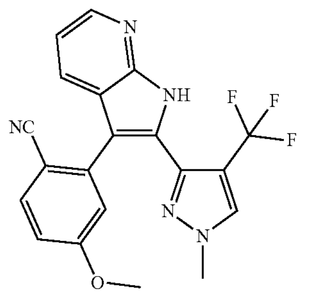
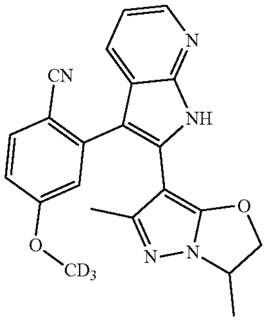
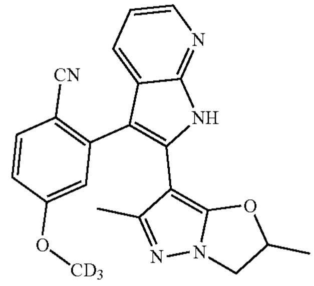
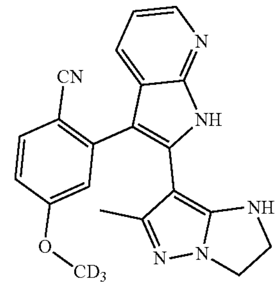
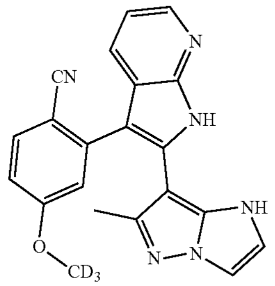
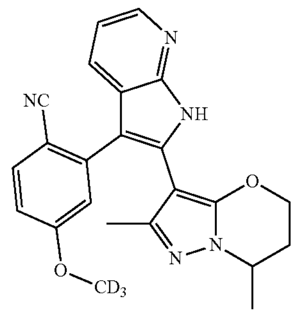

-continued
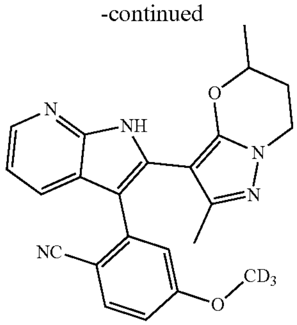
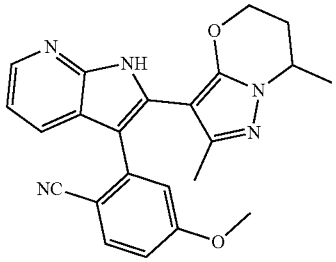
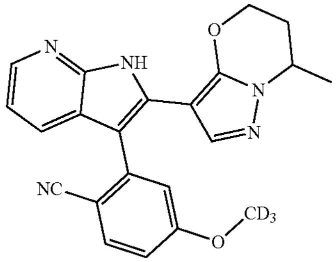
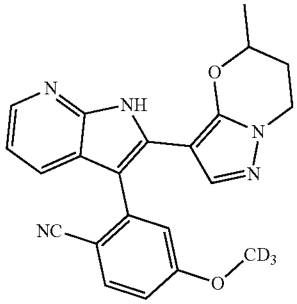
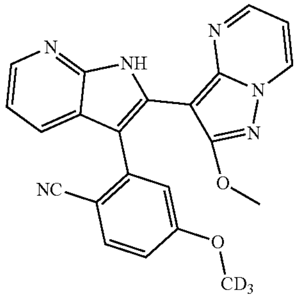
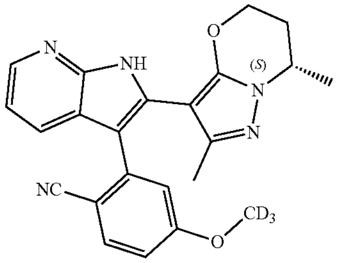
-continued
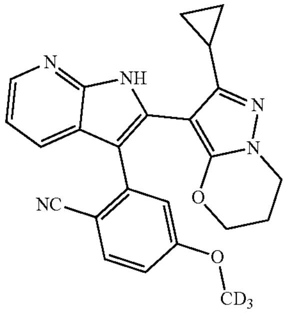
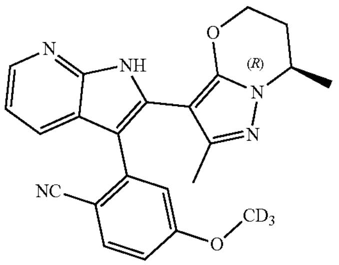
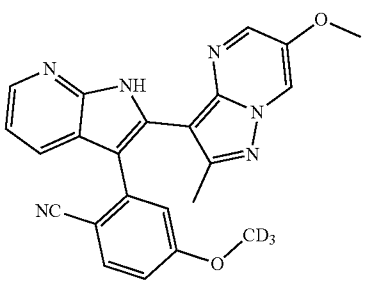
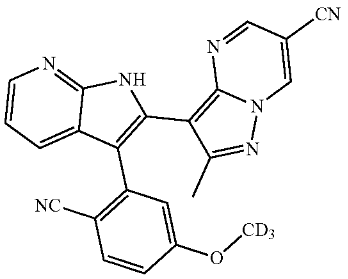
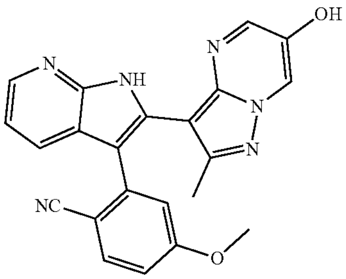
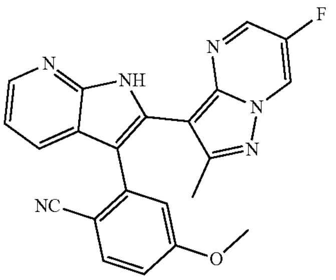

-continued
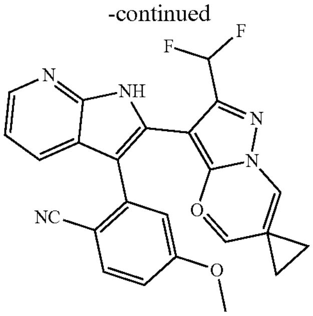
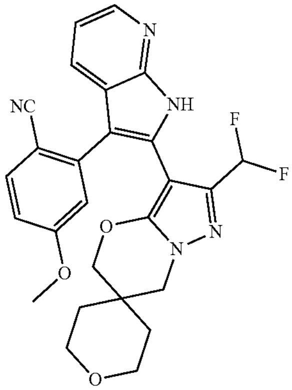
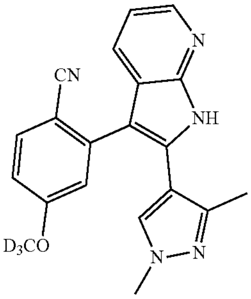
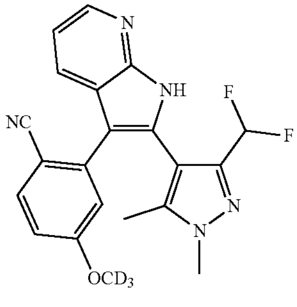
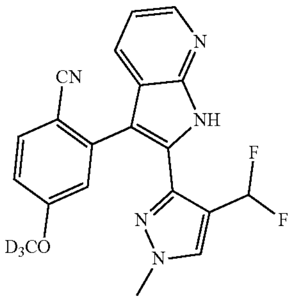
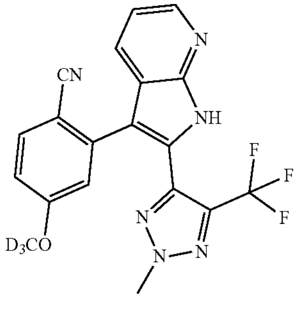
-continued
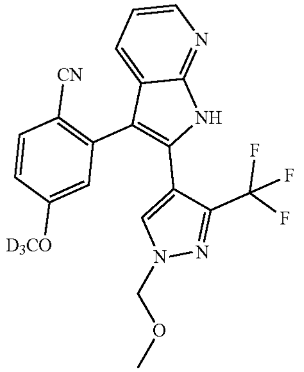
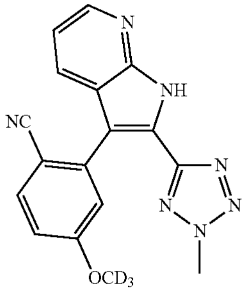
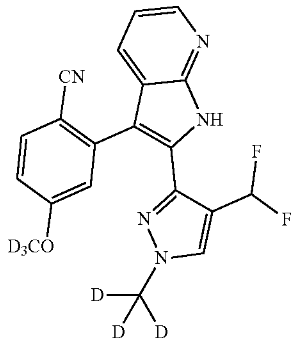
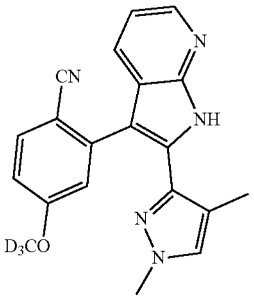
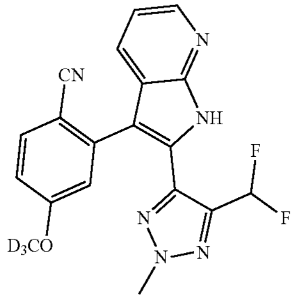
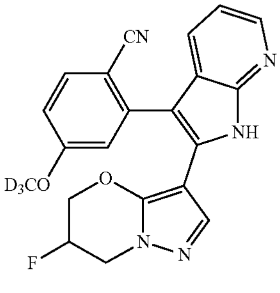
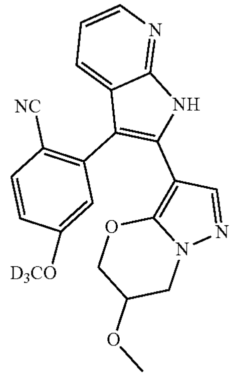
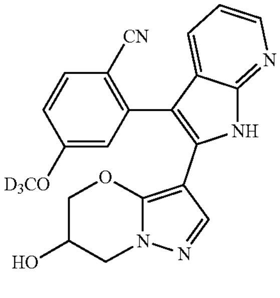
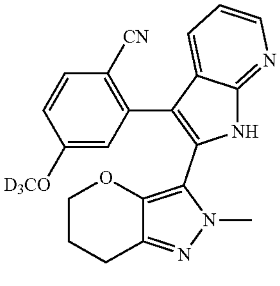

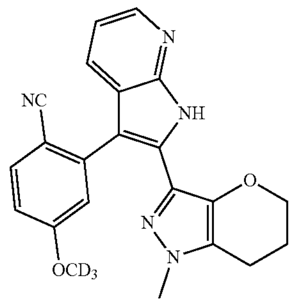
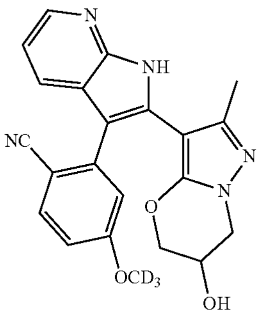
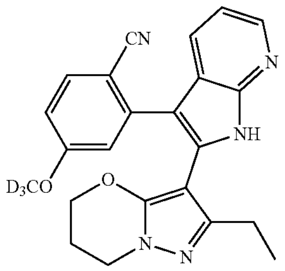
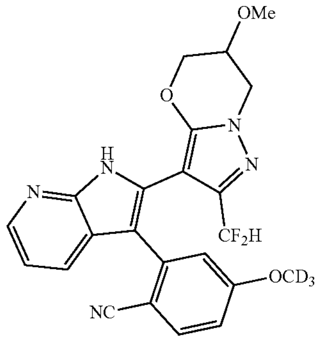
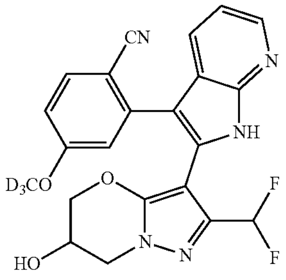
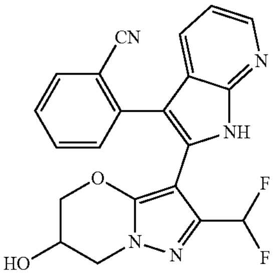
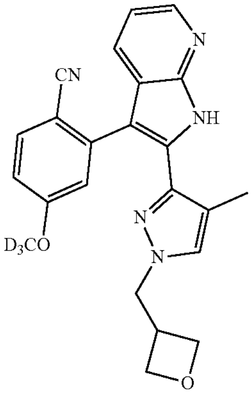
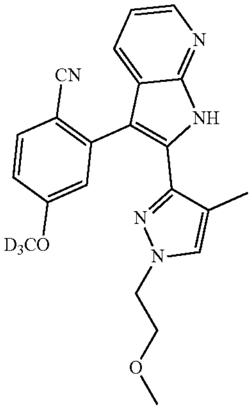
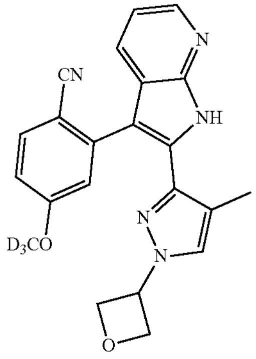
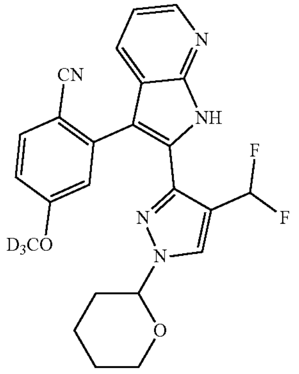
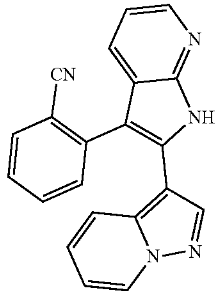
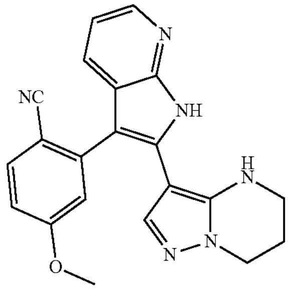
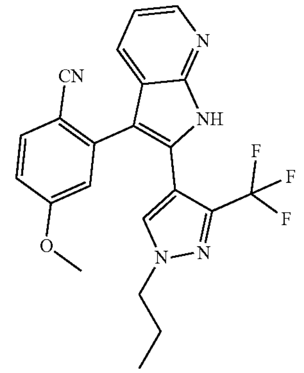
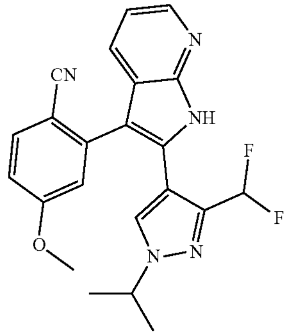
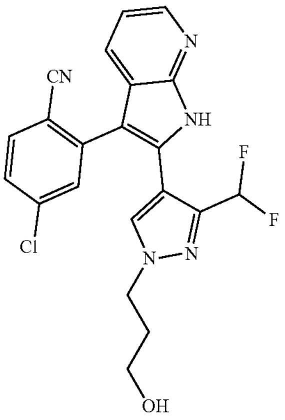

-continued
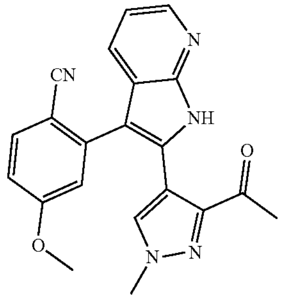
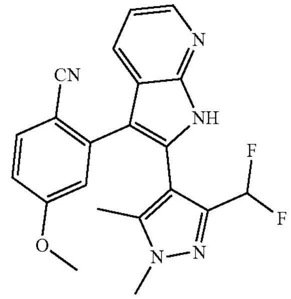
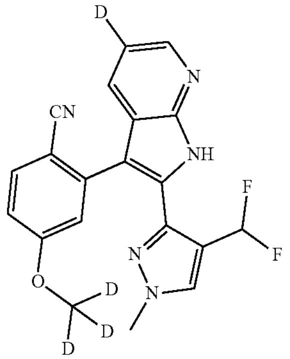
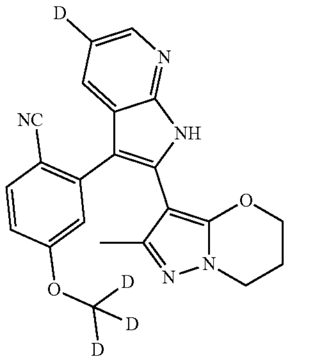
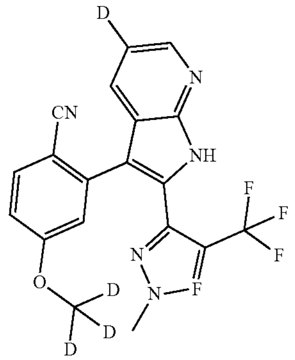
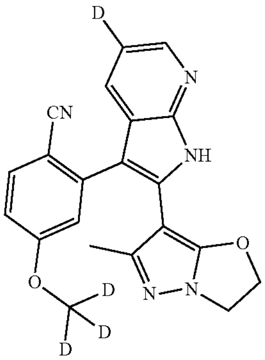
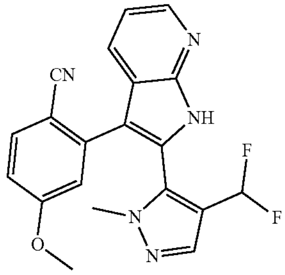
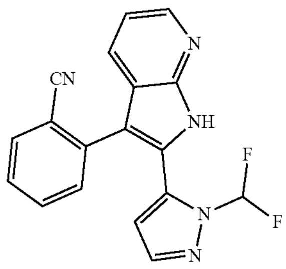
-continued
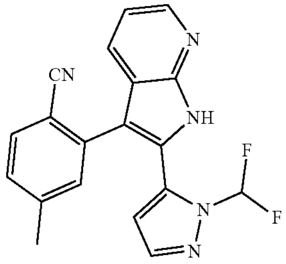
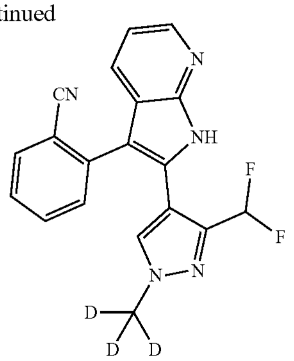
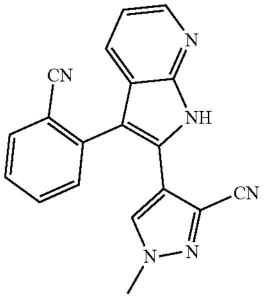
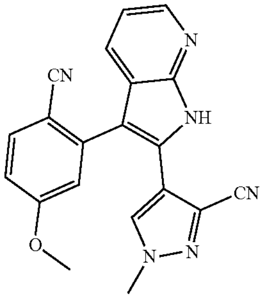
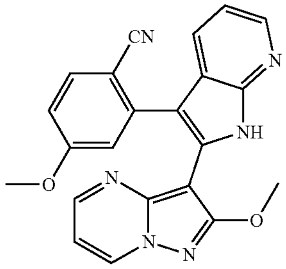
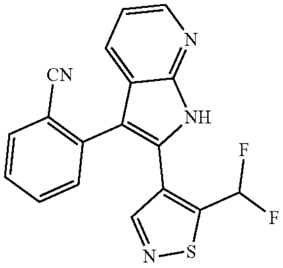
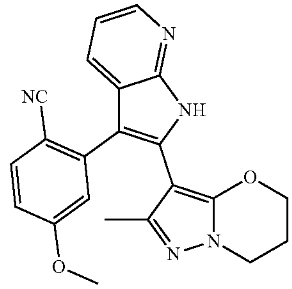
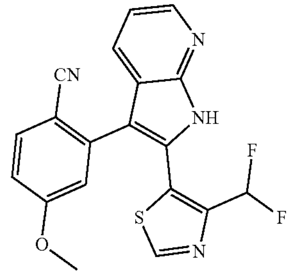

-continued
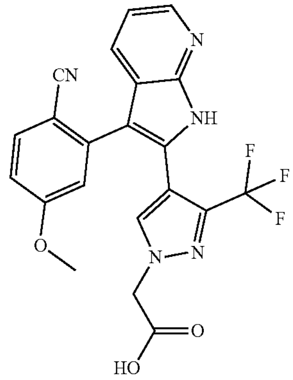
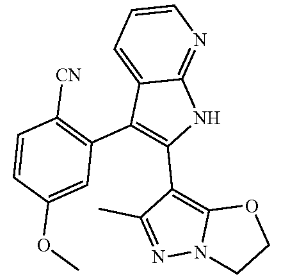
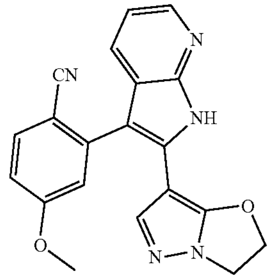
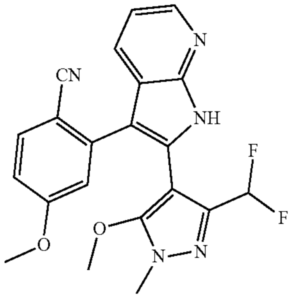
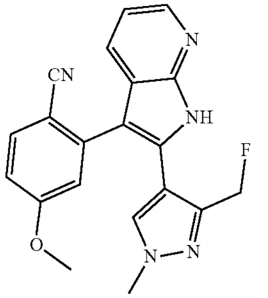
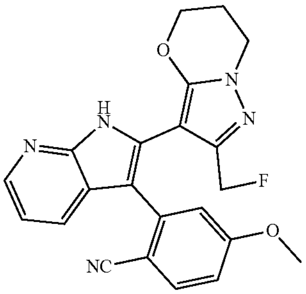
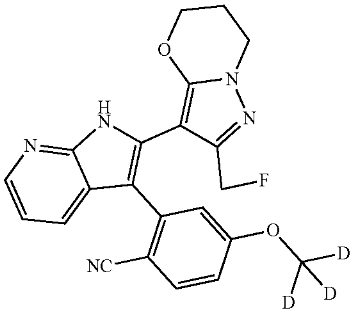
-continued
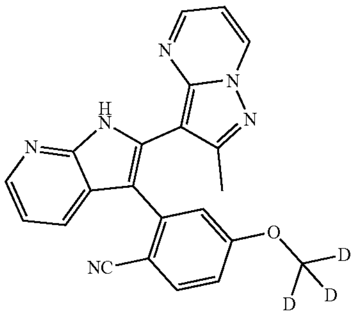
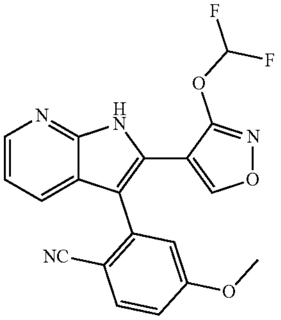
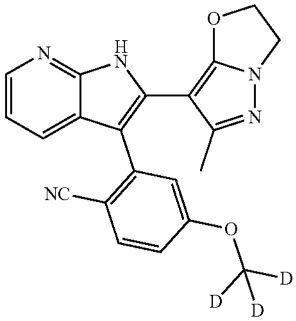
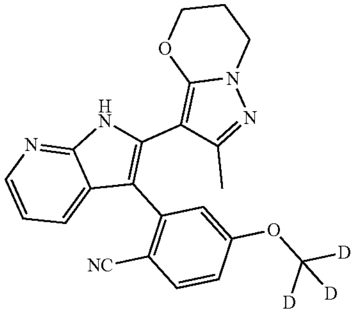
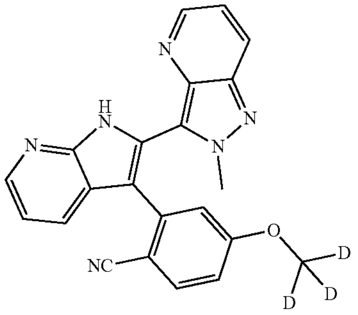

-continued
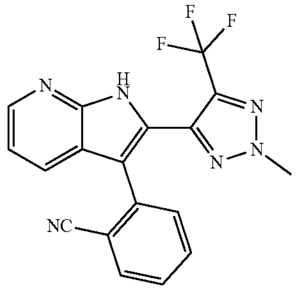
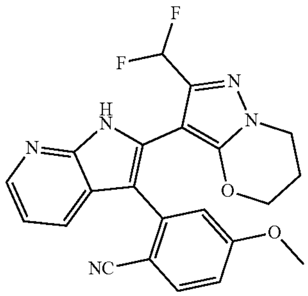
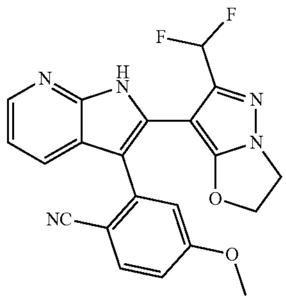
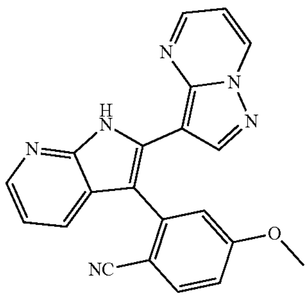
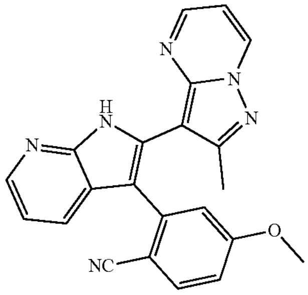
-continued
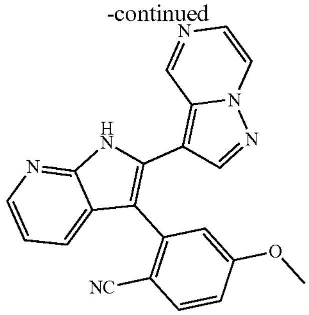
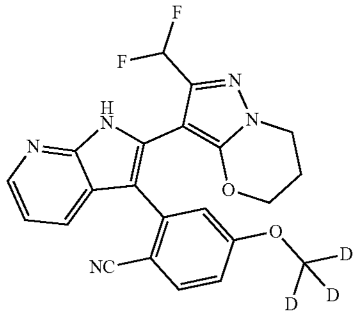
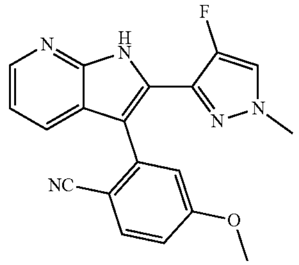
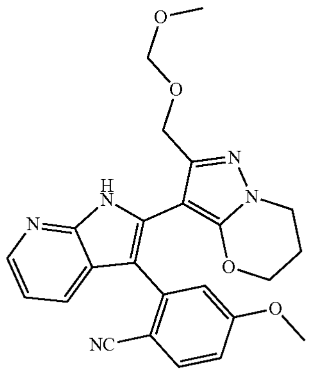
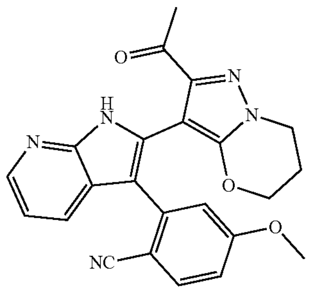

-continued
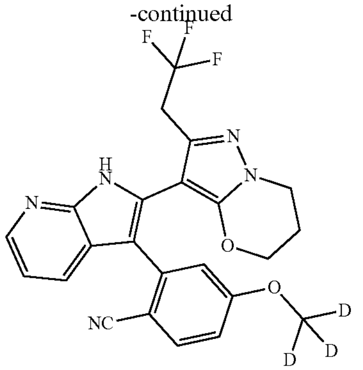
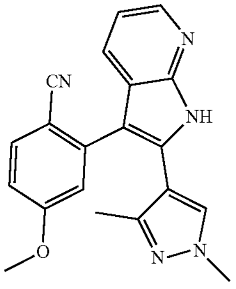
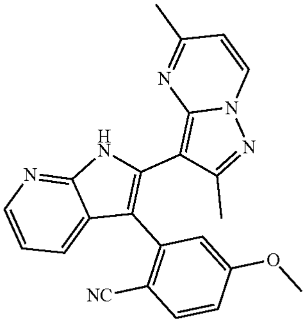
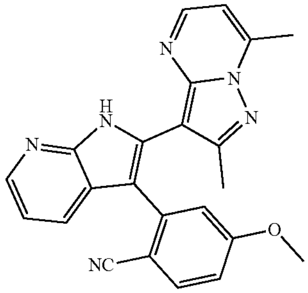
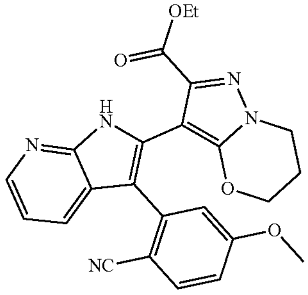
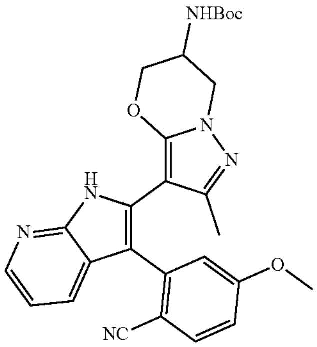
-continued
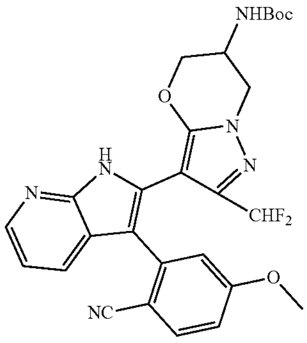
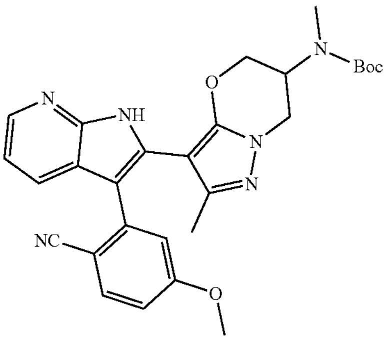
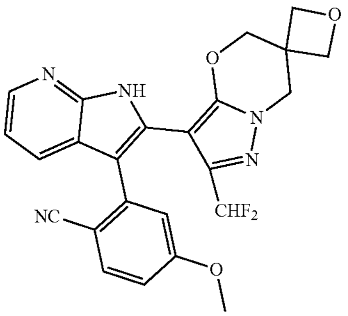
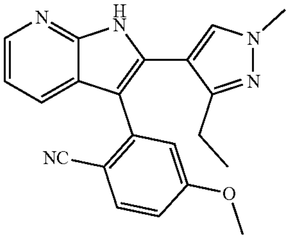
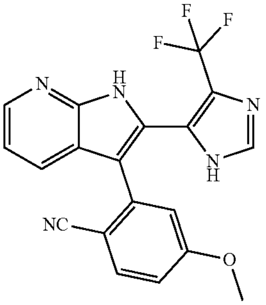

-continued
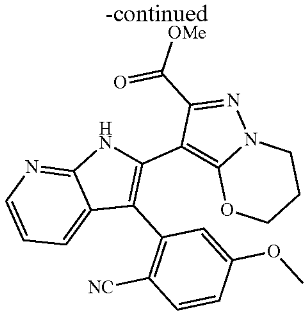
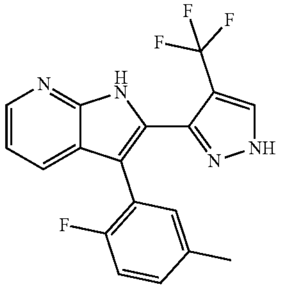
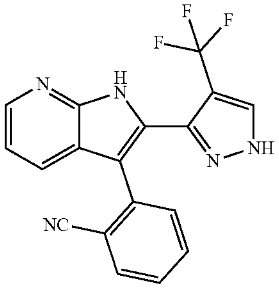
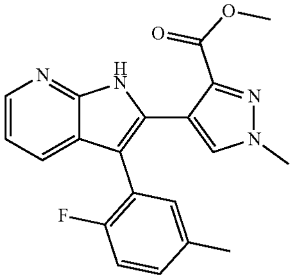
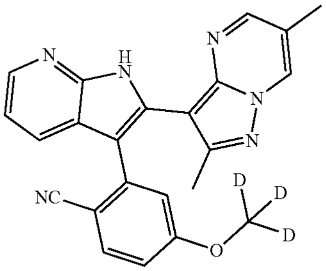
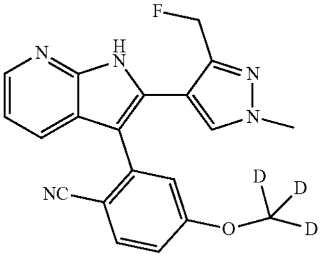
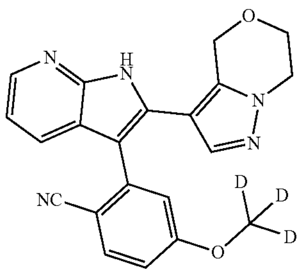
-continued
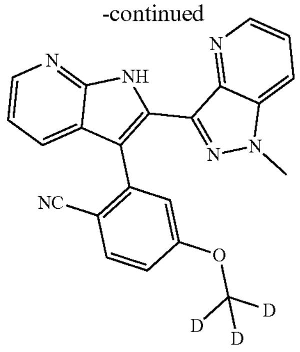
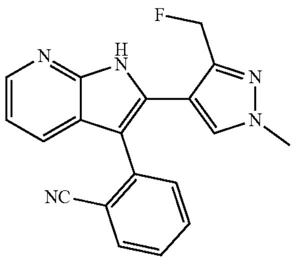
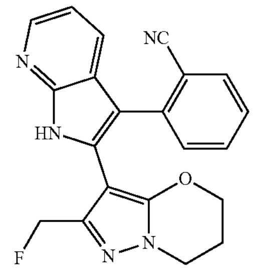
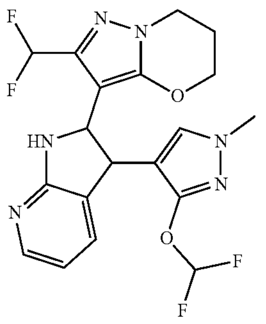
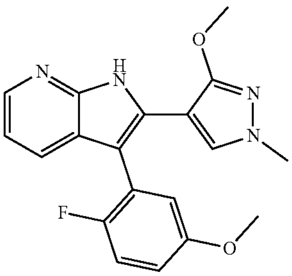
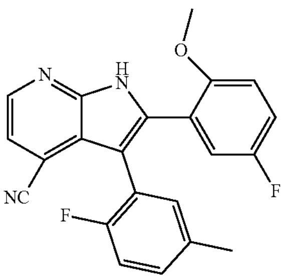
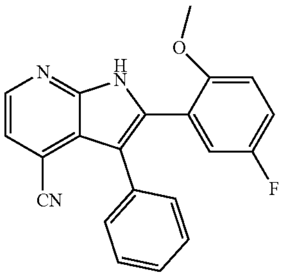
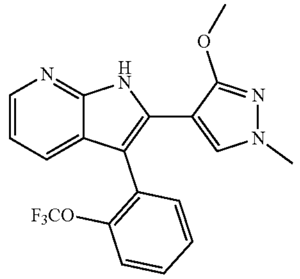

-continued
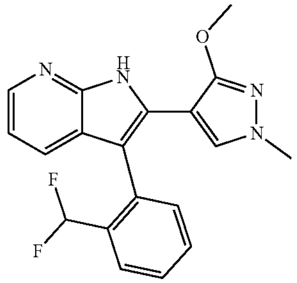
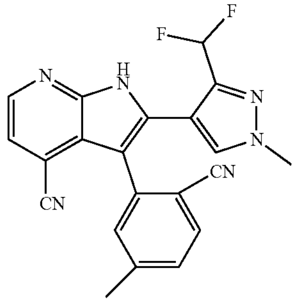
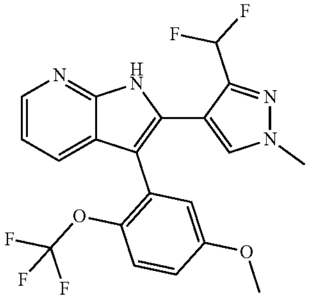
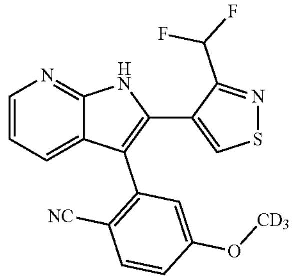
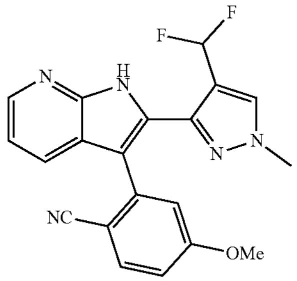
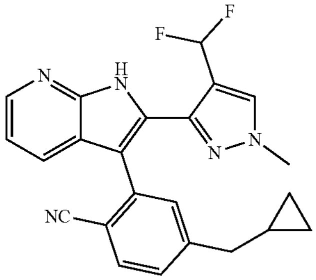
-continued
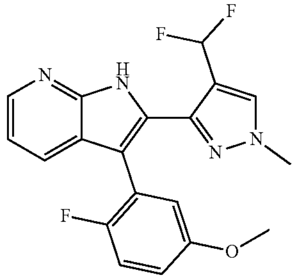
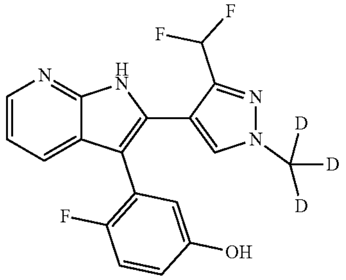
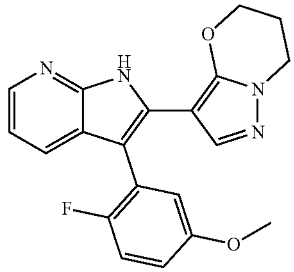
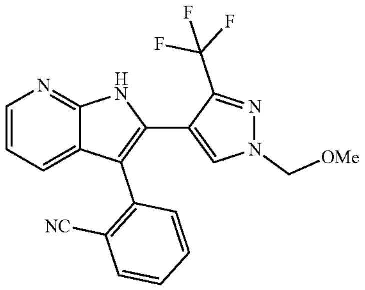
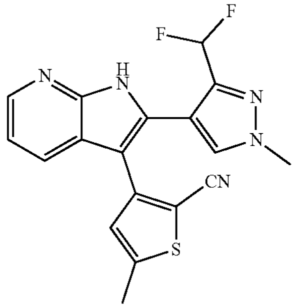
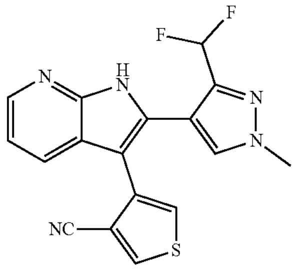

-continued
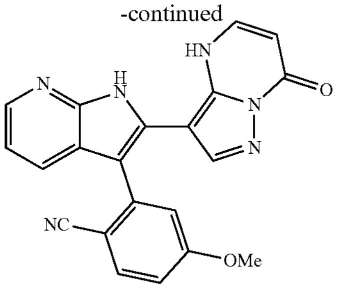
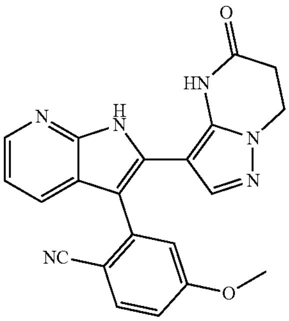
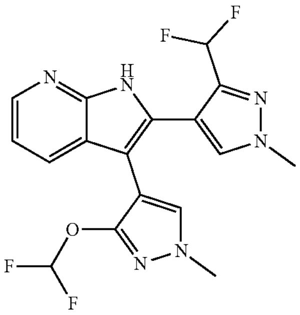
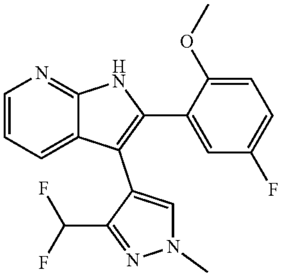
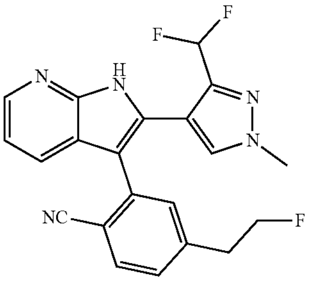
-continued
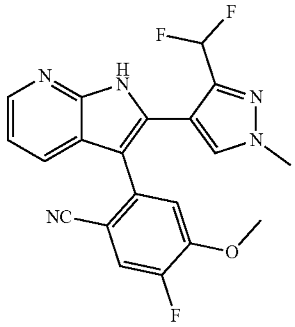
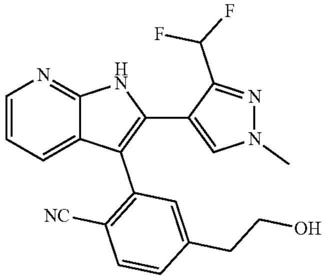
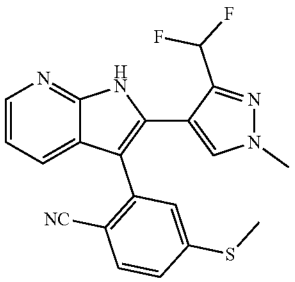
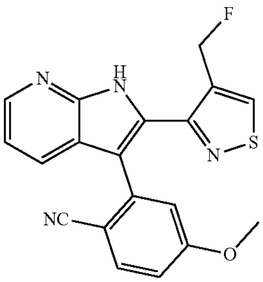
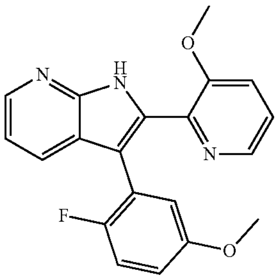
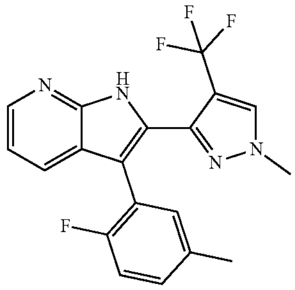
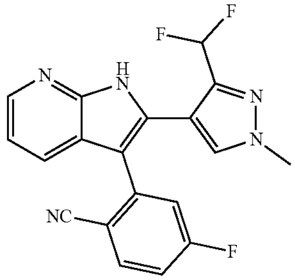

-continued
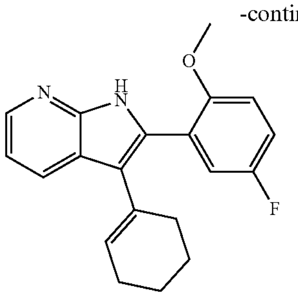
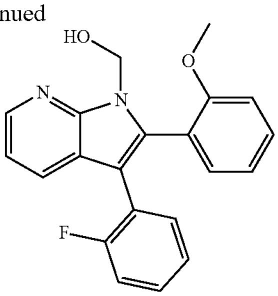
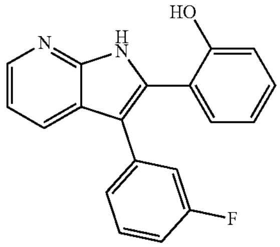
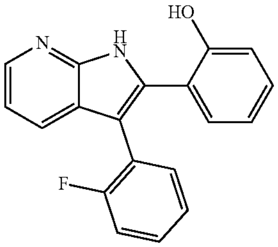
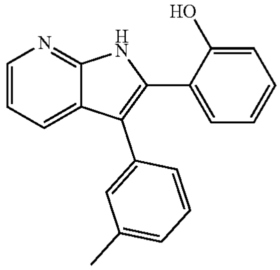
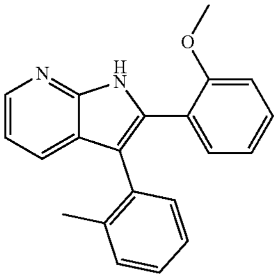
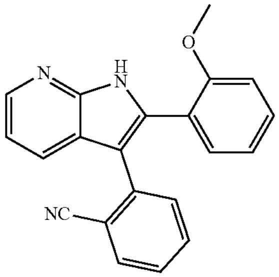
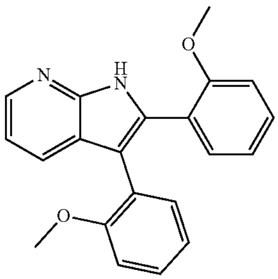
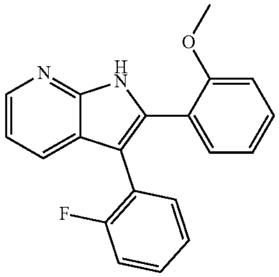
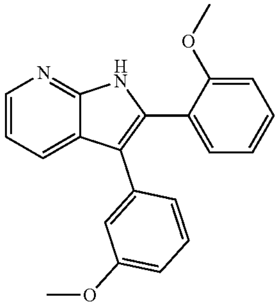
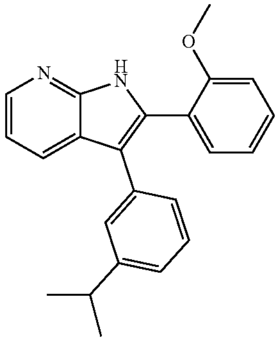
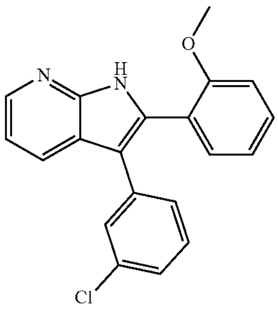
-continued
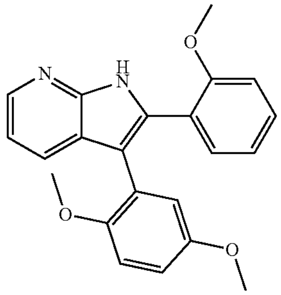
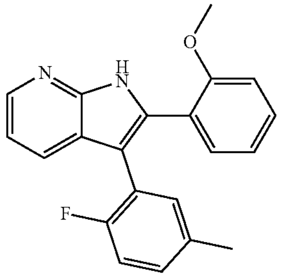
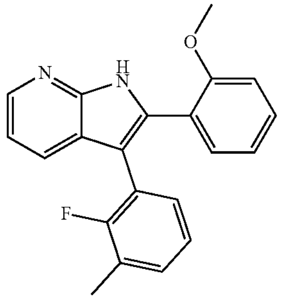
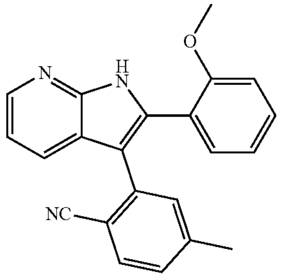
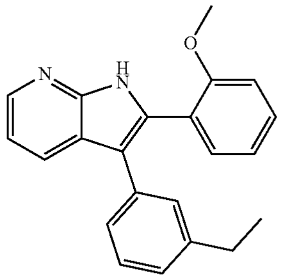
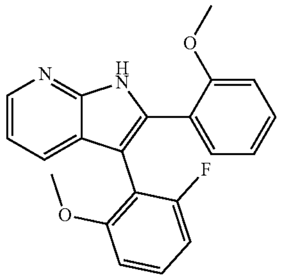
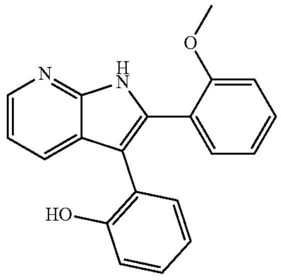
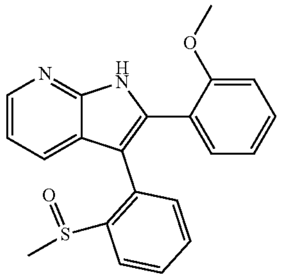
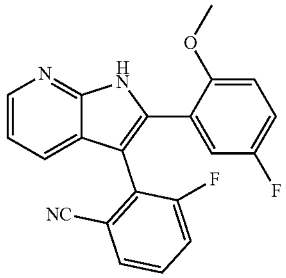
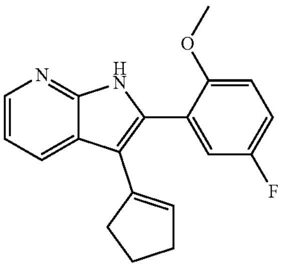

-continued
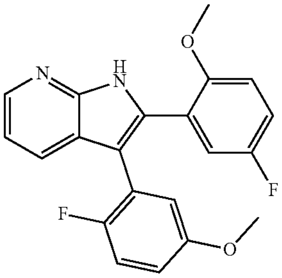
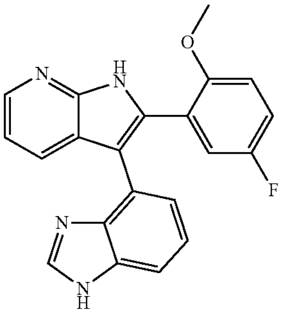
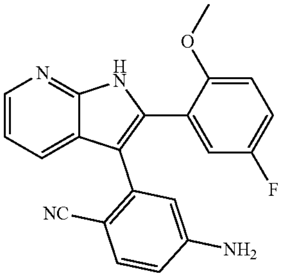
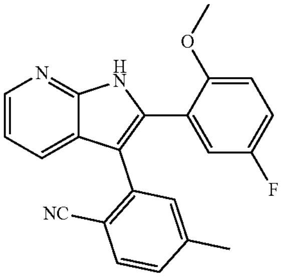
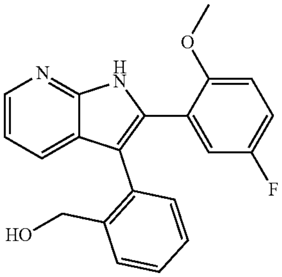
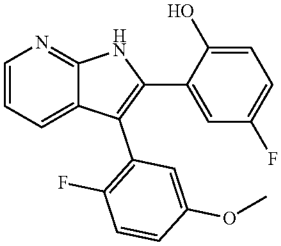
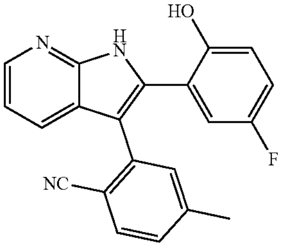
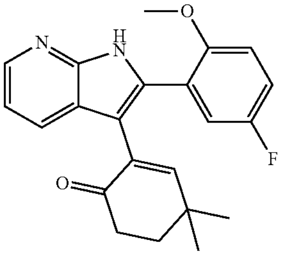
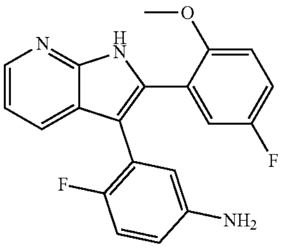
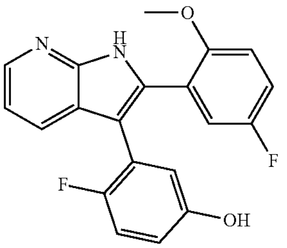
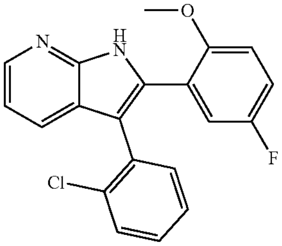
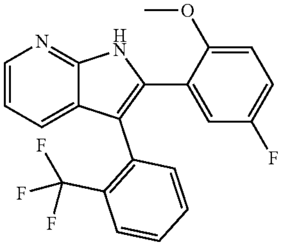
-continued
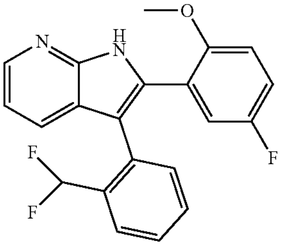
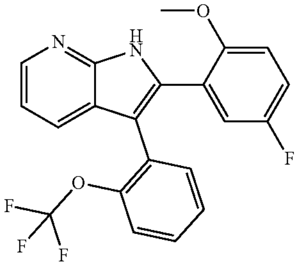
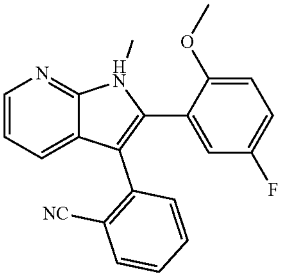
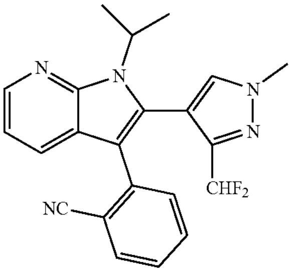
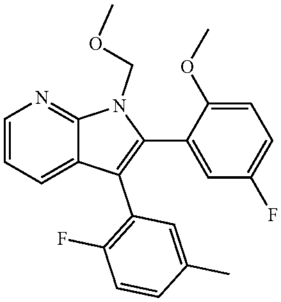
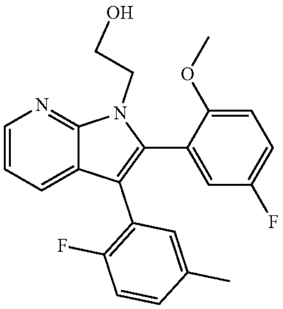
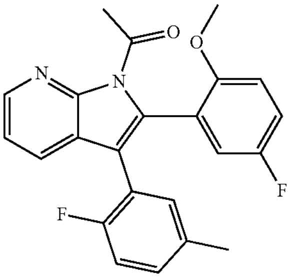

-continued
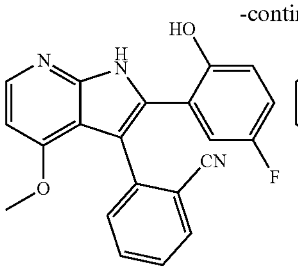
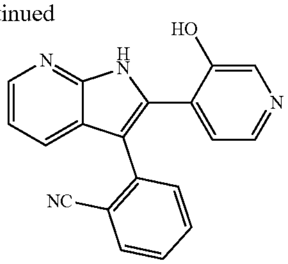
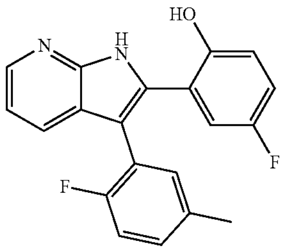
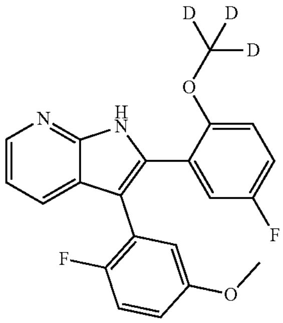
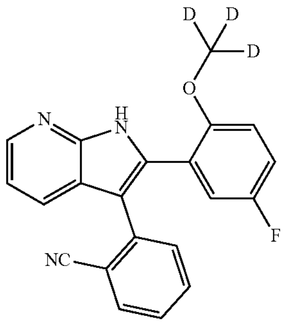
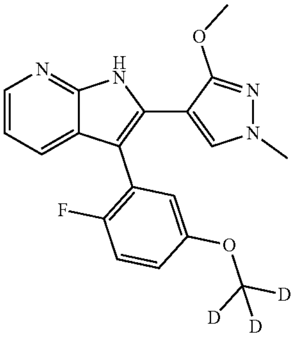
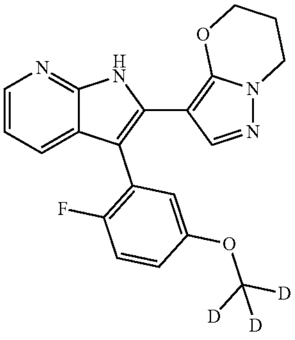
-continued
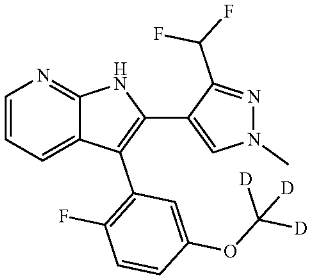
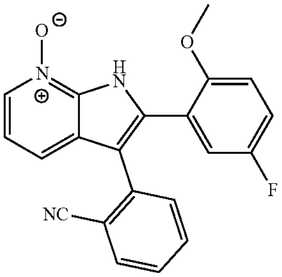
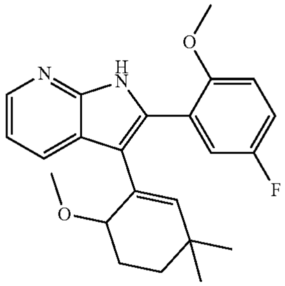
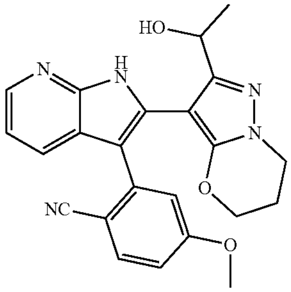
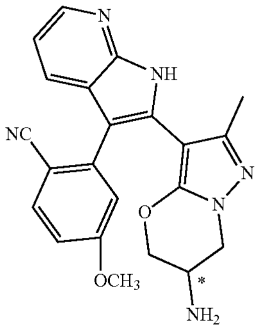
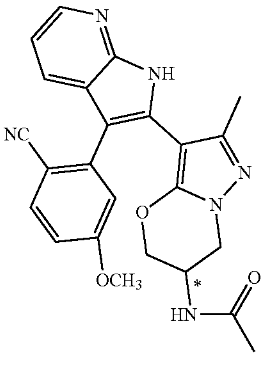
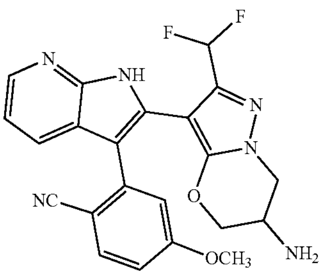

-continued
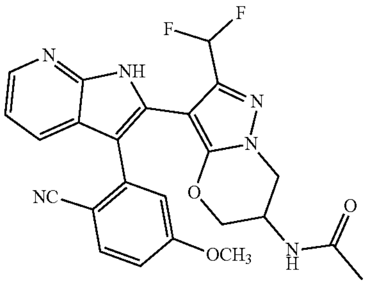
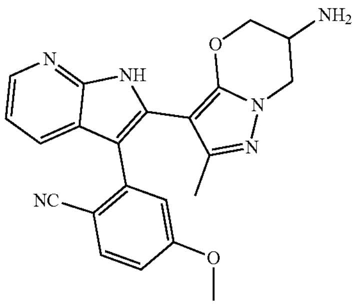
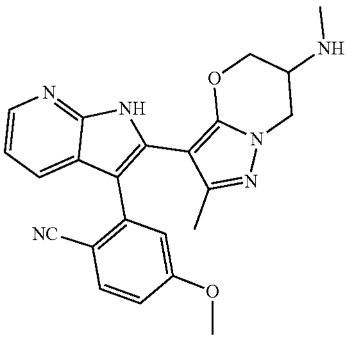
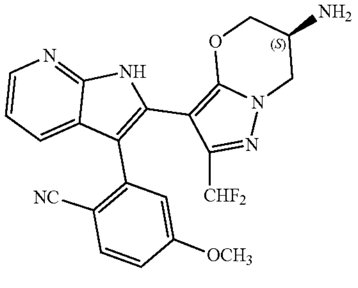
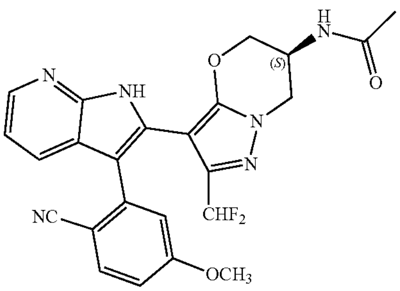
-continued
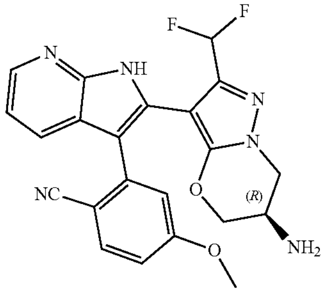
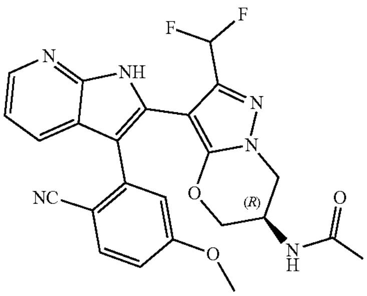
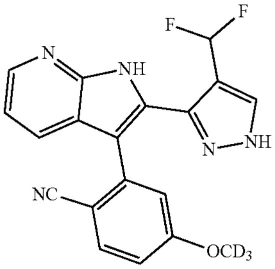
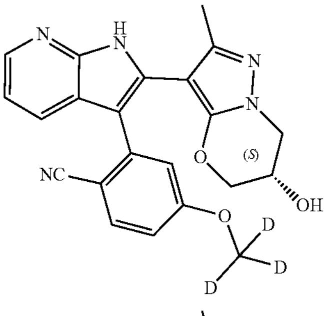
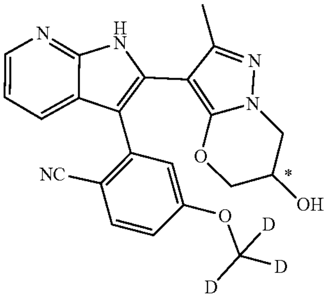

-continued
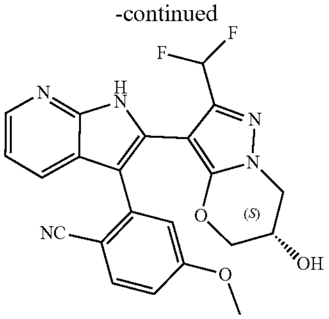
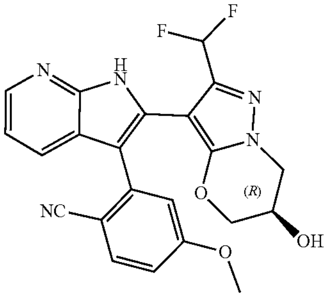
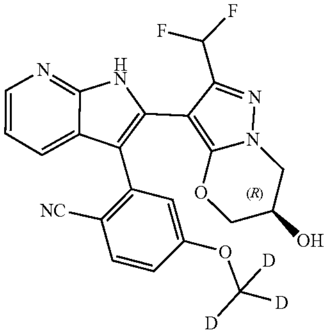
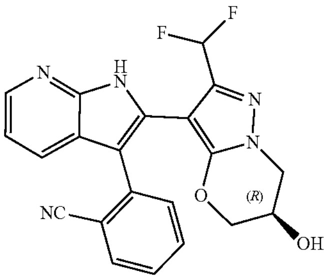
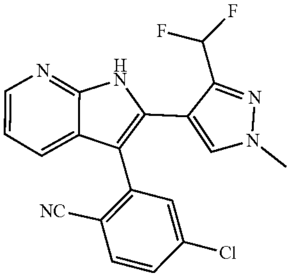
-continued
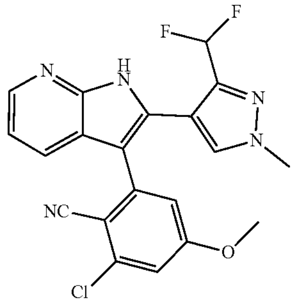
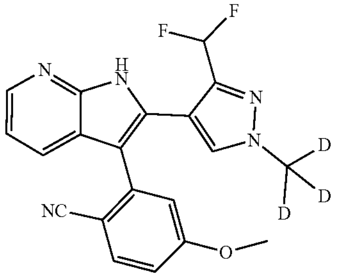
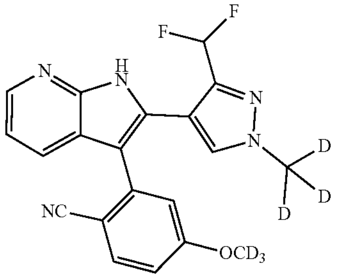
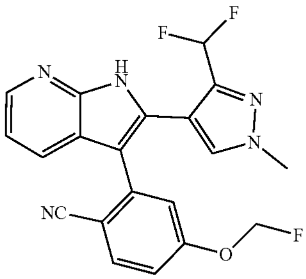
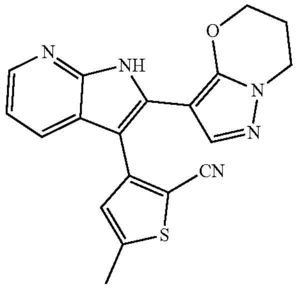
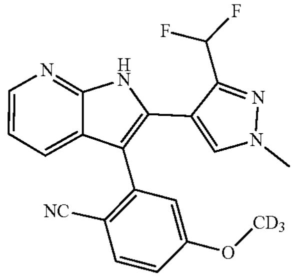

-continued
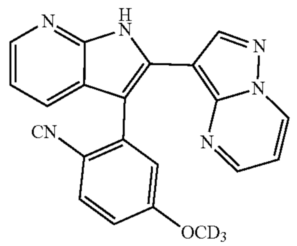
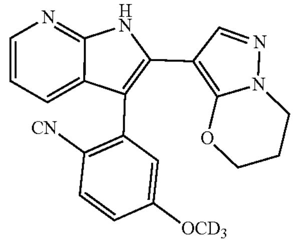
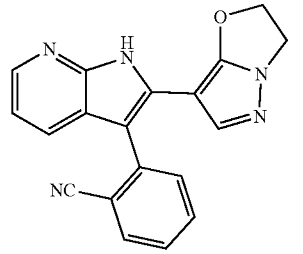
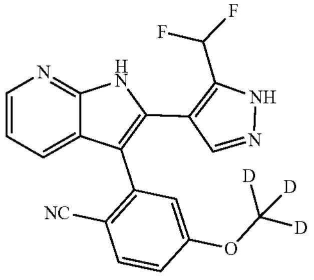
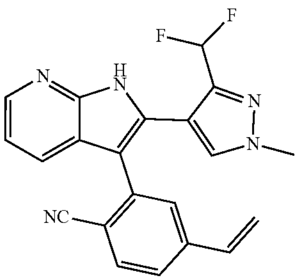
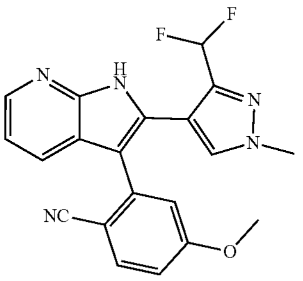
-continued
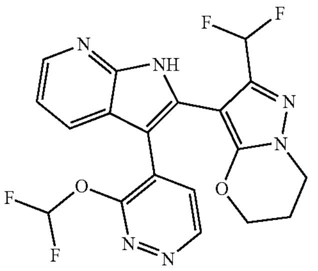
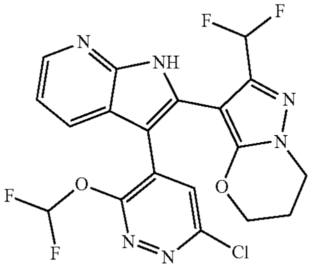
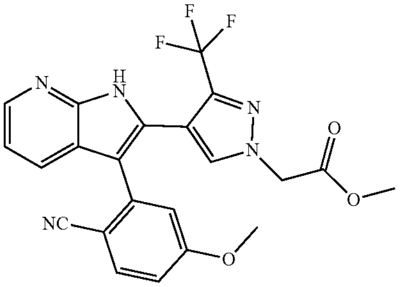
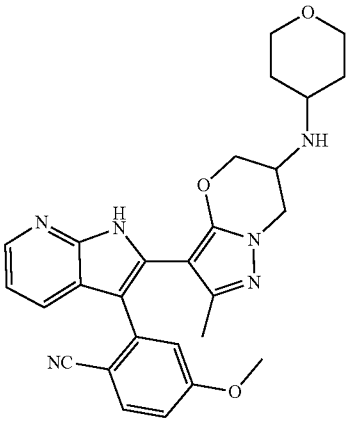
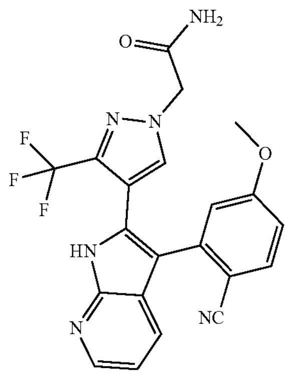

-continued
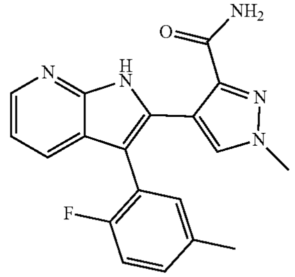
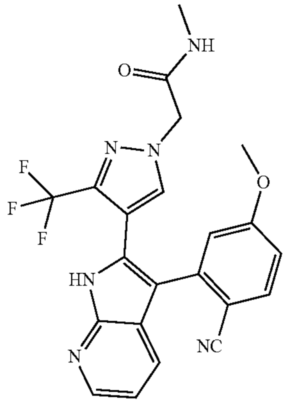
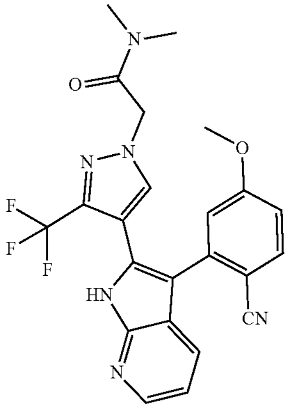
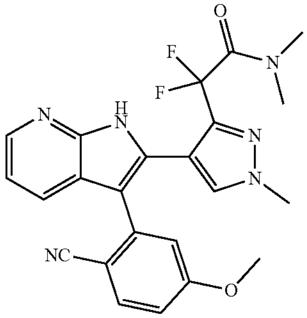
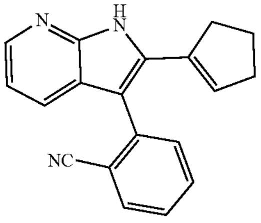
-continued
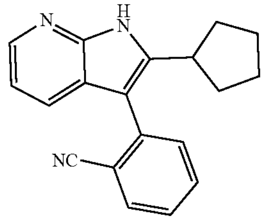
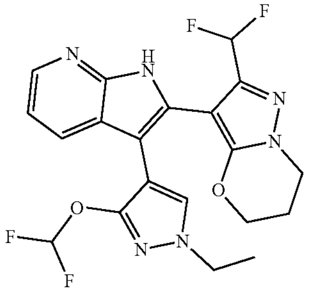
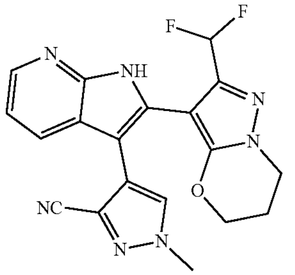
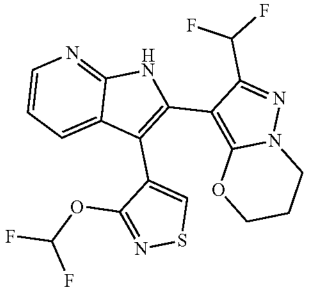
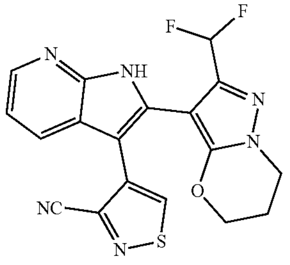
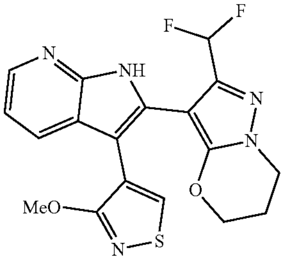

-continued
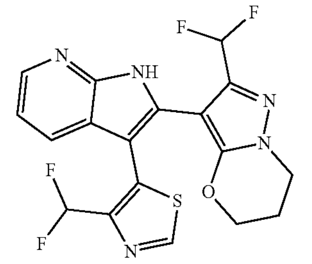
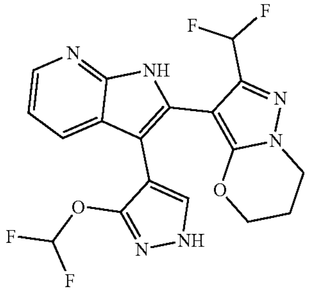
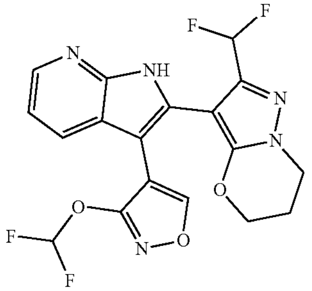
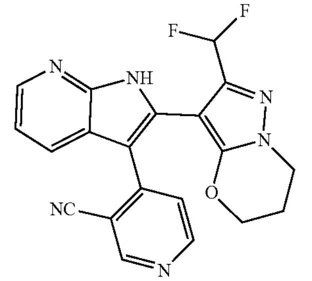
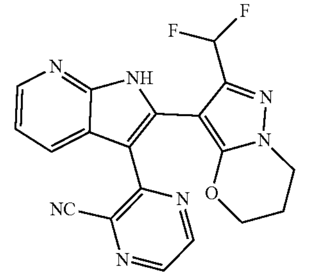
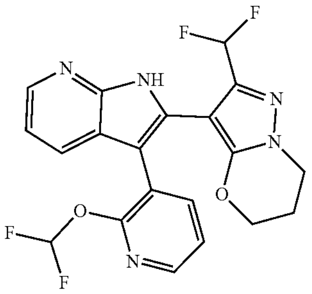
-continued
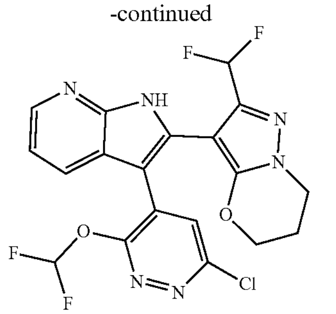
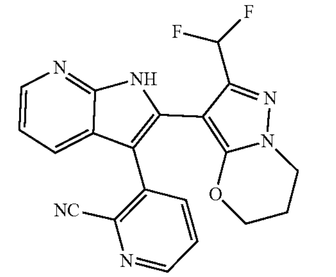
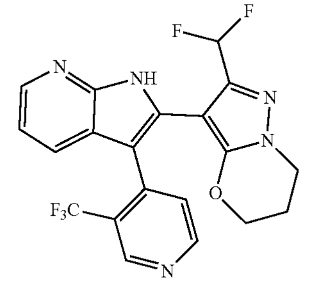
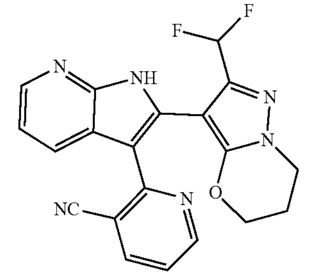
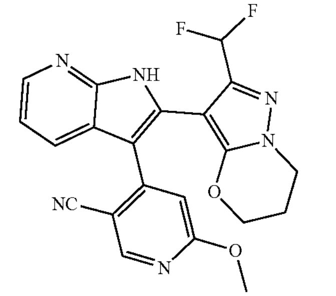
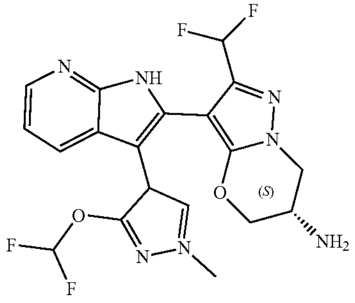

-continued

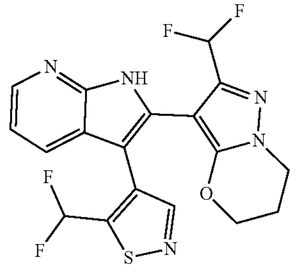

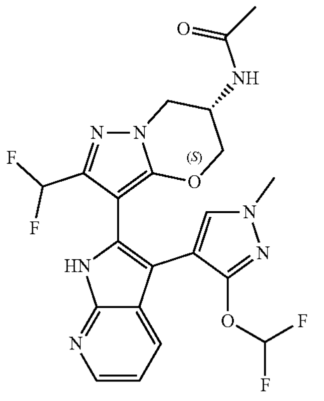

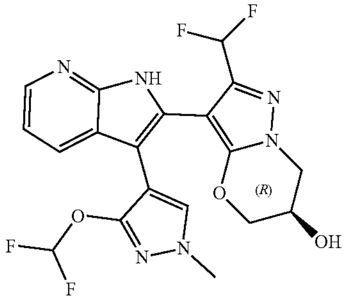

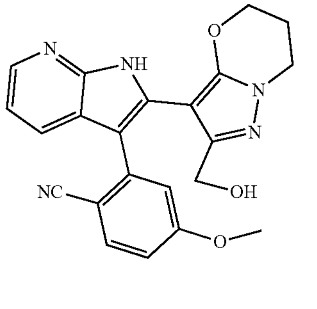

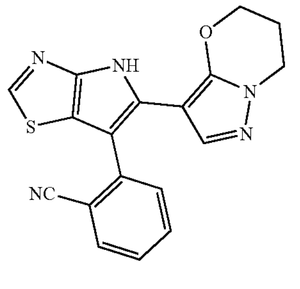

-continued

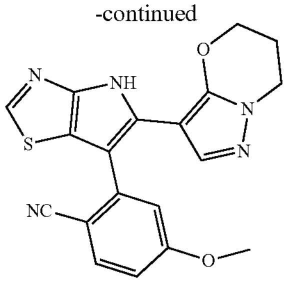

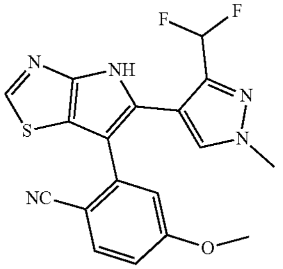

[11] A pharmaceutical composition, comprising: the compound or pharmaceutically acceptable salt thereof according to any one of [1]-[10]; and a pharmaceutically acceptable excipient.

[12] A method of treating an MRGPRX2-mediated disease or disorder, comprising: administering to a patient in need thereof a therapeutically effective amount of the compound or pharmaceutically acceptable salt thereof according to any one of [1]-[10].

[13] The method according to [12], wherein the MRGPRX2-mediated disease or disorder is a pseudo-allergic reaction, an itch-associated condition, a pain-associated condition, or an inflammatory or autoimmune disorder.

[14] The method according to claim [12], wherein the MRGPRX2-mediated disease or disorder is selected from the group consisting of chronic urticaria, (e.g. chronic spontaneous urticaria or chronic inducible urticaria, e.g. cold urticaria, cholinergic urticaria, heat urticaria, solar urticaria, symptomatic demographism urticaria, pressure urticaria or contact urticaria), mastocytosis, atopic dermatitis, rosacea, e.g. papulopustular rosacea, Crohn's disease, ulcerative colitis, irritable bowel syndrome, rheumatoid arthritis, fibromyalgia, nasal polyps, neuropathic pain, inflammatory pain, chronic itch, drug-induced anaphylactoid reactions, metabolic syndrome, oesophagus reflux, asthma, cough, migraine, chronic pruritus, e.g. chronic pruritus of unknown origin, acute pruritus, prurigo nodularis, osteoarthritis, and pseudo anaphylaxis.

[15] The compound or pharmaceutically acceptable salt thereof according to any one of [1]-[10] for use in the treatment of an MRGPRX2-mediated disease or disorder.

[16] The compound or pharmaceutically acceptable salt for use according to [15], wherein the disease or disorder is selected from the group consisting of chronic urticaria, (e.g. chronic spontaneous urticaria or chronic inducible urticaria, e.g. cold urticaria, cholinergic urticaria, heat urticaria, solar urticaria, symptomatic demographism urticaria, pressure urticaria or contact urticaria), mastocytosis, atopic dermatitis, rosacea, e.g. papulopustar rosacea, Crohn's disease, ulcerative colitis, irritable bowel syndrome, rheumatoid arthritis, fibromyalgia, nasal polyps, neuropathic pain, inflammatory pain, chronic itch, drug-induced anaphylactoid reactions, metabolic syndrome, oesophagus reflux, asthma, cough, migraine, chronic pruritus, e.g. chronic pruritus of unknown origin, acute pruritus, prurigo nodularis, osteoarthritis, and pseudo anaphylaxis.

[17] Use of the compound or pharmaceutically acceptable salt thereof according to any one of [1]-[10], in the manufacture of a medicament for use in the treatment of an MRGPRX2-mediated disease or disorder.

[18] The use according to [17], wherein said disease or disorder is chronic urticaria, (e.g. chronic spontaneous urticaria or chronic inducible urticaria, e.g. cold urticaria, cholinergic urticaria, heat urticaria, solar urticaria, symptomatic demographism urticaria, pressure urticaria or contact urticaria), mastocytosis, atopic dermatitis, rosacea, e.g. papulopustular rosacea, Crohn's disease, ulcerative colitis, irritable bowel syndrome, rheumatoid arthritis, fibromyalgia, nasal polyps, neuropathic pain, inflammatory pain, chronic itch, drug-induced anaphylactoid reactions, metabolic syndrome, oesophagus reflux, asthma, cough, migraine, chronic pruritus, e.g. chronic pruritus of unknown origin, acute pruritus, prurigo nodularis, osteoarthritis, or pseudo anaphylaxis.

[19] A compound of Formula (IIa), (IIa)

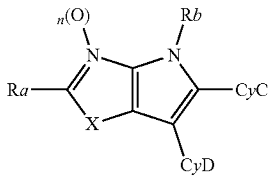

or a pharmaceutically acceptable salt thereof, wherein X is S, —CRd=CRe-, —CRd=N—, or —N=CRd-; Rd and Re are independently hydrogen, deuterium, halo, CN, $C_1$-$C_6$ alkyl, $C_1$-$C_6$ haloalkyl or $C_1$-$C_6$ alkoxy; Ra is hydrogen, halo, $C_1$-$C_6$ alkyl or $C_1$-$C_6$ alkoxy; Rb is hydrogen, $C_1$-$C_6$ alkyl, hydroxy-$C_1$-$C_6$ alkyl, $C_1$-$C_6$ alkoxy-$C_1$-$C_6$ alkyl, $C_1$-$C_6$ alkyl-carbonyl or $C_1$-$C_6$ alkoxy-carbonyl; CyC and CyD are independently $C_6$-$C_{10}$ aryl optionally having at least one substituent selected from a group W, heteroaryl optionally having at least one substituent selected from the group W, $C_3$-$C_8$ cycloalkyl optionally having at least one substituent selected from the group W, $C_3$-$C_8$ cycloalkenyl optionally having at least one substituent selected from the group W, heterocyclyl optionally having at least one substituent selected from the group W, fused heterocyclic ring consisting of 8 to 10 atoms optionally having at least one substituent selected from the group W, where the group W is deuterium, halo, $C_1$-$C_6$ alkyl optionally substituted with one or more deuterium, $C_1$-$C_6$ haloalkyl, $C_1$-$C_6$ alkoxy optionally substituted with one or more deuterium, $C_1$-$C_6$ haloalkoxy, $C_2$-$C_6$ alkenyl, hydroxyl, $C_1$-$C_6$ hydroxyalkyl, $C_1$-$C_6$ hydroxyalkoxy, carboxy-$C_1$-$C_6$ alkyl, amino optionally having at least one $C_1$-$C_3$ alkyl or hydroxy-$C_1$-$C_3$ alkyl, $NO_2$, CN, $CONH_2$, aminocarbonyl substituted with at least one $C_1$-$C_6$ alkyl, oxo, $C_1$-$C_6$ alkyl-carbonyl, $C_1$-$C_6$ alkoxy-carbonyl, aminocarbonyloxy substituted with at least one $C_1$-$C_6$ alkyl, $C_1$-$C_6$ alkyl-carbonylamino, hydroxy-$C_1$-$C_6$ alkyl-carbonylamino, hydroxy-$C_1$-$C_6$ alkyl-carbonyl-N-methylamino, hydroxy-$C_1$-$C_6$ alkyl-N-methylamino-carbonylamino, $C_3$-$C_8$ cycloalkyl-carbonylamino, $C_1$-$C_6$ alkoxy-carbonylamino, heterocycloxy-carbonylamino, hydroxy heterocyclo-carbonylamino, heteroaryl-carbonylamino, $C_1$-$C_6$ alkyl-heteroaryl-carbonylamino, $C_1$-$C_6$ alkyl-carbonyl-N-methylamino, $C_1$-$C_6$ alkoxy-carbonyl-N-methylamino, $C_1$-$C_6$ alkyl-sulfonylamino, hydroxy-$C_1$-$C_6$ alkyl-sulfonylamino, $C_3$-$C_8$ cycloalkyl-sulfonylamino, $C_1$-$C_6$ alkyl-$C_3$-$C_8$ cycloalkyl-sulfonylamino, N,N-dimethylaminosulfonyl amino, $C_1$-$C_6$ alkylsulfanyl, $C_1$-$C_6$ alkylsulfinyl, $C_1$-$C_6$ alkylsulfonyl, $C_1$-$C_6$ alkylaminosulfonyl, $C_1$-$C_6$ alkylsulfinyl-$C_1$-$C_6$ alkyl, $C_1$-$C_6$ alkylsulfonyl-$C_1$-$C_6$ alkyl, $C_3$-$C_8$ cycloalkyl, $C_3$-$C_8$ cycloalkyl-$C_1$-$C_3$ alkoxy, $C_1$-$C_3$ alkoxy-$C_1$-$C_3$ alkyl, $C_1$-$C_3$ alkoxy-$C_1$-$C_3$alkoxy-$C_1$-$C_3$ alkyl, $C_1$-$C_3$ alkoxy-carbonyl-$C_1$-$C_3$ alkyl, phenyl-$C_1$-$C_6$ alkoxy, $C_1$-$C_6$ alkoxy-carbonyl-$C_1$-$C_6$ alkoxy, amino-carbonyl-$C_1$-$C_6$ alkoxy, $C_1$-$C_6$ alkoxy-$C_1$-$C_6$ alkoxy, $C_1$-$C_6$ alkylsulfonylamino-$C_1$-$C_6$ alkoxy, $C_1$-$C_6$ alkyl-carbonylamino-$C_1$-$C_6$ alkoxy, N,N-dimethylamino-$C_1$-$C_6$ alkoxy, N-methylamino-carbonyl-$C_1$-$C_6$ alkyl, N,N-dimethylaminocarbonyl-$C_1$-$C_6$ alkyl, heterocyclyl optionally substituted with one or more oxo group, heterocyclyl-$C_1$-$C_3$ alkyl, ureido, or a spiro ring, where $C_3$-$C_8$ cycloalkyl of $C_3$-$C_8$ cycloalky-carbonylamino may be substituted by one or more substituents selected from a halogen atom, a hydroxy group, a cyano group, a $C_1$-$C_6$ alkyl, and an aminocarboxyl group, where $C_1$-$C_6$ alkoxy of $C_1$-$C_6$ alkoxy-carbonylamino may be substituted by one or more substituents selected from a hydroxy group, an amino group, a N-methylamino group, an amino-carbonyl group, a N-methylamino-carbonyl group, and oxo group, where ureido may be substituted by one or more substituents selected from a $C_1$-$C_6$ alkyl and a hydroxy-$C_1$-$C_6$ alkyl group; and n is 0 or 1.

DETAILED DESCRIPTION OF THE EMBODIMENTS

The present embodiments are described in more detail below.

The terms used herein are described below.

Halo

The term "halo" as used herein means fluorine, chlorine, bromine or iodine.

$C_1$-$C_6$ alkyl

In a preferred embodiment, the term "$C_1$-$C_6$ alkyl" as used herein means a straight- or branched-chain alkyl group having 1 to 6 carbon atoms. Examples include methyl, ethyl, propyl, isopropyl, butyl, isobutyl, sec-butyl, tert-butyl, pentyl, isopentyl, neopentyl, 1-methylbutyl, 2-methylbutyl, 1,2-dimethylpropyl, hexyl, and isohexyl.

In other embodiments, the term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{14}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

$C_1$-$C_6$ haloalkyl

In a preferred embodiment, the term "$C_1$-$C_6$ haloalkyl" as used herein means a $C_1$-$C_6$ alkyl group substituted with 1 to 5 same or different halogen atoms. Examples of the $C_1$-$C_6$ haloalkyl group include a fluoromethyl group, a difluoromethyl group, a trifluoromethyl group, a 2-fluoroethyl group, a 2-chloroethyl group, a 2,2-difluoroethyl group, a 1,1-difluoroethyl group, a 1,2-difluoroethyl group, a 2,2,2-trifluoroethyl group, a 1,1,2,2,2-pentafluoroethyl group, a 2,2,2-trichloroethyl group, a 3-fluoropropyl group, a 2-fluoropropyl group, a 1-fluoropropyl group, a 3,3-difluoropropyl group, a 2,2-difluoropropyl group, a 1,1-difluoropropyl group, a 4-fluorobutyl group, a 5-fluoropentyl group and a 6-fluorohexyl group.

In a other embodiments, the term "haloalkyl" refers to a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

$C_1$-$C_6$ Alkoxy

In a preferred embodiment, the term "$C_1$-$C_6$ alkoxy" as used herein means a straight- or branched-chain alkoxy group having 1 to 6 carbon atoms; that is, a $C_1$-$C_6$ alkyl —O— group. Examples include methoxy, ethoxy, propoxy, isopropoxy, isobutoxy, butoxy, sec-butoxy, tert-butoxy, pentyloxy, and hexyloxy.

In other embodiments, the term "alkoxy" refers to an alkyl group, as defined herein, appended to the parent molecular moiety through an oxygen atom. In some embodiments, the alkoxy moiety has 1 to 8 carbon atoms ("$C_{1-8}$ alkoxy"). In some embodiments, the alkoxy moiety has 1 to 6 carbon atoms ("$C_{1-6}$ alkoxy"). In some embodiments, the alkoxy moiety has 1 to 4 carbon atoms ("$C_{1-4}$ alkoxy"). In some embodiments, the alkoxy moiety has 1 to 3 carbon atoms ("$C_{1-3}$ alkoxy"). In some embodiments, the alkoxy moiety has 1 to 2 carbon atoms ("$C_{1-2}$ alkoxy"). Representative examples of alkoxy include, but are not limited to, methoxy, ethoxy, propoxy, 2-propoxy, butoxy and tert-butoxy.

Hydroxy $C_1$-$C_6$ alkyl

In a preferred embodiment, the term "hydroxy-$C_1$-$C_6$ alkyl" as used herein means a $C_1$-$C_6$ alkyl group substituted with a hydroxyl group. Examples of the $C_1$-$C_6$ hydroxyalkyl group include a 2-hydroxyethyl group, a 1-hydroxyethyl group, a 3-hydroxypropyl group, a 2-hydroxypropyl group, a 1-hydroxypropyl group, a 4-hydroxybutyl group, a 3-hydroxybutyl group, a 2-hydroxybutyl group, a 1-hydroxybutyl group, a 5-hydroxypentyl group and a 6-hydroxyhexyl group.

In other embodiments, the term "hydroxyalkyl" refers to a substituted alkyl group, wherein one or more of the hydrogen atoms are independently replaced by a hydroxyl. In some embodiments, the hydroxyalkyl moiety has 1 to 8 carbon atoms ("$C_{1-8}$ hydroxyalkyl"). In some embodiments, the hydroxyalkyl moiety has 1 to 6 carbon atoms ("$C_{1-6}$ hydroxyalkyl"). In some embodiments, the hydroxyalkyl moiety has 1 to 4 carbon atoms ("$C_{1-4}$ hydroxyalkyl"). In some embodiments, the hydroxyalkyl moiety has 1 to 3 carbon atoms ("$C_{1-3}$ hydroxyalkyl"). In some embodiments, the hydroxyalkyl moiety has 1 to 2 carbon atoms ("$C_{1-2}$ hydroxyalkyl").

$C_1$-$C_6$ alkoxy-$C_1$-$C_6$ alkyl

The term "$C_1$-$C_6$ alkoxy-$C_1$-$C_6$ alkyl" as used herein means a straight-or branched-chain alkyl group having 1 to 6 carbon atoms substituted with a straight-or branched-chain alkoxy group having 1 to 6 carbon atoms.

$C_1$-$C_6$ alkyl-carbonyl

The term "$C_1$-$C_6$ alkyl-carbonyl" as used herein means a straight- or branched-chain alkylcarbonyl group derived from an aliphatic carboxylic acid having 1 to 6 carbon atoms; that is, a $C_1$-$C_6$ alkyl-C(═O)— group. Examples of the $C_1$-$C_6$ alkylcarbonyl include methylcarbonyl, ethylcarbonyl, propylcarbonyl, isopropylcarbonyl, butylcarbonyl, isobutylcarbonyl, sec-butylcarbonyl, tert-butyl carbonyl, pentylcarbonyl, isopentylcarbonyl, neopentylcarbonyl, 1-methylbutylcarbonyl, 2-methylbutylcarbonyl, 1,2-dimethylpropylcarbonyl, hexylcarbonyl, and isohexylcarbonyl.

$C_1$-$C_6$ alkoxy-carbonyl

The term "$C_1$-$C_6$ alkoxy-carbonyl" as used herein means a straight- or branched-chain alkoxycarbonyl group having 1 to 6 carbon atoms; that is, a $C_1$-$C_6$ alkyl-O—C(═O)— group. Examples include methoxycarbonyl, ethoxycarbonyl, propoxycarbonyl, isopropoxycarbonyl, isobutoxycarbonyl, butoxycarbonyl, sec-butoxycarbonyl, tert-butoxycarbonyl, pentyloxycarbonyl, and hexyloxycarbonyl.

$C_1$-$C_6$ alkylaminosulfonyl

The term "$C_1$-$C_6$ alkylaminosulfonyl" as used herein means an amino-substituted sulfonyl group containing a straight- or branched-chain alkyl group having 1 to 6 carbon atoms; that is, a $C_1$-$C_6$ alkyl-$NHSO_2$— group. Examples include methylaminosulfonyl, ethylaminosulfonyl, propylaminosulfonyl, isopropylaminosulfonyl, butylaminosulfonyl, isobutylaminosulfonyl, sec-butylaminosulfonyl, and tert-butylaminosulfonyl.

Carbocyclyl

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like.

Exemplary $C_{3-8}$ carbocyclyl groups include, without limitation, the aforementioned $C_{3-8}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some preferred embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

$C_3$-$C_8$ cycloalkyl

The term "$C_3$-$C_8$ cycloalkyl" as used herein means a monocyclic, saturated cycloalkyl group having 3 to 8 carbon atoms. Examples include cyclopropyl, cyclobutyl, cyclopentyl, cyclohexyl, cycloheptyl, and cyclooctyl.

$C_6$-$C_{10}$ aryl

In a preferred embodiment, the term "$C_6$-$C_{10}$ aryl" as used herein means a phenyl group or naphthyl group.

In a other embodiments, the term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-14 aryl"). In some embodiments, an aryl group has 6 ring carbon atoms ("$C_6$ aryl"; e.g., phenyl). In some embodiments, an aryl group has ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

Heteroaryl

In a preferred embodiment, the term "heteroaryl" as used herein means a 5-membered heteroaromatic ring or 6-membered heteroaromatic ring. The term "5-membered heteroaromatic ring" as used herein means a 5-membered heteroaromatic ring containing 1 to 4 atoms selected from a sulfur atom, an oxygen atom, and a nitrogen atom. The nitrogen atom(s) in the aromatic ring may be N-oxide. Examples of the 5-membered heteroaromatic ring include furyl, thienyl, pyrrolyl, pyrazolyl, imidazolyl, oxazolyl, isoxazolyl, thiazolyl, isothiazolyl, 1, 2, 3-oxadiazolyl, 1,3, 4-oxadiazolyl, triazolyl, tetrazolyl, and thiadiazolyl. The term "6-membered heteroaromatic ring" as used herein means a 6-membered heteroaromatic ring containing 1 to 4 nitrogen atoms. The nitrogen atom(s) in the aromatic ring may be N-oxide. Examples of the 6-membered heteroaromatic ring include pyridyl, pyridazinyl, pyrimidinyl, and pyrazinyl.

In other embodiments, the term "heteroaryl" refers to a radical of a 5-14 membered monocyclic or polycyclic (e.g., bicyclic, tricyclic) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-12 membered aromatic ring system having ring carbon atoms and 1-4 ring heteroatoms provided in the aromatic ring system, wherein each heteroatom is independently selected from nitrogen, oxygen, and sulfur ("5-12 membered heteroaryl"). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

Heterocyclyl

In a preferred embodiment, the term "heterocyclyl" as used herein means a 5- to 7-membered non-aromatic heterocyclic ring containing 1 to 4 heteroatoms selected from a sulfur atom, an oxygen atom, and a nitrogen atom and optionally containing 1 to 3 carbonyls. Examples include unsaturated heterocyclic rings such as pyrrolinyl, imidazolinyl, pyrazolinyl, dihydropyranyl, dihydrothiopyranyl, and dihydropyridyl; and saturated heterocyclic rings such as morpholinyl, thiomorpholinyl, pyrrolidinyl, imidazolidinyl, pyrazolidinyl, piperidinyl, piperazinyl, tetrahydrofuranyl, oxathiolanyl, oxazinanyl, oxooxathiolanyl, dioxooxathiolanyl, oxothiazolidinyl, dioxothiazolidinyl, dithiepanyl, oxathiepanyl, and thiazepanyl.

In other embodiments, the term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 4-10 membered non-aromatic ring system having ring carbon atoms and 1-4 ring heteroatoms, wherein each heteroatom is independently selected from nitrogen, oxygen, and sulfur ("4-10 membered heterocyclyl"). In some embodiments, a heterocyclyl group is a 4-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, aziridinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

Fused Heterocyclic Ring Consisting of 9 or 10 Atoms

The term "fused heterocyclic ring consisting of 9 or 10 atoms" as used herein means a fused aromatic or non-aromatic ring constituted with 9 or 10 atoms of which 1 to 5 are heteroatoms containing 1 to 4 heteroatoms selected from a sulfur atom, an oxygen atom, and a nitrogen atom and optionally containing 1 to 4 double bonds and 1 to 3 carbonyls. Examples of the fused heterocyclic ring consisting of 9 or 10 atoms include 2,3-dihydropyrazolo[5,1-b]oxazolyl, pyrazolo[1,5-a]pyrimidinyl, 1H-imidazo[1,2-b]pyrazolyl, 2H-pyrazolo[4,3-b]pyridinyl, 6,7-dihydro-5H-pyrazolo[5,1-b][1,3]oxazinyl, 6,7-dihydro-4H-pyrazolo[5,1-c][1,4]oxazinyl, 1,2,5,6,7,7a-hexahydropyrano[3,2-c]pyrazolyl, 4,5,6,7-tetrahydropyrazolo[1,5-a]pyridinyl, 5,6,7,8-tetrahydro-4H-pyrazolo[1,5-a]azepinyl, pyrazolo[1,5-a]pyrazinyl, 4,5,6,7-tetrahydropyrazolo[1,5-a]pyrimidinyl, 2,4-dihydro-1H-pyrazolo[4,3-b]pyridinyl, and 4,7-dihydropyrazolo[1,5-a]pyrimidinyl.

Preferable examples of the fused heterocyclic ring consisting of 9 or 10 atoms include 2,3-dihydropyrazolo[5,1-b]oxazole-7-yl, 6,7-dihydro-5H-pyrazolo[5,1-b][1,3]oxazine-3-yl, and pyrazolo[1,5-a]pyrimidine-3-yl.

Fused Heterocyclic Ring Consisting of 8 to 10 Atoms

The terms "fused heterocyclic ring consisting of 8 to 10 atoms" as used herein means a fused aromatic or non-aromatic heterocyclic rings constituted with 8 to 10 atoms including from 1 to 5 heteroatoms selected from a sulfur atom, an oxygen atom, and a nitrogen atom and optionally containing 1 to 4 double bonds and/or 1 to 3 carbonyls. The heteroatoms may be shared by the fused rings. Examples of the fused heterocyclic ring consisting of 8-10 atoms include, but are not limited to, 2,3-dihydropyrazolo[5,1-b]oxazolyl, pyrazolo[1,5-a]pyrimidinyl, 1H-imidazo[1,2-b]pyrazolyl, 2H-pyrazolo[4,3-b]pyridinyl, 6,7-dihydro-5H-pyrazolo[5,1-b][1,3]oxazinyl, 6,7-dihydro-4H-pyrazolo[5,1-c][1,4]oxazinyl, 1,2,5,6,7,7a-hexahydropyrano[3,2-c]pyrazolyl, 4,5,6,7-tetrahydropyrazolo[1,5-a]pyridinyl, 5,6,7,8-tetrahydro-4H-pyrazolo[1,5-a]azepinyl, pyrazolo[1,5-a]pyrazinyl, 4,5,6,7-tetrahydropyrazolo[1,5-a]pyrimidinyl, 2,4-dihydro-1H-pyrazolo[4,3-b]pyridinyl, and 4,7-dihydropyrazolo[1,5-a]pyrimidinyl. Preferable examples of the fused heterocyclic ring consisting of 8 to 10 atoms include 2,3-dihydropyrazolo[5,1-b]oxazole-7-yl, 6,7-dihydro-5H-pyrazolo[5,1-b][1,3]oxazine-3-yl, and pyrazolo[1,5-a]pyrimidine-3-yl.

$C_1$-$C_6$ haloalkoxy

In a preferred embodiment, the term "$C_1$-$C_6$ haloalkoxy" as used herein means a $C_1$-$C_6$ alkoxy group substituted with 1 to 5 same or different halogen atoms. Examples of the halo $C_1$-$C_6$ alkoxy group include a fluoromethoxy group, a difluoromethoxy group, a trifluoromethoxy group, a 2-fluoroethoxy group, a 2-chloroethoxy group, a 2,2-difluoroethoxy group, a 1,1-difluoroethoxy group, a 1,2-difluorocthoxy group, a 2,2,2-trifluoroethoxy group, a 1,1,2,2,2-pentafluoroethoxy group, a 2,2,2-trichloroethoxy group, a 3-fluoropropoxy group, a 2-fluoropropoxy group, a 1-fluoropropoxy group, a 3,3-difluoropropoxy group, a 2,2-difluoropropoxy group, a 1,1-difluoropropoxy group, a 4-fluorobutoxy group, a 5-fluoropentoxy group and a 6-fluorohexyloxy group.

In other embodiments, the term "haloalkoxy" refers to a haloalkyl group, as defined herein, appended to the parent molecular moiety through an oxygen atom. In some embodiments, the alkoxy moiety has 1 to 8 carbon atoms ("$C_{1-8}$ haloalkoxy"). In some embodiments, the alkoxy moiety has 1 to 6 carbon atoms ("$C_{1-6}$ haloalkoxy"). In some embodiments, the alkoxy moiety has 1 to 4 carbon atoms ("$C_{1-4}$ haloalkoxy"). In some embodiments, the alkoxy moiety has 1 to 3 carbon atoms ("$C_{1-3}$ haloalkoxy"). In some embodiments, the alkoxy moiety has 1 to 2 carbon atoms ("$C_{1-2}$ haloalkoxy"). Representative examples of haloalkoxy include, but are not limited to, difluoromethoxy, trifluoromethoxy, and 2,2,2-trifluoroethoxy.

$C_2$-$C_6$ alkenyl

In a preferred embodiment, the term "$C_2$-$C_6$ alkenyl" as used herein means a straight- or branched-chain alkenyl group having 2 to 6 carbon atoms. Examples include ethenyl, propenyl, isopropenyl, butenyl, isobutenyl, sec-butenyl, pentenyl, isopentenyl, 1-methylbutenyl, 2-methylbutenyl, 1,2-dimethylpropenyl, hexenyl, and isohexenyl.

In other embodiments, the term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C═C double bond for which the stereochemistry is not specified (e.g., —CH═CHCH$_3$ or

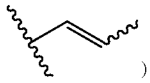

)

may be an (E)- or (Z)-double bond.

Hydroxy $C_1$-$C_6$ alkoxy

The terms "hydroxy $C_1$-$C_6$ alkoxyl" or "$C_1$-$C_6$ hydroxyalkoxy" can be used interchangeably and, as used herein, mean a $C_1$-$C_6$ alkoxy group substituted with a hydroxyl group. Examples of the $C_1$-$C_6$ hydroxyalkoxy group a 2-hydroxyethoxy group, a 1-hydroxyethoxy group, a 3-hydroxypropoxy group, a 2-hydroxypropoxy group, a 1-hydroxypropoxy group, a 4-hydroxybutoxy group, a 3-hydroxybutoxy group, a 2-hydroxybutoxy group, a 1-hydroxybutoxy group, a 5-hydroxypentoxygroup, a 6-hydroxyhexoxy group, 2-hydroxy-2-methylpropoxy group, (3-hydroxybutan-2-yl)oxy group, (1-hydroxy-2-methylpropan-2-yl)oxy group, 1-hydroxy-2-methylpropoxy group, (2-hydroxybutan-2-yl)oxy group, (2-hydroxypropan-2-yl)oxy group, and (1-hydroxypropan-2-yl)oxy group.

N,N-dimethylamino-$C_1$-$C_6$ alkoxy

The term "N,N-dimethylamino-$C_1$-$C_6$ alkoxy" means an alkoxy group having a straight- or branched-carbon chain of from 1-6 carbon atoms substituted with a dimethylamino group. The dimethylamino group may be bonded to a chain carbon or bonded to a terminal carbon. Examples of N,N-dimethylamino-$C_1$-$C_6$ alkoxy include, but are not limited to, a dimethylaminomethoxy group, a 2-(dimethylamino)ethoxy group, a 3-(dimethylamino)propoxy group, a 2-(dimethylamino)propoxy group, a 4-(dimethylamino)butoxy group, a 3-(dimethylamino)butoxy group, a 5-(dimethylamino)pentoxy group, a 4-(dimethylamino)pentoxy group, a 3-(dimethylamino)pentoxy group, a 6-(dimethylamino)hexoxy group, a 5-(dimethylamino)hexoxy group, a 5-(dimethylamino)hexoxy group, a 4-(dimethylamino)hexoxy group and a 3-(dimethylamino)hexoxy group.

Heterocycloxy

The term "heterocycloxy" means an alkoxy group derived from a heterocyclic alcohol. Examples of the heterocyclic ring structure include 5- to 7-membered non-aromatic heterocyclic rings containing 1 to 4 heteroatoms selected from a sulfur atom, an oxygen atom, and a nitrogen atom. Examples include but are not limited to oxy heterocycles derived from unsaturated heterocyclic rings such as pyrrolinyl, imidazolinyl, pyrazolinyl, dihydropyranyl, dihydrothiopyranyl, and dihydropyridyl; and saturated heterocyclic rings such as morpholinyl, thiomorpholinyl, pyrrolidinyl, imidazolidinyl, pyrazolidinyl, piperidinyl, piperazinyl, tetrahydrofuranyl, oxathiolanyl, oxazinanyl, oxooxathiolanyl, dioxooxathiolanyl, oxothiazolidinyl, dioxothiazolidinyl, dithiepanyl, oxathiepanyl, and thiazepanyl.

Heterocyclo-carbonylamino

The term "heterocyclo-carbonylamino" means an amido group substituent bonded through the amido N and having a hetercyclic group bonded to the amidocarbonyl carbon. Examples of the heterocyclic ring structure include 5- to 7-membered non-aromatic heterocyclic rings containing 1 to 4 heteroatoms selected from a sulfur atom, an oxygen atom, and a nitrogen atom. Examples include but are not limited to aminocarbonyl heterocycles derived from unsaturated heterocyclic rings such as pyrrolinyl, imidazolinyl, pyrazolinyl, dihydropyranyl, dihydrothiopyranyl, and dihydropyridyl; and saturated heterocyclic rings such as morpholinyl, thiomorpholinyl, pyrrolidinyl, imidazolidinyl, pyrazolidinyl, piperidinyl, piperazinyl, tetrahydrofuranyl, oxathiolanyl, oxazinanyl, oxooxathiolanyl, dioxooxathiolanyl, oxothiazolidinyl, dioxothiazolidinyl, dithiepanyl, oxathiepanyl, and thiazepanyl.

$C_1$-$C_6$ alkylsulfanyl

The term "$C_1$-$C_6$ alkylsulfanyl" as used herein means a straight- or branched-chain alkylsulfanyl group having 1 to 6 carbon atoms; that is, a $C_1$-$C_6$ alkyl-S— group. Examples include methylsulfanyl, ethylsulfanyl, propylsulfanyl, isopropylsulfanyl, butylsulfanyl, isobutylsulfanyl, sec-butylsulfanyl, and tert-butylsulfanyl $C_1$-$C_6$ alkylsulfinyl The term "$C_1$-$C_6$ alkylsulfinyl" as used herein means a straight- or branched-chain alkylsulfinyl group having 1 to 6 carbon atoms; that is, a $C_1$-$C_6$ alkyl-SO— group. Examples include methylsulfinyl, ethylsulfinyl, propylsulfinyl, isopropylsulfinyl, butylsulfinyl, isobutylsulfinyl, sec-butylsulfinyl, and tert-butylsulfinyl.

$C_1$-$C_6$ alkylsulfonyl

The term "$C_1$-$C_6$ alkylsulfonyl" as used herein means a straight- or branched-chain alkylsulfonyl group having 1 to 6 carbon atoms; that is, a $C_1$-$C_6$ alkyl-$SO_2$— group. Examples include methylsulfonyl, ethylsulfonyl, propylsulfonyl, isopropylsulfonyl, butylsulfonyl, isobutylsulfonyl, sec-butylsulfonyl, and tert-butylsulfonyl.

The term "$C_1$-$C_6$ alkyl-carbonylamino" as used herein means amino substituted with $C_1$-$C_6$ alkyl-carbonyl group.

The term "$C_1$-$C_6$ alkoxy-carbonylamino" as used herein means amino substituted with $C_1$-$C_6$ alkoxy-carbonyl group.

The term "$C_1$-$C_6$ alkyl-carbonyl-N-methylamino" as used herein means amino substituted with $C_1$-$C_6$ alkyl-carbonyl group and methyl.

The term "$C_1$-$C_6$ alkoxy-carbonyl-N-methylamino" as used herein means amino substituted with $C_1$-$C_6$ alkoxy-carbonyl group and methyl.

The term "$C_3$-$C_8$ cycloalkyl-$C_1$-$C_3$ alkoxy" as used herein means a $C_1$-$C_3$ alkoxy group substituted with a $C_3$-$C_8$ cycloalkyl group.

The term "$C_1$-$C_3$ alkoxy-$C_1$-$C_3$ alkyl" as used herein means a $C_1$-$C_3$ alkyl group substituted with a $C_1$-$C_3$ alkoxy group.

The term "$C_1$-$C_3$ alkoxy-$C_1$-$C_3$ alkoxy-$C_1$-$C_3$ alkyl" as used herein means a $C_1$-$C_3$ alkoxy-$C_1$-$C_3$ alkyl group substituted with a $C_1$-$C_3$ alkoxy group.

The term "$C_1$-$C_3$ alkoxy-carbonyl-$C_1$-$C_3$ alkyl" as used herein means a $C_1$-$C_3$ alkyl group substituted with a $C_1$-$C_3$ alkoxy-carbonyl group.

The term "phenyl-$C_1$-$C_3$ alkoxy" as used herein means a $C_1$-$C_3$ alkoxy group substituted with phenyl.

The term "heterocyclyl-$C_1$-$C_3$ alkyl" as used herein means a $C_1$-$C_3$ alkyl substituted with a heterocyclyl.

Spiro Ring

In a preferred embodiment, the term "spiro ring" as used herein means a monocyclic, saturated cyclic group having 3 to 8 atoms optionally containing an oxygen atom and/or nitrogen atom.

In other embodiments, a spirocyclic carbocyclyl (e.g., cycloalkyl) or heterocyclyl refers to a bicyclic or polycyclic ring system where two or more rings are connected through a single atom.

Pharmacologically Acceptable Salt

The term "pharmacologically acceptable salt" means a salt of a compound with a pharmaceutically acceptable non-toxic base or acid (e.g., with an inorganic or organic base or an inorganic or organic acid). Examples of salts derived from a pharmaceutically acceptable non-toxic base include those with an inorganic base such as sodium salts, potassium salts, calcium salts and magnesium salts and those with an organic base such as piperidine, morpholine, pyrrolidine, arginine, and lysine. Examples of salts derived from a pharmaceutically acceptable non-toxic acid includes acid salts of a mineral acid such as hydrochloric acid, hydrobromic acid, sulfuric acid, and nitric acid and salts formed by the combination of a compound with an organic acid such as formic acid, acetic acid, maleic acid, fumaric acid, succinic acid, lactic acid, malic acid, tartaric acid, citric acid, methanesulfonic acid, p-toluenesulfonic acid, salicylic acid, stearic acid, and palmitic acid.

MRGPRX2 Antagonist:

"MRGPRX2 antagonist" used in the present embodiment has a function of inhibiting the degranulation of human mast cells (MCs) induced by basic secretagogues and pseudoallergic drug. MRGPRX2 antagonists are expected as therapeutic agents for inflammatory diseases including IgE-independent allergic reactions.

Compound

According to one aspect of the present disclosure, a compound of Formula (Ia), (Ia)

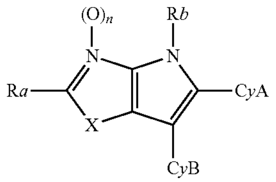

or a pharmaceutically acceptable salt thereof. In Formula (Ia),

X is S, —CRd-CRe-, —CRd=N—, or —N=CRd-;

Rd and Re are independently hydrogen, deuterium, halo, CN, $C_1$-$C_6$ alkyl, $C_1$-$C_6$ haloalkyl or $C_1$-$C_6$ alkoxy;

Ra is hydrogen, halo, $C_1$-$C_6$ alkyl or $C_1$-$C_6$ alkoxy;

Rb is hydrogen, $C_1$-$C_6$ alkyl, hydroxy-$C_1$-$C_6$ alkyl, $C_1$-$C_6$ alkoxy-$C_1$-$C_6$ alkyl, $C_1$-$C_6$ alkyl-carbonyl or $C_1$-$C_6$ alkoxy-carbonyl;

CyA and CyB are independently $C_6$-$C_{10}$ aryl optionally having at least one substituent selected from a group Q, heteroaryl optionally having at least one substituent selected from the group Q, $C_3$-$C_8$ cycloalkyl optionally having at least one substituent selected from the group Q, $C_3$-$C_8$ cycloalkenyl optionally having at least one substituent selected from the group Q, heterocyclyl optionally having at least one substituent selected from the group Q, fused heterocyclic ring consisting of 9 or 10 atoms optionally having at least one substituent selected from the group Q, where the group Q is deuterium, halo, $C_1$-$C_6$ alkyl optionally substituted with one or more deuterium, $C_1$-$C_6$ haloalkyl, $C_1$-$C_6$ alkoxy optionally substituted with one or more deuterium, $C_1$-$C_6$ haloalkoxy, $C_2$-$C_6$ alkenyl, hydroxyl, $C_1$-$C_6$ hydroxyalkyl, $C_1$-$C_6$ hydroxyalkoxy, carboxy-$C_1$-$C_6$ alkyl, amino optionally having at least one $C_1$-$C_3$ alkyl, $NO_2$, CN, $CONH_2$, aminocarbonyl substituted with at least one $C_1$-$C_6$ alkyl, oxo, $C_1$-$C_6$ alkyl-carbonyl, $C_1$-$C_6$ alkoxy-carbonyl, $C_1$-$C_6$ alkyl-carbonylamino, $C_1$-$C_6$ alkoxy-carbonylamino, $C_1$-$C_6$ alkyl-carbonyl-N-methylamino, $C_1$-$C_6$ alkoxy-carbonyl-N-methylamino, $C_1$-$C_6$ alkylsulfanyl, $C_1$-$C_6$ alkylsulfinyl, $C_1$-$C_6$ alkylsulfonyl, $C_3$-$C_8$ cycloalkyl, $C_3$-$C_8$ cycloalkyl-$C_1$-$C_3$ alkoxy, $C_1$-$C_3$ alkoxy-$C_1$-$C_3$ alkyl, $C_1$-$C_3$ alkoxy-$C_1$-$C_3$ alkoxy-$C_1$-$C_3$ alkyl, $C_1$-$C_3$ alkoxy-carbonyl-$C_1$-$C_3$ alkyl, phenyl-$C_1$-$C_6$ alkoxy, N-methylamino-carbonyl-$C_1$-$C_6$ alkyl, N,N-dimethylaminocarbonyl-$C_1$-$C_6$ alkyl, heterocyclyl, heterocyclyl-$C_1$-$C_3$ alkyl or a spiro ring; and n is 0 or 1.

In an embodiment of a compound of formula (Ia), or a pharmaceutically acceptable salt thereof, X is S.

In an embodiment of a compound of formula (Ia), or a pharmaceutically acceptable salt thereof, X is-CRd=CRe-.

In an embodiment of a compound of formula (Ia), or a pharmaceutically acceptable salt thereof, X is-CRd=N—.

In an embodiment of a compound of formula (Ia), or a pharmaceutically acceptable salt thereof, X is —N=CRd-.

In an embodiment of a compound of formula (Ia), or a pharmaceutically acceptable salt thereof, X is —CH=CH—.

In an embodiment of a compound of formula (Ia), or a pharmaceutically acceptable salt thereof, Rd is hydrogen.

In an embodiment of a compound of formula (Ia), or a pharmaceutically acceptable salt thereof, Rd is deuterium.

In an embodiment of a compound of formula (Ia), or a pharmaceutically acceptable salt thereof, Rd is halo.

In an embodiment of a compound of formula (Ia), or a pharmaceutically acceptable salt thereof, Rd is CN.

In an embodiment of a compound of formula (Ia), or a pharmaceutically acceptable salt thereof, Rd is $C_1$-$C_6$ alkyl.

In an embodiment of a compound of formula (Ia), or a pharmaceutically acceptable salt thereof, Rd is $C_1$-$C_6$ haloalkyl.

In an embodiment of a compound of formula (Ia), or a pharmaceutically acceptable salt thereof, Rd is $C_1$-$C_6$ alkoxy.

In an embodiment of a compound of formula (Ia), or a pharmaceutically acceptable salt thereof, Re is hydrogen.

In an embodiment of a compound of formula (Ia), or a pharmaceutically acceptable salt thereof, Re is deuterium.

In an embodiment of a compound of formula (Ia), or a pharmaceutically acceptable salt thereof, Re is halo.

In an embodiment of a compound of formula (Ia), or a pharmaceutically acceptable salt thereof, Re is CN.

In an embodiment of a compound of formula (Ia), or a pharmaceutically acceptable salt thereof, Re is $C_1$-$C_6$ alkyl.

In an embodiment of a compound of formula (Ia), or a pharmaceutically acceptable salt thereof, Re is $C_1$-$C_6$ haloalkyl.

In an embodiment of a compound of formula (Ia), or a pharmaceutically acceptable salt thereof, Re is $C_1$-$C_6$ alkoxy.

In an embodiment of a compound of formula (Ia), or a pharmaceutically acceptable salt thereof, Rd is hydrogen; and Re is hydrogen.

In an embodiment of a compound of formula (Ia), or a pharmaceutically acceptable salt thereof, Ra is hydrogen.

In an embodiment of a compound of formula (Ia), or a pharmaceutically acceptable salt thereof, Ra is halo.

In an embodiment of a compound of formula (Ia), or a pharmaceutically acceptable salt thereof, Ra is $C_1$-$C_6$ alkyl.

In an embodiment of a compound of formula (Ia), or a pharmaceutically acceptable salt thereof, Ra is $C_1$-$C_6$ alkoxy.

In an embodiment of a compound of formula (Ia), or a pharmaceutically acceptable salt thereof, Rb is hydrogen.

In an embodiment of a compound of formula (Ia), or a pharmaceutically acceptable salt thereof, Rb is $C_1$-$C_6$ alkyl.

In an embodiment of a compound of formula (Ia), or a pharmaceutically acceptable salt thereof, Rb is hydroxy-$C_1$-$C_6$ alkyl.

In an embodiment of a compound of formula (Ia), or a pharmaceutically acceptable salt thereof, Rb is $C_1$-$C_6$ alkoxy-$C_1$-$C_6$ alkyl.

In an embodiment of a compound of formula (Ia), or a pharmaceutically acceptable salt thereof, Rb is $C_1$-$C_6$ alkyl-carbonyl.

In an embodiment of a compound of formula (Ia), or a pharmaceutically acceptable salt thereof, Rb is $C_1$-$C_6$ alkoxy-carbonyl.

In an embodiment of a compound of formula (Ia), or a pharmaceutically acceptable salt thereof, Ra is hydrogen; and Rb is hydrogen.

In an embodiment of a compound of formula (Ia), or a pharmaceutically acceptable salt thereof, Rd is hydrogen; Re is hydrogen; Ra is hydrogen; and Rb is hydrogen.

In an embodiment of a compound of formula (Ia), or a pharmaceutically acceptable salt thereof, X is —CH═CH—; Ra is hydrogen; and Rb is hydrogen.

In an embodiment of a compound of formula (Ia), or a pharmaceutically acceptable salt thereof, X is —CH═CH—; Ra is hydrogen; Rb is hydrogen; and n is 0.

In an embodiment of a compound of formula (Ia), or a pharmaceutically acceptable salt thereof, CyA is heteroaryl optionally having at least one substituent selected from the group Q, or fused heterocyclic ring consisting of 9 or 10 atoms optionally having at least one substituent selected from the group Q.

In an embodiment of a compound of formula (Ia), or a pharmaceutically acceptable salt thereof, CyA is heteroaryl optionally having at least one substituent selected from the group Q.

In an embodiment of a compound of formula (Ia), or a pharmaceutically acceptable salt thereof, CyA is selected from the group consisting of

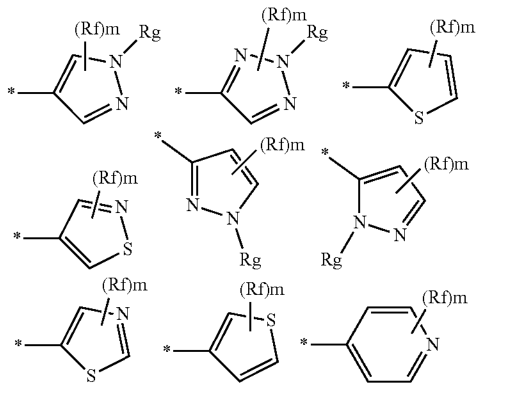

-continued

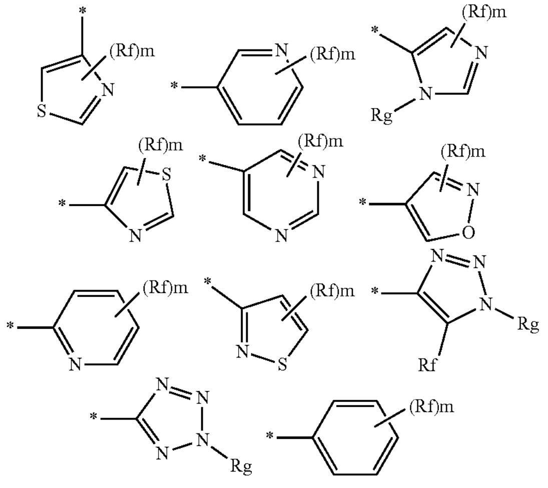

wherein each Rf is independently hydrogen, C1-C6 alkyl, C1-C6 haloalkyl, C1-C6 alkoxy, C1-C6 haloalkoxy, hydroxyl, C1-C6 hydroxyalkyl, C1-C6 hydroxyalkoxy, carboxy-C1-6 alkyl, amino optionally having at least one C1-3 alkyl, $NO_2$, CN, CONH2, oxo, C1-C6 alkyl-carbonyl, C1-C6 alkoxy-carbonyl, C1-C6 alkyl-carbonylamino, C1-C6 alkoxy-carbonylamino, C1-C6 alkyl-carbonyl-N-methylamino, C1-C6 alkoxy-carbonyl-N-methylamino, C3-C8 cycloalkyl, C3-C8 cycloalkyl-C1-C3 alkoxy, C1-C3 alkoxy-C1-C3 alkyl, C1-C3 alkoxy-C1-C3-alkoxy-C1-C3 alkyl, C1-C3 alkoxy-carbonyl-C1-C3 alkyl, or phenyl-C1-C6 alkoxy or two Rf are taken together with the carbon atom to which they are attached to form a spiro ring; Rg is hydrogen, C1-C6 alkyl, C1-C6 haloalkyl, carboxy-C1-C6 alkyl, amino optionally having at least one C1-C3 alkyl, C1-C3 alkoxy-C1-C3 alkyl, C1-C3 alkoxy-carbonyl-C1-C3 alkyl, carboxy-C1-C6 alkyl, N-methylamino-carbonyl-C1-C6 alkyl, N,N-dimethylaminocarbonyl-C1-C6 alkyl, heterocyclyl or heterocyclyl-C1-C3 alkyl; m is an integer of 0 to 5; and asterisks denote the points of attachment.

In an embodiment of a compound of formula (Ia), or a pharmaceutically acceptable salt thereof, CyA is selected from the group consisting of

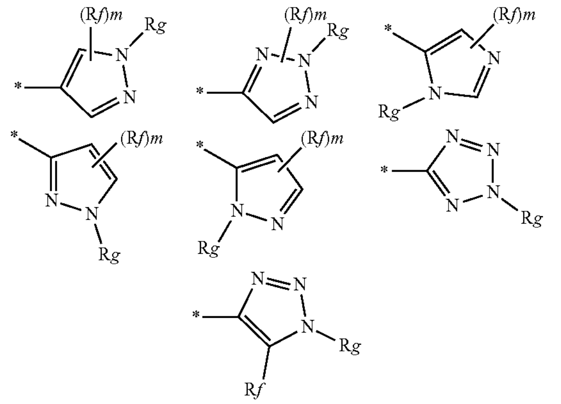

wherein each Rf is independently hydrogen, C1-C6 alkyl, C1-C6 haloalkyl, hydroxyl, amino optionally having at least one C1-3 alkyl, or C1-C6 alkyl-carbonylamino; Rg is hydrogen or C1-C6 alky; m is an integer of 0 to 5; and asterisks denote the points of attachment.

In an embodiment of a compound of formula (Ia), or a pharmaceutically acceptable salt thereof, CyA is

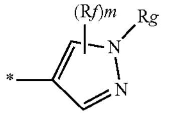

wherein each Rf is independently hydrogen, C1-C6 alkyl or C1-C6 haloalkyl; Rg is C1-C6 alky; m is an integer of 0 to 2; and asterisks denote the points of attachment.

In an embodiment of a compound of formula (Ia), or a pharmaceutically acceptable salt thereof, CyA is

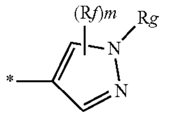

wherein each Rf is C1-C6 haloalkyl; Rg is methyl; m is 1; and asterisks denote the points of attachment.

In an embodiment of a compound of formula (Ia), or a pharmaceutically acceptable salt thereof, CyA is fused heterocyclic ring consisting of 9 or 10 atoms optionally having at least one substituent selected from the group Q.

In an embodiment of a compound of formula (Ia), or a pharmaceutically acceptable salt thereof, CyA is fused non-aromatic heterocyclyl-aryl optionally having at least one substituent selected from the group Q, fused non-aromatic heterocyclyl-heteroaryl optionally having at least one substituent selected from the group Q, fused arylheteroaryl optionally having at least one substituent selected from the group Q, or fused heteroarylheteroaryl optionally having at least one substituent selected from the group Q.

In an embodiment of a compound of formula (Ia), or a pharmaceutically acceptable salt thereof, CyA is fused non-aromatic heterocyclyl-heteroaryl optionally having at least one substituent selected from the group Q.

In an embodiment of a compound of formula (Ia), or a pharmaceutically acceptable salt thereof, CyA is selected from the group consisting of

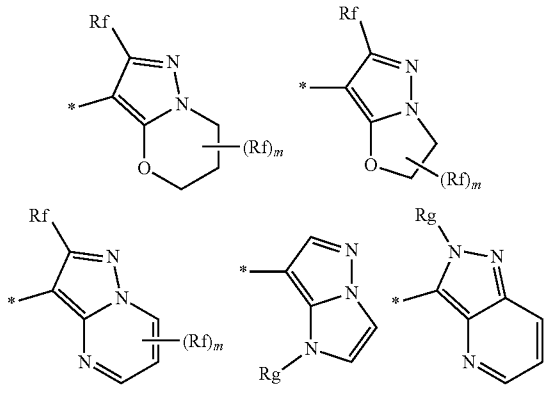

-continued

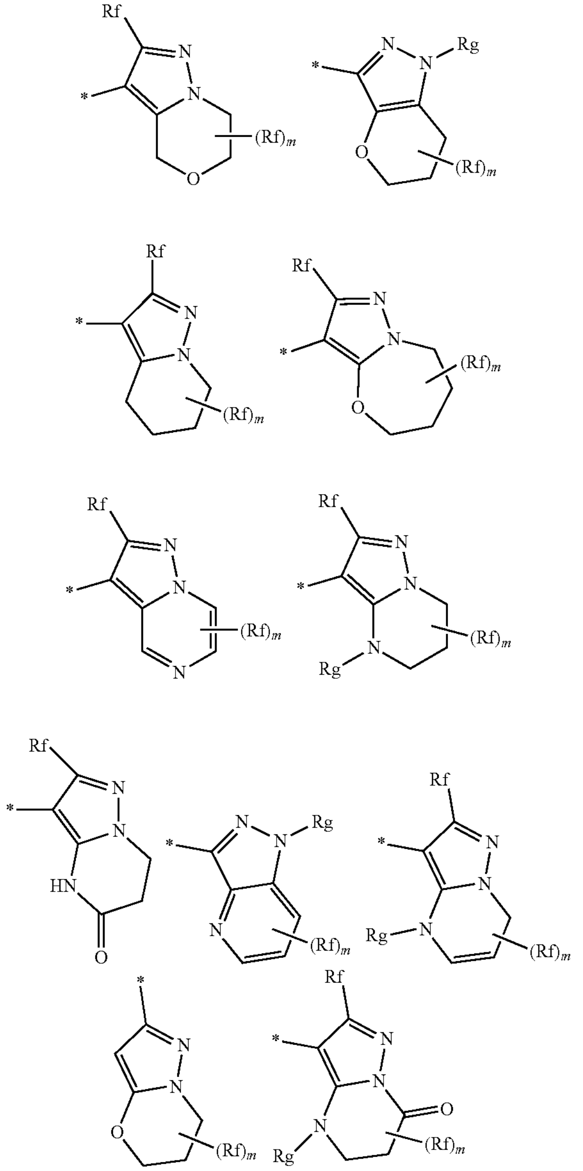

wherein each Rf is independently hydrogen, C1-C6 alkyl, C1-C6 haloalkyl, C1-C6 alkoxy, C1-C6 haloalkoxy, hydroxyl, C1-C6 hydroxyalkyl, C1-C6 hydroxyalkoxy, carboxy-C1-6 alkyl, amino optionally having at least one C1-3 alkyl, $NO_2$, CN, CONH2, oxo, C1-C6 alkyl-carbonyl, C1-C6 alkoxy-carbonyl, C1-C6 alkyl-carbonylamino, C1-C6 alkoxy-carbonylamino, C1-C6 alkyl-carbonyl-N-methylamino, C1-C6 alkoxy-carbonyl-N methylamino, C3-C8 cycloalkyl, C3-C8 cycloalkyl-C1-C3 alkoxy, C1-C3 alkoxy-C1-C3 alkyl, C1-C3 alkoxy-C1-C3-alkoxy-C1-C3 alkyl, C1-C3 alkoxy-carbonyl-C1-C3 alkyl, or phenyl-C1-C6 alkoxy or two Rf are taken together with the carbon atom to which they are attached to form a spiro ring; Rg is hydrogen, C1-C6 alkyl, C1-C6 haloalkyl, carboxy-C1-C6 alkyl, amino optionally having at least one C1-C3 alkyl, C1-C3 alkoxy-C1-C3 alkyl, C1-C3 alkoxy-carbonyl-C1-C3 alkyl, carboxy-C1-C6 alkyl, N-methylamino-carbonyl-C1-C6 alkyl, N,N-dimethylaminocarbonyl-C1-C6 alkyl, heterocyclyl or heterocyclyl-C1-C3 alkyl; m is an integer of 0 to 5; and asterisks denote the points of attachment.

In an embodiment of a compound of formula (Ia), or a pharmaceutically acceptable salt thereof, CyA is

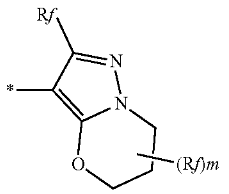

wherein each Rf is independently hydrogen, C1-C6 alkyl, C1-C6 haloalkyl, hydroxyl, amino optionally having at least one C1-3 alkyl, or C1-C6 alkyl-carbonylamino; m is an integer of 0 to 3; and asterisks denote the points of attachment.

In an embodiment of a compound of formula (Ia), or a pharmaceutically acceptable salt thereof, CyA is

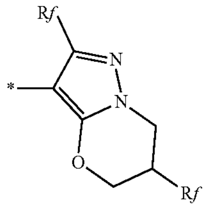

wherein each Rf is independently hydrogen, C1-C6 alkyl, C1-C6 haloalkyl, hydroxyl, amino optionally having at least one C1-3 alkyl, or C1-C6 alkyl-carbonylamino; and asterisks denote the points of attachment.

In an embodiment of a compound of formula (Ia), or a pharmaceutically acceptable salt thereof, CyA is

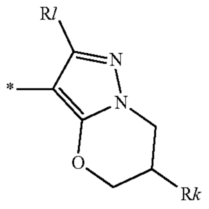

wherein each Rl is C1-C6 alkyl or C1-C6 haloalkyl; Rk is hydrogen, hydroxyl, amino or C1-C6 alkyl-carbonylamino; and asterisks denote the points of attachment. In an embodiment of a compound of formula (Ia), or a pharmaceutically acceptable salt thereof, CyB is C6-C10 aryl optionally having at least one substituent selected from a group Q or heteroaryl optionally having at least one substituent selected from the group Q.

In an embodiment of a compound of formula (Ia), or a pharmaceutically acceptable salt thereof, CyB is C6-C10 aryl optionally having at least one substituent selected from a group Q.

In an embodiment of a compound of formula (Ia), or a pharmaceutically acceptable salt thereof, CyB is phenyl optionally having at least one substituent selected from the group Q.

In an embodiment of a compound of formula (Ia), or a pharmaceutically acceptable salt thereof, CyB is

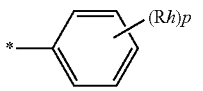

wherein each Rh is independently halo, C1-C6 alkyl, C1-C6 haloalkyl, C1-C6 alkoxy, C1-C6 haloalkoxy, or CN; p is an integer of 0 to 2; and asterisks denote the points of attachment.

In an embodiment of a compound of formula (Ia), or a pharmaceutically acceptable salt thereof, CyB is

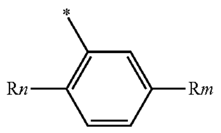

wherein Rn is CN; Rm is C1-C6 alkoxy; and asterisks denote the points of attachment.

In an embodiment of a compound of formula (Ia), or a pharmaceutically acceptable salt thereof, CyB is heteroaryl optionally having at least one substituent selected from the group Q.

In an embodiment of a compound of formula (Ia), or a pharmaceutically acceptable salt thereof, CyB is

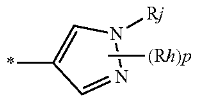

wherein each Rh is independently halo, C1-C6 alkyl, C1-C6 haloalkyl, C1-C6 alkoxy, C1-C6 haloalkoxy, C2-C6 alkenyl, hydroxyl, C1-C6 hydroxyalkyl, amino optionally having at least one C1-C3 alkyl, CN, oxo, C1-C6 alkylsulfonyl, or C3-C8 cycloalkyl; Rj is hydrogen or C1-C6 alkyl; p is an integer of 0 to 2; and asterisks denote the points of attachment.

In an embodiment of a compound of formula (Ia), or a pharmaceutically acceptable salt thereof, CyB is

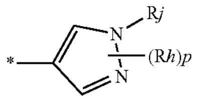

wherein each Rh is independently C1-C6 haloalkoxy or CN; Rj is hydrogen or C1-C6 alkyl; p is an integer of 0 to 1; and asterisks denote the points of attachment.

In an embodiment of a compound of formula (Ia), or a pharmaceutically acceptable salt thereof, CyB is

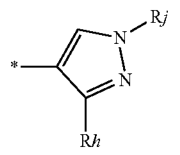

wherein Rh is C1-C6 haloalkoxy; Rj is hydrogen or methyl; and asterisks denote the points of attachment.

In an embodiment of a compound of formula (Ia), or a pharmaceutically acceptable salt thereof, CyA is

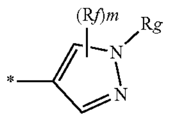

wherein each Rf is C1-C6 haloalkyl; Rg is methyl; m is 1; CyB is

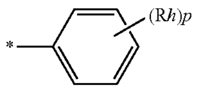

wherein each Rh is independently halo, C1-C6 alkyl, C1-C6 haloalkyl, C1-C6 alkoxy, C1-C6 haloalkoxy or CN; p is an integer of 0 to 2; and asterisks denote the points of attachment.

In an embodiment of a compound of formula (Ia), or a pharmaceutically acceptable salt thereof, CyA is

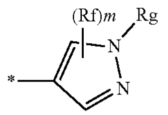

wherein each Rf is C1-C6 haloalkyl; Rg is methyl; m is 1; CyB is

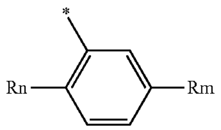

wherein Rn is CN; Rm is C1-C6 alkoxy; and asterisks denote the points of attachment.

In an embodiment of a compound of formula (Ia), or a pharmaceutically acceptable salt thereof, X is —CH═CH—; Ra is hydrogen; Rb is hydrogen; n is 0; CyA is

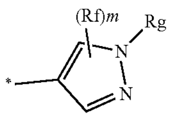

wherein each Rf is C1-C6 haloalkyl; Rg is methyl; m is 1; CyB is

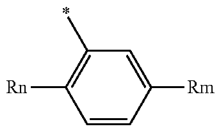

wherein Rn is CN; Rm is C1-C6 alkoxy; and asterisks denote the points of attachment.

In an embodiment of a compound of formula (Ia), or a pharmaceutically acceptable salt thereof, CyA is

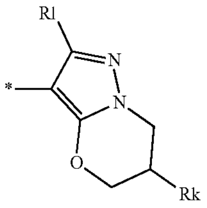

wherein each Rl is C1-C6 alkyl or C1-C6 haloalkyl; Rk is hydrogen, hydroxyl, amino or C1-C6 alkyl-carbonylamino; CyB is

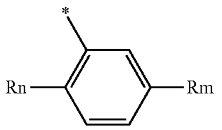

wherein Rn is CN; Rm is C1-C6 alkoxy; and asterisks denote the points of attachment.

In an embodiment of a compound of formula (Ia), or a pharmaceutically acceptable salt thereof, X is —CH═CH—; Ra is hydrogen; Rb is hydrogen; n is 0; CyA is

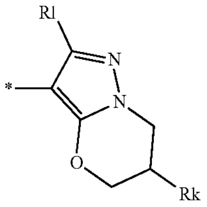

wherein each Rl is C1-C6 alkyl or C1-C6 haloalkyl; Rk is hydrogen, hydroxyl, amino or C1-C6 alkyl-carbonylamino; CyB is

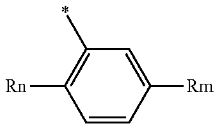

wherein Rn is CN; Rm is C1-C6 alkoxy; and asterisks denote the points of attachment.

In an embodiment of a compound of formula (Ia), or a pharmaceutically acceptable salt thereof, CyA is

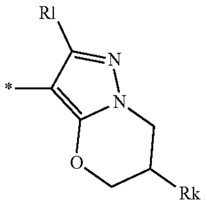

wherein Rl is C1-C6 alkyl or C1-C6 haloalkyl; Rk is hydrogen, hydroxyl, amino or C1-C6 alkyl-carbonylamino; CyB is

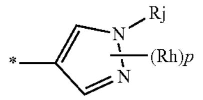

wherein Rj is hydrogen or C1-C6 alkyl; Rh is independently halo, C1-C6 alkyl, C1-C6 haloalkyl, C1-C6 alkoxy, C1-C6 haloalkoxy or CN: p is an integer of 0 to 2; and asterisks denote the points of attachment.

In an embodiment of a compound of formula (Ia), or a pharmaceutically acceptable salt thereof, X is —CH═CH—; Ra is hydrogen; Rb is hydrogen; n is 0; CyA is

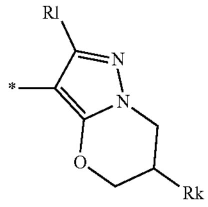

wherein Rl is C1-C6 alkyl or C1-C6 haloalkyl; Rk is hydrogen, hydroxyl, amino or C1-C6 alkyl-carbonylamino; CyB is

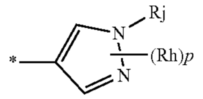

wherein Rj is hydrogen or C1-C6 alkyl; Rh is independently C1-C6 haloalkoxy or CN; p is an integer of 0 to 2; and asterisks denote the points of attachment.

In an embodiment of a compound of formula (Ia), or a pharmaceutically acceptable salt thereof, X is —CH═CH—; Ra is hydrogen; Rb is hydrogen; n is 0; CyA is

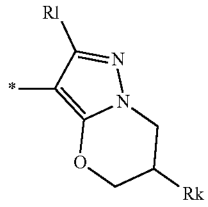

wherein Rl is C1-C6 alkyl or C1-C6 haloalkyl; Rk is hydrogen, hydroxyl, amino or C1-C6 alkyl-carbonylamino; CyB is

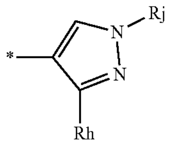

wherein Rj is hydrogen or mehyl; Rh is C1-C6 haloalkoxy; and asterisks denote the points of attachment.

In some aspects, the present disclosure relates to one of the following embodiments:

Embodiment 1. A compound represented by structural formula (I*):

(I*)

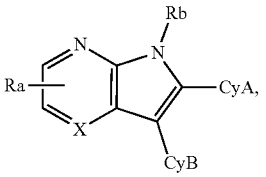

or a pharmaceutically acceptable salt thereof, wherein:

X is CH or N;

Rb is selected from H, $C_1$-$C_6$ alkyl, and C(═O)O($C_1$-$C_6$ alkyl), wherein each $C_1$-$C_6$ alkyl is optionally substituted with one or more substituents independently selected from group Q;

CyA is selected from one of the following moieties:

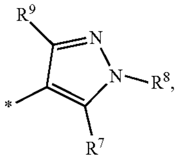

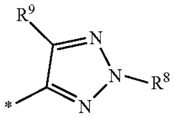

,

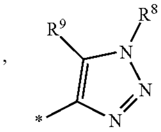

,

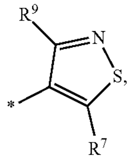

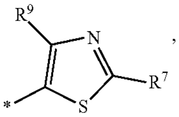

,

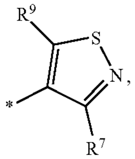

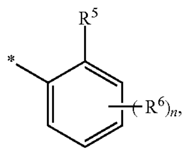

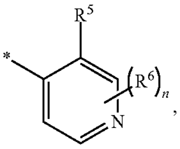

, and

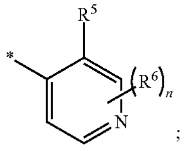

;

CyB is selected from 5- to 12-membered heteroaryl and $C_6$-$C_{12}$ aryl, wherein the 5- to 12-membered heteroaryl or $C_6$-$C_{12}$ aryl is optionally substituted with one or more substituents independently selected from group Q;

Ra is selected from H, deuterium, F, Cl, Br, CN, $NO_2$, $C_1$-$C_6$ alkyl, and $C_1$-$C_6$ alkoxy, wherein each $C_1$-$C_6$ alkyl or $C_1$-$C_6$ alkoxy is optionally substituted with one or more substituents independently selected from group Q;

$R^5$ and $R^6$ are each independently selected from deuterium, F, Cl, Br, OH, CN, $NO_2$, $NR^{10a}R^{10b}$, C(=O)$NR^{11a}R^{11b}$, $C_1$-$C_6$ alkyl, $C_1$-$C_6$ alkoxy, $C_2$-$C_6$ alkenyl, $C_2$-$C_6$ alkynyl, $C_3$-$C_{12}$ cycloalkyl, $C_6$-$C_{12}$ aryl, 5- to 12-membered heteroaryl, and 4- to 12-membered heterocyclyl, wherein each $C_1$-$C_6$ alkyl, $C_1$-$C_6$ alkoxy, $C_2$-$C_6$ alkenyl, $C_2$-$C_6$ alkynyl, $C_3$-$C_{12}$ cycloalkyl, $C_6$-$C_{12}$ aryl, 5- to 12-membered heteroaryl, or 4- to 12-membered heterocyclyl is optionally substituted with one or more substituents independently selected from group Q, or $R^5$ and $R^6$ together with the atoms to which they are attached form $C_4$-$C_{12}$ carbocyclyl, 5- to 12-membered heteroaryl, or 4- to 12-membered heterocyclyl, wherein the $C_4$-$C_{12}$ carbocyclyl, 5- to 12-membered heteroaryl, or 4- to 12-membered heterocyclyl is optionally substituted with one or more substituents independently selected from group Q;

n is 0, 1, 2, 3, or 4;

$R^7$ and $R^8$ together with the atoms to which they are attached form 4- to 12-membered heterocyclyl or 5- to 12-membered heteroaryl, wherein the 4- to 12-membered heterocyclyl or 5- to 12-membered heteroaryl is optionally substituted with one or more substituents independently selected from group Q;

$R^7$ is selected from H, deuterium, F, Cl, Br, OH, CN, $NO_2$, $NR^{10c}R^{10d}$, C(=O)$NR^{11c}R^{11c}$, $C_1$-$C_6$ alkyl, $C_1$-$C_6$ alkoxy, $C_2$-$C_6$ alkenyl, $C_2$-$C_6$ alkynyl, $C_3$-$C_{12}$ cycloalkyl, $C_6$-$C_{12}$ aryl, 5- to 12-membered heteroaryl, and 4- to 12-membered heterocyclyl, wherein each $C_1$-$C_6$ alkyl, $C_1$-$C_6$ alkoxy, $C_2$-$C_6$ alkenyl, $C_2$-$C_6$ alkynyl, $C_3$-$C_{12}$ cycloalkyl, $C_6$-$C_{12}$ aryl, 5- to 12-membered heteroaryl, or 4- to 12-membered heterocyclyl is optionally substituted with one or more substituents independently selected from a group Q;

$R^8$ is selected from H and $C_{1-6}$ alkyl optionally substituted with one or more substituents independently selected from a group Q;

$R^9$ is selected from $C_1$-$C_6$ alkyl, F, Cl, Br, OH, CN, $NO_2$, $NR^{10e}R^{10f}$, C(=O)$NR^{11e}R^{11f}$, $C_1$-$C_6$ alkoxy, $C_2$-$C_6$ alkenyl, $C_2$-$C_6$ alkynyl, $C_3$-$C_{12}$ cycloalkyl, $C_6$-$C_{12}$ aryl, 5- to 12-membered heteroaryl, and 4- to 12-membered heterocyclyl, wherein each $C_1$-$C_6$ alkyl, $C_1$-$C_6$ alkoxy, $C_2$-$C_6$ alkenyl, $C_2$-$C_6$ alkynyl, $C_3$-$C_{12}$ cycloalkyl, $C_6$-$C_{12}$ aryl, 5- to 12-membered heteroaryl, and 4- to 12-membered heterocyclyl is optionally substituted with one or more substituents independently selected from a group Q; and $R^{10a}$, $R^{10b}$, $R^{10c}$, $R^{10d}$, $R^{10e}$, $R^{10f}$, $R^{11a}$, $R^{11b}$, $R^{11c}$, $R^{11d}$, $R^{11e}$, and $R^{11f}$ are each independently selected from H and $C_1$-$C_6$ alkyl optionally substituted with one or more substituents independently selected from a group Q, or one or more of the pairs of variables selected from $R^{10a}$ and $R^{10b}$, $R^{10c}$ and $R^{10d}$, $R^{10c}$ and $R^{10f}$, $R^{11a}$ and $R^{11b}$, $R^{11c}$ and $R^{11d}$, and $R^{11e}$ and $R^{11f}$, together with the nitrogen to which they are attached, form 5- to 12-membered heteroaryl or 4- to 12-membered heterocyclyl, wherein each 5- to 12-membered heteroaryl or 4- to 12-membered heterocyclyl is optionally substituted with one or more substituents independently selected from a group Q;

wherein each of the one or more substituents of group Q is independently selected from deuterium, F, Cl, Br, OH, $NH_2$, NH(C=O)($C_1$-$C_6$ alkyl), NH(C=O)($C_3$-$C_8$ cycloalkyl), NH(C=O)(O—$C_1$-$C_6$ alkyl), $C_1$-$C_6$ alkyl optionally substituted with one or more deuterium, $C_1$-$C_6$ haloalkyl, $C_1$-$C_6$ alkoxy optionally substituted with one or more deuterium, $C_1$-$C_6$ haloalkoxy, $C_2$-$C_6$ alkenyl, $C_1$-$C_6$ hydroxyalkyl, $C_1$-$C_6$ hydroxyalkoxy, carboxy-$C_1$-$C_6$ alkyl, amino optionally having at least one $C_1$-$C_3$ alkyl, $NO_2$, CN, $CONH_2$, aminocarbonyl substituted with at least one $C_1$-$C_6$ alkyl, oxo, $C_1$-$C_6$ alkyl-carbonyl, $C_1$-$C_6$ alkoxy-carbonyl, $C_1$-$C_6$ alkyl-carbonylamino, $C_1$-$C_6$ alkoxy-carbonylamino, $C_1$-$C_6$ alkyl-carbonyl-N-methylamino, $C_1$-$C_6$ alkoxy-carbonyl-N-methylamino, $C_1$-$C_6$ alkylsulfanyl, $C_1$-$C_6$ alkylsulfinyl, $C_1$-$C_6$ alkylsulfonyl, $C_1$-$C_6$ alkylamino-sulfonyl, $C_1$-$C_6$ alkylsulfinyl-$C_1$-$C_6$ alkyl, $C_1$-$C_6$ alkylsulfonyl-$C_1$-$C_6$ alkyl, $C_3$-$C_8$ cycloalkyl, $C_3$-$C_8$ cycloalkyl-$C_1$-$C_3$ alkoxy, $C_1$-$C_3$ alkoxy-$C_1$-$C_3$ alkyl, $C_1$-$C_3$ alkoxy-$C_1$-$C_3$alkoxy-$C_1$-$C_3$ alkyl, $C_1$-$C_3$ alkoxy-carbonyl-$C_1$-$C_3$ alkyl, phenyl-$C_1$-$C_6$ alkoxy, N-methyl-amino-carbonyl-$C_1$-$C_6$ alkyl, N,N-dimethylaminocarbonyl-$C_1$-$C_6$ alkyl, heterocyclyl, heterocyclyl-$C_1$-$C_3$ alkyl or a spiro ring.

Embodiment 2. The compound of embodiment 1, wherein Ra is selected from H, F, Cl, Br, CN, and $NO_2$.

Embodiment 3. The compound of embodiment 1, wherein Ra is $C_1$-$C_6$ alkyl.

Embodiment 4. The compound of embodiment 1, wherein Ra is $C_1$-$C_6$ alkoxy.

Embodiment 5. The compound of embodiment 1, wherein the compound is represented by structural formula (Ia*):

(Ia*)

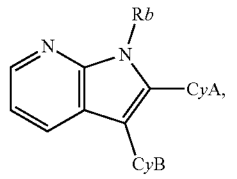

or a pharmaceutically acceptable salt thereof.

Embodiment 6. The compound of any one of embodiments 1-5, wherein Rb is $C_1$-$C_3$ alkyl.

Embodiment 7. The compound of embodiment 1, wherein the compound is represented by structural formula (Ib*):

(Ib*)

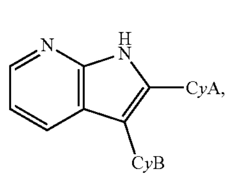

or a pharmaceutically acceptable salt thereof.

Embodiment 8. The compound of any one of embodiments 1-7, wherein CyB is $C_6$-$C_{12}$ aryl.

Embodiment 9. The compound of embodiment 8, wherein CyB is phenyl optionally substituted with one or more substituents independently selected from group Q.

Embodiment 10. The compound of any one of embodiments 1-7, wherein CyB is

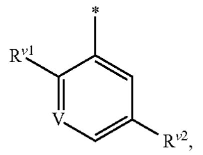

wherein

V is CH or N;

$R^{v1}$ is selected from CN, F, Cl, Br, $C_1$-$C_3$ haloalkyl, and $C_1$-$C_3$ haloalkoxy; and $R^{v2}$ is selected from H, F, Cl, Br, $NH_2$, $C_1$-$C_3$ alkyl, $C_1$-$C_3$ alkoxy, and $C_1$-$C_3$ deteuroalkoxy.

Embodiment 11. The compound of embodiment 10, wherein V is CH.

Embodiment 12. The compound of embodiment 10, wherein V is N.

Embodiment 13. The compound of any one of embodiments 10-12, wherein $R^{v1}$ is selected from CN, F, and $OCHF_2$.

Embodiment 14. The compound of embodiment 13, wherein $R^{v1}$ is $OCHF_2$.

Embodiment 15. The compound of embodiment 13, wherein $R^{v1}$ is CN.

Embodiment 16. The compound of any one of embodiments 10-15, wherein $R^{v2}$ is H.

Embodiment 17. The compound of any one of embodiments 10-15, wherein $R^{v2}$ is $OCH_3$.

Embodiment 18. The compound of any one of embodiments 10-15, wherein $R^{v2}$ is $OCD_3$.

Embodiment 19. The compound of any one of embodiments 1-7, wherein CyB is 5- to 12-membered heteroaryl.

Embodiment 20. The compound of embodiment 19, wherein CyB is 5- to 6-membered heteroaryl optionally substituted with one or more substituents independently selected from group Q.

Embodiment 21. The compound of embodiment 20, wherein CyB is 5-membered heteroaryl.

Embodiment 22. The compound of embodiment 20, wherein CyB is selected from the following moieties:

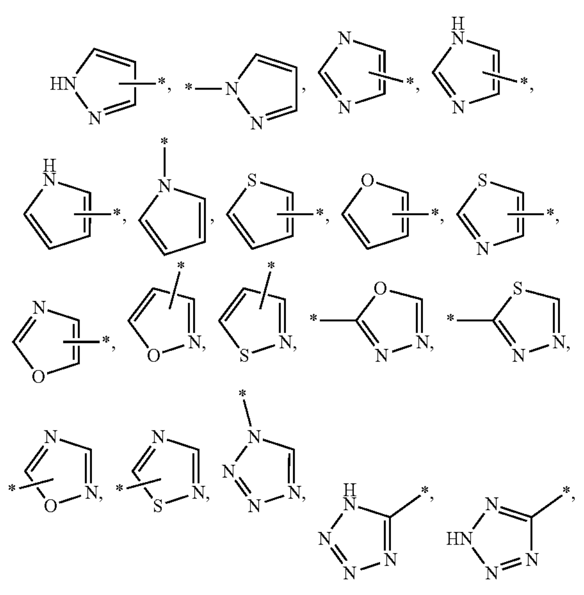

-continued

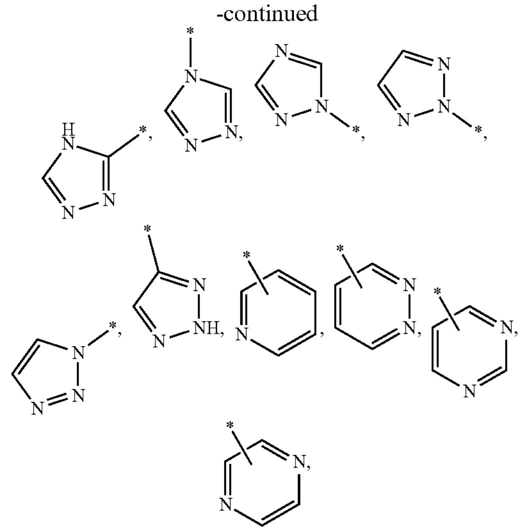

and wherein each of the listed moieties, as valence permits, is optionally substituted with one or more substituents independently selected from group Q.

Embodiment 23. The compound of embodiment 22, wherein CyB is

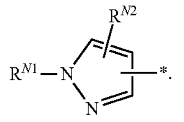

wherein $R^{N1}$ is selected from H and $C_1$-$C_3$ alkyl; and $R^{N2}$ is selected from CN and $C_1$-$C_3$ haloalkoxy.

Embodiment 24. The compound of embodiment 23, wherein the compound is represented by structural formula (Ic*):

(Ic*)

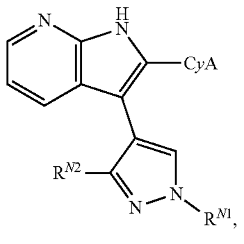

or a pharmaceutically acceptable salt thereof.

Embodiment 25. The compound of embodiment 23 or 24, wherein $R^{N1}$ is $C_1$-$C_3$ alkyl.

Embodiment 26. The compound of embodiment 25, wherein $R^{N1}$ is methyl.

Embodiment 27. The compound of any one of embodiments 23-26, wherein $R^{N2}$ is CN.

Embodiment 28. The compound of any one of embodiments 23-26, wherein $R^{N2}$ is $C_1$-$C_3$ haloalkoxy.

Embodiment 29. The compound of embodiment 28, wherein $R^{N2}$ is $OCHF_2$.

Embodiment 30. The compound of embodiment 1, wherein the compound is represented by structural formula (Id*):

(Id*)

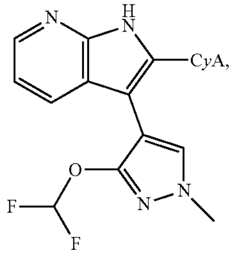

or a pharmaceutically acceptable salt thereof.

Embodiment 31. The compound of any one of embodiments 1-30, wherein the compound is represented by structural formula (Ie*):

(Ie*)

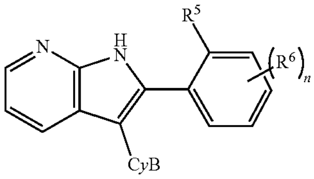

, or a pharmaceutically acceptable salt thereof.

Embodiment 32. The compound of embodiment 31, wherein the compound is represented by structural formula (If*):

(If*)

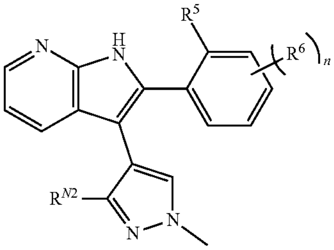

, or a pharmaceutically acceptable salt thereof.

Embodiment 33. The compound of any one of embodiments 1-30, wherein CyA is selected from

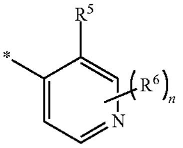

and

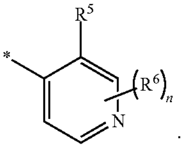

.

Embodiment 34. The compound of any one of embodiments 31-33, wherein $R^5$ is selected from F, OH, $C_1$-$C_3$ alkoxy, and $C_1$-$C_3$ haloalkyl, wherein the $C_1$-$C_3$ alkyl and $C_1$-$C_3$ haloalkyl optionally substituted with one or more substituents independently selected from group Q.

Embodiment 35. The compound of any one of embodiments 31-34, wherein $R^5$ is selected from F, deuterium, $C_1$-$C_3$ alkyl, $C_1$-$C_3$ alkoxy, and $C_1$-$C_3$ haloalkyl.

Embodiment 36. The compound of any one of embodiments 31-35, wherein $R^6$ is selected from deuterium and F.

Embodiment 37. The compound of embodiment 31 or 32, wherein $R^5$ and $R^6$ together with the atoms to which they are attached form 5- to 6-membered heteroaryl.

Embodiment 38. The compound of any one of embodiments 31-35, wherein n is 0.

Embodiment 39. The compound of any one of embodiments 1-30, wherein CyA is selected from

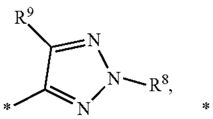

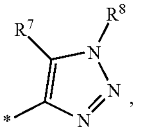

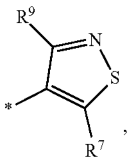

and

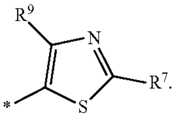

Embodiment 40. The compound of any one of embodiments 1-30, wherein the compound is represented by structural formula (Ig*):

(Ig*)

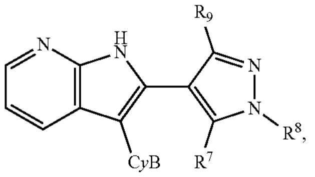

or a pharmaceutically acceptable salt thereof.

Embodiment 41. The compound of embodiment 1, wherein the compound is represented by structural formula (Ih*):

(Ih*)

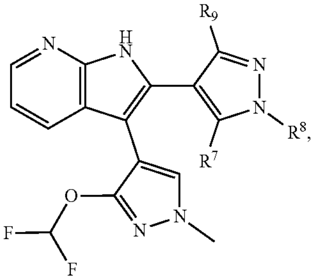

or a pharmaceutically acceptable salt thereof.

Embodiment 42. The compound of any one of embodiments 39-41, wherein $R^9$ is selected from F, Cl, Br, OH, CN, $NO_2$, $C_1$-$C_6$ alkyl, $C_1$-$C_6$ alkoxy, $C_1$-$C_6$ haloalkyl, and $C_1$-$C_6$ haloalkoxy.

Embodiment 43. The compound of embodiment 42, wherein $R^9$ is selected from $C_1$-$C_3$ alkyl, $C_1$-$C_3$ alkoxy, and $C_1$-$C_3$ haloalkyl.

Embodiment 44. The compound of embodiment 43, wherein $R^9$ is $C_1$-$C_3$ haloalkyl.

Embodiment 45. The compound of embodiment 44, wherein $R^9$ is selected from $CH_2F$, $CHF_2$, and $CF_3$.

Embodiment 46. The compound of embodiment 45, wherein $R^9$ is $CHF_2$.

Embodiment 47. The compound of embodiment 43, wherein $R^9$ is $C_1$-$C_3$ alkyl.

Embodiment 48. The compound of embodiment 47, wherein $R^9$ is ethyl.

Embodiment 49. The compound of any one of embodiments 39-48, wherein $R^8$ is H.

Embodiment 50. The compound of any one of embodiments 39-48, wherein $R^8$ is $C_1$-$C_3$ alkyl.

Embodiment 51. The compound of any one of embodiments 39-50, wherein $R^7$ is selected from H, F, Cl, Br, OH, CN, $NO_2$, $C_1$-$C_6$ alkyl, $C_1$-$C_6$ alkoxy, $C_1$-$C_6$ haloalkyl, and $C_1$-$C_6$ haloalkoxy.

Embodiment 52. The compound of any one of embodiments 39-50, wherein $R^7$ is H.

Embodiment 53. The compound of any one of embodiments 39-50, wherein $R^7$ is selected from $C_1$-$C_3$ alkyl, $C_1$-$C_3$ alkoxy, and $C_1$-$C_3$ haloalkyl.

Embodiment 54. The compound of any one of embodiments 39-48, wherein $R^7$ and $R^8$ together with the atoms to which they are attached form 5- to 12-membered heteroaryl.

Embodiment 55. The compound of embodiment 54, wherein $R^7$ and $R^8$ together with the atoms to which they are attached form 5- to 6-membered heteroaryl optionally substituted, as valence permits, with one or more substituents independently selected from group Q.

Embodiment 56. The compound of any one of embodiments 39-48, wherein $R^7$ and $R^8$ together with the atoms to which they are attached form 4- to 12-membered heterocyclyl.

Embodiment 57. The compound of any one of embodiments 38-44, wherein $R^7$ and $R^8$ together with the atoms to which they are attached form 5- to 8-membered heterocyclyl optionally substituted with one or more substituents independently selected from group Q.

Embodiment 58. The compound of any one of embodiments 1-30, wherein the compound is represented by structural formula (Ii*):

(Ii*)

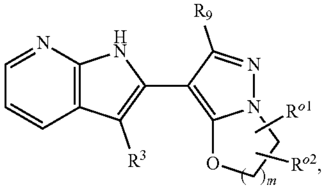

or a pharmaceutically acceptable salt thereof, wherein m is 1, 2, or 3; and $R^{o1}$ and $R^{o2}$ are each independently selected from H, OH, F, Cl, Br, $C_1$-$C_3$ alkyl, $C_1$-$C_3$ alkoxy, $NR^{x1}R^{x2}$, $NR^{x3}C(=O)R^{x5}$, and $NR^{x6}C(=O)OR^{x7}$, wherein $R^{x1}$, $R^{x2}$, $R^{x3}$, $R^{x5}$, $R^{x6}$, and $R^{x7}$ is each independently selected from H, $C_{1-3}$ alkyl, and $C_3$-$C_6$ cycloalkyl, and wherein each $C_1$-$C_3$ alkyl, $C_1$-$C_3$ alkoxy, or $C_3$-$C_6$ cycloalkyl is substituted with one or more substituents independently selected from group Q.

Embodiment 59. The compound of embodiment 58, wherein the compound is represented by structural formula (Ij*):

(Ij*)

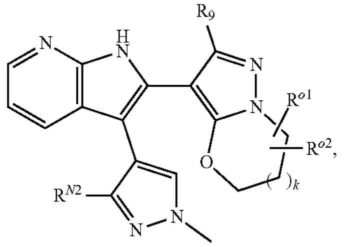

or a pharmaceutically acceptable salt thereof, wherein k is 1 or 2;

$R^9$ is selected from $C_1$-$C_3$ alkyl and $C_1$-$C_3$ haloalkyl.

$R^{N2}$ is selected from $OCHF_2$ and CN; and $R^{o1}$ and $R^{o2}$ are each independently selected from H, OH, F, Cl, Br, $C_1$-$C_3$ alkyl, $C_1$-$C_3$ alkoxy, $NR^{x1}R^{x2}$, $NR^{x3}C(=O)R^{x5}$, and $NR^{x6}C(=O)OR^{x7}$, wherein $R^{x1}$, $R^{x2}$, $R^{x3}$, $R^{x5}$, $R^{x6}$, and $R^{x7}$ is each independently selected from H, $C_1$-$C_3$ alkyl, and $C_3$-$C_6$ cycloalkyl, and wherein each $C_1$-$C_3$ alkyl, $C_1$-$C_3$ alkoxy, or $C_3$-$C_6$ cycloalkyl is substituted with one or more substituents independently selected from group Q.

Embodiment 60. The compound of embodiment 59, wherein the compound is represented by structural formula (Ik*):

(Ik*)

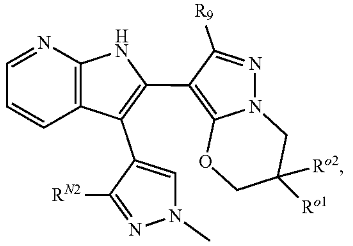

or a pharmaceutically acceptable salt thereof, wherein $R^{o1}$ is selected from H and $C_1$-$C_2$ alkyl; and $R^{o2}$ is selected from OH, F, $NHC(=O)O(C_1$-$C_2$ alkyl), $NHC(=O)O(C_3$-$C_6$ cycloalkyl), $C_1$-$C_3$ alkoxy, and $—O(C_1$-$C_3$ hydroxyalkyl).

Embodiment 61. The compound of embodiment 59 or 60, wherein $R^{N2}$ is $OCHF_2$.

Embodiment 62. The compound of embodiment 69 or 60, wherein $R^{N2}$ is CN.

Embodiment 63. The compound of any one of embodiments 59-62, wherein $R^{o1}$ is H.

Embodiment 64. The compound of any one of embodiments 59-62, wherein $R^{o1}$ is methyl.

Embodiment 65. The compound of any one of embodiments 59-63, wherein $R^{o1}$ and $R^{o2}$ are each H.

Embodiment 66. The compound of embodiment any one of embodiments 54-57, wherein $R^{o2}$ is OH.

Embodiment 67. The compound of any one of embodiments 59-64, wherein $R^{o2}$ is F.

Embodiment 68. The compound of any one of embodiments 59-64, wherein $R^{o2}$ is methoxy.

Embodiment 69. The compound of any one of embodiments 59-64, wherein $R^{o2}$ is $—OCH_2CH_2OH$.

Embodiment 70. The compound of any one of embodiments 59-64, wherein $R^{o2}$ is $—OCH_2C(Me)_2OH$.

Embodiment 71. The compound of any one of embodiments 59-64, wherein $R^{o2}$ is NHC(=O)OCH$_3$.

Embodiment 72. The compound of any one of embodiments 59-64, wherein $R^{o2}$ is NHC(=O)O(C$_3$ cycloalkyl).

Embodiment 73. The compound of any one of embodiments 58-72, wherein $R^9$ is CHF$_2$.

Embodiment 74. The compound of any one of embodiments 58-72, wherein $R^9$ is ethyl.

Embodiment 75. The compound of embodiment 1, wherein the compound is selected from

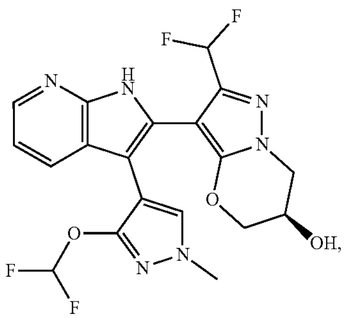

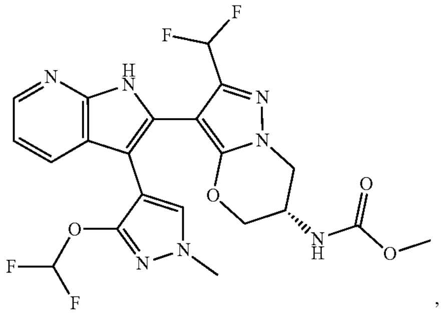

,

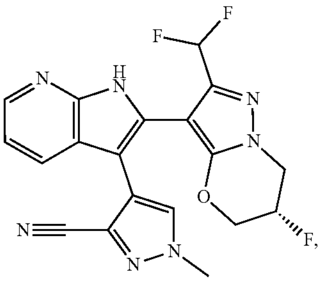

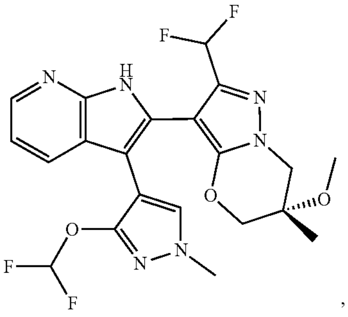

,

-continued

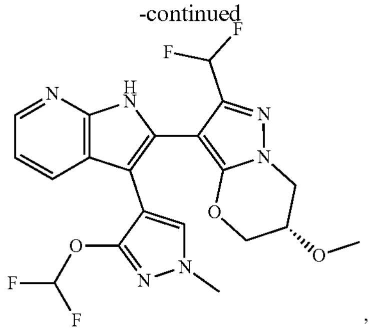

,

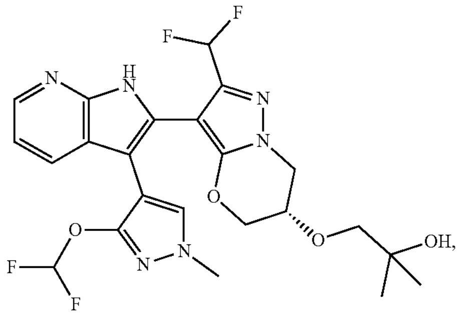

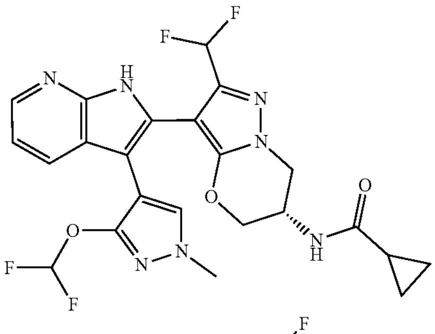

,

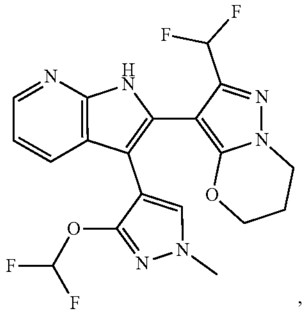

,

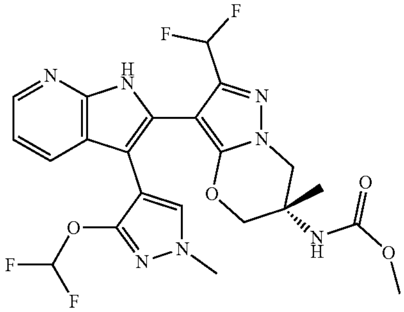

,

-continued

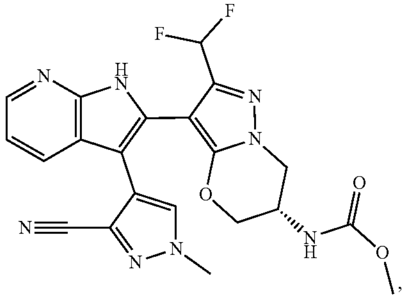

, and

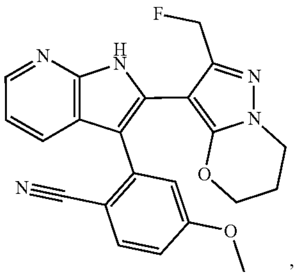

,

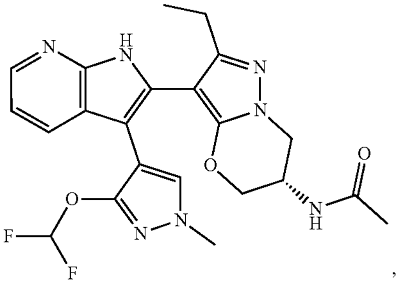

,

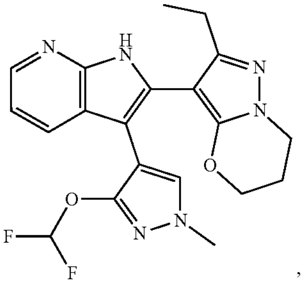

,

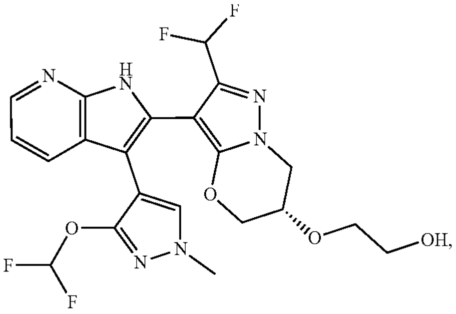

or a pharmaceutically acceptable salt thereof.

Embodiment 76. The compound of embodiment 1, wherein the compound is

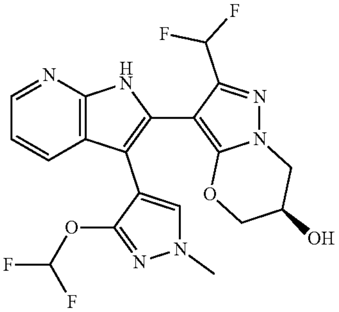 [SMILES: Cn1cc(-c2c(-c3c(C(F)F)nn4c3OC[C@H](O)C4)[nH]c3ncccc23)c(OC(F)F)n1]

or a pharmaceutically acceptable salt thereof.

Embodiment 77. The compound of embodiment 1, wherein the compound is

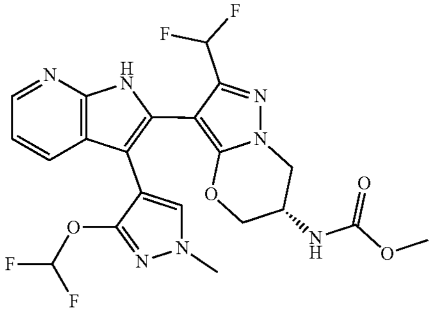 [SMILES: COC(=O)N[C@@H]1COc2c(-c3[nH]c4ncccc4c3-c3cn(C)nc3OC(F)F)c(C(F)F)nn2C1]

or a pharmaceutically acceptable salt thereof.

Embodiment 78. The compound of embodiment 1, wherein the compound is

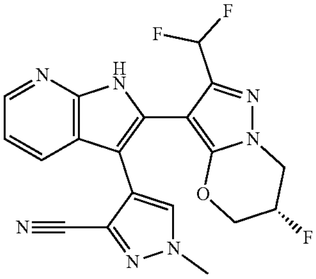 [SMILES: Cn1cc(-c2c(-c3c(C(F)F)nn4c3OC[C@@H](F)C4)[nH]c3ncccc23)c(C#N)n1]

or a pharmaceutically acceptable salt thereof.

Embodiment 79. The compound of embodiment 1, wherein the compound is

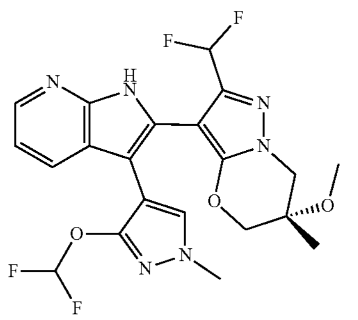 [SMILES: CO[C@]1(C)COc2c(-c3[nH]c4ncccc4c3-c3cn(C)nc3OC(F)F)c(C(F)F)nn2C1]

or a pharmaceutically acceptable salt thereof.

Embodiment 80. The compound of embodiment 1, wherein the compound is

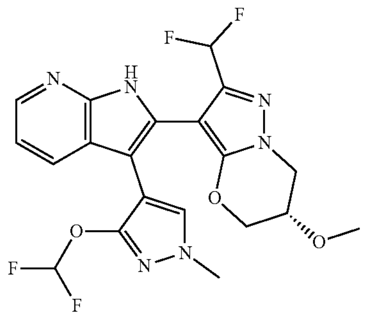 [SMILES: CO[C@@H]1COc2c(-c3[nH]c4ncccc4c3-c3cn(C)nc3OC(F)F)c(C(F)F)nn2C1]

or a pharmaceutically acceptable salt thereof.

Embodiment 81. The compound of embodiment 1, wherein the compound is

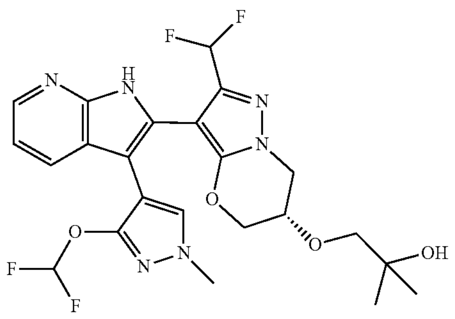 [SMILES: Cn1cc(-c2c(-c3c(C(F)F)nn4c3OC[C@@H](OCC(C)(C)O)C4)[nH]c3ncccc23)c(OC(F)F)n1]

or a pharmaceutically acceptable salt thereof.

Embodiment 82. The compound of embodiment 1, wherein the compound is

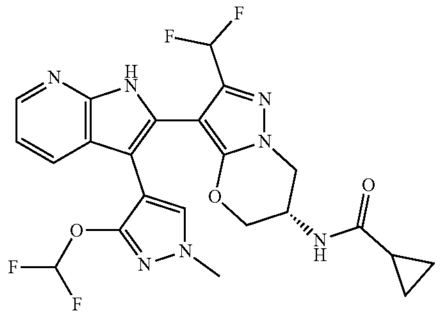 [SMILES: Cn1cc(-c2c(-c3c(C(F)F)nn4c3OC[C@@H](NC(=O)C3CC3)C4)[nH]c3ncccc23)c(OC(F)F)n1]

or a pharmaceutically acceptable salt thereof.

Embodiment 83. The compound of embodiment 1, wherein the compound is

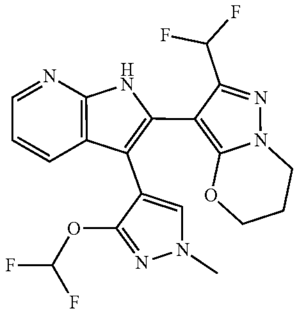 [SMILES: Cn1cc(-c2c(-c3c(C(F)F)nn4c3OCCC4)[nH]c3ncccc23)c(OC(F)F)n1]

or a pharmaceutically acceptable salt thereof.

Embodiment 84. The compound of embodiment 1, wherein the compound is

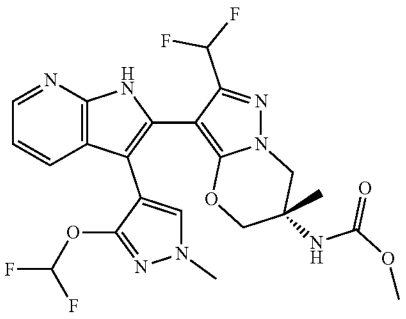 [SMILES: COC(=O)N[C@]1(C)COc2c(-c3[nH]c4ncccc4c3-c3cn(C)nc3OC(F)F)c(C(F)F)nn2C1]

or a pharmaceutically acceptable salt thereof.

Embodiment 85. The compound of embodiment 1, wherein the compound is

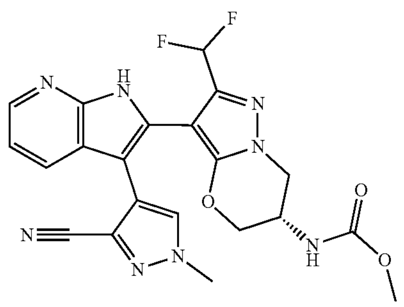 [SMILES: COC(=O)N[C@@H]1COc2c(-c3[nH]c4ncccc4c3-c3cn(C)nc3C#N)c(C(F)F)nn2C1]

or a pharmaceutically acceptable salt thereof.

Embodiment 86. The compound of embodiment 1, wherein the compound is

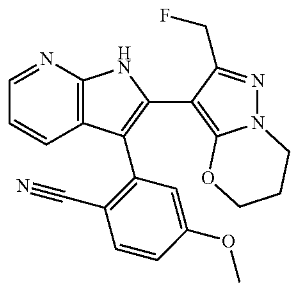 [SMILES: COc1ccc(C#N)c(-c2c(-c3c(CF)nn4c3OCCC4)[nH]c3ncccc23)c1]

or a pharmaceutically acceptable salt thereof.

Embodiment 87. The compound of embodiment 1, wherein the compound is

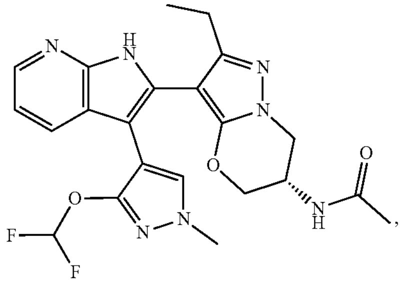 [SMILES: CCc1nn2c(c1-c1[nH]c3ncccc3c1-c1cn(C)nc1OC(F)F)OC[C@@H](NC(C)=O)C2]

or a pharmaceutically acceptable salt thereof.

Embodiment 88. The compound of embodiment 1, wherein the compound is

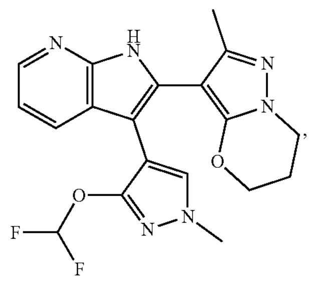 [SMILES: Cc1nn2c(c1-c1[nH]c3ncccc3c1-c1cn(C)nc1OC(F)F)OCCC2]

or a pharmaceutically acceptable salt thereof.

Embodiment 89. The compound of embodiment 1, wherein the compound is

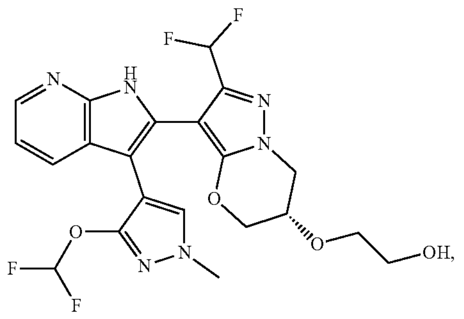 [SMILES: Cn1cc(-c2c(-c3c(C(F)F)nn4c3OC[C@@H](OCCO)C4)[nH]c3ncccc23)c(OC(F)F)n1]

or a pharmaceutically acceptable salt thereof.

Embodiment 90. A pharmaceutical composition, comprising a compound of any one of embodiments 1-89 and a pharmaceutically acceptable carrier.

Embodiment 91. The pharmaceutical composition of embodiment 90, wherein the pharmaceutical composition is formulated for the treatment of MRGPRX2-mediated disease or disorder.

Embodiment 92. The pharmaceutical composition of embodiment 91, wherein the MRGPRX2-mediated disease or disorder is selected from the group consisting of chronic spontaneous urticaria, chronic inducible urticaria, mastocytosis, atopic dermatitis, rosacea, Crohn's disease, ulcerative colitis, irritable bowel syndrome, rheumatoid arthritis, fibromyalgia, nasal polyps, neuropathic pain, inflammatory pain, chronic itch, drug-induced anaphylactoid reactions, metabolic syndrome, oesophagus reflux, asthma, cough, migraine, chronic pruritus, acute pruritus, prurigo nodularis, osteoarthritis, and pseudo anaphylaxis.

Embodiment 93. The pharmaceutical composition of embodiment 92, wherein the MRGPRX2-mediated disease or disorder is chronic spontaneous urticaria or chronic inducible urticaria.

Embodiment 94. The pharmaceutical composition of embodiment 93, wherein the chronic inducible urticaria is cold urticaria, cholinergic urticaria, heat urticaria, solar urticaria, symptomatic demographism urticaria, pressure urticaria, or contact urticaria.

Embodiment 95. The pharmaceutical composition of embodiment 92, wherein the chronic pruritus is chronic pruritus of unknown origin.

Embodiment 96. The pharmaceutical composition of embodiment 92, wherein the rosacea is papulopustular rosacea.

Embodiment 97. A method of treating an MRGPRX2-mediated disease or disorder, comprising administering to a patient in need thereof a therapeutically effective amount of a compound of any one of embodiments 1-89 or a pharmaceutically acceptable composition of embodiment 90.

Embodiment 98. The method of embodiment 96, wherein the MRGPRX2-mediated disease or disorder is selected from the group consisting of chronic spontaneous urticaria, chronic inducible urticaria, mastocytosis, atopic dermatitis, rosacea, Crohn's disease, ulcerative colitis, irritable bowel syndrome, rheumatoid arthritis, fibromyalgia, nasal polyps, neuropathic pain, inflammatory pain, chronic itch, drug-induced anaphylactoid reactions, metabolic syndrome, oesophagus reflux, asthma, cough, migraine, chronic pruritus, acute pruritus, prurigo nodularis, osteoarthritis, and pseudo anaphylaxis.

Embodiment 99. The method of embodiment 98, wherein the MRGPRX2-mediated disease or disorder is chronic spontaneous urticaria or chronic inducible urticaria.

Embodiment 100. The method of embodiment 99, wherein the chronic inducible urticaria is cold urticaria, cholinergic urticaria, heat urticaria, solar urticaria, symptomatic demographism urticaria, pressure urticaria, or contact urticaria.

Embodiment 101. The method of embodiment 98, wherein the chronic pruritus is chronic pruritus of unknown origin.

Embodiment 102. The method of embodiment 98, wherein the rosacea is papulopustular rosacea.

Embodiment 103. A compound of any one of embodiments 1-89 or a pharmaceutical composition of embodiment 90 for use in the treatment of an MRGPRX2-mediated disease or disorder.

Embodiment 104. The compound of embodiment 103, wherein the MRGPRX2-mediated disease or disorder is selected from the group consisting of chronic spontaneous urticaria, chronic inducible urticaria, mastocytosis, atopic dermatitis, rosacea, Crohn's disease, ulcerative colitis, irritable bowel syndrome, rheumatoid arthritis, fibromyalgia, nasal polyps, neuropathic pain, inflammatory pain, chronic itch, drug-induced anaphylactoid reactions, metabolic syndrome, oesophagus reflux, asthma, cough, migraine, chronic pruritus, acute pruritus, prurigo nodularis, osteoarthritis, and pseudo anaphylaxis.

Embodiment 105. The compound of embodiment 104, wherein the MRGPRX2-mediated disease or disorder is chronic spontaneous urticaria or chronic inducible urticaria.

Embodiment 106. The compound of embodiment 105, wherein the chronic inducible urticaria is cold urticaria, cholinergic urticaria, heat urticaria, solar urticaria, symptomatic demographism urticaria, pressure urticaria, or contact urticaria.

Embodiment 107. The compound of embodiment 104, wherein the chronic pruritus is chronic pruritus of unknown origin.

Embodiment 108. The compound of embodiment 104, wherein the rosacea is papulopustular rosacea.

Embodiment 109. Use of a compound of any one of embodiments 1-89 or a pharmaceutical composition of embodiment 90 in the manufacture of a medicament for use in the treatment of an MRGPRX2-mediated disease or disorder.

Embodiment 110. The use of embodiment 109, wherein the MRGPRX2-mediated disease or disorder is selected from the group consisting of chronic spontaneous urticaria, chronic inducible urticaria, mastocytosis, atopic dermatitis, rosacea, Crohn's disease, ulcerative colitis, irritable bowel syndrome, rheumatoid arthritis, fibromyalgia, nasal polyps, neuropathic pain, inflammatory pain, chronic itch, drug-induced anaphylactoid reactions, metabolic syndrome, oesophagus reflux, asthma, cough, migraine, chronic pruritus, acute pruritus, prurigo nodularis, osteoarthritis, and pseudo anaphylaxis.

Embodiment 111. The use of embodiment 110, wherein the MRGPRX2-mediated disease or disorder is chronic spontaneous urticaria or chronic inducible urticaria.

Embodiment 112. The use of embodiment 111, wherein the chronic inducible urticaria is cold urticaria, cholinergic urticaria, heat urticaria, solar urticaria, symptomatic demographism urticaria, pressure urticaria, or contact urticaria.

Embodiment 113. The use of embodiment 110, wherein the chronic pruritus is chronic pruritus of unknown origin.

Embodiment 114. The compound of embodiment 110, wherein the rosacea is papulopustular rosacea.

Embodiment 115. A compound of Formula (IIa), (IIa)

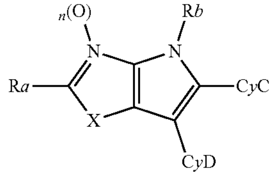

or a pharmaceutically acceptable salt thereof, wherein X is S, —CRd=CRe-, —CRd=N—, or —N=CRd-; Rd and Re are independently hydrogen, deuterium, halo, CN, $C_1$-$C_6$ alkyl, $C_1$-$C_6$ haloalkyl or $C_1$-$C_6$ alkoxy; Ra is hydrogen, halo, $C_1$-$C_6$ alkyl or $C_1$-$C_6$ alkoxy; Rb is hydrogen, $C_1$-$C_6$ alkyl, hydroxy-$C_1$-$C_6$ alkyl, $C_1$-$C_6$ alkoxy-$C_1$-$C_6$ alkyl, $C_1$-$C_6$ alkyl-carbonyl or $C_1$-$C_6$ alkoxy-carbonyl; CyC and CyD are independently $C_6$-$C_{10}$ aryl optionally having at least one substituent selected from a group W, heteroaryl optionally having at least one substituent selected from the group W, $C_3$-$C_8$ cycloalkyl optionally having at least one substituent selected from the group W, $C_3$-$C_8$ cycloalkenyl optionally having at least one substituent selected from the group W, heterocyclyl optionally having at least one substituent selected from the group W, fused heterocyclic ring consisting of 8 to 10 atoms optionally having at least one substituent selected from the group W, where the group W is deuterium, halo, $C_1$-$C_6$ alkyl optionally substituted with one or more deuterium, $C_1$-$C_6$ haloalkyl, $C_1$-$C_6$ alkoxy optionally substituted with one or more deuterium, $C_1$-$C_6$ haloalkoxy, $C_2$-$C_6$ alkenyl, hydroxyl, $C_1$-$C_6$ hydroxyalkyl, $C_1$-$C_6$ hydroxyalkoxy, carboxy-$C_1$-$C_6$ alkyl, amino optionally having at least one $C_1$-$C_3$ alkyl or hydroxy-$C_1$-$C_3$ alkyl, $NO_2$, CN, $CONH_2$, aminocarbonyl substituted with at least one $C_1$-$C_6$ alkyl, oxo, $C_1$-$C_6$ alkyl-carbonyl, $C_1$-$C_6$ alkoxy-carbonyl, aminocarbonyloxy substituted with at least one $C_1$-$C_6$ alkyl, $C_1$-$C_6$ alkyl-carbonylamino, hydroxy-$C_1$-$C_6$ alkyl-carbonylamino, hydroxy-$C_1$-$C_6$ alkyl-carbonyl-N-methylamino, hydroxy-$C_1$-$C_6$ alkyl-N-methyl-amino-carbonylamino, $C_3$-$C_8$ cycloalkyl-carbonylamino, $C_1$-$C_6$ alkoxy-carbonylamino, heterocycloxy-carbonylamino, hydroxy heterocyclo-carbonylamino, heteroaryl-carbonylamino, $C_1$-$C_6$ alkyl-heteroaryl-carbonylamino, $C_1$-$C_6$ alkyl-carbonyl-N-methylamino, $C_1$-$C_6$ alkoxy-carbonyl-N-methyl-amino, $C_1$-$C_6$ alkyl-sulfonylamino, hydroxy-$C_1$-$C_6$ alkyl-sulfonylamino, $C_3$-$C_8$ cycloalkyl-sulfonylamino, $C_1$-$C_6$ alkyl-$C_3$-$C_8$ cycloalkyl-sulfonylamino, N,N-dimethylaminosulfonyl amino, $C_1$-$C_6$ alkylsulfanyl, $C_1$-$C_6$ alkylsulfinyl, $C_1$-$C_6$ alkylsulfonyl, $C_1$-$C_6$ alkylaminosulfonyl, $C_1$-$C_6$ alkylsulfinyl-$C_1$-$C_6$ alkyl, $C_1$-$C_6$ alkylsulfonyl-$C_1$-$C_6$ alkyl, $C_3$-$C_8$ cycloalkyl, $C_3$-$C_8$ cycloalkyl-$C_1$-$C_3$ alkoxy, $C_1$-$C_3$ alkoxy-$C_1$-$C_3$ alkyl, $C_1$-$C_3$ alkoxy-$C_1$-$C_3$alkoxy-$C_1$-$C_3$ alkyl, $C_1$-$C_3$ alkoxy-carbonyl-$C_1$-$C_3$ alkyl, phenyl-$C_1$-$C_6$ alkoxy, $C_1$-$C_6$ alkoxy-carbonyl-$C_1$-$C_6$ alkoxy, amino-carbonyl-$C_1$-$C_6$ alkoxy, $C_1$-$C_6$ alkoxy-$C_1$-$C_6$ alkoxy, $C_1$-$C_6$ alkylsulfonylamino-$C_1$-$C_6$ alkoxy, $C_1$-$C_6$ alkyl-carbonylamino-$C_1$-$C_6$ alkoxy, N,N-dimethylamino-$C_1$-$C_6$ alkoxy, N-methylamino-carbonyl-$C_1$-$C_6$ alkyl, N,N-dimethylaminocarbonyl-$C_1$-$C_6$ alkyl, heterocyclyl optionally substituted with one or more oxo group, heterocyclyl-$C_1$-$C_3$ alkyl, ureido, or a spiro ring, where $C_3$-$C_8$ cycloalkyl of $C_3$-$C_8$ cycloalky-carbonylamino may be substituted by one or more substituents selected from a halogen atom, a hydroxy group, a cyano group, a $C_1$-$C_6$ alkyl, and an aminocarboxyl group, where $C_1$-$C_6$ alkoxy of $C_1$-$C_6$ alkoxy-carbonylamino may be substituted by one or more substituents selected from a hydroxy group, an amino group, a N-methylamino group, an amino-carbonyl group, a N-methylamino-carbonyl group, and oxo group, where ureido may be substituted by one or more substituents selected from a $C_1$-$C_6$ alkyl and a hydroxy-$C_1$-$C_6$ alkyl group; and n is 0 or 1.

Embodiment 116. The compound or a pharmaceutically acceptable salt thereof according to embodiment 115, wherein the Formula (IIa) is selected from the group consisting of Formulas (IIb), (IIc), (IId) and (IIe), (IIb)

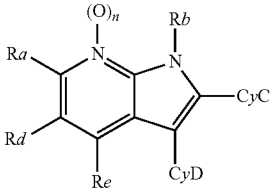

(IIc)

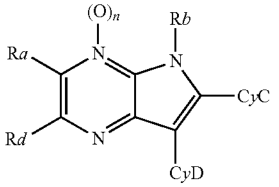

(IId)

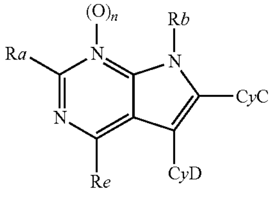

(IIe)

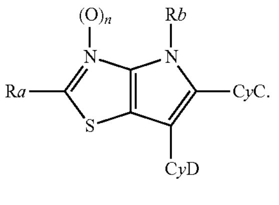

Embodiment 117. The compound or a pharmaceutically acceptable salt thereof according to embodiment 115 or 116, wherein CyC is fused non-aromatic heterocyclyl-aryl optionally having at least one substituent selected from the group W, fused non-aromatic heterocyclyl-heteroaryl optionally having at least one substituent selected from the group W, fused arylheteroaryl optionally having at least one substituent selected from the group W, or fused heteroaryl-heteroaryl optionally having at least one substituent selected from the group W, wherein the group W is halo, $C_3$-$C_8$ cycloalkyl-carbonylamino, $C_1$-$C_6$ alkyl, $C_1$-$C_6$ haloalkyl, $C_1$-$C_6$ alkoxy, $C_1$-$C_6$ haloalkoxy, hydroxyl, $C_1$-$C_6$ hydroxyalkyl, $C_1$-$C_6$ hydroxyalkoxy, carboxy-$C_{1-6}$ alkyl, amino optionally having at least one $C_{1-3}$ alkyl, $NO_2$, CN, $CONH_2$, aminocarbonyl substituted with at least one $C_1$-$C_6$ alkyl, oxo, $C_1$-$C_6$ alkyl-carbonyl, $C_1$-$C_6$ alkoxy-carbonyl, $C_1$-$C_6$ alkyl-carbonylamino, $C_1$-$C_6$ alkoxy-carbonylamino, $C_1$-$C_6$ alkyl-carbonyl-N-methylamino, $C_1$-$C_6$ alkoxy-carbonyl-N-methylamino, $C_3$-$C_8$ cyloalkyl, $C_3$-$C_8$ cyloalkyl-$C_1$-$C_3$ alkoxy, $C_1$-$C_3$ alkoxy-$C_1$-$C_3$ alkyl, $C_1$-$C_3$ alkoxy-$C_1$-$C_3$-alkoxy-$C_1$-$C_3$ alkyl, $C_1$-$C_3$ alkoxy-carbonyl-$C_1$-$C_3$ alkyl, phenyl-$C_1$-$C_6$ alkoxy, $C_1$-$C_3$ alkoxy-carbonyl-$C_1$-$C_3$ alkyl, N-methylamino-carbonyl-$C_1$-$C_6$ alkyl, N,N-dimethylaminocarbonyl-$C_1$-$C_6$ alkyl, heterocyclyl, heterocyclyl-$C_1$-$C_3$ alkyl or a spiro ring.

Embodiment 118. The compound or a pharmaceutically acceptable salt thereof according to embodiment 115 or 116, wherein CyC is selected from the group consisting of

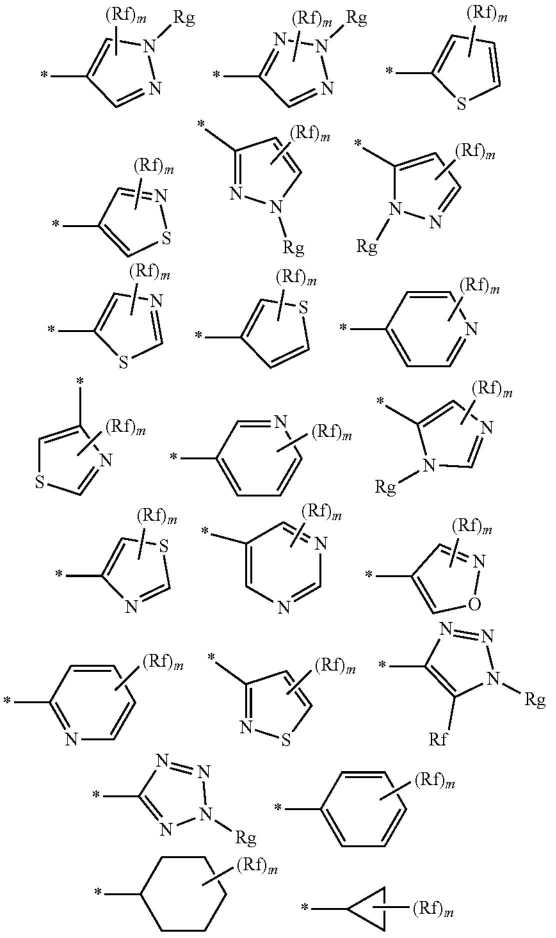

-continued

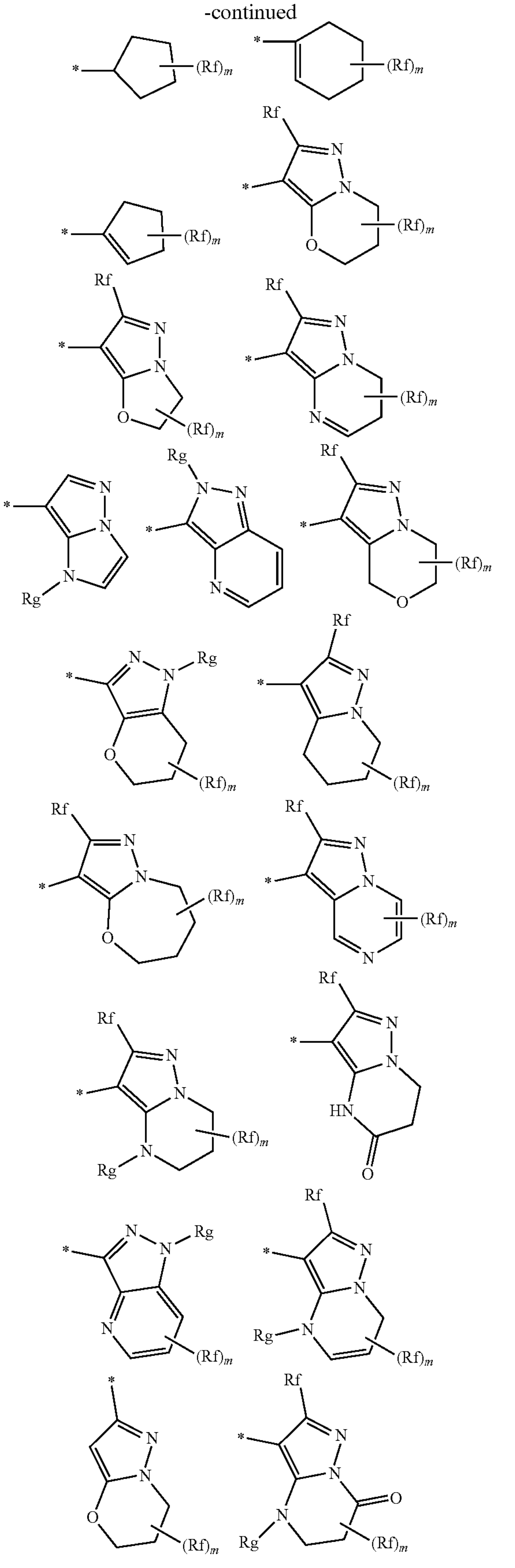

wherein each $R^f$ is independently hydrogen, halo, $C_3$-$C_8$ cycloalkyl-carbonylamino, $C_1$-$C_6$ alkyl, $C_1$-$C_6$ haloalkyl, $C_1$-$C_6$ alkoxy, $C_1$-$C_6$ haloalkoxy, hydroxyl, $C_1$-$C_6$ hydroxyalkyl, $C_1$-$C_6$ hydroxyalkoxy, carboxy-$C_{1-6}$ alkyl, amino optionally having at least one $C_{1-3}$ alkyl, $NO_2$, CN, $CONH_2$, oxo, $C_1$-$C_6$ alkyl-carbonyl, $C_1$-$C_6$ alkoxy-carbonyl, $C_1$-$C_6$ alkyl-carbonylamino, $C_1$-$C_6$ alkoxy-carbonylamino, $C_1$-$C_6$ alkyl-carbonyl-N-methylamino, $C_1$-$C_6$ alkoxy-carbonyl-N-methylamino, $C_3$-$C_8$ cycloalkyl, $C_3$-$C_8$ cycloalkyl-$C_1$-$C_3$ alkoxy, $C_1$-$C_3$ alkoxy-$C_1$-$C_3$ alkyl, $C_1$-$C_3$ alkoxy-$C_1$-$C_3$-alkoxy-$C_1$-$C_3$ alkyl, $C_1$-$C_3$ alkoxy-carbonyl-$C_1$-$C_3$ alkyl, or phenyl-$C_1$-$C_6$ alkoxy or two Rf are taken together with the carbon atom to which they are attached to form a spiro ring; Rg is hydrogen, $C_1$-$C_6$ alkyl, $C_1$-$C_6$ haloalkyl, carboxy-$C_1$-$C_6$ alkyl, amino optionally having at least one $C_1$-$C_3$ alkyl, $C_1$-$C_3$ alkoxy-$C_1$-$C_3$ alkyl, $C_1$-$C_3$ alkoxy-carbonyl-$C_1$-$C_3$ alkyl, carboxy-$C_1$-$C_6$ alkyl, N-methylamino-carbonyl-$C_1$-$C_6$ alkyl, N,N-dimethylaminocarbonyl-$C_1$-$C_6$ alkyl, heterocyclyl or heterocyclyl-$C_1$-$C_3$ alkyl; m is an integer of 0 to 5; and asterisks denote the points of attachment.

Embodiment 119. The compound or a pharmaceutically acceptable salt thereof according to embodiment 115 or 116, wherein CyD is $C_6$-$C_{10}$ aryl optionally having at least one substituent selected from the group W, or heteroaryl optionally having at least one substituent selected from the group W, and the group W is halo, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, hydroxyl, $C_1$-$C_6$ hydroxyalkyl, amino optionally having at least one $C_1$-$C_3$ alkyl, CN, oxo, $C_1$-$C_6$ alkylsulfanyl, $C_1$-$C_6$ alkylsulfinyl, $C_1$-$C_6$ alkylsulfonyl, $C_1$-$C_6$ alkoxy-carbonylamino, $C_1$-$C_6$ hydroxyalkoxy, $C_3$-$C_8$ cycloalkyl-carbonylamino, or $C_3$-$C_8$ cycloalkyl.

Embodiment 120. The compound or a pharmaceutically acceptable salt thereof according to embodiment 115, 116 or 118, wherein CyD is selected from the group consisting of

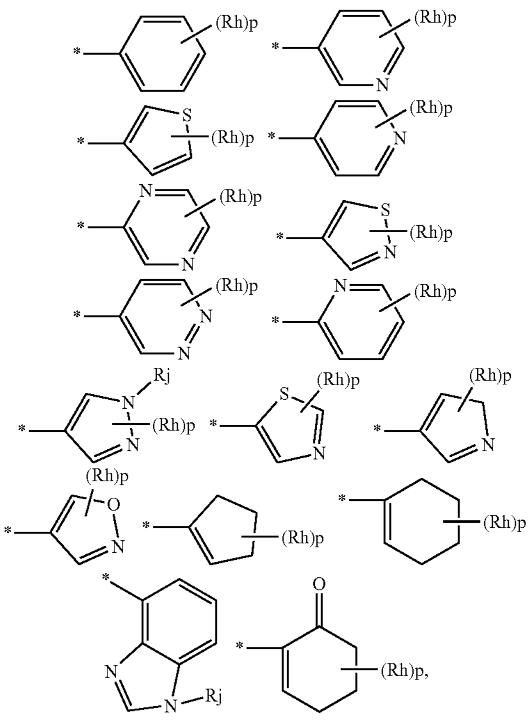

wherein each Rh is independently halo, $C_1$-$C_6$ alkyl, $C_1$-$C_6$ haloalkyl, $C_1$-$C_6$ alkoxy, $C_1$-$C_6$ haloalkoxy, $C_2$-$C_6$ alkenyl, hydroxyl, $C_1$-$C_6$ hydroxyalkyl, amino optionally having at least one $C_1$-$C_3$ alkyl, CN, oxo, $C_1$-$C_6$ alkylsulfonyl, or $C_3$-$C_8$ cycloalkyl; Rj is hydrogen, $C_1$-$C_6$ alkyl, or $C_1$-$C_6$ haloalkyl;

p is an integer of 0 to 5; and asterisks denote the points of attachment.

Embodiment 121. The compound or a pharmaceutically acceptable salt thereof according to embodiment 115 or 120, wherein the Formula (IIa) is Formula (IIb)

(IIb)

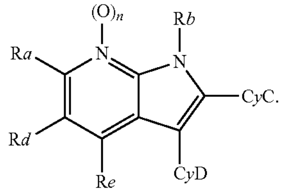

Embodiment 122. The compound or a pharmaceutically acceptable salt thereof according to embodiment 121, wherein Ra, Rb, Rd and Re are hydrogens; and n is 0.

Embodiment 123. The compound or a pharmaceutically acceptable salt thereof according to embodiment 122, wherein CyD is phenyl optionally having at least one substituent selected from the group W, pyridyl optionally having at least one substituent selected from the group W, or pyrazolyl optionally having at least one substituent selected from the group W.

(1) General Procedure 1

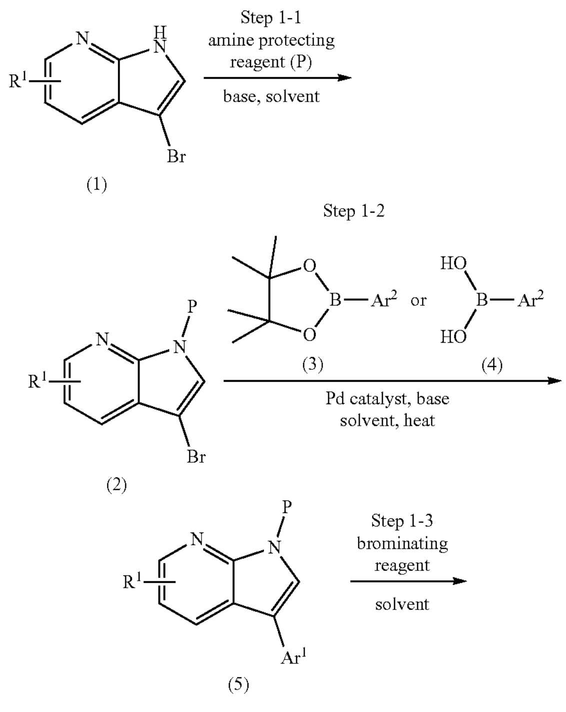

-continued

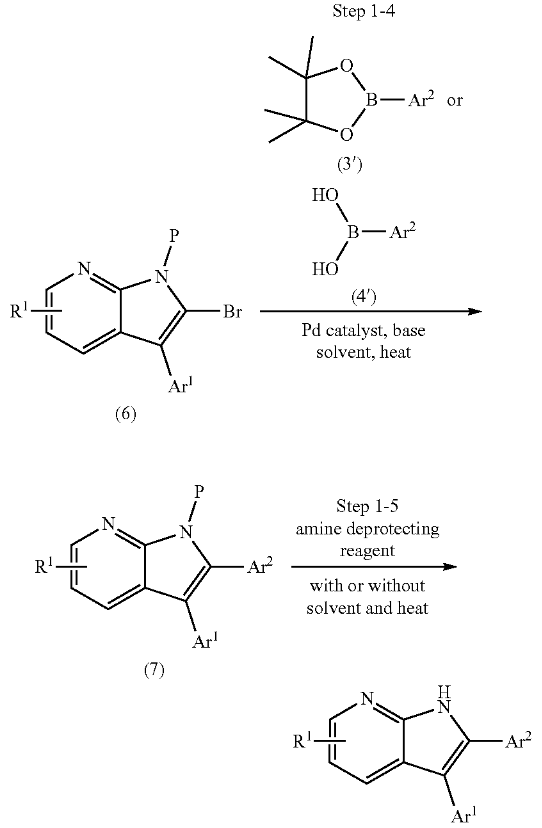

$R^1$ = H, OME, F, Cl
$Ar^1$, $Ar^2$ = aryl optionally stubstituted, heteroaryl optionally substituted etc.
P = Boc, SEM Step 1-1

This step is a step of protecting 1H—N of the 7-azaindole compound (1) to produce the compound (2) by the reaction with an amine protecting agent in a solvent in the presence of a base. The amine protecting reagents used may include di-tert-butyl dicarbonate ($Boc_2O$), 2-(trimethylsilyl) ethoxymethyl chloride (SEM-Cl), fluorenlmethyloxycarbonyl chloride (Fmoc-Cl), benzyl chloroformate (Cbz-Cl), benzyl chloride (BnCl) and the like. The base used may include triethylamine (TEA), N,N-diisopropylethylamine (DIPEA), 4-dimethylaminopyridine (DMAP), sodium hydride (NaH) and the like. The amount of the amine protecting agent used is about 1.1 to 1.5 molar equivalents with respect to 1 mole of the compound (1). The amount of the base used is about 1 to 2 molar equivalents with respect to 1 mole of the compound (1). The reaction can be usually performed at room temperature in the solvent such as DMF, THF and the like. The reaction time varies depending on the starting materials, the amine protecting agent, the base and the solvent used.

Step 1-2

This step is a step of reacting the compound (2) with a pinacol boronic ester as compound (3) or a boronic acid as compound (4) to produce the compound (5) using a palladium catalyst in the presence of a base in mixed solvents such as 1,4-dioxane and water. The palladium catalyst used may include dichloro[1,1'-bis(diphenylphosphino)ferrocene]palladium(II)-DCM adduct ($Pd(dppf)Cl_2$-DCM), tris (dibenzylideneacetone)dipalladium(0) ($Pd_2(dba)_3$) with 2-dicyclohexylphosphino-2',4',6'-triisopropylbiphenyl (XPhos), tetrakis(triphenylphosphine)palladium (0) (Pd $(PPh_3)_4$) and the like. Examples of base may include cesium carbonate ($Cs_2CO_3$), potassium carbonate ($K_2CO_3$) and the like. The amount of compound (3) or (4) used is about 1 to 2 molar equivalents with respect to 1 mole of the compound (2). The reaction can be usually performed at 70° C. to the reflux temperature of the solvent, and usually goes to completion in 1-2 hours.

Step 1-3

This step is a step of bromination at 2-position of 7-azaindole (5) to produce the compound (6) using a brominating agent such as N-bromosuccinimide (NBS) and/or bromine ($Br_2$). The reaction can be usually performed at room temperature in a solvent such as DCM, DCE and the like. The amount of the brominating agent used is usually about 1 to 5 molar equivalents with respect to 1 mole of the compound (5). The reaction time varies depending on the starting materials, the brominating agent and the solvent used.

Step 1-4

This step is a step of reacting the compound (6) with a pinacol boronic ester as compound (3') or a boronic acid as compound (4') to produce the compound (7) using a palladium catalyst in the presence of a base in mixed solvents such as 1,4-dioxane and water. The palladium catalyst used may include $Pd(dppf)Cl_2$-DCM, $Pd_2(dba)_3$ with XPhos, $Pd(PPh_3)_4$ and the like. Examples of base may include $Cs_2CO_3$, $K_2CO_3$ and the like. The amount of compound (3') or (4') used is about 1 to 2 molar equivalents with respect to 1 mole of the compound (6). The reaction can be usually performed at 70° C. to the reflux temperature of the solvent, and usually goes to completion in 1-2 hours.

Step 1-5

This step is a step of deprotecting amine of the compound (7) to produce the final compound by the reaction with an amine deprotecting agent. The amine deprotecting agent can be acid with or without base such as trifluoroacetic acid (TFA), hydrochloric acid (HCl) with or without ethylene diamine, ammonium hydroxide ($NH_4OH$), ammonia ($NH_3$) and the like depending on the protecting groups. The reaction can be usually performed at room temperature to 50° C. with or without a solvent such as MeOH, 1,4-dioxane and water. The reaction time varies depending on the substrate, acid/base and reaction temperature.

(2) General Procedure 2

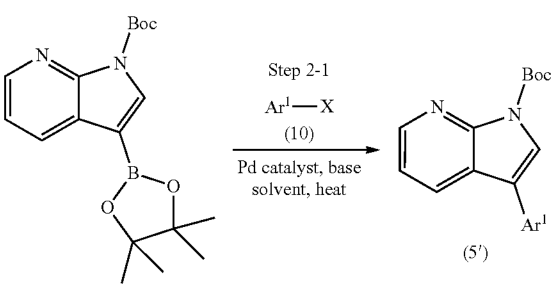

(9)

(5')

$Ar^1$, $Ar^2$ = aryl optionally substituted, heteroaryl optionally substituted, etc X = Br, I Step 2-1

This step is a step of reacting the compound (9) with an aryl halide or a heteroaryl halide compound (10) to produce the compound (5') using a palladium catalyst in the presence of a base in mixed solvents such as 1,4-dioxane and water. The palladium catalyst used may include $Pd(dppf)Cl_2$-DCM, $Pd_2(dba)_3$ with XPhos, $Pd(PPh_3)_4$ and the like. Examples of base may include $Cs_2CO_3$, $K_2CO_3$ and the like. The amount of compound (10) used is about 1 to 2 molar equivalents with respect to 1 mole of the compound (9). The reaction can be usually performed at 80° C. to the reflux temperature of the solvent, and usually goes to completion in 1-2 hours.

(3) General Procedure 3

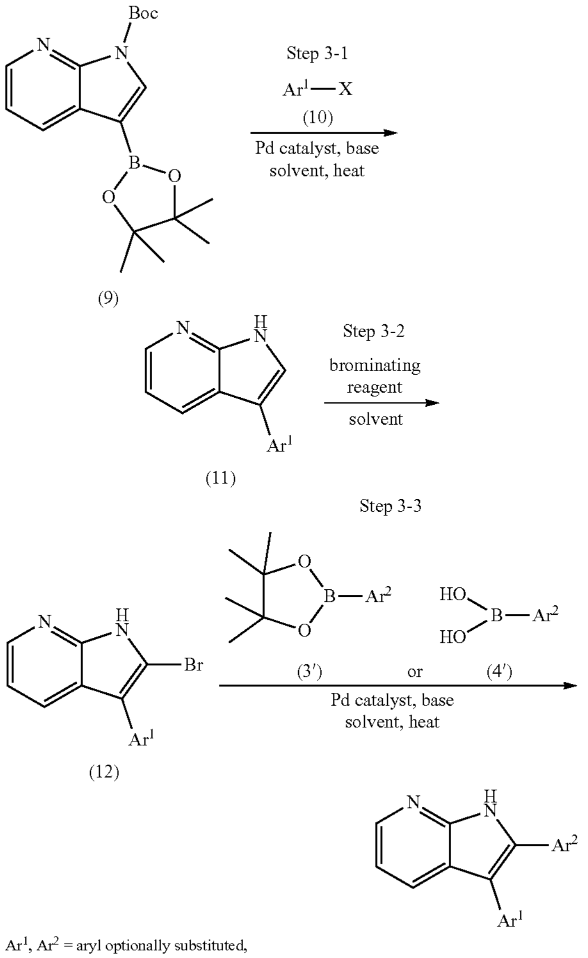

(9)

(11)

(12)

$Ar^1$, $Ar^2$ = aryl optionally substituted, heteroaryl optionally substituted, etc Step 3-1

This step is a step of reacting the compound (9) with an aryl halide or heteroaryl halide compound (10) to produce the compound (11) using a palladium catalyst in the presence of a base in mixed solvents such as 1,4-dioxane and water. The palladium catalyst used may include dichloro[1, 1'-bis(diphenylphosphino)ferrocene]palladium(II)-DCM adduct ($Pd(dppf)Cl_2$-DCM), tris(dibenzylideneacetone)dipalladium(0) ($Pd_2(dba)_3$) with 2-dicyclohexylphosphino-2',4',6'-triisopropylbiphenyl (XPhos), tetrakis(triphenylphosphine)palladium (0) ($Pd(PPh_3)_4$) and the like. Examples of base may include cesium carbonate ($Cs_2CO_3$), potassium carbonate ($K_2CO_3$) and the like. The amount of compound (10) used is about 1 to 2 molar equivalents with respect to 1 mole of the compound (9). The reaction can be usually performed at 80° C. to the reflux temperature of the solvent, and usually goes to completion in 1-2 hours.

Step 3-2

This step is a step of bromination at 2-position of 7-azaindole (11) to produce the compound (12) using a brominating agent such as N-bromosuccinimide (NBS) and/or bromine ($Br_2$). The reaction can be usually performed at room temperature in a solvent such as DCM, DCE and the like. The amount of the brominating agent used is usually about 1 to 5 molar equivalents with respect to 1 mole of the compound (11). The reaction time varies depending on the starting materials, the brominating agent and the solvent used.

Step 3-3

This step is a step of reacting the compound (12) with a pinacol boronic ester as compound (3') or a boronic acid as compound (4') to produce the final compound using a palladium catalyst in the presence of a base in mixed solvents such as 1, 4-dioxane and water. The palladium catalyst used may include Pd(dppf)$Cl_2$-DCM, $Pd_2(dba)_3$) with XPhos, $Pd(PPh_3)_4$ and the like. Examples of base may include $Cs_2CO_3$, $K_2CO_3$ and the like. The amount of compound (3') or (4') used is about 1 to 2 molar equivalents with respect to 1 mole of the compound (12). The reaction can be usually performed at 80° C. to the reflux temperature of the solvent, and usually goes to completion in 1-2 hours.

(4) General Procedure 4

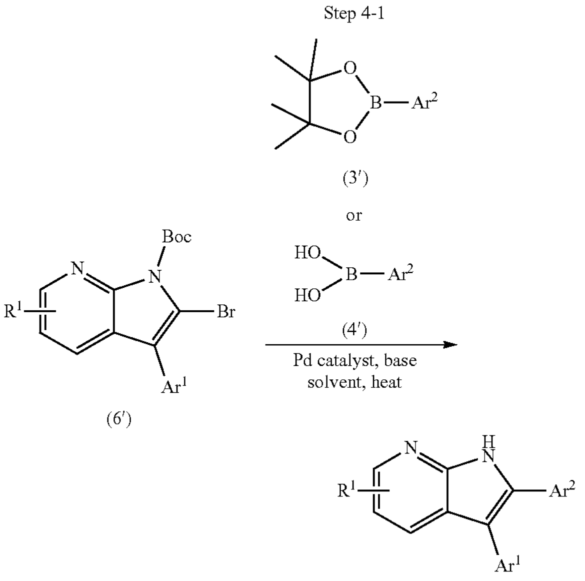

(3')

(4')

(6')

$R^1$ = OMe, Me, F
$Ar^1$, $Ar^2$ = aryl optionally substituted, heteroaryl optionally substituted, etc Step 4-1

This step is a step of reacting the compound (6') with a pinacol boronic ester as compound (3') or a boronic acid as compound (4') to produce the final compound using a palladium catalyst in the presence of a base in mixed solvents such as 1,4-dioxane and water. The palladium catalyst used may include Pd(dppf)$Cl_2$-DCM, $Pd_2(dba)_3$ with XPhos, $Pd(PPh_3)_4$ and the like. Examples of base may include $Cs_2CO_3$, $K_2CO_3$ and the like. The amount of compound (3') or (4') used is about 1 to 2 molar equivalents with respect to 1 mole of the compound (6'). The reaction can be usually performed at 80° C. to the reflux temperature of the solvent, and usually goes to completion in 1-2 hours.

(5) General Procedure 5

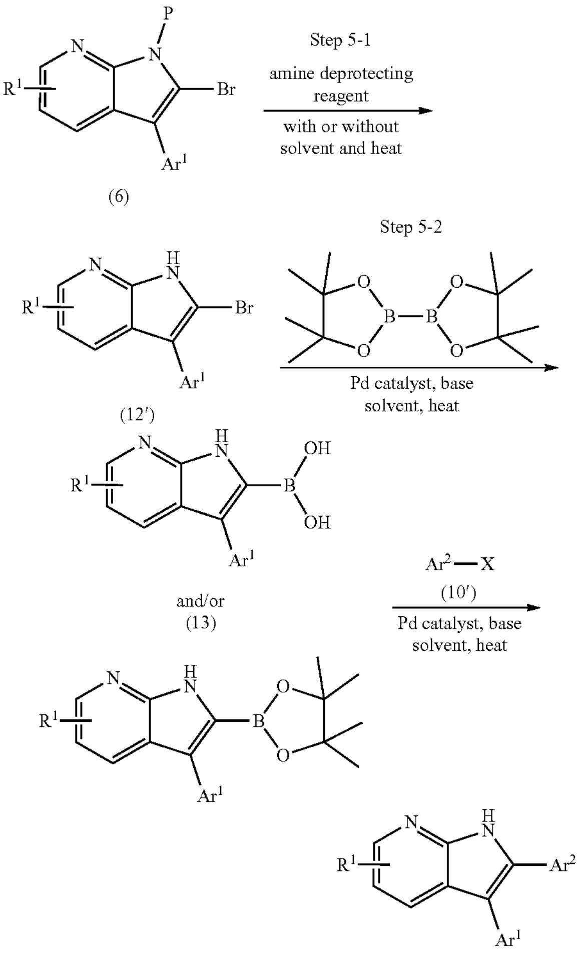

(6)

(12')

and/or (13)

$R^1$ = OME, Me, F, H
$Ar^1$, $Ar^2$ = aryl optionally substituted, heteroaryl optionally substituted, etc
X = Br, I
P = Boc, SEM Step 5-1

This step is a step of deprotecting amine of the compound (6) to produce the compound (12') by the reaction with an amine deprotecting agent. The amine deprotecting agent can be acid with or without base such as TFA, HCl with or without ethylene diamine, $NH_4OH$, $NH_3$ and the like depending on the protecting groups. The reaction can be usually performed at room temperature to 50° C. with or without a solvent such as MeOH, 1,4-dioxane, and water. The reaction time varies depending on the substrate, acid/base and reaction temperature.

Step 5-2

This step is a step of reacting the compound (12') with bis(pinacolato)diboron in a solvent to produce the compound (13) using a palladium catalyst in the presence of a base such as potassium acetate (KOAc). Examples of palladium catalyst used may include Pd(dppf)$Cl_2$ and the like. Examples of solvent used may include 1,4-dioxane, toluene and the like. The amount of bis(pinacolato)diboron used is usually about 1 to 2 molar equivalents with respect to 1 mole of the compound (12'). The reaction can be usually performed at 90° C. to the reflux temperature of the solvent. The reaction time varies depending on the starting material, the catalyst system, the base, the solvent, and the reaction temperature used.

Step 5-3

This step is a step of reacting the compound (13) with an aryl halide or a heteroaryl halide compound (10') to produce the final compound. The final compound can be produced by reacting the boronic acid compound (13) with the aryl halide or heteroaryl halide compound (10') using a palladium catalyst in the presence of a base in mixed solvents such as 1,4-dioxane and water. The palladium catalyst used may include Pd(dppf)$Cl_2$-DCM, $Pd_2(dba)_3$ with XPhos, $Pd(PPh_3)_4$ and the like. Examples of base may include $Cs_2CO_3$, $K_2CO_3$ and the like. The amount of compound (10') used is about 1 to 2 molar equivalents with respect to 1 mole of the compound (13). The reaction can be usually performed at 60° C. to the reflux temperature of the solvent, and usually goes to completion in 1-2 hours.

(6) General Procedure 6

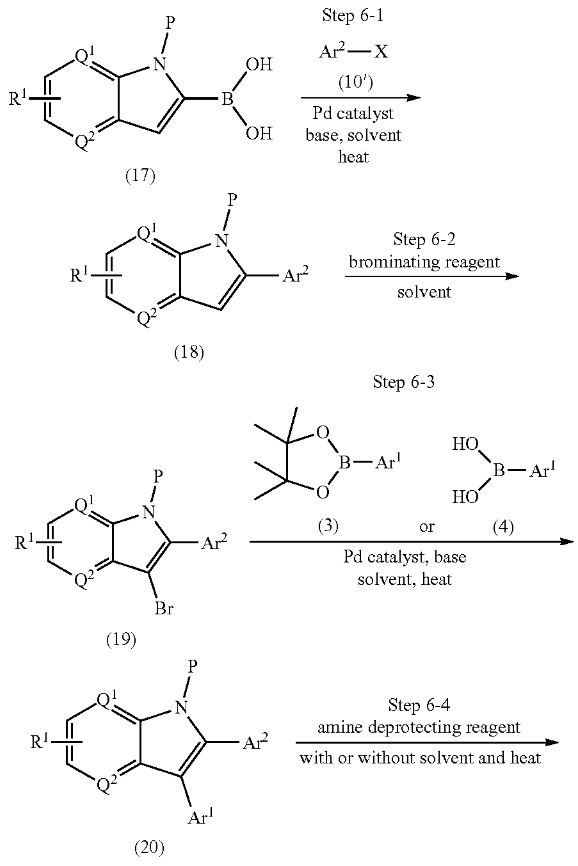

-continued

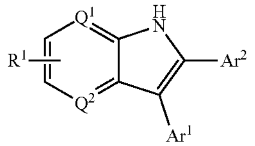

$Q^1$, $Q^2$ = C(R), N
$R^1$ = H, F, CN
$Ar^1$, $Ar^2$ = aryl optionally substituted, heteroaryl optionally substituted, etc
P = Boc, SEM Step 6-1

This step is a step of reacting the boronic acid compound (17) with the aryl halide or heteroaryl halide compound (10') to produce the compound (18). The compound (18) can be produced by reacting the boronic acid compound (17) with aryl halide or heteroaryl halide compound (10') using a palladium catalyst in the presence of a base in mixed solvents such as 1,4-dioxane and water. The palladium catalyst used may include Pd(dppf)$Cl_2$-DCM, $Pd_2(dba)_3$ with XPhos, $Pd(PPh_3)_4$ and the like. Examples of base may include $Cs_2CO_3$, $K_2CO_3$ and the like. The amount of compound (10') used is about 1 to 2 molar equivalents with respect to 1 mole of the compound (17). The reaction can be usually performed at 80° C. to the reflux temperature of the solvent, and usually goes to completion in 1-2 hours.

Step 6-2

This step is a step of bromination at 3-position of the compound (18) to produce the compound (19) using a brominating agent such as NBS and/or $Br_2$. The reaction can be usually performed at room temperature in a solvent such as DCM, DCE and the like. The amount of the brominating agent used is usually about 1 to 5 molar equivalents with respect to 1 mole of the compound (18). The reaction time varies depending on the starting materials, the brominating agent and the solvent used.

Step 6-3

This step is a step of reacting the compound (19) with a pinacol boronic ester as compound (3) or a boronic acid as compound (4) to produce the compound (20) using a palladium catalyst in the presence of a base in mixed solvents such as 1,4-dioxane and water. The palladium catalyst used may include Pd(dppf)$Cl_2$-DCM, $Pd_2(dba)_3$ with XPhos, $Pd(PPh_3)_4$ and the like. Examples of base may include $Cs_2CO_3$, $K_2CO_3$ and the like. The amount of compound (3) or (4) used is about 1 to 2 molar equivalents with respect to 1 mole of the compound (19). The reaction can be usually performed at 80° C. to the reflux temperature of the solvent, and usually goes to completion in 1-2 hours.

Step 6-4

This step is a step of deprotecting amine of the compound (20) to produce the final compound by the reaction with an amine deprotecting agent. The amine deprotecting agent can be acid with or without base such as TFA, HCl with or without ethylene diamine, $NH_4OH$, $NH_3$ and the like depending on the protecting groups. The reaction can be usually performed at room temperature to 50° C. with or without a solvent such as MeOH, 1,4-dioxane and water. The reaction time varies depending on the substrate, acid/base and reaction temperature.

(7) General Procedure 7

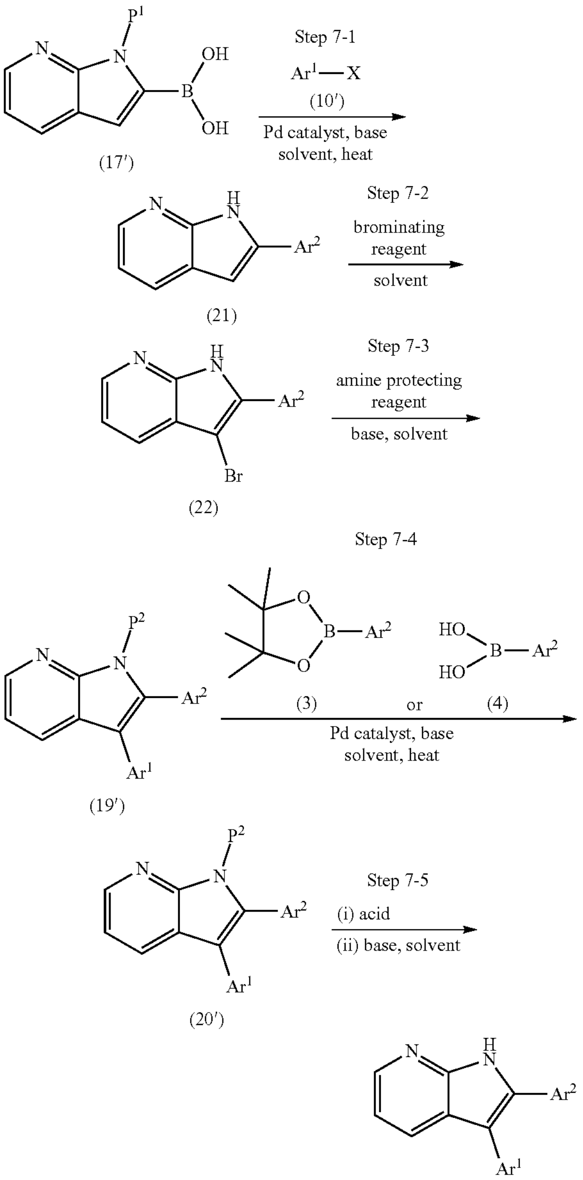

$P^1$ = Boc
$P^2$ = SEM
$Ar^1$, $Ar^2$ = aryl optionally substituted, heteroaryl optionally substituted, etc Step 7-1

This step is a step of reacting the boronic acid compound (17') with the compound (10') to produce the compound (21). The compound (21) can be produced by reacting the boronic acid compound (17') with aryl halide or heteroaryl halide compound (10') using a palladium catalyst in the presence of a base in mixed solvents such as 1, 4-dioxane and water. The palladium catalyst used may include $Pd(dppf)Cl_2$-DCM, $Pd_2(dba)_3$ with XPhos, $Pd(PPh_3)_4$ and the like. Examples of base may include $Cs_2CO_3$, $K_2CO_3$ and the like. The amount of compound (10') used is about 1 to 2 molar equivalents with respect to 1 mole of the compound (17'). The reaction can be usually performed at 80° C. to the reflux temperature of the solvent, and usually goes to completion in 1-2 hours.

Step 7-2

This step is a step of bromination at 3-position of the compound (21) to produce the compound (22) using a brominating agent such as NBS and/or $Br_2$. The reaction can be usually performed at room temperature in a solvent such as DCM, DCE and the like. The amount of the brominating agent used is usually about 1 to 5 molar equivalents with respect to 1 mole of the compound (21). The reaction time varies depending on the starting materials, the brominating agent and the solvent used.

Step 7-3

This step is a step of protecting 1H—N of the 7-azaindole compound (22) to produce the compound (19') by the reaction with an amine protecting agent such as SEM-$C_1$ in a solvent in the presence of a base such as NaH. The amount of SEM-$C_1$ used is about 1.1 to 1.5 molar equivalents with respect to 1 mole of the compound (22). The amount of NaH is about 1 to 2 molar equivalents with respect to 1 mole of the compound (22). The reaction can be usually performed at room temperature in the solvent such as DMF and the like. The reaction usually goes to completion in 1-2 hours.

Step 7-4

This step is a step of reacting the compound (19') with a pinacol boronic ester as compound (3) or a boronic acid as compound (4) to produce the compound (20') using a palladium catalyst in the presence of a base in mixed solvents such as 1,4-dioxane and water. The palladium catalyst used may include $Pd(dppf)Cl_2$-DCM, $Pd_2(dba)_3$ with XPhos, $Pd(PPh_3)_4$ and the like. Examples of base may include $Cs_2CO_3$, $K_2CO_3$ and the like. The amount of compound (3) or (4) used is about 1 to 2 molar equivalents with respect to 1 mole of the compound (19'). The reaction can be usually performed at 80° C. to the reflux temperature of the solvent, and usually goes to completion in 1-2 hours.

Step 7-5

This step is a step of deprotecting amine of the compound (20') to produce the final compound by the reaction with an amine deprotecting agent. The amine deprotecting agent can be an acid such as TFA, HCl followed by treating with a base such as ethylene diamine, $NH_4OH$, $NH_3$ and the like. The reaction can be usually performed at room temperature to 50° C. with or without a solvent such as MeOH, 1,4-dioxane and water. The reaction time varies depending on the substrate, acid/base and reaction temperature.

(8) General Procedure 8

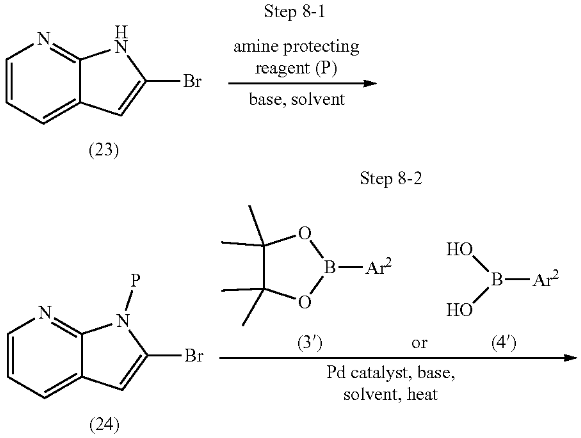

-continued

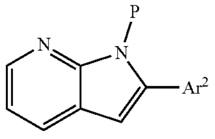

(18')

Step 8-1

This step is a step of protecting 1H-amine of 2-bromo-7-azaindole (23) to produce the compound (24) by the reaction with an amine protecting agent in a solvent in the presence of a base. The amine protecting agents used may include $Boc_2O$, SEM-Cl, Fmoc-Cl, Cbz-Cl, BnCl and the like. The base used may include TEA, DIPEA, DMAP, NaH and the like. The amount of the amine protecting agent used is about 1.1 to 1.5 molar equivalents with respect to 1 mole of the compound (23). The amount of the base used is about 1.1 to 2.0 molar equivalents with respect to 1 mole of the compound (23). The reaction can be usually performed at room temperature in solvents such as DMF, THF and the like. The reaction time varies depending on the starting materials, the amine protecting agent, the base and the solvent used.

Step 8-2

This step is a step of reacting the compound (24) with a pinacol boronic ester as compound (3') or a boronic acid as compound (4') to produce the compound (18') using a palladium catalyst in the presence of a base in mixed solvents such as 1,4-dioxane and water. The palladium catalyst used may include $Pd(dppf)Cl_2$-DCM, $Pd_2(dba)_3$ with XPhos, $Pd(PPh_3)_4$ and the like. Examples of base may include $Cs_2CO_3$, $K_2CO_3$ and the like. The amount of compound (3') or (4') used is about 1 to 2 molar equivalents with respect to 1 mole of the compound (24). The reaction can be usually performed at 80° C. to the reflux temperature of the solvent, and usually goes to completion in 1-2 hours.

(9) General Procedure 9

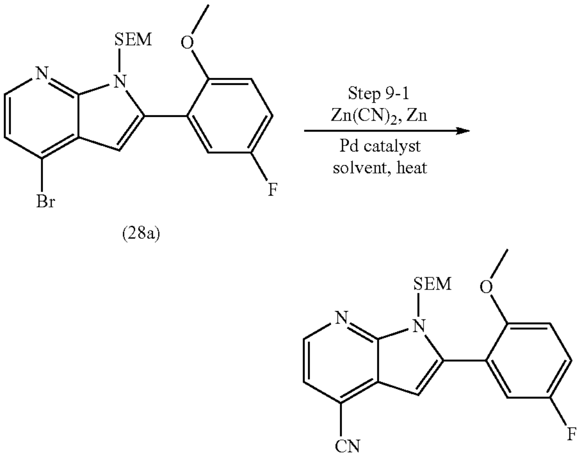

(28a)

(18c)

Step 9-1

This step is a step of converting the bromo group of the compound (28a) to the cyano group to produce the compound (18c). The compound (18c) can be produced by the reaction of the compound (28a) with zinc cyanide ($Zn(CN)_2$) in the presence of Zn and Pd catalysts in a solvent such as DMF and the like. The amount $Zn(CN)_2$ used is usually 3 molar equivalents with respect to 1 mole of the compound (28a). The palladium catalyst used may include Pd(dppf) $Cl_2$-DCM, $Pd(PPh_3)_4$ and the like. The reaction can be usually performed at 90° C. to the reflux temperature of the solvent, and usually goes to completion in 1-2 hours.

(10) General Procedure 10

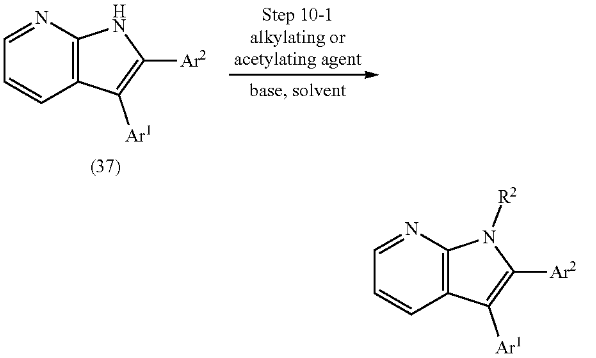

(37)

$R^2$ = Me, $CH_2OCH_3$, Ac $Ar^1$, $Ar^2$ = aryl optionally substituted, heteroaryl optionally substituted, etc Step 10-1

This step is a step of N-alkylation or N-acetylation of the compound (37) to produce the final compound by the reaction with an alkylating agent in the presence of a base. Examples of the alkylating agents may include methyl iodide, MOM-$C_1$ and the like, base may include NaH, $K_2CO_3$, NaOtBu and the like. Examples of the solvent may include DMF, THF and the like. The amount of the alkylating agent used is usually about 1 to 2 molar equivalents with respect to 1 mole of the compound (37). The reaction can be performed at room temperature, and usually goes to completion in 1-2 hours.

(11) General Procedure 11

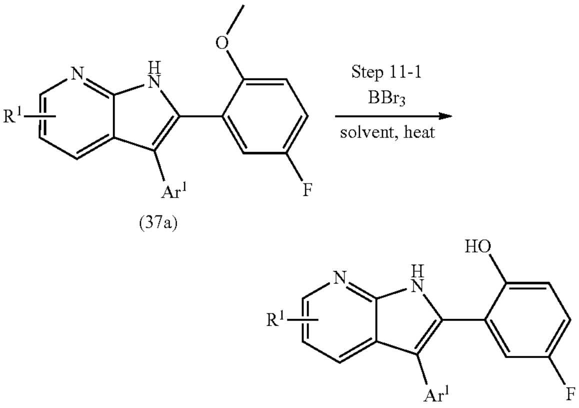

(37a)

Step 11-1

This step is a step of O-demethylation of the compound (37a) to produce the final compound by the reaction of the compound (37a) with $BBr_3$ in a solvent. Examples of the solvent may include DCM, 1,4-dioxane and the like. The amount of $BBr_3$ used is usually about 1 to 20 molar equivalents with respect to 1 mole of the compound (37a). The reaction can be performed at room temperature to the reflux temperature of the solvent. The reaction time and temperature vary depending on the starting materials and the solvent used.

(12) General Procedure 12

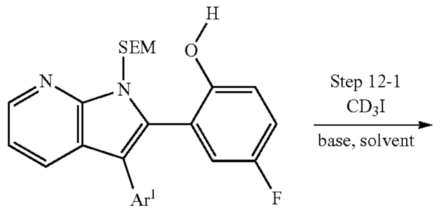

(7e)

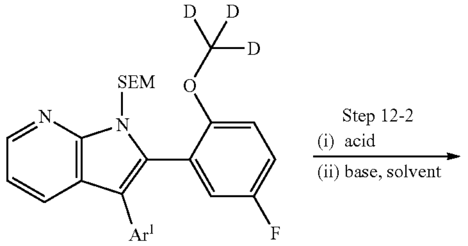

(7f)

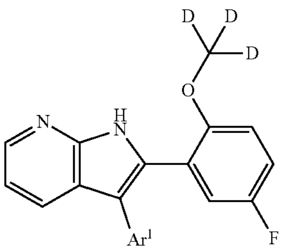

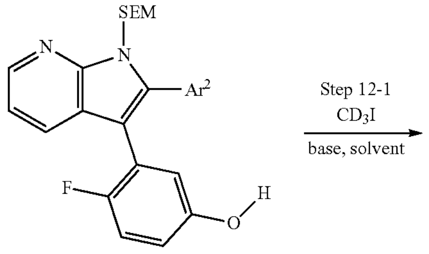

(7g)

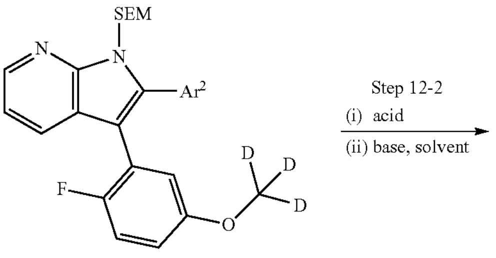

(7h)

-continued

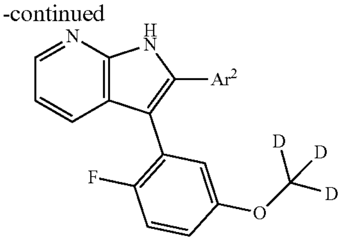

Step 12-1

This step is a step of O-trideuteriomethylation of the compound (7e or 7g) to produce the compound (7f or 7h) by the reaction with $CD_3I$ in the presence of a base. Examples of the base may include NaH, $K_2CO_3$, NaOtBu and the like. Examples of the solvent may include DMF, THF and the like. The amount of $CD_3I$ used is usually about 1 to 2 molar equivalents with respect to 1 mole of the compound (7e or 7g). The reaction can be performed at room temperature, and usually goes to completion in 1-2 hours.

Step 12-2

This step is a step of deprotecting amine of the compound (7f or 7h) by the removal of SEM group to produce the final compound. The compound (7f or 7h) can be treated with an acid such as TFA, HCl and the like followed by a base such as ethylene diamine, $NH_4OH$, $NH_3$ and the like in a solvent such as MeOH, 1,4-dioxane and water. The reaction time varies depending on the substrate, acid/base and reaction temperature.

(13) General Procedure 13

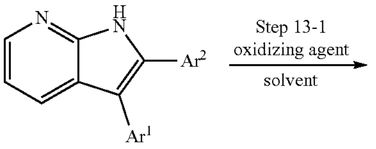

(37)

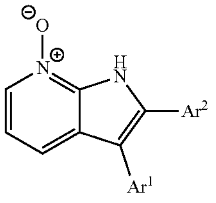

Step 13-1

This step is a step of oxidizing pyridine-N of the 7-azaindole compound (37) to produce N-oxide derivative by the reaction with an oxidizing agent such as meta-chloroperoxybenzoic acid (mCPBA) in a solvent. Examples of the solvent used may include dimethoxyethane (DME), DCM and the like. The reaction can be usually performed at room temperature. The reaction time varies depending on the starting material, the oxidizing agent, the solvent, and the reaction temperature used.

(14) General Procedure 14

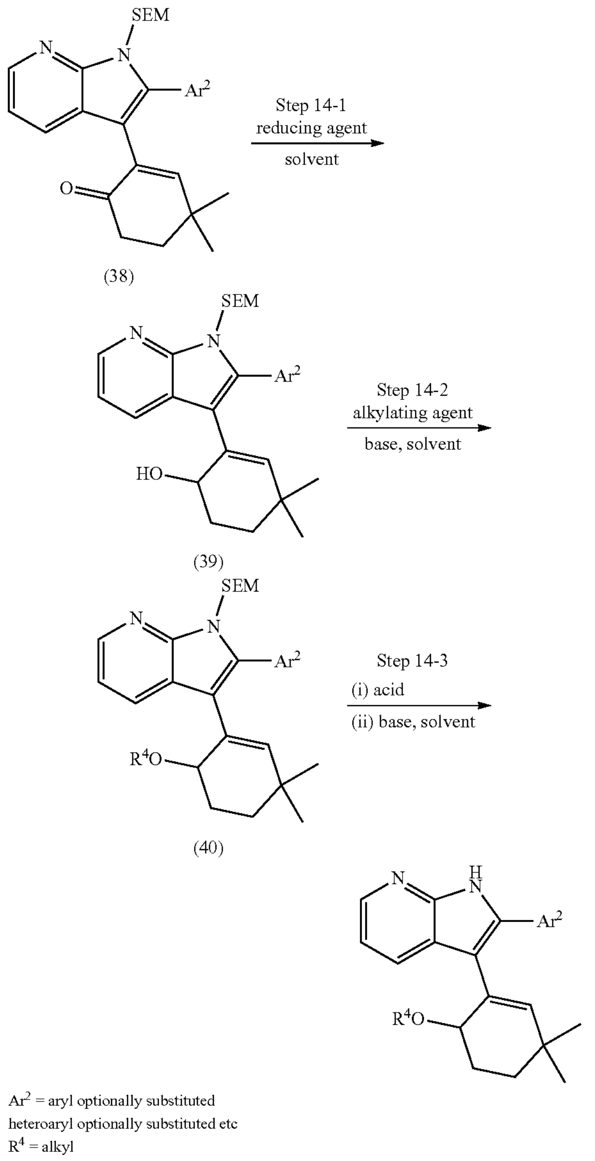

(38) (39) (40)

Step 14-1

This step is a step of reducing the ketone moiety of the compound (38) to produce compound (39) according to general procedure 6. The reduced compound can be produced by the reaction with a reducing agent such as sodium borohydride ($NaBH_4$), lithium borohydride ($LiBH_4$), and the like in a solvent. Examples of the solvent may include MeOH and the like. The reaction can be usually performed at 0° C. to room temperature The reaction time varies depending on the starting materials, the reducing agent, the solvent, and the reaction temperature used.

Step 14-2

This step is a step of O-alkylation of the compound (39) to produce the compound (40) by the reaction with an alkylating agent in the presence of a base. Examples of the base may include NaH, $K_2CO_3$, NaOtBu and the like. Examples of alkylating agent may include iodomethane (MeI), Iodoethane (EtI) and the like. Examples of the solvent may include DMF, THF and the like. The amount of the alkylating agent used is usually about 1 to 2 molar equivalents with respect to 1 mole of the compound (39). The reaction can be performed at room temperature, and usually goes to completion in 1-2 hours.

Step 14-3

This step is a step of deprotecting amine of the compound (40) by the removal of SEM group to produce the final compound. The compound (40) can be treated with an acid such as TFA, HCl and the like followed by a base such as ethylene diamine, $NH_4OH$, $NH_3$ and the like in a solvent such as MeOH, 1,4-dioxane and water. The reaction time varies depending on the substrate, acid/base and at 0° C. to room temperature.

(15) General Procedure 15

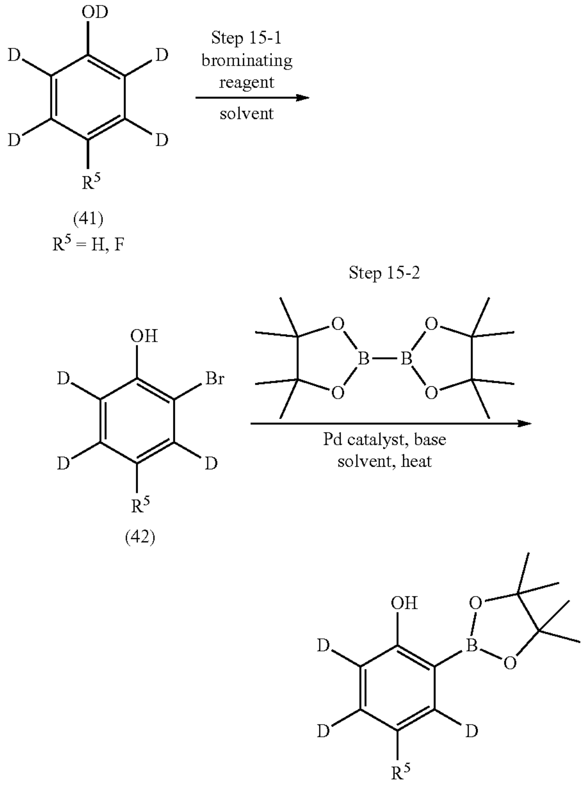

(41)
$R^5$ = H, F (42)

(3b) or (3c)

Step 15-1

This step is a step of bromination of the compound (41) to produce the compound (42) using a brominating agent such as $Br_2$. The reaction can be usually performed at room temperature in a solvent such as DCM, DCE and the like. The amount of the brominating agent used is usually about 1.0 to 1.5 molar equivalents with respect to 1 mole of the compound (41). The reaction time varies depending on the starting materials and the brominating agent.

Step 15-2

This step is a step of reacting the compound (42) with bis(pinacolato)diboron in a solvent to produce the compound (3b) or (3c) using a palladium catalyst in the presence of a base such as KOAc. Examples of palladium catalysts used may include $Pd(ppf)Cl_2$ and the like. Examples of solvents used may include 1,4-dioxane, toluene, and the like.

The amount of bis(pinacolato)diboron used is usually about 1 to 2 molar equivalents with respect to 1 mole of the compound (42). The reaction can be usually performed at 90° C. to the reflux temperature of the solvent. The reaction time varies depending on the starting material, the catalyst system, the base, the solvent, and the reaction temperature used.

(16) General Procedure 16

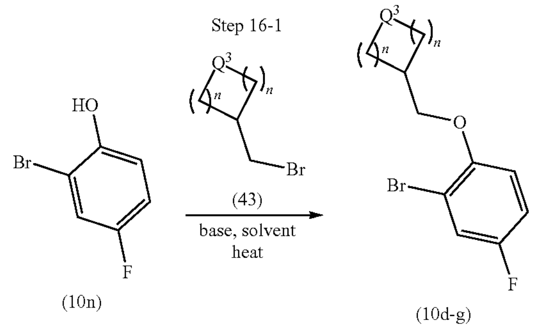

(10n) (10d-g)

$Q^3$ = O, NAc, NBoc
n = 1-2

Step 16-1

This step is a step of alkylating the hydroxyl group of 2-bromo-4-fluorophenol (10n) to produce the ether compounds (10d-g). The ether compounds can be produced by reacting the compound (10n) with heterocyclic methyl bromide (43) in the presence of base in a solvent such as DMF. Examples of base may include $K_2CO_3$, potassium t-butoxide (KOtBu) and the like. The amount of heterocyclic methyl bromide (43) used is about 1.1 to 1.5 molar equivalents with respect to 1 mole of the compound (10n). The reaction can be usually performed at 60° C. to the reflux temperature of the solvent. The reaction time varies depending on the heterocyclic methyl bromide compound (43), the base and the solvent used.

(17) General Procedure 17

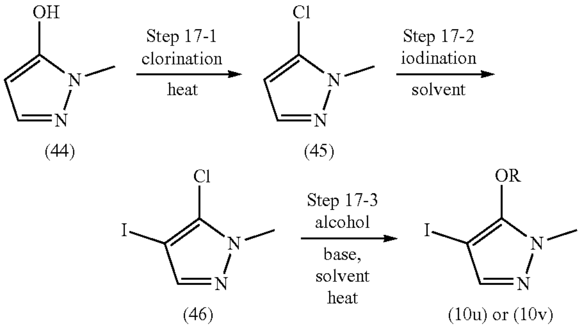

(44) (45) (46) (10u) or (10v)

R = ethyl, cyclopropylmethyl

Step 17-1

This step is a step of converting the compound (44) to the chloride derivative (45). The compound (45) can be produced by reacting the compound (44) with phosphoryl chloride. The reaction is usually performed under heated conditions (90° C. to 100° C.) overnight.

Step 17-2

This step is a step of iodination of the compound (45) to produce the compound (46) using N-iodosuccinimide (NIS). The reaction can be usually performed at room temperature in a solvent such as DCM, DCE and the like. The amount of NIS used is 1.05 molar equivalents with respect to 1 mole of the compound (45). The reaction usually goes to completion in 1 hour.

Step 17-3

This step is a step of converting the chloro pyrazole compound (46) to produce the alkoxy pyrazole compound (10u) or (10v). The compound (10u) or (10v) can be produced by reacting the compound (46) with an alcohol in the presence of base. Examples of base may include KOtBu, $K_2CO_3$ and the like. The amount of alcohol used is about 2 molar equivalents with respect to 1 mole of the compound (46) or excess amount as a solvent. Examples of other solvents may include 1,4-dioxane, THF and the like. The reaction can be usually performed at reflux temperature of the solvent. The reaction time varies depending on the alcohol, the base and the solvent used.

(18) General Procedure 18

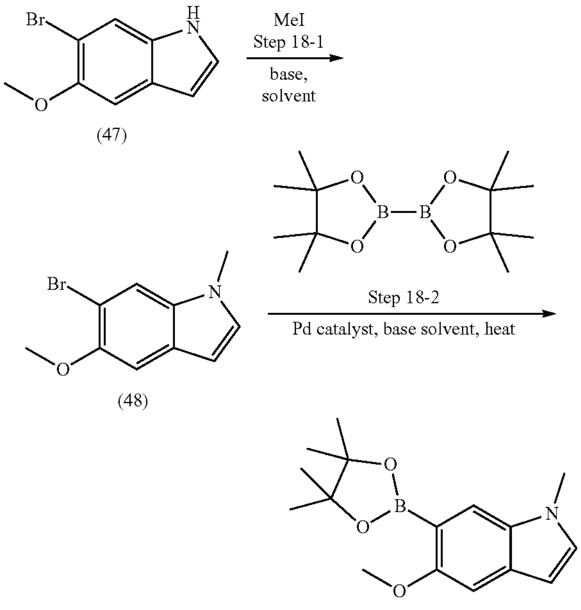

(47) (48) (3a)

Step 18-1

This step is a step of N-methylation of the compound (47) to produce the compound (48) by the reaction with MeI in the presence of a base. Examples of the base may include NaH, $K_2CO_3$, NaOtBu and the like. Examples of the solvent may include DMF, THF and the like. The amount of MeI used is usually about 1 to 2 molar equivalents with respect to 1 mole of the compound (47). The reaction can be performed at room temperature, and usually goes to completion in 1-2 hours.

Step 18-2

This step is a step of reacting the compound (48) with bis(pinacolato)diboron in a solvent to produce the compound (3a) using a palladium catalyst in the presence of a base such as KOAc. Examples of palladium catalyst used may include Pd(dppf)$Cl_2$ and the like. Examples of solvent used may include 1,4-dioxane, toluene and the like. The amount of bis(pinacolato)diboron used is usually about 1 to 2 molar equivalents with respect to 1 mole of the compound (48). The reaction can be usually performed at 90° C. to the reflux temperature of the solvent. The reaction time varies depending on the catalyst system, the base, the solvent, and the reaction temperature used.

(19) General Procedure 19

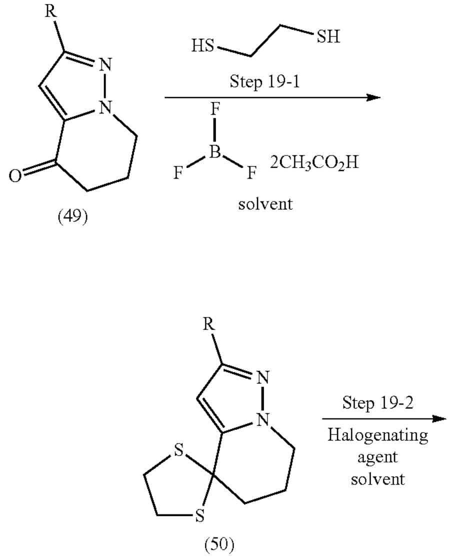

-continued

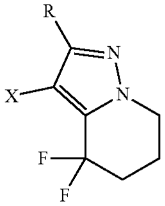

(10w)

X = Br, I
R = $CH_3$, $CF_3$, $CHF_2$, $CH_2F$

Step 19-1

This step is a step where the carbonyl of (49) is protected as a spiro-dithiane. The compound (50) can be produced by reacting the compound (49) with 1, 2-ethanedithiol, in the presence of a Lewis acid such as boron trifluoride acetic acid complex, Dibutylboron trifluoromethanesulfonate and the likes. The amount of 1, 2-ethanedithiol used is usually about 1 to 1.5 molar equivalents with respect to 1 mole of the compound (49). The reaction can be usually performed at room temperature overnight or longer and in solvents such as DCM, DCE and the like.

Step 19-2

This step is a step where compound (50) is converted to (10w) in the presence of halogenating agent and HF.pyridine. Examples of halogenating agent used may include NBS, NIS and the like. The reaction can be usually performed at −78° C. in a solvent such as DCM, DCE and the like.

(20) General Procedure 20

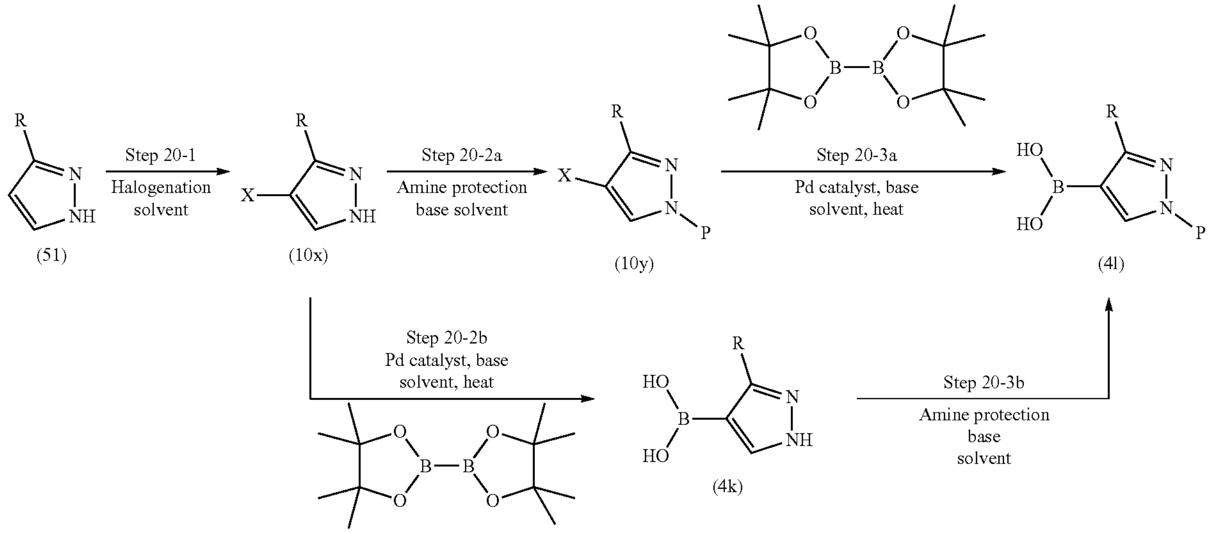

R = $CH_3$, $CF_3$, $OCHF_2$
P = Boc, SEM
X = Br, I

Step 20-1

This step is a step of halogenation of compound (51) to produce compound (10x) using a halogenating agent such as N-iodosuccinimide (NIS) or N-bromosuccinimide (NBS) and/or Br. The reaction can be usually performed at room temperature in a solvent such as DMF, DCM, DCE and the like. The amount of the halogenating agent used is usually about 1 equivalent with respect to 1 mole of the compound (51).

Step 20-2a

This step is a step of protecting pyrazole-NH of compound (10x) to produce compound (10y) by the reaction of a protecting agent and a base. The protecting agents used may include $Boc_2O$, SEM-Cl and the like. Examples of the base may include NaH, $K_2CO_3$, NaOtBu and the like. Examples of the solvent may include DMF, THF and the like. The amount of the $Boc_2O$ used is usually about 1 to 2 molar equivalents with respect to 1 mole of the compound (10x). The reaction is usually performed at 0° C.

Step 20-2b

This step is a step of reacting compound (10x) with bis(pinacolato)diboron in a solvent to produce compound (4k) using a palladium catalyst in the presence of a base such as KOAc. Examples of palladium catalyst used may include $Pd(dppf)Cl_2$ and the like. Examples of solvent used may include 1,4-dioxane, toluene and the like. The amount of bis(pinacolato)diboron used is usually about 1 to 2 molar equivalents with respect to 1 mole of the compound (10x). The reaction can be usually performed at 90° C. to the reflux temperature of the solvent. The reaction time varies depending on the starting material, the catalyst system, the base, the solvent, and the reaction temperature used.

Step 20-3a

This step is a step of reacting compound (10y) with bis(pinacolato)diboron in a solvent to produce compound (41) using a palladium catalyst in the presence of a base such as KOAc. Examples of palladium catalyst used may include $Pd(dppf)Cl_2$ and the like. Examples of solvent used may include 1,4-dioxane, toluene and the like. The amount of bis(pinacolato)diboron used is usually about 1 to 2 molar equivalents with respect to 1 mole of the compound (10y). The reaction can be usually performed at 90° C. to the reflux temperature of the solvent. The reaction time varies depending on the starting material, the catalyst system, the base, the solvent, and the reaction temperature used.

Step 20-3b

This step is a step of protecting pyrazole-NH of compound (4k) to produce the compound (41) by the reaction of a protecting agent and a base. The protecting agents used may include $Boc_2O$, $SEM\text{-}C_1$ and the like. Examples of the base may include NaH, $K_2CO_3$, NaOtBu and the like. Examples of the solvent may include DMF, THF and the like. The amount of the $Boc_2O$ used is usually about 1 to 2 molar equivalents with respect to 1 mole of the compound (4k). The reaction is usually performed at 0° C.

(21) General Procedure 21

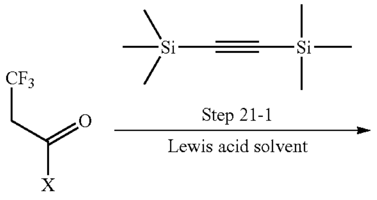

(52)

-continued

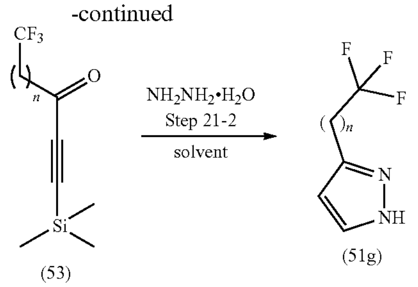

(53) (51g)

X = Cl, Br
n = 1, 2, 3

Step 21-1

This step is a step that converts 3,3,3-trifluoropropanoyl halide (52) into compound (53) using 1,2-bis(trimethylsilyl) ethyne in the presence of Lewis acid such as $AlCl_3$ and solvents such as DCM, DCE and the like. The reaction is performed at 0° C. for 1-3 h.

Step 21-2

This step is a step that converts compound (53) to the corresponding pyrazole (51g) by the reaction with hydrazine in the presence of solvents such as ethanol, $CH_3CN$ and the like. The reaction is performed at room temperature and reaction goes to completion in 1-2 h.

(22) General Procedure 22

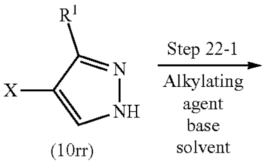

(10rr)

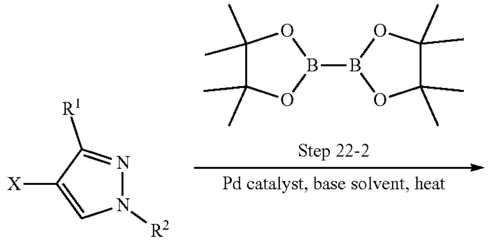

(10ss)

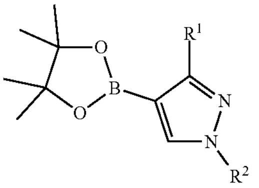

(3q)

X = Br, I
$R^1$ = $OCHF_2$, $CF_3$, $CHF_2$, $CH_2F$
$R^2$ = Alkyl

Step 22-1

This step is a step of N-alkylation of the compound (10rr) to produce the compound (10ss) by the reaction with alkylating agent in the presence of a base. Examples of the base may include $K_2CO_3$ and the like. The alkylating agent used may include iodomethane (MeI), Iodoethane (EtI) and the like. The reaction can be usually performed at room temperature to 50° C. in a solvent such as DMSO, THF and the like. The reaction time varies depending on the starting materials, the alkylating agent, the base, the solvent used, and the reaction temperature.

Step 22-2

This step is a step of reacting the compound (10ss) with bis(pinacolato)diboron in a solvent to produce the compound (3q) using a palladium catalyst in the presence of a base such as KOAc. Examples of palladium catalyst used may include Pd(dppf)$Cl_2$ and the like. Examples of solvent used may include 1,4-dioxane, toluene and the like. The amount of bis(pinacolato)diboron used is usually about 1 to 2 molar equivalents with respect to 1 mole of the compound (10ss). The reaction can be usually performed at 90° C. to the reflux temperature of the solvent. The reaction time varies depending on the starting material, the catalyst system, the base, the solvent, and the reaction temperature used.

(23) General Procedure 23

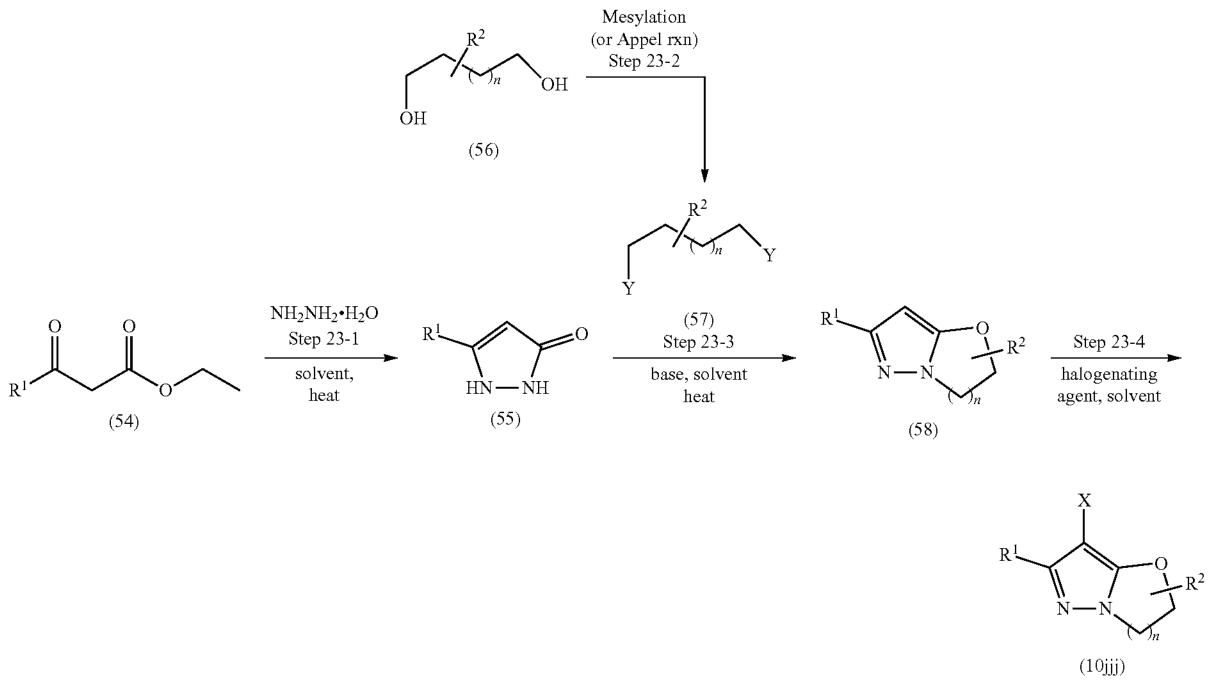

(56) (57) (54) (55) (58) (10jjj)

$R^1$ = H, $CH_3$, Et, Cyclopropyl, $CH_2CF_3$, $CHF_2$
$R^2$ = H, $CH_3$, Et, Cyclopropyl, OH
Y = OMs, via Appel rxn (Br, Cl)
X = halogen
n = 2-4

Step 23-1

This step is a step that converts compound (54) to compound (55) using hydrazine in Ethanol. The reaction is usually heated at 110° C. to 115° C. for 2-16 h.

Step 23-2

This step is a step where compound (56) is converted to compound (57) via mesylation in the presence of a base and in a solvent such as DCM, THF and the like. Examples of the base may include $Et_3N$, pyridine and the like. Alternatively, compound (57) can also be generated from compound (56) via Appel reaction where Y═Br or Cl (Angew. Chem. Int. Engl. 1975, 14, 801-811).

Step 23-3

This step is a step where compounds (55) and (57) are heated together in a solvent such as DMF and in the presence of a base to form bicyclic compound (58). Examples of base may include $K_2CO_3$, $Cs_2CO_3$ and the likes. The reaction can be usually performed at 110 to 120° C. The reaction time varies depending on the substrates and reaction temperature.

Step 23-4

This step is a step of halogenating compound (58) to produce the compound (10jjj) using a halogenating agent such as NIS or NBS and/or $Br_2$. The reaction can be usually performed at room temperature in a solvent such as $CH_3CN$, DCM, DCE and the like. The amount of the halogenating agent used is usually about 1-1.5 equivalent with respect to 1 mole of the compound (58)

(24) General Procedure 24

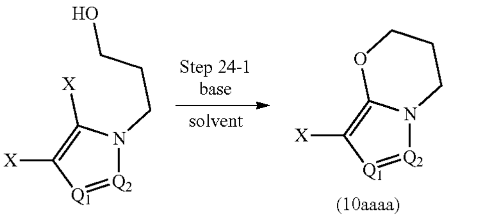

(10zzz)

(10aaaa)

X = Br, I
Q1, Q2 = C(H), N

Step 24-1

This step is a step of cyclization of compound (10zzz) to compound (10aaaa) in the presence of a base and at temperature between 60° C. to 100° C. Examples of the base may include $Cs_2CO_3$ and the like. The solvent used may include DMF, DMSO and the like. The reaction time varies depending on the substrate and reaction temperature.

(25) General Procedure 25

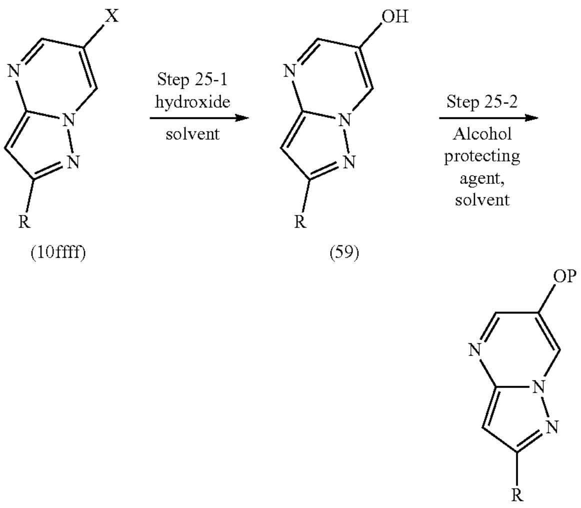

(10ffff)

(59)

(60)

R = $CH_3$, $CF_3$, Et
X = halogen
P = Silyl group

Step 25-1

This step is a step where compound (10ffff) is converted to compound (59) in the presence of a hydroxide and at temperature between 60° C. to 70° C. Examples of hydroxide my include potassium hydroxide (KOH), sodium hydroxide and the like. The solvent used may include DMF and the like. The reaction time varies depending on the starting material and the solvent used.

Step 25-2

This step is a step of protecting the alcohol moiety of compound (59) to produce compound (60) in the presence of a base. The alcohol protecting reagents used may include tert-butyldimethylsilane (TBDMS), SEM-Cl and the likes. The base used may include imidazole, diisopropylethylamine, pyridine and the like. Examples of the solvent may include DMF, DCM and the like. The reaction time varies depending on the starting material, reaction temperature and the protecting reagent used.

(26) General Procedure 26

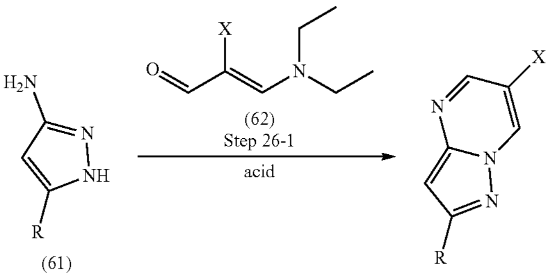

(61)

(62)

(10iiii)

X = F, Cl
R = $CH_3$, Et, $CF_3$
$CHF_2$, $CH_2F$

Step 26-1

This step is a step where compound (61) is reacted with compound (62) in the presence of an acid at 100° C. to obtain cyclized product (10iiii). Examples of the acid may include AcOH, p-Toluenesulfonic acid and the like.

(27) General Procedure 27

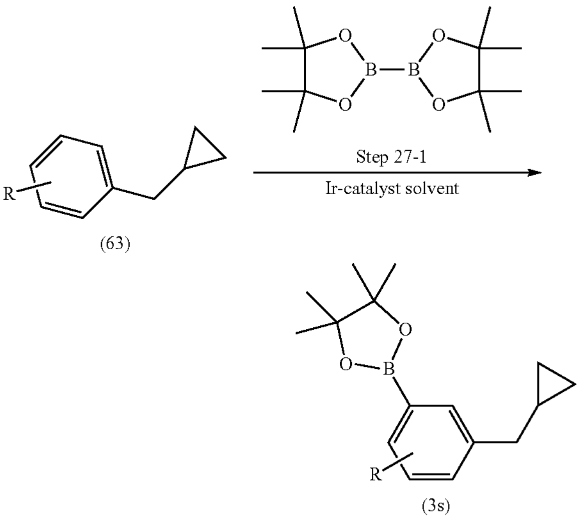

(63)

(3s)

R = CN, OMe, $OCD_3$

Step 27-1

This step is a step that converts compound (63) to compound (3s) in the presence of a Ir-catalyst and solvent. The Ir-catalyst may be $[Ir(OMe)(cod)]_2$ and the like. Examples of solvent used may include p-xylene, THF and the like. (J. Am. Chem. Soc. 2005, 127, 10539-10544)

(28) General Procedure 28

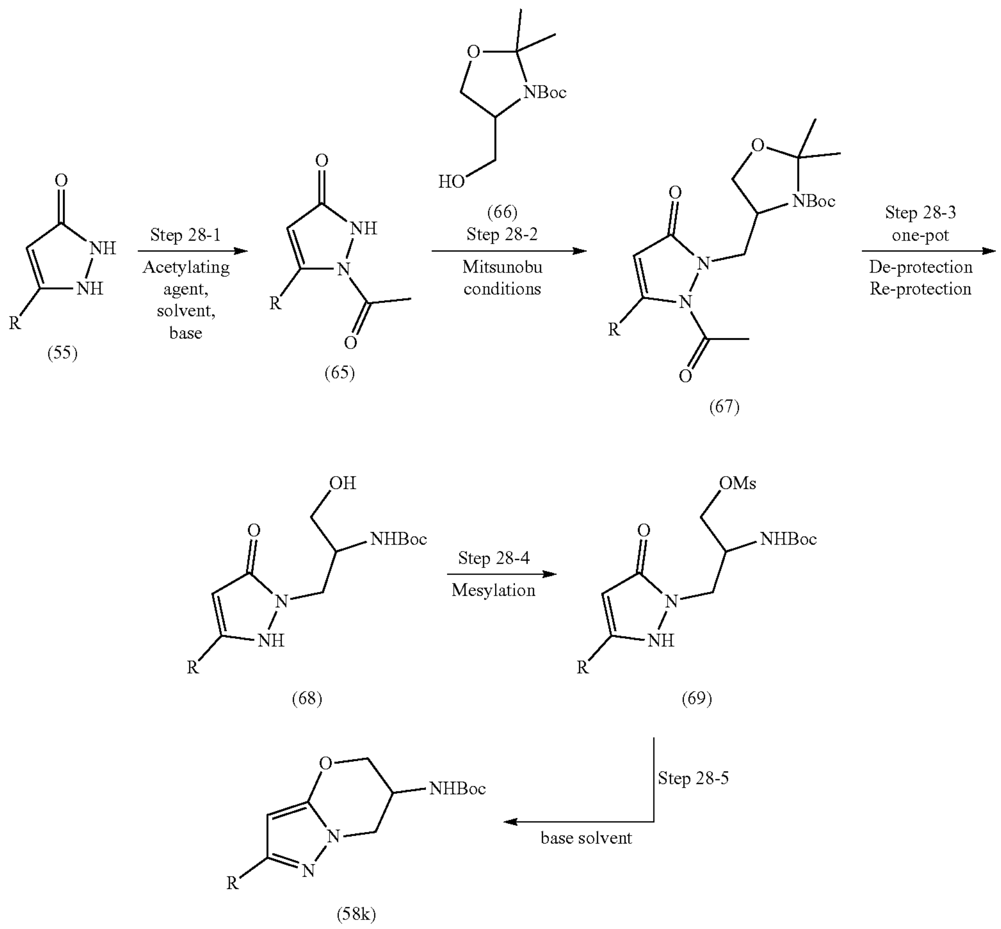

(55) (65) (66) (67) (68) (69) (58k)

R = $CH_3$, $CF_3$, $CHF_2$, $CH_2F$

The reaction conditions of Step 28-1 and 28-2 are carried out by utilizing of the method described in Example 25 of WO2018/136890.

Step 28-1

This step is a step of N-acetylation of compound (55) to produce compound (65) by the reaction with an acylating agent in the presence of a base. Examples of the base may include pyridine, triethyl amine and the like. Examples of the solvent may include DCM, MeCN and the like. Examples of the acetylating agent may include acetyl chloride, acetic anhydride and the like. The amount of the acylating agent used is usually about 1 to 1.05 molar equivalents with respect to 1 mole of the compound (55). The reaction can be performed at 0° C. to 95° C. The reaction time varies depending on the starting materials, the acylating agent, the base and the solvent used.

Step 28-2

This step is a step where compound (65) is reacted with compound (66) under Mitsunobu conditions at room temperature to obtain compound (67) in the presence of a solvent. The reagents used may include diethyl azodicarboxylate (DEAD), diisopropyl azodicarboxylate (DIAD) and the like in the presence of triphenylphosphine (TPP). Examples of the solvent may include THF, DCM and the like. The reaction time varies depending on the starting materials.

Step 28-3

This step is a step where deprotection of Boc and acetonide groups of compounds (67) was achieved by the reaction of p-toluenesulfonic acid (pTSA) at room temperature in a solvent. Examples of the solvent may include MeOH and the like. After complete deprotection of acetyl and Boc groups, protection of the amine with a Boc group was achieved by reaction with $Boc_2O$ in the presence of base and solvent at room temperature. Examples of the base may include $Et_3N$, and the like. Examples of the solvent may include THF and the like.

Step 28-4

This step is a step where the alcohol of compound (68) is converted to a mesyl group in the presence of MesylCl and a base to generate compound (69) at room temperature. Examples of the base may include $Et_3N$, pyridine and the like. Examples of the solvent may include THE, DCM and the like. The reaction time varies depending on the starting material.

Step 28-5

This step is a step where compound (69) is converted to compound (58k) in the presence of base and solvent. Examples of the base may include $K_2CO_3$, and the like. Examples of the solvent may include DMF and the like. The reaction time varies depending on the starting material and temperature of the reaction (80° C.~100° C.).

(29) General Procedure 29

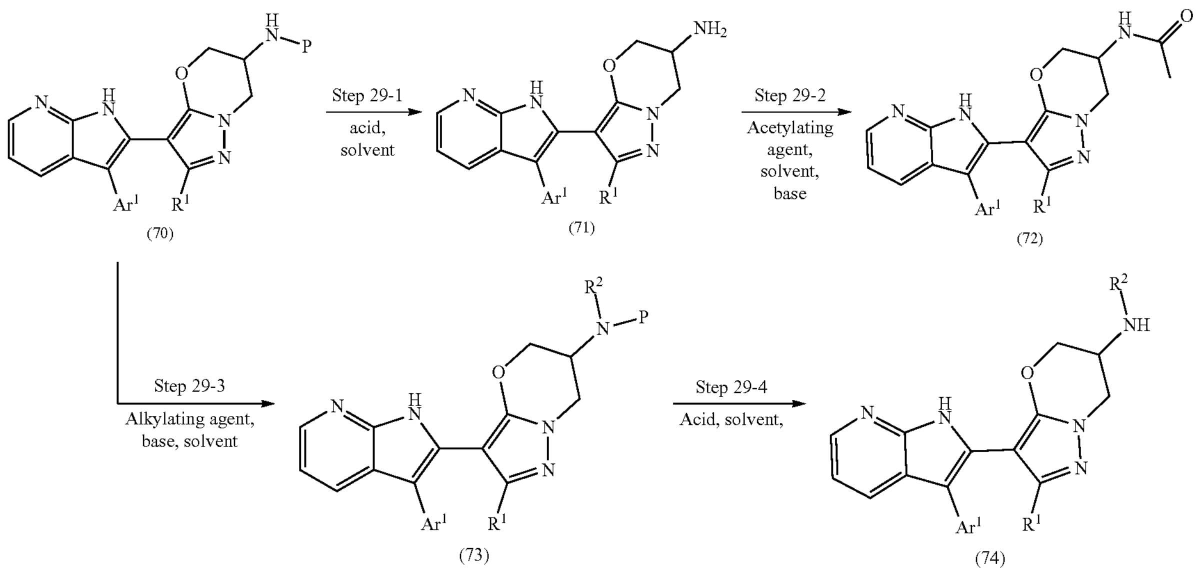

(70) (71) (72) (73) (74)

$R^1$ = H, $CH_3$, $CF_3$, $CHF_2$, $OCHF_2$
= $CH_2F$
$R^2$ = $CH_3$, Et
$Ar^1$, $Ar^2$ = aryl optionally substituted, heteroaryl optionally subsituted, etc.
P = Boc, Cbz Step 29-1

This step is a deprotection step of compound (70) to produce compound (71) at room temperature. The deprotecting agent can be an acid such as TFA, HCl in a solvent such as DCM, THF and the like. The reaction time varies depending on the starting material and the acid used.

Step 29-2

This step is a step where compound (71) is converted to compound (72) in the presence of acetyl chloride, base and solvent at room temperature. Examples of base include $Et_3N$, DIPEA and the like. Examples of solvent include THE, DCM, and the like.

Step 29-3

This step is a step of compound (70) to produce compound (73) by the reaction with an alkylating agent in the presence of a base. Examples of the base may include sodium hydride (NaH), $K_2CO_3$, NaOtBu and the like. Examples of the solvent may include DMF, THF and the like. The alkylating agent used may include MeI, EtI and the like. The amount of the alkylating agent used is usually about 1 to 2 molar equivalents with respect to 1 mole of the compound (70). The reaction can be performed at room temperature, and usually goes to completion in 1-2 hours.

Step 29-4

This step is a step where compound (73) is converted to compound (74) in the presence of TFA, HCl and the like at room temperature. Examples of solvent include DCM, THF and the like.

(30) General Procedure 30

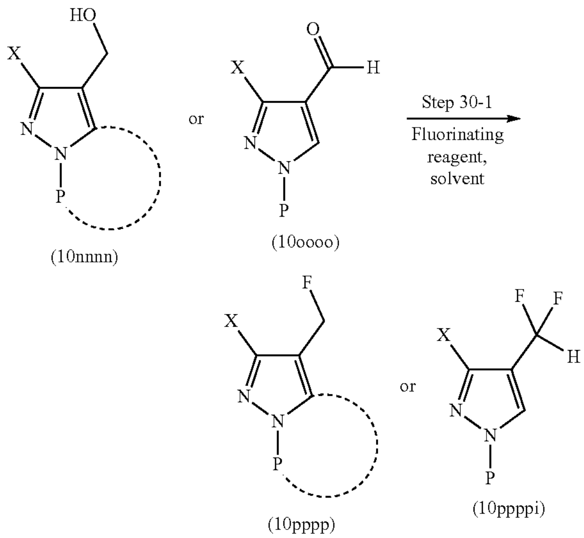

(10nnnn) or (10oooo) (10pppp) or (10ppppi)

X = Br, I
P = THP, SEM, Boc, cyclo-

Step 30-1

This step is a step of fluorinating compound (10nnnn) to produce compound (10pppp) using a fluorinating reagent such as diethylaminosulfur trifluoride (DAST) and the like.

The reaction can be usually performed at −78° C. to room temperature in a solvent such as DCM, DCE and the like. The amount of the fluorinating agent used is usually about 2 to 3 molar equivalents with respect to 1 mole of the compound (10nnnn). The reaction time varies depending on the starting material and reaction temperature.

(31) General Procedure 31

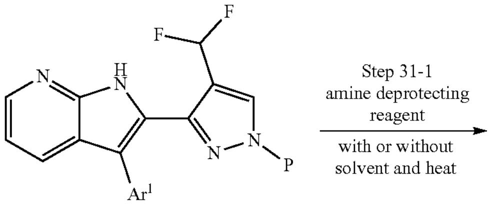

(75)

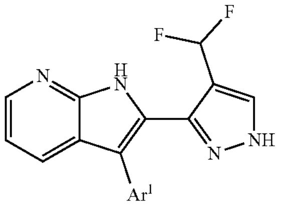

(76)

X = Halogen
$Ar^1$ = aryl optionally substituted, heteroaryl optionally substituted, etc
P = THP, Boc, SEM Step 31-1

This step is a step of deprotecting amine moiety of compound (75) to produce compound (76) by the reaction with an amine deprotecting agent. The amine deprotecting agent can be acid with or without base such as TFA, HCl with or without ethylene diamine, $NH_4OH$, $NH_3$ and the like depending on the protecting groups. The reaction can be usually performed at room temperature to 50° C. with or without a solvent such as MeOH, 1,4-dioxane and water. The reaction time varies depending on the substrate, acid/base and reaction temperature.

(32) General Procedure 32

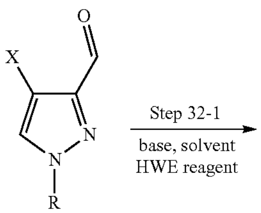

(10aaaaa)

-continued

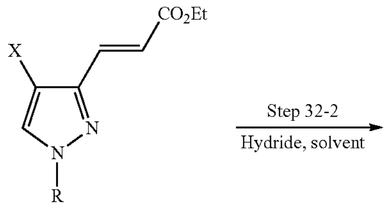

(10bbbbb)

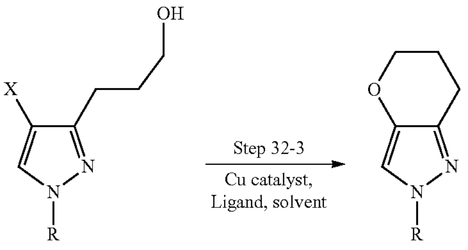

(10ccccc) (58m)

X = Br, I
$R^1$ = H, Me, Et

Step 32-1

This step is a step of converting compound (10aaaaa) to compound (10bbbbb) under Horner-Wadsworth-Emmons (HWE) conditions. The HWE reagent and base used are triethylphosphonoacetate and sodium hydride (NaH) respectively. Examples of solvent used are THF and the like. The amount of HWE reagent used is usually about 1.0 to 1.5 molar equivalents with respect to 1 mole of the compound (10aaaaa). The amount of NaH used is usually about 1.0 to 1.5 molar equivalents with respect to 1 mole of the compound (10aaaaa). The reaction is performed at 0° C. to room temperature and usually goes to completion overnight.

Step 32-2

This step is a step of reducing the α, β-unsaturated ethyl ester moiety of compound (10bbbbb) to produce compound (10ccccc). The compound (10ccccc) can be generated by the reaction of compound (10bbbbb) with a reducing agent such as lithium aluminum hydride ($LiAlH_4$), super hydride ($Li(C_2H_5)_3BH$) and the like. Examples of the solvent may include THF and the like. The reaction can be performed at −78° C. to room temperature and usually goes to completion from 30 min. to 18 h.

Step 32-3

This step is a step of converting compound (10ccccc) to compound (58m) under Glaser coupling conditions. The catalyst and ligand used are copper Iodide (CuI) and 3, 4, 7, 8-tetramethyl-1,10-phenanthroline respectively. Examples of the solvent may include toluene, and the like. The reaction can be usually performed at 100° C. to 110° C. The reaction time is usually 1 to 2 days.

(33) General Procedure 33

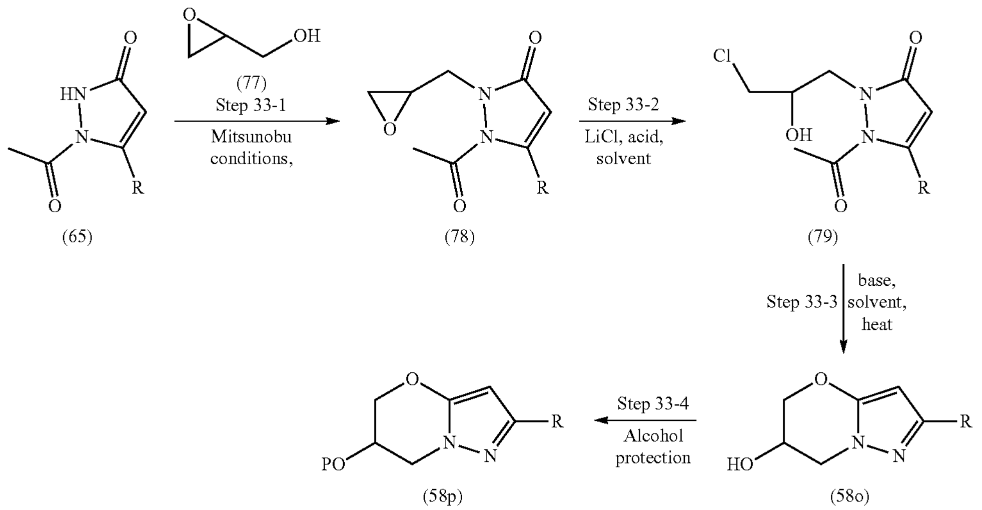

(65) (78) (79) (58o) (58p)

R = $CH_3$, $CF_3$, $CHF_2$, $CH_2F$
P = SEM, TBDPS, Boc

The reaction conditions of Step 33-1, 33-2 and 33-3 are carried out by utilizing of the method described in Example 25 of WO2018/136890.

Step 33-1

This step is a step of N-alkylation of compound (65) with Glycidol (77) under Mitsunobu conditions to produce compound (78). Examples of the solvent may include THF, diethyl ether and the like. The amount of the Glycidol used is usually about 1 to 1.2 molar equivalents with respect to 1 mole of the compound (65). The reaction can be performed at 0° C. and usually goes to completion in 3-4 hours.

Step 33-2

This step is a step to ring opening of epoxide moiety in compound (78) in the presence of LiCl and acetic acid to produce compound (79). The reaction can be performed in THF at room temperature and usually goes to completion in 18-24 hours.

Step 33-3

This step is a step to formation of compound (580) from compound (79) in the presence of $K_2CO_3$. The reaction can be performed in DMF at 125° C. to 135° C. and usually goes to completion in 24 to 36 hours.

Step 33-4

This step is a step of protecting alcohol moiety in compound (580) to produce the compound (58p) by the reaction with an alcohol protecting agent in a solvent in the presence of a base and catalyst. The alcohol protecting reagents used may include tert-butyl-chloro-diphenyl-silane (TBDPS-Cl) and the like. The base and catalyst used are imidazole and DMAP respectively. The amount of the alcohol protecting agent used is about 1.5 molar equivalents with respect to 1 mole of the compound (580). The amount of the base used is about 2 to 2.2 molar equivalents with respect to 1 mole of compound (580). The reaction can be usually performed at room temperature in the solvent such as DMF and the like. The reaction time varies depending on the starting materials, the alcohol protecting agent, the base and the solvent used.

(34) General Procedure 34

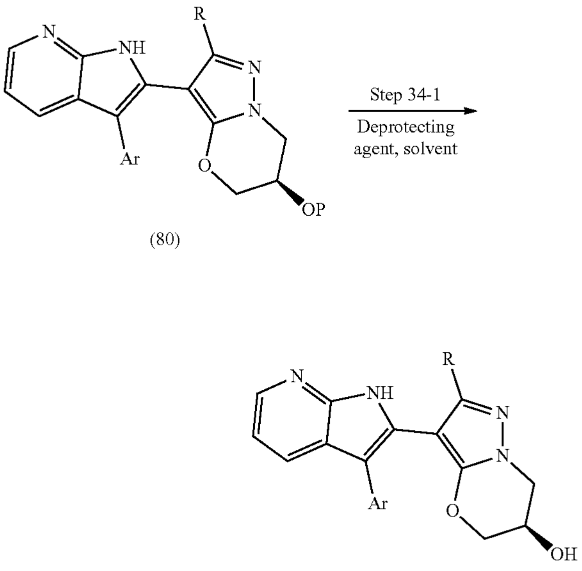

(80) (81)

R = $CH_3$, $CH_2F$, $CHF_2$, $CF_3$
Ar = aryl optionally substituted heteroaryl optionally substituted
P = Boc, SEM Step 34-1

This step is a step of deprotecting alcohol moiety in compound (80) to produce compound (81) by the reaction with an alcohol deprotecting agent. The alcohol deprotecting agent may include tetra-n-butylammonium fluoride (TBAF), HCl and the like. The reaction can be usually performed at 0° C. to room temperature with a solvent such as THE, DCM and the like. The reaction usually goes to completion in 1 h.

(35) General Procedure 35

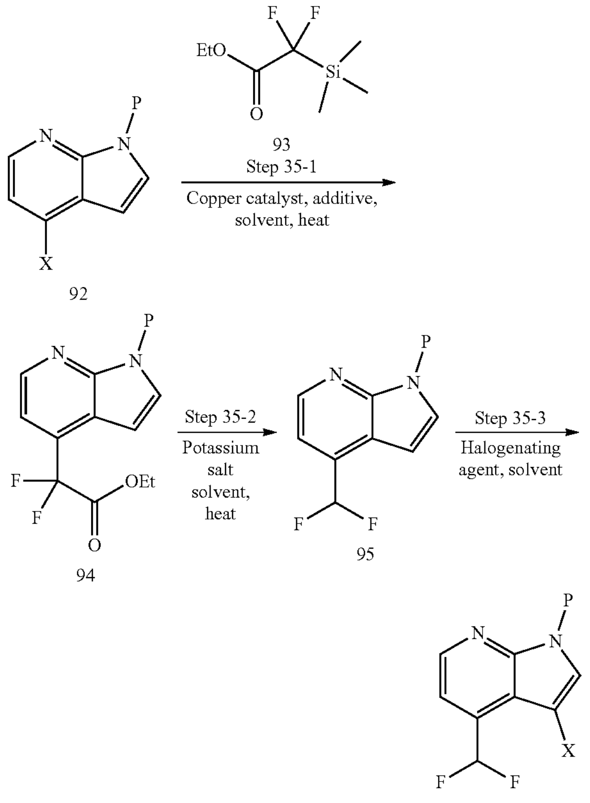

93, 92, 94, 95, 96

P = SEM, Boc
X = I, Br

Step 35-1

This step is a step of reacting the compound (92) with silyl-ester compound (93) to produce the compound (94) using a copper halide in the presence of an additive heated at 80° C. The copper used may include CuI, copper and the like. Examples of additive may include potassium fluoride, sodium fluoride and the like. Examples of solvent may include DMF, DMSO and the like. The amount of copper halide and additive are about 1 to 3 molar equivalents each with respect to 1 mole of the compound (92). The amount of compound (93) used is about 1 to 3 molar equivalents with respect to 1 mole of the compound (92). The reaction time varies depending on the starting materials, the additive and the solvent used.

Step 35-2

This step is a step of de-acetylation of the compound (94) to produce the compound (95) using an potassium salt in aqueous solvent. The potassium salt used may include potassium fluoride (KF), potassium chloride, and the like. The reaction can be usually performed at 100° C. to 130° C. in a solvent such as DMSO, DMF and the like. The amount of potassium salt and water used are about 3 to 5 molar equivalents each with respect to 1 mole of the compound (94). The reaction time varies depending on the starting materials, potassium halide and the solvent used.

Step 35-3

This step is a step of halogenation of compound (95) to produce the compound (96) using a halogenating agent such as N-iodosuccinimide (NIS), N-bromosuccinimide (NBS) and/or bromine ($Br_2$). The reaction can be usually performed at room temperature in a solvent such as DCM, DCE and the like. The amount of the halogenating agent used is usually about 1 to 5 molar equivalents with respect to 1 mole of the compound (95). The reaction time varies depending on the starting materials, the halogenating agent and the solvent used.

(36) General Procedure 36

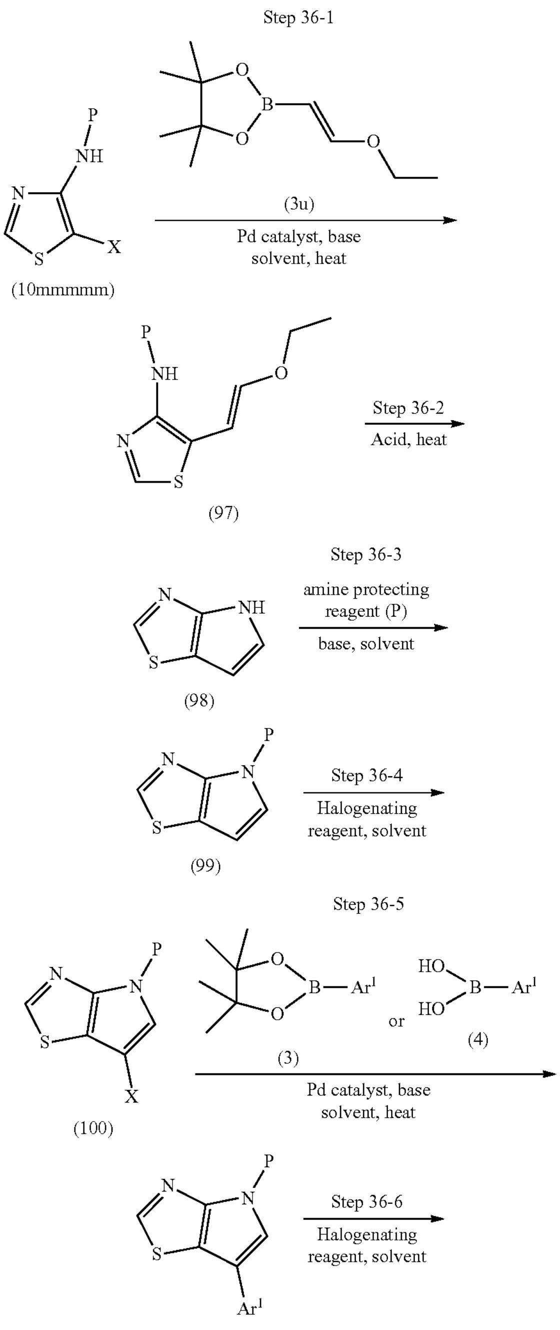

(3u), (10mmmmm), (97), (98), (99), (100), (3), (4), (101)

-continued

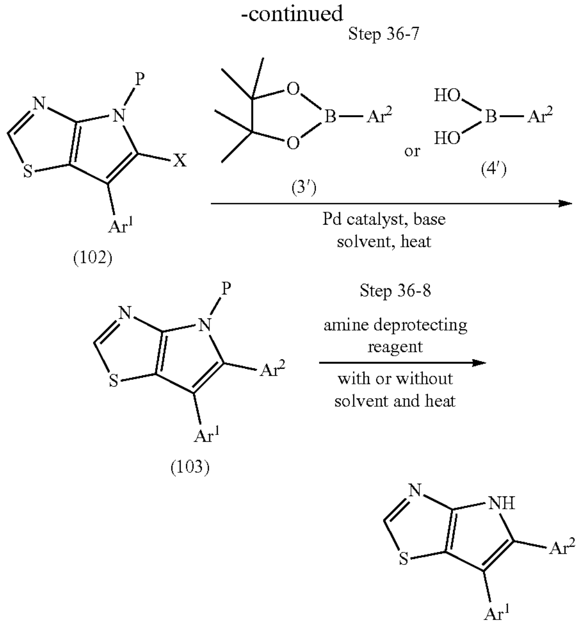

(3')

(4')

(102)

(103)

(104)

$Ar^1$, $Ar^2$ = aryl optionally substituted, heteroaryl optionally substituted, etc
P = Boc, SEM
X = I, Br Step 36-1

This step is a step of reacting the compound (10mmmmm) with a pinacol boronic ester compound (3u) to produce the compound (97) using a palladium catalyst in the presence of a base in mixed solvents such as 1,4-dioxane and water. The palladium catalyst used may include $Pd(dppf)Cl_2$-DCM, $Pd_2(dba)_3$ with XPhos, $Pd(PPh_3)_4$ and the like. Examples of base may include $Cs_2CO_3$, $K_2CO_3$ and the like. The amount of compound (3u) used is about 1 to 2 molar equivalents with respect to 1 mole of the compound (10mmmmm). The reaction can be usually performed at 70° C. to the reflux temperature of the solvent, and usually goes to completion in 1-2 hours.

Step 36-2

This step is a step of converting the compound (97) to the compound (98) using mineral acid. Examples of mineral acid may include HCl, sulfuric acid ($H_2SO_4$) and the like. The reaction can be usually performed at 70° C. to 100° C. The reaction time varies depending on the temperature of the reaction and the starting materials.

Step 36-3

This step is a step of protecting 1H—N of the compound (98) to produce the compound (99) by the reaction with an amine protecting agent in a solvent in the presence of a base. The amine protecting reagents used may include $Boc_2O$, SEM-Cl, Fmoc-Cl, Cbz-Cl, BnCl and the like. The base used may include TEA, DIPEA, DMAP, NaH and the like. The amount of the amine protecting agent used is about 1.1 to 1.5 molar equivalents with respect to 1 mole of the compound (98). The amount of the base used is about 1 to 2 molar equivalents with respect to 1 mole of the compound (98). The reaction can be usually performed at room temperature in the solvent such as DMF, THF and the like. The reaction time varies depending on the starting materials, the amine protecting agent, the base and the solvent used.

Step 36-4

This step is a step is halogenation of the compound (99) to produce the compound (100) using a halogenating agent such as NIS, NBS and/or $Br_2$. The reaction can be usually performed at room temperature in a solvent such as DCM, MeCN and the like. The amount of the halogenating agent used is usually about 1 to 5 molar equivalents with respect to 1 mole of the compound (99). The reaction time varies depending on the starting materials, the halogenating agent and the solvent used.

Step 36-5

This step is a step of reacting the compound (100) with a pinacol boronic ester as compound (3) or a boronic acid as compound (4) to produce the compound (101) using a palladium catalyst in the presence of a base in mixed solvents such as 1,4-dioxane and water. The palladium catalyst used may include $Pd(dppf)Cl_2$-DCM, $Pd_2(dba)_3$ with XPhos, $Pd(PPh_3)_4$ and the like. Examples of base may include $Cs_2CO_3$, $K_2CO_3$ and the like. The amount of compound (3) or (4) used is about 1 to 2 molar equivalents with respect to 1 mole of the compound (100). The reaction can be usually performed at 70° C. to the reflux temperature of the solvent, and usually goes to completion in 1-2 hours.

Step 36-6

This step is a step is halogenation of the compound (101) to produce the compound (102) using a halogenating agent such as NIS, NBS and/or $Br^2$. The reaction can be usually performed at room temperature in a solvent such as DCM, DCE and the like. The amount of the halogenating agent used is usually about 1 to 5 molar equivalents with respect to 1 mole of the compound (101). The reaction time varies depending on the starting materials, the halogenating agent and the solvent used.

Step 36-7

This step is a step of reacting the compound (102) with a pinacol boronic ester as compound (3') or a boronic acid as compound (4') to produce the compound (103) using a palladium catalyst in the presence of a base in mixed solvents such as 1,4-dioxane and water. The palladium catalyst used may include $Pd(dppf)Cl_2$-DCM, $Pd_2(dba)_3$ with XPhos, $Pd(PPh_3)_4$ and the like. Examples of base may include $Cs_2CO_3$, $K_2CO_3$ and the like. The amount of compound (3') or (4') used is about 1 to 2 molar equivalents with respect to 1 mole of the compound (102). The reaction can be usually performed at 70° C. to the reflux temperature of the solvent, and usually goes to completion in 1-2 hours.

Step 36-8

This step is a step of deprotecting amine of the compound (103) to produce compound (104) by the reaction with an amine deprotecting agent. The amine deprotecting agent can be acid with or without base such as TFA, HCl with or without ethylene diamine, $NH_4OH$, $NH_3$ and the like depending on the protecting groups. The reaction can be usually performed at room temperature to 50° C. with or without a solvent such as MeOH, 1,4-dioxane and water. The reaction time varies depending on the substrate, acid/base and reaction temperature.

(37) General Procedure 37

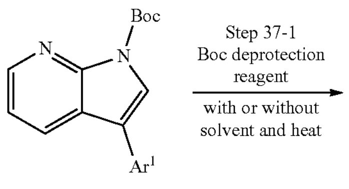

(5d)

-continued

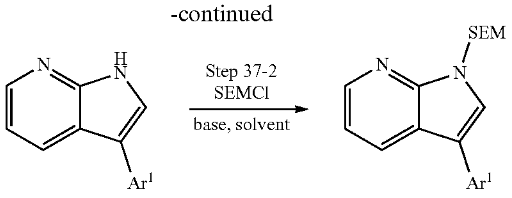

(11) (5e)

$Ar^1$, $Ar^2$ = aryl optionally substituted, heteroaryl optionally substituted, etc Step 37-1

This step is a step of removing Boc protecting group from compound (5d) to produce compound (11) by the reaction with an acid. The acid used may include TFA, HCl and the like. The reaction can be usually performed at room temperature to 50° C. with a solvent such as DCM, DCE and the like. The reaction time varies depending on the substrate, acid, and reaction temperature.

Step 37-2

This step is a step of protecting 1H—N of the 7-azaindole compound (11) with SEM group to produce the compound (5e) by the reaction with SEM-Cl in a solvent in the presence of a base. The base used may include NaH and the like. The amount of SEM-Cl used is about 1.1 to 1.5 molar equivalents with respect to 1 mole of the compound (11). The amount of the base used is about 1 to 2 molar equivalents with respect to 1 mole of the compound (11). The reaction can be usually performed at room temperature in the solvent such as DMF, THF and the like. The reaction time varies depending on the starting materials, the base and the solvent used.

(38) General Procedure 38

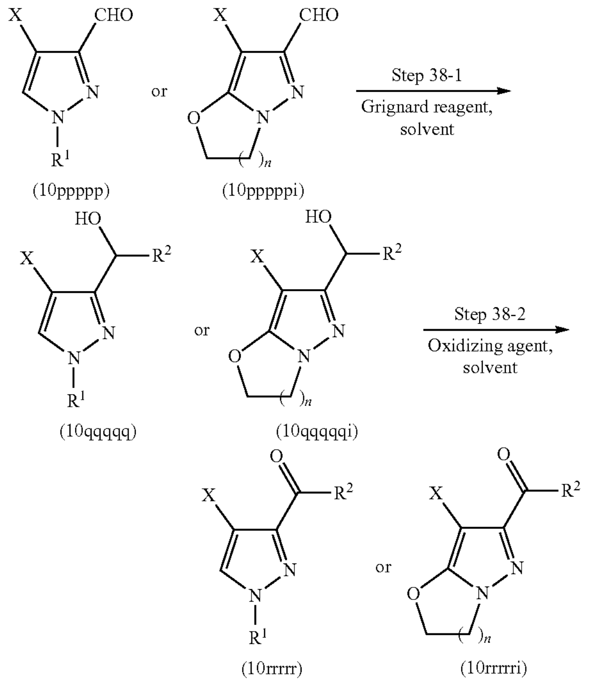

(10ppppp) or (10pppppi)

(10qqqqq) or (10qqqqqi)

(10rrrrr) or (10rrrrri)

-continued

X = Halogen
n = 1, 2
$R^1$ = Me, Et, SEM
$R^2$ = Me, $CF_3$, $CHF_2$

Step 38-1

This step is a step of reacting the compound (10ppppp) with a Grignard reagent to produce the compound (10qqqqq) in solvents such as THE, ether and the like. The Grignard reagent (or its equivalent) used may include methylmagnesium bromide, benzylmagnesium bromide and the like. The amount of Grignard reagent used is about 1 to 2 molar equivalents with respect to 1 mole of the compound (10ppppp). The reaction can be usually performed at 0° C. to room temperature, and usually goes to completion in 0.5-2 hours.

Step 38-2

This step is a step of oxidization of the alcohol moiety in compound (10qqqqq) to produce the compound (10rrrrr) at room temperature. Oxidizing reagent may include Dess-Martin periodinane, 2-Iodoxybenzoic acid (IBX), Pyridinium chlorochromate (PCC) and the like. The solvent used may include DCM, DMSO and the like. The amount of oxidizing reagent used is about 1.5 to 3 molar equivalents with respect to 1 mole of the compound (10qqqqq). The reaction time varies depending on the starting materials, oxidizing reagent and the solvent used.

(1) General Procedure 39

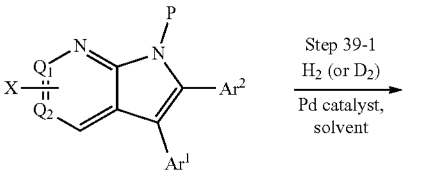

(104)

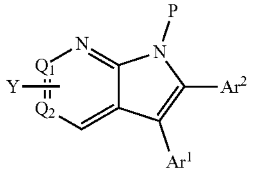

(105)

P = SEM, Boc
$Ar^1$, $Ar^2$ = aryl optionally substituted, heteroaryl optionally substituted, etc
X = halogen
Y = H, D
$Q_1$, $Q_2$ = C(Y), N Step 39-1

This step is a step of reacting the compound (104) with a $H_2$ or $D_2$ (gas) to produce the compound (105) using a palladium catalyst in the presence of a ligand in solvents such as DMSO, DMF and the like. The palladium catalyst used may include Palladium on carbon (Pd/C), $Pd_2(dba)_3$ and the like. Examples of ligand may include $^tBu_3P$, $Me_3P$, $P(Ph)_3$ and the like. The reaction can be usually performed at 80° C. to 90° C., and usually goes to completion in 1-2 hours.

(40) General Procedure 40

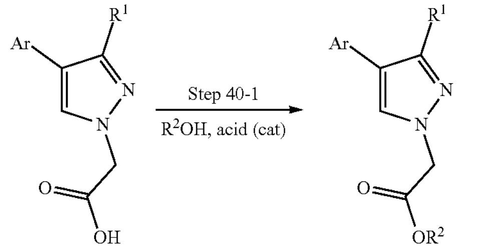

(106) (107)

$R^1$ = $OCHF_2$, $CH_3$, $CF_3$, $CHF_2$, $CH_2F$
$R^2$ = Alkyl
Ar = aryl optionally subsituted, heteroaryl optionally substituted, etc Step 40-1

This step is a step of converting carboxylic acid moiety of compound (106) to the ester of the compound (107) in the presence of alcohol and catalytic amount of acid. The alcohol used, depending on the target ester, may include MeOH, EtOH and the like. The acid used may include $H_2SO_4$, HCl and the like. The reaction can be usually performed at 60° C. to reflux temperature of the alcohol used. The reaction time varies depending on the starting materials, the temperature of the reaction and the solvent used.

(41) General Procedure 41

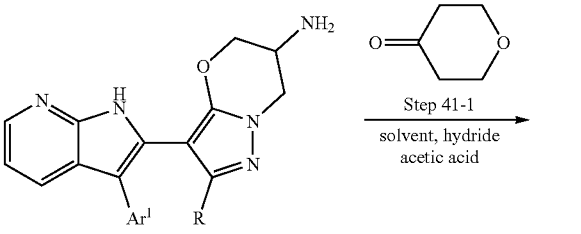

(108)

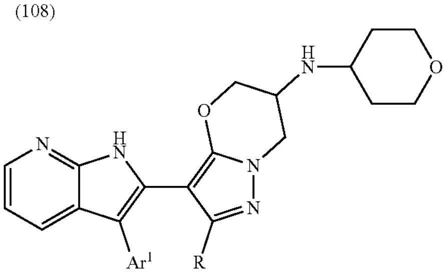

(109)

$Ar^1$ = aryl optionally substituted heteroaryl optinally substituted, etc
R = H, $CH_3$, $CF_3$, $CH_2F$, $CHF_2$ Step 41-1

This step is a reductive amination between compound (108) with tetrahydropyran-4-one to produce the compound (109) in the presence of an acid, reducing agent and in solvent such as methanol. The acid used may include acetic acid, PTSA and the like. The reducing agent used may include Sodium triacetoxyborohydride ($NaBH(OAc)_3$), $NaBH_3CN$ and the like. The amount of the acid and reducing agent used are usually about 1 to 2 molar equivalents each with respect to 1 mole of the compound (108). The reaction time varies depending on the starting materials, the reducing agent and the acid used.

(42) General Procedure 42

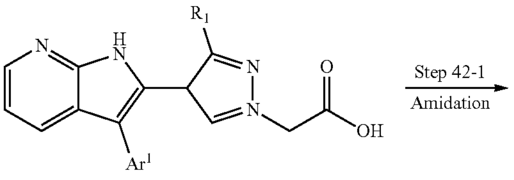

(110)

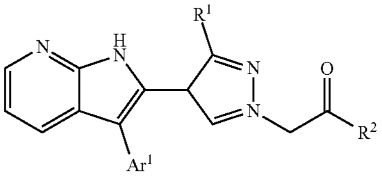

(111)

$Ar^1$ = aryl optionally substituted, heteroaryl optinally substituted, etc
$R^1$ = $CF_3$, $CHF_2$, $CH_2F$, $CH_3$
$R^2$ = amine Step 42-1

This step is a step of converting the carboxylic acid group of the compound (110) to produce the compound (111) by the reaction with an amine in a solvent under the influence of a coupling agent and a base. The coupling agent used may include oxalyl chloride, 1-[bis(dimethylamino)methylene]-1H-1,2,3-triazolo[4,5-b]pyridinium 3-oxid hexafluorophosphate (HATU), N-Ethyl-N'-(3-dimethylaminopropyl) carbodiimide hydrochloride (EDCl), 1-hydroxybenzotriazole (HOBt), dicyclohexylcarbodiimide (DCC), (benzotriazol-1-yl-oxytripyrrolidinophosphonium hexafluorophosphate (PyBOP) and the like. The base used may include TEA, DIPEA and the like. The amount of amine used is about 1 to 2 molar equivalents with respect to 1 mole of the compound (110). The reaction can be usually performed at 0° C. to 50° C. in a solvent such as DMF, $CH_3CN$ and the like. The reaction time varies depending on the starting materials, the coupling agent, the base, the solvent used, and the reaction temperature.

(43) General Procedure 43

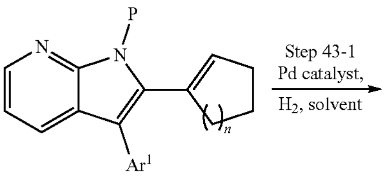

(121)

-continued

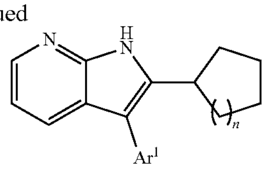

(122)

n = 1, 2

$Ar^1$ = aryl optionally substituted, heteroaryl optinally substituted, etc

P = Boc, SEM

Step 43-1

This step is a step of reducing the isolated olefin in the compound (121) to produce the compound (122) using a palladium catalyst under $H_2$ atmosphere. The palladium catalyst used may include Pd/C, Lindlar catalyst and the like. The reaction can be usually performed at room temperature in a solvent such as MeOH, EtOH and the like. The reaction time varies depending on the starting materials, pressure of $H_2$ gas, and the solvent used.

(44) General Procedure 44

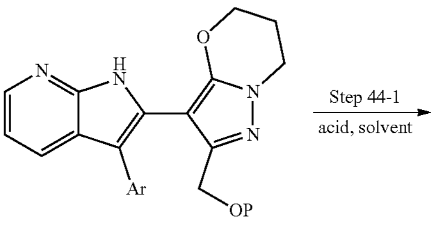

(125)

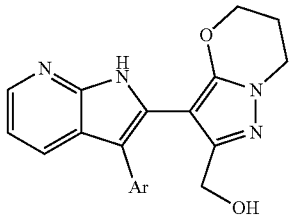

(125a)

Ar = aryl optionally substituted, heteroaryl optinally substituted, etc

P = MOM, THP

Step 44-1

This step is a step of deprotecting alcohol of compound (125) to produce the compound (125a) by the reaction with an alcohol deprotecting agent. The alcohol deprotecting agent used may include HCl, $H_2SO_4$ and the like. The reaction can be usually performed at 0° C. to room temperature with a solvent such as THF. The reaction usually goes to completion in 1-2 h.

(45) General Procedure 45

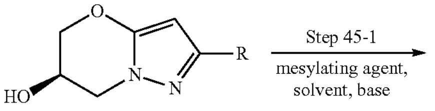

(58q)

-continued

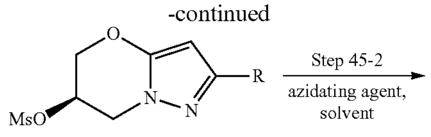

(58r)

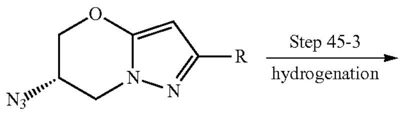

(58s)

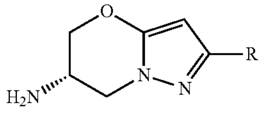

(58t)

The reaction conditions of all steps are carried out by utilizing of the method described in Example 42 of WO2018/136890.

Step 45-1

This step is a step of mesylation of compound (58q) to produce compound (58r) by the reaction with a mesylating reagent in a solvent in the presence of a base. The mesylating reagents used may include methanesulfonyl chloride (MsCl), methanesulfonyl triflate and the like. The base used may include TEA, DIPEA and the like. The amount of the mesylating agent used is about 2 to 2.05 molar equivalents with respect to 1 mole of the compound (58q). The amount of the base used is about 2 to 2.05 molar equivalents with respect to 1 mole of the compound (58q). The reaction can be usually performed at 0° C. to room temperature in the solvent such as DCM, THF and the like. The reaction time varies depending on the starting materials, the mesylating agent, the base and the solvent used.

Step 45-2

This step is a step is azidation of the compound (58r) to produce the compound (58s) by the reaction with an azidation reagent in a solvent. The azidation reagents used may include sodium azide ($NaN_3$), toluenesulfonyl azide ($TsN_3$) and the like. The amount of the azidation agent used is about 2 to 3 molar equivalents with respect to 1 mole of the compound (58r). The reaction can be usually performed at room temperature to 120° C. in the solvent such as DMF, DMSO and the like. The reaction time varies depending on the reaction temperature, starting materials, the azidation agent and the solvent used.

Step 45-3

This step is a step is hydrogenation of the azide moiety of compound (58s) to produce compound (58t) using a palladium catalyst under $H_2$ atmosphere. The palladium catalyst used may include Pd/C, Lindlar catalyst and the like. The reaction can be usually performed at room temperature in a solvent such as MeOH, EtOH and the like. The reaction time varies depending on the starting materials, pressure of $H_2$ gas, and the solvent used.

(46) General Procedure 46

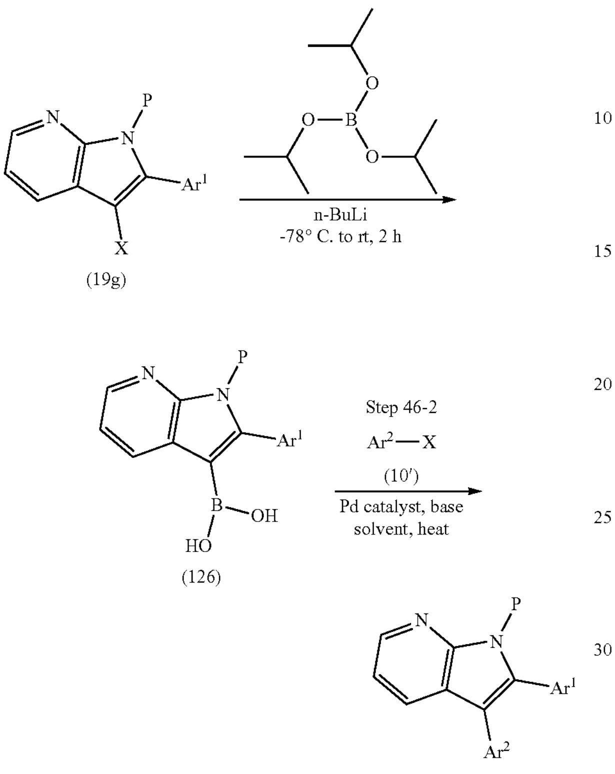

(19g) (126) (10') (7bb)

$Ar^1$, $Ar^2$ = aryl optionally substituted, heteroaryl optionally substituted, etc
X = I, Br
P = Boc, SEM Step 46-1

This step is a step of converting the halide compound (19g) to the boronic acid compound (126). The compound (126) can be produced by first exposing compound (19g) to n-buthyllithium (n-BuLi) at −78° C. then triisopropyl borate. If necessary, HPMC may be used in this step. The amount of n-BuLi and HMPA used is usually about 2 molar equivalents with respect to 1 mole of the compound (19g). The lithiation and borylation can be performed at −78° C. to room temperature, and usually goes to completion in 1-2 hours at room temperature Step 46-2

This step is a step of reacting the compound (126) with an aryl halide or heteroaryl halide compound (10') to produce the compound (7bb), an intermediate used in the procedure 1, using a palladium catalyst in the presence of a base in mixed solvents such as 1,4-dioxane and water. The palladium catalyst used may include Pd(dppf)$Cl_2$-DCM, $Pd_2(dba)_3$ with XPhos, $Pd(PPh_3)_4$ and the like. Examples of base may include $Cs_2CO_3$, $K_2CO_3$ and the like. The amount of aryl halide or heteroaryl halide compound (10') used is about 1 to 2 molar equivalents with respect to 1 mole of the compound (126). The reaction can be usually performed at 80° C. to the reflux temperature of the solvent, and usually goes to completion in 1-2 hours.

(47) General Procedure 47

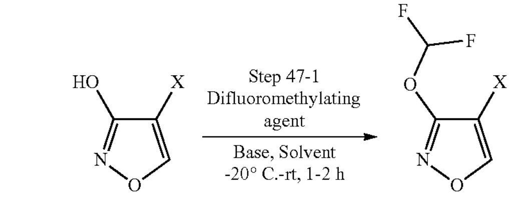

(10qqqqqq) (10rrrrrr)

X = Br, I

Step 47-1

This step is a step of difluoromethylation of compound (10qqqqqq) to produce compound (10rrrrrr) using a difluromethylating agent and base. Examples difluromethylating agent used may include Diethyl (bromodifluoromethyl)phosphonate, 2-halo-2,2-difluoroacetophenone, 2-Bromo-2,2-difluoroacetic acid and the like. The base used may include various bases such as KOH, NaOH, $Cs_2CO_3$, $K_2CO_3$ and the like. The reaction can be usually performed at −20° C. to room temperature in a solvent such as mixture of MeCN, Water and DMF. The amount of the difluromethylating agent used is usually about 1 to 2 molar equivalents with respect to 1 mole of the compound (10qqqqqq). The reaction time varies depending on the starting materials, the difluromethylating agent and the solvent used.

(48) General Procedure 48

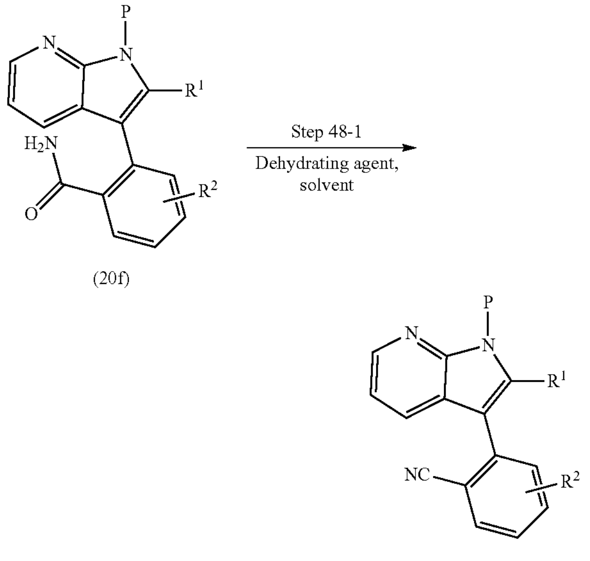

(20f) (20g)

$R^1$ = Alkyl
$R^2$ = H, $OCH_3$, $OCD_3$
P = Boc, SEM

Step 48-1

This step is a step of converting the amide moiety of the compound (20f) to the nitrile in compound (20g) under the influence of dehydrating agent and base. The dehydrating agent used may include Phosphoryl Chloride ($POCl_3$), Phosphorous Chloride ($PCl_3$) and the like. Examples of base may include diethyl amine, pyridine and the like. The reaction can be usually performed at room temperature to the reflux temperature of the solvent such as DCM, $CHCl_3$ and the like. The amount of the dehydrating reagent used is usually about 1 to 1.5 molar equivalents with respect to 1 mole of the compound (20f). The reaction time varies depending on the starting materials, the coupling agents and the solvent used.

(49) General Procedure 49

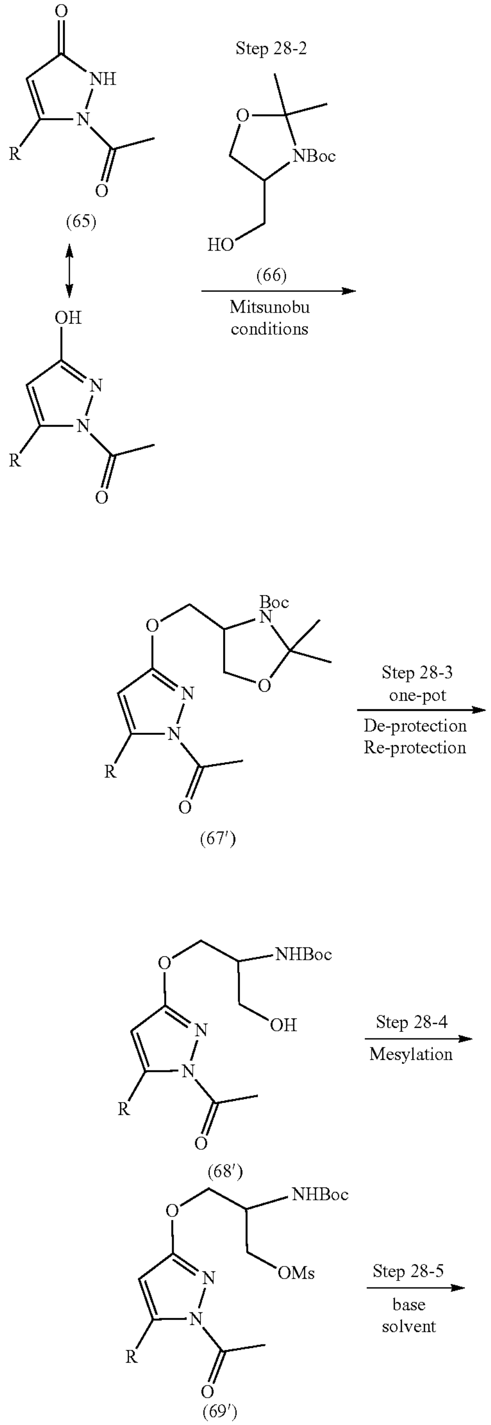

(65) (66) (67') (68') (69')

-continued

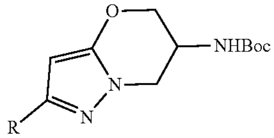

(58k)

R = $CH_3$, $CF_3$, $CHF_2$, $CH_2F$

This procedure is another rout that is different from General Procedure 28 to produce compound (58k). The Mitsunobu reaction is proceeding from the enol form of compound (65) to give the O-alkylating product (67'). The reaction conditions for each step are the same as those described in General Procedure 28.

The reaction conditions of 28-2 are carried out by utilizing of the method described in Example 25 of WO2018/136890.

Step 28-2

This step is a step where compound (65) is reacted with compound (66) under Mitsunobu conditions at room temperature to obtain compound (67') in the presence of a solvent. The reagents used may include diethyl azodicarboxylate (DEAD), diisopropyl azodicarboxylate (DIAD) and the like in the presence of triphenylphosphine (TPP). Examples of the solvent may include THE, DCM and the like. The reaction time varies depending on the starting materials.

Step 28-3

This step is a step where deprotection of Boc and acetonide groups of compounds (67') was achieved by the reaction of p-toluenesulfonic acid (pTSA) at room temperature in a solvent. Examples of the solvent may include MeOH and the like. After complete deprotection of acetyl and Boc groups, protection of the amine with a Boc group was achieved by reaction with $Boc_2O$ in the presence of base and solvent at room temperature. Examples of the base may include $Et_3N$, and the like. Examples of the solvent may include THF and the like.

Step 28-4

This step is a step where the alcohol of compound (68') is converted to a mesyl group in the presence of MesylCl and a base to generate compound (69') at room temperature. Examples of the base may include $Et_3N$, pyridine and the like. Examples of the solvent may include THF, DCM and the like. The reaction time varies depending on the starting material.

Step 28-5

This step is a step where compound (69') is converted to compound (58k) in the presence of base and solvent. Examples of the base may include $K_2CO_3$, and the like. Examples of the solvent may include DMF and the like. The reaction time varies depending on the starting material and temperature of the reaction (80° C.~100° C.).

(50) General Procedure 50

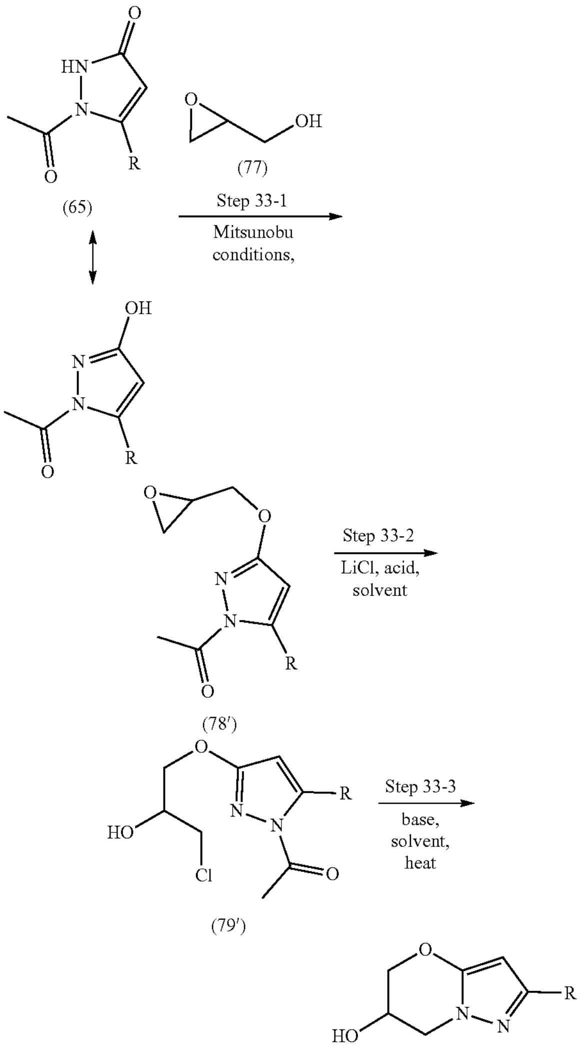

R = $CH_3$, $CF_3$, $CHF_2$, $CH_2F$
P = SEM, TBDPS, Boc

This procedure is another rout that is different from General Procedure 33 to produce compound (580). The Mitsunobu reaction is proceeding from the enol form of compound (65) to give the O-alkylating product (78'). The reaction conditions for each step are the same as those described in General Procedure 33. The same method as above is described in Example A of WO2020018975.

The reaction conditions of Step 33-1, 33-2 and 33-3 are carried out by utilizing of the method described in Example 25 of WO2018/136890.

Step 33-1

This step is a step of N-alkylation of compound (65) with Glycidol (77) under Mitsunobu conditions to produce compound (78'). Examples of the solvent may include THF, diethyl ether and the like. The amount of the Glycidol used is usually about 1 to 1.2 molar equivalents with respect to 1 mole of the compound (65). The reaction can be performed at 0° C. and usually goes to completion in 3-4 hours.

Step 33-2

This step is a step to ring opening of epoxide moiety in compound (78') in the presence of LiCl and acetic acid to produce compound (79'). The reaction can be performed in THF at room temperature and usually goes to completion in 18-24 hours.

Step 33-3

This step is a step to formation of compound (580) from compound (79') in the presence of $K_2CO_3$. The reaction can be performed in DMF at 125° C. to 135° C. and usually goes to completion in 24 to 36 hours.

EXPERIMENTAL PROCEDURES

(1) Experimental Procedure of EX.1

EX. 1 was prepared in accordance with the general procedure 1 using the method described below in detail.

Synthesis of 2-(2-(5-fluoro-2-methoxyphenyl)-1H-pyrrolo[2,3-b]pyridin-3-yl)benzonitrile (EX.1)

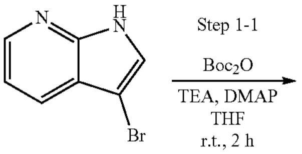

(1a)

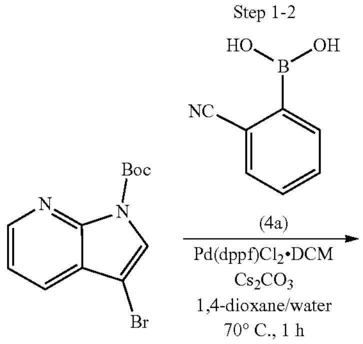

(2a)

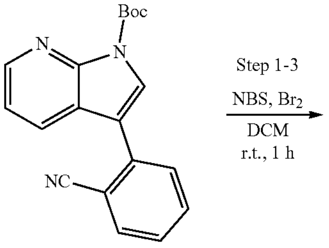

(5a)

-continued

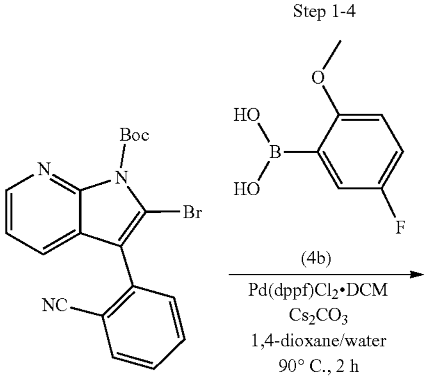

(6a)

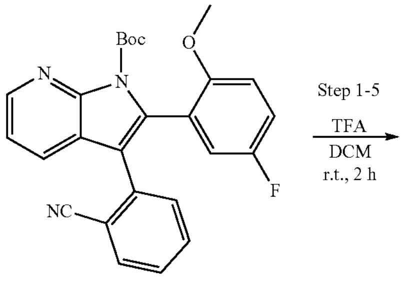

(7a)

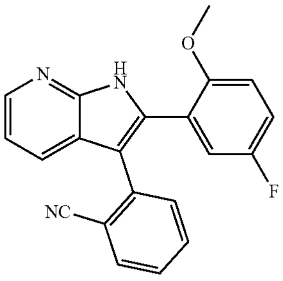

EX. 1

Step 1-1

A mixture of 3-bromo-1H-pyrrolo[2,3-b]pyridine (1.0 g, 5.08 mmol) (1a), $Boc_2O$ (1.33 g, 6.09 mmol), TEA (1.06 mL, 7.61 mmol) and DMAP (61 mg, 0.51 mmol) in THF (20 mL) was stirred at room temperature for 2 h. After concentration, the residue was purified by silica gel column chromatography (0-30% EtOAc/Hexane) to give the expected product as a white solid (1.49 g, 94%); LRMS (ESI): m/z $[M+H]^+$ 297, 299.

Step 1-2

A reaction vessel containing tert-butyl 3-bromo-1H-pyrrolo[2,3-b]pyridine-1-carboxylate (2a) (217 mg, 1.0 mmol), (2-cyanophenyl)boronic acid (4a) (118 mg, 1.1 mmol) and $Cs_2CO_3$ (712 mg, 3.0 mmol) in 1,4-dioxane (3 mL) and water (1 mL) was degassed and backfilled with nitrogen three times. After the addition of Pd(dppf)$Cl_2$·DCM (80 mg, 0.10 mmol), the mixture was purged with nitrogen three times. The resulting mixture was then stirred and heated at 70° C. for 1 h. After cooling to room temperature, the mixture was concentrated. The residue was purified by silica gel column chromatography (0-35% EtOAc/Hexane) to give the expected product as a tan solid (175 mg, 71%); LRMS (ESI): m/z $[M+H]^+$ 320.

Step 1-3

A mixture of tert-butyl 3-(2-cyanophenyl)pyrrolo[2,3-b]pyridine-1-carboxylate (5a) (87 mg, 0.27 mmol), NBS (48 mg, 0.27 mmol) and $Br_2$ (28 μL, 0.54 mmol) in DCM (1 mL) was stirred at room temperature for 1 h. The reaction mixture was adsorbed on silica gel, dried, and purified by silica gel column chromatography (0-30% EtOAc/Hexane) to give the expected product as a light brown solid (54 mg, 47%); LRMS (ESI): m/z $[M+H]^+$ 398, 400.

Step 1-4

A reaction vessel containing tert-butyl 2-bromo-3-(2-cyanophenyl)pyrrolo[2,3-b]pyridine-1-carboxylate (6a) (20 mg, 0.05 mmol), (5-fluoro-2-methoxy-phenyl)boronic acid (4b) (17 mg, 0.10 mmol) and $Cs_2CO_3$ (49 mg, 0.15 mmol) in 1,4-dioxane (0.3 mL) and water (0.1 mL) was degassed and backfilled with nitrogen three times. After the addition of Pd(dppf)$Cl_2$-DCM (4.1 mg, 0.005 mmol), the mixture was purged with nitrogen three times. The resulting mixture was then stirred and heated at 90° C. for 2 h. After cooling to room temperature, the mixture was concentrated. The residue was purified by silica gel column chromatography (0-70% EtOAc/Hexane) to give the expected product as a white solid (12 mg, 50%); LRMS (ESI): m/z $[M+H]^+$ 444.

Step 1-5

A mixture of tert-butyl 3-(2-cyanophenyl)-2-(5-fluoro-2-methoxy-phenyl)pyrrolo[2,3-b]pyridine-1-carboxylate (7a) (12 mg, 0.026 mmol) and neat TFA (0.3 mL) was stirred at room temperature for 2 h. After concentration, the residue was purified by prep HPLC (CH3CN/0.1% TFA-H2O/0.1% TFA) to give EX.1 as a white solid (6 mg, 58%).

$^1$H NMR (400 MHz, DMSO-$d_6$): δ 3.36 (3H, s), 7.01 (1H, dd, J=8.9, 4.3 Hz), 7.09-7.26 (3H, m), 7.37 (1H, d, J=7.8 Hz), 7.49 (1H, t, J=7.7 Hz), 7.68 (1H, t, J=7.7 Hz), 7.81 (1H, d, J=7.9 Hz), 7.87 (1H, d, J=7.8 Hz), 8.33 (1H, dd, J=4.6, 1.4 Hz), 12.29 (1H, s); LRMS (ESI): m/z $[M+H]^+$344.

The following compounds were synthesized using conditions analogous to (7a) in accordance with the general procedure 1.

| Example No. | Chemical structural formula | Spectrum data |
|---|---|---|
| EX.2 | 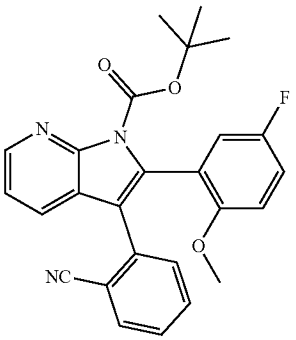 [SMILES: COc1ccc(F)cc1-c1c(-c2ccccc2C#N)c2cccnc2n1C(=O)OC(C)(C)C] | (Mixture of atropisomers)$^{1}$H NMR (400 MHz, DMSO-$d_6$): δ 1.28 (9H, s), 3.63 (1.8H, s), 3.74 (1.2H, s), 6.73-6.82 (0.4H, m), 6.84-6.95 (0.6H, m), 6.98-7.29 (2.4H, m), 7.30-7.43 (1H, m), 7.49-7.90 (4H, m), 7.93-8.05 (0.6H, m), 8.50 (1H, s); LRMS (ESI): m/z $[M + H]^+$ 444. |
| EX.3 | 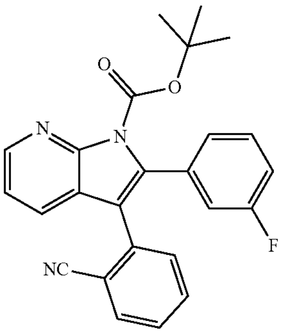 [SMILES: CC(C)(C)OC(=O)n1c(-c2cccc(F)c2)c(-c2ccccc2C#N)c2cccnc21] | $^{1}$H NMR (400 MHz, $CDCl_3$): δ 1.29 (9H, s), 6.95-7.13 (3H, m), 7.19-7.35 (3H, m), 7.43 (1H, td, J = 7.7, 1.3 Hz), 7.53 (1H, td, J = 7.7, 1.3 Hz), 7.67-7.76 (2H, m), 8.61 (1H, dd, J = 4.8, 1.6 Hz); LRMS (ESI): m/z $[M + H\text{-}tBu]^+$ 358, $[M + H]^+$ 414. |
| EX.4 | 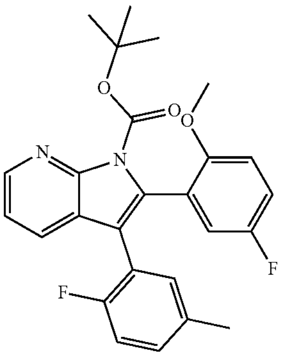 [SMILES: COc1ccc(F)cc1-c1c(-c2cc(C)ccc2F)c2cccnc2n1C(=O)OC(C)(C)C] | $^{1}$H NMR (400 MHz, DMSO-$d_6$): δ 1.27 (9H, s), 2.23 (3H, s), 3.71 (3H, s), 6.91 (1H, dd, J = 8.8, 3.2 Hz), 7.05-7.25 (5H, m), 7.33 (1H, dd, J = 7.9, 4.7 Hz), 7.78-7.80 (1H, m), 8.46 (1H, dd, J = 4.7, 1.6 Hz); LRMS (ESI): m/z $[M + H]^+$ 451. |

The following compounds were synthesized using conditions analogous to EX.1 in accordance with the general procedure 1.

| Example No. | Chemical structural formula | Spectrum data |
|---|---|---|
| EX.5 | 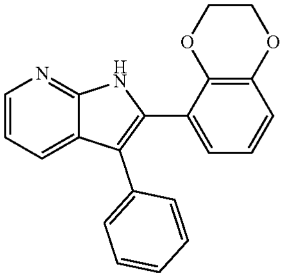 [SMILES: c1ccc(-c2c(-c3cccc4c3OCCO4)[nH]c3ncccc23)cc1] | $^{1}$H NMR (400 MHz, DMSO-$d_6$): δ 3.97 (2H, s), 4.18 (2H, s), 6.77-6.85 (2H, m), 6.87-6.92 (1H, m), 7.13 (1H, dd, J = 4.7, 7.9 Hz), 7.22 (1H, t, J = 7.9 Hz), 7.28 (2H, d, J = 7.2 Hz), 7.35 (2H, t, J = 7.5 Hz), 8.00 (1H, d, J = 8.0 Hz), 8.27 (1H, d, J = 3.9 Hz), 11.93 (1H, s); LRMS (ESI): m/z $[M + H]^+$ 329. |

-continued

| Example No. | Chemical structural formula | Spectrum data |
|---|---|---|
| EX.6 | 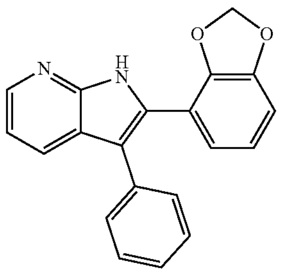 [SMILES: c1ccc(-c2c(-c3cccc4c3OCO4)[nH]c3ncccc23)cc1] | $^{1}$H NMR (400 MHz, DMSO-$d_6$): δ 5.83 (2H, s), 6.81-6.90 (2H, m), 6.94 (1H, dd, J = 8.2, 4.1 Hz), 7.15 (1H, dd, J = 7.9, 4.6 Hz), 7.27 (1H, t, J = 7.9 Hz), 7.30-7.43 (4H, m), 8.00 (1H, d, J = 6.6 Hz), 8.30 (1H, dd, J = 4.6, 1.4 Hz), 12.03 (1H, s); LRMS (ESI): m/z [M + H]$^+$ 315. |
| EX.7 | 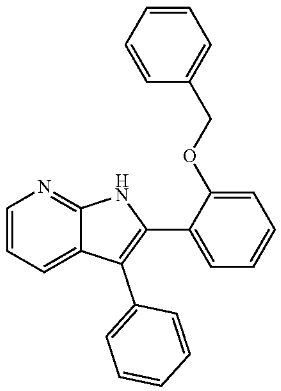 [SMILES: c1ccc(COc2ccccc2-c2[nH]c3ncccc3c2-c2ccccc2)cc1] | $^{1}$H NMR (400 MHz, DMSO-$d_6$); δ 4.99 (2H, s), 6.98 (1 H, t, J = 7.7 Hz), 7.11-7.40 (14H, m), 8.03 (1 H, d, J = 7.7 Hz), 8.25 (1 H, s), 11.96 (1H, s); LRMS (ESI): m/z [M + H]$^+$ 377. |
| EX.8 | 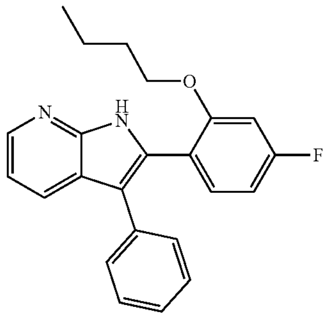 [SMILES: CCCCOc1cc(F)ccc1-c1[nH]c2ncccc2c1-c1ccccc1] | $^{1}$H NMR (400 MHz, DMSO-$d_6$): δ 0.74 (3H, t, J = 7.3 Hz), 1.11-1.18 (2H, m), 1.25-1.33 (2H, m), 3.76 (2H, t, J = 6.5 Hz), 6.82 (1H, t, J = 8.2 Hz), 6.99 (1H, d, J = 11.7 Hz), 7.13 (1H, dd, J = 7.9, 4.7 Hz), 7.20 (1H, td, J = 7.5, 1.3 Hz), 7.26 (2H, d, J = 8.0 Hz), 7.32 (3H, t, J = 6.9 Hz), 8.04 (1H, d, J = 7.9 Hz), 8.26 (1H, d, J = 4.6 Hz), 11.88 (1H, s); LRMS (ESI): m/z [M + H]$^+$ 361. |
| EX.9 | 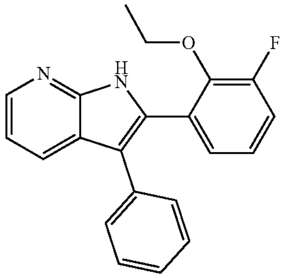 [SMILES: CCOc1c(F)cccc1-c1[nH]c2ncccc2c1-c1ccccc1] | $^{1}$H NMR (400 MHz, DMSO-$d_6$): δ 0.99 (3H, t, J = 7.0 Hz), 3.77 (2H, q, J = 7.0 Hz), 7.12 (2H, t, J = 3.5 Hz), 7.16 (1H, dd, J = 8.0, 4.6 Hz), 7.22 (1H, t, J = 7.4 Hz), 7.26-7.38 (5H, m), 8.05 (1H, d, J = 7.9 Hz), 8.30 (1H, d, J = 3.9 Hz), 12.03 (1H, br s); LRMS (ESI): m/z [M + H]$^+$ 333. |
| EX.10 | 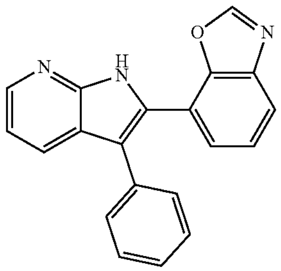 [SMILES: c1ccc(-c2c(-c3cccc4ncoc34)[nH]c3ncccc23)cc1] | $^{1}$H NMR (400 MHz, DMSO-$d_6$) δ 7.15-7.36 (6H, m), 7.40-7.53 (2H, m), 7.84 (1H, dd, J = 7.4, 1.3 Hz), 8.06 (1H, d, J = 8.0 Hz), 8.30 (1H, d, J = 4.8 Hz), 8.65 (1H, s), 12.30 (NH, s); LRMS (ESI): m/z [M + H]$^+$ 312. |

-continued

| Example No. | Chemical structural formula | Spectrum data |
|---|---|---|
| EX.11 | 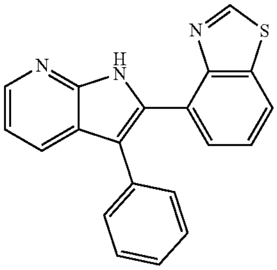 [SMILES: c1ccc(-c2c(-c3cccc4scnc34)[nH]c3ncccc23)cc1] | $^1$H NMR (400 MHz, DMSO-d$_6$): δ 7.14-7.24 (2H, m), 7.25-7.36 (4H, m), 7.38-7.53 (2H, m), 8.03 (1H, d, J = 7.5 Hz), 8.22 (1H, dd, J = 5.6, 2.8 Hz), 8.32 (1H, d, J = 4.5 Hz), 9.42 (1H, s), 12.12 (1H, s); LRMS (ESI): m/z [M + H]$^+$ 328. |
| EX.12 | 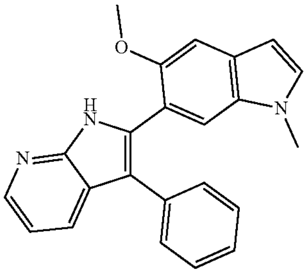 [SMILES: COc1cc2ccn(C)c2cc1-c1[nH]c2ncccc2c1-c1ccccc1] | $^1$H NMR (400 MHz, DMSO-d$_6$): δ 3.57 (3H, s), 3.71 (3H, s), 6.40 (1H, dd, J = 3.0, 0.8 Hz), 7.12-7.37 (9H, m), 7.97-8.07 (1H, d, J = 7.2 Hz), 8.27 (1H, dd, J = 4.7, 1.6 Hz), 11.61 (1H, br s); LRMS (ESI): m/z [M + H]$^+$ 354. |
| EX.13 | 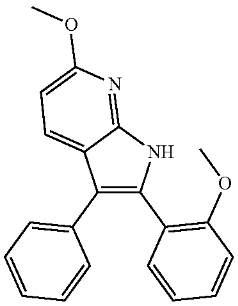 [SMILES: COc1ccc2c(-c3ccccc3)c(-c3ccccc3OC)[nH]c2n1] | $^1$H NMR (400 MHz, DMSO-d$_6$): δ 3.57 (3H, s), 3.90 (3H, s), 6.58 (1H, d, J = 8.5 Hz), 6.90 (1H, t, J = 7.3 Hz), 7.07 (1H, d, J = 8.1 Hz), 7.11-7.39 (7H, m), 7.89 (1H, d, J = 8.6 Hz), 11.70 (1H, br s); LRMS (ESI): m/z [M + H]$^+$ 331. |
| EX.14 | 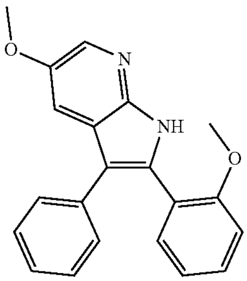 [SMILES: COc1cnc2[nH]c(-c3ccccc3OC)c(-c3ccccc3)c2c1] | $^1$H NMR (400 MHz, DMSO-d$_6$): δ 3.55 (3H, s), 3.83 (3H, s), 6.93 (1H, t, J = 7.4 Hz), 7.08 (1H, d, J = 8.5 Hz), 7.15-7.41 (7H, m), 7.48 (1H, s), 8.01 (1H, s), 11.76 (1H, br s); LRMS (ESI): m/z [M + H]$^+$ 331. |
| EX.15 | 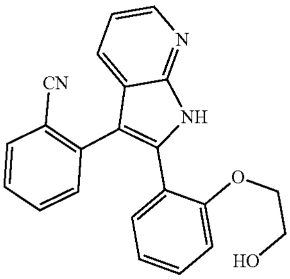 [SMILES: N#Cc1ccccc1-c1c(-c2ccccc2OCCO)[nH]c2ncccc12] | $^1$H NMR (400 MHz, DMSO-d$_6$): δ 3.52-3.55 (2H, m), 3.87-3.90 (2H, m), 4.99 (1H, t, J = 5.5 Hz), 6.92 (1H, t, J = 7.5 Hz), 7.08-7.18 (3H, m), 7.34 (1H, t, J = 7.5 Hz), 7.39 (1H, d, J = 7.7 Hz), 7.48 (1H, t, J = 7.6 Hz), 7.66 (1H, t, J = 7.6 Hz), 7.81 (1H, d, J = 8.0 Hz), 7.86 (1H, d, J = 7.7 Hz), 8.31 (1H, d, J = 4.8 Hz), 12.13 (1H, s); LRMS (ESI): m/z [M + H]$^+$ 356. |

-continued

| Example No. | Chemical structural formula | Spectrum data |
|---|---|---|
| EX.16 | 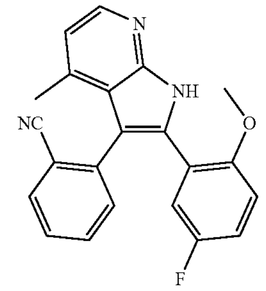 [SMILES: COc1ccc(F)cc1-c1[nH]c2nccc(C)c2c1-c1ccccc1C#N] | $^1$H NMR (400 MHz, DMSO-$d_6$): δ 2.09 (3H, s), 3.45 (3H, s), 6.90 (1H, d, J = 4.6 Hz), 6.96 (1H, dd, J = 9.0, 4.6 Hz), 7.02 (1H, dd, J = 9.1, 3.0 Hz), 7.16 (1H, td, J = 8.7, 3.0 Hz), 7.41 (1H, d, J = 7.3 Hz), 7.49 (1H, t, J = 7.8 Hz), 7.63 (1H, t, J = 7.4 Hz), 7.84 (1H, d, J = 7.3 Hz), 8.16 (1H, d, J = 4.6 Hz), 12.15 (1H, br s); LRMS (ESI): m/z $[M + H]^+$ 358. |
| EX.17 | 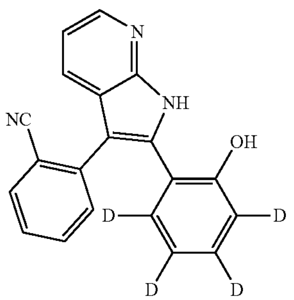 [SMILES: [2H]c1c([2H])c([2H])c(-c2[nH]c3ncccc3c2-c2ccccc2C#N)c(O)c1[2H]] | $^1$H NMR (400 MHz, DMSO-$d_6$): δ 7.11 (1H, dd, J = 7.8, 4.3 Hz), 7.47-7.60 (2H, m), 7.67 (1H, d, J = 7.8 Hz), 7.75 (1H, t, J = 7.8 Hz), 7.91 (1H, d, J = 7.8 Hz), 8.27 (1H, d, J = 4.3 Hz), 9.75 (1H, br s), 12.28 (1H, br s); LRMS (ESI): m/z $[M + H]^+$ 316. |
| EX.18 | 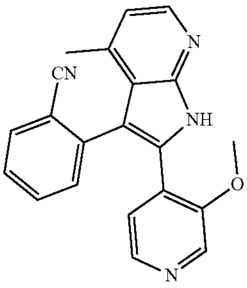 [SMILES: COc1cnccc1-c1[nH]c2nccc(C)c2c1-c1ccccc1C#N] | $^1$H NMR (400 MHz, DMSO-$d_6$): δ 2.09 (3H, s), 3.59 (3H, s), 6.92 (1H, d, J = 4.5 Hz), 7.17 (1H, d, J = 4.5 Hz), 7.41 (1H, d, J = 7.5 Hz), 7.52 (1H, t, J = 7.5 Hz), 7.64 (1H, t, J = 7.5 Hz), 7.86 (1H, d, J = 7.5 Hz), 8.14-8.24 (2H, m), 8.35 (1H, s), 12.30 (1H, br s); LRMS (ESI): m/z $[M + H]^+$ 341. |

(2) Experimental Procedure of EX.19

EX.19 was prepared in accordance with the general procedure 1 using the method described below in detail.

Synthesis of 2-(5-fluoro-2-(2-methoxyphenyl)-1H-pyrrolo[2,3-b]pyridine-3-yl)benzonitrile (EX.19)

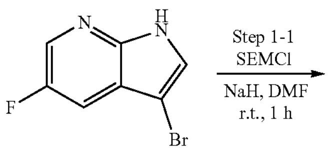

(1b)

-continued

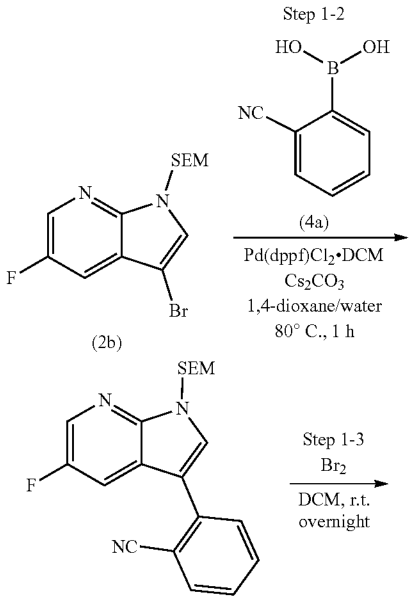

(5b)

-continued

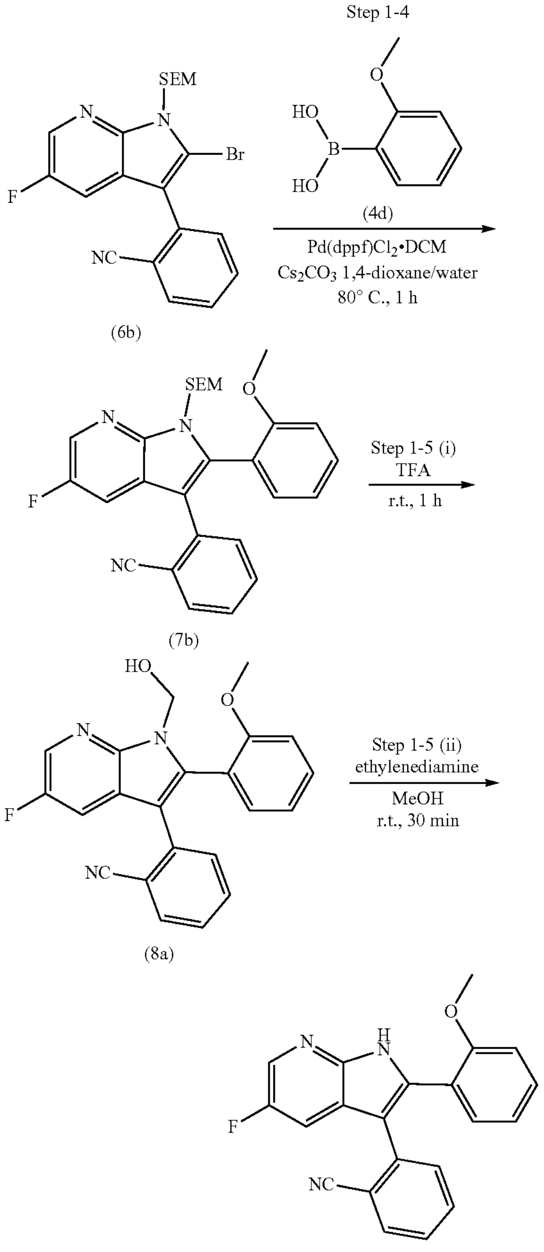

EX. 19

Step 1-1

To a solution of 3-bromo-5-fluoro-1H-pyrrolo[2,3-b]pyridine (1b) (158 mg, 0.73 mmol) in DMF (3.5 mL) was added NaH, 60% dispersion in mineral oil (44.1 mg, 1.10 mmol) and the mixture was stirred at room temperature for 10 min. To this, SEM-Cl (0.16 mL, 0.88 mmol) was added dropwise, and the mixture was stirred at room temperature for 1 h. The mixture was poured into brine and the product was extracted with DCM (×2). The combined organic extracts were dried over $Na_2SO_4$ and concentrated. The residue was used for the next reaction without further purification (235 mg, quantitative yield);

LRMS (ESI): m/z $[M+H]^+$ 345, 347.

Step 1-2

A reaction vessel containing 2-[(3-bromo-5-fluoro-pyrrolo[2,3-b]pyridin-1-yl)methoxy]ethyl-trimethyl-silane (2b) (100.0 mg, 0.29 mmol), (2-cyanophenyl)boronic acid (4a) (46.8 mg, 0.32 mmol) and $Cs_2CO_3$ (283.1 mg, 0.87 mmol) in 1,4-dioxane (3 mL) and water (1 mL) was degassed and backfilled with nitrogen three times. After the addition of Pd(dppf)$Cl_2$-DCM (23.6 mg, 0.03 mmol), the mixture was purged with nitrogen three times. The resulting mixture was stirred and heated at 80° C. for 1 h. After cooling to room temperature, the mixture was filtered through Celite, and the filtrate was concentrated. The residue was purified by silica gel column chromatography (0-20% EtOAc/Hexane) to give the expected product as colorless oil (20.4 mg, 19%); LRMS (ESI): m/z $[M+H]^+$ 368.

Step 1-3

To a solution of 2-[5-fluoro-1-(2-trimethylsilylethoxymethyl)pyrrolo[2,3-b]pyridin-3-yl]benzonitrile (5b) (20.4 mg, 0.06 mmol) in DCM (1 mL) was added 2M $Br_2$ in DCM (0.09 mL, 0.18 mmol) at room temperature and the mixture was stirred at room temperature overnight. The mixture was then diluted with DCM and washed with sat. aq. $NaHCO_3$ (×2). The organic layer was dried over $Na_2SO_4$ and concentrated. The residue was purified by silica gel column chromatography (0-20% EtOAc/Hexane) to give the expected product as yellow oil (14.2 mg, 57%); LRMS (ESI): m/z $[M+H]^+$ 446, 448.

Step 1-4

A reaction vessel containing 2-[2-bromo-5-fluoro-1-(2-trimethylsilylethoxymethyl)pyrrolo[2,3-b]pyridin-3-yl]benzonitrile (6b) (14.2 mg, 0.03 mmol), O-methoxyphenylboronic acid (4d) (4.8 mg, 0.03 mmol) and $Cs_2CO_3$ (31.1 mg, 0.10 mmol) in 1,4-dioxane (0.5 mL) and water (0.1 mL) was degassed and backfilled with nitrogen three times. After the addition of Pd(dppf)$Cl_2$-DCM (2.6 mg, 3.20 μmol), the mixture was purged with nitrogen three times. The resulting mixture was then stirred and heated at 80° C. for 1 h. After cooling to room temperature, the mixture was filtered through Celite, and the filtrate was concentrated. The residue was purified by silica gel column chromatography (0-10% EtOAc/Hexane) to give the expected product as yellow oil (9.4 mg, 62%); LRMS (ESI): m/z $[M+H]^+$ 474.

Step 1-5 (i)

A mixture of 2-[5-fluoro-2-(2-methoxyphenyl)-1-(2-trimethylsilylethoxymethyl)pyrrolo[2,3-b]pyridin-3-yl]benzonitrile (7b) (9.4 mg, 0.02 mmol) and neat TFA (0.15 mL, 1.98 mmol) was stirred at room temperature for 1 h. After concentration to dryness, the residue was used for the next reaction without further purification; LRMS (ESI): m/z $[M+H]^+$374.

Step 1-5 (ii)

To a solution of 2-(5-fluoro-1-(hydroxymethyl)-2-(2-methoxyphenyl)-1H-pyrrolo[2,3-b]pyridin-3-yl)benzonitrile (8a) in MeOH (0.15 mL) was added ethylenediamine (0.13 mL, 1.98 mmol) at room temperature and the mixture was stirred at room temperature for 30 min. The mixture was then poured into brine and the product was extracted with DCM (×2). The combined organic extracts were dried over $Na_2SO_4$ and concentrated. The residue was purified by silica gel column chromatography (0-25% EtOAc/Hexane) to give the expected product as a white solid (6.0 mg, 85%).

$^1H$ NMR (400 MHz, DMSO-$d_6$): δ 3.37 (3H, br s), 6.97 (1H, t, J=7.5 Hz), 7.03 (1H, d, J=8.3 Hz), 7.25 (1H, dd, J=7.6, 1.6 Hz), 7.32 (1H, d, J=7.9 Hz), 7.35-7.42 (1H, m), 7.47 (1H, td, J=7.7, 1.2 Hz), 7.60-7.70 (2H, m), 7.86 (1H, d, J=7.8 Hz), 8.30 (1H, dd, J=2.7, 1.6 Hz), 12.37 (1H, br s); LRMS (ESI): m/z $[M+H]^+$ 344.

The following compounds were synthesized using conditions analogous to EX.19 in accordance with the general procedure 1.

| Example No. | Chemical structural formula | Spectrum data |
|---|---|---|
| EX.20 | 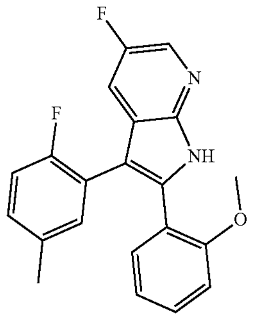 [SMILES: COc1ccccc1-c1[nH]c2ncc(F)cc2c1-c1cc(C)ccc1F] | $^{1}$H NMR (400 MHz, DMSO-$d_6$): δ 2.20 (3H, s), 3.56 (3H, s), 6.93 (1H, t, J = 7.4 Hz), 7.02 (1H, d, J = 6.5 Hz), 7.04-7.13 (3H, m), 7.20 (1H, dd, J = 7.5, 1.4 Hz), 7.37 (1H, t, J = 7.1 Hz), 7.58 (1H, d, J = 9.3 Hz), 8.25 (1H, s), 12.17 (1H, br s); LRMS (ESI): m/z $[M + H]^+$ 351. |
| EX.21 | 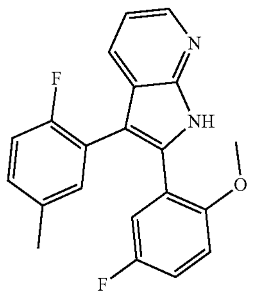 [SMILES: COc1ccc(F)cc1-c1[nH]c2ncccc2c1-c1cc(C)ccc1F] | $^{1}$H NMR (400 MHz, DMSO-$d_6$): δ 2.23 (3H, s), 3.50 (3H, s), 7.04-7.09 (3H, m), 7.09-7.16 (3H, m), 7.21 (1H, td, J = 7.4, 3.8 Hz), 7.80 (1H, d, J = 8.0 Hz), 8.29 (1H, dd, J = 4.7, 1.6 Hz), 12.08 (1H, s); LRMS (ESI): m/z $[M + H]^+$ 351. |
| EX.22 | 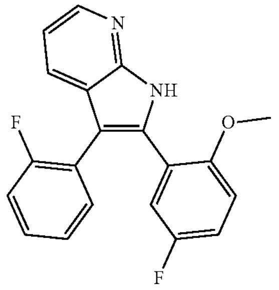 [SMILES: COc1ccc(F)cc1-c1[nH]c2ncccc2c1-c1ccccc1F] | $^{1}$H NMR (400 MHz, DMSO-$d_6$): δ 3.46 (3H, s), 7.04-7.36 (8H, m), 7.79 (1H, dd, J = 7.9, 1.6 Hz), 8.29 (1H, dd, 4.6, 1.6 Hz), 12.12 (1H, br s); LRMS (ESI): m/z $[M + H]^+$ 337. |
| EX.23 | 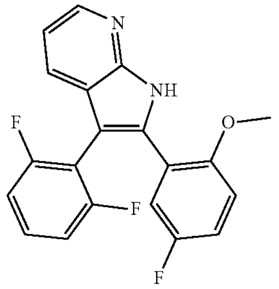 [SMILES: COc1ccc(F)cc1-c1[nH]c2ncccc2c1-c1c(F)cccc1F] | $^{1}$H NMR (400 MHz, DMSO-$d_6$): δ 3.45 (3H, s), 7.03-7.23 (6H, m), 7.37-7.45 (1H, m), 7.70 (1H, dd, J = 7.9, 1.6 Hz), 8.31 (1H, dd, J = 4.7, 1.6 Hz), 12.26 (1H, br s); LRMS (ESI): m/z $[M + H]^+$ 355. |
| EX.24 | 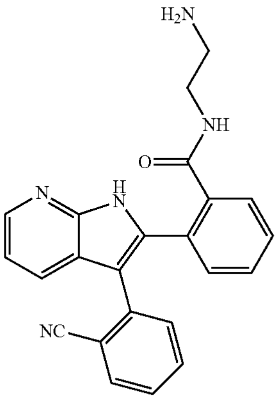 [SMILES: N#Cc1ccccc1-c1c(-c2ccccc2C(=O)NCCN)[nH]c2ncccc12] | $^{1}$H NMR (400 MHz, DMSO-$d_6$): δ 2.47 (2H, t, J = 6.6 Hz) (partially overlapping with DMSO-$d_6$ peak), 2.92(4H, br s), 6.69 (0.5H, br s), 7.15 (1H, dd, J = 7.9, 4.7 Hz), 7.24-7.31 (1H, m), 7.35 (1H, d, J = 6.2 Hz), 7.40-7.62 (5H, m), 7.78 (1H, dd, J = 7.9, 1.5 Hz), 7.80-7.84 (1H, m), 8.04 (0.5H, br s), 8.28-8.30 (1H, m); LRMS (ESI): m/z $[M + H]^+$ 382. |

-continued

| Example No. | Chemical structural formula | Spectrum data |
|---|---|---|
| EX.25 | 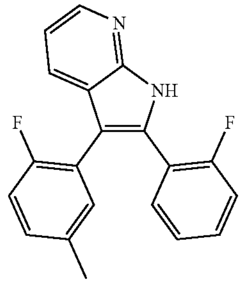 [SMILES: Cc1ccc(F)c(-c2c(-c3ccccc3F)[nH]c3ncccc23)c1] | $^1$H NMR (400 MHz, DMSO-d$_6$): δ 2.25 (3H, s), 7.11-7.20 (4H, m), 7.20-7.31 (2H, m), 7.34-45 (2H, m), 7.83 (1H, d, J = 7.4 Hz), 8.32 (1H, d, J = 4.7 Hz), 12.29 (1H, s); LRMS (ESI): m/z [M + H]$^+$ 321. |
| EX.26 | 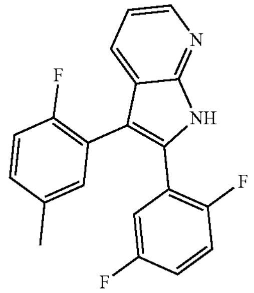 [SMILES: Cc1ccc(F)c(-c2c(-c3cc(F)ccc3F)[nH]c3ncccc23)c1] | $^1$H NMR (400 MHz, DMSO-d$_6$): δ 2.26 (3H, s), 7.14-7.31 (5H, m), 7.32-7.36 (2H, m), 7.86 (1H, d, J = 8.0 Hz), 8.34 (1H, d, J = 4.4 Hz), 12.39 (1H, s); LRMS (ESI): m/z [M + H]$^+$ 339. |
| EX.27 | 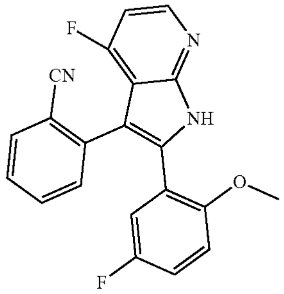 [SMILES: COc1ccc(F)cc1-c1[nH]c2nccc(F)c2c1-c1ccccc1C#N] | $^1$H NMR (400 MHz, DMSO-d$_6$): δ 3.37 (3H, s), 6.96-7.07 (2H, m), 7.14 (1H, dd, J = 9.0, 3.1 Hz), 7.23 (1H, td, J = 8.6, 3.1 Hz), 7.29 (1H, d, J = 7.6 Hz), 7.48 (1H, td, J = 7.7, 1.3 Hz), 7.59 (1H, td, J = 7.7, 1.3 Hz), 7.88 (1H, d, J = 7.8 Hz), 8.31 (1H, dd, J = 8.0, 5.5 Hz), 12.63 (1H, br s); LRMS (ESI): m/z [M + H]$^+$ 362. |
| EX.28 | 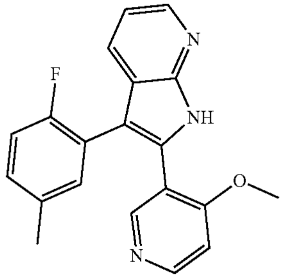 [SMILES: COc1ccncc1-c1[nH]c2ncccc2c1-c1cc(C)ccc1F] | $^1$H NMR (400 MHz, DMSO-d$_6$): δ 2.24 (3H, s), 3.70 (3H, s), 6.97-7.28 (5H, m), 7.81 (1H, d, J = 7.9 Hz), 8.24 (1H, s), 8.30 (1H, dd, J = 4.6, 1.2 Hz), 8.44 (1H, d, J = 5.8 Hz), 11.89 (1H, br s); LRMS (ESI): m/z [M + H]$^+$ 334. |
| EX.29 | 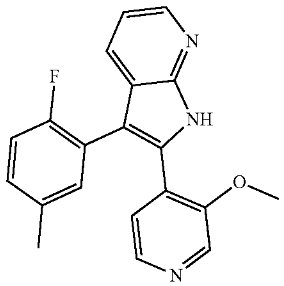 [SMILES: COc1cnccc1-c1[nH]c2ncccc2c1-c1cc(C)ccc1F] | $^1$H NMR (400 MHz, DMSO-d$_6$): δ 2.25 (3H, s), 3.65 (3H, s), 7.03-7.18 (4H, m), 7.22 (1H, d, J = 4.8 Hz), 7.74 (1H, dt, J = 7.4 Hz), 8.20 (1H, d, J = 4.8 Hz), 8.33 (1H, dd, J = 4.7, 1.6 Hz), 8.44 (1H, s), 12.01 (1H, br s); LRMS (ESI): m/z [M + H]$^+$ 334. |

-continued

| Example No. | Chemical structural formula | Spectrum data |
| --- | --- | --- |
| EX.30 | 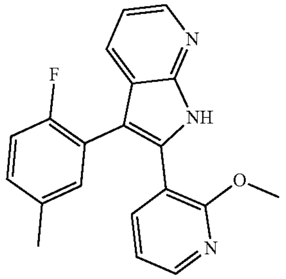 [SMILES: COc1ncccc1-c1[nH]c2ncccc2c1-c1cc(C)ccc1F] | $^1$H NMR (400 MHz, DMSO-$d_6$): δ 2.24 (3H, s), 3.68 (3H, s), 7.01 (1H, dd, J = 7.9, 4.7 Hz), 7.07-7.15 (4H, m), 7.60 (1H, dd, J = 7.9, 1.8 Hz), 7.82 (1H, d, J = 7.9 Hz), 8.19 (1H, dd, J = 4.8, 1.8 Hz), 8.30 (1H, dd, J = 4.8, 1.8 Hz), 12.13 (1H, br s); LRMS (ESI): m/z $[M + H]^+$ 334. |
| EX.31 | 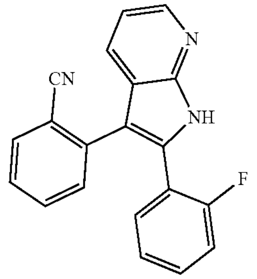 [SMILES: N#Cc1ccccc1-c1c(-c2ccccc2F)[nH]c2ncccc12] | $^1$H NMR (400 MHz, DMSO-$d_6$): δ 7.18 (1H, dd, J = 7.6, 4.2 Hz), 7.22-7.28 (2H, m), 7.37 (1H, td, J = 7.6, 1.5 Hz), 7.42-7.48 (2H, m), 7.50 (1H, t, J = 7.6 Hz), 7.70 (1H, td, J = 7.6, 1.2 Hz), 7.87 (2H, t, J = 7.9 Hz), 8.36 (1H, dd, J = 4.6, 1.5 Hz), 12.49 (1H, br s); LRMS (ESI): m/z $[M + H]^+$ 314. |
| EX.32 | 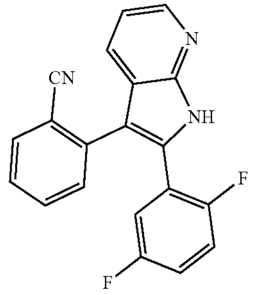 [SMILES: N#Cc1ccccc1-c1c(-c2cc(F)ccc2F)[nH]c2ncccc12] | $^1$H NMR (400 MHz, DMSO-$d_6$): δ 7.10-7.19 (1H, m), 7.23-7.35 (3H, m), 7.46-7.52 (2H, m), 7.71 (1H, t, J = 7.7 Hz), 7.78-7.94 (2H, m), 8.35 (1H, d, J = 4.2 Hz), 12.55 (1H, br s); LRMS (ESI): m/z $[M + H]^+$ 332. |
| EX.33 | 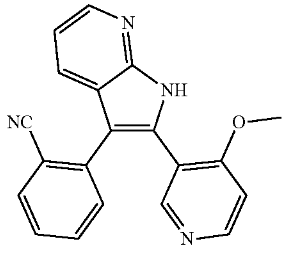 [SMILES: COc1ccncc1-c1[nH]c2ncccc2c1-c1ccccc1C#N] | $^1$H NMR (400 MHz, DMSO-$d_6$): δ 3.56 (3H, s), 7.10 (1H, d, J = 5.6 Hz), 7.17 (1H, dd, J = 7.9, 4.4 Hz), 7.42 (1H, d, J = 8.1 Hz), 7.50 (1H, t, J = 8.2 Hz), 7.69 (1H, t, J = 7.7 Hz), 7.82-7.87 (2H, m), 8.27 (1H, s), 8.34 (1H, d, J = 4.4 Hz), 8.44 (1H, d, J = 5.6 Hz), 12.37 (1H, br s); LRMS (ESI): m/z $[M + H]^+$ 327. |
| EX.34 | 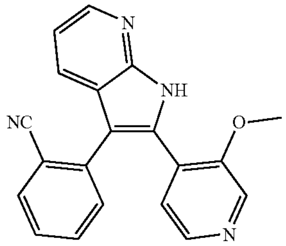 [SMILES: COc1cnccc1-c1[nH]c2ncccc2c1-c1ccccc1C#N] | $^1$H NMR (400 MHz, DMSO-$d_6$): δ 3.52 (3H, s), 7.18 (1H, dd, J = 7.9, 4.6 Hz), 7.27 (1H, d, J = 4.8 Hz), 7.39 (1H, d, J = 7.8 Hz), 7.51 (1H, t, J = 7.7 Hz), 7.70 (1H, t, J = 7.7 Hz), 7.84 (1H, d, J = 7.9 Hz), 7.88 (1H, d, J = 7.8 Hz), 8.24 (1H, d, J = 4.8 Hz), 8.37 (1H, d, J = 4.6 Hz), 8.39 (1H, s), 12.38 (1H, br s); LRMS (ESI): m/z $[M + H]^+$ 327. |

-continued

| Example No. | Chemical structural formula | Spectrum data |
|---|---|---|
| EX.35 | 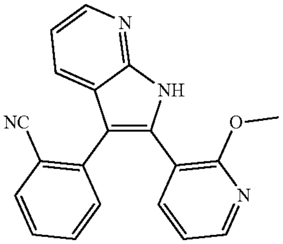 [SMILES: COc1ncccc1-c1[nH]c2ncccc2c1-c1ccccc1C#N] | $^1$H NMR (400 MHz, DMSO-$d_6$): δ 3.55 (3H, s), 7.04 (1H, dd, J = 7.3, 4.9 Hz), 7.17 (1H, dd, J = 7.6, 4.9 Hz ), 7.41 (1H, d, J = 7.7 Hz), 7.49 (1H, t, J = 7.7 Hz) 7.65 (1H, dd, J = 7.3, 1.8 Hz), 7.70 (1H, td, J = 7.3, 1.2 Hz), 7.83 (1H, dd, J = 7.6, 0.9 Hz), 7.87 (1H, dd, J = 7.6, 0.9 Hz), 8.19 (1H, dd, J = 4.9, 1.8 Hz), 8.33 (1H, d, J = 4.7 Hz), 12.35 (1H, s); LRMS (ESI): m/z $[M + H]^+$ 327. |
| EX.36 | 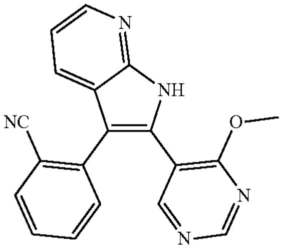 [SMILES: COc1ncncc1-c1[nH]c2ncccc2c1-c1ccccc1C#N] | $^1$H NMR (400 MHz, DMSO-$d_6$): δ 3.66 (3H, s), 7.20 (1H, dd, J = 8.1, 4.6 Hz), 7.48-7.58 (2H, m), 7.75 (1H, td, J = 7.6, 1.3 Hz), 7.88 (2H, d, J = 8.1 Hz), 8.38 (1H, dd, J = 4.7, 1.3 Hz), 8.45 (1H, s), 8.81 (1H, s), 12.1 (1H, br s). LRMS (ESI): m/z $[M + H]^+$ 328. |
| EX.37 | 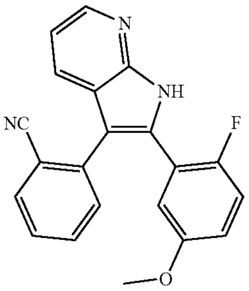 [SMILES: COc1ccc(F)c(-c2[nH]c3ncccc3c2-c2ccccc2C#N)c1] | $^1$H NMR (400 MHz, DMSO-$d_6$): δ 3.68 (3H, s), 6.90-7.02 (2H, m), 7.11-7.24 (2H, m), 7.46 (1H, d, J = 7.9 Hz), 7.52 (1H, t, J = 7.7 Hz), 7.71 (1H, t, J = 7.7 Hz), 7.84 (1H, d, J = 7.9 Hz), 7.88 (1H, d, J = 7.8 Hz), 8.36 (1H, d, J = 4.5 Hz), 12.50 (1H, br s); LRMS (ESI): m/z $[M + H]^+$ 344. |
| EX.38 | 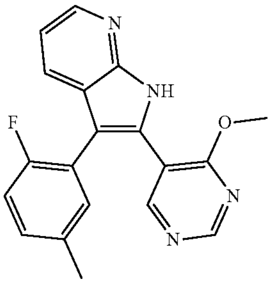 [SMILES: COc1ncncc1-c1[nH]c2ncccc2c1-c1cc(C)ccc1F] | $^1$H NMR (400 MHz, DMSO-$d_6$): δ 2.27 (3H, s), 3.76 (3H, s), 7.08-7.22 (4H, m), 7.87 (1H, d, J = 7.9 Hz), 8.34 (1H, dd, J = 4.8, 1.1 Hz) 8.43 (1H, s), 8.80 (1H, s), 12.28 (1H, s); LRMS (ESI): m/z $[M + H]^+$ 335. |
| EX.39 | 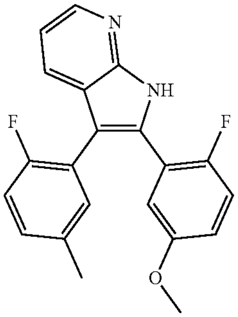 [SMILES: COc1ccc(F)c(-c2[nH]c3ncccc3c2-c2cc(C)ccc2F)c1] | $^1$H NMR (400 MHz, DMSO-$d_6$): δ 2.25 (3H, s), 3.70 (3H, s), 6.96-6.99 (2H, m), 7.09-7.20 (5H, m), 7.82 (1H, d, J = 7.6 Hz), 8.33 (1H, dd, J = 4.6, 1.4 Hz), 12.30 (1H, br s); LRMS (ESI): m/z $[M + H]^+$ 351. |

-continued

| Example No. | Chemical structural formula | Spectrum data |
|---|---|---|
| EX.40 | 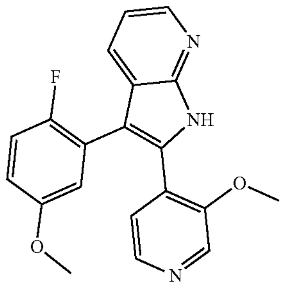 [SMILES: COc1ccc(F)c(-c2c(-c3ccncc3OC)[nH]c3ncccc23)c1] | $^1$H NMR (400 MHz, DMSO-d$_6$): δ 3.65 (3H, s), 3.67 (3H, s), 6.75 (1H, dd, J = 6.0, 3.1 Hz), 6.84-6.94 (1H, m), 7.13-7.19 (2H, m), 7.26 (1H, t, J = 6.0 Hz), 7.87 (1H, d, J = 7.8 Hz), 8.23 (1H, dd, J = 10.5, 3.0 Hz), 8.33 (1H, dd, J = 4.7, 1.4 Hz ), 8.45 (1H, s), 12.33 (1H, br s); LRMS (ESI): m/z [M + H]$^+$ 350. |
| EX.41 | 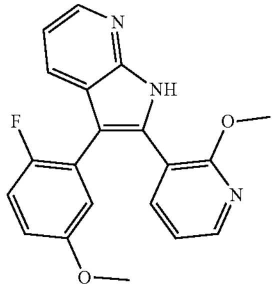 [SMILES: COc1ccc(F)c(-c2c(-c3cccnc3OC)[nH]c3ncccc23)c1] | $^1$H NMR (400 MHz, DMSO-d$_6$): δ 3.64 (3H, s), 3.68 (3H, s), 6.75 (1H, dd, J = 7.4, 4.5 Hz), 6.83-6.91 (1H, m), 7.03 (1H, dd, J = 7.3, 5.0 Hz), 7.11-7.19 (2H, m), 7.64 (1H, dd, J = 7.4, 1.2 Hz), 7.86 (1H, t, J = 9.2 Hz), 8.20 (1H, dd, J = 5.0, 1.8 Hz), 8.30 (1H, dd, J = 4.6, 1.4 Hz), 12.17 (1H, s); LRMS (ESI): m/z [M + H]$^+$ 350. |
| EX.42 | 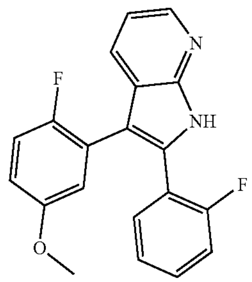 [SMILES: COc1ccc(F)c(-c2c(-c3ccccc3F)[nH]c3ncccc23)c1] | $^1$H NMR (400 MHz, DMSO-d$_6$): δ 3.65 (3H, s), 6.75 (1H, dd, J = 7.9, 4.5 Hz), 6.88 (1H, dt, J = 9.0, 3.5 Hz), 7.13-7.16 (2H, m), 7.22-7.27 (2H, m), 7.42-7.49 (2H, m), 7.87 (1H, dd, J = 7.9, 1.5 Hz), 8.32 (1H, dd, J = 4.2, 1.5 Hz ), 12.34 (1H, s); LRMS (ESI): m/z [M + H]$^+$ 337. |
| EX.43 | 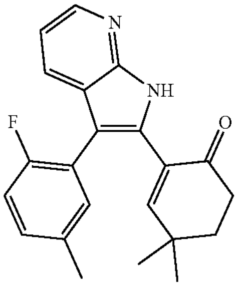 [SMILES: Cc1ccc(F)c(-c2c(C3=CC(C)(C)CCC3=O)[nH]c3ncccc23)c1] | $^1$H NMR (400 MHz, DMSO-d$_6$): δ 1.04 (6H, s), 1.86 (2H, t, J = 6.8 Hz), 2.31 (3H, s), 2.53 (2H, t, J = 6.8 Hz), 6.59 (1H, s), 7.08-7.18 (4H, m), 7.80 (1H, dt, J = 7.6, 1.6 Hz), 8.25 (1H, dd, J = 4.6, 1.6 Hz), 11.79 (1H, s); LRMS (ESI): m/z [M + H]$^+$ 349. |
| EX.44 | 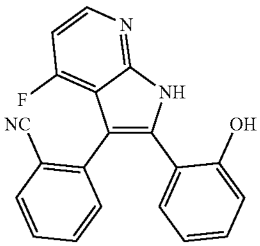 [SMILES: N#Cc1ccccc1-c1c(-c2ccccc2O)[nH]c2nccc(F)c12] | $^1$H NMR (400 MHz, DMSO-d$_6$): δ 6.76 (1H, t, J = 7.1 Hz), 6.85 (1H, d, J = 7.9 Hz), 7.00 (1H, dd, J = 11.0, 5.4 Hz), 7.06 (1H, d, J = 6.2 Hz), 7.18 (1H, t, J = 7.8 Hz), 7.29 (1H, d, J = 7.7 Hz), 7.43 (1H, t, J = 7.7 Hz), 7.55 (1H, t, J = 7.7 Hz), 7.84 (1H, d, J = 7.7 Hz), 8.27 (1H, dd, J = 8.0, 5.5 Hz), 9.76 (1H, br s), 12.41 (1H, br s); LRMS (ESI): m/z [M + H]$^+$ 330. |

-continued

| Example No. | Chemical structural formula | Spectrum data |
| --- | --- | --- |
| EX.45 | 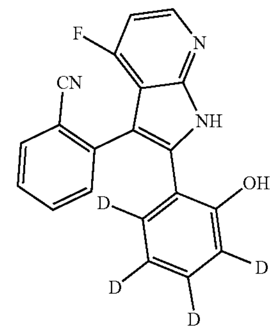 [SMILES: [2H]c1c([2H])c([2H])c(-c2[nH]c3nccc(F)c3c2-c2ccccc2C#N)c(O)c1[2H]] | $^1$H NMR (400 MHz, DMSO-d$_6$): δ 6.98 (1H, dd, J = 10.8, 5.6 Hz), 7.49 (1H, d, J = 7.5 Hz), 7.54 (1H, t, J = 7.5 Hz), 7.69 (1H, t, J = 7.5 Hz), 7.90 (1H, d, J = 7.5 Hz), 8.25 (1H, dd, J = 7.4, 5.6 Hz), 9.76 (1H, br s), 12.59 (1H, br s); LRMS (ESI): m/z [M + H]$^+$ 334. |
| EX.46 | 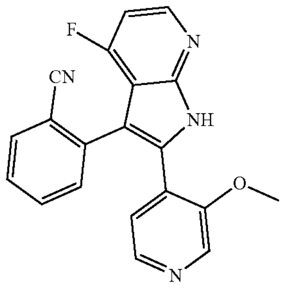 [SMILES: COc1cnccc1-c1[nH]c2nccc(F)c2c1-c1ccccc1C#N] | $^1$H NMR (400 MHz, CD$_3$OD): δ 3.71 (3H, s), 6.97 (1H, dd, J = 10.6, 5.5 Hz), 7.26 (1H, d, J = 4.9 Hz), 7.42 (1H, d, J = 7.4 Hz), 7.50 (1H, t, J = 7.7 Hz), 7.62 (1H, t, J = 7.4 Hz), 7.79 (1H, d, J = 7.7 Hz), 8.16 (1H, d, J = 4.9 Hz), 8.28-8.37 (2H, m); LRMS (ESI): m/z [M + H]$^+$ 345. |
| EX.47 | 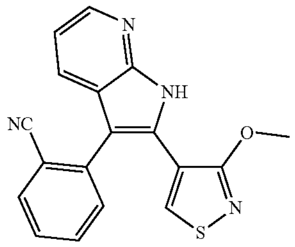 [SMILES: COc1nscc1-c1[nH]c2ncccc2c1-c1ccccc1C#N] | $^1$H NMR (400 MHz, DMSO-d$_6$): δ 3.65 (3H, s), 7.16 (1H, dd, J = 8.0, 4.7 Hz), 7.47 (1H, d, J = 7.8 Hz), 7.54 (1H, t, J = 7.6 Hz), 7.74 (1H, td, J = 7.8, 1.2 Hz), 7.80 (1H, d, J = 8.0 Hz), 7.91 (1H, d, J = 7.8 Hz), 8.34 (1H, dd, J = 4.7, 1.5 Hz), 8.83 (1H, s), 12.31 (1H, s); LRMS (ESI): m/z [M + H]$^+$ 333. |
| EX.48 | 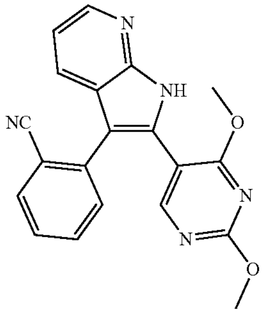 [SMILES: COc1ncc(-c2[nH]c3ncccc3c2-c2ccccc2C#N)c(OC)n1] | $^1$H NMR (400 MHz, DMSO-d$_6$): δ 3.65 (3H, s), 3.93 (3H, s), 7.18 (1H, dd, J = 7.9, 4.7 Hz), 7.49-7.54 (2H, m), 7.74 (1H, td, J = 7.7, 1.3 Hz), 7.85 (1H, dd, J = 7.9, 1.6 Hz), 7.89 (1H, d, J = 7.7 Hz), 8.22 (1H, s), 8.34 (1H, dd, J = 4.7, 1.6 Hz), 12.38 (1H, br s); LRMS (ESI): m/z [M + H]$^+$ 358. |
| EX.49 | 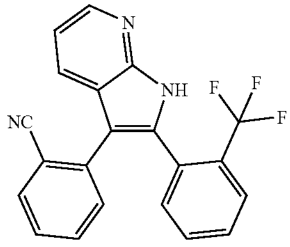 [SMILES: N#Cc1ccccc1-c1c(-c2ccccc2C(F)(F)F)[nH]c2ncccc12] | $^1$H NMR (400 MHz, DMSO-d$_6$): δ 7.20 (2H, dd, J = 8.0, 5.1 Hz), 7.44 (1H, t, J = 7.2 Hz), 7.51-7.58 (1H, m), 7.61-8.01 (6H, m), 8.36 (1H, dd, J = 4.5, 1.4 Hz), 12.43 (1H, s); LRMS (ESI): m/z [M + H]$^+$ 364. |

-continued

| Example No. | Chemical structural formula | Spectrum data |
|---|---|---|
| EX.50 | 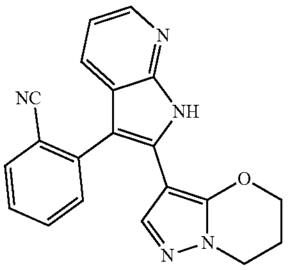 [SMILES: N#Cc1ccccc1-c1c(-c2cnn3c2OCCC3)[nH]c2ncccc12] | $^{1}$H NMR (400 MHz, DMSO-$d_6$): δ 2.01-2.12 (2H, m), 3.90-4.01 (2H, m), 4.07 (2H, dd, J = 12.2, 7.3 Hz), 7.08 (1H, dd, J = 7.9, 4.7 Hz), 7.39 (1H, s), 7.47 (1H, d, J = 7.9 Hz), 7.51 (1H, dd, J = 7.6, 0.9 Hz), 7.66 (1H, dd, J = 7.9, 1.5 Hz), 7.71 (1H, dd, J = 7.9, 1.4 Hz), 7.89 (1H, dd, J = 7.6, 1.2 Hz), 8.22 (1H, dd, J = 4.7, 1.5 Hz), 11.93 (1H, s); LRMS (ESI): m/z $[M + H]^+$ 342. |
| EX.51 | 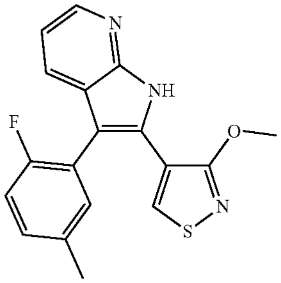 [SMILES: COc1nscc1-c1[nH]c2ncccc2c1-c1cc(C)ccc1F] | $^{1}$H NMR (400 MHz, DMSO-$d_6$): δ 2.29 (3H, s), 3.78 (3H, s), 7.08-7.27 (4H, m), 7.78 (1H, d, J = 7.6 Hz), 8.30 (1H, dd, J = 4.6, 1.5 Hz), 8.79 (1H, s), 12.07 (1H, s); LRMS (ESI): m/z $[M + H]^+$ 340. |
| EX.52 | 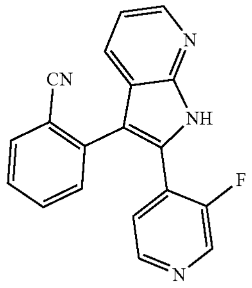 [SMILES: N#Cc1ccccc1-c1c(-c2ccncc2F)[nH]c2ncccc12] | $^{1}$H NMR (400 MHz, DMSO-$d_6$): δ 7.23 (1H, dd, J = 7.8, 5.4 Hz ), 7.44 (1H, dd, J = 5.8, 5.4 Hz), 7.54 (1H, d, J = 7.8 Hz), 7.58 (1H, dd, J = 7.8, 0.7 Hz), 7.76 (1H, td, J = 7.6, 0.7 Hz), 7.91 (2H, dd, J = 7.2, 0.7 Hz), 8.44 (1H, dd, J = 4.8, 1.2 Hz), 8.49 (1H, d, J = 5.0 Hz), 8.63 (1H, d, J = 2.0 Hz), 12.71 (1H, s); LRMS (ESI): m/z $[M + H]^+$ 315. |
| EX.53 | 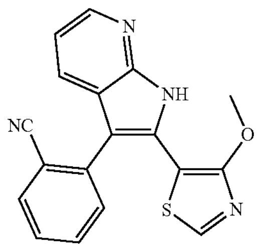 [SMILES: COc1ncsc1-c1[nH]c2ncccc2c1-c1ccccc1C#N] | $^{1}$H NMR (400 MHz, DMSO-$d_6$): δ 3.64 (3H, s), 7.06 (1H, d, J = 5.5 Hz), 7.12 (1H, dd, J = 7.9, 4.7 Hz), 7.49 (1H, dd, J = 7.8, 0.4 Hz), 7.52-7.60 (2H, m), 7.67 (1H, dd, J = 8.0, 1.3 Hz), 7.75 (1H, td, J = 8.0, 1.3 Hz), 7.92 (1H, dd, J = 7.8, 0.4 Hz), 8.29 (1H, dd, J = 4.6, 1.3 Hz), 11.95 (1H, s); LRMS (ESI): m/z $[M + H]^+$ 332. |
| EX.54 | 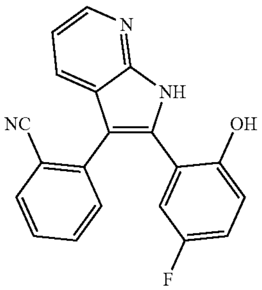 [SMILES: N#Cc1ccccc1-c1c(-c2cc(F)ccc2O)[nH]c2ncccc12] | $^{1}$H NMR (400 MHz, DMSO-$d_6$): δ 6.76 (1H, dd, J = 8.8, 4.9 Hz), 6.84 (1H, dd, J = 10.0, 3.1 Hz), 6.95 (1H, td, J = 8.4, 2.8 Hz), 7.05 (1H, dd, J = 7.7, 4.6 Hz), 7.44 (1H, d, J = 7.8 Hz), 7.49 (1H, td, J = 7.6, 1,2 Hz), 7.58-7.74 (2H, m), 7.83-7.94 (1H, m), 8.24 (1H, dd, J = 4.5, 1.3 Hz); LRMS (ESI): m/z $[M + H]^+$ 330. |

-continued

| Example No. | Chemical structural formula | Spectrum data |
|---|---|---|
| EX.55 | 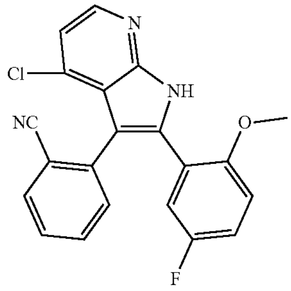 [SMILES: COc1ccc(F)cc1-c1[nH]c2nccc(Cl)c2c1-c1ccccc1C#N] | $^1$H NMR (400 MHz, DMSO-$d_6$): δ 3.45 (3H, s), 6.99 (1H, dd, J = 9.2, 4.5 Hz), 7.10 (1H, dd, J = 9.0, 3.2 Hz), 7.20 (1H, dd, J = 8.4, 3.2 Hz), 7.24 (1H, d, J = 5.2 Hz), 7.33 (1H, dd, J = 7.7, 0.7 Hz), 7.49 (1H, td, J = 7.7, 1.3 Hz), 7.59 (1H, td, J = 7.7, 1.4 Hz), 7.86 (1H, dd, J = 7.7, 0.9 Hz), 8.26 (1H, d, J = 5.1 Hz), 12.63 (1H, s); LRMS (ESI): m/z [M + H]$^+$ 378. |
| EX.56 | 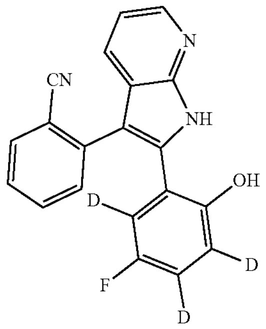 [SMILES: [2H]c1c([2H])c(F)c([2H])c(-c2[nH]c3ncccc3c2-c2ccccc2C#N)c1O] | $^1$H NMR (400 MHz, DMSO-$d_6$): δ 7.14 (1H, dd, J = 7.8, 4.6 Hz), 7.39 (1H, d, J = 7.8 Hz), 7.48 (1H, t, J = 7.8 Hz), 7.66 (1H, t, J = 7.8 Hz), 7.78 (1H, d, J = 7.8 Hz), 7.86 (1H, d, J = 7.8 Hz), 8.27 (1H, d, J = 4.6 Hz), 9.68 (1H, br s), 12.15 (1H, br s); LRMS (ESI): m/z [M + H]$^+$ 333. |
| EX.57 | 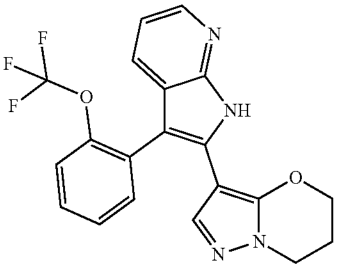 [SMILES: FC(F)(F)Oc1ccccc1-c1c(-c2cnn3c2OCCC3)[nH]c2ncccc12] | $^1$H NMR (400 MHz, DMSO-$d_6$): δ 2.08 (2H, t, J = 6.1 Hz), 3.97-4.04 (2H, m), 4.06 (2H, t, J = 6.1 Hz), 7.04 (1H, dd, J = 7.8, 4.7 Hz), 7.26 (1H, s), 7.38-7.41 (2H, m), 7.41-7.51 (2H, m), 7.53-7.60 (1H, m), 8.15-8.20 (1H, m), 11.67 (1H, s); LRMS (ESI): m/z [M + H]$^+$ 401. |
| EX.58 | 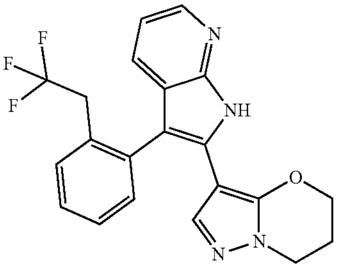 [SMILES: FC(F)(F)Cc1ccccc1-c1c(-c2cnn3c2OCCC3)[nH]c2ncccc12] | $^1$H NMR (400 MHz, DMSO-$d_6$): δ 2.12 (2H, dt, J = 10.6, 5.9 Hz), 3.37-3.51 (2H, m), 4.05 (2H, t, J = 6.0 Hz), 4.09-4.21 (2H, m), 6.95 (1H, s), 7.02 (1H, dd, J = 7.8, 4.7 Hz), 7.23-7.28 (1H, m), 7.41 (3H, td, J = 7.5, 4.2 Hz), 7.51 (1H, d, J = 7.1 Hz), 8.15-8.20 (1H, m), 11.43 (1H, s); LRMS (ESI): m/z [M + H]$^+$ 399. |
| EX.59 | 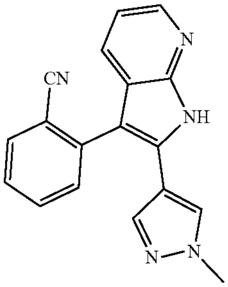 [SMILES: Cn1cc(-c2[nH]c3ncccc3c2-c2ccccc2C#N)cn1] | $^1$H NMR (400 MHz, DMSO-$d_6$): δ 3.83 (3H, s), 7.07-7.11 (1H, m), 7.41 (1H, s), 7.59-7.66 (3H, m), 7.74 (1H, s), 7.80-7.84 (1H, m), 8.00 (1H, d, J = 8.1 Hz), 8.24-8.25 (1H, m), 12.27 (1H, br s); LRMS (ESI): m/z [M + H]$^+$ 300. |

-continued

| Example No. | Chemical structural formula | Spectrum data |
|---|---|---|
| EX.60 | 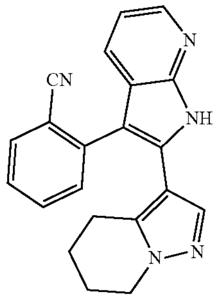 [SMILES: N#Cc1ccccc1-c1c(-c2cnn3c2CCCC3)[nH]c2ncccc12] | $^1$H NMR (400 MHz, DMSO-$d_6$): δ 1.61-1.69 (2H, br m), 1.83-1.94 (2H, br m), 2.22-2.38 (2H, m), 4.04-4.09 (2H, m), 7.11-7.14 (1H, m), 7.34 (1H, s), 7.49-7.54 (2H, m), 7.72-7.75 (2H, m), 7.90 (1H, d, J = 8.0 Hz), 8.26-8.28 (1H, m), 12.10 (1H, br s); LRMS (ESI): m/z $[M + H]^+$ 340. |
| EX.61 | 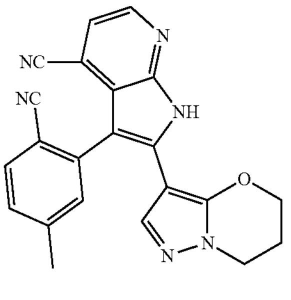 [SMILES: Cc1ccc(C#N)c(-c2c(-c3cnn4c3OCCC4)[nH]c3nccc(C#N)c23)c1] | $^1$H NMR (400 MHz, DMSO-$d_6$): δ 2.05-2.14 (2H, m), 2.41 (3H, s), 3.96-4.08 (4H, m), 7.29 (1H, s), 7.35-7.36 (1H, m), 7.41-7.44 (1H, m), 7.50 (1H, d, J = 5.0 Hz), 7.81 (1H, d, J = 8.0 Hz), 8.35 (1H, d, J = 5.0 Hz), 12.46 (1H, br s); LRMS (ESI): m/z $[M + H]^+$ 381. |
| EX.62 | 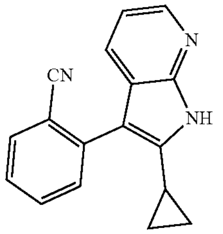 [SMILES: N#Cc1ccccc1-c1c(C2CC2)[nH]c2ncccc12] | $^1$H NMR (400 MHz, DMSO-$d_6$): δ 0.95-1.01 (4H, m), 1.96-2.03 (1H, m), 7.07 (1H, dd, J = 7.8, 4.7 Hz), 7.54-7.58 (1H, m), 7.65 (2H, d, J = 7.8 Hz), 7.79-7.82 (1H, m), 7.97 (1H, d, J = 7.6 Hz), 8.19 (1H, d, J = 4.7 Hz), 11.63 (1H, br s); LRMS (ESI): m/z $[M + H]^+$ 260. |
| EX.63 | 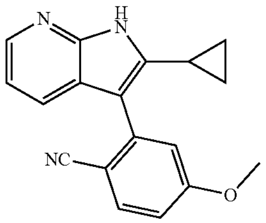 [SMILES: COc1ccc(C#N)c(-c2c(C3CC3)[nH]c3ncccc23)c1] | $^1$H NMR (400 MHz, DMSO-$d_6$): δ 0.95-1.01 (4H, m), 1.99-2.06 (1H, m), 3.89 (3H, s), 7.05-7.12 (3H, m), 7.68 (1H, dd, J = 7.9, 1.5 Hz), 7.88-7.90 (1H, m), 8.18 (1H, dd, J = 4.7, 1.5 Hz), 11.62 (1H, br s); LRMS (ESI): m/z $[M + H]^+$ 290. |
| EX.64 | 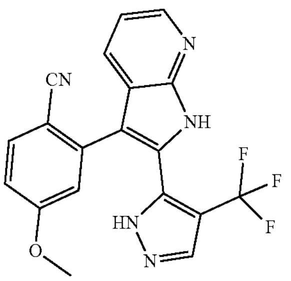 [SMILES: COc1ccc(C#N)c(-c2c(-c3[nH]ncc3C(F)(F)F)[nH]c3ncccc23)c1] | $^1$H NMR (400 MHz, DMSO-$d_6$): δ 3.73 (3H, s), 6.75 (1H, d, J = 2.8 Hz), 7.04 (1H, dd, J = 8.7, 2.5 Hz), 7.21 (1H, dd, J = 8.1, 4.7 Hz), 7.82 (1H, d, J = 8.7 Hz), 7.90 (1H, dd, J = 8.1, 1.6 Hz), 8.38-8.43 (2H, m), 12.45 (1H, br s), 13.73 (1H, br s); LRMS (ESI): m/z $[M + H]^+$ 384. |

-continued

| Example No. | Chemical structural formula | Spectrum data |
|---|---|---|
| EX.65 | 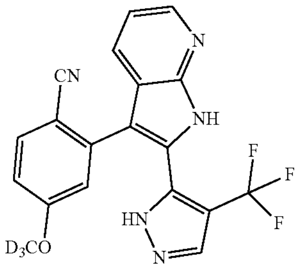 | $^1$H NMR (400 MHz, DMSO-$d_6$): δ 6.75 (1H, d, J = 2.6 Hz), 7.04 (1H, d, J = 8.3 Hz), 7.20-7.23 (1H, m), 7.82 (1H, d, J = 8.7 Hz), 7.90 (1H, d, J = 7.0 Hz), 8.39 (1H, s), 8.50 (1H, s), 12.43 (1H, br s), 13.88 (1H, br s); LRMS (ESI): m/z $[M + H]^+$ 387. |
| EX.66 | 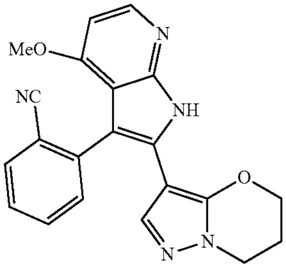 [SMILES: COc1ccnc2[nH]c(-c3cnn4c3OCCC4)c(-c3ccccc3C#N)c12] | $^1$H NMR (400 MHz, DMSO-$d_6$): δ 1.96-2.14 (2H, m), 3.73 (3H, s), 3.87 (1H, m), 3.96-4.07 (3H, m), 6.68 (1H, d, J = 5.6 Hz), 7.22 (1H, s), 7.37 (1H, d, J = 8.3 Hz), 7.45 (1H, apparent t, J = 7.5 Hz), 7.59 (1H, apparent t, J = 7.5 Hz), 7.81 (1H, d, J = 7.8 Hz), 8.10 (1H, d, J = 5.6 Hz), 11.75 (1H, br s); LRMS (ESI): m/z $[M + H]^+$ 372. |
| EX.67 | 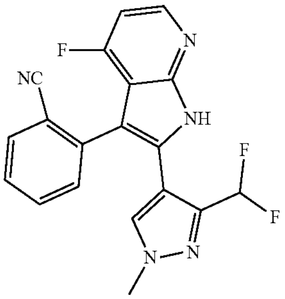 [SMILES: Cn1cc(-c2[nH]c3nccc(F)c3c2-c2ccccc2C#N)c(C(F)F)n1] | $^1$H NMR (400 MHz, DMSO-$d_6$): δ 3.90 (3H, s), 6.63 (1H, t, $J_{H\text{-}F}$ = 53.8 Hz), 7.04 (1H, dd, J = 10.9, 5.4 Hz), 7.38 (1H, d, J = 7.9 Hz), 7.50 (1H, apparent t, J = 7.7 Hz), 7.64 (1H, apparent t, J = 7.6 Hz), 7.89 (1H, d, J = 7.8 Hz), 7.97 (1H, s), 8.31 (1H, dd, J = 7.8, 5.7 Hz), 12.05 (1H, br s); LRMS (ESI): m/z $[M + H]^+$ 368. |
| EX.68 | 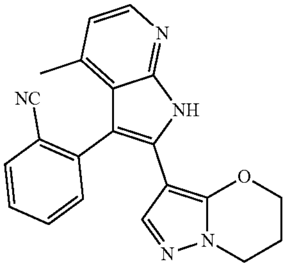 [SMILES: Cc1ccnc2[nH]c(-c3cnn4c3OCCC4)c(-c3ccccc3C#N)c12] | $^1$H NMR (400 MHz, DMSO-$d_6$): δ 1.96-2.15 (5H, m), 3.92-4.10 (4H, m), 6.83 (1H, d, J = 4.9 Hz), 7.12 (1H, s), 7.51 (1H, d, J = 7.8 Hz), 7.57 (1H, apparent t, J = 7.5 Hz), 7.71 (1H, apparent t, J = 7.5 Hz), 7.89 (1H, d, J = 7.5 Hz), 8.07 (1H, d, J = 4.7 Hz), 11.67 (1H, s); LRMS (ESI): m/z $[M + H]^+$ 356. |
| EX.69 | 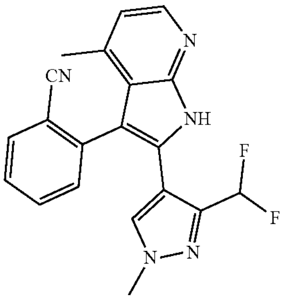 [SMILES: Cc1ccnc2[nH]c(-c3cn(C)nc3C(F)F)c(-c3ccccc3C#N)c12] | $^1$H NMR (400 MHz, DMSO-$d_6$): δ 2.05 (3H, s), 3.86 (3H, s), 6.74 (1H, t, $J_{H\text{-}F}$ = 53.9 Hz), 6.90 (1H, d, J = 4.6 Hz), 7.48-7.58 (2H, m), 7.69 (1H, apparent t, J = 7.8 Hz), 7.78 (1H, s), 7.86 (1H, d, J = 7.4 Hz), 8.16 (1H, d, J = 4.7 Hz), 12.09 (1H, s); LRMS (ESI): m/z $[M + H]^+$ 364. |

-continued

| Example No. | Chemical structural formula | Spectrum data |
|---|---|---|
| EX.70 | 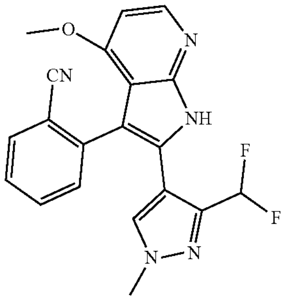 [SMILES: COc1ccnc2[nH]c(-c3cn(C)nc3C(F)F)c(-c3ccccc3C#N)c12] | $^1$H NMR (400 MHz, DMSO-$d_6$): δ 3.75 (3H, s), 3.87 (3H, s), 6.51 (1H, t, $J_{H-F}$ = 55.0 Hz), 6.73 (1H, d, J = 5.5 Hz), 7.28 (1H, d, J = 8.0 Hz), 7.43 (1H, apparent t, J = 7.8 Hz), 7.56 (1H, apparent t, J = 7.8 Hz), 7.81 (1H, d, J = 7.6 Hz), 7.85 (1H, s), 8.18 (1H, d, J = 5.4 Hz), 12.07 (1H, s); LRMS (ESI): m/z $[M + H]^+$ 380. |
| EX.71 | 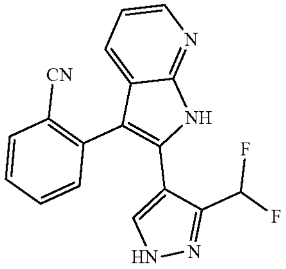 [SMILES: N#Cc1ccccc1-c1c(-c2c[nH]nc2C(F)F)[nH]c2ncccc12] | $^1$H NMR (400 MHz, DMSO-$d_6$): δ 6.62 (1H, t, $J_{H-F}$ = 53.9 Hz), 7.16 (1H, dd, J = 8.1, 4.8 Hz), 7.41 (1H, d, J = 7.3 Hz), 7.51 (1H, apparent t, J = 7.7 Hz), 7.69 (1H, apparent t, J = 7.6 Hz), 7.79 (1H, d, J = 7.7 Hz), 7.88 (1H, d, J = 7.7 Hz), 7.98 (1H, s), 8.32 (1H, d, J = 4.4 Hz), 12.21 (1H, s), 13.59 (1H, s); LRMS (ESI): m/z $[M + H]^+$ 336. |
| EX.72 | 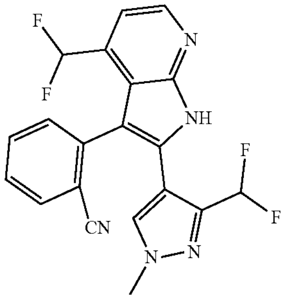 [SMILES: Cn1cc(-c2[nH]c3nccc(C(F)F)c3c2-c2ccccc2C#N)c(C(F)F)n1] | $^1$H NMR (400 MHz, DMSO-$d_6$): δ 3.86 (3H, s), 6.77 (2H, td, $J_{H-F}$ = 55.3, 54.8, 8.5 Hz), 7.35 (1H, d, J = 4.6 Hz), 7.50-7.60 (2H, m), 7.72 (1H, t, J =7.3 Hz), 7.80 (1H, s), 7.83 (1H, d, J = 7.5 Hz), 8.47 (1H, d, J = 4.8 Hz), 12.50 (1H, br s); LRMS (ESI): m/z $[M + H]^+$ 400. |
| EX.73 | 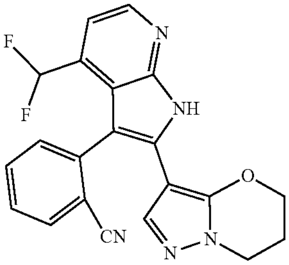 [SMILES: N#Cc1ccccc1-c1c(-c2cnn3c2OCCC3)[nH]c2nccc(C(F)F)c12] | $^1$H NMR (400 MHz, DMSO-$d_6$): δ 2.04-2.14 (2H, m), 4.00-4.10 (4H, m), 6.70 (1H, t, $J_{H-F}$ = 55.0 Hz), 7.03 (1H, s), 7.27 (1H, d, J = 4.7 Hz), 7.52-7.65 (2H, m), 7.69-7.79 (1H, m), 7.85-7.93 (1H, m), 8.35 (1H, d, J = 4.8 Hz); LRMS (ESI): m/z $[M + H]^+$ 392. |
| EX.74 | 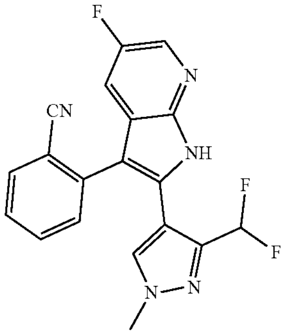 [SMILES: Cn1cc(-c2[nH]c3ncc(F)cc3c2-c2ccccc2C#N)c(C(F)F)n1] | $^1$H NMR (400 MHz, DMSO-$d_6$): δ 3.91 (3H, s), 6.58 (1H, t, $J_{H-F}$ = 54.2 Hz), 7.41 (1H, d, J = 7.6 Hz), 7.52 (1H, apparent t, J = 7.7 Hz), 7.66-7.72 (2H, m), 7.90 (1H, d, J = 7.8 Hz), 7.98 (1H, s), 8.32 (1H, s), 12.36 (1H, br s); LRMS (ESI): m/z $[M + H]^+$ 368. |

-continued

| Example No. | Chemical structural formula | Spectrum data |
|---|---|---|
| EX.75 | 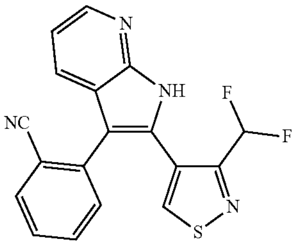 [SMILES: N#Cc1ccccc1-c1c(-c2csnc2C(F)F)[nH]c2ncccc12] | $^1$H NMR (400 MHz, DMSO-d$_6$): δ 6.84 (1H, t, $J_{H-F}$ = 53.5 Hz), 7.20 (1H, dd, J = 7.8, 4.7 Hz), 7.43 (1H, d, J = 7.8 Hz), 7.51 (1H, apparent t, J = 7.6 Hz), 7.70 (1H, apparent t, J = 7.6 Hz), 7.87 (2H, dd, J = 14.4, 7.8 Hz), 8.37 (1H, d, J = 4.5 Hz), 9.19 (1H, s), 12.49 (1H, s); LRMS (ESI): m/z [M + H]$^+$ 353. |
| EX.76 | 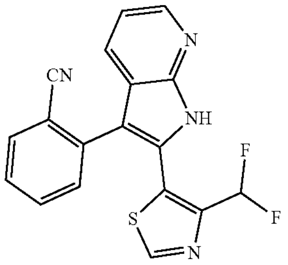 [SMILES: N#Cc1ccccc1-c1c(-c2scnc2C(F)F)[nH]c2ncccc12] | $^1$H NMR (400 MHz, DMSO-d$_6$): δ 6.77 (1H, t, $J_{H-F}$ = 53.0 Hz), 7.20 (1H, s), 7.51-7.59 (2H, m), 7.75 (1H, apparent t, J = 7.2 Hz), 7.83-7.85 (1H, m), 7.89 (1H, d, J = 7.8 Hz) 8.35-8.43 (1H, m), 9.27 (1H, s), 12.78 (1H, br s); LRMS (ESI): m/z [M + H]$^+$ 353. |
| EX.77 | 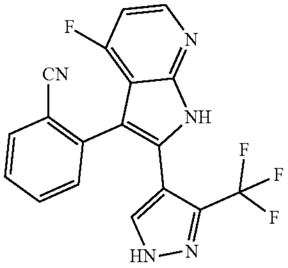 [SMILES: N#Cc1ccccc1-c1c(-c2c[nH]nc2C(F)(F)F)[nH]c2nccc(F)c12] | $^1$H NMR (400 MHz, DMSO-d$_6$): δ 7.04 (1H, dd, J = 11.1, 5.5 Hz), 7.31 (1H, d, J = 7.4 Hz), 7.47 (1H, apparent t, J = 7.7 Hz), 7.60 (1H, apparent t, J = 8.1 Hz), 7.86 (1H, d, J = 7.8 Hz), 8.11 (1H, s), 8.28-8.35 (1H, m), 12.60 (1H, br s); LRMS (ESI): m/z [M + H]$^+$ 372. |
| EX.78 | 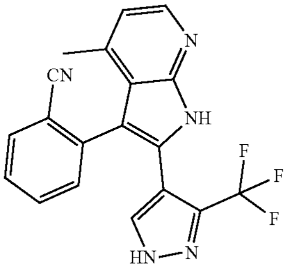 [SMILES: Cc1ccnc2[nH]c(-c3c[nH]nc3C(F)(F)F)c(-c3ccccc3C#N)c12] | $^1$H NMR (400 MHz, DMSO-d$_6$): δ 2.07 (3H, s), 6.92 (1H, d, J = 5.0 Hz), 7.49-7.53 (2H, m), 7.64 (1H, m), 7.84 (1H, d, J = 7.9 Hz), 8.01 (1H, s), 8.18 (1H, d, J = 4.9 Hz), 12.16 (1H, s), 13.70 (1H, br s); LRMS (ESI): m/z [M + H]$^+$ 368. |
| EX.79 | 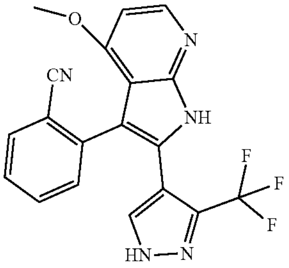 [SMILES: COc1ccnc2[nH]c(-c3c[nH]nc3C(F)(F)F)c(-c3ccccc3C#N)c12] | $^1$H NMR (400 MHz, DMSO-d$_6$): δ 3.76 (3H, s), 6.75 (1H, d, J = 5.1 Hz), 7.23 (1H, d, J = 7.5 Hz), 7.40 (1H, apparent t, J = 7.6 Hz), 7.52 (1H, apparent t, J = 7.4 Hz), 7.78 (1H, d, J = 7.7 Hz), 8.10 (1H, s), 8.20 (1H, d, J = 5.1 Hz), 12.16 (1H, s), 13.77 (1H, br s); LRMS (ESI): m/z [M + H]$^+$ 384. |

-continued

| Example No. | Chemical structural formula | Spectrum data |
|---|---|---|
| EX.80 | 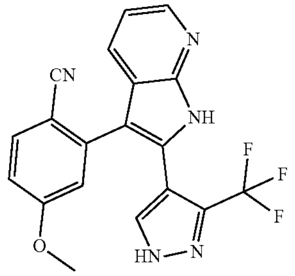 [SMILES: COc1ccc(C#N)c(-c2c(-c3c[nH]nc3C(F)(F)F)[nH]c3ncccc23)c1] | $^1$H NMR (400 MHz, DMSO-$d_6$): δ 3.75 (3H, s), 6.83 (1H, s), 7.01-7.09 (1H, m), 7.18 (1H, dd, J = 7.8, 4.6 Hz), 7.77-7.86 (2H, m), 8.18 (1H, s), 8.33 (1H, d, J = 4.5 Hz), 12.29 (1H, s), 13.91 (1H, s); LRMS (ESI): m/z $[M + H]^+$ 384. |
| EX.81 | 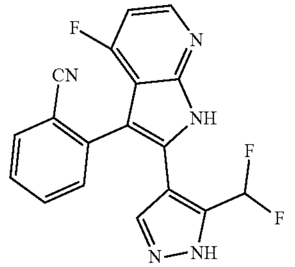 [SMILES: N#Cc1ccccc1-c1c(-c2cn[nH]c2C(F)F)[nH]c2nccc(F)c12] | $^1$H NMR (400 MHz, DMSO-$d_6$): δ 6.66 (1H, t, $J_{H-F}$ = 54.3 Hz), 7.04 (1H, dd, J = 10.8, 5.3 Hz), 7.38 (1H, d, J = 7.7 Hz), 7.49 (1H, apparent t, J = 7.7 Hz), 7.63 (1H, apparent t, J = 7.9 Hz), 7.88 (1H, d, J = 7.7 Hz), 7.98 (1H, s), 8.28-8.35 (1H, m), 12.54 (1H, br s); LRMS (ESI): m/z $[M + H]^+$ 354. |
| EX.82 | 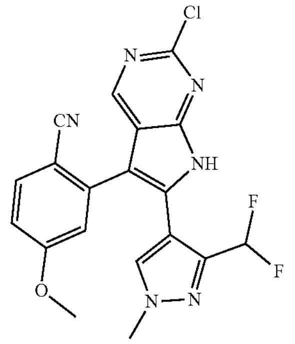 [SMILES: COc1ccc(C#N)c(-c2c(-c3cn(C)nc3C(F)F)[nH]c3nc(Cl)ncc23)c1] | $^1$H NMR (400 MHz, DMSO-$d_6$): δ 3.80 (3H, s), 3.93 (3H, s), 6.67 (1H, t, $J_{H-F}$ = 53.8 Hz), 6.99 (1H, d, J = 2.0 Hz), 7.11 (1H, dd, J = 8.5, 2.2 Hz), 7.84 (1H, d, J = 8.6 Hz), 8.06 (1H, s), 8.84 (1H, s), 12.96 (1H, s); LRMS (ESI): m/z $[M + H]^+$ 415. |
| EX.83 | 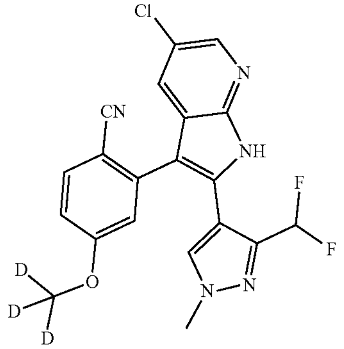 [SMILES: [2H]C([2H])([2H])Oc1ccc(C#N)c(-c2c(-c3cn(C)nc3C(F)F)[nH]c3ncc(Cl)cc23)c1] | $^1$H NMR (400 MHz, DMSO-$d_6$): δ 3.92 (3H, s), 6.64 (1H, t, $J_{H-F}$ = 53.9 Hz), 6.94 (1H, d, J = 2.6 Hz), 7.08 (1H, dd, J = 8.7, 2.6 Hz), 7.81 (1H, d, J = 8.7 Hz), 7.88 (1H, d, J = 2.3 Hz), 8.00 (1H, s), 8.33 (1H, d, J = 2.3 Hz), 12.49 (1H, s); LRMS (ESI): m/z $[M + H]^+$ 417. |
| EX.84 | 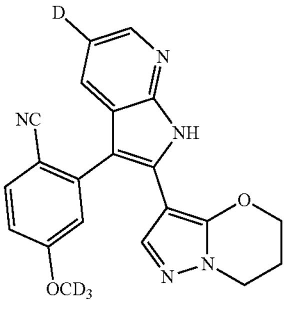 | $^1$H NMR (400 MHz, DMSO-$d_6$): δ 2.07-2.11 (2H, m), 4.01-4.10 (4H, m), 6.98 (1H, d, J = 2.3 Hz), 7.08 (1H, dd, J = 8.7, 2.5 Hz), 7.37 (1H, s), 7.69 (1H, s), 7.82 (1H, d, J = 8.7 Hz), 8.22 (1H, s), 11.86 (1H, s); LRMS (ESI): m/z $[M + H]^+$ 376. |

-continued

| Example No. | Chemical structural formula | Spectrum data |
|---|---|---|
| EX.85 | 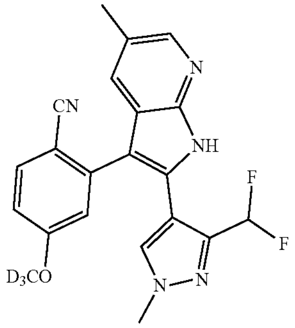 | $^1$H NMR (400 MHz, DMSO-$d_6$): δ 2.38 (3H, s), 3.92 (3H, s), 6.61 (1H, t, JH-J = 53.9 Hz), 6.92 (1H, d, J = 2.6 Hz), 7.06 (1H, dd, J = 8.7, 2.6 Hz), 7.59-7.60 (1H, m), 7.79 (1H, d, J = 8.7 Hz), 7.95 (1H, s), 8.17 (1H, d, J = 1.9 Hz), 12.05 (1H, s); LRMS (ESI): m/z $[M + H]^+$ 397. |
| EX.86 | 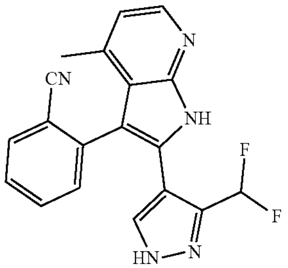 [SMILES: Cc1ccnc2[nH]c(-c3c[nH]nc3C(F)F)c(-c3ccccc3C#N)c12] | $^1$H NMR (400 MHz, $CD_3OD$): δ 2.18 (3H, s), 6.68 (1H, t, $J_{H-F}$ = 54.2 Hz), 6.97 (1H, d, J = 4.6 Hz), 7.56 (2H, d, J = 8.0 Hz), 7.62 (1H, s), 7.70 (1H, t, J = 7.7 Hz), 7.80 (1H, d, J = 7.7 Hz), 8.16 (1H, d, J = 4.9 Hz); LRMS (ESI): m/z $[M + H]^+$ 350. |
| EX.87 | 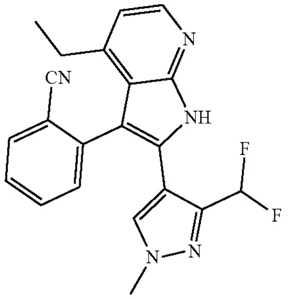 [SMILES: CCc1ccnc2[nH]c(-c3cn(C)nc3C(F)F)c(-c3ccccc3C#N)c12] | (Mixture of atropisomers) $^1$H NMR (400 MHz, DMSO-$d_6$): δ 0.88 (3H, t, J = 7.5 Hz), 2.33-2.47 (2H, m), 3.85 (3H, s), 6.75 (1H, t, $J_{H-F}$ = 54.0 Hz), 6.96 (1H, d, J = 4.9 Hz), 7.56 (2H, d, J = 7.6 Hz), 7.70 (1H, apparent t, J = 7.7 Hz), 7.76 (1H, s), 7.86 (1H, d, J = 7.7 Hz), 8.21 (1H, d, J = 4.8 Hz), 12.10 (1H, s); LRMS (ESI): m/z $[M + H]^+$ 378. |
| EX.88 | 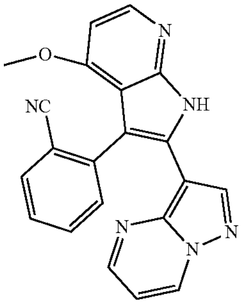 [SMILES: COc1ccnc2[nH]c(-c3cnn4cccnc34)c(-c3ccccc3C#N)c12] | (Mixture of atropisomers) $^1$H NMR (400 MHz, DMSO-$d_6$): 83.76 (3H, s), 6.74 (1H, d, J = 5.5 Hz), 7.09 (1H, dd, J = 6.8, 4.1 Hz), 7.46 (2H, apparent t, J = 8.4 Hz), 7.57 (1H, apparent t, J = 7.7 Hz), 7.83 (1H, d, J = 7.5 Hz), 7.95 (1H, s), 8.18 (1H, d, J = 5.5 Hz), 8.50 (1H, d, J = 4.0 Hz), 9.14 (1H, d, J = 7.0 Hz), 11.92 (1H, s); LRMS (ESI): m/z $[M + H]^+$ 367. |
| EX.89 | 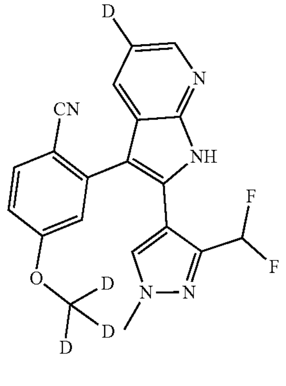 [SMILES: [2H]c1cnc2[nH]c(-c3cn(C)nc3C(F)F)c(-c3cc(OC([2H])([2H])[2H])ccc3C#N)c2c1] | $^1$H NMR (400 MHz, DMSO-$d_6$): δ 3.92 (3H, s), 6.63 (1H, t, $J_{H-F}$ = 53.9 Hz), 6.90-6.95 (1H, m), 7.03-7.10 (1H, m), 7.77-7.86 (2H, m), 7.97 (1H, s), 8.32 (1H, s), 12.22 (1H, s); LRMS (ESI): m/z $[M + H]^+$ 384. |

-continued

| Example No. | Chemical structural formula | Spectrum data |
|---|---|---|
| EX.90 | 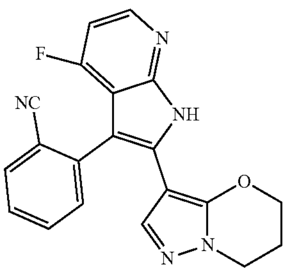 [SMILES: N#Cc1ccccc1-c1c(-c2cnn3c2OCCC3)[nH]c2nccc(F)c12] | $^1$H NMR (400 MHz, DMSO-$d_6$): δ 1.96-2.14 (2H, m), 3.82-3.92 (1H, m), 3.95-4.10 (3H, m), 6.96 (1H, dd, J = 11.2, 5.5 Hz), 7.35 (1H, s), 7.46 (1H, d, J = 7.7 Hz), 7.52 (1H, apparent t, J = 7.8 Hz), 7.67 (1H, apparent t, J = 7.5 Hz), 7.88 (1H, d, J = 7.6 Hz), 8.21 (1H, dd, J = 7.6, 5.7 Hz), 12.25 (1H, br s); LRMS (ESI): m/z $[M + H]^+$ 360. |
| EX.91 | 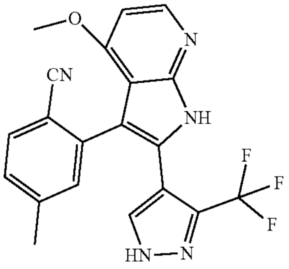 [SMILES: COc1ccnc2[nH]c(-c3c[nH]nc3C(F)(F)F)c(-c3cc(C)ccc3C#N)c12] | (Mixture of atropisomers) $^1$H NMR (400 MHz, DMSO-$d_6$): δ 2.27 (3H, s), 3.76 (3H, s), 6.74 (1H, d, J = 5.6 Hz), 7.07 (1H, s), 7.21 (1H, d, J = 8.0 Hz), 7.65 (1H, d, J = 8.1 Hz), 8.12 (1H, s), 8.19 (1H, d, J = 5.6 Hz), 12.12 (1H, s), 13.81 (1H, s); LRMS (ESI): m/z $[M + H]^+$ 398. |
| EX.92 | 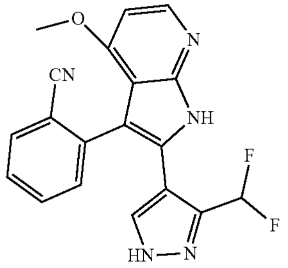 [SMILES: COc1ccnc2[nH]c(-c3c[nH]nc3C(F)F)c(-c3ccccc3C#N)c12] | (Mixture of atropisomers) $^1$H NMR (400 MHz, DMSO-$d_6$): δ 3.76 (3H, s), 6.59 (1H, t, $J_{H-F}$ = 54.0 Hz), 6.74 (1H, d, J = 5.9 Hz), 7.29 (1H, d, J = 7.4 Hz), 7.42 (1H, apparent t, J = 7.5 Hz), 7.55 (1H, apparent t, J = 7.2 Hz), 7.75-7.91 (2H, m), 8.19 (1H, d, J = 5.4 Hz), 12.08 (1H, s), 13.54 (1H, s); LRMS (ESI): m/z $[M + H]^+$ 366. |
| EX.93 | 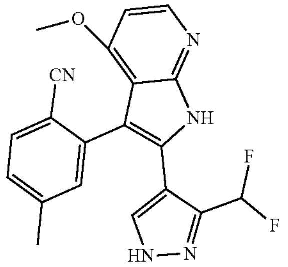 [SMILES: COc1ccnc2[nH]c(-c3c[nH]nc3C(F)F)c(-c3cc(C)ccc3C#N)c12] | (Mixture of atropisomers) $^1$H NMR (400 MHz, DMSO-$d_6$): δ 2.29 (3H, s), 3.75 (3H, s), 6.59 (1H, t, $J_{H-F}$ = 54.0 Hz), 6.73 (1H, d, J = 5.8 Hz), 7.13 (1H, s), 7.24 (1H, d, J = 7.5 Hz), 7.67 (1H, d, J = 8.0 Hz), 7.89 (1H, s), 8.18 (1H, d, J = 5.4 Hz), 12.02 (1H, s), 13.48 (1H, s); LRMS (ESI): m/z $[M + H]^+$ 380. |
| EX.94 | 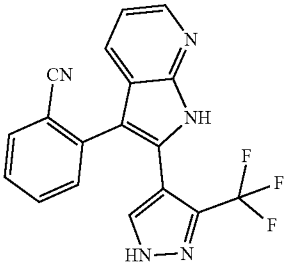 [SMILES: N#Cc1ccccc1-c1c(-c2c[nH]nc2C(F)(F)F)[nH]c2ncccc12] | $^1$H NMR (400 MHz, DMSO-$d_6$): δ 7.17 (1H, dd, J = 7.8, 4.8 Hz), 7.34 (1H, d, J = 7.5 Hz), 7.49 (1H, apparent t, J = 7.7 Hz), 7.66 (1H, apparent t, J = 7.8 Hz), 7.81 (1H, d, J = 7.8 Hz), 7.88 (1H, d, J = 7.5 Hz), 8.17 (1H, s), 8.34 (1H, d, J = 4.8 Hz), 12.30 (1H, s), 13.91 (1H, s); LRMS (ESI): m/z $[M + H]^+$ 354. |

-continued

| Example No. | Chemical structural formula | Spectrum data |
|---|---|---|
| EX.95 | 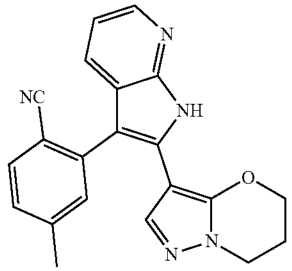 | $^1$H NMR (400 MHz, DMSO-$d_6$): δ 2.03-2.14 (2H, m), 2.41 (3H, s), 3.97-4.10 (4H, m), 7.14 (1H, dd, J = 7.8, 4.9 Hz), 7.34-7.37 (3H, m), 7.74 (1H, d, J = 7.6 Hz), 7.78 (1H, d, J = 7.8 Hz) 8.25 (1H, d, J = 4.6 Hz), 11.99 (1H, br s); LRMS (ESI): m/z $[M + H]^+$ 356. |
| EX.96 | 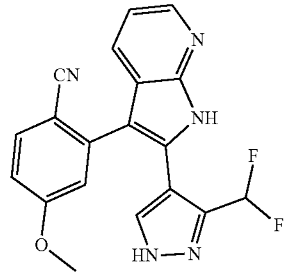 [SMILES: COc1ccc(C#N)c(-c2c(-c3c[nH]nc3C(F)F)[nH]c3ncccc23)c1] | $^1$H NMR (400 MHz, (CD3)2CO): δ 3.86 (3H, s), 6.73 (1H, t, $J_{H-F}$ = 54.2 Hz), 7.03 (1H, d, J = 2.6 Hz), 7.09 (1H, dd, J = 8.7, 2.6 Hz), 7.19 (1H, dd, J = 7.9, 4.7 Hz), 7.76 (1H, d, J = 8.7 Hz), 7.89 (1H, dd, J = 7.9, 1.5 Hz), 7.96 (1H, s), 8.35 (1H, dd, J = 4.7, 1.6 Hz) LRMS (ESI): m/z $[M + H]^+$ 366. |
| EX.97 | 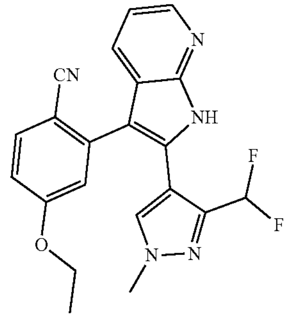 [SMILES: CCOc1ccc(C#N)c(-c2c(-c3cn(C)nc3C(F)F)[nH]c3ncccc23)c1] | $^1$H NMR (400 MHz, ($CDCl_3$): δ 1.44 (3H, t, J = 7.0 Hz), 3.90 (3H, s), 4.03-4.12 (2H, m), 6.74 (1H, t, $J_{H-F}$ = 54.2 Hz), 6.97-6.99 (2H, m), 7.16 (1H, dd, J = 7.9, 4.8 Hz), 7.25 (1H, s), 7.67 -7.74 (1H, m), 7.80 (1H, dd, J = 7.9, 1.5 Hz), 8.33-8.35 (1H, m), 9.73 (1H, br s); LRMS (ESI): m/z $[M + H]^+$ 394. |
| EX.98 | 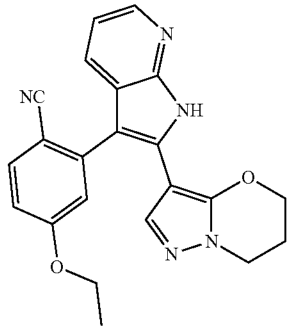 [SMILES: CCOc1ccc(C#N)c(-c2c(-c3cnn4c3OCCC4)[nH]c3ncccc23)c1] | $^1$H NMR (400 MHz, $CDCl_3$): δ 1.47 (3H, t, J = 6.9 Hz), 2.40 (2H, br s), 4.07-4.30 (4H, m), 4.59 (2H, br s), 7.06 (3H, d, J = 9.6 Hz), 7.30-7.40 (1H, m), 7.79 (1H, d, J = 8.8 Hz), 8.01-8.16 (2H, m), 13.28 (1H, br s); LRMS (ESI): m/z $[M + H]^+$ 386. |
| EX.99 | 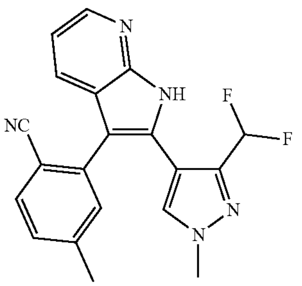 [SMILES: Cc1ccc(C#N)c(-c2c(-c3cn(C)nc3C(F)F)[nH]c3ncccc23)c1] | $^1$H (400 MHz, DMSO-$d_6$): δ 2.36 (3H, s), 3.91 (3H, s), 6.57 (1H, t, $J_{H-F}$ = 54.0 Hz), 7.15 (1H, dd, J = 7.9, 4.7 Hz), 7.28 (1H, s), 7.33 (1H, d, J = 8.0 Hz), 7.75 (1H, d, J = 8.0 Hz), 7.76 (1H, dd, J = 8.2, 1.7 Hz), 7.94 (1H, s), 8.31 (1H, dd, J = 4.7, 1.5 Hz), 12.17 (1H, s); LRMS (ESI): m/z $[M + H]^+$ 364. |

-continued

| Example No. | Chemical structural formula | Spectrum data |
|---|---|---|
| EX.100 | 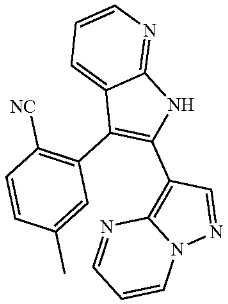 [SMILES: Cc1ccc(C#N)c(-c2c(-c3cnn4cccnc34)[nH]c3ncccc23)c1] | $^1$H (400 MHz, DMSO-$d_6$): δ 2.38 (3H, s), 7.05 -7.19 (2H, m), 7.35 (1H, d, J = 8.0 Hz), 7.43 (1H, s), 8.08 (1H, s), 7.75 (1H, d, J = 8.0 Hz), 7.76 (1H, dd, J = 7.9, 1.3 Hz), 8.30 (1H, dd, J = 4.7, 1.5 Hz), 8.53 (1H, dd, J = 4.0, 1.7 Hz), 9.18 (1H, dd, J = 7.0, 1.7 Hz), 12.01 (1H, s); LRMS (ESI): m/z $[M + H]^+$ 351. |
| EX.101 | 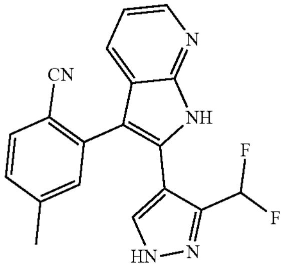 [SMILES: Cc1ccc(C#N)c(-c2c(-c3c[nH]nc3C(F)F)[nH]c3ncccc23)c1] | $^1$H (400 MHz, DMSO-$d_6$): δ 2.35 (3H, s), 6.61 (1H, t, $J_{H-F}$ = 54.0 Hz), 7.15 (1H, dd, J = 7.8, 4.6 Hz), 7.27 (1H, s), 7.32 (1H, d, J = 7.7 Hz), 7.68-7.80 (2H, m), 7.94 (1H, s), 8.31 (1H, d, J = 4.3 Hz), 12.17 (1H, s), 13.58 (1H, s); LRMS (ESI): m/z $[M + H]^+$ 350. |
| EX.102 | 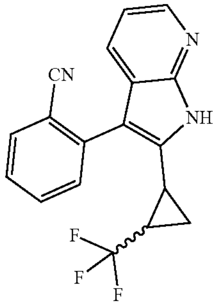 [SMILES: N#Cc1ccccc1-c1c(C2CC2C(F)(F)F)[nH]c2ncccc12] | $^1$H (400 MHz, DMSO-$d_6$): δ 1.40-1.51 (1H, m), 1.54-1.67 (1H, m), 2.30-2.47 (2H, m), 7.11 (1H, dd, J = 7.8, 4.8 Hz), 7.55-7.75 (3H, m), 7.82 (1H, t, J = 7.5 Hz), 8.00 (1H, d, J = 7.2 Hz), 8.26 (1H, d, J = 4.7 Hz), 11.94 (1H, s); LRMS (ESI): m/z $[M + H]^+$ 328. |
| EX.103 | 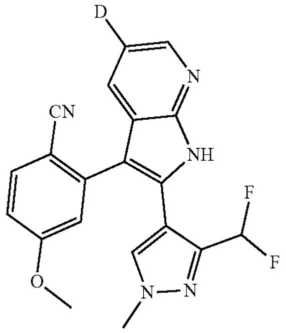 [SMILES: [2H]c1cnc2[nH]c(-c3cn(C)nc3C(F)F)c(-c3cc(OC)ccc3C#N)c2c1] | $^1$H (400 MHz, DMSO-$d_6$): δ 3.78 (3H, s), 3.92 (3H, s), 6.63 (1H, t, $J_{H-F}$ = 53.8 Hz), 6.92 (1H, d, J = 2.5 Hz), 7.06 (1H, dd, J = 8.7, 2.6 Hz), 7.77-7.83 (2H, m), 7.96 (1H, s), 8.31 (1H, d, J = 1.6 Hz), 12.20 (1H, s); LRMS (ESI): m/z $[M + H]^+$ 381. |
| EX.104 | 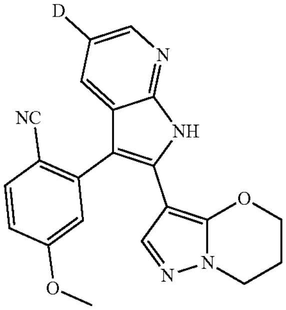 [SMILES: [2H]c1cnc2[nH]c(-c3cnn4c3OCCC4)c(-c3cc(OC)ccc3C#N)c2c1] | $^1$H (400 MHz, DMSO-$d_6$): δ 2.02-2.17 (2H, m), 3.82 (3H, s), 3.92-4.06 (2H, m), 4.08 (2H, t, J = 6.1 Hz), 6.98 (1H, d, J = 2.5 Hz), 7.08 (1H, dd, J = 8.7, 2.6 Hz), 7.36 (1H, s), 7.68 (1H, d, J = 1.6 Hz), 7.81 (1H, d, J = 8.7 Hz), 8.21 (1H, d, J = 1.6 Hz), 11.84 (1H, s); LRMS (ESI): m/z $[M + H]^+$ 373. |

-continued

| Example No. | Chemical structural formula | Spectrum data |
|---|---|---|
| EX.105 | 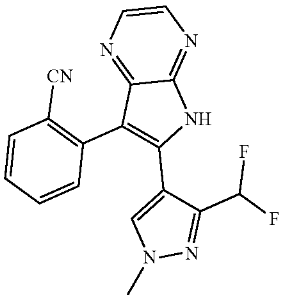 [SMILES: Cn1cc(-c2[nH]c3nccnc3c2-c2ccccc2C#N)c(C(F)F)n1] | $^1H$ (400 MHz, DMSO-$d_6$): δ 3.92 (3H, s), 6.63 (1H, t, $J_{H-F}$ = 54.0 Hz), 7.44 (1H, ddd, J = 7.8, 1.2, 0.5 Hz), 7.53 (1H, td, J = 7.7, 1.3 Hz), 7.70 (1H, td, J = 7.7, 1.4 Hz), 7.88 (1H, ddd, J = 7.8, 1.4, 0.5 Hz), 8.05 (1H, s), 8.35 (1H, d, J = 2.6 Hz), 8.44 (1H, d, J = 2.6 Hz), 12.58 (1H, s); LRMS (ESI): m/z $[M + H]^+$ 351. |

(3) Experimental Procedure of EX.106

EX.106 was prepared in accordance with the general procedures 2 and 1 using the method described below in detail.

Synthesis of 2-(5-fluoro-2-methoxyphenyl)-3-(4-methylpyridin-2-yl)-1H-pyrrolo[2,3-b]pyridine (EX.106)

Step 2-1

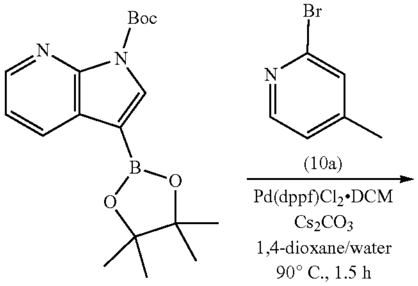

(9)

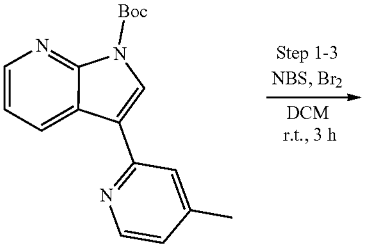

(5c)

-continued

Step 1-4

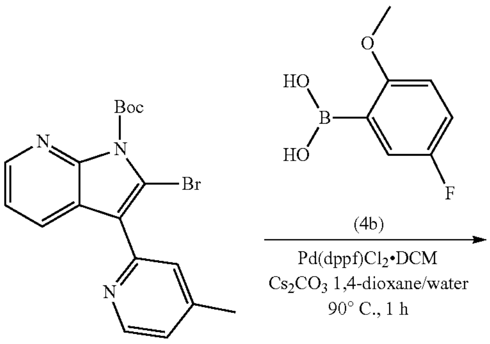

(6c)

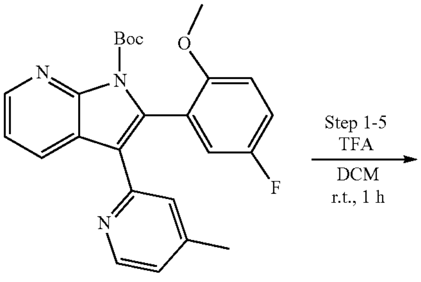

(7e)

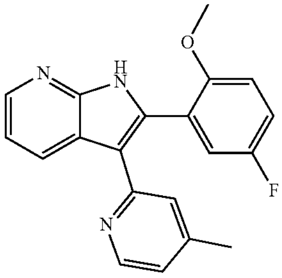

EX. 106

Step 2-1

A reaction vessel containing tert-butyl 3-(4,4,5,5-tetramethyl-1,3,2-dioxaborolan-2-yl)-1H-pyrrolo[2,3-b]pyridine-1-carboxylate (9) (150 mg, 0.44 mmol), 2-bromo-4-methylpyridine (10a) (97.4 mg, 0.57 mmol) and $Cs_2CO_3$ (426 mg, 1.31 mmol) in 1,4-dioxane (1 mL) and water (0.5 mL) was degassed and backfilled with nitrogen three times. After the addition of Pd(dppf)$Cl_2$-DCM (71.2 mg, 0.09 mmol), the mixture was purged with nitrogen three times. The resulting mixture was then stirred and heated at 90° C. for 1.5 h. After cooling to room temperature, the mixture was filtered through Celite and the filtrate was concentrated. The residue was purified by silica gel column chromatography (0-60% EtOAc/Hexane) to give the expected product as colorless oil (79 mg, 59%); LRMS (ESI): m/z $[M+H]^+$ 310.

Step 1-3

A mixture of tert-butyl 3-(4-methyl-2-pyridyl)pyrrolo[2,3-b]pyridine-1-carboxylate (5c) (79 mg, 0.26 mmol), NBS (50 mg, 0.28 mmol) and 1M $Br_2$ in DCM (0.38 mL, 0.38 mmol) in DCM (1 mL) was stirred at room temperature for 3 h. The reaction mixture was then quenched with sat. aq. $Na_2S_2O_3$, and the product was extracted with DCM (×3). The combined organic extracts were dried over $Na_2SO_4$ and concentrated. The residue was purified by silica gel column chromatography (0-70% EtOAc/Hexane) to give the expected product as pale yellow oil (60 mg, 60%); LRMS (ESI): m/z $[M+H]^+$ 389, 391.

Step 1-4

A reaction vessel containing tert-butyl 2-bromo-3-(4-methylpyridin-2-yl)-1H-pyrrolo[2,3-b]pyridine-1-carboxylate (6c) (60 mg, 0.15 mmol), (5-fluoro-2-methoxy-phenyl) boronic acid (4b) (34 mg, 0.20 mmol) and $Cs_2CO_3$ (151 mg, 0.46 mmol) in 1,4-dioxane (0.4 mL) and water (0.2 mL) was degassed and backfilled with nitrogen three times. After the addition of Pd(dppf)$Cl_2$-DCM (25.2 mg, 0.03 mmol), the mixture was purged with nitrogen three times. The resulting mixture was then stirred and heated at 90° C. for 1 h. After cooling to room temperature, the mixture was concentrated. The residue was purified by silica gel column chromatography (0-70% EtOAc/Hexane) to give the expected product as a white solid (16 mg, 24%); LRMS (ESI): m/z $[M+H]^+$ 434.

Step 1-5

A mixture of tert-butyl 2-(5-fluoro-2-methoxy-phenyl)-3-(4-methyl-2-pyridyl)pyrrolo[2,3-b]pyridine-1-carboxylate (7e) (16 mg, 0.04 mmol) and TFA (0.2 mL) in DCM (0.3 mL) was stirred at room temperature for 1 h. After concentration, the residue was purified by prep HPLC ($CH_3CN$/0.1% TFA-$H_2O$/0.1% TFA) to give EX.106 as a white solid (12.4 mg, 73%).

$^1H$ NMR (400 MHz, DMSO-$d_6$) δ 2.54 (3H, s), 3.33 (3H, s), 7.08 (1H, dd, J=9.2, 4.6 Hz), 7.29 (1H, dd, J=8.0, 4.7 Hz), 7.35 (1H, td, J=8.7, 3.1 Hz), 7.45 (1H, dd, J=9.1, 3.1 Hz), 7.69-7.70 (2H, m), 8.24 (1H, dd, J=8.2, 1.5 Hz), 8.42 (1H, dd, J=4.6, 1.5 Hz), 8.63 (1H, d, J=6.5 Hz), 12.80 (NH, br s); LRMS (ESI): m/z $[M+H]^+$ 334.

(4) Experimental Procedure of EX.107

EX.107 was prepared in accordance with the general procedure 3 using the method described below in detail.

Synthesis of 2-(2-(5-fluoro-2-methoxyphenyl)-1H-pyrrolo[2,3-b]pyridin-3-yl)-4-methoxybenzonitrile (EX.107)

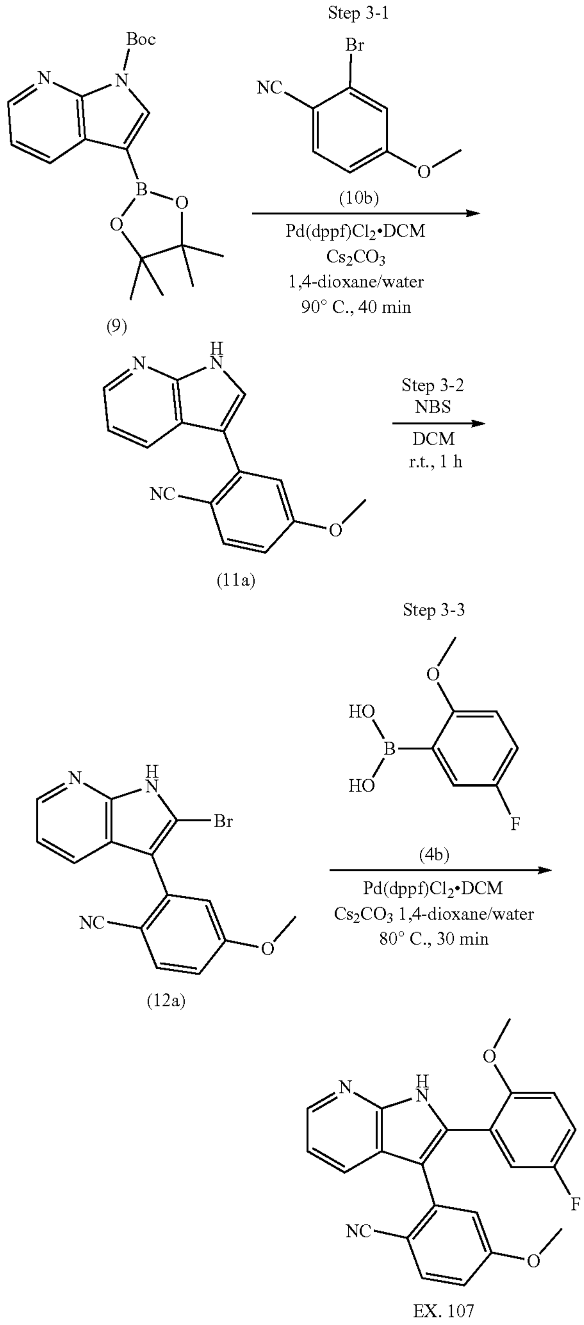

Step 3-1

A reaction vessel containing tert-butyl 3-(4,4,5,5-tetramethyl-1,3,2-dioxaborolan-2-yl)pyrrolo[2,3-b]pyridine-1-carboxylate (9) (100 mg, 0.29 mmol), 2-bromo-4-methoxybenzonitrile (10b) (73.9 mg, 0.35 mmol) and $Cs_2CO_3$ (236.6 mg, 0.73 mmol) in 1,4-dioxane (1.5 mL) and water (0.8 mL) was degassed and backfilled with nitrogen three times. After the addition of Pd(dppf)$Cl_2$-DCM (47.5 mg, 0.058 mmol), the mixture was purged with nitrogen three times. The resulting mixture was then stirred and heated at 90° C. for 40 min. After cooling to room temperature, the mixture was purified by prep HPLC ($CH_3CN$/0.1% TFA-$H_2O$/0.1% TFA) to give the expected product as an off-white solid (50 mg, 69%); LRMS (ESI): m/z $[M+H]^+$ 250.

Step 3-2

A solution of 4-methoxy-2-(1H-pyrrolo[2,3-b]pyridin-3-yl)benzonitrile (11a) (48 mg, 0.19 mmol) and NBS (41.1 mg, 0.23 mmol) in DCM (2.4 mL) was stirred at room temperature for 1 h. After concentration, the residue was purified by prep HPLC ($CH_3CN$/0.1% TFA-$H_2O$/0.1% TFA) to give the expected product as a white solid (20.4 mg, 32%); LRMS (ESI): m/z $[M+H]^+$ 328, 330.

Step 3-3

A reaction vessel containing 2-(2-bromo-1H-pyrrolo[2,3-b]pyridin-3-yl)-4-methoxy-benzonitrile (12a) (12.9 mg, 0.039 mmol), (5-fluoro-2-methoxy-phenyl)boronic acid (4b) (8.7 mg, 0.051 mmol), and $Cs_2CO_3$ (32 mg, 0.098 mmol) in 1,4-dioxane (1 mL) and water (0.5 mL) was degassed and backfilled with nitrogen three times. After the addition of $Pd(dppf)Cl_2$-DCM (6.4 mg, 0.008 mmol), the mixture was purged with nitrogen three times. The resulting mixture was then stirred and heated at 80° C. for 30 minutes. After cooling to room temperature, the mixture was purified by prep HPLC ($CH_3CN$/0.1% TFA-$H_2O$/0.1% TFA) to give EX.107 as a pale-yellow solid (0.82 mg, 5%).

$^1H$ NMR (400 MHz, DMSO-$d_6$) δ 3.42 (3H, s), 3.76 (3H, s), 6.86 (1H, d, J=2.6 Hz), 7.01-7.03 (1H, m), 7.03-7.06 (1H, m), 7.11 (1H, dd, J=9.1, 3.1 Hz), 7.16 (1H, dd, J=7.9, 4.7 Hz), 7.22 (1H, td, J=8.6, 3.2 Hz), 7.78 (1H, d, J=8.7 Hz), 7.85 (1H, d, J=6.4 Hz), 8.32 (1H, dd, J=4.7, 1.5 Hz), 12.27 (NH, s); LRMS (ESI): m/z $[M+H]^+$ 374.

The following compounds were synthesized in a similar manner to EX.107 using $Br_2$ instead of NBS in step 3-2 in accordance with the general procedure 3.

| Example No. | Chemical structuralformula | Spectrum data |
|---|---|---|
| EX. 108 | 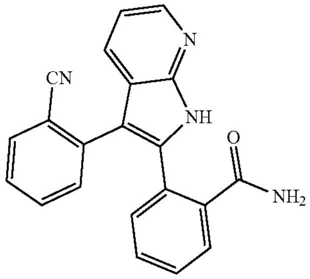 [SMILES: N#Cc1ccccc1-c1c(-c2ccccc2C(N)=O)[nH]c2ncccc12] | $^1H$ NMR (400 MHz, DMSO-$d_6$): δ 7.16 (1H, dd, J = 7.9, 4.7 Hz), 7.19 (1H, br s), 7.25-7.28 (1H, m), 7.31 (1H, dd, J = 7.9, 1.3 Hz), 7.35 (1H, br s), 7.41-7.47 (3H, m), 7.53-7.57 (2H, m), 7.79 (1H, dd, J = 7.9, 1.5 Hz), 7.84 (1H, dd, J = 7.7, 1.3 Hz), 8.30 (1H, dd, J = 4.7, 1.5 Hz), 12.15 (1H, br s); LRMS (ESI): m/z $[M + H]^+$ 339. |
| EX. 109 | 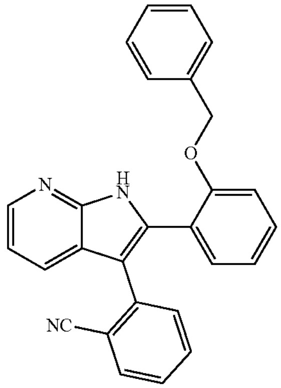 [SMILES: N#Cc1ccccc1-c1c(-c2ccccc2OCc2ccccc2)[nH]c2ncccc12] | $^1H$ NMR (400 MHz, $CDCl_3$): δ 5.15 (2H, s), 6.84 (1H, td, J = 7.6, 1.1 Hz), 7.05 (1H, d, J = 8.3 Hz), 7.08-7.17 (2H, m), 7.27-7.36 (6H, m), 7.40 (1H, td, J = 7.6, 1.3 Hz), 7.45-7.49 (1H, m), 7.58 (1H, td, J = 7.7, 1.4 Hz), 7.67-7.72 (1H, m), 7.84 (1H, dd, J = 7.9, 1.5 Hz), 8.30 (1H, dd, J = 4.8, 1.5 Hz), 10.24 (1H, s); LRMS (ESI): m/z $[M + H]^+$ 402. |
| EX. 110 | 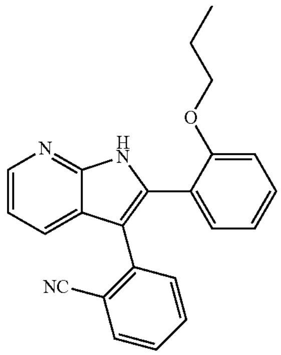 [SMILES: CCCOc1ccccc1-c1[nH]c2ncccc2c1-c1ccccc1C#N] | $^1H$ NMR (400 MHz, $CDCl_3$): δ 1.00 (3H, t, J = 7.4 Hz), 1.70-1.89 (2H, m), 3.97-4.08 (2H, m), 6.79 (1H, td, J = 7.5, 1.1 Hz), 7.00-7.06 (2H, m), 7.21 (1H, dd, J = 7.6, 4.8 Hz), 7.27-7.34 (1H, m), 7.43 (1H, td, J = 7.6, 1.3 Hz), 7.50 (1H, t, J = 7.2 Hz), 7.61 (1H, td, J = 7.7, 1.4 Hz), 7.74 (1H, dd, J = 7.8, 0.9 Hz), 7.94 (1H, d, J = 7.5 Hz), 8.31 (1H, d, J = 4.9 Hz), 10.79 (NH, br s); LRMS (ESI): m/z $[M + H]^+$ 354. |

-continued

| Example No. | Chemical structuralformula | Spectrum data |
|---|---|---|
| EX. 111 | 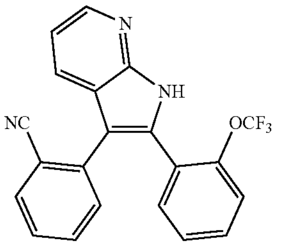 [SMILES: N#Cc1ccccc1-c1c(-c2ccccc2OC(F)(F)F)[nH]c2ncccc12] | $^1$H NMR (400 MHz, $CDCl_3$): δ 7.18-7.68 (8H, m), 7.74-7.82 (1H, m), 8.10-8.51 (2H, m), 13.48 (NH, br s); LRMS (ESI): m/z $[M + H]^+$ 380. |
| EX. 112 | 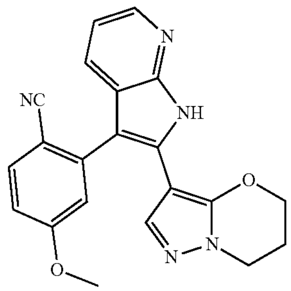 [SMILES: COc1ccc(C#N)c(-c2c(-c3cnn4c3OCCC4)[nH]c3ncccc23)c1] | $^1$H NMR (400 MHz, DMSO-$d_6$): δ 2.02-2.14 (2H, m), 3.82 (3H, s), 3.97-4.04 (2H, m), 4.08 (2H, t, J = 6.2 Hz), 6.98 (1H, d, J = 2.6 Hz), 7.05-7.14 (2H, m), 7.36 (1H, s), 7.70 (1H, dd, J = 7.9, 1.2 Hz), 7.81 (1H, d, J = 8.7 Hz), 8.22 (1H, dd, J = 4.7, 1.5 Hz), 11.89 (1H, s); LRMS (ESI): m/z $[M + H]^+$ 372. |
| EX. 113 | 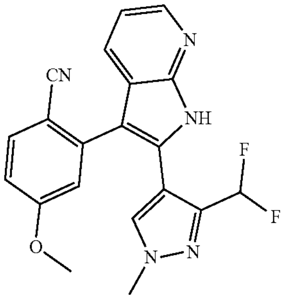 [SMILES: COc1ccc(C#N)c(-c2c(-c3cn(C)nc3C(F)F)[nH]c3ncccc23)c1] | $^1$H NMR (400 MHz, $CD_3OD$): δ 3.83 (3H, s), 3.94 (3H, s), 6.50 (1H, t, $J_{H-F}$ = 54.2 Hz), 6.98 (1H, d, J = 2.6 Hz), 7.05 (1H, dd, J = 8.7, 2.6 Hz), 7.21 (1H, dd, J = 8.0, 4.8 Hz), 7.72 (1H, dd, J = 8.7, 0.3 Hz), 7.76 (1H, s), 7.89 (1H, dd, J = 7.9, 1.5 Hz), 8.29 (1H, dd, J = 4.9, 1.5 Hz); LRMS (ESI): m/z $[M + H]^+$ 380. |
| EX. 114 | 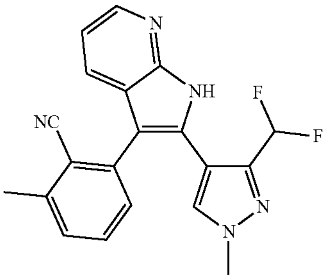 [SMILES: Cc1cccc(-c2c(-c3cn(C)nc3C(F)F)[nH]c3ncccc23)c1C#N] | [1]H (400 MHz, DMSO-$d_6$): δ 2.51 (3H, s), 3.90 (3H, s), 6.60 (1H, t, $J_{H-F}$ = 54.1 Hz), 7.16 (1H, dd, J = 7.9, 4.7 Hz), 7.18 (1H, d, J = 7.8 Hz), 7.41 (1H, dt, J = 7.7, 0.9 Hz), 7.56 (1H, t, J = 7.7 Hz), 7.78 (1H, dd, J = 7.9, 1.5 Hz), 7.94 (1H, s), 8.32 (1H, dd, J = 4.7, 1.5 Hz), 12.21 (1H, s); LRMS (ESI): m/z $[M + H]^+$ 364. |
| EX. 115 | 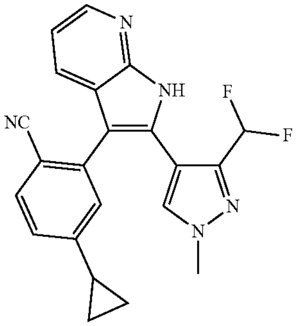 [SMILES: Cn1cc(-c2[nH]c3ncccc3c2-c2cc(C3CC3)ccc2C#N)c(C(F)F)n1] | [1]H (400 MHz, DMSO-$d_6$): δ 0.44-0.86 (2H, m), 1.03 (2H, ddd, J = 8.2, 3.5, 1.3 Hz), 1.97 (1H, ddd, J = 13.0, 8.2, 4.9 Hz), 3.91 (3H, s), 6.58 (1H, t, $J_{H-F}$ = 54.0 Hz), 7.02 (1H, d, J = 1.7 Hz), 7.15 (1H, dd, J = 7.9, 4.7 Hz), 7.22 (1H, dd, J = 8.1, 1.9 Hz), 7.71 (1H, d, J = 8.1 Hz), 7.77 (1H, dd, J = 7.9, 1.1 Hz), 7.94 (1H, s), 8.31 (1H, dd, J = 4.7, 1.6 Hz), 12.18 (1H, s); LRMS (ESI): m/z $[M + H]^+$ 390. |

-continued

| Example No. | Chemical structuralformula | Spectrum data |
|---|---|---|
| EX. 116 | 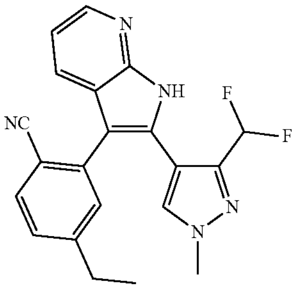 [SMILES: CCc1ccc(C#N)c(-c2c(-c3cn(C)nc3C(F)F)[nH]c3ncccc23)c1] | [1]H (400 MHz, DMSO-$d_6$): δ 1.11 (3H, t, J = 7.6 Hz), 2.64 (2H, q, J = 7.5 Hz), 3.90 (3H, s), 6.55 (1H, t, $J_{H\text{-}F}$ = 54.1 Hz), 7.15 (1H, dd, J = 7.9, 4.7 Hz), 7.26 (1H, d, J = 1.3 Hz), 7.35 (1H, dd, J = 8.0, 1.8 Hz), 7.78 (1H, d, J = 7.9 Hz), 7.78 (1H, dd, J = 8.0, 1.6 Hz), 7.95 (1H, s), 8.31 (1H, dd, J = 4.7, 1.6 Hz), 12.18 (1H, s); LRMS (ESI): m/z $[M + H]^+$ 378. |
| EX. 117 | 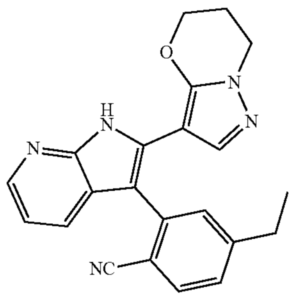 [SMILES: CCc1ccc(C#N)c(-c2c(-c3cnn4c3OCCC4)[nH]c3ncccc23)c1] | [1]H (400 MHz, DMSO-$d_6$): δ 1.19 (3H, t, J = 7.6 Hz), 1.98-2.17 (2H, m), 2.69 (2H, q, J = 7.5 Hz), 3.89-4.03 (2H, m), 4.06 (2H, t, J = 5.6 Hz), 7.09 (1H, dd, J = 7.9, 4.8 Hz), 7.31 - 7.33 (1H, m), 7.37 (1H, dd, J = 8.0, 1.8 Hz), 7.37 (1H, S), 7.67 (1H, dd, J = 7.9, 1.1 Hz), 7.79 (1H, d, J = 8.2 Hz), 8.22 (1H, dd, J = 4.8, 1.6 Hz), 11.87 (1H, s); LRMS (ESI): m/z $[M + H]^+$ 370. |

(5) Experimental Procedure of EX.118

EX.118 was prepared in accordance with the general procedure 4 using the method described below in detail.

Synthesis of 2-(6-methyl-3-phenyl-1H-pyrrolo[2,3-b]pyridin-2-yl) phenol (EX.118)

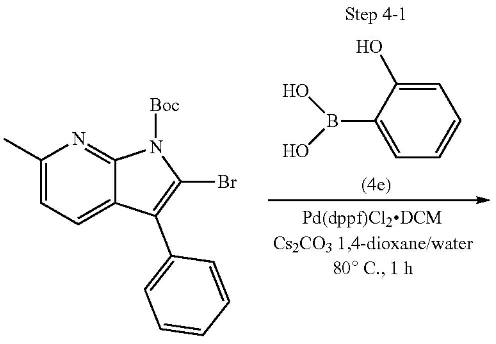

(6d)

-continued

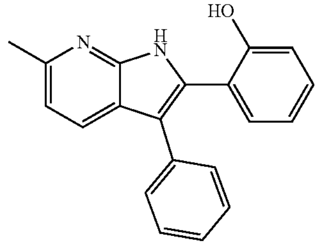

EX. 118

Step 4-1

A reaction vessel containing tert-butyl 2-bromo-6-methyl-3-phenyl-pyrrolo[2,3-b]pyridine-1-carboxylate (6d) (35 mg, 0.09 mmol), O-hydroxyphenylboronic acid (4e) (15 mg, 0.11 mmol) and $Cs_2CO_3$ (88.3 mg, 0.27 mmol) in 1,4-dioxane (0.5 mL) and water (0.1 mL) was degassed and backfilled with nitrogen three times. After the addition of Pd(dppf)$Cl_2$-DCM (7.4 mg, 0.01 mmol), the mixture was purged with nitrogen three times. The resulting mixture was then stirred and heated at 80° C. for 1 h. After cooling to room temperature, the mixture was filtered through Celite, and the filtrate was concentrated. The residue was purified by prep HPLC ($CH_3CN$/0.1% TFA-$H_2O$/0.1% TFA) to give EX.118 as a pale-yellow solid (3.8 mg, 13%).

$^1$H NMR (400 MHz, DMSO-$d_6$): δ 2.54 (3H, s), 6.73 (1H, t, J=7.4 Hz), 6.92 (1H, d, J=8.1 Hz), 6.98 (1H, d, J=7.9 Hz), 7.08 (1H, d, J=6.6 Hz), 7.13-7.24 (2H, m), 7.26-7.37 (4H, m), 7.87 (1H, d, J=7.9 Hz), 9.80 (1H, br s), 11.53 (1H, br s); LRMS (ESI): m/z $[M+H]^+$ 301.

The following compounds were synthesized using conditions analogous to EX.118 in accordance with the general procedure 4.

| Example No. | Chemical structural formula | Spectrum data |
|---|---|---|
| EX. 119 | 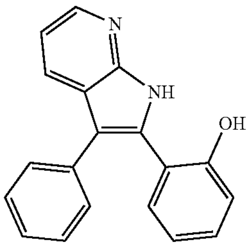 [SMILES: Oc1ccccc1-c1[nH]c2ncccc2c1-c1ccccc1] | $^{1}$H NMR (400 MHz, DMSO-$d_6$): δ 6.77 (1H, t, J = 7.4 Hz), 6.94 (1H, d, J = 8.1 Hz), 7.08-7.15 (2H, m), 7.16-7.26 (2H, m), 7.29-7.33 (4H, m), 8.00 (1H, d, J = 8.1 Hz), 8.25 (1H, dd, J = 4.7, 1.4 Hz), 9.72 (1H, br s), 11.82 (1H, br s); LRMS (ESI): m/z $[M + H]^+$ 287. |
| EX. 120 | 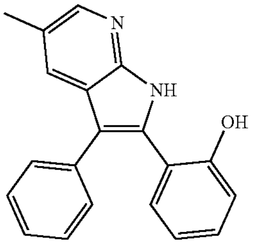 [SMILES: Cc1cnc2[nH]c(-c3ccccc3O)c(-c3ccccc3)c2c1] | $^{1}$H NMR (400 MHz, DMSO-$d_6$): δ 2.39 (3H, s), 6.75 (1H, t, J = 7.4 Hz), 6.93 (1H, d, J = 8.1 Hz), 7.09 (1H, d, J = 7.4 Hz), 7.13-7.24 (2H, m), 7.26-7.34 (4H, m), 7.80 (1H, s), 8.09 (1H, s), 9.69 (1H, br s), 11.64 (1H, br s); LRMS (ESI): m/z $[M + H]^+$ 301. |
| EX. 121 | 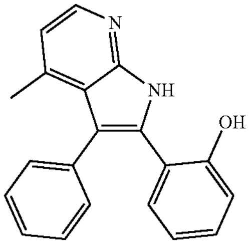 [SMILES: Cc1ccnc2[nH]c(-c3ccccc3O)c(-c3ccccc3)c12] | $^{1}$H NMR (400 MHz, DMSO-$d_6$): δ 2.09 (3H, s), 6.58 (1H, t, J = 7.1 Hz), 6.79 (1H, d, J = 4.5 Hz), 6.85 (1H, d, J = 7.6 Hz), 6.94 (1H, d, J = 7.6 Hz), 7.08 (1H, t, J = 7.9 Hz), 7.19-7.34 (5H, m), 8.06 (1H, d, J = 4.5 Hz), 11.05 (1H, br s); LRMS (ESI): m/z $[M + H]^+$ 301. |
| EX. 122 | 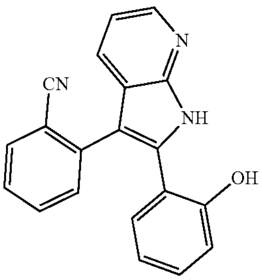 [SMILES: N#Cc1ccccc1-c1c(-c2ccccc2O)[nH]c2ncccc12] | $^{1}$H NMR (400 MHz, DMSO-$d_6$): δ 6.71 (1H, t, J = 7.0 Hz), 6.84 (1H, d, J = 8.2 Hz), 7.01-7.19 (3H, m), 7.35 (1H, d, J = 7.7 Hz), 7.45 (1H, td, J = 7.7, 1.3 Hz), 7.63 (1H, td, J = 7.7, 1.3 Hz), 7.73 (1H, d, J = 7.7 Hz), 7.85 (1H, d, J = 7.7 Hz), 8.26 (1H, dd, J = 4.7, 1.4 Hz); LRMS (ESI): m/z $[M + H]^+$ 312. |

(6) Experimental Procedure of EX.123

EX.123 was prepared in accordance with general procedure 5 using the method described below in detail.

Synthesis of 2-[2-(5-methoxy-1-methyl-pyrazol-4-yl)-1H-pyrrolo[2,3-b]pyridin-3-yl]benzonitrile (EX.123)

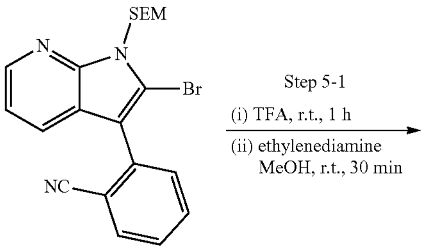

(6e)

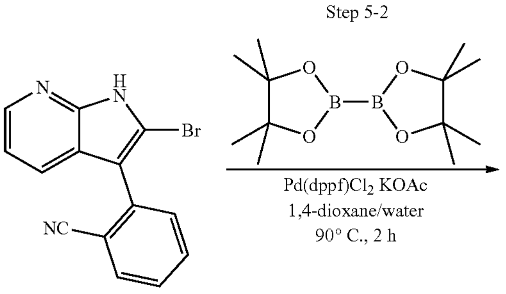

(12b)

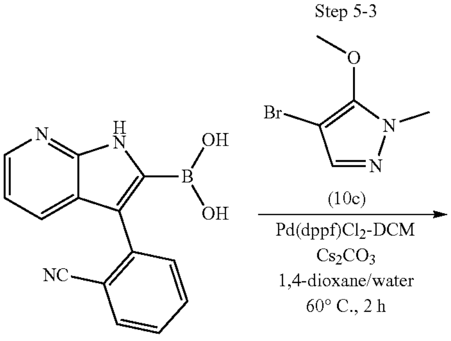

(13a)

-continued

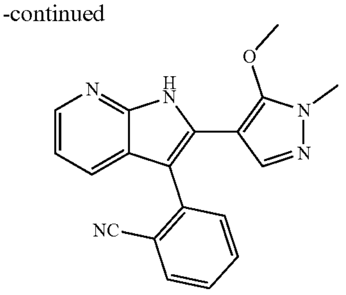

EX. 123

Step 5-1

A mixture of 2-[2-bromo-1-(2-trimethylsilylethoxymethyl)pyrrolo[2,3-b]pyridin-3-yl]benzonitrile (6e) (1.92 g, 4.48 mmol) and neat TFA (10.29 mL, 134.45 mmol) was stirred at room temperature for 1 h. After concentration to dryness, the residue was dissolved in MeOH (10 mL) and ethylenediamine (9.0 mL, 134.45 mmol) was added. The mixture was then stirred at room temperature for 30 min. The mixture was poured into brine and the product was extracted with DCM (×2). The combined organic extracts were dried over $Na_2SO_4$ and concentrated. The residue was purified by silica gel column chromatography (0-100% EtOAc/Hexane, then 0-10% MeOH/DCM) to give the expected product as a white solid (1.30 g, 97%); LRMS (ESI): m/z $[M+H]^+$ 298, 300.

Step 5-2

A reaction vessel containing 2-(2-bromo-1H-pyrrolo[2,3-b]pyridin-3-yl)benzonitrile (12b) (507 mg, 1.70 mmol), bis(pinacolato)diboron (518.2 mg, 2.04 mmol) and potassium acetate (334.0 mg, 3.40 mmol) in 1,4-dioxane (8 mL) and water (2 mL) was degassed and backfilled with nitrogen three times. After the addition of Pd(dppf)$Cl_2$-DCM (138.9 mg, 0.17 mmol), the reaction mixture was purged with nitrogen three times. The resulting mixture was then stirred and heated at 90° C. for 2 h. After cooling to room temperature, the mixture was filtered through Celite, and the filtrate was concentrated. The residue was purified by silica gel column chromatography (0-30% MeOH/DCM/0.5% TFA) to give the expected product as a beige solid (145 mg, 32%);

LRMS (ESI): m/z $[M+H]^+$ 264.

Step 5-3

A reaction vessel containing [3-(2-cyanophenyl)-1H-pyrrolo[2,3-b]pyridin-2-yl]boronic acid (13a) (35 mg, 0.13 mmol), 4-bromo-5-methoxy-1-methyl-pyrazole (10c) (28 mg, 0.15 mmol), and $Cs_2CO_3$ (78 mg, 0.24 mmol) in 1,4-dioxane (1.4 mL) and water (0.7 mL) was degassed and backfilled with nitrogen three times. After the addition of Pd(dppf)$Cl_2$-DCM (21.7 mg, 0.027 mmol), the mixture was purged with nitrogen three times. The resulting mixture was then stirred and heated at 60° C. for 1 h. After cooling to room temperature, the mixture was purified by prep HPLC ($CH_3CN$/0.1% TFA-$H_2O$/0.1% TFA) to give EX.123 as a pale-yellow solid (1.3 mg, 3%).

$^1H$ NMR (400 MHz, DMSO-$d_6$): δ 3.48 (3H, s), 3.70 (3H, s), 7.09 (1H, dd, J=7.9, 4.7 Hz), 7.45 (1H, d, J=7.2 Hz), 7.52 (1H, td, J=7.9, 1.6 Hz), 7.63 (1H, s), 7.64-7.73 (2H, m), 7.89 (1H, d, J=7.8 Hz), 8.23 (1H, dd, J=4.6, 1.5 Hz), 11.86 (NH, s);

LRMS (ESI): m/z $[M+H]^+$ 330.

The following compounds were synthesized using conditions analogous to EX.123 in accordance with the general procedure 5.

| Example No. | Chemical structural formula | Spectrum data |
|---|---|---|
| EX.124 | 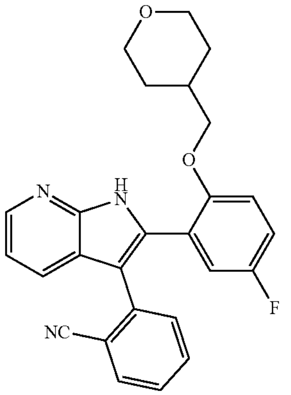 [SMILES: N#Cc1ccccc1-c1c(-c2cc(F)ccc2OCC2CCOCC2)[nH]c2ncccc12] | $^1$H NMR (400 MHz, DMSO-$d_6$): δ 0.95-1.13 (2H, m), 1.36 (2H, br s), 1.54 (1H, br s), 3.19 (2H, td, J = 11.7, 2.2 Hz), 3.41-3.60 (2H, m), 3.67-3.80 (2H, m), 7.05 (1H, dd, J = 9.1, 4.5 Hz), 7.11-7.24 (3H, m), 7.34 (1H, d, J = 7.8 Hz), 7.47 (1H, td, J = 7.7, 1.1 Hz), 7.65 (1H, td, J = 7.7, 1.2 Hz), 7.88 (2H, td, J = 7.8, 1.4 Hz), 8.33 (1H, dd, J = 4.7, 1.5 Hz), 12.27 (NH, s); LRMS (ESI): m/z $[M + H]^+$ 428. |
| EX.125 | 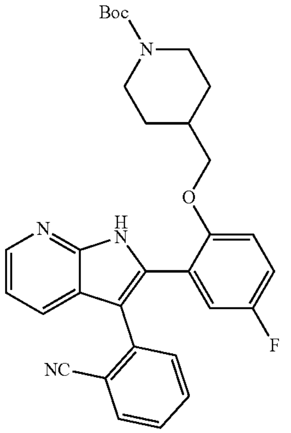 [SMILES: CC(C)(C)OC(=O)N1CCC(COc2ccc(F)cc2-c2[nH]c3ncccc3c2-c2ccccc2C#N)CC1] | $^1$H NMR (400 MHz, DMSO-$d_6$): δ 0.88 (2H, qd, J = 12.5, 3.8 Hz), 1.35 (9H, s), 1.44 (3H, br s), 2.67 (2H, br s), 3.47 (2H, br s), 3.81 (2H, br s), 7.04 (1H, dd, J = 9.2, 4.6 Hz), 7.09-7.29 (3H, m), 7.35 (1H, d, J = 7.9 Hz), 7.47 (1H, td, J = 7.7, 1.1 Hz), 7.66 (1H, td, J = 7.6, 1.2 Hz), 7.87 (2H, td, J = 8.1, 1.5 Hz), 8.33 (1H, dd, J = 4.7, 1.5 Hz), 12.27 (NH, s); LRMS (ESI): m/z $[M + H]^+$ 527. |
| EX.126 | 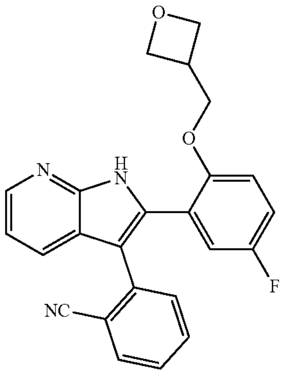 [SMILES: N#Cc1ccccc1-c1c(-c2cc(F)ccc2OCC2COC2)[nH]c2ncccc12] | $^1$H NMR (400 MHz, DMSO-$d_6$): δ 2.97 (1H, dt, J = 13.7, 6.7 Hz), 3.95 (2H, m), 4.10-4.19 (2H, m), 4.51 (2H, dd, J = 7.8, 6.2 Hz), 7.06-7.15 (2H, m), 7.15-7.27 (2H, m), 7.35-7.39 (1H, m), 7.42-7.52 (1H, m), 7.67 (1H, td, J = 7.7, 1.4 Hz), 7.87 (2H, ddd, J = 9.7, 7.9, 1.2 Hz), 8.33 (1H, dd, J = 4.7, 1.6 Hz), 12.28 (NH, s); LRMS (ESI): m/z $[M + H]^+$ 400. |

-continued

| Example No. | Chemical structural formula | Spectrum data |
|---|---|---|
| EX.127 | 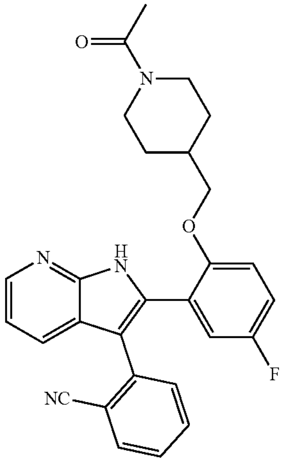 [SMILES: CC(=O)N1CCC(COc2ccc(F)cc2-c2[nH]c3ncccc3c2-c2ccccc2C#N)CC1] | $^1H$ NMR (400 MHz, DMSO-$d_6$): δ 0.74-1.07 (2H, m), 1.33-1.59 (3H, br s), 1.91 (3H, s), 2.34-2.45 (1H, m), 2.83-2.96 (1H, m), 3.52 (2H, d, J = 26.7 Hz), 3.69 (1H, d, J = 15.0 Hz), 4.26 (1H, d, J = 10.6 Hz), 7.05 (1H, dd, J = 9.1, 4.7 Hz), 7.10-7.27 (3H, m), 7.35 (1H, d, J = 6.3 Hz), 7.48 (1H, td, J = 7.7, 1.1 Hz), 7.61-7.71 (1H, m), 7.84-7.93 (2H, m), 8.34 (1H, dd, J = 4.7, 1.5 Hz), 12.30 (NH, s); LRMS (ESI): m/z $[M + H]^+$ 469. |
| EX.128 | 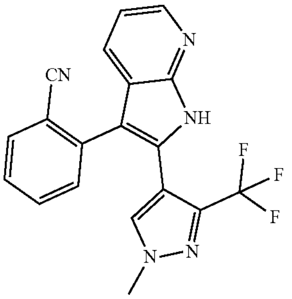 [SMILES: Cn1cc(-c2[nH]c3ncccc3c2-c2ccccc2C#N)c(C(F)(F)F)n1] | $^1H$ NMR (400 MHz, DMSO-$d_6$): δ 3.97 (3H, s). 7.17 (1H, dd, J = 7.9, 4.7 Hz), 7.34 (1H, d, J = 7.5 Hz), 7.50 (1H, t, J = 7.8 Hz), 7.67 (1H, t, J = 7.7 Hz), 7.80 (1H, d, J = 8.0 Hz), 7.90 (1H, t, J = 7.1 Hz), 8.15 (1H, s), 8.33 (1H, d, J = 4.7 Hz), 12.32 (NH, s); LRMS (ESI): m/z $[M + H]^+$ 368. |
| EX.129 | 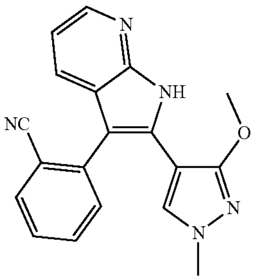 [SMILES: COc1nn(C)cc1-c1[nH]c2ncccc2c1-c1ccccc1C#N] | $^1H$ NMR (400 MHz, DMSO-$d_6$): δ 3.49 (3H, s), 3.70 (3H, s), 7.09 (1H, dd, J = 7.9, 4.7 Hz), 7.38-7.58 (2H, m), 7.60-7.76 (3H, m), 7.90 (1H, d, J = 7.6 Hz), 8.23 (1H, d, J = 4.7 Hz), 11.90 (NH, s); LRMS (ESI): m/z $[M + H]^+$ 330. |
| EX.130 | 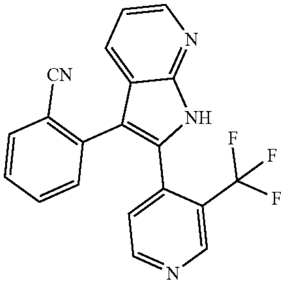 [SMILES: N#Cc1ccccc1-c1c(-c2ccncc2C(F)(F)F)[nH]c2ncccc12] | $^1H$ NMR (400 MHz, DMSO-$d_6$): δ 7.21-7.35 (2H, m), 7.49 (1H, t, J = 7.7 Hz), 7.61 (1H, t, J = 7.7 Hz), 7.73 (1H, s), 7.87-7.98 (2H, m), 8.41 (1H, dd, J = 4.9, 1.2 Hz), 8.95 (1H, d, J = 4.9 Hz), 9.05 (1H, s), 12.59 (NH, s); LRMS (ESI): m/z $[M + H]^+$ 365. |

-continued

| Example No. | Chemical structural formula | Spectrum data |
|---|---|---|
| EX.131 | 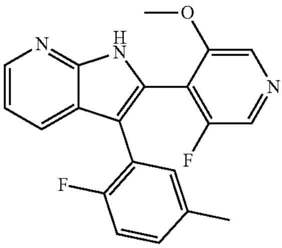 [SMILES: COc1cncc(F)c1-c1[nH]c2ncccc2c1-c1cc(C)ccc1F] | $^1$H NMR (400 MHz, DMSO-$d_6$): 2.23 (3H, s), 3.74 (3H, s), 7.07 (1H, dd, J = 7.6, 4.7 Hz), 7.10-7.15 (2H, m), 7.17 (1H, dd, J = 8.5, 7.4 Hz), 7.89 (1H, d, J = 7.6 Hz), 8.32 (1H, s), 8.35 (1H, d, J = 4.7 Hz), 8.39 (1H, s), 12.28 (NH, s); LRMS (ESI): m/z $[M + H]^+$ 352. |
| EX.132 | 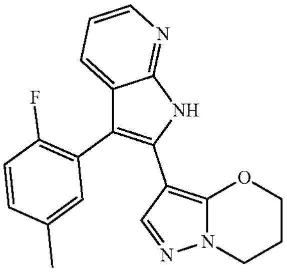 [SMILES: Cc1ccc(F)c(-c2c(-c3cnn4c3OCCC4)[nH]c3ncccc23)c1] | $^1$H NMR (400 MHz, DMSO-$d_6$): δ 2.08-2.17 (2H, m), 2.30 (3H, s), 4.07-4.10 (4H, m), 7.04 (1H, dd, J = 7.8, 4.7 Hz), 7.11-7.18 (3H, m), 7.35 (1H, s), 7.62 (1H, d, J = 7.8 Hz), 8.18 (1H, dd, J = 4.8, 1.5 Hz), 11.61 (1H, s); LRMS (ESI): m/z $[M + H]^+$ 349. |
| EX.133 | 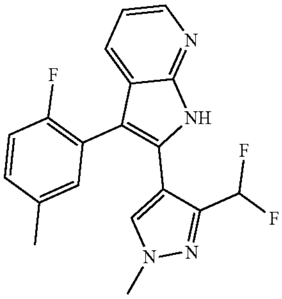 [SMILES: Cc1ccc(F)c(-c2c(-c3cn(C)nc3C(F)F)[nH]c3ncccc23)c1] | $^1$H NMR (400 MHz, DMSO-$d_6$): δ 2.26 (3H, s), 3.91 (3H, s), 6.63 (1H, t, $J_{H-F}$ = 54.2 Hz), 7.12 (4H, m), 7.75 (1H, d, J = 8.0 Hz), 7.93 (1H, s), 8.28 (1H, dd, J = 4.7, 1.1 Hz), 12.04 (1H, s); LRMS (ESI): m/z $[M + H]^+$ 357. |
| EX.134 | 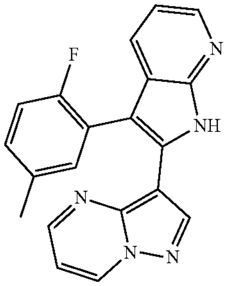 [SMILES: Cc1ccc(F)c(-c2c(-c3cnn4cccnc34)[nH]c3ncccc23)c1] | $^1$H NMR (400 MHz, DMSO-$d_6$): δ 2.28 (3H, s), 7.08-7.24 (4H, m), 7.28 (1H, d, J = 6.1 Hz), 7.74 (1H, d, J = 8.0 Hz), 8.10 (1H, s), 8.27 (1H, dd, J = 4.7, 1.5 Hz), 8.62 (1H, dd, J = 4.0, 1.7 Hz), 9.20 (1H, dd, J = 7.0, 1.7 Hz), 11.77 (1H, s); LRMS (ESI): m/z $[M + H]^+$ 344. |
| EX.135 | 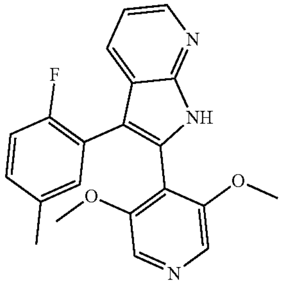 [SMILES: COc1cncc(OC)c1-c1[nH]c2ncccc2c1-c1cc(C)ccc1F] | $^1$H NMR (400 MHz, DMSO-$d_6$) δ 2.18 (3H, s), 3.66 (6H, s), 6.95 (1H, d, J = 7.4 Hz), 7.08 (2H, d, J = 8.3 Hz), 7.12 (1H, dd, J = 7.9, 4.7 Hz), 7.80 (1H, d, J = 7.9 Hz), 8.15 (2H, s), 8.28 (1H, dd, J = 4.6, 1.6 Hz), 12.00 (1H, s); LRMS (ESI): m/z $[M + H]^+$ 364. |

-continued

| Example No. | Chemical structural formula | Spectrum data |
|---|---|---|
| EX.136 | 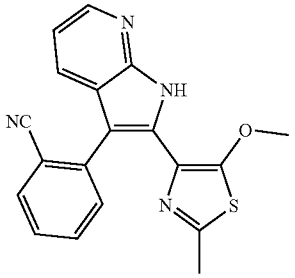 [SMILES: COc1sc(C)nc1-c1[nH]c2ncccc2c1-c1ccccc1C#N] | $^{1}$H NMR (400 MHz, DMSO-$d_6$): δ 2.53 (3H, s), 3.52 (3H, s), 7.09-7.17 (1H, m), 7.45 (1H, d, J = 7.7 Hz), 7.51 (1H, apparent t, J = 7.9 Hz), 7.71-7.75 (2H, m), 7.88 (1H, d, J = 7.1 Hz), 8.30 (1H, d, J = 4.2 Hz), 12.06 (1H, br s); LRMS (ESI): m/z $[M + H]^+$ 347. |
| EX.137 | 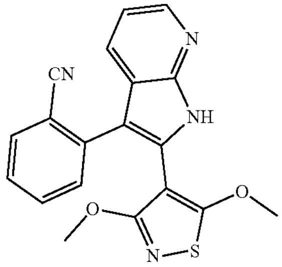 [SMILES: COc1nsc(OC)c1-c1[nH]c2ncccc2c1-c1ccccc1C#N] | $^{1}$H NMR (400 MHz, DMSO-$d_6$): δ 3.68 (3H, s), 3.71 (3H, s), 7.15 (1H, dd, J = 7.9, 4.7 Hz), 7.43 (1H, d, J = 7.9 Hz), 7.49 (1H, td, J = 7.7, 1.2 Hz), 7.71 (1H, td, J = 7.6, 1.3 Hz), 7.79-7.91 (2H, m), 8.31 (1H, dd, J = 4.6, 1.6 Hz), 12.12 (s, 1H); LRMS (ESI): m/z [M+H] 363. |
| EX.138 | 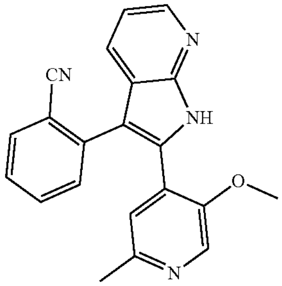 [SMILES: COc1cnc(C)cc1-c1[nH]c2ncccc2c1-c1ccccc1C#N] | $^{1}$H NMR (400 MHz, DMSO-$d_6$): δ 2.39 (3H, s), 3.43 (3H, s), 7.14-7.20 (2H, m), 7.35 (1H, d, J = 7.8 Hz), 7.52 (1H, apparent t, J = 7.8 Hz), 7.69 (1H, apparent t, J = 7.9 Hz), 7.84 (1H, d, J = 6.8 Hz), 7.89 (1H, d, J = 7.6 Hz), 8.21 (1H, s), 8.36 (1H, dd, J = 4.6, 1.6 Hz), 12.38 (1H, s); LRMS (ESI): m/z $[M + H]^+$ 341. |
| EX.139 | 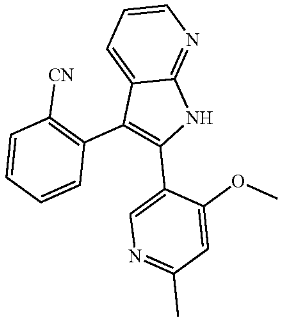 [SMILES: COc1cc(C)ncc1-c1[nH]c2ncccc2c1-c1ccccc1C#N] | $^{1}$H NMR (400 MHz, DMSO-$d_6$): δ 2.45 (3H, s), 3.54 (3H, s), 6.98 (1H, s), 7.16 (1H, dd, J = 7.9, 4.7 Hz), 7.41 (1H, d, J = 8.0 Hz), 7.49 (1H, apparent t, J = 7.7 Hz), 7.69 (1H, apparent t, J = 7.8 Hz), 7.81 (1H, d, J = 7.8 Hz), 7.85 (1H, d, J = 7.9 Hz), 8.11 (1H, s), 8.32 (1H, d, J = 4.5 Hz), 12.18 (1H, s); LRMS (ESI): m/z [M+H] 341. |
| EX.140 | 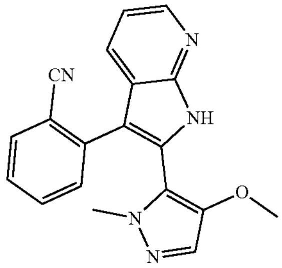 [SMILES: COc1cnn(C)c1-c1[nH]c2ncccc2c1-c1ccccc1C#N] | $^{1}$H NMR (400 MHz, DMSO-$d_6$): δ 3.25 (3H, s), 3.75 (3H, s), 7.15-7.25 (1H, m), 7.33 (1H, s), 7.44-7.54 (2H, m), 7.73 (1H, apparent t, J = 8.4 Hz), 7.80-7.95 (2H, m), 8.31-8.41 (1H, d, J = 4.4 Hz); LRMS (ESI): m/z $[M + H]^+$ 330. |

-continued

| Example No. | Chemical structural formula | Spectrum data |
|---|---|---|
| EX.141 | 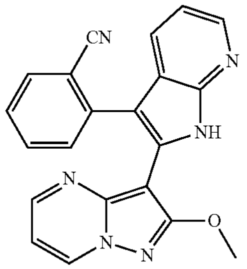 [SMILES: COc1nn2cccnc2c1-c1[nH]c2ncccc2c1-c1ccccc1C#N] | $^1H$ NMR (400 MHz, DMSO-$d_6$): δ 3.72 (3H, s), 6.97 (1H, dd, J = 6.9, 4.4 Hz), 7.15 (1H, dd, J = 7.8, 4.7 Hz), 7.45 (2H, d, J = 7.8 Hz), 7.64 (1H, apparent t, J = 7.8 Hz), 7.81 (2H, d, J = 6.8 Hz), 8.29 (1H, dd, J = 4.5, 1.8 Hz), 8.41 (1H, dd, J = 4.1, 1.8 Hz), 9.02 (1H, dd, J = 7.0, 1.8 Hz), 12.01 (1H, s); LRMS (ESI): m/z $[M + H]^+$ 367. |
| EX.142 | 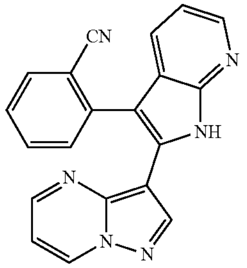 [SMILES: N#Cc1ccccc1-c1c(-c2cnn3cccnc23)[nH]c2ncccc12] | $^1H$ NMR (400 MHz, DMSO-$d_6$): δ 7.11 (1H, dd, J = 7.0, 4.0 Hz), 7.16 (1H, dd, J = 7.9, 4.7 Hz), 7.48-7.59 (2H, m), 7.70 (1H, td, J = 7.7, 1.5 Hz), 7.78 (1H, dd, J = 7.9, 1.6 Hz), 7.88 (1H, dd, J = 7.8, 1.4 Hz), 8.16 (1H, s) 8.31 (1H, dd, J = 4.7, 1.5 Hz), 8.47 (1H, dd, J = 4.0, 1.7 Hz), 9.18 (1H, dd, J = 7.0, 1.7 Hz), 12.11 (1H, s); LRMS (ESI): m/z $[M + H]^+$ 337. |
| EX.143 | 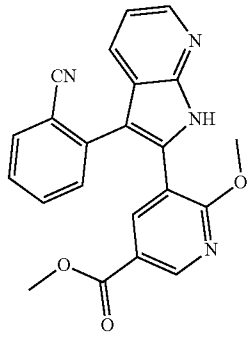 [SMILES: COC(=O)c1cnc(OC)c(-c2[nH]c3ncccc3c2-c2ccccc2C#N)c1] | $^1H$ NMR (400 MHz, DMSO-$d_6$): δ 3.61 (3H, s), 3.83 (3H, s), 7.19 (1H, dd, J = 8.0, 4.8 Hz), 7.45-7.54 (2H, m), 7.72 (1H, apparent t, J = 7.5 Hz), 7.85-7.87 (2H, m), 8.13 (1H, d, J = 2.2 Hz), 8.35-8.37 (1H, m), 8.75 (1H, d, J = 2.3 Hz); LRMS (ESI): m/z $[M + H]^+$ 385. |
| EX.144 | 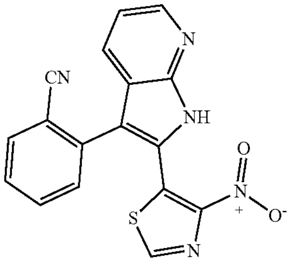 | $^1H$ NMR (400 MHz, DMSO-$d_6$): δ 7.24 (1H, dd, J = 8.0, 4.7 Hz), 7.51-7.61 (2H, m), 7.76 (1H, t, J = 7.6 Hz), 7.88-7.99 (2H, m), 8.44 (1H, d, J = 4.6 Hz), 9.18 (1H, s); LRMS (ESI): m/z $[M + H]^+$ 348. |
| EX.145 | 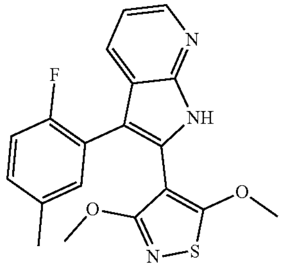 [SMILES: COc1nsc(OC)c1-c1[nH]c2ncccc2c1-c1cc(C)ccc1F] | $^1H$ NMR (400 MHz, DMSO-$d_6$): δ 2.25 (3H, s), 3.68-3.83 (6H, m), 7.02-7.20 (4H, m), 7.78 (1H, d, J = 8.1 Hz), 8.27 (1H, d, J = 4.7 Hz), 11.93 (1H, s); LRMS (ESI): m/z $[M + H]^+$ 370. |

-continued

| Example No. | Chemical structural formula | Spectrum data |
|---|---|---|
| EX.146 | 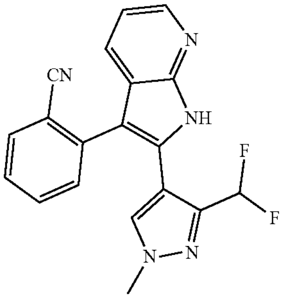 [SMILES: Cn1cc(-c2[nH]c3ncccc3c2-c2ccccc2C#N)c(C(F)F)n1] | $^1$H NMR (400 MHz, DMSO-$d_6$): δ 3.91 (3H, s), 6.62 (1H, t, J = 54.3 Hz), 7.14 (1H, dd, J = 7.9, 4.7 Hz), 7.41 (1H, d, J = 7.7 Hz), 7.51 (1H, apparent t, J = 7.7 Hz), 7.70 (1H, td, J = 7.8, 1.3 Hz), 7.76 (1H, dd, J = 8.0, 1.3 Hz), 7.89 (1H, d, J = 7.7 Hz), 7.94 (1H, s), 8.31 (1H, dd, J = 4.8, 1.2 Hz), 12.24 (NH, s); LRMS (ESI): m/z [M + H]$^+$ 350. |
| EX.147 | 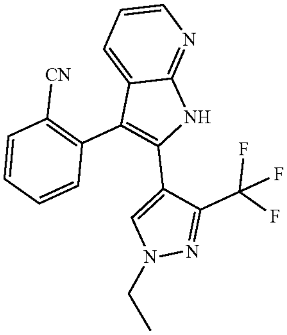 [SMILES: CCn1cc(-c2[nH]c3ncccc3c2-c2ccccc2C#N)c(C(F)(F)F)n1] | $^1$H NMR (400 MHz, DMSO-$d_6$): δ 1.39 (3H, t, J = 7.3 Hz). 4.26 (2H, q, J = 7.3 Hz), 7.18 (1H, dd, J = 7.9, 4.7 Hz), 7.35 (1H, dd, J = 7.3, 0.5 Hz), 7.50 (1H, td, J = 7.7, 1.2 Hz), 7.67 (1H, td, J = 7.7, 1.2 Hz), 7.81 (1H, dd, J = 8.0, 1.5 Hz), 7.88 (1H, dd, J = 7.0, 1.0 Hz), 8.20 (1H, s), 8.34 (1H, dd, J = 4.7, 1.5 Hz), 12.31 (NH, s); LRMS (ESI): m/z [M + H]$^+$ 382. |
| EX.148 | 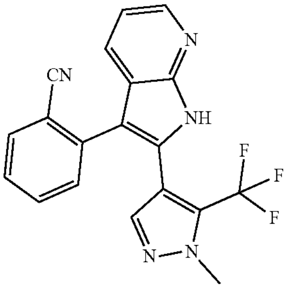 [SMILES: Cn1ncc(-c2[nH]c3ncccc3c2-c2ccccc2C#N)c1C(F)(F)F] | $^1$H NMR (400 MHz, DMSO-$d_6$): δ 3.98 (3H, s), 7.62 (1H, s), 7.17 (1H, dd, J = 8.0, 4.7 Hz), 7.40 (1H, d, J = 7.9 Hz), 7.51 (1H, t, J = 7.6 Hz), 7.70 (1H, td, J = 7.7, 1.3 Hz), 7.82 (1H, dd, J = 7.9, 1.5 Hz), 7.88 (1H, dd, J = 7.7, 0.8 Hz), 8.34 (1H, dd, J = 4.7, 1.5 Hz), 12.47 (NH, s); LRMS (ESI): m/z [M + H]$^+$ 368. |
| EX.149 | 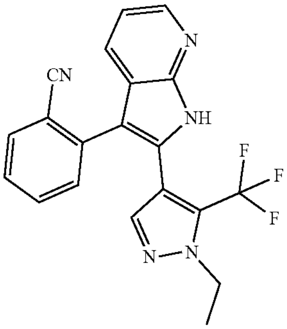 [SMILES: CCn1ncc(-c2[nH]c3ncccc3c2-c2ccccc2C#N)c1C(F)(F)F] | $^1$H NMR (400 MHz, DMSO-$d_6$): δ 1.38 (3H, t, J = 7.2 Hz), 4.28 (2H, q, J = 7.2 Hz), 7.18 (1H, dd, J = 7.9, 4.5 Hz), 7.39 (1H, dd, J = 7.8, 0.4 Hz), 7.51 (1H, td, J = 7.6, 1.2 Hz), 7.68 (1H, s), 7.70 (1H, td, J = 7.7, 1.4 Hz), 7.83 (1H, dd, J = 7.9, 1.5 Hz), 7.88 (1H, d, J = 7.9 Hz), 8.35 (1H, dd, J = 4.6, 1.5 Hz), 12.44 (NH, s); LRMS (ESI): m/z [M + H]$^+$ 382. |
| EX.150 | 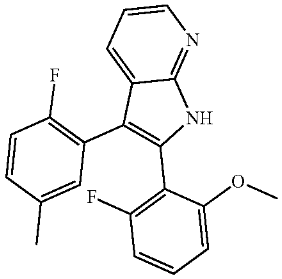 [SMILES: COc1cccc(F)c1-c1[nH]c2ncccc2c1-c1cc(C)ccc1F] | $^1$H NMR (400 MHz, DMSO-$d_6$): δ 2.18 (3H, s), 3.63 (3H, s), 6.84 (1H, t, J = 8.8 Hz), 6.93-6.99 (2H, m), 7.03-7.09 (2H, m), 7.13 (1H, dd, J = 7.9, 4.7 Hz), 7.43 (1H, td, J = 8.4, 6.9 Hz), 7.81 (1H, d, J = 8.0 Hz), 8.29 (1H, dd, J = 4.7, 1.6 Hz), 12.08 (1H, br s); LRMS (ESI): m/z [M + H]$^+$ 351. |

-continued

| Example No. | Chemical structural formula | Spectrum data |
|---|---|---|
| EX.151 | 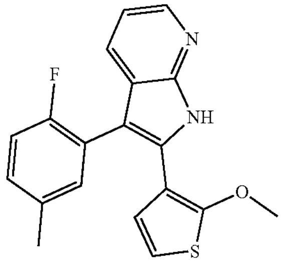 [SMILES: COc1sccc1-c1[nH]c2ncccc2c1-c1cc(C)ccc1F] | $^1$H NMR (400 MHz, CDC13): δ 2.37 (3H, s), 4.12 (3H, s), 6.51 (1H, d, J = 6.0 Hz), 6.66 (1H, d, J = 6.0 Hz), 7.08 (1H, dd, J = 7.8, 4.9 Hz), 7.12 (1H, t, J = 9.2 Hz), 7.16-7.21 (1H, m), 7.24 (1H, dd, J = 7.0, 1.9 Hz), 7.72 (1H, d, J = 7.8 Hz), 8.29 (1H, dd, J = 4.8, 1.5 Hz), 9.97 (NH, s); LRMS (ESI): m/z $[M + H]^+$ 339. |
| EX.152 | 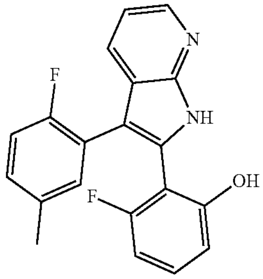 | $^1$H NMR (400 MHz, DMSO-$d_6$): δ 2.21 (3H, s), 6.97-7.15 (3H, m), 7.19 (1H, dd, J = 7.9, 4.7 Hz), 7.77 (1H, dd, J = 7.8, 4.7 Hz), 7.89 (1H, d, J = 7.9 Hz), 8.03 (1H, d, J = 6.9 Hz), 8.35 (1H, dd, J = 4.7, 1.6 Hz), 8.82 (1H, d, J = 3.1 Hz), 12.36 (NH, s); LRMS (ESI): m/z $[M + H]^+$ 372. |
| EX.153 | 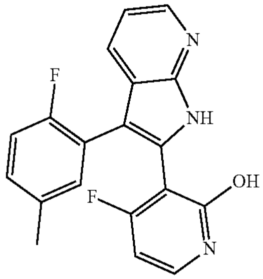 [SMILES: Cc1ccc(F)c(-c2c(-c3c(F)ccnc3O)[nH]c3ncccc23)c1] | $^1$H NMR (400 MHz, DMSO-$d_6$): δ 2.18 (3H, s), 6.64 (1H, t, J = 8.6 Hz), 6.74 (1H, d, J = 8.4 Hz), 6.97-7.16 (3H, m), 7.19-7.32 (1H, m), 7.80 (1H, d, J = 7.9 Hz), 8.27 (1H, dd, J = 4.7, 1.6 Hz), 10.14 (OH, s), 12.02 (NH, s); LRMS (ESI): m/z $[M + H]^+$ 337. |
| EX.154 | 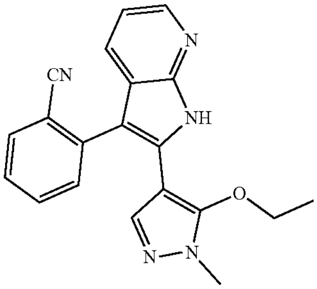 [SMILES: CCOc1c(-c2[nH]c3ncccc3c2-c2ccccc2C#N)cnn1C] | $^1$H NMR (400 MHz, $CD_3OD$): δ 1.18 (3H, t, J = 7.1 Hz), 3.66 (3H, s), 3.99 (2H, q, J = 7.1 Hz), 7.18 (1H, dd, J = 8.0, 4.8 Hz), 7.29 (1H, s), 7.52 (1H, t, J = 7.6 Hz), 7.58 (1H, d, J = 7.6 Hz), 7.72 (1H, t, J = 7.6 Hz), 7.79-7.86 (2H, m), 8.26 (1H, d, J = 4.8 Hz); LRMS (ESI): m/z $[M + H]^+$ 344. |
| EX.155 | 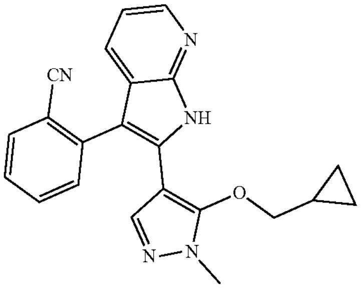 [SMILES: Cn1ncc(-c2[nH]c3ncccc3c2-c2ccccc2C#N)c1OCC1CC1] | $^1$H NMR (400 MHz, $CD_3OD$): δ 0.09-0.16 (2H, m), 0.42-0.51 (2H, m), 1.01-1.12 (1H, m), 3.70 (3H, s), 3.71-3.83 (2H, m), 7.18 (1H, dd, J = 7.7, 4.5 Hz), 7.28 (1H, s), 7.53 (1H, t, J = 7.7 Hz), 7.58 (1H, d, J = 7.7 Hz), 7.74 (1H, t, J = 7.7 Hz), 7.78-7.85 (2H, m), 8.25 (1H, d, J = 4.5 Hz); LRMS (ESI): m/z $[M + H]^+$ 370. |

-continued

| Example No. | Chemical structural formula | Spectrum data |
|---|---|---|
| EX.156 | 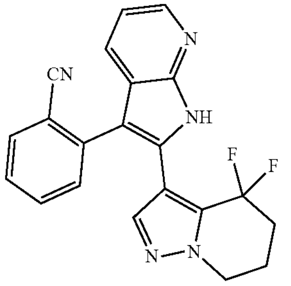 [SMILES: N#Cc1ccccc1-c1c(-c2cnn3c2C(F)(F)CCC3)[nH]c2ncccc12] | $^1$H NMR (400 MHz, DMSO-$d_6$): δ 2.08-2.12 (2H, m), 2.29-2.35 (2H, m), 4.21-4.24 (2H, m), 7.14-7.17 (1H, m), 7.35 (1H, d, J = 8.0 Hz), 7.46-7.50 (1H, m), 7.63-7.67 (2H, m), 7.76 (1H, d, J = 8.1 Hz), 7.86 (1H, d, J = 8.0 Hz), 8.31-8.33 (1H, m), 12.07 (1H, br s); LRMS (ESI): m/z $[M + H]^+$ 376. |
| EX.157 | 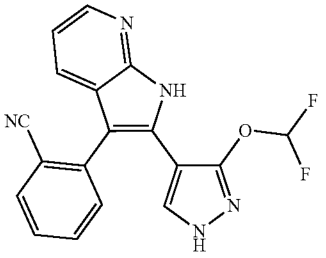 [SMILES: N#Cc1ccccc1-c1c(-c2c[nH]nc2OC(F)F)[nH]c2ncccc12] | 'HNMR (400 MHz, DMSO-$d_6$): δ 6.83-7.19 (2H, m), 7.45 (1H, d, J = 7.8 Hz), 7.51 (1H, td, J = 7.7, 1.2 Hz), 7.68-7.75 (2H, m), 7.88 (1H, dd, J = 7.9, 1.4 Hz), 7.93 (1H, d, J = 1.9 Hz), 8.29 (1H, dd, J = 4.7, 1.6 Hz), 12.17 (1H, 1H, br s), 12.82 (1H, br s); LRMS (ESI): m/z $[M + H]^+$ 352. |
| EX.158 | 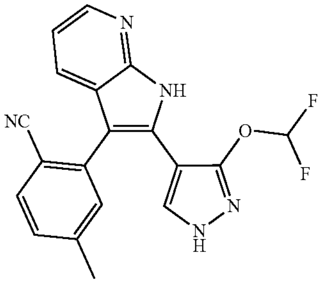 [SMILES: Cc1ccc(C#N)c(-c2c(-c3c[nH]nc3OC(F)F)[nH]c3ncccc23)c1] | $^1$H NMR (400 MHz, DMSO-$d_6$): δ 2.38 (3H, s), 6.80-7.20 (2H, m), 7.30 (1H, s), 7.33 (1H, d, J = 8.0 Hz), 7.72-7.75 (2H, m), 7.91 (1H, d, J = 2.0 Hz), 8.28 (1H, dd, J = 4.8, 1.6 Hz), 12.12 (1H, br s), 12.80 (1H, br s); LRMS (ESI): m/z $[M + H]^+$ 366. |
| EX.159 | 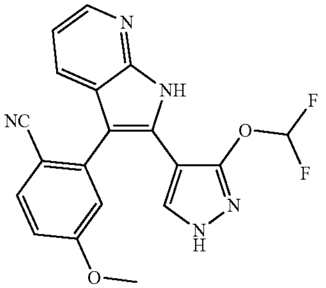 [SMILES: COc1ccc(C#N)c(-c2c(-c3c[nH]nc3OC(F)F)[nH]c3ncccc23)c1] | $^1$H NMR (400 MHz, DMSO-$d_6$): δ 3.80 (3H, s), 6.80-7.14 (5H, m), 7.76-7.80 (2H, m), 7.91 (1H, s), 12.15 (1H, br s), 12.81 (1H, br s); LRMS (ESI): m/z $[M + H]^+$ 382. |
| EX.160 | 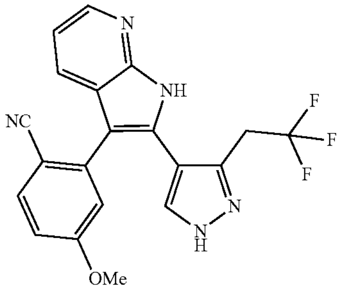 [SMILES: COc1ccc(C#N)c(-c2c(-c3c[nH]nc3CC(F)(F)F)[nH]c3ncccc23)c1] | $^1$H NMR (400 MHz, $CD_3CN$): δ 3.29 (2H, q, J = 10.9 Hz), 3.80 (3H, s), 6.92 (1H, d, J = 2.6 Hz), 7.05 (1H, dd, J = 8.7, 2.6 Hz), 7.19 (1H, dd, J = 7.9, 4.7 Hz), 7.74-7.79 (2H, m), 7.88 (1H, dd, J = 7.9, 1.3 Hz), 8.34 (1H, dd, J = 4.7, 1.4 Hz), 10.16 (1H, br s), 11.36 (1H, br s); LRMS (ESI): m/z $[M + H]^+$ 398. |

-continued

| Example No. | Chemical structural formula | Spectrum data |
|---|---|---|
| EX.161 | 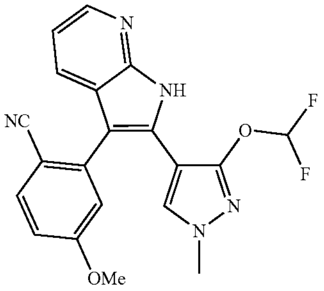 [SMILES: COc1ccc(C#N)c(-c2c(-c3cn(C)nc3OC(F)F)[nH]c3ncccc23)c1] | $^1$H NMR (400 MHz, DMSO-$d_6$): δ 3.80 (3H, s), 3.81 (3H, s), 6.83-7.19 (4H, m), 7.77 (1H, dd, J = 7.9, 1.6 Hz), 7.80 (1H, d, J = 8.7 Hz), 7.88 (1H, s), 8.29 (1H, dd, J = 4.7, 1.6 Hz), 12.16 (1H, s); LRMS (ESI): m/z $[M + H]^+$ 396. |
| EX.162 | 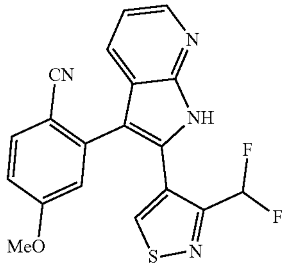 [SMILES: COc1ccc(C#N)c(-c2c(-c3csnc3C(F)F)[nH]c3ncccc23)c1] | $^1$H NMR (400 MHz, $CD_3OD$): δ 3.82 (3H, s), 6.67 (1H, t, J = 53.0 Hz), 6.96 (1H, d, J = 2.5 Hz), 7.06 (1H, dd, J = 8.7, 2.6 Hz), 7.27 (1H, dd, J = 8.0, 4.8 Hz), 7.73 (1H, d, J = 8.7 Hz), 7.98 (1H, dd, J = 8.0, 1.5 Hz), 8.37 (1H, dd, J = 4.8, 1.4 Hz), 9.09 (1H, s); LRMS (ESI): m/z $[M + H]^+$ 383. |
| EX.163 | 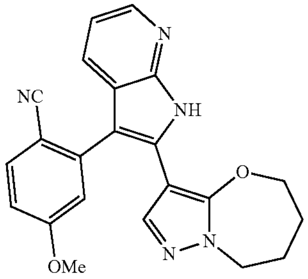 [SMILES: COc1ccc(C#N)c(-c2c(-c3cnn4c3OCCCC4)[nH]c3ncccc23)c1] | $^1$H NMR (400 MHz, DMSO-$d_6$): δ 1.71-1.75 (2H, m), 1.85-1.90 (2H, m), 3.54-3.63 (2H, m), 3.84 (3H, s), 4.11-4.15 (2H, m), 7.01 (1H, d, J = 2.5 Hz), 7.08-7.11 (2H, m), 7.32 (1H, s), 7.68 (1H, dd, J = 7.9, 1.1 Hz), 7.84 (1H, d, J = 8.7 Hz), 8.25 (1H, dd, J = 4.7, 1.5 Hz ), 11.96 (1H, br s); LRMS (ESI): m/z $[M + H]^+$ 386. |
| EX.164 | 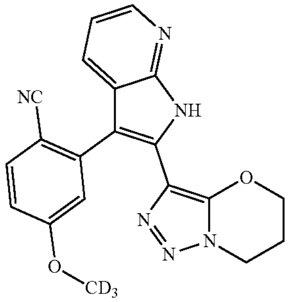 [SMILES: [2H]C([2H])([2H])Oc1ccc(C#N)c(-c2c(-c3nnn4c3OCCC4)[nH]c3ncccc23)c1] | $^1$H NMR (400 MHz, $CD_3OD$): δ 2.26-2.30 (2H, m), 4.26-4.30 (2H, m), 4.45-4.48 (2H, m), 7.07-7.09 (2H, m), 7.20 (1H, dd, J = 8.0, 4.8 Hz), 7.73 (1H, d, J = 8.4 Hz), 7.90 (1H, dd, J = 8.0, 1.3 Hz), 8.29 (1H, dd, J = 4.8, 1.4 Hz); LRMS (ESI): m/z $[M + H]^+$ 376. |
| EX.165 | 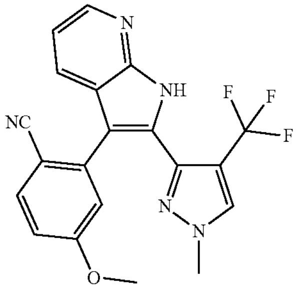 [SMILES: COc1ccc(C#N)c(-c2c(-c3nn(C)cc3C(F)(F)F)[nH]c3ncccc23)c1] | $^1$H NMR (400 MHz, DMSO-$d_6$): δ 3.75 (3H, s), 3.94 (3H, s), 6.77 (1H, d, J = 2.7 Hz), 7.05 (1H, dd, J = 8.6, 2.6 Hz), 7.20 (1H, dd, J = 8.0, 4.6 Hz), 7.82 (1H, d, J = 8.7 Hz), 7.88 (1H, dd, J = 8.0, 1.5 Hz), 8.37 (1H, dd, J = 4.6, 1.6 Hz), 8.45 (1H, s), 12.43 (NH, br s); LRMS (ESI): m/z $[M + H]^+$ 398. |

-continued

| Example No. | Chemical structural formula | Spectrum data |
|---|---|---|
| EX.166 | 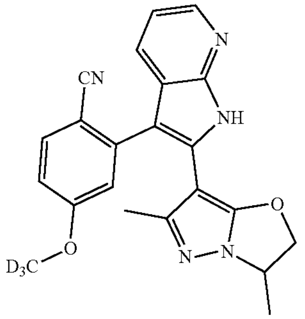 [SMILES: [2H]C([2H])([2H])Oc1ccc(C#N)c(-c2c(-c3c(C)nn4c3OCC4C)[nH]c3ncccc23)c1] | $^1$H NMR (400 MHz, DMSO-$d_6$): δ 1.34 (3H, d, J = 6.2 Hz), 1.96 (3H, s), 4.39-4.43 (1H, m), 4.53-4.59 (1H, m), 4.95-4.99 (1H, m), 6.96 (1H, d, J = 2.6 Hz), 7.04 (1H, dd, J = 8.7, 2.6 Hz), 7.12 (1H, dd, J = 7.8, 4.7 Hz), 7.77-7.82 (2H, m), 8.26 (1H, dd, J = 4.7, 1.5 Hz), 12.00 (1H, br s); LRMS (ESI): m/z $[M + H]^+$ 389. |
| EX.167 | 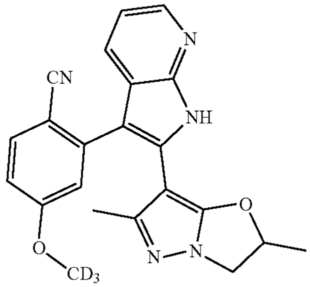 [SMILES: [2H]C([2H])([2H])Oc1ccc(C#N)c(-c2c(-c3c(C)nn4c3OC(C)C4)[nH]c3ncccc23)c1] | $^1$H NMR (400 MHz, DMSO-$d_6$): δ 1.24 (3H, d, J = 6.1 Hz), 2.04 (3H, s), 3.75-3.79 (1H, m), 4.28-4.33 (1H, m), 5.22-5.30 (1H, m), 6.92-7.06 (2H, m), 7.12 (1H, dd, J = 7.8, 4.7 Hz), 7.78-7.80 (2H, m), 8.25 (1H, d, J = 4.6 Hz ), 11.98 (1H, br s); LRMS (ESI): m/z $[M + H]^+$ 389. |
| EX.168 | 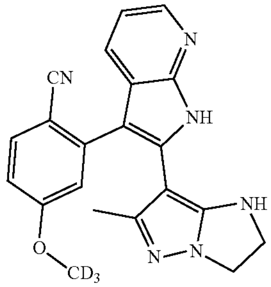 [SMILES: [2H]C([2H])([2H])Oc1ccc(C#N)c(-c2c(-c3c(C)nn4c3NCC4)[nH]c3ncccc23)c1] | $^1$H NMR (400 MHz, DMSO-$d_6$): δ 1.70 (3H, s), 3.75-3.80 (2H, m), 3.99-4.03 (2H, m), 2.51-2.52 (1H, m), 6.94 (1H, d, J = 2.5 Hz), 7.04 (1H, dd, J = 8.6, 2.7 Hz), 7.11 (1H, dd, J = 7.9, 4.8 Hz), 7.77 (1H, dd, J = 7.9, 1.5 Hz), 7.80 (1H, d, J = 8.6 Hz), 8.23 (1H, dd, J = 4.6, 1.5 Hz), 11.81 (1H, br s); LRMS (ESI): m/z $[M + H]^+$ 374. |
| EX.169 | 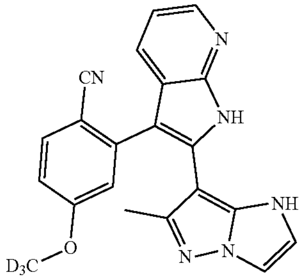 [SMILES: [2H]C([2H])([2H])Oc1ccc(C#N)c(-c2c(-c3c(C)nn4cc[nH]c34)[nH]c3ncccc23)c1] | $^1$H NMR (400 MHz, $CD_3OD$): δ 1.99 (3H, s), 7.00-7.03 (2H, m), 7.09 (1H, d, J = 2.3 Hz), 7.20 (1H, dd, J = 7.8, 4.9 Hz), 7.35 (1H, d, J = 2.2 Hz), 7.67 (1H, d, J = 8.6 Hz), 7.95 (1H, dd, J = 7.8, 1.5 Hz), 8.25 (1H, dd, J = 4.8, 1.5 Hz); LRMS (ESI): m/z $[M + H]^+$ 372. |
| EX.170 | 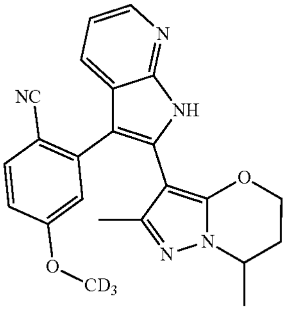 [SMILES: [2H]C([2H])([2H])Oc1ccc(C#N)c(-c2c(-c3c(C)nn4c3OCCC4C)[nH]c3ncccc23)c1] | $^1$H NMR (400 MHz, DMSO-$d_6$): δ 1.42 (3H, d, J = 6.4 Hz), 1.79-1.84 (4H, m), 2.18-2.26 (1H, m), 3.94-3.98 (1H, m), 4.07-4.24 (2H, m), 6.93 (1H, d, J = 2.6 Hz), 7.03 (1H, dd, J = 8.6, 2.6 Hz), 7.12 (1H, dd, J = 7.9, 4.6 Hz), 7.78 (1H, d, J = 8.7 Hz), 7.81 (1H, dd, J = 7.8, 1.5 Hz), 8.25 (1H, dd, J = 4.7, 1.5 Hz), 11.90 (1H, br s); LRMS (ESI): m/z $[M + H]^+$ 403. |

-continued

| Example No. | Chemical structural formula | Spectrum data |
|---|---|---|
| EX.171 | 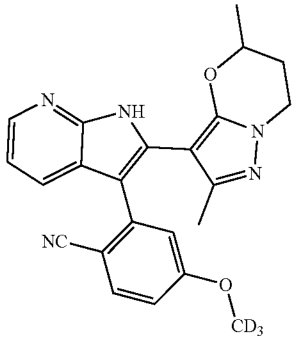 [SMILES: [2H]C([2H])([2H])Oc1ccc(C#N)c(-c2c(-c3c(C)nn4c3OC(C)CC4)[nH]c3ncccc23)c1] | $^1$H NMR (400 MHz, DMSO-$d_6$): δ 1.04 (3H, d, J = 6.2 Hz), 1.65-1.74 (1H, m), 2.04-2.09 (4H, m), 3.90-4.03 (3H, m), 6.93 (1H, d, J = 2.7 Hz), 7.04 (1H, dd, J = 8.7, 2.6 Hz), 7.11 (1H, dd, J = 8.0, 4.6 Hz), 7.76 (1H, d, J = 8.7 Hz), 7.80 (1H, dd, J = 7.9, 1.5 Hz), 8.25 (1H, dd, J = 4.7, 1.6 Hz), 11.92 (1H, br s); LRMS (ESI): m/z [M + H]$^+$ 403. |
| EX.172 | 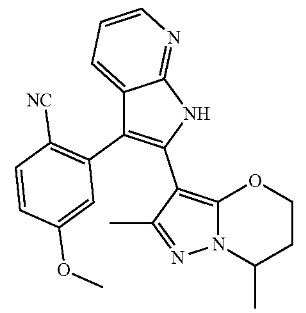 [SMILES: COc1ccc(C#N)c(-c2c(-c3c(C)nn4c3OCCC4C)[nH]c3ncccc23)c1] | $^1$H NMR (400 MHz, DMSO-$d_6$): δ 1.42 (3H, d, J = 6.4 Hz), 1.77-1.86 (4H, m), 2.20-2.26 (1H, m), 3.80 (3H, s), 3.94-3.99 (1H, m), 4.07-4.24 (2H, m), 6.93 (1H, d, J = 2.1 Hz), 7.04 (1H, dd, J = 8.8, 2.5 Hz), 7.11 (1H, dd, J = 7.9, 4.8 Hz), 7.77-7.82 (2H, m), 8.25 (1H, d, J = 4.7 Hz), 11.91 (1H, br s); LRMS (ESI): m/z [M + H]$^+$ 400. |
| EX.173 | 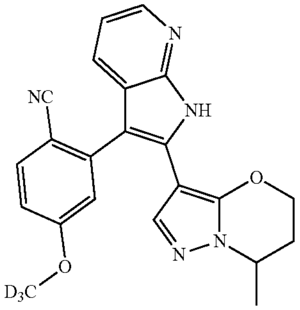 [SMILES: [2H]C([2H])([2H])Oc1ccc(C#N)c(-c2c(-c3cnn4c3OCCC4C)[nH]c3ncccc23)c1] | $^1$H NMR (400 MHz, DMSO-$d_6$): δ 1.44 (3H, d, J = 6.4 Hz), 1.79-1.88 (1H, m), 2.19-2.28 (1H, m), 3.95-4.10 (2H, m), 4.25-4.34 (1H, m), 6.98 (1H, s), 7.06-7.10 (2H, m), 7.38 (1H, s), 7.69 (1H, d, J = 7.8 Hz), 7.82 (1H, d, J = 8.6 Hz), 8.22 (1H, dd, J = 4.7, 1.5 Hz), 11.85 (1H, br s); LRMS (ESI): m/z [M+H] 389. |
| EX.174 | 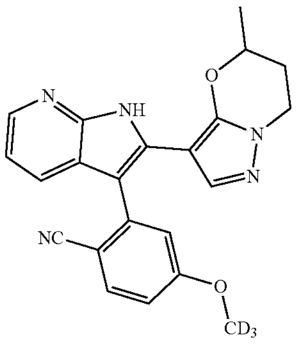 [SMILES: [2H]C([2H])([2H])Oc1ccc(C#N)c(-c2c(-c3cnn4c3OC(C)CC4)[nH]c3ncccc23)c1] | $^1$H NMR (400 MHz, DMSO-$d_6$): δ 0.95-1.00 (3H, m), 1.70-1.82 (1H, m), 2.08-2.14 (1H, m), 4.00-4.12 (3H, m), 6.95 (1H, d, J = 4.2 Hz), 7.06-7.09 (2H, m), 7.56 (1H, s), 7.69 (1H, dd, J = 7.9, 1.3 Hz), 7.80 (1H, d, J = 8.4 Hz), 8.21 (1H, dd, J = 4.7, 1.5 Hz), 11.96 (1H, br s); LRMS (ESI): m/z [M + H]$^+$ 389. |

-continued

| Example No. | Chemical structural formula | Spectrum data |
|---|---|---|
| EX.175 | 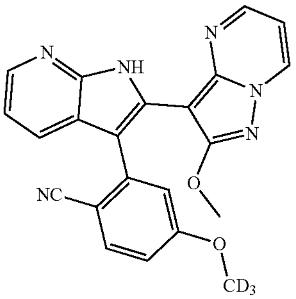 [SMILES: [2H]C([2H])([2H])Oc1ccc(C#N)c(-c2c(-c3c(OC)nn4cccnc34)[nH]c3ncccc23)c1] | $^{1}H$ NMR (400 MHz, DMSO-$d_6$): δ 3.77 (3H, s), 6.97-7.01 (3H, m), 7.15 (1H, dd, J = 7.9, 4.7 Hz), 7.73 (1H, J = 8.3, 0.6 Hz), 7.85 (1H, dd, J = 7.9, 1.1 Hz), 8.29-8.30 (1H, m), 8.44 (1H, dd, J = 4.2, 1.7 Hz), 9.03 (1H, dd, J = 6.9, 1.7 Hz), 11.99 (1H, br s); LRMS (ESI): m/z $[M + H]^+$ 400. |
| EX.176 | 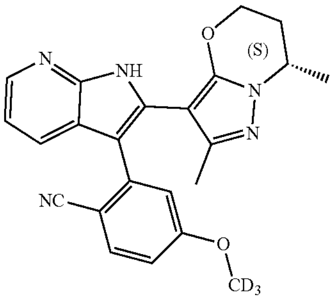 | $^{1}H$ NMR (400 MHz, DMSO-$d_6$): δ 1.42 (3H, d, J = 6.3 Hz), 1.78-1.85 (4H, m), 2.20-2.24 (1H, m), 3.94-3.99 (1H, m), 4.09-4.24 (2H, m), 6.93 (1H, d, J = 2.4 Hz), 7.03 (1H, dd, J = 8.7, 2.5 Hz), 7.12 (1H, dd, J = 7.8, 4.7 Hz), 7.77-7.82 (2H, m), 8.25 (1H, d, J = 4.7 Hz), 11.90 (1H, br s); LRMS (ESI): m/z $[M + H]^+$ 403. |
| EX.177 | 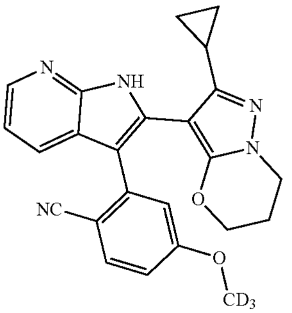 [SMILES: [2H]C([2H])([2H])Oc1ccc(C#N)c(-c2c(-c3c(C4CC4)nn4c3OCCC4)[nH]c3ncccc23)c1] | $^{1}H$ NMR (400 MHz, DMSO-$d_6$): δ 0.37-0.38 (2H, m), 0.46-0.47 (2H, m), 1.31-1.37 (1H, m), 2.10-2.16 (2H, m), 3.98-4.01 (2H, m), 4.13-4.18 (2H, m), 6.92 (1H, d, J = 2.6 Hz), 7.04 (1H, dd, J = 8.7, 2.6 Hz), 7.12 (1H, dd, J = 7.9, 4.7 Hz), 7.78 (1H, d, J = 8.7 Hz), 7.81 (1H, dd, J = 7.9, 1.1 Hz), 8.25 (1H, dd, J = 4.7, 1.5 Hz), 11.94 (1H, br s); LRMS (ESI): m/z $[M + H]^+$ 415. |
| EX.178 | 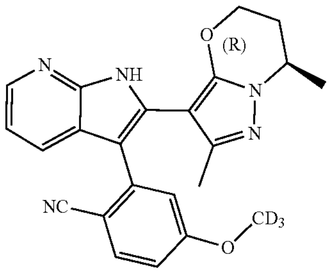 | $^{1}H$ NMR (400 MHz, DMSO-$d_6$): δ 1.42 (3H, d, J = 6.4 Hz), 1.77-1.85 (4H, m), 2.20-2.23 (1H, m), 3.94-3.99 (1H, m), 4.07-4.24 (2H, m), 6.93 (1H, d, J = 2.6 Hz), 7.03 (1H, dd, J = 8.7, 2.6 Hz), 7.12 (1H, dd, J = 7.9, 4.7 Hz), 7.77-7.82 (2H, m), 8.25 (1H, dd, J = 4.7, 1.5 Hz), 11.90 (1H, br s); LRMS (ESI): m/z $[M + H]^+$ 403. |
| EX.179 | 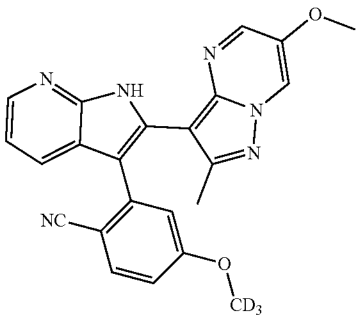 [SMILES: [2H]C([2H])([2H])Oc1ccc(C#N)c(-c2c(-c3c(C)nn4cc(OC)cnc34)[nH]c3ncccc23)c1] | $^{1}H$ NMR (400 MHz, DMSO-$d_6$): δ 2.09 (3H, s), 3.87 (3H, s), 6.95-7.01 (2H, m), 7.17 (1H, dd, J = 7.9, 4.7 Hz), 7.71 (1H, d, J = 8.6 Hz), 7.90 (1H, dd, J = 7.9, 1.1 Hz), 8.32 (1H, dd, J = 4.7, 1.5 Hz), 8.38 (1H, d, J = 2.7 Hz), 8.84 (1H, d, J = 2.7 Hz), 12.19 (1H, br s); LRMS (ESI): m/z $[M + H]^+$ 414. |

-continued

| Example No. | Chemical structural formula | Spectrum data |
|---|---|---|
| EX.180 | 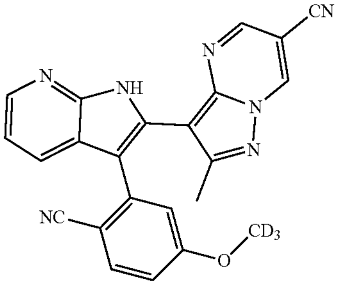 [SMILES: [2H]C([2H])([2H])Oc1ccc(C#N)c(-c2c(-c3c(C)nn4cc(C#N)cnc34)[nH]c3ncccc23)c1] | $^1$H NMR (400 MHz, DMSO-$d_6$): δ 2.24 (3H, s), 7.0-7.02 (2H, m), 7.21 (1H, dd, J = 7.9, 4.7 Hz), 7.69-7.72 (1H, m), 7.94 (1H, dd, J = 7.9, 1.4 Hz), 8.36 (1H, dd, J = 4.7, 1.5 Hz), 8.72 (1H, d, J = 2.1 Hz), 9.92 (1H, d, J = 2.0 Hz), 12.36 (1H, br s); LRMS (ESI): m/z $[M + H]^+$ 409. |
| EX.181 | 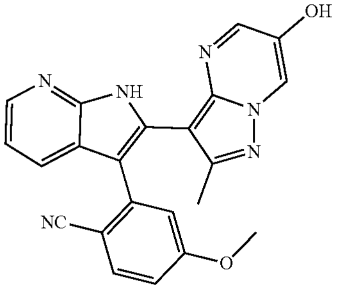 [SMILES: COc1ccc(C#N)c(-c2c(-c3c(C)nn4cc(O)cnc34)[nH]c3ncccc23)c1] | $^1$H NMR (400 MHz, DMSO-$d_6$): δ 2.04 (3H, s), 3.75 (3H, s), 6.94-6.95 (1H, m), 6.99 (1H, dd, J = 8.7, 2.6 Hz), 7.17 (1H, dd, J = 7.9, 4.7 Hz), 7.72 (1H, d, J = 8.6 Hz), 7.89 (1H, d, J = 7.8 Hz), 8.27 (1H, d, J = 2.6 Hz), 8.31 (1H, dd, J = 4.7, 1.5 Hz), 8.45 (1H, d, J = 2.5 Hz), 10.42 (1H, br s), 12.13 (1H, br s); LRMS (ESI): m/z $[M + H]^+$ 397. |
| EX.182 | 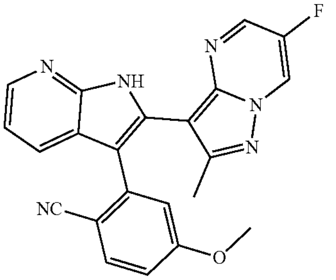 [SMILES: COc1ccc(C#N)c(-c2c(-c3c(C)nn4cc(F)cnc34)[nH]c3ncccc23)c1] | $^1$H NMR (400 MHz, DMSO-$d_6$): δ 2.14 (3H, s), 3.77 (3H, s), 6.97-7.02 (2H, m), 7.19 (1H, dd, J = 7.9, 4.7 Hz), 7.71 (1H, d, J = 8.5 Hz), 7.92 (1H, d, J = 7.9 Hz), 8.34 (1H, d, J = 4.6 Hz), 8.72 (1H, d, J = 2.4 Hz), 9.51 (1H, dd, J = 4.5, 2.6 Hz), 12.26 (1H, br s); LRMS (ESI): m/z $[M + H]^+$ 399. |
| EX.183 | 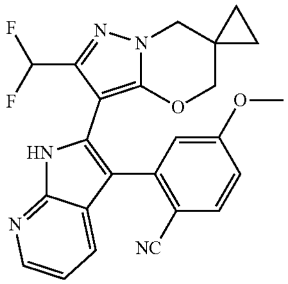 [SMILES: COc1ccc(C#N)c(-c2c(-c3c(C(F)F)nn4c3OCC3(CC3)C4)[nH]c3ncccc23)c1] | $^1$H NMR (400 MHz, DMSO-$d_6$): δ 0.65-0.74 (4H, m), 3.77 (3H, s), 3.87-4.05 (4H, m), 6.54-6.81 (1H, m), 6.84 (1H, d, J = 2.6 Hz), 7.05 (1H, dd, J = 8.7, 2.6 Hz), 7.15 (1H, dd, J = 7.9, 4.7 Hz), 7.78-7.84 (2H, m), 8.30 (1H, dd, J = 4.6, 1.5 Hz), 12.10 (1H, br s); LRMS (ESI): m/z $[M + H]^+$ 448. |
| EX.184 | 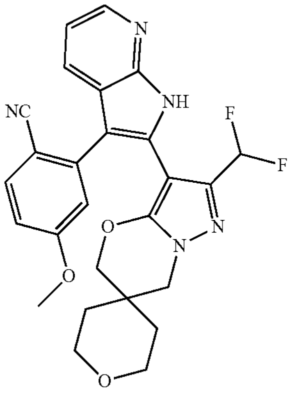 [SMILES: COc1ccc(C#N)c(-c2c(-c3c(C(F)F)nn4c3OCC3(CCOCC3)C4)[nH]c3ncccc23)c1] | $^1$H NMR (400 MHz, $CD_3OD$): δ 1.44-1.56 (4H, m), 3.63-3.74 (4H, m), 3.84 (3H, s), 4.09 (4H, s), 6.53 (1H, t, J = 54.3 Hz), 6.93 (1H, d, J = 2.6 Hz), 7.05 (1H, dd, J = 8.8, 2.5 Hz), 7.22 (1H, dd, J = 7.9, 4.8 Hz), 7.73 (1H, d, J = 8.6 Hz), 7.93 (1H, dd, J = 7.9, 1.5 Hz), 8.29 (1H, dd, J = 4.8, 1.5 Hz ); LRMS (ESI): m/z $[M + H]^+$ 492. |

-continued

| Example No. | Chemical structural formula | Spectrum data |
|---|---|---|
| EX.185 | 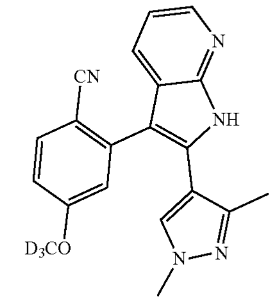 | $^1H$ NMR (400 MHz, DMSO-$d_6$): δ 1.82 (3H, s), 3.78 (3H, s), 6.96 (1H, d, J = 2.6 Hz), 7.07 (1H, dd, J = 8.7, 2.6 Hz), 7.13 (1H, dd, J = 7.9, 4.7 Hz), 7.66 (1H, s), 7.78 (1H, dd, J = 7.9, 1.5 Hz), 7.81 (1H, d, J = 8.7 Hz), 8.27 (1H, dd, J = 4.7, 1.5 Hz), 12.06 (1H, s); LRMS (ESI): m/z $[M + H]^+$ 347. |
| EX.186 | 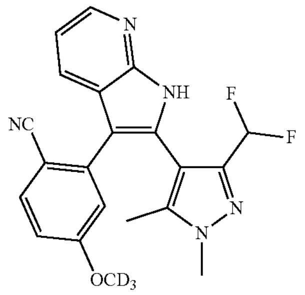 | $^1H$ NMR (400 MHz, $CD_3OD$): δ 2.11 (3H, s), 3.84 (3H, s), 6.54 (1H, t, $J_{H-F}$ = 54.2 Hz), 6.93 (1H, d, J = 2.6 Hz), 7.03 (1H, dd, J = 8.7, 2.6 Hz), 7.24 (1H, dd, J = 8.1, 4.8 Hz), 7.72 (1H, d, J = 8.9 Hz), 7.97 (1H, dd, J = 8.0, 1.5 Hz), 8.32 (1H, dd, J = 4.9, 1.5 Hz); LRMS (ESI): m/z $[M + H]^+$ 397. |
| EX.187 | 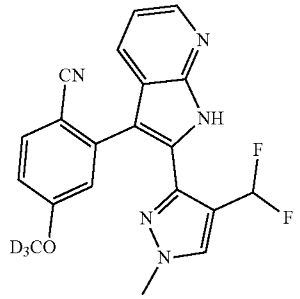 | $^1H$ NMR (400 MHz, DMSO-$d_6$): δ 3.91 (3H, s), 6.48 (1H, t, $J_{H-F}$ = 56.0 Hz), 6.92 (1H, s), 7.06-7.21 (2H, m), 7.80-7.87 (2H, m), 8.17 (1H, s), 8.35 (1H, s), 12.40 (1H, s); LRMS (ESI): m/z $[M + H]^+$ 383. |
| EX.188 | 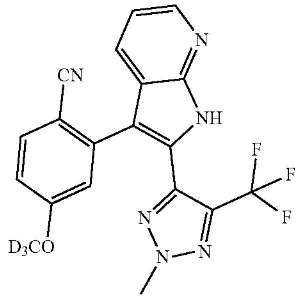 | $^1H$ NMR (400 MHz, $CD_3OD$): δ 4.33 (3H, s), 6.92 (1H, d, J = 2.6 Hz), 7.08 (1H, dd, J = 8.7, 2.6 Hz), 7.28 (1H, dd, J = 8.1, 4.7 Hz), 7.74 (1H, d, J = 8.7 Hz), 8.01 (1H, dd, J = 8.0, 1.5 Hz), 8.40 (1H, dd, J = 4.8, 1.5 Hz); LRMS (ESI): m/z $[M + H]^+$ 402. |
| EX.189 | 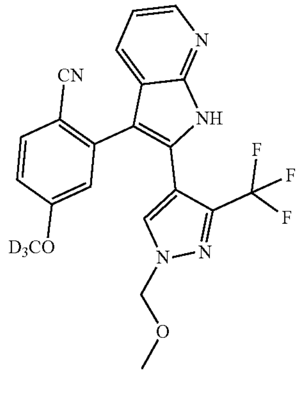 | $^1H$ NMR (400 MHz, $CD_3OD$): δ 3.34 (3H, s, overlapping with solvent residual peak), 5.49 (2H, s), 6.93 (1H, d, J = 2.6 Hz), 7.05 (1H, dd, J = 8.7, 2.6 Hz), 7.24 (1H, dd, J = 8.1, 4.9 Hz), 7.72 (1H, d, J = 8.8 Hz), 7.95 (1H, dd, J = 8.0, 1.6 Hz), 8.10 (1H, d, J = 0.8 Hz), 8.34 (1H, dd, J = 4.8, 1.5 Hz); LRMS (ESI): m/z $[M + H]^+$ 431. |

-continued

| Example No. | Chemical structural formula | Spectrum data |
|---|---|---|
| EX.190 | 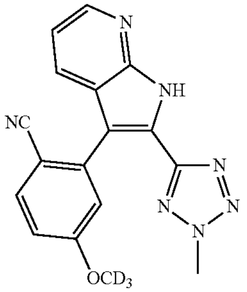 | $^1$H NMR (400 MHz, DMSO-$d_6$): δ 4.40 (3H, s,), 7.13-7.37 (3H, m), 7.86-7.88 (2H, m), 8.41-8.43 (1H, m), 12.97 (1H, s); LRMS (ESI): m/z $[M + H]^+$ 335. |
| EX.191 | 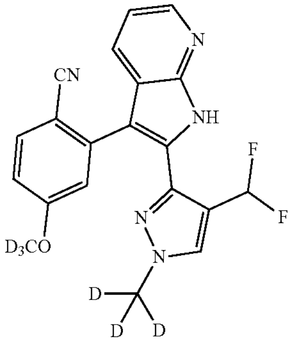 | $^1$H NMR (400 MHz, DMSO-$d_6$): δ 6.49 (1H, t, $J_{H-F}$ = 55.6 Hz), 6.92 (1H, d, J = 2.7 Hz), 7.07 (1H, dd, J = 8.6 Hz, 2.5 Hz), 7.18 (1H, dd, J = 8.0 Hz, 4.8 Hz), 7.81 (1H, d, J = 8.7 Hz), 7.86 (1H, dd, J = 8.1, 1.5 Hz), 8.17 (1H, s), 8.35 (1H, dd, J = 4.6 Hz, 1.6 Hz), 12.39 (1H, br s); LRMS (ESI): m/z $[M + H]^+$ 386. |
| EX.192 | 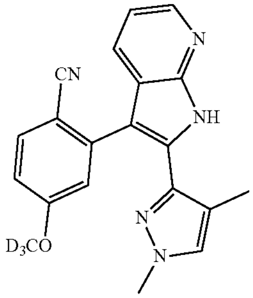 | $^1$H NMR (400 MHz, DMSO-$d_6$): δ 1.60 (3H, s), 3.82 (3H, s), 6.89 (1H, d, J = 2.8 Hz), 7.06 (1H, dd, J = 8.8 Hz, 2.5 Hz), 7.15 (1H, dd, J = 7.9 Hz, 4.7 Hz), 7.53 (1H, s), 7.81-7.86 (2H, m), 8.30 (1H, dd, J = 4.6 Hz, 1.4 Hz), 12.20 (1H, br s); LRMS (ESI): m/z [M+H] 347. |
| EX.193 | 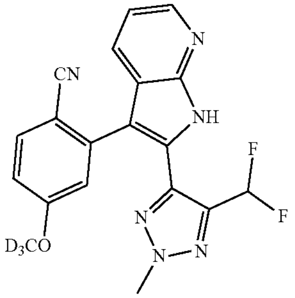 | $^1$H NMR (400 MHz, $CD_3OD$): δ 4.29 (3H, s), 6.52 (1H, t, $J_{H-F}$ = 53.7 Hz), 7.02 (1H, d, J = 2.5 Hz) 7.10 (1H, dd, J = 8.7, 2.6 Hz), 7.27 (1H, dd, J = 8.0, 4.8 Hz) 7.75 (1H, d, J = 8.7 Hz), 7.99 (1H, dd, J = 8.0, 1.5 Hz), 8.39 (1H, dd, J = 4.8, 1.5 Hz); LRMS (ESI): m/z $[M + H]^+$ 384. |
| EX.194 | 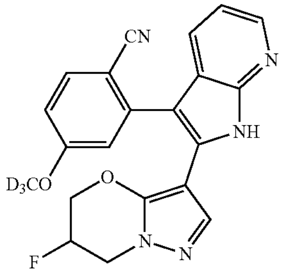 | $^1$H NMR (400 MHz, $CD_3CN$): δ 4.22-4.45 (3H, m), 4.51-4.65 (1H, m), 5.37 (1H, d, $J_{H-F}$ = 44.4 Hz), 7.33-6.96 (4H, m), 7.85-7.66 (2H, m), 8.26 (1H, dd, J = 4.7 Hz, 1.5 Hz), 9.93 (1H, s); LRMS (ESI): m/z $[M + H]^+$ 393. |

-continued

| Example No. | Chemical structural formula | Spectrum data |
|---|---|---|
| EX.195 | 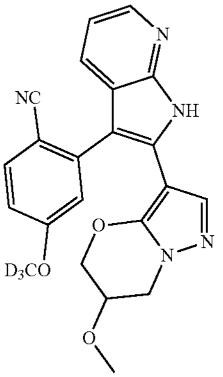 | $^1$H NMR (400 MHz, $CD_3CN$): δ 3.42 (3H, d, J = 9.9 Hz), 4.00 (1H, s), 4.15-4.29 (3H, m), 4.45-4.55 (1H, m), 7.04-7.19 (4H, m), 7.68-7.72 (1H, m), 7.80 (1H, d, J = 8.6 Hz), 8.20-8.28 (1H, m), 9.89 (1H, s); LRMS (ESI): m/z $[M + H]^+$ 405. |
| EX.196 | 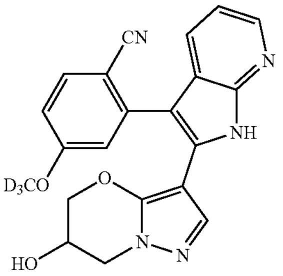 | $^1$H NMR (400 MHz, $CD_3CN$): δ 3.74-4.12 (2H, m), 4.21-4.44 (4H, m), 7.00-7.22 (4H, m), 7.70 (1H, apparent t, J = 8.1 Hz), 7.80 (1H, d, 9.2 Hz), 8.25 (1H, s), 10.04 (1H, s); LRMS (ESI): m/z $[M + H]^+$ 391. |
| EX.197 | 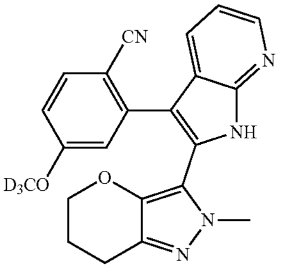 | $^1$H NMR (400 MHz, DMSO-$d_6$): δ 1.76-1.85 (2H, m), 2.60 (2H, t, J = 6.4 Hz), 3.61 (3H, s), 3.72 (2H, br s), 6.98 (1H, d, J = 2.5 Hz), 7.06 (1H, dd, J = 8.9, 2.6 Hz), 7.20 (1H, dd, J = 8.0, 4.5 Hz), 7.78 (1H, d, J = 8.8 Hz), 7.93 (1H, dd, J = 8.0, 1.5 Hz), 8.36 (1H, dd, J = 4.7, 1.6 Hz), 12.40 (1H, s); LRMS (ESI): m/z $[M + H]^+$ 389. |
| EX.198 | 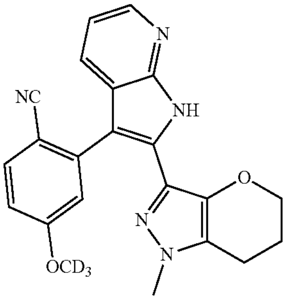 | $^1$H NMR (400 MHz, DMSO-$d_6$): δ 1.82 (2H, s), 2.47-2.53 (2H, m), 3.71 (5H, s), 6.97-7.16 (3H, m), 7.71-7.84 (2H, m), 8.23-8.32 (1H, m), 11.93 (1H, s); LRMS (ESI): m/z $[M + H]^+$ 389. |
| EX.199 | 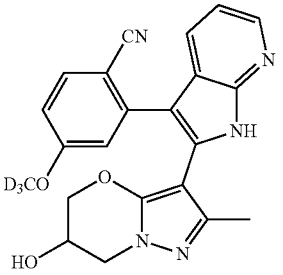 | (Mixture of atropisomers) $^1$H NMR (400 MHz, DMSO-$d_6$): δ 1.79 (1.5H, br s), 1.83 (1.5H, br s), 3.83-3.97 (3H, m), 4.09-4.22 (2H, m), 5.50 (1H, br s), 6.89 (1H, br s), 7.03 (1H, dd, J = 8.6, 2.2 Hz), 7.12 (1H, dd, J = 8.0, 4.7 Hz), 7.75-7.85 (2H, m), 8.25 (1H, dd, J = 4.7, 1.5 Hz), 11.94 (1H, s) ; LRMS (ESI): m/z $[M + H]^+$ 405. |

-continued

| Example No. | Chemical structural formula | Spectrum data |
|---|---|---|
| EX.200 | 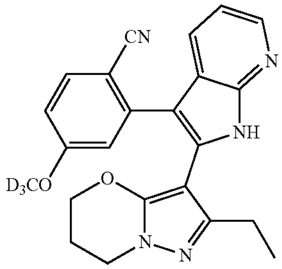 | (Mixture of atropisomers) $^1$H NMR (400 MHz, DMSO-$d_6$): δ 0.86 (3H, t, J = 7.5 Hz), 2.05-2.23 (4H, m), 3.99-4.14 (4H, m), 6.90 (1H, d, J = 2.6 Hz), 7.04 (1H, dd, J = 8.6, 2.6 Hz), 7.12 (1H, dd, J = 7.9, 4.7 Hz), 7.79 (2H, d, J = 8.5 Hz), 8.25 (1H, dd, J = 4.6, 1.5 Hz), 11.92 (1H, s); LRMS (ESI): m/z [M + H]$^+$ 403. |
| EX.201 | 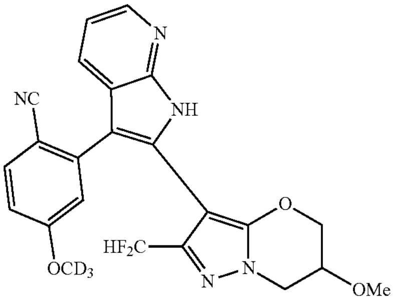 | (Mixture of atropisomers) $^1$H NMR (400 MHz, DMSO-$d_6$): δ 3.35 (3H, s, overlapped with water peak), 3.94-4.08 (2H, m), 4.18-4.48 (3H, m), 6.64 (1H, br s), 6.79 (1H, s), 7.02 (1H, dd, J = 8.7, 2.6 Hz), 7.15 (1H, dd, J = 7.9, 4.7 Hz), 7.74-7.86 (2H, m), 8.30 (1H, dd, J = 4.6, 1.5 Hz), 12.07 (1H, s); LRMS (ESI): m/z [M + H]$^+$ 455. |
| EX.202 | 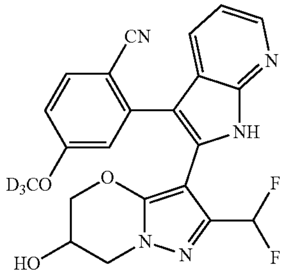 | (Mixture of atropisomers) $^1$H NMR (400 MHz, DMSO-$d_6$): δ 3.99-4.02 (3H, m), 4.27-4.33 (2H, m), 5.60 (1H, s), 6.63 (1H, t, $J_{H-F}$ = 54 Hz), 6.83 (1H, s), 7.03 (1H, dd, J = 8.7, 2.6 Hz), 7.15 (1H, dd, J = 8.0, 4.6 Hz), 7.78-7.82 (2H, m), 8.30 (1H, dd, J = 4.7, 1.5 Hz), 12.08 (1H, s); LRMS (ESI): m/z [M + H]$^+$ 441. |
| EX.203 | 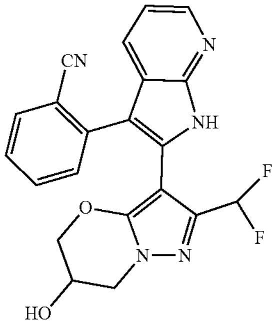 [SMILES: N#Cc1ccccc1-c1c(-c2c(C(F)F)nn3c2OCC(O)C3)[nH]c2ncccc12] | $^1$H NMR (400 MHz, DMSO-$d_6$): δ 3.83-4.12 (3H, m), 4.21-4.34 (2H, m), 5.60 (1H, br s), 6.66 (1H, t, $JJ_{H-F}$ = 52.0 Hz), 7.15 (1H, dd, J = 8.0, 4.6 Hz), 7.35 (1H, br s), 7.48 (1H, m) 7.62-7.71 (1H, m), 7.79 (1H, dd, J = 7.9, 1.1 Hz), 7.87 (1H, d, J = 7.4 Hz), 8.30 (1H, dd, J = 4.7, 1.6 Hz), 12.05 (1H, s); LRMS (ESI): m/z [M + H]$^+$ 408. |
| EX.204 | 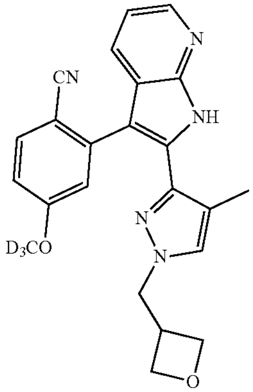 | $^1$H NMR (400 MHz, DMSO-$d_6$): δ 1.76 (3H, s), 3.25-3.32 (1H, m), 4.37-4.28 (4H, m), 4.50-4.54 (2H, m), 6.90 (1H, d, J = 2.5 Hz), 7.05 (1H, dd, J = 8.7, 2.7 Hz), 7.16 (1H, dd, J = 8.0, 4.6 Hz), 7.60 (1H, d, J = 0.6Hz), 7.79 (1H, d, J = 8.5 Hz), 7.86 (1H, dd, J = 8.0, 1.2 Hz), 8.31 (1H, dd, J = 4.6, 1.4 Hz), 12.20 (1H, s); LRMS (ESI): m/z [M + H]$^+$ 403. |

-continued

| Example No. | Chemical structural formula | Spectrum data |
| --- | --- | --- |
| EX.205 | 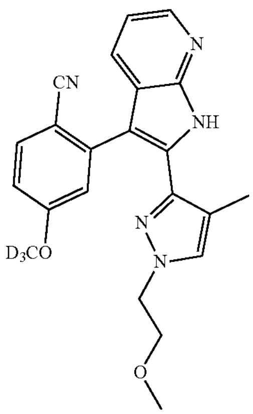 | $^1$H NMR (400 MHz, DMSO-$d_6$): δ 1.69 (3H, s), 3.20 (3H, s), 3.61 (2H, t, J = 5.3 Hz), 4.20 (2H, t, J = 5.3 Hz), 6.88 (1H, d, J = 2.7 Hz), 7.04 (1H, dd, J = 8.7, 2.5 Hz), 7.16 (1H, dd, J = 8.0, 4.7 Hz), 7.55 (1H, s), 7.80 (1H, d, J = 8.7 Hz), 7.85 (1H, dd, J = 7.9, 1.4 Hz), 8.31 (1H, dd, J = 4.6, 1.5 Hz), 12.21 (1H, s) ; LRMS (ESI): m/z [M+H] 391. |
| EX.206 | 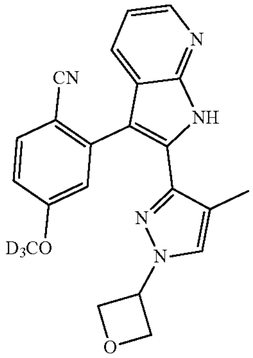 | $^1$H NMR (400 MHz, DMSO-$d_6$): δ 1.68 (3H, s), 4.92-4.79 (m, 4H), 5.58-5.48 (m, 1H), 6.98 (d, J = 2.6 Hz, 1H), 7.06 (dd, J = 8.7, 2.6 Hz, 1H), 7.18 (dd, J = 7.9, 4.7 Hz, 1H), 7.72 (d, J = 0.7 Hz, 1H), 7.80 (d, J = 8.7 Hz, 1H), 7.89 (dd, J = 8.0, 1.2 Hz, 1H), 8.34 (dd, J = 4.7, 1.6 Hz, 1H), 12.27 (s, 1H), LRMS (ESI): m/z $[M + H]^+$ 389. |
| EX.207 | 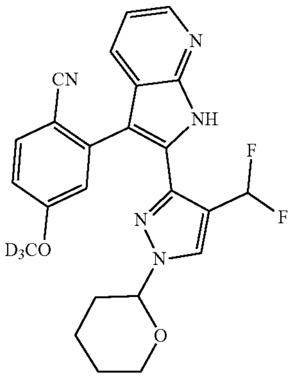 | $^1$H NMR (400 MHz, DMSO-$d_6$): δ 1.42-1.70 (3H, m), 1.83-1.89 (2H, m), 1.97-2.11 (1H, m), 3.57-3.67 (1H, m), 3.82-3.86 (1H, m), 5.52 (1H, dd, J = 9.0, 1.9 Hz), 6.69 (1H, t, $J_{H-F}$ = 55.7 Hz), 6.91 (1H, d, J = 2.6 Hz), 7.05 (1H, dd, J = 8.7, 2.7 Hz), 7.20 (1H, dd, J = 8.1, 4.7 Hz), 7.80 (1H, d, J = 8.5 Hz), 7.88 (1H, dd, J = 8.0 Hz, 1.7 Hz), 8.33 (1H, s), 8.37 (1H, dd, J = 4.7, 1.5 Hz), 12.41 (1H, s); LRMS (ESI): m/z $[M + H]^+$ 453. |
| EX.208 | 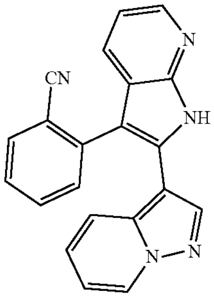 [SMILES: N#Cc1ccccc1-c1c(-c2cnn3ccccc23)[nH]c2ncccc12] | $^1$H NMR (400 MHz, DMSO-$d_6$): δ 6.90-6.94 (1H, m), 7.00 (1H, d, J = 8.7 Hz), 7.10-7.20 (2H, m), 7.50 (1H, td, J = 7.7, 1.0 Hz), 7.57 (1H, d, J = 7.5 Hz), 7.70-7.74 (1H, m), 7.81 (1H, dd, J = 7.9, 1.5 Hz), 7.86 (1H, d, J = 7.5 Hz), 8.08 (1H, s), 8.31 (1H, dd, J = 4.7, 1.5 Hz), 8.73 (1H, d, J = 7.1 Hz), 12.41 (1H, s); LRMS (ESI): m/z $[M + H]^+$ 336. |

-continued

| Example No. | Chemical structural formula | Spectrum data |
| --- | --- | --- |
| EX.209 | 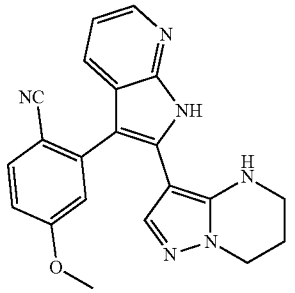 [SMILES: COc1ccc(C#N)c(-c2c(-c3cnn4c3NCCC4)[nH]c3ncccc23)c1] | $^1$H NMR (400 MHz, DMSO-$d_6$): δ 1.93-2.02 (2H, m), 3.15 (2H, s), 3.84 (3H, s), 4.00 (2H, t, J = 6.1 Hz), 5.78 (1H, s), 6.89 (1H, s), 7.06 (3H, m), 7.66 (1H, d, J = 7.8 Hz), 7.82 (1H, d, J = 8.7 Hz), 8.19 (1H, d, J = 4.9 Hz), 11.71 (1H, s); LRMS (ESI): m/z $[M + H]^+$ 371. |
| EX.210 | 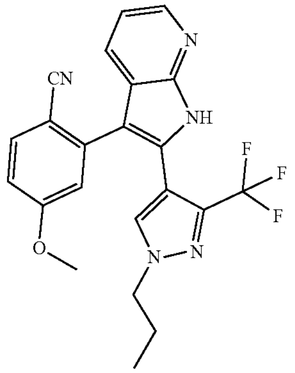 [SMILES: CCCn1cc(-c2[nH]c3ncccc3c2-c2cc(OC)ccc2C#N)c(C(F)(F)F)n1] | $^1$H NMR (400 MHz, DMSO-$d_6$): δ 0.78 (3H, t, J = 7.4 Hz), 1.79 (2H, m), 3.76 (3H, s), 4.19 (2H, t, J = 6.8 Hz), 6.83 (1H, d, J = 2.6 Hz), 7.05 (1H, dd, J = 8.7, 2.6 Hz), 7.18 (1H, dd, J = 7.9, 4.7 Hz), 7.79 (1H, d, J = 8.7 Hz), 7.84 (1H, dd, J = 8.0, 1.1 Hz), 8.11-8.16 (1H, m), 8.34 (1H, dd, J = 4.7, 1.5 Hz), 12.30 (1H, s); LRMS (ESI): m/z $[M + H]^+$ 426. |
| EX.211 | 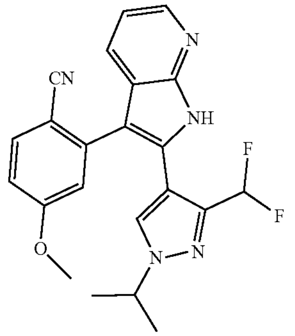 [SMILES: COc1ccc(C#N)c(-c2c(-c3cn(C(C)C)nc3C(F)F)[nH]c3ncccc23)c1] | $^1$H NMR (400 MHz, DMSO-$d_6$) δ 1.42 (6H, d, J = 6.8 Hz), 3.76 (3H, s), 4.55-4.65 (1H, m), 6.62 (1H, t, $J_{H-F}$ = 54.0 Hz), 6.90 (1H, d, J = 2.6 Hz), 7.05 (1H, dd, J = 8.7, 2.6 Hz), 7.17 (1H, dd, J = 7.9, 4.7 Hz), 7.80 (1H, d, J = 8.7 Hz), 7.83 (1H, dd, J = 7.9, 1.5 Hz), 8.05 (1H, s), 8.32 (1H, dd, J = 4.7, 1.5 Hz), 12.19 (1H, s); LRMS (ESI): m/z $[M + H]^+$ 408. |
| EX.212 | 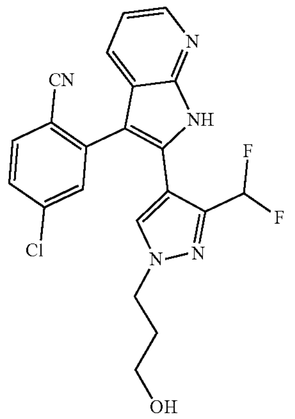 [SMILES: N#Cc1ccc(Cl)cc1-c1c(-c2cn(CCCO)nc2C(F)F)[nH]c2ncccc12] | $^1$H NMR (400 MHz, DMSO-$d_6$): δ 1.91 (2H, p, J = 6.5 Hz), 3.38 (2H, q, J = 6.0 Hz), 4.25 (2H, t, J = 6.9 Hz), 4.60 (1H, t, J = 5.2 Hz), 6.72 (1H, t, $J_{H-F}$ = 53.9 Hz), 7.19 (1H, dd, J = 7.9, 4.7 Hz), 7.46 (1H, d, J = 2.0 Hz), 7.59 (1H, dd, J = 8.4, 2.2 Hz), 7.85 (1H, dd, J = 8.0, 1.3 Hz), 7.92 (1H, d, J = 8.4 Hz), 8.01 (1H, s), 8.34 (1H, dd, J = 4.7, 1.5 Hz), 12.30 (1H, s); LRMS (ESI): m/z $[M + H]^+$ 428. |

-continued

| Example No. | Chemical structural formula | Spectrum data |
|---|---|---|
| EX.213 | 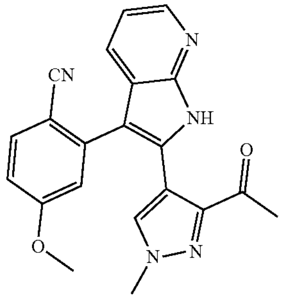 [SMILES: COc1ccc(C#N)c(-c2c(-c3cn(C)nc3C(C)=O)[nH]c3ncccc23)c1] | $^1$H NMR (400 MHz, DMSO-$d_6$): δ 2.44 (3H, s), 3.79 (3H, s), 3.92 (3H, s), 6.90 (1H, d, J = 2.5 Hz), 7.07 (1H, dd, J = 8.7, 2.6 Hz), 7.14 (1H, dd, J = 7.9, 4.7 Hz), 7.70-7.86 (3H, m), 8.30 (1H, dd, J = 4.7, 1.4 Hz), 12.13 (1H, s); LRMS (ESI): m/z $[M + H]^+$ 372. |
| EX.214 | 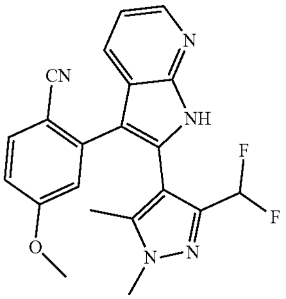 [SMILES: COc1ccc(C#N)c(-c2c(-c3c(C(F)F)nn(C)c3C)[nH]c3ncccc23)c1] | $^1$H NMR (400 MHz, DMSO-$d_6$): δ 2.06 (3H, s), 3.76 (3H, s), 3.81 (3H, s), 6.64 (1H, t, $J_{H-F}$ = 54.0 Hz), 6.86 (1H, d, J = 2.4 Hz), 7.04 (1H, dd, J = 8.7, 2.5 Hz), 7.17 (1H, dd, J = 7.9, 4.7 Hz), 7.80 (1H, d, J = 8.7 Hz), 7.85 (1H, dd, J = 7.9, 1.3 Hz), 8.32 (1H, d, J = 3.4 Hz), 12.19 (1H, s); LRMS (ESI): m/z $[M + H]^+$ 394. |
| EX.215 | 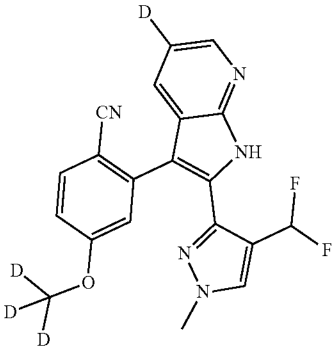 [SMILES: [2H]c1cnc2[nH]c(-c3nn(C)cc3C(F)F)c(-c3cc(OC([2H])([2H])[2H])ccc3C#N)c2c1] | $^1$H NMR (400 MHz, DMSO-$d_6$): δ 3.91 (3H, s), 6.48 (1H, t, $J_{H-F}$ = 55.8 Hz), 6.92 (1H, d, J = 2.6 Hz), 7.07 (1H, dd, J = 8.7, 2.6 Hz), 7.82 (1H, d, J = 8.7 Hz), 7.87 (1H, d, J = 1.6 Hz), 8.17 (1H, s), 8.36 (1H, d, J = 1.6 Hz), 12.40 (1H, s); LRMS (ESI): m/z $[M + H]^+$ 384. |
| EX.216 | 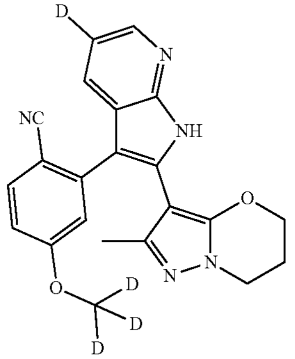 [SMILES: [2H]c1cnc2[nH]c(-c3c(C)nn4c3OCCC4)c(-c3cc(OC([2H])([2H])[2H])ccc3C#N)c2c1] | $^1$H NMR (400 MHz, DMSO-$d_6$): δ 1.80 (3H, s), 2.05-2.10 (2H, m), 3.99-4.06 (4H, m), 6.94 (1H, d, J = 2.6 Hz), 7.04 (1H, dd, J = 8.7, 2.6 Hz), 7.78 (1H, d, J = 8.7 Hz), 7.80 (1H, d, J = 1.6 Hz), 8.25 (1H, d, J = 1.6 Hz), 11.92 (1H, br s); LRMS (ESI): m/z $[M + H]^+$ 390. |

-continued

| Example No. | Chemical structural formula | Spectrum data |
|---|---|---|
| EX.217 | 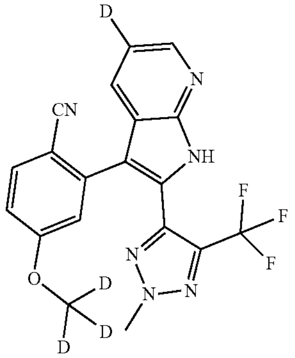 [SMILES: [2H]c1cnc2[nH]c(-c3nn(C)nc3C(F)(F)F)c(-c3cc(OC([2H])([2H])[2H])ccc3C#N)c2c1] | $^1$H NMR (400 MHz, DMSO-$d_6$): δ 4.33 (3H, s), 6.85 (1H, d, J = 2.6 Hz), 7.09 (1H, dd, J = 8.7, 2.6 Hz), 7.82 (1H, d, J = 8.7 Hz), 7.94 (1H, d, J = 1.4 Hz), 8.42 (1H, d, J = 1.4 Hz), 12.68 (1H, s); LRMS (ESI): m/z $[M + H]^+$ 403. |
| EX.218 | 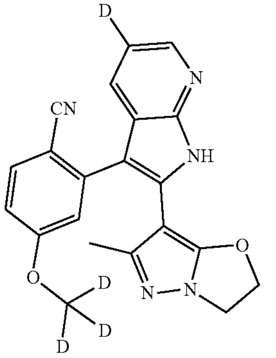 [SMILES: [2H]c1cnc2[nH]c(-c3c(C)nn4c3OCC4)c(-c3cc(OC([2H])([2H])[2H])ccc3C#N)c2c1] | $^1$H NMR (400 MHz, DMSO-$d_6$): δ 1.95 (3H, s), 4.19 (2H, t, J = 7.7 Hz), 4.88 (2H, t, J = 7.9 Hz), 6.97 (1H, d, J = 2.6 Hz), 7.05 (1H, dd, J = 8.7, 2.6 Hz), 7.78-7.80 (2H, m), 8.26 (1H, d, J = 1.6 Hz), 11.99 (1H, s); LRMS (ESI): m/z $[M + H]^+$ 376. |
| EX.219 | 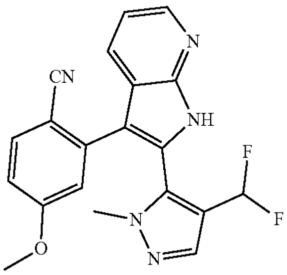 [SMILES: COc1ccc(C#N)c(-c2c(-c3c(C(F)F)cnn3C)[nH]c3ncccc23)c1] | $^1$H NMR (400 MHz, CDC13): δ 3.66 (3H, s), 3.81 (3H, s), 6.55 (1H, t, $J_{H\text{-}F}$ = 55.6 Hz), 6.87 (1H, s), 6.99 (1H, dd, J = 8.7, 2.6 Hz), 7.23-7.30 (1H, m), 7.71 (1H, d, J = 8.7 Hz), 7.83 (1H, s), 8.06 (1H, dd, J = 8.0, 1.5 Hz), 8.37 (1H, dd, J = 4.7, 1.4 Hz), 11.05 (1H, br s); LRMS (ESI): m/z [M+H] 380. |
| EX.220 | 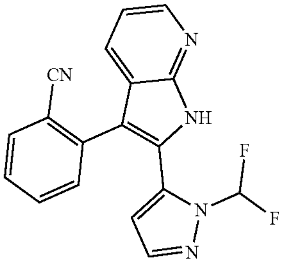 [SMILES: N#Cc1ccccc1-c1c(-c2ccnn2C(F)F)[nH]c2ncccc12] | $^1$H NMR (400 MHz, (CD3)2CO): δ 6.70 (1H, d, J = 1.7 Hz), 7.29-7.34 (1H, m), 7.55-7.63 (2M, m), 7.76 (1H, td, J = 7.7, 1.4 Hz), 7.83 (1H, d, J = 1.7 Hz), 7.89 (1H, dd, J = 7.8, 1.4 Hz), 8.03 (1H, dd, J = 8.0, 1.5 Hz), 8.50 (1H, dd, J = 4.7, 1.5 Hz); LRMS (ESI): m/z $[M + H]^+$ 336. |
| EX.221 | 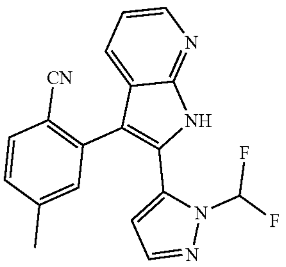 [SMILES: Cc1ccc(C#N)c(-c2c(-c3ccnn3C(F)F)[nH]c3ncccc23)c1] | $^1$H NMR (400 MHz, (CD3)2CO): δ 2.44 (3H, s), 6.73 (1H, apparent t, J = 1.7 Hz), 7.29-7.58 (4H, m), 7.77 (1H, d, J = 7.9 Hz), 7.85 (1H, s), 8.17-8.22 (1H, m), 8.58 (1H, br s); LRMS (ESI): m/z $[M + H]^+$ 350. |

-continued

| Example No. | Chemical structural formula | Spectrum data |
|---|---|---|
| EX.222 | 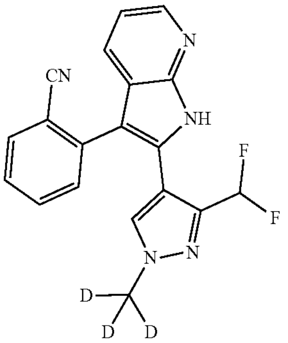 [SMILES: [2H]C([2H])([2H])n1cc(-c2[nH]c3ncccc3c2-c2ccccc2C#N)c(C(F)F)n1] | $^{1}$H NMR (400 MHz, DMSO-$d_6$): δ 6.97 (1H, t, $J_{H\text{-}F}$ = 54.2 Hz), 7.28 (1H, dd, J = 8.0, 4.7 Hz), 7.59-7.67 (2H, m), 7.79-7.83 (1H, m), 7.87 (1H, ddd, J = 7.8, 1.4, 0.6 Hz), 7.99 (1H, dd, J = 8.0, 1.6 Hz), 8.45 (1H, dd, J = 4.6, 1.5 Hz), 8.60-8.61 (1H, m), 11.62 (1H, s); LRMS (ESI): m/z $[M + H]^+$ 353. |
| EX.223 | 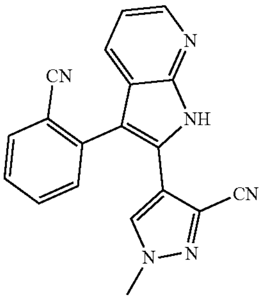 [SMILES: Cn1cc(-c2[nH]c3ncccc3c2-c2ccccc2C#N)c(C#N)n1] | $^{1}$H NMR (400 MHz, DMSO-$d_6$): δ 3.99 (3H, s), 7.20 (1H, dd, J = 7.9, 4.7 Hz), 7.47 (1H, m), 7.52-7.60 (1H, m), 7.70-7.79 (1H, m), 7.82-7.89 (1H, m), 7.89-7.96 (1H, m), 8.18 (1H, s), 8.37 (1H, dd, J = 4.7, 1.6 Hz), 12.52 (1H, s); LRMS (ESI): m/z $[M + H]^+$ 325. |
| EX.224 | 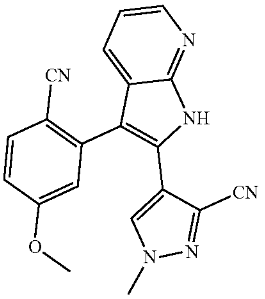 [SMILES: COc1ccc(C#N)c(-c2c(-c3cn(C)nc3C#N)[nH]c3ncccc23)c1] | $^{1}$H NMR (400 MHz, DMSO-$d_6$): δ 3.75 (3H, s), 3.93 (3H, s), 6.90 (1H, d, J = 2.6 Hz), 7.08 (1H, dd, J = 8.8, 2.6 Hz), 7.24 (1H, dd, J = 8.0, 4.8 Hz), 7.77 (1H, d, J = 8.7 Hz), 7.90 (1H, dd, J = 8.0, 1.5 Hz), 8.08 (1H, s), 8.31 (1H, dd, J = 4.8, 1.4 Hz), 12.51 (1H, br s); LRMS (ESI): m/z $[M + H]^+$ 355. |
| EX.225 | 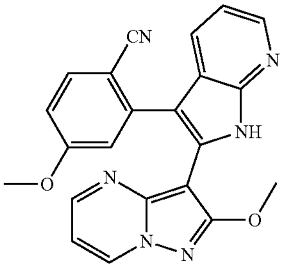 | $^{1}$H NMR (400 MHz, DMSO-$d_6$): δ 3.76 (3H, d, J = 2.0 Hz), 4.04 (1H, s), 6.95-7.04 (3H, m), 7.15 (1H, dd, J = 7.9, 4.9 Hz), 7.47-7.56 (1H, m), 7.73 (1H, d, J = 8.5 Hz), 7.82-7.89 (1H, m), 7.92-7.99 (1H, m), 8.26-8.33 (1H, m), 8.44 (1H, dd, J = 4.2, 1.8 Hz), 8.99-9.06 (1H, m), 12.01 (1H, s); LRMS (ESI): m/z $[M + H]^+$ 397. |
| EX.226 | 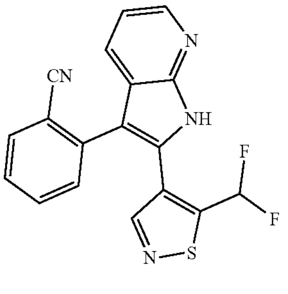 [SMILES: N#Cc1ccccc1-c1c(-c2cnsc2C(F)F)[nH]c2ncccc12] | $^{1}$H NMR (400 MHz, (CD3)2CO): δ 6.97 (1H, t, $J_{H\text{-}F}$ = 54.2 Hz), 7.28 (1H, dd, J = 8.0, 4.7 Hz), 7.58-7.69 (2H, m), 7.77-7.84 (1H, m), 7.87 (1H, m), 7.99 (1H, dd, J = 8.0, 1.6 Hz), 8.45 (1H, dd, J = 4.6, 1.5 Hz), 8.61 (1H, t, J = 2.4 Hz); LRMS (ESI): m/z $[M + H]^+$ 353. |

-continued

| Example No. | Chemical structural formula | Spectrum data |
|---|---|---|
| EX.227 | 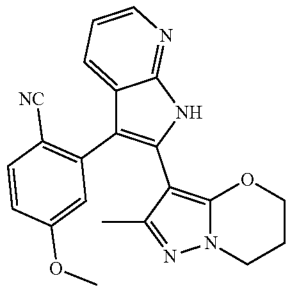 [SMILES: COc1ccc(C#N)c(-c2c(-c3c(C)nn4c3OCCC4)[nH]c3ncccc23)c1] | $^1$H (400 MHz, DMSO-d$_6$): δ 1.79 (3H, s), 2.02-2.12 (2H, m), 3.81 (3H, s), 3.94-4.08 (4H, m), 6.93 (1H, d, J = 2.5 Hz), 7.03 (1H, dd, J = 8.7, 2.6 Hz), 7.11 (1H, dd, J = 7.8, 4.7 Hz), 7.74-7.83 (2H, m), 8.24 (1H, dd, J = 4.7, 1.5 Hz), 11.91 (1H, s); LRMS (ESI): m/z [M + H]$^+$ 386. |
| EX.228 | 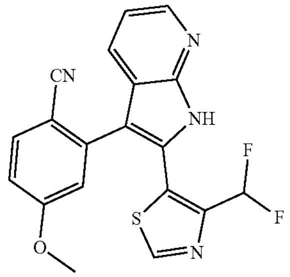 [SMILES: COc1ccc(C#N)c(-c2c(-c3scnc3C(F)F)[nH]c3ncccc23)c1] | $^1$H NMR (400 MHz, CD$_3$OD): δ 3.83 (3H, s), 6.61 (1H, t, JH-J = 53.4 Hz), 7.01 (1H, d, J = 2.5 Hz), 7.09 (1H, dd, J = 8.7, 2.6 Hz), 7.28 (1H, dd, J = 8.0, 4.8 Hz), 7.73 (1H, d, J = 8.7 Hz), 7.97 (1H, dd, J = 8.0, 1.6 Hz), 8.40 (1H, dd, J = 4.8, 1.5 Hz), 9.18 (1H, s); LRMS (ESI): m/z [M + H]$^+$ 383. |
| EX.229 | 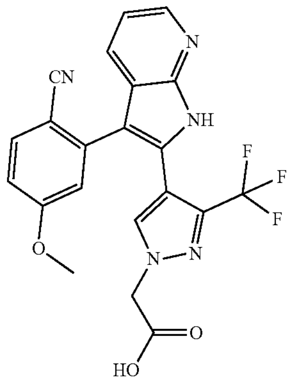 [SMILES: COc1ccc(C#N)c(-c2c(-c3cn(CC(=O)O)nc3C(F)(F)F)[nH]c3ncccc23)c1] | $^1$H (400 MHz, DMSO-d$_6$): δ 3.73 (3H, s), 5.14 (2H, s), 6.80 (1H, d, J = 2.6 Hz), 7.02 (1H, dd, J = 8.7, 2.6 Hz), 7.18 (1H, dd, J = 8.0, 4.7 Hz), 7.79 (1H, d, J = 8.7 Hz), 7.83 (1H, dd, J = 8.0, 1.1 Hz), 8.15 (1H, d, J = 0.9 Hz), 8.34 (1H, dd, J = 4.7, 1.6 Hz), 12.38 (1H, s), 13.34 (1H, br s); LRMS (ESI): m/z [M + H]$^+$ 442. |
| EX.230 | 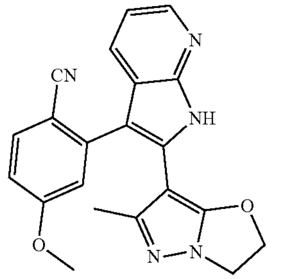 [SMILES: COc1ccc(C#N)c(-c2c(-c3c(C)nn4c3OCC4)[nH]c3ncccc23)c1] | $^1$H (400 MHz, DMSO-d$_6$): δ 1.94 (3H, s), 3.82 (3H, s), 4.19 (2H, t, J = 7.9 Hz), 4.88 (2H, t, J = 8.0 Hz), 6.96 (1H, d, J = 2.5 Hz), 7.04 (1H, dd, J = 8.7, 2.6 Hz), 7.12 (1H, dd, J = 7.9, 4.7 Hz), 7.78 (1H, d, J = 8.7 Hz), 7.79 (1H, dd, J = 8.0, 1.2 Hz), 8.25 (1H, dd, J = 4.7, 1.6 Hz), 11.99 (1H, s); LRMS (ESI): m/z [M + H]$^+$ 372. |
| EX.231 | 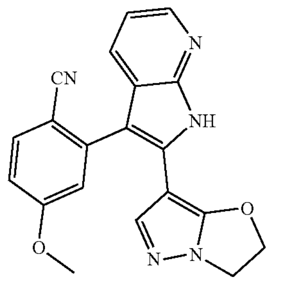 [SMILES: COc1ccc(C#N)c(-c2c(-c3cnn4c3OCC4)[nH]c3ncccc23)c1] | $^1$H (400 MHz, DMSO-d$_6$): δ 3.83 (3H, s), 4.25 (2H, t, J = 8.3 Hz), 4.88 (2H, q, J = 7.7 Hz), 7.00 (1H, d, J = 2.5 Hz), 7.05-7.11 (2H, m), 7.67 (1H, dd, J = 7.6, 1.6 Hz), 7.68 (1H, s), 7.81 (1H, d, J = 8.6 Hz), 8.21 (1H, dd, J = 4.7, 1.6 Hz), 12.09 (1H, s); LRMS (ESI): m/z [M + H]$^+$ 358. |

-continued

| Example No. | Chemical structural formula | Spectrum data |
|---|---|---|
| EX.232 | 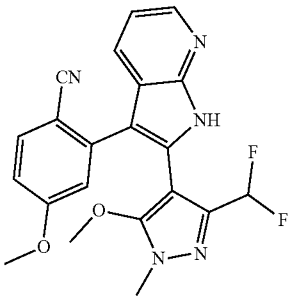 [SMILES: COc1ccc(C#N)c(-c2c(-c3c(C(F)F)nn(C)c3OC)[nH]c3ncccc23)c1] | $^1H$ (400 MHz, DMSO-$d_6$): δ 3.65 (3H, s), 3.69 (3H, s), 3.75 (3H, s), 6.65 (1H, t, $J_{H-F}$ = 53.6 Hz), 6.84 (1H, d, J = 2.6 Hz), 7.05 (1H, dd, J = 8.7, 2.6 Hz), 7.17 (1H, dd, J = 7.9, 4.7 Hz), 7.80-7.87 (2H, m), 8.33 (1H, dd, J = 4.7, 1.6 Hz), 12.29 (1H, s); LRMS (ESI): m/z $[M + H]^+$ 410. |
| EX.233 | 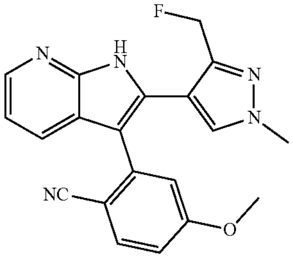 [SMILES: COc1ccc(C#N)c(-c2c(-c3cn(C)nc3CF)[nH]c3ncccc23)c1] | $^1H$ (400 MHz, DMSO-$d_6$): δ 3.79 (3H, s), 3.88 (3H, d, J = 1.5 Hz), 5.00 (2H, d, $J_{H-F}$ = 48.6 Hz), 6.93 (1H, d, J = 2.5 Hz), 7.07 (1H, dd, J = 8.7, 2.6 Hz), 7.15 (1H, dd, J = 7.9, 4.7 Hz), 7.79 (1H, dd, J = 7.9, 1.6 Hz), 7.82 (1H, d, J = 8.7 Hz), 7.86 (1H, s), 8.30 (1H, dd, J = 4.7, 1.6 Hz), 12.14 (1H, s); LRMS (ESI): m/z $[M + H]^+$ 362. |
| EX.234 | 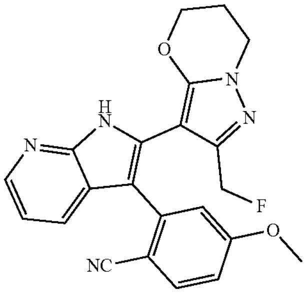 [SMILES: COc1ccc(C#N)c(-c2c(-c3c(CF)nn4c3OCCC4)[nH]c3ncccc23)c1] | $^1H$ (400 MHz, DMSO-$d_6$) δ 2.12 (2H, bs), 3.79 (3H, s), 4.12 (4H, apparent t, J = 5.6 Hz), 4.81-5.11 (2H, m), 6.89 (1H, d, J = 2.6 Hz), 7.04 (1H, dd, J = 8.7, 2.6 Hz), 7.13 (1H, dd, J = 7.9, 4.7 Hz), 7.79 (1H, d, J = 8.7 Hz) 7.82 (1H, dd, J = 7.9, 1.6 Hz), 8.28 (1H, dd, J = 4.7, 1.5 Hz), 12.00 (1H, br s); LRMS (ESI): m/z $[M + H]^+$ 404. |
| EX.235 | 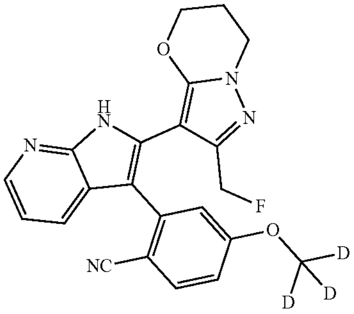 [SMILES: [2H]C([2H])([2H])Oc1ccc(C#N)c(-c2c(-c3c(CF)nn4c3OCCC4)[nH]c3ncccc23)c1] | $^1H$ NMR (400 MHz, DMSO-$d_6$) δ 2.08 (2H, bs), 4.11 (4H, apparent t, J = 5.5 Hz), 4.95 (2H, $J_{H-F}$ = 41.3 Hz), 6.89 (1H, d, J = 2.6 Hz), 7.04 (1H, dd, J = 8.7, 2.6 Hz), 7.13 (1H, dd, J = 7.9, 4.7 Hz), 7.79 (1H, d, J = 8.7 Hz), 7.81 (1H, dd, J = 7.9, 1.6 Hz), 8.27 (1H, dd, J = 4.7, 1.65 Hz), 12.02 (1H, s); LRMS (ESI): m/z $[M + H]^+$ 407. |
| EX.236 | 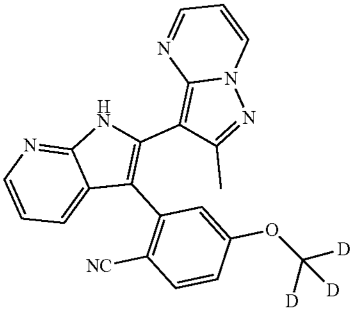 [SMILES: [2H]C([2H])([2H])Oc1ccc(C#N)c(-c2c(-c3c(C)nn4cccnc34)[nH]c3ncccc23)c1] | $^1H$ NMR (400 MHz, DMSO-$d_6$): δ 2.14 (3H, s), 6.96-7.04 (3H, m), 7.18 (1H, dd, J = 7.9, 4.7 Hz), 7.71 (1H, dd, J = 8.3, 0.6 Hz), 7.91 (1H, dd, J = 7.9, 1.2 Hz), 8.33 (1H, dd, J = 4.7, 1.5 Hz), 8.45 (1H, dd, J = 4.1, 1.7 Hz), 9.06 (1H, dd, J = 7.0, 1.7 Hz), 12.21 (1H, s); LRMS (ESI): m/z $[M + H]^+$ 384. |

-continued

| Example No. | Chemical structural formula | Spectrum data |
|---|---|---|
| EX.237 | 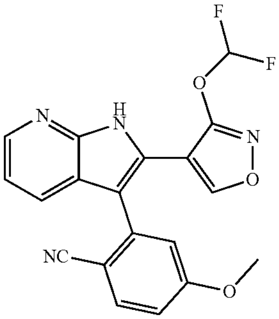 [SMILES: COc1ccc(C#N)c(-c2c(-c3conc3OC(F)F)[nH]c3ncccc23)c1] | $^1$H NMR (400 MHz, $CD_3OD$): δ 3.88 (3H, s), 7.06 (1H, t, J = 71.6 Hz), 7.07 (2H, d, J = 2.4 Hz), 7.11 (1H, dd, J = 8.6, 2.6 Hz), 7.23 (2H, dd, J = 7.9, 4.8 Hz), 7.76 (1H, d, J = 8.6 Hz), 7.93 (1H, dd, J = 8.0, 1.5 Hz), 8.34 (1H, dd, J = 3.4, 1.4 Hz), 8.77 (1H, s); LRMS (ESI): m/z $[M + H]^+$ 383. |
| EX.238 | 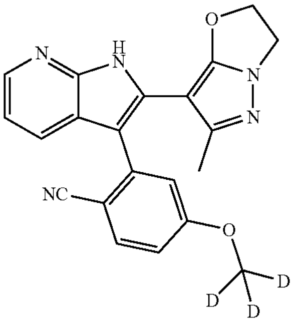 [SMILES: [2H]C([2H])([2H])Oc1ccc(C#N)c(-c2c(-c3c(C)nn4c3OCC4)[nH]c3ncccc23)c1] | $^1$H (400 MHz, DMSO-$d_6$) δ 1.94 (3H, s), 4.19 (2H, t, J = 9.0 Hz), 4.87 (2H, t, J = 7.6 Hz), 6.96 (1H, d, J = 2.4 Hz), 7.04 (1H, dd, J = 8.7, 2.6 Hz), 7.12 (1H, dd, J = 7.9, 4.7 Hz), 7.78 (1H, d, J = 8.5 Hz), 7.79 (1H, dd, J = 7.9, 1.6 Hz), 8.25 (1H, dd, J = 4.7, 1.5 Hz), 12.00 (1H, s); LRMS (ESI): m/z $[M + H]^+$ 375. |
| EX.239 | 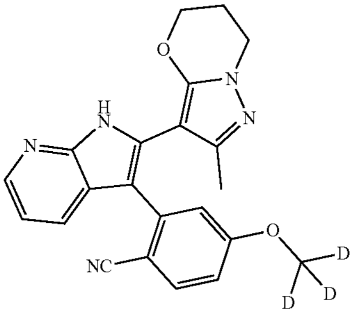 [SMILES: [2H]C([2H])([2H])Oc1ccc(C#N)c(-c2c(-c3c(C)nn4c3OCCC4)[nH]c3ncccc23)c1] | $^1$H (400 MHz, DMSO-$d_6$): δ 1.80 (3H, s), 2.02-2.12 (2H, m), 4.01 (4H, dt, J = 17.1, 5.6 Hz), 6.93 (1H, d, J = 2.6 Hz), 7.03 (1H, dd, J = 8.7, 2.6 Hz), 7.11 (1H, dd, J = 7.9, 4.7 Hz), 7.77 (1H, d, J = 8.7 Hz), 7.80 (1H, dd, J = 7.9, 1.4 Hz), 8.24 (1H, dd, J = 4.7, 1.6 Hz), 11.91 (1H, s); LRMS (ESI): m/z $[M + H]^+$ 389. |
| EX240 | 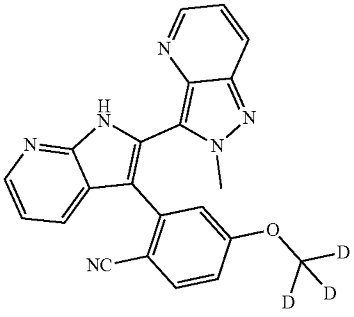 [SMILES: [2H]C([2H])([2H])Oc1ccc(C#N)c(-c2c(-c3c4ncccc4nn3C)[nH]c3ncccc23)c1] | $^1$H (400 MHz, DMSO-$d_6$): δ 4.10 (3H, s), 6.96 (1H, dd, J = 8.7, 2.6 Hz), 7.04 (1H, d, J = 2.5 Hz), 7.26 (2H, td, J = 8.6, 4.4 Hz), 7.65 (1H, d, J = 8.7 Hz), 8.04 (1H, dd, J = 8.0, 1.5 Hz), 8.11 (1H, dd, J = 8.7, 1.4 Hz), 8.37 (1H, dd, J = 4.0, 1.4 Hz), 8.45 (1H, dd, J = 4.7, 1.5 Hz), 12.69 (1H, s); LRMS (ESI): m/z $[M + H]^+$ 384. |
| EX.241 | 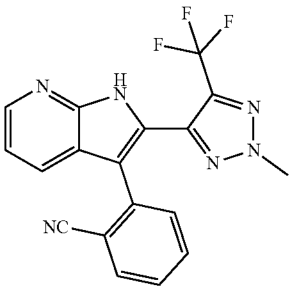 [SMILES: Cn1nc(-c2[nH]c3ncccc3c2-c2ccccc2C#N)c(C(F)(F)F)n1] | $^1$H NMR (400 MHz, DMSO-$d_6$): δ 4.33 (3H, s), 7.25 (1H, dd, J = 8.0, 4.6 Hz), 7.35 (1H, d, J = 7.8 Hz), 7.55 (1H, td, J = 7.7, 1.2 Hz), 7.70 (1H, td, J = 7.7, 1.4 Hz), 7.91 (1H, dd, J = 2.8, 1.1 Hz), 7.93 (1H, dd, J = 3.1, 1.1 Hz), 8.43 (1H, s), 12.72 (1H, s). LRMS (ESI): m/z $[M + H]^+$ 369. |

-continued

| Example No. | Chemical structural formula | Spectrum data |
|---|---|---|
| EX.242 | 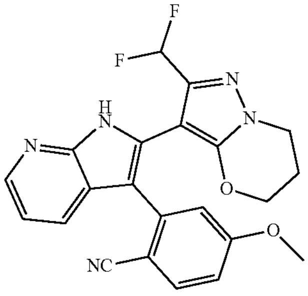 [SMILES: COc1ccc(C#N)c(-c2c(-c3c(C(F)F)nn4c3OCCC4)[nH]c3ncccc23)c1] | $^1$H NMR (400 MHz, DMSO-$d_6$): δ 2.10-2.25 (2H, m), 3.79 (3H, s), 4.01-4.31 (4H, m), 6.56 (1H, t, $J_{H-F}$ = 54.0 Hz), 6.88 (1H, d, J = 2.6 Hz), 7.04 (1H, dd, J = 8.7, 2.6 Hz), 7.15 (1H, dd, J = 7.9, 4.7 Hz), 7.79 (1H, d, J = 8.7 Hz), 7.82 (1H, dd, J = 8.0, 1.0 Hz), 8.30 (1H, dd, J = 4.7, 1.5 Hz), 12.05 (1H, s). LRMS (ESI): m/z $[M + H]^+$ 422. |
| EX243 | 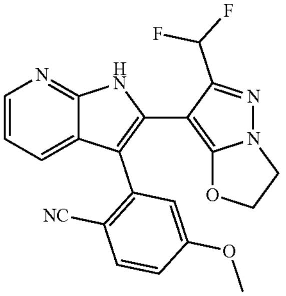 [SMILES: COc1ccc(C#N)c(-c2c(-c3c(C(F)F)nn4c3OCC4)[nH]c3ncccc23)c1] | $^1$H NMR (400 MHz, DMSO-$d_6$): δ 3.80 (3H, s), 4.40 (2H, t, J = 8.0 Hz), 5.04 (2H, t, J = 8.0 Hz), 6.66 (1H, t, $J_{H-F}$ = 53.8 Hz), 6.90 (1H, d, J = 2.6 Hz), 7.06 (1H, dd, J = 8.7, 2.6 Hz), 7.16 (1H, dd, J = 7.9, 4.7 Hz), 7.78-7.84 (2H, m), 8.31 (1H, dd, J = 4.7, 1.6 Hz), 12.11 (1H, s). LRMS (ESI): m/z $[M + H]^+$ 408. |
| EX.244 | 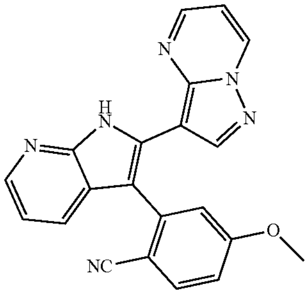 [SMILES: COc1ccc(C#N)c(-c2c(-c3cnn4cccnc34)[nH]c3ncccc23)c1] | $^1$H NMR (400 MHz, DMSO-$d_6$): δ 3.80 (3H, s), 7.06-7.11 (2H, m), 7.15 (2H, m), 7.72-7.85 (2H, m), 8.14 (1H, s), 8.31 (1H, dd, J = 4.7, 1.5 Hz), 8.54 (1H, dd, J = 4.0, 1.7 Hz), 9.20 (1H, dd, J = 7.0, 1.7 Hz), 12.05 (1H, s). LRMS (ESI): m/z $[M + H]^+$ 367. |
| EX.245 | 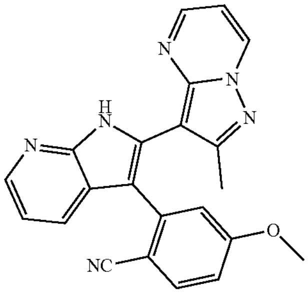 [SMILES: COc1ccc(C#N)c(-c2c(-c3c(C)nn4cccnc34)[nH]c3ncccc23)c1] | $^1$H NMR (400 MHz, DMSO-$d_6$): δ 2.14 (3H, s), 3.75 (3H, s), 6.94-7.06 (3H, m), 7.18 (1H, dd, J = 7.9, 4.7 Hz), 7.64-7.76 (1H, m), 7.91 (1H, dd, J = 7.9, 1.1 Hz), 8.33 (1H, dd, J = 4.7, 1.5 Hz), 8.45 (1H, dd, J = 4.1, 1.7 Hz), 9.07 (1H, dd, J = 7.0, 1.7 Hz), 12.22 (1H, s). LRMS (ESI): m/z $[M + H]^+$ 381. |
| EX.246 | 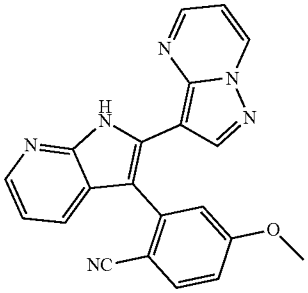 [SMILES: COc1ccc(C#N)c(-c2c(-c3cnn4cccnc34)[nH]c3ncccc23)c1] | $^1$H NMR (400 MHz, DMSO-$d_6$): δ 3.84 (3H, s), 7.10 (1H, dd, J = 8.7, 2.6 Hz), 7.17-7.25 (2H, m), 7.77 (1H, d, J = 8.7 Hz), 7.91 (1H, dd, J = 7.9, 1.5 Hz), 7.95 (1H, d, J = 4.7 Hz), 8.21 (1H, s), 8.36 (1H, dd, J = 4.7, 1.5 Hz), 8.56 (1H, d, J = 1.4 Hz), 8.85 (1H, dd, J = 4.7, 1.4 Hz), 12.61 (1H, s). LRMS (ESI): m/z $[M + H]^+$ 367. |

-continued

| Example No. | Chemical structural formula | Spectrum data |
|---|---|---|
| EX.247 | 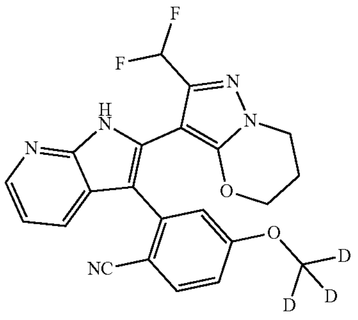 [SMILES: [2H]C([2H])([2H])Oc1ccc(C#N)c(-c2c(-c3c(C(F)F)nn4c3OCCC4)[nH]c3ncccc23)c1] | $^1$H NMR (400 MHz, DMSO-$d_6$): δ 2.15 (2H, s), 4.15-4.18 (4H, m), 6.56 (1H, t, $J_{H-F}$ = 54.0 Hz), 6.88 (1H, d, J = 2.6 Hz), 7.04 (1H, dd, J = 8.7, 2.6 Hz), 7.15 (1H, dd, J = 7.9, 4.7 Hz), 7.79 (1H, d, J = 8.7 Hz), 7.82 (1H, dd, J = 7.9, 1.4 Hz), 8.30 (1H, dd, J = 4.7, 1.6 Hz), 12.07 (1H, s). LRMS (ESI): m/z [M + H]$^+$ 425. |
| EX.248 | 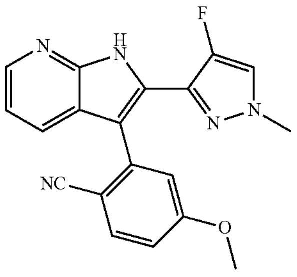 [SMILES: COc1ccc(C#N)c(-c2c(-c3nn(C)cc3F)[nH]c3ncccc23)c1] | $^1$H NMR (400 MHz, DMSO-$d_6$): δ 3.83 (3H, s), 3.84 (3H, s), 7.01 (1H, d, J = 2.6 Hz), 7.09 (1H, dd, J = 8.7, 2.6 Hz), 7.15 (1H, dd, J = 7.9, 4.7 Hz), 7.74-7.87 (2H, m), 7.91 (1H, d, J = 4.7 Hz), 8.32 (1H, dd, J = 4.7, 1.5 Hz), 12.35 (1H, s). LRMS (ESI): m/z [M + H]$^+$ 348. |
| EX.249 | 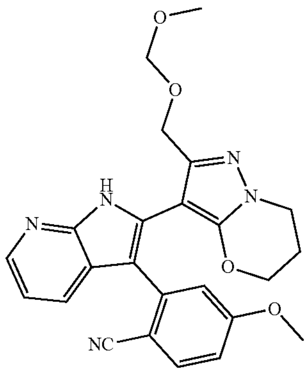 [SMILES: COCOCc1nn2c(c1-c1[nH]c3ncccc3c1-c1cc(OC)ccc1C#N)OCCC2] | $^1$H NMR (400 MHz, DMSO-$d_6$): δ 2.10 (2H, bs), 3.03 (3H, s), 3.78 (3H, s), 4.08 (6H, m), 4.39 (2H, s), 6.90 (1H, s), 7.04 (1H, d, J = 8.6 Hz), 7.08-7.19 (1H, m), 7.65-7.96 (2H, m), 8.26 (1H, d, J = 4.7 Hz), 11.84 (1H, s). LRMS (ESI): m/z [M + H]$^+$ 446. |
| EX.250 | 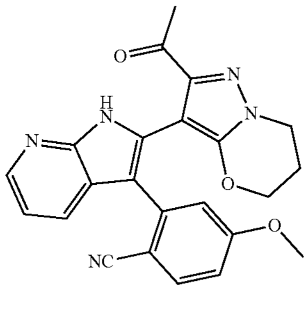 [SMILES: COc1ccc(C#N)c(-c2c(-c3c(C(C)=O)nn4c3OCCC4)[nH]c3ncccc23)c1] | $^1$H NMR (400 MHz, DMSO-$d_6$): 82.11 (2H, s), 2.34 (3H, s), 3.78 (3H, s), 4.03 (2H, s), 4.20 (2H, t, J = 6.0 Hz), 6.82 (1H, d, J = 2.6 Hz), 7.01 (1H, dd, J = 8.7, 2.6 Hz), 7.12 (1H, dd, J = 7.9, 4.7 Hz), 7.75 (1H, d, J = 8.7 Hz), 7.82 (1H, dd, J = 7.9, 1.3 Hz), 8.27 (1H, dd, J = 4.7, 1.5 Hz), 11.89 (1H, s). LRMS (ESI): m/z [M + H]$^+$ 414. |

-continued

| Example No. | Chemical structural formula | Spectrum data |
|---|---|---|
| EX.251 | 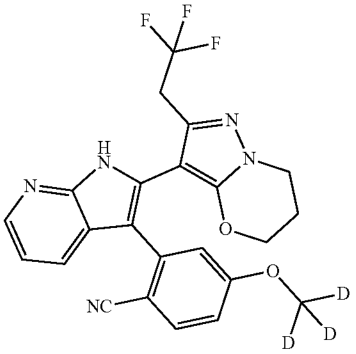 [SMILES: [2H]C([2H])([2H])Oc1ccc(C#N)c(-c2c(-c3c(CC(F)(F)F)nn4c3OCCC4)[nH]c3ncccc23)c1] | $^1$H NMR (400 MHz, DMSO-$d_6$): δ 2.08 (2H, bs), 2.89-3.32 (2H, m), 3.87-4.31 (4H, m), 6.81 (1H, d, J = 2.6 Hz), 7.05 (1H, dd, J = 8.7, 2.6 Hz), 7.13 (1H, dd, J = 7.9, 4.7 Hz), 7.75-7.87 (2H, m), 8.27 (1H, dd, J = 4.7, 1.5 Hz), 12.07 (1H, s). LRMS (ESI): m/z [M + H]$^+$ 457. |
| EX.252 | 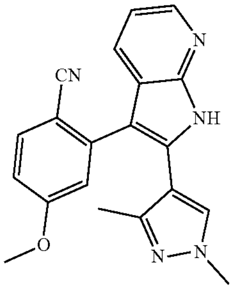 | $^1$H NMR (400 MHz, DMSO-$d_6$): δ 1.82 (3H, s), 3.78 (3H, s), 3.81 (3H, s), 6.96 (1H, d, J = 2.6 Hz), 7.07 (1H, dd, J = 8.7, 2.6 Hz), 7.13 (1H, dd, J = 7.9, 4.7 Hz), 7.67 (1H, s), 7.79 (1H, dd, J = 7.9, 1.2 Hz), 7.82 (1H, d, J = 8.7 Hz), 8.27 (1H, dd, J = 4.7, 1.5 Hz), 12.06 (1H, s). LRMS (ESI): m/z [M + H]$^+$ 344. |
| EX.253 | 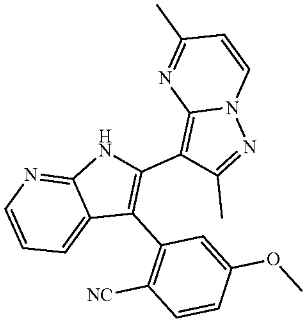 [SMILES: COc1ccc(C#N)c(-c2c(-c3c(C)nn4ccc(C)nc34)[nH]c3ncccc23)c1] | $^1$H NMR (400 MHz, DMSO-$d_6$): δ 2.21 (3H, s), 2.35 (3H, s), 3.74 (3H, s), 6.87 (1H, d, J = 7.1 Hz), 6.93-7.03 (2H, m), 7.17 (1H, dd, J = 7.9, 4.7 Hz), 7.61-7.74 (1H, m), 7.89 (1H, dd, J = 7.9, 1.2 Hz), 8.32 (1H, dd, J = 4.7, 1.5 Hz), 8.88 (1H, d, J = 7.1 Hz), 12.17 (1H, S). LRMS (ESI): m/z [M + H]$^+$ 395. |
| EX.254 | 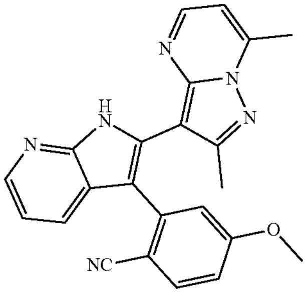 [SMILES: COc1ccc(C#N)c(-c2c(-c3c(C)nn4c(C)ccnc34)[nH]c3ncccc23)c1] | $^1$H NMR (400 MHz, DMSO-$d_6$): δ 2.16 (3H, s), 2.74 (3H, s), 3.74 (3H, s), 6.93-7.03 (3H, m), 7.18 (1H, dd, J = 7.9, 4.7 Hz), 7.72 (1H, d, J = 8.3 Hz), 7.90 (1H, dd, J = 7.9, 1.2 Hz), 8.33 (1H, dd, J = 4.7, 1.5 Hz), 8.37 (1H, d, J = 4.2 Hz), 12.19 (1H, s). LRMS (ESI): m/z [M + H]$^+$ 395. |
| EX.255 | 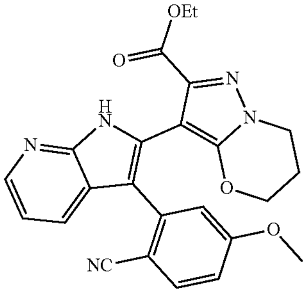 [SMILES: CCOC(=O)c1nn2c(c1-c1[nH]c3ncccc3c1-c1cc(OC)ccc1C#N)OCCC2] | $^1$H NMR (400 MHz, DMSO-$d_6$): δ 1.04 (3H, t, J = 7.1 Hz), 2.13 (2H, s), 3.79 (3H, s), 4.00 (2H, q, J = 7.1 Hz), 4.11 (2H, s), 4.18 (2H, t, J = 6.1 Hz), 6.85 (1H, d, J = 2.6 Hz), 7.02 (1H, dd, J = 8.7, 2.6 Hz), 7.12 (1H, dd, J = 7.9, 4.7 Hz), 7.76 (1H, d, J = 8.7 Hz), 7.82 (1H, dd, J = 7.9, 1.5 Hz), 8.27 (1H, dd, J = 4.7, 1.5 Hz), 11.98 (1H, s). LRMS (ESI): m/z [M + H]$^+$ 444. |

-continued

| Example No. | Chemical structural formula | Spectrum data |
|---|---|---|
| EX.256 | 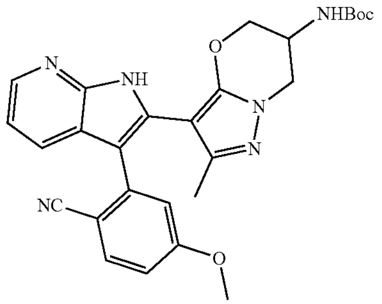 [SMILES: COc1ccc(C#N)c(-c2c(-c3c(C)nn4c3OCC(NC(=O)OC(C)(C)C)C4)[nH]c3ncccc23)c1] | $^1$H NMR (400 MHz, DMSO-$d_6$): δ 1.40 (9H, s), 1.70 (3H, s), 3.82 (3H, s), 3.86 (1H, dt, J = 8.6, 4.6 Hz), 3.92-4.02 (1H, m), 4.10 (2H, s), 4.23 (1H, dd, J = 12.0, 4.5 Hz), 6.97 (1H, bs), 7.05 (1H, dd, J = 8.7, 2.5 Hz), 7.13 (1H, dd, J = 7.9, 4.7 Hz), 7.15 (1H, bs), 7.72-7.88 (2H, m), 8.26 (1H, dd, J = 4.7, 1.5 Hz), 11.87 (1H, s). LRMS (ESI): m/z [M + H]$^+$ 501. |
| EX.257 | 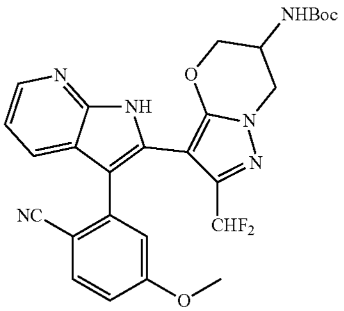 [SMILES: COc1ccc(C#N)c(-c2c(-c3c(C(F)F)nn4c3OCC(NC(=O)OC(C)(C)C)C4)[nH]c3ncccc23)c1] | $^1$H NMR (400 MHz, DMSO-$d_6$): δ 1.41 (9H, s), 3.80 (3H, s), 3.93-4.28 (4H, m), 4.40 (2H, m), 6.48 (1H, t, $J_{H\text{-}F}$ = 53.9 Hz), 6.92 (1H, d, J = 2.4 Hz), 7.05 (1H, dd, J = 8.7, 2.6 Hz), 7.16 (1H, dd, J = 7.9, 4.7 Hz), 7.79 (1H, d, J = 8.7 Hz), 7.83-7.87 (1H, m), 8.31 (1H, dd, J = 4.7, 1.5 Hz), 12.01 (1H, s). LRMS (ESI): m/z [M + H]$^+$ 537. |
| EX.258 | 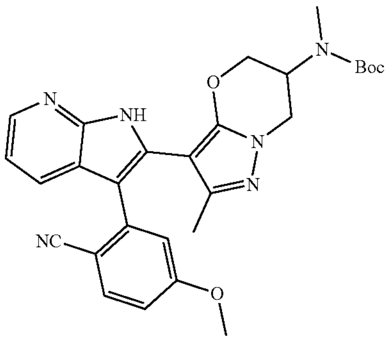 [SMILES: COc1ccc(C#N)c(-c2c(-c3c(C)nn4c3OCC(N(C)C(=O)OC(C)(C)C)C4)[nH]c3ncccc23)c1] | $^1$H NMR (400 MHz, DMSO-$d_6$): δ 1.42 (9H, s), 1.87 (3H, s), 2.61 (3H, s), 3.82 (3H, s), 4.15 (3H, d, J = 3.7 Hz), 4.30 (1H, dd, J = 12.8, 6.1 Hz), 4.46 (1H, s), 6.95 (1H, d, J = 22.2 Hz), 7.04 (1H, dd, J = 8.7, 2.6 Hz), 7.12 (1H, dd, J = 7.9, 4.7 Hz), 7.80 (2H, d, J = 7.0 Hz), 8.27 (1H, dd, J = 4.7, 1.5 Hz), 11.99 (1H, s). LRMS (ESI): m/z [M + H]$^+$ 515. |
| EX.259 | 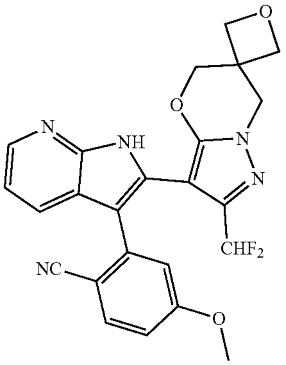 [SMILES: COc1ccc(C#N)c(-c2c(-c3c(C(F)F)nn4c3OCC3(COC3)C4)[nH]c3ncccc23)c1] | $^1$H NMR (400 MHz, DMSO-$d_6$): δ 3.77 (3H, s), 4.14-4.65 (8H, m), 6.62 (1H, t, JH-F = 54.0 Hz), 6.83 (1H, d, J = 2.6 Hz), 7.05 (1H, dd, J = 8.7, 2.6 Hz), 7.15 (1H, dd, J = 7.9, 4.7 Hz), 7.79 (1H, d, J = 8.7 Hz), 7.85 (1H, dd, J = 7.9, 1.4 Hz), 8.31 (1H, dd, J = 4.7, 1.5 Hz), 12.11 (1H, s). LRMS (ESI): m/z [M + H]$^+$ 464. |

-continued

| Example No. | Chemical structural formula | Spectrum data |
|---|---|---|
| EX.260 | 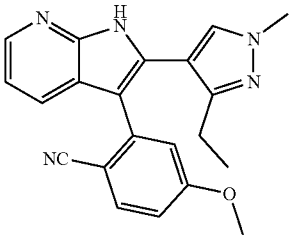 [SMILES: CCc1nn(C)cc1-c1[nH]c2ncccc2c1-c1cc(OC)ccc1C#N] | $^{1}H$ NMR (400 MHz, DMSO-$d_6$): δ 0.88 (3H, t, J = 7.5 Hz), 2.21 (2H, d, J = 7.2 Hz), 3.80 (6H, s), 6.85-6.97 (1H, m), 7.02-7.10 (1H, m), 7.13 (1H, dd, J = 7.8, 4.7 Hz), 7.71 (1H, s), 7.77 (1H, d, J = 7.8 Hz), 7.83 (1H, d, J = 8.7 Hz), 8.27 (1H, d, J = 4.6 Hz), 12.07 (1H, s). LRMS (ESI): m/z $[M + H]^+$ 358. |

3-Bromo-7-methyl-6,7-dihydro-5H-pyrazolo[5,1-b][1,3]oxazine for preparation of EX.173 was synthesized according to literature procedure WO2018/136890. 3-Bromo-5-methyl-6,7-dihydro-5H-pyrazolo[5,1-b][1,3]oxazine for preparation of EX.174 was synthesized according to literature procedure WO2018/136890. 3-Bromo-6-methoxy-6,7-dihydro-5H-pyrazolo[5,1-b][1,3]oxazine for preparation of EX.195 was obtained according to the method described in the patent WO 2018/136890 (PCT/US2018/014728).

3-Bromo-6,7-dihydro-5H-pyrazolo[5,1-b][1,3]oxazin-6-ol (10wwww) for preparation of EX.196 was obtained according to the method described in the patent WO 2018/136890 (PCT/US2018/014728).

EX.261 was synthesized using conditions analogous to EX.123 in accordance with general procedure 5 (using 10ee and 10ff in step 5-3), followed by SEM-deprotection step in accordance with methods used in step 6-4 of making EX.273.

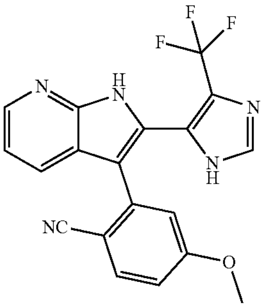 [SMILES: COc1ccc(C#N)c(-c2c(-c3[nH]cnc3C(F)(F)F)[nH]c3ncccc23)c1]

$^{1}$HNMR (400 MHz, $CDCl_3$): δ 3.78 (3H, s), 6.79 (1H, s), 6.94 (1H, d, J=8.3 Hz), 7.09-7.18 (1H, m), 7.55-7.66 (2H, m), 7.90 (1H, d, J=7.9 Hz), 8.16-8.23 (1H, m), 11.60 (2H, br s); LRMS (ESI): m/z $[M+H]^+$ 384.

Methyl 3-(3-(2-cyano-5-methoxyphenyl)-1H-pyrrolo[2,3-b]pyridin-2-yl)-6,7-dihydro-5H-pyrazolo[5,1-b][1,3]oxazine-2-carboxylate (EX.262)

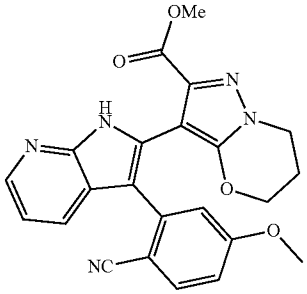

EX.262 is a transesterification product of EX.255 during purification via silica gel column chromatography (eluent: 0%-30% MeOH/DCM). $^{1}H$ NMR (400 MHz, DMSO-$d_6$): δ 2.14 (2H, s), 3.53 (3H, s), 3.79 (3H, s), 3.98-4.28 (4H, m), 6.85 (1H, d, J=2.6 Hz), 7.02 (1H, dd, J=8.7, 2.6 Hz), 7.13 (1H, dd, J=7.9, 4.7 Hz), 7.75 (1H, d, J=8.7 Hz), 7.83 (1H, dd, J=7.9, 1.5 Hz), 8.28 (1H, dd, J=4.7, 1.5 Hz), 12.00 (1H, s). LRMS (ESI): m/z $[M+H]^+$ 430.

The following compounds were synthesized in accordance with procedure 5 (steps 5-1, 5-2, 5-3) using 2-[[3-bromo-4-(trifluoromethyl)pyrazol-1-yl]methoxy]ethyl-trimethyl-silane in step 5-3, followed by SEM-deprotection as described in step 7-5.

| Example No. | Chemical structural formula | Spectrum data |
|---|---|---|
| EX.263 | 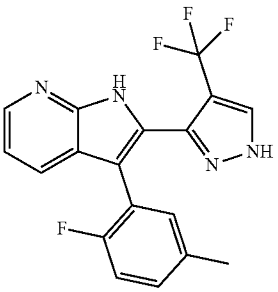 [SMILES: Cc1ccc(F)c(-c2c(-c3n[nH]cc3C(F)(F)F)[nH]c3ncccc23)c1] | $^{1}H$ NMR (400 MHz, DMSO-$d_6$): δ 7.04 (1H, d, J = 8.0 Hz), 7.08-7.10 (2H, m), 7.16 (1H, dd, J = 8.0, 4.2 Hz), 7.84 (1H, d, J = 8.0 Hz), 7.88 (2H, t, J = 7.3 Hz), 8.26 (1H, br s), 8.33 (1H, dd, J = 4.6 Hz, J = 1.4 Hz). LRMS (ESI): m/z $[M + H]^+$ 361. |

-continued

| Example No. | Chemical structural formula | Spectrum data |
|---|---|---|
| EX.264 | 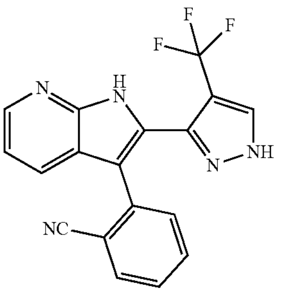 [SMILES: N#Cc1ccccc1-c1c(-c2n[nH]cc2C(F)(F)F)[nH]c2ncccc12] | $^1$H NMR (400 MHz, DMSO-$d_6$): δ 7.20 (1H, dd, J = 8.0, 4.7 Hz), 7.26 (1H, d, J = 7.8 Hz), 7.49 (1H, apparent t, J-7.6 Hz), 7.62 (1H, apparent t, J = 8.0 Hz), 7.88 (2H, t, J = 7.3 Hz), 8.31 (1H, br s), 8.38 (1H, dd, J = 4.6, 1.4 Hz). LRMS (ESI): m/z [M + H]$^+$ 354. |

The following compounds were synthesized in accordance with the general procedures 1 (steps 1-1, 1-2, 1-3) and 5.

| Example No. | Chemical structural formula | Spectrum data |
|---|---|---|
| EX.265 | 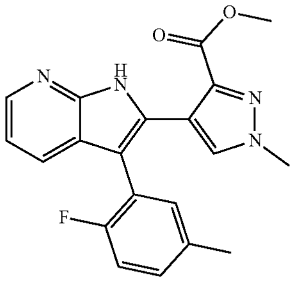 | $^1$H (400 MHz, DMSO-$d_6$): δ 2.24 (3H, s), 3.55 (3H, s), 3.91 (3H, s), 7.07 (1H, d, J = 6.0 Hz), 7.09-7.20 (3H, m), 7.81 (1H, d, J = 8.0 Hz), 7.87 (1H, s), 8.29 (1H, dd, J = 4.8, 1.5 Hz), 12.14 (1H, s); LRMS (ESI): m/z [M + H]$^+$ 351. |
| EX.266 | 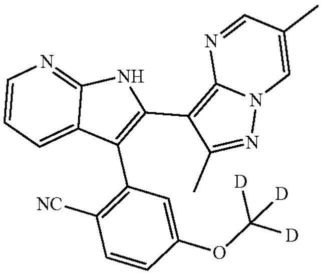 [SMILES: [2H]C([2H])([2H])Oc1ccc(C#N)c(-c2c(-c3c(C)nn4cc(C)cnc34)[nH]c3ncccc23)c1] | $^1$H (400 MHz, DMSO-$d_6$): δ 2.10 (3H, s), 2.30 (3H, s), 6.95 (1H, d, J = 2.3 Hz), 6.98 (1H, dd, J = 8.5, 2.6 Hz), 7.17 (1H, dd, J = 7.9, 4.7 Hz), 7.70 (1H, d, J = 8.5 Hz), 7.89 (1H, dd, J = 7.9, 1.4 Hz), 8.31 (1H, dd, J = 4.7, 1.5 Hz), 8.36 (1H, d, J = 2.1 Hz), 8.90 (1H, dd, J = 2.1, 1.1 Hz), 12.17 (1H, s); LRMS (ESI): m/z [M + H]$^+$ 398. |
| EX.267 | 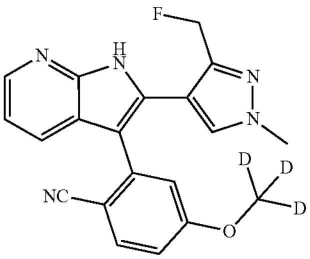 [SMILES: [2H]C([2H])([2H])Oc1ccc(C#N)c(-c2c(-c3cn(C)nc3CF)[nH]c3ncccc23)c1] | $^1$H (400 MHz, DMSO-$d_6$): δ 3.88 (3H, d, J = 1.5 Hz), 5.00 (2H, d, JH-F = 48.6 Hz), 6.93 (1H, d, J = 2.6 Hz), 7.07 (1H, dd, J = 8.7, 2.6 Hz), 7.15 (1H, dd, J = 7.9, 4.7 Hz), 7.76-7.84 (2H, m), 7.86 (1H, s), 8.30 (1H, dd, J = 4.7, 1.6 Hz), 12.15 (1H, s); LRMS (ESI): m/z [M + H]$^+$ 365. |

-continued

| Example No. | Chemical structural formula | Spectrum data |
|---|---|---|
| EX.268 | 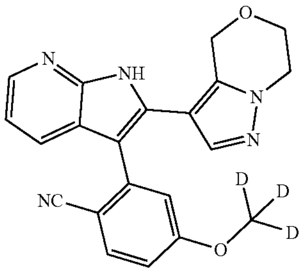 [SMILES: [2H]C([2H])([2H])Oc1ccc(C#N)c(-c2c(-c3cnn4c3COCC4)[nH]c3ncccc23)c1] | $^{1}H$ (400 MHz, DMSO-$d_6$): δ 3.96 (2H, t, J = 5.2 Hz), 4.13 (2H, t, J = 5.1 Hz), 4.32 (2H, d, J = 2.9 Hz), 7.06 (1H, d, J = 2.5 Hz), 7.08-7.15 (2H, m), 7.47 (1H, s), 7.77 (1H, dd, J = 7.9, 1.3 Hz), 7.82 (1H, d, J = 8.7 Hz), 8.28 (1H, dd, J = 4.7, 1.5 Hz), 12.16 (1H, s); LRMS (ESI): m/z $[M + H]^+$ 375. |
| EX.269 | 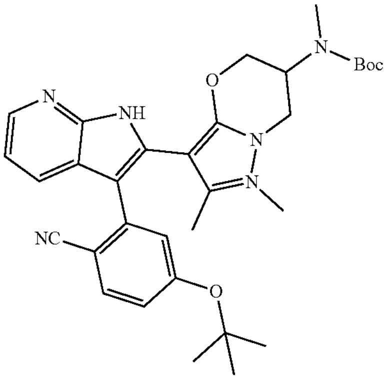 | $^{1}H$ (400 MHz, DMSO-$d_6$): δ 4.08 (3H, s), 7.06 (1H, dd, J = 8.7, 2.6 Hz), 7.16 (1H, dd, J = 2.6, 0.3 Hz), 7.20 (1H, dd, J = 7.9, 4.7 Hz), 7.48 (1H, dd, J = 8.6, 4.3 Hz), 7.78 (1H, dd, J = 8.7, 0.3 Hz), 7.88 (1H, ddd, J = 8.0, 1.7, 0.8 Hz), 8.24 (1H, dd, J = 8.6, 1.3 Hz), 8.37 (1H, dd, J = 4.7, 1.6 Hz), 8.55 (1H, dd, J = 4.3, 1.3 Hz), 12.21 (1H, s); LRMS (ESI): m/z $[M + H]^+$ 384.+PS |

The following compounds were synthesized in accordance with the general procedures 2 (step 2-1), 1 (step 1-3), and 5 (step 5-1, step 5-2, and step 5-3).

| Example No. | Chemical structural formula | Spectrum data |
|---|---|---|
| EX.270 | 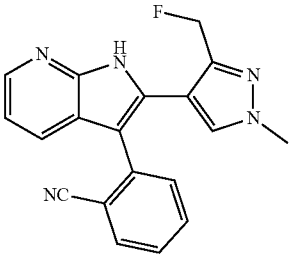 [SMILES: Cn1cc(-c2[nH]c3ncccc3c2-c2ccccc2C#N)c(CF)n1] | $^{1}H$ (400 MHz, DMSO-$d_6$) δ 3.87 (3H, d, J = 1.5 Hz), 4.95 (2H, dd, J = 48.7, 1.8 Hz), 7.15 (1H, dd, J = 7.9, 4.7 Hz), 7.42 (1H, ddd, J = 7.8, 1.2, 0.6 Hz), 7.52 (1H, td, J = 7.7, 1.2 Hz), 7.70 (1H, td, J = 7.7, 1.4 Hz), 7.76 (1H, ddd, J = 7.9, 1.5, 0.6 Hz), 7.86 (1H, s), 7.91 (1H, ddd, J = 7.8, 1.4, 0.5 Hz), 8.30 (1H, dd, J = 4.7, 1.6 Hz), 12.19 (1H, s); LRMS (ESI): m/z $[M + H]^+$ 332. |
| EX.271 | 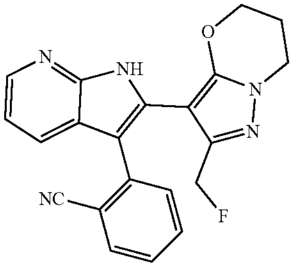 [SMILES: N#Cc1ccccc1-c1c(-c2c(CF)nn3c2OCCC3)[nH]c2ncccc12] | $^{1}H$ (400 MHz, DMSO-$d_6$) δ 1.93-2.29 (2H, m), 3.76-4.34 (4H, m), 4.97 (2H, t, $J_{H-F}$ = 49.9 Hz), 7.13 (1H, dd, J = 7.9, 4.7 Hz), 7.38 (1H, d, J = 7.8 Hz), 7.48 (1H, td, J = 7.7, 1.2 Hz), 7.69 (1H, td, J = 7.7, 1.4 Hz), 7.79 (1H, dd, J = 7.9, 1.0 Hz), 7.87 (1H, dd, J = 7.8, 1.0 Hz), 8.28 (1H, dd, J = 4.7, 1.5 Hz), 12.03 (1H, s); LRMS (ESI): m/z $[M + H]^+$ 374. |

The following compounds were synthesized in accordance with the general procedures 3 (steps 3-1, 3-2), and 5 (steps 5-2, 5-3).

| Example No. | Chemical structural formula | Spectrum data |
| --- | --- | --- |
| EX.272 | 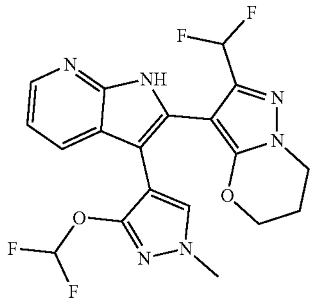 [SMILES: Cn1cc(-c2c(-c3c(C(F)F)nn4c3OCCC4)[nH]c3ncccc23)c(OC(F)F)n1] | $^1$HNMR (400 MHz, $CD_3OD$): δ 2.28-2.34 (2H, m), 3.81 (3H, s), 4.22 (2H, apparent t, J = 6.2 Hz), 4.30-4.33 (2H, m), 6.44 (1H, t, $J_{H-F}$ = 54.1 Hz), 6.82 (1H, t, $J_{H-F}$ = 74.0 Hz), 7.15 (1H, dd, J = 7.9, 4.8 Hz), 7.52 (1H, s), 7.97 (1H, dd, J = 7.9, 1.5 Hz), 8.21 (1H, dd, J = 4.8, 1.5 Hz); LRMS (ESI): m/z [M + H]$^+$ 437. |

(7) Experimental Procedure of EX.273

EX.273 was prepared in accordance with general procedure 6 using the method described below in detail.

Synthesis of 3-(2-fluoro-5-methoxyphenyl)-2-(3-methoxy-1-methyl-1H-pyrazol-4-yl)-1H-pyrrolo[2,3-b]pyridine (EX.273)

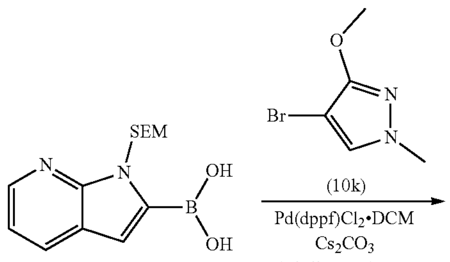

(17b) (10k)

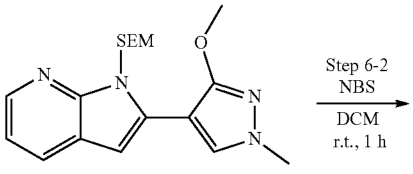

(18b)

-continued

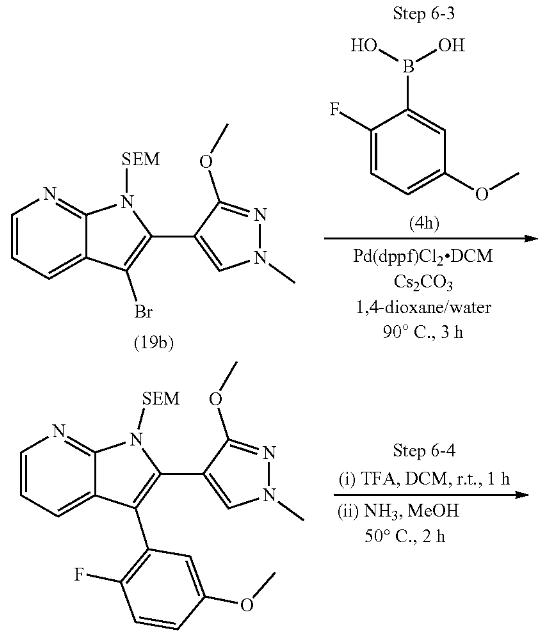

(4h) (19b) (20b)

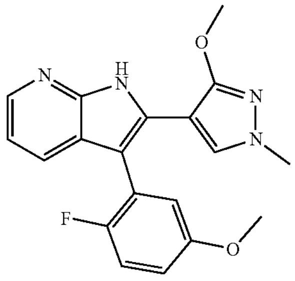

EX.273

Step 6-1

A reaction vessel containing [1-(2-trimethylsilylethoxymethyl)pyrrolo[2,3-b]pyridin-2-yl]boronic acid (17b) (360 mg, 1.23 mmol), 4-bromo-3-methoxy-1-methylpyrazole (10k) (254.2 mg, 1.33 mmol) and $Cs_2CO_3$ (1.20 g, 3.70 mmol) in 1,4-dioxane (2 mL) and water (0.5 mL) was degassed and backfilled with nitrogen three times. After the addition of Pd(dppf)$Cl_2$-DCM (100.6 mg, 0.12 mmol), the mixture was purged with nitrogen three times. The resulting mixture was stirred and heated at 80° C. for 2 h. After cooling to room temperature, the mixture was filtered through Celite, and the filtrate was concentrated. The residue was purified by silica gel column chromatography (0-50% EtOAc/Hexane) to give the expected product as a white solid (50 mg, 11%); LRMS (ESI): m/z $[M+H]^+$ 359.

Step 6-2

A mixture of 2-[2-(3-methoxy-1-methyl-pyrazol-4-yl) pyrrolo[2,3-b]pyridin-1-yl]methoxyethyltrimethylsilane (18b) (142 mg, 0.40 mmol) and NBS (69.6 mg, 0.44 mmol) in DCM (2 mL) was stirred at room temperature for 1 h. After concentration, the residue was purified by silica gel column chromatography (0-40% EtOAc/Hexane) to give the expected product as colorless oil (149 mg, 86%); LRMS (ESI): m/z $[M+H]^+$ 438, 440.

Step 6-3

A reaction vessel containing 2-[3-bromo-2-(3-methoxy-1-methyl-pyrazol-4-yl)pyrrolo[2,3-b]pyridin-1-yl]methoxyethyltrimethylsilane (19b) (50 mg, 0.11 mmol), (2-fluoro-5-methoxy-phenyl)boronic acid (4h) (25.2 mg, 0.15 mmol) and $Cs_2CO_3$ (111.7 mg, 0.34 mmol) in 1,4-dioxane (1 mL) and water (0.3 mL) was degassed and backfilled with nitrogen three times. After the addition of Pd(dppf)$Cl_2$-DCM (18.7 mg, 0.02 mmol), the mixture was purged with nitrogen three times. The resulting mixture was then stirred and heated at 90° C. for 3 h. After cooling to room temperature, the mixture was filtered through Celite, and the filtrate was concentrated. The residue was purified by prep HPLC ($CH_3CN$/0.1% TFA-$H_2O$/0.1% TFA) to give the expected product as a white solid (19 mg, 34%); LRMS (ESI): m/z $[M+H]^+$ 483.

Step 6-4

A mixture of 2-[3-(2-fluoro-5-methoxy-phenyl)-2-(3-methoxy-1-methyl-pyrazol-4-yl)pyrrolo[2,3-b]pyridin-1-yl] methoxyethyltrimethylsilane (20b) (12 mg, 0.02 mmol) and TFA (0.2 mL, 2.58 mmol) in DCM (0.3 mL) was stirred at room temperature for 1 h. After concentration to dryness, the residue was treated with $NH_3$ in methanol (1 mL), and the mixture was stirred at 50° C. for 2 h. After concentration, the residue was purified by prep HPLC ($CH_3CN$/0.1% TFA-$H_2O$/0.1% TFA) to give EX.273 as a white solid (2.2 mg, 25%); LRMS (ESI): m/z $[M+H]^+$ 353.

$^1$H NMR (400 MHz, DMSO-$d_6$): δ 4.21 (3H, s), 4.32 (3H, s), 4.55 (3H, s), 7.55 (1H, dd, J=5.8, 3.2 Hz), 7.56-7.66 (1H, m), 7.76-7.86 (2H, m), 7.96 (1H, dd, J=7.9, 5.8 Hz), 8.71 (1H, d, J=7.8 Hz), 8.77 (1H, d, J=5.8 Hz), 13.24 (NH, br s); LRMS (ESI): m/z $[M+H]^+$ 353.

The following compounds were synthesized using conditions analogous to EX.273 in accordance with general procedure 6.

| Example No. | Chemical structural formula | Spectrum data |
|---|---|---|
| EX. 274 | 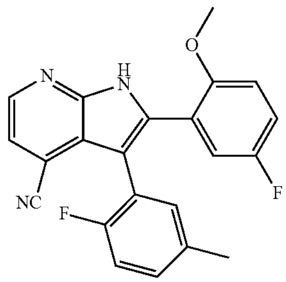 [SMILES: COc1ccc(F)cc1-c1[nH]c2nccc(C#N)c2c1-c1cc(C)ccc1F] | $^1$H NMR (400 MHz, DMSO-$d_6$): δ 2.20 (3H, s), 3.52 (3H, s), 6.99 (1H, dd, J = 7.3, 1.9 Hz), 7.04-7.20 (4H, m), 7.25 (1H, td, J = 8.7, 3.2 Hz), 7.58 (1H, d, J = 4.9 Hz), 8.45 (1H, d, J = 4.9 Hz), 12.79 (NH, br s); LRMS (ESI): m/z $[M + H]^+$ 376. |
| EX. 275 | 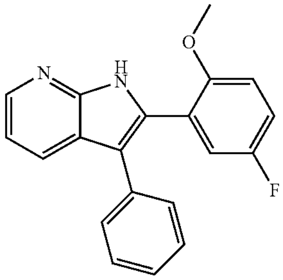 | $^1$H NMR (400 MHz, DMSO-$d_6$): δ 3.54 (3H, s), 7.00-7.11 (2H, m), 7.19-7.40 (6H, m), 7.58 (1H, dd, J = 4.9 Hz), 8.45 (1H, dd, J = 4.9 Hz), 12.69 (NH, br s); LRMS (ESI): m/z $[M + H]^+$ 344. |
| EX. 276 | 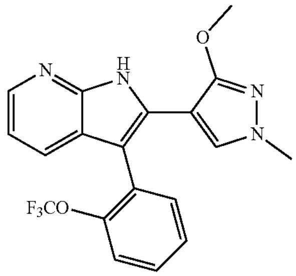 [SMILES: COc1nn(C)cc1-c1[nH]c2ncccc2c1-c1ccccc1OC(F)(F)F] | $^1$H NMR (400 MHz, Acetone-$d_6$): δ 3.72 (3H, s), 3.99 (3H, s), 7.25 (1H, s), 7.39-7.46 (1H, m), 7.49-7.70 (4H, m), 8.04 (1H, dd, J = 7.8, 2.4 Hz), 8.38 (1H, d, J = 5.5 Hz), 12.60 (NH, br s); LRMS (ESI): m/z $[M + H]^+$ 389. |

-continued

| Example No. | Chemical structural formula | Spectrum data |
|---|---|---|
| EX. 277 | 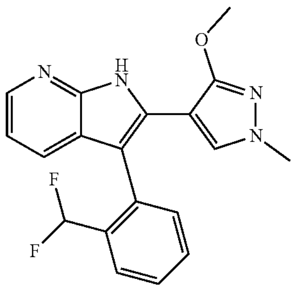 [SMILES: COc1nn(C)cc1-c1[nH]c2ncccc2c1-c1ccccc1C(F)F] | $^1$H NMR (400 MHz, Acetone-$d_6$): δ 3.65 (3H, s), 3.99 (3H, s), 6.63 (1H, t, J = 55.0 Hz), 6.92 (1H, s), 7.43-7.50 (2H, m), 7.67-7.78 (2H, m), 7.84-7.92 (1H, m), 7.96 (1H, d, J = 7.8 Hz), 8.38 (1H, d, J = 4.6 Hz), 12.82 (NH, br s); LRMS (ESI): m/z $[M + H]^+$ 355. |
| EX. 278 | 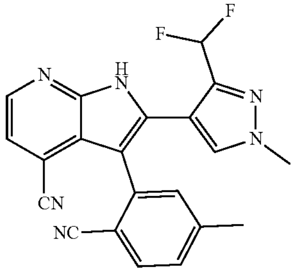 [SMILES: Cc1ccc(C#N)c(-c2c(-c3cn(C)nc3C(F)F)[nH]c3nccc(C#N)c23)c1] | $^1$H NMR (400 MHz, $CD_3OD$): δ 2.45 (3H, s), 3.93 (3H, s), 6.57 (1H, t, $J_{H-F}$ = 54.2 Hz), 7.37-7.42 (2H, m), 7.50 (1H, d, J = 4.9 Hz), 7.70 (1H, d, J = 8.0 Hz), 7.75 (1H, s), 8.46 (1H, d, J = 4.9 Hz); LRMS (ESI): m/z $[M + H]^+$ 389. |
| EX. 279 | 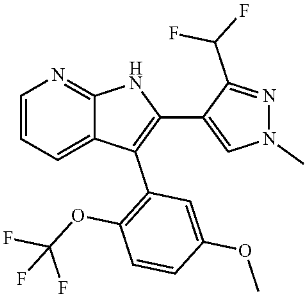 [SMILES: COc1ccc(OC(F)(F)F)c(-c2c(-c3cn(C)nc3C(F)F)[nH]c3ncccc23)c1] | $^1$H NMR (400 MHz, DMSO-$d_6$): δ 3.73 (3H, s), 3.91 (3H, s), 6.73 (1H, t, $J_{H-F}$ = 54.0 Hz), 6.89 (1H, d, J = 3.1 Hz), 6.99 (1H, dd, J = 9.0, 3.2 Hz), 7.13 (1H, dd, J = 7.9, 4.7 Hz), 7.34 (1H, dd, J = 9.0, 1.3 Hz), 7.75 (1H, dd, J = 7.9, 1.2 Hz), 7.80 (1H, s), 8.29 (1H, dd, J = 4.7, 1.6 Hz), 12.04 (1H, br s); LRMS (ESI): m/z $[M + H]^+$ 439. |
| EX. 280 | 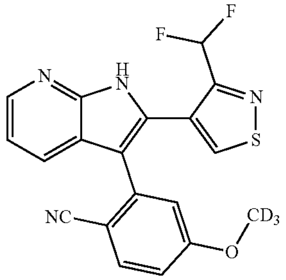 [SMILES: [2H]C([2H])([2H])Oc1ccc(C#N)c(-c2c(-c3csnc3C(F)F)[nH]c3ncccc23)c1] | $^1$H NMR (400 MHz, DMSO-$d_6$): δ 6.67-6.95 (2H, m), 7.06 (1H, dd, J = 8.7, 2.5 Hz), 7.21 (1H, dd, J = 7.9, 4.6 Hz), 7.80 (1H, d, J = 8.7 Hz), 7.90 (1H, d, J = 7.9 Hz), 8.38 (1H, d, J = 3.3 Hz), 9.26 (1H, s), 12.47 (1H, br s); LRMS (ESI): m/z $[M + H]^+$ 386. |
| EX. 281 | 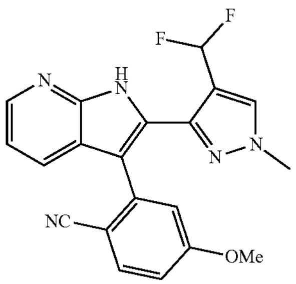 [SMILES: COc1ccc(C#N)c(-c2c(-c3nn(C)cc3C(F)F)[nH]c3ncccc23)c1] | $^1$H NMR (400 MHz, DMSO-$d_6$): δ 3.79 (3H, s), 3.91 (3H, s), 6.48 (1H, t, $J_{H-F}$ = 55.8 Hz), 6.92 (1H, d, J = 2.6 Hz), 7.07 (1H, dd, J = 8.7, 2.6 Hz), 7.19 (1H, dd, J = 8.0, 4.7 Hz), 7.82 (1H, d, J = 8.7 Hz), 7.87 (1H, dd, J = 8.0, 1.5 Hz), 8.17 (1H, s), 8.36 (1H, dd, J = 4.7, 1.6 Hz ), 12.40 (1H, br s); LRMS (ESI): m/z $[M + H]^+$ 380. |

-continued

| Example No. | Chemical structural formula | Spectrum data |
|---|---|---|
| EX. 282 | 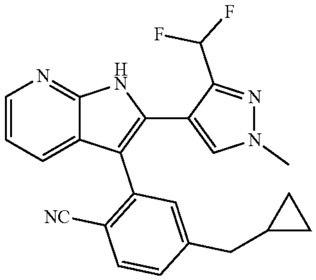 [SMILES: Cn1cc(-c2[nH]c3ncccc3c2-c2cc(CC3CC3)ccc2C#N)c(C(F)F)n1] | $^1$H NMR (400 MHz, $CD_3OD$): δ 0.16-0.18 (2H, m), 0.50-0.52 (2H, m), 0.91-0.99 (1H, m), 2.60-2.64 (2H, m), 3.95 (3H, s), 6.45 (1H, t, $J_{H-F}$ = 54.3 Hz), 7.23 (1H, dd, J = 8.0, 4.8 Hz), 7.39-7.42 (2H, m), 7.73- 7.77 (2H, m), 7.90 (1H, dd, J = 7.9, 1.6 Hz), 8.31 (1H, dd, J = 4.8, 1.5 Hz); LRMS (ESI): m/z [M + H]$^+$ 404. |
| EX. 283 | 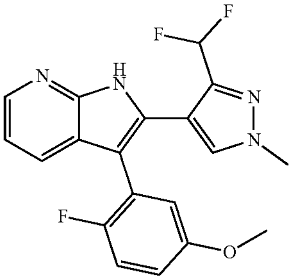 [SMILES: COc1ccc(F)c(-c2c(-c3cn(C)nc3C(F)F)[nH]c3ncccc23)c1] | $^1$H NMR (400 MHz, DMSO-$d_6$): δ 3.67 (3H, s), 3.92 (3H, s), 6.66 (1H, t, $J_{H-F}$ = 53.9 Hz), 6.75-6.81 (1H, m), 6.87-6.94 (1H, m), 7.11-7.23 (2H, m), 7.79 (1H, d, J = 7.4 Hz), 7.96 (1H, s), 8.29 (1H, d, J = 4.7 Hz), 12.09 (1H, s); LRMS (ESI): LRMS (ESI): m/z [M + H]$^+$ 373. |
| EX. 284 | 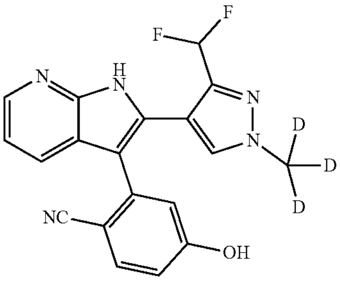 [SMILES: [2H]C([2H])([2H])n1cc(-c2[nH]c3ncccc3c2-c2cc(O)ccc2C#N)c(C(F)F)n1] | $^1$H NMR (400 MHz, DMSO-$d_6$): δ 6.59 (1H, t, $J_{H-F}$ = 54.1 Hz), 6.73 (1H, d, J = 2.4 Hz), 6.86 (1H, dd, J = 8.6, 2.5 Hz), 7.16 (1H, dd, J = 7.9, 4.7 Hz), 7.69 (1H, d, J = 8.6 Hz), 7.77 (1H, dd, J = 7.9, 1.5 Hz), 7.95 (1H, s), 8.31 (1H, dd, J = 4.7, 1.6 Hz), 10.42 (1H, s), 12.17 (1H, s); LRMS (ESI): m/z [M + H]$^+$ 369. |
| EX. 285 | 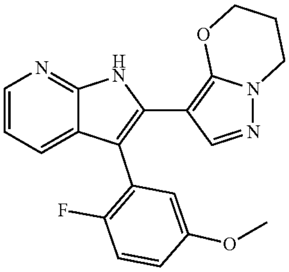 [SMILES: COc1ccc(F)c(-c2c(-c3cnn4c3OCCC4)[nH]c3ncccc23)c1] | $^1$H NMR (400 MHz, DMSO-$d_6$): δ 2.11-2.16 (2H, m), 3.73 (3H, s), 4.09-4.15 (4H, m), 6.89 (1H, dd, J = 6.0, 3.2 Hz), 6.92-6.96 (1H, m), 7.13 (1H, dd, J = 7.9, 4.9 Hz), 7.21 (1H, t, J = 9.3 Hz), 7.37 (1H, s), 7.78 (1H, dt, J = 7.6, 1.4 Hz), 8.23 (1H, dd, J = 4.9, 1.5 Hz), 11.86 (1H, s); LRMS (ESI): m/z [M + H]$^+$ 365. |
| EX. 286 | 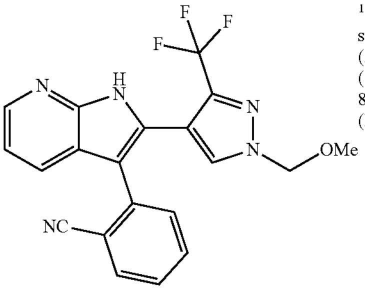 | $^1$H NMR (400 MHz, Acetone-$d_6$): δ 3.33 (3H, s), 5.54 (2H, s), 7.37-7.41 (1H, m), 7.53-7.60 (2H, m), 7.74 (1H, td, J = 7.7, 1.3 Hz), 7.87 (1H, d, J = 7.8 Hz), 8.13 (1H, d, J = 8.0 Hz), 8.23 (1H, s), 8.50 (1H, d, J = 4.9 Hz); LRMS (ESI): m/z [M + H]$^+$ 398. |

-continued

| Example No. | Chemical structural formula | Spectrum data |
|---|---|---|
| EX. 287 | 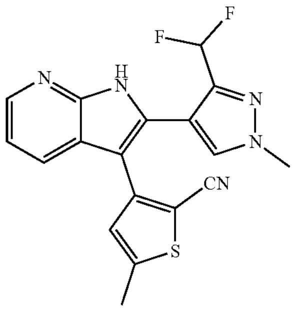 [SMILES: Cc1cc(-c2c(-c3cn(C)nc3C(F)F)[nH]c3ncccc23)c(C#N)s1] | $^1$H NMR (400 MHz, Acetone-$d_6$): δ 2.57 (3H, d, J = 1.1 Hz), 4.00 (3H, s) 6.66 (1H, t, $J_{H\text{-}F}$ = 54.2 Hz), 6.93 (1H, q, J = 1.1 Hz), 7.21 (1H, dd, J = 7.9, 4.7 Hz), 7.94 (1H, s), 7.99 (1H, dd, J = 7.9, 1.6 Hz), 8.33 (1H, dd, J = 4.7, 1.6 Hz), 11.9 (0.4 H, br s); LRMS (ESI): m/z $[M + H]^+$ 370. |
| EX. 288 | 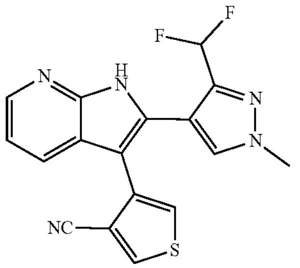 [SMILES: Cn1cc(-c2[nH]c3ncccc3c2-c2cscc2C#N)c(C(F)F)n1] | $^1$H NMR (400 MHz, DMSO-$d_6$): δ 3.93 (3H, s), 6.61 (1H, t, $J_{H\text{-}F}$ = 54.1 Hz), 7.16 (1H, dd, J = 7.9, 4.7 Hz), 7.59 (1H, d, J = 3.1 Hz), 7.84 (1H, dd, J = 7.9, 1.6 Hz), 8.01 (1H, s), 8.31 (1H, dd, J = 4.7, 1.6 Hz), 8.64 (1H, d, J = 3.1 Hz), 12.16 (1H, s); LRMS (ESI): m/z $[M + H]^+$ 356. |
| EX. 289 | 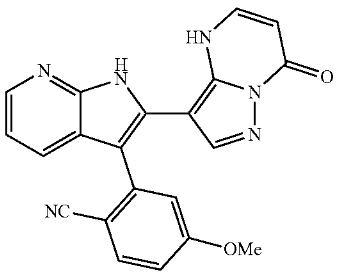 [SMILES: COc1ccc(C#N)c(-c2c(-c3cnn4c(=O)cc[nH]c34)[nH]c3ncccc23)c1] | $^1$H NMR (400 MHz, Acetone-$d_6$): δ 2.10 (3H, s), 6.15 (1H, d, J = 8.3 Hz), 7.12 (1H, dd, J = 8.0, 2.6 Hz), 7.16 (1H, dd, J = 8.0, 4.7 Hz), 7.23 (1H, d, 2.6 Hz), 7.64 (1H, s), 7.77 (1H, d, J = 8.7 Hz), 7.86 (1H, dd, J = 7.8, 1.5 Hz), 8.31 (1H, dd, J = 4.7, 1.6 Hz), 8.44 (1H, d, J = 8.3 Hz); LRMS (ESI): m/z $[M + H]^+$ 383. |
| EX. 290 | 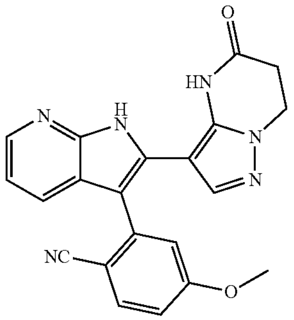 [SMILES: COc1ccc(C#N)c(-c2c(-c3cnn4c3NC(=O)CC4)[nH]c3ncccc23)c1] | $^1$H NMR (400 MHz, $CD_3OD$): δ 2.79-2.90 (2H, m), 3.89 (3H, s), 4.34 (2H, t, J = 6.7 Hz), 7.04 (1H, dd, J = 8.7, 2.6 Hz), 7.16 (1H, d, J = 2.6 Hz), 7.19 (1H, dd, J = 7.9, 4.8 Hz), 7.26 (1H, s), 7.69 (1H, d, J = 8.7 Hz), 7.90 (1H, dd, J = 7.9, 1.5 Hz), 8.26 (1H, dd, J = 4.8, 1.5 Hz); LRMS (ESI): m/z $[M + H]^+$ 385. |
| EX. 291 | 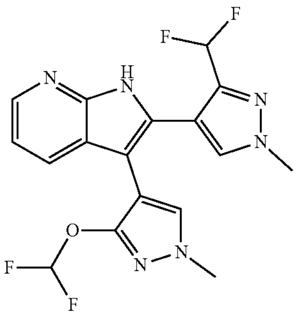 [SMILES: Cn1cc(-c2c(-c3cn(C)nc3C(F)F)[nH]c3ncccc23)c(OC(F)F)n1] | $^1$H NMR (400 MHz, $CD_3OD$): δ 3.81 (3H, s), 3.96 (3H, s), 6.59 (1H, t, $J_{H\text{-}F}$ = 54.5 Hz), 6.86 (1H, t, J = 73.8 Hz), 7.16 (1H, dd, J = 7.9, 4.8 Hz), 7.50 (1H, s), 7.81 (1H, s), 7.94 (1H, dd, J = 7.9, 1.5 Hz), 8.23 (1H, dd, J = 4.8, 1.5 Hz); LRMS (ESI): m/z $[M + H]^+$ 395. |

-continued

| Example No. | Chemical structural formula | Spectrum data |
|---|---|---|
| EX. 292 | 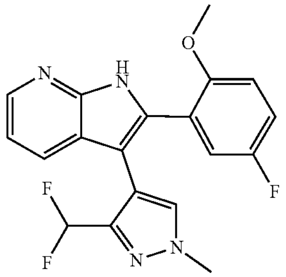 [SMILES: COc1ccc(F)cc1-c1[nH]c2ncccc2c1-c1cn(C)nc1C(F)F] | $^{1}$H NMR (400 MHz, DMSO-$d_6$): δ 3.63 (3H, s), 3.89 (3H, s), 6.51 (1H, t, $J_{H\text{-}F}$ = 53.9 Hz), 7.03 (1H, dd, J = 9.1, 3.2 Hz), 7.08 (1H, dd, J = 4.7, 1.3 Hz), 7.10 (1H, d, J = 4.7 Hz), 7.20 (1H, ddd, J = 9.0, 8.3, 3.2 Hz), 7.70-7.73 (1H, m), 7.73 (1H, s), 8.26 (1H, dd, J = 4.7, 1.6 Hz), 11.94 (1H, s); LRMS (ESI): m/z $[M + H]^+$ 373. |
| EX. 293 | 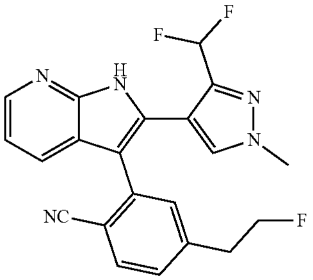 [SMILES: Cn1cc(-c2[nH]c3ncccc3c2-c2cc(CCF)ccc2C#N)c(C(F)F)n1] | $^{1}$H NMR (400 MHz, $CD_3OD$): δ 3.03 (1H, t, J = 5.9 Hz), 3.09 (1H, t, J = 6.0 Hz), 3.92 (3H, s), 4.55 (1H, t, J = 6.0 Hz), 4.67 (1H, t, J = 6.0 Hz), 6.46 (1H, t, $J_{H\text{-}F}$ = 54.2 Hz), 7.21 (1H, dd, J = 7.9, 4.8 Hz), 7.40 (1H, s), 7.42 (1H, dd, J = 7.8, 1.8 Hz), 7.73 (1H, s), 7.74 (1H, d, J = 7.9 Hz), 7.88 (1H, dd, J = 7.9, 1.5 Hz), 8.29 (1H, dd, J = 4.8, 1.4 Hz); LRMS (ESI): m/z $[M + H]^+$ 396. |
| EX. 294 | 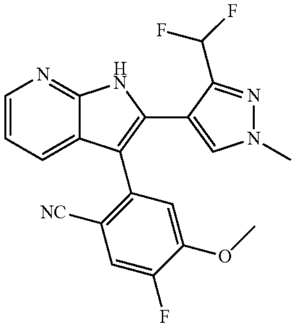 [SMILES: COc1cc(-c2c(-c3cn(C)nc3C(F)F)[nH]c3ncccc23)c(C#N)cc1F] | $^{1}$H NMR (400 MHz, $CD_3OD$): δ 3.85 (3H, s), 3.94 (3H, s), 6.57 (1H, t, $J_{H\text{-}F}$ = 54.1 Hz), 7.13 (1H, d, J = 8.2 Hz), 7.21 (1H, dd, J = 7.9, 4.8 Hz), 7.57 (1H, d, J = 10.9 Hz), 7.77 (1H, s), 7.91 (1H, dd, J = 7.9, 1.5 Hz), 8.30 (1H, dd, J = 4.8, 1.5 Hz); LRMS (ESI): m/z $[M + H]^+$ 398. |
| EX. 295 | 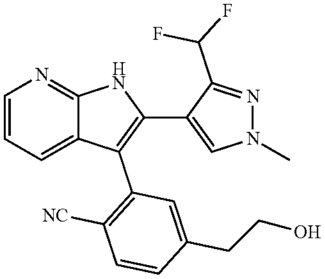 [SMILES: Cn1cc(-c2[nH]c3ncccc3c2-c2cc(CCO)ccc2C#N)c(C(F)F)n1] | $^{1}$H NMR (400 MHz, $CD_3OD$): δ 2.88 (2H, t, J = 6.6 Hz), 3.76 (2H, t, J = 6.6 Hz), 3.93 (3H, s), 6.48 (1H, t, $J_{H\text{-}F}$ = 54.3 Hz), 7.20 (1H, dd, J = 7.9, 4.8 Hz), 7.39 (1H, s), 7.39-7.43 (1H, m), 7.70-7.73 (1H, m), 7.74 (1H, s), 7.89 (1H, dd, J = 7.9, 1.5 Hz), 8.29 (1H, dd, J = 4.8, 1.5 Hz); LRMS (ESI): m/z $[M + H]^+$ 394. |
| EX. 296 | 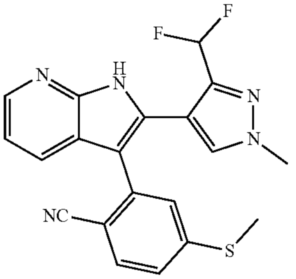 [SMILES: CSc1ccc(C#N)c(-c2c(-c3cn(C)nc3C(F)F)[nH]c3ncccc23)c1] | $^{1}$H NMR (400 MHz, DMSO-$d_6$): δ 2.42 (3H, s), 3.91 (3H, s), 6.65 (1H, t, $J_{H\text{-}F}$ = 53.9 Hz), 7.14-7.18 (1H, m), 7.18 (1H, s), 7.34 (1H, dd, J = 8.3, 1.9 Hz), 7.76 (1H, d, J = 8.3 Hz), 7.81 (1H, dd, J = 7.9, 1.4 Hz), 7.97 (1H, s), 8.32 (1H, dd, J = 4.7, 1.3 Hz), 12.25 (1H, s); LRMS (ESI): m/z $[M + H]^+$ 396. |

-continued

| Example No. | Chemical structural formula | Spectrum data |
|---|---|---|
| EX. 297 | 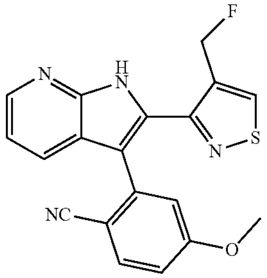 [SMILES: COc1ccc(C#N)c(-c2c(-c3nscc3CF)[nH]c3ncccc23)c1] | $^1$H NMR (400 MHz, CD3OD) δ 3.82 (3H, s), 5.18 (2H, d, J = 47.5 Hz), 6.97 (1H, d, J = 2.5 Hz), 7.05 (1H, dd, J = 8.7, 2.6 Hz), 7.27 (1H, dd, J = 8.0, 4.8 Hz), 7.71 (1H, d, J = 8.7 Hz), 8.03 (1H, dd, J = 8.0, 1.5 Hz), 8.39 (1H, dd, J = 4.8, 1.5 Hz), 9.09 (1H, dd, J = 1.7, 0.7 Hz); LRMS (ESI): m/z [M + H]$^+$ 365. |

(8) Experimental Procedure of EX.298

EX.298 was prepared in accordance with general procedure 7 using the method described below in detail.

Synthesis of 3-(2-fluoro-5-methoxyphenyl)-2-(3-methoxypyridin-2-yl)-1H-pyrrolo[2,3-b]pyridine (EX.298)

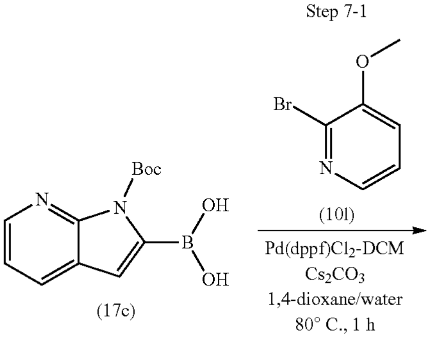

(17c)

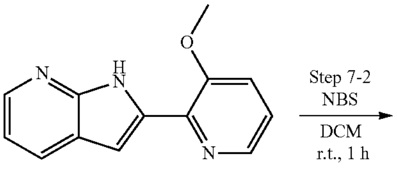

(21a)

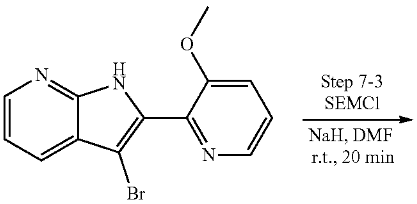

(22a)

-continued

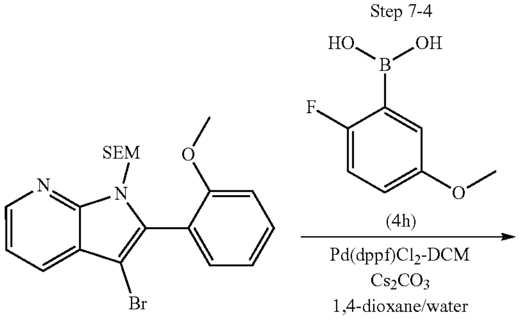

(19c)

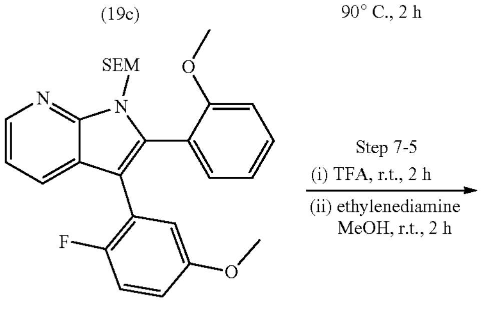

(20c)

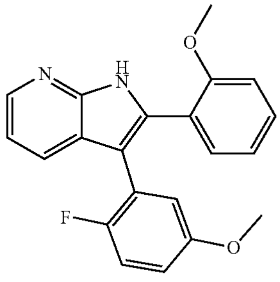

EX.298

Step 7-1

A reaction vessel containing (1-(tert-butoxycarbonyl)-1H-pyrrolo[2,3-b]pyridin-2-yl) boronic acid (17c) (489 mg, 1.86 mmol), 2-bromo-3-methoxypyridine (101) (421 mg, 2.24 mmol) and $Cs_2CO_3$ (1.83 g, 5.60 mmol) in 1,4-dioxane (2 mL) and water (0.7 mL) was degassed and backfilled with nitrogen three times. After the addition of Pd(dppf)$Cl_2$-DCM (152 mg, 0.18 mmol), the mixture was purged with nitrogen three times. The resulting mixture was stirred and heated at 80° C. for 1 h. After cooling to room temperature, the mixture was filtered through Celite, and the filtrate was concentrated. The residue was purified by silica gel column chromatography (0-100% EtOAc/Hexane) to give the expected product as a tan solid (308 mg, 67%); LRMS (ESI): m/z $[M+H]^+$ 226.

Step 7-2

A mixture of 2-(3-methoxypyridin-2-yl)-1H-pyrrolo[2,3-b]pyridine (21a) (306 mg, 1.36 mmol) and NBS (242 mg, 1.36 mmol) in DCM (5 mL) was stirred at room temperature for 1 h. After concentration, the residue was purified by silica gel column chromatography (0-100% EtOAc/Hexane) to give the expected product as a light brown solid (378 mg, 87%); LRMS (ESI): m/z $[M+H]^+$ 304, 306.

Step 7-3

To a solution of 3-bromo-2-(3-methoxy-2-pyridyl)-1H-pyrrolo[2,3-b]pyridine (22a) (378 mg, 1.24 mmol) in DMF (5 mL) was added NaH, 60% dispersion in mineral oil (32.8 mg, 1.37 mmol) at room temperature and the mixture was stirred at room temperature for 10 min. To this, SEMCl (0.16 mL, 1.86 mmol) was added dropwise, and the mixture was stirred at room temperature for 20 min. The mixture was poured into brine and the product was extracted with EtOAc (×2). The combined organic extracts were dried over $Na_2SO_4$ and concentrated. The residue was purified by silica gel column chromatography (0-25% EtOAc/Hexane) to give the expected product as colorless oil (90 mg, 17%); LRMS (ESI): m/z $[M+H]^+$ 434.

Step 7-4

A reaction vessel containing 3-bromo-2-(3-methoxypyridin-2-yl)-1-((2-(trimethylsilyl)ethoxy)methyl)-1H-pyrrolo[2,3-b]pyridine (19c) (90 mg, 0.20 mmol), (2-fluoro-5-methoxy-phenyl)boronic acid (4h) (39 mg, 0.22 mmol) and $Cs_2CO_3$ (195 mg, 0.60 mmol) in 1,4-dioxane (1 mL) and water (0.3 mL) was degassed and backfilled with nitrogen three times. After the addition of $Pd(dppf)Cl_2$-DCM (16 mg, 0.02 mmol), the mixture was purged with nitrogen three times. The resulting mixture was then stirred and heated at 90° C. for 2 h. After cooling to room temperature, the mixture was filtered through Celite, and the filtrate was concentrated. The residue was purified by silica gel column chromatography (0-50% EtOAc/Hexane) to give the expected product as colorless oil (3 mg, 1.5%); LRMS (ESI): m/z $[M+H]^+$ 480.

Step 7-5

A mixture of 2-[[3-(2-fluoro-5-methoxy-phenyl)-2-(3-methoxy-2-pyridyl)pyrrolo[2,3-b]pyridin-1-yl]methoxy]ethyl-trimethyl-silane (20c) (3 mg, 0.01 mmol) and neat TFA (0.25 mL, 3.30 mmol) was stirred at room temperature for 2 h. After concentration to dryness, the residue was dissolved in MeOH (0.25 mL). To this, ethylenediamine (0.22 mL, 3.30 mmol) was added at room temperature and the mixture was stirred at room temperature for 2 h. The mixture was purified by prep HPLC ($CH_3CN$/0.1% TFA-$H_2O$/0.1% TFA) to give EX.298 as a white solid (1.3 mg, 56%).

$^1H$ NMR (400 MHz, DMSO-$d_6$) δ 3.49 (3H, s), 3.64 (3H, s), 6.74 (1H, dd, J=6.0, 3.2 Hz), 6.82-6.86 (1H, m), 7.07-7.20 (2H, m), 7.41 (1H, dd, J=8.4, 4.8 Hz), 7.50 (1H, d, J=8.4 Hz), 7.87 (1H, d, J=8.3 Hz), 8.22 (1H, d, J=4.7 Hz), 8.32 (1H, dd, J=4.7, 1.2), 12.20 (NH, br s); LRMS (ESI): m/z $[M+H]^+$ 350.

The following compounds were synthesized using the appropriate starting materials and reaction conditions analogous to EX.298, in accordance with general procedure 7.

| Example No. | Chemical structural formula | Spectrum data |
|---|---|---|
| EX.299 | 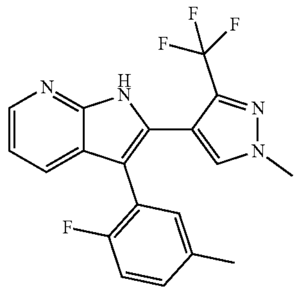 [SMILES: Cc1ccc(F)c(-c2c(-c3cn(C)nc3C(F)(F)F)[nH]c3ncccc23)c1] | $^1H$ NMR (400 MHz, DMSO-$d_6$) δ 2.25 (3H, s), 3.97 (3H, s), 7.05-7.19 (4H, m), 7.78 (1H, d, J = 7.6 Hz), 8.08 (1H, s), 8.30 (1H, dd, J = 4.7, 1.6 Hz), 12.12 (NH, s); LRMS (ESI): m/z $[M + H]^+$ 375. |
| EX.300 | 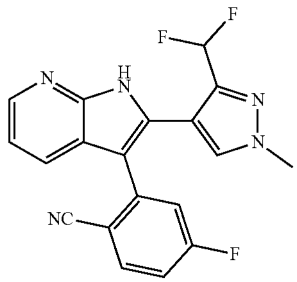 [SMILES: Cn1cc(-c2[nH]c3ncccc3c2-c2cc(F)ccc2C#N)c(C(F)F)n1] | $^1H$ (400 MHz, DMSO-$d_6$): δ 3.93 (3H, s), 6.65 (1H, t, $J_{H\text{-}F}$ = 53.9 Hz), 7.17 (1H, dd, J = 7.9, 4.7 Hz), 7.27 (1H, dd, J = 9.6, 2.6 Hz), 7.40 (1H, td, J = 8.6, 2.7 Hz), 7.83 (1H, dd, J = 7.9, 1.1 Hz), 7.98 (1H, dd, J = 8.7, 5.8 Hz), 8.01 (1H, s), 8.33 (1H, dd, J = 4.7, 1.6 Hz), 12.30 (1H, s); LRMS (ESI): m/z $[M + H]^+$ 368. |

(9) Experimental Procedure of EX.301

EX.301 was prepared in accordance with the general procedure 8 and procedure 6 using the method described below in detail.

Synthesis of 3-(cyclohex-1-en-1-yl)-2-(5-fluoro-2-methoxyphenyl)-1H-pyrrolo[2,3-b]pyridine (EX.301)

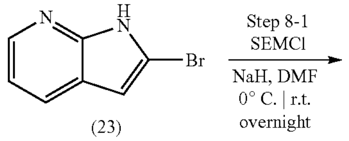

(23)

Step 8-2

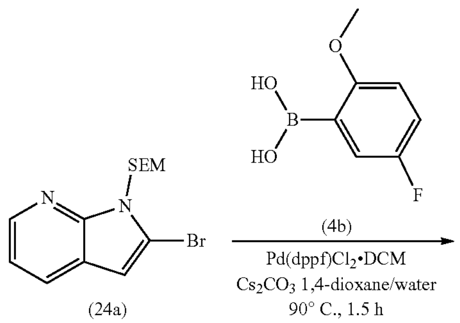

(4b)

(24a)

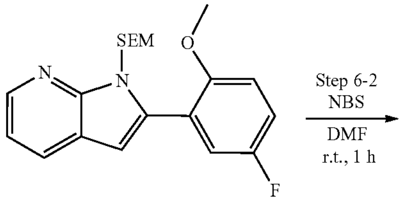

(18d)

Step 6-3

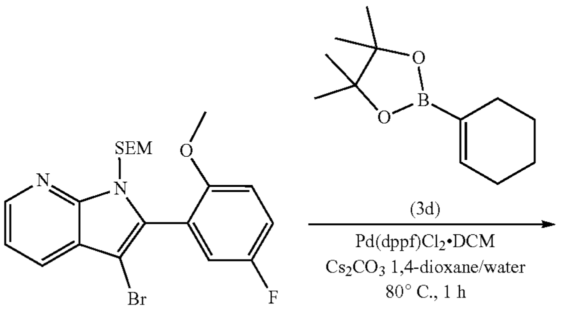

(3d)

(19d)

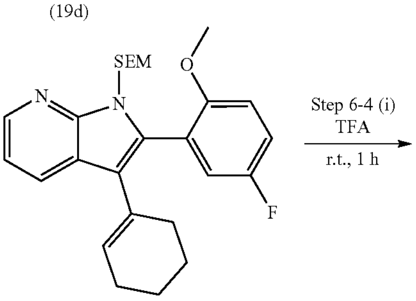

(20d)

-continued

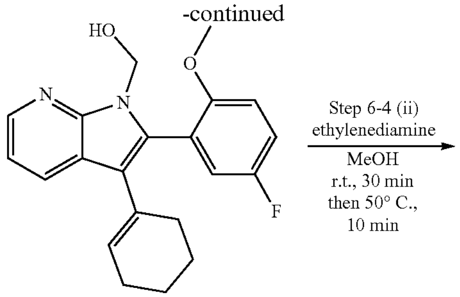

(25)

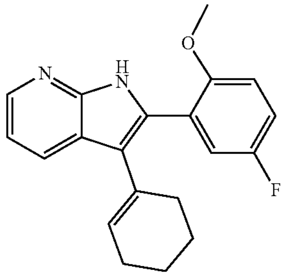

EX.301

Step 8-1

To a suspension of NaH, 60% dispersion in mineral oil (609 mg, 15.23 mmol) in DMF (16 mL) was added 2-bromo-1H-pyrrolo[2,3-b]pyridine (23) (2.0 g, 15.23 mmol) at 0° C. and the mixture was stirred for 20 min. To this, SEMCl (2.34 mL, 13.20 mmol) was added dropwise, and the mixture was stirred at room temperature overnight. The mixture was poured into brine and the product was extracted with EtOAc (×2). The combined organic extracts were dried over $Na_2SO_4$ and concentrated. The residue was purified by silica gel column chromatography (0-15% EtOAc/Hexane) to give the expected product as colorless oil (2.58 g, 78%); LRMS (ESI): m/z $[M+H]^+$ 327, 329.

Step 8-2

A reaction vessel containing 2-[(2-bromopyrrolo[2,3-b]pyridin-1-yl)methoxy]ethyl-trimethyl-silane (24a) (1.35 g, 4.12 mmol), (5-fluoro-2-mehoxyphenyl)boronic acid (4b) (911.3 mg, 5.36 mmol) and $Cs_2CO_3$ (4.03 g, 12.37 mmol) in 1,4-dioxane (9 mL) and water (4 mL) was degassed and backfilled with nitrogen three times. After the addition of $Pd(dppf)Cl_2$-DCM (673.7 mg, 0.82 mmol), the mixture was purged with nitrogen three times. The resulting mixture was stirred and heated at 90° C. for 1.5 h. After cooling to room temperature, the mixture was filtered through Celite, and the filtrate was concentrated. The residue was purified by silica gel column chromatography (0-30% EtOAc/Hexane) to give the expected product as colorless oil (2.77 g, 67%); LRMS (ESI): m/z $[M+H]^+$ 373.

Step 6-2

To a solution of 2-[[2-(5-fluoro-2-methoxyphenyl)pyrrolo[2,3-b]pyridin-1-yl]methoxy]ethyl-trimethyl-silane (18d) (1.03 g, 2.77 mmol) in DMF (7 mL) was added NBS (541.4 mg, 3.04 mmol) at room temperature and the mixture was stirred at room temperature for 1 h. The mixture was then diluted with EtOAc and washed with sat. aq. $NaHCO_3$ (×2). The organic layer was dried over $Na_2SO_4$ and concentrated. The residue was purified by silica gel column chromatography (0-30% EtOAc/Hexane) to give the expected product as red oil (1.13 g, 91%); LRMS (ESI): m/z $[M+H]^+$ 451, 453.

Step 6-3

A reaction vessel containing 2-[[3-bromo-2-(5-fluoro-2-methoxy-phenyl)pyrrolo[2,3-b]pyridin-1-yl]methoxy]ethyl-trimethyl-silane (19d) (20.0 mg, 0.04 mmol), 2-(cyclo-hexen-1-yl)-4,4,5,5-tetramethyl-1,3,2-dioxaborolane (3d) (11.1 mg, 0.05 mmol) and $Cs_2CO_3$ (43.3 mg, 0.13 mmol) in 1,4-dioxane (0.5 mL) and water (0.1 mL) was degassed and backfilled with nitrogen three times. After the addition of $Pd(dppf)Cl_2$-DCM (3.6 mg, 4.40 μmol), the mixture was purged with nitrogen three times. The resulting mixture was then stirred and heated at 80° C. for 1 h. After cooling to room temperature, the mixture was filtered through Celite, and the filtrate was concentrated. The residue was purified by silica gel column chromatography (0-15% EtOAc/Hexane) to give the expected product as yellow oil (16.7 mg, 83%); LRMS (ESI): m/z $[M+H]^+$ 453.

Step 6-4 (i)

A mixture of 2-[[3-(cyclohexen-1-yl)-2-(5-fluoro-2-methoxy-phenyl)pyrrolo[2,3-b]pyridin-1-yl]methoxy]ethyl-trimethyl-silane (20d) (16.7 mg, 0.04 mmol) and neat TFA (0.28 mL, 3.69 mmol) was stirred at room temperature for 1 h. After concentration to dryness, the residue was used for the next reaction without further purification; LRMS (ESI): m/z $[M+H]^+$ 353.

Step 6-4 (ii)

To a solution of (3-(cyclohex-1-en-1-yl)-2-(5-fluoro-2-methoxyphenyl)-1H-pyrrolo[2,3-b]pyridin-1-yl)methanol (25) in MeOH (0.5 mL) was added ethylenediamine (0.25 mL, 3.69 mmol) at room temperature and the mixture was stirred at room temperature for 30 min, then 50° C. for 10 min. The mixture was then poured into brine and the product was extracted with DCM (×2). The combined organic extracts were dried over $Na_2SO_4$ and concentrated. The residue was purified by prep HPLC ($CH_3CN$/0.1% TFA-$H_2O$/0.1% TFA) to give EX.301 as an off-white solid (9.2 mg, 73%).

$^1H$ NMR (400 MHz, DMSO-$d_6$): δ 1.60 (4H, br s), 2.08 (4H, br s), 3.76 (3H, s), 5.65 (1H, s), 7.05 (1H, dd, J=7.9, 4.7 Hz), 7.11 (1H, dd, J=9.0, 4.7 Hz), 7.15-7.27 (2H, m), 7.94 (1H, dd, J=7.9, 1.5 Hz), 8.20 (1H, dd, J=4.6, 1.5 Hz), 11.64 (NH, br s); LRMS (ESI): m/z $[M+H]^+$ 323.

The following compound was synthesized using conditions analogous to the compound (25) in accordance with the general procedure 8 and procedure 6.

| Example No. | Chemical structural formula | Spectrum data |
|---|---|---|
| EX.302 | 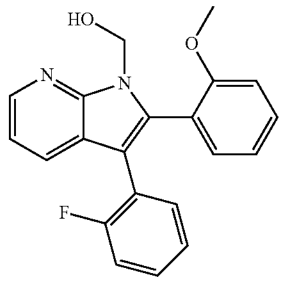 [SMILES: COc1ccccc1-c1c(-c2ccccc2F)c2cccnc2n1CO] | $^1H$ NMR (400 MHz, DMSO-$d_6$): δ 3.61 (3H, s), 5.15 (1H, d, J = 10.7 Hz), 5.84 (1H, d, J = 10.6 Hz), 6.97 (1H, t, J = 7.4 Hz), 7.03-7.14 (3H, m), 7.16-7.33 (4H, m), 7.39-7.47 (1H, m), 7.79 (1H, dt, J = 7.6, 1.5 Hz), 8.33-8.40 (1H, m); LRMS (ESI): m/z $[M + H]^+$ 349. |

The following compounds were synthesized using conditions analogous to EX.301 in accordance with general procedure 8 and procedure 6.

| Example No. | Chemical structural formula | Spectrum data |
|---|---|---|
| EX.303 | 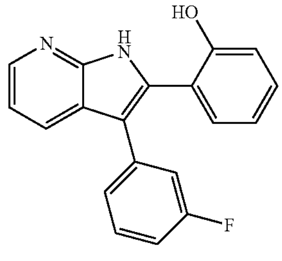 [SMILES: Oc1ccccc1-c1[nH]c2ncccc2c1-c1cccc(F)c1] | $^1H$ NMR (400 MHz, DMSO-$d_6$): δ 6.77 (1H, t, J = 7.4 Hz), 6.92 (1H, d, J = 8.2 Hz), 6.98-7.24 (6H, m), 7.33-7.39 (1H, m), 8.01 (1H, d, J = 8.1 Hz), 8.25 (1H, dd, J = 4.8, 1.1 Hz); LRMS (ESI): m/z $[M + H]^+$ 305. |
| EX.304 | 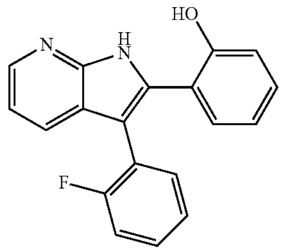 [SMILES: Oc1ccccc1-c1[nH]c2ncccc2c1-c1ccccc1F] | $^1H$ NMR (400 MHz, DMSO-$d_6$): δ 6.72 (1H, t, J = 7.4 Hz), 6.89 (1H, d, J = 8.4 Hz), 7.08-7.33 (7H, m), 7.73 (1H, dt, J = 7.8, 2.0 Hz), 8.25 (1H, dd, J = 4.8, 1.8 Hz); LRMS (ESI): m/z $[M + H]^+$ 305. |

-continued

| Example No. | Chemical structural formula | Spectrum data |
|---|---|---|
| EX.305 | 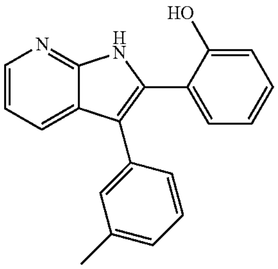 [SMILES: Cc1cccc(-c2c(-c3ccccc3O)[nH]c3ncccc23)c1] | $^1$H NMR (400 MHz, DMSO-$d_6$): δ 2.26 (3H, s), 6.74 (1H, t, J = 7.6 Hz), 6.92 (1H, d, J = 8.0 Hz), 7.00 (1H, d, J = 8.1 Hz), 7.04 (1H, d, J = 7.8 Hz), 7.08-7.22 (5H, m), 7.98 (1H, d, J = 7.3 Hz), 8.23 (1H, d, J = 4.3 Hz); LRMS (ESI): m/z $[M + H]^+$ 301. |
| EX.306 | 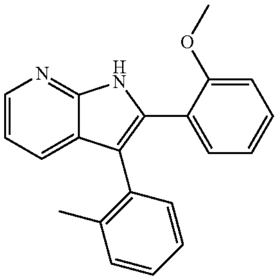 [SMILES: COc1ccccc1-c1[nH]c2ncccc2c1-c1ccccc1C] | $^1$H NMR (400 MHz, DMSO-$d_6$): δ 1.95 (3H, s), 3.60 (3H, s), 6.86 (1H, t, J = 7.5 Hz), 7.02-7.15 (5H, m), 7.15-7.20 (1H, m), 7.20-7.27 (1H, m), 7.28-7.36 (1H, m), 7.66 (1H, d, J = 7.5 Hz), 8.27 (1H, dd, J = 4.9, 1.1 Hz), 12.02 (1H, s); LRMS (ESI): m/z $[M + H]^+$ 315. |
| EX.307 | 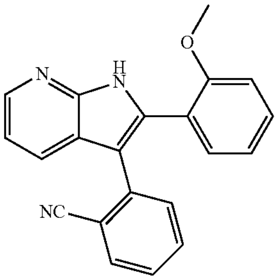 [SMILES: COc1ccccc1-c1[nH]c2ncccc2c1-c1ccccc1C#N] | $^1$H NMR (400 MHz, DMSO-$d_6$): δ 3.45 (3H, s), 6.96 (1H, t, J = 7.5 Hz), 7.02 (1H, d, J = 8.4 Hz), 7.14 (1H, dd, J = 7.9, 4.7 Hz), 7.23 (1H, dd, J = 7.5, 1.7 Hz), 7.32 (1H, d, J = 7.2 Hz), 7.36 (1H, td, J = 8.3, 7.5, 1.6 Hz), 7.46 (1H, td, J = 7.5, 1.1 Hz), 7.64 (1H, td, J = 7.6, 1.2 Hz), 7.79 (1H, dd, J = 7.9, 1.5 Hz), 7.85 (1H, dd, J = 7.8, 1.4 Hz), 8.30 (1H, dd, J = 4.8, 1.6 Hz), 12.21 (1H, s); LRMS (ESI): m/z $[M + H]^+$ 326. |
| EX.308 | 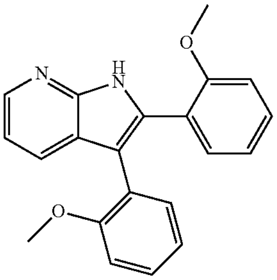 [SMILES: COc1ccccc1-c1[nH]c2ncccc2c1-c1ccccc1OC] | $^1$H NMR (400 MHz, DMSO-$d_6$): δ 3.57 (6H, d, J = 19.0 Hz), 6.86 (2H, dt, J = 11.8, 7.4 Hz), 7.00 (1H, dd, J = 7.5, 1.7 Hz), 7.06 (2H, t, J = 8.4 Hz), 7.10-7.14 (1H, m), 7.14-7.18 (1H, m), 7.25 (1H, td, J = 8.3, 7.5, 1.8 Hz), 7.30-7.39 (1H, m), 7.80 (1H, dd, J = 7.9, 1.5 Hz), 8.27 (1H, dd, J = 4.9, 1.5 Hz), 12.08 (1H, s); LRMS (ESI): m/z $[M + H]^+$ 331. |
| EX.309 | 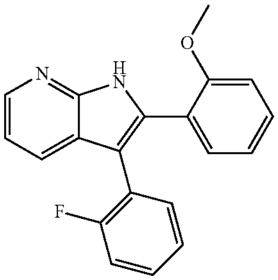 [SMILES: COc1ccccc1-c1[nH]c2ncccc2c1-c1ccccc1F] | $^1$H NMR (400 MHz, DMSO-$d_6$): δ 3.54 (3H, s), 6.94 (1H, td, J = 7.5, 1.1 Hz), 7.06 (1H, d, J = 8.4 Hz), 7.09-7.20 (3H, m), 7.20-7.28 (2H, m), 7.28-7.34 (1H, m), 7.34-7.41 (1H, m), 7.82 (1H, d, J = 7.8 Hz), 8.29 (1H, dd, J = 4.7, 1.5 Hz), 12.15 (1H, s); LRMS (ESI): m/z $[M + H]^+$ 319. |

-continued

| Example No. | Chemical structural formula | Spectrum data |
|---|---|---|
| EX.310 | 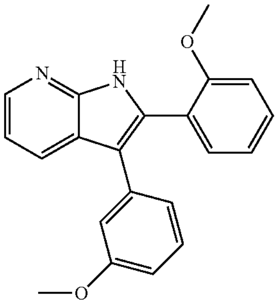 [SMILES: COc1cccc(-c2c(-c3ccccc3OC)[nH]c3ncccc23)c1] | $^1$H NMR (400 MHz, DMSO-$d_6$): δ 3.61 (3H, s), 3.62 (3H, s), 6.76-6.77 (2H, m), 6.86 (1H, d, J = 7.6 Hz), 6.94-6.98 (1H, m), 7.11-7.14 (2H, m), 7.20-7.25 (2H, m), 7.39-7.43 (1H, m), 8.03 (1H, dd, J = 7.9, 1.5 Hz), 8.26 (1H, dd, J = 4.7, 1.5 Hz), 11.92 (1H, s); LRMS (ESI): m/z $[M + H]^+$ 331. |
| EX.311 | 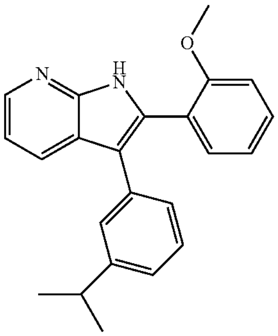 [SMILES: COc1ccccc1-c1[nH]c2ncccc2c1-c1cccc(C(C)C)c1] | $^1$H NMR (400 MHz, DMSO-$d_6$): δ 1.06 (6H, d, J = 6.9 Hz), 2.73-2.78 (1H, m), 3.55 (3H, s), 6.94-6.98 (1H, m), 7.04-7.06 (2H, m), 7.09-7.16 (3H, m), 7.22-7.26 (2H, m), 7.38-7.42 (1H, m), 8.02 (1H, dd, J = 7.9, 1.6 Hz), 8.26 (1H, dd, J = 4.7, 1.6 Hz), 11.90 (1H, s); LRMS (ESI): m/z $[M + H]^+$ 343. |
| EX.312 | 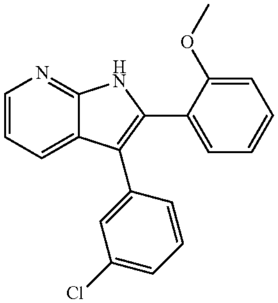 [SMILES: COc1ccccc1-c1[nH]c2ncccc2c1-c1cccc(Cl)c1] | $^1$H NMR (400 MHz, DMSO-$d_6$): δ 3.58 (3H, s), 6.98-7.01 (1H, m), 7.12-7.17 (2H, m), 7.22-7.27 (4H, m), 7.33-7.37 (1H, m), 7.41-7.45 (1H, m), 8.02 (1H, J = 8.0, 1.2 Hz), 8.28 (1H, dd, J = 4.5, 1.3 Hz), 12.05 (1H, s); LRMS (ESI): m/z $[M + H]^+$ 335. |
| EX.313 | 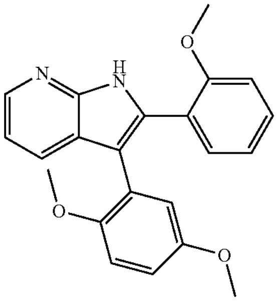 [SMILES: COc1ccc(OC)c(-c2c(-c3ccccc3OC)[nH]c3ncccc23)c1] | $^1$H NMR (400 MHz, DMSO-$d_6$): δ 3.47 (3H, s), 3.55 (3H, s), 3.62 (3H, s), 6.57 (1H, d, J = 3.0 Hz), 6.79 (1H, dd, J = 8.8, 3.2 Hz), 6.88-6.91 (1H, m), 6.95 (1H, d, J = 9.0 Hz), 7.04-7.09 (2H, m), 7.14 (1H, dd, J = 7.6, 1.7 Hz), 7.32-7.36 (1H, m), 7.69 (1H, d, J = 7.7 Hz), 8.22 (1H, dd, J = 4.7, 1.6 Hz), 11.80 (1H, s); LRMS (ESI): m/z $[M + H]^+$ 361. |
| EX.314 | 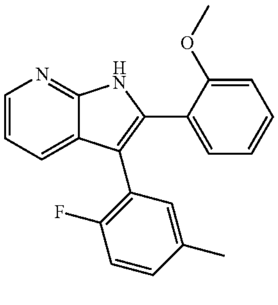 [SMILES: COc1ccccc1-c1[nH]c2ncccc2c1-c1cc(C)ccc1F] | $^1$H NMR (400 MHz, DMSO-$d_6$): δ 2.21 (3H, s), 3.58 (3H, s), 6.91-6.95 (1H, m), 7.02-7.12 (5H, m), 7.20 (1H, dd, J = 7.5, 1.7 Hz), 7.34-7.38 (1H, m), 7.77 (1H, d, J = 7.8 Hz), 8.26 (1H, dd, J = 4.7, 1.5 Hz), 11.99 (1H, s); LRMS (ESI): m/z $[M + H]^+$ 333. |

-continued

| Example No. | Chemical structural formula | Spectrum data |
|---|---|---|
| EX.315 | 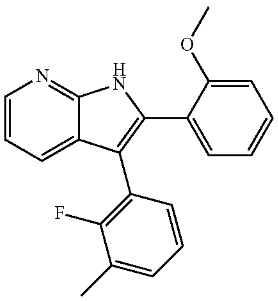 [SMILES: COc1ccccc1-c1[nH]c2ncccc2c1-c1cccc(C)c1F] | $^1$H NMR (400 MHz, DMSO-d6): δ 2.25 (3H, s), 3.56 (3H, s), 6.91-7.00 (3H, m), 7.06-7.12 (2H, m), 7.15-7.21 (2H, m), 7.34-7.38 (1H, m), 7.75 (1H, d, J = 8.1 Hz), 8.26 (1H, dd, J = 4.7, 1.5 Hz), 11.99 (1H, s); LRMS (ESI): m/z $[M + H]^+$ 333. |
| EX.316 | 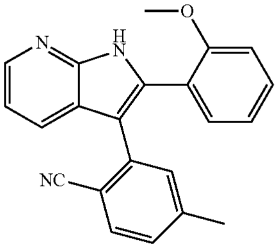 [SMILES: COc1ccccc1-c1[nH]c2ncccc2c1-c1cc(C)ccc1C#N] | $^1$H NMR (400 MHz, DMSO-$d_6$): δ 2.33 (3H, s), 3.49 (3H, s), 6.95 (1H, td, J = 7.5, 0.9 Hz), 7.03 (1H, d, J = 8.4 Hz), 7.15 (1H, dd, J = 7.8, 4.7 Hz), 7.18-7.25 (2H, m), 7.28 (1H, dd, J = 8.0, 1.6 Hz), 7.32-7.41 (1H, m), 7.70 (1H, d, J = 7.9 Hz), 7.81 (1H, dd, J = 7.9, 1.4 Hz), 8.30 (1H, dd, J = 4.6, 1.4 Hz), 12.21 (1H, s); LRMS (ESI): m/z $[M + H]^+$ 340. |
| EX317 | 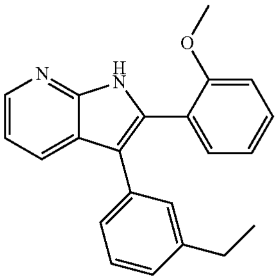 [SMILES: CCc1cccc(-c2c(-c3ccccc3OC)[nH]c3ncccc23)c1] | $^1$H NMR (400 MHz, DMSO-$d_6$): δ 1.07 (3H, t, J = 7.6 Hz), 2.49-2.54 (2H, m), 3.57 (3H, s), 6.95 (1H, td, J = 7.5, 1.0 Hz), 7.03 (1H, d, J = 7.8 Hz), 7.07-7.14 (4H, m), 7.20-7.23 (2H, m), 7.38-7.42 (1H, m), 8.01 (1H, dd, J = 7.9, 1.6 Hz), 8.26 (1H, dd, J = 4.7, 1.6 Hz), 11.89 (1H, br s); LRMS (ESI): m/z $[M + H]^+$ 329. |
| EX.318 | 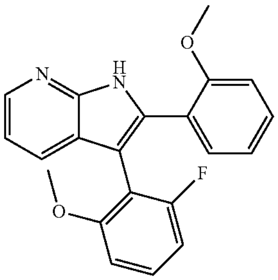 [SMILES: COc1ccccc1-c1[nH]c2ncccc2c1-c1c(F)cccc1OC] | $^1$H NMR (400 MHz, DMSO-$d_6$): δ 3.51 (3H, s), 3.60 (3H, s), 6.78 (1H, t, J = 8.8 Hz), 6.85-6.88 (2H, m), 7.04-7.07 (2H, m), 7.11 (1H, dd, J = 7.4, 1.9 Hz), 7.27-7.33 (2H, m), 7.55 (1H, d, J = 7.9 Hz), 8.23 (1H, dd, J = 4.7, 1.6 Hz), 11.89 (1H, br s); LRMS (ESI): m/z $[M + H]^+$ 349. |
| EX.319 | 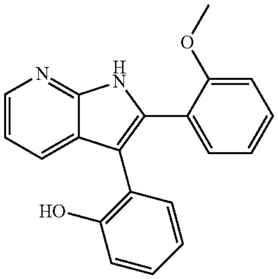 [SMILES: COc1ccccc1-c1[nH]c2ncccc2c1-c1ccccc1O] | $^1$H NMR (400 MHz, DMSO-$d_6$): δ 3.65 (3H, s), 6.66 (1H, t, J = 7.4 Hz), 6.84-6.90 (3H, m), 7.02-7.09 (3H, m), 7.16 (1H, dd, J = 7.5, 1.7 Hz), 7.28-7.33 (1H, m), 7.67 (1H, dd, J = 7.8, 1.6 Hz), 8.21 (1H, dd, J = 4.7, 1.6 Hz), 9.10 (1H, br s), 11.68 (1H, s); LRMS (ESI): m/z $[M + H]^+$ 317. |

-continued

| Example No. | Chemical structural formula | Spectrum data |
|---|---|---|
| EX.320 | 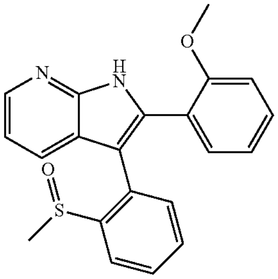 [SMILES: COc1ccccc1-c1[nH]c2ncccc2c1-c1ccccc1S(C)=O] | (Mixture of atropisomers) $^{1}$H NMR (400 MHz, DMSO-$d_6$): δ 2.11 (1.8H, s), 2.15 (1.2H, s), 3.56 (1.8H, s), 3.57 (1.2H, s), 6.88 (0.4H, t, J = 7.5 Hz), 6.95 (0.6H, t, J = 7.5 Hz), 7.06 (1H, dd, J = 12.5, 8.0 Hz), 7.09-7.19 (1.4H, m), 7.23 (0.6H, dd, J = 7.5, 1.8 Hz), 7.31 (1H, d, J = 8.1 Hz), 7.33-7.42 (0.6H, m), 7.41-7.48 (0.4H, m), 7.53 (0.6H, td, J = 7.5, 1.3 Hz), 7.56-7.66 (1.4H, m), 7.68 (0.4H, dd, J = 8.0, 1.3 Hz), 7.74 (0.6H, dd, J = 6.5 Hz), 7.76-7.83 (0.4H, m), 7.97 (0.6H, dd, J = 7.9, 1.4 Hz), 8.30 (1H, d, J = 4.7 Hz), 12.16 (0.4H, s), 12.21 (0.6H, s); LRMS (ESI): m/z $[M + H]^{+}$ 363. |
| EX.321 | 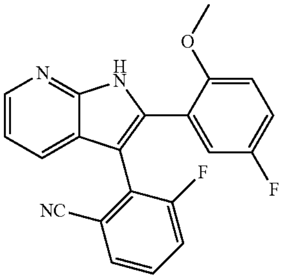 [SMILES: COc1ccc(F)cc1-c1[nH]c2ncccc2c1-c1c(F)cccc1C#N] | $^{1}$H NMR (400 MHz, DMSO-$d_6$): δ 3.34 (3H, s), 6.96-7.03 (1H, m), 7.13-7.19 (2H, m), 7.22 (1H, td, J = 8.7, 3.8 Hz), 7.57 (1H, td, J = 8.0, 5.3 Hz), 7.61-7.69 (1H, m), 7.70-7.77 (2H, m), 8.34 (1H, dd, J = 4.7, 1.6 Hz), 12.43 (1H, s); LRMS (ESI): m/z $[M + H]^{+}$ 362. |
| EX.322 | 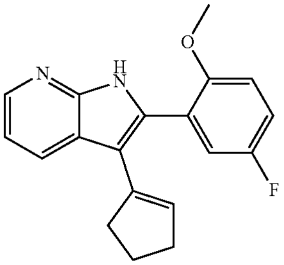 [SMILES: COc1ccc(F)cc1-c1[nH]c2ncccc2c1C1=CCCC1] | $^{1}$H NMR (400 MHz, DMSO-$d_6$): δ 1.74-1.82 (2H, m), 2.23-2.27 (2H, m), 2.38-2.43 (2H, m), 3.73 (3H, s), 5.90-5.92 (1H, m), 7.09-7.15 (2H, m), 7.18 (1H, dd, J = 8.9, 3.2 Hz), 7.29 (1H, td, J = 8.7, 3.2 Hz), 8.10 (1H, dd, J = 8.0, 1.4 Hz), 8.22 (1H, dd, J = 4.7, 1.5 Hz), 11.75 (1H, s); LRMS (ESI): m/z $[M + H]^{+}$ 309. |
| EX323 | 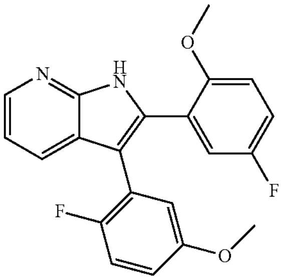 [SMILES: COc1ccc(F)c(-c2c(-c3cc(F)ccc3OC)[nH]c3ncccc23)c1] | $^{1}$H NMR (400 MHz, DMSO-$d_6$): δ 3.51 (3H, s), 3.63 (3H, s), 6.72 (1H, dd, J = 6.0, 3.2 Hz), 6.85-6.89 (1H, m), 7.06-7.25 (5H, m), 7.83 (1H, d, J = 7.9 Hz), 8.29 (1H, d, J = 4.8, 1.5 Hz), 12.13 (1H, s); LRMS (ESI): m/z $[M + H]^{+}$ 367. |
| EX.324 | 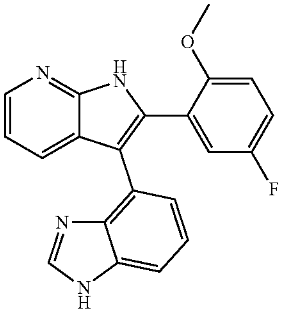 [SMILES: COc1ccc(F)cc1-c1[nH]c2ncccc2c1-c1cccc2[nH]cnc12] | $^{1}$H NMR (400 MHz, $CD_3OD$): δ 3.41 (3H, s), 6.97 (1H, dd, J = 8.9, 4.0 Hz), 7.06-7.17 (2H, m), 7.33 (1H, dd, J = 7.9, 5.2 Hz), 7.44 (1H, dd, J = 7.5, 0.9 Hz), 7.64 (1H, dd, J = 8.3, 7.5 Hz), 7.84 (1H, dd, J = 8.3, 1.0 Hz), 7.98 (1H, dd, J = 7.9, 1.4 Hz), 8.40 (1H, dd, J = 5.2, 1.4 Hz), 9.32 (1H, s); LRMS (ESI): m/z $[M + H]^{+}$ 359. |

-continued

| Example No. | Chemical structural formula | Spectrum data |
|---|---|---|
| EX.325 | 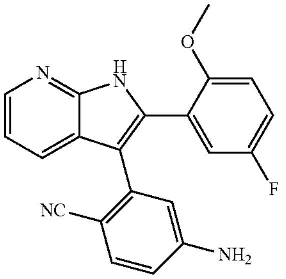 [SMILES: COc1ccc(F)cc1-c1[nH]c2ncccc2c1-c1cc(N)ccc1C#N] | $^1$H NMR (400 MHz, DMSO-$d_6$): δ 3.51 (3H, s), 6.45 (1H, d, J = 2.2 Hz), 6.55 (1H, dd, J = 8.5, 2.3 Hz), 6.94-7.26 (6H, m), 7.42 (1H, d, J = 8.5 Hz), 7.79 (1H, dd, J = 8.0, 1.2 Hz), 8.30 (1H, dd, J = 4.7, 1.6 Hz), 12.14 (1H, s); LRMS (ESI): m/z $[M + H]^+$ 359. |
| EX.326 | 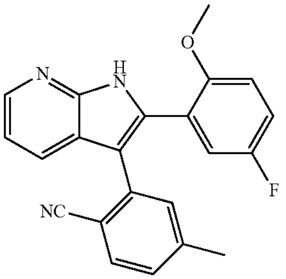 [SMILES: COc1ccc(F)cc1-c1[nH]c2ncccc2c1-c1cc(C)ccc1C#N] | $^1$H NMR (400 MHz, DMSO-$d_6$): δ 2.35 (3H, s), 3.39 (3H, s), 7.02 (1H, dd, J = 9.2, 4.6 Hz), 7.08 (1H, dd, J = 9.2, 3.1 Hz), 7.15 (1H, dd, J = 7.9, 4.6 Hz), 7.20 (1H, dd, J = 8.6, 3.1 Hz), 7.24 (1H, s), 7.30 (1H, d, J = 8.1 Hz), 7.72 (1H, d, J = 7.9 Hz), 7.80 (1H, d, J = 8.1 Hz), 8.32 (1H, d, J = 4.6 Hz), 12.24 (1H, br s); LRMS (ESI): m/z $[M + H]^+$ 358. |
| EX.327 | 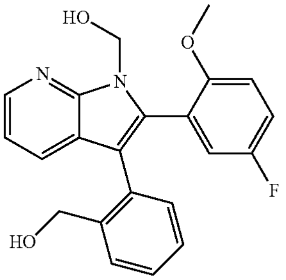 | $^1$H NMR (400 MHz, DMSO-$d_6$): δ 3.55 (3H, s), 4.03 (1H, d, J = 14.1 Hz), 4.30 (1H, d, J = 14.1 Hz), 4.98 (1H, br s), 6.94 (1H, dd, J = 9.2, 3.1 Hz), 6.99-7.11 (3H, m), 7.15 (1H, td, J = 8.8, 3.1 Hz), 7.21 (1H, t, J = 7.3 Hz), 7.33 (1H, t, J = 7.3 Hz), 7.58 (2H, t, J = 8.8 Hz), 8.27 (1H, d, J = 4.5 Hz), 11.95 (1H, br s); LRMS (ESI): m/z $[M + H]^+$ 349. |
| EX.328 | 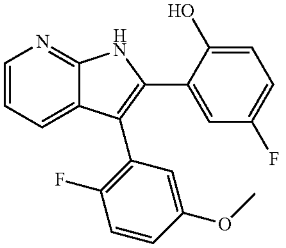 [SMILES: COc1ccc(F)c(-c2c(-c3cc(F)ccc3O)[nH]c3ncccc23)c1] | $^1$H NMR (400 MHz, DMSO-$d_6$): δ 3.63 (3H, s), 6.78 (1H, dd, J = 6.1, 3.0 Hz), 6.81-6.91 (2H, m), 6.94 (1H, dd, J = 9.1, 3.1 Hz), 7.05 (1H, td, J = 8.3, 3.1Hz), 7.09-7.19 (2H, m), 7.80 (1H, d, J = 7.9 Hz), 8.27 (1H, d, J = 4.3 Hz), 9.76 (1H, s), 12.01 (1H, br s); LRMS (ESI): m/z $[M + H]^+$ 353. |
| EX.329 | 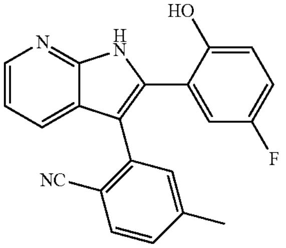 [SMILES: Cc1ccc(C#N)c(-c2c(-c3cc(F)ccc3O)[nH]c3ncccc23)c1] | $^1$H NMR (400 MHz, DMSO-$d_6$): δ 2.35 (3H, s), 6.83 (1H, dd, J = 8.2, 4.5 Hz), 6.89 (1H, dd, J = 9.4, 3.1 Hz), 7.04 (1H, td, J = 8.5, 3.1Hz), 7.14 (1H, dd, J = 8.5, 4.8 Hz), 7.27 (1H, s), 7.30 (1H, d, J = 8.0 Hz), 7.72 (1H, d, J = 8.0 Hz), 7.78 (1H, d, J = 8.2 Hz), 8.30 (1H, d, J = 4.5 Hz), 9.67 (1H, br s), 12.10 (1H, br s); LRMS (ESI): m/z $[M + H]^+$ 344. |

-continued

| Example No. | Chemical structural formula | Spectrum data |
|---|---|---|
| EX.330 | 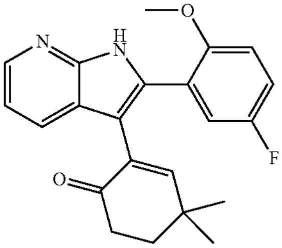 [SMILES: COc1ccc(F)cc1-c1[nH]c2ncccc2c1C1=CC(C)(C)CCC1=O] | $^1$H NMR (400 MHz, DMSO-$d_6$): δ 1.04 (6H, s), 1.85 (2H, t, J = 6.8 Hz), 2.48-2.54 (2H, m), 3.68 (3H, s), 6.35 (1H, s), 7.01-7.09 (2H, m), 7.15 (1H, dd, J = 9.2, 3.1 Hz), 7.17-7.26 (1H, m), 7.64 (1H, dd, J = 7.5, 1.7 Hz), 8.22 (1H, dd, J = 4.7, 1.6 Hz), 11.84 (1H, s); LRMS (ESI): m/z $[M + H]^+$ 365. |
| EX.331 | 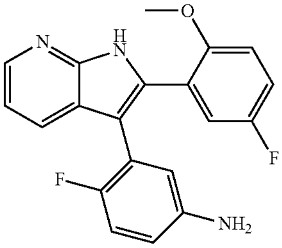 [SMILES: COc1ccc(F)cc1-c1[nH]c2ncccc2c1-c1cc(N)ccc1F] | $^1$H NMR (400 MHz, DMSO-$d_6$): δ 3.59 (3H, s), 4.90 (2H, br s), 6.42-6.56 (2H, m), 6.87 (1H, dd, J = 9.8, 8.6 Hz), 7.00 (1H, dd, J = 9.2, 3.2 Hz), 7.06-7.13 (2H, m), 7.19 (1H, td, J = 8.7, 3.2 Hz), 7.77 (1H, d, J = 8.0 Hz), 8.27 (1H, dd, J = 4.7, 1.6 Hz), 11.97 (1H, s); LRMS (ESI): m/z $[M + H]^+$ 352. |
| EX.332 | 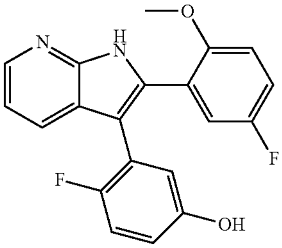 [SMILES: COc1ccc(F)cc1-c1[nH]c2ncccc2c1-c1cc(O)ccc1F] | $^1$H NMR (400 MHz, DMSO-$d_6$): δ 3.53 (3H, s), 6.58 (1H, dd, J = 6.1, 3.0 Hz), 6.64-6.70 (1H, m), 6.97-7.17 (4H, m), 7.22 (1H, td, J = 8.7, 3.2 Hz), 7.78 (1H, d, J = 8.1 Hz), 8.28 (1H, dd, J = 4.7, 1.5 Hz), 9.29 (1H, s), 12.06 (1H, s); LRMS (ESI): m/z $[M + H]^+$ 353. |
| EX.333 | 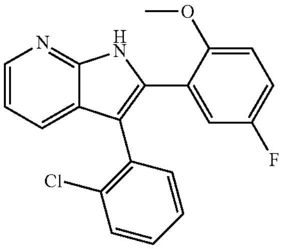 [SMILES: COc1ccc(F)cc1-c1[nH]c2ncccc2c1-c1ccccc1Cl] | $^1$H NMR (400 MHz, DMSO-$d_6$): δ 3.47 (3H, s), 6.98-7.06 (2H, m), 7.10 (1H, dd, J = 7.9, 4.7 Hz), 7.14-7.22 (2H, m), 7.29 (1H, td, J = 7.5, 1.5 Hz), 7.34 (1H, td, J = 7.5, 1.9 Hz), 7.55 (1H, dd, J = 7.8, 1.5 Hz), 7.66 (1H, dd, J = 7.9, 1.5 Hz), 8.28 (1H, dd, J = 4.7, 1.6 Hz), 12.07 (1H, br s); LRMS (ESI): m/z $[M + H]^+$ 353. |
| EX.334 | 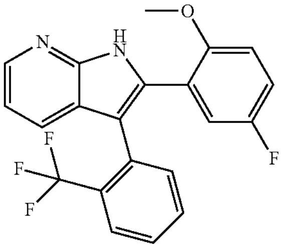 [SMILES: COc1ccc(F)cc1-c1[nH]c2ncccc2c1-c1ccccc1C(F)(F)F] | $^1$H NMR (400 MHz, DMSO-$d_6$): δ 3.56 (3H, s), 6.93 (1H, dd, J = 9.3, 3.2 Hz), 7.02 (1H, dd, J = 9.2, 4.6 Hz), 7.06 (1H, dd, J = 7.9, 4.7 Hz), 7.11-7.20 (1H, m), 7.35 (1H, d, J = 7.6 Hz), 7.53 (1H, d, J = 7.2 Hz), 7.57 (1H, t, J = 7.7 Hz), 7.65 (1H, t, J = 7.5 Hz), 7.81 (1H, d, J = 7.0 Hz), 8.27 (1H, dd, J = 4.7, 1.6 Hz), 12.03 (1H, s); LRMS (ESI): m/z $[M + H]^+$ 387. |
| EX.335 | 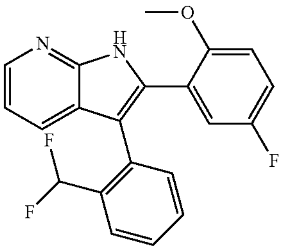 [SMILES: COc1ccc(F)cc1-c1[nH]c2ncccc2c1-c1ccccc1C(F)F] | $^1$H NMR (400 MHz, DMSO-$d_6$): 3.43 (3H, s), 6.58 (1H, t, $J_{H-F}$ = 55.1 Hz), 7.00 (1H, dd, J = 9.2, 4.6 Hz), 7.10 - 7.14 (2H, m), 7.17 - 7.21 (2H, m), 7.51 (2H, dd, J = 6.1, 3.0 Hz), 7.61 (1H, d, J = 7.8 Hz), 7.70 - 7.72 (1H, m), 8.31 (1H, dd, J = 4.7, 1.6 Hz), 12.19 (1H, s); LRMS (ESI): m/z $[M + H]^+$ 369. |

-continued

| Example No. | Chemical structural formula | Spectrum data |
|---|---|---|
| EX.336 | 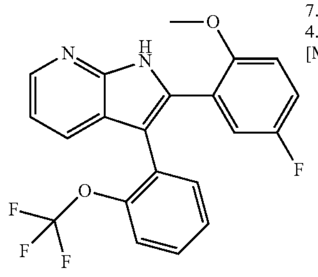 | $^1$H NMR (400 MHz, DMSO-$d_6$): δ 3.48 (3H, s), 6.96 (1H, dd, J = 9.1, 3.2 Hz), 7.06 (1H, dd, J = 9.1, 4.6 Hz), 7.13 (1H, dd, J = 7.9, 4.7 Hz), 7.21 (1H, td, J = 8.7, 3.2 Hz), 7.31-7.49 (4H, m), 7.76 (1H, dd, J = 8.0, 1.3 Hz), 8.30 (1H, dd, J = 4.7, 1.2 Hz), 12.13 (1H, s); LRMS (ESI): m/z $[M + H]^+$ 403. |

(10) Experimental Procedure of EX.337

EX.337 was prepared in accordance with the general procedure 10 using the method described below in detail.

Synthesis of 2-(2-(5-fluoro-2-methoxyphenyl)-1-methyl-1H-pyrrolo[2,3-b]pyridin-3-yl)benzonitrile (EX.337)

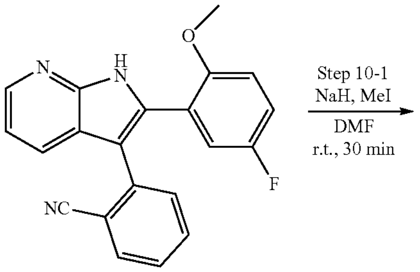

EX. 1

-continued

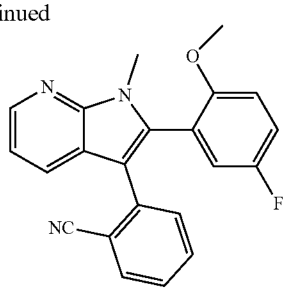

EX. 337

Step 10-1

To a solution of 2-(2-(5-fluoro-2-methoxyphenyl)-1H-pyrrolo[2,3-b]pyridin-3-yl)benzonitrile (EX.1) (14 mg, 0.041 mmol) in DMF (0.2 mL) was added NaH, 60% dispersion in mineral oil (1.8 mg, 0.045 mmol). After the addition of MeI (5.1 μL, 0.081 mmol), the mixture was stirred at room temperature for 30 min. The mixture was quenched with MeOH and purified by silica gel chromatography to give EX.337 as a white solid (11 mg, 72%).

(Mixture of atropisomers) $^1$H NMR (400 MHz, DMSO-$d_6$): δ 3.58-3.70 (6H, m), 6.97-7.30 (5H, m), 7.46 (1H, m), 7.64 (1H, br s), 7.85 (1H, d, J=7.6 Hz), 8.40 (1H, dd, J=4.7, 1.5 Hz); LRMS (ESI): m/z $[M+H]^+$ 358.

The following compounds were synthesized using conditions analogous to EX.337 and the appropriate alkylating reagents in accordance with the general procedure 10.

| Example No. | Chemical structural formula | Spectrum data |
|---|---|---|
| EX.338 | 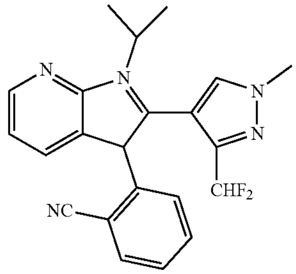 | (Mixture of atropisomers) $^1$H NMR (400 MHz, DMSO-$d_6$): 1.65 (6H, br s), 3.95 (3H, s), 4.42 - 4.57 (1H, m), 6.64 (1H, t, $J_{H-F}$ = 53.8 Hz ), 7.16-7.19 (1H, m), 7.37 (1H, s), 7.47 (1H, t, J =7.7 Hz), 7.60-7.64 (1H, m), 7.76 (1H, d, J =7.8 Hz), 7.82 (1H, d, J =7.9 Hz), 8.08 (1H, s), 8.35 - 8.40 (1H, m) LRMS (ESI): m/z $[M + H]^+$ 392. |

-continued

| Example No. | Chemical structural formula | Spectrum data |
|---|---|---|
| EX.339 | 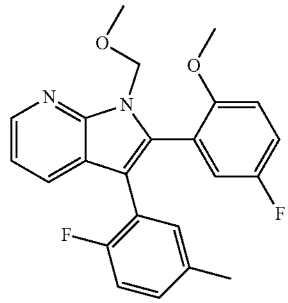 [SMILES: COCn1c(-c2cc(F)ccc2OC)c(-c2cc(C)ccc2F)c2cccnc21] | $^1$H NMR (400 MHz, DMSO-$d_6$): δ 2.19 (3H, s), 3.10 (3H, s), 3.61 (3H, s), 5.24 (1H, d, J = 10.8 Hz), 5.73 (1H, d, J = 10.8 Hz), 7.03 (1H, d, J = 6.4 Hz), 7.06-7.15 (4H, m), 7.23-7.32 (2H, m), 7.84 (1H, d, J = 7.9 Hz), 8.38-8.40 (1H, m); LRMS (ESI): m/z [M + H]$^+$ 395. |

2-(2-(5-Fluoro-2-methoxyphenyl)-3-(2-fluoro-5-methylphenyl)-1H-pyrrolo[2,3-b]pyridin-1-yl) ethan-1-ol (EX.340)

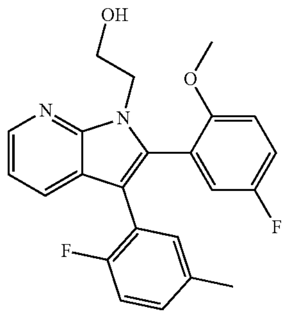 [SMILES: COc1ccc(F)cc1-c1c(-c2cc(C)ccc2F)c2cccnc2n1CCO]

2-(2-(5-Fluoro-2-methoxyphenyl)-3-(2-fluoro-5-methylphenyl)-1H-pyrrolo[2,3-b]pyridin-1-yl) ethan-1-ol (EX.340) was prepared by reacting EX.21 with 2-(2-bromoethoxy)tetrahydropyran in accordance with the general procedure 10, followed by treatment with 4M HCl.

$^1$H NMR (400 MHz, DMSO-$d_6$): δ 2.18 (3H, s), 3.48-3.56 (1H, m), 3.57-3.66 (1H, m), 3.70 (3H, s), 3.94 (1H, dt, J=14.0, 7.1 Hz), 4.31-4.41 (1H, m), 4.86 (OH, t, J=5.6 Hz), 6.97 (1H, d, J=7.6 Hz), 7.03-7.10 (3H, m), 7.13-7.22 (2H, m), 7.31 (1H, td, J=8.7, 3.2 Hz), 7.82 (1H, d, J=7.8 Hz), 8.35 (1H, dd, J=4.7, 1.5 Hz); LRMS (ESI): m/z [M+H]$^+$ 395.

(11) Experimental Procedure of EX.341

EX.341 was prepared in accordance with the general procedure 10 using the method described below in detail.

Synthesis of 1-[2-(5-fluoro-2-methoxyphenyl)-3-(2-fluoro-5-methylphenyl)pyrrolo[2,3-b]pyridin-1-yl] ethanone (EX.341)

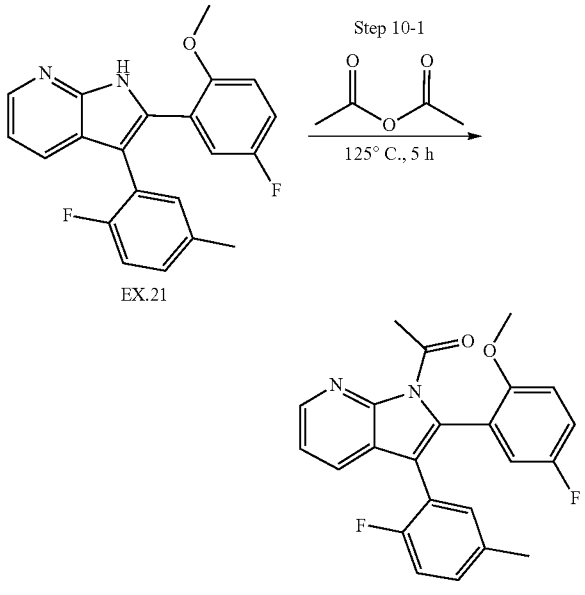

Step 10-1

The solution of 2-(5-fluoro-2-methoxy-phenyl)-3-(2-fluoro-5-methyl-phenyl)-1H-pyrrolo[2,3-b]pyridine (EX.21) (15 mg, 0.04 mmol) in acetic anhydride (0.2 mL) was heated at 125° C. for 5 h. After cooling to room temperature, the mixture was purified by prep HPLC ($CH_3CN$/0.1% TFA-$H_2O$/0.1% TFA) to give EX.341 as a white solid (12 mg, 71%).

$^1$H NMR (400 MHz, DMSO-$d_6$): δ 2.22 (3H, s), 3.04 (3H, s), 3.68 (3H, s), 6.87 (1H, dd, J=8.9, 3.1 Hz), 7.00-7.03 (2H, m), 7.09-7.20 (3H, m), 7.38 (1H, dd, J=7.9, 4.8 Hz), 7.81-7.84 (1H, m), 8.49 (1H, dd, J=4.8, 1.6 Hz); LRMS (ESI): m/z [M+H]$^+$ 393.

(12) Experimental Procedure of EX.342

EX.342 was prepared in accordance with the general procedure 11 using the method described below in detail.

Synthesis of 2-(2-(5-fluoro-2-hydroxyphenyl)-4-methoxy-1H-pyrrolo[2,3-b]pyridine-3-yl)benzonitrile (EX.342)

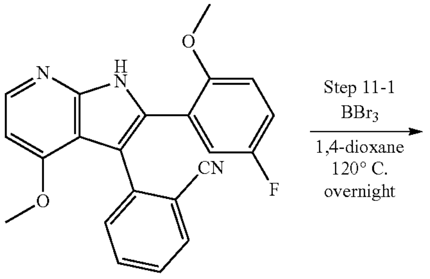

(37b)

-continued

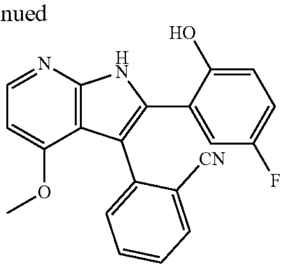

EX.342

Step 11-1

To a suspension of 2-[2-(5-fluoro-2-methoxy-phenyl)-4-methoxy-1H-pyrrolo[2,3-b]pyridine-3-yl]benzonitrile (37b) (22.0 mg, 0.06 mmol) in 1,4-dioxane (2 mL) was added 1M $BBr_3$ in DCM (1.2 mL, 1.20 mmol) at room temperature and the mixture was stirred at 120° C. overnight. After cooling to room temperature, the mixture was concentrated. The residue was purified by silica gel column chromatography (0-20% MeOH/DCM) to give the expected product as a tan solid (7.8 mg, 36%).

$^1$H NMR (400 MHz, DMSO-$d_6$): δ 3.75 (3H, s), 6.72 (1H, d, J=5.4 Hz), 6.76-6.83 (2H, m), 6.99 (1H, td, J=8.6, 3.1 Hz), 7.24 (1H, d, J=7.8 Hz), 7.40 (1H, t, J=7.7 Hz), 7.51 (1H, t, J=7.7 Hz), 7.78 (1H, d, J=7.7 Hz), 8.17 (1H, d, J=5.4 Hz), 9.62 (OH, s), 12.01 (1H, br s); LRMS (ESI): m/z $[M+H]^+$ 360.

The following compounds were synthesized using conditions analogous to EX.342 in accordance with the general procedure 11.

| Example No. | Chemical structural formula | Spectrum data |
|---|---|---|
| EX.343 | 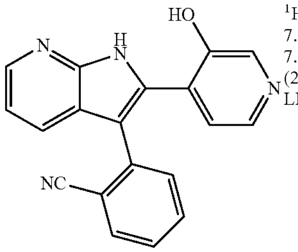 | $^1$H NMR (400 MHz, DMSO-$d_6$): δ 7.15 (1H, s), 7.21-7.29 (1H, m), 7.57 (2H, d, J = 7.4 Hz), 7.72-7.76 (1H, m), 7.84 (1H, d, J = 6.8 Hz), 7.93 (2H, d, J = 7.6 Hz), 8.19 (1H, s), 8.37 (1H, s); LRMS (ESI): m/z $[M + H]^+$ 327. |
| EX.344 | 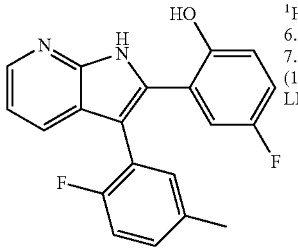 | $^1$H NMR (400 MHz, DMSO-$d_6$): δ 2.24 (3H, s), 6.84-6.94 (2H, m), 7.01 (1H, dt, J = 8.5, 3.2 Hz), 7.05-7.15 (4H, m), 7.74 (1H, d, J = 7.9 Hz), 8.25 (1H, dd, J = 4.7, 1.6 Hz), 11.19 (1H, br s); LRMS (ESI): m/z $[M + H]^+$ 337. |

(13) Experimental Procedure of EX.345

EX.345 was prepared in accordance with the general procedure 12 using the method described below in detail.

Synthesis of 2-(5-fluoro-2-(methoxy-$d_3$)phenyl)-3-(2-fluoro-5-methoxyphenyl-1H-pyrrolo[2,3-b]pyridine (EX.345)

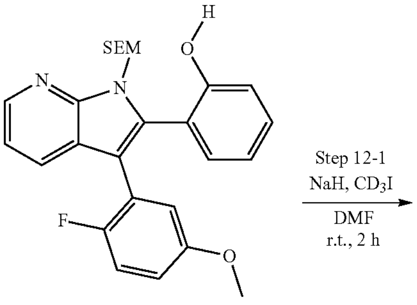

(7i)

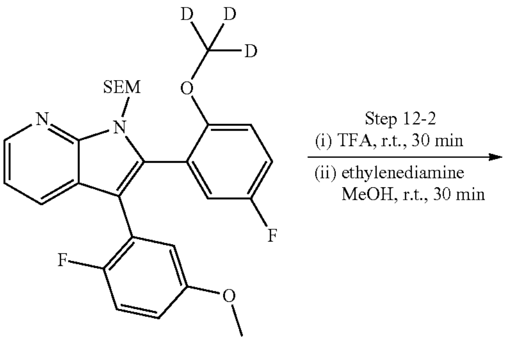

(7j)

-continued

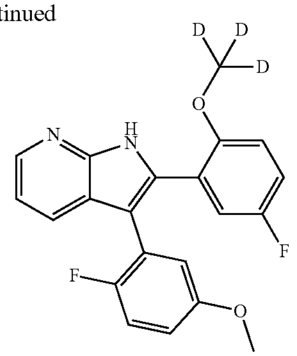

EX.345

Step 12-1

To a solution of 4-fluoro-2-[3-(2-fluoro-5-methoxyphenyl)-1-(2-trimethylsilylethoxymethyl)pyrrolo[2,3-b]pyridine-2-yl]phenol (7i) (16.8 mg, 0.03 mmol) in DMF (1 mL) was added NaH, 60% dispersion in mineral oil (2.1 mg, 0.05 mmol) and the mixture was stirred at room temperature for 10 min. After the addition of $CD_3I$ (6.5 μL, 0.10 mmol), the mixture was further stirred at room temperature for 2 h. The mixture was quenched with brine and the product was extracted with DCM (×3). The combined organic extracts were dried over $Na_2SO_4$ and concentrated. The residue was used for the next reaction without further purification (16.5 mg, 95%); LRMS (ESI): m/z $[M+H]^+$ 500.

Step 12-2

2-[[3-(2-fluoro-5-methoxy-phenyl)-2-[5-fluoro-2-(trideuteriomethoxy)phenyl]pyrrolo[2,3-b]pyridin-1-yl]methoxy]ethyl-trimethyl-silane (7j) (16.5 mg, 0.03 mmol) and neat TFA (0.25 mL, 3.30 mmol) was stirred at room temperature for 30 min. After concentration to dryness, the residue was dissolved in MeOH (0.25 mL). To this, ethylenediamine (0.22 mL, 3.30 mmol) was added at room temperature and the mixture was stirred at room temperature for 30 min. The mixture was then poured into brine and the product was extracted with DCM (×2). The combined organic extracts were dried over $Na_2SO_4$ and concentrated. The residue was purified by silica gel column chromatography (0-100% EtOAc/Hexane) to give the expected product as a white solid (6.3 mg, 49%).

$^1$H NMR (400 MHz, DMSO-$d_6$): δ 3.62 (3H, s), 6.71 (1H, dd, J=5.5, 3.1 Hz), 6.81-6.90 (1H, m), 7.03-7.27 (5H, m), 7.82 (1H, d, J=7.5 Hz), 8.29 (1H, d, J=4.2 Hz), 12.12 (1H, br s); LRMS (ESI): m/z $[M+H]^+$ 370.

The following compounds were synthesized using conditions analogous to EX.345 in accordance with the general procedure 12.

| Example No. | Chemical structural formula | Spectrum data |
|---|---|---|
| EX.346 | 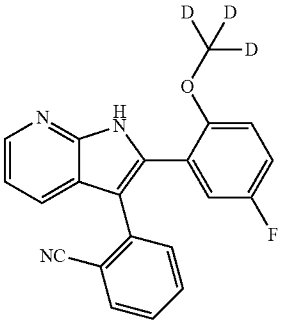 [SMILES: [2H]C([2H])([2H])Oc1ccc(F)cc1-c1[nH]c2ncccc2c1-c1ccccc1C#N] | $^1$H NMR (400 MHz, DMSO-$d_6$): δ 7.01 (1H, dd, J = 9.1, 4.6 Hz), 7.08-7.28 (3H, m), 7.37 (1H, d, J = 7.9 Hz), 7.49 (1H, t, J = 7.7 Hz), 7.68 (1H, t, J = 7.6 Hz), 7.78-7.84 (1H, m), 7.87 (1H, d, J = 7.8 Hz), 8.28-8.37 (1H, m), 12.28 (1H, br s); LRMS (ESI): m/z [M + H]$^+$ 347. |

-continued
| Example No. | Chemical structural formula | Spectrum data |
| --- | --- | --- |
| EX.347 | 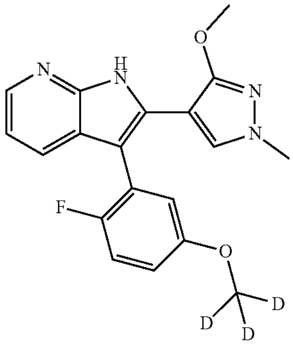 [SMILES: [2H]C([2H])([2H])Oc1ccc(F)c(-c2c(-c3cn(C)nc3OC)[nH]c3ncccc23)c1] | $^1$H NMR (400 MHz, Acetone-$d_6$): δ 3.73 (3H, s), 4.01 (3H, s), 6.91-7.12 (2H, m), 7.18-7.32 (1H, m), 7.39-7.49 (2H, m), 8.15 (1H, d, J = 7.7 Hz), 8.37 (1H, s), 12.69 (1H, br s); LRMS (ESI): m/z [M + H]$^+$ 356. |
| EX.348 | 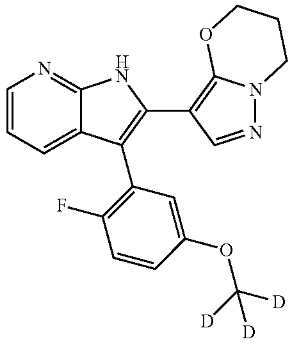 [SMILES: [2H]C([2H])([2H])Oc1ccc(F)c(-c2c(-c3cnn4c3OCCC4)[nH]c3ncccc23)c1] | $^1$H NMR (400 MHz, DMSO-$d_6$): δ 2.10-2.16 (2H, m), 4.08-4.13 (4H, m), 6.87 (1H, dd, J = 6.0, 3.2 Hz), 6.90-6.94 (1H, m), 7.09 (1H, dd, J = 7.8, 4.8 Hz), 7.20 (1H, t, J = 9.3 Hz), 7.37 (1H, s), 7.72 (1H, d, J = 7.7 Hz), 8.21 (1H, dd, J = 4.8, 1.5 Hz), 11.75 (1H, s); LRMS (ESI): m/z [M + H]$^+$ 368. |
| EX.349 | 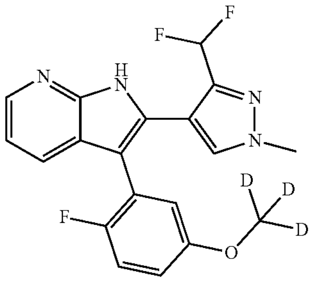 [SMILES: [2H]C([2H])([2H])Oc1ccc(F)c(-c2c(-c3cn(C)nc3C(F)F)[nH]c3ncccc23)c1] | $^1$H NMR (400 MHz, DMSO-$d_6$): δ 3.92 (3H, s), 6.52-6.79 (2H, m), 6.87-6.91 (1H, m), 7.12-7.21 (2H, m), 7.79 (1H, d, J = 7.8 Hz), 7.96 (1H, s), 8.29 (1H, dd, J = 4.7, 1.6 Hz), 12.10 (1H, s); LRMS (ESI): m/z [M + H]$^+$ 376. |

(14) Experimental Procedure of EX.350

EX.350 was prepared in accordance with the general procedure 13 using the method described below in detail.

Synthesis of 3-(2-cyanophenyl)-2-(5-fluoro-2-methoxyphenyl)-1H-pyrrolo[2,3-b]pyridine 7-oxide (EX.350)

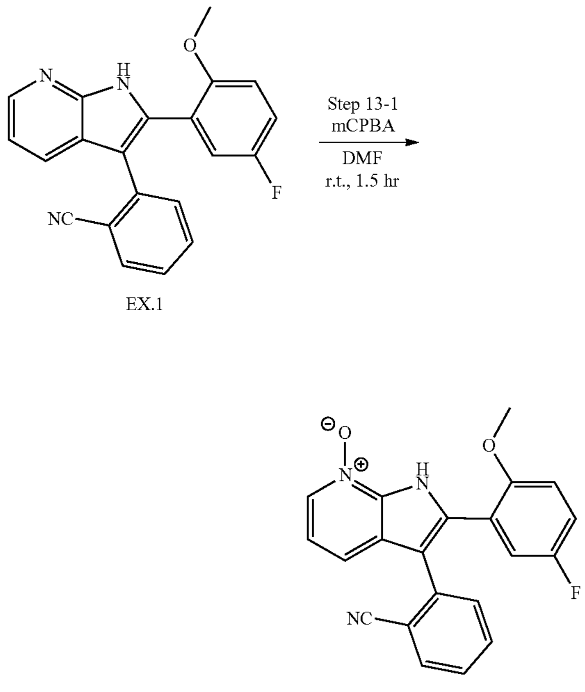

EX.1

EX.350

Step 13-1

To a solution of 2-(2-(5-fluoro-2-methoxyphenyl)-1H-pyrrolo[2,3-b]pyridin-3-yl)benzonitrile (EX.1) (50 mg, 0.15 mmol) in DME (2 mL) was added mCPBA (40.2 mg, 0.23 mmol) and the mixture was stirred at room temperature for 1.5 h. The mixture was then poured into water and basified to pH 9-10 with sat. aq. $K_2CO_3$. The precipitate was filtered off and the filtrate was extracted with DCM (×3). The combined organic extracts were dried over $Na_2SO_4$ and concentrated. The residue was purified by prep HPLC ($CH_3CN$/0.1% TFA-$H_2O$/0.1% TFA) to give EX.350 as a white solid (5 mg, 10%).

$^1H$ NMR (400 MHz, $CD_3CN$): δ 3.38 (3H, s), 6.81-7.33 (3H, m), 7.35-7.56 (2H, m), 7.57-7.85 (3H, m), 7.87-8.01 (1H, m), 8.06-8.27 (1H, m); LRMS (ESI): m/z $[M+H]^+$ 360.

(15) Experimental Procedure of EX.351

EX.351 was prepared in accordance with the general procedure 14 using the method described below in detail.

Synthesis of 2-(5-fluoro-2-methoxyphenyl)-3-(6-methoxy-3,3-dimethylcyclohex-1-en-1-yl)-1H-pyrrolo[2,3-b]pyridine (EX.351)

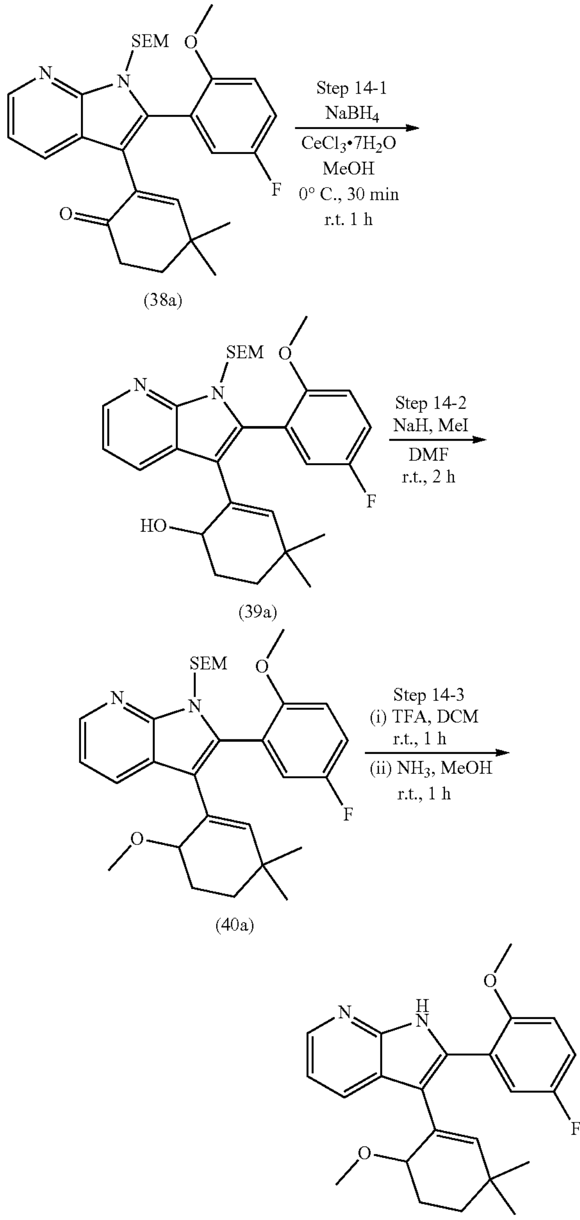

(38a)

(39a)

(40a)

EX.351

Step 14-1

To a solution of 2-[2-(5-fluoro-2-methoxy-phenyl)-1-(2-trimethylsilylethoxymethyl)pyrrolo[2,3-b]pyridin-3-yl]-4,4-dimethyl-cyclohex-2-en-1-one (38a) (127 mg, 0.26 mmol) in methanol (3 mL) was added $CeCl_3 \cdot 7H_2O$ (114.8 mg, 0.31 mmol) and $NaBH_4$ (11.6 mg, 0.31 mmol) under nitrogen at 0° C. The mixture was stirred at 0° C. for 30 min then room temperature for 1 h. After concentration, the residue was partitioned between EtOAc and water. The organic layer was dried over $Na_2SO_4$ and concentrated. The residue was purified by silica gel column chromatography (0-50% EtOAc/Hexane) to give the expected product as colorless oil (102 mg, 80%); LRMS (ESI): m/z $[M+H]^+$ 497.

Step 14-2

To a solution of 2-[2-(5-fluoro-2-methoxy-phenyl)-1-(2-trimethylsilylethoxymethyl)pyrrolo[2,3-b]pyridin-3-yl]-4,4-dimethyl-cyclohex-2-en-1-ol (39a) (25 mg, 0.05 mmol) in DMF (0.5 mL) was added NaH, 60% dispersion in mineral oil (2.6 mg, 0.07 mmol) and the mixture was stirred at room temperature for 10 min. After the addition of MeI (4.1 μL, 0.065 mmol), the mixture was further stirred at room temperature for 2 h. The mixture was then poured into water and the product was extracted with EtOAc (×2). The combined organic extracts were dried over $Na_2SO_4$ and concentrated. The residue was used for the next reaction without further purification (20 mg, 47%); LRMS (ESI): m/z $[M+H]^+$ 511.

Step 14-3

A mixture of 2-[[2-(5-fluoro-2-methoxy-phenyl)-3-(6-methoxy-3,3-dimethyl-cyclohexen-1-yl)pyrrolo[2,3-b]pyridin-1-yl]methoxy]ethyl-trimethyl-silane (40a) (20 mg, 0.02 mmol) and TFA (0.3 mL, 3.92 mmol) in DCM (0.5 mL) was stirred at room temperature for 1 h. After concentration to dryness, the residue was treated with $NH_3$ in methanol (1 mL), and the mixture was stirred at room temperature for 1 h. After concentration, the residue was purified by prep HPLC ($CH_3CN$/0.1% TFA-$H_2O$/0.1% TFA) to give EX.351 as a white solid (5.6 mg, 61%).

$^1$H NMR (400 MHz, DMSO-$d_6$): δ 0.88 (3H, s), 0.92 (3H, s), 1.30-1.41 (1H, m), 1.51-1.63 (1H, m), 1.65-1.77 (1H, m), 1.78-1.89 (1H, m), 2.99 (3H, s), 3.74-3.79 (4H, m), 5.31 (1H, s), 7.06 (1H, dd, J=7.9, 4.7 Hz), 7.11 (1H, dd, J=8.9, 4.5 Hz), 7.18-7.31 (2H, m), 7.95 (1H, dd, J=8.1, 1.3 Hz), 8.21 (1H, dd, J=4.7, 1.6 Hz), 11.67 (1H, s); LRMS (ESI): m/z $[M+H]^+$ 381.

(16) Experimental Procedure of EX.352

EX.352 was prepared in accordance with the general procedure 14 using the method described below in detail.

Synthesis of 2-[2-[2-(1-hydroxyethyl)-6,7-dihydro-5H-pyrazolo[5,1-b][1,3]oxazin-3-yl]-1H-pyrrolo[2,3-b]pyridin-3-yl]-4-methoxy-benzonitrile: (EX.352)

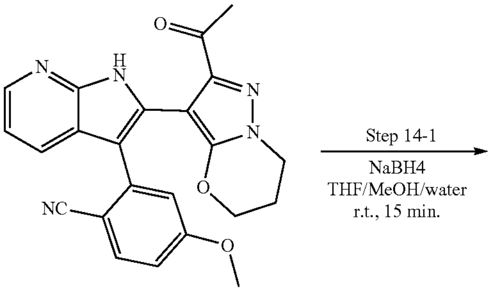

38b

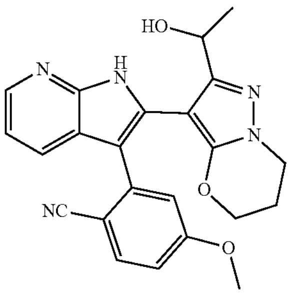

EX. 352

Step 14-1 (ref.: Angew. Chem. Int. Ed. 2019, 58, 17567)

To a solution of the 2-[2-(2-acetyl-6,7-dihydro-5H-pyrazolo[5,1-b][1,3]oxazin-3-yl)-1H-pyrrolo[2,3-b]pyridin-3-yl]-4-methoxy-benzonitrile (38b) (19.6 mg, 0.05 mmol) in THF (3 mL) and Methanol (1 mL) with $H_2O$ (3.42 μL, 0.19 mmol) was added $NaBH_4$ (3.59 mg, 0.09 mmol) at once. After 15 min, the reaction mixture was quenched with 1 mL of sat. $NH_4Cl$ and concentrated under reduced pressure. The crude material was purified by ISCO-column chromatography (normal-phase silica gel) using 0-30% MeOH on DCM gave pure compound EX.352 as an off-white solid, 18 mg 90% yield.

$^1$H NMR (400 MHz, DMSO-$d_6$) δ 1.26 (3H, s), 2.03 (2H, bs), 3.66-3.96 (5H, m), 4.03 (2H, t, J=5.8 Hz), 4.65 (1H, bs), 5.63-5.83 (1H, m), 6.80-7.01 (1H, m), 7.05 (1H, dd, J=8.7, 2.6 Hz), 7.12 (1H, dd, J=7.9, 4.7 Hz), 7.79 (2H, d, J=7.7 Hz), 8.24 (1H, dd, J=4.7, 1.5 Hz), 11.76 (1H, s). LRMS (ESI): m/z $[M+H]^+$ 416.

(17) Experimental Procedure of EX.353 and EX.354

EX.353 and EX.354 were prepared in accordance with the general procedures 5 and 29 using the method described below in detail.

Synthesis of 2-[2-[6-amino-2-methyl-6,7-dihydro-5H-pyrazolo[5,1-b][1,3]oxazin-3-yl]-1H-pyrrolo[2,3-b]pyridin-3-yl]-4-methoxy-benzonitrile (EX.353) and N-[3-[3-(2-cyano-5-methoxy-phenyl)-1H-pyrrolo[2,3-b]pyridin-2-yl]-2-methyl-6,7-dihydro-5H-pyrazolo[5,1-b][1,3]oxazin-6-yl]acetamide (EX.354)

Step 5-3

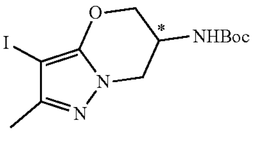

(10IIII)

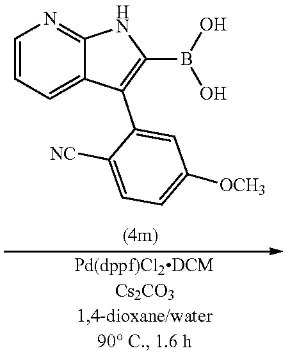

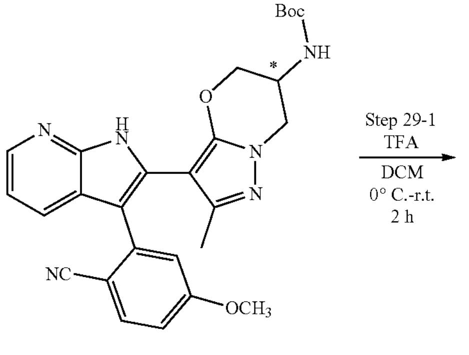

(70a)

-continued

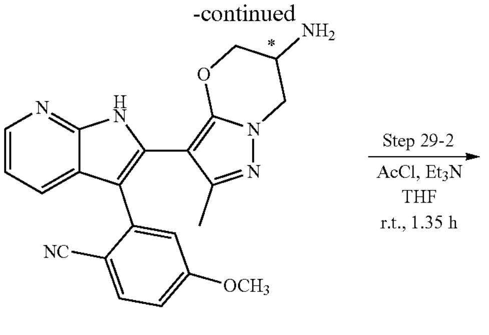

EX.353

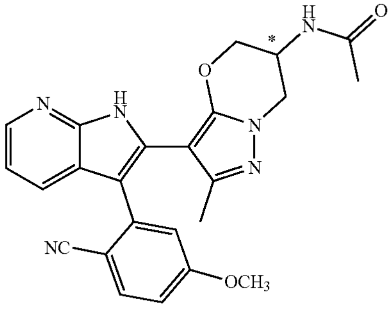

EX.354

Step 5-3

A reaction vessel containing (3-(2-cyano-5-methoxyphenyl)-1H-pyrrolo[2,3-b]pyridin-2-yl) boronic acid (4m) (220 mg, 0.59 mmol), tert-butyl N-[3-iodo-2-methyl-6,7-dihydro-5H-pyrazolo[5,1-b][1,3]oxazin-6-yl]carbamate (10llll) (244.5 mg, 0.64 mmol) and $Cs_2CO_3$ (573 mg, 1.76 mmol) in 1,4-dioxane (8 mL) and water (2 mL) was degassed and backfilled with $N_2$ three times. After the addition of $PdCl_2$(dppf).DCM (95.7 mg, 0.12 mmol), the mixture was purged with $N_2$ three times again, and heated at 90° C. for 98 min. The reaction mixture was concentrated in vacuo and purified by silica gel column chromatography (0-100% EtOAc/hexanes) to obtain expected product as a brown solid (130 mg, 44%); LCMS (ESI): m/z $[M+H]^+$ 501.

Step 29-1

A solution containing tert-butyl N-3-[3-(2-cyano-5-methoxy-phenyl)-1H-pyrrolo[2,3-b]pyridin-2-yl]-2-methyl-6,7-dihydro-5H-pyrazolo[5,1-b][1,3]oxazin-6-yl]carbamate (70a) (178 mg, 0.36 mmol) in DCM (3.7 mL) was cooled to 0° C. and added TFA (0.54 mL, 7.11 mmol). After addition ice bath was removed and reacted at room temperature for 2 h. The reaction mixture was cooled at 0° C., added sat. $NaHCO_3$ dropwise (pH=~7-8) and extracted with EtOAc. Organic extracts were combined, dried over anhydrous $Na_2SO_4$, filtered and concentrated under reduced pressure to afford an orange oil which was further purified by prep-HPLC ($CH_3CN$/0.1% TFA-$H_2O$/0.1% TFA). Fractions containing product were combined, concentrated, and added saturated $NaHCO_3$ (pH 7-8). Resulting solution was transferred to a separatory funnel and extracted with EtOAc. Combined organic layers were further washed with water (×3), dried over anhydrous $Na_2SO_4$ and concentrated under reduced pressure to afford EX.353 as a white solid (31 mg, 21%); $^1$H NMR (400 MHz, DMSO-$d_6$): δ 1.77-1.92 (5H, m), 3.28-3.32 (1H, m), 3.64-3.69 (2H, m), 3.82 (3H, s), 3.95-4.14 (2H, m), 6.96 (1H, d, J=2.5 Hz), 7.04 (1H, dd, J=8.7, 2.6 Hz), 7.12 (1H, dd, J=7.9, 4.7 Hz), 7.77-7.83 (2H, m), 8.25 (1H, dd, J=4.7, 1.6 Hz), 11.93 (1H, br s); LRMS (ESI): m/z $[M+H]^+$ 401.

Step 29-2

A solution of 4-methoxy-2-[2-[6-amino-2-methyl-6,7-dihydro-5H-pyrazolo[5,1-b][1,3]oxazin-3-yl]-1H-pyrrolo[2,3-b]pyridin-3-y]benzonitrile (EX.353) (47 mg, 0.12 mmol), THF (3.3 mL), $Et_3N$ (18 μL, 0.13 mmol) was cooled to 0° C. and stirred for 6 min, added dropwise $CH_3COCl$ (8.3 μL, 0.12 mmol) in THF (0.67 mL). Reacted at 0° C. for 4 min and then at room temperature for 46 min additional $CH_3COCl$ (0.8 μL) was added and stirred for 15 min. Further addition of $CH_3COCl$ (2.2 μL) and reacted for another 35 min. The reaction was partitioned between water and extracted with EtOAc. Organic layer was washed with water (×3) and evaporated solvent in vacuo. Crude residue was purified by silica gel column chromatography (0-8% MeOH/DCM), fractions were dried and lyophilized. The white solid was further dried in the rotavapor at 50° C. for 2 h to obtain EX.354 as an off-white solid (37.5 mg, 70%); $^1$H NMR (400 MHz, DMSO-$d_6$): δ 1.80 (3H, br s), 1.82 (3H, br s), 3.79-3.90 (4H, m), 3.98-4.04 (2H, m), 4.21-4.28 (2H, m), 6.93-7.02 (1H, m), 7.05 (1H, dd, J=8.7, 2.5 Hz), 7.13 (1H, dd, J=7.9, 4.7 Hz), 7.78-7.84 (2H, m), 8.04 (0.5H, br s), 8.26 (1H, dd, J=4.7, 1.5 Hz), 8.31 (0.5H, br s), 11.94 (1H, br s); LRMS (ESI): m/z $[M+H]^+$ 443.

The following compounds were synthesized using conditions analogous to EX.353 and EX.354 in accordance with the general procedures 5 and 29.

| Example No. | Chemical structural formula | Spectrum data |
|---|---|---|
| EX.355 | 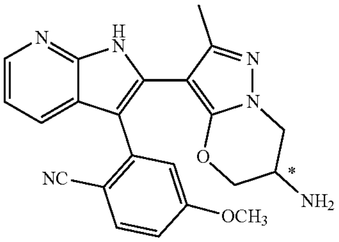 [SMILES: COc1ccc(C#N)c(-c2c(-c3c(C)nn4c3OCC(N)C4)[nH]c3ncccc23)c1] | (Mixture of atropisomers) $^1$H NMR (400 MHz, DMSO-$d_6$): δ 1.77 (5H, bs), 3.32 (1H, s), 3.60-3.72 (2H, m), 3.82 (3H, s), 4.00 (1H, bs), 4.05-4.17 (1H, m), 6.96 (1H, d, J = 2.6 Hz), 7.04 (1H, dd, J = 8.7, 2.6 Hz), 7.12 (1H, dd, J = 7.9, 4.7 Hz), 7.78 (1H, d, J = 8.7 Hz), 7.82 (1H, d, J = 7.0 Hz), 8.25 (1H, dd, J = 4.7, 1.5 Hz), 11.94 (1H, s). LRMS (ESI): m/z $[M + H]^+$ 401. |

-continued

| Example No. | Chemical structural formula | Spectrum data |
| --- | --- | --- |
| EX.356 | 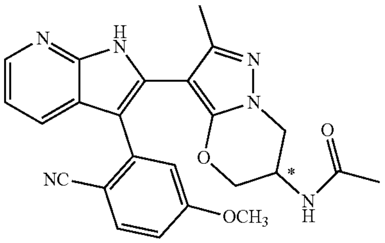 [SMILES: COc1ccc(C#N)c(-c2c(-c3c(C)nn4c3OCC(NC(C)=O)C4)[nH]c3ncccc23)c1] | (Mixture of atropisomers) $^{1}$H NMR (400 MHz, DMSO-$d_6$): δ 1.81 (3H, br s), 1.83 (3H, s), 3.76-3.91 (4H, m), 3.94-4.09 (2H, m), 4.17-4.32 (2H, m), 6.97 (1H, br s), 7.05 (1H, dd, J = 8.7, 2.6 Hz), 7.13 (1H, dd, J = 7.9, 4.7 Hz), 7.66-7.89 (2H, m), 8.02 (0.6H, br s), 8.26 (1.4H, br s), 11.91 (1H, s). LRMS (ESI): m/z $[M + H]^+$ 443. |
| EX.357 | 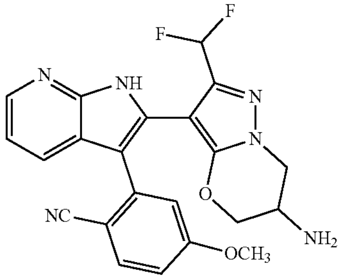 [SMILES: COc1ccc(C#N)c(-c2c(-c3c(C(F)F)nn4c3OCC(N)C4)[nH]c3ncccc23)c1] | $^{1}$H NMR (400 MHz, DMSO-$d_6$): δ 3.43-3.57 (1H, m), 3.79 (3H, s), 3.83-4.22 (3H, m), 4.31 (1H, dd, J = 12.3, 4.7 Hz), 6.56 (1H, t, $J_{H-F}$ = 54.0 Hz), 6.89 (1H, s), 7.05 (1H, dd, J = 8.7, 2.6 Hz), 7.15 (1H, dd, J = 7.9, 4.7 Hz), 7.79 (1H, d, J = 8.7 Hz), 7.84 (1H, dd, J = 7.9, 1.3 Hz), 8.31 (1H, dd, J = 4.7, 1.5 Hz), 12.06 (1H, s). LRMS (ESI): m/z $[M + H]^+$ 437. |
| EX.358 | 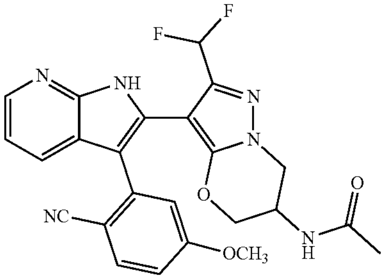 [SMILES: COc1ccc(C#N)c(-c2c(-c3c(C(F)F)nn4c3OCC(NC(C)=O)C4)[nH]c3ncccc23)c1] | (Mixture of atropisomers) $^{1}$H NMR (400 MHz, DMSO-$d_6$): δ 1.84 (3H, s), 3.78 (3H, bs), 3.93-4.24 (3H, (br m) m), 4.25-4.50 (2H, (br m) m), 6.58 (1H, t, $J_{H-F}$ = 53.8 Hz), 6.78-7.01 (1H, (br m) m), 7.06 (1H, dd, J = 8.7, 2.6 Hz), 7.15 (1H, dd, J = 7.9, 4.7 Hz), 7.71-7.92 (2H, m), 8.01 (0.5H, bs), 8.31 (1H, dd, J = 4.7, 1.5 Hz), 8.40 (0.5H, bs). LRMS (ESI): m/z $[M + H]^+$ 479. |
| EX.359 | 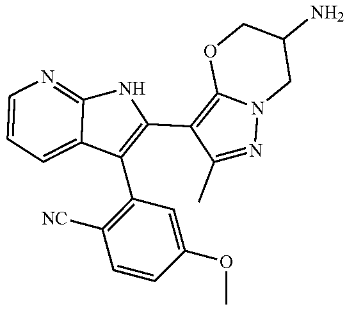 [SMILES: COc1ccc(C#N)c(-c2c(-c3c(C)nn4c3OCC(N)C4)[nH]c3ncccc23)c1] | $^{1}$H NMR (400 MHz, DMSO-$d_6$) δ 1.80 (3H, s), 3.32 (1H, s), 3.70 (2H, dd, J = 12.0, 6.1 Hz), 3.82 (3H, s), 3.99 (1H, d, J = 9.7 Hz), 4.14 (1H, dd, J = 11.9, 4.7 Hz), 6.96 (1H, d, J = 2.2 Hz), 7.04 (1H, dd, J = 8.7, 2.6 Hz), 7.12 (1H, dd, J = 7.9, 4.7 Hz), 7.78 (1H, d, J = 8.7 Hz), 7.82 (1H, d, J = 6.9 Hz), 8.26 (1H, dd, J = 4.7, 1.5 Hz), 11.92 (1H, s). LRMS (ESI): m/z $[M + H]^+$ 401. |
| EX.360 | 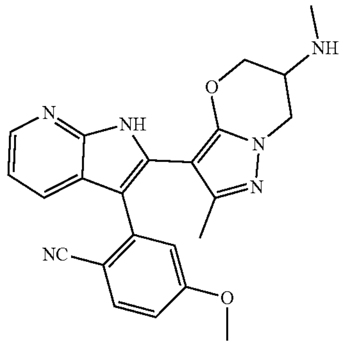 [SMILES: CNC1COc2c(-c3[nH]c4ncccc4c3-c3cc(OC)ccc3C#N)c(C)nn2C1] | $^{1}$H NMR (400 MHz, DMSO-$d_6$): δ 1.83 (3H, s), 2.34 (3H, s), 3.16 (1H, s), 3.31 (1H, s), 3.81 (3H, s), 3.84-3.91 (1H, m), 3.96 (1H, s), 4.03 (1H, dd, J = 11.0, 2.2 Hz), 4.18 (1H, dd, J = 12.3, 4.7 Hz), 6.94 (1H, s), 7.04 (1H, dd, J = 8.7, 2.6 Hz), 7.12 (1H, dd, J = 7.9, 4.7 Hz), 7.78 (1H, d, J = 8.7 Hz), 7.80 (1H, s), 8.26 (1H, dd, J = 4.7, 1.5 Hz), 11.92 (1H, s). LRMS (ESI): m/z $[M + H]^+$ 415. |

-continued

| Example No. | Chemical structural formula | Spectrum data |
|---|---|---|
| EX.361 | 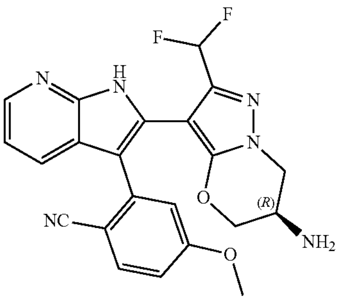 | $^1$H NMR (400 MHz, DMSO-$d_6$): δ 1.86 (2H, bs), 3.40 (1H, br s), 3.79 (3H, s), 3.80-3.91 (2H, m), 4.13 (1H, br s), 4.21-4.33 (1H, m), 6.54 (1H, t, $J_{H-F}$ = 53.9 Hz), 6.90 (1H, d, J = 2.3 Hz), 7.04 (1H, dd, J = 8.7, 2.6 Hz), 7.15 (1H, dd, J = 7.9, 4.7 Hz), 7.79 (1H, d, J = 8.7 Hz), 7.84 (1H, dd, J = 7.9, 1.2 Hz), 8.30 (1H, dd, J = 4.7, 1.5 Hz), 12.09 (1H, s). LCMS (ESI): m/z $[M + H]^+$ 437. |
| EX.362 | 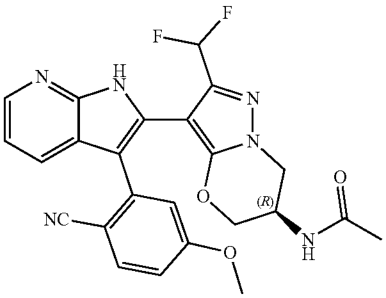 | $^1$H NMR (400 MHz, DMSO-$d_6$): δ 1.84 (3H, s), 3.79 (3H, s), 3.94-4.24 (3H, m), 4.29-4.45 (2H, m), 6.58 (1H, t, $J_{H-F}$ = 54.1 Hz), 6.90 (1H, br s), 7.06 (1H, dd, J = 8.7, 2.4 Hz), 7.15 (1H, dd, J = 7.9, 4.7 Hz), 7.75-7.89 (2H, m), 8.01 (0.5H, br s), 8.31 (1H, d, J = 4.6 Hz), 8.33 (0.5H, br s), 12.05 (1H, s). LRMS (ESI): m/z $[M + H]^+$ 479. |
| EX.363 | 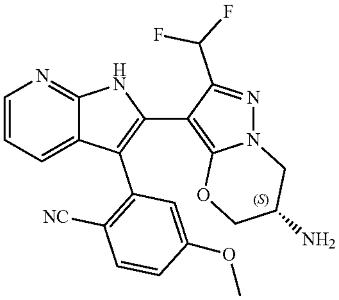 | $^1$H NMR (400 MHz, DMSO-$d_6$) 1.89 (2H, s), 3.40 (1H, br s), 3.79 (3H, s), 3.80-3.85 (2H, m), 4.10 (1H, br s), 4.21-4.33 (1H, m), 6.54 (1H, d, $J_{H-F}$ = 53.9 Hz), 6.89 (1H, d, J = 2.6 Hz), 7.04 (1H, dd, J = 8.7, 2.6 Hz), 7.15 (1H, dd, J = 7.9, 4.7-Hz), 7.78 (1H, d, J = 8.7 Hz), 7.84 (1H, dd, J = 7.9, 1.6 Hz), 8.30 (1H, dd, J = 4.7, 1.6 Hz), 12.05 (1H, s); LRMS (ESI): m/z $[M + H]^+$ 437. |
| EX.364 | 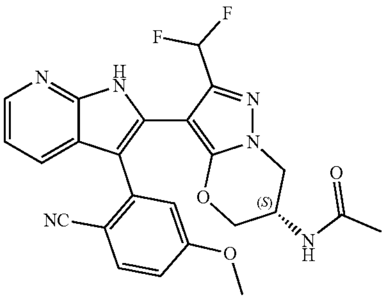 | $^1$H NMR (400 MHz, DMSO-$d_6$): δ 1.84 (3H, s), 3.79 (3H, s), 3.99-4.22 (3H, m), 4.29-4.45 (2H, m), 6.58 (1H, t, $J_{H-F}$ = 52 Hz), 6.89 (1H, s), 7.06 (1H, dd, J = 8.7, 2.6 Hz), 7.15 (1H, dd, J = 8.0, 4.7 Hz), 7.77-7.88 (2H, m), 8.00 (0.5H, br s), 8.31 (1H, dd, J = 4.7, 1.5 Hz), 8.37 (0.5H, br s), 12.05 (1H, s); LRMS (ESI): m/z $[M + H]^+$ 479. |

(18) Experimental Procedure of EX.365

EX.365 was prepared in accordance with the general procedure 31 using the method described below in detail.

Synthesis of 2-[2-[4-(difluoromethyl)-1H-pyrazol-3-yl]-1H-pyrrolo[2,3-b]pyridin-3-yl]-4-(trideuteri-omethoxy)benzonitrile (EX.365)

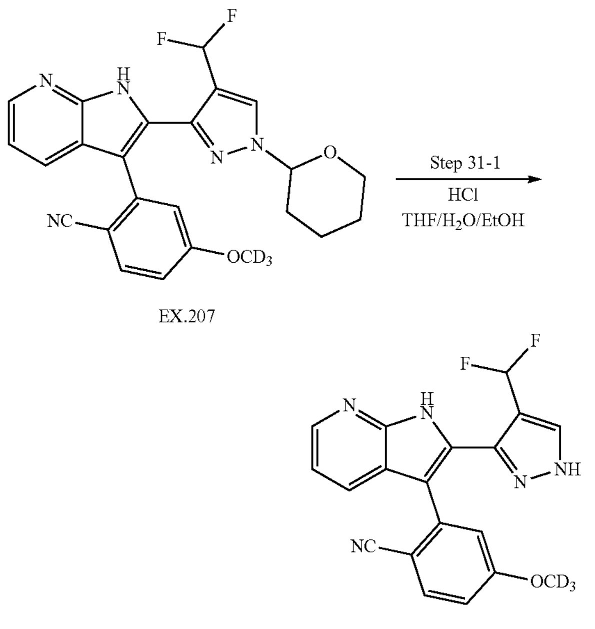

EX.207

EX. 365

Step 31-1

To a solution of 2-[2-[4-(difluoromethyl)-1-tetrahydropyran-2-yl-pyrazol-3-yl]-1H-pyrrolo[2,3-b]pyridin-3-yl]-4-(trideuteriomethoxy)benzonitrile (EX.207) in THF/$H_2O$/EtOH (0.5 mL/0.1 mL/0.5 mL) was added conc. HCl (25 μL of 12.4 M, 0.31 mmol). Resulting solution was stirred at room temperature for 48 h. Thereafter, reaction mixture was slowly poured to a 30 mL saturated solution of sodium bicarbonate and extracted thrice with EtOAc. The combined organic extracts were dried over $Na_2SO_4$, filtered, and concentrated to afford a white solid which was purified by prep-HPLC [Kinetex 5u C18 100A RXI, 150×21.20 mm, 30-70% $CH_3CN$ w/0.1% TFA in $H_2O$ w/0.1% TFA over 20 min, flow rate 20 mL/min, UV 225]. Pure fractions were passed through the PL-$HCO_3$ MP flash, concentrated, and lyophilized to afford a white solid (3.5 mg, 28%) as product (EX.365).

$^1H$ NMR (400 MHz, DMSO-$d_6$): δ 6.59 (1H, t, $J_{H-F}$=55.8 Hz), 6.90 (1H, d, J=2.6 Hz), 7.06 (1H, dd, J=8.7, 2.6 Hz), 7.20 (1H, dd, J=8.0, 4.7 Hz), 7.81 (1H, d, J=8.7 Hz), 7.89 (1H, dd, J=8.0, 1.1 Hz), 8.13 (1H, s), 8.37 (1H, dd, J=4.6, 1.4 Hz), 12.62 (1H, s), 13.53 (1H, s); LRMS (ESI): m/z $[M+H]^+$ 369.

(19) Experimental Procedure of EX.366

EX.366 was prepared in accordance with the general procedures 5 and 34 using the method described below in detail.

Synthesis of 2-[2-[(6S)-6-hydroxy-2-methyl-6,7-dihydro-5H-pyrazolo[5,1-b][1,3]oxazin-3-yl]-1H-pyrrolo[2,3-b]pyridin-3-yl]-4-(trideuteriomethoxy) benzonitrile (EX.366)

Step 5-3

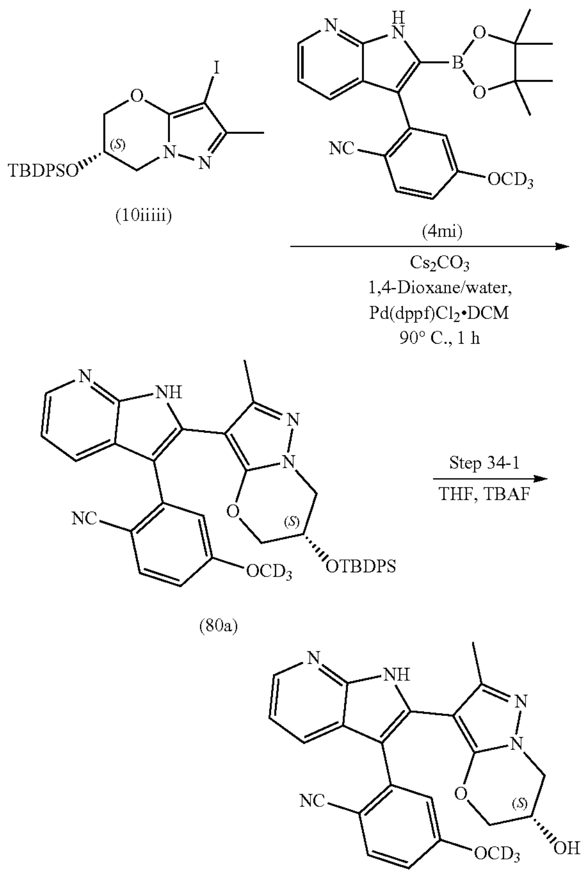

(10iiiii)

(4mi)

(80a)

EX.366

Step 5-3

A 10 ml round bottom flask containing 4-(methoxy-d3)-2-(2-(4,4,5,5-tetramethyl-1,3,2-dioxaborolan-2-yl)-1H-pyrrolo[2,3-b]pyridin-3-yl)benzonitrile (4 mi) (50 mg, 0.13 mmol), tert-butyl-[[(6S)-3-iodo-2-methyl-6,7-dihydro-5H-pyrazolo[5,1-b][1,3]oxazin-6-yl]oxy]-diphenyl-silane (10iiiii) (133 mg, 0.26 mmol) and $Cs_2CO_3$ (180 mg, 0.55 mmol) in 1,4-Dioxane/$H_2O$ (1 mL/0.2 mL) was thrice evacuated and backfilled with nitrogen. After the addition of Pd(dppf)$Cl_2$-DCM (32 mg, 0.04 mmol), the mixture was again thrice evacuated and backfilled with nitrogen and stirred at 90° C. for 1 h. Thereafter, the aqueous layer was pipetted out and the remaining liquid (dark colored) was purified by silica gel column chromatography [4g pre-pack silica gel column (gold), eluted with 100% Hexanes (2 min.), 70% EtOAc/Hexanes (5 min.), 80% EtOAc/Hexanes (5 min.), 90% EtOAc/Hexanes (5 min.), 100% EtOAc/Hexanes (5 min.), 0 to 5% MeOH/DCM (5 min.), 10% MeOH/DCM (5 min.), 30% MeOH/DCM (5 min.)] to afford a light tan colored oil (20.5 mg, 24%) as product. LRMS (ESI): m/z $[M+H]^+$ 643.

Step 34-1

A 10 mL round bottom flask containing 2-[2-[(6S)-6-[tert-butyl(diphenyl) silyl]oxy-2-methyl-6,7-dihydro-5H-pyrazolo[5,1-b][1,3]oxazin-3-yl]-1H-pyrrolo[2,3-b]pyridin-3-yl]-4-(trideuteriomethoxy)benzonitrile (80a) (20 mg, 0.03 mmol) in THF (1.5 mL) at 0° C. was treated with TBAF (0.09 mL, 0.09 mmol) and stirred for 1 h at 0° C. Thereafter, the reaction mixture was quenched with cold water and extracted thrice with EtOAc. The combined organic extracts were dried over $Na_2SO_4$, filtered, and concentrated. Residue was purified by silica gel chromatography [4g pre-pack silica gel column (gold), eluted with 100% Hexanes (2 min.), 70% EtOAc/Hexanes (5 min.), 80% EtOAc/Hexanes (5 min.), 90% EtOAc/Hexanes (5 min.), 100% EtOA EtOAc/Hexanes (5 min.), 0 to 5% MeOH/DCM (5 min.), 10% MeOH/DCM (5 min.), 30% MeOH/DCM (5 min.)] to afford a yellow oil which was re-purified by prep-HPLC [Kinetex 5u C18 100A RXI, 150×21.20 mm, 30-70% $CH_3CN$ w/0.1% TFA in $H_2O$ w/0.1% TFA over 20 min, flow rate 20 mL/min, UV 240]. Pure fractions were passed through the PL-$HCO_3$ MP column, concentrated, and lyophilized to afford a white solid (3.6 mg, 28%) as product.

(mixture of atropisomers) $^1H$ NMR (400 MHz, DMSO-$d_6$): δ 1.80 (1.5H, br s), 1.92 (1.5H, br s), 3.83-3.97 (3H, m), 4.11-4.23 (2H, m), 5.49 (1H, br s), 6.90 (1H, br s), 7.03 (1H, dd, J=8.6, 2.6 Hz), 7.12 (1H, dd, J=7.9, 4.7 Hz), 7.72-7.86 (2H, m), 8.25 (1H, dd, J=4.7 Hz, 1.5 Hz), 11.93 (1H, s); LRMS (ESI): m/z $[M+H]^+$ 405.

The following compounds were synthesized using conditions analogous to EX.366 in accordance with the general procedures 5 (step 5-3) and 34.

| Example No. | Chemical structural formula | Spectrum data |
|---|---|---|
| EX.367 | 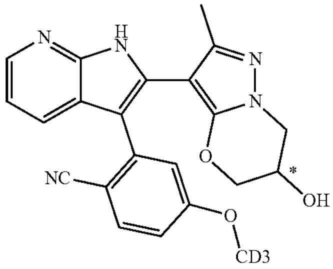 [SMILES: [2H]C([2H])([2H])Oc1ccc(C#N)c(-c2c(-c3c(C)nn4c3OCC(O)C4)[nH]c3ncccc23)c1] | (Mixture of atropisomers) $^1H$ NMR (400 MHz, DMSO-$d_6$): δ 1.80 (1.5H, br s), 1.92 (1.5H, br s), 3.83-3.97 (3H, m), 4.11-4.23 (2H, m), 5.49 (1H, br s), 6.90 (1H, br s), 7.03 (1H, dd, J = 8.6, 2.6 Hz), 7.12 (1H, dd, J = 7.9, 4.7 Hz), 7.72-7.86 (2H, m), 8.25 (1H, dd, J = 4.7 Hz, 1.5 Hz), 11.93 (1H, s); LRMS (ESI): m/z $[M + H]^+$ 405. |
| EX.368 | 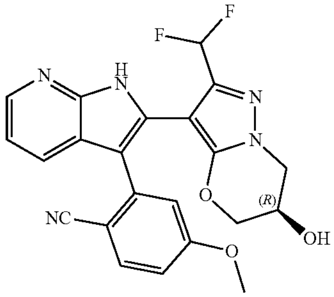 | $^1H$ NMR (400 MHz, DMSO-$d_6$): δ 3.77 (3H, s), 3.95-4.16 (3H, m), 4.25-4.35 (2H, m), 5.61 (1H, br s), 6.63 (1H, t, $J_{H-F}$ = 53.2 Hz) 6.83 (1H, br s), 7.03 (1H, dd, J = 8.8 Hz, 2.4 Hz), 7.15 (1H, dd, J = 7.89, 4.7 Hz), 7.79 (1H, d, J = 8.8 Hz), 7.80 (1H, dd, J = 7.9, 1.6 Hz), 8.30 (1H, d, J = 4.7, 1.6 Hz), 12.10 (1H, br s); LRMS (ESI): m/z $[M + H]^+$ 438. |
| EX.369 | 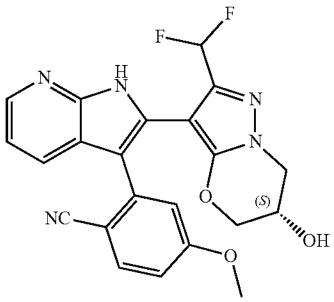 | $^1H$ NMR (400 MHz, DMSO-$d_6$): δ 3.77 (3H, s), 3.95-4.16 (3H, m), 4.25-4.35 (2H, m), 5.61 (1H, br s), 6.63 (1H, t, $J_{H-F}$ = 52 Hz), 6.83 (1H, br s), 7.03 (1H, dd, J = 8.8 Hz, 2.4 Hz), 7.15 (1H, dd, J = 7.8 Hz, 4.7 Hz), 7.76-7.84 (2H, m), 8.28-8.31 (1H, m), 12.10 (1H, s); LRMS (ESI): m/z $[M + H]^+$ 438. |

-continued

| Example No. | Chemical structural formula | Spectrum data |
|---|---|---|
| EX.370 | 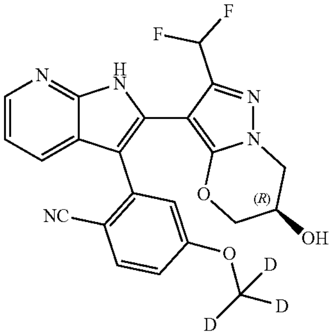 | $^1$H NMR (400 MHz, DMSO-d$_6$): δ 3.93-4.17 (3H, m), 4.23-4.36 (2H, m), 5.60 (1H, br s), 6.63 (1H, t, $J_{H\text{-}F}$ = 52.0 Hz), 6.83 (1H, br s), 7.03 (1H, dd, J = 8.7, 2.6 Hz), 7.15 (1H, dd, J = 8.0, 4.6 Hz), 7.75-7.84 (2H, m), 8.30 (1H, dd, J = 4.7, 1.5 Hz), 12.08 (1H, s); LRMS (ESI): m/z [M + H]$^+$ 441. |
| EX.371 | 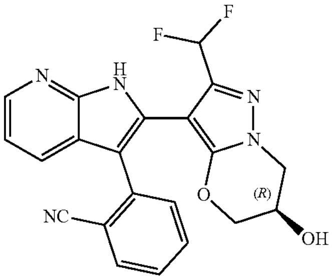 | $^1$H NMR (400 MHz, DMSO-d$_6$): δ 3.83-4.12 (3H, m), 4.21-4.34 (2H, m), 5.60 (1H, br s,), 6.66 (1H, t, $J_{H\text{-}F}$ = 52.0 Hz), 7.15 (1H, dd, J = 8.0, 4.6 Hz), 7.35 (1H, br s), 7.48 (1H, m) 7.62-7.71 (1H, m), 7.79 (1H, dd, J = 7.9, 1.1 Hz), 7.87 (1H, d, J =7.4 Hz), 8.30 (1H, dd, J = 4.7, 1.6 Hz), 12.05 (1H, s); LRMS (ESI): m/z [M + H]$^+$ 408. |

(20) Experimental Procedure of EX.372

EX.372 was prepared in accordance with the general procedures 36 using the method described below in detail.

Synthesis of 2-[5-(6,7-dihydro-5H-pyrazolo[5,1-b][1,3]oxazin-3-yl)-4H-pyrrolo[2,3-d]thiazol-6-yl]benzonitrile (EX.372)

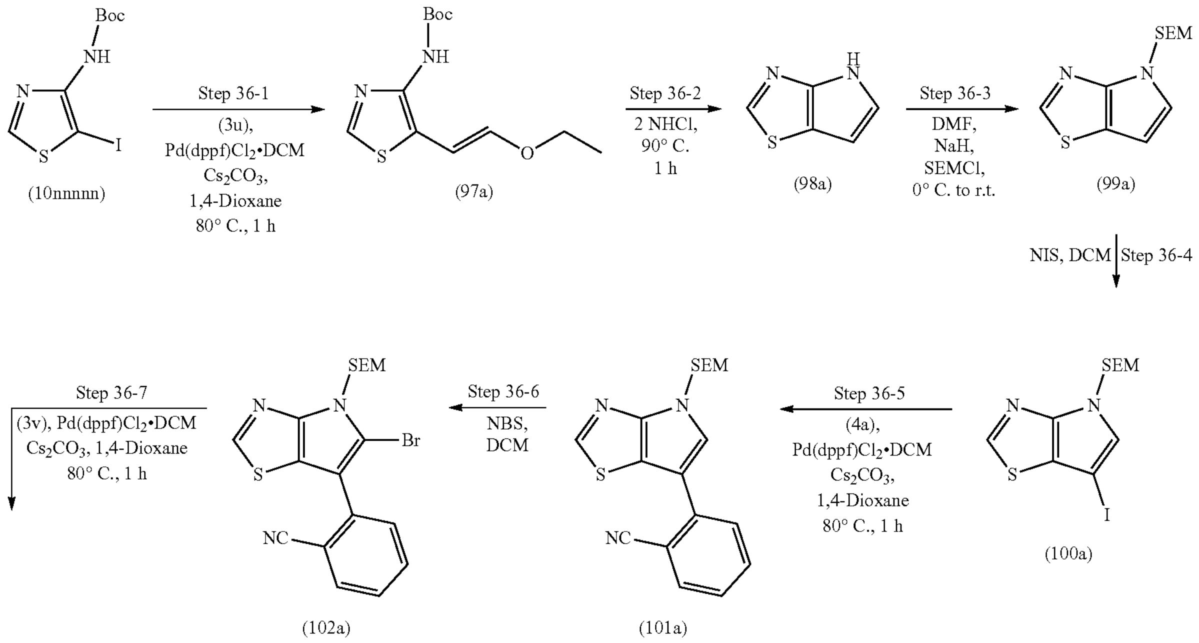

-continued

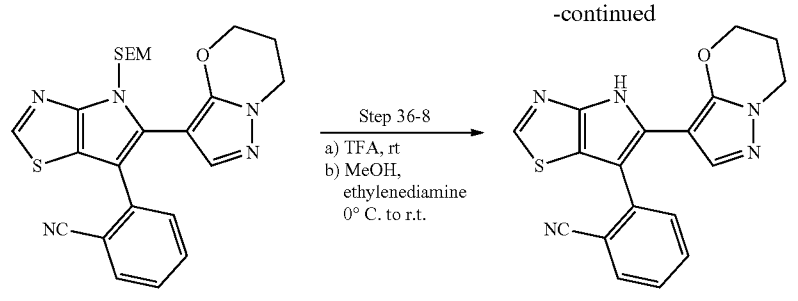

(103a) EX. 372

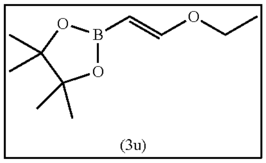
(3u)

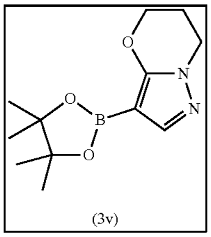
(3v)

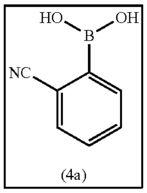
(4a)

Step 36-1

A reaction vessel containing tert-butyl N-(5-iodothiazol-4-yl) carbamate (10nnnnn) (1.6 g, 4.91 mmol), 2-[(E)-2-ethoxyvinyl]-4,4,5,5-tetramethyl-1,3,2-dioxaborolane (3u) (1.17 g, 5.89 mmol) and $Cs_2CO_3$ (4.8 g, 14.72 mmol) in 1,4-dioxane (12 mL) and water (4 mL) was thrice evacuated and backfilled with nitrogen. After the addition of Pd(dppf) $Cl_2$-DCM (600 mg, 0.74 mmol), mixture was again thrice evacuated & backfilled with nitrogen and stirred at 80° C. for 1 h. Thereafter, the aqueous layer was pipetted out and remaining liquid (dark colored) was concentrated. The residue was purified by silica gel column chromatography (eluted with 0-50% EtOAc/Hexanes) to afford a red oil (1.15 g, 87%) as the expected product. LRMS (ESI): m/z $[M+H-tBu]^+$ 215.

Step 36-2

A mixture of tert-butyl N-[5-[(E)-2-ethoxyvinyl]thiazol-4-yl]carbamate (97a) (7.38 g, 27.3 mmol) and 70 ml (2N HCl, 140 mmol) was stirred at 90° C. for 1 h. Thereafter, mixture was decanted to a separatory funnel and extracted thrice with EtOAc. The combined organic extracts were dried over $Na_2SO_4$, filtered, and concentrated. The residue was purified by silica gel column chromatography (eluted with 0-40% EtOAc/Hexanes) to afford a brown oil (1.08 g, 32%); LRMS (ESI): m/z $[M+H]^+$ 125.

Step 36-3

To a solution of 4H-pyrrolo[2,3-d]thiazole (98a) (500 mg, 4.03 mmol) in DMF (15 mL) at 0° C. was added slowly NaH (60% in mineral oil) (193 mg, 4.83 mmol) and stirred at 0° C. for 10 min. Afterwards, SEM-Cl (0.78 mL, 4.43 mmol) was added and stirred at room temperature for 1 h. The mixture was then diluted with DCM, decanted into a separatory funnel, and washed with water. The organic layer was dried over $Na_2SO_4$, filtered, and concentrated. The residue was purified by silica gel column chromatography (eluted with 0-30% EtOAc/Hexanes) to afford a tan-colored oil (965 mg, 94%) as the expected product. LRMS (ESI): m/z $[M+H]^+$ 255.

Step 36-4

A mixture of trimethyl-[2-(pyrrolo[2,3-d]thiazol-4-yl-methoxy)ethyl]silane (99a) (965 mg, 3.79 mmol) and NIS (896 mg, 3.98 mmol) in DCM (20 ml) was stirred for 1 h. Afterwards, additional 500 mg of NIS was added and further stirred for 1 h. Thereafter, mixture was decanted into a separatory funnel containing $Na_2S_2O_3$ (sat. aqueous) and extracted twice with DCM. The combined organic extracts were dried over $Na_2SO_4$, filtered, and concentrated. The residue was purified by silica gel column chromatography (eluted with 0-20% EtOAc/Hexanes) to afford a red oil (1.12 g, 77%); LRMS (ESI): m/z $[M+H]^+$ 381.

Step 36-5

A reaction vessel containing 2-[(6-iodopyrrolo[2,3-d]thiazol-4-yl)methoxy]ethyl-trimethyl-silane (100a) (400 mg, 1.05 mmol), (2-cyanophenyl)boronic acid (4a) (185 mg, 1.26 mmol) and $Cs_2CO_3$ (1.03 g, 3.16 mmol) in 1,4-dioxane (3 mL) and water (1 mL) was thrice evacuated and backfilled with nitrogen. After the addition of Pd(dppf)$Cl_2$-DCM (171 mg, 0.21 mmol), mixture was again thrice evacuated and backfilled with nitrogen and stirred at 80° C. for 1 h Thereafter, the aqueous layer was pipetted out and remaining liquid (dark colored) was concentrated. The residue was purified by silica gel column chromatography (eluted with 0-70% EtOAc/Hexanes) to afford a yellow oil (127.3 mg, 34%) as the expected product. LRMS (ESI): m/z $[M+H]^+$ 356.

Step 36-6

A mixture of 2-[4-(2-trimethylsilylethoxymethyl)pyrrolo[2,3-d]thiazol-6-yl]benzonitrile (101a) (127 mg, 0.36 mmol) and NBS (76 mg, 0.43 mmol) in DCM (2 mL) was stirred at room temperature for 1 h. Afterwards, mixture was concentrated and purified by silica gel column chromatography (eluted with 0-20% EtOAc/Hexanes) to afford a dark brown oil (119.7 mg, 77%) as the expected product. LRMS (ESI): m/z $[M+H]^+$ 434, 436.

Step 36-7

A reaction vessel containing 2-[5-bromo-4-(2-trimethylsilylethoxymethyl)pyrrolo[2,3-d]thiazol-6-yl]benzonitrile (102a) (50 mg, 0.12 mmol), 3-(4,4,5,5-tetramethyl-1,3,2-dioxaborolan-2-yl)-6,7-dihydro-5H-pyrazolo[5,1-b][1,3]oxazine (3v) (58 mg, 0.23 mmol) and $Cs_2CO_3$ (112 mg, 0.35 mmol) in 1,4-dioxane (1 mL) and water (0.3 mL) was thrice evacuated and backfilled with nitrogen. After the addition of Pd(dppf)$Cl_2$-DCM (18.8 mg, 0.02 mmol), mixture was again thrice evacuated and backfilled with nitrogen and stirred at 80° C. for 1 h. Thereafter, the aqueous layer was pipetted out and remaining liquid (dark colored) was concentrated. The residue was purified by silica gel column chromatography (eluted with 0-50% EtOAc/Hexanes) to afford a dark brown oil (25.2 mg, 46%) as the expected product. LRMS (ESI): m/z $[M+H]^+$ 478.

Step 36-8

A mixture of 2-[5-(6,7-dihydro-5H-pyrazolo[5,1-b][1,3]oxazin-3-yl)-4-(2-trimethylsilylethoxymethyl)pyrrolo[2,3-d]thiazol-6-yl]benzonitrile (103a) (25 mg, 0.05 mmol) and neat TFA (0.2 mL, 2.64 mmol) was stirred at room temperature for 30 min. Afterwards, mixture was concentrated, dissolved in MeOH (0.5 mL), treated with ethylenediamine (0.12 mL, 1.75 mmol) and stirred for 30 min at room temperature Thereafter, mixture was directly purified by silica gel column chromatography (eluted with 0-100% EtOAc/Hexanes). Fractions with product were concentrated and re-purified by prep-HPLC (Kinetex 5u C18 100A RXI, 150×21.20 mm, 30-70% $CH_3CN$ w/0.1% TFA in $H_2O$ w/0.1% TFA for 8 min, flow rate 20 mL/min). Pure fractions of product were passed through a PL-$HCO_3$ MP column and lyophilized to afford an off-white solid (10.2 mg, 54%) as the expected product.

$^1H$ NMR (400 MHz, DMSO-$d_6$) δ 2.03 2.11 (2H, m), 3.93-4.01 (2H, m), 4.06 (2H, t, J=6.0 Hz), 7.28 (1H, s), 7.46 (2H, apparent t, J=7.3 Hz), 7.65 (1H, apparent t, J=7.6 Hz), 7.85 (1H, d, J=7.9 Hz), 8.79 (1H, s), 12.20 (1H, s); LRMS (ESI): m/z $[M+H]^+$ 348.

The following compound was synthesized using conditions analogous to EX.372 in accordance with the general procedure 36.

| Example No. | Chemical structural formula | Spectrum data |
|---|---|---|
| EX.373 | 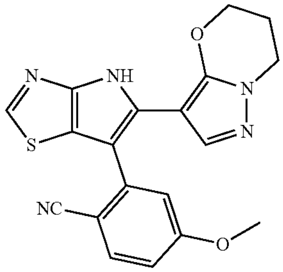 [SMILES: COc1ccc(C#N)c(-c2c(-c3cnn4c3OCCC4)[nH]c3ncsc23)c1] | $^1H$ NMR (400 MHz, DMSO-$d_6$) δ 2.04-2.14 (2H, m), 3.78 (3H, s), 4.02-4.12 (4H, m), 6.94 (1H, s), 7.02 (1H, d, J = 7.3 Hz), 7.28 (1H, s), 7.78 (1H, d, J = 8.8 Hz). 8.79 (1H, s). 12.18 (1H, s); LRMS (ESI): m/z $[M + H]^+$ 378. |
| EX.374 | 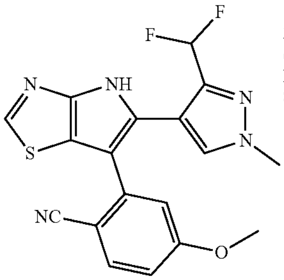 [SMILES: COc1ccc(C#N)c(-c2c(-c3cn(C)nc3C(F)F)[nH]c3ncsc23)c1] | $^1H$ NMR (400 MHz, DMSO-d6) δ 3.71 (3H, s), 3.91 (3H, s), 6.66 (1H, t, $J_{H-F}$ = 53.6 Hz), 6.81 (1H, d, J = 1.9 Hz), 7.01 (1H, dd, J = 8.3, 2.0 Hz), 7.79 (1H, d, J = 8.5 Hz), 7.94 (1H, s), 8.90 (1H, s), 12.46 (1H, s); LRMS (ESI): m/z $[M + H]^+$ 386. |

(21) Experimental Procedure of EX.375

EX.375 was prepared in accordance with the general procedures 3, 37 and 1 using the method described below in detail.

Synthesis of 4-chloro-2-[2-[3-(difluoromethyl)-1-methyl-pyrazol-4-yl]-1H-pyrrolo[2,3-b]pyridin-3-yl]benzonitrile (EX.375)

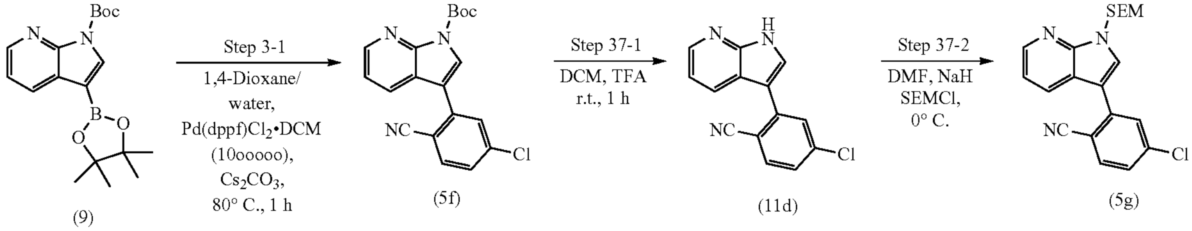

(9) (5f) (11d) (5g)

-continued

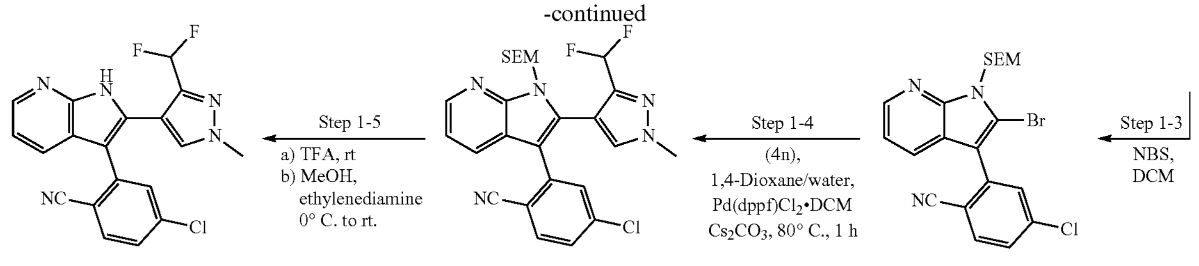

EX. 375 (7z) (6f)

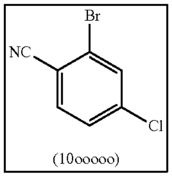

(10ooooo)

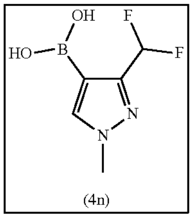

(4n)

Step 3-1

A reaction vessel containing tert-butyl 3-(4,4,5,5-tetramethyl-1,3,2-dioxaborolan-2-yl)pyrrolo[2,3-b]pyridine-1-carboxylate (9) (5 g, 14.53 mmol), 2-bromo-4-chloro-benzonitrile (1000000) (3.77 g, 17.43 mmol) and $Cs_2CO_3$ (14.2 g, 43.58 mmol) in 1,4-dioxane (30 mL) and water (10 mL) was thrice evacuated & backfilled with nitrogen. After the addition of Pd(dppf)$Cl_2$-DCM (1.78 g, 2.18 mmol), mixture was again thrice evacuated & backfilled with nitrogen and stirred at 80° C. for 1 h. Thereafter, the aqueous layer was pipetted out and remaining liquid (dark colored) was concentrated. The residue was purified by silica gel column chromatography (eluted with 0-100% EtOAc/Hexanes) to afford an orange solid (4.87 g, 95%) as the expected product. LRMS (ESI): m/z $[M+H]^+$ 354.

Step 37-1

To a solution of tert-butyl 3-(5-chloro-2-cyano-phenyl) pyrrolo[2,3-b]pyridine-1-carboxylate (5f) (5.09 g, 14.39 mmol) in DCM (50 mL) was added TFA (22 mL, 287.73 mmol) at room temperature and stirred for 1 h. Afterwards, mixture was concentrated, treated with saturated aqueous solution of $NaHCO_3$ and stirred vigorously for 10 min. Thereafter, solids were filtered, washed with water and dried to afford product as a TFA salt (5.13 g, 97%, orange solid); LRMS (ESI): m/z $[M+H]^+$ 254.

Step 37-2

To a solution of 4-chloro-2-(1H-pyrrolo[2,3-b]pyridin-3-yl)benzonitrile (11d) (2.07 g, 8.16 mmol) in DMF (40 mL) was added NaH (60% in mineral oil) (489.57 mg, 12.24 mmol) at 0° C. and stirred for 10 min. Afterwards, SEM-Cl (1.73 mL, 9.79 mmol) was added slowly, and the resulting mixture was stirred further at 0° C. for 1 h. The reaction was quenched with water and extracted thrice with DCM (×3). The combined organic extracts were dried over $Na_2SO_4$, filtered, and concentrated. The residue was purified by silica gel column chromatography (eluted with 0-30% EtOAc/Hexanes) to afford a pale-yellow solid (824 mg, 26%) as the expected product. LRMS (ESI): m/z $[M+H]^+$ 384.

Step 1-3

To a solution of 4-chloro-2-[1-(2-trimethylsilylethoxymethyl)pyrrolo[2,3-b]pyridin-3-yl]benzonitrile (5g) (824 mg, 2.15 mmol) in DCM (10 mL) was added NBS (420 mg, 2.36 mmol, see note) and stirred for a total 2 h and 40 min. at room temperature. Reaction mixture diluted with DCM, washed with $NaHCO_3$ (sat. aqueous solution), dried over $Na_2SO_4$, filtered, and concentrated. The residue was then purified by silica gel column chromatography (eluted with 0-20% EtOAc/Hexanes) to afford a peach-colored oil (956 mg, 96%) as the expected product. LRMS (ESI): $[M+H]^+$ 462, 464.

Note: Additional 2 drops of bromine were added after 2 h and followed by 5 drops after 10 min.

Step 1-4

A reaction vessel containing 2-[2-bromo-1-(2-trimethylsilylethoxymethyl)pyrrolo[2,3-b]pyridin-3-yl]-4-chloro-benzonitrile (6f) (50 mg, 0.11 mmol), [3-(difluoromethyl)-1-methyl-pyrazol-4-yl]boronic acid (4n) (23 mg, 0.13 mmol) and $Cs_2CO_3$ (105 mg, 0.32 mmol) in 1,4-dioxane (1 mL) and water (0.3 mL) was thrice evacuated and backfilled with nitrogen. After the addition of Pd(dppf)$Cl_2$-DCM (18 mg, 0.02 mmol), mixture was again thrice evacuated and backfilled with nitrogen and stirred at 80° C. for 1 h. Thereafter, the aqueous layer was pipetted out and remaining liquid (dark colored) was directly purified by silica gel column chromatography (eluted with 0-70% EtOAc/Hexanes) to afford a colorless oil (32.8 mg, 59%) as the expected product. LRMS (ESI): m/z $[M+H]^+$ 514.

Step 1-5

A mixture of 4-chloro-2-[2-[3-(difluoromethyl)-1-methyl-pyrazol-4-yl]-1-(2-trimethylsilylethoxymethyl)pyrrolo[2,3-b]pyridin-3-yl]benzonitrile (7z) (32.8 mg, 0.06 mmol) and neat TFA (0.24 mL, 3.19 mmol) was stirred at room temperature for 30 min. Afterwards. Afterwards, the mixture was concentrated, dissolved in MeOH (0.5 mL) treated with ethylenediamine (0.12 mL, 1.75 mmol), and stirred for 30 min at room temperature. Thereafter, mixture was directly purified by silica gel column chromatography (eluted with 0-100% EtOAc/Hexanes). Fractions with product were concentrated and re-purified by prep HPLC (Kinetex 5u C18 100A RXI, 150×21.20 mm, 20-70% $CH_3CN$ w/0.1% TFA in $H_2O$ w/0.1% TFA for 8 min, flow rate 20 mL/min). Pure fractions of product were passed through a PL-$HCO_3$ MP column and lyophilized to afford a white solid (3.9 mg, 15%) as the expected product. LRMS (ESI): m/z $[M+H]^+$ 384.

$^1H$ NMR (400 MHz, DMSO-$d_6$): δ 3.93 (3H, s), 6.69 (1H, t, $J_{H-F}$=53.9 Hz), 7.18 (1H, dd, J=7.9, 4.7 Hz), 7.49 (1H, d, J=2.1 Hz), 7.60 (1H, dd, J=8.4, 2.1 Hz), 7.82 (1H, dd, J=7.9, 1.5 Hz), 7.93 (1H, d, J=8.4 Hz), 8.01 (1H, s), 8.33 (1H, dd, J=4.7, 1.5 Hz), 12.30 (1H, s); LRMS (ESI): m/z $[M+H]^+$ 384.

The following compounds were synthesized analogous to EX.375 in accordance with the general procedures 1, 3 and 37 using the appropriate starting material.

| Example No. | Chemical structural formula | Spectrum data |
|---|---|---|
| EX.376 | 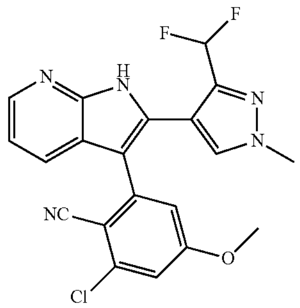 [SMILES: COc1cc(Cl)c(C#N)c(-c2c(-c3cn(C)nc3C(F)F)[nH]c3ncccc23)c1] | $^1$H NMR (400 MHz, DMSO-$d_6$): δ 3.82 (3H, s), 3.94 (3H, s), 6.71 (1H, t, $J_{H-F}$ = 53.9 Hz), 6.89 (1H, d, J = 2.4 Hz), 7.17 (1H, dd, J = 7.9, 4.7 Hz), 7.32 (1H, d, J = 2.4 Hz), 7.84 (1H, dd, J = 7.9, 1.5 Hz), 8.01 (1H, s), 8.33 (1H, dd, J = 4.7, 1.5 Hz), 12.27 (1H, s); LRMS (ESI): m/z $[M + H]^+$ 414. |
| EX.377 | 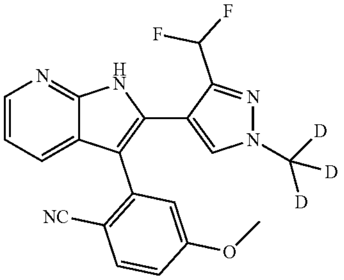 [SMILES: [2H]C([2H])([2H])n1cc(-c2[nH]c3ncccc3c2-c2cc(OC)ccc2C#N)c(C(F)F)n1] | $^1$H NMR (400 MHz, DMSO-$d_6$): δ 3.79 (3H, s), 6.62 (1H, t, $J_{H-F}$ = 54.0 Hz), 6.93 (1H, d, J = 2.6 Hz), 7.07 (1H, dd, J = 8.7, 2.6 Hz), 7.16 (1H, dd, J = 7.9, 4.7 Hz), 7.77-7.85 (2H, m), 7.96 (1H, s), 8.32 (1H, dd, J = 4.7, 1.6 Hz), 12.19 (1H, br s); LRMS (ESI): m/z $[M + H]^+$ 383. |
| EX.378 | 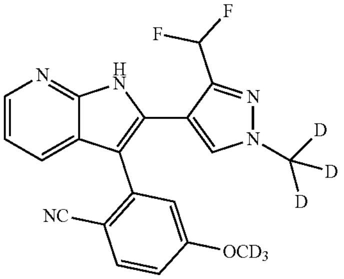 | $^1$H NMR (400 MHz, DMSO-$d_6$): δ 6.62 (1H, t, $J_{H-F}$ = 54.0 Hz), 6.92 (1H, d, J = 2.5 Hz), 7.07 (1H, dd, J = 8.7, 2.6 Hz), 7.16 (1H, dd, J = 7.9, 4.7 Hz), 7.78-7.84 (2H, m), 7.96 (1H, s), 8.32 (1H, dd, J = 4.7, 1.6 Hz); LRMS (ESI): m/z $[M + H]^+$ 386. |
| EX.379 | 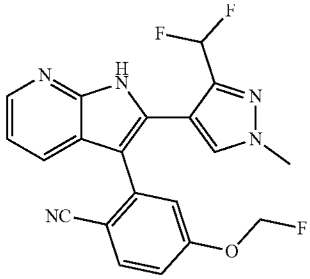 [SMILES: Cn1cc(-c2[nH]c3ncccc3c2-c2cc(OCF)ccc2C#N)c(C(F)F)n1] | $^1$H NMR (400 MHz, $(CD_3)_2CO$): δ 3.97 (3H, s), 5.92 (2H, d, $J_{H-F}$ = 53.0 Hz), 6.67 (1H, t, $J_{H-F}$ = 54.0 Hz), 7.16-7.30 (3H, m), 7.81-7.93 (3H, m), 8.36 (1H, s); LRMS (ESI): m/z $[M + H]^+$ 398. |
| EX.380 | 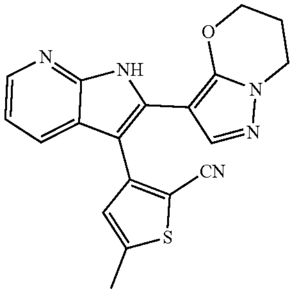 [SMILES: Cc1cc(-c2c(-c3cnn4c3OCCC4)[nH]c3ncccc23)c(C#N)s1] | $^1$H NMR (400 MHz, DMSO-$d_6$): δ 2.09-2.21 (2H, m), 2.56 (3H, s), 4.12 (4H, m), 7.00 (1H, s), 7.12 (1H, dd, J = 7.8, 4.7 Hz), 7.49 (1H, s), 7.81 (1H, d, J = 7.2 Hz), 8.23 (1H, d, J = 3.6 Hz), 12.00 (1H, s) ; LRMS (ESI): m/z $[M + H]^+$ 362. |

-continued

| Example No. | Chemical structural formula | Spectrum data |
|---|---|---|
| EX.381 | 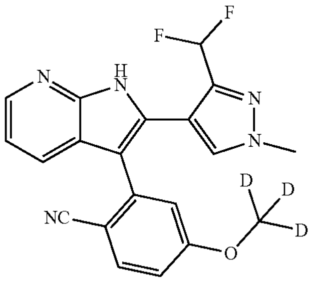 [SMILES: [2H]C([2H])([2H])Oc1ccc(C#N)c(-c2c(-c3cn(C)nc3C(F)F)[nH]c3ncccc23)c1] | $^1H$ (400 MHz, DMSO-$d_6$): δ 3.92 (3H, s), 6.61 (1H, t, $J_{H-F}$ = 53.9 Hz), 6.92 (1H, d, J = 2.6 Hz), 7.06 (1H, dd, J = 8.7, 2.6 Hz), 7.16 (1H, dd, J = 7.9, 4.7 Hz), 7.80 (2H, d, J = 8.7 Hz), 7.97 (1H, s), 8.31 (1H, dd, J = 4.7, 1.6 Hz), 12.21 (1H, s); LRMS (ESI): m/z $[M + H]^+$ 383. |
| EX.382 | 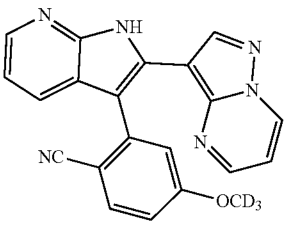 | $^1H$ (400 MHz, DMSO-$d_6$): δ 7.04-7.11 (2H, m), 7.09-7.19 (2H, m), 7.77-7.82 (2H, m), 8.13 (1H, s), 8.30 (1H, dd, J = 4.6, 1.4 Hz), 8.54 (1H, dd, J = 4.3, 1.8 Hz), 9.18 (1H, dd, J = 7.1, 1.8 Hz), 12.03 (1H, s); LRMS (ESI): m/z $[M + H]^+$ 370. |
| EX.383 | 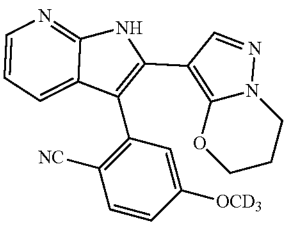 | $^1H$ (400 MHz, $CD_3OD$): δ 2.29 (2H, qd, J = 6.4, 4.3 Hz), 4.17 (2H, t, J = 6.2 Hz), 4.34 (2H, ddd, J = 6.8, 4.8, 2.9 Hz), 7.13 (1H, d, J = 2.6 Hz), 7.17 (1H, dd, J = 8.7, 2.6 Hz), 7.21 (1H, s), 7.46 (1H, dd, J = 7.9, 5.7 Hz), 7.82 (1H, d, J = 8.7 Hz), 8.20 (1H, dd, J = 7.9, 1.2 Hz), 8.31 (1H, d, J = 5.8 Hz); LRMS (ESI): m/z $[M + H]^+$ 375. |
| EX.384 | 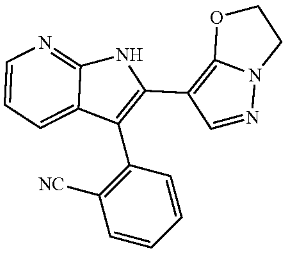 [SMILES: N#Cc1ccccc1-c1c(-c2cnn3c2OCC3)[nH]c2ncccc12] | $^1H$ (400 MHz, DMSO-$d_6$): δ 4.15-4.32 (2H, m), 4.70-4.96 (2H, m), 7.08 (1H, dd, J =7.9, 4.7 Hz), 7.45-7.58 (2H, m), 7.63 (1H, d, J=7.9 Hz), 7.68 (1H, s), 7.72 (1H, t, J = 7.7 Hz), 7.89 (1H, d, J = 7.6 Hz), 8.22 (1H, dd, J = 4.7, 1.4 Hz), 12.12 (1H, s); LRMS (ESI): m/z $[M + H]^+$ 328. |
| EX.385 | 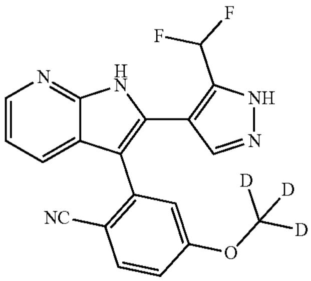 [SMILES: [2H]C([2H])([2H])Oc1ccc(C#N)c(-c2c(-c3cn[nH]c3C(F)F)[nH]c3ncccc23)c1] | $^1H$ (400 MHz, DMSO-$d_6$): δ 6.65 (1H, t, $J_{H-F}$ = 54.0 Hz), 6.90 (1H, d, J = 2.6 Hz), 7.05 (1H, dd, J = 8.7, 2.6 Hz), 7.16 (1H, dd, J = 7.9, 4.7 Hz), 7.79 (1H, d, J = 8.6 Hz), 7.81 (1H, dd, J = 7.9, 1.5 Hz), 7.96 (1H, s), 8.31 (1H, dd, J = 4.7, 1.6 Hz), 12.20 (1H, s), 13.61 (1H, s); LRMS (ESI): m/z $[M + H]^+$ 369. |

-continued

| Example No. | Chemical structural formula | Spectrum data |
| --- | --- | --- |
| EX.386 | 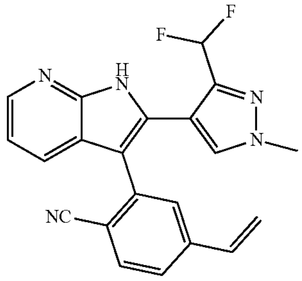 [SMILES: C=Cc1ccc(C#N)c(-c2c(-c3cn(C)nc3C(F)F)[nH]c3ncccc23)c1] | [1]H (400 MHz, DMSO-$d_6$): δ 3.90 (3H, s), 5.45 (1H, d, J = 11.4 Hz), 5.96 (1H, d, J = 17.1 Hz), 6.62 (1H, t, $J_{H\text{-}F}$ = 54.0 Hz), 6.79 (1H, dd, J = 16.6, 10.0 Hz), 7.16 (1H, dd, J = 7.9, 4.7 Hz), 7.51 (1H, d, J = 1.7 Hz), 7.62 (1H, dd, J = 8.1, 1.7 Hz), 7.78 (1H, dd, J = 8.2, 1.2 Hz), 7.84 (1H, d, J = 8.1 Hz), 7.96 (1H, s), 8.32 (1H, dd, J = 4.7, 1.6 Hz), 12.21 (1H, s); LRMS (ESI): m/z $[M + H]^+$ 376. |

(22) Experimental Procedure of EX.387

EX.387 was prepared in accordance with the general procedure 39 using the method described below in detail.

Synthesis of 2-[6-[3-(difluoromethyl)-1-methyl-pyrazol-4-yl]-7H-pyrrolo[2,3-d]pyrimidin-5-yl]-4-methoxy-benzonitrile (EX.387)

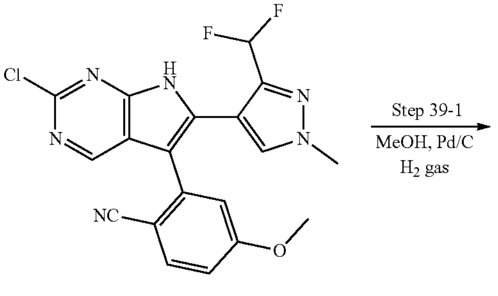

EX.82

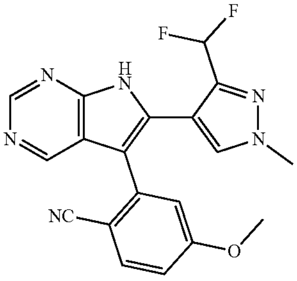

EX.387

Step 39-1

To a solution of 2-[2-chloro-6-[3-(difluoromethyl)-1-methyl-pyrazol-4-yl]-7H-pyrrolo[2,3-d]pyrimidin-5-yl]-4-methoxy-benzonitrile (EX.82) (6.4 mg, 0.02 mmol) in methanol (0.5 mL) was added 10% Pd/C (1.64 mg, 0.015 mmol) under $N_2$ was thrice evacuated and backfilled with hydrogen and the mixture was stirred under $H_2$ atmosphere (balloon) at room temperature for a total of ~4 days. Thereafter, mixture was filtered through a pad of Celite, concentrated and purified by silica gel column chromatography (eluted with 0-100% EtOAc/Heaxnes followed by 0-20% MeOH in DCM). Fractions with product was concentrated and re-purified by prep-HPLC (Kinetex 5u C18 100A RXI, 150×21.20 mm, 20-70% $CH_3CN$ w/0.1% TFA in $H_2O$ w/0.1% TFA for 8 min, flow rate 20 mL/min). Pure fractions were passed through a PL-$HCO_3$ MP column and lyophilized to afford EX.387 (3.5 mg, 59%) as a white solid. $^1$H NMR (400 MHz, DMSO-$d_6$): δ 3.80 (3H, s), 3.93 (3H, s), 6.67 (1H, t, $J_{H\text{-}F}$=53.9 Hz), 6.98 (1H, d, J=2.6 Hz), 7.10 (1H, dd, J=8.7, 2.6 Hz), 7.83 (1H, d, J=8.7 Hz), 8.03 (1H, s), 8.87 (2H, d, J=9.7 Hz), 12.69 (1H, s); LRMS (ESI): m/z $[M+H]^+$ 381.

(23) Experimental Procedure of EX.388

EX.388 was prepared in accordance with the general procedure 39 using the method described below in detail.

Synthesis of 3-(3-(3-(difluoromethoxy)pyridazin-4-yl)-1H-pyrrolo[2,3-b]pyridin-2-yl)-2-(difluoromethyl)-6,7-dihydro-5H-pyrazolo[5,1-b][1,3]oxazine (EX.388)

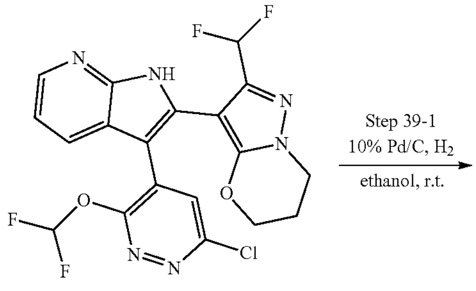

EX. 389

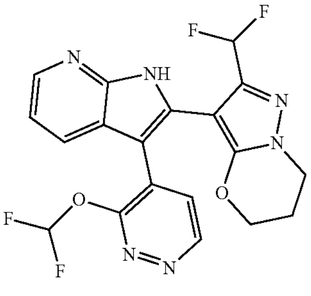

EX. 388

Step 39-1

A solution of 3-(3-(6-chloro-3-(difluoromethoxy)pyridazin-4-yl)-1H-pyrrolo[2,3-b]pyridin-2-yl)-2-(difluoromethyl)-6,7-dihydro-5H-pyrazolo[5,1-b][1,3]oxazine (EX.389) (2 mg) and 10% Pd/C (1 mg) in ethanol (0.2 mL) was thrice degassed and backfilled with $N_2$. Afterwards, mixture was thrice degassed and backfilled with hydrogen (balloon). The reaction mixture was stirred at room temperature overnight. Thereafter, mixture was filtered through celite and purified by prep-HPLC to afford EX.388 (1.18 mg, 62%) as a yellow oil.

$^1$H NMR (400 MHz, $CD_3OD$): δ 2.15-2.30 (2H, m), 4.08-4.25 (4H, m), 6.59 (2H, t, J=54.1 Hz), 7.31 (1H, dd, J=8.0, 5.0 Hz), 7.68 (1H, d, J=4.9 Hz), 7.73 (1H, t, J=72.1 Hz), 8.14 (1H, dd, J=8.0, 1.4 Hz), 8.34 (1H, d, J=4.4 Hz), 8.96 (1H, d, J=4.9 Hz); LRMS (ESI): m/z $[M+H]^+$ 435.

(24) Experimental Procedure of 2-(2-(cyclopropanecarbonyl)-1H-pyrrolo[2,3-b]pyridin-3-yl)-4-methoxybenzonitril 2-(2-(cyclopropanecarbonyl)-1H-pyrrolo[2,3-b]pyridin-3-yl)-4-methoxybenzonitrile was prepared in accordance with the general procedures 38, 6 and 48 using the method described below in detail.

Synthesis of 2-(2-(cyclopropanecarbonyl)-1H-pyrrolo[2,3-b]pyridin-3-yl)-4-methoxybenzonitrile

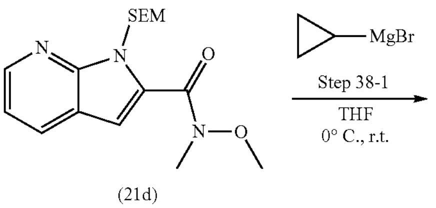

(21d)

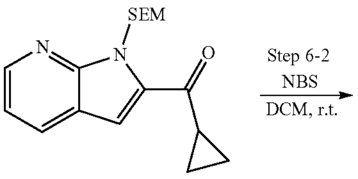

(21e)

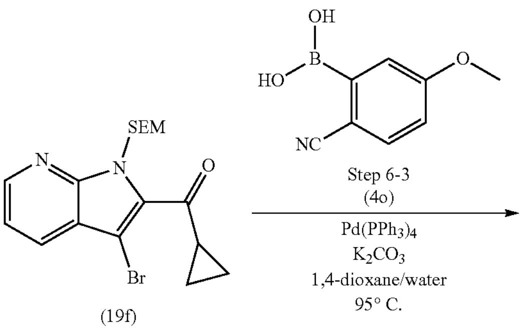

(19f)

-continued

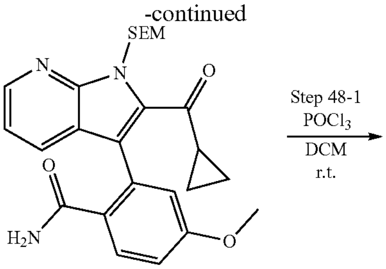

(20j)

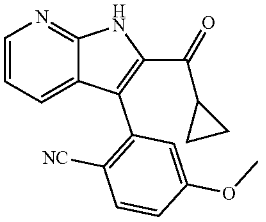

Step 38-1

To a solution of N-methoxy-N-methyl-1-(2-trimethylsilylethoxymethyl)pyrrolo[2,3-b]pyridine-2-carboxamide (21d) (130 mg, 0.39 mmol) in THF (5 mL) in ice bath was slowly added cyclopropylmagnesium bromide solution (1M in 2-methyltetrahydrofuran) (2.6 mL, 2.6 mmol). Then the reaction was warmed up to room temperature and stirred for 3.5 hr. The mixture was concentrated and purified by ISCO normal-phase silica flash chromatography (0~40% EA in HX) to obtain product (21e) as yellow solid (88 mg, 71%); LRMS (ESI): m/z $[M+H]^+$ 317; m/z $[M+Na]^+$ 339.

Step 6-2 as Per General Procedure 6.

Step 6-3

A vial containing of (2-cyano-5-methoxy-phenyl)boronic acid (40) (12.1 mg, 0.07 mmol), [3-bromo-1-(2-trimethylsilylethoxymethyl)pyrrolo[2,3-b]pyridin-2-yl]-cyclopropylmethanone (19f) (17 mg, 0.04 mmol), potassium carbonate (17.8 mg, 0.13 mmol) and tetrakis(triphenylphosphine)palladium(0) (7.5 mg, 0.01 mmol) was vacuumed and refilled with $N_2$ three times. Afterwards, 1,4-Dioxane (2 mL) and Water (0.5 mL) were added into the vial and the mixture was again vacuumed and refilled with $N_2$ three times. The resulting mixture was heated at 95° C. for 2h 43 min. After reaction was cooled down, the organic layer was separated, concentrated, and purified by silica gel column chromatography (0~90% EtOAc/Hexanes) to obtain product (20j) as colorless film (12.8 mg, 60%); LRMS (ESI): m/z $[M+H]^+$ 466.

Step 48-1

To a solution of 2-[2-(cyclopropanecarbonyl)-1-(2-trimethylsilylethoxymethyl)pyrrolo[2,3-b]pyridin-3-yl]-4-methoxy-benzamide (20j) (12.8 mg, 0.03 mmol) in DCM (0.6 mL) was added $POCl_3$ (1.14 mL). The mixture was stirred at room temperature for ~3 h. Then it was concentrated and purified by silica gel column chromatography (0~65% ethyl acetate/hexanes) and then prep-TLC plate to obtain 2-(2-(cyclopropanecarbonyl)-1H-pyrrolo[2,3-b]pyridin-3-yl)-4-methoxybenzonitrile as white solid (0.58 mg, 6%).

$^1$H (400 MHz, DMSO-$d_6$) δ 0.86-0.99 (2H, m), 0.99-1.13 (2H, m), 2.19-2.29 (1H, m), 3.89 (3H, s), 7.18 (1H, dd, J=8.7, 2.6 Hz), 7.20-7.25 (2H, m), 7.87 (1H, dd, J=8.1, 1.5 Hz), 7.90 (1H, d, J=8.6 Hz), 8.52 (1H, dd, J=4.6, 1.6 Hz), 12.78 (1H, s); LRMS (ESI): m/z $[M+H]^+$ 318.

(25) Experimental Procedure of EX.391

EX.391 were prepared in accordance with the general procedures 40 using the method described below in detail.

Synthesis of methyl 2-(4-(3-(2-cyano-5-methoxyphenyl)-1H-pyrrolo[2,3-b]pyridin-2-yl)-3-(trifluoromethyl)-1H-pyrazol-1-yl)acetate (EX.391)

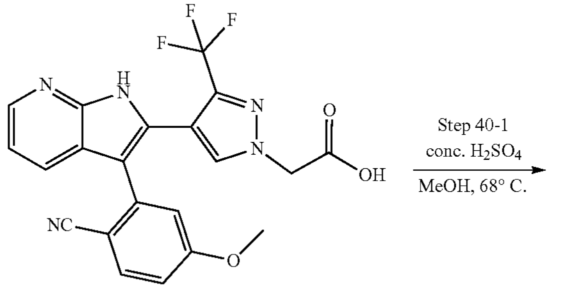

EX.229

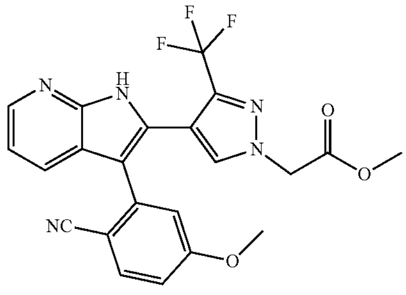

EX.391

Step 40-1

To a solution of 2-[4-[3-(2-cyano-5-methoxy-phenyl)-1H-pyrrolo[2,3-b]pyridin-2-yl]-3-(trifluoromethyl)pyrazol-1-yl]acetic acid (EX.229) (40 mg, 0.09 mmol) in methanol (2 mL) was added conc. $H_2SO_4$ (0.03 mL). The solution was heated at 68° C. for 1 h. After the mixture was cooled down, it was purified by Prep HPLC to obtain EX.391 as white solid (2.86 mg, 7%).

$^1H$ (400 MHz, DMSO-$d_6$) δ 3.70 (3H, s), 3.75 (3H, s), 5.28 (2H, s), 6.81 (1H, d, J=2.5 Hz), 7.04 (1H, dd, J=8.7, 2.6 Hz), 7.18 (1H, dd, J=8.0, 4.7 Hz), 7.80 (1H, d, J=8.7 Hz), 7.83 (1H, dd, J=8.0, 1.5 Hz), 8.16 (1H, d, J=0.9 Hz), 8.34 (1H, dd, J=4.7, 1.6 Hz), 12.38 (1H, s); LRMS (ESI): m/z $[M+H]^+$ 456.

(26) Experimental Procedure of EX.392

EX.392 was prepared in accordance with the general procedures 41 using the method described below in detail.

Synthesis of 4-methoxy-2-(2-(2-methyl-6-((tetrahydro-2H-pyran-4-yl)amino)-6,7-dihydro-5H-pyrazolo[5,1-b][1,3]oxazin-3-yl)-1H-pyrrolo[2,3-b]pyridin-3-yl)benzonitrile (EX.392)

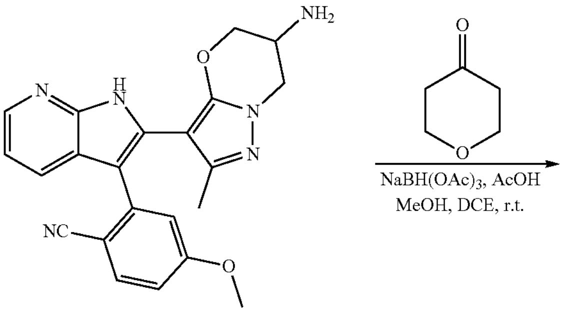

(108a)

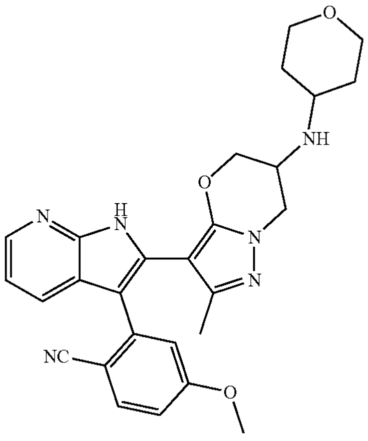

EX.392

Step 41-1 (J. Med. Chem. 2019, 62, 1761-1780)

A solution of 2-[2-(6-amino-2-methyl-6,7-dihydro-5H-pyrazolo[5,1-b][1,3]oxazin-3-yl)-1H-pyrrolo[2,3-b]pyridin-3-yl]-4-methoxy-benzonitrile (108a) (36 mg, 0.09 mmol) and tetrahydropyran-4-one (0.01 mL, 0.06 mmol) and NaBH (OAc) 3 (25.4 mg, 0.12 mmol) and AcOH (0.01 mL, 0.12 mmol) in DCE (1 mL) and methanol (0.2 mL) was stirred at room temperature overnight. The mixture was concentrated and purified by silica gel column chromatography (0-12% MeOH in DCM) to obtain EX.392 as light-yellow solid (1.25 mg, 4%).

$^1$HNMR (400 MHz, $CD_3OD$) δ 1.29 (3H, s), 1.63-1.91 (4H, m), 2.84-2.97 (1H, m), 3.44 (2H, td, J=11.8, 2.1 Hz), 3.50-3.58 (1H, m), 3.89 (3H, s), 3.90-4.09 (3H, m), 4.13-4.38 (3H, m), 7.03 (1H, dd, J=8.7, 2.6 Hz), 7.11 (1H, s), 7.18 (1H, dd, J=7.9, 4.9 Hz), 7.68 (1H, d, J=8.6 Hz), 7.94 (1H, d, J=6.9 Hz), 8.24 (1H, d, J=4.0 Hz); LRMS (ESI): m/z $[M+H]^+$ 485.

(27) Experimental Procedure of EX.393

EX.393 was prepared in accordance with the general procedure 42 using the method described below in detail.

Synthesis of 2-(4-(3-(2-cyano-5-methoxyphenyl)-1H-pyrrolo[2,3-b]pyridin-2-yl)-3-(trifluoromethyl)-1H-pyrazol-1-yl) acetamide (EX.393)

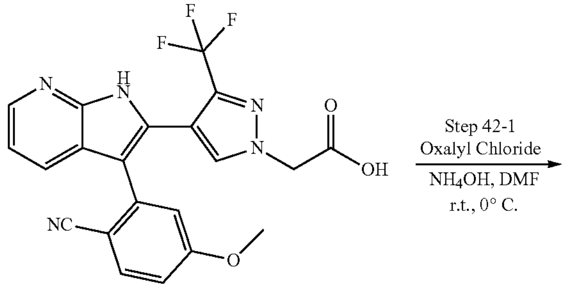

EX.229

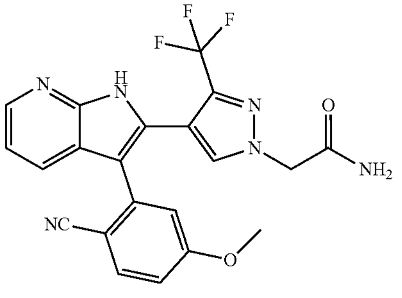

EX.393

Step 42-1

A solution of 2-[4-[3-(2-cyano-5-methoxy-phenyl)-1H-pyrrolo[2,3-b]pyridin-2-yl]-3-(trifluoromethyl)pyrazol-1-yl]acetic acid (EX.229) (40 mg, 0.09 mmol) in DMF (1.5 mL) was stirred in ice bath for 10 minutes before oxalyl chloride (0.01 mL, 0.1 mmol) was added. The mixture was stirred in ice bath for another 10 minutes before $NH_4OH$ (28% aq. solution) (0.22 mL, 1.72 mmol) was added. The reaction was warmed up to room temperature and stopped after 1h 40 min. The reaction mixture was concentrated and purified by silica gel column chromatography (0~8% MeOH in DCM) and then by Agilent Prep HPLC to obtain EX.393 as white solid (2.9 mg, 7%).

$^1$HNMR (400 MHz, DMSO-$d_6$) δ 3.74 (3H, s), 4.92 (2H, s), 6.81 (1H, d, J=2.6 Hz), 7.02 (1H, dd, J=8.7, 2.6 Hz), 7.17 (1H, dd, J=8.0, 4.7 Hz), 7.39 (1H, s), 7.65 (1H, s), 7.79 (1H, d, J=8.7 Hz), 7.82 (1H, dd, J=7.9, 1.6 Hz), 8.13 (1H, d, J=0.8 Hz), 8.33 (1H, dd, J=4.7, 1.6 Hz), 12.34 (1H, s); LRMS (ESI): m/z $[M+H]^+$ 441.

EX.394 was synthesized using conditions analogous to EX.393 in accordance with the general procedure 42.

4-(3-(2-fluoro-5-methylphenyl)-1H-pyrrolo[2,3-b]pyridin-2-yl)-1-methyl-1H-pyrazole-3-carboxamide

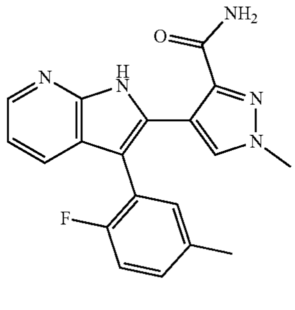 [SMILES: Cc1ccc(F)c(-c2c(-c3cn(C)nc3C(N)=O)[nH]c3ncccc23)c1]

$^1$H (400 MHz, $CD_3OD$) δ 2.40 (3H, s), 3.87 (3H, s), 7.22 (1H, dd, J=9.6, 8.5 Hz), 7.29 (1H, dd, J=6.6, 1.9 Hz), 7.33-7.40 (2H, m), 7.45 (1H, s), 8.07 (1H, d, J=7.9 Hz), 8.32 (1H, dd, J=5.5, 1.3 Hz); LRMS (ESI): m/z $[M+H]^+$ 350.

(28) Experimental Procedure of EX.395

EX.395 was prepared in accordance with the general procedure 42 using the method described below in detail.

Synthesis of 2-(4-(3-(2-cyano-5-methoxyphenyl)-1H-pyrrolo[2,3-b]pyridin-2-yl)-3-(trifluoromethyl)-1H-pyrazol-1-yl)-N-methylacetamide (EX.395)

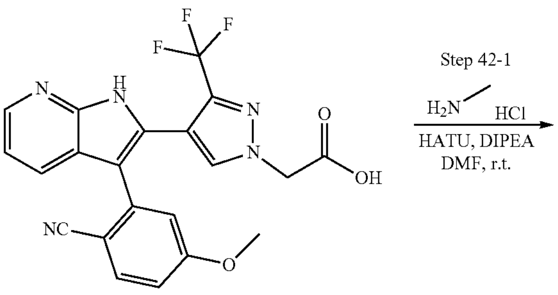

EX. 229

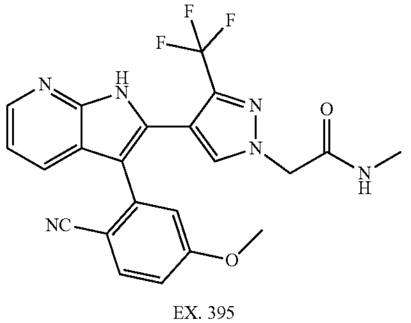

EX. 395

Step 42-1

To a solution of 2-[4-[3-(2-cyano-5-methoxy-phenyl)-1H-pyrrolo[2,3-b]pyridin-2-yl]-3-(trifluoromethyl)pyrazol-1-yl]acetic acid (EX.229) (15 mg, 0.03 mmol) and methylamine HCl salt (3.1 mg, 0.05 mmol) in DMF (1.5 mL) was added DIPEA (0.01 mL, 0.07 mmol) and then HATU (19.6 mg, 0.05 mmol). The mixture was stirred at room temperature for ~2 h before it was concentrated and purified by Agilent Prep HPLC to obtain EX.395 as white solid (5.6 mg, 36%).

$^1$H (400 MHz, DMSO-$d_6$) δ 2.64 (3H, d, J=4.6 Hz), 3.75 (3H, s), 4.92 (2H, s), 6.82 (1H, d, J=2.6 Hz), 7.03 (1H, dd, J=8.7, 2.6 Hz), 7.18 (1H, dd, J=8.0, 4.7 Hz), 7.80 (1H, d, J=8.7 Hz), 7.83 (1H, dd, J=7.9, 1.5 Hz), 8.15 (1H, s), 8.22 (1H, q, J=4.5 5 Hz), 8.33 (1H, dd, J=4.7, 1.6 Hz), 12.37 (1H, s); LRMS (ESI): m/z $[M+H]^+$ 455.

The following compounds were synthesized using conditions analogous to EX.395 in accordance with the general procedure 42.

| Example No. | Chemical structural formula | Spectrum data |
|---|---|---|
| EX.396 | 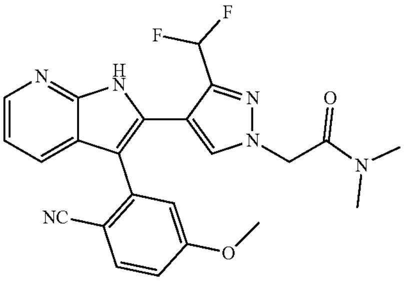 | $^1$H (400 MHz, DMSO-$d_6$) δ 2.86 (3H, s), 3.01 (3H, s), 3.75 (3H, s), 5.30 (2H, s), 6.81 (1H, d, J = 2.6 Hz), 7.03 (1H, dd, J = 8.7, 2.6 Hz), 7.18 (1H, dd, J = 8.0, 4.7 Hz), 7.80 (1H, d, J = 8.7 Hz), 7.82 (1H, dd, J = 8.0, 1.1 Hz), 8.05 (1H, d, J = 0.9 Hz), 8.33 (1H, dd, J = 4.7, 1.6 Hz), 12.38 (1H, s); LRMS (ESI): m/z $[M + H]^+$ 469. |
| EX.397 | 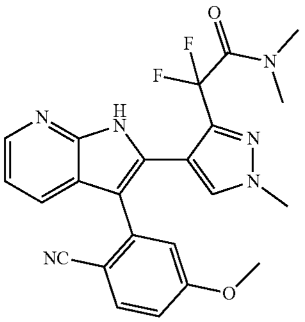 [SMILES: COc1ccc(C#N)c(-c2c(-c3cn(C)nc3C(F)(F)C(=O)N(C)C)[nH]c3ncccc23)c1] | $^1$H NMR (400 MHz, DMSO-$d_6$) δ 2.70 (3H, s), 2.88 (3H, s), 3.76 (3H, s), 3.91 (3H, s), 6.85 (1H, d, J = 2.6 Hz), 7.04 (1H, dd, J = 8.7, 2.6 Hz), 7.16 (1H, dd, J = 7.9, 4.7 Hz), 7.75-7.85 (2H, m), 8.08 (1H, s), 8.32 (1H, dd, J = 4.7, 1.6 Hz), 12.15 (1H, s). LRMS (ESI): m/z $[M + H]^+$ 451. |

(29) Experimental Procedure of EX.398 and EX.399

EX.398 and EX.399 were prepared in accordance with the general procedures 1 and 43 using the method described below in detail.

Synthesis of 2-[2-(cyclopenten-1-yl)-1H-pyrrolo[2,3-b]pyridin-3-yl]benzonitrile (EX.398) and 2-(2-cyclopentyl-1H-pyrrolo[2,3-b]pyridin-3-yl)benzonitrile (EX.399)

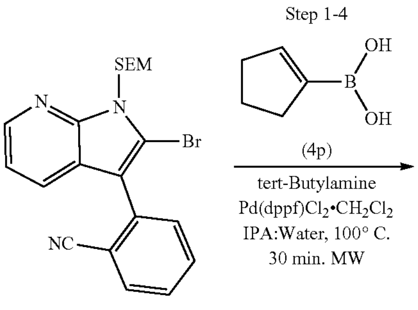

(6e)

-continued

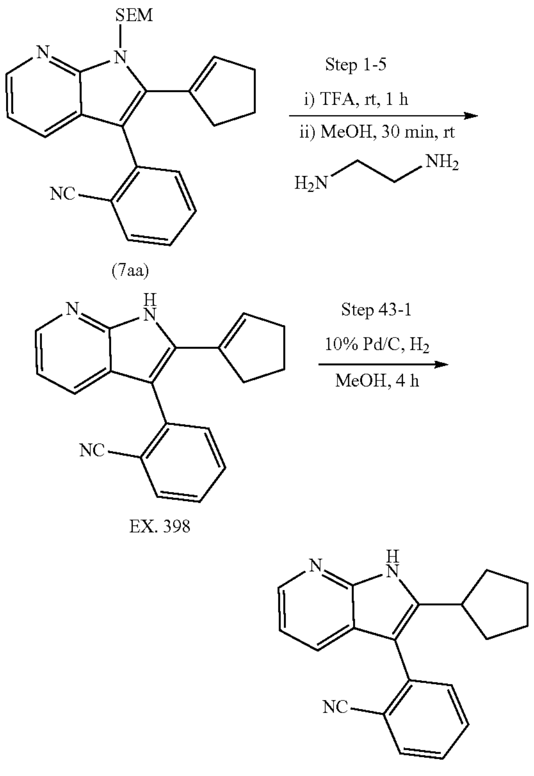

(7aa)

EX. 398

EX. 399

Step 1-4 (J. Nat. Prod., 2017, 80. 2561-2565.)

A reaction vial containing 2-[2-bromo-1-(2-trimethylsilylethoxymethyl)pyrrolo[2,3-b]pyridin-3-yl]benzonitrile (6e) (100 mg, 0.23 mmol), cyclopenten-1-ylboronic acid (4p) (52.3 mg, 0.47 mmol), and tert-butylamine (0.07 mL, 0.7 mmol), IPA (2 mL), Water (1 mL) was degassed for two minutes. Subsequently, added Pd(dppf)$Cl_2$-DCM (9.5 mg, 0.01 mmol) and the reaction mixture was degassed for two minutes. The resulting mixture was then heated at 100° C. for 30 min. under microwave conditions. The reaction mixture was directly concentrated and purified by silica gel column chromatography (0-30% EtOAc/hex), pure fraction was concentrated and dried to obtain product (7aa) as a pale, yellow oil, (71 mg, 73%).

Step 1-5

A mixture of 2-[2-(cyclopenten-1-yl)-1-(2-trimethylsilylethoxymethyl)pyrrolo[2,3-b]pyridin-3-yl]benzonitrile (7aa) (70 mg, 0.17 mmol) and neat TFA (0.77 mL, 10.11 mmol) was stirred at room temperature for 1 h. After concentration, the residue was dissolved in MeOH (0.5 mL) and reacted with ethylenediamine (0.67 mL, 10.11 mmol) at room temperature for 30 min. Thereafter, mixture was concentrated and directly subjected to prep HPLC (Kinetex 5u C18 100A RXI, 150×21.20 mm, 30-80% $CH_3CN$ w/0.1% TFA in $H_2O$ w/0.1% TFA for 8 min run, flow rate 20 mL/min). Fractions containing the expected product were passed through a PL-$HCO_3$ MP column and lyophilized to give the product EX.398 as a light brown solid (36 mg, 73%).

$^1$HNMR (400 MHz, DMSO-$d_6$) δ 1.88-1.78 (2H, m), 2.30 (2H, dt, J=7.9, 3.7 Hz), 2.36-2.46 (2H, m), 6.18-6.32 (1H, m), 7.06 (1H, dd, J=7.9, 4.7 Hz), 7.49-7.68 (3H, m), 7.78 (1H, td, J=7.7, 1.4 Hz), 7.88-8.01 (1H, m), 8.27 (1H, dd, J=4.7, 1.5 Hz), 12.07 (1H, s). LRMS (ESI): m/z $[M+H]^+$ 286.

Step 43-1

In a 25 mL RB flask, 2-[2-(cyclopenten-1-yl)-1H-pyrrolo[2,3-b]pyridin-3-yl]benzonitrile (EX.398) (12 mg, 0.04 mmol) was dissolved in 3 mL of MeOH and added carefully 10% Pd/C (0.45 mg, 0.0042 mmol). The mixture was degassed four times using $N_2$ purging and charged with the $H_2$ balloon to the RB, purged the $H_2$ gas for two times, sealed and stirred at room temperature for 4 h. After concentration, the residue was dissolved in MeOH (0.5 mL) and the mixture was directly subjected to prep-HPLC. Pure fractions containing the expected product were passed through a PL-$HCO_3$ MP column and lyophilized to give the product EX.399 as a white solid (6.5 mg, 52%).

$^1$H NMR (400 MHz, DMSO-$d_6$) δ 1.44-1.68 (2H, m), 1.68-2.00 (5H, m), 2.14-2.09 (1H, m), 2.98-3.14 (1H, m), 7.07 (1H, dd, J=7.9, 4.7 Hz), 7.44-7.69 (3H, m), 7.79 (1H, td, J=7.7, 1.4 Hz), 7.89-8.05 (1H, m), 8.22 (1H, dd, J=4.7, 1.5 Hz), 11.98 (1H, s). LRMS (ESI): m/z $[M+H]^+$ 288.

(30) Experimental Procedure of EX.400

EX.400 was prepared in accordance with general procedures 6, 46, and 1 using the method described below in detail.

Synthesis of 3-[3-[3-(difluoromethoxy)-1-ethylpyrazol-4-yl]-1H-pyrrolo[2,3-b]pyridin-2-yl]-2-(difluoromethyl)-6,7-dihydro-5H-pyrazolo[5,1-b][1,3]oxazine (EX.400)

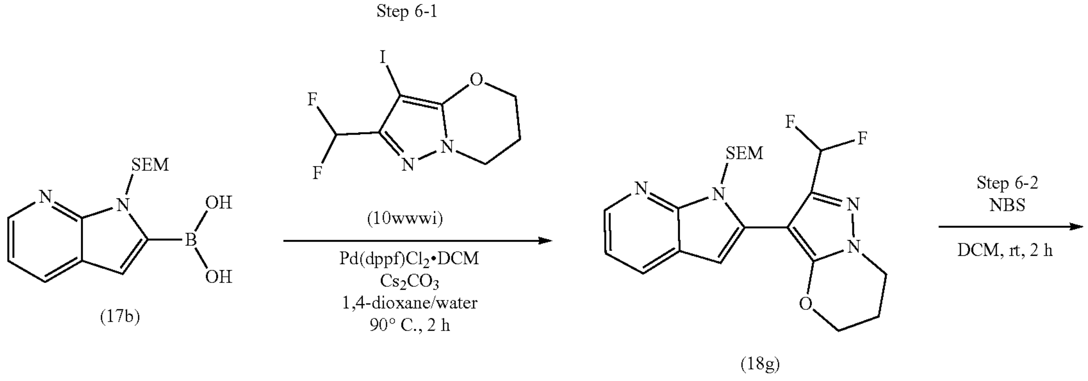

(17b)

(18g)

-continued

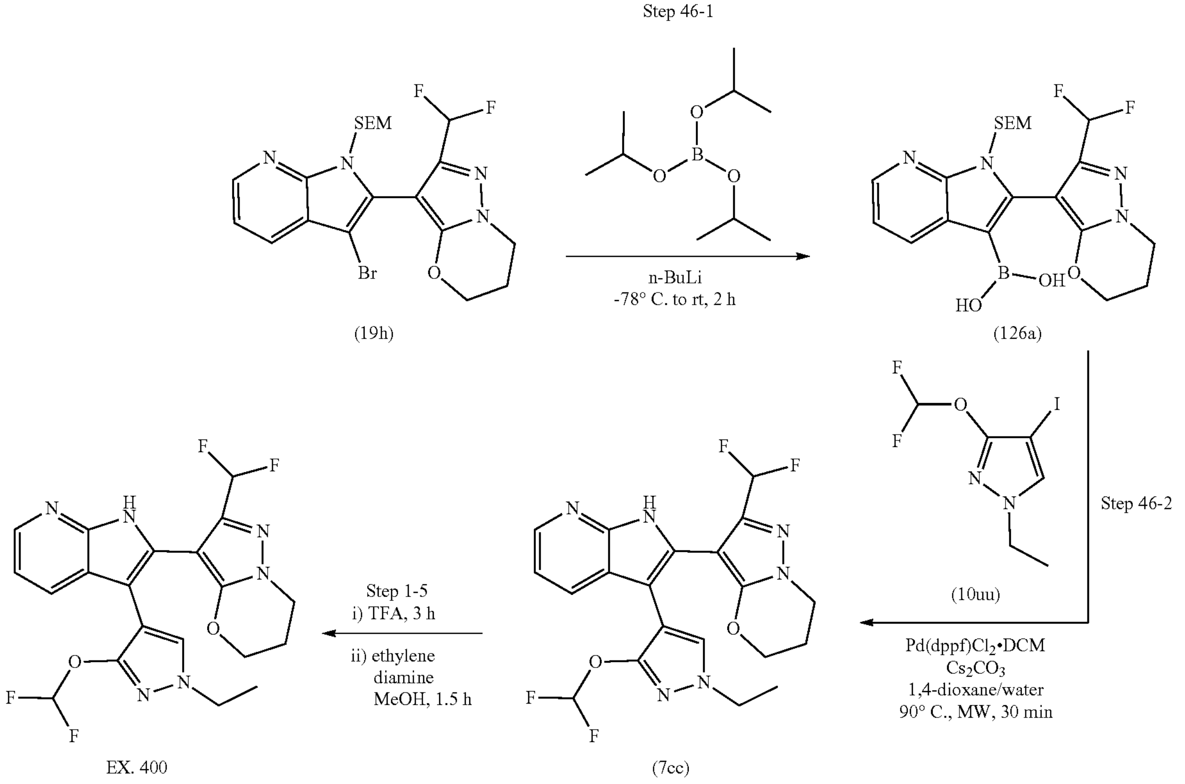

(19h) (126a) (10uu) (7cc) EX. 400

Step 6-1

A vial containing of 2-(difluoromethyl)-3-iodo-6,7-dihydro-5H-pyrazolo[5,1-b][1,3]oxazine (10wwwi) (924 mg, 3.08 mmol), [1-(2-trimethylsilylethoxymethyl)pyrrolo[2,3-b]pyridin-2-yl]boronic acid (17b) (750 mg, 2.57 mmol), $Cs_2CO_3$ (2.5 g, 7.7 mmol) and Pd(dppf)$Cl_2$-DCM (314 mg, 0.38 mmol) was vacuumed and refilled with $N_2$ three times. Thereafter, 1,4-Dioxane (8 mL) and Water (2 mL) were added into the vial and the resulting mixture was vacuumed and refilled with $N_2$ three times. Mixture was then heated at 90° C. for 2.0 h. Afterwards, it was cooled down to rt and concentrated. Crude residue was purified by silica gel chromatography using ethyl acetate in hexanes to give the expected product (18g) as dark brown oil, 650 mg (60%). LRMS (ESI): m/z $[M+H]^+$ 421.

Step 6-2

A solution containing 2-[[2-[2-(difluoromethyl)-6,7-dihydro-5H-pyrazolo[5,1-b][1,3]oxazin-3-yl]pyrrolo[2,3-b]pyridin-1-yl]methoxy]ethyl-trimethyl-silane (18g) (650 mg, 1.55 mmol) and NBS (296 mg, 1.85 mmol) in DCM (15 mL) was stirred at room temperature for 2 h. The reaction mixture was quenched with water, diluted with 50 mL of DCM and 50 mL of water and shaken. Layers were separated, and the organic layer was washed with saturated bicarbonate and followed by brine. The organic layer was concentrated and purified by silica gel chromatography to give the expected product (19h) as a yellow oil, 600 mg (78% yield). LRMS (ESI): m/z $[M+H]^+$ 499, 500.

Step 46-1

A solution of 2-[[3-bromo-2-[2-(difluoromethyl)-6,7-dihydro-5H-pyrazolo[5,1-b][1,3]oxazin-3-yl]pyrrolo[2,3-b]pyridin-1-yl]methoxy]ethyl-trimethyl-silane (19h) (520 mg, 1.04 mmol) in diethyl ether (10 mL) was cooled to −78° C. with a dry ice/acetone bath. To the stirred, heterogeneous mixture was added n-BuLi (0.83 mL, 2.08 mmol) dropwise. The mixture was stirred for a further 15 min at −78° C., and then triisopropyl borate (0.48 mL, 2.08 mmol) was added slowly via syringe. After 15 min of stirring, the reaction mixture was allowed to warm to rt and stirred further for 1 h. Thereafter, reaction mixture was quenched with methanol, dried under vacuum to get crude product (126a) and used as for next step without further purifications. LRMS (ESI): m/z $[M+H]^+$ 465.

Step 46-2

A microwave vial containing of 3-(difluoromethoxy)-1-ethyl-4-iodo-pyrazole (10uu) (30 mg, 0.1 mmol), [2-[2-(difluoromethyl)-6,7-dihydro-5H-pyrazolo[5,1-b][1,3]oxazin-3-yl]-1-(2-trimethylsilylethoxymethyl)pyrrolo[2,3-b]pyridin-3-yl]boronic acid (126a) (40 mg, 0.09 mmol), $Cs_2CO_3$ (85 mg, 0.26 mmol) and Pd(dppf)$Cl_2$-DCM (11 mg, 0.01 mmol) was vacuumed and refilled with $N_2$ three times. Then 1, 4-Dioxane (1 mL) and Water (0.25 mL) were added into the vial and the mixture was thrice evacuated and refilled with $N_2$. The resulting mixture was heated at 90° C. in microwave for 30 min. Thereafter, the reaction vial was removed from microwave and water phase was discarded. The organic phase was concentrated and purified by silica gel column chromatography using MeOH/DCM to obtain 38 mg (76%) of compound (7cc). LRMS (ESI): m/z $[M+H]^+$ 581.

Step 1-5

A solution of 2-[[3-[3-(difluoromethoxy)-1-ethyl-pyrazol-4-yl]-2-[2-(difluoromethyl)-6,7-dihydro-5H-pyrazolo[5,1-b][1,3]oxazin-3-yl]pyrrolo[2,3-b]pyridin-1-yl]methoxy]ethyl-trimethyl-silane (7cc) (38 mg, 0.07 mmol) in TFA (1 mL, 13.1 mmol) was stirred at room temperature for 3 h. Afterwards, the mixture was concentrated and used for the next step. The above concentrated crude reaction mixture was dissolved in methanol (1.5 mL) followed by the addition of ethylenediamine (0.44 mL, 6.54 mmol). 1). The mixture was stirred at room temperature for 1.5 h, and then the clear reaction mixture was turned into a white-color cloudy suspension. The reaction mixture was concentrated under reduced pressure and purified the solid material by silica gel column chromatography using MeOH/DCM gave the desired compound (EX.400) as a white solid (22.1 mg, 74% yield).

$^1$H NMR (400 MHz, DMSO-$d_6$): δ 1.35 (3H, t, J=7.2 Hz), 2.13-2.28 (2H, m), 4.05 (2H, q, J=7.2 Hz), 4.18 (2H, t, J=6.0 Hz), 4.22-4.33 (2H, m), 6.62 (1H, t, $J_{H-F}$=54.0 Hz), 6.89-7.32 (2H, m), 7.63 (1H, s), 7.83 (1H, dd, J=7.9, 1.5 Hz), 8.23 (1H, dd, J=4.7, 1.6 Hz), 11.75 (1H, s). LRMS (ESI): m/z $[M+H]^+$ 451.

The following compounds were synthesized using conditions analogous to EX.400 in accordance with the general procedures 6, 46 and 1.

| Example No. | Chemical structural formula | Spectrum data |
|---|---|---|
| EX.401 | 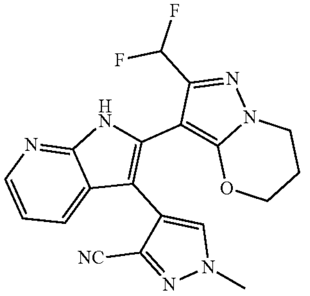 [SMILES: Cn1cc(-c2c(-c3c(C(F)F)nn4c3OCCC4)[nH]c3ncccc23)c(C#N)n1] | $^1$H NMR (400 MHz, DMSO-$d_6$): δ 2.08-2.28 (2H, m), 3.97 (3H, s), 4.18 (2H, t, J = 6.0 Hz), 4.23-4.35 (2H, m), 6.60 (1H, t, $J_{H-F}$ = 54.0 Hz), 7.15 (1H, dd, J = 7.9, 4.7 Hz), 7.91 (1H, dd, J = 7.9, 1.1 Hz), 8.02 (1H, s), 8.28 (1H, dd, J = 4.7, 1.5 Hz). LRMS (ESI): m/z $[M + H]^+$ 396. |
| EX.402 | 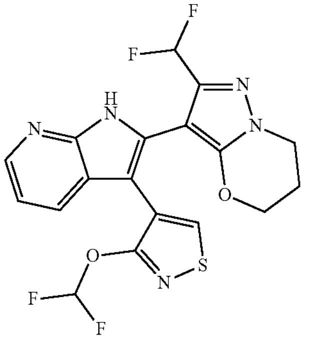 [SMILES: FC(F)Oc1nscc1-c1c(-c2c(C(F)F)nn3c2OCCC3)[nH]c2ncccc12] | $^1$H NMR (400 MHz, DMSO-$d_6$): δ 2.10-2.24 (2H, m), 4.05-4.30 (4H, m), 6.73 (1H, t, $J_{H-F}$ = 54.0 Hz), 7.14 (1H, dd, J = 7.9, 4.7 Hz), 7.60 (1H, t, $J_{H-F}$ = 72.5 Hz), 7.86 (1H, dd, J = 7.9, 1.1 Hz), 8.28 (1H, dd, J = 4.7, 1.5 Hz), 8.74 (1H, s), 11.99 (1H, s). LRMS (ESI): m/z $[M + H]^+$ 440. |
| EX.403 | 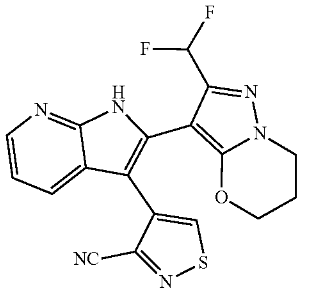 [SMILES: N#Cc1nscc1-c1c(-c2c(C(F)F)nn3c2OCCC3)[nH]c2ncccc12] | $^1$H NMR (400 MHz, DMSO-$d_6$): δ 2.18 (2H, p, J = 5.8 Hz), 4.07-4.28 (4H, m), 6.69 (1H, t, $J_{H-F}$ = 53.8 Hz), 7.18 (1H, dd, J = 7.9, 4.7 Hz), 7.91 (1H, dd, J = 7.9, 1.0 Hz), 8.32 (1H, dd, J = 4.7, 1.6 Hz), 9.11 (1H, s), 12.19 (1H, s). LRMS (ESI): m/z $[M + H]^+$ 399. |
| EX.404 | 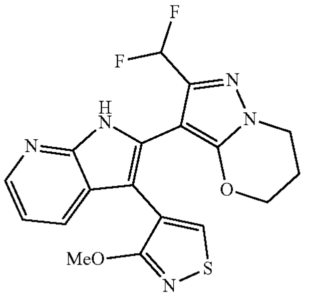 [SMILES: COc1nscc1-c1c(-c2c(C(F)F)nn3c2OCCC3)[nH]c2ncccc12] | $^1$H NMR (400 MHz, DMSO-$d_6$): δ 2.05-2.31 (2H, m), 3.86 (3H, s), 4.16-4.23 (4H, m), 6.69 (1H, t, $J_{H-F}$ = 54.0 Hz), 7.10 (1H, dd, J = 7.9, 4.7 Hz), 7.81 (1H, dd, J = 7.9, 1.2 Hz), 8.24 (1H, dd, J = 4.7, 1.6 Hz), 8.50 (1H, s), 11.85 (1H, s). LRMS (ESI): m/z $[M + H]^+$ 404. |

-continued

| Example No. | Chemical structural formula | Spectrum data |
|---|---|---|
| EX.405 | 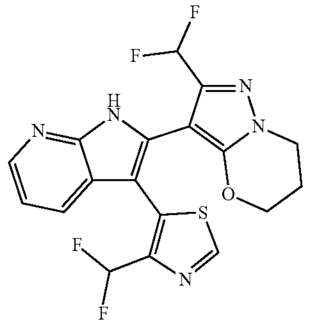 [SMILES: FC(F)c1ncsc1-c1c(-c2c(C(F)F)nn3c2OCCC3)[nH]c2ncccc12] | $^1$H NMR (400 MHz, $CD_3OD$): δ 2.20-2.26 (2H, m), 4.15-4.19 (4H, m), 6.43 (1H, $J_{H-F}$ = 53.1 Hz), 6.66 (1H, t, $J_{H-F}$ = 54.1 Hz), 7.25 (1H, dd, J = 8.0, 4.8 Hz), 7.94 (1H, dd, J = 7.9, 1.5 Hz), 8.33 (1H, dd, J = 4.8, 1.5 Hz), 9.13 (1H, s). LRMS (ESI): m/z [M + H]$^+$ 424. |
| EX.406 | 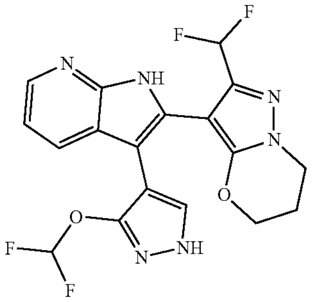 [SMILES: FC(F)Oc1n[nH]cc1-c1c(-c2c(C(F)F)nn3c2OCCC3)[nH]c2ncccc12] | $^1$H NMR (400 MHz, $CD_3OD$): δ 2.29-2.35 (2H, m), 4.23 (2H, apparent t, J = 6.2 Hz), 4.31-4.33 (2H, m), 6.45 (1H, t, $J_{H-F}$ = 54.2 Hz), 6.85 (1H, t, $J_{H-F}$ = 74.1 Hz), 7.17 (1H, dd, J = 7.9, 4.8 Hz), 7.58 (1H, s), 7.99 (1H, dd, J = 7.9, 1.4 Hz), 8.23 (1H, br s). LRMS (ESI): m/z [M + H]$^+$ 423. |
| EX.407 | 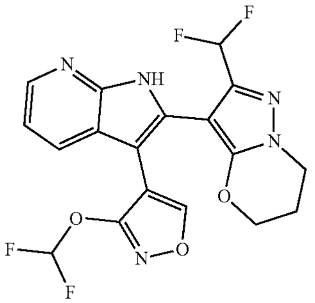 [SMILES: FC(F)Oc1nocc1-c1c(-c2c(C(F)F)nn3c2OCCC3)[nH]c2ncccc12] | $^1$H NMR (400 MHz, $CD_3OD$): δ 2.29-2.35 (2H, m), 4.23 (2H, t, J = 6.2 Hz), 4.31-4.34 (2H, m), 6.59 (1H, t, $J_{H-F}$ = 54.1 Hz), 7.18 (1H, t, $J_{H-F}$ = 72.0 Hz), 7.21 (1H, dd, J =7.9, 4.8 Hz), 8.00 (1H, dd, J = 7.9, 1.5 Hz), 8.28 (1H, dd, J= 7.9, 1.5 Hz) 8.65 (1H, s). LRMS (ESI): m/z [M + H]$^+$ 424. |
| EX.408 | 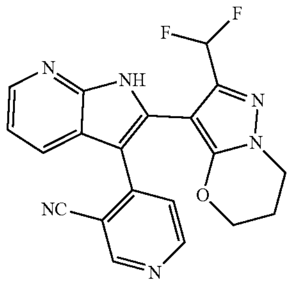 [SMILES: N#Cc1cnccc1-c1c(-c2c(C(F)F)nn3c2OCCC3)[nH]c2ncccc12] | $^1$H NMR (400 MHz, DMSO-$d_6$): δ 2.13-2.16 (2H, m), 4.13-4.18 (4H, m), 6.73 (1H, t, $J_{H-F}$ = 53.8 Hz), 7.19 (1H, dd, J = 7.9, 4.7 Hz), 7.40 (1H, d, J = 5.2 Hz), 7.94 (1H, dd, J = 7.9, 1.4 Hz), 8.33 (1H, dd, J = 4.6, 1.3 Hz), 8.75 (1H, d, J = 5.3 Hz), 8.99 (1H, s). LRMS (ESI): m/z [M + H]$^+$ 393. |
| EX.409 | 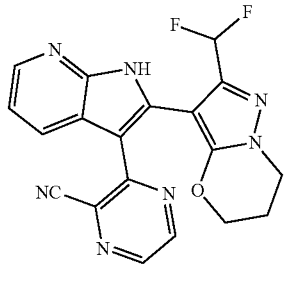 [SMILES: N#Cc1nccnc1-c1c(-c2c(C(F)F)nn3c2OCCC3)[nH]c2ncccc12] | $^1$H NMR (400 MHz, $CDCl_3$): δ 2.21-2.27 (2H, m), 4.03-4.05 (2H, m), 4.25 (2H, t, J = 6.2 Hz), 6.60 (1H, t, $J_{H-F}$ = 54.2 Hz), 7.22 (1H, dd, J = 7.9, 4.8 Hz), 8.15 (1H, dd, J = 7.9, 1.3 Hz), 8.40 (1H, d, J = 3.7 Hz), 8.57 (1H, d, J = 2.3 Hz), 8.87 (1H, d, J = 2.3 Hz), 9.46 (1H, s). LRMS (ESI): m/z [M + H]$^+$ 394. |

-continued

| Example No. | Chemical structural formula | Spectrum data |
|---|---|---|
| EX.410 | 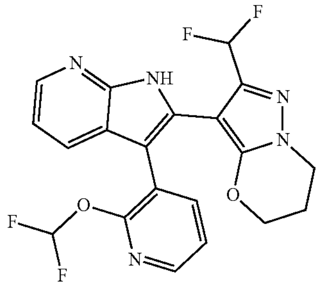 [SMILES: FC(F)Oc1ncccc1-c1c(-c2c(C(F)F)nn3c2OCCC3)[nH]c2ncccc12] | $^1$H NMR (400 MHz, DMSO-$d_6$): δ 2.08-2.14 (2H, m), 4.12 (4H, m), 6.69 (1H, t, $J_{H\text{-}F}$ = 54.0 Hz), 7.12 (1H, dd, J = 7.9, 4.7 Hz), 7.25 (1H, dd, J = 7.5, 4.9 Hz), 7.62 (1H, dd, J = 7.5, 1.9 Hz), 7.70 (1H, t, $J_{H\text{-}F}$ = 72.0 Hz), 7.78 (1H, dd, J = 7.9, 1.5 Hz), 8.19 (1H, dd, J = 4.9, 1.9 Hz), 8.27 (1H, dd, J = 4.7, 1.6 Hz), 11.96 (1H, s). LRMS (ESI): m/z $[M + H]^+$ 434. |
| EX.389 | 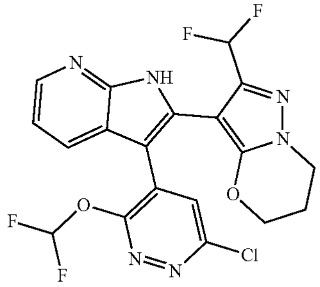 [SMILES: FC(F)Oc1nnc(Cl)cc1-c1c(-c2c(C(F)F)nn3c2OCCC3)[nH]c2ncccc12] | $^1$H NMR (400 MHz, $CD_3OD$): δ 2.21-2.32 (2H, m), 4.15-4.29 (4H, m), 6.61 (1H, t, $J_{H\text{-}F}$ = 54.0 Hz), 7.35 (1H, dd, J = 8.0, 5.1 Hz), 7.68 (1H, t, J = 71.7 Hz), 7.76 (1H, s), 8.20 (1H, dd, J = 8.0, 1.4 Hz), 8.36 (1H, dd, J = 5.1, 1.4 Hz); LRMS (ESI): m/z $[M + H]^+$ 469. |
| EX.411 | 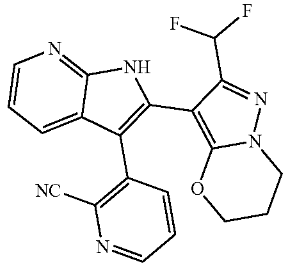 [SMILES: N#Cc1ncccc1-c1c(-c2c(C(F)F)nn3c2OCCC3)[nH]c2ncccc12] | $^1$H NMR (400 MHz, $CD_3OD$) δ 2.14-2.32 (2H, m), 4.06-4.28 (4H, m), 6.50 (1H, t, $J_{H\text{-}F}$ = 54.1 Hz), 7.41 (1H, dd, J = 8.0, 5.3 Hz), 7.71 (1H, dd, J = 8.0, 4.7 Hz), 7.95 (1H, dd, J = 8.0, 1.6 Hz), 8.21 (1H, dd, J = 8.0, 1.4 Hz), 8.39 (1H, dd, J = 5.3, 1.3 Hz), 8.67 (1H, dd, J = 4.7, 1.6 Hz); LRMS (ESI): m/z $[M + H]^+$ 393. |
| EX.412 | 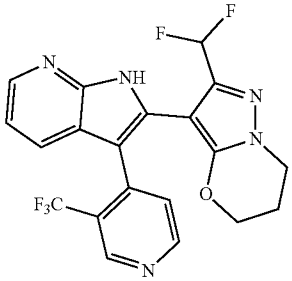 [SMILES: FC(F)c1nn2c(c1-c1[nH]c3ncccc3c1-c1ccncc1C(F)(F)F)OCCC2] | $^1$H NMR (400 MHz, DMSO-$d_6$): δ 1.97-2.17 (2H, m), 3.94-4.03 (1H, m), 4.03-4.15 (3H, m), 6.83 (1H, t, $J_{H\text{-}F}$ = 54.0 Hz), 7.10 (1H, dd, J = 7.9, 4.7 Hz), 7.31 (1H, d, J = 5.1 Hz), 7.63 (1H, d, J = 7.9 Hz), 8.28 (1H, dd, J = 4.7, 1.5 Hz), 8.79 (1H, d, J = 5.1 Hz), 8.98 (1H, s), 12.05 (1H, s). LRMS (ESI): m/z $[M + H]^+$ 436. |
| EX.413 | 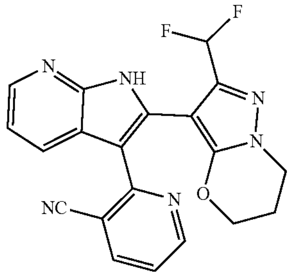 [SMILES: N#Cc1cccnc1-c1c(-c2c(C(F)F)nn3c2OCCC3)[nH]c2ncccc12] | $^1$HNMR (400 MHz, DMSO-$d_6$): δ 2.09-2.20 (2H, m), 4.12 (2H, t, J = 5.5 Hz), 4.16 (2H, t, J = 6.0 Hz), 6.65 (1H, t, $J_{H\text{-}F}$ = 54.1 Hz), 7.17 (1H, dd, J = 7.9, 4.7 Hz), 7.47 (1H, dd, J = 7.9, 4.9 Hz), 7.98 (1H, dd, J = 7.9, 1.6 Hz), 8.27 (1H, dd, J = 7.9, 1.8 Hz), 8.31 (1H, dd, J = 4.7, 1.6 Hz), 8.87 (1H, dd, J = 4.9, 1.8 Hz), 12.14 (1H, s). LRMS (ESI): m/z $[M + H]^+$ 393. |

-continued

| Example No. | Chemical structural formula | Spectrum data |
|---|---|---|
| EX.414 | 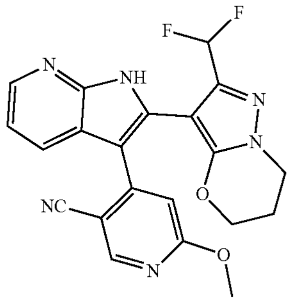 [SMILES: COc1cc(-c2c(-c3c(C(F)F)nn4c3OCCC4)[nH]c3ncccc23)c(C#N)cn1] | $^1H$ NMR (400 MHz, DMSO-$d_6$): δ 2.11-2.22 (2H, m), 3.94 (3H, s), 4.14-4.23 (4H, m), 6.70 (1H, t, $J_{H-F}$ = 54.0 Hz), 6.75 (1H, s), 7.16 (1H, dd, J = 7.9, 4.7 Hz), 7.90 (1H, dd, J = 7.9, 1.2 Hz), 8.31 (1H, d, J = 4.7 Hz), 8.69 (1H, s), 12.26 (1H, s). LRMS (ESI): m/z $[M + H]^+$ 423. |
| EX.415 | 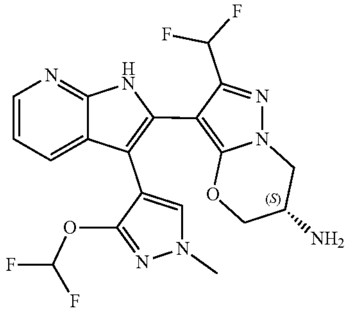 | $^1H$ NMR (400 MHz, DMSO-$d_6$): δ 1.96 (2H, br s), 3.49 (1H, br s), 3.86 (1H, dd, J = 12.0, 5.9 Hz), 3.96 (1H, dd, J = 10.6, 6.4 Hz), 4.20 (1H, dd, J = 10.7, 2.6 Hz), 4.28 (1H, dd, J = 12.0, 4.7 Hz), 6.65 (1H, t, $J_{H-F}$ = 54.1 Hz), 7.09 (1H, dd, J = 7.9, 4.7 Hz), 7.12 (1H, t, $J_{H-F}$ = 73.8 Hz), 7.60 (1H, s), 7.84 (1H, dd, J = 7.9, 1.2 Hz), 8.24 (1H, dd, J = 4.7, 1.6 Hz), 11.72 (1H, s); LRMS (ESI): m/z $[M + H]^+$ 452. |
| EX.416 | 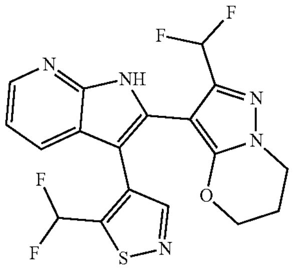 [SMILES: FC(F)c1nn2c(c1-c1[nH]c3ncccc3c1-c1cnsc1C(F)F)OCCC2] | $^1HNMR$ (400 MHz, $CD_3OD$): δ 2.15-2.28 (2H, m), 4.11-4.24 (4H, m), 6.68 (2H, td, J = 54.1, 25.7 Hz), 7.41 (1H, dd, J = 7.9, 5.3 Hz), 8.15 (1H, dd, J = 7.9, 1.3 Hz), 8.39 (1H, d, J = 5.3 Hz), 8.47 (1H, t, J = 2.3 Hz). LRMS (ESI): m/z $[M + H]^+$ 424. |
| EX.417 | 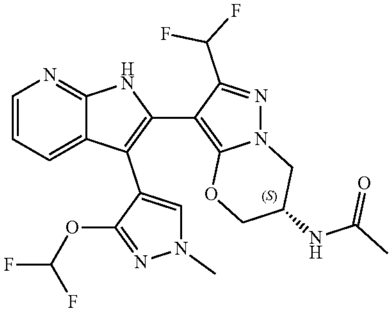 | $^1H$ NMR (400 MHz, DMSO-$d_6$): δ 1.88 (3H, s), 3.77 (3H, s), 4.03-4.14 (1H, m), 4.14-4.27 (2H, m), 4.41 (2H, d, J = 9.0 Hz), 6.69 (2H, t, $J_{H-F}$ = 54.0 Hz), 7.10 (1H, dd, J = 7.9, 4.8 Hz), 7.12 (1H, t, $J_{H-F}$ = 73.8 Hz), 7.83 (1H, dd, J = 7.9, 1.5 Hz), 8.24 (1H, dd, J = 4.6, 1.5 Hz), 8.37 (1H, d, J = 5.7 Hz), 11.71 (1H, s); LRMS (ESI): m/z [M + H]+ 494. |
| EX.418 | 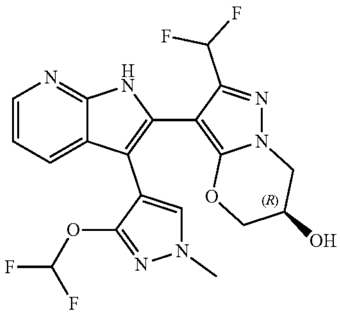 | $^1HNMR$ (400 MHz, DMSO-$d_6$): δ 3.74 (3H, s), 4.04 (1H, d, J = 11.3 Hz), 4.20 (2H, s), 4.33 (2H, d, J = 11.8 Hz), 5.71 (1H, d, J = 2.9 Hz), 6.71 (1H, t, $J_{H-F}$ = 54.1 Hz), 7.10 (1H, dd, J = 7.9, 4.7 Hz), 7.14 (1H, t, $J_{H-F}$ = 73.8 Hz), 7.54 (1H, s), 7.83 (1H, d, J = 7.9 Hz), 8.24 (1H, dd, J = 4.7, 1.5 Hz), 11.78 (1H, s); ; LRMS (ESI): m/z $[M + H]^+$ 453. |

(31) Experimental Procedure of EX.419

EX.419 was prepared in accordance with the general procedure 44 using the method described below in detail.

Synthesis of 2-[2-[2-(Hydroxymethyl)-6,7-dihydro-5H-pyrazolo[5,1-b][1,3]oxazin-3-yl]-1H-pyrrolo[2,3-b]pyridin-3-yl]-4-methoxy-benzonitrile (EX.419)

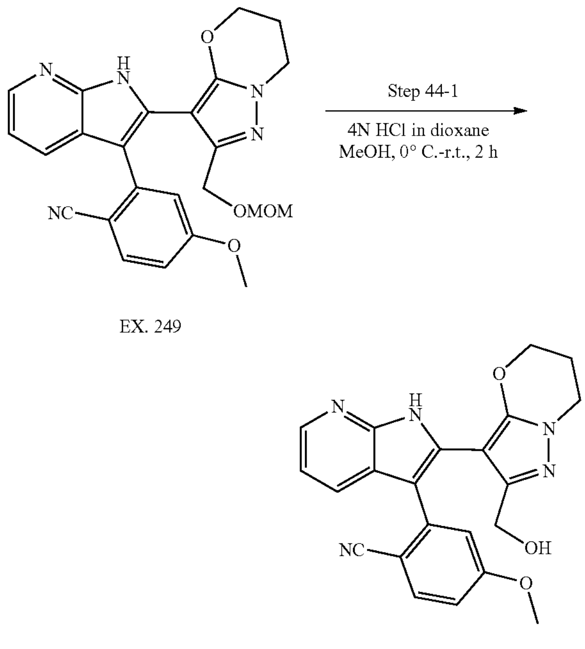

EX. 249

EX. 419

Step 44-1

To a stirred solution of 4-methoxy-2-[2-[2-(methoxymethoxymethyl)-6,7-dihydro-5H-pyrazolo[5,1-b][1,3]oxazin-3-yl]-1H-pyrrolo[2,3-b]pyridin-3-yl]benzonitrile (EX.249) (26 mg, 0.06 mmol) in methanol (2 mL), was added 4 N HCl in 1,4-dioxane (146 μL, 0.58 mmol) at 0° C. and ice bath removed and stirring was continued for 2 h at rt. Reaction mixture was evaporated and added water (2 mL) and sat. bicarbonate, to adjust the pH to 8-9 and extracted with 5% MeOH in $CH_2Cl_2$ (2x5 mL) and combined organic layers were washed with brine (10 mL), dried over $Na_2SO_4$ and concentrated. The crude was purified by silica gel column chromatography using 0-5% MeOH in $CH_2Cl_2$ gave pale yellow solid which was repurified by prep-HPLC to afford pure EX.419 as white solid (6 mg, 25%).

$^1$H NMR (400 MHz, DMSO-$d_6$) δ 2.04 (2H, s), 3.80 (3H, s), 3.91 (2H, d, J=21.0 Hz), 4.03 (2H, t, J=6.1 Hz), 4.25 (2H, d, J=17.9 Hz), 5.46 (1H, s), 6.95 (1H, d, J=2.6 Hz), 7.04 (1H, dd, J=8.7, 2.6 Hz), 7.12 (1H, dd, J=7.9, 4.7 Hz), 7.79 (2H, dd, J=8.2, 1.8 Hz), 8.24 (1H, dd, J=4.7, 1.5 Hz), 11.70 (1H, s). LRMS (ESI): m/z $[M+H]^+$ 402.

(32) Reference Procedure of (18'd)

2-[3-(Difluoromethyl)-1-methyl-pyrazol-4-yl]-1-(2 trimethylsilylethoxymethyl)pyrrolo[2,3-b]pyridine-4-carbonitrile (18'd) for preparation of EX.278 was prepared in accordance with the general procedure 9 using the method described below in detail.

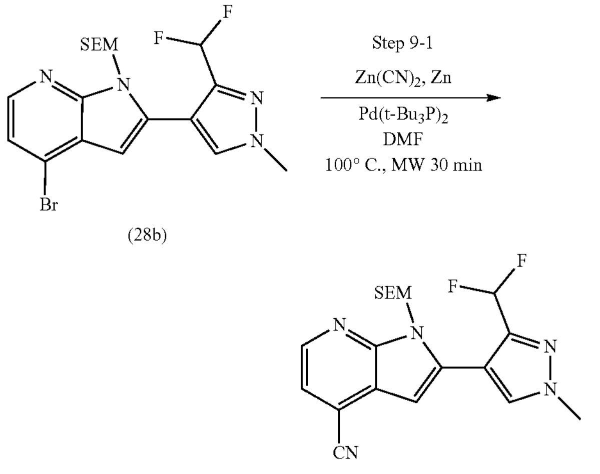

(28b)

(18'd)

Step 9-1

A reaction vessel containing 2-[[4-bromo-2-[3-(difluoromethyl)-1-methyl-pyrazol-4-yl]pyrrolo[2,3-b]pyridin-1-yl]methoxy]ethyl-trimethyl-silane (28b) (121.6 mg, 0.27 mmol), $Zn(CN)_2$ (93.6 mg, 0.8 mmol) and Zn (3.4 mg, 0.05 mmol) in DMF (1.6 mL) was degassed and backfilled with $N_2$ three times. After the addition of Pd(dppf)$Cl_2$-DCM (21.7 mg, 0.03 mmol), the reaction mixture was purged with $N_2$ three times. The resulting mixture was then stirred and heated at 90° C. for 1 h. No product formation was observed. The reaction mixture was transferred to a MW vial, degassed and back filled with $N_2$ three times and added bis(tri-tert-butylphosphine)palladium (27.1 mg, 0.05 mmol). The reaction was degassed and back filled with $N_2$ three times and heated at 100° C. for 30 min under microwave irradiation. Solvent was evaporated in vacuo and purified by silica gel column chromatography (0-13% EtOAc/hexane) to obtain product as a yellow oil (69.2 mg, 64%); LRMS (ESI): m/z $[M+H]^+$ 404.

(33) Reference Procedure of (18f)

2-Methylpyrazolo[1,5-a]pyrimidine-6-carbonitrile (18f) for preparation of EX.180 was prepared in accordance with the general procedure 9 using the method described below in detail.

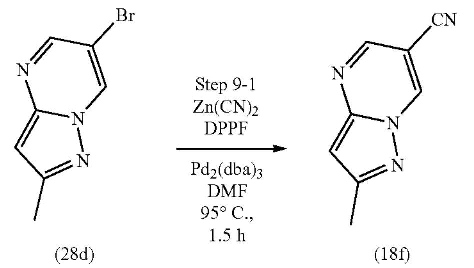

(28d)

(18f)

Step 9-1

A reaction vessel containing 6-bromo-2-methyl-pyrazolo[1,5-a]pyrimidine (28d) (400 mg, 1.89 mmol), dppf (209.1 mg, 0.38 mmol), $Zn(CN)_2$ (443 mg, 3.77 mmol) in DMF (15 mL) was degassed and backfilled with $N_2$ three times. After the addition of $Pd_2(dba)_3$ (172.7 mg, 0.19 mmol), the reaction mixture was purged with $N_2$ three times. The resulting mixture was then stirred and heated at 95° C. for 1.5 h. The reaction was partitioned between water and extracted with ether, evaporated solvent and purified by silica gel column chromatography (0-21% EtOAc/Hexane) to obtain product as a yellow solid (160.2 mg, 54%); LRMS (ESI): m/z $[M+H]^+$ 159.

(34) Reference Procedure of (18c)

2-(5-fluoro-2-methoxyphenyl)-1-((2-(trimethylsilyl)ethoxy)methyl)-1H-pyrrolo[2,3-b]pyridine-4-carbonitrile (18c) for the preparation of EX.274 was prepared in accordance with the general procedure 9 using the method described below in detail.

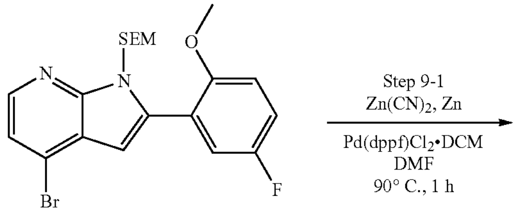

(28a)

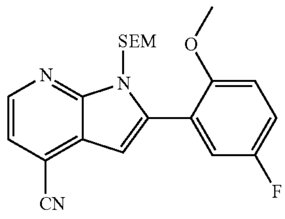

(18c)

Step 9-1

A reaction vessel containing 2-[[4-bromo-2-(5-fluoro-2-methoxy-phenyl)pyrrolo[2,3-b]pyridin-1-yl]methoxy]ethyl-trimethyl-silane (28a) (110 mg, 0.24 mmol), $Zn(CN)_2$ (85.8 mg, 0.73 mmol) and Zn (3.2 mg, 0.05 mmol) in DMF (1.5 mL) was degassed and backfilled with nitrogen three times. After the addition of Pd(dppf)$Cl_2$-DCM (19.9 mg, 0.02 mmol), the mixture was purged with nitrogen three times. The resulting mixture was then stirred and heated at 90° C. for 1 h. After cooling to room temperature, the mixture was filtered through Celite, and the filtrate was concentrated. The residue was purified by silica gel column chromatography (0-20% EtOAc/Hexane) to give the expected product as a pale-yellow solid (91.2 mg, 94%); LRMS (ESI): m/z $[M+H]^+$ 398.

(35) Reference Procedure of (3b)

2-(4,4,5,5-Tetramethyl-1,3,2-dioxaborolan-2-yl) phen-3,4,5,6-$d_4$-ol (3b) for the preparation of EX.17 was prepared in accordance with the general procedure 15 using the method described below in detail.

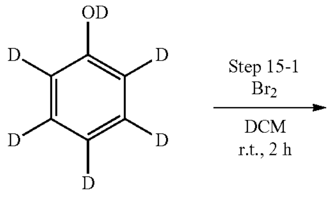

(41a)

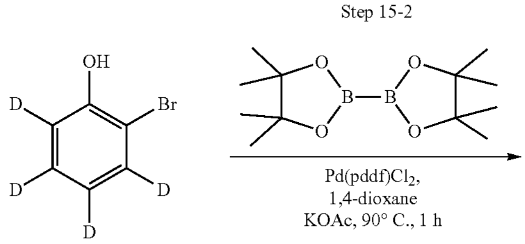

(42a)

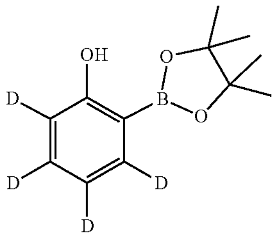

(3b)

Step 15-1

To a solution of 1,2,3,4,5-pentadeuterio-6-deuteriooxy-benzene (41a) (318 mg, 3.18 mmol) in DCM (10 mL) was added 2M $Br_2$ in DCM (1.75 mL, 3.49 mmol) at room temperature and the mixture was stirred at room temperature for 2 h. The reaction mixture was directly loaded onto prepacked silica column and was purified by silica gel column chromatography (0-20% EtOAc/Hexane) to give the expected product as red oil (462 mg, 82%); LRMS (ESI): m/z $[M+H]^+$ 177, 179.

Step 15-2

A reaction vessel containing 2-bromo-3,4,5,6-tetradeuterio-phenol (42a) (99.4 mg, 0.56 mmol), bis(pinacolato) diboron (171.2 mg, 0.67 mmol) and potassium acetate (110.3 mg, 1.12 mmol) in 1,4-dioxane (3 mL) was degassed and backfilled with nitrogen three times. After the addition of [1,1-bis(diphenylphosphino) ferrocene]dichloropalladium (II) (41.1 mg, 0.06 mmol), the reaction mixture was purged with nitrogen three times. The resulting mixture was then stirred and heated at 90° C. for 1 h. After cooling to room temperature, the mixture was filtered through Celite, and the filtrate was concentrated. The residue was purified by silica gel column chromatography (0-30% EtOAc/Hexane) to give the expected product (3b) as an off-white solid (79.1 mg, 62%); LRMS (ESI): m/z $[M+H]^+$ 225.

(36) Reference Procedure of (3c)

5-fluoro-2-(4,4,5,5-tetramethyl-1,3,2-dioxaborolan-2-yl) phen-3,4,6-d3-ol (3c) for the preparation of EX.56 was synthesized from commercially available 4-fluorophen-2,3,5,6-$d_4$-ol in accordance with the methods described in the procedure 15 for the preparation of EX.56.

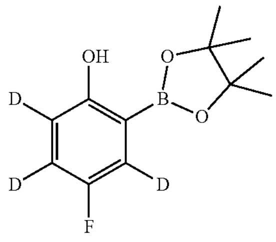 [SMILES: [2H]c1c([2H])c(F)c([2H])c(B2OC(C)(C)C(C)(C)O2)c1O]

3c

LRMS (ESI): m/z $[M+H]^+$ 242.

(37) Reference Procedure of (10d)

4-((2-bromo-4-fluorophenoxy)methyl)tetrahydro-2H-pyran (10d) for preparation of EX.124 was prepared in accordance with the general procedure 16 using the method described below in detail.

Step 16-1

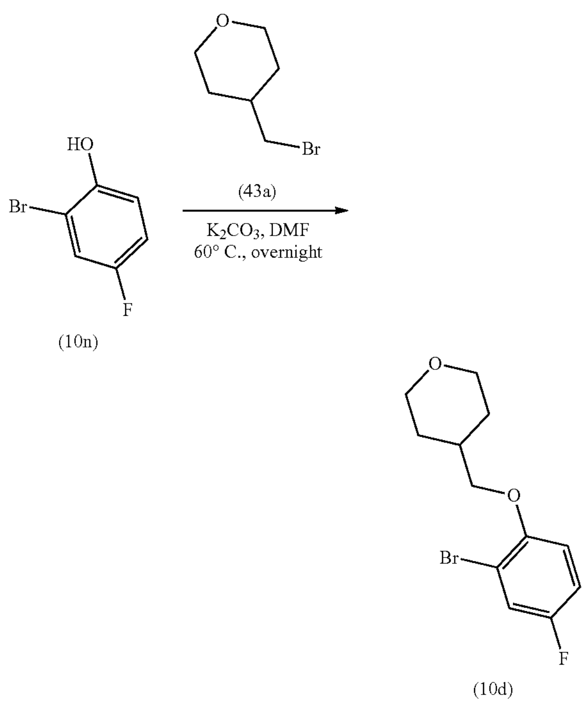

Step 16-1

A mixture of 2-bromo-4-fluoro-phenol (10n) (50 mg, 0.26 mmol), 4-(bromomethyl)tetrahydropyran (43a) (51.6 mg, 0.29 mmol) and $K_2CO_3$ (65.1 mg, 0.47 mmol) in DMF (3 mL) was stirred and heated at 60° C. overnight. After cooling to room temperature, the mixture was concentrated. The residue was purified by silica gel column chromatography (0-70% EtOAc/Hexane) to give the expected product as colorless oil (50.8 mg, 67%); LRMS (ESI): m/z $[M+H]^+$ 289, 291.

The following compounds were synthesized using conditions analogous to (10d) in accordance with the general procedure 16.

Tert-butyl 4-((2-bromo-4-fluorophenoxy)methyl) piperidine-1-carboxylate (10e) (for preparation of EX.125)

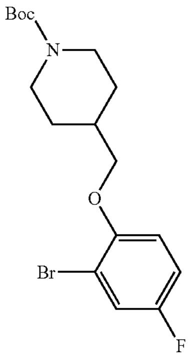 [SMILES: CC(C)(C)OC(=O)N1CCC(COc2ccc(F)cc2Br)CC1]

(10e)

LRMS (ESI): m/z $[M+H]^+$ 388, 390.

3-((2-Bromo-4-fluorophenoxy)methyl) oxetane (10f) (for preparation of EX.126)

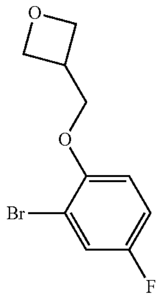 [SMILES: Fc1ccc(OCC2COC2)c(Br)c1]

(101)

LRMS (ESI): m/z $[M+H]^+$ 261, 263.

1-(4-((2-Bromo-4-fluorophenoxy)methyl) piperidin-1-yl) ethan-1-one (10g) (for preparation of EX.127)

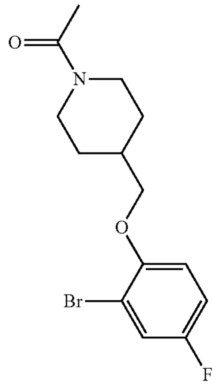 [SMILES: CC(=O)N1CCC(COc2ccc(F)cc2Br)CC1]

(10g)

LRMS (ESI): m/z $[M+H]^+$ 330, 332.

(38) Reference Procedure of (3f) and (4j)

2-(4,4,5,5-Tetramethyl-1,3,2-dioxaborolan-2-yl)-4-(trideuteriomethoxy)benzonitrile (3f) and [2-cyano-5-(trideuteriomethoxy)phenyl]boronic acid (4j) were prepared in accordance with the general procedures 15 and 16 using the method described below in detail.

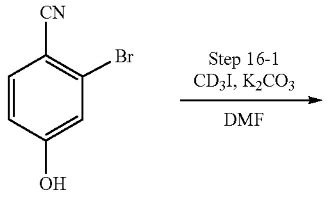

(10o)

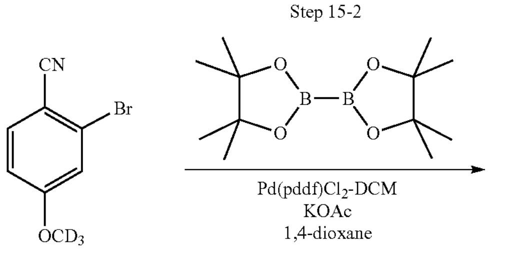

(10p)

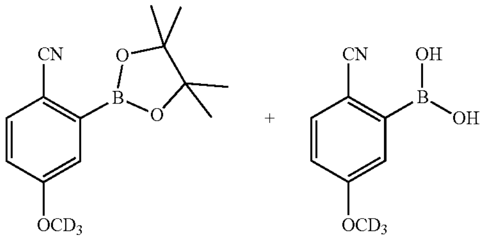

(3f) + (4j)

Step 16-1

A round bottom flask containing a pre-stirred (20 min) mixture of 2-bromo-4-hydroxy-benzonitrile (100) (5 g, 25.25 mmol) and $K_2CO_3$ (6.98 g, 50.5 mmol) in DMF (50 mL) was added $CD_3I$ (2.39 mL, 37.87 mmol) and stirred for 4.5 h. Thereafter, reaction mixture was filtered through a pad of Celite and washed twice with EtOAc. Filtrate and washes were combined, concentrated, and purified by silica gel column chromatography (eluted with 0-50% EtOAc/Hexanes) to afford a white solid (5.25 g, 96%) as the expected product. LRMS (ESI): m/z $[M+H]^+$ 216.

Step 15-2

A round bottom flask containing 2-bromo-4-(trideuteriomethoxy)benzonitrile (10p) (2.5 g, 11.62 mmol), bis(pinacolato)diboron (3.84 g, 15.11 mmol) and KOAc (3.42 g, 34.87 mmol) in 1,4-dioxane (40 mL) was thrice evacuated and backfilled with nitrogen. After addition of Pd(dppf)$Cl_2$-DCM (1.9 g, 2.32 mmol), mixture was again thrice evacuated and backfilled with nitrogen. The resulting mixture was vigorously stirred overnight at 90° C. Thereafter, the mixture was cooled to room temperature, diluted with DCM, and extracted thrice with 2N NaOH. Aqueous layers were combined and treated with conc. HCl until precipitate formed (~pH 4.5). The resulting slurry was filtered, washed twice with water, and vacuum dried to afford 1.2 g of an off-white solid (labeled as P1). The remaining filtrate and washes were combined and extracted thrice with DCM. The combined organic extracts were dried over $Na_2SO_4$, filtered, and concentrated to afford a greyish oil material that solidified under vacuum drying (labeled as P2). Solids P1 and P2 were combined to afford 2-(4, 4, 5, 5-tetramethyl-1,3,2-dioxaborolan-2-yl)-4-(trideuteriomethoxy)benzonitrile (3f) (2.07 g, 67%) and [2-cyano-5-(trideuteriomethoxy)phenyl]boronic acid (4j) (0.69 g, 32%). LRMS (ESI): m/z $[M+H]^+$ 263, 181.

(39) Reference Procedure of (10r)

2-Bromo-4-(fluoromethoxy)benzonitrile (10r) for preparation of EX.379 was prepared in accordance with the general procedure 16 using the method described below in detail.

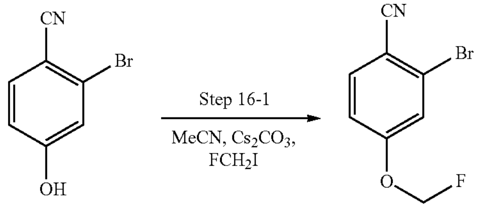

(10q) (10r)

Step 16-1

To a mixture of the 2-bromo-4-hydroxy-benzonitrile (10q) (600 mg, 3.03 mmol) and $Cs_2CO_3$ (1.085 g, 3.33 mmol) in dry acetonitrile, was treated slowly with fluoro (iodo) methane (0.23 mL, 3.33 mmol) and stirred for 12 h. Thereafter, reaction mixture was quenched with water and extracted thrice with $Et_2O$. The combined organic extracts were washed with 1N NaOH, brine, dried over anhydrous $Na_2SO_4$, filtered and concentrated. The residue was purified by silica gel column chromatography (eluted with 30% EtOAc/Hexanes) to afford an off-white solid (638 mg, 92%) as the expected product. LRMS (ESI): m/z $[M+H]^+$ 230, 232.

(40) Reference Procedure of (10t)

3-Iodo-2-(methoxymethoxymethyl)-6,7-dihydro-5H-pyrazolo[5,1-b][1,3]oxazine (10t) for preparation of EX.249 was prepared in accordance with the general procedure 16 using the method described below in detail.

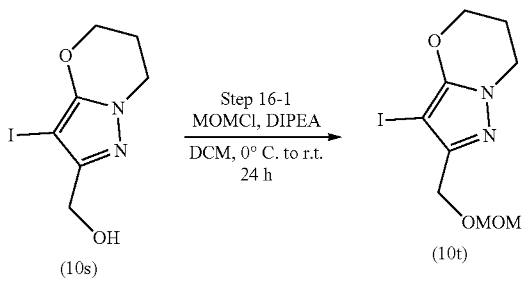

(10s) (10t)

Step 16-1

To the stirred solution of (3-iodo-6,7-dihydro-5H-pyrazolo[5,1-b][1,3]oxazin-2-yl) methanol (10s) (100 mg, 0.36 mmol) in $CH_2Cl_2$ (6 mL) was added DIPEA (124 μL, 0.71 mmol) and after stirring for 5 min, reaction mixture was cooled to 0° C. and added chloromethyl methyl ether (35 μL, 0.46 mmol). The reaction mixture was stirred at room temperature for 24 h. The mixture was concentrated and purified by silica gel column chromatography using 0-100% EtOAc in hexanes to give brown solid (10t), 106 mg 91% yield.

(41) Reference Procedure of (10u)

5-Ethoxy-4-iodo-1-methyl-1H-pyrazole (10u) for preparation of EX.154 was prepared in accordance with the general procedure 17 using the method described below in detail.

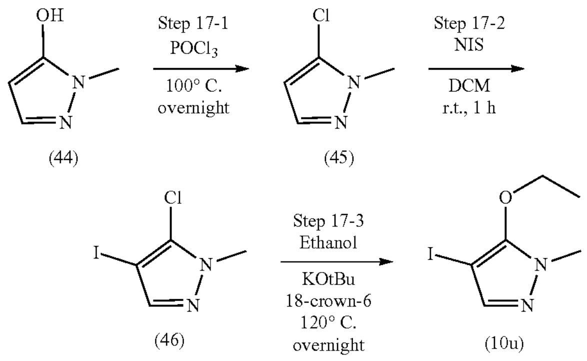

Step 17-1

A mixture of 2-methylpyrazol-3-ol (44) (2.0 g, 20.39 mmol) and neat $POCl_3$ (19 mL, 203.87 mmol) was stirred and heated at 100° C. overnight. After cooling to room temperature, extra $POC_3$ was evaporated in vacuo. To the residue, water was added at 0° C. and the product was extracted with DCM (x3). The combined organic extracts were dried over $Na_2SO_4$ and concentrated. The residue was used for the next reaction without further purification (1.23 g, 52%); LRMS (ESI): m/z $[M+H]^+$ 117.

Step 17-2

A mixture of 5-chloro-1-methyl-pyrazole (45) (227 mg, 1.95 mmol) and NIS (460 mg, 2.05 mmol) in DCM (10 mL) was stirred at room temperature for 1 h. After concentration, the residue was purified by silica gel column chromatography (0-20% EtOAc/Hexane) to give the expected product as a tan solid (275.8 mg, 58%); LRMS (ESI): m/z $[M+H]^+$ 243.

Step 17-3

A mixture of 5-chloro-4-iodo-1-methyl-pyrazole (46) (100.0 mg, 0.41 mmol), KOtBu (139 mg, 1.24 mmol) and 18-crown-6 (163.5 mg, 0.62 mmol) in ethanol (1.2 mL) was stirred and heated at 120° C. overnight. After cooling to room temperature, the mixture was poured into brine and the product was extracted with DCM (x3). The combined organic extracts were dried over $Na_2SO_4$ and concentrated. The residue was purified by silica gel column chromatography (0-100% DCM/Hexane) to give the expected product as a yellow oil (8.2 mg, 7.9%); LRMS (ESI): m/z $[M+H]^+$ 253.

(42) Reference Procedure of (10v)

5-(Cyclopropylmethoxy)-4-iodo-1-methyl-1H-pyrazole (10v) for preparation of EX.155 was prepared in accordance with the general procedure 17, step 17-3 using the method described below in detail.

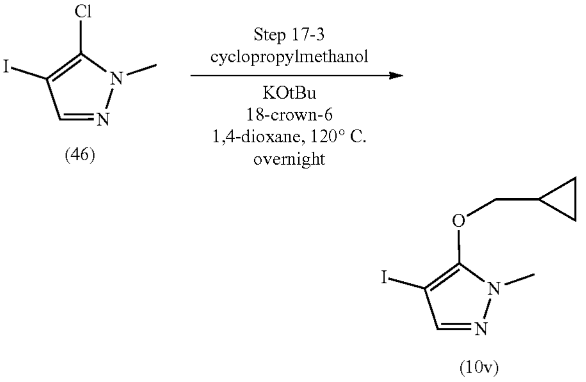

Step 17-3

A mixture of 5-chloro-4-iodo-1-methyl-pyrazole (46) (150.0 mg, 0.62 mmol), cyclopropylmethanol (0.1 mL, 1.24 mmol), KOtBu (138.8 mg, 1.24 mmol) and 18-crown-6 (327.1 mg, 1.24 mmol) in 1,4-dioxane (2 mL) was stirred and heated at 120° C. overnight. After cooling to room temperature, the mixture was poured into brine and the product was extracted with DCM (x3). The combined organic extracts were dried over $Na_2SO_4$ and concentrated. The residue was purified by silica gel column chromatography (0-100% DCM/Hexane) to give the expected product as yellow oil (22.0 mg, 12.8%); LRMS (ESI): m/z $[M+H]^+$ 279.

(43) Reference Procedure of (3a)

5-Methoxy-1-methyl-6-(4,4,5,5-tetramethyl-1,3,2-dioxaborolan-2-yl)-1H-indole (3a) for preparation of EX.12 was prepared in accordance with the general procedure 18 using the method described below in detail.

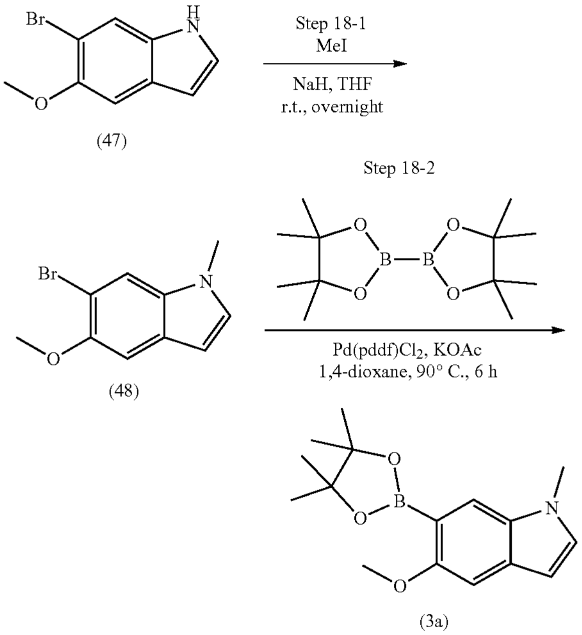

Step 18-1

To a solution of 6-bromo-5-methoxy-1H-indole (47) (30 mg, 0.13 mmol) in THF (1 mL) was added NaH, 60% dispersion in mineral oil (3.5 mg, 0.15 mmol) and the mixture was stirred at room temperature for 10 min. After the addition of MeI (12.3 μL, 0.20 mmol), the mixture was further stirred at room temperature overnight. After concentration, the residue was purified by silica gel column chromatography (0-10% EtOAc/Hexane) to give the expected product as a white solid (25 mg, 75%); LRMS (ESI): m/z $[M+H]^+$ 240, 242.

Step 18-2

A reaction vessel containing 6-bromo-5-methoxy-1-methyl-indole (48) (25 mg, 0.099 mmol), bis(pinacolato) diboron (39 mg, 0.15 mmol) and potassium acetate (29 mg, 0.3 mmol) in 1,4-dioxane (0.4 mL) was degassed and backfilled with nitrogen three times. After the addition of $Pd(dppf)Cl_2$-DCM (8 mg, 0.01 mmol), the reaction mixture was purged with nitrogen three times. The resulting mixture was then stirred and heated at 90° C. for 6 h. After cooling to room temperature and concentration, the residue was purified by silica gel column chromatography (0-5% EtOAc/Hexane) to give the expected product as a white solid (12 mg, 40%); LRMS (ESI): m/z $[M+H]^+$ 288.

(44) Reference Procedure of (10wi)

3-Bromo-4,4-difluoro-4,5,6,7-tetrahydropyrazolo[1,5-a] pyridine (10wi) for preparation of EX.156 was prepared in accordance with the general procedure 19 using the method described below in detail.

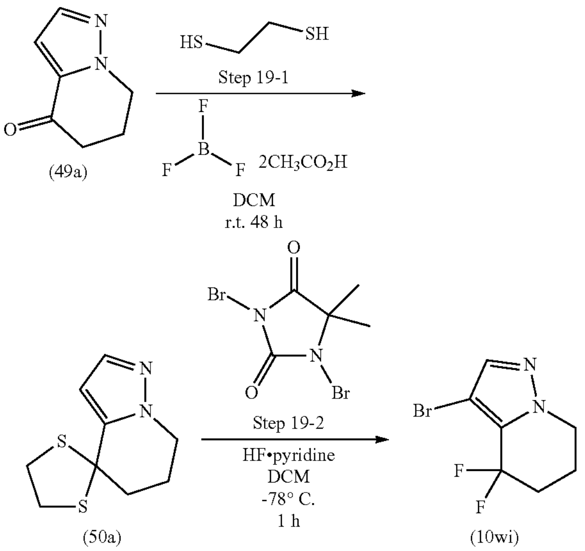

(49a) (50a) (10wi)

Step 19-1

To a mixture of 6,7-dihydro-5H-pyrazolo[1,5-a]pyridin-4-one (49a) (700 mg, 5.14 mmol) in DCM (29 mL) was added 1,2-ethanedithiol (0.65 mL, 7.71 mmol) and $BF_3 \cdot 2AcOH$ (1.07 mL, 7.71 mmol) at room temperature. The reaction was stirred at room temperature over the weekend. The reaction was partitioned between brine and extracted with DCM. The combined organic layers were dried over $Na_2SO_4$ and concentrated in vacuo. The crude residue was purified by silica gel column chromatography (0-50% EtOAc/Hexane) to obtain the expected product as a yellow solid (942 mg, 86%); LRMS (ESI): m/z $[M+H]^+$ 213.

Step 19-2

To a solution of 1,3-dibromo-5,5-dimethyl-imidazolidine-2,4-dione (DBDMH) (1.09 g, 3.82 mmol) in DCM (2.18 mL) was added HF.pyridine (1.81 mL, 20.06 mmol) dropwise at −78° C., followed by spiro[1,3-dithiolane-2,4'-6,7-dihydro-5H-pyrazolo[1,5-a]pyridine] (50a) (200 mg, 0.94 mmol). After stirring for 1 h at −78° C. the reaction was quenched with water, extracted with DCM, dried over $Na_2SO_4$ and concentrated in vacuo. Crude was purified by silica gel column chromatography (0-20% EtOAc/hexane) to obtain the expected product as a white solid (56.3 mg, 25%); LRMS (ESI): m/z $[M+H]^+$ 237, 239.

(45) Reference Procedure of (10aa)

Tert-butyl 3-(difluoromethoxy)-4-iodo-1H-pyrazole-1-carboxylate (10aa) for preparation of EX.157 was prepared in accordance with the general procedures 20 using the method described below in detail.

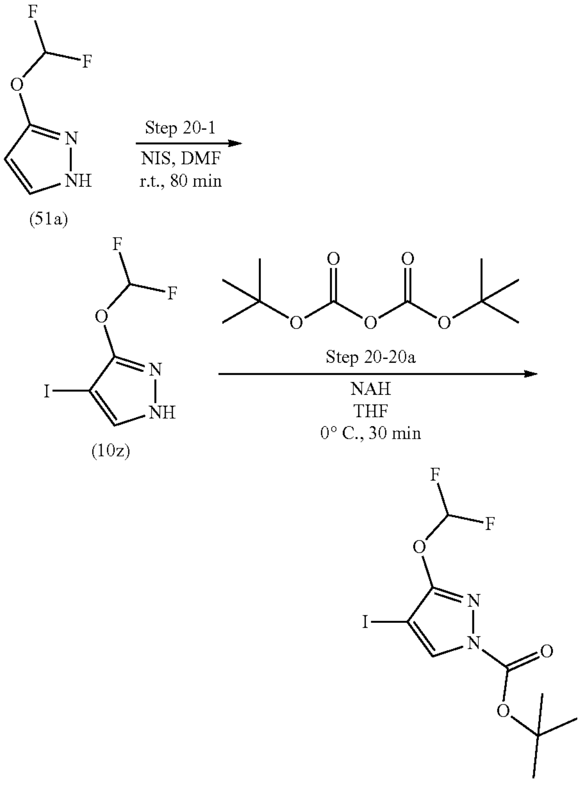

(51a) (10z) (10aa)

Step 20-1

To a solution of 3-(difluoromethoxy)-1H-pyrazole (51a) (0.14 mL, 1.49 mmol) in DMF (3 mL) added NIS (336 mg, 1.49 mmol) and reacted at room temperature for 80 min. The reaction was quenched with water and extracted thrice with EtOAc. The combined organic layers were dried over $Na_2SO_4$, filtered, and concentrated to afford a light-yellow color semisolid compound (261 mg, 67%) as a crude product which was used for the next step without further purification. LRMS (ESI): m/z $[M+H]^+$ 261.

Step 20-2a

A solution of 3-(difluoromethoxy)-4-iodo-1H-pyrazole (10z) (289 mg, 0.97 mmol) in THF (4.6 mL) was cooled to 0° C. and added NaH (93.1 mg, 2.33 mmol) and stirred at 0° C. for 10 min. Subsequently, $Boc_2O$ (329.4 mg, 1.51 mmol) was added and stirred at 0° C. for 30 min. The reaction was quenched with water and extracted with EtOAc. The combined organic layers were dried over $Na_2SO_4$ and concentrated in vacuo. The crude residue was purified by silica gel column chromatography (0-11% EtOAc/hexanes) to obtain the expected product as an orange oil (176.6 mg, 50%); LRMS (ESI): m/z $[M+H-tBu]^+$ 304.9.

(461) Reference Procedure of (3g) and (3h)

4-(4,4,5,5-Tetramethyl-1,3,2-dioxaborolan-2-yl)-3-(trifluoromethyl)-1H-pyrazole (3g) and tert-butyl 4-(4,4,5,5-tetramethyl-1,3,2-dioxaborolan-2-yl)-3-(trifluoromethyl) pyrazole-1-carboxylate (3h) were prepared in accordance with the general procedure 20 using the method described below in detail.

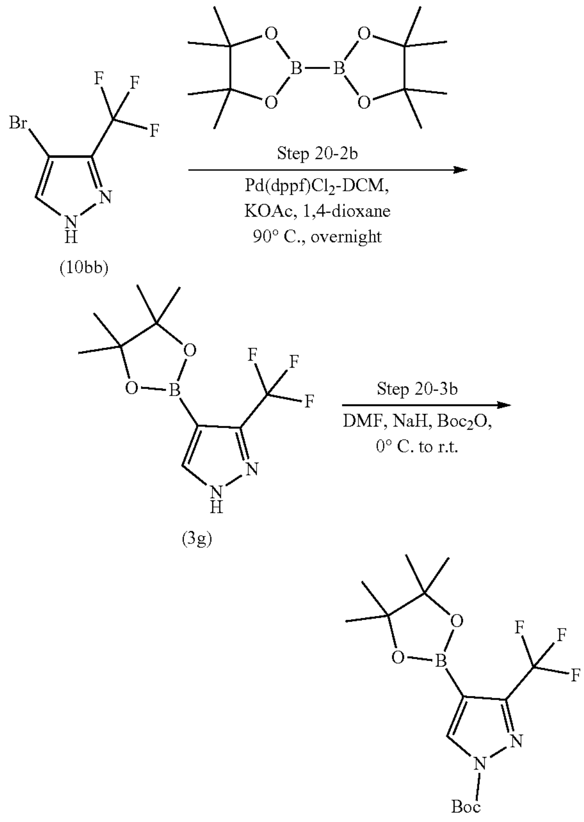

(10bb)

(3g)

(3h)

Step 20-2b

A reaction vessel containing 4-bromo-3-(trifluoromethyl)-1H-pyrazole (10bb) (200 mg, 0.93 mmol), bis(pinacolato)diboron (284 mg, 1.12 mmol) and potassium acetate (183 mg, 1.86 mmol) in 1,4-dioxane (5 mL) was thrice evacuated and backfilled with nitrogen. After addition of $Pd(dppf)Cl_2$-DCM (76 mg, 0.09 mmol), mixture was again thrice evacuated and backfilled with nitrogen and stirred at 90° C. overnight. Thereafter, mixture was concentrated and purified by silica gel column chromatography (eluted with 0-70% EtOAc/Hexanes) to afford the expected product (64 mg, 26%). LRMS (ESI): m/z $[M+H]^+$ 263.

Step 20-3b

To a solution of 4-(4,4,5,5-tetramethyl-1,3,2-dioxaborolan-2-yl)-3-(trifluoromethyl)-1H-pyrazole (3g) (500 mg, 1.91 mmol) in DMF (7 mL) was added 60% NaH in mineral oil (83 mg, 2.1 mmol) at 0° C., and stirred at the same temperature for 10 min. Afterwards, $Boc_2O$ (499 mg, 2.29 mmol) was added at 0° C. and stirred at room temperature for 1 h. Thereafter, mixture was slowly treated with water and extracted thrice with 5% MeOH/DCM. The combined organic extracts were dried over $Na_2SO_4$, filtered, and concentrated. The residue was purified by silica gel column chromatography (eluted with 0-30% EtOAc/Hexanes) to afford a white solid (320 mg, 46%) as the expected product. LRMS (ESI): m/z [M+H-Boc]+263, $[M+H-tBu]^+$ 307, $[M+Na]_+$ 385.

(47) Reference Procedure of (3j) and (4ja)

Tert-butyl 5-(difluoromethyl)-4-(4,4,5,5-tetramethyl-1,3,2-dioxaborolan-2-yl)pyrazole-1-carboxylate (3j) and [1-tert-butoxycarbonyl-5-(difluoromethyl)pyrazol-4-yl]boronic acid (4ja) were prepared in accordance with the general procedure 20 using the method described below in detail.

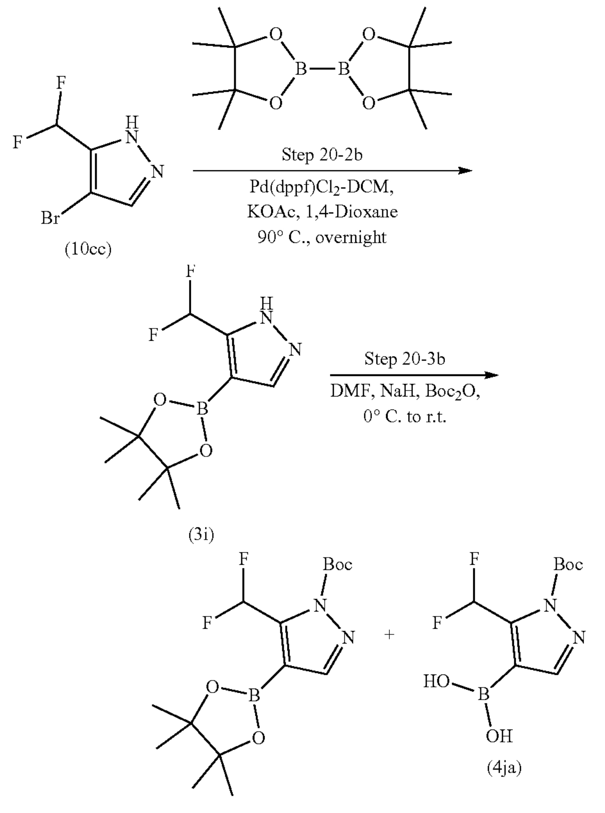

(10cc)

(3i)

(3j)

+

(4ja)

Step 20-2b

A reaction vessel containing 4-bromo-5-(difluoromethyl)-1H-pyrazole (10cc) (2 g, 10.15 mmol), bis(pinacolato)diboron (3.35 g, 13.2 mmol) and KOAc (2.99 g, 30.46 mmol) in 1,4-dioxane (40 mL) was thrice evacuated a backfilled with nitrogen. After addition of $Pd(dppf)Cl_2$-DCM (0.83 g, 1.02 mmol), mixture was again thrice evacuated and backfilled with nitrogen. Resulting mixture was stirred overnight at 90° C. Thereafter, mixture was concentrated and purified by silica gel column chromatography (eluted with 0-100% EtOAc/Hexanes) to afford a red oil (2.13 g, 86%) as the expected product. LRMS (ESI): $[M+H]^+$ 245.

Step 20-3b

To a solution of 5-(difluoromethyl)-4-(4,4,5,5-tetramethyl-1,3,2-dioxaborolan-2-yl)-1H-pyrazole (3i) (2 g, 8.2 mmol) in DMF (30 mL) at 0° C. was added 60% NaH in mineral oil (0.36 g, 9.01 mmol) at 0° C. and stirred at the same temperature for 10 min. Afterwards, $Boc_2O$ (2.15 g, 9.83 mmol) was added and stirred at room temperature for 1 h. Thereafter, mixture was slowly treated with water and extracted thrice with 5% MeOH/DCM. The combined organic extracts were dried over $Na_2SO_4$, filtered, and concentrated. The residue was purified by silica gel column chromatography (eluted with 0-100% EtOAc/Hexanes) to afford a mixture of tert-butyl 5-(difluoromethyl)-4-(4,4,5,5-tetramethyl-1,3,2-dioxaborolan-2-yl)pyrazole-1-carboxylate (3j) (630 mg, 22%) and [1-tert-butoxycarbonyl-5-(difluoromethyl)pyrazol-4-yl]boronic acid (4ja) (200 mg, 9%) which was used in the next step without further purification. LRMS (ESI): m/z $[M+H-^tBu]^+$289 for (3j), $[M+H-^tBu]^+$ 207 for (4ja).

(48) Reference Procedure of (10ee) and (10ff)

2-[[4-Bromo-5-(trifluoromethyl) imidazol-1-yl]methoxy] ethyl-trimethyl-silane (10ee) and 2-[[5-bromo-4-(trifluoromethyl) imidazol-1-yl]methoxy]ethyl-trimethyl-silane (10ff) were prepared in accordance with the general procedure 20 using the method described below in detail.

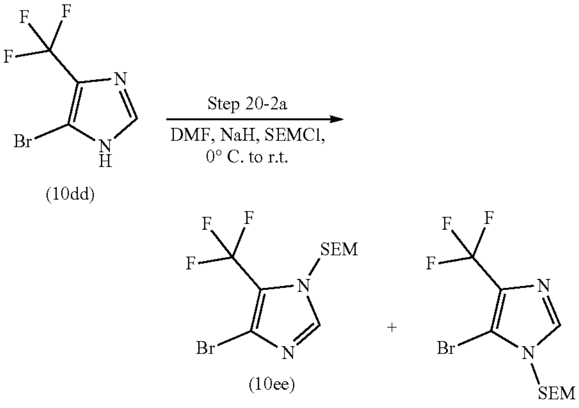

(10dd) (10ee) (10ff)

Step 20-2a

To a solution of 5-bromo-4-(trifluoromethyl)-1H-imidazole (10dd) (700 mg, 3.26 mmol) in DMF (10 mL) stirred at 0° C. and was added NaH (60% in mineral oil) (143.28 mg, 3.58 mmol) and stirring continued for 10 min. Afterwards, SEM-Cl (570 mg, 3.42 mmol) was added and stirred for another 1 h (during that time was allowed to warm to room temperature). The mixture was then poured into water and extracted twice with DCM. The combined organic extracts were dried over $Na_2SO_4$, filtered, and concentrated. The residue was purified by silica gel column chromatography (0-100% DCM/Hexanes) to afford a colorless oil (651 mg, 57.8%, mixture of 2-[[4-bromo-5-(trifluoromethyl) imidazol-1-yl]methoxy]ethyl-trimethyl-silane (10ee) and 2-[[5-bromo-4-(trifluoromethyl) imidazol-1-yl]methoxy]ethyl-trimethyl-silane (10ff) with approximately 1:1 ratio by 1HNMR analysis) as products. LRMS (ESI): m/z $[M+H]^+$ 345, 347.

(49) Reference Procedure of (3k)

5-Methyl-3-(4, 4, 5, 5-tetramethyl-1,3,2-dioxaborolan-2-yl)thiophene-2-carbonitrile (3k) was prepared in accordance with the general procedure 20 using the method described below in detail.

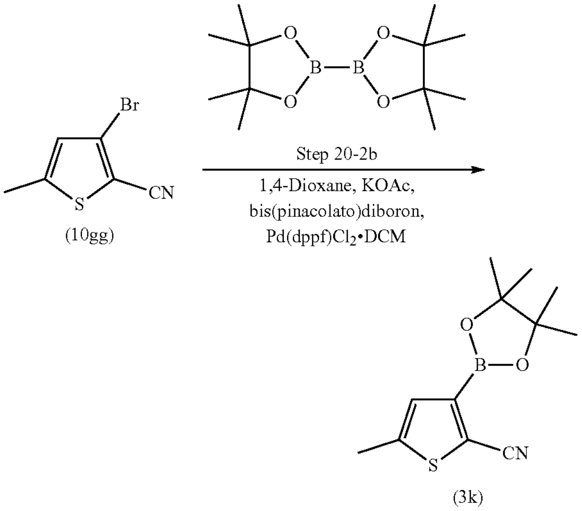

(10gg) (3k)

Step 20-2b

To a 20 mL vial containing 3-bromo-5-methyl-thiophene-2-carbonitrile (10gg) (500 mg, 2.47 mmol), bis(pinacolato) diboron (816 mg, 3.22 mmol) and KOAc (728 mg, 7.42 mmol) in 1,4-dioxane (10 mL) was degassed by bubbling $N_2$ for 5 min. Afterwards, mixture was treated with Pd(dppf) $Cl_2$.DCM (404 mg, 0.49 mmol) and stirred overnight at 90° C. Thereafter, mixture the mixture was diluted with water (20 mL) and extracted thrice with EtOAc (20 mL each time). The combined organic extracts were dried over $Na_2SO_4$, filtered and concentrated. The residue was purified by silica gel column chromatography (20% EtOAc/Hexanes) to afford the expected product (466 mg, 76%). LRMS (ESI): m/z: 250 and $(M+Na)^+$ 277.

(50) Reference Procedure of (10ii)

3-Bromo-4-(2-trimethylsilylethoxymethyl)pyrazolo[1,5-a]pyrimidin-7-one (10ii) for preparation of EX.289 was prepared in accordance with the general procedure 20 using the method described below in detail.

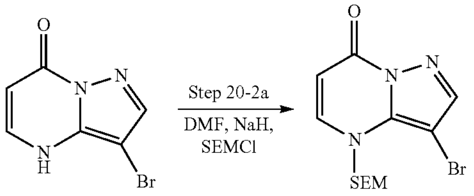

(10hh) (10ii)

Step 20-2a

To a solution of 3-bromo-4H-pyrazolo[1,5-a]pyrimidin-7-one (10 hh) (500 mg, 2.34 mmol) in DMF (5 mL) was added NaH (120 mg, 4.68 mmol) and stirred at 0° C. for min. Afterwards, mixture was treated slowly (over 10 min.) at 0°

C. with the 2-(trimethylsilyl)ethoxymethyl chloride (408 mg, 2.45 mmol) and further at room temperature for 3 h. Thereafter, mixture was diluted with water (20 mL) and extracted thrice with (20 mL each time). The organic extracts were combined, dried over $Na_2SO_4$, filtered, and concentrated. The residue was purified by silica gel column chromatography (0-15% EtOAc/Hexanes) to afford a yellow oil (529 mg, 66%) as product. LRMS (ESI): m/z $[M+H-2CH_3]^+$ 316.

(51) Reference Procedure of (3m)

3-(Difluoromethoxy)-1-methyl-4-(4,4,5,5-tetramethyl-1,3,2-dioxaborolan-2-yl)pyrazole (3m) for preparation of EX.291 was prepared in accordance with the general procedure 20 using the method described below in detail.

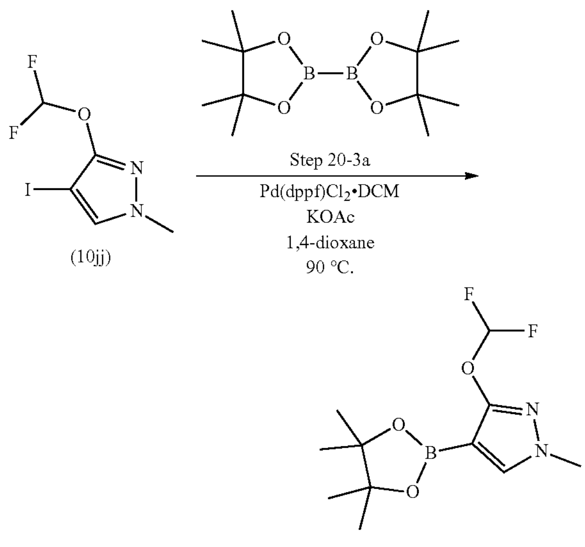

(10jj)

(3m)

Step 20-3a

A vial containing 3-(difluoromethoxy)-4-iodo-1-methyl-pyrazole (10jj) (200 mg, 0.73 mmol) and 4,4,5,5-tetramethyl-2-(4,4,5,5-tetramethyl-1,3,2-dioxaborolan-2-yl)-1,3,2-dioxaborolane (222.4 mg, 0.88 mmol), KOAc (215 mg, 2.19 mmol) and $Pd(dppf)Cl_2$-DCM (119.2 mg, 0.15 mmol) was vacuumed and backfilled with $N_2$ three times. Then, 1,4-dioxane (5 mL) was added, and the solution was vacuumed and backfilled with $N_2$ three times. The final mixture was stirred at 90° C. for 4 h. After the reaction was cooled down, the mixture was diluted with DCM and extracted with 2N NaOH aqueous solution (25 mL×2). The combined aqueous layers were combined and washed with DCM one more time. The aqueous phase was separated, filtered through Celite, and then acidified with 12 N HCl aq. solution to pH 3. This acidic aqueous solution was then extracted with DCM (30 mL×2) and with EtOAc (30 mL×2). The organic layers were combined, dried over $Na_2SO_4$, filtered, and concentrated to obtain product as brown oil (102 mg, 50%); LRMS (ESI): m/z $[M+H]^+$ 275. It was used as is in the next step without further purification.

(52) Reference Procedure of (10kk)

3-Ethyl-4-iodo-1-methyl-1H-pyrazole (10kk) for preparation of EX.260 was prepared in accordance with the general procedure 20 using the method described below in detail.

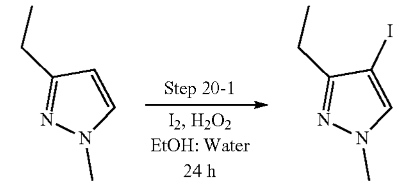

51b (10kk)

Step 20-1

To a stirred solution of 3-ethyl-1-methyl-pyrazole (51b) (250 mg, 2.27 mmol), in ethanol (1 mL) and water (2 mL) was added molecular iodine (288 mg, 1.13 mmol), and cooled it to 15-20° C., added $H_2O_2$ (0.14 mL, 1.36 mmol) stirred at rt for 24 h. The reaction was quenched with $NaHSO_3$ solution (0.1 mL) and concentrate in vacuo. The crude was purified by flash chromatography using 0-5% MeOH in DCM to obtain the expected compound as brown oil, 295 mg, 55%. LCMS (ESI): m/z $[M+H]^+$ 237.

(53) Reference Procedure of (10ll)

3-Iodo-6-methoxy-2-methylpyrazolo[1,5-a]pyrimidine (10ll) for preparation of EX.179 was prepared in accordance with the general procedures 16 and 20 using the method described below in detail.

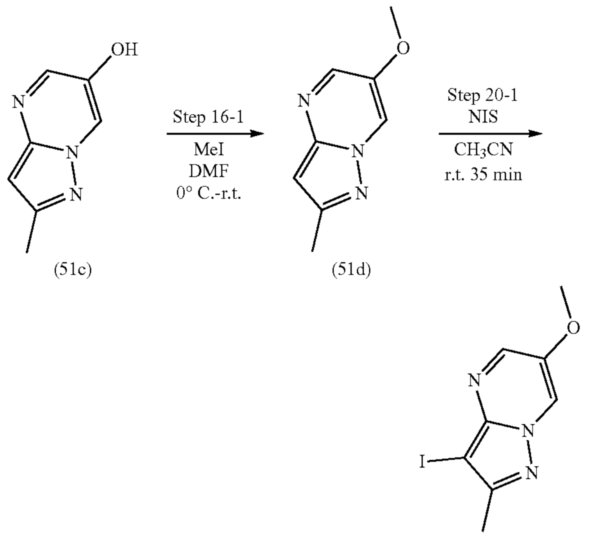

(51c) (51d)

(10ll)

Step 16-1

A vial containing 2-methylpyrazolo[1,5-a]pyrimidin-6-ol (51c) (63.3 mg, 0.42 mmol) was dissolved in DMF (1.6 mL) cooled to 0° C. and added NaH (28.8 mg, 0.72 mmol). Reaction was stirred at 0° C. for 5 min and then added $CH_3I$ (0.04 mL, 0.72 mmol) and reacted at 0° C. for 40 min and then at room temperature for 1.25 h. Additional $CH_3I$ (12.4 uL), NaH (10.7 mg) was added at 0° C. and reacted at 0° C. for 1 h and then at room temperature for 2.15 h. The reaction was quenched with water, extracted with ether and purified by silica gel column chromatography (0-25% EtOAc/hexanes) to obtain the expected product as a white solid (47 mg, 68%); LRMS (ESI): m/z $[M+H]^+$ 164.

Step 20-1

A reaction vial containing 6-methoxy-2-methyl-pyrazolo [1,5-a]pyrimidine (51d) (47 mg, 0.29 mmol) was dissolved in MeCN (0.79 mL), added NIS (72.2 mg, 0.32 mmol) and reacted at room temperature for 35 min. Crude reaction mixture was purified by silica gel column chromatography (0-30% EtOAc/hexanes) to obtain the expected product as a yellow solid (78.4 mg, 94%); LRMS (ESI): m/z [M+H]$^+$ 290.

(54) Reference Procedure of (10 mm)

4-Bromo-3-(difluoromethyl)-5-methoxy-1-methyl-pyrazole (10 mm) for preparation of EX.232 was prepared in accordance with the general procedures 16 and 20 using the method described below in detail.

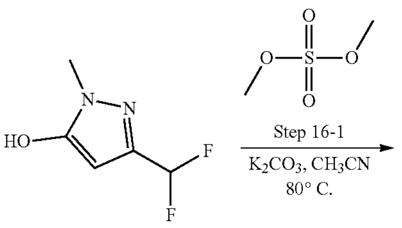

(51e)

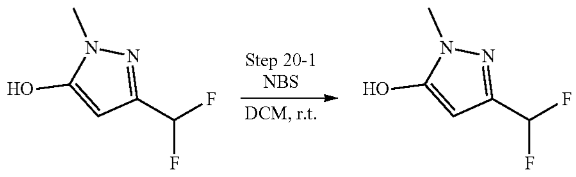

(51h) (10mm)

Step 16-1 (following procedure in Journal of Fluorine Chemistry, 218 (2019), P1-10)

To a solution of 5-(difluoromethyl)-2-methyl-pyrazol-3-ol (51e) (300 mg, 2.03 mmol) and $K_2CO_3$ (420 mg, 3.04 mmol) in MeCN (5 mL) was added dimethyl sulfate (0.19 mL, 2.03 mmol). The mixture was refluxed at 80° C. for 2.5 h. After the reaction was cooled down, the mixture was diluted with water and then extracted with ethyl ether twice. The organic layers were combined, dried over $Na_2SO_4$, filtered, and concentrated to obtain product (51f) as colorless liquid (310 mg, 94%). It was used as is in next step without further purification. 1H (400 MHz, DMSO-d$_6$): δ 3.57 (3H, t, J=1.2 Hz), 3.89 (3H, s), 5.96 (1H, t, J=0.9 Hz), 6.78 (1H, t, $J_{H-F}$=54.6 Hz); LRMS (ESI): m/z [M+H]$^+$ 163.

Step 20-1

A solution containing 3-(difluoromethyl)-5-methoxy-1-methyl-pyrazole (51f) (150 mg, 0.93 mmol) and NBS (177.4 mg, 1.11 mmol) in DCM (5 mL) was stirred at room temperature for 1 h. It was concentrated and purified by ISCO normal-phase silica flash chromatography (0-40% ethyl acetate in hexanes) to obtain product (10 mm) as light yellow oil (140 mg, 62%); LRMS (ESI): m/z [M+H]$^+$ 241, 243.

(55) Reference Procedure of (3o)

Trimethyl-[2-[[5-(4,4,5,5-tetramethyl-1,3,2-dioxaborolan-2-yl)-4-(trifluoromethyl) pyrazol-1-yl]methoxy]ethyl] silane (3o) for preparation of EX.64 and EX.65 was prepared in accordance with the general procedure 20 using the method described below in detail.

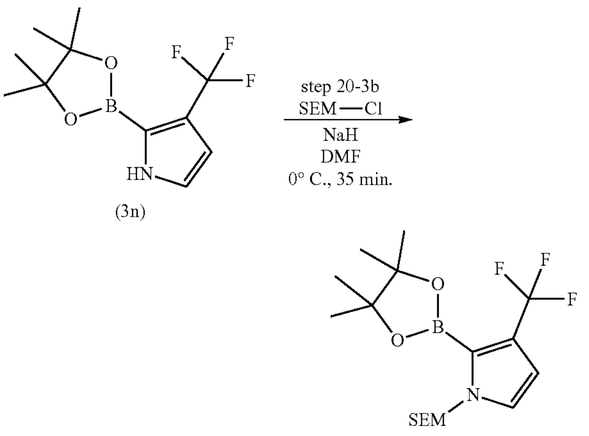

(3n)

(3o)

Step 20-3b 5-(4,4,5,5-tetramethyl-1,3,2-dioxaborolan-2-yl)-4-(trifluoromethyl)-1H-pyrazole (3n) (200 mg, 0.76 mmol) was dissolved in DMF (0.5 mL) and cooled to 0° C., added NaH (33.5 mg, 0.84 mmol) and reacted for 10 min. Subsequently, added (2-(chloromethoxy)ethyl)trimethylsilane (0.16 mL, 0.92 mmol) and reacted at 0° C. for 35 min. The reaction mixture was quenched with MeOH and purified by silica gel chromatography (0-15% EtOAc/hexanes) to obtain the expected product as a clear oil (128.3 mg, 43%); LRMS (ESI): m/z [M+H]$^+$ 393.

Tert-butyl 7-iodo-6-methyl-2,3-dihydroimidazo[1,2-b] pyrazole-1-carboxylate (10nn) for preparation of EX.168 was prepared in accordance with the general procedure 20.

(10nn)

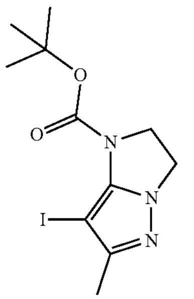

LRMS (ESI): m/z [M+H]$^+$ 350.

Tert-butyl 7-iodo-6-methyl-imidazo[1,2-b]pyrazole-1-carboxylate (1000) for the preparation of EX.169 was prepared in accordance with the general procedure 20.

(10oo)

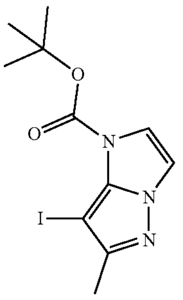

LRMS (ESI): m/z $[M+H]^+$ 348.

3-(4-(4,4,5,5-Tetramethyl-1,3,2-dioxaborolan-2-yl)-1H-pyrazol-1-yl) propan-1-ol (3qa) was prepared in accordance with the general procedure 22.

(3qa)

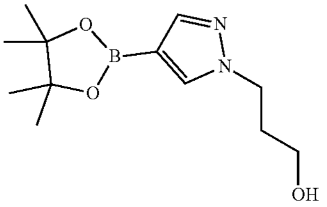

LRMS (ESI): m/z $[M+H]^+$ 253.

3-(3-(Difluoromethyl)-4-(4,4,5,5-tetramethyl-1,3,2-dioxaborolan-2-yl)-1H-pyrazol-1-yl) propan-1-ol (3qb) was prepared in accordance with the general procedure 22.

(3qb)

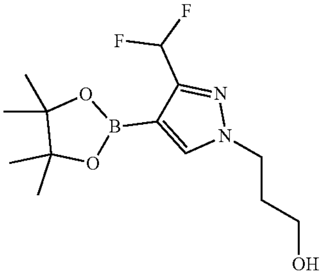

LRMS (ESI): m/z $[M+H]^+$ 303.

(56) Reference Procedure of (10qq)

Tert-butyl 4-iodo-3-(2,2,2-trifluoroethyl)-1H-pyrazole-1-carboxylate (10qq) for preparation of EX.160 was prepared in accordance with the general procedures 21 and 20 using the method described below in detail.

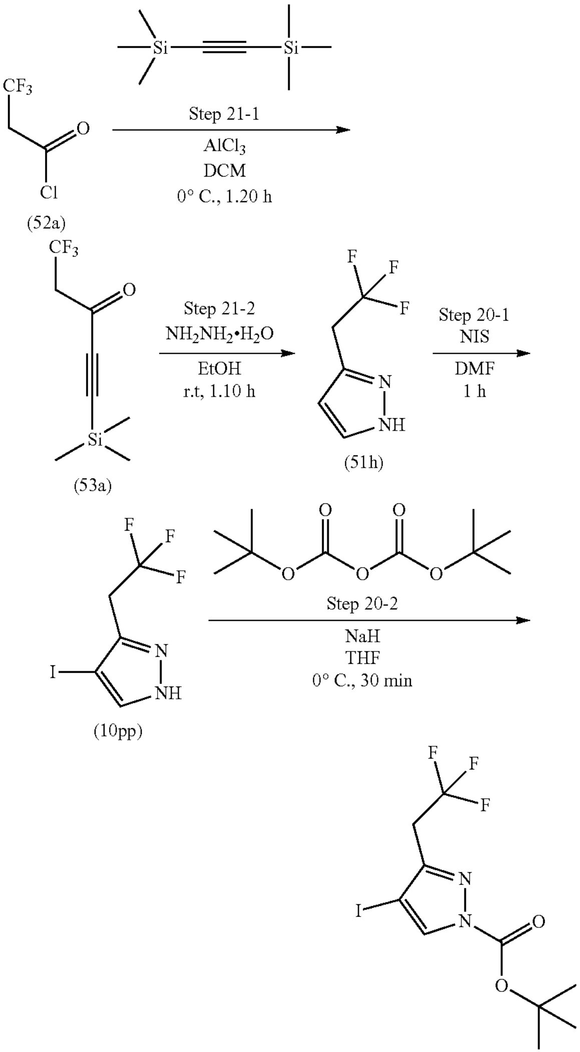

(52a) (53a) (51h) (10pp) (10qq)

Step 21-1

A reaction vessel under $N_2$ containing trimethyl(2-trimethylsilylethynyl) silane (1.3 mL, 5.87 mmol), 3,3,3-trifluoropropanoyl chloride (52a) (0.67 mL, 6.46 mmol) was dissolved in DCM (15 mL), cooled to 0° C., and added $AlCl_3$ (939 mg, 7.04 mmol). The reaction was stirred at 0° C. for 1.20 h. The reaction mixture was then poured into a mixture of 2M HCl (20 mL), ice, DCM. The mixture was left standing for 15 min. The aqueous layer was extracted with DCM. The organic layer was dried over $Na_2SO_4$ and evaporated solvent in vacuo to obtain the expected product as a yellow oil (732 mg, 60%) which was used for the next step without further purification.

Step 21-2

A reaction vessel containing 5, 5, 5-trifluoro-1-trimethylsilyl-pent-1-yn-3-one (53a) (0.73 g, 3.51 mmol) was dissolved in EtOH (10 mL), cooled to 0° C. and added $NH_2NH_2 \cdot H_2O$ (0.46 mL, 9.46 mmol). The reaction was stirred at room temperature for 1.10 h. Evaporated solvent in vacuo, added brine and extracted with DCM. Organic layer was dried over $Na_2SO_4$ and evaporated in vacuo. The residue was purified by silica gel column chromatography (0-3.5% MeOH/DCM) to obtain the expected product as a brown oily solid (193.2 mg, 36%); LRMS (ESI): m/z $[M+H]^+$ 151.

Step 20-1

To a solution of 3-(2,2,2-trifluoroethyl)-1H-pyrazole (51h) (190 mg, 1.27 mmol) in DMF (0.3 mL) was added NIS (281.6 mg, 1.25 mmol) and reacted at room temperature for 1 h. The reaction was partitioned between brine and extracted with EtOAc. The combined organic layers were dried over $Na_2SO_4$ and concentrated in vacuo to obtain the expected product as a red solid (342.4 mg, 98%); LRMS (ESI): m/z $[M+H]^+$ 276.9.

Step 20-2

A solution of 4-iodo-3-(2,2,2-trifluoroethyl)-1H-pyrazole (10pp) (342.4 mg, 1.24 mmol) in THF (5.6 mL) was cooled to 0° C., added NaH (74.4 mg, 1.86 mmol) and stirred at 0° C. for 15 min. Subsequently $Boc_2O$ (431 mg, 1.97 mmol) was added and stirred at 0° C. for 30 min then at room temperature for 55 min. Additional $Boc_2O$ (18 mg) was added and reacted at room temperature for another 1.15 h. The reaction was quenched with water and extracted with EtOAc. The combined organic layers were dried over $Na_2SO_4$ and concentrated in vacuo. The crude residue was purified by silica gel column chromatography (0-11% EtOAc/hexanes) to obtain the expected product as a pale-yellow solid (257.1 mg, 55%); LRMS (ESI): m/z $[M+Na]^+$ 398.9.

(57) Reference Procedure of (10jj) and (10Uu)

3-(Difluoromethoxy)-4-iodo-1-methyl-1H-pyrazole (10jj) for preparation of EX.161 and 3-(difluoromethoxy)-1-ethyl-4-iodo-1H-pyrazole (10uu) for preparation of EX.400 were prepared in accordance with the general procedure 22 using the method described below in detail.

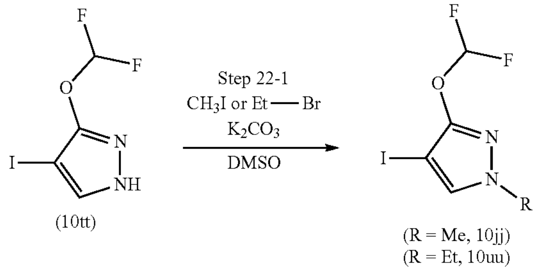

(10tt)

(R = Me, 10jj)
(R = Et, 10uu)

Step 22-1

3-(difluoromethoxy)-4-iodo-1H-pyrazole (10tt) (84.4 mg, 0.32 mmol) was dissolved in DMSO (0.19 mL), cooled to 0° C., added $K_2CO_3$ (68.5 mg, 0.5 mmol) and iodomethane (0.02 mL, 0.39 mmol). The reaction was stirred from 0° C. to room temperature. After 1 h additional $CH_3I$ (20 μL) was added and reacted at room temperature for 1.20 h. Further addition of $CH_3I$ (9.9 μL) and reacted at room temperature for another 1.5 h. The reaction was partitioned between water and extracted with EtOAc. The combined organic layers were dried over $Na_2SO_4$ and concentrated in vacuo. The crude residue was purified by silica gel column chromatography (0-1% EtOAc/DCM) to afford a yellow oil (52.6 mg, 59%) as product (10jj). LRMS (ESI): m/z $[M+H]^+$ 274.9.

Note: Iodoethane was used instead of Iodomethane for the conversion of compound (10tt) to product (10uu).

(58) Reference Procedure of (10ww)

3-Bromo-1-methyl-4-(trifluoromethyl)-1H-pyrazole (10ww) for preparation of EX.165 was prepared in accordance with the general procedure 22 using the method described below in detail.

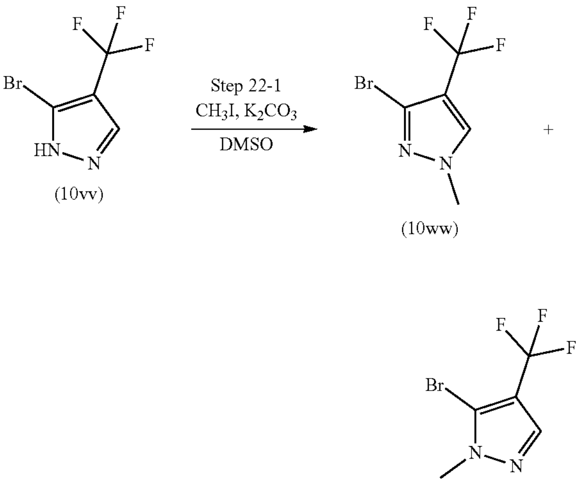

(10vv) (10ww) + (10xx)

Step 22-1

5-bromo-4-(trifluoromethyl)-1H-pyrazole (10vv) (300 mg, 1.4 mmol) was dissolved in DMSO (1.0 mL) and cooled to 0° C., added $K_2CO_3$ (231.4 mg, 1.67 mmol) and iodomethane (0.1 mL, 1.54 mmol) and reacted from 0° C. to room temperature overnight. Additional $CH_3I$ (55 μL) was added and reacted for another 1.05 h. The reaction was partitioned between water and extracted with EtOAc. The combined organic layers were dried over $Na_2SO_4$ and concentrated in vacuo. The crude residue was purified by silica gel column chromatography (0-35% EtOAc/hexanes) to afford: (10xx) as a clear oil (41 mg, 13%); $^1H$ NMR (400 MHz, $CDCl_3$): δ 3.94 (3H, s), 7.72 (1H, s). (10ww) as a yellow oil (55.1 mg, 17%); $^1H$ NMR (400 MHz, $CDCl_3$): δ 3.92 (3H, s), 7.62 (1H, s); LRMS (ESI): m/z $[M+H]^+$ 229, 231. Structures confirmed by HSQC and HMBC experiments.

(59) Reference Procedure of (10yy)

3-[4-Bromo-3-(difluoromethyl)pyrazol-1-yl]propan-1-ol (10yy) for preparation of EX.212 and (7t) was prepared in accordance with the general procedure 22 using the method described below in detail.

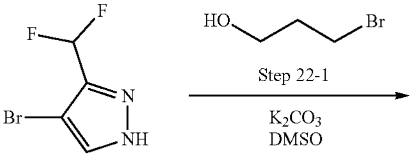

(10cc)

-continued

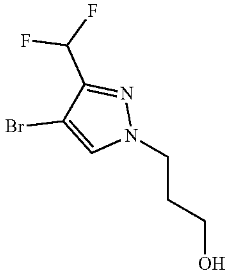

+

(10yy)

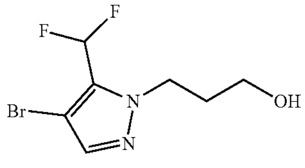

(10zz)

Step 22-1

To a solution of 3-bromo-1-propanol (0.25 mL, 2.83 mmol) in DMSO (1.2 mL) cooled to 0° C. added $K_2CO_3$ (391 mg, 2.83 mmol) and 4-bromo-3-(difluoromethyl)-1H-pyrazole (10cc) (464 mg, 2.36 mmol) and reacted from 0° C. to room temperature overnight. Additional 3-bromo-1-propanol (41.2 μL) was added and reacted for 55 min. Additional $K_2CO_3$ (60.8 mg) was added at room temperature and reacted at room temperature for 3 h. The reaction mixture was partitioned between water and extracted with EtOAc. The combined organic layers were dried over $Na_2SO_4$, concentrated in vacuo and purified by silica gel column chromatography (0-32% EtOAc/hexanes) to afford: 3-[4-bromo-3-(difluoromethyl)pyrazol-1-yl]propan-1-ol (10yy) (300.2 mg, 50%) and 3-[4-bromo-5-(difluoromethyl)pyrazol-1-yl]propan-1-ol (10zz) (44.2 mg, 7%) as clear oils. (10xx): $^1$H NMR (400 MHz, $CDCl_3$): δ 2.00-2.07 (2H, m), 3.22 (1H, br s), 3.56-3.60 (2H, m), 4.23-4.27 (2H, m), 6.66 (1H, t, $J_{H-F}$=53.7 Hz), 7.51 (1H, s).

(10yy): $^1$H NMR (400 MHz, $CDCl_3$): δ 2.07-2.13 (2H, m), 2.63 (1H, br s), 3.63-3.66 (2H, m), 4.46-4.49 (2H, m), 6.80 (1H, t, $J_{H-F}$=52.3 Hz), 7.50 (1H, s).

LRMS (ESI): m/z $[M+H]^+$ 255, 257. Structure confirmed by HSQC and HMBC.

(60) Reference Procedure of (10Ccc)

3-Iodo-4-methyl-1-(oxetan-3-ylmethyl)pyrazole (10ccc) for preparation of EX.204 was prepared in accordance with the general procedure 22.

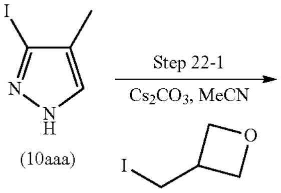

(10aaa)

-continued

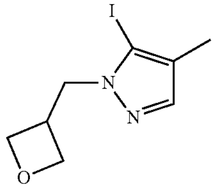

+

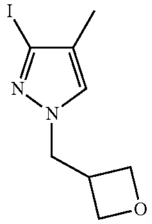

(10bbb) (10ccc)

Step 22-1

To a round bottom flask containing 3-iodo-4-methyl-1H-pyrazole (10aaa) (300 mg, 1.44 mmol), $Cs_2CO_3$ (1.03 g, 3.16 mmol) in MeCN (6.5 mL) was added 3-(iodomethyl) oxetane (0.29 mL, 2.88 mmol). Resulting mixture was stirred for 2 days at room temperature. Thereafter, mixture was filtered through a pad of Celite and washed twice with DCM. Filtrate and washes were combined, concentrated, and purified by prep-TLC (30% EtOAc/hexanes) to afford a colorless oil (153 mg, 38%) as the expected product (10ccc).

$^1$H NMR (400 MHz, $CDCl_3$): δ 1.97 (3H, d, J=0.7 Hz), 4.37 (2H, d, J=7.6 Hz), 4.46 (2H, t, J=6.2 Hz), 4.80 (2H, dd, J=7.7, 6.5 Hz), 7.07 (1H, s); $^{13}$C NMR (101 MHz, $CDCl_3$): δ 11.01, 35.5, 54.8, 74.6, 100.4, 121.6, 128.4. HMBC confirmed correct regiochemistry of (10ccc). LRMS (ESI): m/z $[M+H]^+$ 279. TLC analysis: Rf=0.07 in 30% EtOAc/hexanes.

Note: Compound (10bbb) eluted with unreacted starting material (10aaa).

3-Iodo-1-(2-methoxyethyl)-4-methyl-pyrazole (10ddd) was synthesized from commercially available 3-iodo-4-methyl-1H-pyrazole and 2-bromoethyl methyl ether in accordance with the methods described in the general procedure 22 for the preparation of EX.205.

(10ddd)

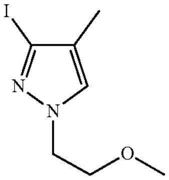

LRMS (ESI): m/z $[M+H]^+$ 267.

The coupling agent, 3-iodo-4-methyl-1-(oxetan-3-yl) pyrazole (10eee) was synthesized from commercially available 3-iodo-4-methyl-1H-pyrazole and 3-iodooxetane in accordance with the methods described in the general procedure 22 for the preparation of EX.206.

(10eee)

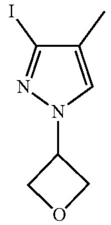

LRMS (ESI): m/z $[M+H]^+$ 265.

(61) Reference Procedure of (10hhh)

The coupling agent, 4-(difluoromethyl)-5-iodo-1-methyl-pyrazole (10hhh) for preparation of EX.219 was prepared in accordance with the general procedure 22 using the method described below in detail.

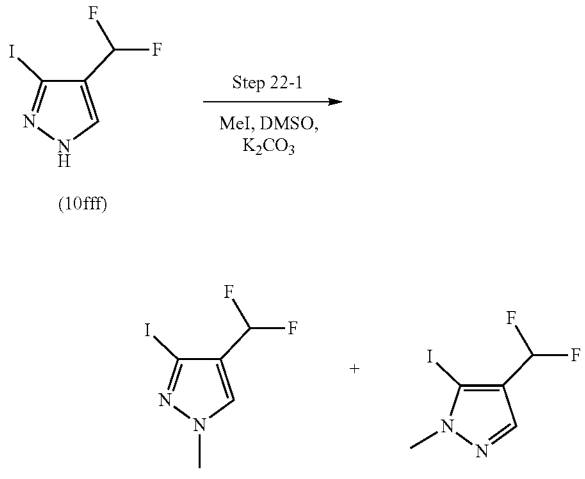

(10fff)

(10ggg) (10hhh)

Step 22-1

To a mixture of 4-(difluoromethyl)-3-iodo-1H-pyrazole (10fff) (307 mg, 1.26 mmol) and $K_2CO_3$ (347 mg, 2.52 mmol) in DMSO (5 mL) was added iodomethane (0.12 mL, 1.89 mmol) and stirred at room temperature for 2 h. Thereafter, mixture was poured into water and extracted thrice with EtOAc. The combined organic extracts were dried over $Na_2SO_4$, filtered, and concentrated. The residue was purified by silica gel column chromatography (0-10% EtOAc/Hexanes) to afford product (10hhh) (113 mg, purity=~55%, yield=19%) followed by compound (10ggg) (120 mg, 37%). LRMS (ESI): m/z $[M+H]^+$ 259.

(62) Reference Procedure of (10iii) and (3r)

4-Bromo-3-(difluoromethyl)-1-(trideuteriomethyl)pyrazole (10iii) (for preparation of EX.222 and EX.284) and 3-(Difluoromethyl)-4-(4,4,5,5-tetramethyl-1,3,2-dioxaborolan-2-yl)-1-(trideuteriomethyl)pyrazole (3r) (for preparation of EX.377 and EX.378) were prepared in accordance with the general procedures 22 and 20 using the method described below in detail.

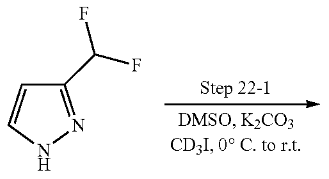

(51i)

-continued

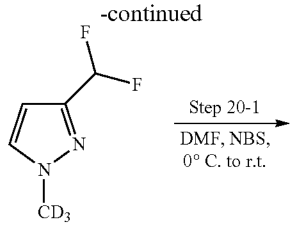

(51j)

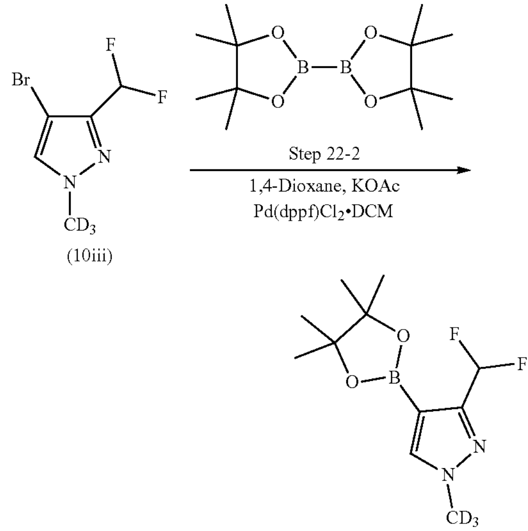

(10iii)

(3r)

Step 22-1

A vial containing 3-(difluoromethyl)-1H-pyrazole (51i) (600 mg, 5.08 mmol), $K_2CO_3$ (842 mg, 6.1 mmol), trideuterio (iodo) methane (0.35 mL, 5.59 mmol) at 0° C. was diluted with 4 mL of DMSO. The resulting mixture was slowly warmed to room temperature and stirred for 24 h. Thereafter, the reaction mixture was quenched with iced water (10 mL) and extracted twice with EtOAc (15 mL each time). The organic extracts were combined, washed with brine (20 mL), dried over $Na_2SO_4$, filtered and concentrated to afford crude product (150 mg, 22%) which was used in the next step without further purification. LRMS (ESI): m/z $[M+H]^+$ 136.

Step 20-1

A solution of NBS (591 mg, 3.7 mmol) in dry DMF (2 mL) was added dropwise to a stirring solution of compound 3-(difluoromethyl)-1-(trideuteriomethyl)pyrazole (51j) (500 mg, 3.7 mmol) in dry DMF (1 mL) at 0° C. and stirred for 2 h at room temperature thereafter, reaction mixture was quenched with water and extracted with diethyl ether. The organic extract was washed with brine, dried over $Na_2SO_4$, filtered, and concentrated to afford crude product (512 mg, 64%) which was used in the next step without further purification. LRMS (ESI): m/z $[M+H]^+$ 196, 198.

Step 22-2

A reaction vessel containing 4-bromo-3-(difluoromethyl)-1-(trideuteriomethyl)pyrazole (10iii) (300 mg, 1.4 mmol), bis(pinacolato)diboron (462 mg, 1.82 mmol) and KOAc (413 mg, 4.21 mmol) in 1,4-dioxane (15 mL) was thrice evacuated and backfilled with nitrogen. After addition of $Pd(dppf)Cl_2$-DCM (114 mg, 0.14 mmol), mixture was purged thrice with nitrogen and then stirred at 90° C. overnight. Thereafter, mixture was concentrated, and residue was purified by silica gel column chromatography (eluted with 0-25% EtOAc/Hexanes) to afford a red oil (210 mg, 57%) as the expected product. LRMS (ESI): $[M+H]^+$ 262.

(63) Reference Procedure of (10'jjj)

3-Iodo-5,6,7,8-tetrahydropyrazolo[5,1-b][1,3]oxazepine (10'jjj) for preparation of EX.163 was prepared in accordance with the general procedure 23 using the method described below in detail.

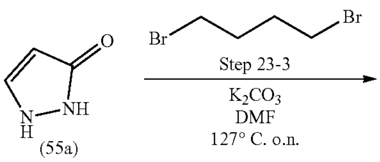

(55a)

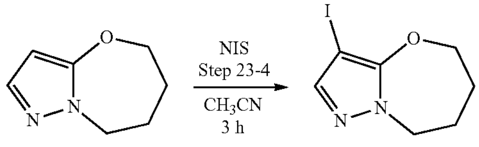

(58a) (10'jjj)

Step 23-3

To a solution of 1,2-dihydropyrazol-3-one (2.0 g, 23.7 mmol) (55a), DMF (66 mL), $K_2CO_3$ (11.5 g, 83.2 mmol) was added 1,4-dibromobutane (57a) (3.4 mL, 28.5 mmol) dropwise at room temperature, then the resulting reaction mixture was heated at 127° C. overnight. The reaction was partitioned between brine and extracted with EtOAc and $CHCl_3$. The combined organic layers were dried over $Na_2SO_4$ and concentrated in vacuo. The crude residue was purified by silica gel column chromatography (0-11% EtOAc/hexanes) to obtain the expected product as a yellow oil (849 mg, 25%); LRMS (ESI): m/z $[M+H]^+$ 139.

Step 23-4

A reaction vial containing 5,6,7,8-tetrahydropyrazolo[5,1-b][1,3]oxazepine (58a) (276.2 mg, 2.0 mmol) was dissolved in MeCN (4.4 mL) and added NIS (458.7 mg, 2.04 mmol) at room temperature The reaction was stirred at room temperature for 1.40 h. Additional NIS (35.3 mg) was added and reacted at room temperature for another 1.10 h. After concentration, the residue was purified by silica gel column chromatography (0-10% EtOAc/hexanes) to obtain the expected product as a white solid (269.3 mg, 51%);

LRMS (ESI): m/z $[M+H]^+$ 264.9.

(64) Reference Procedure of (10kkk) and (10lll)

7-iodo-2,6-dimethyl-2,3-dihydropyrazolo[5,1-b]oxazole (10kkk) for preparation of EX.167 and 7-iodo-3,6-dimethyl-2,3-dihydropyrazolo[5,1-b]oxazole (10lll) for preparation of EX.166 were prepared in accordance with the general procedure 23 using the method described below in detail.

Step 23-3

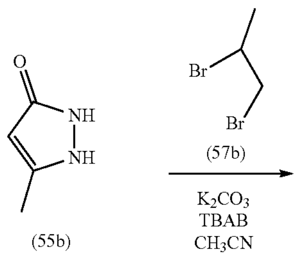

(55b)

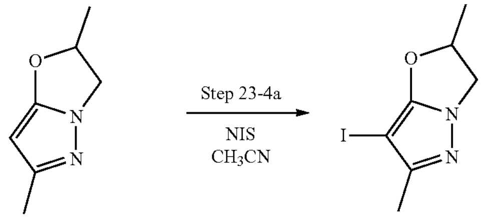

(58b-1) (10kkk)

+

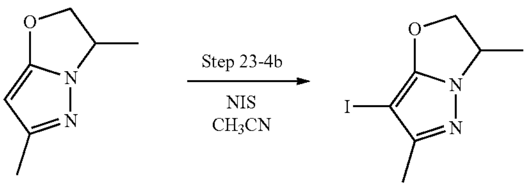

(58b-2) (10lll)

Step 23-3

5-methyl-1, 2-dihydropyrazol-3-one (55b) (1 g, 10.19 mmol) was dissolved in MeCN (20 mL), added $K_2CO_3$ (2.8 g, 20.26 mmol), TBAB (657.2 mg, 2.04 mmol), 1,2-dibromopropane (57b) (1.59 mL, 15.3 mmol) and heated at 50° C. overnight. Additional 1,2-dibromopropane (1.59 mL), $K_2CO_3$ (1.38 g) was added and heated at 95° C. for 2 h. To the solution DMF (1 mL) was added and heated at 90° C. overnight. After concentration, the residue was purified by silica gel column chromatography (0-28% EtOAc/hexanes) to obtain 3,6-dimethyl-2,3-dihydropyrazolo[5,1-b]oxazole (58b-2) (73 mg, 5%) and 2,6-dimethyl-2,3-dihydropyrazolo[5,1-b]oxazole (58b-1) (81.8 mg, 6%) both as clear oils.

(58b-2): $^1H$ NMR (400 MHz, $CDCl_3$): δ 1.44 (3H, d, J=6.0 Hz), 2.13 (3H, s), 4.37-4.42 (2H, m), 4.93-4.99 (1H, m), 5.06 (1H, s).

(58b-1): $^1H$ NMR (400 MHz, $CDCl_3$): δ 1.52 (3H, d, J=6.4 Hz), 2.13 (3H, s), 3.67-3.71 (1H, m), 4.20-4.24 (1H, m), 5.06 (1H, s), 5.21-5.30 (1H, m); LRMS (ESI): m/z $[M+H]^+$ 139.

Step 23-4a

A reaction vial containing 2,6-dimethyl-2,3-dihydropyrazolo[5,1-b]oxazole (58b-1) (75 mg, 0.54 mmol) was dissolved in MeCN (1.8 mL) and added NIS (122 mg, 0.54 mmol) at room temperature and reacted at room temperature for 55 min. Additional NIS (11 mg) was added and reacted for another 2 h. Solvent was evaporated in vacuo and was purified by silica gel column chromatography (0-50% EtOAc/hexanes) to obtain product (10kkk) as a clear oil (138.1 mg, 96%); LRMS (ESI): m/z $[M+H]^+$ 265.

Step 23-4b

A reaction vial containing 3,6-dimethyl-2,3-dihydropyrazolo[5,1-b]oxazole (58b-2) (72 mg, 0.52 mmol) was dissolved in MeCN (1.1 mL) and added NIS (117 mg, 0.52 mmol) at room temperature and reacted at room temperature for 40 min. Solvent was evaporated in vacuo and was purified by silica gel column chromatography (0-51% EtOAc/hexanes) to obtain product (10lll) as a white solid (104.5 mg, 76%); LRMS (ESI): m/z $[M+H]^+$ 265

(65) Reference Procedure of (10mmm) and (10nnn)

(1) 3-Bromo-2, 7-dimethyl-6,7-dihydro-5H-pyrazolo[5,1-b][1,3]oxazine (10mmm) for preparation of EX.170 and EX.172, (2) 3-bromo-2,5-dimethyl-6,7-dihydro-5H-pyrazolo[5,1-b][1,3]oxazine (10nnn) for preparation of EX.171 were prepared in accordance with the general procedure 23 using the method described below in detail.

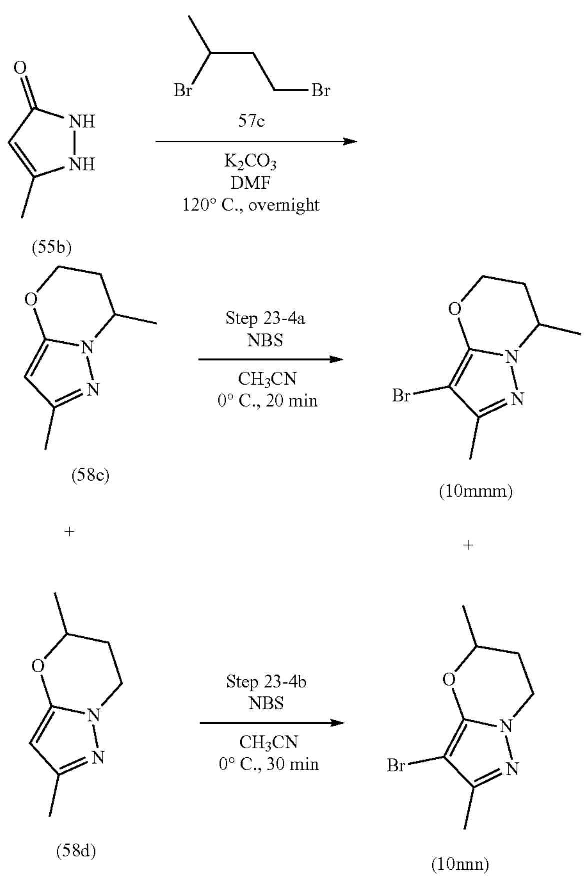

(55b)

(58c) + (10mmm) +

(58d) (10nnn)

Step 23-3

A solution containing 5-methyl-1, 2-dihydropyrazol-3-one (55b) (1 g, 10.19 mmol), $K_2CO_3$ (4.9 g, 35.6 mmol) in DMF (25 mL) was heated at 120° C. for 20 min, and then added 1,3-dibromobutane (57c) (1.47 mL, 12.2 mmol) dropwise at room temperature and heated at 120° C. overnight. The reaction mixture was partitioned between water and extracted with DCM, EtOAc and ether. The combined organic layers were dried over $Na_2SO_4$, concentrated in vacuo and purified by silica gel column chromatography (0-100% EtOAc/hexanes) to obtain 2,7-dimethyl-6,7-dihydro-5H-pyrazolo[5,1-b][1,3]oxazine (58c) (415.5 mg, 27%) and 2,5-dimethyl-6,7-dihydro-5H-pyrazolo[5,1-b][1,3]oxazine (58d) (60 mg, 4%) both as clear oils.

(58c): $^1$H NMR (400 MHz, $CDCl_3$): δ 1.58 (3H, d, J=6.5 Hz), 1.92-2.00 (1H, m), 2.20 (3H, s), 2.26-2.33 (1H, m), 4.17-4.22 (1H, m), 4.26-4.34 (2H, m), 5.29 (1H, s); $^{13}$C (100 MHz, $CDCl_3$): δ 13.6, 20.3, 29.4, 49.2, 63.5, 85.7, 147.3, 151.3.

(58d): $^1$H NMR (400 MHz, $CDCl_3$): δ 1.32 (3H, d, J=6.3 Hz), 1.90-1.93 (2H, m), 1.99-2.02 (1H, m), 2.05 (3H, s), 3.88-3.95 (1H, m), 4.15-4.23 (1H, m), 5.13 (1H, s);

LRMS (ESI): m/z $[M+H]^+$ 153.

Step 23-4a

A reaction vial containing 2,7-dimethyl-6,7-dihydro-5H-pyrazolo[5,1-b][1,3]oxazine (58c) (407.6 mg, 2.68 mmol) was dissolved in MeCN (4.8 mL) cooled to 0° C. and added NBS (427.2 mg, 2.67 mmol) and reacted at 0° C. for 22 min. Solvent was evaporated in vacuo and the residue was purified by silica gel column chromatography (0-48% EtOAc/hexanes) to obtain product (10mmm) as a clear oil (547 mg, 88%); $^1$H NMR (400 MHz, $CDCl_3$): δ 1.58 (3H, d, J=6.5 Hz), 1.96-2.04 (1H, m), 2.20 (3H, s), 2.30-2.37 (1H, m), 4.25-4.33 (2H, m), 4.39-4.44 (1H, m); LRMS (ESI): m/z $[M+H]^+$ 231, 233.

Step 23-4b

A reaction vial containing 2,5-dimethyl-6,7-dihydro-5H-pyrazolo[5,1-b][1,3]oxazine (58d) (60 mg, 0.39 mmol) was dissolved in MeCN (0.7 mL), cooled to 0° C. and added NBS (62.8 mg, 0.39 mmol) and reacted at 0° C. for 30 min. Solvent was evaporated in vacuo and the residue was purified by silica gel column chromatography (0-100% EtOAc/hexanes) to obtain product (10nnn) as a clear oil (77.3 mg, 85%); $^1$H NMR (400 MHz, $CDCl_3$): δ 1.53 (3H, d, J=6.3 Hz), 2.03-2.13 (1H, m), 2.16-2.18 (1H, m), 2.20 (3H, s), 4.04-4.11 (1H, m), 4.13-4.18 (1H, m), 4.37-4.45 (1H, m); LRMS (ESI): m/z $[M+H]^+$ 231, 233.

(66) Reference Procedure of (10oooo)

(7S)-3-iodo-2, 7-dimethyl-6,7-dihydro-5H-pyrazolo[5,1-b][1,3]oxazine (10000) for preparation of EX.176 was prepared in accordance with the general procedure 23 using the method described below in detail.

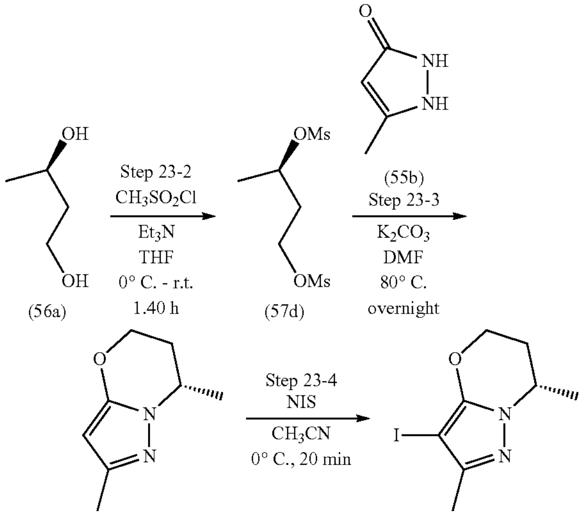

(56a) (57d)

(58e) (10ooo)

Step 23-2

A solution containing (3R)-butane-1,3-diol (56a) (1 mL, 11.1 mmol), $Et_3N$ (6.1 mL, 44.3 mmol) in THF (24 mL) was cooled to 0° C. and added methanesulfonyl chloride (1.8 mL, 24.4 mmol) dropwise. After addition, reaction was stirred at 0° C. for 6 min and then at room temperature for 1.40 h. The reaction was partitioned between water and extracted with EtOAc, dried over $Na_2SO_4$, concentrated to obtain a brown oil, which was used for the next step without further purification. Consumption of SM was monitored by TLC (10% MeOH/DCM).

Step 23-3

A solution containing 5-methyl-1,2-dihydropyrazol-3-one (55b) (1.08 g, 11.0 mmol), [(3R)-3-methylsulfonyloxybutyl] methanesulfonate (57d) (2.71 g, 11.0 mmol), $K_2CO_3$ (6.09 g, 44.0 mmol) in DMF (25 mL) was heated at 80° C. overnight. The reaction was partitioned between water and extracted with EtOAc and ether. Combined organic layers were washed again with fresh water, dried over $Na_2SO_4$, concentrated and purified by silica gel column chromatography (0-35% EtOAc/hexanes) to afford the expected product as a yellow liquid (387 mg, 23%); $^1$H NMR (400 MHz, $CDCl_3$): δ 1.52 (3H, d, J=6.5 Hz), 1.86-1.94 (1H, m), 2.15 (3H, s), 2.20-2.28 (1H, m), 4.11-4.17 (1H, m), 4.19-4.28 (2H, m), 5.23 (1H, s); $^{13}$C NMR (100 MHz, $CDCl_3$): δ 14.3, 20.8, 29.8, 49.5, 63.8, 85.8, 147.5, 151.3; LRMS (ESI): m/z $[M+H]^+$ 153. Step 23-4

A reaction vial containing (7S)-2,7-dimethyl-6,7-dihydro-5H-pyrazolo[5,1-b][1,3]oxazine (58e) (150 mg, 0.99 mmol) was dissolved in MeCN (2.9 mL) cooled to 0° C. and added NIS (221.7 mg, 0.99 mmol) and reacted at 0° C. for 20 min. Solvent was evaporated in vacuo and the residue was purified by silica gel column chromatography (0-45% EtOAc/hexanes) to obtain the expected product as a yellow solid (178.3 mg, 65%); $^1$H NMR (400 MHz, $CDCl_3$): δ 1.57 (3H, d, J=6.5 Hz), 1.95-2.04 (1H, m), 2.20 (3H, s), 2.29-2.37 (1H, m), 4.27-4.34 (2H, m), 4.39-4.44 (1H, m); LRMS (ESI): m/z $[M+H]^+$ 279.

(7R)-3-iodo-2,7-dimethyl-6,7-dihydro-5H-pyrazolo[5,1-b][1,3]oxazine (10'ooo) for preparation of EX.178 was obtained using (3S)-butane-1,3-diol (56'a) according to the procedure described for 10000.

(56'a)

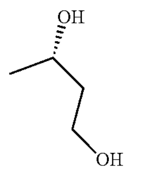

(10'ooo)

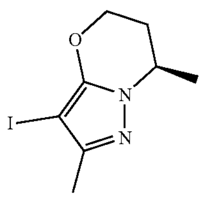

LRMS (ESI): m/z $[M+H]^+$ 279.

(67) Reference Procedure of (10Ppp)

2'-(Difluoromethyl)-3'-iodo-5'H,7'H-spiro[cyclopropane-1,6'-pyrazolo[5,1-b][1,3]oxazine] (10ppp) for preparation of EX.183 was prepared in accordance with the general procedure 23 using the method described below in detail.

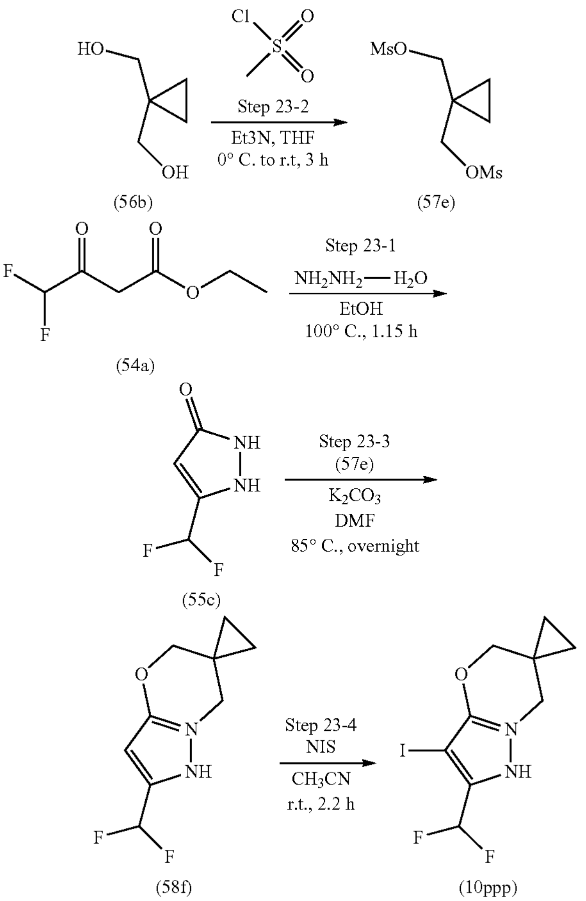

Step 23-1

A solution of $NH_2NH_2 \cdot H_2O$ (4 mL, 64.5 mmol) in absolute ethanol (8.7 mL) was added dropwise to a solution of ethyl 4, 4-difluoro-3-oxo-butanoate (54a) (6 mL, 43.0 mmol) at room temperature. Resulting mixture was slightly exothermic. After heat generation stopped (~10 minutes), reaction mixture was heated at 100° C. for 1.15 h. Thereafter, reaction mixture was cooled to r.t, concentrated and purified by silica gel column chromatography (5% MeOH/DCM) to obtain the expected product as a white solid (2.42 g, 42%); LRMS (ESI): m/z $[M+H]^+$ 135.

Step 23-2

A solution containing [1-(hydroxymethyl)cyclopropyl] methanol (56b) (0.71 mL, 7.45 mmol), $Et_3N$ (4.1 mL, 29.8 mmol) in THF (22 mL) was cooled to 0° C., and then added methanesulfonyl chloride (1.27 mL, 16.39 mmol) dropwise and reacted at 0° C. for min and then at room temperature for 3.10 h. The reaction was concentrated, partitioned between water, and extracted with EtOAc to obtain pale yellow solid (1.9 g), which was used for the next step without further purification.

Step 23-3

A solution containing [1-(methylsulfonyloxymethyl)cyclopropyl]methyl methanesulfonate (57e) (1.92 g, 7.45 mmol), 5-(difluoromethyl)-1,2-dihydropyrazol-3-one (55c) (1 g, 7.45 mmol), $K_2CO_3$ (4.1 g, 29.8 mmol) in DMF (16.9 mL) was heated at 85° C. overnight. The reaction was partitioned between water and extracted with ether, dried and purified by silica gel column chromatography (0-100% EtOAc/hexanes) to obtain the expected product as a yellow liquid (379.1 mg, 25%); $^1$H NMR (400 MHz, $CDCl_3$): δ 0.80-0.88 (4H, m), 4.00-4.03 (4H, m), 5.77 (1H, s), 6.55 (1H, t, $J_{H-F}$=55.1 Hz);

LRMS (ESI): m/z $[M+H]^+$ 201.

Step 23-4

A reaction vial containing 2-(difluoromethyl)spiro[5,7-dihydropyrazolo[5,1-b][1,3]oxazine-6,1'-cyclopropane] (58f) (190 mg, 0.95 mmol) was dissolved in MeCN (2.8 mL) added NIS (213.8 mg, 0.95 mmol) and reacted at room temperature for 2.20 h. The reaction was purified by silica gel column chromatography (0-10% EtOAc/hexanes) to obtain a yellow oil (290 mg, 94%); LRMS (ESI): m/z $[M+H]^+$ 326.9.

(68) Reference Procedure of (10qqq)

3-Bromo-2-methyl-6-tetrahydropyran-2-yloxy-6,7-dihydro-5H-pyrazolo[5,1-b][1,3]oxazine (10qqq) for preparation of EX.199 was prepared in accordance with the general procedure 23.

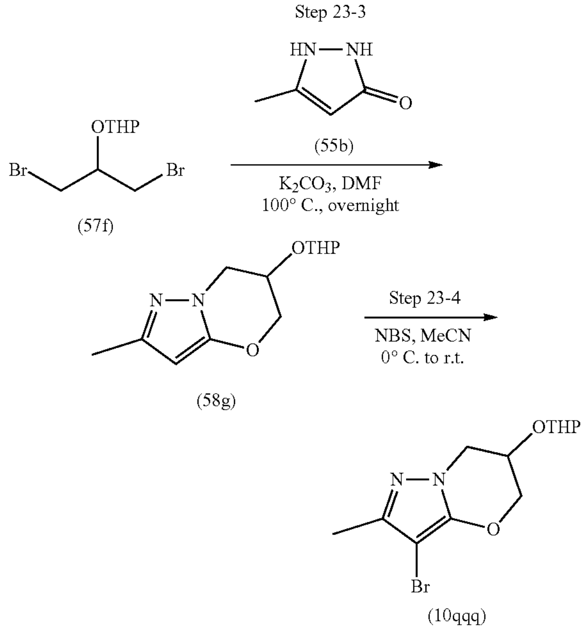

Step 23-3

A 100 mL round bottom flask containing 2-[2-bromo-1-bromomethyl)ethoxy]tetrahydropyran (57f) (2.39 g, 7.14 mmol), 5-methyl-1,2-dihydropyrazol-3-one (55b) (0.7 g, 7.14 mmol) and $K_2CO_3$ (3.45 g, 24.97 mmol) in DMF (36 mL) was heated to 100° C. overnight. Thereafter, mixture was concentrated, diluted with water and extracted thrice with EtOAc. The combined organic extracts were washed with brine, dried over $Na_2SO_4$, filtered, and concentrated. The residue was purified by silica gel column chromatography using EtOAc in hexanes to afford the expected product as a yellowish oil [563 mg, yield=21%]. LRMS (ESI): m/z $[M+H]^+$ 239.

Note: Compound 57f preparation: WO 2018/136890 (PCT/US2018/014728).

Step 23-4

To a solution of 2-methyl-6-tetrahydropyran-2-yloxy-6,7-dihydro-5H-pyrazolo[5,1-b][1,3]oxazine (58g) (580 mg, 1.54 mmol) in MeCN (10 mL) at 0° C., was added (in two portions) NBS (0.38 g, 2.15 mmol). Reaction mixture was removed from the ice bath and stirred at room temperature for 1 h. Thereafter, mixture was diluted with water and extracted thrice with EtOAc. The combined organic extracts were dried over $Na_2SO_4$, filtered, and concentrated. The residue was purified by silica gel column chromatography using EtOAc in hexanes to afford a dark orange oil (86 mg, 18%) as the expected product. LRMS (ESI): m/z $[M+H]^+$ 317, 319.

(69) Reference Procedure of (10rrr)

2-(Difluoromethyl)-3-iodo-6-methoxy-6,7-dihydro-5H-pyrazolo[5,1-b][1,3]oxazine (10rrr) for preparation of EX.201 was prepared in accordance with the general procedures 23 and 16.

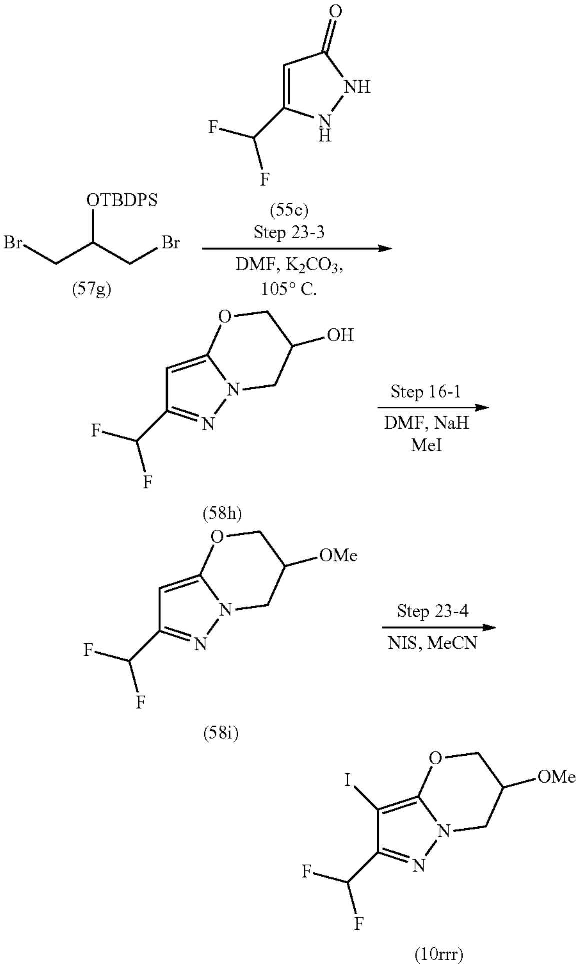

Step 23-3

A round bottom flask containing a pre-heated (45 min., 105° C.) mixture of 5-(difluoromethyl)-1, 2-dihydropyrazol-3-one (55c) (1.2 g, 8.92 mmol) and $K_2CO_3$ (1.55 g, 11.24 mmol) in DMF (30 mL) was added [2-bromo-1-(bromomethyl) ethoxy]-tert-butyl-diphenyl-silane (57g) (0.855 g, 1.87 mmol) in 3 mL of DMF. The reaction mixture was stirred overnight at 105° C. Thereafter, mixture was cooled down to room temperature, filtered through a pad of Celite and washed twice with DCM. Filtrate and washings were combined and diluted with water. The phases were separated, and the aqueous layer extracted twice with DCM. The combined organic extracts were dried over $Na_2SO_4$, filtered, and concentrated. Residue was purified by silica gel column chromatography [0% to 100% EtOAc/Hexanes] to afford the expected product as a brownish oil (45 mg, 12%). LRMS (ESI): m/z $[M+H]^+$ 191.

Note: Compound 57g preparation: WO 2012/068450 A1

Step 16-1 22-1

To a solution of 2-(difluoromethyl)-6,7-dihydro-5H-pyrazolo[5,1-b][1,3]oxazin-6-ol (58h) (45 mg, 0.24 mmol) in DMF (2 mL) was added NaH (37 mg, 0.95 mmol) and stirred for 1 h. Afterwards, iodomethane (0.03 mL, 0.47 mmol) was added and the mixture was further stirred for 18 h. Thereafter, mixture was quenched with water and extracted thrice with EtOAc. The combined organic extracts were washed with brine, dried over $Na_2SO_4$, filtered, and concentrated. The resulting residue (48 mg) was used in the next step without further purification. LRMS (ESI): m/z $[M+H]^+$ 205.

Step 23-4

To a solution of 2-(difluoromethyl)-6-methoxy-6,7-dihydro-5H-pyrazolo[5,1-b][1,3]oxazine (58i) (48 mg, 0.24 mmol) in MeCN (1.5 mL) was added NIS (68 mg, 0.31 mmol). After 30 min., reaction mixture was quenched with water and extracted thrice with EtOAc. The combined organic extracts were washed with brine, dried over $Na_2SO_4$, filtered, and concentrated. Resulting residue was purified by silica gel column chromatography [0-100% EtOAc in hexanes] to afford an orange oil (88 mg, 71%) as the expected product.

$^1H$ NMR (400 MHz, $CDCl_3$): δ 3.50 (3H, s), 3.95-4.00 (1H, m), 4.22-4.39 (3H, m), 4.57 (1H, ddd, J=11.9, 3.6, 1.9 Hz), 6.55 (1H, t, $J_{H-F}$=53.9 Hz); LRMS (ESI): m/z $[M+H]^+$ 331.

2-Ethyl-3-iodo-6,7-dihydro-5H-pyrazolo[5,1-b][1,3]oxazine (10qqqi) for the preparation of EX.200 was prepared in accordance with the general procedures 23 and 16.

(10qqqi)

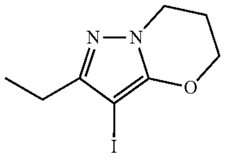

$^1H$ NMR (400 MHz, $CDCl_3$): δ 1.21 (3H, t, J=7.6 Hz), 2.21-2.27 (2H, m), 2.52 (2H, q, J=7.6 Hz), 4.12 (2H, t, J=6.2 Hz), 4.31-4.35 (2H, m). LRMS (ESI): m/z $[M+H]^+$ 279.

3-Bromo-2-methyl-6,7-dihydro-5H-pyrazolo[5,1-b][1,3]oxazine (10qqqii) for the preparation of EX.227 was synthesized in accordance with the general procedures 23 and 16.

(10qqqii)

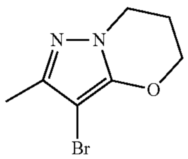

$^1H$ NMR (400 MHz, $CDCl_3$): δ 2.19 (3H, s), 2.24-2.31 (2H, m), 4.12 (2H, t, J=6.2 Hz), 4.33-4.39 (2H, m). LRMS (ESI): m/z $[M+H]^+$ 217, 219.

(70) Reference Procedure of (10sss) and (10ttt)

Tert-butyl N-(3-iodo-2-methyl-6,7-dihydro-5H-pyrazolo[5,1-b][1,3]oxazin-6-yl) carbamate (10sss) and tert-butyl N-(3-iodo-2-methyl-6,7-dihydro-5H-pyrazolo[5,1-b][1,3]oxazin-6-yl)-N-methyl-carbamate (10ttt) for preparation of EX.256 and EX.258 respectively were prepared in accordance with the general procedures 23 and 22 using the method described below in detail.

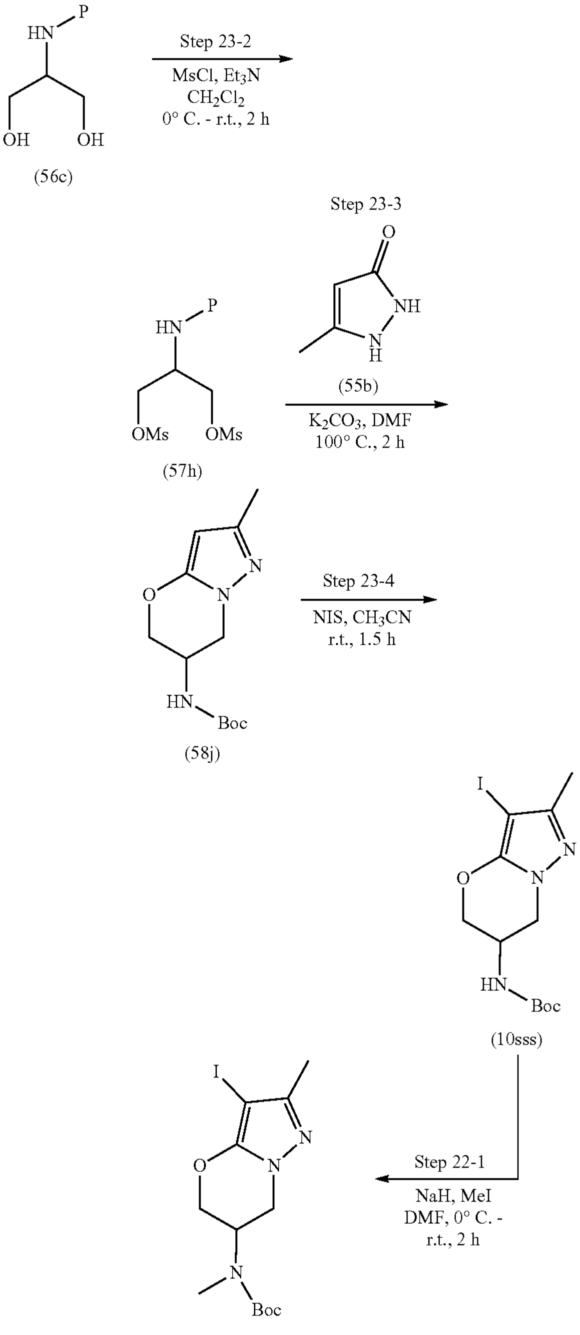

(56c)
(55b)
(57h)
(58j)
(10sss)
(10ttt)

Step 23-2

A solution containing methane sulfonyl chloride (2.67 mL, 34.52 mmol), $Et_3N$ (8.76 mL, 62.75 mmol) in DCM (20 mL) was cooled to 0° C., and then added tert-butyl N-[2-hydroxy-1-(hydroxymethyl)ethyl]carbamate (56c) (3 g, 15.69 mmol) dropwise and reacted at 0° C. for 10 min and then at rt for 2 h. Added water and extracted with DCM (2×20 mL) to obtain a brown oil, which was purified by flash chromatography using 0-5% MeOH in DCM, gave 3.2 g of white solid (57h), 59% yield.

Step 23-3

A mixture of 5-methyl-1,2-dihydropyrazol-3-one (55b) (0.6 g, 6.12 mmol), $K_2CO_3$ (1.61 g, 11.62 mmol), in DMF (15 mL) were heated at 100° C. for 20 min. and added [2-(tert-butoxycarbonylamino)-3-methylsulfonyloxy-propyl]methane sulfonate (57h) (1.28 mL, 7.34 mmol) in 8 mL of DMF to the reaction mixture and was stirred at 80° C. for 2 h. The reaction was cooled to rt and quenched by the addition of water (80 mL) and the product was extracted with DCM (3×60 mL). The combined organic extracts were dried over $Na_2SO_4$ and concentrated. The crude product was purified by flash chromatography using MeOH in DCM gave target compound (58j) as a pale-yellow solid, 810 mg, 52%. LRMS (ESI): m/z $[M+H]^+$: 254, 198.

Step 23-4

A mixture of tert-butyl N-(2-methyl-6,7-dihydro-5H-pyrazolo[5,1-b][1,3]oxazin-6-yl) carbamate (58j) (800 mg, 3.16 mmol), and N-iodosuccinimide (0.4 mL, 3.47 mmol) in MeCN (15 mL) was stirred at rt for 1.5 h. The reaction was concentrated in vacuo and crude was purified by flash chromatography using 0-5% MeOH in DCM to obtain target compound (10sss) as yellow solid, 945 mg, 79%. LRMS (ESI): m/z $[M+H]^+$: 380 and 324.

Step 22-1

A vial containing tert-butyl N-(3-iodo-2-methyl-6,7-dihydro-5H-pyrazolo[5,1-b][1,3]oxazin-6-yl) carbamate (10sss) (500 mg, 1.32 mmol) in DMF (15 mL) at 0° C., was treated slowly with 60% NaH (79 mg, 1.98 mmol) and stirred for 20 min. Afterwards, iodomethane (0.33 mL, 5.27 mmol) was added dropwise and stirred further for 2 h at room temperature, Thereafter, reaction mixture was quenched at 0° C. by slow addition of a saturated aqueous solution of $NH_4Cl$ (10 mL), diluted with water (50 mL) and extracted thrice with DCM (3×30 mL). The combined organic layers were washed twice with cold water (30 mL each time), dried with $Na_2SO_4$, filtered, and concentrated. The residue was purified by silica gel column chromatography (eluted with 0-5% MeOH/DCM for 10 min and 5-30% MeOH/DCM for 10 min) to afford a light-yellow oil product (10ttt) which solidified in storage (511 mg, 98%). LRMS (ESI): m/z $[M+H]^+$: 394.

Tert-butyl N-[2-(difluoromethyl)-3-iodo-6,7-dihydro-5H-pyrazolo[5,1-b][1,3]oxazin-6-yl]carbamate (10uuu) for preparation of EX.257 was prepared in accordance with the methods described in the procedure 23.

(10uuu)

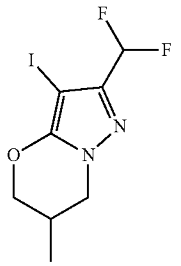

NHBoc

LRMS (ESI): m/z $[M-t-Bu]^+$: 380, $[M+Na]^+$: 438

2'-(Difluoromethyl)-3'-iodo-5'H,7'H-spiro[oxetane-3,6'-pyrazolo[5,1-b][1,3]oxazine] (10vvv) for preparation of EX.259 was prepared in accordance with the methods described in general procedure 23.

(10vvv)

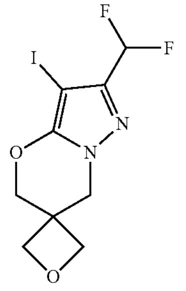

LRMS (ESI): m/z 343.

3-Iodo-2-(2,2,2-trifluoroethyl)-6,7-dihydro-5H-pyrazolo[5,1-b][1,3]oxazine (10www) for preparation of EX.251 was prepared in accordance with the general procedure 23.

10www

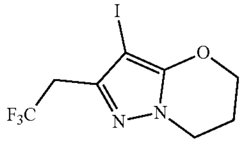

LRMS (ESI): m/z $[M+H]^+$: 333.

2-(Difluoromethyl)-3-iodo-6,7-dihydro-5H-pyrazolo[5,1-b][1,3]oxazine (10wwwi) for preparation of EX.242 was prepared in accordance with the general procedure 23 steps 23-1 to step 23-4.

(10wwwi)

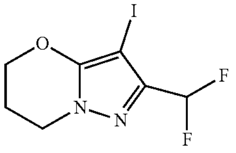

LRMS (ESI): m/z $[M+H]^+$: 301.

2-(Difluoromethyl)-3-iodo-6,7-dihydro-5H-pyrazolo[5,1-b][1,3]oxazin-6-ol (10xxx) for preparation of EX.203 was prepared in accordance with the general procedure 23.

(10xxx)

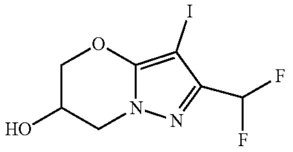

LRMS (ESI): m/z $[M+H]^+$: 317.

Tert-butyl-[[2-(difluoromethyl)-3-iodo-6,7-dihydro-5H-pyrazolo[5,1-b][1,3]oxazin-6-yl]oxy]-diphenyl-silane (10yyy) for preparation of EX.202 was prepared in accordance with the general procedures 23 (step 23-1 to step 23-4) and 33 (step 33-4).

(10yyy)

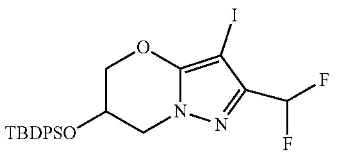

LRMS (ESI): m/z [M+H]$^+$: 555.

(71) Reference Procedure of (10eeee)

3-Bromo-6,7-dihydro-5H-triazolo[5,1-b][1,3]oxazine (10eeee) for preparation of EX.164 was prepared in accordance with the general procedure 22 and 24 using the method described below in detail.

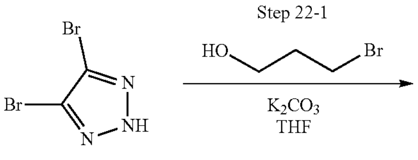

(10bbbb)

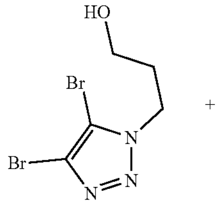

(10cccc)

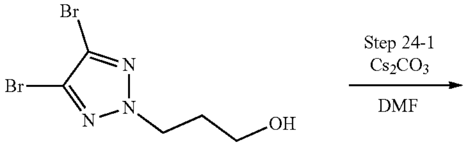

(10dddd)

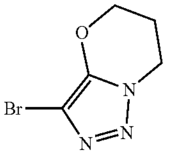

(10eeee)

Step 22-1

To the stirred solution of 4,5-dibromo-2H-triazole (10bbbb) (800 mg, 3.53 mmol) in THF (7 mL) added $K_2CO_3$ (487 mg, 3.53 mmol) and cooled to 0° C. Subsequently added 3-bromo-1-propanol (0.38 mL, 4.23 mmol) and reacted at 0° C. for 1.35 h (turbid solution) and then at room temperature for 1.20 h. Added dioxane (2.7 mL) and: additional 3-bromopropanol (10 μL) and reacted at room temperature overnight. The reaction was heated at 94° C. for 35 min. The reaction was filtered, filtrate concentrated in vacuo and purified by silica gel column chromatography (0-8% EtOAc/DCM) to obtain the expected product (10cccc) as a white solid (223.9 mg, 22%); $^1$H NMR (400 MHz, $CDCl_3$): δ 2.12-2.19 (2H, m), 3.68-3.71 (2H, m), 4.54-4.57 (2H, m), 5.31 (1H, s) and product (10dddd), as a clear oil (189.9 mg, 19%); LRMS (ESI): m/z [M+H]$^+$ 285.

Step 24-1

To the stirred solution of 3-(4,5-dibromotriazol-1-yl) propan-1-ol (10cccc) (80 mg, 0.28 mmol) in DMF (1 mL) was added $Cs_2CO_3$ (191.8 mg, 0.59 mmol) and heated at 78° C. overnight. Additional $Cs_2CO_3$ (223.5 mg) was added and heated at 100° C. for 3.20 h. Further addition of $Cs_2CO_3$ (407 mg) and heated for another 4 h. The reaction was partitioned between water and extracted with $CHCl_3$. The combined organic layers were dried over $Na_2SO_4$ and concentrated in vacuo to obtain the expected product as an orange solid (54.8 mg, 76%); LRMS (ESI): m/z [M+H]$^+$ 204, 206.

(72) Reference Procedure of (10hhhh)

6-((Tert-butyldimethylsilyl)oxy)-3-iodo-2-methylpyrazolo[1,5-a]pyrimidine (10hhhh) for preparation of EX.181 was prepared in accordance with the general procedures 25 and 20 using the method described below in detail.

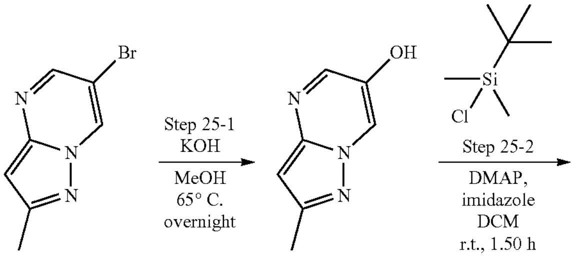

(10gggg) (59a)

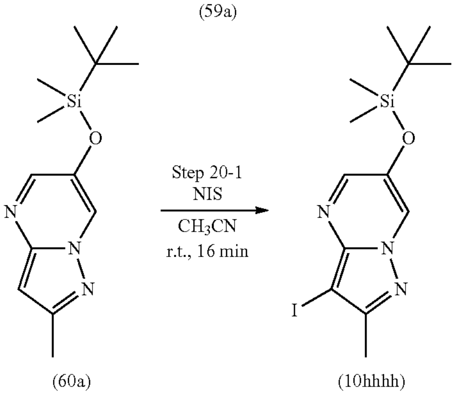

(60a) (10hhhh)

Step 25-1

A vial containing of 6-bromo-2-methyl-pyrazolo[1,5-a]pyrimidine (10gggg) (500 mg, 2.36 mmol) was dissolved in methanol (11 mL), added KOH (798 mg, 14.25 mmol) and heated at 65° C. overnight. The mixture was concentrated, added 2M HCl until acidic and extracted with EtOAc. Organic layer was dried over $Na_2SO_4$, concentrated and purified by silica gel column chromatography (0-41% EtOAc/hexanes) to obtain the expected product as a white solid (177.6 mg, 50%); LRMS (ESI): m/z [M+H]$^+$ 150.

Step 25-2

A vial containing 2-methylpyrazolo[1,5-a]pyrimidin-6-ol (59a) (71 mg, 0.48 mmol), was dissolved in DCM (2.26 mL), added imidazole (94.9 mg, 1.39 mmol), DMAP (11.6 mg, 0.1 mmol), tert-butylchlorodimethylsilane (107.6 mg, 0.71 mmol) and reacted at room temperature for 1.50 h (starting material was consumed after 1 h). The reaction mixture was partitioned between water and extracted with DCM. The combined organic layers were dried over $Na_2SO_4$ and concentrated. The residue was purified by silica gel column chromatography (0-16% EtOAc/hexanes) to obtain the expected product as a white solid (81 mg, 65%); LRMS (ESI): m/z $[M+H]^+$ 264.

Step 20-1

A reaction vial containing tert-butyl-dimethyl-(2-methylpyrazolo[1,5-a]pyrimidin-6-yl)oxy-silane (60a) (81 mg, 0.31 mmol) was dissolved in MeCN (0.85 mL), added NIS (77.2 mg, 0.34 mmol) and reacted at room temperature for 16 min. The reaction was concentrated and purified by silica gel column chromatography (0-14% EtOAc/hexanes) to obtain the expected product as a white solid (105.9 mg, 88%); LRMS (ESI): m/z $[M+H]^+$ 390.

(73) Reference Procedure of (10kkkk)

6-Fluoro-3-iodo-2-methylpyrazolo[1,5-a]pyrimidine (10kkkk) for preparation of EX.182 was prepared in accordance with the general procedure 26 and 20 using the method described below in detail.

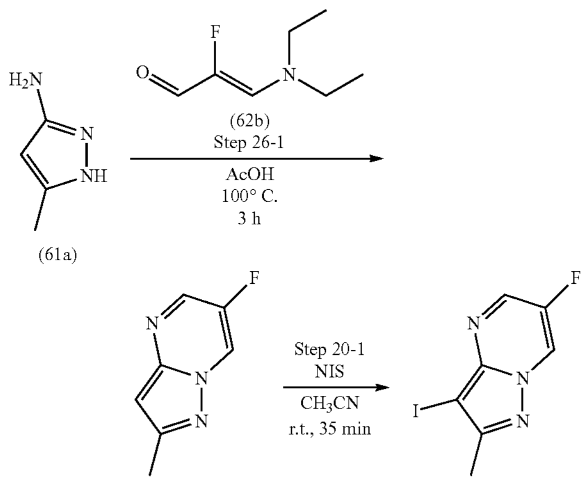

(61a) (10jjjj) (10kkkk)

Step 26-1

A vial containing 5-methyl-1H-pyrazol-3-amine (61a) (300 mg, 3.09 mmol), (Z)-3-(diethylamino)-2-fluoro-prop-2-enal (62b) (0.45 mL, 3.18 mmol) in acetic acid (12 mL) was heated at 100° C. for 3 h. The reaction mixture was partitioned between water and extracted with DCM. The reaction was concentrated and purified by silica gel column chromatography (0-10% EtOAc/hexanes) to obtain the expected product as a white solid (142.3 mg, 30%); LRMS (ESI): m/z $[M+H]^+$ 152.

Step 20-1

A vial containing 6-fluoro-2-methyl-pyrazolo[1,5-a]pyrimidine (10jjjj) (80 mg, 0.53 mmol) was dissolved in MeCN (1.4 mL), added NIS (133.1 mg, 0.59 mmol) and reacted at room temperature for 35 min. The reaction was concentrated and purified by silica gel column chromatography (0-18% EtOAc/hexanes) to obtain the expected product as a white solid (123.6 mg, 84%); LRMS (ESI): m/z $[M+H]^+$ 278.

(74) Reference Procedure of (3t)

4-(Cyclopropylmethyl)-2-(4,4,5,5-tetramethyl-1,3,2-dioxaborolan-2-yl)benzonitrile (3t) for preparation of EX.282 was obtained according to the methods described in procedures 1 (step 1-2) and 27 (step 27-1).

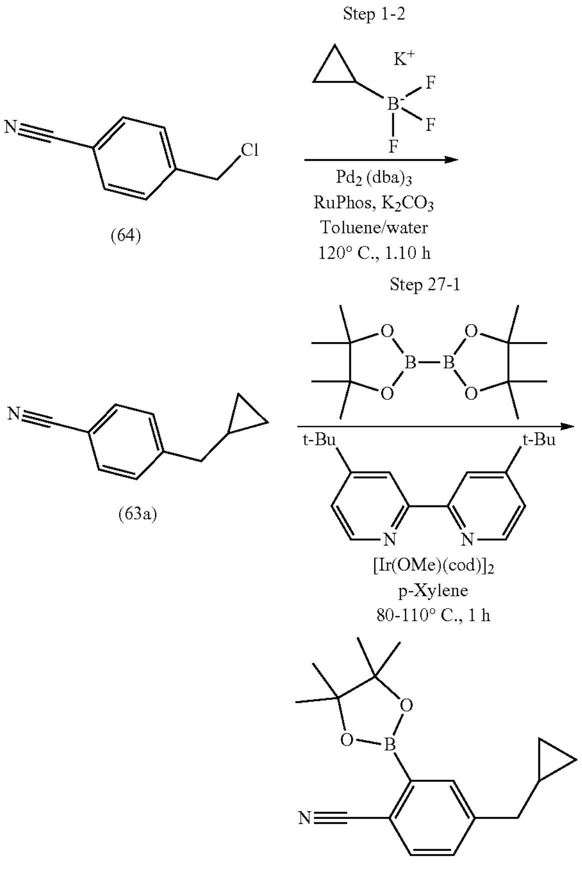

(64) (63a) (3t)

Step 1-2

A MW vial containing 4-(chloromethyl)benzonitrile (64) (800 mg, 5.28 mmol), potassium cyclopropyltrifluoroborate (1.17 g, 7.92 mmol), RuPhos (492.5 mg, 1.06 mmol), $K_2CO_3$ (1.46 g, 10.5 mmol) was dissolved in toluene (19 mL), water (1 mL) degassed and back filled with $N_2$ three times. Subsequently added $Pd_2(dba)_3$ (483.2 mg, 0.53 mmol) degassed and back filled with $N_2$ three times and heated at 120° C. for 1.10 h. The reaction was concentrated and purified by silica gel column chromatography (0-5% EtOAc/hexanes) to obtain the expected product as a clear oil (203.6 mg, 24%); LRMS (ESI): m/z $[M+H]^+$ 158.

Step 27-1

A vial containing of 4,4,5,5-tetramethyl-2-(4,4,5,5-tetramethyl-1,3,2-dioxaborolan-2-yl)-1,3,2-dioxaborolane (152.3 mg, 0.6 mmol), 4,4'-Bis(1,1-dimethylethyl)-2,2'-bipyridine (19.3 mg, 0.07 mmol) was dissolved in p-xylene (3 mL), degassed, and back filled with $N_2$ three times. Subsequently added (1,5-Cyclooctadiene)(methoxy) iridium (I) Dimer (25.15 mg, 0.04 mmol) degassed and back filled with $N_2$ three times and finally added 4-(cyclopropylmethyl) benzonitrile (63a) (123 mg, 0.78 mmol) heated at 110° C. for 30 min and then 80° C. for 1 h. The reaction was concentrated and purified by silica gel column chromatography (0-11% EtOAc/hexanes) to obtain the expected product as a clear oil (29.8 mg, 17%); LRMS (ESI): m/z $[M+H]^+$ 284.

(75) Reference Procedure of (10llll)

The coupling agent, tert-butyl N-[3-iodo-2-methyl-6,7-dihydro-5H-pyrazolo[5,1-b][1,3]oxazin-6-yl]carbamate (10IIII) for preparation of EX.354 was prepared in accordance with the general procedures 28 and 23 using the method described below in detail.

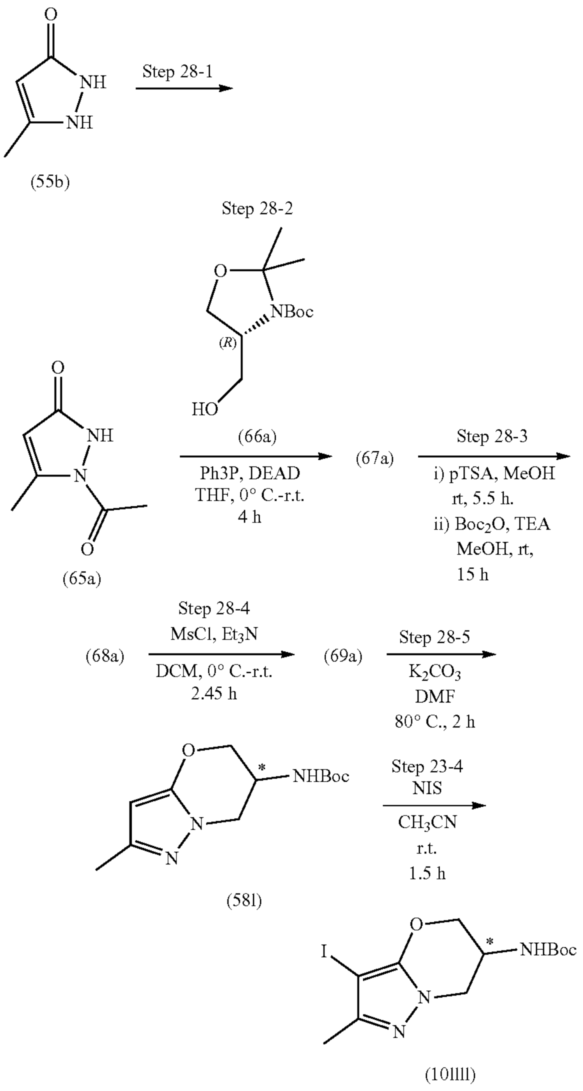

Step 28-1

A round bottom flask containing of 5-methyl-1,2-dihydropyrazol-3-one (55b) (4 g, 40.77 mmol) in pyridine (24 mL) was heated at 95° C. and added slowly (~30 min.) acetic anhydride (3.85 mL, 40.77 mmol) in pyridine (8 mL). The resulting mixture was heated further for 1 h at the same temperature. Thereafter, mixture was concentrated and triturated with MeOH (25 mL). The resulting precipitate was filtered to afford a light-yellow solid (874 mg, 15%) as the expected product. LRMS (ESI): m/z $[M+H]^+$ 141.

Step 28-2

A mixture of 2-acetyl-3-methyl-1H-pyrazol-5-one (65a) (1 g, 7.14 mmol) and triphenylphosphine (2.81 g, 10.7 mmol) in THF (47.5 mL) was cooled to 0° C. The mixture was de-gassed, filled with $N_2$ three times and DEAD (4.8 mL, 10.7 mmol) was added dropwise to the above mixture (~18 minutes) degassed twice and filled with $N_2$. The reaction was stirred for an additional 1 hour at 0° C. To this a solution of tert-butyl (4R)-4-(hydroxymethyl)-2,2-dimethyl-oxazolidine-3-carboxylate (66a) (2.64 g, 11.42 mmol) in dry THF (6 mL) was added dropwise (10 min). After 30 min ice bath was removed, and the reaction was stirred at room temperature for 4 h. Solvent was evaporated in vacuo and purified by silica gel column chromatography (0-13% EtOAc/hexanes) to obtain the expected product as a clear oil (4.91 g, 97%); $^1H$ NMR (400 MHz, $CDCl_3$): δ 1.50-1.65 (15H, m), 2.54 (3H, s), 2.60 (3H, s), 4.00-4.38 (5H, m), 5.74 (1H, d, J=13.4 Hz); LRMS (ESI): m/z $[M+H]^+$ 354.

Step 28-3

A solution of the Mitsunobu reaction product (67a) in Step 28-2 (4.8 g, 13.5 mmol) in methanol (27 mL) was cooled to 0° C., added PTSA (monohydrate) (8.2 g, 43.1 mmol), stirred at 0° C. for 25 min and then at room temperature for 5.5 h. Evaporated solvent in vacuo and added THF (30.6 mL), cooled to 0° C. and added $Et_3N$ (9.4 mL, 67.71 mmol) and $Boc_2O$ (2.67 g, 12.22 mmol) and reacted at 0° C. for 12 min and then at room temperature overnight. Evaporated solvent in vacuo and purified by silica gel column chromatography (0-1.8% MeOH/DCM) to obtain product as an oil, 3.74g. The product contained trace amount of TsOH. To the above oil added $Et_3N$ (0.39 mL, to neutralize acid) and 10 mL DCM and re purified by silica gel column chromatography (0-4.8% MeOH/DCM) to obtain the expected product as a clear oil (2.65 g, 72%); $^1H$ NMR (400 MHz, $CDCl_3$): δ 1.47 (9H, s), 2.37 (3H, s), 3.57-3.61 (1H, m), 3.75-3.79 (1H, m), 3.96 (1H, br s), 4.23-4.27 (1H, m), 4.35-4.39 (1H, m), 5.20 (1H, d, J=8.2 Hz), 5.53 (1H, s); LRMS (ESI): m/z $[M+H]^+$ 272.

Step 28-4

The compound (68a) that was obtained in Step 28-3 (2.3 mL, 9.16 mmol), $Et_3N$ (1.79 mL, 12.82 mmol) in DCM (38.3 mL) was cooled to 0° C., and added $CH_3SO_2Cl$ (0.71 mL, 9.16 mmol) and reacted at 0° C. for 12 min and then at room temperature for 6 min. Additional $Et_3N$ (0.3 mL) was added and reacted at room temperature for 1 h. SM still remaining. Additional $CH_3SO_2Cl$ (50 μL) was added and reacted for 16 min. Further addition of $CH_3SO_2Cl$ (22 μL) and reacted at room temperature for 17 min. Further addition of $Et_3N$ (0.6 mL) and reacted at room temperature for 8 min (now turbid solution). Additional $CH_3SO_2Cl$ (65 μL) was added and reacted for 45 min. Evaporated solvent in vacuo to obtain a white solid (~2.88g), which was used for the next step without further purification; LRMS (ESI): m/z $[M+H]^+$ 350.

Step 28-5

To a solution of the compound (69a) that was obtained in Step 28-4 (2.88 g, 8.24 mmol) in DMF (18 mL) added $K_2CO_3$ (3.42 g, 24.72 mmol) and heated in an oil bath at 78° C. for 2 h. The reaction was partitioned between water and extracted with ether. Combined organic layers were dried over anhydrous $Na_2SO_4$ and evaporated solvent in vacuo. Crude was purified by silica gel column chromatography (0-1.7% MeOH/DCM) to obtain the expected product as a white solid (970 mg, 46%); $^1H$ NMR (400 MHz, $CDCl_3$): δ 1.43 (9H, s), 2.18 (3H, s), 4.07-4.33 (5H, m), 5.20 (1H, d, J=7.8 Hz), 5.34 (1H, s); $^{13}C$ NMR (100 MHz, $CDCl_3$): δ 14.3, 28.3, 43.1, 49.6, 68.2, 80.4, 86.5, 148.5, 150.6, 154.9; LRMS (ESI): m/z $[M+H]^+$ 254.

Step 23-4

A mixture of the compound (581) that was obtained in Step 28-5 (510 mg, 2.01 mmol), NIS (498.2 mg, 2.21 mmol) in MeCN (15 mL) was stirred at room temperature for 90 min. The reaction was concentrated in vacuo. The crude was purified by silica gel column chromatography (0-40% EtOAc/hexanes) to obtain the expected compound as an off white solid (660 mg, 86%); LRMS (ESI): m/z $[M+H]^+$ 380.

Tert-butyl N-[3-iodo-2-methyl-6,7-dihydro-5H-pyrazolo [5,1-b][1,3]oxazin-6-yl]carbamate (10mmmm) for the preparation of key intermediate in the synthesis of EX.355 was obtained from tert-butyl (4S)-4-(hydroxymethyl)-2,2-dimethyl-oxazolidine-3-carboxylate (66'a) according to the methods described for the preparation of (10llll)

(66'a)

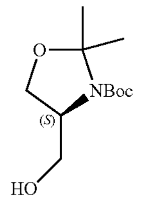

(10mmmm)

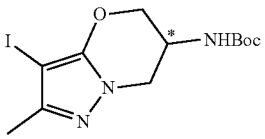

LRMS (ESI): m/z $[M+H]^+$ 380.

(76) Reference Procedure of (10ssss)

4-(Difluoromethyl)-3-iodo-1-tetrahydropyran-2-yl-pyrazole (10ssss) for preparation of EX.207 was prepared in accordance with the general procedure 30 using the method described below in detail.

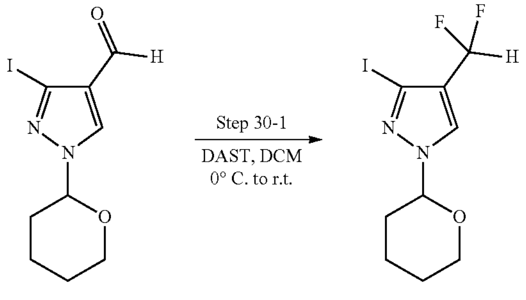

(10rrrr) (10ssss)

Step 30-1

DAST (0.76 mL, 5.74 mmol) was added slowly to a stirring solution of 3-iodo-1-tetrahydropyran-2-yl-pyrazole-4-carbaldehyde (10rrrr) (878 mg, 2.87 mmol) in DCM (5 mL) at 0° C. The resulting mixture was stirred for two days and during that time was allowed to warm to room temperature. Thereafter, reaction mixture was quenched slowly with water at 0° C. and extracted thrice with DCM. The combined organic extracts were dried over $Na_2SO_4$, filtered and concentrated. Residue was purified by silica gel column chromatography [12g pre-pack column, eluted with 100% hexanes (3 min.), 0% to 10% EtOAc/Hexanes (2 min.), 10% EtOAc/Hexanes (5 min.), 10% to 20% EtOAc/Hexanes (2 min.), 20% EtOAc/Hexanes (5 min.), 20% to 30% EtOAc/Hexanes (2 min.), 30% EtOAc/Hexanes (5 min.)] to afford the expected product as a colorless oil (661 mg, 70%). $^1H$ NMR (400 MHz, $CDCl_3$): δ 1.62-177 (3H, m), 1.99-2.15 (3H, m), 3.68-3.76 (1H, m), 4.04-4.12 (1H, m), 5.40 (1H, dd, J=8.6 Hz, 3.4 Hz), 6.55 (1H, t, $J_{H-F}$=55.3 Hz), 7.76 (1H, apparent t, J=1.5 Hz); LRMS (ESI): m/z $[M+H]^+$ 329.

(77) Reference Procedure of (10ffffff)

4-Bromo-5-(difluoromethyl) isothiazole (10ffffff) for preparation of EX.226 and EX.416 was prepared in accordance with the general procedures 30 using the method described below in detail.

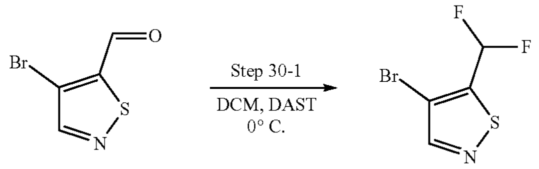

(10eeeeee) (10ffffff)

Step 30-1

To a solution DAST (0.06 mL, 0.47 mmol) in DCM (1 ml) was added 4-bromoisothiazole-5-carbaldehyde (10eeeeee) (30 mg, 0.16 mmol) at 0° C. and stirred for 2 h at the same temperature. Thereafter, 5 mL of $NaHCO_3$ (sat. solution) and 10 mL water were added at 0° C. The mixture was thrice extracted with DCM, and the organic extracts were combined, dried over $Na_2SO_4$ and concentrated. The residue was used in the next step without further purification. LRMS (ESI): m/z $[M+H]^+$ not detected.

4-Bromo-5-(difluoromethyl)-2-methyl-triazole (10tttt) for preparation of EX.193 was prepared in accordance with the general procedure 30.

(10tttt)

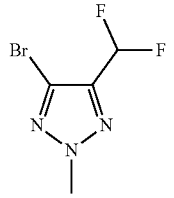

LRMS (ESI): m/z $[M+H]^+$: not detected.

4-Bromo-3-(difluoromethyl) isothiazole (10uuuu) for preparation of EX.75 and EX.280 was prepared in accordance with the general procedure 30.

(10uuuu)

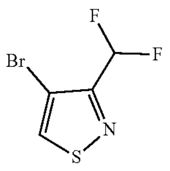

LRMS (ESI): m/z $[M+H]^+$: not detected.

5-Bromo-4-(difluoromethyl) thiazole (10vvvv) for the preparation of EX.76 and EX.228 was prepared in accordance with the general procedure 30.

(10vvvv)

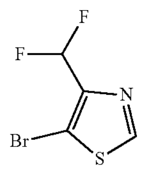

LRMS (ESI): m/z $[M+H]^+$: 214, 216.

(78) Reference Procedure of (10xxxx)

3-Bromo-6-fluoro-6,7-dihydro-5H-pyrazolo[5,1-b][1,3]oxazine (10xxxx) for preparation of EX.194 was prepared in accordance with the general procedure 30 using the method described below in detail.

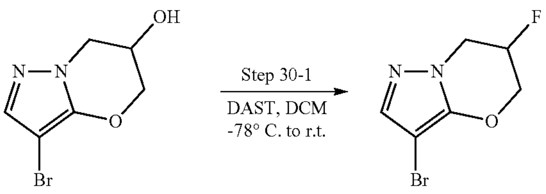

(10wwww) (10xxxx)

Step 30-1

To a solution of 3-bromo-6,7-dihydro-5H-pyrazolo[5,1-b][1,3]oxazin-6-ol (10wwww) (150 mg, 0.68 mmol) in DCM (5 mL) at −78° C., was slowly added DAST (0.18 mL, 1.37 mmol). The resulting solution was stirred overnight and during that time was allowed to warm to room temperature, thereafter, water was added slowly, stirred for 2 minutes, phases were separated, and aqueous layer was extracted thrice with DCM. The combined organic extracts were washed with brine, dried over $Na_2SO_4$, and conc, and concentrated. The residues purified by silica gel column chromatography (5% EtOAc/Hexanes to 100% EtOAc) to afford a light tan colored oil (115 mg, 76%) as the expected product.

$^1H$ NMR (400 MHz, DMSO-$d_6$): δ 4.30-4.50 (2H, m), 4.71-4.61 (1H, m), 4.61-4.71 (1H, m), 5.48 (1H, dd, J=44.7, 2.6 Hz), 7.45 (1H, s); LRMS (ESI): m/z $[M+H]^+$ 221, 223.

4-Bromo-3-(fluoromethyl)-1-methyl-pyrazole (10yyyy) for preparation of EX.233, EX.270 and EX.267 was prepared in accordance with the general procedure 30.

(10yyyy)

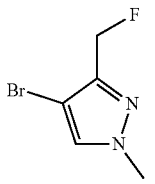

(10yyyy)

LRMS (ESI): m/z $[M+H]^+$ 193, 195.

(79) Reference Procedure of (10zzzz)

2-(Fluoromethyl)-3-iodo-6,7-dihydro-5H-pyrazolo[5,1-b][1,3]oxazine (10zzzz) for the preparation of EX.234, EX.235 and EX.271 was prepared in accordance with the general procedure 30 using the method described below in detail.

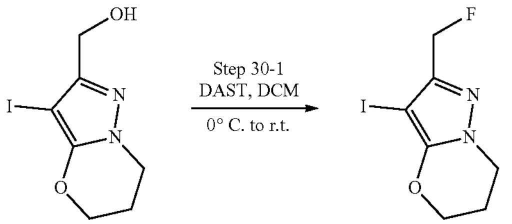

(10nnnna) (10zzzz)

Step 30-1

To a solution of (3-iodo-6,7-dihydro-5H-pyrazolo[5,1-b][1,3]oxazin-2-yl) methanol (10nnnna) (100 mg, 0.36 mmol) in DCM (4 mL) at 0° C. was added DAST (0.09 mL, 0.71 mmol). The resulting mixture was stirred at 0° C. for 10 mins and then, at room temperature for 55 min. Thereafter, reaction mixture was concentrated, and residue was directly purified by silica gel column chromatography (0-66% EtOAc/hexane) to afford a white solid as the expected product (36 mg, 36%): LRMS (ESI): m/z $[M+H]^+$ 283.

(80) Reference Procedure of (10gggggg)

3-Iodo-2-methyl-6,7-dihydro-5H-pyrano[3,2-c]pyrazole (10ggggg) for preparation of EX.197 was prepared in accordance with the general procedures 20 and 32 using the method described below in detail.

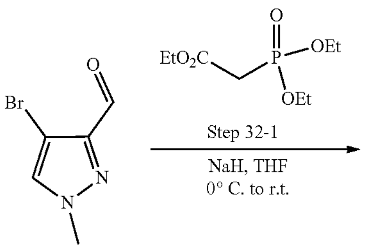

(10dddddd)

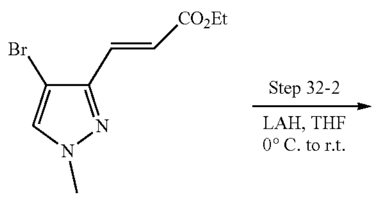

(10eeeee)

-continued

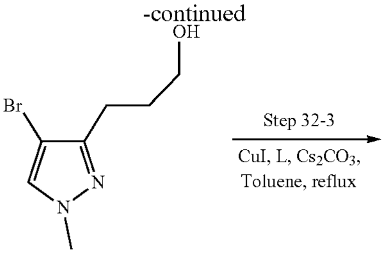

(10fffff)

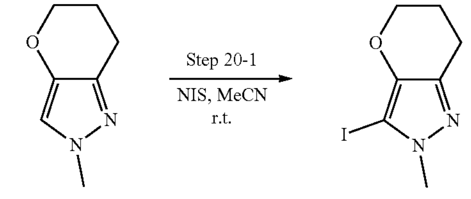

(58n) (10ggggg)

Step 32-1

Triethyl phosphonoacetate (1.46 mL, 7.67 mmol) was added dropwise to a stirring suspension of NaH (0.42 g, 10.5 mmol) in THF (5 mL) at 0° C. After stirring for 20 minutes, 4-bromo-1-methyl-pyrazole-3-carbaldehyde (10ddddd) (1 g, 5.29 mmol) in THF (3 mL) was added slowly. The resulting mixture was stirred overnight and during that time was allowed to warm to room temperature. Thereafter, reaction mixture was quenched slowly with water and extracted thrice with EtOAc. The combined organic extracts were dried over $Na_2SO_4$, filtered and concentrated. Residue was purified by silica gel column chromatography [12g pre-pack column, 0% hexanes (3 min.), 0% to 100% EtOAc/Hexanes (10 min.)] to afford a white solid (900 mg, 65%) as the expected product.

$^1$H NMR (400 MHz, $CDCl_3$): δ 1.35 (3H, t, J=7.0 Hz), 3.93 (3H, s), 4.28 (2H, q, J=7.2 Hz), 6.80 (1H, d, J=16.0 Hz), 7.43 (1H, s), 7.61 (1H, d, J=16.2 Hz); LRMS (ESI): m/z $[M+H]^+$ 259, 261.

Step 32-2

To a stirring solution of ethyl (E)-3-(4-bromo-1-methyl-pyrazol-3-yl) prop-2-enoate (10eeeee) (900 mg, 3.47 mmol) in THF (5 mL) at 0° C., was added dropwise $LiAlH_4$ (17 mL, 17.34 mmol). Reaction mixture was stirred overnight and during that time was allowed to warm to room temperature. Thereafter, the reaction mixture was quenched slowly with water at 0° C., diluted with 60 mL of 1M HCl and extracted thrice with EtOAc. The combined organic extracts were dried over $Na_2SO_4$, filtered and concentrated. The residue was purified by silica gel column chromatography (5% EtOAc/Hexanes to 100% EtOAc/Hexanes) to afford a colorless oil (256 mg, 33%) as product.

$^1$H NMR (400 MHz, $CDCl_3$): δ 2.10-1.89 (3H, m), 2.75 (2H, t, J=7.1 Hz), 3.72 (2H, t, J=6.1 Hz), 3.85 (3H, s), 7.34 (1H, s); LRMS (ESI): m/z $[M+H]^+$ 219, 221.

Step 32-3

A sealed tube containing 3-(4-bromo-1-methyl-pyrazol-3-yl) propan-1-ol (10fffff) (128 mg, 0.58 mmol), copper (I) iodide (11 mg, 0.06 mmol), 3,4,7,8-tetramethyl-1,10-phenanthroline (ligand) (27 mg, 0.12 mmol) and $Cs_2CO_3$ (285 mg, 0.88 mmol) in toluene (3 mL) was heated to 110° C. for 36 h. Thereafter, reaction mixture was concentrated and purified by silica gel column chromatography [4g pre-pack column, 0% to 100% EtOAc/Hexanes (10 min), 100% EtOAc (5 min.), 0% to 30% MeOH/DCM (2 min.), 30% MeOH/DCM (5 min.)] to afford a colorless oil (36 mg, 44%) as the expected product.

$^1$H NMR (400 MHz, $CDCl_3$): δ 2.05-1.99 (2H, m), 2.76 (2H, t, J=6.5 Hz), 3.78 (3H, s), 4.12-4.07 (2H, m), 6.92 (1H, s); LRMS (ESI): m/z $[M+H]^+$ 139.

Step 20-1

NIS (234 mg, 1.04 mmol) was added to a stirring solution of 2-methyl-6,7-dihydro-5H-pyrano[3,2-c]pyrazole (58n) (36 mg, 0.26 mmol) in MeCN (1.5 mL) at 0° C. Reaction mixture was removed from the ice bath and stirred overnight. Thereafter, reaction mixture was concentrated and purified by silica gel column chromatography [4g pre-pack column (gold), 100% Hexanes (3 min.), 0% to 25% EtOAc/Hexanes (1 min.), 25% EtOAc/Hexanes (7 min.), 25% to 30% EtOAc/Hexanes (7 min.)] to afford a yellowish-solid (25 mg, 36%) as the expected product.

$^1$H NMR (400 MHz, $CDCl_3$): δ 4.22-4.12 (2H, m), 3.83 (3H, s), 2.76 (2H, t, J=6.5 Hz, 1H), 2.06 (2H, m); LRMS (ESI): m/z $[M+H]^+$ 265.

3-Iodo-1-methyl-6,7-dihydro-5H-pyrano[3,2-c]pyrazole (10hhhhh) for preparation of EX.198 was synthesized from commercially available 4-bromo-2-methyl-pyrazole-3-carbaldehyde in accordance with the methods described in the procedures 32 (step 32-1 to 32-3) and 20 (step 20-1).

(10hhhhh)

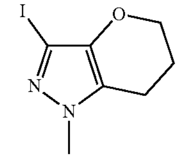

(10hhhhh)

LRMS (ESI): m/z $[M+H]^+$ 265

(81) Reference Procedure of (10iiiii)

Tert-butyl-[[(6S)-3-iodo-2-methyl-6,7-dihydro-5H-pyrazolo[5,1-b][1,3]oxazin-6-yl]oxy]-diphenyl-silane (10iiiii) for preparation of EX.366 was prepared in accordance with the general procedures 28, 33 and 20 using the method described below in detail.

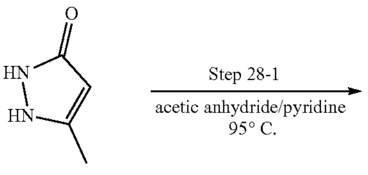

(55b)

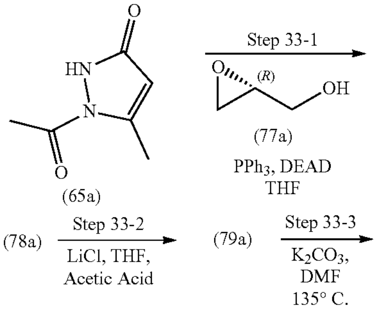

(65a) (78a) (79a)

-continued

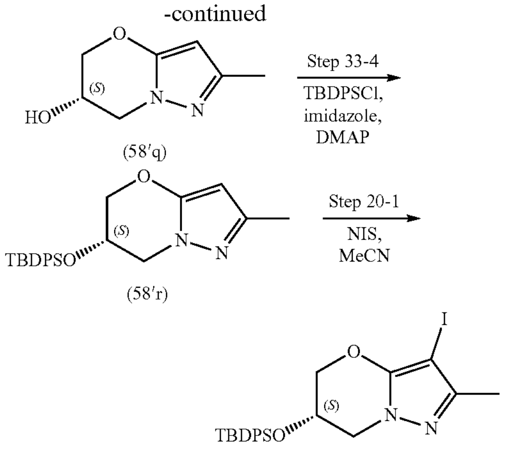

(58'q)

(58'r)

(10iiiiii)

Step 28-1

A mixture of acetic anhydride (3.85 mL, 40.77 mmol)/pyridine (8 mL) was added slowly (30 min.) to a pre-heated (95° C.) solution of 5-methyl-1,2-dihydropyrazol-3-one (55b) (4 g, 40.77 mmol) in pyridine (24 mL). The mixture was then heated further for 1 h at 95° C. Thereafter, reaction mixture was concentrated in a rotary evaporator to afford a dark red oil which was triturated with MeOH (25 mL). The resulting light-yellow solid was filtered and vacuumed dried overnight to give 874 mg of product. LRMS (ESI): m/z $[M+H]^+$ 141.

Step 33-1

A mixture of 2-acetyl-3-methyl-1H-pyrazol-5-one (65a) (874 mg, 6.24 mmol) and triphenylphosphine (2.45 g, 9.35 mmol) in THF (10 mL) at 0° C. under $N_2$ was added slowly (~10 min.) ethyl (NE)-N-ethoxycarbonyliminocarbamate (4.26 mL, 9.35 mmol) and stirred for 1 hour at the same temperature. Afterwards, R-glycidol (77a) (0.5 mL, 7.48 mmol) was added slowly (~15 min.) and stirred overnight (during that time was allowed to warm to room temperature). Thereafter, mixture was concentrated and purified by silica gel column chromatography (10% EtOAc/Hexanes) to afford the expected product as a white solid (1.02 g, 83%).

$^1H$ NMR (400 MHz, $CDCl_3$): δ 2.52 (3H, d, J=1.0 Hz), 2.56 (3H, s), 2.74 (1H, dd, J=5.0, 2.7 Hz), 2.90 (1H, dd, J=4.9, 4.2 Hz), 3.34-3.38 (1H, m), 4.13 (1H, dd, J=11.9, 6.0 Hz), 4.48 (1H, dd, J=11.8, 3.2 Hz), 5.72 (1H, d, J=0.9 Hz); LRMS (ESI): m/z $[M+H]^+$ 197.

Step 33-2

To a solution of the Mitsunobu reaction product (78a) in Step 33-1 (1.02 g, 5.2 mmol), glacial acetic acid (0.9 mL, 15.6 mmol) in THF (6 mL) was added lithium chloride (0.35 g, 8.32 mmol) and was stirred overnight. Thereafter, the mixture was diluted with water and extracted thrice with EtOAc. The combined organic extracts were washed with sat. $NaHCO_3$, brine, dried over $Na_2SO_4$, filtered, and concentrated to afford a colorless oil which was used for next step without further purification.

Step 33-3

A mixture of the compound (79a) that was obtained in Step 33-2 (1.2 g, 5.16 mmol) and $K_2CO_3$ (2.14 g, 15.47 mmol) in DMF (12 mL) was stirred overnight at 135° C. Thereafter, reaction mixture was filtered through a pad Celite and washed down twice with EtOAc. Filtrate and washing were combined and diluted with water. The phases were separated, and the aqueous layer was extracted thrice with EtOAc. The combined organic extracts were dried over $Na_2SO_4$, filtered, and concentrated. The residue was purified by silica gel column chromatography [12 g silica gel pre-pack column, eluted with 100% Hexanes (3 min.), 100% EtOAc (15 min.), 30% MeOH/DCM (10 min.)] to afford a tan colored oil (315 mg, 39%) as the expected product. LRMS (ESI): m/z $[M+H]^+$ 155.

The absolute structure of (58'q) was determined S-form by the results of X-ray analysis.

Step 33-4

A 20 mL round bottom flask containing tert-butyl-chloro-diphenyl-silane (0.79 mL, 3.06 mmol) was added to a stirring solution of (6S)-2-methyl-6,7-dihydro-5H-pyrazolo[5,1-b][1,3]oxazin-6-ol (58'q) (315 mg, 2.04 mmol), imidazole (280 mg, 4.11 mmol) and DMAP (70 mg, 0.57 mmol) in DCM (3 mL). Resulting mixture was stirred overnight at room temperature. Thereafter, mixture was concentrated and purified by silica gel column chromatography [12 g silica gel pre-pack column, eluted with 100% hexanes (3 min.), 10% EtOAc/hexanes (5 min.), 10% to 100% EtOAc/hexanes (5 min.), 100% EtOAc (10 min.)] to afford a colorless oil (565 mg, 70%) as the expected product. LRMS (ESI): m/z $[M+H]^+$ 393.

Step 20-1

A 10 mL round bottom flask containing tert-butyl-[[(6S)-2-methyl-6,7-dihydro-5H-pyrazolo[5,1-b][1,3]oxazin-6-yl]oxy]-diphenyl-silane (58'r) (565 mg, 1.44 mmol) in MeCN (2 mL) was treated with NIS (971 mg, 4.32 mmol). The resulting mixture was stirred at room temperature for 1 h. Afterwards, reaction mixture was diluted with $NaHCO_3$ (sat. solution) and extracted thrice with DCM. The combined organic extracts were dried over $Na_2SO_4$, filtered, and concentrated. Residue was purified by silica gel column chromatography [24g pre-pack silica gel column, eluted with 100% hexanes (2 min.), 10% EtOAc/Hexanes (5 min.), 20% EtOAc/Hexanes (5 min.), 30% EtOAc/Hexanes (5 min.), 40% EtOAc/Hexanes (5 min.)] to afford a light tan colored oil (606 mg, 81%) as the expected product. LRMS (ESI): m/z $[M+H]^+$ 519.

Tert-butyl-[[3-iodo-2-methyl-6,7-dihydro-5H-pyrazolo[5,1-b][1,3]oxazin-6-yl]oxy]-diphenyl-silane (10jjjjj) for the preparation of EX.367 was synthesized using commercially available S-glycidol according to the procedure described for 10iiiii.

(10jjjjj)

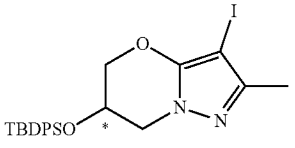

(10jjjj)

LRMS (ESI): m/z $[M+H]^+$ 519.

(82) Reference Procedure of (10kkkkk)

Tert-butyl-[[(6R)-2-(difluoromethyl)-3-iodo-6,7-dihydro-5H-pyrazolo[5,1-b][1,3]oxazin-6-yl]oxy]-diphenyl-silane (10kkkkk) for preparation of EX.368, EX.370, EX.371 and EX.418 was prepared in accordance with the general procedures 28, 33 and 20 using the method described below in detail.

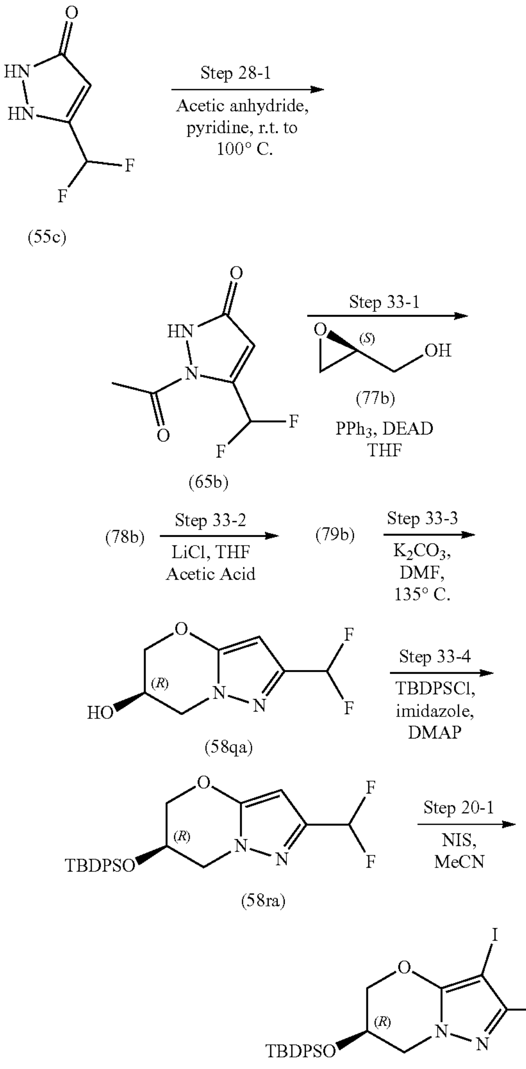

(10kkkkk)

Step 28-1

Acetic anhydride (17.0 mL, 180 mmol) was added to a solution of 5-(difluoromethyl)-1,2-dihydropyrazol-3-one (22.9 g, 170 mmol) in pyridine (114 mL) at ambient temperature under an argon atmosphere. After stirring for 2 h at 100° C., reaction mixture was concentrated under reduced pressure. The residue was purified by silica gel chromatography to afford 16.1 g (54%) of product. $^1H$ NMR (400 MHz, $CDCl_3$): δ 2.59 (s, 3H), 6.35 (s, 1H), 7.21 (t, J=53.9 Hz, 1H), 9.93 (s, 1H).

Steps 33-1 to 33-4 and 20-1 were performed in a similar manner as reported for 10iiiii.

LRMS (ESI): m/z $[M+H]^+$ 555.

The absolute structure of (58qa) was determined R-form by the results of X-ray analysis.

(6S)-2-(difluoromethyl)-6,7-dihydro-5H-pyrazolo[5,1-b][1,3]oxazin-6-ol (58u) was synthesized from R-glycidol in accordance with the methods described for (58qa).

The absolute structure of (58u) was determined S-form by the results of X-ray analysis.

(58u)

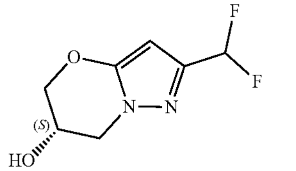

LRMS (ESI): m/z $[M+H]^+$ $XXX^-$

Tert-butyl-[[(6S)-2-(difluoromethyl)-3-iodo-6,7-dihydro-5H-pyrazolo[5,1-b][1,3]oxazin-6-yl]oxy]-diphenyl-silane (10lllll) for preparation of EX.369 was synthesized from (58u) in accordance with the methods described for 10kkkkk.

(10lllll)

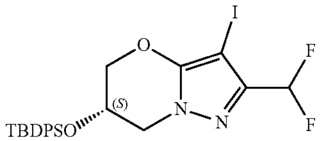

(10lllll)

LRMS (ESI): m/z $[M+H]^+$ 555.

(83) Reference Procedure of (96a)

2-[[3-Bromo-4-(difluoromethyl)pyrrolo[2,3-b]pyridin-1-yl]methoxy]ethyl-trimethyl-silane (96a) for preparation of EX.72 and EX.73 was prepared in accordance with the general procedure 35 using the method described below in detail.

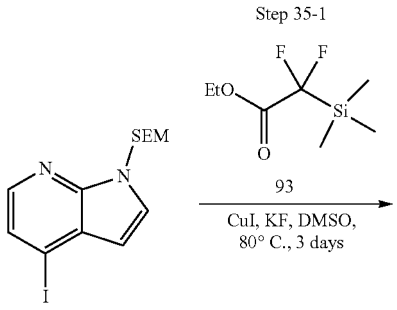

(92a)

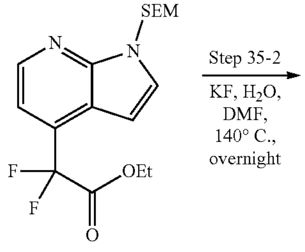

(94a)

-continued

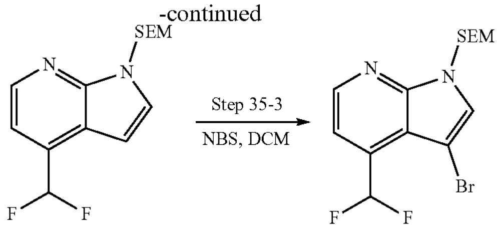

(95a) (96a)

Step 35-1

To a mixture of 2-[(4-iodopyrrolo[2,3-b]pyridin-1-yl)methoxy]ethyl-trimethyl-silane (92a) (1.2 g, 3.21 mmol), CuI (634 mg, 6.41 mmol) and KF (372 mg, 6.41 mmol) in DMSO (7 mL) was added ethyl 2,2-difluoro-2-trimethylsilyl-acetate (93) (1.49 mL, 9.62 mmol) at room temperature and stirred at 80° C. for 3 days. Thereafter, mixture was diluted with DCM, brine and filtered through a sintered glass (padded with Celite). Filtrate was decanted to separatory funnel, and the phases were separated. The organic phase was dried over $Na_2SO_4$, filtered, and concentrated. The residue was purified by silica gel column chromatography (eluted with 0-20% EtOAc/Hexanes) to afford a yellow oil (574 mg, 48%) as the expected product. LRMS (ESI): m/z $[M+H]^+$ 371.

Step 35-2

A mixture of ethyl 2,2-difluoro-2-[1-(2-trimethylsilylethoxymethyl)pyrrolo[2,3-b]pyridin-4-yl]acetate (94a) (2.21 g, 5.97 mmol), KF (1.73 g, 29.83 mmol) and $H_2O$ (0.54 mL, 29.83 mmol) in DMF (8 mL) was heated at 140° C. overnight. Thereafter, mixture was partitioned between water and EtOAc. The organic layer was dried over $Na_2SO_4$, filtered, and concentrated. The residue was purified silica gel column chromatography (eluted with 0-100% EtOAc/Hexanes) to afford a yellow oil (348 mg, 19%) as product. LRMS (ESI): m/z $[M+H]^+$ 299.

Step 35-3

A mixture of 2-[[4-(difluoromethyl)pyrrolo[2,3-b]pyridin-1-yl]methoxy]ethyl-trimethyl-silane (95a) (348 mg, 1.17 mmol) and NBS (195 mg, 1.22 mmol) in DCM (5 mL) was stirred at room temperature for 1 h. Thereafter, mixture was concentrated and purified by silica gel column chromatography (eluted with 0-20% EtOAc/Hexanes) to afford a yellow oil (401 mg, 91%) as the expected product. LRMS (ESI): m/z $[M+H]^+$ 377, 379.

(84) Reference Procedure of (10ttttt)

1-(4-Bromo-1-methyl-pyrazol-3-yl) ethanone (10ttttt) for preparation of EX.213, was prepared in accordance with the general procedure 38 using the method described below in detail.

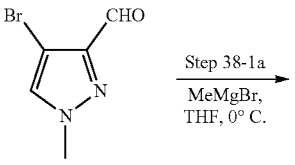

(10ddddd)

-continued

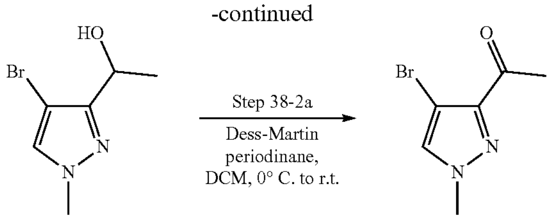

(10sssss) (10ttttt)

Step 38-1a

To a solution of 4-bromo-1-methyl-pyrazole-3-carbaldehyde (10ddddd) (1 g, 5.29 mmol) in THF (20 mL) was added 1.94 mL of MeMgBr (3M in ether, 5.82 mmol) at 0° C. and stirred at 0° C. for 1 h. Thereafter, mixture was then poured into sat. aq. $NH_4Cl$ (sat. aqueous solution) and extracted thrice with EtOAc. The combined organic extracts were dried over $Na_2SO_4$, filtered, and concentrated. The residue was used for the next reaction without further purification; LRMS (ESI): m/z $[M+, M+2]^+$ 205, 207.

Step 38-2a

To a solution of 1-(4-bromo-1-methyl-pyrazol-3-yl) ethanol (10sssss) (1.08 g, 5.29 mmol) in DCM (20 mL) was added Dess-Martin periodinane (2.91 g, 6.87 mmol) at 0° C. and stirred for 3 days (during that time was allowed to warm to room temperature). Thereafter, Celite (~5 g) was added to the mixture, stirred for 30 min., filtered, and concentrated. The residue was purified by silica gel column chromatography (eluted with 0-100% EtOAc/Hexanes) to afford a pale-yellow solid (959 mg, 89%) as product.

LRMS (ESI): m/z $[M+, M+2]^+$ 203, 205.

(85) Reference Procedure of (10xxxxx)

1-(3-Bromo-6,7-dihydro-5H-pyrazolo[5,1-b][1,3]oxazin-2-yl) etanone for preparation of EX.250 (10xxxxx) was prepared in accordance with the general procedure 38 using the method described below in detail.

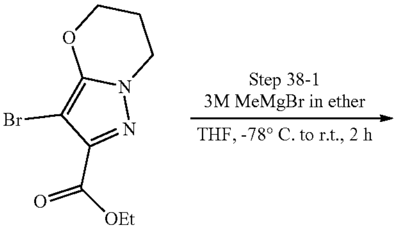

(10wwwww)

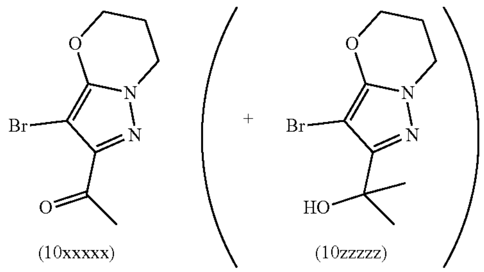

(10xxxxx) (10zzzzz)

Step 38-1

A solution of ethyl 3-bromo-6,7-dihydro-5H-pyrazolo[5,1-b][1,3]oxazine-2-carboxylate (10wwwww) (500 mg, 1.82 mmol) in THF (10 mL) was cooled to −78° C., and added 3

M MeMgBr in diethyl ether (1.21 mL, 3.64 mmol) dropwise under $N_2$ atmosphere. After addition, the dry ice bath was removed, and mixture was stirred at rt for 2 h. The mixture was quenched by adding saturated $NH_4Cl$ (2 mL) and extracted with EtOAc (3×10 mL). The organic phases were dried over anhydrous $Na_2SO_4$, filtered, and concentrated in vacuo. The crude was purified by silica gel column chromatography using 0-100% ethyl acetate in hexanes afforded the pure products. (10xxxxx) is a white solid, 140 mg 32% yield, whereas (10zzzzz) is a thick oil which solidified when stored in the freezer to give the brown solid, 98 mg 20% yield. LCMS (ESI): m/z $[M+H]^+$ 245, 261.

(86) Reference Procedure of (10hhhhhh)

Methyl 2-[4-bromo-3-(trifluoromethyl)pyrazol-1-yl]acetate (10hhhhhh) for preparation of EX.229 was prepared in accordance with the general procedure 40 using the method described below in detail.

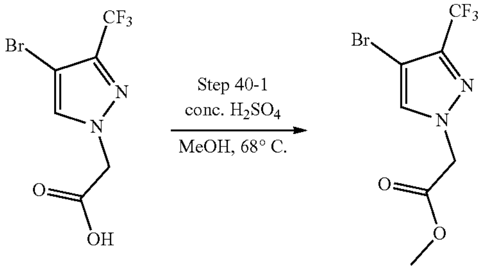

(10gggggg) (10hhhhhh)

Step 40-1

To a solution of 2-[4-bromo-3-(trifluoromethyl)pyrazol-1-yl]acetic acid (10gggggg) (500 mg, 1.83 mmol) in methanol (6 mL) was slowly added conc. $H_2SO_4$ (0.4 mL). The mixture was stirred at 68° C. for 1h 18 min. After the reaction mixture was cooled down, concentrated and then neutralized with saturated $NaHCO_3$ aqueous solution. The solution was extracted with DCM three times and the organic phases were combined, dried over $Na_2SO_4$, filtered and finally concentrated to obtain product (10hhhhhh) as light-yellow solid (508.8 mg, 96%); LRMS (ESI): m/z $[M+H]^+$ 287, 289.

(87) Reference Procedure of (10ooooooo)

Tert-butyl N-[(6R)-2-(difluoromethyl)-3-iodo-6,7-dihydro-5H-pyrazolo[5,1-b][1,3]oxazin-6-yl]carbamate (10ooooooo) was prepared in accordance with the general procedures 45 and 20 using the method described below in detail.

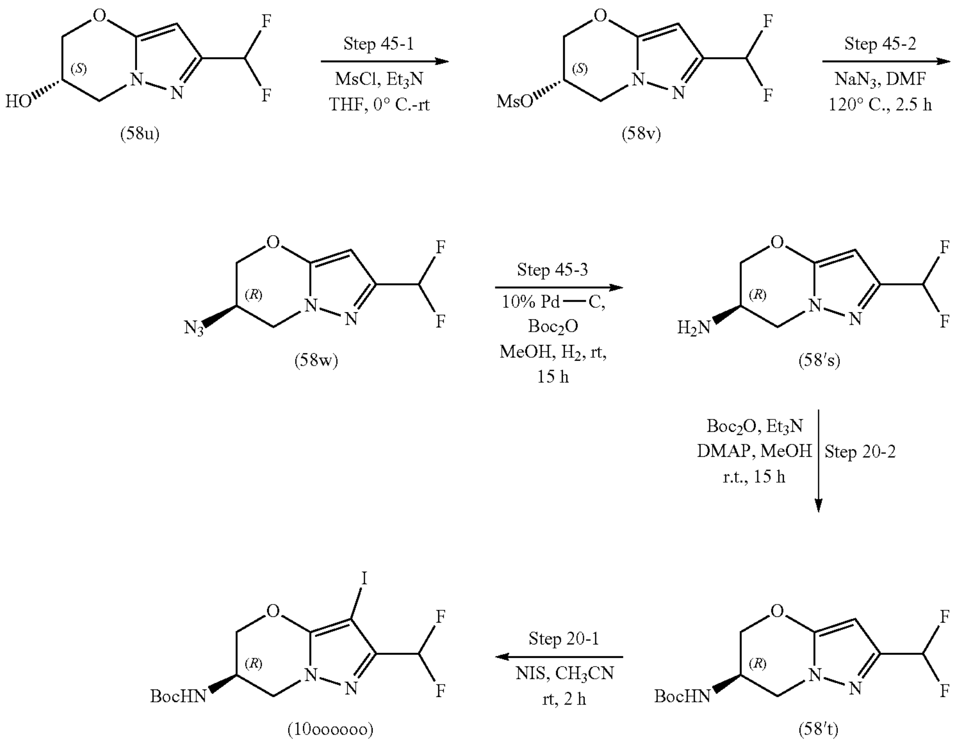

(58u) (58v) (58w) (58's) (10ooooooo) (58't)

Step 45-1

To a solution of (6S)-2-(difluoromethyl)-6,7-dihydro-5H-pyrazolo[5,1-b][1,3]oxazin-6-ol (58u) (0.63 g, 3.29 mmol) and $Et_3N$ (1.38 mL, 9.86 mmol) in THF (8 mL) at 0° C. was added dropwise methane sulfonyl chloride (0.31 mL, 3.94 mmol) and stirred at room temperature for 1.5 h. Thereafter, reaction mixture was concentrated under reduced pressure and added 50 mL of water and extracted with ethyl acetate (2×50 mL) and 10% MeOH in DCM (2×50 mL). The combined organic extracts were dried over $Na_2SO_4$, filtered, and concentrated to afford solid white material which was directly used for next reaction without further purification.

Step 45-2 Procedure as per: WO 2020/102096 PCT/US2019/060770, page 754.

In a 50 mL pear shaped flask with the empty condenser, was added (6S)-2-(difluoromethyl)-6,7-dihydro-5H-pyra zolo[5,1-b][1,3]oxazin-6-yl]methanesulfonate (58v) (725 mg, 2.7 mmol) in DMF (9 mL) and $NaN_3$ (351 mg, 5.41 mmol) at room temperature, flushed with $N_2$ and reaction was placed in pre-heated oil bath and heated at 120° C. for 2.5 h. After 5 min, the reaction mixture was turned form light yellow to light peach color. Later it turned to purple color. The reaction mixture was cooled after 2.5 hours, and reaction mixture was directly used for next step without any work up/purification.

Step 45-3

Crude reaction mixture from step 45-2 was taken in to a 100 mL, 24 neck-RB and added Methanol (18 mL), $Boc_2O$ (836 mg, 3.83 mmol) followed by Pd—C (27 mg, 0.26 mmol) and reaction was placed under $N_2$ atm. The mixture was degassed two times using $N_2$ purging and charged with the $H_2$ balloon to the RB flask, purged the $H_2$ gas for two times, sealed and stirred at room temperature for overnight. After 15 hours azide starting material was completed and free-amine (58's) was the major product and very minor Boc-protected product (58't).

Step 20-2

The crude reaction mixture of (6R)-2-(difluoromethyl)-6,7-dihydro-5H-pyrazolo[5,1-b][1,3]oxazin-6-amine (58's) was filtered through Celite and rinsed with MeOH, the low boiling volatile are removed (MeOH) and was added Methanol (15 mL), TEA (0.92 mL, 5.29 mmol) and DMAP (16 mg, 0.13 mmol). The reaction was placed under $N_2$ atm and added $Boc_2O$ (865 mg, 3.96 mmol). The mixture was stirred at room temperature for 15 h. MeOH was evaporated, and water (50 mL) was added to the reaction mixture and extracted with DCM (3×20 mL), combined organic layer was dried over $Na_2SO_4$, concentrated and purified by silica gel column chromatography using 0-10% MeOH in DCM to give 435 mg of product (58't) as a light brown solid.

Step 20-1

A mixture of tert-butyl N-[(6R)-2-(difluoromethyl)-6,7-dihydro-5H-pyrazolo[5,1-b][1,3]oxazin-6-yl]carbamate (58't) (260 mg, 0.9 mmol) and NIS (303 mg, 1.35 mmol) in MeCN (12 mL) was stirred at rt for 120 min. The reaction mixture was concentrated in vacuo. The crude was purified by silica gel column chromatography using 0-5% MeOH in DCM, to obtain target compound (10oooooo) as pale pink solid, 286 mg, 76%.

Tert-butyl N-[(6S)-2-(difluoromethyl)-3-iodo-6,7-dihydro-5H-pyrazolo[5,1-b][1,3]oxazin-6-yl]carbamate (10pppppp) (for preparation of EX.363, EX.415) was synthesized from commercially available S-glycidol in accordance with the methods described in the procedures 45 (step 45-1 to step 45-3) and 20 (20-1).

(10pppppp)

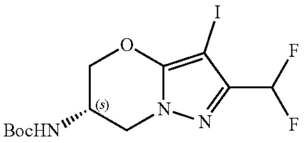

(10pppppp)

LRMS (ESI): m/z $[M+H]^+$ 417.

(88) Reference Procedure of (10tttttt)

4-Bromo-3-(difluoromethoxy) isoxazole (10tttttt) for preparation of EX.407 and EX.237 was prepared in accordance with the general procedure 47 using the method described below in detail.

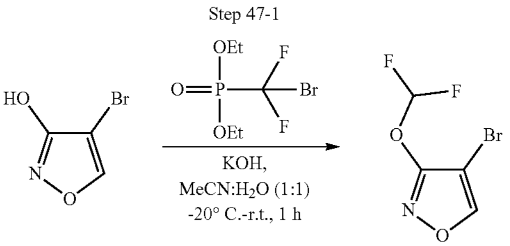

(10ssssss) (10tttttt)

Step 47-1

A reaction vessel containing KOH (1.36 g, 20 mmol), acetonitrile (3 mL) and water (3 mL) was stirred at room temperature until the KOH is completely dissolved. Then cooled the reaction mixture to −20° C. using ice bath and added the 4-bromoisoxazol-3-ol (10ssssss) (200 mg, 1.0 mmol), followed by diethyl (bromodifluoromethyl)phosphonate (10tttttt) (651.4 mg, 2.0 mmol). The resulting mixture was then stirred at the same temperature for 15 min then removed the ice bath and continued the stirring at room temperature for another 45 min. After completion of the reaction, diluted the reaction mixture with more water (10 mL) and extracted with ethyl acetate (3×15 mL). The combined organic layers were washed with brine (10 mL), dried over sodium sulfate, and concentrated and used in the next step without further purification.

(89) Reference Procedure of 4-iodoisothiazol-3 (2H)-one (127)

(127)

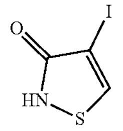

(127)

NIS (2.25 g, 10.0 mmol) was added to a solution of isothiazol-3-one (1.00 g, 9.89 mmol) in DMF (19 mL) at 0° C. After stirring at 0° C. for 0.5 h, another portion of NIS (2.25 g, 10.0 mmol) was added. The reaction mixture was then stirred for 2 h at room temperature. Sat. aq. $Na_2S_2O_3$ was added to quench the reaction, and the resulting mixture was extracted with EtOAc. The organic layer was washed with brine, dried over $Na_2SO_4$, and concentrated. $CHCl_3$ was added to the residue, and the resulting insoluble solid was collected by filtration to yield compound 127 (651 mg) as a pale yellow solid. The filtrate was concentrated, and the residue was purified by silica gel column chromatography (8-64% EtOAc/hexane) to yield compound 127 (242 mg) as a white solid. In total, 893 mg (40%) of compound 127 was obtained; $^1H$-NMR (400 MHz, DMSO-$d_6$) δ 8.92 (s, 1H), 12.17 (s, 1H); MS (ESI−): 226 [M−H]−.

(90) Reference Procedure of 3-(difluoromethoxy)-4-iodo-isothiazole (128)

(128)

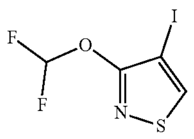

(128)

A mixture of compound 127 (650 mg, 2.86 mmol), 5 mol/L aq. KOH (14 mL, 70.0 mmol), and diethyl (bromodifluoromethyl)phosphate (1.3 mL, 7.30 mmol) was stirred at room temperature for 16 h. 3 mol/L HCl was added, and the resulting mixture was extracted with $Et_2O$. The organic layer was washed with brine, dried over $Na_2SO_4$, and concentrated to yield compound 128 (779 mg) as a brown oil, which was used directly in the next step without purification.

(91) Reference Procedure of 3-(difluoromethoxy)-4-(4,4,5,5-tetramethyl-1,3,2-dioxaborolan-2-yl) isothiazole (129)

(129)

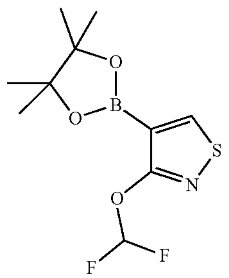

(129)

A mixture of 3-(difluoromethoxy)-4-iodo-isothiazole (933 mg, crude), bis(pinacolato)diboron (1.10 g, 4.33 mmol), $PdCl_2(dppf)\text{-}CH_2Cl_2$ (238 mg, 0.288 mmol), and AcOK (850 mg, 8.66 mmol, 3.01 eq) in dioxane (11 mL) was stirred at 100° C. for 5.5 h under Ar atmosphere. The reaction mixture was filtered off through a pad of Celite and the filtrate was concentrated. The residue was purified by silica gel column chromatography (0-10% methanol/EtOAc) to yield compound 129 (794 mg, quant.) as a brown oil; $^1$H-NMR (400 MHz, $CDCl_3$) δ 1.34 (s, 12H), 7.13-7.49 (m, 1H), 8.99 (s, 1H).

(92) Reference Procedure of 3-bromo-1-methylpyrrole-2-carboxamide (130)

(130)

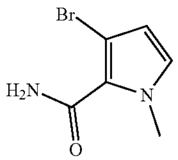

(130)

A mixture of 3-bromo-1-methylpyrrole-2-carboxlic acid (100 mg, 0.49 mmol), EDCl-HCl (141 mg, 0.736 mmol), DIEPA (0.125 mL, 0.735 mmol), and 1H-1,2,3-benzotriazol-1-ol amine (123 mg, 0.835 mmol) in DMF (2 mL) was stirred at room temperature for 2 h. Water was added, and the resulting solid was removed by filtration. The filtrate was concentrated, and the residue was purified by silica gel column chromatography (1-10% MeOH/$CHCl_3$) to yield compound 130 (102 mg) along with some impurities. The product, containing impurities, was used in the next step without further purification.

(93) Reference Procedure of 3-bromo-1-methylpyrrole-2-carbonitrile (131)

(131)

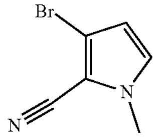

(131)

$SOCl_2$ (0.071 mL, 0.980 mmol) was added to a solution of compound 130 (101 mg) in DMF (2.5 mL). After stirring at room temperature for 1 h, water was added, and the resulting mixture was extracted with $CHCl_3$-MeOH (9:1). The organic layer was washed with brine, dried over $Na_2SO_4$, and concentrated. The residue was purified by silica gel column chromatography (0-100% MeCN/$H_2O$) to yield compound 131 (12 mg, 13%); $^1$H-NMR (400 MHz, DMSO-$d_6$) δ 3.74 (s, 3H), 6.37 (s, 1H), 7.22 (s, 1H).

(94) Reference Procedure of 3-(difluoromethoxy)-4-iodopyridine (132)

(132)

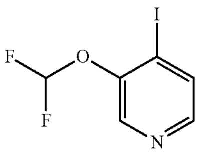

(132)

A mixture of 4-iodo-3-hydroxypyridine (1.00 g, 4.52 mmol), sodium chlorodifluoroacetate (1.04 g, 6.82 mmol), and cesium carbonate (2.21 g, 6.78 mmol) in DMF (22.6 mL) was stirred at 80° C. for 2 h under Ar atmosphere. The reaction mixture was filtered off through a pad of Celite and the filtrate was concentrated. The residue was purified by silica gel column chromatography (8-66% EtOAc/hexane) to yield compound 132 (220 mg, 18%) as a white solid; $^1$H-NMR (400 MHz, $CDCl_3$) δ 6.60 (t, J=72.3 Hz, 1H), 7.83 (d, J=5.0 Hz, 1H), 8.11 (d, J=5.1 Hz, 1H), 8.41 (t, J=1.2 Hz, 1H); MS (ESI$^+$): 272 $[M+H]^+$.

(95) Reference Procedure of 3-(difluoromethoxy)-4-(4,4,5,5-tetramethyl-1,3,2-dioxaborolan-2-yl)pyridine (133)

(133)

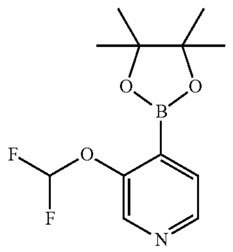

(133)

n-Butyllithium was slowly added to a stirred solution of compound 132 (105 mg, 0.387 mmol) and 2-isopropoxy-4,4,5,5-tetramethyl-1,3,2-dioxaborolane (0.12 mL, 0.583 mmol) in $Et_2O$ (1.94 mL) at −78° C. The reaction mixture was allowed to warm gradually to room temperature over 2 h. AcOH (0.044 mL, 0.769 mmol) was added, and the resulting mixture was stirred for 1 h. The mixture was filtered off through a pad of Celite, and the filtrate was concentrated to yield compound 133 as a yellow solid, which was used directly in the next step without purification.

(96) Reference Procedure of 2-(2-chloro-5-methyl-3-thienyl)-4,4,5,5-tetramethyl-1,3,2-dioxaborolane (134)

(134)

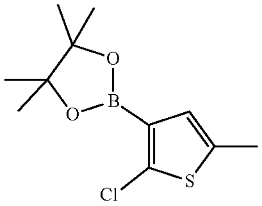

(134)

Compound 134 was synthesized from the corresponding bromide using conditions analogous to compound 129; $^1$H-NMR (400 MHz, $CDCl_3$) δ 1.33 (12H, s), 2.38 (3H, d, J=1.1 Hz), 6.79 (1H, q, J=1.1 Hz).

(97) Reference Procedure of 5-cyclopropyl-1,2-dihydro-3H-pyrazol-3-one (135)

(135)

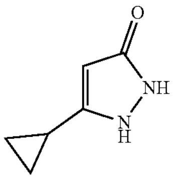

(135)

Hydrazine hydrate (0.79 mL, 16.3 mmol) was slowly added to a stirred mixture of ethyl 3-cyclopropyl-3-oxopropanoate (1.00 g, 6.40 mmol) in EtOH (5 mL) at room temperature. After stirring at 60° C. for 1.5 h, the resulting mixture was cooled to room temperature, and the resulting solid was collected by filtration to yield compound 135 (500 mg, 63%) as a white solid; $^1$H-NMR (400 MHz, DMSO-$d_6$) δ 0.53-0.57 (2H, m), 0.77-0.82 (2H, m), 1.66-1.72 (1H, m), 5.07 (1H, s), 9.69 (1H, s), 10.80 (1H, s).

The following compounds were synthesized from the corresponding starting materials and keto-esters using conditions analogous to compound 135.

| Compound No. | Chemical structural formula | Spectrum data |
|---|---|---|
| 136 | 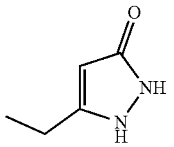 | $^1$H-NMR (400 MHz, DMSO-$d_6$) δ 1.12 (3H, t, J = 7.6 Hz), 2.44 (2H, q, J = 7.6 Hz), 5.22 (1H, s); MS (ESI$^+$): 113 [M + H]$^+$ |
| 137 | 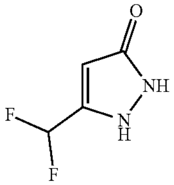 | $^1$H-NMR (400 MHz, DMSO-$d_6$) δ 5.51 (s, 1H), 6.72 (t, J = 56.3 Hz, 1H), 10.84 (s, 1H), 12.46 (s, 1H); MS (ESI$^-$): 133 [M − H]$^-$. |

(98) Reference Procedure of 1-acetyl-5-cyclopropyl-1,2-dihydro-3H-pyrazol-3-one (138)

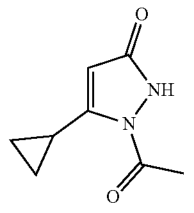

(138)

A mixture of compound 135 (100 mg, 0.806 mmol) and acetic anhydride (0.079 mL, 0.838 mmol) in pyridine (1 mL) was stirred at room temperature for 0.5 h, followed by stirring at 95° C. for 2 h. The resulting mixture was concentrated. The residue was purified by silica gel column chromatography (5-100% EtOAc/hexane) to yield compound 138 (33 mg, 25%) as a white solid; $^1$H-NMR (400 MHz, $CDCl_3$) δ 0.66-0.70 (2H, m), 1.02-1.07 (2H, m), 2.55 (3H, s), 2.56-2.63 (1H, m), 5.48 (1H, d, J=0.8 Hz); MS ($ESI^+$): 167 $[M+H]^+$.

The following compounds were synthesized from the corresponding starting materials using conditions analogous to compound 138.

(99) Reference Procedure of (2-methyl-3-methylsulfonyloxy-2-nitro-propyl) methanesulfonate (141)

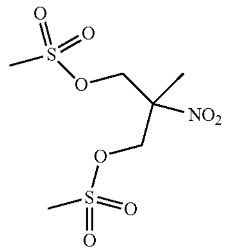

(141)

Triethyl amine (3.1 mL, 22.2 mmol) and methanesulfonyl chloride (1.2 mL, 15.6 mmol) were added to a solution of 2-methyl-2-nitropropane-1,3-diol (1.00 g, 7.40 mmol) in $CH_2Cl_2$ (18.5 mL) at 0° C. After stirring at room temperature for 3 h, water was added, and the resulting mixture was extracted with EtOAc. The organic layer was washed with brine, dried over $Na_2SO_4$, and concentrated to yield compound 141 (1.92 g, 89%) as a white solid; $^1$H-NMR (400 MHz, $CDCl_3$) δ 1.74 (s, 3H), 3.10 (s, 6H), 4.60 (d, J=11.0 Hz, 2H), 4.64 (d, J=11.0 Hz, 2H).

| Compound No. | Chemical structural formula | Spectrum data |
|---|---|---|
| 139 | 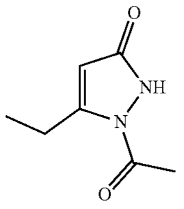 | $^1$H-NMR (400 MHz, DMSO-$d_6$) δ 1.14 (t, J = 7.4 Hz, 3H), 2.46 (s, 3H), 2.86 (qd, J = 7.4, 1.0 Hz, 2H), 5.79 (t, J = 1.0 Hz, 1H), 10.75 (s, 1H); MS ($ESI^+$): 155 $[M + H]^+$. |
| 140 | 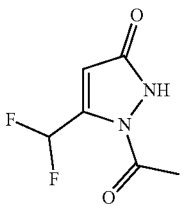 | $^1$H-NMR (400 MHz, $CDCl_3$) δ 2.58 (3H, s), 6.34 (1H, s), 7.19 (1H, t, J = 53.9 Hz), 9.55 (1H, s); MS ($ESI^-$): 175 $[M - H]^-$. |

(99) Reference Procedure of 2-(difluoromethyl)-6-methyl-6-nitro-5,7-dihydropyrazolo[5,1-b][1,3]oxazine (142)

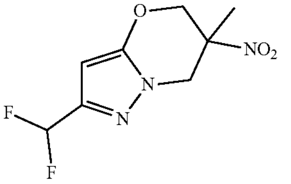 [SMILES: CC1([N+](=O)[O-])COc2cc(C(F)F)nn2C1]

A mixture of compound 141 (1.92 g, 6.59 mmol), compound 137 (803 mg, 5.99 mmol), and $K_2CO_3$ (3.31 g, 23.9 mmol) in DMF (29.9 mL) was stirred at 80° C. for 14 h under Ar atmosphere. The reaction mixture was filtered off through a pad of Celite, and the filtrate was concentrated. The residue was purified by silica gel column chromatography (25-100% EtOAc/hexane) to yield compound 142 (1.19 mg, 85%) as a colorless oil; MS ($ESI^+$): 234 $[M+H]^+$.

(100) Reference Procedure of 2-cyclopropyl-6,7-dihydro-5H-pyrazolo[5,1-b][1,3]oxazine (143)

(143)

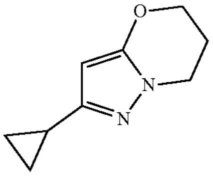

A mixture of compound 135 (200 mg, 1.61 mmol), 1,3-dibromopropane (0.181 mL, 1.78 mmol), and $K_2CO_3$ (668 mg, 4.83 mmol) in DMA (16 mL) was stirred at 70° C. for 1 h under Ar atmosphere. The reaction was quenched with sat. aq. $NH_4Cl$, and NaCl was added to saturate the mixture. The resulting mixture was extracted with EtOAc. The organic layer was washed with brine, dried over $Na_2SO_4$, and concentrated. The residue was purified by silica gel column chromatography (5-100% EtOAc/hexane then 0-30% MeOH/EtOAc) to yield compound 143 (160 mg, 61%) as a white solid; $^1$H-NMR (400 MHz, $CDCl_3$) δ 0.60-0.71 (2H, m), 0.78-0.90 (2H, m), 1.77-1.83 (1H, m), 2.19 (2H, dt, J=11.6, 5.2 Hz), 4.07 (2H, t, J=6.1 Hz), 4.21 (2H, t, J=5.5 Hz), 5.13 (1H, s); MS ($ESI^+$): 165 $[M+H]^+$.

The following compounds were synthesized from the corresponding starting materials and reagents using conditions analogous to compound 143.

| Compound No. | Chemical structural formula | Spectrum data |
|---|---|---|
| 144 | 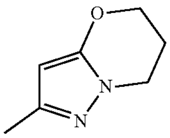 | $^1$H-NMR (400 MHz, $CDCl_3$) δ 2.16 (3H, s), 2.20 (2H, qd, J = 6.3, 4.0 Hz), 4.08 (2H, t, J = 6.1 Hz), 4.21-4.24 (2H, m), 5.28 (1H, s). |
| 145 | 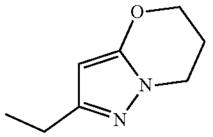 | $^1$H-NMR (400 MHz, $CDCl_3$) δ 1.19 (3H, t, J = 7.6 Hz), 2.18-2.24 (2H, m), 2.53 (2H, q, J = 7.5 Hz), 4.09 (2H, t, J = 6.1 Hz), 4.23 (2H, t, J = 5.2 Hz), 5.30 (1H, s). |
| 146 | 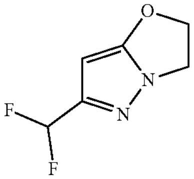 [SMILES: FC(F)c1cc2n(n1)CCO2] | $^1$H-NMR (400 MHz, $CDCl_3$) δ 4.33 (tt, J = 8.0, 1.7 Hz, 2H), 5.08 (t, J = 8.1 Hz, 2H), 5.61 (s, 1H), 6.51 (t, J = 54.9 Hz, 1H); MS ($ESI^+$): 161 $[M + H]^+$. |
| 147 | 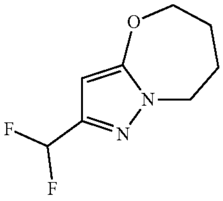 [SMILES: FC(F)c1cc2n(n1)CCCCO2] | $^1$H-NMR (400 MHz, $CDCl_3$) δ 1.84-1.92 (m, 2H), 2.03-2.11 (m, 2H), 4.08 (t, J = 5.0 Hz, 2H), 4.23 (t, J = 5.3 Hz, 2H), 5.93 (s, 1H), 6.51 (t, J = 55.2 Hz, 1H); MS ($ESI^+$): 189 $[M + H]^+$. |

-continued

| Compound No. | Chemical structural formula | Spectrum data |
|---|---|---|
| 148 | 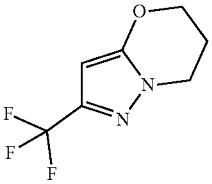 [SMILES: FC(F)(F)c1cc2n(n1)CCCO2] | $^1$H-NMR (400 MHz, DMSO-$d_6$) δ 2.18-2.25 (m, 2H), 4.16 (t, J = 6.1 Hz, 2H), 4.34 (t, J = 5.3 Hz, 2H), 5.97 (s, 1H) MS (FI$^+$): 192 [M$^+$]. |

(101) Reference Procedure of (S)-1-(5-cyclopropyl-3-(oxiran-2-ylmethoxy)-1H-pyrazol-1-yl) ethan-1-one (149)

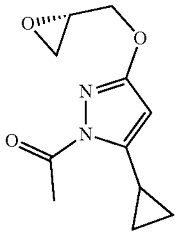

(149)

[(2R)-Oxiran-2-yl]methanol (0.35 mL, 5.29 mmol), followed by diisopropyl azodicarboxylate (1.5 mL, 7.79 mmol) were added to a stirred solution of compound 135 (720 mg, 4.33 mmol) in THF (20 mL) at 0° C. After stirring at the same temperature for 1 h, triphenylphosphine (2.05 g, 7.82 mmol) was added, and the reaction mixture was stirred at room temperature for 2 h. The reaction mixture was directly purified by silica gel column chromatography (5-20% EtOAc/hexane) to yield compound 149 (830 mg, 86%) as a white solid; $^1$H-NMR (400 MHz, $CDCl_3$) δ 0.61-0.65 (2H, m), 0.98-1.03 (2H, m), 2.55-2.62 (4H, m), 2.72 (1H, q, J=2.5 Hz), 2.86-2.89 (1H, m), 3.32-3.36 (1H, m), 4.10 (1H, q, J=5.9 Hz), 4.45 (1H, dd, J=11.8, 3.3 Hz), 5.48 (1H, d, J=0.8 Hz); MS (ESI$^+$): 223 [M+H]$^+$.

The following compounds were synthesized from the corresponding starting materials and reagents using conditions analogous to compound 149.

| Compound No. | Chemical structural formula | Spectrum data |
|---|---|---|
| 150 | 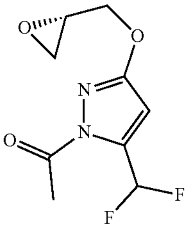 [SMILES: CC(=O)n1nc(OC[C@@H]2CO2)cc1C(F)F] | $^1$H-NMR (400 MHz, $CDCl_3$) δ 2.59 (3H, s), 2.74 (1H, q, J = 2.5 Hz), 2.90 (1H, dd, J = 4.8, 4.2 Hz), 3.34-3.38 (1H, m), 4.16 (1H, dd, J = 11.8, 6.1 Hz), 4.52 (1H, dd, J = 11.8, 3.1 Hz), 6.32 (1H, d, J = 0.7 Hz), 7.19 (1H, td, J = 54.0, 0.6 Hz); MS (ESI$^+$): 233 [M + H]$^+$. |
| 151 | 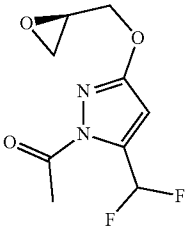 [SMILES: CC(=O)n1nc(OC[C@H]2CO2)cc1C(F)F] | $^1$H-NMR (400 MHz, $CDCl_3$) δ 2.59 (3H, s), 2.73-2.75 (1H, m), 2.90 (1H, dd, J = 4.9, 4.2 Hz), 3.34-3.38 (1H, m), 4.16 (1H, dd, J = 11.8, 6.1 Hz), 4.52 (1H, dd, J = 11.8, 3.1 Hz), 6.32 (1H, d, J = 0.6 Hz), 7.19 (1H, td, J = 54.0, 0.5 Hz). |
| 152 | 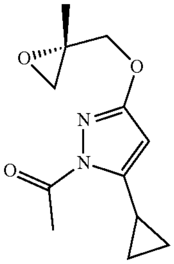 [SMILES: CC(=O)n1nc(OC[C@]2(C)CO2)cc1C1CC1] | $^1$H-NMR (400 MHz, $CDCl_3$) δ 0.59-0.70 (m, 2H), 0.96-1.08 (m, 2H), 1.45 (s, 3H), 2.54-2.66 (m, 4H), 2.72 (d, J = 4.8 Hz, 1H), 2.87 (d, J = 4.8 Hz, 1H), 4.15 (d, J = 11.3 Hz, 1H), 4.27 (d, J = 11.3 Hz, 1H), 5.50 (s, 1H); MS (ESI$^+$): 237 [M + H]$^+$. |

-continued

| Compound No. | Chemical structural formula | Spectrum data |
|---|---|---|
| 153 | 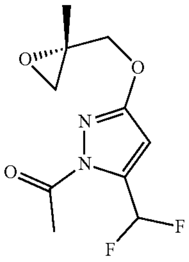 [SMILES: CC(=O)n1nc(OC[C@]2(C)CO2)cc1C(F)F] | $^1$H-NMR (400 MHz, $CDCl_3$) δ 1.48 (s, 3H), 2.60 (s, 3H), 2.74 (d, J = 4.7 Hz, 1H), 2.89 (d, J = 4.7 Hz, 1H), 4.20 (d, J = 11.3 Hz, 1H), 4.34 (d, J = 11.3 Hz, 1H), 6.34 (d, J = 0.6 Hz, 1H), 7.21 (td, J = 54.0, 0.5 Hz, 1H); MS (ESI$^+$): 247 [M + H]$^+$. |
| 154 | 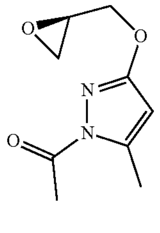 | $^1$H-NMR (400 MHz, $CDCl_3$) δ 2.53 (3H, s), 2.57 (3H, s), 2.75 (1H, dd, J = 4.9, 2.6 Hz), 2.90 (1H, t, J = 4.5 Hz), 3.33-3.40 (1H, m), 4.14 (1H, dd, J = 11.8, 6.0 Hz), 4.48 (1H, dd, J = 11.9, 3.2 Hz), 5.72 (1H, s); MS (ESI$^+$): 197 [M + H]$^+$. |
| 155 | 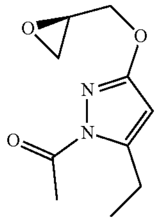 | $^1$H-NMR (400 MHz, DMSO-$d_6$) δ 1.16 (3H, t, J = 7.4 Hz), 2.48-2.53 (3H, m), 2.71 (1H, dd, J = 5.0, 2.6 Hz), 2.83 (1H, t, J = 4.6 Hz), 2.89 (2H, qd, J = 7.4, 0.8 Hz), 3.31-3.38 (1H, m), 3.96 (1H, dd, J = 11.8, 6.8 Hz), 4.51 (1H, dd, J = 11.8, 2.7 Hz), 6.05 (1H, s); MS (ESI$^+$): 211 [M + H]$^+$. |

(102) Reference Procedure of (R)-1-(3-(3-chloro-2-hydroxypropoxy)-5-cyclopropyl-1H-pyrazol-1-yl)ethan-1-one (156)

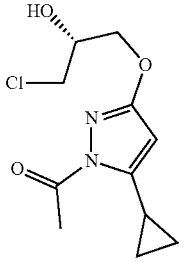

(156)

A mixture of 149 (820 mg, 3.69 mmol), AcOH (0.64 mL, 11.2 mmol), and LiCl (257 mg, 6.06 mmol) in THF (15 mL) was stirred at 50° C. for 2 h. Then, LiCl (129 mg, 3.04 mmol) was added and the reaction mixture was stirred at 60° C. for 1 h. The reaction was quenched by brine, and the resulting mixture was extracted with EtOAc. The organic layer was washed with sat. aq. $NaHCO_3$, brine, dried over $Na_2SO_4$, and concentrated to yield compound 156 (960 mg, quant.) as a slightly yellow oil; $^1$H-NMR (400 MHz, $CDCl_3$) δ 0.62-0.66 (2H, m), 1.00-1.04 (2H, m), 2.55-2.63 (4H, m), 3.24 (1H, s), 3.62-3.71 (2H, m), 4.15-4.20 (1H, m), 4.35 (2H, d, J=4.7 Hz), 5.49 (1H, d, J=0.8 Hz); MS (ESI$^+$): 223 [M+H]$^+$.

The following compounds were synthesized from the corresponding starting materials and reagents using conditions analogous to compound 156.

| Compound No. | Chemical structural formula | Spectrum data |
|---|---|---|
| 157 | 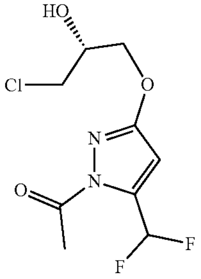 [SMILES: CC(=O)n1nc(OC[C@@H](O)CCl)cc1C(F)F] | $^1$H-NMR (400 MHz, $CDCl_3$) δ 2.60 (3H, s), 2.66 (1H, s), 3.66-3.76 (2H, m), 4.19-4.26 (1H, m), 4.38 (2H, d, J = 5.1 Hz), 6.32 (1H, s), 7.19 (1H, t, J = 54.0 Hz); MS ($ESI^-$): 267 $[M - H]^-$. |
| 158 | 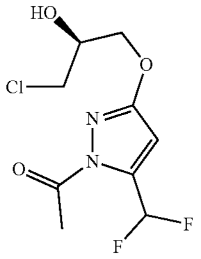 [SMILES: CC(=O)n1nc(OC[C@H](O)CCl)cc1C(F)F] | $^1$H-NMR (400 MHz, $CDCl_3$) δ 2.60 (3H, s), 2.66 (1H, s), 3.71 (2H, dq, J = 19.9, 5.6 Hz), 4.20-4.27 (1H, m), 4.38 (2H, d, J = 4.9 Hz), 6.32 (1H, s), 7.19 (1H, t, J = 54.1 Hz); MS ($EI^+$): 268 $[M^+]$. |
| 159 | 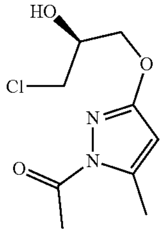 | $^1$H-NMR (400 MHz, DMSO-$d_6$) δ 1.16 (3H, t, J = 7.3 Hz), 2.46-2.53 (3H, m), 2.88 (2H, q, J = 7.4 Hz), 3.64 (1H, dd, J = 11.2, 5.3 Hz), 3.70 (1H, dd, J = 11.2, 5.0 Hz), 3.99-4.08 (1H, m), 4.11-4.23 (2H, m), 5.58 (1H, d, J = 5.3 Hz), 6.02 (1H, s). |
| 160 | 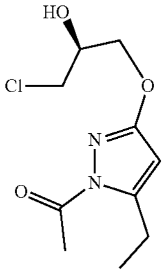 [SMILES: CCc1cc(OC[C@H](O)CCl)nn1C(C)=O] | $^1$H-NMR (400 MHz, $CDCl_3$) δ 1.16 (3H, t, J = 7.3 Hz), 2.46-2.53 (3H, m), 2.88 (2H, q, J = 7.4 Hz), 3.64 (1H, dd, J = 11.2, 5.3 Hz), 3.70 (1H, dd, J = 11.2, 5.0 Hz), 3.99-4.08 (1H, m), 4.11-4.23 (2H, m), 5.58 (1H, d, J = 5.3 Hz), 6.02 (1H, s); MS ($ESI^+$): 247 $[M + H]^+$. |
| 161 | 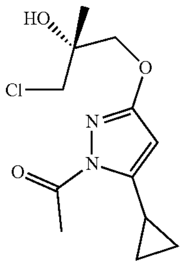 [SMILES: CC(=O)n1nc(OC[C@@](C)(O)CCl)cc1C1CC1] | $^1$H-NMR (400 MHz, $CDCl_3$) δ 0.60-0.71 (m, 2H), 0.97-1.09 (m, 2H), 1.38 (s, 3H), 2.55-2.67 (m, 4H), 3.09 (s, 1H), 3.62 (s, 2H), 4.18 (d, J = 10.7 Hz, 1H), 4.26 (d, J = 10.9 Hz, 1H), 5.51 (d, J = 0.7 Hz, 1H); MS ($ESI^+$): 273 $[M + H]^+$. |

-continued

| Compound No. | Chemical structural formula | Spectrum data |
|---|---|---|
| 162 | 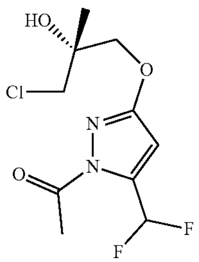 [SMILES: CC(=O)n1nc(OC[C@@](C)(O)CCl)cc1C(F)F] | $^1$H-NMR (400 MHz, $CDCl_3$) δ 1.41 (s, 3H), 2.58 (s, 1H), 2.62 (s, 3H), 3.64 (d, J = 11.1 Hz, 1H), 3.68 (d, J = 11.2 Hz, 1H), 4.23 (d, J = 10.5 Hz, 1H), 4.29 (d, J = 10.5 Hz, 1H), 6.35 (d, J = 0.6 Hz, 1H), 7.21 (t, J = 54.0 Hz, 1H); MS ($ESI^+$): 283 $[M + H]^+$. |

(103) Reference Procedure of (S)-2-cyclopropyl-6,7-dihydro-5H-pyrazolo[5,1-b][1,3]oxazin-6-ol (163)

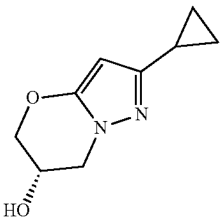 [SMILES: O[C@@H]1COc2cc(C3CC3)nn2C1]

A mixture of 156 (950 mg, 3.67 mmol) and $K_2CO_3$ (1.53 g, 11.1 mmol) in DMF (40 mL) was stirred at 135° C. for 2 h. The reaction mixture was cooled to room temperature, and MeOH (40 mL) was added. After stirring at 50° C. for 0.5 h, the reaction mixture was concentrated. Brine was added to the residue, and the resulting mixture was extracted with EtOAc. The organic layer was dried over $Na_2SO_4$ and concentrated. The residue was purified by silica gel column chromatography (0-30% MeOH/EtOAc) to yield compound 163 (120 mg, 15%) as a white solid; $^1$H-NMR (400 MHz, $CDCl_3$) δ 0.64-0.68 (2H, m), 0.84-0.89 (2H, m), 1.77-1.84 (1H, m), 2.28 (1H, s), 4.08-4.26 (4H, m), 4.35 (1H, ddd, J=7.0, 4.0, 1.8 Hz), 5.19 (1H, s); MS ($ESI^+$): 181 $[M+H]^+$.

The following compounds were synthesized from the corresponding starting materials and reagents using conditions analogous to compound 163.

| Compound No. | Chemical structural formula | Spectrum data |
|---|---|---|
| 164 | 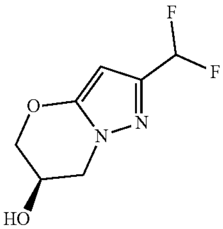 [SMILES: O[C@H]1COc2cc(C(F)F)nn2C1] | $^1$H-NMR (400 MHz, $CDCl_3$) δ 1.91 (1H, s), 4.18-4.34 (4H, m), 4.44 (1H, qd, J = 3.6, 1.5 Hz), 5.76 (1H, s), 6.52 (1H, t, J = 55.0 Hz); MS ($ESI^+$): 191 $[M + H]^+$. |
| 165 | 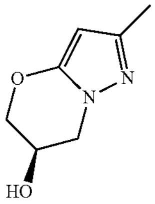 | $^1$H-NMR (400 MHz, DMSO-$d_6$) δ 2.02 (3H, s), 3.77-3.85 (1H, m), 4.03-4.23 (4H, m), 5.24 (1H, s), 5.45-5.62 (1H, m); MS ($ESI^+$): 155 $[M + H]^+$. |
| 166 | 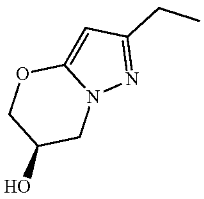 | $^1$H-NMR (400 MHz, DMSO-$d_6$) δ 1.10 (3H, t, J = 7.6 Hz), 2.39 (2H, q, J = 7.6 Hz), 3.78-3.85 (1H, m), 4.02-4.16 (3H, m), 4.17-4.23 (1H, m), 5.28 (1H, s), 5.48 (1H, d, J = 3.5 Hz); MS ($ESI^+$): 169 $[M + H]^+$. |

-continued

| Compound No. | Chemical structural formula | Spectrum data |
|---|---|---|
| 167 | 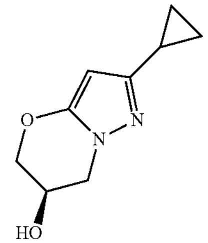 [SMILES: O[C@H]1COc2cc(C3CC3)nn2C1] | $^1$H-NMR (400 MHz, $CDCl_3$) δ 0.64-0.73 (m, 2H), 0.85-0.93 (m, 2H), 1.78-1.87 (m, 1H), 4.08-4.29 (m, 4H), 4.33-4.42 (m, 1H), 5.20 (s, 1H); MS (ESI$^+$): 181 [M + H]$^+$. |
| 168 | 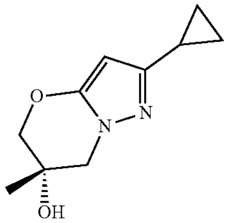 | $^1$H-NMR (400 MHz, $CDCl_3$) δ 0.64-0.73 (m, 2H), 0.82-0.90 (m, 2H), 1.40 (s, 3H), 1.80-1.86 (m, 1H), 2.41 (s, 1H), 3.92-3.99 (m, 2H), 4.02-4.06 (m, 2H), 5.22 (s, 1H); MS (ESI$^+$): 195 [M + H]$^+$. |
| 169 | 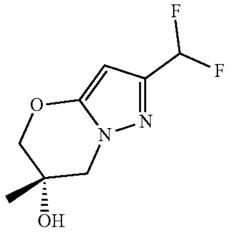 | $^1$H-NMR (400 MHz, $CDCl_3$) δ 1.44 (s, 3H), 2.36 (s, 1H), 4.02-4.18 (m, 4H), 5.79 (s, 1H), 6.53 (t, J = 55.1 Hz, 1H); MS (ESI$^+$): 205 [M + H]$^+$. |

(104) Reference Procedure of (S)-2-(difluoromethyl)-6-fluoro-6,7-dihydro-5H-pyrazolo[5,1-b][1,3]oxazine (170)

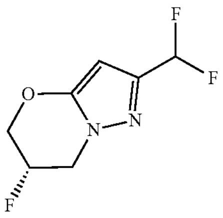 [SMILES: FC(F)c1cc2n(n1)C[C@H](F)CO2]

Diethylaminosulfur trifluoride (DAST) (0.413 mL, 3.15 mmol) was added to a stirred suspension of compound 164 (300 mg, 1.58 mmol) in $CH_2Cl_2$ (6 mL) at 0° C. under Ar atmosphere. After stirring at room temperature for 46.5 h. The reaction mixture was poured into sat. aq. $NaHCO_3$. The resulting mixture was then extracted with $CH_2Cl_2$. The organic layer was washed with brine, dried over $Na_2SO_4$, and concentrated. The residue was purified by silica gel column chromatography (10-100% EtOAc/hexane) to yield compound 170 (100 mg, 33%) as a white solid; $^1$H-NMR (400 MHz, $CDCl_3$) δ 4.21 (1H, ddd, J=36.7, 12.7, 0.8 Hz), 4.28-4.42 (1H, m), 4.47-4.55 (1H, m), 4.58-4.65 (1H, m), 5.16-5.30 (1H, m), 5.79 (1H, s), 6.54 (1H, t, J=55.0 Hz); MS (ESI$^+$): 193 [M+H]$^+$.

(105) Reference Procedure of (R)-2-(difluoromethyl)-6,7-dihydro-5H-pyrazolo[5,1-b][1,3]oxazin-6-yl methanesulfonate (171)

(171)

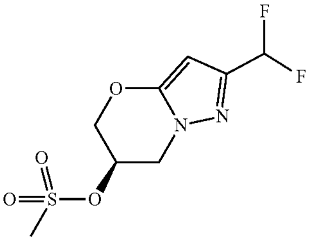

To a stirred solution of compound 164 (1.00 g, 5.26 mmol) in THF (40 mL) at 0° C. under Ar atmosphere, triethylamine (0.88 mL, 6.35 mmol) was added, followed by the addition of methanesulfonyl chloride (0.45 mL, 5.81 mmol). After stirring at room temperature for 1 h, ice-water was added. The resulting mixture was extracted with EtOAc. The organic layer was dried over $Na_2SO_4$, and concentrated to yield compound 171 (1.41 g) as a white solid; $^1$H-NMR (400 MHz, $CDCl_3$) § 3.13 (3H, s), 4.27 (1H, d, J=12.6 Hz), 4.40-4.51 (2H, m), 4.63 (1H, ddd, J=12.5, 3.0, 2.2 Hz), 5.35-5.37 (1H, m), 5.80 (1H, s), 6.52 (1H, t, J=55.0 Hz); MS (ESI$^+$): 269 [M+H]$^+$.

The following compounds were synthesized from the corresponding starting materials and reagents using conditions analogous to compound 171.

| Compound No. | Chemical structural formula | Spectrum data |
|---|---|---|
| 172 | 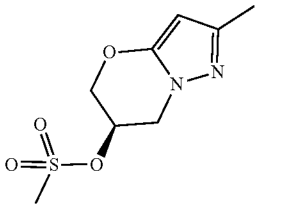 | The crude compound obtained was used directly in the next step without purification. |
| 173 | 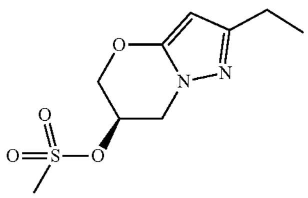 [SMILES: CCc1cc2n(n1)C[C@@H](OS(C)(=O)=O)CO2] | The crude compound obtained was used directly in the next step without purification. |
| 174 | 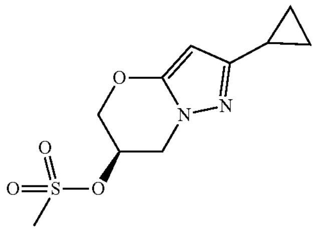 [SMILES: CS(=O)(=O)O[C@H]1COc2cc(C3CC3)nn2C1] | The crude compound obtained was used directly in the next step without purification. |

(106) Reference Procedure of (S)-6-azido-2-(difluoromethyl)-6,7-dihydro-5H-pyrazolo[5,1-b][1,3]oxazine (175)

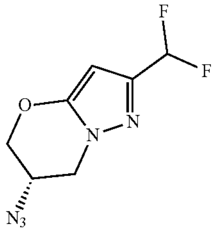

(175)

A mixture of compound 171 (1.41 g) and sodium azide (700 mg, 10.8 mmol) in DMF (20 mL) was stirred at 120° C. for 3 h. The reaction mixture was cooled to room temperature, and brine was added. The resulting mixture was extracted with EtOAc. The organic layer was dried over $Na_2SO_4$, and concentrated. The residue was purified by silica gel column chromatography (5-100% EtOAc/hexane) to yield compound 175 (960 mg, 84%) as a slightly yellow oil; $^1$H-NMR (400 MHz, $CDCl_3$) δ 4.18-4.24 (2H, m), 4.28-4.40 (3H, m), 5.77 (1H, s), 6.52 (1H, t, J=55.1 Hz); MS (ESI$^+$): 216 $[M+H]^+$.

The following compounds were synthesized from the corresponding starting materials and reagents using conditions analogous to compound 175.

| Compound No. | Chemical structural formula | Spectrum data |
|---|---|---|
| 176 | 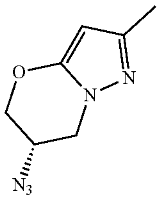 | $^1$H-NMR (400 MHz, $CDCl_3$) δ 2.19 (3H, s), 4.11-4.19 (2H, m), 4.23-4.38 (3H, m), 5.36 (1H, s); MS (ESI$^+$): 154 $[M + H]^+$. |

-continued

| Compound No. | Chemical structural formula | Spectrum data |
|---|---|---|
| 177 | 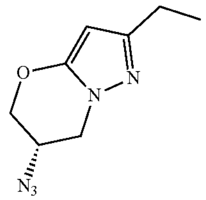 | $^1$H-NMR (400 MHz, $CDCl_3$) δ 1.21 (3H, t. J = 7.6 Hz), 2.55 (2H, q, J = 7.6 Hz), 4.12-4.19 (2H, m), 4.23-4.38 (3H, m), 5.39 (1H, s); MS (ESI$^+$): 194 [M + H]$^+$. |
| 178 | 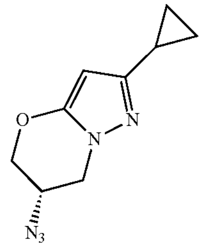 [SMILES: [N-]=[N+]=N[C@@H]1COc2cc(C3CC3)nn2C1] | $^1$H-NMR (400 MHz, $CDCl_3$) δ 0.63-0.75 (m, 2H), 0.83-0.95 (m, 2H), 1.76-1.89 (m, 1H), 4.08-4.34 (m, 5H), 5.22 (s, 1H); MS (ESI$^+$): 206 [M + H]$^+$. |

(107) Reference Procedure of (S)-2-(difluoromethyl)-6,7-dihydro-5H-pyrazolo[5,1-b][1,3]oxazin-6-amine (179)

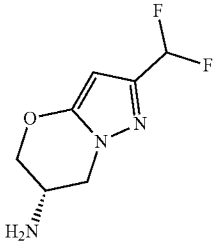

(179)

A mixture of compound 175 (950 mg, 4.42 mmol) and 10% Pd—C (95 mg) in EtOH (30 mL) was stirred at room temperature for 2 h under $H_2$ atmosphere (1 atm). The reaction mixture was purged and backfilled with Ar, and filtered off through a pad of Celite. The filtrate was concentrated to yield compound 179 (835 mg, quant.) as a slightly brown oil; $^1$H-NMR (400 MHz, $CDCl_3$) δ 1.51 (2H, s), 3.60-3.63 (1H, m), 3.90 (1H, dd, J=12.3, 5.5 Hz), 4.03 (1H, dd, J=10.9, 6.2 Hz), 4.25 (1H, d, J=11.0 Hz), 4.34 (1H, dd, J=12.3, 4.7 Hz), 5.73 (1H, s), 6.51 (1H, t, J=55.1 Hz); MS (ESI$^+$): 190 [M+H]$^+$.

The following compounds were synthesized from the corresponding starting materials and reagents using conditions analogous to compound 179.

| Compound No. | Chemical structural formula | Spectrum data |
|---|---|---|
| 180 | 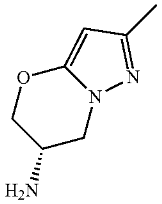 | $^1$H-NMR (400 MHz, $CDCl_3$) δ 2.19 (3H, s), 3.53-3.60 (1H, m), 3.81-3.88 (1H, m), 3.96-4.03 (1H, m), 4.18-4.24 (1H, m), 4.28 (1H, dd, J = 12.1, 4.9 Hz), 5.33 (1H, s). |
| 181 | 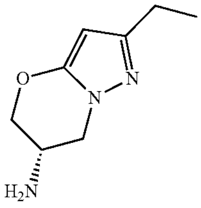 | $^1$H-NMR (400 MHz, $CDCl_3$) δ 1.21 (3H, t, J = 7.6 Hz), 1.41 (2H, s), 2.55 (2H, q, J = 7.6 Hz), 3.50-3.61 (1H, m), 3.81-3.88 (1H, m), 3.96-4.02 (1H, m), 4.17-4.23 (1H, m), 4.26-4.33 (1H, m), 5.35 (1H, s); MS (ESI$^+$): 168 [M + H]$^+$. |

-continued

| Compound No. | Chemical structural formula | Spectrum data |
|---|---|---|
| 182 | 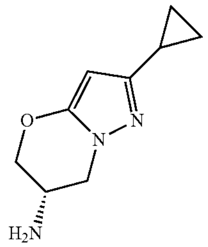 | $^1$H-NMR (400 MHz, $CDCl_3$) δ 0.62-0.73 (m, 2H), 0.83-0.93 (m, 2H), 1.77-1.89 (m, 1H), 3.46-3.59 (m, 1H), 3.83 (ddd, J = 12.1, 5.4, 1.1 Hz, 1H), 3.98 (ddd, J = 10.9, 6.2, 1.1 Hz, 1H), 4.19 (ddd, J = 10.8, 2.7, 0.8 Hz, 1H), 4.27 (ddd, J = 12.1, 5.0, 0.7 Hz, 1H), 5.18 (s, 1H). |

(108) Reference Procedure of (S)-2-(difluoromethyl)-6,7-dihydro-5H-pyrazolo[5,1-b][1,3]oxazin-6-amine (183) and tert-butyl (S)-(tert-butoxycarbonyl)(2-(difluoromethyl)-6,7-dihydro-5H-pyrazolo[5,1-b][1,3]oxazin-6-yl)carbamate (183')

(183)

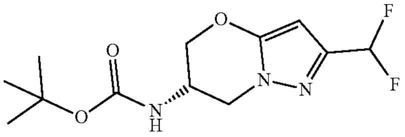

-continued (183')

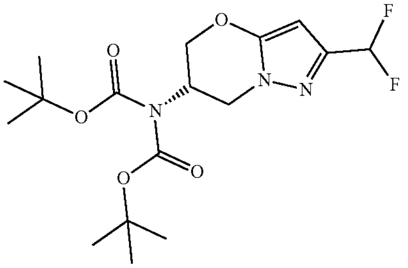

A mixture of compound 179 (730 mg, 3.86 mmol), $(Boc)_2O$ (2.11 g, 9.67 mmol), triethylamine (1.60 mL, 11.6 mmol), and 4-dimethylaminopyridine (95.0 mg, 0.778 mmol) in THF (40 mL) was stirred at room temperature for 2 h. The reaction mixture was directly purified by silica gel column chromatography (5-100% EtOAc/hexane) to yield compound 183 (155 mg, 14%) as a slightly yellow oil and compound 183' (747 mg, 50%) as a white solid; 183: $^1$H-NMR (400 MHz, $CDCl_3$) δ 1.45 (s, 9H), 4.17-4.43 (m, 5H), 5.06 (s, 1H), 5.78 (s, 1H), 6.53 (t, J=55.1 Hz, 1H); MS ($ESI^-$): 288 $[M-H]^-$. 183': $^1$H-NMR (400 MHz, $CDCl_3$) δ 1.49 (18H, s), 4.30 (2H, dd, J=10.6, 6.9 Hz), 4.48 (1H, t, J=10.7 Hz), 4.61-4.66 (1H, m), 4.83-4.91 (1H, m), 5.72 (1H, s), 6.50 (1H, t, J=55.1 Hz); MS ($ESI^+$): 390 $[M+H]^+$.

The following compounds were synthesized from the corresponding starting materials and reagents using conditions analogous to compound 183.

| Compound No. | Chemical structural formula | Spectrum data |
|---|---|---|
| 184 | 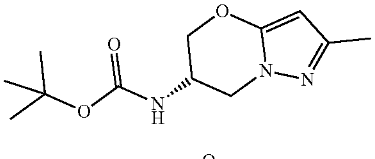 | $^1$H-NMR (400 MHz, $CDCl_3$) δ 1.44 (9H, s), 2.19 (3H, s), 4.05-4.38 (5H, m), 5.08 (1H, d, J = 7.6 Hz), 5.36 (1H, s); MS ($ESI^+$): 254 $[M + H]^+$. |
| 185 | 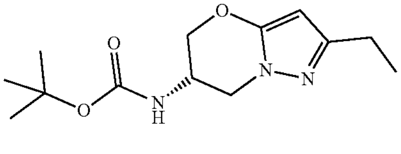 | $^1$H-NMR (400 MHz, $CDCl_3$) δ 1.22 (3H, t, J = 7.6 Hz), 1.45 (9H, s), 2.56 (2H, q, J = 7.6 Hz), 4.04-4.41 (5H, m), 5.09 (1H, d, J = 7.8 Hz), 5.38 (1H, s); MS ($ESI^+$): 268 $[M + H]^+$. |
| 186 | 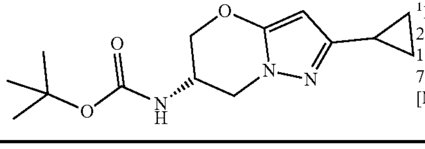 | $^1$H-NMR (400 MHz, $CDCl_3$) δ 0.63-0.74 (m, 2H), 0.84-0.93 (m, 2H), 1.44 (s, 9H), 1.80-1.86 (m, IH), 4.05-4.38 (m, 5H), 5.07 (d, J = 7.7 Hz, 1H), 5.21 (s, 1H); MS ($ESI^+$): 280 $[M + H]^+$. |

(109) Reference Procedure of 2-(difluoromethyl)-5H-pyrazolo[5,1-b][1,3]oxazin-6 (7H)-one (187)

(187)

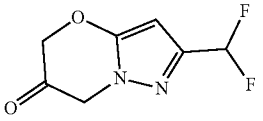

To a stirred solution of compound 58u (30.0 mg, 0.158 mmol) in $CH_2Cl_2$ (3 mL) at room temperature, Dess-Martin periodinane (100 mg, 0.236 mmol) was added. After stirring at room temperature for 2 days, the reaction mixture was filtered off to remove the precipitate, and the filtrate was concentrated. The residue was purified by silica gel column chromatography (5-100% EtOAc/hexane) to yield compound 187 (30.0 mg, 99%) as a colorless oil; $^1$H-NMR (400 MHz, $CDCl_3$) δ 4.62 (2H, s), 4.82 (2H, t, J=1.5 Hz), 5.95 (1H, s), 6.54 (1H, t, J=54.7 Hz); MS (ESI): 187 $[M-H]^-$.

(110) Reference Procedure of 2-(difluoromethyl)-6,7-dihydro-5H-pyrazolo[5,1-b][1,3]oxazin-6-ol (188)

(188)

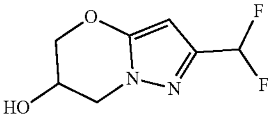

To a stirred solution of compound 187 (20.0 mg, 0.106 mmol) in MeOH (1 mL) at room temperature, $NaBH_4$ (8.00 mg, 0.211 mmol) was added. After stirring at room temperature for 2 h, the reaction was quenched with sat. aq. $NH_4Cl$. The resulting mixture was stirred for 0.5 h, saturated with NaCl, and extracted with EtOAc. The organic layer was dried over $Na_2SO_4$, and concentrated. The residue was purified by silica gel column chromatography (0-30% MeOH/EtOAc) to yield compound 188 (15.0 mg, 74%) as a white solid; $^1$H-NMR (400 MHz, $CDCl_3$) δ 2.38 (1H, s), 4.17-4.35 (4H, m), 4.42-4.45 (1H, m), 5.76 (1H, s), 6.52 (1H, t, J=55.0 Hz); MS (ESI$^+$): 191 $[M+H]^+$.

(110) Reference Procedure of (S)-6-((tert-butyldiphenylsilyl)oxy)-2-(difluoromethyl)-6,7-dihydro-5H-pyrazolo[5,1-b][1,3]oxazine (189)

(189)

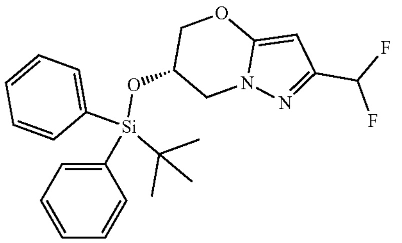

A mixture of compound 58u (420 mg, 2.21 mmol), TBDPSCl (0.85 mL, 3.32 mmol), imidazole (331 mg, 4.86 mmol), and 4-dimethylaminopyridine (80.0 mg, 0.655 mmol) in $CH_2Cl_2$ (6 mL) was stirred at room temperature for 1 h. Water was added, and the resulting mixture was extracted with $CH_2Cl_2$. The organic layer was dried over $Na_2SO_4$, and concentrated. The residue was purified by silica gel column chromatography (5-60% EtOAc/hexane) to yield compound 189 (915 mg, 97%) as a colorless oil; $^1$H-NMR (400 MHz, $CDCl_3$) δ 1.03 (9H, s), 4.00-4.12 (4H, m), 4.29 (1H, qd, J=4.5, 2.4 Hz), 5.73 (1H, s), 6.51 (1H, t, J=55.3 Hz), 7.36-7.49 (6H, m), 7.56-7.58 (2H, m), 7.64-7.67 (2H, m); MS (ESI$^+$): 429 $[M+H]^+$.

The following compounds were synthesized from the corresponding starting materials and reagents using conditions analogous to compound 190.

| Compound No. | Chemical structural formula | Spectrum data |
|---|---|---|
| 190 | 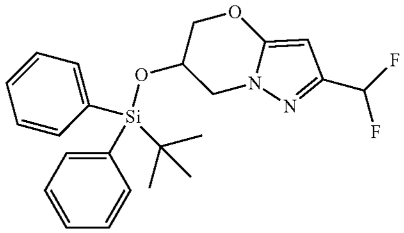 [SMILES: CC(C)(C)[Si](OC1COc2cc(C(F)F)nn2C1)(c1ccccc1)c1ccccc1] | $^1$H-NMR (400 MHz, $CDCl_3$) δ 1.03 (9H, s), 4.00-4.12 (4H, m), 4.29 (1H, qd, J = 4.5, 2.4 Hz), 5.73 (1H, s), 6.51 (1H, t, J = 55.3 Hz), 7.36-7.49 (6H, m), 7.56-7.58 (2H, m), 7.64-7.67 (2H, m); MS (ESI$^+$): 429 $[M + H]^+$. |
| 191 | 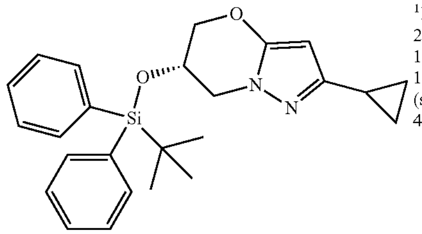 | $^1$H-NMR (400 MHz, $CDCl_3$) δ 0.62-0.73 (m, 2H), 0.81-0.91 (m, 2H), 1.05 (s, 9H), 1.77-1.84 (m, 1H), 3.94-4.01 (m, 3H), 4.06 (dd, J = 12.1, 4.6 Hz, 1H), 4.22-4.26 (m, 1H), 5.16 (s, 1H), 7.36-7.52 (m, 6H), 7.59-7.69 (m, 4H); MS (ESI$^+$): 419 $[M + H]^+$. |

(111) Reference Procedure of 2-cyclopropyl-3-iodo-6,7-dihydro-5H-pyrazolo[5,1-b][1,3]oxazine (192)

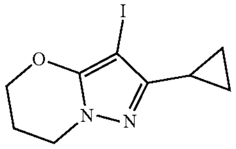

(192)

To a stirred solution of compound 143 (155 mg, 0.944 mmol) in MeCN (3 mL) at room temperature, NIS (640 mg, 2.84 mmol) was added. After stirring at room temperature for 1 h, the reaction was quenched with sat. aq. $NaHCO_3$ and sat. aq. $Na_2S_2O_3$, and the resulting mixture was extracted with EtOAc. The organic layer was washed with water, followed by brine, dried over $Na_2SO_4$, and concentrated. The residue was purified by silica gel column chromatography (5-100% EtOAc/hexane) to yield compound 192 (271 mg, 99%) as a colorless oil; $^1$H-NMR (400 MHz, $CDCl_3$) δ 0.79-0.90 (4H, m), 1.72-1.79 (1H, m), 2.19-2.25 (2H, m), 4.06 (2H, q, J=6.1 Hz), 4.31 (2H, t, J=5.2 Hz); MS (ESI$^+$): 291 [M+H]$^+$.

The following compounds were synthesized from the corresponding starting materials and reagents using conditions analogous to compound 192.

| Compound No. | Chemical structural formula | Spectrum data |
|---|---|---|
| 193 | 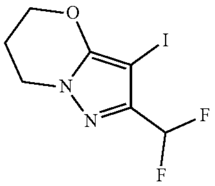 [SMILES: FC(F)c1nn2c(c1I)OCCC2] | $^1$H-NMR (500 MHz, $CDCl_3$) δ 2.28-2.32 (m, 2H), 4.20 (t, J = 6.1 Hz, 2H), 4.39 (t, J = 5.4 Hz, 2H), 6.52 (t, J = 53.9 Hz, 2H); MS (ESI$^+$): 301 [M + H]$^+$. |
| 194 | 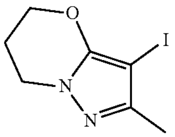 | $^1$H-NMR (400 MHz, $CDCl_3$) δ 2.16 (3H, s), 2.23 (2H, dt, J = 11.8, 5.5 Hz), 4.10 (2H, t, J = 6.4 Hz), 4.32 (2H, t, J = 5.2 Hz); MS (ESI$^+$): 265 [M + H]$^+$. |
| 195 | 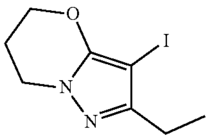 | $^1$H-NMR (400 MHz, $CDCl_3$) δ 1.21 (3H, t, J = 7.6 Hz), 2.24 (2H, dt, J = 11.6, 5.2 Hz), 2.52 (2H, q, J = 7.5 Hz), 4.12 (2H, t, J = 6.1 Hz), 4.32 (2H, dd, J = 6.1, 4.9 Hz); MS (ESI$^+$): 279 [M + H]$^+$. |
| 196 | 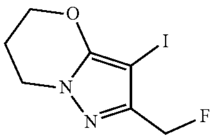 [SMILES: FCc1nn2c(c1I)OCCC2] | $^1$H-NMR (500 MHz, $CDCl_3$) δ 2.26-2.32 (m, 2H), 4.17-4.22 (m, 2H), 4.36-4.39 (m, 2H), 5.24 (t, J = 48.5 Hz, 2H). |
| 197 | 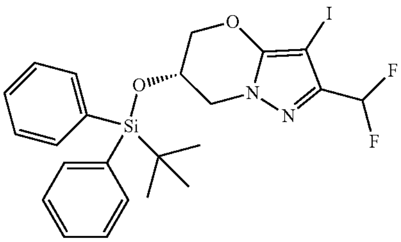 [SMILES: CC(C)(C)[Si](O[C@@H]1COc2c(I)c(C(F)F)nn2C1)(c1ccccc1)c1ccccc1] | $^1$H-NMR (400 MHz, $CDCl_3$) δ 1.03 (9H, s), 4.09-4.18 (4H, m), 4.29-4.33 (1H, m), 6.51 (1H, t, J = 53.8 Hz), 7.37-7.51 (6H, m), 7.55-7.57 (2H, m), 7.64 (2H, dd, J = 7.9, 1.2 Hz); MS (ESI$^+$): 555 [M + H]$^+$. |
| 198 | 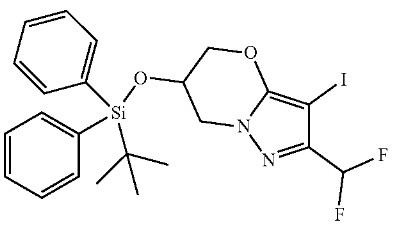 [SMILES: CC(C)(C)[Si](OC1COc2c(I)c(C(F)F)nn2C1)(c1ccccc1)c1ccccc1] | $^1$H-NMR (400 MHz, $CDCl_3$) δ 1.03 (9H, s), 4.06-4.18 (4H, m), 4.31 (1H, qd, J = 4.5, 1.8 Hz), 6.51 (1H, t, J = 53.8 Hz), 7.36-7.51 (6H, m), 7.55-7.58 (2H, m), 7.63-7.65 (2H, m); MS (ESI$^+$): 555 [M + H]$^+$. |

-continued

| Compound No. | Chemical structural formula | Spectrum data |
|---|---|---|
| 199 | 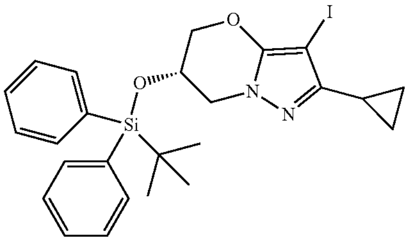 [SMILES: CC(C)(C)[Si](O[C@@H]1COc2c(I)c(C3CC3)nn2C1)(c1ccccc1)c1ccccc1] | $^1$H-NMR (400 MHz, $CDCl_3$) δ 0.78-0.91 (m, 4H), 1.04 (s, 9H), 1.71-1.80 (m, 1H), 3.97 (dd, J = 12.1, 5.3 Hz, 1H), 4.03-4.07 (m, 3H), 4.23-4.28 (m, 1H), 7.36-7.49 (m, 6H), 7.57-7.59 (m, 2H), 7.64-7.66 (m, 2H); MS (ESI$^+$): 545 [M + H]$^+$. |
| 200 | 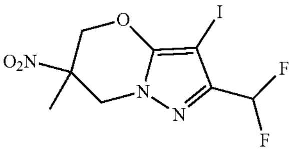 [SMILES: CC1([N+](=O)[O-])COc2c(I)c(C(F)F)nn2C1] | $^1$H-NMR (400 MHz, $CDCl_3$) δ 1.81 (s, 3H), 4.27 (d, J = 12.1 Hz, 2H), 5.05 (dd, J = 12.3, 2.2 Hz, 1H), 5.18 (dd, J = 14.0, 2.0 Hz, 1H), 6.52 (t, J = 53.7 Hz, 1H); MS (ESI$^+$): 360 [M + H]$^+$. |
| 201 | 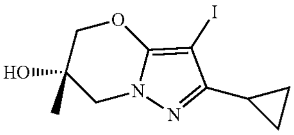 | $^1$H-NMR (400 MHz, $CDCl_3$) δ 0.81-0.92 (m, 4H), 1.41 (s, 3H), 1.74-1.81 (m, 1H), 3.92-4.17 (m, 4H); MS (ESI$^+$): 321 [M + H]$^+$. |
| 202 | 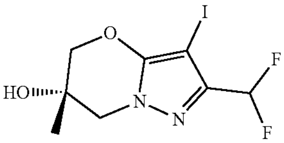 | $^1$H-NMR (400 MHz, $CDCl_3$) δ 1.46 (s, 3H), 2.27 (s, 1H), 4.02-4.25 (m, 4H), 6.53 (t, J = 53.7 Hz, 1H); MS (ESI$^+$): 331 [M + H]$^+$. |
| 203 | 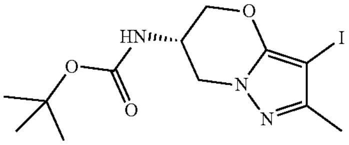 [SMILES: Cc1nn2c(c1I)OC[C@@H](NC(=O)OC(C)(C)C)C2] | $^1$H-NMR (400 MHz, $CDCl_3$) δ 1.45 (9H, s), 2.18 (3H, s), 4.08-4.43 (5H, m); 5.06 (1H, d, J = 7.3 Hz). |
| 204 | 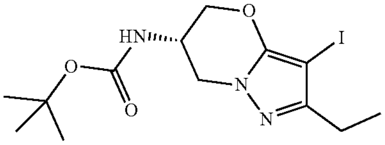 [SMILES: CCc1nn2c(c1I)OC[C@@H](NC(=O)OC(C)(C)C)C2] | $^1$H-NMR (400 MHz, $CDCl_3$) δ 1.23 (3H, t, J = 7.6 Hz), 1.45 (9H, s), 2.54 (2H, q, J = 7.6 Hz), 4.06-4.49 (5H, m), 5.08 (1H, d, J = 6.6 Hz); MS (ESI$^+$): 394 [M + H]$^+$. |
| 205 | 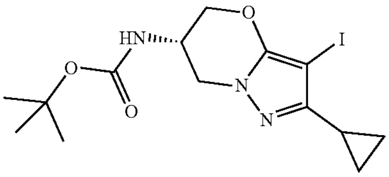 [SMILES: CC(C)(C)OC(=O)N[C@@H]1COc2c(I)c(C3CC3)nn2C1] | $^1$H-NMR (400 MHz, $CDCl_3$) δ 0.80-0.92 (m, 4H), 1.44 (s, 9H), 1.73-1.82 (m, 1H), 4.07-4.40 (m, 4H), 5.06 (d, J = 6.6 Hz, 1H); MS (ESI$^+$): 406 [M + H]$^+$. |
| 206 | 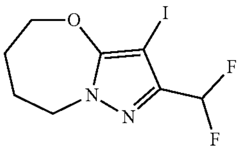 [SMILES: FC(F)c1nn2c(c1I)OCCCC2] | $^1$H-NMR (400 MHz, $CDCl_3$) δ 1.85-1.94 (m, 2H), 2.05-2.14 (m, 2H), 4.11-4.16 (m, 2H), 4.24-4.30 (m, 2H), 6.50 (t, J = 53.9 Hz, 1H); MS (ESI$^+$): 315 [M + H]$^+$. |
| 207 | 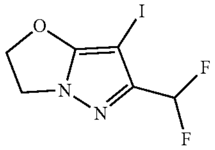 [SMILES: FC(F)c1nn2c(c1I)OCC2] | $^1$H-NMR (400 MHz, $CDCl_3$) δ 4.42 (tt, J = 8.1, 1.6 Hz, 2H), 5.14 (t, J = 8.1 Hz, 2H), 6.50 (t, J = 53.6 Hz, 1H); MS (ESI$^+$): 287 [M + H]$^+$. |

-continued

| Compound No. | Chemical structural formula | Spectrum data |
|---|---|---|
| 208 | 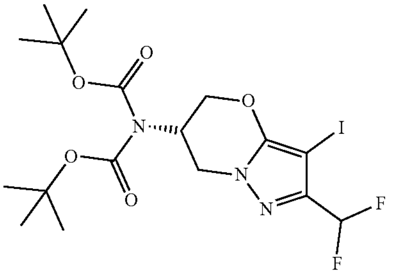 | $^1$H-NMR (400 MHz, $CDCl_3$) δ 1.49 (18H, s), 4.32 (1H, ddd, J = 11.5, 6.3, 0.9 Hz), 4.37 (1H, ddd, J = 10.5, 3.7, 1.1 Hz), 4.50-4.56 (1H, m), 4.67-4.72 (1H, m), 4.83-4.91 (1H, m), 6.50 (1H, t, J = 53.7 Hz); MS (ESI$^+$): 516 [M + H]$^+$. |
| 209 | 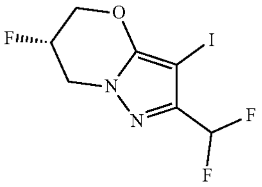 [SMILES: FC(F)c1nn2c(c1I)OC[C@@H](F)C2] | $^1$H-NMR (400 MHz, $CDCl_3$) δ 4.21-4.44 (2H, m), 4.54 (1H, t, J = 15.7 Hz), 4.69-4.76 (1H, m), 5.19-5.33 (1H, m), 6.54 (1H, t, J = 53.7 Hz); MS (ESI$^+$): 319 [M + H]$^+$. |
| 210 | 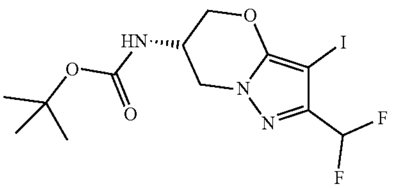 | $^1$H-NMR (400 MHz, $CDCl_3$) δ 1.45 (s, 9H), 4.22-4.47 (m, 5H), 5.02-5.08 (m, 1H), 6.53 (t, J = 53.7 Hz, 1H); MS (ESI$^+$): 416 [M + H]$^+$. |
| 211 | 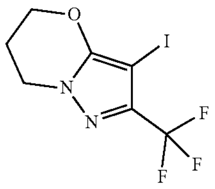 [SMILES: FC(F)(F)c1nn2c(c1I)OCCC2] | $^1$H-NMR (400 MHz, DMSO-$d_6$) δ 2.19-2.25 (m, 2H), 4.17 (t, J = 6.0 Hz, 2H), 4.41 (t, J = 5.3 Hz, 2H); MS (ESI$^+$): 319 [M + H]$^+$. |

(112) Reference Procedure of (S)-2-(difluoromethyl)-3-iodo-6-methoxy-6-methyl-6,7-dihydro-5H-pyrazolo[5,1-b][1,3]oxazine (212)

(212)

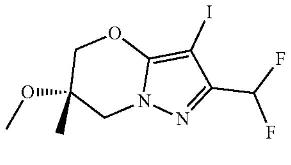

To a stirred solution of compound 202 (100 mg, 0.303 mmol) in THF (1.52 mL) at 0° C. under Ar atmosphere, 60% sodium hydride (15.0 mg, 0.332 mmol) was added. After stirring at 0° C. for 0.5 h, iodomethane (0.025 mL, 0.402 mmol) was added to the reaction mixture, which was stirred at room temperature for 2 h, followed by stirring at 40° C. for an additional 2 h. The reaction was quenched with sat. aq. $NH_4Cl$, and the resulting mixture was extracted with EtOAc. The organic layer was washed with brine, dried over $Na_2SO_4$, and concentrated. The residue was purified by silica gel column chromatography (8-66% EtOAc/hexane) to yield compound 212 (86.0 mg, 83%) as a white solid; $^1$H-NMR (400 MHz, $CDCl_3$) δ 1.35 (s, 3H), 3.30 (s, 3H), 3.94 (dt, J=12.9, 1.4 Hz, 1H), 3.98 (d, J=11.8 Hz, 1H), 4.28 (dd, J=12.9, 2.1 Hz, 1H), 4.40 (dd, J=11.8, 2.4 Hz, 1H), 6.52 (t, J=53.9 Hz, 1H); MS (ESI$^+$): 345 [M+H]$^+$.

(113) Reference Procedure of methyl (S)-2-((2-(difluoromethyl)-3-iodo-6-methyl-6,7-dihydro-5H-pyrazolo[5,1-b][1,3]oxazin-6-yl)oxy)acetate (213)

(213)

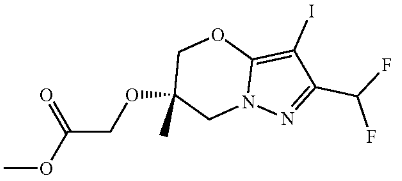

To a stirred solution of compound 201 (100 mg, 0.303 mmol) in THF (1.52 mL) at 0° C. under Ar atmosphere, 60% sodium hydride (15.0 mg, 0.332 mmol) was added. After stirring at 0° C. for 0.5 h, methyl bromoacetate (0.038 mL, 0.402 mmol) was added to the reaction mixture, which was stirred at room temperature for 1 h, followed by stirring at 40° C. for an additional 6 h. The reaction was quenched with sat. aq. $NH_4Cl$, and the resulting mixture was extracted with EtOAc. The organic layer was washed with brine, dried over $Na_2SO_4$, and concentrated. The residue was purified by silica gel column chromatography (25-100% EtOAc/hexane) to yield compound 213 (87.0 mg, 72%) as a colorless oil; $^1$H-NMR (400 MHz, $CDCl_3$) δ 1.40 (s, 3H), 3.72 (s, 3H), 3.97-4.05 (m, 2H), 4.07-4.28 (m, 2H), 4.33 (dd, J=13.7, 1.3 Hz, 1H), 4.41 (dd, J=11.9, 2.3 Hz, 1H), 6.52 (t, J=53.8 Hz, 1H); MS (ESI$^+$): 403 [M+H]$^+$.

(114) Reference Procedure of methyl (S)-2-((2-(difluoromethyl)-3-iodo-6-methyl-6,7-dihydro-5H-pyrazolo[5,1-b][1,3]oxazin-6-yl)oxy) acetic acid (214)

(214)

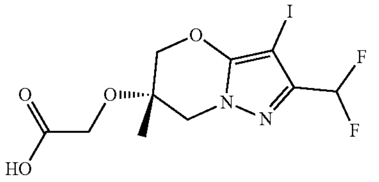

To a stirred solution of compound 213 (87.0 mg, 0.217 mmol) in MeOH (1.1 mL) at room temperature, 2 mol/L aq. NaOH (15.0 mg, 0.030 mmol) was added. After stirring at room temperature for 14 h, the reaction mixture was concentrated, and 1 mol/L HCl was added to adjust the pH to 4-5. The resulting precipitate was collected by filtration to yield compound 214 (56.0 mg, 67%) as a white solid; $^1$H-NMR (400 MHz, DMSO-$d_6$) δ 1.25 (s, 3H), 4.00-4.26 (m, 5H), 4.43-4.51 (m, 1H), 6.77 (t, J=53.3 Hz, 1H); MS (ESI$^+$): 389 [M+H]$^+$.

(115) Reference Procedure of (S)-2-((2-(difluoromethyl)-3-iodo-6-methyl-6,7-dihydro-5H-pyrazolo[5,1-b][1,3]oxazin-6-yl)oxy) acetamide (215)

(215)

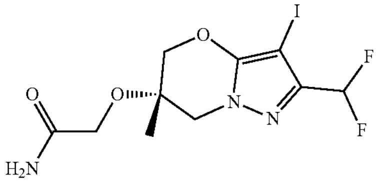

A mixture of compound 214 (56.0 mg, 0.144 mmol), EDCI-HCl (42.0 mg, 0.216 mmol), 1H-1,2,3-benzotriazol-1-ol amine (33.0 mg, 0.218 mmol), and N,N-diisopropylethylamine (0.037 mL, 0.218 mmol) in DMF (1.44 mL) was stirred at room temperature for 4 h under Ar atmosphere. The residue was directly purified by silica gel column chromatography (25-100% EtOAc/hexane) to yield compound 215 (44 mg, 78%) as a white solid; $^1$H-NMR (400 MHz, DMSO-$d_6$) δ 1.25 (s, 3H), 3.81 (d, J=15.4 Hz, 1H), 3.85 (d, J=15.3 Hz, 1H), 4.07 (d, J=12.8 Hz, 1H), 4.15 (d, J=11.8 Hz, 1H), 4.35 (d, J=13.3 Hz, 1H), 4.55 (dd, J=11.8, 2.2 Hz, 1H), 6.77 (t, J=53.3 Hz, 1H), 7.14 (s, 1H), 7.31 (s, 1H); MS (ESI$^+$): 388 [M+H]$^+$.

(116) Reference Procedure of (S)-2-(difluoromethyl)-3-iodo-6-methyl-6-nitro-6,7-dihydro-5H-pyrazolo[5,1-b][1,3]oxazine (216)

(216)

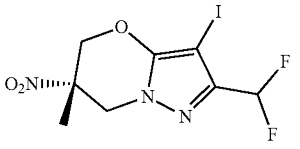

Compound 216 was prepared by optical resolution of compound 200 using chiral HPLC (DAICEL CHIRALPAK IG column; eluent: EtOH/hexane=50/50; flow rate: 1 mL/min; retention time: 8.92 min); $^1$H-NMR (400 MHz, $CDCl_3$) δ 1.79 (s, 3H), 4.22-4.30 (m, 2H), 5.03 (dd, J=12.2, 2.3 Hz, 1H), 5.16 (dd, J=14.0, 2.0 Hz, 1H), 6.51 (t, J=53.7 Hz, 1H); MS (ESI$^+$): 360 [M+H]$^+$.

(117) Reference Procedure of (S)-2-cyclopropyl-3-iodo-6,7-dihydro-5H-pyrazolo[5,1-b][1,3]oxazin-6-amine (217)

(217)

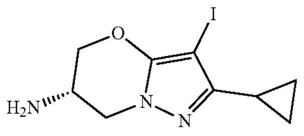

To a stirred solution of compound 205 (446 mg, 1.10 mmol) in $CH_2Cl_2$ (2.75 mL) at room temperature, TFA (2.75 mL) was added. After stirring at room temperature for 1 h, the reaction mixture was concentrated. The residue was purified by silica gel column chromatography (25-100% EtOAc/hexane) to yield compound 217 (257 mg, 77%) as a white solid; $^1$H-NMR (400 MHz, $CDCl_3$) δ 0.81-0.92 (m, 4H), 1.74-1.82 (m, 1H), 3.52-3.62 (m, 1H), 3.78-3.87 (m, 1H), 4.03-4.11 (m, 1H), 4.23-4.32 (m, 2H); MS (ESI$^+$): 306 [M+H]$^+$.

(118) Reference Procedure of methyl (S)-(2-cyclopropyl-3-iodo-6,7-dihydro-5H-pyrazolo[5,1-b][1,3]oxazin-6-yl) carbamate (218)

(218)

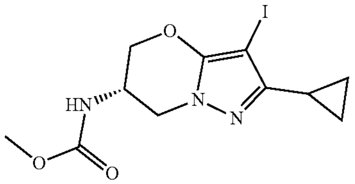

To a stirred solution of compound 217 (103 mg, 0.247 mmol) in $CH_2Cl_2$ (1.23 mL) at room temperature under Ar atmosphere, methyl chloroformate (0.023 mL, 0.299 mmol) and N,N-diisopropylethylamine (0.084 mL, 0.494 mmol) were added. After stirring at the same temperature for 14 h, the resulting mixture was concentrated. The residue was directly purified by silica gel column chromatography (25-100% EtOAc/hexane) to yield compound 218 (75.0 mg, 84%) as a colorless oil; $^1$H-NMR (400 MHz, $CDCl_3$) δ 0.80-0.92 (m, 4H), 1.71-1.83 (m, 1H), 3.69 (s, 3H), 4.10-4.14 (m, 1H), 4.20-4.29 (m, 2H), 4.35-4.43 (m, 2H), 5.21 (d, J=8.8 Hz, 1H); MS (ESI$^+$): 364 $[M+H]^+$.

(119) Reference Procedure of (S)—N-(2-cyclopropyl-3-iodo-6,7-dihydro-5H-pyrazolo[5,1-b][1,3]oxazin-6-yl) methanesulfonamide (219)

(219)

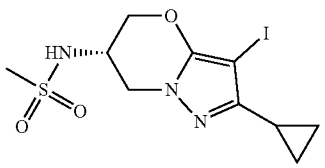

To a stirred solution of compound 217 (100 mg, 0.328 mmol) in $CH_2Cl_2$ (1.64 mL) at room temperature under Ar atmosphere, triethylamine (0.068 mL, 0.491 mmol) and methanesulfonyl chloride (0.026 mL, 0.336 mmol) were added. After stirring at the same temperature for 14 h, the resulting mixture was concentrated. The residue was directly purified by silica gel column chromatography (25-100% EtOAc/hexane) to yield compound 219 (65.0 mg, 52%) as a white solid; $^1$H-NMR (400 MHz, $CDCl_3$) δ 0.80-0.93 (m, 4H), 1.73-1.81 (m, 1H), 3.05 (s, 3H), 4.14-4.19 (m, 1H), 4.22-4.33 (m, 3H), 4.41 (ddd, J=11.4, 3.4, 1.9 Hz, 1H), 4.95 (d, J=7.2 Hz, 1H); MS (ESI$^+$): 384 $[M+H]^+$.

(120) Reference Procedure of 2-methyl-3-(4,4,5,5-tetramethyl-1,3,2-dioxaborolan-2-yl)-6,7-dihydro-5H-pyrazolo[5,1-b][1,3]oxazine (220)

(220)

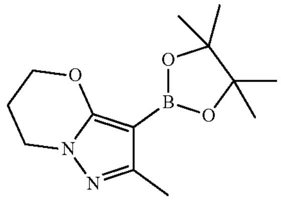

To a stirred solution of compound 194 (570 mg, 2.16 mmol) and 2-isopropoxy-4,4,5,5-tetramethyl-1,3,2-dioxaborolane (0.68 mL, 3.36 mmol) in THF (10 mL) at 0° C. under Ar atmosphere, 2 mol/L isopropylmagnesium chloride in THF (1.30 mL, 2.67 mmol) was slowly added. After stirring at 0° C. for 2 h, the reaction was quenched with sat. aq. $NH_4Cl$, and the resulting mixture was extracted with EtOAc. The organic layer was dried over $Na_2SO_4$, and concentrated. The residue was purified by silica gel column chromatography (0-30% MeOH/EtOAc) to yield compound 220 (290 mg, 51%) as a white solid; $^1$H-NMR (400 MHz, $CDCl_3$) δ 1.28 (12H, s), 2.15-2.21 (2H, m), 2.28 (3H, s), 4.06 (2H, t, J=6.4 Hz), 4.32 (2H, t, J=5.2 Hz); MS (ESI$^+$): 265 $[M+H]^+$.

The following compounds were synthesized from the corresponding starting materials and reagents using conditions analogous to compound 220.

| Compound No. | Chemical structural formula | Spectrum data |
| --- | --- | --- |
| 221 | 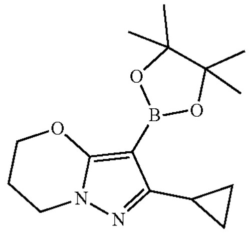 [SMILES: CC1(C)OB(c2c(C3CC3)nn3c2OCCC3)OC1(C)C] | $^1$H-NMR (400 MHz, $CDCl_3$) δ 0.81-0.88 (4H, m), 1.29 (12H, s), 2.17 (2H, dt, J = 11.6, 5.2 Hz), 2.25-2.32 (1H, m), 4.02 (2H, t, J = 6.1 Hz), 4.30 (2H, t, J = 5.2 Hz); MS (ESI$^+$): 291 $[M + H]^+$. |
| 222 | 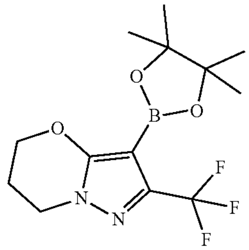 [SMILES: CC1(C)OB(c2c(C(F)(F)F)nn3c2OCCC3)OC1(C)C] | $^1$H-NMR (400 MHz, DMSO-$d_6$) δ 1.21 (s, 12H), 2.16-2.23 (m, 2H), 4.13 (t, J = 6.1 Hz, 2H), 4.37 (t, J = 5.2 Hz, 2H); MS (ESI$^+$): 319 $[M + H]^+$. |
| 223 | 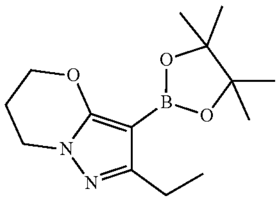 [SMILES: CCc1nn2c(c1B1OC(C)(C)C(C)(C)O1)OCCC2] | $^1$H-NMR (400 MHz, $CDCl_3$) δ 1.20 (3H, t, J = 7.6 Hz), 1.28 (12H, s), 2.19 (2H, dt, J = 11.8, 5.5 Hz), 2.69 (2H, q, J = 7.5 Hz), 4.08 (2H, t, J = 6.4 Hz), 4.32 (2H, t, J = 5.2 Hz); MS (ESI$^+$): 279 $[M + H]^+$. |

-continued

| Compound No. | Chemical structural formula | Spectrum data |
| --- | --- | --- |
| 224 | 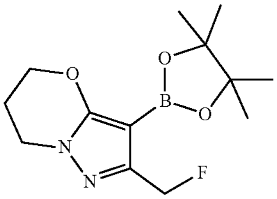 | $^1$H-NMR (500 MHz, $CDCl_3$) δ 1.30 (s, 12H), 2.21-2.27 (m, 2H), 4.14-4.18 (m, 2H), 4.35-4.39 (m, 2H), 5.41 (t, J = 47.8 Hz, 2H). |
| 225 | 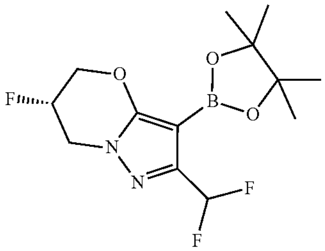 [SMILES: CC1(C)OB(c2c(C(F)F)nn3c2OC[C@@H](F)C3)OC1(C)C] | $^1$H-NMR (400 MHz, $CDCl_3$) δ 1.31-1.37 (m, 12H), 4.21-4.59 (m, 3H), 4.72-4.79 (m, 1H), 5.25 (d, J = 45.4 Hz, 1H), 6.94 (t, J = 54.2 Hz, 1H); MS (ESI$^+$): 319 $[M + H]^+$. |
| 226 | 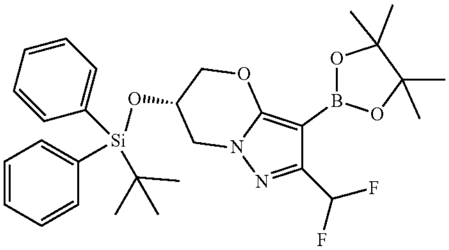 [SMILES: CC1(C)OB(c2c(C(F)F)nn3c2OC[C@@H](O[Si](c2ccccc2)(c2ccccc2)C(C)(C)C)C3)OC1(C)C] | $^1$H-NMR (400 MHz, $CDCl_3$) δ 1.03 (9H, s), 1.28 (12H, s), 4.02-4.17 (4H, m), 4.25-4.30 (1H, m), 6.88 (1H, t, J = 54.3 Hz), 7.35-7.48 (6H, m), 7.56-7.64 (4H, m); MS (ESI$^+$): 555 $[M + H]^+$. |
| 227 | 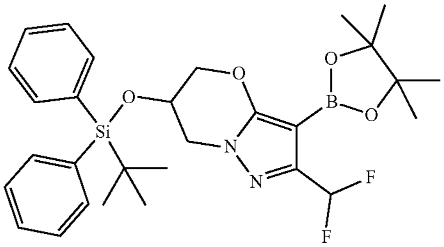 [SMILES: CC1(C)OB(c2c(C(F)F)nn3c2OCC(O[Si](c2ccccc2)(c2ccccc2)C(C)(C)C)C3)OC1(C)C] | $^1$H-NMR (400 MHz, $CDCl_3$) δ 1.03 (9H, s), 1.28 (12H, d, J = 1.8 Hz), 4.02-4.18 (4H, m), 4.25-4.30 (1H, m), 6.88 (1H, t, J = 54.3 Hz), 7.36-7.48 (6H, m), 7.57 (2H, dd, J = 7.9, 1.2 Hz), 7.63 (2H, dd, J = 7.9, 1.2 Hz); MS (ESI$^+$): 555 $[M + H]^+$. |
| 228 | 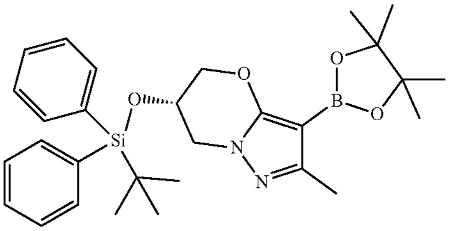 [SMILES: Cc1nn2c(c1B1OC(C)(C)C(C)(C)O1)OC[C@@H](O[Si](c1ccccc1)(c1ccccc1)C(C)(C)C)C2] | $^1$H-NMR (400 MHz, DMSO-$d_6$) δ 0.97 (s, 9H), 1.22 (s, 12H), 2.12 (s, 3H), 3.74-3.81 (m, 1H), 3.97-4.07 (m, 1H), 4.09-4.16 (m, 2H), 4.38-4.43 (m, 1H), 7.37-7.64 (m, 10H); MS (ESI$^+$): 519 $[M + H]^+$. |
| 229 | 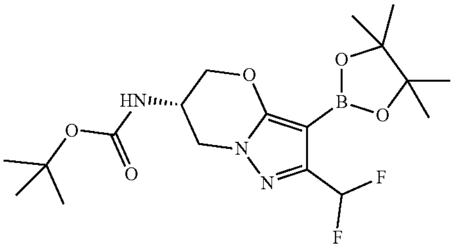 [SMILES: CC(C)(C)OC(=O)N[C@@H]1COc2c(B3OC(C)(C)C(C)(C)O3)c(C(F)F)nn2C1] | $^1$H-NMR (400 MHz, $CDCl_3$) δ 1.29 (12H, s), 1.42 (9H, s), 4.08-4.45 (5H, m), 5.10 (1H, s), 6.89 (1H, t, J = 54.2 Hz); MS (ESI$^+$): 416 $[M + H]^+$. |

-continued

| Compound No. | Chemical structural formula | Spectrum data |
| --- | --- | --- |
| 230 | 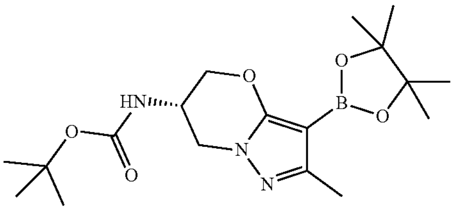 [SMILES: Cc1nn2c(c1B1OC(C)(C)C(C)(C)O1)OC[C@@H](NC(=O)OC(C)(C)C)C2] | $^1$H-NMR (400 MHz, $CDCl_3$) δ 1.30 (s, 12H), 1.43 (s, 9H), 2.31 (s, 3H), 4.08-4.42 (m, 5H), 5.10-5.16 (m, 1H); MS ($ESI^+$): 380 $[M + H]^+$. |
| 231 | 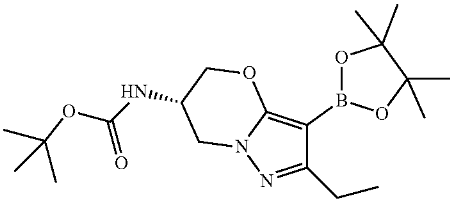 [SMILES: CCc1nn2c(c1B1OC(C)(C)C(C)(C)O1)OC[C@@H](NC(=O)OC(C)(C)C)C2] | $^1$H-NMR (400 MHz, $CDCl_3$) δ1.21 (t, J = 7.5 Hz, 3H), 1.30 (s, 6H), 1.31 (s, 6H), 1.44 (s, 9H), 2.71 (q, J = 7.4 Hz, 2H), 4.07-4.10 (m, 1H), 4.18-4.25 (m, 2H), 4.30-4.43 (m, 2H), 5.14 (d, J = 5.1 Hz, 1H); MS ($ESI^+$): 394 $[M + H]^+$. |
| 232 | 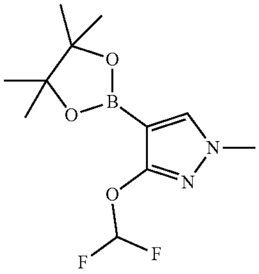 | $^1$H-NMR (500 MHz, $CDCl_3$) δ 1.30 (s, 12H), 3.77 (s, 3H), 6.96 (t, J = 73.8 Hz, 1H), 7.49 (s, 1H); MS ($ESI^+$): 275 $[M + H]^+$. |

(121) Reference Procedure of 2-methyl-3-(4,4,5,5-tetramethyl-1,3,2-dioxaborolan-2-yl)-6,7-dihydro-5H-pyrazolo[5,1-b][1,3]oxazine (233)

(233)

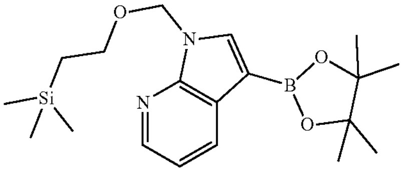

To a stirred solution of 3-bromo-1-((2-(trimethylsilyl)ethoxy)methyl)-1H-pyrrolo[2,3-b]pyridine (Journal of Organic Chemistry (2020), 85 (17), 11519-11530) (157 mg, 0.480 mmol) and 2-isopropoxy-4,4,5,5-tetramethyl-1,3,2-dioxaborolane (0.15 mL, 0.722 mmol) in THF (2.4 mL) at −78° C. under Ar atmosphere, 1.6 mol/L n-butyllithium in hexane (0.48 mL, 0.767 mmol) was slowly added. After stirring at −78° C. for 2 h, the reaction was quenched with sat. aq. $NH_4Cl$, and the resulting mixture was extracted with EtOAc. The organic layer was washed with brine, dried over $Na_2SO_4$, and concentrated. The residue was purified by silica gel column chromatography (0-20% EtOAc/hexane) to yield compound 233 (65.0 mg, 41%) as a colorless oil; $^1$H-NMR (400 MHz, $CDCl_3$) δ −0.07 (s, 9H), 0.87-0.94 (m, 2H), 1.37 (s, 12H), 3.51-3.56 (m, 2H), 5.67 (s, 2H), 7.14 (dd, J=7.8, 4.7 Hz, 1H), 7.80 (s, 1H), 8.27 (dd, J=7.8, 1.6 Hz, 1H), 8.33 (dd, J=4.7, 1.6 Hz, 1H); MS ($ESI^+$): 375 $[M+H]^+$.

(121) Reference Procedure of 3-(3-(difluoromethoxy)-1-methyl-1H-pyrazol-4-yl)-1-((2-(trimethylsilyl)ethoxy)methyl)-1H-pyrrolo[2,3-b]pyridine (234)

(234)

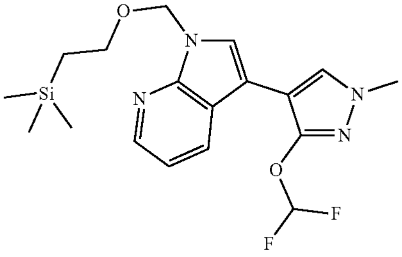

A mixture of compound 233 (2.43 g, 6.49 mmol), compound 10z (1.94 g, 7.08 mmol), 2-dicyclohexylphosphino-2',6'-dimethoxybiphenyl (SPhos) (136 mg, 0.331 mmol), $Pd_2(dba)_3$ (198 mg, 0.162 mmol), $K_3PO_4$ (4.14 g, 19.5 mmol), and water (1.2 mL, 67.7 mmol) in toluene (25 mL) was stirred at 80° C. for 4 h. The reaction mixture was cooled to room temperature and directly purified by silica gel column chromatography (5-80% EtOAc/hexane) to yield compound 234 (708 mg, 28%) as a brown solid; $^1$H-NMR (400 MHz, $CDCl_3$) δ −0.08 (9H, s), 0.85-0.94 (2H, m), 3.54-3.58 (2H, m), 3.86 (3H, s), 5.70 (2H, s), 7.01 (1H, t, J=74.0 Hz), 7.13 (1H, q, J=4.3 Hz), 7.57 (1H, s), 7.60 (1H, s), 7.99 (1H, dd, J=7.9, 1.8 Hz), 8.36 (1H, dd, J=4.6, 1.5 Hz).

(122) Reference Procedure of 2-bromo-3-(3-(difluoromethoxy)-1-methyl-1H-pyrazol-4-yl)-1-((2-(trimethylsilyl)ethoxy)methyl)-1H-pyrrolo[2,3-b]pyridine (235)

(235)

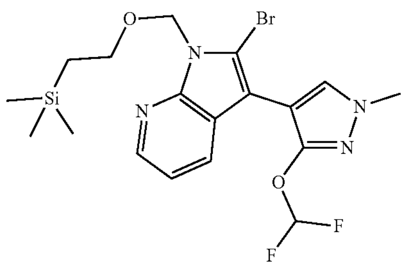

(235)

To a stirred solution of compound 234 (650 mg, 1.65 mmol) in MeCN (6.5 mL) at room temperature, NBS (294 mg, 1.65 mmol) was added portionwise. After stirring at room temperature for 0.5 h, the reaction was quenched with sat. aq. $NaHCO_3$ and sat. aq. $Na_2S_2O_3$, and the resulting mixture was extracted with EtOAc. The organic layer was washed with water, followed by brine, dried over $Na_2SO_4$, and concentrated. The residue was purified by silica gel column chromatography (5-70% EtOAc/hexane) to yield compound 235 (720 mg, 92%) as a slightly yellow oil; $^1$H-NMR (400 MHz, $CDCl_3$) δ −0.09 (9H, s), 0.90-0.95 (2H, m), 3.61-3.65 (2H, m), 3.88 (3H, s), 5.79 (2H, s), 6.97 (1H, t), 7.11 (1H, q, J=4.3 Hz), 7.52 (1H, s), 7.88 (1H, dd, J=7.9, 1.2 Hz), 8.32 (1H, dd, J=4.9, 1.2 Hz).

(123) Reference Procedure of 2-cyclopropyl-3-(3-(3-(difluoromethoxy)-1-methyl-1H-pyrazol-4-yl)-1-((2-(trimethylsilyl)ethoxy)methyl)-1H-pyrrolo[2,3-b]pyridin-2-yl)-6,7-dihydro-5H-pyrazolo[5,1-b][1,3]oxazine (236)

(236)

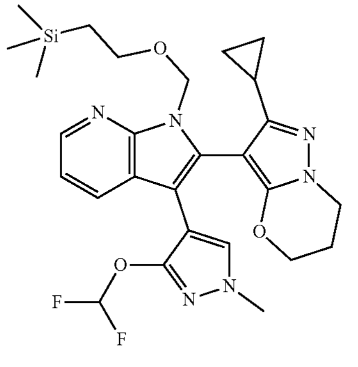

A mixture of compound 235 (130 mg, 0.275 mmol), compound 221 (95.0 mg, 0.327 mmol), SPhos Pd G4 (23.0 mg, 0.0290 mmol), and $K_3PO_4$ (180 mg, 0.848 mmol) in toluene (3 mL) was stirred at 100° C. for 1 h under microwave irradiation. Brine was added and the resulting mixture was extracted with EtOAc. The organic layer was dried over $Na_2SO_4$, and concentrated. The residue was purified by silica gel column chromatography (5-100% EtOAc/hexane) to yield compound 236 (65 mg, 43%) as a slightly yellow oil; $^1$H-NMR (400 MHz, $CDCl_3$) δ −0.13 (9H, s), 0.47-0.67 (3H, m), 0.74-0.87 (3H, m), 1.39-1.46 (1H, m), 2.22-2.28 (2H, m), 3.37-3.49 (2H, m), 3.79 (3H, s), 4.08-4.15 (2H, m), 4.19-4.30 (2H, m), 5.55 (1H, d, J=11.0 Hz), 5.76 (1H, d, J=10.4 Hz), 6.78 (1H, t, J=74.0 Hz), 7.09-7.14 (1H, m), 7.20 (1H, s), 7.91 (1H, d, J=7.3 Hz), 8.35 (1H, q, J=2.2 Hz); MS (ESI$^+$): 557 [M+H]$^+$.

(124) Experimental procedure of 2-cyclopropyl-3-(3-(3-(difluoromethoxy)-1-methyl-1H-pyrazol-4-yl)-1-((2-(trimethylsilyl)ethoxy)methyl)-1H-pyrrolo[2,3-b]pyridin-2-yl)-6,7-dihydro-5H-pyrazolo[5,1-b][1,3]oxazine (EX.420)

EX. 420

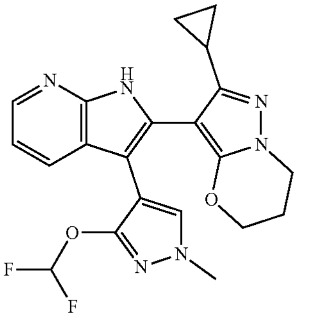

To a stirred solution of compound 236 (58.0 mg, 0.104 mmol) in $CH_2Cl_2$ (1.5 mL) at room temperature, TFA (3 mL) was added. After stirring at room temperature for 2 h, the reaction mixture was concentrated. The residue was dissolved in MeOH (3 mL) and then 5 mol/L aq. NaOH was added to the resulting solution. After stirring at 50° C. for 0.5 h, the resulting mixture was neutralized with sat. aq. $NH_4Cl$, and extracted with $CHCl_3$/MeOH (9/1). The organic layer was dried over $Na_2SO_4$, and concentrated. The residue was purified by silica gel column chromatography (0-30% MeOH/$CHCl_3$) to yield EX.420 (33.0 mg, 74%) as a white solid; $^1$H-NMR (400 MHz, DMSO-$d_6$) δ 0.43-0.49 (2H, m), 0.53 (2H, td, J=5.3, 3.7 Hz), 1.38-1.45 (1H, m), 2.09-2.15 (2H, m), 3.37-3.43 (1H, m), 3.72 (3H, s), 3.96 (2H, t, J=6.1 Hz), 4.18 (2H, t, J=5.2 Hz), 7.02 (1H, dd, J=7.9, 4.9 Hz), 7.08 (1H, t, J=74.0 Hz), 7.49 (1H, s), 7.74 (1H, dd, J=7.9, 1.2 Hz), 8.14 (1H, dd, J=4.6, 1.5 Hz), 11.57 (1H, s); MS (ESI$^+$): 427 [M+H]$^+$.

(125) Reference Procedure of 3-(1-((2-(trimethylsilyl)ethoxy)methyl)-1H-pyrrolo[2,3-b]pyridin-3-yl)picolinonitrile (237)

(237)

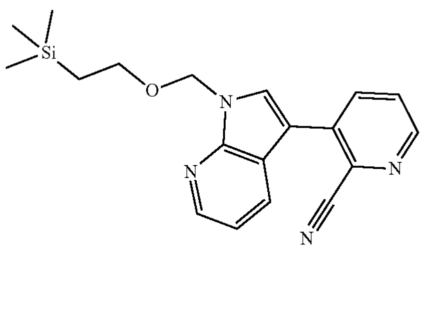

A mixture of compound 233 (400 mg, 1.07 mmol), 3-bromopyridine-2-carbonitrile (292 g, 1.60 mmol), $PdCl_2$(dppf)-$CH_2Cl_2$ (87.2 mg, 0.107 mmol), and $K_3PO_4$ (680 mg, 3.20 mmol) in dioxane/water (10/1, 9.9 mL) was stirred at 100° C. for 16 h. The reaction mixture was cooled to room temperature and filtered off through a pad of Celite. The filtrate was concentrated and the residue was purified by silica gel column chromatography (8-64% EtOAc/hexane) to yield compound 243 (135 mg, 36%) as a brown solid; $^1$H-NMR (400 MHz, $CDCl_3$) δ −0.05 (s, 9H), 0.96 (t, J=8.3 Hz, 2H), 3.61-3.66 (m, 2H), 5.79 (s, 2H), 7.23 (dd, J=7.9, 4.7 Hz, 1H), 7.61 (dd, J=8.0, 4.7 Hz, 1H), 7.91 (s, 1H), 8.02 (dd, J=8.0, 1.5 Hz, 1H), 8.05 (dd, J=8.1, 1.7 Hz, 1H), 8.46 (dd, J=4.7, 1.5 Hz, 1H), 8.67 (dd, J=4.6, 1.6 Hz, 1H).

(126) Reference Procedure of 3-(difluoromethoxy)-4-(1-((2-(trimethylsilyl)ethoxy)methyl)-1H-pyrrolo[2,3-b]pyridin-3-yl) isothiazole (238)

(238)

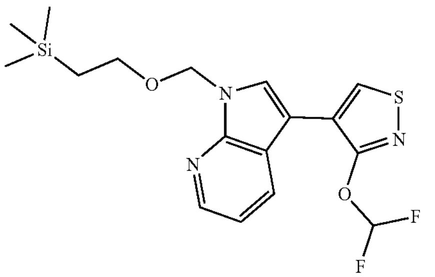

The compound 238 was synthesized from the corresponding starting materials and reagents using conditions analogous to compound 237; $^1$H-NMR (400 MHz, $CDCl_3$) δ −0.07--0.03 (m, 9H), 0.92-0.96 (m, 2H), 3.58-3.62 (m, 2H), 5.75 (s, 2H), 7.22 (dd, J=8.0, 4.7 Hz, 1H), 7.47 (t, J=72.3 Hz, 1H), 7.85 (s, 1H), 8.12 (dd, J=7.9, 1.3 Hz, 1H), 8.42 (dd, J=4.7, 1.4 Hz, 1H), 8.71 (s, 1H); MS (ESI$^+$): 398 [M+H]$^+$.

(126) Reference Procedure of 3-(2-bromo-1-((2-(trimethylsilyl)ethoxy)methyl)-1H-pyrrolo[2,3-b]pyridin-3-yl) picolinonitrile (239)

(239)

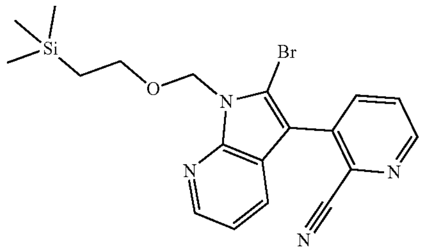

The compound 239 was synthesized from compound 237 using conditions analogous to compound 235; $^1$H-NMR (400 MHz, $CDCl_3$) δ −0.07--0.04 (m, 9H), 0.94-1.00 (m, 2H), 3.65-3.75 (m, 2H), 5.81-5.94 (m, 2H), 7.19 (dd, J=7.9, 4.7 Hz, 1H), 7.52-7.66 (m, 1H), 7.75 (dd, J=7.9, 1.5 Hz, 1H), 7.96 (dd, J=8.0, 1.7 Hz, 1H), 8.42 (dd, J=4.8, 1.5 Hz, 1H), 8.78 (dd, J=4.7, 1.7 Hz, 1H); MS (ESI$^+$): 429 [M+H]$^+$.

(127) Reference Procedure of 4-(2-bromo-1-((2-(trimethylsilyl)ethoxy)methyl)-1H-pyrrolo[2,3-b]pyridin-3-yl)-3-(difluoromethoxy) isothiazole (240)

(240)

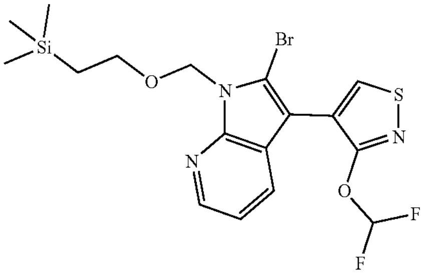

The compound 240 was synthesized from compound 238 using conditions analogous to compound 235; $^1$H-NMR (400 MHz, $CDCl_3$) δ −0.06--0.04 (m, 9H), 0.95 (t, J=8.2 Hz, 2H), 3.67 (t, J=8.2 Hz, 2H), 5.83 (s, 2H), 7.14-7.60 (m, 2H), 7.82 (dd, J=7.9, 1.5 Hz, 1H), 8.37 (dd, J=4.7, 1.5 Hz, 1H), 8.72 (s, 1H).

(128) Reference Procedure of 3-(3-(3-(difluoromethoxy)-1-methyl-1H-pyrazol-4-yl)-1-((2-(trimethylsilyl)ethoxy)methyl)-1H-pyrrolo[2,3-b]pyridin-2-yl)-2-methyl-6,7-dihydro-5H-pyrazolo[5,1-b][1,3]oxazine (241)

(241)

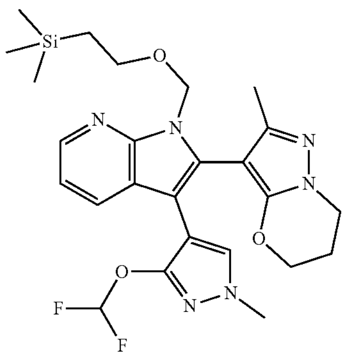

The compound 241 was synthesized from compounds 220 and 235 using conditions analogous to compound 236; $^1$H-NMR (400 MHz, $CDCl_3$) δ −0.13 (9H, s), 0.71-0.91 (2H, m), 1.87 (3H, s), 2.17-2.32 (4H, m), 3.37-3.49 (2H, m), 3.78 (3H, s), 4.06-4.32 (6H, m), 5.44 (1H, d, J=10.4 Hz), 5.75 (1H, d, J=10.4 Hz), 6.78 (1H, t, J=74.3 Hz), 7.10 (1H, q, J=4.3 Hz), 7.17 (1H, s), 7.88 (1H, dd, J=7.9, 1.8 Hz), 8.34 (1H, q, J=2.1 Hz); MS (ESI$^+$): 531 [M+H]$^+$.

The following compounds were also synthesized from the corresponding starting materials and reagents using conditions analogous to compound 236.

| Compound No. | Chemical structural formula | Spectrum data |
|---|---|---|
| 242 | 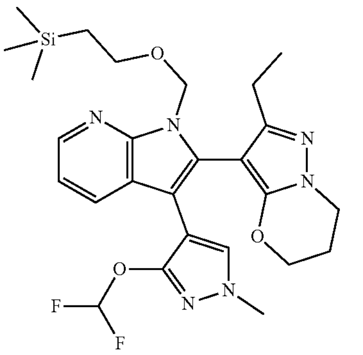 [SMILES: CCc1nn2c(c1-c1c(-c3cn(C)nc3OC(F)F)c3cccnc3n1COCC[Si](C)(C)C)OCCC2] | $^1$H-NMR (400 MHz, $CDCl_3$) δ −0.11 (9H, s), 0.73-0.89 (2H, m), 0.93 (3H, t, J = 7.6 Hz), 1.20 (3H, t, J = 7.6 Hz), 2.19-2.27 (2H, m), 2.54 (2H, q, J = 7.7 Hz), 3.39-3.51 (2H, m), 3.78 (3H, s), 4.11 (2H, t, J = 6.1 Hz), 4.17 (2H, t, J = 6.7 Hz), 4.24 (2H, t, J = 5.2 Hz), 5.48 (1H, d, J = 10.4 Hz), 5.71 (1H, d, J = 11.0 Hz), 6.79 (1H, t, J = 74.0 Hz), 7.10 (1H, q, J = 4.3 Hz), 7.16 (1H, s), 7.89 (1H, dd, J = 7.9, 1.8 Hz), 8.34 (1H, dd, J = 4.9, 1.8 Hz); MS (ESI$^+$): 545 [M + H]$^+$. |
| 243 | 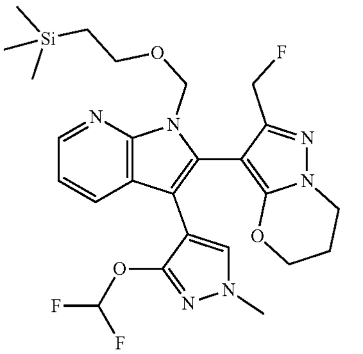 [SMILES: Cn1cc(-c2c(-c3c(CF)nn4c3OCCC4)n(COCC[Si](C)(C)C)c3ncccc23)c(OC(F)F)n1] | $^1$H-NMR (400 MHz, $CDCl_3$) δ −0.11 (9H, s), 0.73-0.91 (2H, m), 2.24-2.34 (2H, m), 3.41-3.51 (2H, m), 3.78 (3H, s), 4.18-4.33 (4H, m), 4.96 (1H, dd, J = 18.0, 10.7 Hz), 5.09 (1H, dd, J = 17.6, 10.6 Hz), 5.43 (1H, d, J = 10.9 Hz), 5.73 (1H, d, J = 10.9 Hz), 6.77 (1H, t, J = 74.0 Hz), 7.11 (1H, dd, J = 7.8, 4.7 Hz), 7.23 (1H, s), 7.88 (1H, dd, J = 7.9, 1.5 Hz), 8.35 (1H, dd, J = 4.7, 1.5 Hz); MS (ESI$^+$): 549 [M + H]$^+$. |
| 244 | 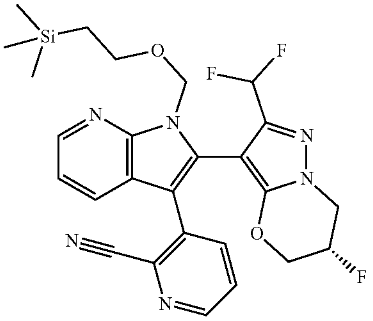 [SMILES: C[Si](C)(C)CCOCn1c(-c2c(C(F)F)nn3c2OC[C@@H](F)C3)c(-c2cccnc2C#N)c2cccnc21] | $^1$H-NMR (400 MHz, CDCl3) δ −0.13-−0.07 (m, 9H), 0.72-0.93 (m, 2H), 3.34-3.72 (m, 2H), 4.24-4.66 (m, 4H), 5.17-6.68 (m, 4H), 7.18-7.24 (m, 1H), 7.41-7.98 (m, 3H), 8.46 (ddd, J = 7.7, 4.7, 1.5 Hz, 1H), 8.61-8.64 (m, 1H); MS (ESI$^+$): 541 [M + H]$^+$. |
| 245 | 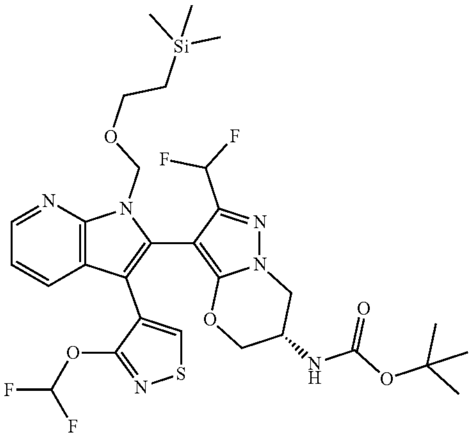 [SMILES: CC(C)(C)OC(=O)N[C@@H]1COc2c(-c3c(-c4csnc4OC(F)F)c4cccnc4n3COCC[Si](C)(C)C)c(C(F)F)nn2C1] | The crude compound obtained was used directly in the next step without purification. |

-continued

| Compound No. | Chemical structural formula | Spectrum data |
| --- | --- | --- |
| 246 | 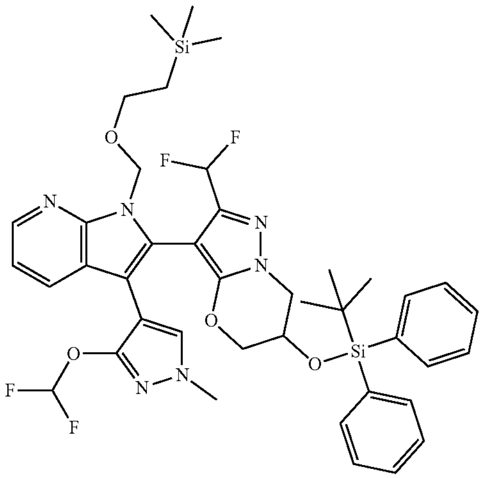 [SMILES: Cn1cc(-c2c(-c3c(C(F)F)nn4c3OCC(O[Si](c3ccccc3)(c3ccccc3)C(C)(C)C)C4)n(COCC[Si](C)(C)C)c3ncccc23)c(OC(F)F)n1] | The crude compound obtained was used directly in the next step without purification. |

(128) Reference Procedure of ethyl 6-bromo-4H-pyrrolo[2,3-d]thiazole-5-carboxylate (247)

(247)

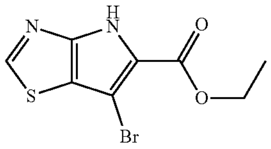

The compound 247 was synthesized from commercially available ethyl 4H-pyrrolo[2,3-d]thiazole-5-carboxylate using conditions analogous to compound 235; $^{1}$H-NMR (400 MHz, DMSO-$d_6$) δ 1.33 (3H, t, J=7.1 Hz), 4.32 (2H, q, J=7.1 Hz), 9.16 (1H, s), 13.20 (1H, s); MS (ESI$^+$): 275 $[M+H]^+$.

(128) Reference Procedure of ethyl 6-bromo-4-((2-(trimethylsilyl)ethoxy)methyl)-4H-pyrrolo[2,3-d]thiazole-5-carboxylate (248)

(248)

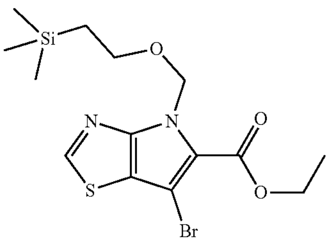

To a stirred solution of compound 247 (1.34 g, 4.89 mmol) in DMF (20 mL) at 0° C. under Ar atmosphere, 2-(trimethylsilyl)ethoxymethyl chloride (1.3 mL, 7.41 mmol) and 60% sodium hydride (256 mg, 5.87 mmol) were added. After stirring at room temperature for 2 h, the reaction was quenched with sat. aq. $NH_4Cl$, and the resulting mixture was extracted with EtOAc. The organic layer was washed with brine, dried over $Na_2SO_4$, and concentrated. The residue was purified by silica gel column chromatography (2-20% EtOAc/hexane) to yield compound 248 (1.89 mg, 95%) as a yellow oil; $^{1}$H-NMR (400 MHz, $CDCl_3$) δ −0.03-0.06 (9H, m), 0.90 (2H, t, J=7.8 Hz), 1.48 (3H, t, J=7.1 Hz), 3.57 (2H, t, J=7.8 Hz), 4.47 (2H, q, J=7.1 Hz), 6.04 (2H, s), 9.40 (1H, s); MS (ESI$^+$): 405 $[M+H]^+$.

(129) Reference Procedure of ethyl 6-(3-(difluoromethoxy)-1-methyl-1H-pyrazol-4-yl)-4-((2-(trimethylsilyl)ethoxy)methyl)-4H-pyrrolo[2,3-d]thiazole-5-carboxylate (249)

(249)

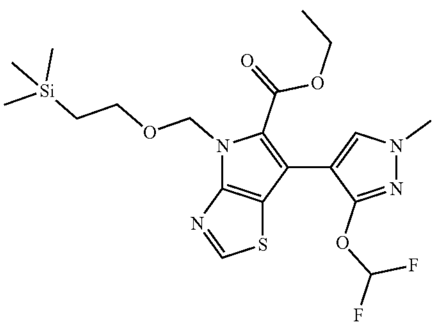

The compound 249 was synthesized from compounds 232 and 248 using conditions analogous to compound 236; $^{1}$H-NMR (400 MHz, DMSO-$d_6$) δ −0.00 (9H, s), 0.90 (2H, t, J=7.9 Hz), 1.36 (3H, t, J=7.1 Hz), 3.57 (2H, t, J=7.9 Hz), 3.95 (3H, s), 4.37 (2H, q, J=7.1 Hz), 6.05 (2H, s), 7.46 (1H, t, J=73.1 Hz), 8.15 (1H, s), 9.31 (1H, s); MS (ESI$^+$): 473 $[M+H]^+$.

(130) Reference Procedure of 6-(3-(difluoromethoxy)-1-methyl-1H-pyrazol-4-yl)-4-((2-(trimethylsilyl)ethoxy)methyl)-4H-pyrrolo[2,3-d]thiazole-5-carboxylic acid (250)

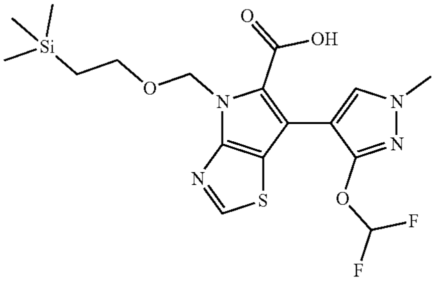

(250)

The compound 250 was synthesized from compound 249 using conditions analogous to compound 214; $^1$H-NMR (400 MHz, DMSO-$d_6$) δ 0.00 (9H, s), 0.90 (2H, t, J=7.9 Hz), 3.58 (2H, t, J=7.9 Hz), 3.93 (3H, s), 6.07 (2H, s), 7.42 (1H, t, J=73.2 Hz), 8.14 (1H, s), 9.26 (1H, s), 13.18 (1H, s); MS (ESI$^-$): 443 [M−H]$^-$.

(131) Experimental procedure of 3-(3-(3-(difluoromethoxy)-1-methyl-1H-pyrazol-4-yl)-1H-pyrrolo[2,3-b]pyridin-2-yl)-2-methyl-6,7-dihydro-5H-pyrazolo[5,1-b][1,3]oxazine (EX.421)

EX. 421

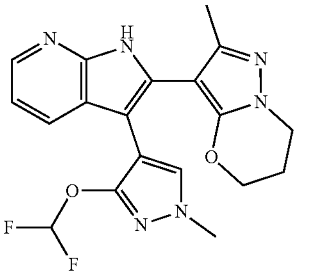

EX.421 was synthesized from compound 241 using conditions analogous to EX.420; $^1$H-NMR (400 MHz, DMSO-$d_6$) δ 1.82 (3H, s), 2.08-2.14 (2H, m), 3.73 (3H, s), 3.98 (2H, t, J=6.1 Hz), 4.15 (2H, t, J=5.2 Hz), 7.01 (1H, dd, J=7.6, 4.6 Hz), 7.09 (1H, t, J=74.0 Hz), 7.52 (1H, s), 7.73 (1H, dd, J=7.9, 1.2 Hz), 8.14 (1H, q, J=4.6, 1.5 Hz), 11.55 (1H, s); MS (ESI$^+$): 401 [M+H]$^+$.

The following compounds were also synthesized from the corresponding starting materials and reagents using conditions analogous to EX.420.

| Compound No. | Chemical structural formula | Spectrum data |
|---|---|---|
| EX.422 | 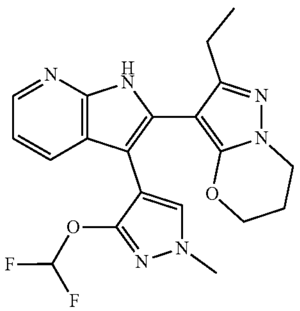 [SMILES: CCc1nn2c(c1-c1[nH]c3ncccc3c1-c1cn(C)nc1OC(F)F)OCCC2] | $^1$H-NMR (400 MHz, DMSO-$d_6$) δ 0.84 (3H, t, J = 7.6 Hz), 2.09-2.15 (2H, m), 2.23 (2H, q, J = 7.5 Hz), 3.72 (3H, s), 4.00 (2H, t, J = 6.1 Hz), 4.16 (2H, t, J = 4.9 Hz), 7.01 (1H, dd, J = 7.9, 4.9 Hz), 7.10 (1H, t, J = 74.0 Hz), 7.50 (1H, s), 7.73 (1H, dd, J = 7.9, 1.2 Hz), 8.14 (1H, dd, J = 4.6, 1.5 Hz), 11.56 (1H, s); MS (ESI$^+$): 415 [M + H]$^+$. |
| EX.423 | 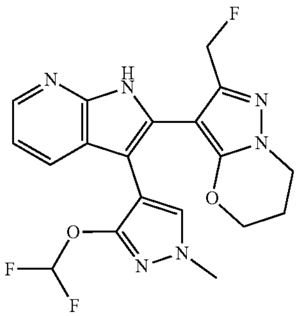 [SMILES: Cn1cc(-c2c(-c3c(CF)nn4c3OCCC4)[nH]c3ncccc23)c(OC(F)F)n1] | $^1$H-NMR (400 MHz, $CD_3OD$) δ 2.25-2.30 (2H, m), 3.78 (3H, s), 4.17 (2H, td, J = 6.2, 2.2 Hz), 4.28 (2H, t, J = 5.2 Hz), 5.02 (2H, d, J = 48.5 Hz), 6.78 (1H, t, J = 74.0 Hz), 7.11 (1H, dd, J = 7.9, 4.8 Hz), 7.50 (1H, s), 7.92 (1H, dd, J = 7.9, 1.5 Hz), 8.17 (1H, dd, J = 4.8, 1.5 Hz); MS (ESI$^+$): 419 [M + H]$^+$. |

-continued

| Compound No. | Chemical structural formula | Spectrum data |
|---|---|---|
| EX.424 | 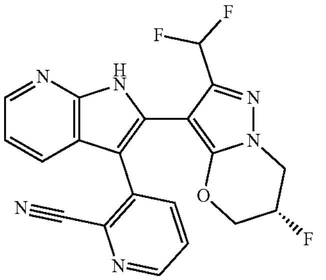 [SMILES: N#Cc1ncccc1-c1c(-c2c(C(F)F)nn3c2OC[C@@H](F)C3)[nH]c2ncccc12] | $^1$H-NMR (400 MHz, DMSO-$d_6$) δ 4.07-4.54 (m, 4H), 5.41 (d, J = 44.9 Hz, 1H), 6.64-6.91 (m, 1H), 7.17 (dd, J = 7.9, 4.7 Hz, 1H), 7.69 (dd, J = 7.8, 4.7 Hz, 1H), 7.79-7.87 (m, 2H), 8.32 (dd, J = 4.7, 1.5 Hz, 1H), 8.66 (dd, J = 4.7, 1.6 Hz, 1H), 12.26 (s, 1H); MS (ESI$^+$): 411 [M + H]$^+$. |
| EX.425 | 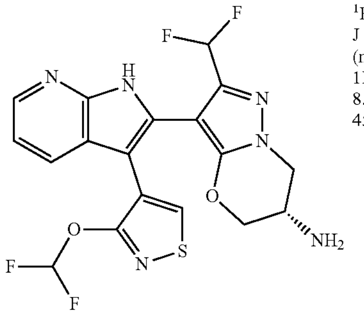 | $^1$H-NMR (400 MHz, DMSO-$d_6$) δ 1.86 (d, J = 6.4 Hz, 2H), 3.52-3.62 (m, 2H), 3.76-3.84 (m, 2H), 4.03-4.09 (m, 1H), 4.19-4.25 (m, 1H), 6.82-7.07 (m, 2H), 7.39-7.79 (m, 2H), 8.18-8.30 (m, 1H), 8.66 (s, 1H); MS (ESI$^+$): 455 [M + H]$^+$. |

(132) Experimental procedure of 3-(3-(3-(difluoromethoxy)-1-methyl-1H-pyrazol-4-yl)-1H-pyrrolo[2,3-b]pyridin-2-yl)-2-(difluoromethyl)-6,7-dihydro-5H-pyrazolo[5,1-b][1,3]oxazin-6-ol (EX.426)

EX. 426

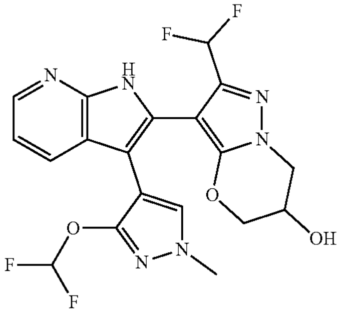

To a stirred solution of compound 246 (40.0 mg, 0.0487 mmol) in THF (1 mL) at room temperature under Ar atmosphere, 1.0 mol/L TBAF in THF (0.24 mL, 0.24 mmol) was added. After stirring at room temperature for 1 h, the reaction was quenched with sat. aq. $NH_4Cl$, and the resulting mixture was extracted with EtOAc. The organic layer was washed with brine, dried over $Na_2SO_4$, and concentrated. The residue was purified by silica gel column chromatography (0-40% MeOH/$CHCl_3$) to yield the desilylated compound. The compound was dissolved in $CH_2Cl_2$ (1 mL), and TFA (2 mL) was added to the resulting solution. After stirring at room temperature for 1 h, the reaction mixture was concentrated. The residue was dissolved in MeOH (1 mL), and 5 mol/L aq. NaOH (0.2 mL) was added to the resulting solution. After stirring at 50° C. for 0.5 h, the reaction mixture was concentrated. Brine was added to the residue, and the resulting mixture was extracted with $CHCl_3$. The organic layer was dried over $Na_2SO_4$, and concentrated. The residue was purified by silica gel column chromatography (0-40% MeOH/$CHCl_3$) to yield EX.426 (13.0 mg, 59%) as a white solid; $^1$H-NMR (400 MHz, DMSO-$d_6$) δ 3.69 (3H, s), 3.99 (1H, d, J=11.1 Hz), 4.15 (2H, s), 4.29 (2H, d, J=11.8 Hz), 5.66 (1H, d, J=3.2 Hz), 6.66 (1H, t, J=54.0 Hz), 7.05 (1H, dd, J=7.9, 4.7 Hz), 7.09 (1H, t, J=74.0 Hz), 7.49 (1H, s), 7.79 (1H, dd, J=7.9, 1.1 Hz), 8.19 (1H, dd, J=4.7, 1.6 Hz), 11.73 (1H, s); MS (ESI$^+$): 453 [M+H]$^+$.

(133) Reference Procedure of 5-bromo-6-(3-(difluoromethoxy)-1-methyl-1H-pyrazol-4-yl)-4-((2-(trimethylsilyl)ethoxy)methyl)-4H-pyrrolo[2,3-d]thiazole (251)

(251)

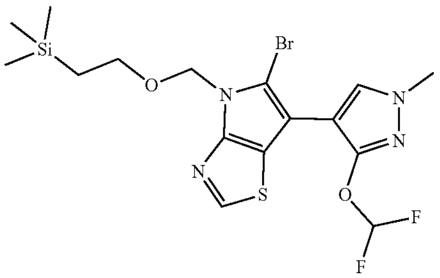

To a stirred solution of compound 250 (43.0 mg, 0.96 mmol) in DMF (0.96 mL) at room temperature, NBS (21.0 mg, 0.116 mmol) and iodobenzene diacetate (16.0 mg, 0.0481 mmol) were added. After stirring at room temperature for 2.5 h, the reaction mixture was diluted with EtOAc, and sat. aq. $Na_2S_2O_3$ was added. The resulting mixture was stirred for 0.5 h, and then filtered off through diatomaceous earth. The filtrate was concentrated, and the residue was purified by silica gel column chromatography (8-66% EtOAc/hexane) to yield compound 251 (19.0 mg, 41%) as a brown oil; $^1$H-NMR (400 MHz, DMSO-$d_6$) δ 0.00 (9H, s), 0.93 (2H, t, J=7.9 Hz), 3.66 (2H, t, J=7.9 Hz), 3.93 (3H, s), 5.71 (2H, s), 7.48 (1H, t, J=73.1 Hz), 8.26 (1H, s), 9.05 (1H, s); MS (ESI$^+$): 479 $[M+H]^+$.

(134) Reference Procedure of (S)-6-((tert-butyldiphenylsilyl)oxy)-3-(6-(3-(difluoromethoxy)-1-methyl-1H-pyrazol-4-yl)-4-((2-(trimethylsilyl)ethoxy)methyl)-4H-pyrrolo[2,3-d]thiazol-5-yl)-2-(difluoromethyl)-6,7-dihydro-5H-pyrazolo[5,1-b][1,3]oxazine (252)

(252)

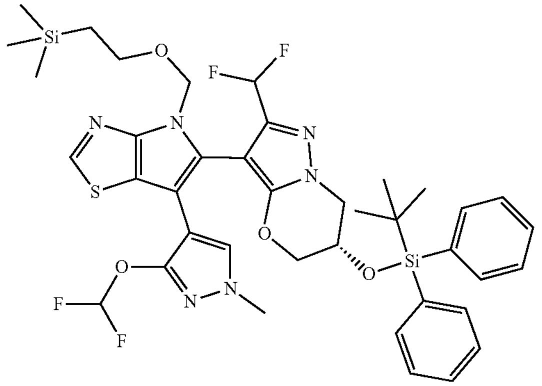

The compound 252 was synthesized from compounds 226 and 251 using conditions analogous to compound 236. The crude compound obtained was used directly in the next step without purification.

(135) Reference Procedure of tert-butyl (S)-(3-(6-(3-(difluoromethoxy)-1-methyl-1H-pyrazol-4-yl)-4-((2-(trimethylsilyl)ethoxy)methyl)-4H-pyrrolo[2,3-d]thiazol-5-yl)-2-(difluoromethyl)-6,7-dihydro-5H-pyrazolo[5,1-b][1,3]oxazin-6-yl) carbamate (253)

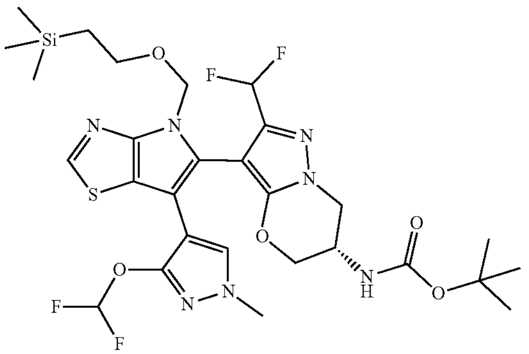 [SMILES: Cn1cc(-c2c(-c3c(C(F)F)nn4c3OC[C@@H](NC(=O)OC(C)(C)C)C4)n(COCC[Si](C)(C)C)c3ncsc23)c(OC(F)F)n1]

The compound 253 was synthesized from compounds 229 and 251 using conditions analogous to compound 236. The crude compound obtained was used directly in the next step without purification.

(136) Experimental procedure of (S)-3-(6-(3-(difluoromethoxy)-1-methyl-1H-pyrazol-4-yl)-4H-pyrrolo[2,3-d]thiazol-5-yl)-2-(difluoromethyl)-6,7-dihydro-5H-pyrazolo[5,1-b][1,3]oxazin-6-ol (EX.427)

EX. 427

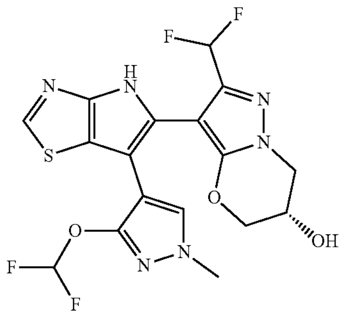

EX.427

EX.427 was synthesized from compound 252 using conditions analogous to EX.420; $^1$H-NMR (400 MHz, DMSO-$d_6$) δ 3.67 (3H, s), 4.04-4.13 (1H, m), 4.19-4.30 (2H, m), 4.33-4.45 (2H, m), 5.73-5.78 (1H, m), 6.60-6.87 (1H, m), 7.10-7.54 (2H, m), 8.76 (1H, s), 11.90 (1H, s); MS (ESI$^+$): 459 $[M+H]^+$.

(137) Experimental procedure of (S)-3-(6-(3-(difluoromethoxy)-1-methyl-1H-pyrazol-4-yl)-4H-pyrrolo[2,3-d]thiazol-5-yl)-2-(difluoromethyl)-6,7-dihydro-5H-pyrazolo[5,1-b][1,3]oxazin-6-amine (EX.428)

EX. 428

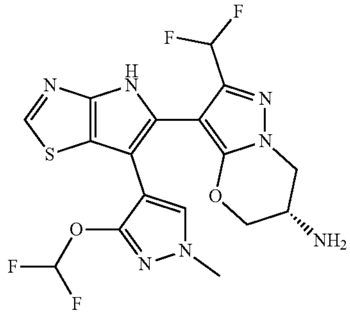

EX.428 was synthesized from compound 253 using conditions analogous to EX.420; $^1$H-NMR (400 MHz, DMSO-$d_6$) δ 1.87-2.07 (2H, m), 3.50-3.60 (1H, m), 3.68 (3H, s), 3.92 (1H, dd, J=11.9, 4.9 Hz), 4.03 (1H, dd, J=10.5, 5.5 Hz), 4.18-4.33 (2H, m), 6.70 (1H, t, J=53.8 Hz), 7.08-7.51 (2H, m), 8.75 (1H, s), 11.87 (1H, s); MS (ESI$^+$): 458 $[M+H]^+$.

(138) Reference Procedure of 3-(difluoromethoxy)-4-(2-(4,4,5,5-tetramethyl-1,3,2-dioxaborolan-2-yl)-1-((2-(trimethylsilyl)ethoxy)methyl)-1H-pyrrolo[2,3-b]pyridin-3-yl)isothiazole (254)

(254)

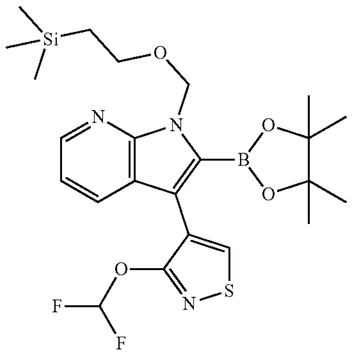

The compound 254 was synthesized from compound 240 using conditions analogous to compound 220. The crude compound obtained was used directly in the next step without purification.

(139) Reference Procedure of 3-(3-(difluoromethoxy)-1-methyl-1H-pyrazol-4-yl)-2-(4,4,5,5-tetramethyl-1,3,2-dioxaborolan-2-yl)-1-((2-(trimethylsilyl)ethoxy)methyl)-1H-pyrrolo[2,3-b]pyridine (255)

(255)

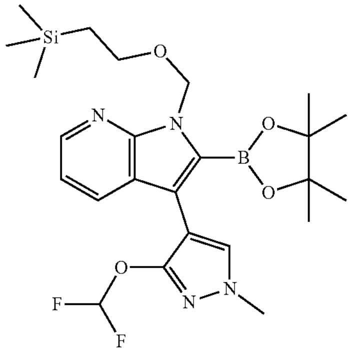

A mixture of compound 235 (100 mg, 0.211 mmol), 4,4,5,5-tetramethyl-1,3,2-dioxaborolane (0.061 mL, 0.424 mmol), SPhos Pd G4 (18.0 mg, 0.0227 mmol), and triethylamine (0.092 mL, 0.664 mmol) in dioxane (2.5 mL) was stirred at 110° C. for 0.5 h under microwave irradiation. The reaction mixture was directly purified by silica gel column chromatography (5-30% EtOAc/hexane) to yield compound 255 (4 mg, 4%) as a yellow oil; $^1$H-NMR (400 MHz, $CDCl_3$) δ -0.11 (9H, s), 0.84-0.89 (2H, m), 1.32 (12H, s), 3.45-3.50 (2H, m), 3.86 (3H, s), 5.97 (2H, s), 6.85 (1H, t, J=73.7 Hz), 7.08 (1H, q, J=4.3 Hz), 7.45 (1H, s), 7.88 (1H, dd, J=7.9, 1.8 Hz), 8.40 (1H, dd, J=4.6, 1.5 Hz); MS (ESI$^+$): 521 $[M+H]^+$.

(140) Reference Procedure of 2-(difluoromethyl)-3-(1-((2-(trimethylsilyl)ethoxy)methyl)-1H-pyrrolo[2,3-b]pyridin-2-yl)-6,7-dihydro-5H-pyrazolo[5,1-b][1,3]oxazine (256)

(256)

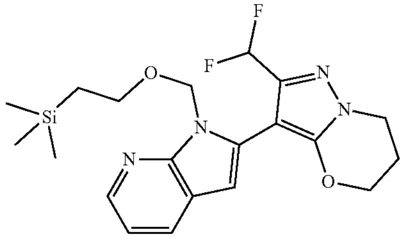

A mixture of compound 193 (330 mg, 1.10 mmol), 2-(4,4,5,5-tetramethyl-1,3,2-dioxaborolan-2-yl)-1-((2-(trimethylsilyl)ethoxy)methyl)-1H-pyrrolo[2,3-b]pyridine (Chemical Science (2021), 12(4), 1528-1534) (374 mg, 0.999 mmol), SPhos Pd G4 (39.7 mg, 0.050 mmol), and $K_3PO_4$ (636 mg, 3.00 mmol) in toluene/water (5/1, 4.44 mL) was stirred at 90° C. for 4 h. The reaction mixture was cooled to room temperature and directly purified by silica gel column chromatography (12-96% EtOAc/hexane) to yield compound 256 (300 mg, 71%) as yellow oil; $^1$H-NMR (400 MHz, $CDCl_3$) δ -0.14 (s, 9H), 0.76-0.81 (m, 2H), 2.33-2.39 (m, 2H), 3.34-3.39 (m, 2H), 4.26-4.38 (m, 4H), 5.67 (s, 2H), 6.39-6.73 (m, 2H), 7.09 (dd, J=7.9, 4.9 Hz, 1H), 7.88 (dd, J=7.9, 1.2 Hz, 1H), 8.33 (dd, J=4.9, 1.2 Hz, 1H); MS (ESI$^+$): 421 $[M+H]^+$.

The following compounds were synthesized from the corresponding starting materials and reagents using conditions analogous to compound 256.

| Compound No. | Chemical structural formula | Spectrum data |
| --- | --- | --- |
| 257 | 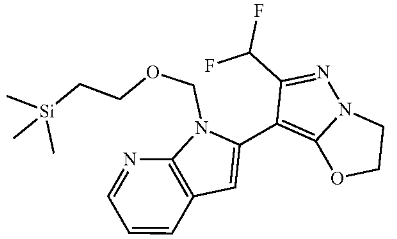 [SMILES: C[Si](C)(C)CCOCn1c(-c2c(C(F)F)nn3c2OCC3)cc2cccnc21] | $^1$H-NMR (400 MHz, $CDCl_3$) δ -0.15 (s, 9H), 0.78 (t, J = 8.3 Hz, 2H), 3.36-3.40 (m, 2H), 4.43-4.47 (m, 2H), 5.17 (t, J = 8.1 Hz, 2H), 5.73 (s, 2H), 6.45-6.72 (m, 2H), 7.09 (dd, J = 7.8, 4.7 Hz, 1H), 7.87 (dd, J = 7.8, 1.5 Hz, 1H), 8.32 (dd, J = 4.7, 1.5 Hz, 1H); MS (ESI$^+$): 407 [M + H]$^+$. |

-continued
| Compound No. | Chemical structural formula | Spectrum data |
|---|---|---|
| 258 | 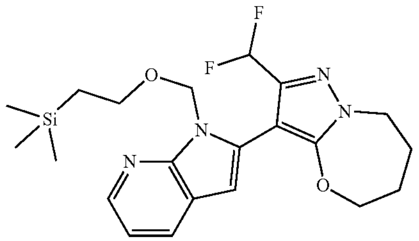 [SMILES: C[Si](C)(C)CCOCn1c(-c2c(C(F)F)nn3c2OCCCC3)cc2cccnc21] | $^1$H-NMR (400 MHz, $CDCl_3$) δ −0.14 (s, 9H), 0.76-0.83 (m, 2H), 1.92-2.00 (m, 2H), 2.07-2.14 (m, 2H), 3.35-3.43 (m, 2H), 4.07-4.11 (m, 2H), 4.30-4.38 (m, 2H), 5.66 (s, 2H), 6.52 (s, 1H), 6.56 (t, J = 54.1 Hz, 1H), 7.10 (dd, J = 7.8, 4.7 Hz, 1H), 7.89 (dd, J = 7.8, 1.6 Hz, 1H), 8.34 (dd, J = 4.7, 1.6 Hz, 1H); MS (ESI$^+$): 435 [M + H]$^+$. |
| 259 | 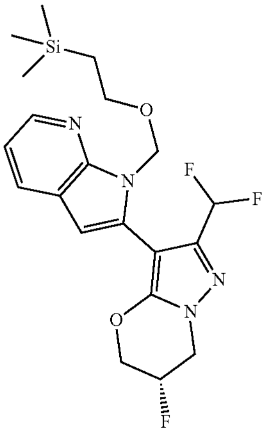 [SMILES: C[Si](C)(C)CCOCn1c(-c2c(C(F)F)nn3c2OC[C@@H](F)C3)cc2cccnc21] | $^1$H-NMR (400 MHz, $CDCl_3$) δ −0.14 (9H, s), 0.73-0.85 (2H, m), 3.33-3.42 (2H, m), 4.21-4.33 (1H, m), 4.38-4.51 (1H, m), 4.58-4.69 (2H, m), 5.24-5.36 (1H, m), 5.60 (1H, d, J = 11.0 Hz), 5.72 (1H, d, J = 11.0 Hz), 6.47-6.74 (2H, m), 7.10 (1H, dd, J = 7.8, 4.9 Hz), 7.89 (1H, dd, J = 7.8, 1.5 Hz), 8.34 (1H, dd, J = 4.7, 1.7 Hz); MS (ESI$^+$): 439 [M + H]$^+$. |
| 260 | 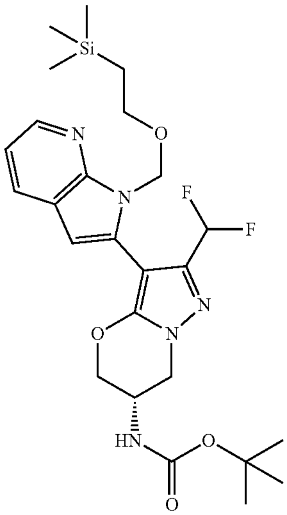 [SMILES: CC(C)(C)OC(=O)N[C@@H]1COc2c(-c3cc4cccnc4n3COCC[Si](C)(C)C)c(C(F)F)nn2C1] | $^1$H-NMR (400 MHz, $CDCl_3$) δ −0.13 (s, 9H), 0.78-0.83 (m, 2H), 1.46 (s, 9H), 3.38-3.43 (m, 2H), 4.27-4.50 (m, 5H), 5.39-5.43 (m, 1H), 5.61 (d, J = 11.1 Hz, 1H), 5.72 (d, J = 11.2 Hz, 1H), 6.45-6.73 (m, 2H), 7.10 (dd, J = 7.8, 4.7 Hz, 1H), 7.90 (dd, J = 7.8, 1.6 Hz, 1H), 8.33 (dd, J = 4.7, 1.5 Hz, 1H); MS (ESI$^+$): 536 [M + H]$^+$. |

-continued

| Compound No. | Chemical structural formula | Spectrum data |
|---|---|---|
| 261 | 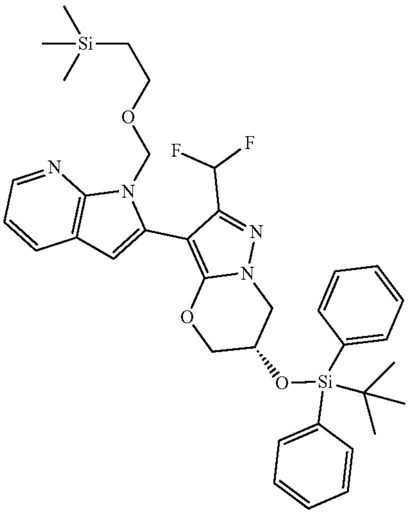 [SMILES: CC(C)(C)[Si](O[C@@H]1COc2c(-c3cc4cccnc4n3COCC[Si](C)(C)C)c(C(F)F)nn2C1)(c1ccccc1)c1ccccc1] | $^1$H-NMR (400 MHz, $CDCl_3$) δ −0.17 (s, 9H), 0.74-0.79 (m, 2H), 1.07 (s, 9H), 3.29-3.39 (m, 2H), 4.05-4.20 (m, 4H), 4.34-4.38 (m, 1H), 5.60 (d, J = 11.0 Hz, 1H), 5.76 (d, J = 11.0 Hz, 1H), 6.47-6.75 (m, 2H), 7.10 (q, J = 4.1 Hz, 1H), 7.39-7.52 (m, 6H), 7.60 (dd, J = 7.9, 1.2 Hz, 2H), 7.67 (dd, J = 8.3, 1.5 Hz, 2H), 7.89 (d, J = 6.7 Hz, 1H), 8.34 (dd, J = 4.6, 1.5 Hz, 1H); MS (ESI$^+$): 675 [M + H]$^+$. |
| 262 | 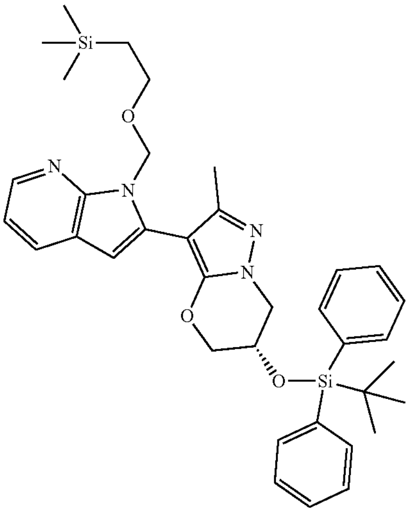 [SMILES: Cc1nn2c(c1-c1cc3cccnc3n1COCC[Si](C)(C)C)OC[C@@H](O[Si](c1ccccc1)(c1ccccc1)C(C)(C)C)C2] | $^1$H-NMR (400 MHz, DMSO-$d_6$) δ −0.24 (s, 9H), 0.62 (t, J = 8.1 Hz, 2H), 1.01 (s, 9H), 2.12 (s, 3H), 3.18-3.26 (m, 2H), 3.88-3.94 (m, 1H), 4.12-4.22 (m, 3H), 4.44-4.48 (m, 1H), 5.50 (d, J = 10.9 Hz, 1H), 5.71 (d, J = 10.9 Hz, 1H), 6.43 (s, 1H), 7.14 (dd, J = 7.7, 4.7 Hz, 1H), 7.41-7.68 (m, 10H), 7.94 (dd, J = 7.8, 1.5 Hz, 1H), 8.25 (dd, J = 4.7, 1.5 Hz, 1H); MS (ESI$^+$): 639 [M + H]$^+$. |
| 263 | 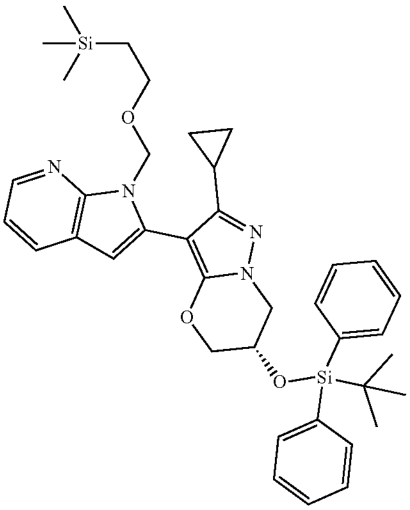 [SMILES: CC(C)(C)[Si](O[C@@H]1COc2c(-c3cc4cccnc4n3COCC[Si](C)(C)C)c(C3CC3)nn2C1)(c1ccccc1)c1ccccc1] | $^1$H-NMR (400 MHz, $CDCl_3$) δ −0.17 (s, 9H), 0.72-0.97 (m, 6H), 1.07 (s, 9H), 1.77-1.85 (m, 1H), 3.30-3.41 (m, 2H), 4.02-4.17 (m, 4H), 4.22-4.34 (m, 1H), 5.63 (d, J = 10.9 Hz, 1H), 5.78 (d, J = 10.9 Hz, 1H), 7.07 (dd, J = 7.7, 4.7 Hz, 1H), 7.36-7.50 (m, 7H), 7.59-7.63 (m, 2H), 7.65-7.69 (m, 2H), 7.86 (dd, J = 7.8, 1.5 Hz, 1H), 8.32 (dd, J = 4.7, 1.5 Hz, 1H); MS (ESI$^+$): 665 [M + H]$^+$. |

-continued

| Compound No. | Chemical structural formula | Spectrum data |
|---|---|---|
| 264 | 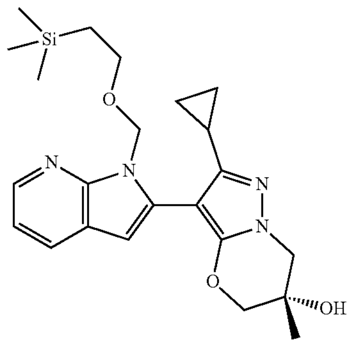 [SMILES: C[C@@]1(O)COc2c(-c3cc4cccnc4n3COCC[Si](C)(C)C)c(C3CC3)nn2C1] | $^1$H-NMR (400 MHz, $CDCl_3$) δ −0.14 (s, 9H), 0.77-0.94 (m, 6H), 1.43 (s, 3H), 1.74-1.83 (m, 1H), 3.41 (dd, J = 9.5, 7.4 Hz, 2H), 3.99-4.15 (m, 4H), 5.68 (d, J = 11.0 Hz, 1H), 5.73 (d, J = 11.0 Hz, 1H), 6.52 (s, 1H), 7.09 (dd, J = 7.8, 4.7 Hz, 1H), 7.87 (dd, J = 7.8, 1.5 Hz, 1H), 8.31 (dd, J = 4.7, 1.5 Hz, 1H); MS (ESI$^+$): 441 [M + H]$^+$. |
| 265 | 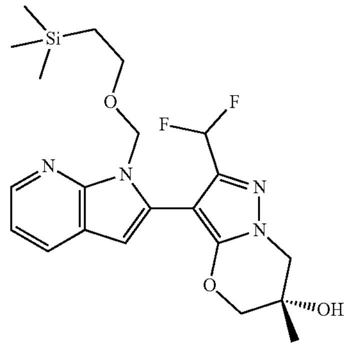 [SMILES: C[C@@]1(O)COc2c(-c3cc4cccnc4n3COCC[Si](C)(C)C)c(C(F)F)nn2C1] | $^1$H-NMR (400 MHz, $CDCl_3$) δ −0.14 (s, 9H), 0.73-0.86 (m, 2H), 1.47 (s, 3H), 3.33-3.46 (m, 2H), 4.08-4.21 (m, 4H), 5.63-5.81 (m, 2H), 6.38-6.75 (m, 3H), 7.10 (dd, J = 7.8, 4.7 Hz, 1H), 7.89-7.91 (m, 1H), 8.33 (dd, J = 4.7, 1.5 Hz, 1H); MS (ESI$^+$): 451 [M + H]$^+$. |
| 266 | 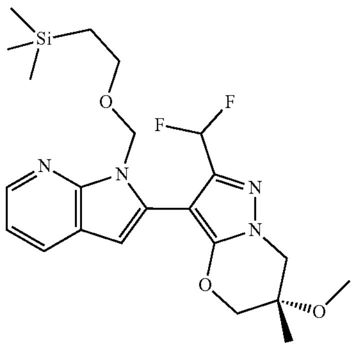 [SMILES: CO[C@]1(C)COc2c(-c3cc4cccnc4n3COCC[Si](C)(C)C)c(C(F)F)nn2C1] | $^1$H-NMR (400 MHz, $CDCl_3$) δ −0.14 (s, 9H), 0.75-0.82 (m, 2H), 1.38 (s, 3H), 3.31-3.41 (m, 5H), 3.97-4.05 (m, 2H), 4.32-4.40 (m, 2H), 5.59 (d, J = 11.0 Hz, 1H), 5.74 (d, J = 11.0 Hz, 1H), 6.55 (s, 1H), 6.60 (t, J = 54.1 Hz, 1H), 7.09 (dd, J = 7.8, 4.8 Hz, 1H), 7.88 (dd, J = 7.8, 1.5 Hz, 1H), 8.33 (dd, J = 4.8, 1.6 Hz, 1H); MS (ESI$^+$): 465 [M + H]$^+$. |
| 267 | 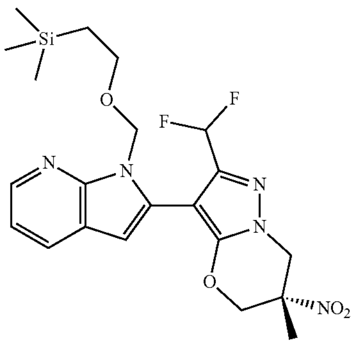 [SMILES: C[C@@]1([N+](=O)[O-])COc2c(-c3cc4cccnc4n3COCC[Si](C)(C)C)c(C(F)F)nn2C1] | $^1$H-NMR (400 MHz, $CDCl_3$) δ −0.13 (s, 9H), 0.74-0.92 (m, 2H), 1.83 (s, 3H), 3.30-3.40 (m, 2H), 4.29 (d, J = 12.2 Hz, 1H), 4.35 (d, J = 14.2 Hz, 1H), 4.98 (dd, J = 12.1, 2.3 Hz, 1H), 5.25 (d, J = 14.0 Hz, 1H), 5.47 (d, J = 11.0 Hz, 1H), 5.66 (d, J = 10.9 Hz, 1H), 6.54 (s, 1H), 6.59 (t, J = 53.9 Hz, 1H), 7.10 (dd, J = 7.8, 4.7 Hz, 1H), 7.89 (dd, J = 7.8, 1.6 Hz, 1H), 8.34 (dd, J = 4.7, 1.5 Hz, 1H); MS (ESI$^+$): 480 [M + H]$^+$. |

-continued
| Compound No. | Chemical structural formula | Spectrum data |
|---|---|---|
| 268 | 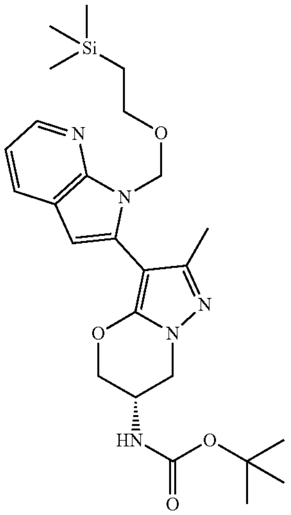 [SMILES: Cc1nn2c(c1-c1cc3cccnc3n1COCC[Si](C)(C)C)OC[C@@H](NC(=O)OC(C)(C)C)C2] | $^{1}$H-NMR (400 MHz, DMSO-$d_6$) δ −0.20 (s, 9H), 0.63-0.70 (m, 2H), 1.41 (s, 9H), 2.09 (s, 3H), 3.27 (t, J = 8.2 Hz, 2H), 3.94-4.33 (m, 5H), 5.57 (s, 2H), 6.42 (s, 1H), 7.13 (dd, J = 7.8, 4.7 Hz, 1H), 7.47 (d, J = 4.6 Hz, 1H), 7.93 (dd, J = 7.8, 1.4 Hz, 1H), 8.24 (dd, J = 4.7, 1.5 Hz, 1H); MS (ESI$^+$): 500 [M + H]$^+$. |
| 269 | 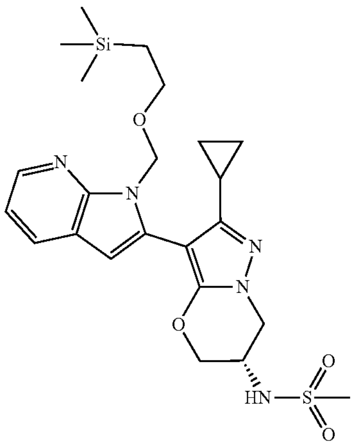 [SMILES: C[Si](C)(C)CCOCn1c(-c2c(C3CC3)nn3c2OC[C@@H](NS(C)(=O)=O)C3)cc2cccnc21] | $^{1}$H-NMR (400 MHz, $CDCl_3$) δ −0.13 (s, 9H), 0.74-0.95 (m, 6H), 1.72-1.82 (m, 1H), 3.04 (s, 3H), 3.38-3.50 (m, 2H), 4.20-4.41 (m, 5H), 5.61 (d, J = 11.1 Hz, 1H), 5.65-5.73 (m, 1H), 5.77 (d, J = 11.1 Hz, 1H), 6.53 (s, 1H), 7.10 (dd, J = 7.8, 4.8 Hz, 1H), 7.89 (dd, J = 7.7, 1.4 Hz, 1H), 8.32 (dd, J = 4.7, 1.2 Hz, 1H); MS (ESI$^+$): 504 [M + H]$^+$. |

(141) Reference Procedure of 3-(3-bromo-1-((2-(trimethylsilyl)ethoxy)methyl)-1H-pyrrolo[2,3-b]pyridin-2-yl)-2-(difluoromethyl)-6,7-dihydro-5H-pyrazolo[5,1-b][1,3]oxazine (270)

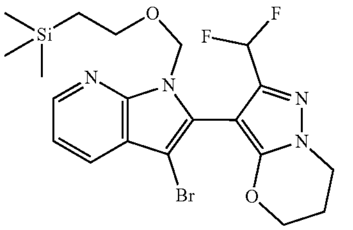

(270)

The compound 270 was synthesized from compound 256 using conditions analogous to compound 235; $^{1}$H-NMR (400 MHz, $CDCl_3$) δ −0.10 (s, 9H), 0.78-0.89 (m, 2H), 2.34-2.40 (m, 2H), 3.40-3.46 (m, 2H), 4.28-4.41 (m, 4H), 5.55-5.65 (m, 2H), 6.42-6.77 (m, 1H), 7.19 (dd, J=7.6, 4.6 Hz, 1H), 7.88 (dd, J=7.9, 1.8 Hz, 1H), 8.38 (dd, J=4.6, 1.5 Hz, 1H); MS (ESI$^+$): 499 [M+H]$^+$.

The following compounds were also synthesized from the corresponding starting materials and reagents using conditions analogous to 235.

| Compound No. | Chemical structural formula | Spectrum data |
|---|---|---|
| 271 | 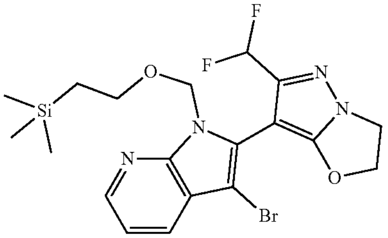 [SMILES: C[Si](C)(C)CCOCn1c(-c2c(C(F)F)nn3c2OCC3)c(Br)c2cccnc21] | $^{1}$H-NMR (400 MHz, $CDCl_3$) δ −0.10 (s, 9H), 0.81-0.90 (m, 2H), 3.40-3.47 (m, 2H), 4.43-4.54 (m, 2H), 5.11-5.25 (m, 2H), 5.57 (d, J = 11.0 Hz, 1H), 5.65 (d, J = 11.0 Hz, 1H), 6.61 (t, J = 54.3 Hz, 1H), 7.19 (dd, J = 7.8, 4.7 Hz, 1H), 7.86 (dd, J = 7.9, 1.6 Hz, 1H), 8.39 (dd, J = 4.7, 1.6 Hz, 1H); MS (ESI$^+$): 485 [M + H]$^+$. |
| 272 | 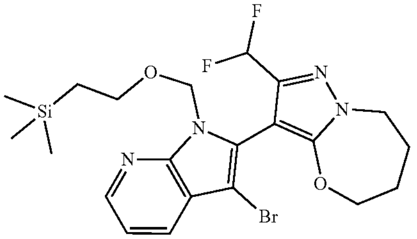 [SMILES: C[Si](C)(C)CCOCn1c(-c2c(C(F)F)nn3c2OCCCC3)c(Br)c2cccnc21] | $^{1}$H-NMR (400 MHz, $CDCl_3$) δ −0.09 (s, 9H), 0.77-0.92 (m, 2H), 1.91-2.15 (m, 4H), 3.38-3.51 (m, 2H), 4.11-4.14 (m, 1H), 4.18-4.25 (m, 1H), 4.26-4.35 (m, 1H), 4.38-4.47 (m, 1H), 5.48 (d, J = 11.1 Hz, 1H), 5.67 (d, J = 11.1 Hz, 1H), 6.57 (t, J = 54.4 Hz, 1H), 7.19 (dd, J = 7.9, 4.8 Hz, 1H), 7.87 (dd, J = 7.9, 1.6 Hz, 1H), 8.39 (dd, J = 4.8, 1.6 Hz, 1H); MS (ESI$^+$): 513 [M + H]$^+$. |
| 273 | 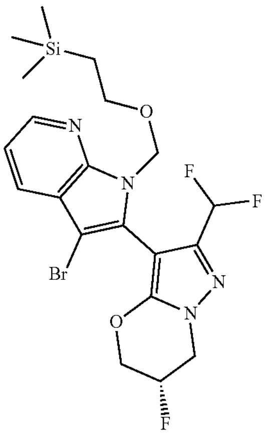 [SMILES: C[Si](C)(C)CCOCn1c(-c2c(C(F)F)nn3c2OC[C@@H](F)C3)c(Br)c2cccnc21] | $^{1}$H-NMR (400 MHz, CDCl3) δ −0.10 (9H, s), 0.76-0.90 (2H, m), 3.38-3.48 (2H, m), 4.20-4.68 (4H, m), 5.25-5.36 (1H, m), 5.53-5.57 (1H, m), 5.62-5.65 (1H, m), 6.51-6.80 (1H, m), 7.17-7.20 (1H, m), 7.86-7.89 (1H, m), 8.37-8.41 (1H, m); MS (ESI$^+$): 517 [M + H]$^+$. |

-continued
| Compound No. | Chemical structural formula | Spectrum data |
|---|---|---|
| 274 | 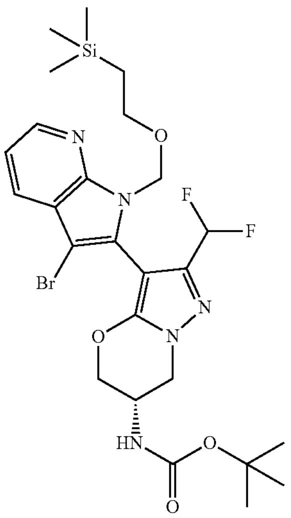 [SMILES: CC(C)(C)OC(=O)N[C@@H]1COc2c(-c3c(Br)c4cccnc4n3COCC[Si](C)(C)C)c(C(F)F)nn2C1] | $^1$H-NMR (400 MHz, $CDCl_3$) δ −0.10−−0.09 (m, 9H), 0.80-1.00 (m, 2H), 1.47 (s, 9H), 3.43-3.52 (m, 2H), 4.28-4.52 (m, 5H), 5.10-5.74 (m, 3H), 6.49-6.79 (m, 1H), 7.18-7.21 (m, 1H), 7.88 (d, J = 7.9 Hz, 1H), 8.37-8.40 (m, 1H); MS (ESI$^+$): 614 [M + H]$^+$. |
| 275 | 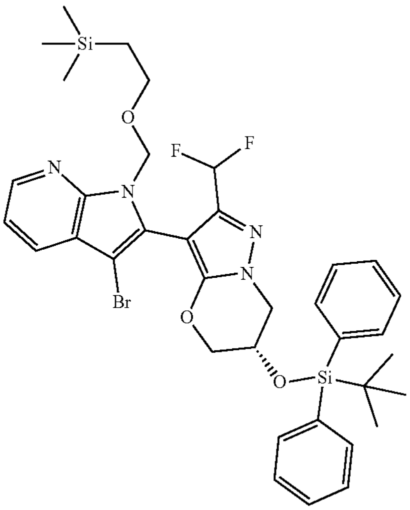 [SMILES: CC(C)(C)[Si](O[C@@H]1COc2c(-c3c(Br)c4cccnc4n3COCC[Si](C)(C)C)c(C(F)F)nn2C1)(c1ccccc1)c1ccccc1] | $^1$H-NMR (400 MHz, $CDCl_3$) δ −0.15−−0.11 (m, 9H), 0.76-0.91 (m, 2H), 1.04-1.10 (m, 9H), 3.34-3.47 (m, 2H), 4.05-4.22 (m, 5H), 4.34-4.39 (m, 1H), 5.42-5.84 (m, 2H), 6.50-6.84 (m, 1H), 7.17-7.20 (m, 1H), 7.37-7.52 (m, 6H), 7.58-7.70 (m, 4H), 7.84-7.90 (m, 1H), 8.37-8.41 (m, 1H); MS (ESI$^+$): 753 [M + H]$^+$. |
| 276 | 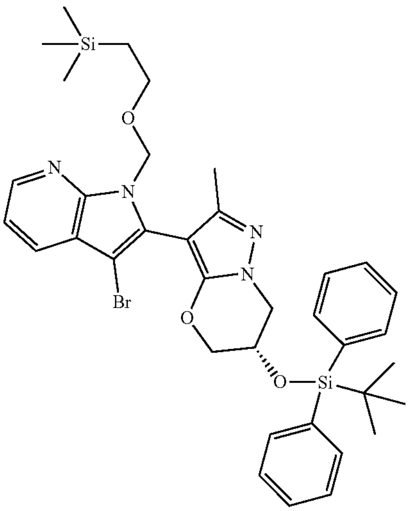 [SMILES: Cc1nn2c(c1-c1c(Br)c3cccnc3n1COCC[Si](C)(C)C)OC[C@@H](O[Si](c1ccccc1)(c1ccccc1)C(C)(C)C)C2] | $^1$H-NMR (400 MHz, DMSO-$d_6$) δ −0.26-0.15 (m, 9H), 0.57-0.78 (m, 2H), 0.95-1.06 (m, 9H), 2.04-2.12 (m, 3H), 3.14-3.38 (m, 2H), 3.84-3.94 (m, 1H), 4.10-4.25 (m, 3H), 4.42-4.51 (m, 1H), 5.28-5.36 (m, 1H), 5.63-5.89 (m, 1H), 7.26-7.31 (m, 1H), 7.40-7.69 (m, 10H), 7.87-7.91 (m, 1H), 8.36-8.40 (m, 1H); MS (ESI$^+$): 717 [M + H]$^+$. |

-continued

| Compound No. | Chemical structural formula | Spectrum data |
|---|---|---|
| 277 | 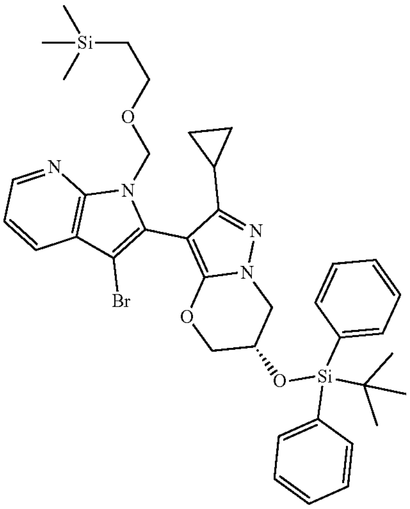 [SMILES: CC(C)(C)[Si](O[C@@H]1COc2c(-c3c(Br)c4cccnc4n3COCC[Si](C)(C)C)c(C3CC3)nn2C1)(c1ccccc1)c1ccccc1] | $^{1}$H-NMR (400 MHz, $CDCl_3$) δ −0.17-−0.11 (m, 9H), 0.74-0.94 (m, 6H), 1.04-1.07 (m, 9H), 1.65-1.76 (m, 1H), 3.32-3.46 (m, 2H), 4.00-4.15 (m, 5H), 5.47-5.89 (m, 2H), 7.16 (ddd, J = 7.9, 4.8, 1.3 Hz, 1H), 7.37-7.49 (m, 6H), 7.57-7.61 (m, 2H), 7.64-7.69 (m, 2H), 7.83-7.87 (m, 1H), 8.35-8.38 (m, 1H); MS ($ESI^+$): 743 $[M + H]^+$. |
| 278 | 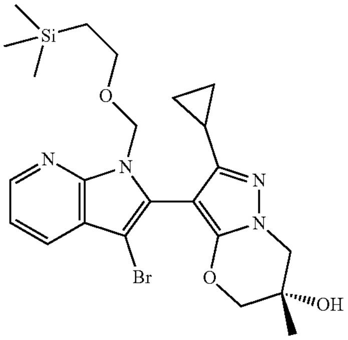 [SMILES: C[C@@]1(O)COc2c(-c3c(Br)c4cccnc4n3COCC[Si](C)(C)C)c(C3CC3)nn2C1] | $^{1}$H-NMR (400 MHz, $CDCl_3$) δ −0.15-−0.07 (m, 9H), 0.72-0.96 (m, 6H), 1.41-1.44 (m, 3H), 1.66-1.74 (m, 1H), 3.41-3.49 (m, 2H), 3.92-4.16 (m, 4H), 5.56-5.70 (m, 2H), 7.18 (dd, J = 7.8, 4.7 Hz, 1H), 7.86 (dt, J = 7.9, 1.5 Hz, 1H), 8.36-8.38 (m, 1H); MS ($ESI^+$): 519 $[M + H]^+$. |
| 279 | 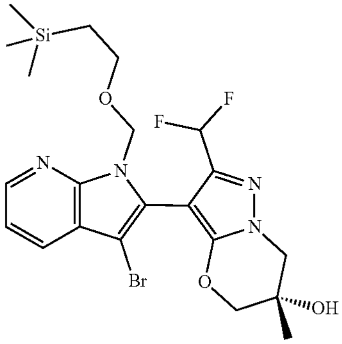 [SMILES: C[C@@]1(O)COc2c(-c3c(Br)c4cccnc4n3COCC[Si](C)(C)C)c(C(F)F)nn2C1] | $^{1}$H-NMR (400 MHz, $CDCl_3$) δ −0.10 (s, 9H), 0.78-0.93 (m, 2H), 1.47 (d, J - 1.9 Hz, 3H), 3.42-3.48 (m, 2H), 4.11-4.18 (m, 4H), 5.47-5.71 (m, 2H), 6.42-6.69 (m, 1H), 7.19 (dd, J = 7.8, 4.7 Hz, 1H), 7.86-7.89 (m, 1H), 8.37-8.39 (m, 1H); MS ($ESI^+$): 529 $[M + H]^+$. |
| 280 | 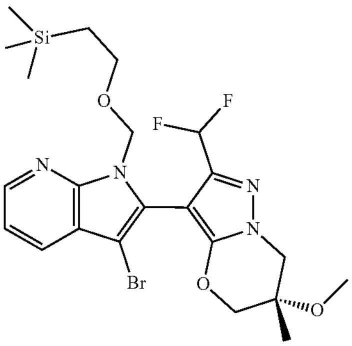 [SMILES: CO[C@]1(C)COc2c(-c3c(Br)c4cccnc4n3COCC[Si](C)(C)C)c(C(F)F)nn2C1] | $^{1}$H-NMR (400 MHz, $CDCl_3$) δ −0.11 (s, 9H), 0.77-0.90 (m, 2H), 1.38 (d, J = 2.5 Hz, 3H), 3.33 (dd, J = 15.9, 5.7 Hz, 3H), 3.38-3.48 (m, 2H), 3.95-4.08 (m, 2H), 4.30-4.41 (m, 2H), 5.41-5.76 (m, 2H), 6.50-6.83 (m, 1H), 7.15-7.20 (m, 1H), 7.84-7.89 (m, 1H), 8.35-8.42 (m, 1H); MS ($ESI^+$): 543 $[M + H]^+$. |

-continued
| Compound No. | Chemical structural formula | Spectrum data |
|---|---|---|
| 281 | 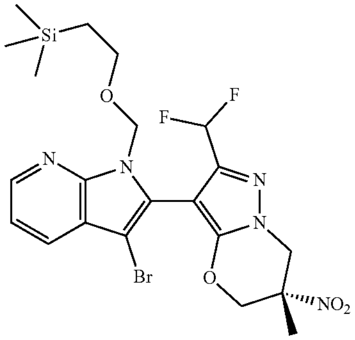 [SMILES: C[C@@]1([N+](=O)[O-])COc2c(-c3c(Br)c4cccnc4n3COCC[Si](C)(C)C)c(C(F)F)nn2C1] | $^1$H-NMR (400 MHz, $CDCl_3$) δ −0.11-−0.08 (m, 9H), 0.78-0.89 (m, 2H), 1.84 (d, J = 2.9 Hz, 3H), 3.34-3.47 (m, 2H), 4.27-4.42 (m, 2H), 4.96 (dt, J = 12.2, 2.1 Hz, 1H), 5.25 (d, J = 14.1 Hz, 1H), 5.41-5.68 (m, 2H), 6.65 (td, J = 54.2, 10.7 Hz, 1H), 7.18 (dd, J = 7.9, 4.7 Hz, 1H), 7.86 (dt, J = 7.9, 2.0 Hz, 1H), 8.39 (ddd, J = 8.3, 4.8, 1.6 Hz, 1H); MS ($ESI^+$): 558 $[M + H]^+$. |
| 282 | 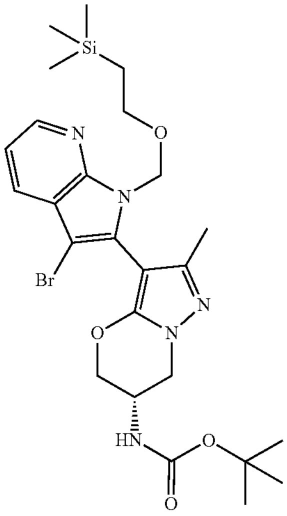 [SMILES: Cc1nn2c(c1-c1c(Br)c3cccnc3n1COCC[Si](C)(C)C)OC[C@@H](NC(=O)OC(C)(C)C)C2] | $^1$H-NMR (400 MHz, DMSO-$d_6$) δ −0.21-0.13 (m, 9H), 0.59-0.80 (m, 2H), 1.36-1.47 (m, 9H), 2.02-2.09 (m, 3H), 3.24-3.37 (m, 2H), 3.96-4.35 (m, 5H), 5.29-5.39 (m, 1H), 5.68-5.74 (m, 1H), 7.25-7.30 (m, 1H), 7.40-7.54 (m, 1H), 7.86-7.90 (m, 1H), 8.35-8.38 (m, 1H). |
| 283 | 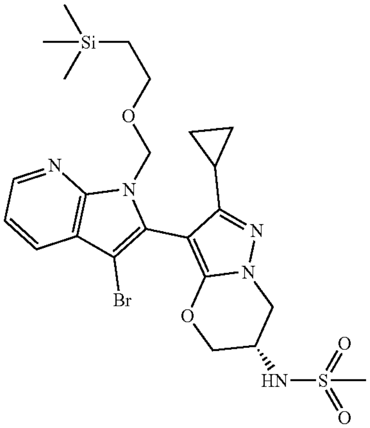 [SMILES: C[Si](C)(C)CCOCn1c(-c2c(C3CC3)nn3c2OC[C@@H](NS(C)(=O)=O)C3)c(Br)c2cccnc21] | $^1$H-NMR (400 MHz, $CDCl_3$) δ −0.11-−0.07 (m, 9H), 0.77-1.01 (m, 6H), 1.67-1.69 (m, 1H), 3.01-3.07 (m, 3H), 3.42-3.54 (m, 2H), 4.23-4.40 (m, 5H), 5.39-5.68 (m, 1H), 5.77-5.80 (m, 1H), 7.19 (dd, J = 7.8, 4.7 Hz, 1H), 7.86-7.89 (m, 1H), 8.36-8.38 (m, 1H); MS ($ESI^+$): 582 $[M + H]^+$. |

(142) Reference Procedure of 3-(3-(2-chlorothiophen-3-yl)-1-((2-(trimethylsilyl)ethoxy)methyl)-1H-pyrrolo[2,3-b]pyridin-2-yl)-2-(difluoromethyl)-6,7-dihydro-5H-pyrazolo[5,1-b][1,3]oxazine (284)

(284)

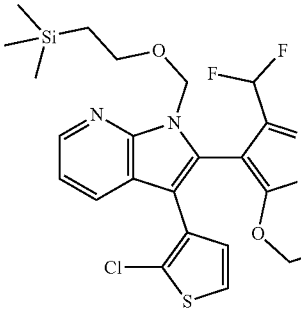

The compound 284 was synthesized from compound 270 and the corresponding boronic acid using conditions analogous to compound 237; MS ($ESI^+$): 537 $[M+H]^+$.

(143) Reference Procedure of (S)-6-((tert-butyldiphenylsilyl)oxy)-3-(3-(2-chloro-5-methylthiophen-3-yl)-1-((2-(trimethylsilyl)ethoxy)methyl)-1H-pyrrolo[2,3-b]pyridin-2-yl)-2-(difluoromethyl)-6,7-dihydro-5H-pyrazolo[5,1-b][1,3]oxazine (285)

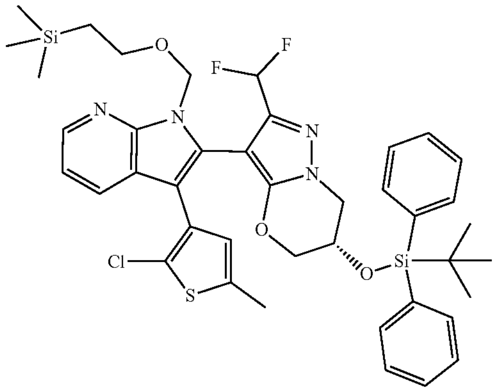 [SMILES: Cc1cc(-c2c(-c3c(C(F)F)nn4c3OC[C@@H](O[Si](c3ccccc3)(c3ccccc3)C(C)(C)C)C4)n(COCC[Si](C)(C)C)c3ncccc23)c(Cl)s1]

The compound 285 was synthesized from compounds 275 and 134 using conditions analogous to compound 237; $^1$H-NMR (400 MHz, DMSO-$d_6$) δ −0.26-−0.16 (m, 9H), 0.61-0.76 (m, 2H), 0.97-1.00 (m, 9H), 1.97-2.35 (m, 3H), 3.18-3.29 (m, 2H), 3.93-3.99 (m, 1H), 4.14-4.32 (m, 3H), 4.46-4.53 (m, 1H), 5.37-5.82 (m, 2H), 6.26-6.85 (m, 2H), 7.26 (ddd, J=31.9, 7.9, 4.7 Hz, 1H), 7.36-7.54 (m, 8H), 7.59-7.66 (m, 2H), 7.79-7.92 (m, 1H), 8.35-8.41 (m, 1H); MS ($ESI^+$): 805 $[M+H]^+$.

(144) Reference Procedure of 2-(difluoromethyl)-3-(3-(2-methoxypyridin-3-yl)-1-((2-(trimethylsilyl)ethoxy)methyl)-1H-pyrrolo[2,3-b]pyridin-2-yl)-6,7-dihydro-5H-pyrazolo[5,1-b][1,3]oxazine (286)

(286)

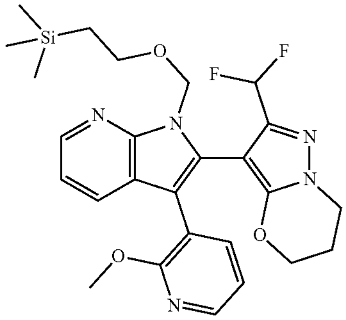

The compound 286 was synthesized from compound 270 and the corresponding boronic acid using conditions analogous to compound 237; $^1$H-NMR (400 MHz, $CDCl_3$) δ −0.08-−0.06 (m, 9H), 0.82-0.97 (m, 2H), 2.13-2.32 (m, 2H), 3.53-3.58 (m, 2H), 3.87 (s, 3H), 4.05-4.10 (m, 1H), 4.17-4.27 (m, 3H), 5.51 (d, J=10.7 Hz, 1H), 5.72 (d, J=10.7 Hz, 1H), 6.55 (t, J=54.4 Hz, 1H), 6.85 (dd, J=7.3, 5.0 Hz, 1H), 7.11 (dd, J=7.9, 4.7 Hz, 1H), 7.45 (dd, J=7.3, 1.9 Hz, 1H), 7.75 (dd, J=7.9, 1.6 Hz, 1H), 8.12 (dd, J=5.0, 1.9 Hz, 1H), 8.38 (dd, J=4.7, 1.6 Hz, 1H); MS ($ESI^+$): 528 $[M+H]^+$.

The following compounds were also synthesized from the corresponding starting materials and reagents using conditions analogous to compound 237.

| Compound No. | Chemical structural formula | Spectrum data |
| --- | --- | --- |
| 287 | 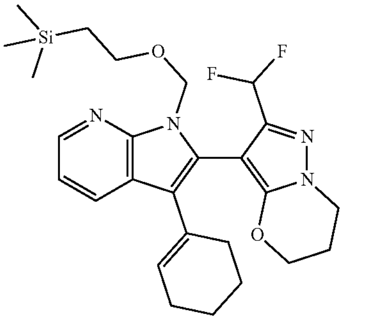 [SMILES: C[Si](C)(C)CCOCn1c(-c2c(C(F)F)nn3c2OCCC3)c(C2=CCCCC2)c2cccnc21] | $^1$H-NMR (400 MHz, $CDCl_3$) δ −0.11-−0.10 (m, 9H), 0.77-0.90 (m, 2H), 1.57-1.73 (m, 4H), 2.08-2.23 (m, 4H), 2.25-2.36 (m, 2H), 3.38-3.48 (m, 2H), 4.26-4.35 (m, 4H), 5.46 (d, J = 10.8 Hz, 1H), 5.62 (d, J = 10.8 Hz, 1H), 5.79-5.82 (m, 1H), 6.55 (t, J = 54.3 Hz, 1H), 7.08 (dd, J = 7.9, 4.8 Hz, 1H), 7.96 (dd, J = 7.9, 1.6 Hz, 1H), 8.32 (dd, J = 4.8, 1.6 Hz, 1H); MS ($ESI^+$): 501 $[M + H]^+$. |

-continued

| Compound No. | Chemical structural formula | Spectrum data |
|---|---|---|
| 288 | 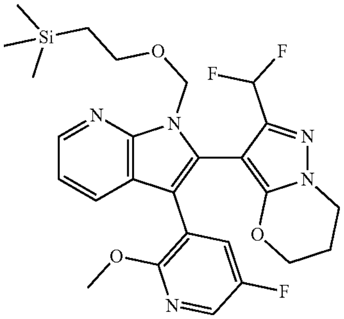 [SMILES: COc1ncc(F)cc1-c1c(-c2c(C(F)F)nn3c2OCCC3)n(COCC[Si](C)(C)C)c2ncccc12] | The crude compound obtained was used directly in the next step without purification. |
| 289 | 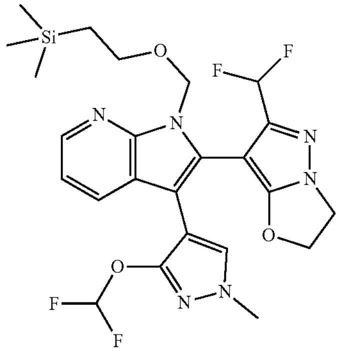 [SMILES: Cn1cc(-c2c(-c3c(C(F)F)nn4c3OCC4)n(COCC[Si](C)(C)C)c3ncccc23)c(OC(F)F)n1] | $^{1}$H-NMR (400 MHz, $CDCl_3$) δ −0.09 (s, 9H), 0.83-0.89 (m, 2H), 3.45-3.52 (m, 2H), 3.81 (s, 3H), 4.39-4.46 (m, 2H), 5.13 (t, J = 8.2 Hz, 2H), 5.60 (d, J = 10.7 Hz, 1H), 5.64 (d, J = 11.0 Hz, 1H), 6.37 (t, J = 54.3 Hz, 1H), 6.82 (t, J = 73.9 Hz, 1H), 7.14 (dd, J = 7.9, 4.7 Hz, 1H), 7.27 (s, 1H), 7.90 (dd, J = 7.9, 1.6 Hz, 1H), 8.38 (dd, J = 4.8, 1.6 Hz, 1H); MS ($ESI^+$): 553 $[M + H]^+$. |
| 290 | 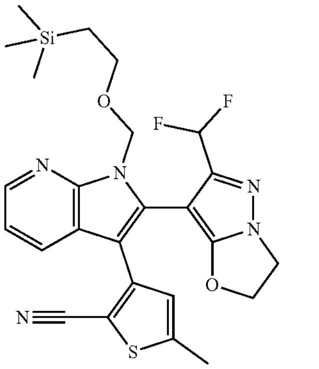 [SMILES: Cc1cc(-c2c(-c3c(C(F)F)nn4c3OCC4)n(COCC[Si](C)(C)C)c3ncccc23)c(C#N)s1] | $^{1}$H-NMR (400 MHz, $CDCl_3$) δ −0.10 (s, 9H), 0.81-0.91 (m, 2H), 2.56 (d, J = 1.0 Hz, 3H), 3.41-3.55 (m, 2H), 4.42-4.47 (m, 2H), 5.15-5.21 (m, 2H), 5.61 (d, J = 11.1 Hz, 1H), 5.79 (d, J = 11.1 Hz, 1H), 6.18 (t, J = 54.3 Hz, 1H), 6.91 (d, J = 1.0 Hz, 1H), 7.18 (dd, J = 7.9, 4.7 Hz, 1H), 7.93 (dd, J = 7.9, 1.6 Hz, 1H), 8.41 (dd, J = 4.7, 1.5 Hz, 1H); MS ($ESI^+$): 528 $[M + H]^+$. |
| 291 | 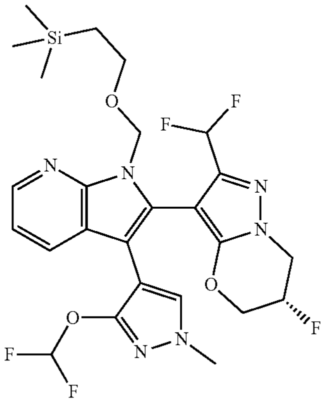 [SMILES: Cn1cc(-c2c(-c3c(C(F)F)nn4c3OC[C@@H](F)C4)n(COCC[Si](C)(C)C)c3ncccc23)c(OC(F)F)n1] | $^{1}$H-NMR (400 MHz, $CDCl_3$) δ −0.11- −0.08 (m, 9H), 0.76-0.93 (m, 2H), 3.38-3.55 (m, 2H), 3.73-3.83 (m, 3H), 4.16-4.65 (m, 4H), 5.20-5.36 (m, 1H), 5.46-5.75 (m, 2H), 6.24-6.99 (m, 2H), 7.08-7.35 (m, 2H), 7.85-8.00 (m, 1H), 8.36-8.41 (m, 1H); MS ($ESI^+$): 585 $[M + H]^+$. |

-continued

| Compound No. | Chemical structural formula | Spectrum data |
|---|---|---|
| 292 | 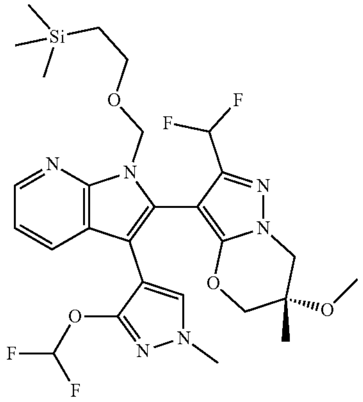 [SMILES: CO[C@]1(C)COc2c(-c3c(-c4cn(C)nc4OC(F)F)c4cccnc4n3COCC[Si](C)(C)C)c(C(F)F)nn2C1] | $^1$H-NMR (400 MHz, $CDCl_3$) δ −0.11-−0.08 (m, 9H), 0.79-0.91 (m, 2H), 1.34-1.36 (m, 3H), 3.23-3.32 (m, 3H), 3.41-3.53 (m, 2H), 3.76-3.80 (m, 3H), 3.92-4.02 (m, 2H), 4.26-4.34 (m, 2H), 5.38-5.83 (m, 2H), 6.26-7.16 (m, 4H), 7.86-7.99 (m, 1H), 8.36-8.39 (m, 1H); MS (ESI$^+$): 611 [M + H]$^+$. |
| 293 | 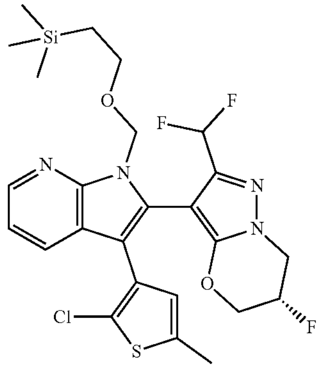 [SMILES: Cc1cc(-c2c(-c3c(C(F)F)nn4c3OC[C@@H](F)C4)n(COCC[Si](C)(C)C)c3ncccc23)c(Cl)s1] | The crude compound obtained was used directly in the next step without purification. |
| 294 | 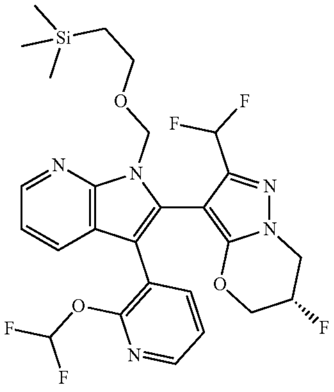 [SMILES: C[Si](C)(C)CCOCn1c(-c2c(C(F)F)nn3c2OC[C@@H](F)C3)c(-c2cccnc2OC(F)F)c2cccnc21] | $^1$H-NMR (400 MHz, $CDCl_3$) δ −0.13-−0.04 (m, 9H), 0.74-0.93 (m, 2H), 3.39-3.58 (m, 2H), 4.09-4.68 (m, 4H), 5.14-5.34 (m, 1H), 5.48-5.87 (m, 2H), 6.16-6.67 (m, 1H), 7.02-7.19 (m, 2H), 7.44-7.90 (m, 3H), 8.10-8.16 (m, 1H), 8.39-8.44 (m, 1H); MS (ESI$^+$): 582 [M + H]$^+$. |
| 295 | 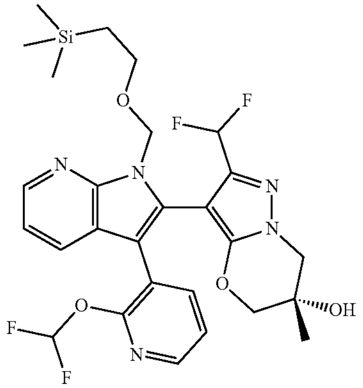 [SMILES: C[C@@]1(O)COc2c(-c3c(-c4cccnc4OC(F)F)c4cccnc4n3COCC[Si](C)(C)C)c(C(F)F)nn2C1] | The crude compound obtained was used directly in the next step without purification. |

-continued

| Compound No. | Chemical structural formula | Spectrum data |
|---|---|---|
| 296 | 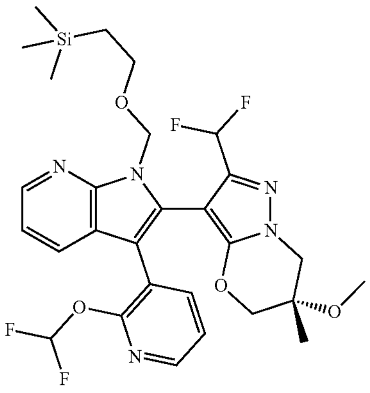 [SMILES: CO[C@]1(C)COc2c(-c3c(-c4cccnc4OC(F)F)c4cccnc4n3COCC[Si](C)(C)C)c(C(F)F)nn2C1] | $^1$H-NMR (400 MHz, $CDCl_3$) δ −0.15- −0.08 (m, 9H), 0.78-0.91 (m, 2H), 1.30-1.37 (m, 3H), 3.08-3.34 (m, 3H), 3.42-3.58 (m, 2H), 3.84-3.96 (m, 2H), 4.17-4.31 (m, 2H), 5.41-6.58 (m, 3H), 7.00-7.17 (m, 2H), 7.45-7.82 (m, 3H), 8.10-8.13 (m, 1H), 8.39-8.42 (m, 1H); MS ($ESI^+$): 608 $[M + H]^+$. |
| 297 | 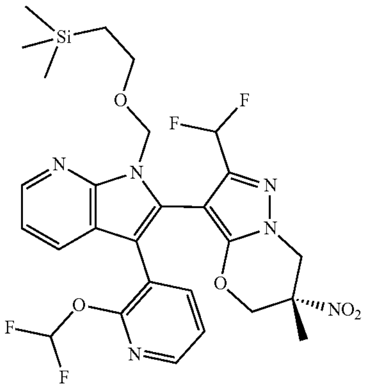 [SMILES: C[C@@]1([N+](=O)[O-])COc2c(-c3c(-c4cccnc4OC(F)F)c4cccnc4n3COCC[Si](C)(C)C)c(C(F)F)nn2C1] | The crude compound obtained was used directly in the next step without purification. |
| 298 | 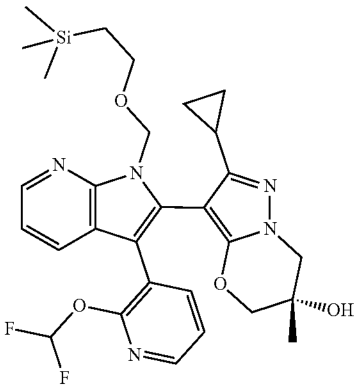 [SMILES: C[C@@]1(O)COc2c(-c3c(-c4cccnc4OC(F)F)c4cccnc4n3COCC[Si](C)(C)C)c(C3CC3)nn2C1] | $^1$H-NMR (400 MHz, $CDCl_3$) δ −0.13- −0.11 (m, 9H), 0.24-0.40 (m, 2H), 0.77-0.88 (m, 4H), 1.30-1.34 (m, 1H), 1.40 (d, J = 2.9 Hz, 3H), 3.46-3.54 (m, 2H), 3.93-4.09 (m, 4H), 5.68 (dd, J = 20.9, 10.9 Hz, 1H), 5.80 (dd, J = 18.9, 10.9 Hz, 1H), 7.07-7.16 (m, 2H), 7.48-7.83 (m, 3H), 8.11-8.14 (m, 1H), 8.38-8.40 (m, 1H); MS ($ESI^+$): 584 $[M + H]^+$. |
| 299 | 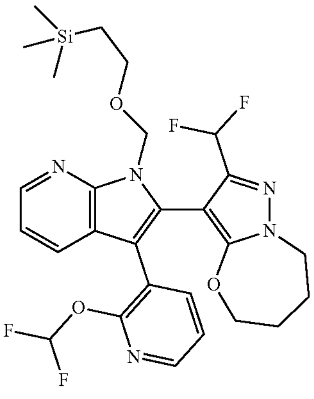 [SMILES: C[Si](C)(C)CCOCn1c(-c2c(C(F)F)nn3c2OCCCC3)c(-c2cccnc2OC(F)F)c2cccnc21] | $^1$H-NMR (400 MHz, $CDCl_3$) δ −0.09 (s, 9H), 0.81-0.91 (m, 2H), 1.68-1.81 (m, 1H), 1.86-2.01 (m, 3H), 3.20-3.33 (m, 1H), 3.45-3.57 (m, 2H), 3.96-4.04 (m, 1H), 4.17-4.24 (m, 1H), 4.26-4.36 (m, 1H), 5.65 (s, 2H), 6.55 (t, J = 54.5 Hz, 1H), 7.07 (dd, J = 7.4, 4.9 Hz, 1H), 7.16 (dd, J = 7.9, 4.7 Hz, 1H), 7.53 (t, J = 73.3 Hz, 1H), 7.61 (dd, J = 7.4, 1.9 Hz, 1H), 7.80 (dd, J = 7.9, 1.6 Hz, 1H), 8.12 (dd, J = 4.9, 1.8 Hz, 1H), 8.41 (dd, J = 4.7, 1.6 Hz, 1H); MS ($ESI^+$): 578 $[M + H]^+$. |

-continued
| Compound No. | Chemical structural formula | Spectrum data |
|---|---|---|
| 300 | 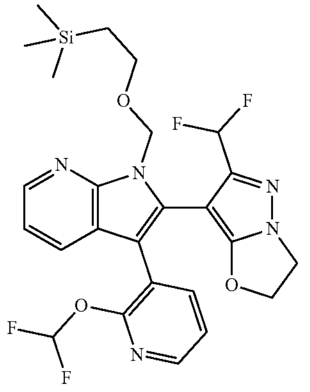 [SMILES: C[Si](C)(C)CCOCn1c(-c2c(C(F)F)nn3c2OCC3)c(-c2cccnc2OC(F)F)c2cccnc21] | $^1$H-NMR (400 MHz, $CDCl_3$) δ −0.10 (s, 9H), 0.83-0.91 (m, 2H), 3.44-3.57 (m, 2H), 4.32-4.47 (m, 2H), 5.06-5.19 (m, 2H), 5.65 (d, J = 11.0 Hz, 1H), 5.72 (d, J = 11.0 Hz, 1H), 6.27 (t, J = 54.2 Hz, 1H), 7.11-7.18 (m, 2H), 7.46 (t, J = 73.4 Hz, 1H), 7.74 (dd, J = 7.4, 1.8 Hz, 1H), 7.80 (dd, J = 7.9, 1.6 Hz, 1H), 8.13 (dd, J = 4.9, 1.9 Hz, 1H), 8.41 (dd, J = 4.7, 1.6 Hz, 1H); MS (ESI$^+$): 550 [M + H]$^+$. |
| 301 | 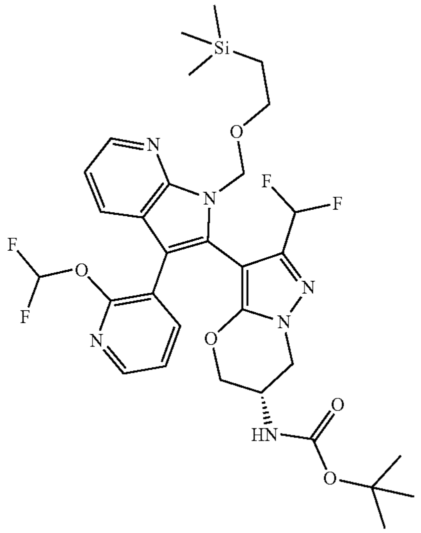 [SMILES: CC(C)(C)OC(=O)N[C@@H]1COc2c(-c3c(-c4cccnc4OC(F)F)c4cccnc4n3COCC[Si](C)(C)C)c(C(F)F)nn2C1] | $^1$H-NMR (400 MHz, $CDCl_3$) δ −0.11- −0.05 (m, 9H), 0.83-0.97 (m, 2H), 1.44-1.51 (m, 9H), 3.53-3.61 (m, 2H), 4.15-4.58 (m, 6H), 5.52-5.77 (m, 3H), 6.19-6.73 (m, 1H), 7.09-7.18 (m, 2H), 7.30-7.83 (m, 2H), 8.12-8.15 (m, 1H), 8.39-8.42 (m, 1H) MS (ESI$^+$): 679 [M + H]$^+$. |
| 302 | 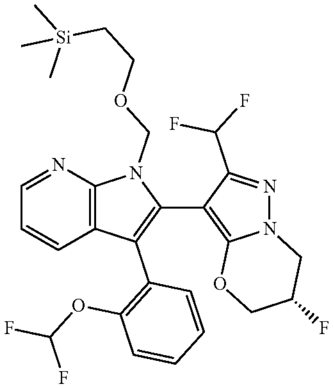 | $^1$H-NMR (400 MHz, $CDCl_3$) δ −0.12- −0.08 (m, 9H), 0.76-0.93 (m, 2H), 3.42-3.53 (m, 2H), 3.78-3.96 (m, 1H), 4.15-4.61 (m, 3H), 5.13-5.30 (m, 1H), 5.55-5.81 (m, 2H), 6.00-6.61 (m, 2H), 7.12-7.25 (m, 3H), 7.27-7.35 (m, 2H), 7.80-7.85 (m, 1H), 8.38-8.43 (m, 1H); MS (ESI$^+$): 581 [M + H]$^+$. |

-continued

| Compound No. | Chemical structural formula | Spectrum data |
|---|---|---|
| 303 | 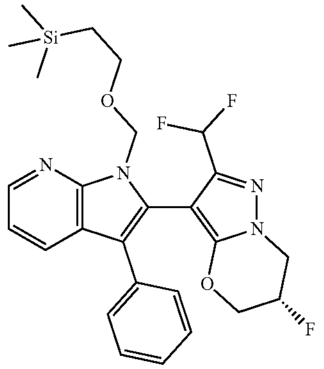 [SMILES: C[Si](C)(C)CCOCn1c(-c2c(C(F)F)nn3c2OC[C@@H](F)C3)c(-c2ccccc2)c2cccnc21] | $^1$H-NMR (400 MHz, $CDCl_3$) δ −0.09-−0.05 (m, 9H), 0.79-0.95 (m, 2H), 3.45-3.55 (m, 2H), 3.69-4.63 (m, 4H), 5.13-5.32 (m, 1H), 5.55-5.71 (m, 2H), 6.16-6.79 (m, 1H), 7.13-7.17 (m, 1H), 7.22-8.27 (m, 6H), 8.38-8.42 (m, 1H); MS (ESI$^+$): 515 [M + H]$^+$. |
| 304 | 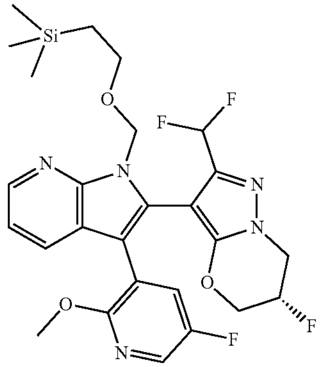 [SMILES: COc1ncc(F)cc1-c1c(-c2c(C(F)F)nn3c2OC[C@@H](F)C3)n(COCC[Si](C)(C)C)c2ncccc12] | $^1$H-NMR (400 MHz, $CDCl_3$) δ −0.07-−0.07 (9H, m), 0.80-0.97 (2H, m), 3.51-3.60 (2H, m), 3.84-3.86 (3H, m), 4.18-4.59 (4H, m), 5.14-5.30 (1H, m), 5.48-5.73 (2H, m), 6.28-6.75 (1H, m), 6.84-6.89 (1H, m), 7.11-7.14 (1H, m), 7.45-7.52 (1H, m), 7.74-7.80 (1H, m), 8.11-8.13 (1H, m), 8.38-8.41 (1H, m); MS (ESI$^+$): 546 [M + H]$^+$. |
| 305 | 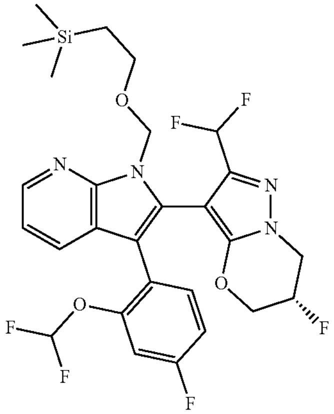 [SMILES: C[Si](C)(C)CCOCn1c(-c2c(C(F)F)nn3c2OC[C@@H](F)C3)c(-c2ccc(F)cc2OC(F)F)c2cccnc21] | $^1$H-NMR (400 MHz, $CDCl_3$) δ −0.10-−0.05 (m, 9H), 0.79-0.96 (m, 2H), 3.47-3.60 (m, 2H), 3.79-3.85 (m, 3H), 3.92-4.32 (m, 1H), 4.32-4.48 (m, 1H), 4.51-4.70 (m, 2H), 5.17-5.34 (m, 1H), 5.50-5.71 (m, 2H), 6.30-6.82 (m, 1H), 7.12-7.17 (m, 1H), 7.25-7.33 (m, 1H), 7.74-7.82 (m, 1H), 7.93-7.96 (m, 1H), 8.38-8.43 (m, 1H); MS (ESI$^+$): 599 [M + H]$^+$. |
| 306 | 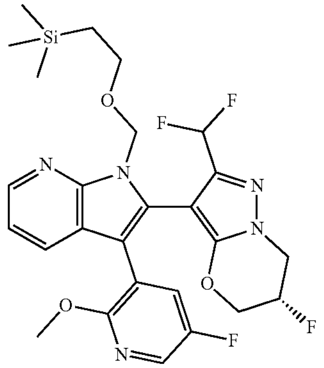 [SMILES: COc1ncc(F)cc1-c1c(-c2c(C(F)F)nn3c2OC[C@@H](F)C3)n(COCC[Si](C)(C)C)c2ncccc12] | $^1$H-NMR (400 MHz, $CDCl_3$) δ −0.10-−0.05 (m, 9H), 0.79-0.96 (m, 2H), 3.47-3.60 (m, 2H), 3.79-3.85 (m, 3H), 3.92-4.32 (m, 1H), 4.32-4.48 (m, 1H), 4.51-4.70 (m, 2H), 5.17-5.34 (m, 1H), 5.50-5.71 (m, 2H), 6.30-6.82 (m, 1H), 7.12-7.17 (m, 1H), 7.25-7.33 (m, 1H), 7.74-7.82 (m, 1H), 7.93-7.96 (m, 1H), 8.38-8.43 (m, 1H); MS (ESI$^+$): 564 [M + H]$^+$. |

-continued

| Compound No. | Chemical structural formula | Spectrum data |
|---|---|---|
| 307 | 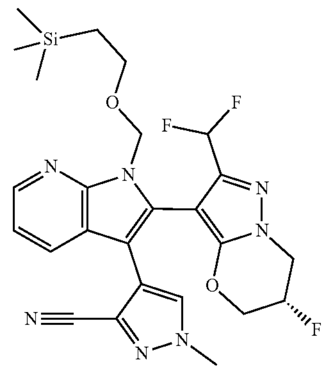 [SMILES: Cn1cc(-c2c(-c3c(C(F)F)nn4c3OC[C@@H](F)C4)n(COCC[Si](C)(C)C)c3ncccc23)c(C#N)n1] | $^1$H-NMR (400 MHz, $CDCl_3$) δ −0.10- −0.06 (m, 9H), 0.74-0.94 (m, 2H), 3.36-3.57 (m, 2H), 3.91-4.04 (m, 3H), 4.09-4.64 (m, 4H), 5.19-5.36 (m, 1H), 5.46-5.88 (m, 2H), 6.11-6.58 (m, 1H), 7.14-7.22 (m, 1H), 7.24-7.65 (m, 1H), 7.84-8.03 (m, 1H), 8.40-8.44 (m, 1H); MS ($ESI^+$): 544 $[M + H]^+$. |
| 308 | 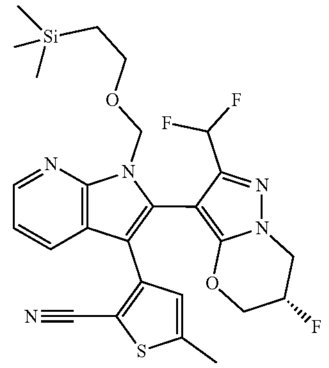 [SMILES: Cc1cc(-c2c(-c3c(C(F)F)nn4c3OC[C@@H](F)C4)n(COCC[Si](C)(C)C)c3ncccc23)c(C#N)s1] | $^1$H-NMR (400 MHz, $CDCl_3$) δ −0.12- −0.08 (m, 9H), 0.72-0.92 (m, 2H), 2.46-2.60 (m, 3H), 3.33-3.55 (m, 2H), 4.20-4.65 (m, 4H), 5.21-5.35 (m, 1H), 5.45-5.70 (m, 1H), 5.92-6.61 (m, 2H), 6.62-7.03 (m, 1H), 7.16-7.23 (m, 1H), 7.90-8.03 (m, 1H), 8.41-8.45 (m, 1H); MS ($ESI^+$): 560 $[M + H]^+$. |
| 309 | 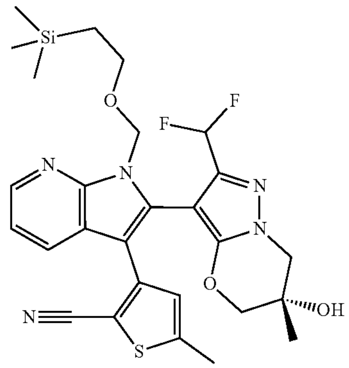 [SMILES: Cc1cc(-c2c(-c3c(C(F)F)nn4c3OC[C@@](C)(O)C4)n(COCC[Si](C)(C)C)c3ncccc23)c(C#N)s1] | $^1$H-NMR (400 MHz, $CDCl_3$) δ −0.12- −0.10 (m, 9H), 0.77-0.93 (m, 2H), 1.39-1.45 (m, 3H), 2.56-2.60 (m, 3H), 3.37-3.54 (m, 2H), 4.16-4.28 (m, 4H), 4.72-7.08 (m, 4H), 7.18 (dd, J = 7.9, 4.7 Hz, 1H), 7.93 (dd, J = 7.9, 1.5 Hz, 1H), 8.40-8.43 (m, 1H); MS ($ESI^+$): 572 $[M + H]^+$. |
| 310 | 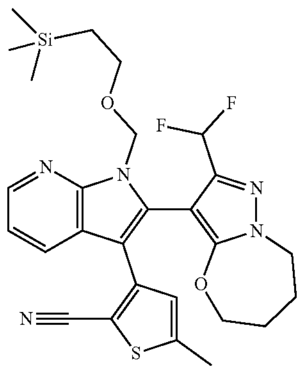 [SMILES: Cc1cc(-c2c(-c3c(C(F)F)nn4c3OCCCC4)n(COCC[Si](C)(C)C)c3ncccc23)c(C#N)s1] | $^1$H-NMR (400 MHz, $CDCl_3$) δ −0.11 (s, 9H), 0.77-0.90 (m, 2H), 1.78-2.04 (m, 4H), 2.51 (d, J = 1.0 Hz, 3H), 3.37-3.48 (m, 2H), 3.61-3.71 (m, 1H), 4.11-4.14 (m, 1H), 4.17-4.26 (m, 1H), 4.31-4.45 (m, 1H), 5.63 (d, J = 11.0 Hz, 1H), 5.74 (d, J = 11.0 Hz, 1H), 6.39 (t, J = 54.5 Hz, 1H), 6.73 (d, J = 1.0 Hz, 1H), 7.20 (dd, J = 7.9, 4.7 Hz, 1H), 7.97 (dd, J = 7.9, 1.5 Hz, 1H), 8.42 (dd, J = 4.7, 1.5 Hz, 1H); MS ($ESI^+$): 556 $[M + H]^+$. |

-continued

| Compound No. | Chemical structural formula | Spectrum data |
|---|---|---|
| 311 | 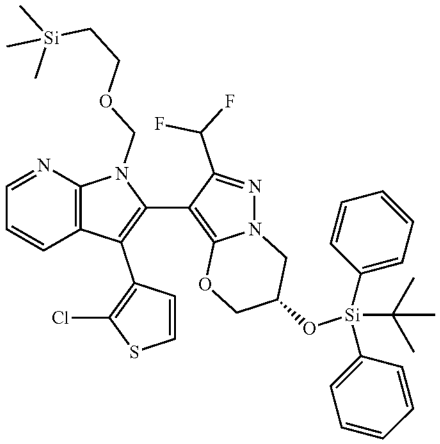 [SMILES: CC(C)(C)[Si](O[C@@H]1COc2c(-c3c(-c4ccsc4Cl)c4cccnc4n3COCC[Si](C)(C)C)c(C(F)F)nn2C1)(c1ccccc1)c1ccccc1] | The crude compound obtained was used directly in the next step without purification. |
| 312 | 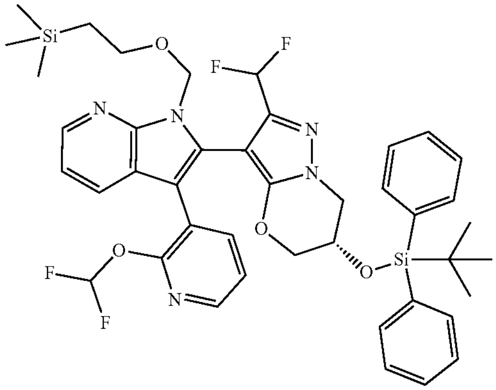 [SMILES: CC(C)(C)[Si](O[C@@H]1COc2c(-c3c(-c4cccnc4OC(F)F)c4cccnc4n3COCC[Si](C)(C)C)c(C(F)F)nn2C1)(c1ccccc1)c1ccccc1] | The crude compound obtained was used directly in the next step without purification. |
| 313 | 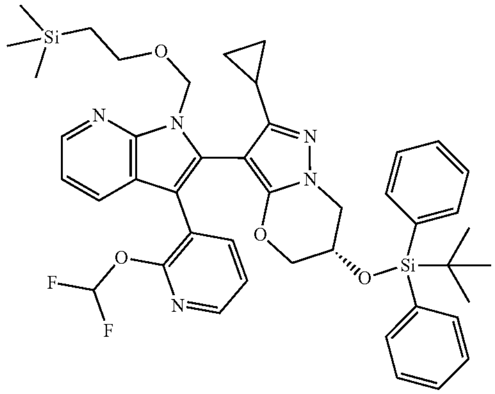 [SMILES: CC(C)(C)[Si](O[C@@H]1COc2c(-c3c(-c4cccnc4OC(F)F)c4cccnc4n3COCC[Si](C)(C)C)c(C3CC3)nn2C1)(c1ccccc1)c1ccccc1] | The crude compound obtained was used directly in the next step without purification. |
| 314 | 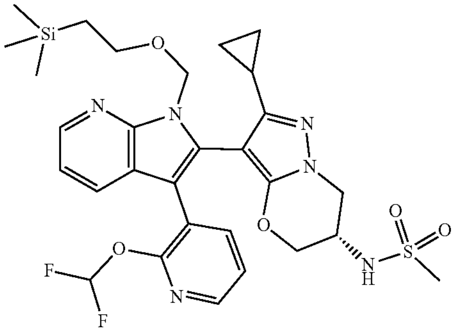 [SMILES: C[Si](C)(C)CCOCn1c(-c2c(C3CC3)nn3c2OC[C@@H](NS(C)(=O)=O)C3)c(-c2cccnc2OC(F)F)c2cccnc21] | The crude compound obtained was used directly in the next step without purification. |

-continued

| Compound No. | Chemical structural formula | Spectrum data |
|---|---|---|
| 315 | 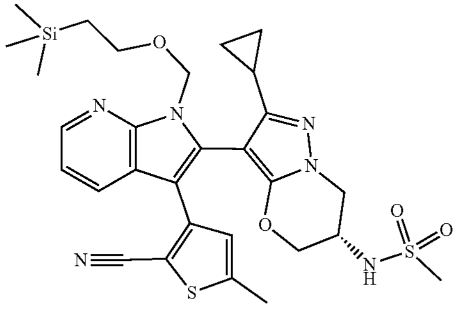 [SMILES: Cc1cc(-c2c(-c3c(C4CC4)nn4c3OC[C@@H](NS(C)(=O)=O)C4)n(COCC[Si](C)(C)C)c3ncccc23)c(C#N)s1] | The crude compound obtained was used directly in the next step without purification. |
| 316 | 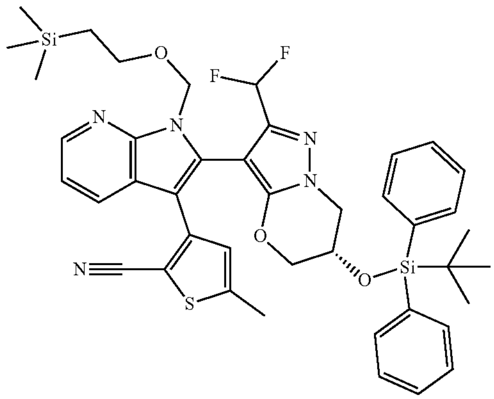 [SMILES: Cc1cc(-c2c(-c3c(C(F)F)nn4c3OC[C@@H](O[Si](c3ccccc3)(c3ccccc3)C(C)(C)C)C4)n(COCC[Si](C)(C)C)c3ncccc23)c(C#N)s1] | The crude compound obtained was used directly in the next step without purification. |
| 317 | 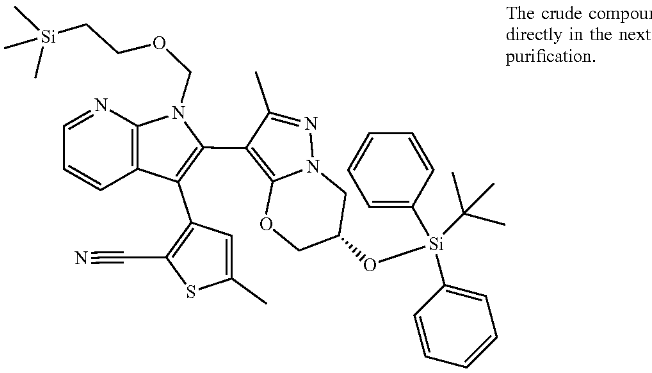 | The crude compound obtained was used directly in the next step without purification. |
| 318 | 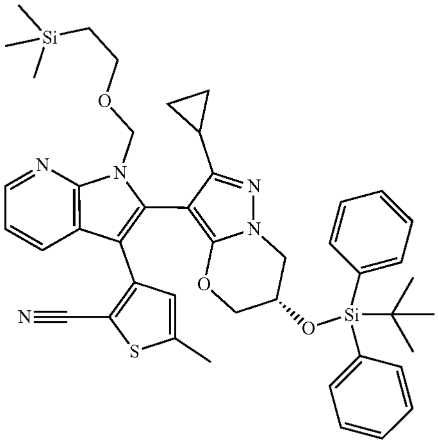 [SMILES: Cc1cc(-c2c(-c3c(C4CC4)nn4c3OC[C@@H](O[Si](c3ccccc3)(c3ccccc3)C(C)(C)C)C4)n(COCC[Si](C)(C)C)c3ncccc23)c(C#N)s1] | The crude compound obtained was used directly in the next step without purification. |

-continued
| Compound No. | Chemical structural formula | Spectrum data |
|---|---|---|
| 319 | 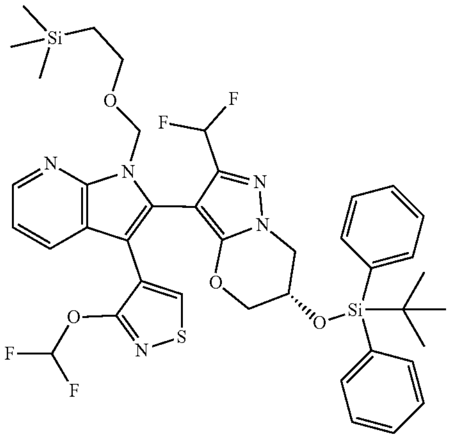 [SMILES: CC(C)(C)[Si](O[C@@H]1COc2c(-c3c(-c4csnc4OC(F)F)c4cccnc4n3COCC[Si](C)(C)C)c(C(F)F)nn2C1)(c1ccccc1)c1ccccc1] | $^1$H-NMR (400 MHz, $CDCl_3$) δ −0.18-−0.08 (m, 9H), 0.74-0.92 (m, 2H), 1.02-1.14 (m, 9H), 3.32-3.52 (m, 2H), 3.98-4.21 (m, 5H), 4.32-4.36 (m, 1H), 5.45-5.96 (m, 2H), 6.26-6.61 (m, 1H), 7.15-7.23 (m, 1H), 7.35-7.69 (m, 10H), 7.85-7.93 (m, 1H), 8.33-8.47 (m, 2H); MS (ESI$^+$): 824 [M + H]$^+$. |
| 320 | 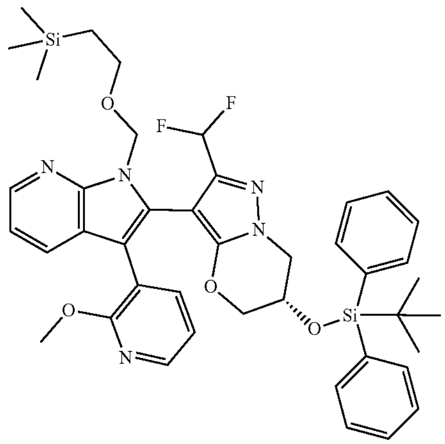 [SMILES: COc1ncccc1-c1c(-c2c(C(F)F)nn3c2OC[C@@H](O[Si](c2ccccc2)(c2ccccc2)C(C)(C)C)C3)n(COCC[Si](C)(C)C)c2ncccc12] | The crude compound obtained was used directly in the next step without purification. |
| 321 | 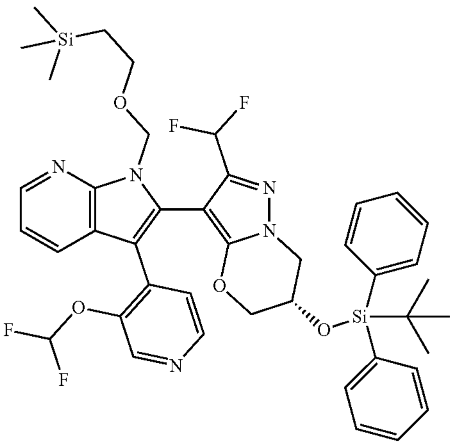 [SMILES: CC(C)(C)[Si](O[C@@H]1COc2c(-c3c(-c4ccncc4OC(F)F)c4cccnc4n3COCC[Si](C)(C)C)c(C(F)F)nn2C1)(c1ccccc1)c1ccccc1] | The crude compound obtained was used directly in the next step without purification. |

-continued
| Compound No. | Chemical structural formula | Spectrum data |
|---|---|---|
| 322 | 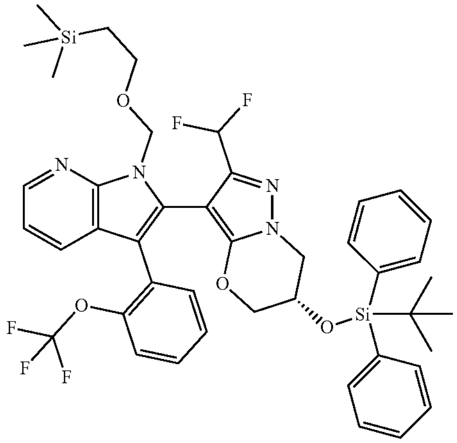 [SMILES: CC(C)(C)[Si](O[C@@H]1COc2c(-c3c(-c4ccccc4OC(F)(F)F)c4cccnc4n3COCC[Si](C)(C)C)c(C(F)F)nn2C1)(c1ccccc1)c1ccccc1] | The crude compound obtained was used directly in the next step without purification. |
| 323 | 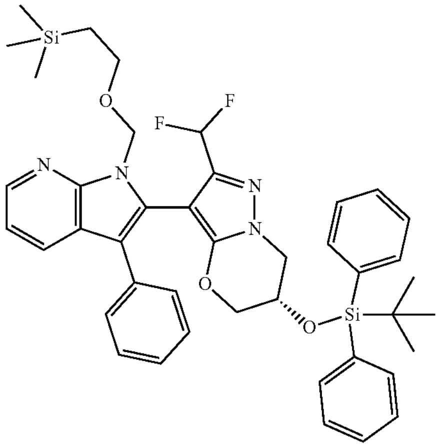 [SMILES: CC(C)(C)[Si](O[C@@H]1COc2c(-c3c(-c4ccccc4)c4cccnc4n3COCC[Si](C)(C)C)c(C(F)F)nn2C1)(c1ccccc1)c1ccccc1] | $^1$H-NMR (400 MHz, $CDCl_3$) δ −0.18-−0.09 (m, 9H), 0.74-0.94 (m, 2H), 1.01-1.11 (m, 9H), 3.31-3.52 (m, 2H), 4.07-4.37 (m, 5H), 5.45-6.75 (m, 3H), 7.08-7.23 (m, 2H), 7.28-7.52 (m, 10H), 7.55-7.69 (m, 4H), 7.80-8.07 (m, 1H), 8.33-8.41 (m, 1H); MS (ESI$^+$): 751 [M + H]$^+$. |
| 324 | 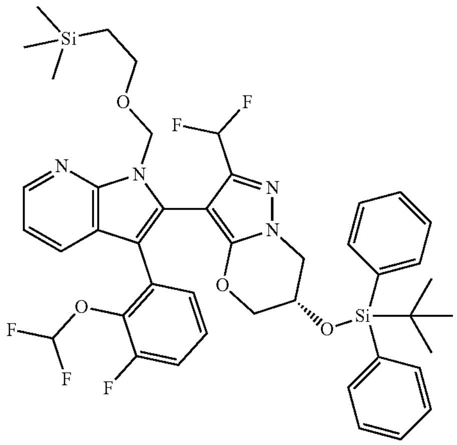 [SMILES: CC(C)(C)[Si](O[C@@H]1COc2c(-c3c(-c4cccc(F)c4OC(F)F)c4cccnc4n3COCC[Si](C)(C)C)c(C(F)F)nn2C1)(c1ccccc1)c1ccccc1] | $^1$H-NMR (400 MHz, $CDCl_3$) δ −0.18-−0.09 (m, 9H), 0.77-0.87 (m, 2H), 1.01-1.10 (m, 9H), 3.41-4.27 (m, 7H), 5.50-6.42 (m, 2H), 6.99-7.17 (m, 4H), 7.35-7.86 (m, 13H), 8.39-8.42 (m, 1H); MS (ESI$^+$): 835 [M + H]$^+$. |

-continued
| Compound No. | Chemical structural formula | Spectrum data |
|---|---|---|
| 325 | 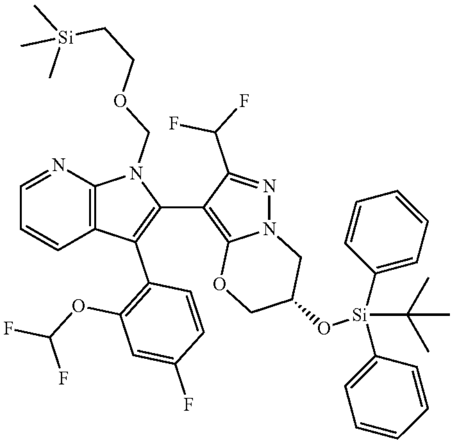 [SMILES: CC(C)(C)[Si](O[C@@H]1COc2c(-c3c(-c4ccc(F)cc4OC(F)F)c4cccnc4n3COCC[Si](C)(C)C)c(C(F)F)nn2C1)(c1ccccc1)c1ccccc1] | $^1$H-NMR (400 MHz, $CDCl_3$) δ −0.13 (dt, J = 8.0, 3.3 Hz, 9H), 0.78-0.88 (m, 2H), 1.01-1.07 (m, 9H), 3.39-3.53 (m, 2H), 4.01-4.11 (m, 4H), 4.28 (d, J = 54.2 Hz, 1H), 5.46-6.45 (m, 2H), 6.97-7.16 (m, 2H), 7.35-7.79 (m, 15H), 8.38-8.42 (m, 1H); MS (ESI$^+$): 835 [M + H]$^+$. |
| 326 | 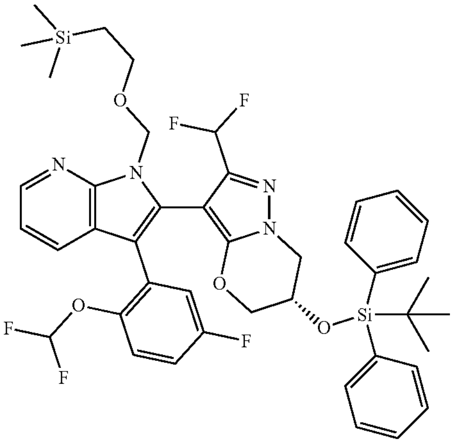 [SMILES: CC(C)(C)[Si](O[C@@H]1COc2c(-c3c(-c4cc(F)ccc4OC(F)F)c4cccnc4n3COCC[Si](C)(C)C)c(C(F)F)nn2C1)(c1ccccc1)c1ccccc1] | The crude compound obtained was used directly in the next step without purification. |
| 327 | 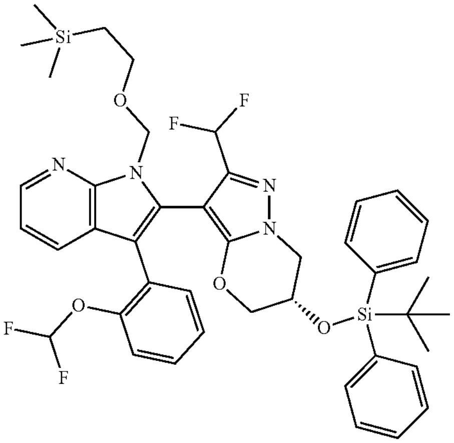 [SMILES: CC(C)(C)[Si](O[C@@H]1COc2c(-c3c(-c4ccccc4OC(F)F)c4cccnc4n3COCC[Si](C)(C)C)c(C(F)F)nn2C1)(c1ccccc1)c1ccccc1] | $^1$H-NMR (400 MHz, $CDCl_3$) δ −0.18- −0.11 (m, 9H), 0.77-0.90 (m, 2H), 1.02- 1.13 (m, 9H), 3.41-3.47 (m, 2H), 4.07- 4.28 (m, 5H), 5.48-6.44 (m, 3H), 7.00- 7.15 (m, 3H), 7.32-7.84 (m, 14H), 8.38- 8.41 (m, 1H); MS (ESI$^+$): 817 [M + H]$^+$. |

-continued
| Compound No. | Chemical structural formula | Spectrum data |
|---|---|---|
| 328 | 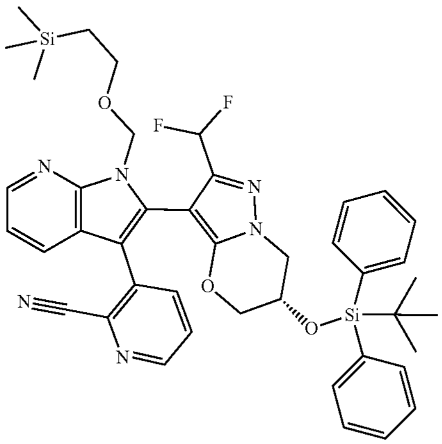 [SMILES: CC(C)(C)[Si](O[C@@H]1COc2c(-c3c(-c4cccnc4C#N)c4cccnc4n3COCC[Si](C)(C)C)c(C(F)F)nn2C1)(c1ccccc1)c1ccccc1] | The crude compound obtained was used directly in the next step without purification. |
| 329 | 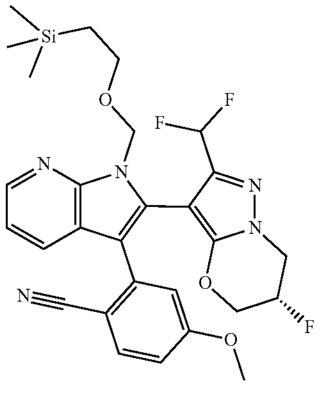 [SMILES: COc1ccc(C#N)c(-c2c(-c3c(C(F)F)nn4c3OC[C@@H](F)C4)n(COCC[Si](C)(C)C)c3ncccc23)c1] | $^1$H-NMR (400 MHz, $CDCl_3$) δ −0.15-−0.04 (m, 9H), 0.71-0.93 (m, 2H), 3.34-3.58 (m, 2H), 3.72-3.91 (m, 3H), 4.19-4.64 (m, 4H), 5.10-6.36 (m, 4H), 6.60-7.13 (m, 2H), 7.15-7.21 (m, 1H), 7.53-7.65 (m, 1H), 7.85-7.90 (m, 1H), 8.41-8.46 (m, 1H); MS (ESI$^+$): 570 [M + H]$^+$. |
| 330 | 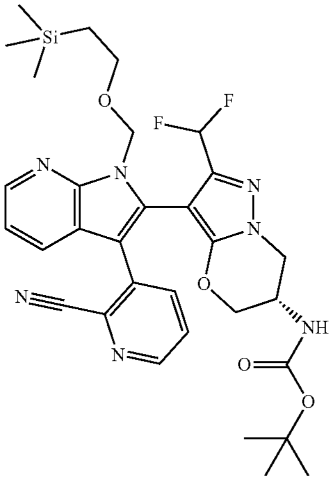 [SMILES: CC(C)(C)OC(=O)N[C@@H]1COc2c(-c3c(-c4cccnc4C#N)c4cccnc4n3COCC[Si](C)(C)C)c(C(F)F)nn2C1] | $^1$H-NMR (400 MHz, $CDCl_3$) δ −0.15-−0.06 (m, 9H), 0.74-0.93 (m, 2H), 1.45-1.52 (m, 9H), 3.37-3.58 (m, 2H), 4.25-4.53 (m, 5H), 5.52-6.42 (m, 3H), 7.20 (dd, J = 7.9, 4.7 Hz, 1H), 7.52-7.60 (m, 1H), 7.81-7.98 (m, 2H), 8.44-8.47 (m, 1H), 8.63-8.66 (m, 1H); MS (ESI$^+$): 638 [M + H]$^+$. |

-continued
| Compound No. | Chemical structural formula | Spectrum data |
| --- | --- | --- |
| 331 | 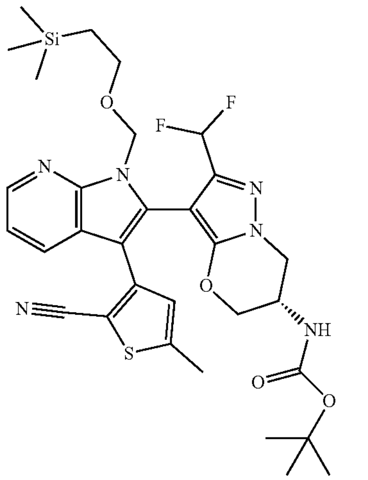 [SMILES: Cc1cc(-c2c(-c3c(C(F)F)nn4c3OC[C@@H](NC(=O)OC(C)(C)C)C4)n(COCC[Si](C)(C)C)c3ncccc23)c(C#N)s1] | The crude compound obtained was used directly in the next step without purification. |
| 332 | 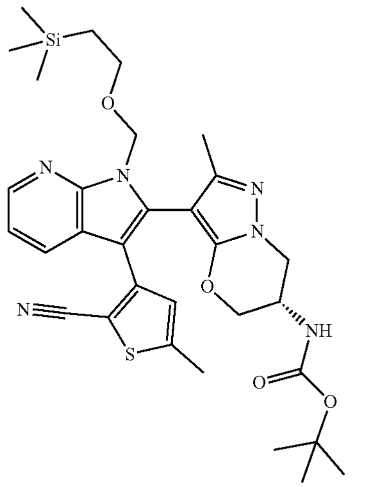 [SMILES: Cc1cc(-c2c(-c3c(C)nn4c3OC[C@@H](NC(=O)OC(C)(C)C)C4)n(COCC[Si](C)(C)C)c3ncccc23)c(C#N)s1] | $^1$H-NMR (400 MHz, $CDCl_3$) δ −0.15-−0.09 (m, 9H), 0.70-0.88 (m, 2H), 1.44-1.50 (m, 9H), 1.57-1.71 (m, 6H), 2.57-2.60 (m, 2H), 4.10-4.54 (m, 5H), 5.46-5.97 (m, 2H), 6.43-6.49 (m, 1H), 6.93-7.19 (m, 2H), 7.85-7.94 (m, 1H), 8.31-8.41 (m, 1H); MS ($ESI^+$): 621 $[M + H]^+$. |
| 333 | 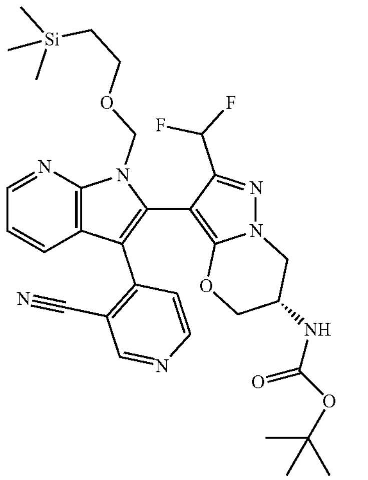 [SMILES: CC(C)(C)OC(=O)N[C@@H]1COc2c(-c3c(-c4ccncc4C#N)c4cccnc4n3COCC[Si](C)(C)C)c(C(F)F)nn2C1] | The crude compound obtained was used directly in the next step without purification. |

-continued
| Compound No. | Chemical structural formula | Spectrum data |
|---|---|---|
| 334 | 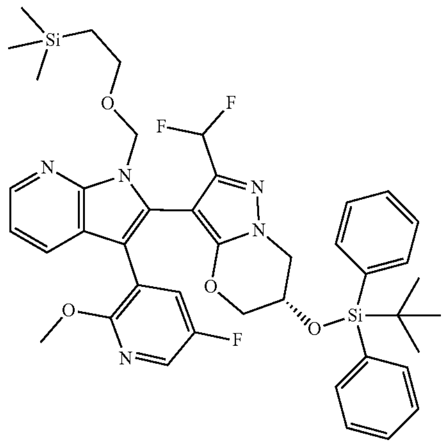 [SMILES: COc1ncc(F)cc1-c1c(-c2c(C(F)F)nn3c2OC[C@@H](O[Si](c2ccccc2)(c2ccccc2)C(C)(C)C)C3)n(COCC[Si](C)(C)C)c2ncccc12] | $^1$H-NMR (400 MHz, $CDCl_3$) δ −0.13-−0.07 (m, 9H), 0.77-0.97 (m, 2H), 0.99-1.10 (m, 9H), 3.46-3.59 (m, 2H), 3.74-4.30 (m, 8H), 5.38-5.88 (m, 2H), 6.35-6.67 (m, 1H), 7.13 (dd, J = 7.4, 4.7 Hz, 1H), 7.22-7.30 (m, 1H), 7.36-7.50 (m, 6H), 7.52-7.66 (m, 4H), 7.73-7.77 (m, 1H), 7.90 (d, J = 3.0 Hz, 1H), 8.37-8.42 (m, 1H); MS (ESI$^+$): 800 [M + H]$^+$. |
| 335 | 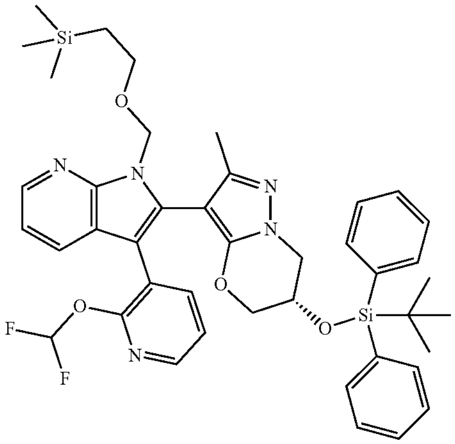 [SMILES: Cc1nn2c(c1-c1c(-c3cccnc3OC(F)F)c3cccnc3n1COCC[Si](C)(C)C)OC[C@@H](O[Si](c1ccccc1)(c1ccccc1)C(C)(C)C)C2] | $^1$H-NMR (400 MHz, $CDCl_3$) δ −0.18-−0.12 (m, 9H), 0.67-0.93 (m, 2H), 1.04-1.11 (m, 9H), 1.72-1.78 (m, 3H), 3.33-3.50 (m, 2H), 3.95-4.15 (m, 4H), 4.25-4.30 (m, 1H), 5.44-5.50 (m, 1H), 5.77-6.05 (m, 1H), 6.92-7.16 (m, 2H), 7.36-7.83 (m, 13H), 8.07-8.09 (m, 1H), 8.39 (ddd, J = 8.2, 4.7, 1.6 Hz, 1H); MS (ESI$^+$): 782 [M + H]$^+$. |
| 336 | 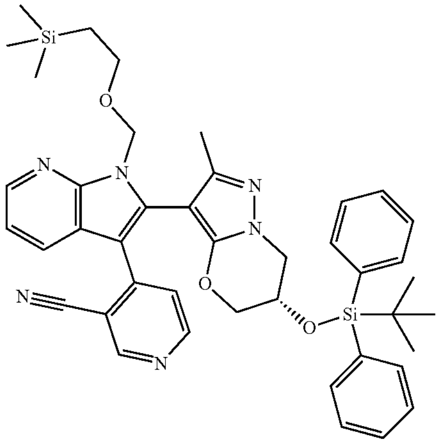 [SMILES: Cc1nn2c(c1-c1c(-c3ccncc3C#N)c3cccnc3n1COCC[Si](C)(C)C)OC[C@@H](O[Si](c1ccccc1)(c1ccccc1)C(C)(C)C)C2] | The crude compound obtained was used directly in the next step without purification. |

(145) Experimental procedure of 2-(difluoromethyl)-3-(3-(2-methoxypyridin-3-yl)-1H-pyrrolo[2,3-b]pyridin-2-yl)-6,7-dihydro-5H-pyrazolo[5,1-b][1,3]oxazine (EX.429)

EX. 429

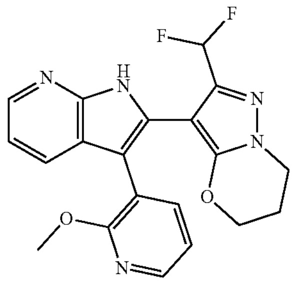

EX.429 was synthesized from compound 286 using conditions analogous to EX.420; $^1$H-NMR (400 MHz, DMSO-$d_6$) δ 2.07-2.20 (m, 2H), 3.74 (s, 3H), 4.07-4.20 (m, 4H), 6.63 (t, J=54.2 Hz, 1H), 6.95 (dd, J=7.2, 5.0 Hz, 1H), 7.07 (dd, J=8.0, 4.8 Hz, 1H), 7.42 (dd, J=7.2, 2.0 Hz, 1H), 7.70 (dd, J=8.0, 1.6 Hz, 1H), 8.10 (dd, J=5.0, 2.0 Hz, 1H), 8.24 (dd, J=4.8, 1.6 Hz, 1H), 11.80 (s, 1H); MS (ESI$^+$): 398 $[M+H]^+$.

The following compounds were also synthesized from the corresponding starting materials and reagents using conditions analogous to EX.420.

| Compound No. | Chemical structural formula | Spectrum data |
|---|---|---|
| EX.430 | 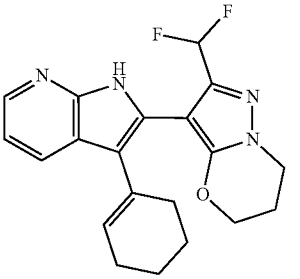 [SMILES: FC(F)c1nn2c(c1-c1[nH]c3ncccc3c1C1=CCCCC1)OCCC2] | $^1$H-NMR (400 MHz, DMSO-d6) δ 1.54-1.70 (m, 4H), 2.04-2.18 (m, 4H), 2.19-2.28 (m, 2H), 4.21 (t, J = 6.1 Hz, 2H), 4.30-4.39 (m, 2H), 5.63-5.69 (m, 1H), 6.80 (t, J = 54.0 Hz, 1H), 7.03 (dd, J = 7.9, 4.7 Hz, 1H), 7.92 (dd, J = 7.9, 1.6 Hz, 1H), 8.17 (dd, J = 4.7, 1.6 Hz, 1H), 11.44 (s, 1H); MS (ESI$^+$): 371 $[M + H]^+$. |
| EX.431 | 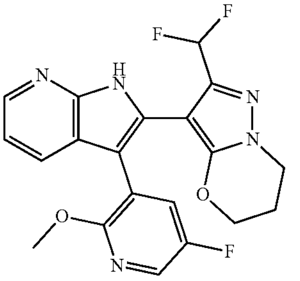 [SMILES: COc1ncc(F)cc1-c1c(-c2c(C(F)F)nn3c2OCCC3)[nH]c2ncccc12] | $^1$H-NMR (400 MHz, DMSO-$d_6$) δ 2.10-2.21 (m, 2H), 3.71 (s, 3H), 4.10-4.23 (m, 4H), 6.68 (t, J = 53.9 Hz, 1H), 7.10 (dd, J = 7.9, 4.7 Hz, 1H), 7.37 (dd, J = 8.8, 3.0 Hz, 1H), 7.76 (dd, J = 7.9, 1.5 Hz, 1H), 8.08 (d, J = 3.0 Hz, 1H), 8.25 (dd, J = 4.7, 1.5 Hz, 1H), 11.90 (s, 1H); MS (ESI$^+$): 416 $[M + H]^+$. |

-continued

| Compound No. | Chemical structural formula | Spectrum data |
| --- | --- | --- |
| EX.432 | 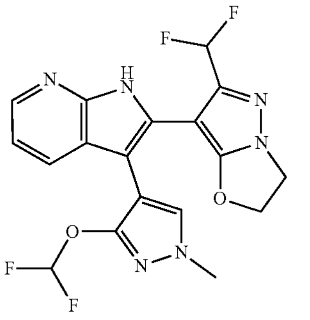 [SMILES: Cn1cc(-c2c(-c3c(C(F)F)nn4c3OCC4)[nH]c3ncccc23)c(OC(F)F)n1] | $^1$H-NMR (400 MHz, DMSO-d$_6$) δ 3.77 (s, 3H), 4.39 (t, J = 8.2 Hz, 2H), 5.12 (t, J = 8.1 Hz, 2H), 6.73 (t, J = 53.9 Hz, 1H), 7.10 (dd, J = 7.9, 4.7 Hz, 1H), 7.14 (t, J = 73.6 Hz, 1H), 7.64 (s, 1H), 7.84 (dd, J = 7.9, 1.2 Hz, 1H), 8.24 (dd, J = 4.6, 1.5 Hz, 1H), 11.79 (s, 1H); MS (ESI$^+$): 423 [M + H]$^+$. |
| EX.433 | 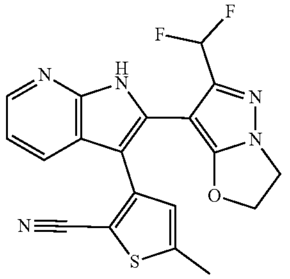 [SMILES: Cc1cc(-c2c(-c3c(C(F)F)nn4c3OCC4)[nH]c3ncccc23)c(C#N)s1] | $^1$H-NMR (400 MHz, DMSO-d$_6$) δ 2.54 (d, J = 0.9 Hz, 3H), 4.41 (t, J = 8.0 Hz, 2H), 5.09 (t, J = 8.1 Hz, 2H), 6.68 (t, J = 53.9 Hz, 1H), 6.96 (d, J = 1.0 Hz, 1H), 7.18 (dd, J = 8.0, 4.7 Hz, 1H), 7.94 (dd, J = 7.9, 1.5 Hz, 1H), 8.31 (dd, J = 4.7, 1.6 Hz, 1H), 12.19 (s, 1H); MS (ESI$^+$): 398 [M + H]$^+$. |
| EX.434 | 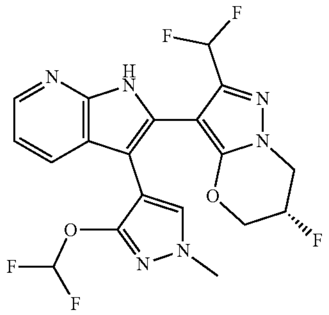 [SMILES: Cn1cc(-c2c(-c3c(C(F)F)nn4c3OC[C@@H](F)C4)[nH]c3ncccc23)c(OC(F)F)n1] | $^1$H-NMR (400 MHz, CDCl$_3$) δ 3.81 (s, 3H), 4.04-4.18 (m, 1H), 4.29-4.61 (m, 3H), 5.16-5.31 (m, 1H), 6.38-7.00 (m, 2H), 7.11 (dd, J = 7.9, 4.8 Hz, 1H), 7.25 (s, 1H), 7.91 (dd, J = 7.9, 1.3 Hz, 1H), 8.30 (dd, J = 4.7, 1.5 Hz, 1H), 9.31 (s, 1H); MS (ESI$^+$): 455 [M + H]$^+$. |
| EX.435 | 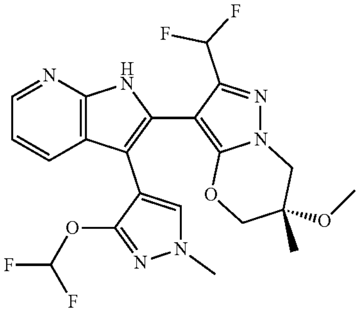 [SMILES: CO[C@]1(C)COc2c(-c3[nH]c4ncccc4c3-c3cn(C)nc3OC(F)F)c(C(F)F)nn2C1] | $^1$H-NMR (400 MHz, DMSO-d$_6$) δ 1.26 (s, 3H), 3.17 (s, 3H), 3.75 (s, 3H), 3.99-4.05 (m, 1H), 4.07-4.14 (m, 1H), 4.16-4.23 (m, 1H), 4.35 (dd, J = 11.9, 2.3 Hz, 1H), 6.75 (t, J = 54.1 Hz, 1H), 6.91-7.28 (m, 2H), 7.49 (s, 1H), 7.81 (dd, J = 8.0, 1.3 Hz, 1H), 8.23 (dd, J = 4.7, 1.6 Hz, 1H), 11.77 (s, 1H); MS (ESI$^+$): 481 [M + H]$^+$. |
| EX.436 | 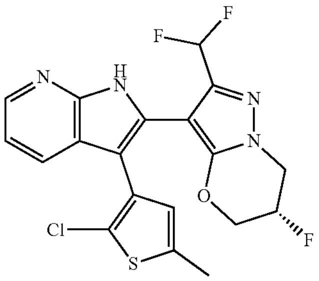 [SMILES: Cc1cc(-c2c(-c3c(C(F)F)nn4c3OC[C@@H](F)C4)[nH]c3ncccc23)c(Cl)s1] | $^1$H-NMR (400 MHz, CDCl$_3$) δ 2.41-2.52 (m, 3H), 3.94-4.13 (m, 1H), 4.30-4.49 (m, 2H), 4.50-4.61 (m, 1H), 5.15-5.31 (m, 1H), 6.29-6.65 (m, 2H), 7.12 (dd, J = 7.9, 4.7 Hz, 1H), 7.86-8.08 (m, 1H), 8.32 (dd, J = 4.7, 1.3 Hz, 1H), 9.06-9.24 (m, 1H); MS (ESI$^+$): 439 [M + H]$^+$. |

-continued

| Compound No. | Chemical structural formula | Spectrum data |
|---|---|---|
| EX.437 | 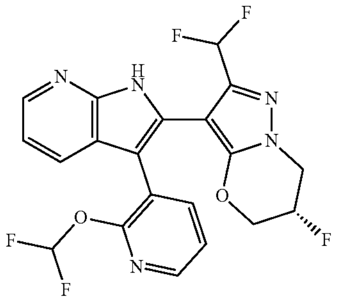 [SMILES: FC(F)Oc1ncccc1-c1c(-c2c(C(F)F)nn3c2OC[C@@H](F)C3)[nH]c2ncccc12] | $^1$H-NMR (400 MHz, DMSO-$d_6$) δ 4.05-4.22 (1H, m), 4.35-4.56 (3H, m), 5.35-5.51 (1H, m), 6.77 (1H, t, J = 54.0 Hz), 7.12 (1H, dd, J = 7.9, 4.7 Hz), 7.22 (1H, dd, J = 7.5, 4.9 Hz), 7.50-7.89 (3H, m), 8.18 (1H, dd, J = 4.9, 1.8 Hz), 8.28 (1H, dd, J = 4.7, 1.5 Hz), 12.01 (1H, s); MS (ESI$^+$): 452 $[M + H]^+$. |
| EX.438 | 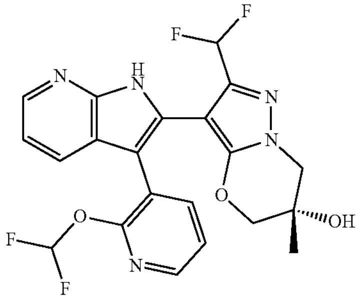 [SMILES: C[C@@]1(O)COc2c(-c3[nH]c4ncccc4c3-c3cccnc3OC(F)F)c(C(F)F)nn2C1] | $^1$H-NMR (400 MHz, DMSO-$d_6$) δ 1.20 (s, 3H), 3.75 (d, J = 10.7 Hz, 1H), 3.84 (dd, J = 11.0, 1.8 Hz, 1H), 3.92 (d, J = 12.2 Hz, 1H), 4.04 (d, J = 12.2 Hz, 1H), 5.39 (s, 1H), 6.78 (t, J = 54.1 Hz, 1H), 7.11 (dd, J = 7.9, 4.7 Hz, 1H), 7.21 (dd, J = 7.4, 4.9 Hz, 1H), 7.52-7.89 (m, 3H), 8.18 (dd, J = 4.9, 1.8 Hz, 1H), 8.27 (dd, J = 4.7, 1.6 Hz, 1H), 11.96 (s, 1H); MS (ESI$^+$): 464 $[M + H]^+$. |
| EX.439 | 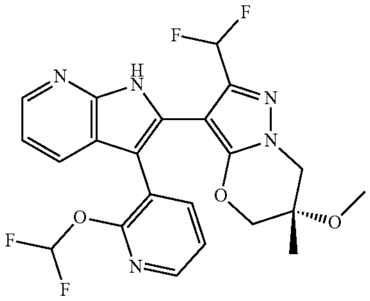 [SMILES: CO[C@]1(C)COc2c(-c3[nH]c4ncccc4c3-c3cccnc3OC(F)F)c(C(F)F)nn2C1] | $^1$H-NMR (400 MHz, DMSO-$d_6$) δ 1.19 (s, 3H), 3.03 (s, 3H), 3.83 (d, J = 11.9 Hz, 1H), 4.02-4.14 (m, 2H), 4.19 (dd, J = 12.0, 1.9 Hz, 1H), 6.83 (t, J = 54.1 Hz, 1H), 7.11 (dd, J = 7.9, 4.6 Hz, 1H), 7.22 (dd, J = 7.4, 4.9 Hz, 1H), 7.50-7.90 (m, 3H), 8.18 (dd, J = 4.9, 1.9 Hz, 1H), 8.27 (dd, J = 4.6, 1.5 Hz, 1H), 11.96 (s, 1H); MS (ESI$^+$): 478 $[M + H]^+$. |
| EX.440 | 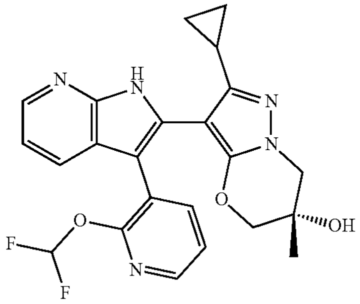 [SMILES: C[C@@]1(O)COc2c(-c3[nH]c4ncccc4c3-c3cccnc3OC(F)F)c(C3CC3)nn2C1] | $^1$H-NMR (400 MHz, DMSO-$d_6$) δ 0.37-0.55 (m, 4H), 1.21 (s, 3H), 1.43-1.53 (m, 1H), 3.74-3.91 (m, 4H), 5.31 (s, 1H), 7.08 (dd, J = 7.9, 4.7 Hz, 1H), 7.22 (dd, J = 7.5, 4.9 Hz, 1H), 7.53-7.93 (m, 3H), 8.18 (dd, J = 4.9, 1.9 Hz, 1H), 8.23 (dd, J = 4.7, 1.6 Hz, 1H), 11.87 (s, 1H); MS (ESI$^+$): 454 $[M + H]^+$. |
| EX.441 | 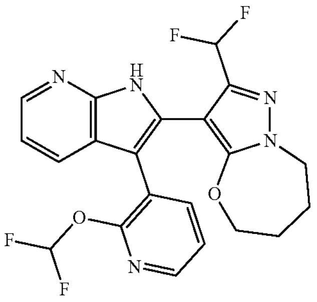 [SMILES: FC(F)Oc1ncccc1-c1c(-c2c(C(F)F)nn3c2OCCCC3)[nH]c2ncccc12] | $^1$H-NMR (400 MHz, DMSO-d6) δ 1.68-1.79 (m, 2H), 1.84-1.94 (m, 2H), 3.50-3.61 (m, 2H), 4.15-4.25 (m, 2H), 6.75 (t, J = 54.0 Hz, 1H), 7.13 (dd, J = 7.9, 4.7 Hz, 1H), 7.26 (dd, J = 7.4, 4.9 Hz, 1H), 7.55-7.92 (m, 3H), 8.20 (dd, J = 4.9, 1.8 Hz, 1H), 8.29 (dd, J = 4.7, 1.6 Hz, 1H), 12.01 (s, 1H); MS (ESI$^+$): 448 $[M + H]^+$. |

-continued

| Compound No. | Chemical structural formula | Spectrum data |
|---|---|---|
| EX.442 | 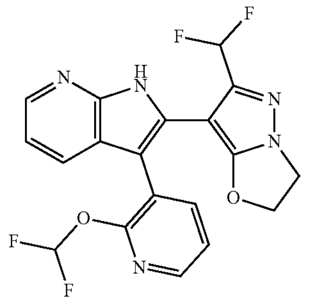 [SMILES: FC(F)Oc1ncccc1-c1c(-c2c(C(F)F)nn3c2OCC3)[nH]c2ncccc12] | $^1$H-NMR (400 MHz, DMSO-$d_6$) δ 4.36 (t, J = 8.1 Hz, 2H), 5.00 (t, J = 8.1 Hz, 2H), 6.75 (t, J = 53.9 Hz, 1H), 7.12 (dd, J = 7.9, 4.7 Hz, 1H), 7.27 (dd, J = 7.4, 4.9 Hz, 1H), 7.51-7.88 (m, 3H), 8.20 (dd, J = 4.9, 1.9 Hz, 1H), 8.28 (dd, J = 4.6, 1.5 Hz, 1H), 12.01 (s, 1H); MS (ESI$^+$): 420 [M + H]$^+$. |
| EX.443 | 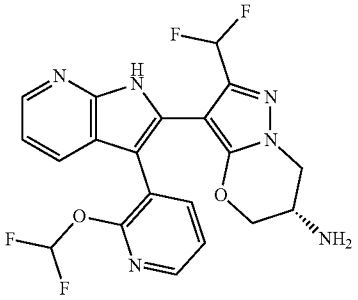 [SMILES: N[C@@H]1COc2c(-c3[nH]c4ncccc4c3-c3cccnc3OC(F)F)c(C(F)F)nn2C1] | $^1$H-NMR (400 MHz, DMSO-$d_6$) δ 1.82 (s, 2H), 3.72-3.79 (m, 2H), 3.99-4.23 (m, 3H), 6.69 (t, J = 54.1 Hz, 1H), 7.08-7.24 (m, 2H), 7.50-7.87 (m, 3H), 8.16-8.26 (m, 2H), 11.93 (s, 1H); MS (ESI$^+$): 449 [M + H]$^+$. |
| EX.444 | 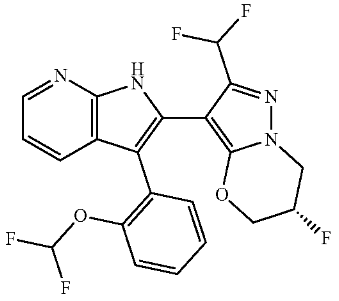 [SMILES: FC(F)Oc1ccccc1-c1c(-c2c(C(F)F)nn3c2OC[C@@H](F)C3)[nH]c2ncccc12] | $^1$H-NMR (400 MHz, $CDCl_3$) δ 3.57-3.90 (m, 1H), 4.09-4.38 (m, 2H), 4.44-4.56 (m, 1H), 5.04-5.19 (m, 1H), 6.04-6.67 (m, 2H), 7.11 (dd, J = 7.9, 4.7 Hz, 1H), 7.18-7.23 (m, 1H), 7.25-7.36 (m, 3H), 7.85 (dd, J = 7.9, 1.5 Hz, 1H), 8.32 (dd, J = 4.7, 1.5 Hz, 1H), 9.51 (s, 1H); MS (ESI$^+$): 451 [M + H]$^+$. |
| EX.445 | 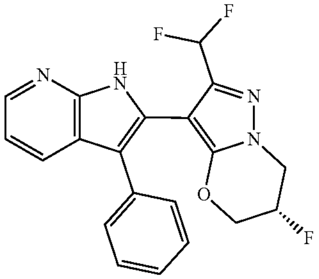 [SMILES: FC(F)c1nn2c(c1-c1[nH]c3ncccc3c1-c1ccccc1)OC[C@@H](F)C2] | $^1$H-NMR (400 MHz, $CDCl_3$) δ 3.75-3.89 (m, 1H), 4.22-4.42 (m, 2H), 4.48-4.59 (m, 1H), 5.08-5.22 (m, 1H), 6.39 (t, J = 54.1 Hz, 1H), 7.11 (dd, J = 7.9, 4.8 Hz, 1H), 7.25-7.31 (m, 1H), 7.34-7.45 (m, 4H), 8.03 (dd, J = 7.9, 1.5 Hz, 1H), 8.32 (dd, J = 4.8, 1.4 Hz, 1H), 9.35 (s, 1H); MS (ESI$^+$): 385 [M + H]$^+$. |
| EX.446 | 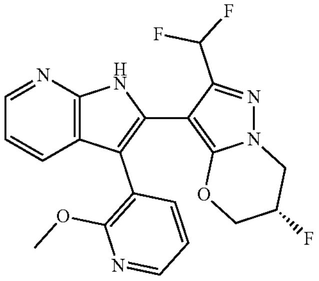 [SMILES: COc1ncccc1-c1c(-c2c(C(F)F)nn3c2OC[C@@H](F)C3)[nH]c2ncccc12] | $^1$H-NMR (400 MHz, $CDCl_3$) δ 3.73-3.93 (m, 4H), 4.19-4.38 (m, 2H), 4.44-4.54 (m, 1H), 5.05-5.19 (m, 1H), 6.57 (t, J = 54.1 Hz, 1H), 6.88 (dd, J = 7.3, 5.0 Hz, 1H), 7.09 (dd, J = 7.9, 4.8 Hz, 1H), 7.48 (dd, J = 7.2, 1.9 Hz, 1H), 7.81 (dd, J = 7.9, 1.5 Hz, 1H), 8.14 (dd, J = 5.0, 1.9 Hz, 1H), 8.31 (dd, J = 4.7, 1.5 Hz, 1H), 9.33 (s, 1H); MS (ESI$^+$): 416 [M + H]$^+$. |

-continued

| Compound No. | Chemical structural formula | Spectrum data |
|---|---|---|
| EX.447 | 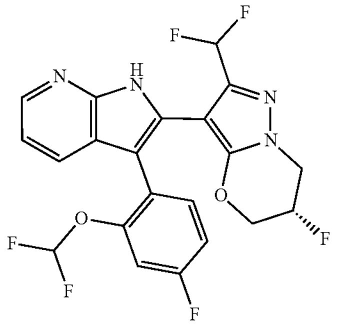 [SMILES: Fc1ccc(-c2c(-c3c(C(F)F)nn4c3OC[C@@H](F)C4)[nH]c3ncccc23)c(OC(F)F)c1] | $^{1}$H-NMR (400 MHz, $CDCl_3$) δ 3.68-3.94 (m, 1H), 4.20-4.39 (m, 2H), 4.44-4.56 (m, 1H), 5.07-5.22 (m, 1H), 6.05-6.71 (m, 2H), 6.91-6.98 (m, 1H), 7.04 (dd, J = 9.4, 2.5 Hz, 1H), 7.11 (dd, J = 7.9, 4.7 Hz, 1H), 7.24-7.30 (m, 1H), 7.81 (dd, J = 7.9, 1.5 Hz, 1H), 8.32 (dd, J = 4.8, 1.5 Hz, 1H), 9.46 (s, 1H); MS ($ESI^+$): 469 $[M + H]^+$. |
| EX.448 | 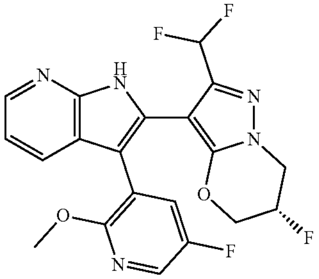 [SMILES: COc1ncc(F)cc1-c1c(-c2c(C(F)F)nn3c2OC[C@@H](F)C3)[nH]c2ncccc12] | $^{1}$H-NMR (400 MHz, $CDCl_3$) δ 3.83-3.97 (m, 4H), 4.23-4.40 (m, 2H), 4.47-4.57 (m, 1H), 5.08-5.23 (m, 1H), 6.60 (t, J = 54.0 Hz, 1H), 7.11 (dd, J = 7.9, 4.7 Hz, 1H), 7.29 (dd, J = 8.3, 3.0 Hz, 1H), 7.81 (dd, J = 7.9, 1.5 Hz, 1H), 7.97 (d, J = 3.0 Hz, 1H), 8.31 (dd, J = 4.7, 1.5 Hz, 1H), 9.45 (s, 1H); MS ($ESI^+$): 434 $[M + H]^+$. |
| EX.449 | 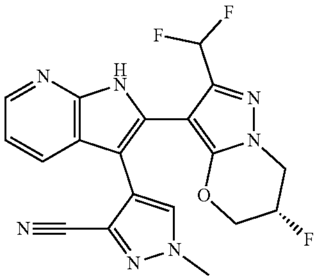 [SMILES: Cn1cc(-c2c(-c3c(C(F)F)nn4c3OC[C@@H](F)C4)[nH]c3ncccc23)c(C#N)n1] | $^{1}$H-NMR (400 MHz, DMSO-$d_6$) δ 3.95 (s, 3H), 4.20-4.38 (m, 1H), 4.39-4.61 (m, 3H), 5.42-5.58 (m, 1H), 6.70 (t, J = 53.9 Hz, 1H), 7.15 (dd, J = 7.9, 4.7 Hz, 1H), 7.90 (dd, J = 7.9, 1.5 Hz, 1H), 7.95 (s, 1H), 8.29 (dd, J = 4.7, 1.6 Hz, 1H), 12.05 (s, 1H); MS ($ESI^+$): 414 $[M + H]^+$. |
| EX.450 | 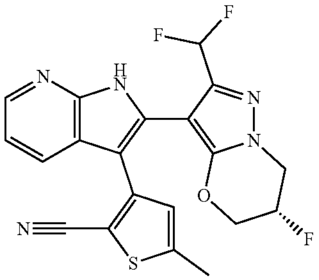 [SMILES: Cc1cc(-c2c(-c3c(C(F)F)nn4c3OC[C@@H](F)C4)[nH]c3ncccc23)c(C#N)s1] | $^{1}$H-NMR (400 MHz, DMSO-$d_6$) δ 2.51 (s, 3H), 4.17-4.32 (m, 1H), 4.43-4.59 (m, 3H), 5.41-5.55 (m, 1H), 6.70 (t, J = 53.9 Hz, 1H), 6.89 (d, J = 1.0 Hz, 1H), 7.18 (dd, J = 8.0, 4.7 Hz, 1H), 7.94 (dd, J = 7.9, 1.5 Hz, 1H), 8.31 (dd, J = 4.7, 1.6 Hz, 1H), 12.20 (s, 1H); MS ($ESI^+$): 430 $[M + H]^+$. |
| EX.451 | 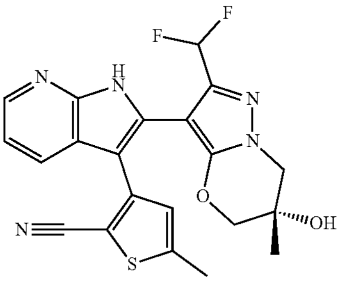 [SMILES: Cc1cc(-c2c(-c3c(C(F)F)nn4c3OC[C@@](C)(O)C4)[nH]c3ncccc23)c(C#N)s1] | $^{1}$H-NMR (400 MHz, DMSO-$d_6$) δ 1.27 (s, 3H), 2.49 (s, 3H), 3.89-4.02 (m, 3H), 4.08-4.15 (m, 1H), 5.42 (s, 1H), 6.70 (t, J = 54.1 Hz, 1H), 6.87 (d, J = 1.1 Hz, 1H), 7.18 (dd, J = 7.9, 4.7 Hz, 1H), 7.93 (dd, J = 7.9, 1.0 Hz, 1H), 8.30 (dd, J = 4.7, 1.5 Hz, 1H), 12.14 (s, 1H); MS ($ESI^+$): 442 $[M + H]^+$. |

-continued

| Compound No. | Chemical structural formula | Spectrum data |
|---|---|---|
| EX.452 | 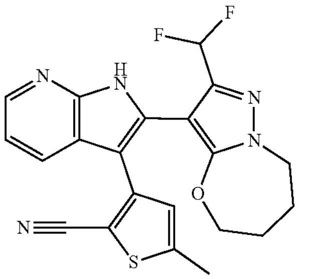 [SMILES: Cc1cc(-c2c(-c3c(C(F)F)nn4c3OCCCC4)[nH]c3ncccc23)c(C#N)s1] | $^1$H-NMR (400 MHz, DMSO-$d_6$) δ 1.77-1.86 (m, 2H), 1.93-2.01 (m, 2H), 2.53 (d, J = 0.9 Hz, 3H), 3.85 (t, J = 4.8 Hz, 2H), 4.25 (t, J = 4.9 Hz, 2H), 6.60 (t, J = 54.0 Hz, 1H), 6.89 (d, J = 1.0 Hz, 1H), 7.19 (dd, J = 8.0, 4.7 Hz, 1H), 7.94 (dd, J = 7.9, 1.4 Hz, 1H), 8.32 (dd, J = 4.7, 1.6 Hz, 1H), 12.19 (s, 1H); MS (ESI$^+$): 426 [M + H]$^+$. |
| EX.453 | 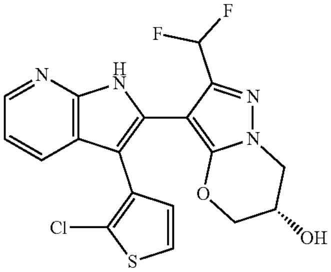 [SMILES: O[C@@H]1COc2c(-c3[nH]c4ncccc4c3-c3ccsc3Cl)c(C(F)F)nn2C1] | $^1$H-NMR (400 MHz, DMSO-$d_6$) δ 3.97-4.13 (m, 3H), 4.26-4.36 (m, 2H), 5.59 (d, J = 3.1 Hz, 1H), 6.57 (t, J = 54.3 Hz, 1H), 6.87 (d, J = 5.5 Hz, 1H), 7.08-7.12 (m, 1H), 7.45 (d, J = 5.5 Hz, 1H), 7.75 (d, J = 7.9 Hz, 1H), 8.25 (d, J = 4.3 Hz, 1H), 11.92 (s, 1H); MS (ESI$^+$): 423 [M + H]$^+$. |
| EX.454 | 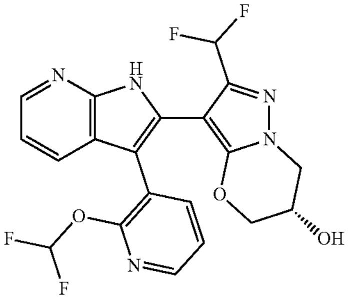 [SMILES: O[C@@H]1COc2c(-c3[nH]c4ncccc4c3-c3cccnc3OC(F)F)c(C(F)F)nn2C1] | $^1$H-NMR (400 MHz, DMSO-$d_6$) δ 3.90-4.03 (m, 3H), 4.21-4.30 (m, 2H), 5.58 (d, J = 3.1 Hz, 1H), 6.75 (t, J = 54.1 Hz, 1H), 7.11 (dd, J = 8.0, 4.7 Hz, 1H), 7.22 (dd, J = 7.5, 4.9 Hz, 1H), 7.60 (dd, J = 7.4, 1.9 Hz, 1H), 7.70 (t, J = 73.4 Hz, 1H), 7.77 (dd, J = 7.9, 1.4 Hz, 1H), 8.18 (dd, J = 4.9, 1.9 Hz, 1H), 8.27 (dd, J = 4.6, 1.5 Hz, 1H), 11.95 (s, 1H); MS (ESI$^+$): 450 [M + H]$^+$. |
| EX.455 | 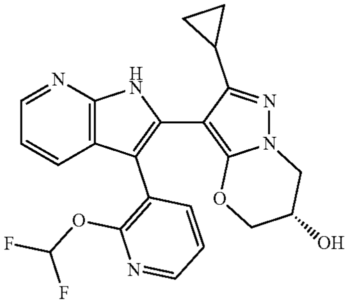 [SMILES: O[C@@H]1COc2c(-c3[nH]c4ncccc4c3-c3cccnc3OC(F)F)c(C3CC3)nn2C1] | $^1$H-NMR (400 MHz, DMSO-$d_6$) δ 0.35-0.53 (m, 4H), 1.39-1.49 (m, 1H), 3.80-3.83 (m, 1H), 3.94-4.06 (m, 2H), 4.12 (dd, J = 12.5, 4.1 Hz, 1H), 4.17-4.24 (m, 1H), 5.52 (d, J = 3.5 Hz, 1H), 7.08 (dd, J = 7.9, 4.7 Hz, 1H), 7.23 (dd, J = 7.4, 4.9 Hz, 1H), 7.53-7.93 (m, 3H), 8.18 (dd, J = 4.9, 1.8 Hz, 1H), 8.23 (dd, J = 4.7, 1.5 Hz, 1H), 11.86 (s, 1H); MS (ESI$^+$): 440 [M + H]$^+$. |
| EX.456 | 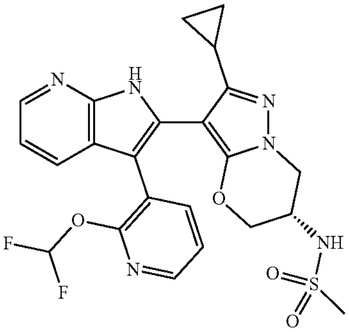 [SMILES: CS(=O)(=O)N[C@@H]1COc2c(-c3[nH]c4ncccc4c3-c3cccnc3OC(F)F)c(C3CC3)nn2C1] | $^1$H-NMR (400 MHz, DMSO-$d_6$) δ 0.28-0.55 (m, 4H), 1.30-1.39 (m, 1H), 3.05 (s, 3H), 3.87-4.30 (m, 5H), 7.09 (dd, J = 7.9, 4.7 Hz, 1H), 7.25 (dd, J = 7.5, 4.9 Hz, 1H), 7.54-7.94 (m, 4H), 8.20 (dd, J = 4.9, 1.9 Hz, 1H), 8.24 (dd, J = 4.7, 1.6 Hz, 1H), 11.80 (s, 1H); MS (ESI$^+$): 517 [M + H]$^+$. |

-continued

| Compound No. | Chemical structural formula | Spectrum data |
|---|---|---|
| EX.457 | 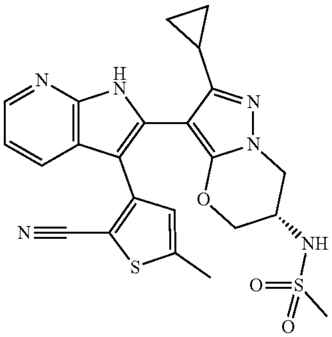 [SMILES: Cc1cc(-c2c(-c3c(C4CC4)nn4c3OC[C@@H](NS(C)(=O)=O)C4)[nH]c3ncccc23)c(C#N)s1] | $^1$H-NMR (400 MHz, DMSO-d$_6$) δ 0.40-0.67 (m, 4H), 1.29-1.40 (m, 1H), 2.54 (s, 3H), 3.07 (s, 3H), 3.90-3.98 (m, 1H), 4.09-4.39 (m, 4H), 6.99 (s, 1H), 7.16 (dd, J = 7.9, 4.7 Hz, 1H), 7.50 (s, 1H), 7.93 (d, J = 7.8 Hz, 1H), 8.27 (d, J = 4.6 Hz, 1H), 11.98 (s, 1H); MS (ESI$^+$): 495 [M + H]$^+$. |
| EX.458 | 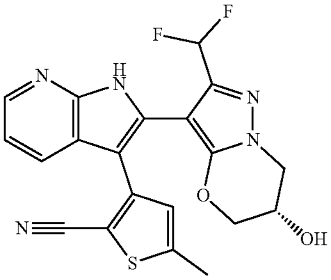 [SMILES: Cc1cc(-c2c(-c3c(C(F)F)nn4c3OC[C@@H](O)C4)[nH]c3ncccc23)c(C#N)s1] | $^1$H-NMR (400 MHz, DMSO-d$_6$) δ 2.45-2.53 (m, 3H), 3.99-4.13 (m, 3H), 4.28-4.36 (m, 2H), 5.60-5.63 (m, 1H), 6.67 (t, J = 54.1 Hz, 1H), 6.86-6.88 (m, 1H), 7.14-7.18 (m, 1H), 7.92 (dd, J = 8.0, 1.5 Hz, 1H), 8.29 (dd, J = 4.6, 1.5 Hz, 1H), 12.13 (s, 1H); MS (ESI$^+$): 428 [M + H]$^+$. |
| EX.459 | 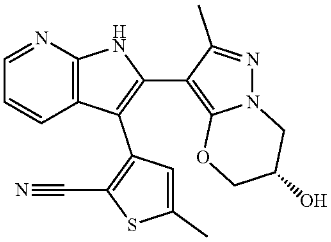 [SMILES: Cc1cc(-c2c(-c3c(C)nn4c3OC[C@@H](O)C4)[nH]c3ncccc23)c(C#N)s1] | $^1$H-NMR (400 MHz, DMSO-d$_6$) δ 1.89 (s, 3H), 2.39-2.76 (m, 3H), 3.79-4.31 (m, 5H), 5.48-5.54 (m, 1H), 6.92 (s, 1H), 7.11-7.17 (m, 1H), 7.88 (d, J = 7.9 Hz, 1H), 8.23-8.28 (m, 1H), 11.99 (s, 1H); MS (ESI$^+$): 392 [M + H]$^+$. |
| EX.460 | 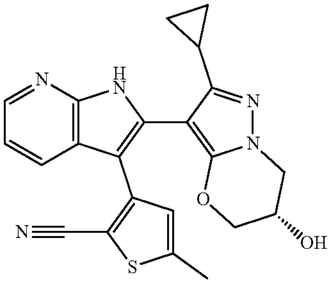 [SMILES: Cc1cc(-c2c(-c3c(C4CC4)nn4c3OC[C@@H](O)C4)[nH]c3ncccc23)c(C#N)s1] | $^1$H-NMR (400 MHz, DMSO-d$_6$) δ 0.46-0.60 (m, 4H), 1.39-1.46 (m, 1H), 2.52 (s, 3H), 3.84-3.89 (m, 1H), 4.07-4.27 (m, 4H), 5.54 (d, J = 3.5 Hz, 1H), 6.93 (s, 1H), 7.15 (dd, J = 7.9, 4.7 Hz, 1H), 7.91 (d, J = 7.9 Hz, 1H), 8.26 (dd, J = 4.7, 1.5 Hz, 1H), 12.04 (s, 1H); MS (ESI$^+$): 418 [M + H]$^+$. |
| EX.461 | 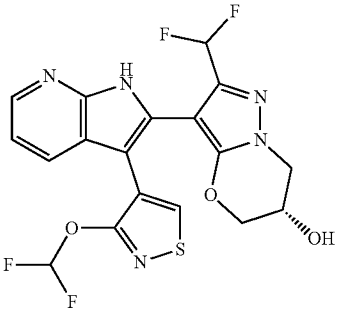 [SMILES: O[C@@H]1COc2c(-c3[nH]c4ncccc4c3-c3csnc3OC(F)F)c(C(F)F)nn2C1] | $^1$H-NMR (400 MHz, DMSO-d$_6$) δ 3.98-4.36 (m, 5H), 5.62 (d, J = 2.9 Hz, 1H), 6.77 (t, J = 54.1 Hz, 1H), 7.12 (dd, J = 8.0, 4.7 Hz, 1H), 7.58 (t, J = 72.5 Hz, 1H), 7.83 (dd, J = 7.9, 1.3 Hz, 1H), 8.26 (dd, J = 4.7, 1.5 Hz, 1H), 8.69 (s, 1H), 11.96 (s, 1H); MS (ESI$^+$): 456 [M + H]$^+$. |

-continued

| Compound No. | Chemical structural formula | Spectrum data |
|---|---|---|
| EX.462 | 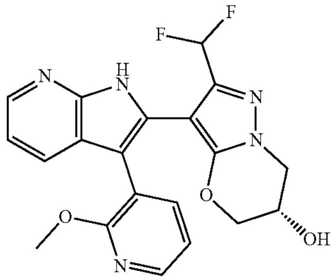 [SMILES: COc1ncccc1-c1c(-c2c(C(F)F)nn3c2OC[C@@H](O)C3)[nH]c2ncccc12] | $^1$H-NMR (400 MHz, DMSO-d$_6$) δ 3.74 (s, 3H), 3.93-4.11 (m, 3H), 4.21-4.33 (m, 2H), 5.58 (d, J = 3.1 Hz, 1H), 6.63 (t, J = 54.1 Hz, 1H), 6.94 (dd, J = 7.2, 5.0 Hz, 1H), 7.08 (dd, J = 7.9, 4.6 Hz, 1H), 7.44 (dd, J = 7.2, 1.8 Hz, 1H), 7.70 (d, J = 7.9 Hz, 1H), 8.09 (dd, J = 5.0, 1.8 Hz, 1H), 8.24 (dd, J = 4.6, 1.2 Hz, 1H), 11.80 (s, 1H); MS (ESI$^+$): 414 [M + H]$^+$. |
| EX.463 | 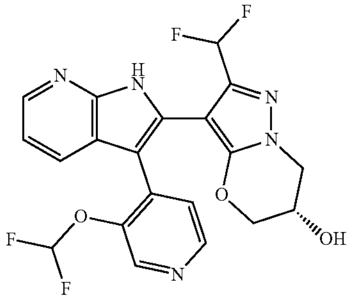 [SMILES: O[C@@H]1COc2c(-c3[nH]c4ncccc4c3-c3ccncc3OC(F)F)c(C(F)F)nn2C1] | $^1$H-NMR (400 MHz, DMSO-d$_6$) δ 3.90-4.07 (m, 3H), 4.20-4.34 (m, 2H), 5.59 (d, J = 2.4 Hz, 1H), 6.65-7.22 (m, 4H), 7.80 (d, J = 7.5 Hz, 1H), 8.29 (dd, J = 4.6, 1.4 Hz, 1H), 8.36 (d, J = 4.9 Hz, 1H), 8.50 (s, 1H), 12.11 (s, 1H); MS (ESI$^+$): 450 [M + H]$^+$. |
| EX.464 | 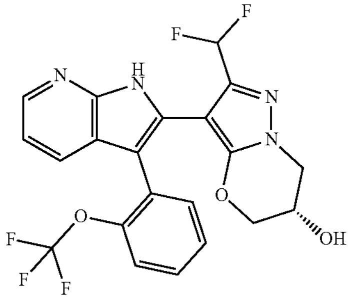 [SMILES: O[C@@H]1COc2c(-c3[nH]c4ncccc4c3-c3ccccc3OC(F)(F)F)c(C(F)F)nn2C1] | $^1$H-NMR (400 MHz, DMSO-d$_6$) δ 3.84-4.01 (m, 3H), 4.20-4.32 (m, 2H), 5.57 (d, J = 2.7 Hz, 1H), 6.67 (t, J = 54.2 Hz, 1H), 7.11 (dd, J = 7.9, 4.7 Hz, 1H), 7.29-7.46 (m, 4H), 7.71 (dd, J = 7.9, 1.3 Hz, 1H), 8.26 (dd, J = 4.7, 1.6 Hz, 1H), 11.91 (s, 1H); MS (ESI$^+$): 467 [M + H]$^+$. |
| EX.465 | 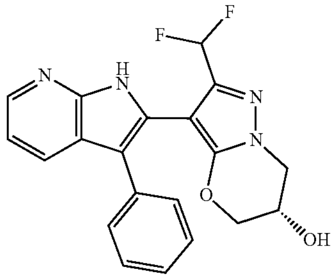 [SMILES: O[C@@H]1COc2c(-c3[nH]c4ncccc4c3-c3ccccc3)c(C(F)F)nn2C1] | $^1$H-NMR (400 MHz, DMSO-d$_6$) δ 3.98-4.15 (3H, m), 4.24-4.39 (2H, m), 5.62 (1H, d, J = 1.8 Hz), 6.52 (1H, t, J = 54.1 Hz), 7.05-7.15 (1H, m), 7.18-7.27 (1H, m), 7.31-7.48 (4H, m), 7.99 (1H, d, J = 7.9 Hz), 8.25 (1H, d, J = 4.6 Hz), 11.80 (1H, s); MS (ESI$^+$): 383 [M + H]$^+$. |
| EX.466 | 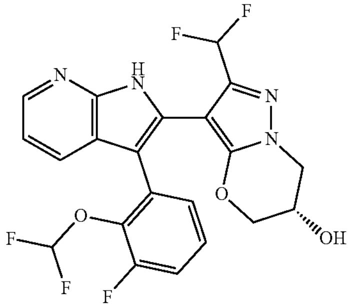 [SMILES: O[C@@H]1COc2c(-c3[nH]c4ncccc4c3-c3cccc(F)c3OC(F)F)c(C(F)F)nn2C1] | $^1$H-NMR (400 MHz, DMSO-d$_6$) δ 3.89-4.08 (m, 3H), 4.20-4.32 (m, 2H), 5.53 (d, J = 2.6 Hz, 1H), 6.51 (t, J = 74.3 Hz, 1H), 6.79 (t, J = 54.1 Hz, 1H), 7.00 (d, J = 7.5 Hz, 1H), 7.11 (dd, J = 7.8, 4.7 Hz, 1H), 7.21-7.36 (m, 2H), 7.74 (dd, J = 7.7, 1.0 Hz, 1H), 8.27 (dd, J = 4.7, 1.1 Hz, 1H), 11.93 (s, 1H); MS (ESI$^+$): 467 [M + H]$^+$. |

-continued

| Compound No. | Chemical structural formula | Spectrum data |
| --- | --- | --- |
| EX.467 | 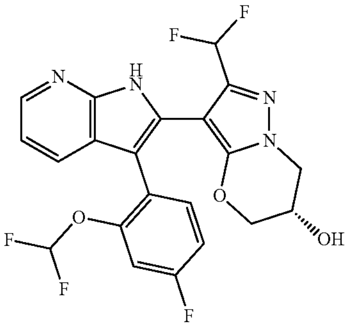 [SMILES: O[C@@H]1COc2c(-c3[nH]c4ncccc4c3-c3ccc(F)cc3OC(F)F)c(C(F)F)nn2C1] | $^1$H-NMR (400 MHz, DMSO-d6) δ 3.91-4.10 (m, 3H), 4.21-4.32 (m, 2H), 5.58 (s, 1H), 6.71 (t, J = 54.1 Hz, 1H), 7.00-7.28 (m, 5H), 7.69 (d, J = 8.0 Hz, 1H), 8.25 (dd, J = 4.6, 1.4 Hz, 1H), 11.87 (s, 1H); MS (ESI$^+$): 467 [M + H]$^+$. |
| EX.468 | 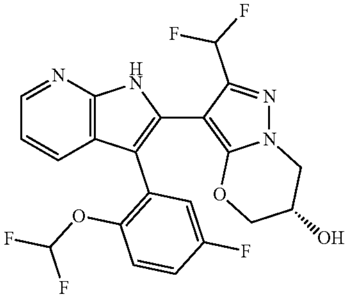 [SMILES: O[C@@H]1COc2c(-c3[nH]c4ncccc4c3-c3cc(F)ccc3OC(F)F)c(C(F)F)nn2C1] | $^1$H-NMR (400 MHz, DMSO-$d_6$) δ 3.95-4.08 (m, 3H), 4.23-4.34 (m, 2H), 5.58 (d, J = 3.0 Hz, 1H), 6.61-6.98 (m, 3H), 7.11 (dd, J = 7.9, 4.7 Hz, 1H), 7.20 (td, J = 8.5, 3.2 Hz, 1H), 7.29 (dd, J = 8.9, 4.9 Hz, 1H), 7.73 (dd, J = 7.9, 1.4 Hz, 1H), 8.26 (dd, J = 4.7, 1.6 Hz, 1H), 11.95 (s, 1H); MS (ESI$^+$): 467 [M + H]$^+$. |
| EX.469 | 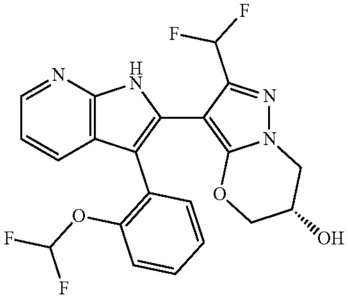 [SMILES: O[C@@H]1COc2c(-c3[nH]c4ncccc4c3-c3ccccc3OC(F)F)c(C(F)F)nn2C1] | $^1$H-NMR (400 MHz, DMSO-$d_6$) δ 3.87-4.05 (m, 3H), 4.20-4.31 (m, 2H), 5.59 (d, J = 2.9 Hz, 1H), 6.65 (t, J = 54.2 Hz, 1H), 6.90 (t, J = 66.0 Hz, 1H), 7.08-7.10 (m, 1H), 7.17-7.26 (m, 3H), 7.33-7.38 (m, 1H), 7.70 (dd, J = 7.9, 1.4 Hz, 1H), 8.25 (dd, J = 4.7, 1.6 Hz, 1H), 11.86 (s, 1H); MS (ESI$^+$): 449 [M + H]$^+$. |
| EX.470 | 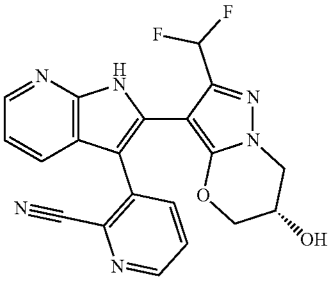 [SMILES: N#Cc1ncccc1-c1c(-c2c(C(F)F)nn3c2OC[C@@H](O)C3)[nH]c2ncccc12] | $^1$H-NMR (400 MHz, DMSO-$d_6$) δ 3.85-4.11 (m, 3H), 4.21-4.32 (m, 2H), 5.58 (s, 1H), 6.79 (t, J = 54.6 Hz, 1H), 7.17 (dd, J = 7.9, 4.7 Hz, 1H), 7.69 (dd, J = 8.0, 4.7 Hz, 1H), 7.78 (dd, J = 7.9, 1.3 Hz, 1H), 7.86 (dd, J = 7.9, 1.5 Hz, 1H), 8.32 (dd, J = 4.7, 1.5 Hz, 1H), 8.67 (dd, J = 4.6, 1.7 Hz, 1H), 12.22 (s, 1H); MS (ESI$^+$): 409 [M + H]$^+$. |
| EX.471 | 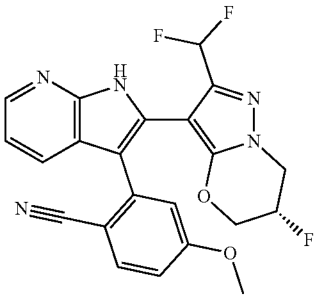 [SMILES: COc1ccc(C#N)c(-c2c(-c3c(C(F)F)nn4c3OC[C@@H](F)C4)[nH]c3ncccc23)c1] | $^1$H-NMR (400 MHz, DMSO-$d_6$) δ 3.76 (s, 3H), 4.07-4.60 (m, 4H), 5.34-5.53 (m, 1H), 6.45-6.90 (m, 2H), 7.03 (dd, J = 8.7, 2.6 Hz, 1H), 7.15 (dd, J = 7.9, 4.7 Hz, 1H), 7.78 (d, J = 8.7 Hz, 1H), 7.82 (dd, J = 7.9, 1.2 Hz, 1H), 8.30 (dd, J = 4.6, 1.5 Hz, 1H), 12.13 (s, 1H) MS (ESI$^+$): 440 [M + H]$^+$. |

-continued

| Compound No. | Chemical structural formula | Spectrum data |
|---|---|---|
| EX.472 | 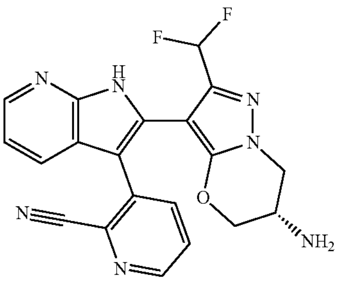 [SMILES: N#Cc1ncccc1-c1c(-c2c(C(F)F)nn3c2OC[C@@H](N)C3)[nH]c2ncccc12] | $^1$H-NMR (400 MHz, DMSO-$d_6$) δ 1.77-1.98 (m, 2H), 3.74-3.83 (m, 2H), 3.96-4.26 (m, 3H), 7.09-7.16 (m, 1H), 7.62-7.87 (m, 4H), 8.27-8.31 (m, 1H), 8.62-8.66 (m, 1H), 12.23 (s, 1H); MS (ESI$^+$): 408 [M + H]$^+$. |
| EX.473 | 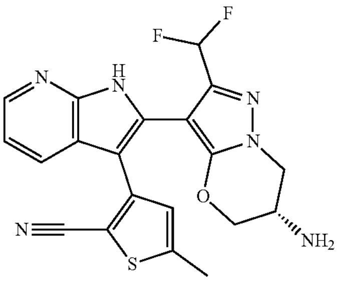 [SMILES: Cc1cc(-c2c(-c3c(C(F)F)nn4c3OC[C@@H](N)C4)[nH]c3ncccc23)c(C#N)s1] | $^1$H-NMR (400 MHz, DMSO-$d_6$) δ 1.92 (s, 2H), 2.52 (s, 3H), 3.44 (s, 1H), 3.83-3.94 (m, 2H), 4.08-4.17 (m, 1H), 4.28 (dd, J = 11.9, 4.7 Hz, 1H), 6.57 (t, J = 54.0 Hz, 1H), 6.96 (s, 1H), 7.16 (dd, J = 7.9, 4.7 Hz, 1H), 7.92 (dd, J = 7.9, 1.4 Hz, 1H), 8.29 (dd, J = 4.7, 1.5 Hz, 1H), 12.12 (s, 1H); MS (ESI$^+$): 425 [M + H]$^+$. |
| EX.475 | 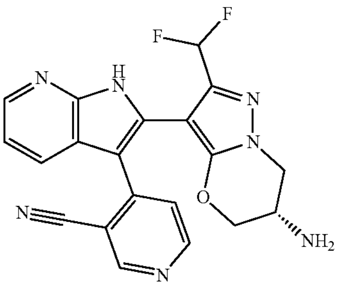 [SMILES: N#Cc1cnccc1-c1c(-c2c(C(F)F)nn3c2OC[C@@H](N)C3)[nH]c2ncccc12] | $^1$H-NMR (400 MHz, DMSO-$d_6$) δ 1.91 (s, 2H), 3.79-3.87 (m, 2H), 4.02-4.29 (m, 3H), 6.68 (t, J = 53.9 Hz, 1H), 7.16-7.21 (m, 1H), 7.41 (d, J = 5.3 Hz, 1H), 7.93 (d, J = 7.9 Hz, 1H), 8.32 (d, J = 4.7 Hz, 1H), 8.73 (d, J = 5.3 Hz, 1H), 8.97 (s, 1H), 12.31 (s, 1H); MS (ESI$^+$): 408 [M + H]$^+$. |
| EX.476 | 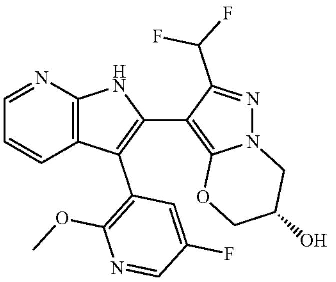 [SMILES: COc1ncc(F)cc1-c1c(-c2c(C(F)F)nn3c2OC[C@@H](O)C3)[nH]c2ncccc12] | $^1$H-NMR (400 MHz, DMSO-$d_6$) δ 3.71 (s, 3H), 3.96-4.13 (m, 3H), 4.24-4.37 (m, 2H), 5.57 (d, J = 3.2 Hz, 1H), 6.70 (t, J = 53.9 Hz, 1H), 7.10 (dd, J = 8.0, 4.7 Hz, 1H), 7.36 (dd, J = 8.7, 3.0 Hz, 1H), 7.76 (dd, J = 8.0, 1.3 Hz, 1H), 8.07 (d, J = 3.0 Hz, 1H), 8.25 (dd, J = 4.7, 1.6 Hz, 1H), 11.91 (s, 1H); MS (ESI$^+$): 432 [M + H]$^+$. |
| EX.477 | 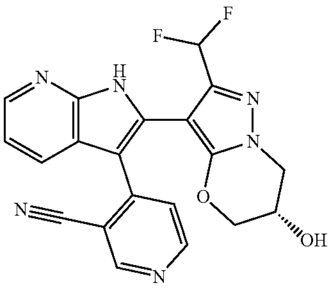 [SMILES: N#Cc1cnccc1-c1c(-c2c(C(F)F)nn3c2OC[C@@H](O)C3)[nH]c2ncccc12] | $^1$H-NMR (400 MHz, DMSO-$d_6$) δ 3.92-4.08 (m, 3H), 4.21-4.34 (m, 2H), 5.58 (s, 1H), 6.81 (t, J = 54.1 Hz, 1H), 7.19 (dd, J = 8.0, 4.6 Hz, 1H), 7.35 (d, J = 5.3 Hz, 1H), 7.93 (dd, J = 7.9, 1.2 Hz, 1H), 8.34 (dd, J = 4.7, 1.4 Hz, 1H), 8.72 (d, J = 5.1 Hz, 1H), 8.99 (s, 1H), 12.33 (s, 1H); MS (ESI$^+$): 409 [M + H]$^+$. |

-continued

| Compound No. | Chemical structural formula | Spectrum data |
|---|---|---|
| EX.478 | 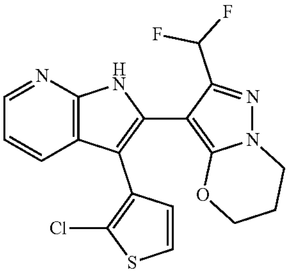 [SMILES: FC(F)c1nn2c(c1-c1[nH]c3ncccc3c1-c1ccsc1Cl)OCCC2] | $^1$H-NMR (400 MHz, DMSO-$d_6$) δ 2.14-2.17 (m, 2H), 4.14-4.20 (m, 4H), 6.55 (t, J = 54.3 Hz, 1H), 6.87 (d, J = 5.5 Hz, 1H), 7.08-7.12 (m, 1H), 7.46 (d, J = 5.5 Hz, 1H), 7.75 (d, J = 6.7 Hz, 1H), 8.24-8.25 (m, 1H), 11.90 (s, 1H); MS (ESI$^+$): 407 [M + H]$^+$. |
| EX.479 | 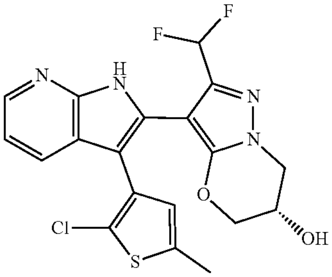 [SMILES: Cc1cc(-c2c(-c3c(C(F)F)nn4c3OC[C@@H](O)C4)[nH]c3ncccc23)c(Cl)s1] | $^1$H-NMR (400 MHz, DMSO-$d_6$) δ 2.38 (d, J = 1.1 Hz, 3H), 4.01-4.19 (m, 3H), 4.27-4.37 (m, 2H), 5.61 (d, J = 3.1 Hz, 1H), 6.60 (t, J = 54.1 Hz, 1H), 6.63 (d, J = 1.1 Hz, 1H), 7.11 (dd, J = 7.9, 4.7 Hz, 1H), 7.76 (dd, J = 7.9, 1.2 Hz, 1H), 8.25 (dd, J = 4.7, 1.6 Hz, 1H), 11.88 (s, 1H); MS (ESI$^+$): 437 [M + H]$^+$. |

(146) Reference Procedure of (S)-3-(3-(2-(difluoromethoxy)pyridin-3-yl)-1-((2-(trimethylsilyl)ethoxy)methyl)-1H-pyrrolo[2,3-b]pyridin-2-yl)-2-(difluoromethyl)-6-methyl-6,7-dihydro-5H-pyrazolo[5,1-b][1,3]oxazin-6-amine (337)

(337)

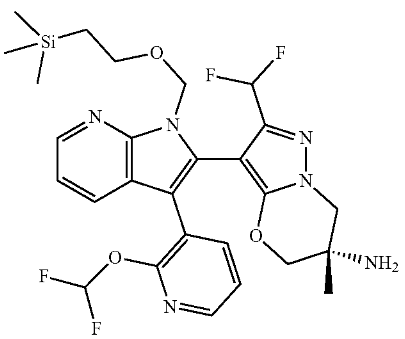

A mixture of compound 297 (335 mg, 0.538 mmol) and iron powder (150 mg, 2.69 mmol) in EtOH and AcOH (1/1, 2.7 mL) was stirred at 80° C. for 5 h under Ar atmosphere. The reaction mixture was filtered off through a pad of Celite, and the filtrate was concentrated. The residue was purified by silica gel column chromatography (25-100% EtOAc/hexane) to yield compound 337 (225 mg, 71%) as a colorless oil; $^1$H-NMR (400 MHz, $CDCl_3$) δ −0.12-−0.07 (m, 9H), 0.80-0.93 (m, 2H), 1.22-1.31 (m, 3H), 3.47-3.56 (m, 2H), 3.79-4.06 (m, 4H), 5.59 (dd, J=16.8, 11.0 Hz, 1H), 5.75 (dd, J=12.6, 10.9 Hz, 1H), 6.30-6.66 (m, 1H), 7.09 (td, J=7.5, 4.9 Hz, 1H), 7.15 (ddd, J=7.9, 4.7, 1.8 Hz, 1H), 7.29-7.70 (m, 2H), 7.80 (dd, J=7.9, 1.6 Hz, 1H), 8.12 (dd, J=4.9, 1.4 Hz, 1H), 8.41 (dt, J=4.7, 1.8 Hz, 1H); MS (ESI$^+$): 593 [M+H]$^+$.

(147) Reference Procedure of 2-(difluoromethyl)-3-(3-(4,4,5,5-tetramethyl-1,3,2-dioxaborolan-2-yl)-1-((2-(trimethylsilyl)ethoxy)methyl)-1H-pyrrolo[2,3-b]pyridin-2-yl)-6,7-dihydro-5H-pyrazolo[5,1-b][1,3]oxazine (338)

(338)

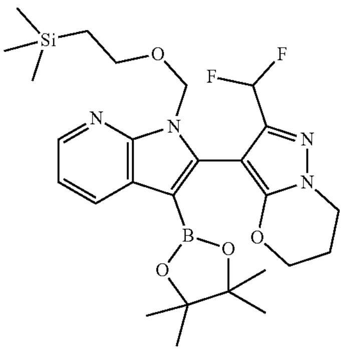

The compound 338 was synthesized from compound 270 using conditions analogous to compound 223; MS (ESI$^+$): 547 [M+H]$^+$.

(148) Reference Procedure of 3-(2-(2-(difluoromethyl)-6,7-dihydro-5H-pyrazolo[5,1-b][1,3]oxazin-3-yl)-1-((2-(trimethylsilyl)ethoxy)methyl)-1H-pyrrolo[2,3-b]pyridin-3-yl)-1-methyl-1H-pyrrole-2-carbonitrile (339)

(339)

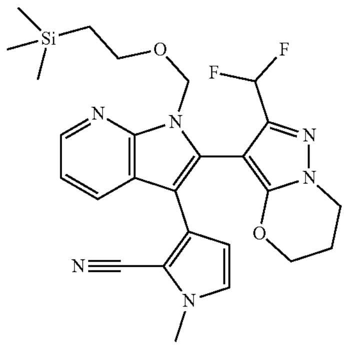

The compound 339 was synthesized from compounds 131 and 270 using conditions analogous to compound 237; $^1$H-NMR (400 MHz, $CDCl_3$) δ −0.11 (s, 9H), 0.74-0.92 (m, 2H), 2.31-2.39 (m, 2H), 3.36-3.51 (m, 2H), 3.74 (s, 3H), 4.29 (t, J=6.1 Hz, 2H), 4.35-4.45 (m, 2H), 5.51 (d, J=11.0 Hz, 1H), 5.89 (d, J=11.0 Hz, 1H), 6.02-6.33 (m, 2H), 6.85 (d, J=2.4 Hz, 1H), 7.15 (dd, J=7.6, 4.6 Hz, 1H), 7.97 (d, J=7.3 Hz, 1H), 8.39 (dd, J=4.9, 1.2 Hz, 1H); MS (ESI$^+$): 525 $[M+H]^+$.

The following compounds were also synthesized from the corresponding starting materials and reagents using conditions analogous to compound 237.

| Compound No. | Chemical structural formula | Spectrum data |
|---|---|---|
| 340 | 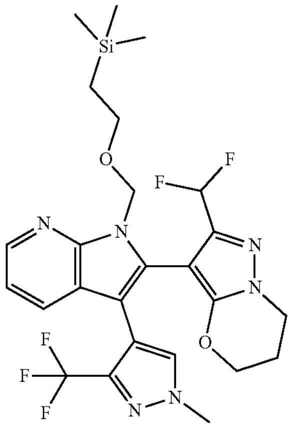 [SMILES: Cn1cc(-c2c(-c3c(C(F)F)nn4c3OCCC4)n(COCC[Si](C)(C)C)c3ncccc23)c(C(F)(F)F)n1] | $^1$H-NMR (400 MHz, $CDCl_3$) δ −0.14-−0.07 (m, 9H), 0.78-0.92 (m, 2H), 2.17-2.32 (m, 2H), 3.41-3.50 (m, 2H), 3.95 (s, 3H), 4.09-4.30 (m, 4H), 5.54 (d, J = 11.0 Hz, 1H), 5.66 (d, J = 11.0 Hz, 1H), 6.52 (t, J = 54.6 Hz, 1H), 7.00-7.13 (m, 1H), 7.28 (s, 1H), 7.71 (dd, J = 7.9, 1.8 Hz, 1H), 8.37 (dd, J = 4.6, 1.5 Hz, 1H); MS (ESI$^+$): 569 $[M + H]^+$. |

-continued

| Compound No. | Chemical structural formula | Spectrum data |
|---|---|---|
| 341 | 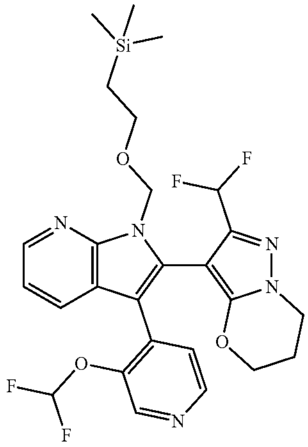 [SMILES: C[Si](C)(C)CCOCn1c(-c2c(C(F)F)nn3c2OCCC3)c(-c2ccncc2OC(F)F)c2cccnc21] | $^1$H-NMR (400 MHz, $CDCl_3$) δ −0.10 (s, 9H), 0.81-0.90 (m, 2H), 2.13-2.35 (m, 2H), 3.44-3.51 (m, 2H), 4.01-4.09 (m, 1H), 4.17-4.28 (m, 3H), 5.64 (d, J = 11.0 Hz, 1H), 5.69 (d, J = 10.9 Hz, 1H), 6.19 (t, J = 74.5 Hz, 1H), 6.57 (t, J = 54.4 Hz, 1H), 7.16-7.21 (m, 2H), 7.84 (dd, J = 7.9, 1.5 Hz, 1H), 8.39 (d, J = 4.9 Hz, 1H), 8.43 (dd, J = 4.7, 1.5 Hz, 1H), 8.55 (s, 1H); MS (ESI$^+$): 564 [M + H]$^+$. |

(149) Reference Procedure of (S)-6-((tert-butyldiphenylsilyl)oxy)-3-(3-(3-(difluoromethoxy)-1-methyl-1H-pyrazol-4-yl)-1-((2-(trimethylsilyl)ethoxy)methyl)-1H-pyrrolo[2,3-b]pyridin-2-yl)-2-methyl-6,7-dihydro-5H-pyrazolo[5,1-b][1,3]oxazine (342)

(342)

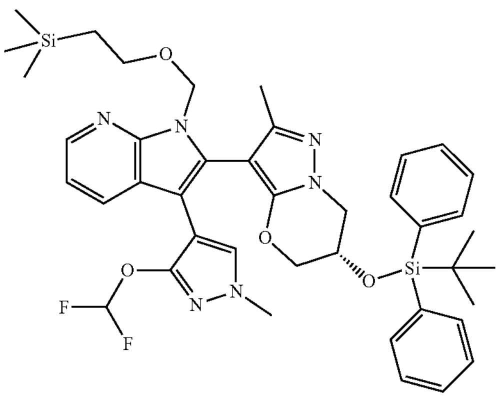

The compound 342 was synthesized from compounds 255 and 10iiiiii using conditions analogous to compound 256. The crude product obtained was used directly in the next step without purification.

The following compounds were also synthesized from the corresponding starting materials and reagents using conditions analogous to compound 256.

| Compound No. | Chemical structural formula | Spectrum data |
|---|---|---|
| 343 | 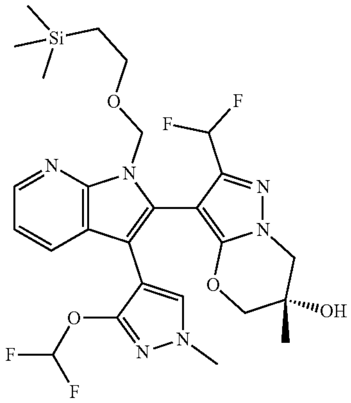 [SMILES: Cn1cc(-c2c(-c3c(C(F)F)nn4c3OC[C@@](C)(O)C4)n(COCC[Si](C)(C)C)c3ncccc23)c(OC(F)F)n1] | The crude compound obtained was used directly in the next step without purification. |
| 344 | 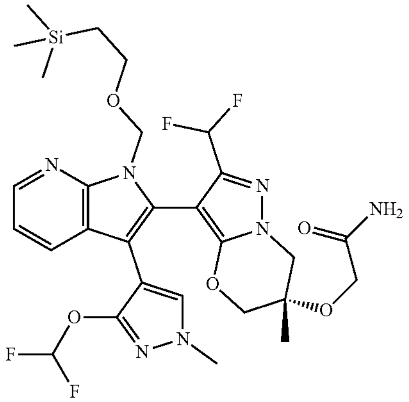 [SMILES: Cn1cc(-c2c(-c3c(C(F)F)nn4c3OC[C@@](C)(OCC(N)=O)C4)n(COCC[Si](C)(C)C)c3ncccc23)c(OC(F)F)n1] | $^1$H-NMR (400 MHz, $CDCl_3$) δ −0.15-−0.08 (m, 9H), 0.78-0.92 (m, 2H), 1.41-1.43 (m, 3H), 3.42-3.53 (m, 1H), 3.76-3.90 (m, 3H), 3.93-4.08 (m, 5H), 4.24-4.44 (m, 2H), 5.29-7.17 (m, 6H), 7.89-7.91 (m, 1H), 8.36-8.39 (m, 1H); MS (ESI$^+$): 654 $[M + H]^+$. |
| 345 | 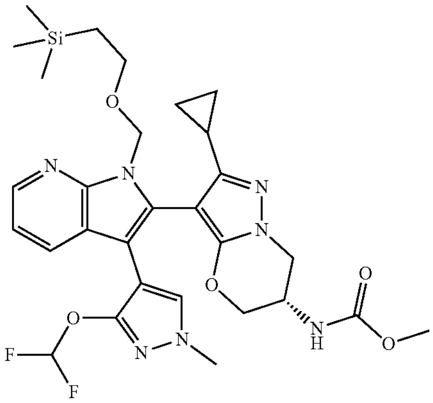 [SMILES: COC(=O)N[C@@H]1COc2c(-c3c(-c4cn(C)nc4OC(F)F)c4cccnc4n3COCC[Si](C)(C)C)c(C3CC3)nn2C1] | The crude compound obtained was used directly in the next step without purification. |
| 346 | 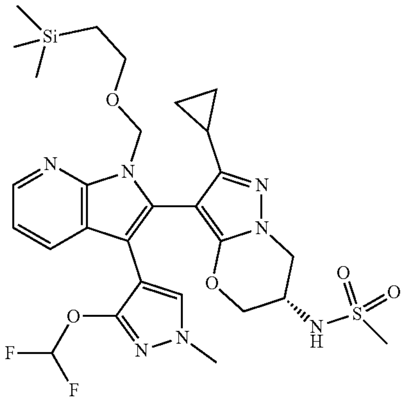 [SMILES: Cn1cc(-c2c(-c3c(C4CC4)nn4c3OC[C@@H](NS(C)(=O)=O)C4)n(COCC[Si](C)(C)C)c3ncccc23)c(OC(F)F)n1] | The crude compound obtained was used directly in the next step without purification. |

-continued

| Compound No. | Chemical structural formula | Spectrum data |
|---|---|---|
| 347 | 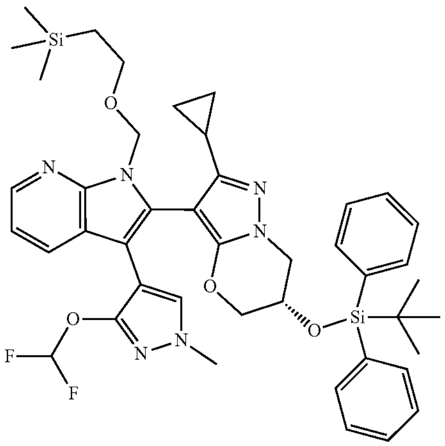 [SMILES: Cn1cc(-c2c(-c3c(C4CC4)nn4c3OC[C@@H](O[Si](c3ccccc3)(c3ccccc3)C(C)(C)C)C4)n(COCC[Si](C)(C)C)c3ncccc23)c(OC(F)F)n1] | The crude compound obtained was used directly in the next step without purification. |

(150) Experimental procedure of (S)-3-(3-(3-(difluoromethoxy)-1-methyl-1H-pyrazol-4-yl)-1H-pyrrolo[2,3-b]pyridin-2-yl)-2-methyl-6,7-dihydro-5H-pyrazolo[5,1-b][1,3]oxazin-6-ol (EX.480)

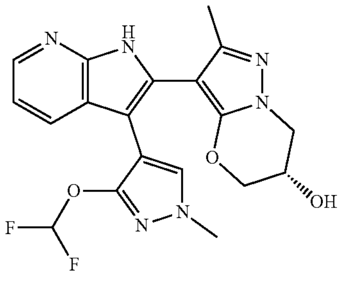

EX.480

EX.480 was synthesized from compound 342 using conditions analogous to EX.420; $^1$H-NMR (400 MHz, DMSO-$d_6$) δ 1.92 (s, 3H), 3.75 (s, 3H), 3.88 (dd, J=12.5, 2.6 Hz, 1H), 4.07-4.12 (m, 2H), 4.18 (dd, J=12.3, 3.9 Hz, 1H), 4.24-4.29 (m, 1H), 5.58 (d, J=3.0 Hz, 1H), 7.06 (dd, J=7.8, 4.7 Hz, 1H), 7.15 (t, J=73.9 Hz, 1H), 7.55 (s, 1H), 7.79 (dd, J=7.9, 1.1 Hz, 1H), 8.19 (dd, J=4.7, 1.6 Hz, 1H), 11.63 (s, 1H); MS (ESI$^+$): 417 $[M+H]^+$.

The following compounds were also synthesized from the corresponding starting materials and reagents using conditions analogous to EX.420.

| Compound No. | Chemical structural formula | Spectrum data |
|---|---|---|
| EX.481 | 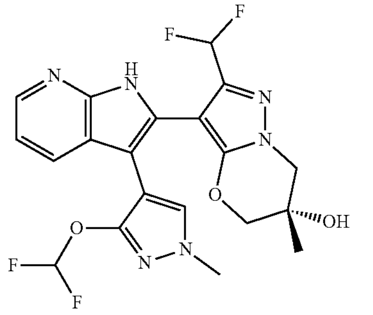 [SMILES: Cn1cc(-c2c(-c3c(C(F)F)nn4c3OC[C@@](C)(O)C4)[nH]c3ncccc23)c(OC(F)F)n1] | $^1$H-NMR (400 MHz, DMSO-$d_6$) δ 1.29 (s, 3H), 3.73 (s, 3H), 3.95-4.14 (m, 4H), 5.49 (s, 1H), 6.71 (t, J = 54.1 Hz, 1H), 7.09 (dd, J = 7.9, 4.7 Hz, 1H), 7.13 (t, J = 73.8 Hz, 1H), 7.52 (s, 1H), 7.83 (dd, J = 7.9, 1.5 Hz, 1H), 8.23 (dd, J = 4.7, 1.6 Hz, 1H), 11.77 (s, 1H); MS (ESI$^+$): 467 [M + H]$^+$. |
| EX.482 | 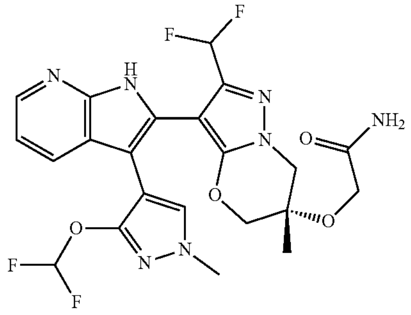 [SMILES: Cn1cc(-c2c(-c3c(C(F)F)nn4c3OC[C@@](C)(OCC(N)=O)C4)[nH]c3ncccc23)c(OC(F)F)n1] | $^1$H-NMR (400 MHz, DMSO-$d_6$) δ 1.29 (s, 3H), 3.71-3.79 (m, 4H), 3.90 (d, J = 15.3 Hz, 1H), 4.03 (d, J = 11.4 Hz, 1H), 4.11 (d, J = 12.9 Hz, 1H), 4.42 (t, J = 13.2 Hz, 2H), 6.70 (t, J = 54.1 Hz, 1H), 6.90-7.27 (m, 3H), 7.34 (d, J = 1.8 Hz, 1H), 7.49 (s, 1H), 7.81 (dd, J = 7.9, 1.2 Hz, 1H), 8.23 (dd, J = 4.7, 1.6 Hz, 1H), 11.78 (s, 1H); MS (ESI$^+$): 524 [M + H]$^+$. |
| EX.483 | 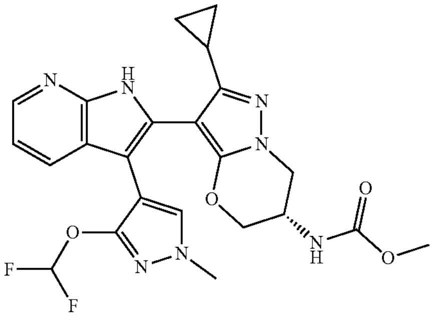 [SMILES: COC(=O)N[C@@H]1COc2c(-c3[nH]c4ncccc4c3-c3cn(C)nc3OC(F)F)c(C3CC3)nn2C1] | $^1$H-NMR (400 MHz, DMSO-$d_6$) δ 0.42-0.68 (m, 4H), 1.37-1.46 (m, 1H), 3.59 (s, 3H), 3.76 (s, 3H), 3.88-3.96 (m, 1H), 4.13-4.27 (m, 4H), 7.07 (dd, J = 7.8, 4.7 Hz, 1H), 7.16 (t, J = 73.8 Hz, 1H), 7.54 (s, 1H), 7.61 (d, J = 5.3 Hz, 1H), 7.80 (dd, J = 7.8, 1.2 Hz, 1H), 8.20 (dd, J = 4.7, 1.6 Hz, 1H), 11.55 (s, 1H); MS (ESI$^+$) : 500 [M + H]$^+$. |
| EX.484 | 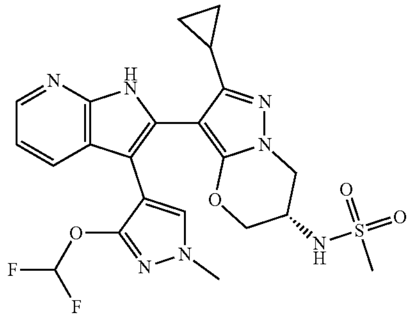 [SMILES: Cn1cc(-c2c(-c3c(C4CC4)nn4c3OC[C@@H](NS(C)(=O)=O)C4)[nH]c3ncccc23)c(OC(F)F)n1] | $^1$H-NMR (400 MHz, DMSO-$d_6$) δ 0.47-0.67 (m, 4H), 1.41-1.51 (m, 1H), 3.07 (s, 3H), 3.76 (s, 3H), 3.96 (dd, J = 12.1, 4.5 Hz, 1H), 4.08-4.19 (m, 2H), 4.22-4.33 (m, 2H), 7.07 (dd, J = 7.8, 4.7 Hz, 1H), 7.17 (t, J = 73.6 Hz, 1H), 7.53 (s, 1H), 7.60 (d, J = 4.8 Hz, 1H), 7.80 (d, J = 7.8 Hz, 1H), 8.20 (dd, J = 4.7, 1.0 Hz, 1H), 11.59 (s, 1H); MS (ESI$^+$): 520 [M + H]$^+$. |

-continued

| Compound No. | Chemical structural formula | Spectrum data |
| --- | --- | --- |
| EX.485 | 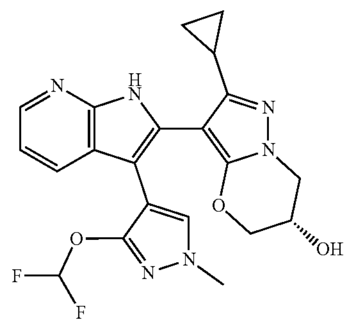 [SMILES: Cn1cc(-c2c(-c3c(C4CC4)nn4c3OC[C@@H](O)C4)[nH]c3ncccc23)c(OC(F)F)n1] | $^1$H-NMR (400 MHz, DMSO-$d_6$) δ 0.50-0.63 (m, 4H), 1.47-1.55 (m, 1H), 3.74 (s, 3H), 3.86 (dd, J = 12.4, 2.6 Hz, 1H), 4.08-4.20 (m, 3H), 4.23-4.30 (m, 1H), 5.57 (d, J = 3.3 Hz, 1H), 7.06 (dd, J = 7.9, 4.7 Hz, 1H), 7.15 (t, J = 73.9 Hz, 1H), 7.52 (s, 1H), 7.79 (dd, J = 7.8, 1.4 Hz, 1H), 8.19 (dd, J = 4.7, 1.6 Hz, 1H), 11.64 (s, 1H); MS (ESI$^+$): 443 [M + H]$^+$. |

(151) Reference Procedure of (S)-3-(2-(2-(difluoromethyl)-6-methoxy-6-methyl-6,7-dihydro-5H-pyrazolo[5,1-b][1,3]oxazin-3-yl)-1-((2-(trimethylsilyl)ethoxy)methyl)-1H-pyrrolo[2,3-b]pyridin-3-yl)-5-methylthiophene-2-carbonitrile (348)

(348)

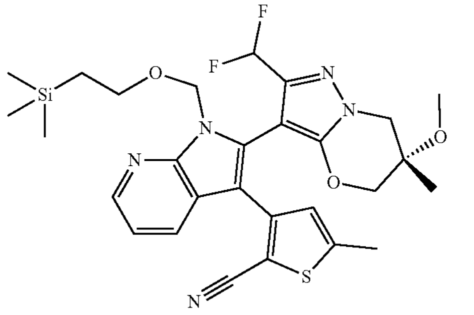

The compound 348 was synthesized from compound 280 and the corresponding borate using conditions analogous to compound 256; $^1$H-NMR (400 MHz, $CDCl_3$) δ −0.16-−0.08 (m, 9H), 0.72-0.90 (m, 2H), 1.34-1.40 (m, 3H), 2.48-2.57 (m, 3H), 3.22-3.53 (m, 5H), 3.94-4.02 (m, 1H), 4.13-4.15 (m, 1H), 4.27-4.35 (m, 2H), 5.39-7.00 (m, 4H), 7.15-7.21 (m, 1H), 7.89-8.02 (m, 1H), 8.40-8.43 (m, 1H); MS (ESI$^+$): 586 [M+H]$^+$.

(152) Reference Procedure of 1-methyl-4-(1-((2-(trimethylsilyl)ethoxy)methyl)-1H-pyrrolo[2,3-b]pyridin-3-yl)-1H-pyrazole-3-carbonitrile (349)

(349)

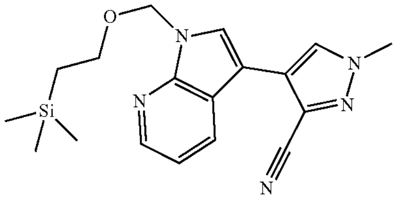

The compound 349 was synthesized from compound 233 and the corresponding halide using conditions analogous to compound 237; $^1$H-NMR (400 MHz, $CDCl_3$) δ −0.06 (s, 9H), 0.90-0.98 (m, 2H), 3.56-3.64 (m, 2H), 4.06 (s, 3H), 5.73 (s, 2H), 7.19 (dd, J=7.9, 4.7 Hz, 1H), 7.74 (s, 1H), 7.81 (s, 1H), 8.00 (dd, J=7.9, 1.5 Hz, 1H), 8.41 (dd, J=4.7, 1.5 Hz, 1H).

(153) Experimental procedure of (S)-3-(2-(2-(difluoromethyl)-6-methoxy-6-methyl-6,7-dihydro-5H-pyrazolo[5,1-b][1,3]oxazin-3-yl)-1H-pyrrolo[2,3-b]pyridin-3-yl)-5-methylthiophene-2-carbonitrile (EX.486)

EX.486

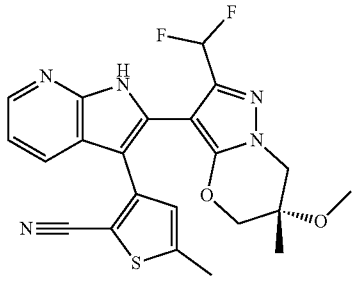

EX.486 was synthesized from compound 348 using conditions analogous to EX.420; $^1$H-NMR (400 MHz, DMSO-$d_6$) δ 1.24 (s, 3H), 2.51 (s, 3H), 3.14 (s, 3H), 3.95 (d, J=11.8 Hz, 1H), 4.08-4.23 (m, 2H), 4.30 (dd, J=11.8, 2.1 Hz, 1H), 6.75 (t, J=54.0 Hz, 1H), 6.83 (d, J=1.1 Hz, 1H), 7.18 (dd, J=7.9, 4.7 Hz, 1H), 7.93 (dd, J=8.0, 1.5 Hz, 1H), 8.30 (dd, J=4.7, 1.5 Hz, 1H), 12.14 (s, 1H); MS (ESI$^+$): 456 [M+H]$^+$.

The following compounds were also synthesized from the corresponding starting materials and reagents using conditions analogous to EX.420.

| Compound No. | Chemical structural formula | Spectrum data |
|---|---|---|
| EX.487 | 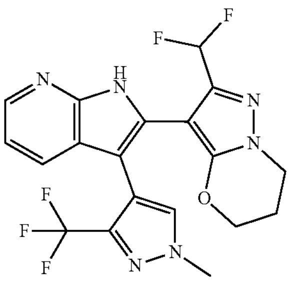 [SMILES: Cn1cc(-c2c(-c3c(C(F)F)nn4c3OCCC4)[nH]c3ncccc23)c(C(F)(F)F)n1] | $^{1}$H-NMR (400 MHz, DMSO-$d_6$) δ 2.12-2.22 (m, 2H), 3.92 (s, 3H), 4.10-4.25 (m, 4H), 6.66 (t, J = 53.9 Hz, 1H), 7.04-7.08 (m, 1H), 7.63 (d, J = 7.3 Hz, 1H), 7.72 (s, 1H), 8.22 (d, J = 4.3 Hz, 1H), 11.78 (s, 1H); MS (ESI$^+$): 439 [M + H]$^+$. |
| EX.488 | 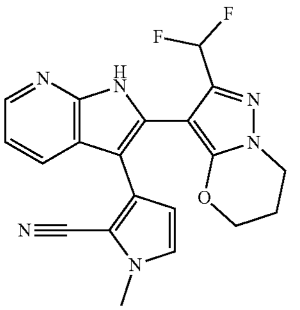 [SMILES: Cn1ccc(-c2c(-c3c(C(F)F)nn4c3OCCC4)[nH]c3ncccc23)c1C#N] | $^{1}$H-NMR (400 MHz, DMSO-$d_6$) δ 2.16-2.23 (m, 2H), 3.67-3.74 (m, 3H), 4.12-4.31 (m, 4H), 6.14 (s, 1H), 6.26-6.55 (m, 1H), 7.07-7.19 (m, 2H), 7.89 (d, J = 7.3 Hz, 1H), 8.24 (s, 1H), 11.86 (s, 1H); MS (ESI$^+$): 395 [M + H]$^+$. |
| EX.489 | 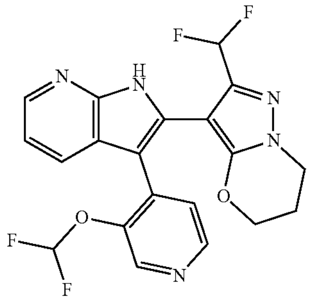 [SMILES: FC(F)Oc1cnccc1-c1c(-c2c(C(F)F)nn3c2OCCC3)[nH]c2ncccc12] | $^{1}$H-NMR (400 MHz, DMSO-$d_6$) δ 2.07-2.18 (m, 2H), 4.06-4.18 (m, 4H), 6.60-7.23 (m, 4H), 7.80 (dd, J = 8.0, 1.4 Hz, 1H), 8.29 (dd, J = 4.6, 1.4 Hz, 1H), 8.38 (d, J = 4.9 Hz, 1H), 8.51 (s, 1H), 12.10 (s, 1H); MS (ESI$^+$): 434 [M + H]$^+$. |
| EX.490 | 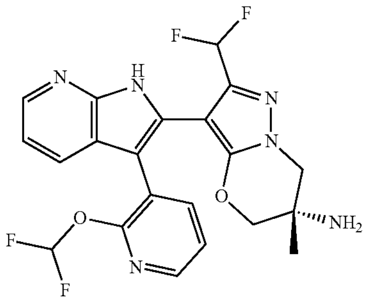 [SMILES: C[C@@]1(N)COc2c(-c3[nH]c4ncccc4c3-c3cccnc3OC(F)F)c(C(F)F)nn2C1] | $^{1}$H-NMR (400 MHz, DMSO-$d_6$) δ 1.04 (s, 3H), 1.83 (s, 2H), 3.73 (s, 2H), 3.84 (d, J = 12.1 Hz, 1H), 3.91 (d, J = 12.2 Hz, 1H), 6.75 (t, J = 54.1 Hz, 1H), 7.11 (dd, J = 7.9, 4.7 Hz, 1H), 7.22 (dd, J = 7.5, 4.9 Hz, 1H), 7.52-7.89 (m, 3H), 8.18 (dd, J = 4.9, 1.9 Hz, 1H), 8.27 (dd, J = 4.7, 1.6 Hz, 1H), 11.95 (s, 1H); MS (ESI$^+$): 463 [M + H]$^+$. |

(154) Reference Procedure of 4-(2-bromo-1-((2-(trimethylsilyl)ethoxy)methyl)-1H-pyrrolo[2,3-b]pyridin-3-yl)-1-methyl-1H-pyrazole-3-carbonitrile (350)

(350)

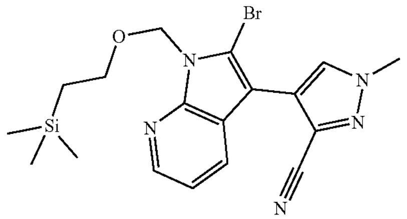

The compound 350 was synthesized from compound 349 using conditions analogous to compound 235; $^1$H-NMR (400 MHz, $CDCl_3$) δ −0.05 (s, 9H), 0.92-0.99 (m, 2H), 3.63-3.70 (m, 2H), 4.08 (s, 3H), 5.83 (s, 2H), 7.17 (dd, J=7.9, 4.7 Hz, 1H), 7.69 (s, 1H), 7.89 (dd, J=7.9, 1.5 Hz, 1H), 8.37 (dd, J=4.7, 1.5 Hz, 1H); MS (ESI$^+$): 432 $[M+H]^+$.

(155) Reference Procedure of (S)-4-(2-(6-((tert-butyldiphenylsilyl)oxy)-2-(difluoromethyl)-6,7-dihydro-5H-pyrazolo[5,1-b][1,3]oxazin-3-yl)-1-((2-(trimethylsilyl)ethoxy)methyl)-1H-pyrrolo[2,3-b]pyridin-3-yl)-1-methyl-1H-pyrazole-3-carbonitrile (351)

(351)

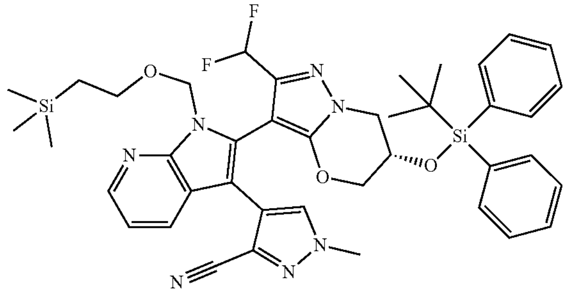

The compound 351 was synthesized from compounds 350 and 226 using conditions analogous to compound 256; $^1$H-NMR (400 MHz, $CDCl_3$) δ −0.14-−0.11 (m, 9H), 0.75-0.94 (m, 2H), 1.03-1.12 (m, 9H), 3.34-3.52 (m, 2H), 3.74-4.01 (m, 3H), 4.03-4.37 (m, 5H), 5.42-6.04 (m, 2H), 6.17-6.59 (m, 1H), 7.14-7.20 (m, 1H), 7.35-7.72 (m, 11H), 7.84-7.98 (m, 1H), 8.38-8.44 (m, 1H) MS (ESI$^+$): 780 $[M+H]^+$.

(156) Reference Procedure of methyl (S)-(3-(3-(2-(difluoromethoxy)pyridin-3-yl)-1-((2-(trimethylsilyl)ethoxy)methyl)-1H-pyrrolo[2,3-b]pyridin-2-yl)-2-(difluoromethyl)-6-methyl-6,7-dihydro-5H-pyrazolo[5,1-b][1,3]oxazin-6-yl) carbamate (352)

(352)

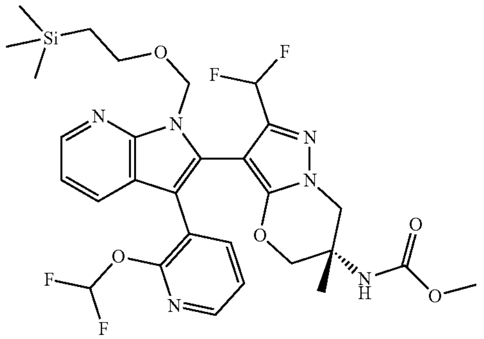

The compound 352 was synthesized from compound 337 using conditions analogous to compound 218; $^1$H-NMR (400 MHz, $CDCl_3$) δ −0.09-−0.06 (m, 9H), 0.85-0.92 (m, 2H), 1.53 (s, 3H), 3.53-3.59 (m, 2H), 3.67 (d, J=9.9 Hz, 3H), 3.86-3.95 (m, 2H), 4.29-4.38 (m, 1H), 4.65-4.71 (m, 1H), 5.35-6.72 (m, 4H), 7.00-7.23 (m, 2H), 7.29-7.52 (m, 1H), 7.55-7.74 (m, 1H), 7.80 (ddd, J=7.9, 5.1, 1.6 Hz, 1H), 8.13 (dd, J=4.9, 1.9 Hz, 1H), 8.40 (dd, J=4.7, 1.4 Hz, 1H); MS (ESI$^+$): 651 $[M+H]^+$.

(157) Reference Procedure of (S)-4-(2-(2-(difluoromethyl)-6-hydroxy-6,7-dihydro-5H-pyrazolo[5,1-b][1,3]oxazin-3-yl)-1-((2-(trimethylsilyl)ethoxy)methyl)-1H-pyrrolo[2,3-b]pyridin-3-yl)-1-methyl-1H-pyrazole-3-carbonitrile (353)

(353)

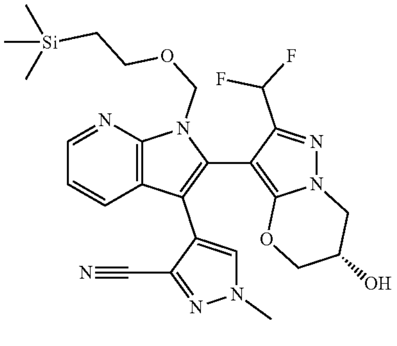

A mixture of compound 328 (334 mg, 0.428 mmol) and $K_3PO_4$ (368 mg, 1.28 mmol) in DMF (4 mL) was stirred at 65° C. at 1 h under Ar atmosphere. The reaction mixture was filtered off through a pad of Celite, and the filtrate was concentrated. The residue was purified by silica gel column chromatography (25-100% EtOAc/hexane) to yield compound 353 (158 mg, 68%) as a brown amorphous; $^1$H-NMR (400 MHz, DMSO-$d_6$) δ −0.18-−0.10 (m, 9H), 0.61-0.81 (m, 2H), 3.23-3.42 (m, 2H), 3.88-3.99 (m, 3H), 4.02-4.11 (m, 1H), 4.18-4.44 (m, 4H), 5.33-5.81 (m, 3H), 6.28-6.79 (m, 1H), 7.23-7.29 (m, 1H), 7.77-8.12 (m, 2H), 8.36-8.41 (m, 1H); MS (ESI+): 542 [M+H]+.

The following compounds were synthesized from the corresponding starting materials and reagents using conditions analogous to compound 353.

| Compound No. | Chemical structural formula | Spectrum data |
|---|---|---|
| 354 | 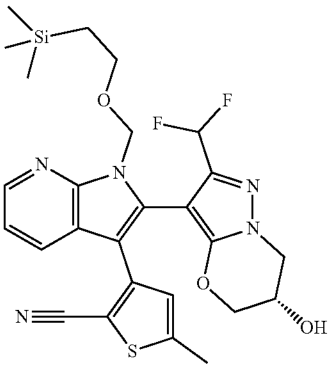 [SMILES: Cc1cc(-c2c(-c3c(C(F)F)nn4c3OC[C@@H](O)C4)n(COCC[Si](C)(C)C)c3ncccc23)c(C#N)s1] | $^1$H-NMR (400 MHz, $CDCl_3$) δ −0.14-−0.07 (m, 9H), 0.76-0.94 (m, 2H), 2.56-2.62 (m, 3H), 3.37-3.55 (m, 2H), 4.30-4.63 (m, 6H), 5.54-6.30 (m, 3H), 6.97-7.20 (m, 2H), 7.93 (dd, J = 7.9, 1.6 Hz, 1H), 8.40-8.43 (m, 1H); MS (ESI+): 558 [M + H]+. |
| 355 | 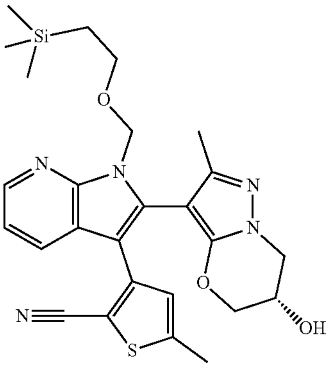 [SMILES: Cc1cc(-c2c(-c3c(C)nn4c3OC[C@@H](O)C4)n(COCC[Si](C)(C)C)c3ncccc23)c(C#N)s1] | $^1$H-NMR (400 MHz, $CDCl_3$) δ −0.14-−0.10 (m, 9H), 0.71-0.90 (m, 2H), 1.61-1.73 (m, 4H), 2.60-2.62 (m, 3H), 3.37-3.53 (m, 2H), 4.31-4.54 (m, 5H), 5.50 (d, J = 11.0 Hz, 1H), 5.99 (d, J = 11.0 Hz, 1H), 7.10-7.18 (m, 2H), 7.90-7.93 (m, 1H), 8.39-8.41 (m, 1H); MS (ESI+): 522 [M + H]+. |
| 356 | 3 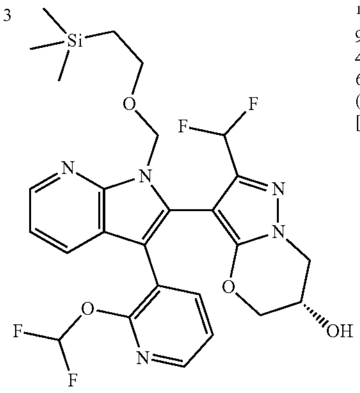 | $^1$H-NMR (400 MHz, $CDCl_3$) δ −0.15-−0.09 (m, 9H), 0.82-0.93 (m, 2H), 3.46-3.68 (m, 3H), 4.18-4.43 (m, 5H), 5.58-5.75 (m, 2H), 6.15-6.59 (m, 1H), 7.08-7.83 (m, 5H), 8.11-8.14 (m, 1H), 8.39-8.40 (m, 1H); MS (ESI+): 580 [M + H]+. |

-continued

| Compound No. | Chemical structural formula | Spectrum data |
|---|---|---|
| 357 | 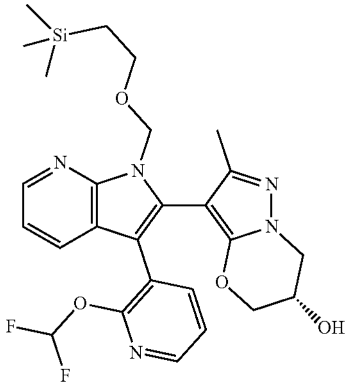 [SMILES: Cc1nn2c(c1-c1c(-c3cccnc3OC(F)F)c3cccnc3n1COCC[Si](C)(C)C)OC[C@@H](O)C2] | $^1$H-NMR (400 MHz, $CDCl_3$) δ −0.15-−0.05 (m, 9H), 0.74-0.92 (m, 2H), 1.53-1.78 (m, 3H), 1.84 (s, 1H), 3.42-3.55 (m, 2H), 4.10-4.44 (m, 5H), 5.52-5.83 (m, 2H), 7.08-7.16 (m, 2H), 7.24-7.52 (m, 1H), 7.64-7.82 (m, 2H), 8.11-8.14 (m, 1H), 8.38-8.40 (m, 1H); MS (ESI$^+$): 544 [M + H]$^+$. |
| 358 | 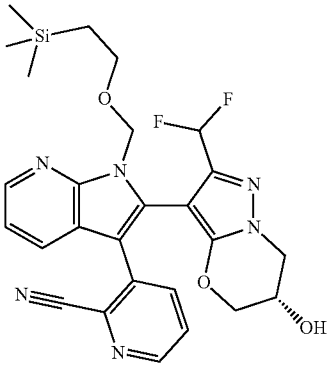 [SMILES: C[Si](C)(C)CCOCn1c(-c2c(C(F)F)nn3c2OC[C@@H](O)C3)c(-c2cccnc2C#N)c2cccnc21] | $^1$H-NMR (400 MHz, $CDCl_3$) δ −0.15-−0.07 (m, 9H), 0.75-0.94 (m, 2H), 3.38-3.55 (m, 2H), 4.27-4.51 (m, 5H), 5.55-6.38 (m, 3H), 7.20 (dd, J = 7.9, 4.7 Hz, 1H), 7.52-7.61 (m, 1H), 7.81-8.04 (m, 2H), 8.44-8.47 (m, 1H), 8.64 (dd, J = 4.6, 1.6 Hz, 1H); MS (ESI$^+$): 539 [M + H]$^+$. |

(158) Reference Procedure of methyl (S)-2-((3-(3-(3-(difluoromethoxy)-1-methyl-1H-pyrazol-4-yl)-1-((2-(trimethylsilyl)ethoxy)methyl)-1H-pyrrolo[2,3-b]pyridin-2-yl)-2-(difluoromethyl)-6-methyl-6,7-dihydro-5H-pyrazolo[5,1-b][1,3]oxazin-6-yl)oxy)acetate (359)

(359)

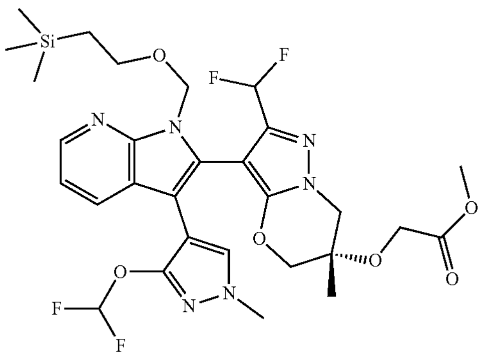

To a stirred solution of compound 343 (100 mg, 0.168 mmol) in THF (0.84 mL) at 0° C. under Ar atmosphere, 60% sodium hydride (8.1 mg, 0.186 mmol) was added. After stirring at the same temperature for 0.5 h, methyl bromoacetate (0.021 mL, 0.222 mmol) was added and the resulting mixture was stirred at room temperature for 1 h, followed by stirring at 40° C. for 6 h. The reaction was quenched with sat. aq. $NH_4Cl$, and the resulting mixture extracted with EtOAc. The organic layer was washed with brine, dried over $Na_2SO_4$, and concentrated. The residue was purified by silica gel column chromatography (25-100% EtOAc/hexane) to yield compound 359 (80.0 mg, 72%) as a colorless oil; $^1$H-NMR (400 MHz, $CDCl_3$) δ −0.12-−0.09 (m, 9H), 0.79-0.89 (m, 2H), 1.38-1.41 (m, 3H), 3.42-3.52 (m, 2H), 3.69-3.80 (m, 6H), 3.96-4.19 (m, 4H), 4.29-4.40 (m, 2H), 5.38-5.82 (m, 2H), 6.28-7.17 (m, 3H), 7.28 (s, 1H), 7.87-7.89 (m, 1H), 8.37-8.40 (m, 1H); MS (ESI$^+$): 669 [M+H]$^+$.

The following compounds also synthesized from the corresponding starting materials and reagents using conditions analogous to compound 359.

| Compound No. | Chemical structural formula | Spectrum data |
|---|---|---|
| 360 | 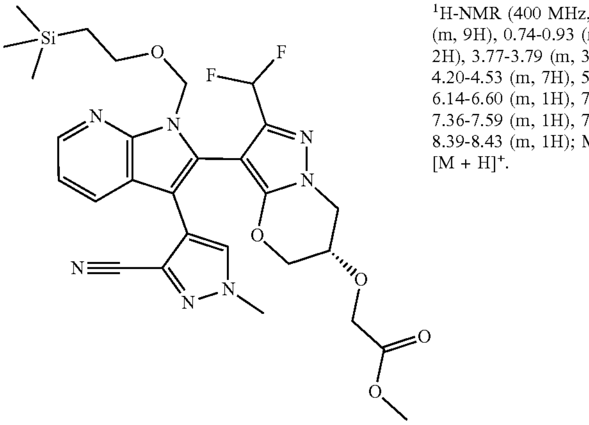 | $^1$H-NMR (400 MHz, $CDCl_3$) δ −0.13-−0.07 (m, 9H), 0.74-0.93 (m, 2H), 3.35-3.53 (m, 2H), 3.77-3.79 (m, 3H), 3.92-4.03 (m, 3H), 4.20-4.53 (m, 7H), 5.42-5.90 (m, 2H), 6.14-6.60 (m, 1H), 7.14-7.20 (m, 1H), 7.36-7.59 (m, 1H), 7.84-7.99 (m, 1H), 8.39-8.43 (m, 1H); MS (ESI$^+$): 614 $[M + H]^+$. |
| 361 | 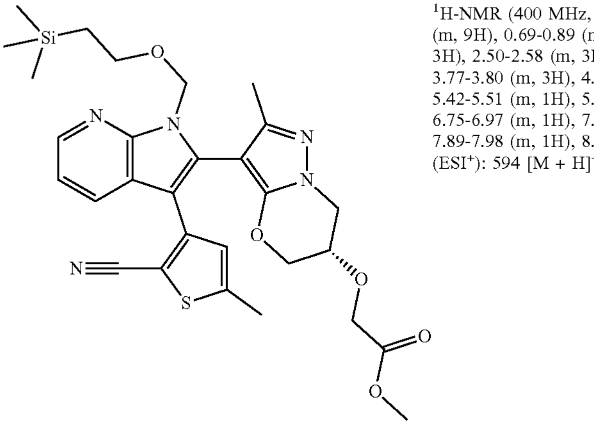 | $^1$H-NMR (400 MHz, $CDCl_3$) δ −0.15-−0.09 (m, 9H), 0.69-0.89 (m, 2H), 1.66-1.80 (m, 3H), 2.50-2.58 (m, 3H), 3.31-3.50 (m, 2H), 3.77-3.80 (m, 3H), 4.22-4.52 (m, 7H), 5.42-5.51 (m, 1H), 5.81-6.02 (m, 1H), 6.75-6.97 (m, 1H), 7.14-7.19 (m, 1H), 7.89-7.98 (m, 1H), 8.38-8.41 (m, 1H); MS (ESI$^+$): 594 $[M + H]^+$. |
| 362 | 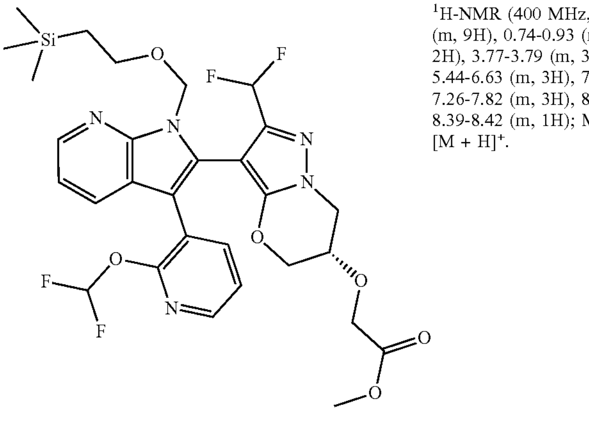 | $^1$H-NMR (400 MHz, $CDCl_3$) δ −0.12-−0.07 (m, 9H), 0.74-0.93 (m, 2H), 3.39-3.55 (m, 2H), 3.77-3.79 (m, 3H), 4.10-4.51 (m, 7H), 5.44-6.63 (m, 3H), 7.00-7.17 (m, 2H), 7.26-7.82 (m, 3H), 8.09-8.13 (m, 1H), 8.39-8.42 (m, 1H); MS (ESI$^+$): 652 $[M + H]^+$. |

-continued

| Compound No. | Chemical structural formula | Spectrum data |
|---|---|---|
| 363 | 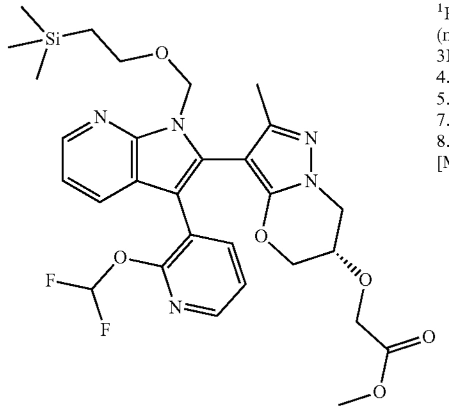 | $^1$H-NMR (400 MHz, $CDCl_3$) δ −0.14-−0.10 (m, 9H), 0.71-0.88 (m, 2H), 1.72-1.85 (m, 3H), 3.35-3.52 (m, 2H), 3.77-3.79 (m, 3H), 4.14-4.49 (m, 7H), 5.43-5.55 (m, 1H), 5.75-5.94 (m, 1H), 7.03-7.15 (m, 2H), 7.32-7.81 (m, 3H), 8.09-8.13 (m, 1H), 8.37-8.41 (m, 1H); MS (ESI$^+$): 616 [M + H]$^+$. |
| 364 | 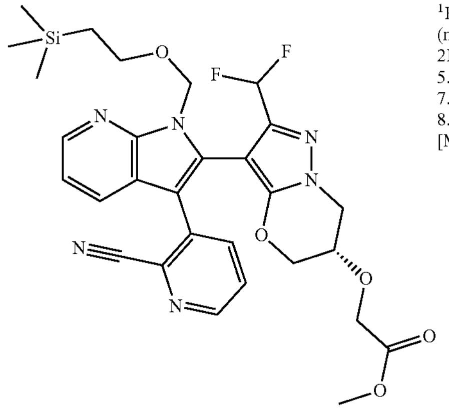 | $^1$H-NMR (400 MHz, $CDCl_3$) δ −0.15-−0.07 (m, 9H), 0.72-0.92 (m, 2H), 3.35-3.60 (m, 2H), 3.77-3.80 (m, 3H), 4.04-4.55 (m, 7H), 5.43-6.59 (m, 3H), 7.17-7.22 (m, 1H), 7.41-7.97 (m, 3H), 8.43-8.47 (m, 1H), 8.59-8.64 (m, 1H); MS (ESI$^+$): 611 [M + H]$^+$. |

(159) Reference Procedure of (S)-4-(2-(2-(difluoromethyl)-6-hydroxy-6,7-dihydro-5H-pyrazolo[5,1-b][1,3]oxazin-3-yl)-1H-pyrrolo[2,3-b]pyridin-3-yl)-1-methyl-1H-pyrazole-3-carbonitrile (365)

(365)

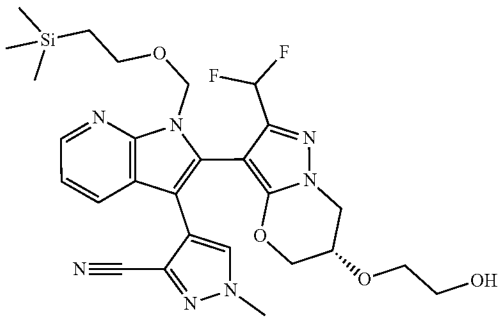

To a stirred solution of compound 360 (254 mg, 0.392 mmol) in THF (2 mL) at 0° C. under Ar atmosphere, 4 mol/L lithium borohydride in THF (0.49 mL, 1.96 mmol) was added. After stirring at room temperature for 1 h, the reaction was quenched with sat. aq. $NH_4Cl$, and the resulting mixture was extracted with EtOAc. The organic layer was washed with brine, dried over $Na_2SO_4$, and concentrated. The residue was purified by silica gel column chromatography (25-100% EtOAc/hexane) to yield compound 365 (163 mg, 71%) as a colorless oil; $^1$H-NMR (400 MHz, DMSO-$d_6$) δ −0.18-−0.12 (m, 9H), 0.61-0.79 (m, 2H), 3.22-3.42 (m, 2H), 3.50-3.56 (m, 2H), 3.58-3.67 (m, 2H), 3.91-3.99 (m, 3H), 4.18-4.59 (m, 5H), 4.69-4.73 (m, 1H), 5.28-5.80 (m, 2H), 6.29-6.78 (m, 1H), 7.23-7.28 (m, 1H), 7.68-8.12 (m, 2H), 8.37-8.40 (m, 1H); MS (ESI$^+$): 586 [M+H]$^+$.

The following compounds were also synthesized from the corresponding starting materials and reagents using conditions analogous to compound 365.

| Compound No. | Chemical structural formula | Spectrum data |
|---|---|---|
| 366 | 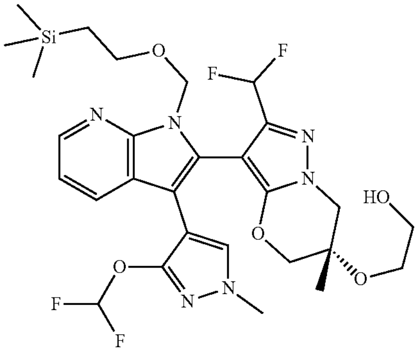 [SMILES: Cn1cc(-c2c(-c3c(C(F)F)nn4c3OC[C@@](C)(OCCO)C4)n(COCC[Si](C)(C)C)c3ncccc23)c(OC(F)F)n1] | $^1$H-NMR (400 MHz, $CDCl_3$) δ −0.15--0.08 (m, 9H), 0.83-0.94 (m, 2H), 1.37-1.38 (m, 3H), 3.39-3.71 (m, 6H), 3.78-3.80 (m, 3H), 3.93-4.06 (m, 2H), 4.25-4.48 (m, 2H), 5.56-5.66 (m, 2H), 6.20-7.00 (m, 2H), 7.11-7.16 (m, 1H), 7.30-7.33 (m, 1H), 7.89-7.93 (m, 1H), 8.35-8.38 (m, 1H); MS ($ESI^+$): 641 $[M + H]^+$. |
| 367 | 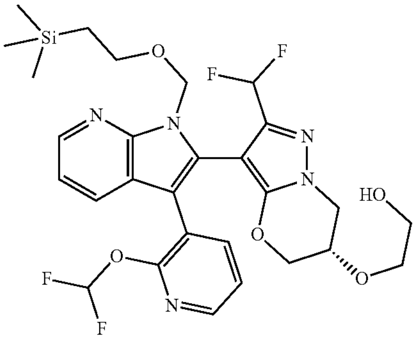 [SMILES: C[Si](C)(C)CCOCn1c(-c2c(C(F)F)nn3c2OC[C@@H](OCCO)C3)c(-c2cccnc2OC(F)F)c2cccnc21] | $^1$H-NMR (400 MHz, $CDCl_3$) δ −0.14--0.06 (m, 9H), 0.77-0.94 (m, 2H), 3.40-3.79 (m, 6H), 4.06-4.52 (m, 5H), 5.57-6.69 (m, 3H), 7.00-7.17 (m, 2H), 7.29-7.82 (m, 3H), 8.11-8.13 (m, 1H), 8.39-8.41 (m, 1H); MS ($ESI^+$): 624 $[M + H]^+$. |
| 368 | 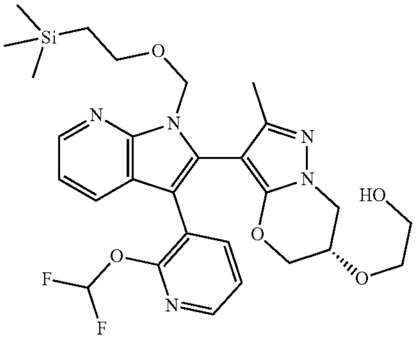 [SMILES: Cc1nn2c(c1-c1c(-c3cccnc3OC(F)F)c3cccnc3n1COCC[Si](C)(C)C)OC[C@@H](OCCO)C2] | $^1$H-NMR (400 MHz, $CDCl_3$) δ −0.15--0.08 (m, 9H), 0.70-0.91 (m, 2H), 1.87-2.05 (m, 3H), 3.39-3.75 (m, 6H), 4.10-4.86 (m, 5H), 5.51-5.92 (m, 2H), 7.10-7.19 (m, 2H), 7.30-7.83 (m, 3H), 8.11-8.17 (m, 1H), 8.37-8.43 (m, 1H); MS ($ESI^+$): 588 $[M + H]^+$. |
| 369 | 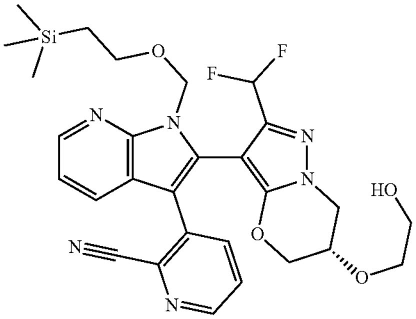 [SMILES: C[Si](C)(C)CCOCn1c(-c2c(C(F)F)nn3c2OC[C@@H](OCCO)C3)c(-c2cccnc2C#N)c2cccnc21] | The crude product was used directly in the next step without purification. |

-continued

| Compound No. | Chemical structural formula | Spectrum data |
|---|---|---|
| 370 | 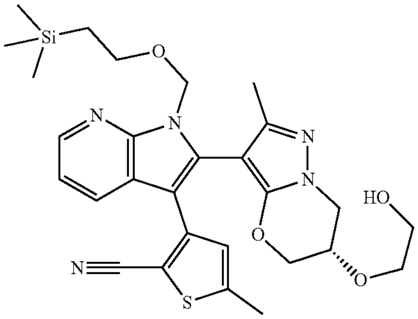 [SMILES: Cc1cc(-c2c(-c3c(C)nn4c3OC[C@@H](OCCO)C4)n(COCC[Si](C)(C)C)c3ncccc23)c(C#N)s1] | The crude product was used directly in the next step without purification. |

(160) Reference Procedure of (S)-4-(2-(2-(difluoromethyl)-6-(2-hydroxy-2-methylpropoxy)-6,7-dihydro-5H-pyrazolo[5,1-b][1,3]oxazin-3-yl)-1-((2-(trimethylsilyl)ethoxy)methyl)-1H-pyrrolo[2,3-b]pyridin-3-yl)-1-methyl-1H-pyrazole-3-carbonitrile (371)

(371)

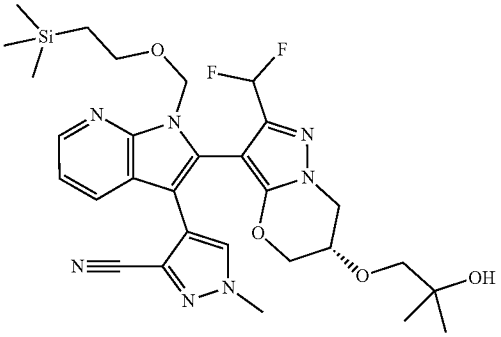

To a stirred solution of compound 360 (150 mg, 0.244 mmol) in THF (2.4 mL) at 0° C. under Ar atmosphere, 3 mol/L methylmagnesium bromide in diethyl ether (0.25 mL, 0.75 mmol) was slowly added. After stirring at room temperature for 3 h, the reaction was quenched with sat. aq. $NH_4Cl$, and the resulting mixture was extracted with EtOAc. The organic layer was washed with brine, dried over $Na_2SO_4$, and concentrated. The residue was purified by silica gel column chromatography (20-100% EtOAc/hexane) to yield compound 371 (124 mg, 83%) as a colorless amorphous; $^1$H-NMR (400 MHz, $CDCl_3$) δ −0.16-−0.05 (m, 9H), 0.79-0.91 (m, 2H), 1.08-1.28 (m, 6H), 2.43-2.53 (m, 1H), 3.35-3.53 (m, 4H), 3.83-4.01 (m, 3H), 4.10-4.51 (m, 5H), 5.48-6.54 (m, 3H), 7.14-7.18 (m, 1H), 7.41-7.91 (m, 2H), 8.40 (dd, J=4.7, 1.5 Hz, 1H); MS (ESI$^+$): 614 $[M+H]^+$.

(161) Reference Procedure of (S)-3-(2-(2-(difluoromethyl)-6-(2-hydroxy-2-methylpropoxy)-6,7-dihydro-5H-pyrazolo[5,1-b][1,3]oxazin-3-yl)-1-((2-(trimethylsilyl)ethoxy)methyl)-1H-pyrrolo[2,3-b]pyridin-3-yl) picolinonitrile (372)

(372)

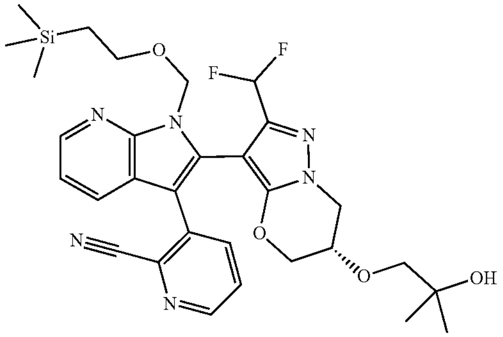

The compound 372 was synthesized from compound 364 using conditions analogous to compound 371. The crude compound was used directly in the next step without purification.

(162) Reference Procedure of (S)-2-((3-(3-(2-cyano-5-methylthiophen-3-yl)-1-((2-(trimethylsilyl)ethoxy)methyl)-1H-pyrrolo[2,3-b]pyridin-2-yl)-2-(difluoromethyl)-6,7-dihydro-5H-pyrazolo[5,1-b][1,3]oxazin-6-yl)oxy) acetic acid (373)

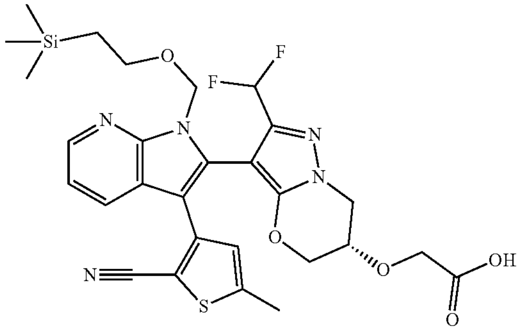

(373)

The compound 373 was synthesized from compound 354 using conditions analogous to compound 359; $^1$H-NMR (400 MHz, $CDCl_3$) δ −0.16-−0.08 (m, 9H), 0.73-0.92 (m, 2H), 2.54-2.61 (m, 3H), 3.85-3.97 (m, 2H), 4.25-4.59 (m, 7H), 5.48-5.59 (m, 1H), 5.85-6.32 (m, 2H), 6.91-7.00 (m, 1H), 7.19-7.23 (m, 1H), 7.94-7.98 (m, 1H), 8.42-8.48 (m, 1H); MS (ESI$^+$): 616 $[M+H]^+$.

(163) Reference Procedure of (S)-3-(2-(2-(difluoromethyl)-6-methoxy-6,7-dihydro-5H-pyrazolo[5,1-b][1,3]oxazin-3-yl)-1-((2-(trimethylsilyl)ethoxy)methyl)-1H-pyrrolo[2,3-b]pyridin-3-yl)-5-methylthiophene-2-carbonitrile (374)

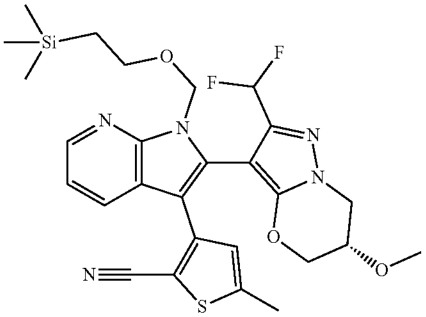

(374)

The compound 373 was synthesized from compound 354 using conditions analogous to compound 212; $^1$H-NMR (400 MHz, $CDCl_3$) δ −0.16-−0.06 (m, 9H), 0.75-0.93 (m, 2H), 3.33-3.56 (m, 5H), 3.89-3.92 (m, 1H), 4.07-4.46 (m, 4H), 5.44-6.65 (m, 3H), 7.00-7.17 (m, 2H), 7.31-7.82 (m, 3H), 8.10-8.14 (m, 1H), 8.39-8.42 (m, 1H); MS (ESI$^+$): 572 $[M+H]^+$.

The following compounds were also synthesized from the corresponding starting materials and reagents using conditions analogous to compound 212.

| Compound No. | Chemical structural formula | Spectrum data |
|---|---|---|
| 375 | 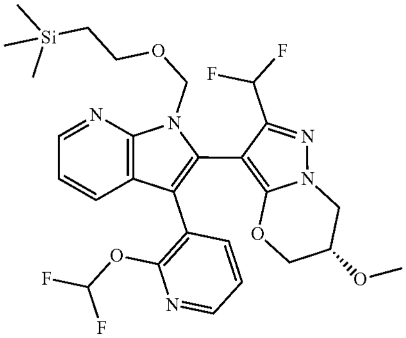 | $^1$H-NMR (400 MHz, $CDCl_3$) δ −0.15-−0.06 (m, 9H), 0.72-0.91 (m, 2H), 2.48-2.60 (m, 3H), 3.33-3.51 (m, 5H), 3.95-4.01 (m, 1H), 4.22-4.51 (m, 4H), 5.41-7.00 (m, 4H), 7.15-7.21 (m, 1H), 7.89-8.00 (m, 1H), 8.40-8.43 (m, 1H); MS (ESI$^+$): 594 $[M + H]^+$. |
| 376 | 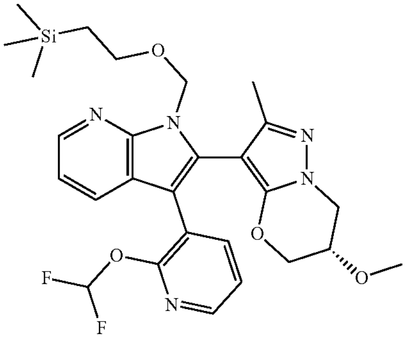 | $^1$H-NMR (400 MHz, $CDCl_3$) δ −0.14-−0.10 (m, 9H), 0.72-0.91 (m, 2H), 1.66 (s, 3H), 3.35-3.53 (m, 5H), 3.87-3.92 (m, 1H), 4.08-4.44 (m, 4H), 5.42-5.55 (m, 1H), 5.74-5.93 (m, 1H), 7.03-7.15 (m, 2H), 7.33-7.81 (m, 3H), 8.09-8.13 (m, 1H), 8.36-8.41 (m, 1H); MS (ESI$^+$): 558 $[M + H]^+$. |

(164) Reference Procedure of (S)-4-(2-(2-(difluoromethyl)-6-ethoxy-6,7-dihydro-5H-pyrazolo[5,1-b][1,3]oxazin-3-yl)-1-((2-(trimethylsilyl)ethoxy)methyl)-1H-pyrrolo[2,3-b]pyridin-3-yl)-1-methyl-1H-pyrazole-3-carbonitrile (377)

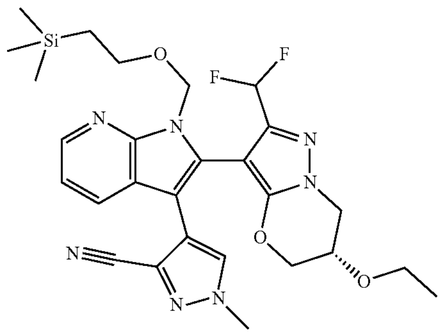 [SMILES: CCO[C@@H]1COc2c(-c3c(-c4cn(C)nc4C#N)c4cccnc4n3COCC[Si](C)(C)C)c(C(F)F)nn2C1]

The compound 377 was synthesized from compound 353 using conditions analogous to compound 212 (iodoethane was used instead of iodomethane); $^1$H-NMR (400 MHz, $CDCl_3$) δ −0.13-−0.06 (m, 9H), 0.74-0.93 (m, 2H), 1.20-1.30 (m, 3H), 3.35-3.53 (m, 2H), 3.60-3.71 (m, 2H), 3.93-4.03 (m, 3H), 4.04-4.10 (m, 1H), 4.18-4.44 (m, 4H), 5.39-5.92 (m, 2H), 6.14-6.61 (m, 1H), 7.13-7.20 (m, 1H), 7.33-7.58 (m, 1H), 7.84-7.98 (m, 1H), 8.39-8.43 (m, 1H); MS (ESI$^+$): 570 [M+H]$^+$.

(165) Reference Procedure of (S)-3-(3-(3-cyano-1-methyl-1H-pyrazol-4-yl)-1-((2-(trimethylsilyl)ethoxy)methyl)-1H-pyrrolo[2,3-b]pyridin-2-yl)-2-(difluoromethyl)-6,7-dihydro-5H-pyrazolo[5,1-b][1,3]oxazin-6-yl methylcarbamate (378)

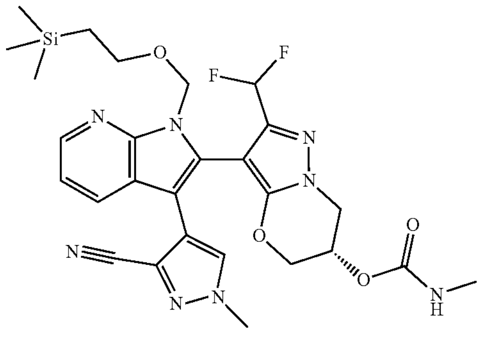

To a stirred solution of compound 353 (125 mg, 0.222 mmol) in THF (1.5 mL) at 0° C. under Ar atmosphere, 60% sodium hydride (12.0 mg, 0.275 mmol) was added. After stirring at 0° C. for 15 min, a solution of N-methylcarbamoyl chloride (42.0 mg, 0.449 mmol) in THF (0.5 mL) was added at 0° C., and the reaction mixture was stirred at room temperature for 1.5 h. The reaction was quenched with sat. aq. $NH_4Cl$, and the resulting mixture was extracted with EtOAc. The organic layer was washed with brine, dried over $Na_2SO_4$, and concentrated. The residue was purified by silica gel column chromatography (0-5% MeOH/EtOAc) to yield compound 378 (93.0 mg, 70%) as a slightly yellow amorphous; $^1$H-NMR (400 MHz, $CDCl_3$) δ −0.13-−0.11 (9H, m), 0.74-0.93 (2H, m), 2.78-2.85 (3H, m), 3.36-3.51 (2H, m), 4.02 (3H, s), 4.26-4.54 (4H, m), 4.95-5.62 (3H, m), 5.79-5.90 (1H, m), 6.14-6.48 (1H, m), 7.14-7.18 (1H, m), 7.56-7.59 (1H, m), 7.81-7.88 (1H, m), 8.40-8.42 (1H, m); MS (ESI$^+$): 599 [M+H]$^+$.

(165) Reference Procedure of (S)-3-(2-(2-(difluoromethyl)-6-(2-hydroxyethoxy)-6,7-dihydro-5H-pyrazolo[5,1-b][1,3]oxazin-3-yl)-1-((2-(trimethylsilyl)ethoxy)methyl)-1H-pyrrolo[2,3-b]pyridin-3-yl)-5-methylthiophene-2-carbonitrile (379)

(379)

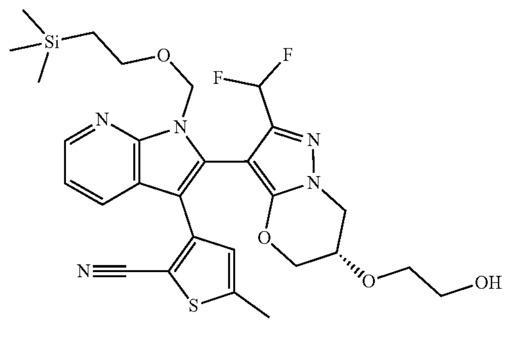

To a stirred solution of compound 373 (105 mg, 0.170 mmol) in THF (1.7 mL) at room temperature, 1,1'-carbonyldiimidazole (33.0 mg, 0.204 mmol) was added. After stirring at the same temperature for 1 h, followed by stirring at 50° C. at 1 h, sodium borohydride (35.0 mg, 0.851 mmol) was added at 0° C., and the reaction mixture was stirred at room temperature for 3 h. The reaction was quenched with sat. aq. $NH_4Cl$, and the resulting mixture extracted with $CHCl_3$/MeOH (10/1). The organic layer was washed with brine, dried over $Na_2SO_4$, and concentrated. The residue was purified by silica gel column chromatography (0-20% MeOH/EtOAc) to yield compound 379 (28.0 mg, 27%) as a slightly yellow amorphous; $^1$H-NMR (400 MHz, $CDCl_3$) δ −0.17-−0.10 (m, 9H), 0.73-0.95 (m, 2H), 2.54-2.60 (m, 3H), 3.35-3.50 (m, 2H), 3.62-3.81 (m, 4H), 4.10-4.61 (m, 6H), 5.52-5.57 (m, 1H), 5.86-5.93 (m, 1H), 6.00-6.28 (m, 1H), 6.91-7.02 (m, 1H), 7.15-7.21 (m, 1H), 7.90-7.96 (m, 1H), 8.40-8.41 (m, 1H); MS (ESI$^+$): 602 [M+H]$^+$.

(166) Reference Procedure of methyl (S)-(3-(3-(2-cyano-5-methylthiophen-3-yl)-1-((2-(trimethylsilyl)ethoxy)methyl)-1H-pyrrolo[2,3-b]pyridin-2-yl)-2-methyl-6,7-dihydro-5H-pyrazolo[5,1-b][1,3]oxazin-6-yl) carbamate (380)

(380)

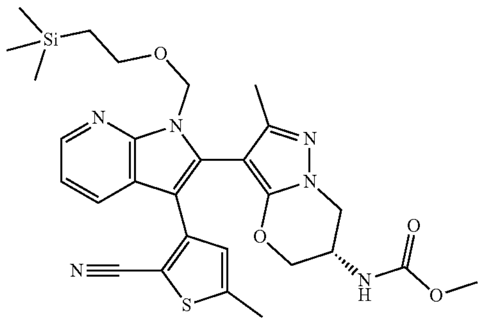

The compound 380 was synthesized from compound 468 using conditions analogous to compound 218; $^1$H-NMR (400 MHz, $CDCl_3$) δ −0.19-−0.06 (m, 9H), 0.70-0.89 (m, 2H), 1.51-1.83 (m, 3H), 2.56-2.67 (m, 2H), 3.35-3.54 (m, 2H), 3.67-3.80 (m, 3H), 4.20-4.61 (m, 6H), 5.46-5.99 (m, 2H), 6.87-7.20 (m, 3H), 7.90 (dd, J=7.9, 1.5 Hz, 1H), 8.40 (dd, J=4.7, 1.5 Hz, 1H); MS (ESI$^+$): 579 [M+H]$^+$.

(167) Reference Procedure of (R)—N-(3-(3-(2-cyano-5-methylthiophen-3-yl)-1-((2-(trimethylsilyl)ethoxy)methyl)-1H-pyrrolo[2,3-b]pyridin-2-yl)-2-methyl-4,5,6,7-tetrahydropyrazolo[1,5-a]pyridin-6-yl)cyclopropanecarboxamide (381)

(381)

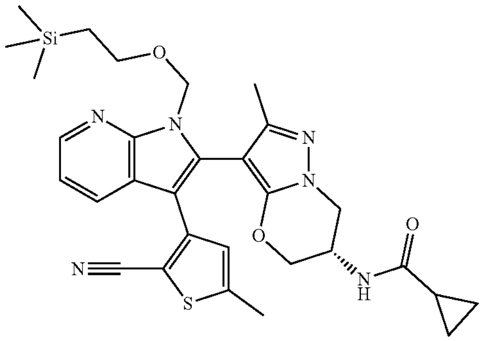

To a stirred solution of compound 468 (50.0 mg, 0.096 mmol) in DMF (1.2 mL) at room temperature, chloro-N,N, N',N'-tetramethylformamidinium hexafluorophosphate (53.9 mg, 0.192 mmol), 1-methylimidazole (0.030 mL, 0.385 mmol), and cyclopropanecarboxylic acid (0.030 mL, 0.385 mmol) were added. After stirring at the same temperature for 1 h, the reaction was quenched with water, and the resulting mixture was extracted with EtOAc. The organic layer was washed with brine, dried over $Na_2SO_4$, and concentrated. The residue was purified by silica gel column chromatography (10-100% EtOAc/hexane) to yield compound 381 (36.0 mg, 64%) as a colorless oil; $^1$H-NMR (400 MHz, $CDCl_3$) δ −0.17-−0.07 (m, 9H), 0.66-1.09 (m, 7H), 1.43-1.49 (m, 1H), 1.53-1.67 (m, 7H), 2.56-2.64 (m, 2H), 3.35-3.56 (m, 2H), 4.10-4.40 (m, 4H), 4.88-4.93 (m, 1H), 5.49 (d, J=10.9 Hz, 1H), 6.00 (d, J=11.0 Hz, 1H), 7.00-7.20 (m, 2H), 7.81-8.02 (m, 2H), 8.35-8.42 (m, 1H); MS (ESI$^+$): 589 [M+H]$^+$.

(168) Experimental procedure of (S)-4-(2-(2-(difluoromethyl)-6-hydroxy-6,7-dihydro-5H-pyrazolo[5,1-b][1,3]oxazin-3-yl)-1H-pyrrolo[2,3-b]pyridin-3-yl)-1-methyl-1H-pyrazole-3-carbonitrile (EX.491)

EX. 491

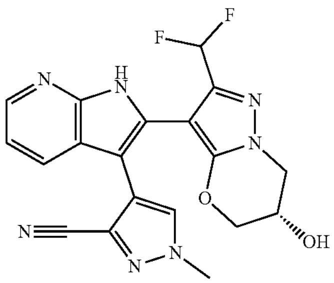

EX.491 was synthesized from compound 353 using conditions analogous to EX.420; $^1$H-NMR (400 MHz, DMSO-$d_6$) δ 3.94 (s, 3H), 3.99-4.07 (m, 1H), 4.13-4.21 (m, 2H), 4.26-4.35 (m, 2H), 5.67 (d, J=3.3 Hz, 1H), 6.70 (t, J=54.0 Hz, 1H), 7.15 (dd, J=8.0, 4.7 Hz, 1H), 7.90-7.94 (m, 2H), 8.28 (dd, J=4.7, 1.6 Hz, 1H), 12.00 (s, 1H); MS (ESI$^+$): 412 [M+H]$^+$.

The following compounds were also synthesized from the corresponding starting materials and reagents using conditions analogous to EX.420.

| Compound No. | Chemical structural formula | Spectrum data |
|---|---|---|
| EX.492 | 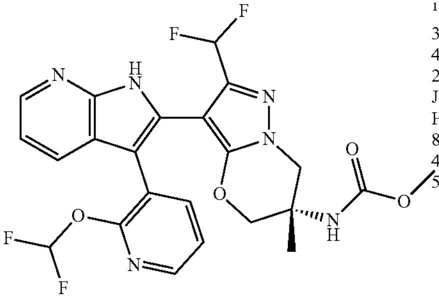 | $^1$H-NMR (400 MHz, DMSO-$d_6$) δ 1.27 (s, 3H), 3.53 (s, 3H), 3.81 (d, J = 11.0 Hz, 1H), 4.04 (d, J = 12.7 Hz, 1H), 4.44-4.48 (m, 2H), 6.78 (t, J = 54.0 Hz, 1H), 7.11 (dd, J = 7.9, 4.7 Hz, 1H), 7.19 (dd, J = 7.4, 4.9 Hz, 1H), 7.42 (s, 1H), 7.51-7.87 (m, 3H), 8.18 (dd, J = 4.9, 1.9 Hz, 1H), 8.27 (dd, J = 4.7, 1.6 Hz, 1H), 11.98 (s, 1H); MS (ESI[+]): 521 [M + H][+]. |
| EX.493 | 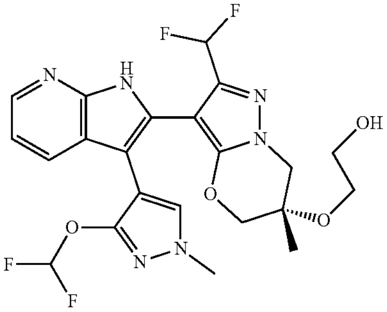 [SMILES: Cn1cc(-c2c(-c3c(C(F)F)nn4c3OC[C@@](C)(OCCO)C4)[nH]c3ncccc23)c(OC(F)F)n1] | $^1$H-NMR (400 MHz, DMSO-$d_6$) δ 1.27 (s, 3H), 3.38-3.45 (m, 4H), 3.75 (s, 3H), 3.99-4.04 (m, 1H), 4.08-4.22 (m, 2H), 4.34 (dd, J = 11.8, 1.9 Hz, 1H), 4.59 (t, J = 5.4 Hz, 1H), 6.71 (t, J = 54.1 Hz, 1H), 6.91-7.28 (m, 2H), 7.48 (s, 1H), 7.81 (dd, J = 7.9, 1.2 Hz, 1H), 8.23 (dd, J = 4.7, 1.6 Hz, 1H), 11.75 (s, 1H); MS (ESI[+]): 511 [M + H][+]. |
| EX.494 | 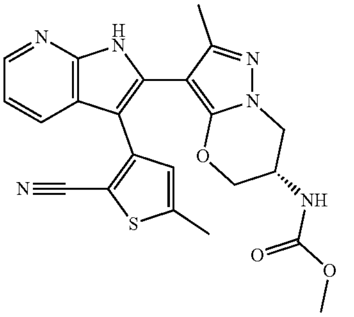 [SMILES: COC(=O)N[C@@H]1COc2c(-c3[nH]c4ncccc4c3-c3cc(C)sc3C#N)c(C)nn2C1] | $^1$H-NMR (400 MHz, DMSO-$d_6$) δ 1.77 (s, 3H), 2.53 (s, 3H), 3.56 (s, 3H), 3.90-4.28 (m, 5H), 7.00 (s, 1H), 7.14 (dd, J = 7.9, 4.7 Hz, 1H), 7.46 (d, J = 6.6 Hz, 1H), 7.89-7.91 (m, 1H), 8.25 (dd, J = 4.7, 1.5 Hz, 1H), 11.92 (s, 1H); MS (ESI[+]): 449 [M + H][+]. |
| EX.495 | 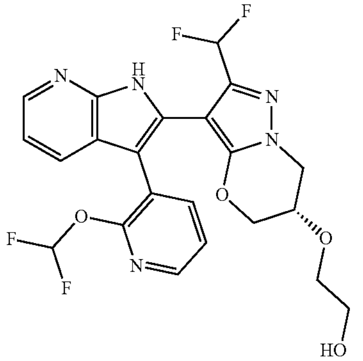 [SMILES: OCCO[C@@H]1COc2c(-c3[nH]c4ncccc4c3-c3cccnc3OC(F)F)c(C(F)F)nn2C1] | $^1$H-NMR (400 MHz, DMSO-$d_6$) δ 3.45-3.50 (m, 4H), 3.94 (d, J = 11.4 Hz, 1H), 4.09-4.30 (m, 4H), 4.65-4.68 (m, 1H), 6.78 (t, J = 54.1 Hz, 1H), 7.10 (dd, J = 8.0, 4.7 Hz, 1H), 7.21 (dd, J = 7.5, 4.9 Hz, 1H), 7.50-7.87 (m, 3H), 8.16 (dd, J = 4.9, 1.9 Hz, 1H), 8.26 (dd, J = 4.7, 1.6 Hz, 1H), 11.94 (s, 1H); MS (ESI[+]): 494 [M + H][+]. |
| EX.496 | 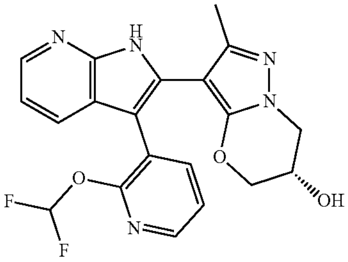 [SMILES: Cc1nn2c(c1-c1[nH]c3ncccc3c1-c1cccnc1OC(F)F)OC[C@@H](O)C2] | $^1$H-NMR (400 MHz, DMSO-$d_6$) δ 1.88 (s, 3H), 3.80-3.89 (m, 3H), 4.09-4.17 (m, 2H), 5.48 (s, 1H), 7.07 (dd, J = 7.8, 4.7 Hz, 1H), 7.21 (dd, J = 7.3, 4.9 Hz, 1H), 7.53-7.91 (m, 3H), 8.17 (dd, J = 4.9, 1.8 Hz, 1H), 8.21 (dd, J = 4.7, 1.5 Hz, 1H), 11.81 (s, 1H); MS (ESI[+]): 414 [M + H][+]. |

-continued

| Compound No. | Chemical structural formula | Spectrum data |
|---|---|---|
| EX.497 | 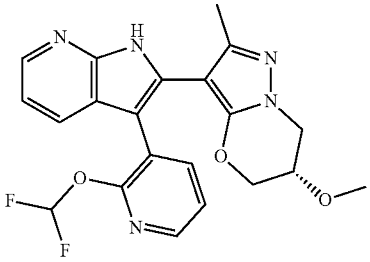 [SMILES: CO[C@@H]1COc2c(-c3[nH]c4ncccc4c3-c3cccnc3OC(F)F)c(C)nn2C1] | $^{1}$H-NMR (400 MHz, DMSO-$d_6$) δ 1.92 (s, 3H), 3.24 (s, 3H), 3.81-3.87 (m, 2H), 3.98-4.18 (m, 3H), 7.06 (dd, J = 7.9, 4.7 Hz, 1H), 7.20 (dd, J = 7.4, 5.0 Hz, 1H), 7.50-7.87 (m, 3H), 8.16 (dd, J = 4.9, 1.8 Hz, 1H), 8.20 (dd, J = 4.7, 1.5 Hz, 1H), 11.82 (s, 1H); MS (ESI$^+$): 428 [M + H]$^+$. |
| EX.498 | 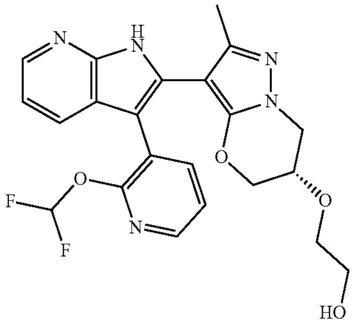 [SMILES: Cc1nn2c(c1-c1[nH]c3ncccc3c1-c1cccnc1OC(F)F)OC[C@@H](OCCO)C2] | $^{1}$H-NMR (400 MHz, DMSO-$d_6$) δ 1.93 (s, 3H), 3.43-3.49 (m, 4H), 3.83 (d, J = 11.5 Hz, 1H), 3.97-4.16 (m, 4H), 4.62-4.67 (m, 1H), 7.07 (dd, J = 7.8, 4.7 Hz, 1H), 7.17-7.24 (m, 1H), 7.51-7.89 (m, 3H), 8.16 (dd, J = 4.9, 1.8 Hz, 1H), 8.21 (dd, J = 4.7, 1.5 Hz, 1H), 11.82 (s, 1H); MS (ESI$^+$): 458 [M + H]$^+$. |
| EX.499 | 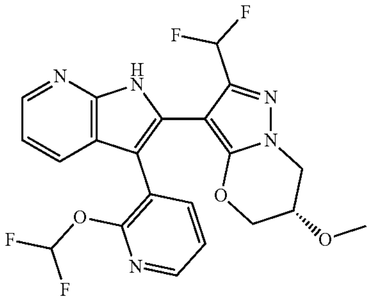 [SMILES: CO[C@@H]1COc2c(-c3[nH]c4ncccc4c3-c3cccnc3OC(F)F)c(C(F)F)nn2C1] | $^{1}$H-NMR (400 MHz, DMSO-$d_6$) δ 3.25 (s, 3H), 3.93-3.96 (m, 2H), 4.16-4.30 (m, 3H), 6.78 (t, J = 54.1 Hz, 1H), 7.10 (dd, J = 7.9, 4.6 Hz, 1H), 7.21 (dd, J = 7.4, 4.9 Hz, 1H), 7.50-7.86 (m, 3H), 8.17 (dd, J = 4.9, 1.9 Hz, 1H), 8.26 (dd, J = 4.7, 1.5 Hz, 1H), 11.94 (s, 1H); MS (ESI$^+$): 464 [M + H]$^+$. |
| EX.500 | 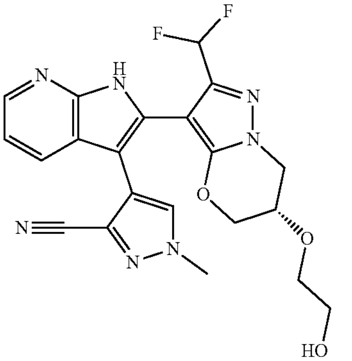 [SMILES: Cn1cc(-c2c(-c3c(C(F)F)nn4c3OC[C@@H](OCCO)C4)[nH]c3ncccc23)c(C#N)n1] | $^{1}$H-NMR (400 MHz, DMSO-$d_6$) δ 3.48-3.55 (m, 2H), 3.56-3.62 (m, 2H), 3.95 (s, 3H), 4.11-4.37 (m, 4H), 4.39-4.46 (m, 1H), 4.69 (t, J = 5.4 Hz, 1H), 6.71 (t, J = 54.1 Hz, 1H), 7.14 (dd, J = 7.9, 4.7 Hz, 1H), 7.89 (dd, J = 7.9, 1.5 Hz, 1H), 7.91 (s, 1H), 8.28 (dd, J = 4.7, 1.6 Hz, 1H), 12.00 (s, 1H); MS (ESI$^+$): 456 [M + H]$^+$. |

-continued

| Compound No. | Chemical structural formula | Spectrum data |
|---|---|---|
| EX.501 | 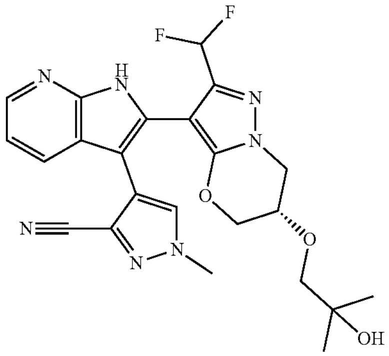 [SMILES: Cn1cc(-c2c(-c3c(C(F)F)nn4c3OC[C@@H](OCC(C)(C)O)C4)[nH]c3ncccc23)c(C#N)n1] | $^1$H-NMR (400 MHz, DMSO-$d_6$) δ 1.04 (s, 6H), 3.30-3.32 (m, 2H), 3.94 (s, 3H), 4.12-4.41 (m, 6H), 6.70 (t, J = 54.0 Hz, 1H), 7.13 (dd, J = 7.9, 4.7 Hz, 1H), 7.86-7.89 (m, 2H), 8.27 (dd, J = 4.7, 1.6 Hz, 1H), 11.98 (s, 1H); MS (ESI$^+$): 484 [M + H]$^+$. |
| EX.502 | 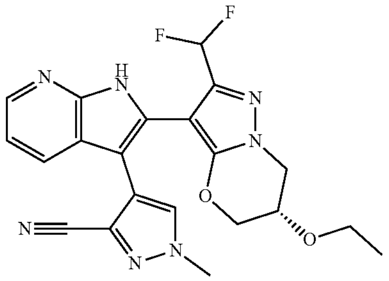 [SMILES: CCO[C@@H]1COc2c(-c3[nH]c4ncccc4c3-c3cn(C)nc3C#N)c(C(F)F)nn2C1] | $^1$H-NMR (400 MHz, $CDCl_3$) δ 1.26 (t, J = 7.0 Hz, 3H), 3.58-3.68 (m, 2H), 3.99-4.03 (m, 4H), 4.09-4.15 (m, 1H), 4.26-4.36 (m, 3H), 6.46 (t, J = 54.2 Hz, 1H), 7.13 (dd, J = 7.9, 4.8 Hz, 1H), 7.49 (s, 1H), 7.89 (dd, J = 7.9, 1.5 Hz, 1H), 8.32 (dd, J = 4.7, 1.5 Hz, 1H), 9.66 (s, 1H); MS (ESI$^+$): 440 [M + H]$^+$. |
| EX.503 | 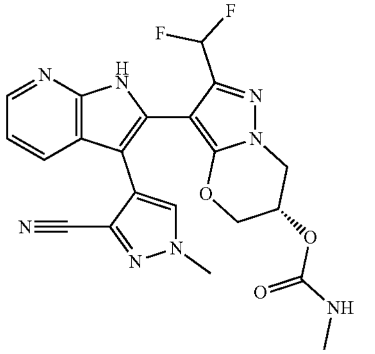 [SMILES: CNC(=O)O[C@@H]1COc2c(-c3[nH]c4ncccc4c3-c3cn(C)nc3C#N)c(C(F)F)nn2C1] | $^1$H-NMR (400 MHz, DMSO-$d_6$) δ 2.59 (d, J = 4.6 Hz, 3H), 3.96 (s, 3H), 4.19-4.29 (m, 2H), 4.35-4.41 (m, 1H), 4.46-4.52 (m, 1H), 5.26-5.30 (m, 1H), 6.74 (t, J = 53.9 Hz, 1H), 7.14 (dd, J = 7.9, 4.7 Hz, 1H), 7.27 (q, J = 4.5 Hz, 1H), 7.88 (dd, J = 7.9, 1.5 Hz, 1H), 7.93 (s, 1H), 8.29 (dd, J = 4.7, 1.5 Hz, 1H), 12.01 (s, 1H); MS (ESI$^+$): 469 [M + H]$^+$. |
| EX.504 | 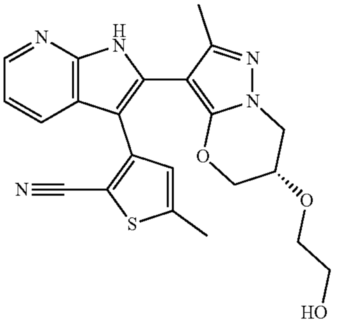 [SMILES: Cc1cc(-c2c(-c3c(C)nn4c3OC[C@@H](OCCO)C4)[nH]c3ncccc23)c(C#N)s1] | $^1$H-NMR (400 MHz, DMSO-$d_6$) δ 1.91 (s, 3H), 2.52-2.54 (m, 3H), 3.46-3.56 (m, 4H), 3.95-4.07 (m, 3H), 4.16-4.26 (m, 2H), 4.62-4.66 (m, 1H), 6.92-6.94 (m, 1H), 7.13 (dd, J = 7.9, 4.7 Hz, 1H), 7.87 (dd, J = 7.9, 1.5 Hz, 1H), 8.24 (dd, J = 4.7, 1.6 Hz, 1H), 12.00 (s, 1H); MS (ESI$^+$): 436 [M + H]$^+$. |

-continued

| Compound No. | Chemical structural formula | Spectrum data |
|---|---|---|
| EX.505 | 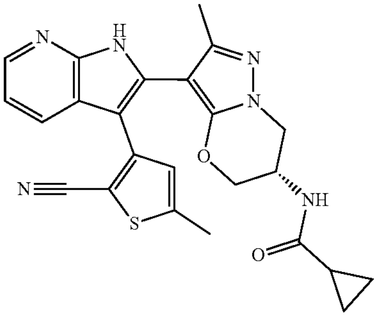 [SMILES: Cc1cc(-c2c(-c3c(C)nn4c3OC[C@@H](NC(=O)C3CC3)C4)[nH]c3ncccc23)c(C#N)s1] | $^1$H-NMR (400 MHz, DMSO-$d_6$) δ 0.64-0.72 (m, 4H), 1.54-1.60 (m, 1H), 1.85 (s, 3H), 2.54 (s, 3H), 3.89-3.94 (m, 1H), 4.06-4.10 (m, 2H), 4.24-4.29 (m, 1H), 4.33-4.37 (m, 1H), 7.00-7.01 (m, 1H), 7.14 (dd, J = 7.9, 4.7 Hz, 1H), 7.90 (dd, J = 7.9, 1.4 Hz, 1H), 8.25 (dd, J = 4.7, 1.5 Hz, 1H), 8.39 (d, J = 6.6 Hz, 1H), 11.99 (s, 1H); MS (ESI$^+$): 459 [M + H]$^+$. |
| EX.506 | 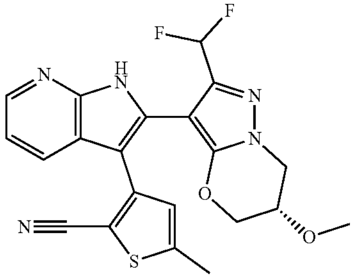 [SMILES: CO[C@@H]1COc2c(-c3[nH]c4ncccc4c3-c3cc(C)sc3C#N)c(C(F)F)nn2C1] | $^1$H-NMR (400 MHz, DMSO-$d_6$) δ 2.51-2.57 (m, 3H), 3.36 (s, 3H), 4.03-4.14 (m, 2H), 4.25-4.46 (m, 3H), 6.60-7.21 (m, 3H), 7.94 (dd, J = 7.9, 1.4 Hz, 1H), 8.32 (dd, J = 4.7, 1.5 Hz, 1H), 12.16 (s, 1H); MS (ESI$^+$): 442 [M + H]$^+$. |
| EX.507 | 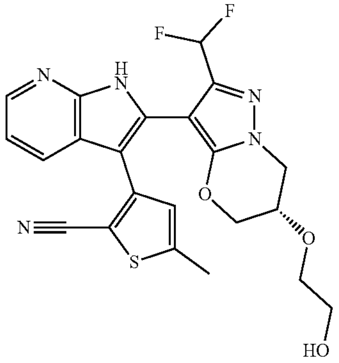 [SMILES: Cc1cc(-c2c(-c3c(C(F)F)nn4c3OC[C@@H](OCCO)C4)[nH]c3ncccc23)c(C#N)s1] | $^1$H-NMR (400 MHz, DMSO-$d_6$) δ 3.30-3.36 (m, 2H), 3.48-3.58 (m, 4H), 3.99-4.39 (m, 6H), 4.66 (t, J = 5.4 Hz, 1H), 6.55-6.86 (m, 2H), 7.16 (dd, J = 7.9, 4.7 Hz, 1H), 7.91 (dd, J = 7.9, 1.4 Hz, 1H), 8.29 (dd, J = 4.6, 1.5 Hz, 1H), 12.13 (s, 1H); MS (ESI$^+$): 472 [M + H]$^+$. |
| EX.508 | 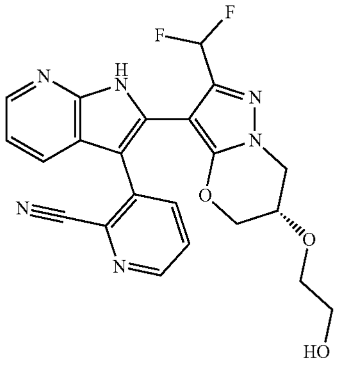 [SMILES: N#Cc1ncccc1-c1c(-c2c(C(F)F)nn3c2OC[C@@H](OCCO)C3)[nH]c2ncccc12] | $^1$H-NMR (400 MHz, DMSO-$d_6$) δ 3.41-3.49 (m, 4H), 3.97-4.30 (m, 5H), 4.65 (s, 1H), 6.67-6.95 (m, 1H), 7.16 (dd, J = 7.9, 4.7 Hz, 1H), 7.66-7.85 (m, 3H), 8.31 (dd, J = 4.6, 1.3 Hz, 1H), 8.65 (dd, J = 4.6, 1.5 Hz, 1H), 12.20 (s, 1H); MS (ESI$^+$): 453 [M + H]$^+$. |

-continued

| Compound No. | Chemical structural formula | Spectrum data |
|---|---|---|
| EX.509 | 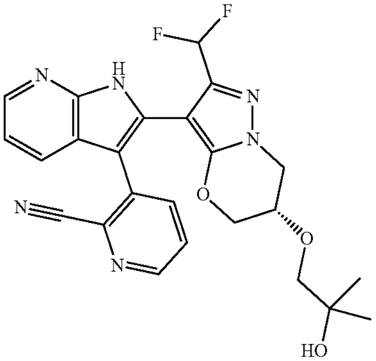 [SMILES: CC(C)(O)CO[C@@H]1COc2c(-c3[nH]c4ncccc4c3-c3cccnc3C#N)c(C(F)F)nn2C1] | $^1$H-NMR (400 MHz, DMSO-$d_6$) δ 0.94-1.06 (m, 6H), 3.23 (s, 2H), 3.92-4.37 (m, 5H), 6.64-6.94 (m, 1H), 7.15 (dd, J = 8.0, 4.7 Hz, 1H), 7.66 (dd, J = 8.1, 4.7 Hz, 1H), 7.74 (dd, J = 8.0, 1.5 Hz, 1H), 7.84 (d, J = 7.8 Hz, 1H), 8.31 (dd, J = 4.7, 1.4 Hz, 1H), 8.64 (dd, J = 4.6, 1.5 Hz, 1H), 12.20 (s, 1H); MS (ESI$^+$): 481 [M + H]$^+$. |

(169) Reference Procedure of tert-butyl (S)-(3-(3-(2-(difluoromethoxy)pyridin-3-yl)-1-(2-((trimethylsilyl) methoxy)ethyl)-1H-pyrrolo[2,3-b]pyridin-2-yl)-2-methyl-6,7-dihydro-5H-pyrazolo[5,1-b][1,3]oxazin-6-yl) carbamate (382)

(382)

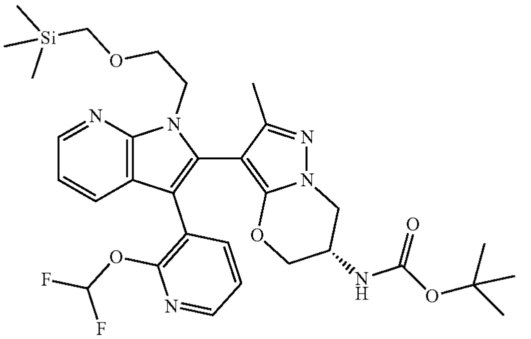

The compound 382 was synthesized from compound 282 and the corresponding boronic acid using conditions analogous to compound 256; $^1$H-NMR (400 MHz, $CDCl_3$) δ −0.13-−0.07 (m, 9H), 0.80-0.89 (m, 2H), 1.44-1.51 (m, 9H), 1.78-1.95 (m, 3H), 3.50-3.57 (m, 2H), 4.10-4.40 (m, 5H), 4.66-5.76 (m, 3H), 7.10-7.16 (m, 2H), 7.31-7.82 (m, 3H), 8.12-8.15 (m, 1H), 8.38-8.41 (m, 1H); MS (ESI$^+$): 643 [M+H]$^+$.

(170) Reference Procedure of tert-butyl (S)-(3-(3-(3-cyano-1-methyl-1H-pyrazol-4-yl)-1-((2-(trimethylsilyl)ethoxy)methyl)-1H-pyrrolo[2,3-b]pyridin-2-yl)-2-(difluoromethyl)-6,7-dihydro-5H-pyrazolo[5,1-b][1,3]oxazin-6-yl) carbamate (383)

(383)

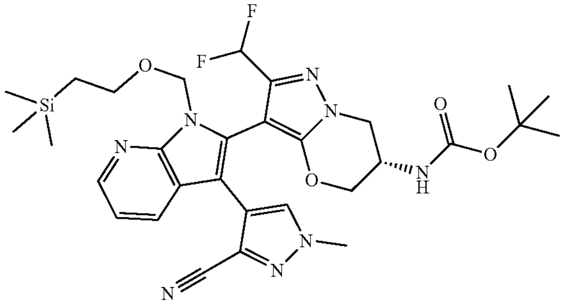

The compound 383 was synthesized from compounds 350 and 229 using conditions analogous to compound 256. $^1$H-NMR (400 MHz, $CDCl_3$) δ −0.12-−0.05 (m, 9H), 0.81-1.01 (m, 2H), 1.42-1.51 (m, 9H), 3.37-3.61 (m, 2H), 3.99-4.06 (m, 3H), 4.24-4.57 (m, 5H), 5.47-5.80 (m, 2H), 6.08-6.53 (m, 2H), 7.14-7.20 (m, 1H), 7.55-7.67 (m, 1H), 7.84-7.93 (m, 1H), 8.39-8.43 (m, 1H).

(171) Experimental procedure of (S)-3-(3-(2-(difluoromethoxy)pyridin-3-yl)-1H-pyrrolo[2,3-b]pyridin-2-yl)-2-methyl-6,7-dihydro-5H-pyrazolo[5,1-b][1,3]oxazin-6-amine (EX.510)

EX. 510

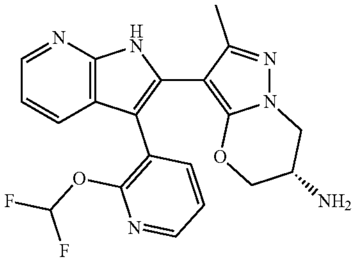

EX.510 was synthesized from compound 382 using conditions analogous to EX.420; $^1$H-NMR (400 MHz, DMSO-$d_6$) δ 1.75-1.87 (m, 3H), 3.15 (d, J=5.1 Hz, 2H), 3.58-3.64 (m, 1H), 3.90-4.13 (m, 3H), 7.05-7.24 (m, 2H), 7.52-7.90 (m, 3H), 8.16-8.22 (m, 2H), 11.80-11.83 (m, 1H); MS (ESI$^+$): 413 [M+H]$^+$.

(171) Experimental procedure of (S)-4-(2-(6-amino-2-(difluoromethyl)-6,7-dihydro-5H-pyrazolo[5,1-b][1,3]oxazin-3-yl)-1H-pyrrolo[2,3-b]pyridin-3-yl)-1-methyl-1H-pyrazole-3-carbonitrile (EX.511)

EX. 511

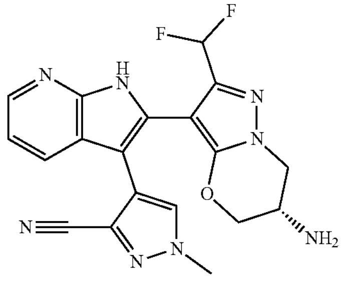

EX.511 was synthesized from compound 383 using conditions analogous to EX.420; $^1$H-NMR (400 MHz, DMSO-$d_6$) δ 1.78-2.07 (m, 2H), 3.42-3.52 (m, 1H), 3.81-3.90 (m, 1H), 3.91-4.00 (m, 4H), 4.20 (dd, J=10.7, 2.7 Hz, 1H), 4.28 (dd, J=12.1, 4.7 Hz, 1H), 6.60 (t, J=54.0 Hz, 1H), 7.14 (dd, J=8.0, 4.7 Hz, 1H), 7.91 (dd, J=7.9, 1.4 Hz, 1H), 8.02 (s, 1H), 8.28 (dd, J=4.7, 1.5 Hz, 1H), 11.97 (s, 1H); MS (ESI$^+$): 411 [M+H]$^+$.

(172) Reference Procedure of (S)-3-(3-(3-(difluoromethoxy) isothiazol-4-yl)-1H-pyrrolo[2,3-b]pyridin-2-yl)-2-(difluoromethyl)-6,7-dihydro-5H-pyrazolo[5,1-b][1,3]oxazin-6-amine (384)

(384)

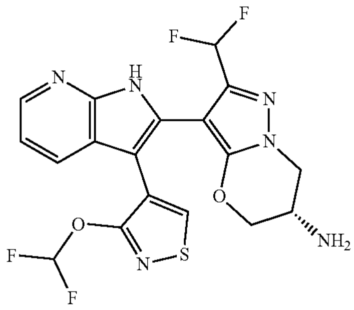

The compound 384 was synthesized from compounds 245 using conditions analogous to EX.420. The crude product was used directly in the next step without purification.

(173) Experimental procedure of methyl(S)-(3-(3-(2-(difluoromethoxy)pyridin-3-yl)-1H-pyrrolo[2,3-b]pyridin-2-yl)-2-(difluoromethyl)-6,7-dihydro-5H-pyrazolo[5,1-b][1,3]oxazin-6-yl)carbamate (EX.512)

EX. 512

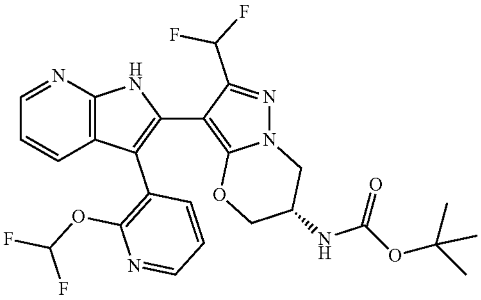

EX.512 was synthesized from EX.443 using conditions analogous to compound 218; $^1$H-NMR (400 MHz, DMSO-$d_6$) δ 3.57 (s, 3H), 4.03-4.16 (m, 4H), 4.36 (dd, J=12.7, 4.2 Hz, 1H), 6.51-6.78 (m, 1H), 7.09-7.23 (m, 2H), 7.51-7.88 (m, 4H), 8.16-8.31 (m, 2H), 11.89 (s, 1H); MS (ESI$^+$): 507 [M+H]$^+$.

The following compounds were also synthesized from the corresponding starting materials and reagents using conditions analogous to compound 218.

| Compound No. | Chemical structural formula | Spectrum data |
|---|---|---|
| EX. 513 | 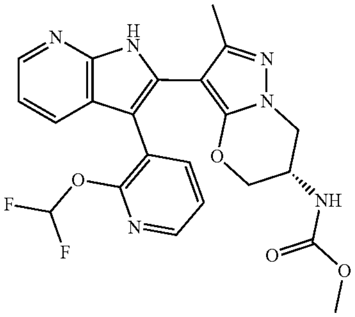 [SMILES: COC(=O)N[C@@H]1COc2c(-c3[nH]c4ncccc4c3-c3cccnc3OC(F)F)c(C)nn2C1] | $^1$H-NMR (400 MHz, DMSO-$d_6$) δ 1.75 (s, 3H),3.56 (s, 3H), 3.87-4.22 (m, 5H), 7.07 (dd, J = 7.9, 4.7 Hz, 1H), 7.22 (dd, J = 7.4, 5.0 Hz, 1H), 7.55-7.92 (m, 4H), 8.17-8.22 (m, 2H), 11.75 (s, 1H); MS (ESI$^+$): 471 [M + H]$^+$. |
| EX. 514 | 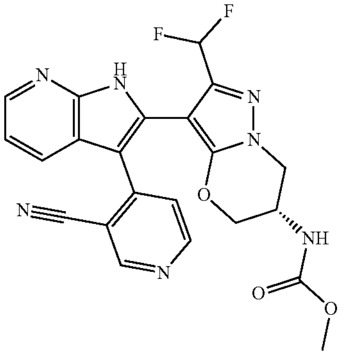 [SMILES: COC(=O)N[C@@H]1COc2c(-c3[nH]c4ncccc4c3-c3ccncc3C#N)c(C(F)F)nn2C1] | $^1$H-NMR (400 MHz, DMSO-$d_6$) δ 3.58 (s, 3H),4.01-4.17 (m, 4H), 4.36-4.41 (m, 1H), 6.67 (t, J = 53.7 Hz, 1H), 7.15-7.19 (m, 1H), 7.67-7.71 (m, 1H), 7.84-7.89 (m, 2H), 8.31-8.34 (m, 1H), 8.65 (d, J = 4.7 Hz, 1H), 12.16 (s, 1H); MS (ESI$^+$): 466 [M + H]$^+$. |
| EX. 515 | 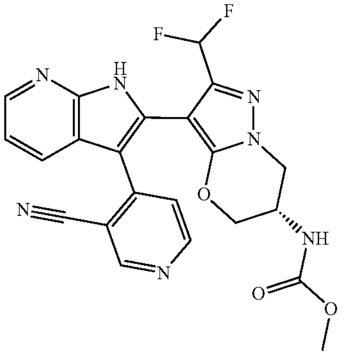 [SMILES: COC(=O)N[C@@H]1COc2c(-c3[nH]c4ncccc4c3-c3ccncc3C#N)c(C(F)F)nn2C1] | $^1$H-NMR (400 MHz, DMSO-$d_6$) δ 3.57 (s, 3H), 3.99-4.22 (m, 4H), 4.40 (dd, J = 12.4, 4.3 Hz, 1H), 6.68 (t, J = 53.9 Hz, 1H), 7.19 (dd, J = 7.9, 4.7 Hz, 1H), 7.42 (d, J = 5.3 Hz, 1H), 7.54 (s, 1H), 7.94 (dd, J = 7.9, 1.3 Hz, 1H), 8.33 (dd, J = 4.7, 1.3 Hz, 1H), 8.72 (d, J = 5.3 Hz, 1H), 8.98 (s, 1H), 12.27 (s, 1H); MS (ESI$^+$): 466 [M + H]$^+$. |
| EX. 516 | 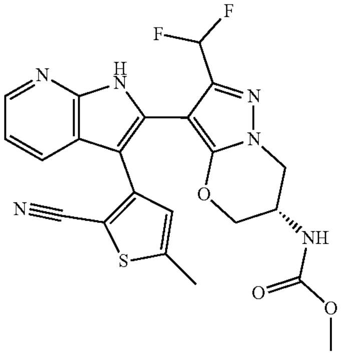 [SMILES: COC(=O)N[C@@H]1COc2c(-c3[nH]c4ncccc4c3-c3cc(C)sc3C#N)c(C(F)F)nn2C1] | $^1$H-NMR (400 MHz, DMSO-$d_6$) δ 2.52 (s, 3H), 3.57 (s, 3H), 4.06-4.26 (m, 4H), 4.42 (dd, J = 12.2, 4.5 Hz, 1H), 6.57 (t, J = 53.9 Hz, 1H), 6.96 (s, 1H), 7.17 (dd, J = 7.9, 4.7 Hz, 1H), 7.48-7.52 (m, 1H), 7.93 (d, J = 7.3 Hz, 1H), 8.28-8.31 (m, 1H), 12.08 (s, 1H); MS (ESI$^+$): 485 [M + H]$^+$. |

-continued
| Compound No. | Chemical structural formula | Spectrum data |
|---|---|---|
| EX. 517 | 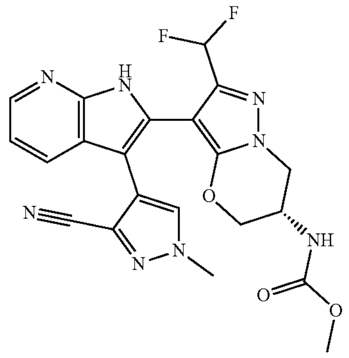 [SMILES: COC(=O)N[C@@H]1COc2c(-c3[nH]c4ncccc4c3-c3cn(C)nc3C#N)c(C(F)F)nn2C1] | $^1$H-NMR (400 MHz, DMSO-$d_6$) δ 3.59 (s, 3H), 3.96 (s, 3H), 4.07-4.15 (m, 1H), 4.17-4.31 (m, 3H), 4.38-4.47 (m, 1H), 6.62 (t, J = 53.9 Hz, 1H), 7.15 (dd, J = 7.9, 4.7 Hz, 1H), 7.51-7.62 (m, 1H), 7.92 (dd, J = 7.9, 1.5 Hz, 1H), 8.00 (s, 1H), 8.29 (dd, J = 4.7, 1.5 Hz, 1H), 11.93 (s, 1H); MS (ESI$^+$): 469 [M + H]$^+$. |
| EX. 518 | 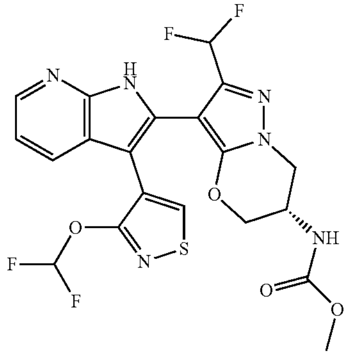 [SMILES: COC(=O)N[C@@H]1COc2c(-c3[nH]c4ncccc4c3-c3csnc3OC(F)F)c(C(F)F)nn2C1] | $^1$H-NMR (400 MHz, DMSO-$d_6$) δ 3.57 (s, 3H), 4.04-4.20 (m, 4H), 4.37 (dd, J = 12.2, 4.4 Hz, 1H), 6.69 (t, J = 54.0 Hz, 1H), 7.12 (dd, J = 7.9, 4.7 Hz, 1H), 7.41-7.77 (m, 2H), 7.84 (dd, J = 7.9, 1.5 Hz, 1H), 8.26 (dd, J = 4.7, 1.6 Hz, 1H), 8.74 (s, 1H), 11.91 (s, 1H); MS (ESI$^+$): 513 [M + H]$^+$. |
| EX. 519 | 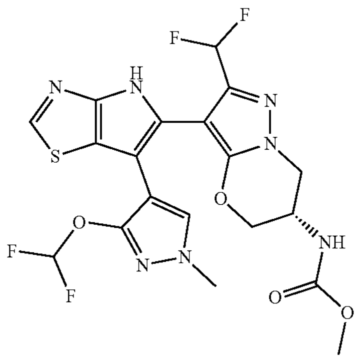 [SMILES: COC(=O)N[C@@H]1COc2c(-c3[nH]c4ncsc4c3-c3cn(C)nc3OC(F)F)c(C(F)F)nn2C1] | $^1$H-NMR (400 MHz, DMSO-$d_6$) δ 3.58 (3H, s), 3.71 (3H, s), 4.11-4.33 (4H, m), 4.39-4.51 (1H, m), 6.73 (1H, t, J = 53.9 Hz), 7.11-7.52 (2H, m), 7.72-7.84 (1H, m), 8.76 (1H, s), 11.84 (1H, s); MS (ESI$^+$): 516 [M + H]$^+$. |

(174) Experimental procedure of (S)—N-(3-(6-(3-(difluoromethoxy)-1-methyl-1H-pyrazol-4-yl)-4H-pyrrolo[2,3-d]thiazol-5-yl)-2-(difluoromethyl)-6,7-dihydro-5H-pyrazolo[5,1-b][1,3]oxazin-6-yl) methanesulfonamide (EX.520)

EX. 520

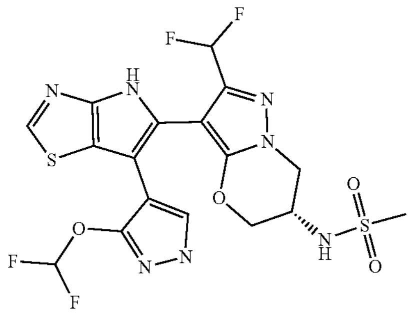

EX.520 was synthesized from EX.428 using conditions analogous to compound 219; $^{1}$H-NMR (400 MHz, DMSO-$d_6$) δ 3.07 (3H, s), 3.71 (3H, s), 4.16-4.30 (3H, m), 4.31-4.40 (1H, m), 4.44-4.53 (1H, m), 6.75 (1H, t, J=53.8 Hz), 7.12-7.53 (2H, m), 7.70 (1H, s), 8.77 (1H, s), 11.88 (1H, s); MS (ESI$^+$): 536 [M+H]$^+$.

The following compounds were also synthesized from the corresponding starting materials and reagents using conditions analogous to compound 219.

| Compound No. | Chemical structural formula | Spectrum data |
|---|---|---|
| EX. 521 | 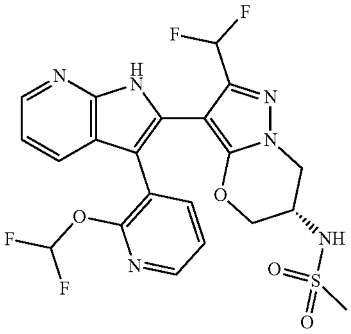 [SMILES: CS(=O)(=O)N[C@@H]1COc2c(-c3[nH]c4ncccc4c3-c3cccnc3OC(F)F)c(C(F)F)nn2C1] | $^{1}$H-NMR (400 MHz, DMSO-$d_6$) δ 3.03 (s, 3H), 4.04-4.14 (m, 4H), 4.38-4.43 (m, 1H), 6.68 (t, J = 53.9 Hz, 1H), 7.11 (dd, J = 8.0, 4.7 Hz, 1H), 7.23 (dd, J = 7.4, 4.9 Hz, 1H), 7.52-7.89 (m, 4H), 8.16-8.19 (m, 1H), 8.25-8.28 (m, 1H), 11.92 (s, 1H); MS (ESI$^+$): 527 [M + H]$^+$. |
| EX. 522 | 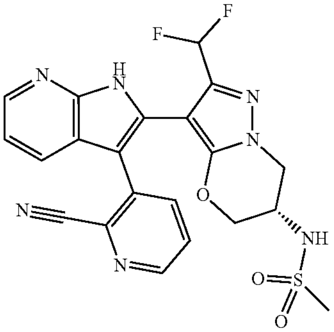 [SMILES: CS(=O)(=O)N[C@@H]1COc2c(-c3[nH]c4ncccc4c3-c3cccnc3C#N)c(C(F)F)nn2C1] | $^{1}$H-NMR (400 MHz, DMSO-$d_6$) δ 3.04 (s, 3H), 4.00-4.27 (m, 4H), 4.40-4.47 (m, 1H), 6.56-6.84 (m, 1H), 7.15-7.19 (m, 1H), 7.69-7.72 (m, 1H), 7.82-7.88 (m, 2H), 8.33 (dd, J = 4.6, 1.4 Hz, 1H), 8.67 (dd, J = 4.7, 1.5 Hz, 1H), 12.20 (s, 1H); MS (ESI$^+$): 486 [M + H]$^+$. |

-continued

| Compound No. | Chemical structural formula | Spectrum data |
|---|---|---|
| EX. 523 | 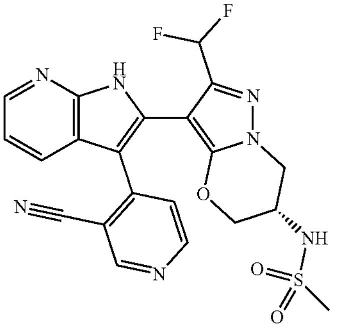 [SMILES: CS(=O)(=O)N[C@@H]1COc2c(-c3[nH]c4ncccc4c3-c3ccncc3C#N)c(C(F)F)nn2C1] | $^1$H-NMR (400 MHz, DMSO-$d_6$) δ 3.03 (s, 3H), 4.05-4.19 (m, 4H), 4.41-4.47 (m, 1H), 6.71 (t, J = 53.9 Hz, 1H), 7.18 (dd, J = 7.9, 4.6 Hz, 1H), 7.40 (d, J = 5.3 Hz, 1H), 7.53-7.62 (m, 1H), 7.93 (dd, J = 7.9, 1.5 Hz, 1H), 8.33 (dd, J = 4.7, 1.5 Hz, 1H), 8.73 (d, J = 5.3 Hz, 1H), 8.98 (s, 1H), 12.30 (s, 1H); MS (ESI$^+$): 486 [M + H]$^+$. |
| EX. 524 | 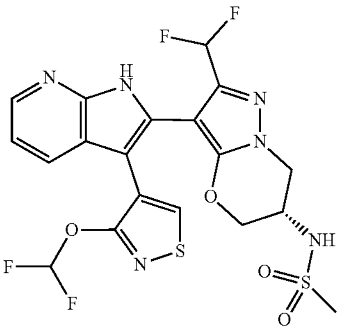 [SMILES: CS(=O)(=O)N[C@@H]1COc2c(-c3[nH]c4ncccc4c3-c3csnc3OC(F)F)c(C(F)F)nn2C1] | $^1$H-NMR (400 MHz, DMSO-$d_6$) δ 3.05 (s, 3H), 4.10-4.23 (m, 4H), 4.41-4.44 (m, 1H), 6.73 (t, J = 53.9 Hz, 1H), 7.13 (dd, J = 7.9, 4.7 Hz, 1H), 7.42-7.79 (m, 2H), 7.84 (dd, J = 7.9, 1.3 Hz, 1H), 8.27 (dd, J = 4.7, 1.2 Hz, 1H), 8.73 (s, 1H), 11.96 (s, 1H); MS (ESI$^+$): 533 [M + H]$^+$. |
| EX. 525 | 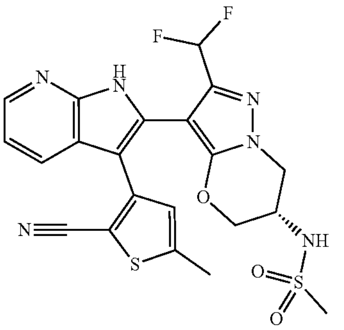 [SMILES: Cc1cc(-c2c(-c3c(C(F)F)nn4c3OC[C@@H](NS(C)(=O)=O)C4)[nH]c3ncccc23)c(C#N)s1] | $^1$H-NMR (400 MHz, DMSO-$d_6$) δ 2.52 (s, 3H), 3.06 (s, 3H), 4.11-4.25 (m, 4H), 4.45-4.49 (m, 1H), 6.62 (t, J = 54.0 Hz, 1H), 6.93 (s, 1H), 7.17 (dd, J = 7.9, 4.6 Hz, 1H), 7.55 (s, 1H), 7.93 (dd, J = 7.9, 1.3 Hz, 1H), 8.30 (dd, J = 4.7, 1.4 Hz, 1H), 12.11 (s, 1H); MS (ESI$^+$): 505 [M + H]$^+$. |

(175) Reference Procedure of 4-iodo-1-methyl-1,2-dihydro-3H-pyrazol-3-one (385)

(385)

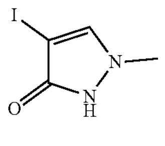

The compound 385 was synthesized from the corresponding starting material using conditions analogous to compound 127; $^1$H-NMR (400 MHz, DMSO-$d_6$) δ 3.62 (3H, s), 7.52 (1H, s), 10.13 (1H, s); MS (ESI$^+$): 225 [M+H]$^+$.

(176) Reference Procedure of 3-(difluoromethoxy)-1-methyl-4-(4,4,5,5-tetramethyl-1,3,2-dioxaborolan-2-yl)-1H-pyrazole (386)

(386)

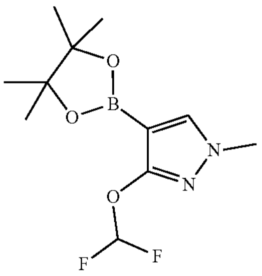

To a stirred suspension of $Cs_2CO_3$ (63.4 g, 195 mmol) in DMF (65 mL) and water (3.6 mL) at 90° C. under Ar atmosphere, a solution of compound 385 (21.8 g, 97.2 mmol) and sodium chlorodifluoroacetate (22.3 g, 146 mmol) in DMF (130 mL) was slowly added. After stirring at the same temperature for 3 h, the reaction mixture was cooled to room temperature, and water was added. The resulting mixture was extracted with EtOAc. The organic layer was washed with water twice, and concentrated. Diisopropyl ether and n-hexane were added to the residue, and the resulting mixture was stirred at 0° C. for 0.5 h. The resulting solid was removed by filtration, and the filtrate was concentrated. The residue was purified by silica gel column chromatography (0-30% EtOAc/hexane) to yield 3-(difluoromethoxy)-4-iodo-1-methyl-1H-pyrazole (11.7 g).

The compound 386 was synthesized from 3-(difluoromethoxy)-4-iodo-1-methyl-1H-pyrazole using conditions analogous to compound 220; $^1$H-NMR (400 MHz, $CDCl_3$) δ 1.30 (s, 12H), 3.77 (s, 3H), 6.96 (t, J=74.0 Hz, 1H), 7.50 (s, 1H).

(177) Reference Procedure of 7-benzyl-3-bromo-7H-pyrrolo[2,3-b]pyridine (387)

(387)

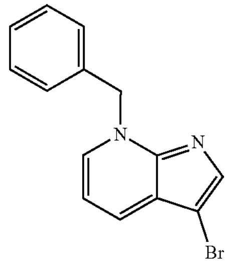

To a stirred suspension of 3-bromo-7-azaindole (10.0 g, 50.8 mmol) in MeCN (40 mL) at room temperature under Ar atmosphere, benzyl bromide (6.4 mL, 53.5 mmol) was added. After stirring at 80° C. for 9.5 h, diisopropyl ether was added, and the resulting mixture was stirred at 0° C. for 0.5 h. The precipitate was collected by filtration, and the solid was washed with MeCN. The solid was dissolved in EtOH-$H_2O$ (2.5/1) at 50° C., and activated charcoal was added. The resulting mixture was stirred at the same temperature for 40 min. The activated charcoal was filtered off through a pad of Celite, and aq. NaOH was added to the filtrate. The resulting mixture was stirred at 0° C. for 1 h. The resulting precipitate was collected by filtration to yield compound 387 (12.9 g, 89%) as a yellow solid; $^1$H-NMR (400 MHz, $CDCl_3$) δ 5.88 (2H, s), 6.93 (1H, dd, J=7.4, 6.3 Hz), 7.34-7.37 (5H, m), 7.64 (1H, d, J=5.5 Hz), 7.85 (1H, s), 8.06 (1H, dd, J=7.5, 1.1 Hz).

(178) Reference Procedure of 7-benzyl-3-(3-(difluoromethoxy)-1-methyl-1H-pyrazol-4-yl)-7H-pyrrolo[2,3-b]pyridine (388)

(388)

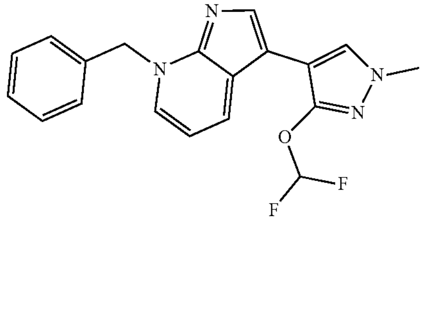

The compound 388 was synthesized from compound 387 using conditions analogous to compound 390; $^1$H-NMR (500 MHz, $CDCl_3$) δ 3.85 (s, 3H), 5.90 (s, 2H), 6.89 (dd, J=6.5 Hz, 7.6 Hz, 1H), 6.97 (t, J=73.8 Hz, 1H), 7.33-7.40 (m, 5H), 7.46 (s, 1H), 7.59 (dd, J=0.8 Hz, 6.1 Hz, 1H), 8.04 (s, 1H), 8.25 (dd, J=0.8 Hz, 7.3 Hz, 1H); MS (ESI$^+$): 355 [M+H]$^+$.

(179) Reference Procedure of 7-benzyl-2-bromo-3-(3-(difluoromethoxy)-1-methyl-1H-pyrazol-4-yl)-7H-pyrrolo[2,3-b]pyridine (389)

(389)

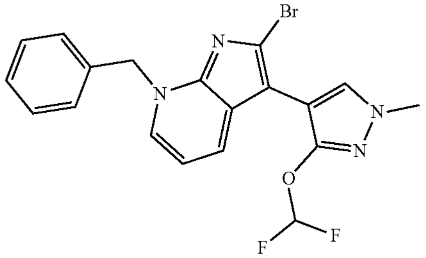

The compound 389 was synthesized from compound 388 using conditions analogous to compound 235; $^1$H-NMR (500 MHz, $CDCl_3$) δ 3.87 (s, 3H), 5.86 (s, 2H), 6.88 (dd, J=6.5 Hz, 7.6 Hz, 1H), 6.97 (t, J=73.8 Hz, 1H), 7.35-7.41 (m, 5H), 7.51 (d, J=6.5 Hz, 1H), 7.62 (s, 1H), 8.12 (d, J=7.6 Hz, 1H); MS (ESI$^+$): 433 [M+H]$^+$.

(180) Reference Procedure of (S)-3-(7-benzyl-3-(3-(difluoromethoxy)-1-methyl-1H-pyrazol-4-yl)-7H-pyrrolo[2,3-b]pyridin-2-yl)-6-((tert-butyldiphenylsilyl)oxy)-2-(difluoromethyl)-6,7-dihydro-5H-pyrazolo[5,1-b][1,3]oxazine (390)

(390)

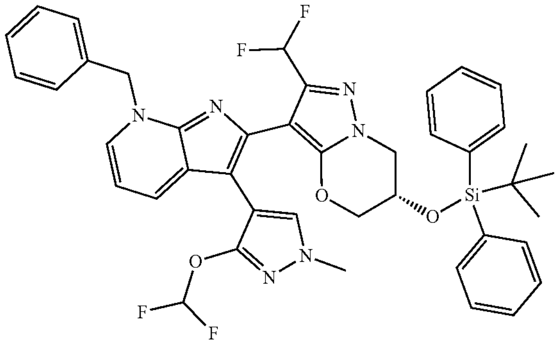

A mixture of compound 389 (70.0 mg, 0.162 mmol), compound 226 (99.0 mg, 0.179 mmol), Pd(amphos)$Cl_2$ (12.0 mg, 0.0169 mmol), and $K_3PO_4$ (103 mg, 0.485 mmol) in DMA (2 mL) was stirred at 60° C. for 2 h under Ar atmosphere. Water was added, and the resulting precipitate was collected by filtration. The solid was dissolved in EtOAc, the resulting solution was dried over $Na_2SO_4$, and concentrated. The residue was purified by silica gel column chromatography (5-100% EtOAc/hexane) to yield compound 390 (56.0 mg, 44%) as a yellow oil; MS (ESI$^+$): 781 [M+H]$^+$.

The following compounds were synthesized from the corresponding starting materials and reagents using conditions analogous to compound 390.

| Compound No. | Chemical structural formula | Spectrum data |
|---|---|---|
| 391 | 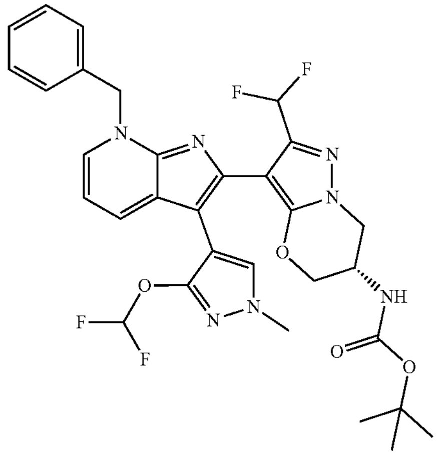 [SMILES: Cn1cc(-c2c3cccn(Cc4ccccc4)c-3nc2-c2c(C(F)F)nn3c2OC[C@@H](NC(=O)OC(C)(C)C)C3)c(OC(F)F)n1] | $^1$H-NMR (400 MHz, $CDCl_3$) δ 1.43 (9H, s), 3.80 (3H, s), 4.06-4.15 (2H, m), 4.30-4.33 (3H, m), 5.05 (1H, d, J = 7.3 Hz), 5.83 (2H, s), 6.79 (1H, t, J = 74.4 Hz), 6.85 (1H, t, J = 6.8 Hz), 7.09 (1H, t, J = 54.4 Hz), 7.17 (1H, s), 7.31-7.39 (3H, m), 7.43-7.46 (2H, m), 7.57 (1H, d, J = 6.1 Hz), 7.99 (1H, d, J = 7.3 Hz); MS (ESI$^+$): 642 [M + H]$^+$. |
| 392 | 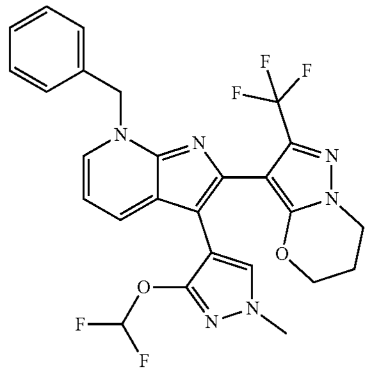 [SMILES: Cn1cc(-c2c3cccn(Cc4ccccc4)c-3nc2-c2c(C(F)(F)F)nn3c2OCCC3)c(OC(F)F)n1] | $^1$H-NMR (400 MHz, DMSO-$d_6$) δ 2.14-2.21 (m, 2H), 3.75 (s, 3H), 4.11-4.21 (m, 4H), 5.83 (s, 2H), 6.89-7.36 (m, 5H), 7.49 (s, 1H), 7.63 (dd, J = 7.6, 1.6 Hz, 2H), 7.99 (dd, J = 7.5, 0.8 Hz, 1H), 8.26 (d, J = 5.3 Hz, 1H); MS (ESI$^+$): 545 [M + H]$^+$. |
| 393 | 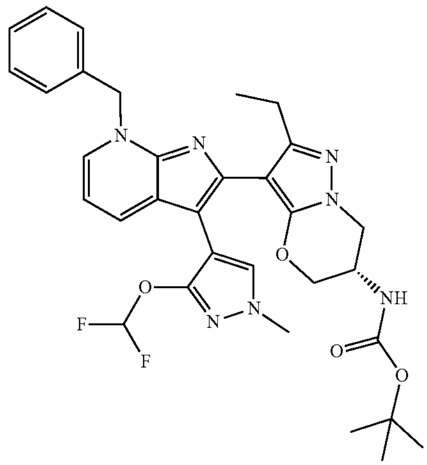 [SMILES: CCc1nn2c(c1-c1nc3n(Cc4ccccc4)cccc-3c1-c1cn(C)nc1OC(F)F)OC[C@@H](NC(=O)OC(C)(C)C)C2] | $^1$H-NMR (400 MHz, $CDCl_3$) δ 1.09-1.17 (m, 3H), 1.44 (s, 9H), 2.62-2.72 (m, 2H), 3.77-3.84 (m, 3H), 4.08-4.33 (m, 4H), 5.17 (d, J = 8.0 Hz, 1H), 5.90 (d, J = 9.4 Hz, 2H), 6.64-7.02 (m, 2H), 7.15 (d, J = 4.3 Hz, 1H), 7.30-7.41 (m, 4H), 7.45-7.48 (m, 2H), 7.52 (dd, J = 6.3, 1.0 Hz, 1H), 8.00-8.04 (m, 1H); MS (ESI$^+$): 620 [M + H]$^+$. |

-continued
| Compound No. | Chemical structural formula | Spectrum data |
|---|---|---|
| 394 | 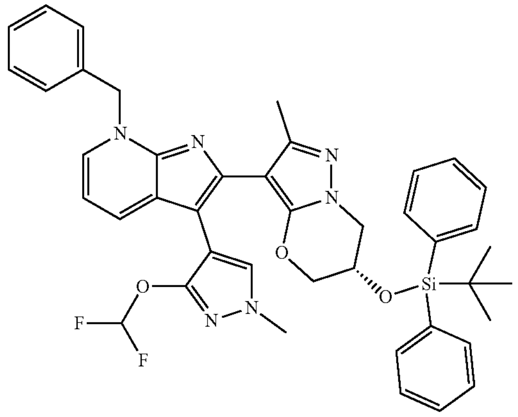 [SMILES: Cc1nn2c(c1-c1nc3n(Cc4ccccc4)cccc-3c1-c1cn(C)nc1OC(F)F)OC[C@@H](O[Si](c1ccccc1)(c1ccccc1)C(C)(C)C)C2] | $^{1}$H-NMR (400 MHz, $CDCl_3$) δ 0.99 (s, 9H), 2.14 (s, 3H), 3.64 (s, 3H), 3.79-4.10 (m, 4H), 4.31-4.37 (m, 1H), 5.84 (dd, J = 25.1, 13.8 Hz, 2H), 6.88-7.67 (m, 18H), 7.86 (dd, J = 7.5, 0.9 Hz, 1H), 8.17-8.18 (m, 1H); MS (ESI$^+$): 745 [M + H]$^+$. |
| 395 | 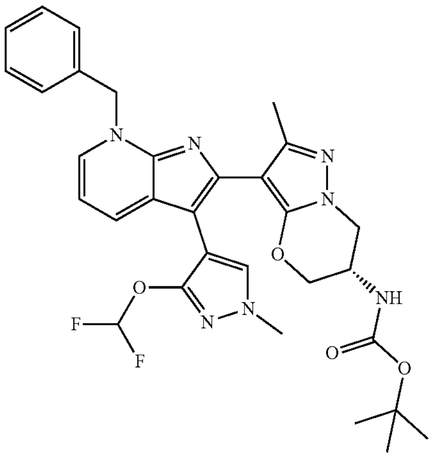 [SMILES: Cc1nn2c(c1-c1nc3n(Cc4ccccc4)cccc-3c1-c1cn(C)nc1OC(F)F)OC[C@@H](NC(=O)OC(C)(C)C)C2] | $^{1}$H-NMR (400 MHz, $CDCl_3$) δ 1.44 (s, 9H), 2.08-2.23 (m, 3H), 3.80 (s, 3H), 4.10-4.36 (m, 5H), 5.31-5.38 (m, 1H), 5.85-5.95 (m, 2H), 6.66-7.05 (m, 2H), 7.16 (s, 1H), 7.32-7.55 (m, 6H), 8.00-8.06 (m, 1H); MS (ESI$^+$): 606 [M + H]$^+$. |

(181) Reference Procedure of (S)-3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-ol (396)

(396)

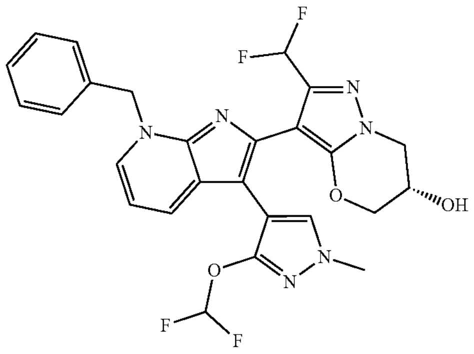

To a stirred solution of compound 390 (45.0 mg, 0.0576 mmol) in THF (0.5 mL) at room temperature, 1 mol/L TBAF in THF (0.17 mL, 0.17 mmol) was added. After stirring at the same temperature for 0.5 h, the reaction was quenched with sat. aq. $NH_4Cl$ and brine. The resulting mixture was extracted with EtOAc, the organic layer was dried over $Na_2SO_4$, and concentrated. The residue was purified by silica gel column chromatography (0-50% MeOH/EtOAc) to yield compound 396 (26.0 mg, 83%) as a yellow amorphous; $^1$H-NMR (400 MHz, $CDCl_3$) δ 1.80 (1H, s), 3.74 (3H, s), 4.00-4.24 (5H, m), 5.81 (2H, s), 6.60-7.03 (3H, m), 7.16 (1H, s), 7.32-7.42 (6H, m), 7.56 (1H, d, J=5.5 Hz), 8.03 (1H, d, J=7.3 Hz); MS (ESI$^+$): 543 $[M+H]^+$.

(181) Reference Procedure of (S)-3-(7-benzyl-3-(3-(difluoromethoxy)-1-methyl-1H-pyrazol-4-yl)-7H-pyrrolo[2,3-b]pyridin-2-yl)-2-methyl-6,7-dihydro-5H-pyrazolo[5,1-b][1,3]oxazin-6-ol (397)

(397)

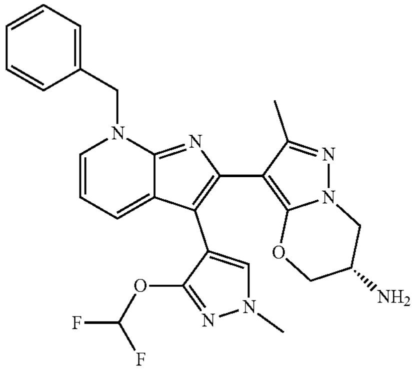

The compound 397 was synthesized from compound 394 using conditions analogous to compound 396; $^1$H-NMR (400 MHz, DMSO-$d_6$) δ 2.15 (s, 3H), 3.74 (s, 3H), 3.83-3.98 (m, 3H), 4.12-4.22 (m, 2H), 5.53 (s, 1H), 5.83 (s, 2H), 6.91-7.36 (m, 5H), 7.45 (s, 1H), 7.57-7.61 (m, 2H), 7.87 (dd, J=7.5, 1.1 Hz, 1H), 8.16 (dd, J=6.3, 1.1 Hz, 1H); MS (ESI$^+$): 507 $[M+H]^+$.

(182) Reference Procedure of (S)-3-(7-benzyl-3-(3-(difluoromethoxy)-1-methyl-1H-pyrazol-4-yl)-7H-pyrrolo[2,3-b]pyridin-2-yl)-6-(difluoromethoxy)-2-(difluoromethyl)-6,7-dihydro-5H-pyrazolo[5,1-b][1,3]oxazine (398)

(398)

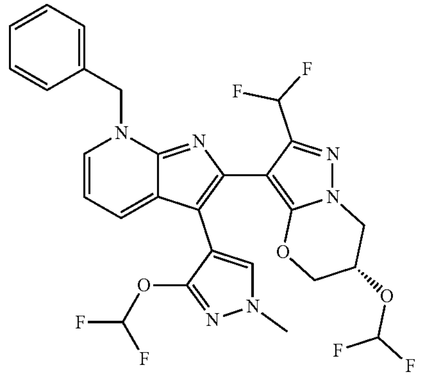

To a stirred solution of compound 396 (50.0 mg, 0.0922 mmol) in THF (0.46 mL) at 0° C. under Ar atmosphere, 60% sodium hydride (4.4 mg, 0.101 mmol) was added. After stirring at 0° C. for 0.5 h, difluoroiodomethane (0.060 mL, 0.12 mmol) was added to the reaction mixture, which was stirred at room temperature for 1 h. The reaction was quenched with sat. aq. $NH_4Cl$, and the resulting mixture was extracted with EtOAc. The organic layer was washed with brine, dried over $Na_2SO_4$, and concentrated. The residue was purified by silica gel column chromatography (25-100% EtOAc/hexane) to yield compound 398 (3.8 mg, 7%) as a yellow oil; $^1$H-NMR (400 MHz, $CDCl_3$) δ 3.79 (s, 3H), 4.10-4.28 (m, 2H), 4.38-4.45 (m, 2H), 4.86-4.92 (m, 1H), 5.82 (d, J=14.3 Hz, 1H), 5.88 (d, J=14.2 Hz, 1H), 6.33 (t, J=72.5 Hz, 1H), 6.62-7.13 (m, 3H), 7.18 (s, 1H), 7.32-7.41 (m, 3H), 7.45-7.49 (m, 2H), 7.58 (dd, J=6.3, 1.0 Hz, 1H), 8.02 (dd, J=7.5, 1.0 Hz, 1H).

(183) Reference Procedure of methyl (S)-2-((3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl)oxy)acetate (399)

(399)

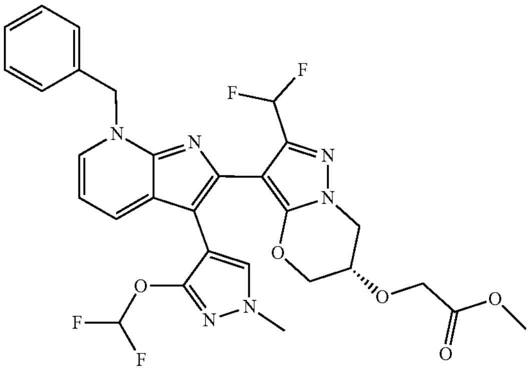

The compound 399 was synthesized from compound 396 using conditions analogous to compound 213; $^1$H-NMR (400 MHz, $CDCl_3$) δ 3.77 (s, 3H), 3.78 (s, 3H), 4.08-4.11 (m, 2H), 4.20 (s, 2H), 4.22-4.42 (m, 3H), 5.80 (d, J=14.2 Hz, 1H), 5.89 (d, J=14.2 Hz, 1H), 6.81 (t, J=74.0 Hz, 1H), 6.85 (dd, J=7.4, 6.3 Hz, 1H), 7.00 (t, J=54.5 Hz, 1H), 7.17 (s, 1H), 7.32-7.42 (m, 3H), 7.44-7.49 (m, 2H), 7.57 (dd, J=6.3, 1.0 Hz, 1H), 8.02 (dd, J=7.5, 1.1 Hz, 1H); MS (ESI$^+$): 615 $[M+H]^+$.

(184) Reference Procedure of methyl (S)-2-((3-(7-benzyl-3-(3-(difluoromethoxy)-1-methyl-1H-pyrazol-4-yl)-7H-pyrrolo[2,3-b]pyridin-2-yl)-2-methyl-6,7-dihydro-5H-pyrazolo[5,1-b][1,3]oxazin-6-yl)oxy) acetate (400)

(400)

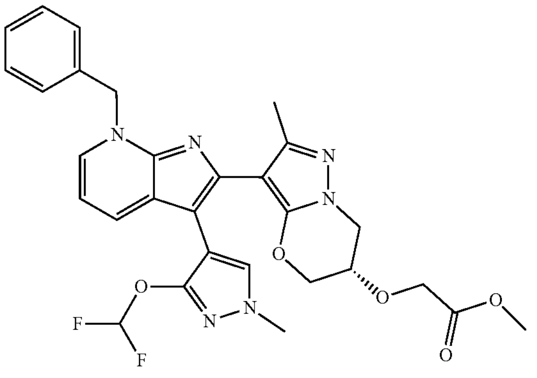

The compound 400 was synthesized from compound 397 using conditions analogous to compound 213; 1H'H-NMR (400 MHz, DMSO-$d_6$) δ 2.16 (s, 3H), 3.66 (s, 3H), 3.73 (s, 3H), 3.98-4.24 (m, 5H), 4.29 (s, 2H), 5.83 (s, 2H), 6.90-7.37 (m, 5H), 7.44 (s, 1H), 7.56-7.61 (m, 2H), 7.86 (dd, J=7.5, 0.9 Hz, 1H), 8.16 (dd, J=6.3, 0.9 Hz, 1H); MS (ESI$^+$): 579 $[M+H]^+$.

(185) Reference Procedure of (S)-3-(7-benzyl-3-(3-(difluoromethoxy)-1-methyl-1H-pyrazol-4-yl)-7H-pyrrolo[2,3-b]pyridin-2-yl)-2-(difluoromethyl)-6-methoxy-6,7-dihydro-5H-pyrazolo[5,1-b][1,3] oxazine (401)

(401)

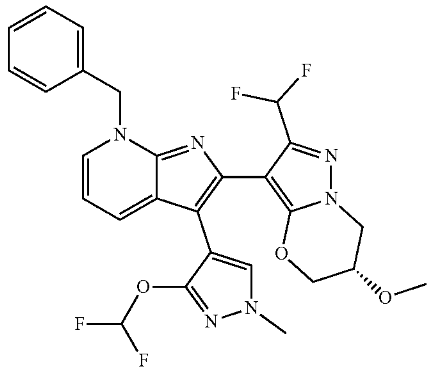

The compound 401 was synthesized from compound 397 using conditions analogous to compound 212; $^1$H-NMR (400 MHz, $CDCl_3$) δ 3.43 (s, 3H), 3.79 (s, 3H), 3.85-3.91 (m, 1H), 4.01-4.07 (m, 1H), 4.20-4.32 (m, 2H), 4.33-4.40 (m, 1H), 5.78 (d, J=14.2 Hz, 1H), 5.90 (d, J=14.2 Hz, 1H), 6.63-7.23 (m, 4H), 7.32-7.41 (m, 3H), 7.45-7.50 (m, 2H), 7.57 (dd, J=6.3, 1.1 Hz, 1H), 8.03 (dd, J=7.5, 1.1 Hz, 1H); MS (ESI$^+$): 557 $[M+H]^+$.

The following compounds were also synthesized from the corresponding starting materials and reagents using conditions analogous to compound 212.

| Compound No. | Chemical structural formula | Spectrum data |
|---|---|---|
| 402 | 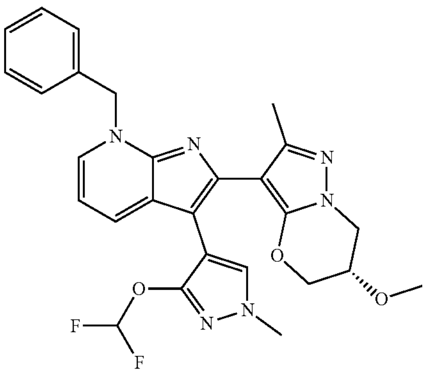 [SMILES: CO[C@@H]1COc2c(-c3nc4n(Cc5ccccc5)cccc-4c3-c3cn(C)nc3OC(F)F)c(C)nn2C1] | $^1$H-NMR (400 MHz, DMSO-$d_6$) δ 2.16 (s, 3H), 3.32 (s, 3H), 3.74 (s, 3H), 3.88-4.24 (m, 5H), 5.83 (s, 2H), 6.89-7.45 (m, 6H), 7.58-7.60 (m, 2H), 7.85-7.87 (m, 1H), 8.15-8.17 (m, 1H); MS (ESI$^+$): 521 $[M + H]^+$. |

-continued

| Compound No. | Chemical structural formula | Spectrum data |
|---|---|---|
| 403 | 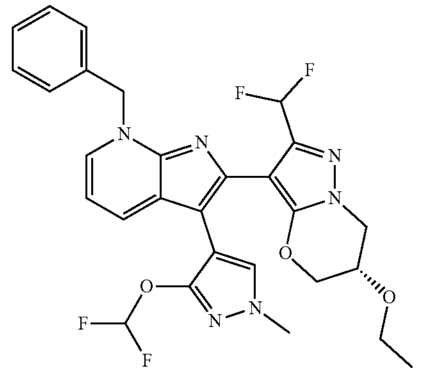 [SMILES: CCO[C@@H]1COc2c(-c3nc4n(Cc5ccccc5)cccc-4c3-c3cn(C)nc3OC(F)F)c(C(F)F)nn2C1] | $^1$H-NMR (400 MHz, DMSO-$d_6$) δ 1.11 (t, J = 7.0 Hz, 3H), 3.48-3.61 (m, 2H), 3.76 (s, 3H), 3.98-4.31 (m, 5H), 5.83 (s, 2H), 6.90-7.58 (m, 9H), 7.93 (dd, J = 7.5, 1.1 Hz, 1H), 8.26 (dd, J = 6.3, 0.9 Hz, 1H); MS (ESI$^+$): 571 [M + H]$^+$. |
| 404 | 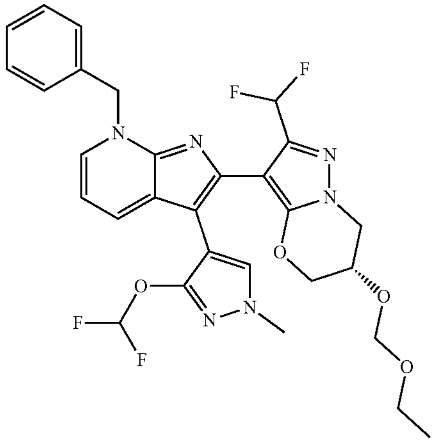 [SMILES: CCOCO[C@@H]1COc2c(-c3nc4n(Cc5ccccc5)cccc-4c3-c3cn(C)nc3OC(F)F)c(C(F)F)nn2C1] | $^1$H-NMR (400 MHz, DMSO-$d_6$) δ 3.22 (s, 3H), 3.44 (t, J = 4.7 Hz, 2H), 3.60-3.69 (m, 2H), 3.76 (s, 3H), 4.00-4.31 (m, 5H), 5.83 (s, 2H), 6.97-7.57 (m, 9H), 7.93 (dd, J = 7.5, 1.1 Hz, 1H), 8.26 (dd, J = 6.3, 0.9 Hz, 1H); MS (ESI$^+$): 601 [M + H]$^+$. |

(186) Reference Procedure of tert-butyl (S)-(3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl)(methyl) carbamate (405)

(405)

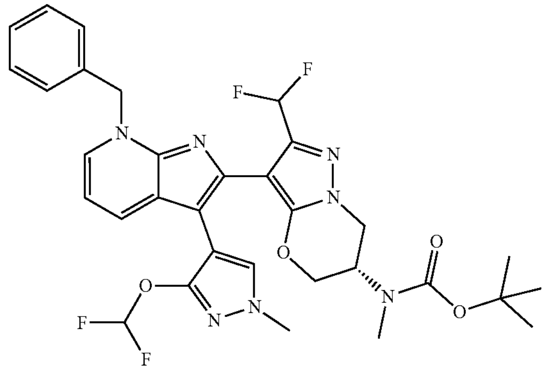

The compound 405 was synthesized from compound 391 using conditions analogous to compound 212; $^1$H-NMR (400 MHz, $CDCl_3$) δ 1.46 (9H, s), 2.77 (3H, s), 3.78 (3H, s), 4.10-4.21 (2H, m), 4.28 (1H, dd, J=13.0, 6.0 Hz), 4.40 (1H, dd, J=12.7, 6.0 Hz), 4.70 (1H, s), 5.84 (2H, s), 6.79 (1H, t, J=74.4 Hz), 6.84 (1H, t, J=6.7 Hz), 7.04 (1H, t, J=54.4 Hz), 7.13 (1H, s), 7.32-7.39 (3H, m), 7.44-7.47 (2H, m), 7.57 (1H, d, J=6.1 Hz), 7.97 (1H, d, J=7.2 Hz); MS (ESI$^+$): 656 [M+H]$^+$.

(187) Reference Procedure of (S)-3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-amine (406)

(406)

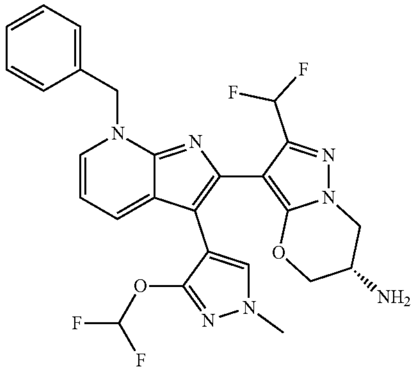

The compound 406 was synthesized from compound 391 using conditions analogous to compound 217; $^1$H-NMR (400 MHz, $CDCl_3$) δ 1.62 (2H, s), 3.55 (1H, qd, J=5.3, 2.8 Hz), 3.78 (3H, s), 3.89 (1H, dd, J=10.7, 5.8 Hz), 3.97 (1H, dd, J=12.5, 5.2 Hz), 4.08-4.13 (2H, m), 4.37 (1H, dd, J=12.2, 4.9 Hz), 5.85 (2H, s), 6.77 (1H, t, J=74.0 Hz), 6.85 (1H, t, J=6.7 Hz), 7.06 (1H, t, J=54.4 Hz), 7.17 (1H, s), 7.31-7.40 (3H, m), 7.46 (2H, dd, J=7.9, 1.8 Hz), 7.56 (1H, d, J=6.7 Hz), 7.99 (1H, d, J=7.9 Hz); MS (ESI$^+$): 542 [M+H]$^+$.

The following compounds were also synthesized from the corresponding starting materials and reagents using conditions analogous to compound 217.

| Compound No. | Chemical structural formula | Spectrum data |
|---|---|---|
| 407 | 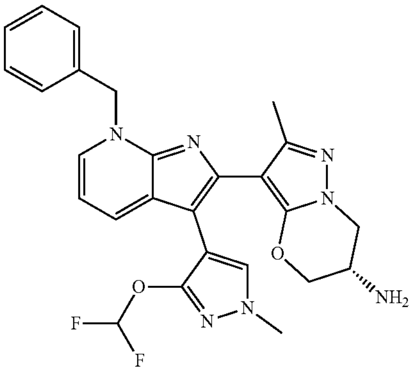 [SMILES: Cc1nn2c(c1-c1nc3n(Cc4ccccc4)cccc-3c1-c1cn(C)nc1OC(F)F)OC[C@@H](N)C2] | $^1$H-NMR (400 MHz, $CDCl_3$) δ 2.16 (s, 3H), 3.53-3.57 (m, 1H), 3.75-3.99 (m, 5H), 4.10-4.35 (m, 2H), 5.91 (s, 2H), 6.64-7.02 (m, 2H), 7.16 (s, 1H), 7.33-7.54 (m, 6H), 8.02 (d, J = 7.2 Hz, 1H); MS (ESI$^+$): 506 [M + H]$^+$. |
| 408 | 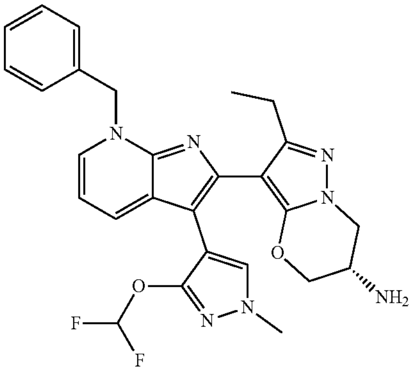 [SMILES: CCc1nn2c(c1-c1nc3n(Cc4ccccc4)cccc-3c1-c1cn(C)nc1OC(F)F)OC[C@@H](N)C2] | $^1$H-NMR (400 MHz, $CDCl_3$) δ 1.10 (t, J = 7.5 Hz, 3H), 2.64 (q, J = 7.6 Hz, 2H), 3.52-3.60 (m, 1H), 3.78 (s, 3H), 3.88-3.95 (m, 2H), 4.13-4.17 (m, 1H), 4.33 (dd, J = 12.2, 5.1 Hz, 1H), 5.89 (s, 2H), 6.62-7.00 (m, 2H), 7.15 (s, 1H), 7.32-7.41 (m, 3H), 7.45-7.52 (m, 3H), 8.01 (dd, J = 7.4, 1.1 Hz, 1H); MS (ESI$^+$): 520 [M + H]$^+$. |

(188) Reference Procedure of methyl (S)-(3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl) carbamate (409)

(409)

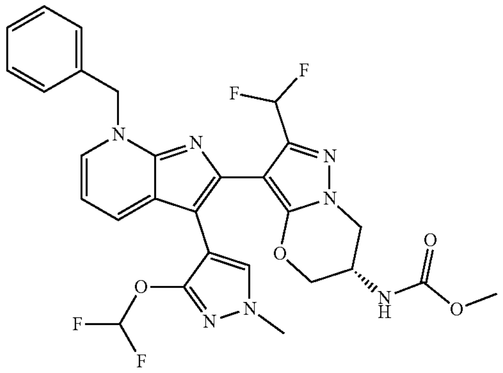

The compound 409 was synthesized from compound 406 using conditions analogous to compound 218; $^{1}$H-NMR (400 MHz, $CDCl_3$) δ 3.71 (s, 3H), 3.83 (s, 3H), 4.11-4.42 (m, 5H), 5.32 (s, 1H), 5.87 (s, 2H), 6.63-7.19 (m, 4H), 7.36-7.61 (m, 6H), 8.02 (d, J=7.3 Hz, 1H); MS (ESI$^+$): 600 $[M+H]^+$.

The following compounds were also synthesized from the corresponding starting materials and reagents using conditions analogous to compound 218.

| Compound No. | Chemical structural formula | Spectrum data |
|---|---|---|
| 410 | 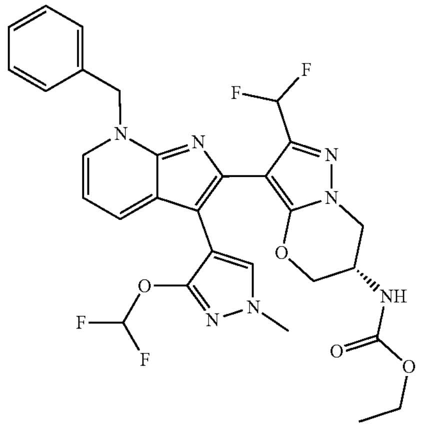 [SMILES: CCOC(=O)N[C@@H]1COc2c(-c3nc4n(Cc5ccccc5)cccc-4c3-c3cn(C)nc3OC(F)F)c(C(F)F)nn2C1] | $^{1}$H-NMR (400 MHz, $CDCl_3$) δ 1.23-1.28 (m, 3H), 3.82 (s, 3H), 4.10-4.23 (m, 5H), 4.33-4.35 (m, 2H), 5.37 (s, 1H), 5.86 (s, 2H), 6.62-7.05 (m, 3H), 7.17-7.48 (m, 6H), 7.58-7.60 (m, 1H), 8.01 (d, J = 7.2 Hz, 1H) MS (ESI$^+$): 614 $[M + H]^+$. |
| 411 | 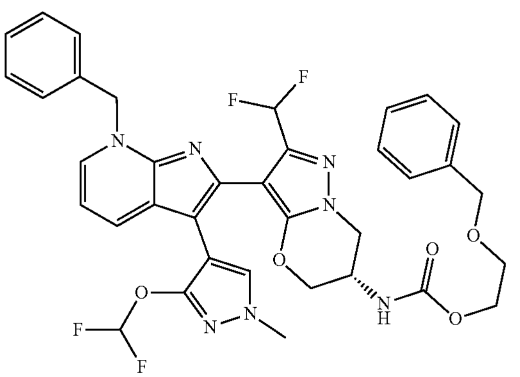 [SMILES: Cn1cc(-c2c3cccn(Cc4ccccc4)c-3nc2-c2c(C(F)F)nn3c2OC[C@@H](NC(=O)OCCOCc2ccccc2)C3)c(OC(F)F)n1] | $^{1}$H-NMR (400 MHz, $CDCl_3$) δ 3.65-3.68 (m, 2H), 3.77 (s, 3H), 4.10-4.40 (m, 7H), 4.54 (s, 2H), 5.44 (s, 1H), 5.86 (s, 2H), 6.63-7.04 (m, 2H), 7.16 (s, 1H), 7.25-7.60 (m, 12H), 8.02 (d, J = 8.8 Hz, 1H); MS (ESI$^+$): 720 $[M + H]^+$. |

-continued
| Compound No. | Chemical structural formula | Spectrum data |
|---|---|---|
| 412 | 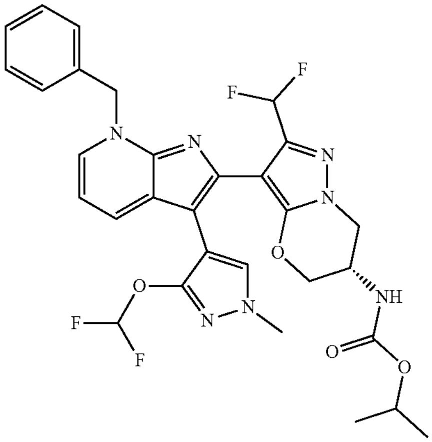 [SMILES: CC(C)OC(=O)N[C@@H]1COc2c(-c3nc4n(Cc5ccccc5)cccc-4c3-c3cn(C)nc3OC(F)F)c(C(F)F)nn2C1] | $^1$H-NMR (400 MHz, $CDCl_3$) δ 1.22-1.33 (m, 6H), 3.83 (s, 3H), 4.10-4.22 (m, 2H), 4.31-4.42 (m, 3H), 4.89-4.96 (m, 1H), 5.16 (s, 1H), 5.86 (s, 2H), 6.64-7.61 (m, 10H), 8.02 (d, J = 7.2 Hz, 1H); MS (ESI$^+$): 628 [M + H]$^+$. |
| 413 | 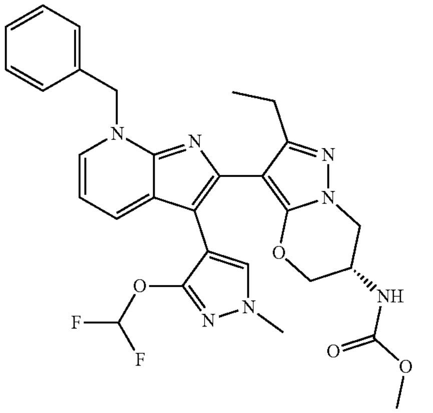 [SMILES: CCc1nn2c(c1-c1nc3n(Cc4ccccc4)cccc-3c1-c1cn(C)nc1OC(F)F)OC[C@@H](NC(=O)OC)C2] | $^1$H-NMR (400 MHz, $CDCl_3$) δ 1.06-1.13 (m, 3H), 2.64 (q, J = 7.6 Hz, 2H), 3.67-3.72 (m, 3H), 3.76-3.84 (m, 3H), 4.18-4.40 (m, 5H), 5.45-5.47 (m, 1H), 5.89 (s, 2H), 6.81-6.86 (m, 1H), 7.15 (s, 1H), 7.35-7.54 (m, 7H), 8.00-8.02 (m, 1H); MS (ESI$^+$): 578 [M + H]$^+$. |

(189) Reference Procedure of methyl (S)-(3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl)(methyl) carbamate (414)

(414)

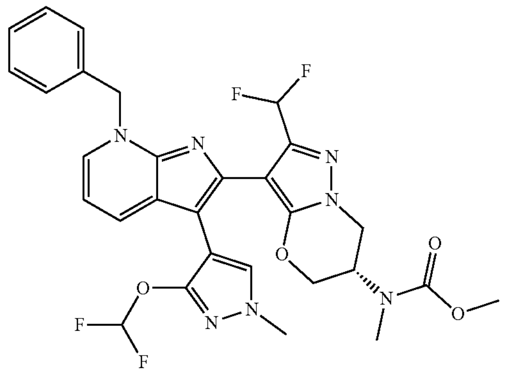

The compound 414 was synthesized from compound 409 using conditions analogous to compound 212; $^1$H-NMR (400 MHz, $CDCl_3$) δ 2.84-2.97 (m, 3H), 3.75 (s, 3H), 3.80 (s, 3H), 4.10-4.47 (m, 5H), 5.86 (s, 2H), 6.61-7.15 (m, 4H), 7.37-7.60 (m, 6H), 7.99 (d, J=7.9 Hz, 1H); MS (ESI$^+$): 614 [M+H]$^+$.

(190) Reference Procedure of (S)-3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl ethylcarbamate (415)

(415)

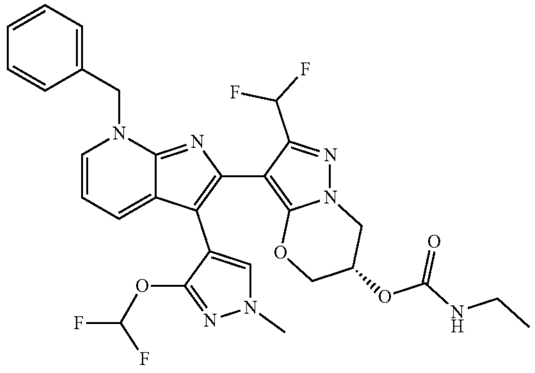

To a stirred solution of compound 396 (50.0 mg, 0.0922 mmol) in THF (0.46 mL) at 0° C. under Ar atmosphere, pyridine (4.4 mg, 0.101 mmol) and 4-nitrophenyl chloroformate (21.0 mg, 0.102 mmol) were added. After stirring at room temperature for 1 h, N,N-diisopropylethylamine (0.024 mL, 0.141 mmol) and ethylamine hydrochloride (11.0 mg, 0.139 mmol) were added to the reaction mixture, which was stirred at room temperature for 14 h. The reaction was quenched with sat. aq. $NH_4Cl$, and the resulting mixture was extracted with EtOAc. The organic layer was washed with brine, dried over $Na_2SO_4$, and concentrated. The residue was purified by silica gel column chromatography (25-100% EtOAc/hexane) to yield compound 415 (10.0 mg, 18%) as a yellow oil; $^1$H-NMR (400 MHz, $CDCl_3$) δ 1.24-1.29 (m, 3H), 3.81 (s, 3H), 4.05-4.20 (m, 3H), 4.27-4.40 (m, 2H), 4.99-5.06 (m, 1H), 5.29-5.33 (m, 1H), 5.84 (d, J=14.4 Hz, 1H), 5.88 (d, J=14.1 Hz, 1H), 6.50-7.09 (m, 3H), 7.24 (s, 1H), 7.34-7.49 (m, 5H), 7.58 (dd, J=6.3, 1.0 Hz, 1H), 7.98 (dd, J=7.4, 1.0 Hz, 1H); MS (ESI$^+$): 614 [M+H]$^+$.

(191) Reference Procedure of (S)-3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl methylcarbamate (416)

(416)

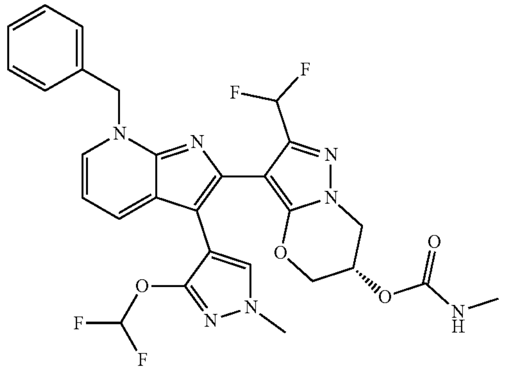

The compound 416 was synthesized from compound 396 using conditions analogous to compound 415; $^1$H-NMR (400 MHz, $CDCl_3$) δ 2.81 (d, J=4.7 Hz, 3H), 3.81 (s, 3H), 4.04-4.43 (m, 4H), 4.96 (d, J=5.7 Hz, 1H), 5.31 (s, 1H), 5.86 (s, 2H), 6.48-7.11 (m, 4H), 7.35-7.62 (m, 6H), 7.97 (d, J=7.4 Hz, 1H); MS (ESI$^+$): 600 [M+H]$^+$.

(192) Reference Procedure of (S)-2-((3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl)oxy)ethan-1-ol (417)

(417)

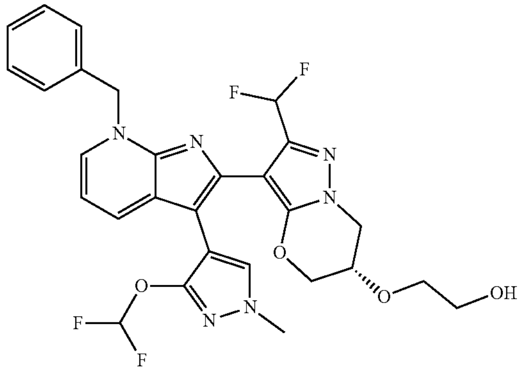

The compound 417 was synthesized from compound 399 using conditions analogous to compound 365; $^1$H-NMR (400 MHz, $CDCl_3$) δ 3.60-3.76 (m, 4H), 3.81 (s, 3H), 4.00-4.08 (m, 2H), 4.23-4.42 (m, 3H), 5.82 (d, J=14.2 Hz, 1H), 5.88 (d, J=14.2 Hz, 1H), 6.57-7.12 (m, 3H), 7.19 (s, 1H), 7.33-7.42 (m, 3H), 7.45-7.51 (m, 2H), 7.57 (d, J=6.2 Hz, 1H), 7.98 (d, J=7.4 Hz, 1H); MS (ESI$^+$): 587 [M+H]$^+$.

(193) Reference Procedure of (S)-2-((3-(7-benzyl-3-(3-(difluoromethoxy)-1-methyl-1H-pyrazol-4-yl)-7H-pyrrolo[2,3-b]pyridin-2-yl)-2-methyl-6,7-dihydro-5H-pyrazolo[5,1-b][1,3]oxazin-6-yl)oxy)ethan-1-ol (418)

(418)

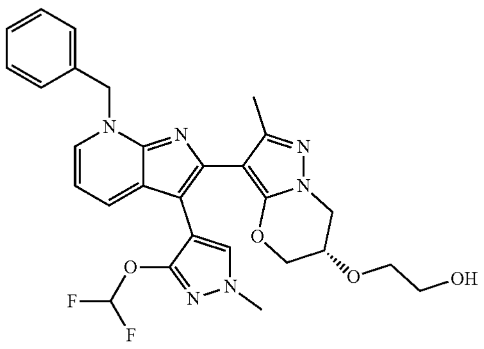

The compound 418 was synthesized from compound 400 using conditions analogous to compound 365; $^1$H-NMR (400 MHz, DMSO-$d_6$) δ 2.32 (s, 3H), 3.45-3.59 (m, 4H), 3.75 (s, 3H), 4.06-4.46 (m, 5H), 4.69-4.75 (m, 1H), 5.85 (s, 2H), 6.90-7.39 (m, 5H), 7.52-7.59 (m, 3H), 8.00 (dd, J=7.5, 1.1 Hz, 1H), 8.29 (dd, J=6.3, 0.9 Hz, 1H); MS (ESI$^+$): 551 [M+H]$^+$.

(194) Reference Procedure of (S)-4-((3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl)oxy)-2-methylbutan-2-ol (419)

(419)

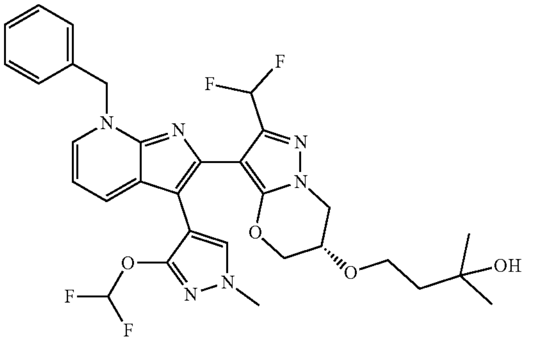

The compound 419 was synthesized from compound 399 using conditions analogous to compound 371; $^1$H-NMR (400 MHz, DMSO-$d_6$) δ 1.03 (s, 6H), 3.29 (s, 2H), 3.76 (s, 3H), 3.98-4.06 (m, 1H), 4.11-4.32 (m, 4H), 4.40 (s, 1H), 5.83 (s, 2H), 6.91-7.57 (m, 9H), 7.93 (dd, J=7.5, 0.9 Hz, 1H), 8.26 (dd, J=6.2, 1.0 Hz, 1H); MS (ESI$^+$): 615 [M+H]$^+$.

(195) Reference Procedure of (S)-2-((3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl)oxy)acetamide (420)

(420)

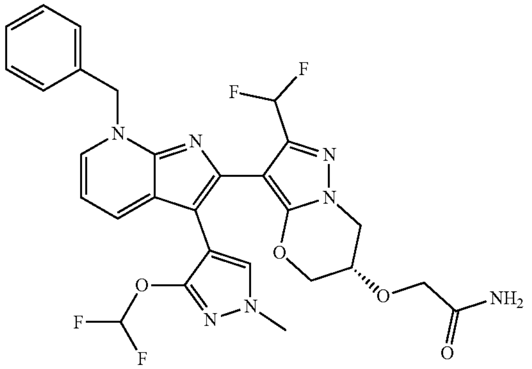

A mixture of compound 417 (62.0 mg, 0.10 mmol) in 7 mol/L ammonia in MeOH (0.50 mL, 3.50 mmol) was stirred at room temperature for 4 h under Ar atmosphere. The reaction mixture was concentrated, and the residue was purified by silica gel column chromatography (0-10% MeOH/EtOAc) to yield compound 420 (60.0 mg, quant.) as a yellow amorphous; $^1$H-NMR (400 MHz, DMSO-$d_6$) δ 3.75 (s, 3H), 3.94 (s, 2H), 3.99-4.06 (m, 1H), 4.15-4.19 (m, 1H), 4.25-4.41 (m, 3H), 5.83 (s, 2H), 6.91-7.58 (m, 11H), 7.93 (dd, J=7.4, 1.0 Hz, 1H), 8.25-8.27 (m, 1H); MS (ESI$^+$): 600 [M+H]$^+$.

(196) Reference Procedure of (S)-2-((3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl)oxy)ethan-1-amine (421)

(421)

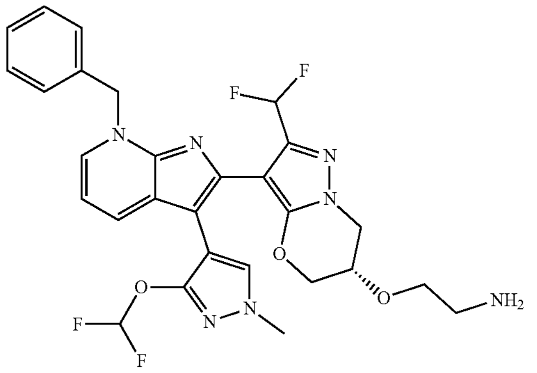

To a stirred solution of compound 420 (192 mg, 0.32 mmol) in THF (2 mL) at room temperature under Ar atmosphere, borane-dimethyl sulfide complex (0.091 mL, 0.961 mmol) was added, and the resulting mixture was stirred at 80° C. for 1 h. The reaction was quenched with MeOH (1 mL) and 2 mol/L aq. NaOH (2 mL), the resulting mixture was stirred at room temperature for 2 h, and extracted with $CHCl_3$/MeOH (9/1). The organic layer was dried over $Na_2SO_4$, and concentrated. The residue was purified by silica gel column chromatography (0-10% MeOH/EtOAc then 10% MeOH/$CHCl_3$) to yield compound 421 (77.0 mg, 41%) as a yellow oil; $^1$H-NMR (400 MHz, DMSO-$d_6$) δ 1.38 (s, 2H), 2.63 (t, J=5.8 Hz, 2H), 3.47 (t, J=5.8 Hz, 2H), 3.76 (s, 3H), 4.00-4.30 (m, 5H), 5.83 (s, 2H), 6.91-7.56 (m, 9H), 7.93 (dd, J=7.4, 1.0 Hz, 1H), 8.26 (dd, J=6.3, 1.1 Hz, 1H); MS (ESI$^+$): 586 [M+H]$^-$.

(197) Reference Procedure of (S)—N-(2-((3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl)oxy)ethyl) methanesulfonamide (422)

(422)

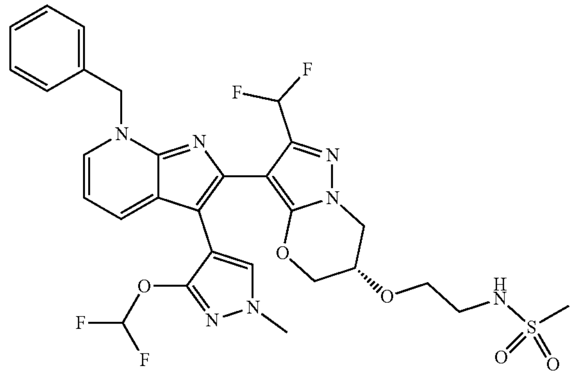

The compound 422 was synthesized from compound 421 using conditions analogous to compound 219; $^1$H-NMR (400 MHz, DMSO-$d_6$) δ 2.83 (s, 3H), 3.07-3.13 (m, 2H), 3.58 (t, J=5.7 Hz, 2H), 3.77 (s, 3H), 4.00-4.05 (m, 1H), 4.11-4.32 (m, 4H), 5.83 (s, 2H), 6.91-7.56 (m, 10H), 7.93 (dd, J=7.6, 1.0 Hz, 1H), 8.27 (dd, J=6.3, 1.1 Hz, 1H); MS (ESI$^+$): 664 [M+H]$^+$.

The following compounds were also synthesized from the corresponding starting materials and reagents using conditions analogous to compound 219.

| Compound No. | Chemical structural formula | Spectrum data |
|---|---|---|
| 423 | 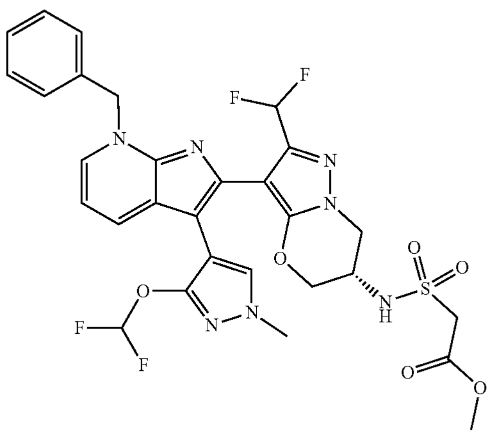 [SMILES: COC(=O)CS(=O)(=O)N[C@@H]1COc2c(-c3nc4n(Cc5ccccc5)cccc-4c3-c3cn(C)nc3OC(F)F)c(C(F)F)nn2C1] | $^1$H-NMR (400 MHz, $CDCl_3$) δ 3.75-3.89 (m, 6H), 4.10-4.24 (m, 3H), 4.33-4.45 (m, 4H), 5.85 (s, 2H), 6.66-7.64 (m, 10H), 8.07 (d, J = 7.4 Hz, 1H); MS (ESI$^+$): 678 [M + H]$^+$. |

-continued
| Compound No. | Chemical structural formula | Spectrum data |
|---|---|---|
| 424 | 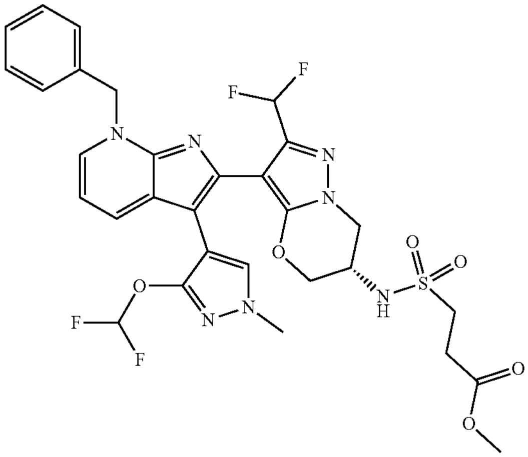 [SMILES: COC(=O)CCS(=O)(=O)N[C@@H]1COc2c(-c3nc4n(Cc5ccccc5)cccc-4c3-c3cn(C)nc3OC(F)F)c(C(F)F)nn2C1] | $^1$H-NMR (400 MHz, $CDCl_3$) δ 2.79-3.03 (m, 2H), 3.36-3.54 (m, 2H), 3.61-3.71 (m, 3H), 3.80-3.97 (m, 3H), 4.06-4.51 (m, 6H), 5.74-5.95 (m, 2H), 6.64-7.11 (m, 3H), 7.17-7.71 (m, 7H), 8.00-8.11 (m, 1H); MS (ESI$^+$): 692 $[M + H]^+$. |
| 425 | 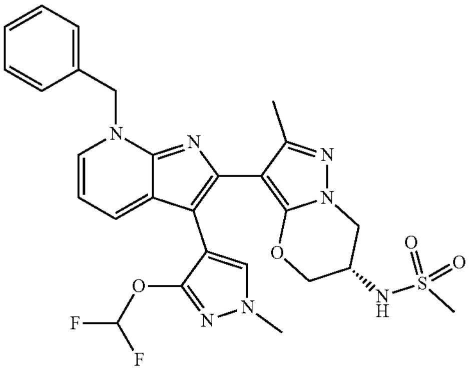 [SMILES: Cc1nn2c(c1-c1nc3n(Cc4ccccc4)cccc-3c1-c1cn(C)nc1OC(F)F)OC[C@@H](NS(C)(=O)=O)C2] | $^1$H-NMR (400 MHz, $CDCl_3$) δ 2.05 (s, 3H), 3.03 (s, 3H), 3.80 (s, 3H), 4.20-4.43 (m, 5H), 5.82-5.96 (m, 2H), 6.67-7.04 (m, 2H), 7.19 (s, 1H), 7.36-7.57 (m, 6H), 8.05 (d, J = 7.3 Hz, 1H); MS (ESI$^+$): 584 $[M + H]^+$. |
| 426 | 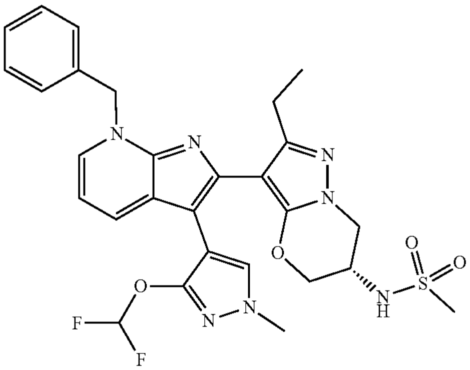 [SMILES: CCc1nn2c(c1-c1nc3n(Cc4ccccc4)cccc-3c1-c1cn(C)nc1OC(F)F)OC[C@@H](NS(C)(=O)=O)C2] | $^1$H-NMR (400 MHz, $CDCl_3$) δ 1.03 (t, J = 7.5 Hz, 3H), 2.42-2.50 (m, 2H), 3.04 (s, 3H), 3.80 (s, 3H), 4.19-4.36 (m, 5H), 5.85-5.91 (m, 2H), 6.67-7.04 (m, 2H), 7.19 (s, 1H), 7.36-7.44 (m, 5H), 7.54 (d, J = 6.4 Hz, 1H), 8.05 (d, J = 7.3 Hz, 1H); MS (ESI$^+$): 598 $[M + H]^+$. |

-continued

| Compound No. | Chemical structural formula | Spectrum data |
|---|---|---|
| 427 | 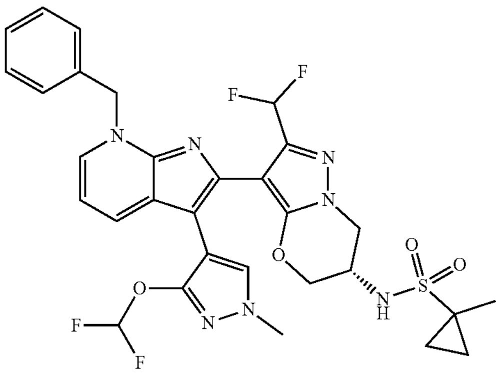 [SMILES: Cn1cc(-c2c3cccn(Cc4ccccc4)c-3nc2-c2c(C(F)F)nn3c2OC[C@@H](NS(=O)(=O)C2(C)CC2)C3)c(OC(F)F)n1] | $^1$H-NMR (400 MHz, $CDCl_3$) δ 0.82-0.88 (m, 2H), 1.41-1.45 (m, 2H), 1.50 (s, 3H), 3.82 (s, 3H), 4.16-4.43 (m, 5H), 5.87 (s, 2H), 6.61-7.00 (m, 2H), 7.23-7.61 (m, 8H), 8.03 (d, J = 6.6 Hz, 1H); MS (ESI$^+$): 660 [M + H]$^+$. |

(198) Reference Procedure of (S)—N-(3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl)-2-hydroxyethane-1-sulfonamide (428)

(428)

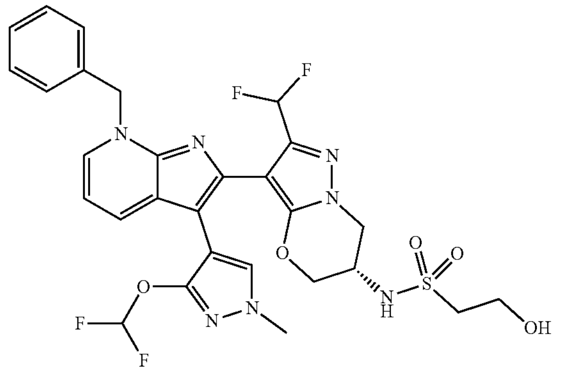

(428)

The compound 428 was synthesized from compound 423 using conditions analogous to compound 365; $^1$H-NMR (400 MHz, $CDCl_3$) δ 3.03-3.25 (m, 2H), 3.81 (s, 3H), 3.94-4.05 (m, 2H), 4.17-4.55 (m, 5H), 5.84-5.87 (m, 2H), 6.53-7.00 (m, 3H), 7.23 (s, 1H), 7.36-7.52 (m, 5H), 7.62 (d, J=6.3 Hz, 1H), 8.11 (d, J=7.5 Hz, 1H); MS (ESI$^+$): 650 [M+H]$^+$.

(199) Reference Procedure of (S)—N-(3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl)-2-hydroxyethane-1-sulfonamide (429)

(429)

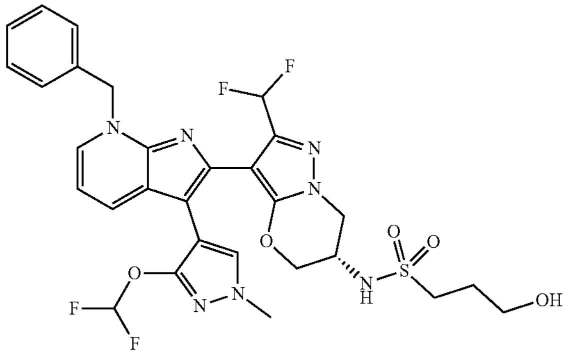

The compound 429 was synthesized from compound 424 using conditions analogous to compound 365; $^1$H-NMR (400 MHz, $CDCl_3$) δ 2.04-2.21 (m, 2H), 2.83-2.90 (m, 1H), 3.02-3.07 (m, 1H), 3.25 (ddd, J=14.7, 7.2, 4.3 Hz, 1H), 3.47-3.52 (m, 1H), 3.80 (s, 3H), 4.27-4.37 (m, 3H), 4.47-4.65 (m, 2H), 5.69 (d, J=14.6 Hz, 1H), 5.87 (d, J=14.6 Hz, 1H), 6.32-7.03 (m, 3H), 7.23 (s, 1H), 7.35-7.43 (m, 5H), 7.59 (d, J=6.3 Hz, 1H), 8.14 (d, J=7.4 Hz, 1H); MS (ESI$^+$): 664 [M+H]$^+$.

(200) Reference Procedure of (S)—N-(2-((3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl)oxy)ethyl) acetamide (430)

(430)

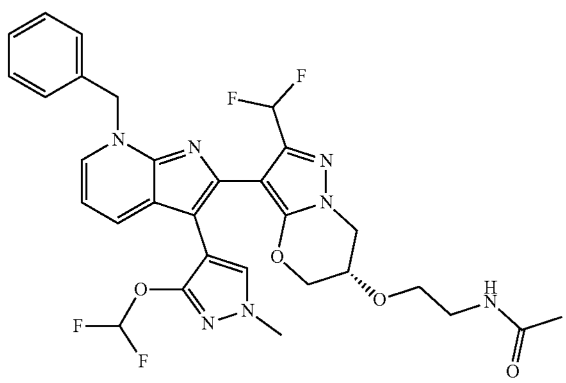

To a stirred solution of compound 421 (36.0 mg, 0.0615 mmol) in $CH_2Cl_2$ (0.5 mL) at room temperature under Ar atmosphere, N,N-diisopropylethylamine (0.016 mL, 0.0923 mmol) and acetyl chloride (0.0053 mL, 0.0743 mmol) were added, and the resulting mixture was stirred at room temperature for 1 h. The reaction mixture was directly purified by silica gel column chromatography (0-10% MeOH/EtOAc) to yield compound 430 (31.0 mg, 81%) as a yellow amorphous; $^1$H-NMR (400 MHz, DMSO-$d_6$) δ 1.78 (s, 3H), 3.14-3.21 (m, 2H), 3.50-3.54 (m, 2H), 3.76 (s, 3H), 3.98-4.31 (m, 5H), 5.83 (s, 2H), 6.91-7.56 (m, 9H), 7.88-7.95 (m, 2H), 8.26 (d, J=6.3 Hz, 1H); MS (ESI$^+$): 628 [M+H]$^+$.

(201) Reference Procedure of (S)-2-((3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl)oxy)-N,N-dimethylethan-1-amine (431)

(431)

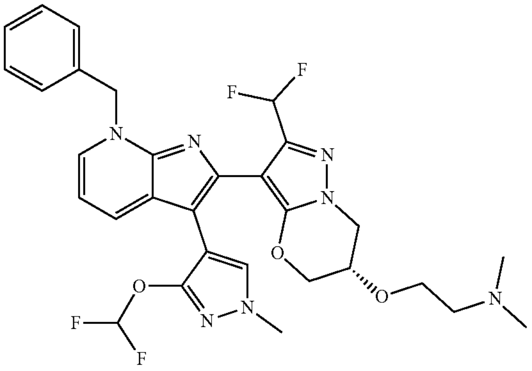

To a stirred solution of compound 421 (36.0 mg, 0.0615 mmol) in THF (1 mL) at room temperature under Ar atmosphere, 37% aq. HCHO (0.055 mL, 0.751 mmol) and sodium triacetocyborohydride (95.0 mg, 0.450 mmol) were added, and the resulting mixture was stirred at room temperature for 1.5 h. The reaction of quenched with 10% aq. $KHCO_3$ and the resulting mixture was extracted with EtOAc. The organic layer was washed with brine, dried over $Na_2SO_4$, and concentrated. The residue was purified by silica gel column chromatography (0-10% MeOH/EtOAc) to yield compound 431 (62.0 mg, 67%) as a yellow amorphous; $^1$H-NMR (400 MHz, DMSO-$d_6$) δ 2.11 (s, 6H), 2.38 (t, J=6.0 Hz, 2H), 3.54-3.63 (m, 2H), 3.76 (s, 3H), 3.99-4.31 (m, 5H), 5.83 (s, 2H), 6.91-7.58 (m, 9H), 7.93 (dd, J=7.5, 0.9 Hz, 1H), 8.26 (dd, J=6.3, 1.1 Hz, 1H); MS (ESI$^+$): 614 [M+H]$^+$.

(202) Reference Procedure of tetrahydrofuran-3-yl ((S)-3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl) carbamate (432)

(432)

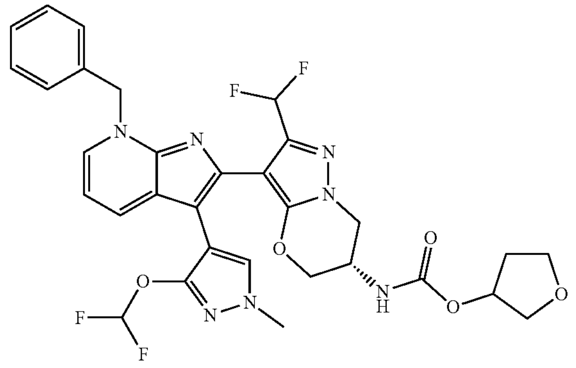

To a stirred solution of tetrahydrofuran-3-ol (0.192 mL, 2.40 mmol) and pyridine (0.32 mL, 3.97 mmol) in $CH_2Cl_2$ (8 mL) at room temperature under Ar atmosphere, 4-nitrophenyl chloroformate (400 mg, 1.99 mmol) was added, and the resulting mixture was stirred at room temperature for 1 h. Water was added and the resulting mixture was extracted with $CH_2Cl_2$. The organic layer was washed with brine, dried over $Na_2SO_4$, and concentrated. The residue was purified by silica gel column chromatography (10-50% EtOAc/hexane) to yield (4-nitrophenyl)tetrahydrofuran-3-yl carbonate (252 mg, 50%) as a colorless oil.

To a stirred solution of (4-nitrophenyl)tetrahydrofuran-3-yl carbonate (77.0 mg, 0.304 mmol) in $CH_2Cl_2$ (1 mL) at room temperature under Ar atmosphere, compound 406 (110 mg, 0.203 mmol) and triethylamine (0.085 mL, 0.611 mmol) were added, and the resulting mixture was stirred at room temperature for 4 h. The reaction mixture was directly purified by silica gel column chromatography (20-100% EtOAc/hexane) to yield compound 432 (62.0 mg, 46%) as a yellow amorphous; $^1$H-NMR (400 MHz, $CDCl_3$) δ 1.98-2.18 (m, 2H), 3.82-3.91 (m, 6H), 4.10-4.20 (m, 3H), 4.34-4.38 (m, 3H), 5.25-5.33 (m, 2H), 5.85 (s, 2H), 6.61-7.23 (m, 4H), 7.35-7.59 (m, 6H), 8.00 (d, J=7.4 Hz, 1H); MS (ESI$^+$): 656 [M+H]$^+$.

The following compounds were synthesized from the corresponding starting materials and reagents using conditions analogous to compound 432.

| Compound No. | Chemical structural formula | Spectrum data |
|---|---|---|
| 433 | 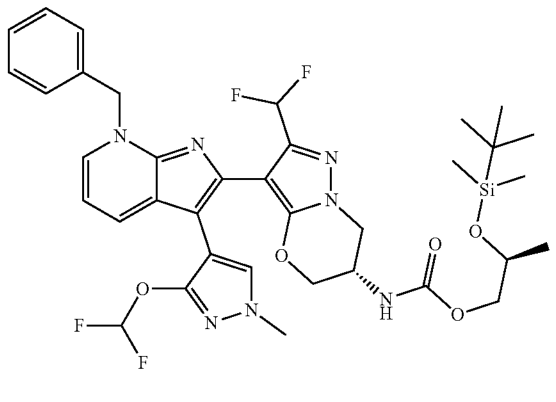 [SMILES: C[C@@H](COC(=O)N[C@@H]1COc2c(-c3nc4n(Cc5ccccc5)cccc-4c3-c3cn(C)nc3OC(F)F)c(C(F)F)nn2C1)O[Si](C)(C)C(C)(C)C] | $^1$H-NMR (400 MHz, $CDCl_3$) δ 0.03-0.08 (m, 6H), 0.87 (s, 9H), 1.14 (d, J = 6.1 Hz, 3H), 3.81 (s, 3H), 3.85-4.20 (m, 5H), 4.29-4.42 (m, 3H), 5.28-5.33 (m, 1H), 5.81-5.90 (m, 2H), 6.62-7.06 (m, 2H), 7.19 (s, 1H), 7.25-7.40 (m, 4H), 7.45-7.47 (m, 2H), 7.58 (d, J = 6.1 Hz, 1H), 8.00 (d, J = 7.3 Hz, 1H); MS (ESI$^+$): 758 $[M + H]^+$. |
| 434 | 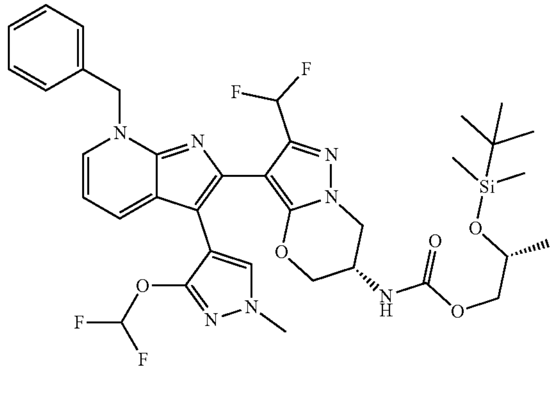 [SMILES: C[C@H](COC(=O)N[C@@H]1COc2c(-c3nc4n(Cc5ccccc5)cccc-4c3-c3cn(C)nc3OC(F)F)c(C(F)F)nn2C1)O[Si](C)(C)C(C)(C)C] | $^1$H-NMR (400 MHz, $CDCl_3$) δ 0.02-0.08 (m, 6H), 0.86 (s, 9H), 1.14 (d, J = 5.8 Hz, 3H), 3.82 (s, 3H), 3.87-4.41 (m, 8H), 5.28 (d, J = 7.7 Hz, 1H), 5.84-5.87 (m, 2H), 6.62-7.26 (m, 4H), 7.35-7.48 (m, 5H), 7.59 (d, J = 5.7 Hz, 1H), 8.00 (d, J = 7.2 Hz, 1H); MS (ESI$^+$): 758 $[M + H]^+$. |
| 435 | 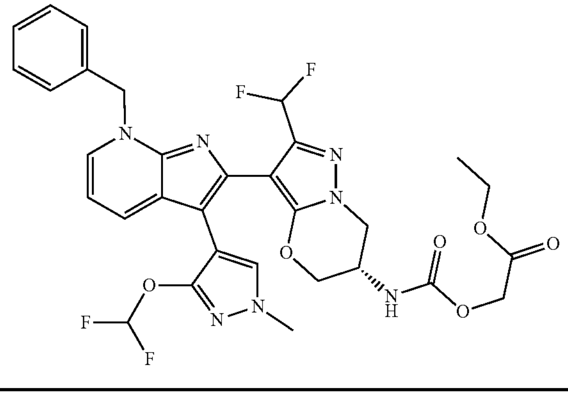 | $^1$H-NMR (400 MHz, $CDCl_3$) δ 1.20-1.38 (m, 3H), 3.76-3.85 (m, 3H), 4.10-4.82 (m, 8H), 5.79-5.93 (m, 2H), 6.66-7.23 (m, 5H), 7.26-7.61 (m, 7H), 8.02-8.07 (m, 1H); MS (ESI$^+$): 672 $[M + H]^+$. |

(203) Reference Procedure of (S)-3-[7-benzyl-3-[3-(difluoromethoxy)-1-methyl-pyrazol-4-yl]pyrrolo[2,3-b]pyridin-2-yl]-2-(difluoromethyl)-6-(dimethylsulfamoylamino)-6,7-dihydro-5H-pyrazolo[5,1-b][1,3]oxazine (436)

(436)

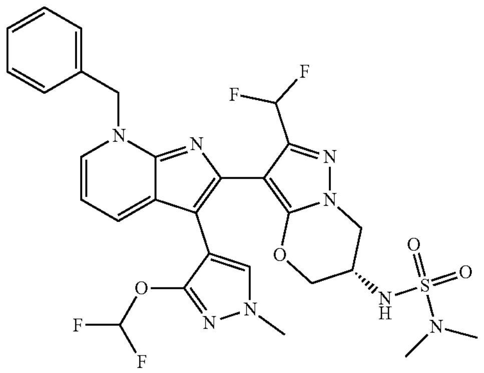

To a stirred solution of compound 406 (40.0 mg, 0.0739 mmol) and N,N-diisopropylethylamine (0.025 mL, 0.148 mmol) in 1,2-dichloroethane (0.7 mL) at room temperature under Ar atmosphere, dimethylsulfamoyl chloride (0.0096 mL, 0.0896 mmol) was added, and the resulting mixture was stirred at room temperature for 1 h, followed by stirring at 50° C. for 17 h. The reaction mixture was concentrated and the residue was purified by silica gel column chromatography (20-100% EtOAc/hexane) to yield compound 436 (36.0 mg, 76%) as a yellow solid; $^1$H-NMR (400 MHz, $CDCl_3$) δ 2.79 (s, 6H), 3.82 (s, 3H), 4.09-4.16 (m, 3H), 4.24-4.44 (m, 3H), 5.85 (s, 2H), 6.61-7.12 (m, 3H), 7.21 (s, 1H), 7.33-7.48 (m, 5H), 7.59 (d, J=5.8 Hz, 1H), 8.02 (d, J=7.4 Hz, 1H); MS (ESI$^+$): 649 [M+H]$^+$.

(204) Reference Procedure of (S)—N-(3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl)-3-hydroxyazetidine-1-carboxamide (437)

(437)

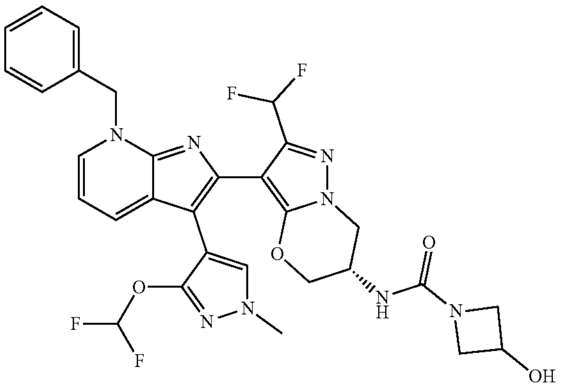

To a stirred solution of compound 406 (55.0 mg, 0.102 mmol) and N,N-diisopropylethylamine (0.035 mL, 0.203 mmol) in $CH_2Cl_2$ (1 mL) at 0° C. under Ar atmosphere, 1,1'-carbonyldiimidazole (33.0 mg, 0.203 mmol) was added, and the resulting mixture was stirred at the same temperature for 0.5 h. A solution of N,N-diisopropylethylamine (0.035 mL, 0.203 mmol) and 3-hydroxyazetidine hydrochloride (17.0 mg, 0.152 mmol) in $CH_2Cl_2$ (0.5 mL) was added, and the reaction mixture was stirred at room temperature for 1.5 h. The reaction mixture was concentrated, and the residue was purified by silica gel column chromatography (0-8% MeOH/EtOAc) to yield compound 437 (65.0 mg, quant.) as a white solid; $^1$H-NMR (400 MHz, $CDCl_3$) δ 3.77-3.87 (m, 4H), 4.00-4.33 (m, 5H), 4.43-4.67 (m, 2H), 5.05 (d, J=7.5 Hz, 1H), 5.76-5.88 (m, 2H), 6.42-7.00 (m, 2H), 7.05-7.14 (m, 1H), 7.29-7.44 (m, 5H), 7.58-7.62 (m, 1H), 7.63-7.70 (m, 1H), 7.99-8.03 (m, 1H); MS (ESI$^+$): 641 [M+H]$^+$.

(205) Reference Procedure of (S)-3-(7-benzyl-3-(3-(difluoromethoxy)-1-methyl-1H-pyrazol-4-yl)-7H-pyrrolo[2,3-b]pyridin-2-yl)-N-(2-((tert-butyldimethylsilyl)oxy)ethyl)-2-(difluoromethyl)-6,7-dihydro-5H-pyrazolo[5,1-b][1,3]oxazin-6-amine (438)

(438)

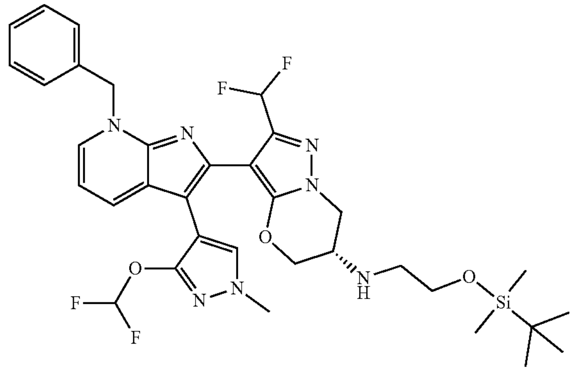

To a stirred solution of compound 406 (60.0 mg, 0.108 mmol) in 1,2-dichloroethane (1 mL) at room temperature under Ar atmosphere, (tert-butyldimethylsilyloxy) acetaldehyde (0.025 mL, 0.0542 mmol), acetic acid (0.0031 mL, 0.0542 mmol), and sodium triacetocyborohydride (69.0 mg, 0.323 mmol) were added, and the resulting mixture was stirred at room temperature for 1 h. The reaction of quenched with sat. aq. $NaHCO_3$ and the resulting mixture was extracted with EtOAc. The organic layer was washed with brine, dried over $Na_2SO_4$, and concentrated. The residue was purified by silica gel column chromatography (10-100% EtOAc/hexane) to yield compound 438 (63.0 mg, 83%) as a yellow oil; $^1$H-NMR (400 MHz, $CDCl_3$) δ −0.06-0.10 (m, 6H), 0.82 (s, 9H), 2.73-2.75 (m, 2H), 3.32-4.31 (m, 11H), 5.78-5.82 (m, 2H), 6.55-7.51 (m, 9H), 7.94 (d, J=7.4 Hz, 1H); MS (ESI$^+$): 700 [M+H]$^+$.

(206) Reference Procedure of (S)—N-(3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl) acetamide (439)

(439)

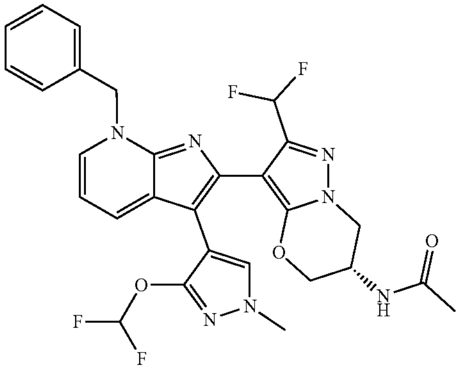

To a stirred solution of compound 406 (10.0 mg, 0.0185 mmol) in THF (0.5 mL) at room temperature under Ar atmosphere, triethylamine (0.020 mL, 0.144 mmol) and acetic anhydride (0.0060 mL, 0.0635 mmol) were added, and the resulting mixture was stirred at room temperature for 0.5 h. The reaction mixture was concentrated, and the residue was purified by silica gel column chromatography (0-15% MeOH/EtOAc) to yield compound 439 (10.0 mg, 93%) as a yellow solid; $^1$H-NMR (400 MHz, $CDCl_3$) δ 2.02 (3H, s), 3.82 (3H, s), 4.10-4.36 (4H, m), 4.69 (1H, d, J=8.1 Hz), 5.85 (2H, s), 6.41-6.98 (3H, m), 7.27 (1H, d, J=5.6 Hz), 7.35-7.40 (3H, m), 7.44-7.48 (2H, m), 7.58 (1H, d, J=6.4 Hz), 7.99 (1H, d, J=6.4 Hz); MS (ESI$^+$): 584 [M+H]$^+$.

(207) Reference Procedure of (S)—N-(3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl) cyclopropanecarboxamide (440)

(440)

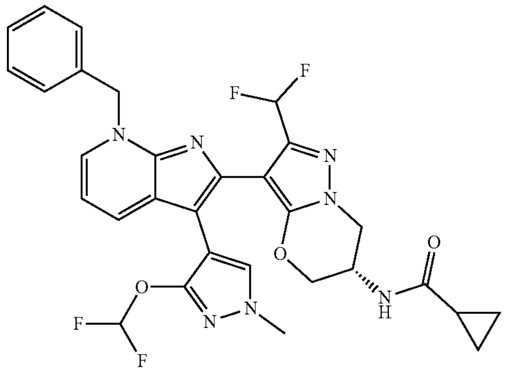

The compound 440 was synthesized from compound 406 and the corresponding acid chlorides using conditions analogous to compound 430; $^1$H-NMR (400 MHz, $CDCl_3$) δ 0.76-0.81 (m, 2H), 0.90-1.00 (m, 2H), 1.39-1.44 (m, 1H), 3.83 (s, 3H), 4.10-4.37 (m, 5H), 4.70-4.75 (m, 1H), 5.82-5.91 (m, 2H), 6.48-6.53 (m, 1H), 6.70-7.02 (m, 2H), 7.29-7.61 (m, 7H), 7.98-8.02 (m, 1H); MS (ESI$^+$): 610 [M+H]$^+$.

The following compounds were also synthesized from the corresponding starting materials and reagents using conditions analogous to compound 430.

| Compound No. | Chemical structural formula | Spectrum data |
|---|---|---|
| 441 | 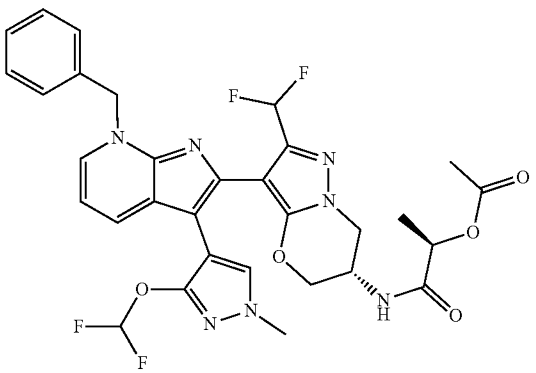 [SMILES: CC(=O)O[C@H](C)C(=O)N[C@@H]1COc2c(-c3nc4n(Cc5ccccc5)cccc-4c3-c3cn(C)nc3OC(F)F)c(C(F)F)nn2C1] | $^1$H-NMR (400 MHz, $CDCl_3$) δ 1.45 (d, J = 6.9 Hz, 3H), 2.09 (s, 3H), 3.83 (s, 3H), 4.10-4.41 (m, 4H), 4.72 (s, 1H), 5.13 (q, J = 6.7 Hz, 1H), 5.81-5.92 (m, 2H), 6.52-6.96 (m, 4H), 7.26-7.61 (m, 7H), 8.02 (d, J = 7.0 Hz, 1H); MS (ESI$^+$): 656 [M + H]$^+$. |

-continued

| Compound No. | Chemical structural formula | Spectrum data |
|---|---|---|
| 442 | 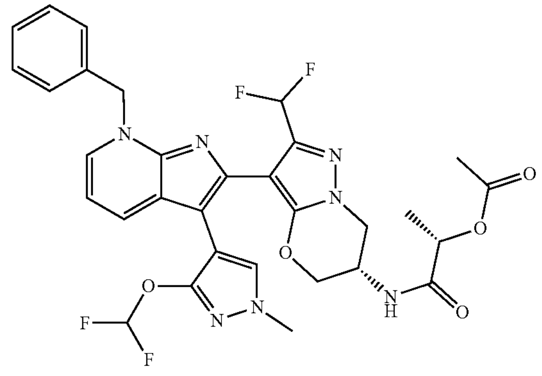 [SMILES: CC(=O)O[C@@H](C)C(=O)N[C@@H]1COc2c(-c3nc4n(Cc5ccccc5)cccc-4c3-c3cn(C)nc3OC(F)F)c(C(F)F)nn2C1] | $^1$H-NMR (400 MHz, $CDCl_3$) δ 1.45 (d, J = 6.9 Hz, 3H), 2.11 (s, 3H), 3.82 (s, 3H), 4.09-4.42 (m, 4H), 4.65-4.71 (m, 1H), 5.16 (q, J = 6.8 Hz, 1H), 5.78-5.94 (m, 2H), 6.54-7.13 (m, 4H), 7.25-7.49 (m, 6H), 7.60 (d, J = 5.9 Hz, 1H), 8.01 (d, J = 7.2 Hz, 1H); MS ($ESI^+$): 656 $[M + H]^+$. |

(208) Reference Procedure of (S)—N-(3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl)-1-methyl-1H-pyrazole-4-carboxamide (443)

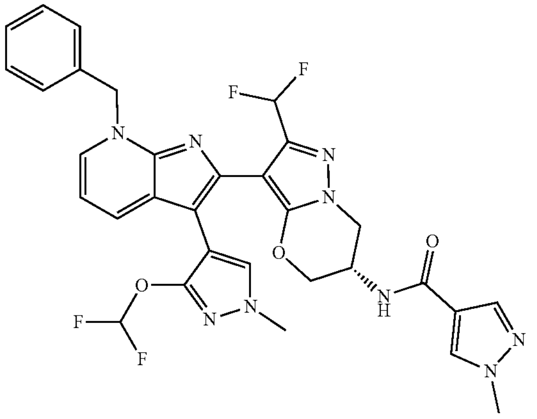 [SMILES: Cn1cc(C(=O)N[C@@H]2COc3c(-c4nc5n(Cc6ccccc6)cccc-5c4-c4cn(C)nc4OC(F)F)c(C(F)F)nn3C2)cn1]

The compound 443 was synthesized from compound 406 and the corresponding carboxylic acids using conditions analogous to compound 381; $^1$H-NMR (400 MHz, $CDCl_3$) δ 3.81 (s, 3H), 3.92 (s, 3H), 4.16-4.29 (m, 2H), 4.36-4.46 (m, 2H), 4.84-4.92 (m, 1H), 5.86 (s, 2H), 6.41-6.82 (m, 2H), 6.84-6.91 (m, 1H), 7.06 (t, J=54.4 Hz, 1H), 7.29-7.42 (m, 4H), 7.44-7.50 (m, 2H), 7.58-7.62 (m, 1H), 7.88-7.91 (m, 1H), 7.96-8.03 (m, 2H); MS ($ESI^+$): 650 $[M+H]^+$.

(209) Reference Procedure of (1R,2R)—N—((S)-3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl)-2-fluorocyclopropane-1-carboxamide (444)

(444)

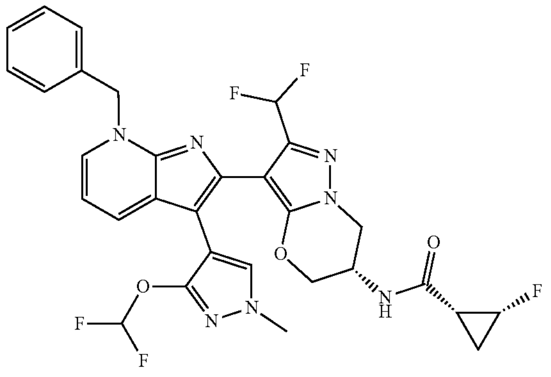

To a stirred solution of compound 406 (60.0 mg, 0.111 mmol) and cis-(1R,2R)-2-fluorocyclopropanecarboxylic acid (18.0 mg, 0.173 mmol) in DMF (1 mL) at room temperature under Ar atmosphere, N,N-diisopropylethylamine (0.038 mL, 0.223 mmol) and HATU (64.0 mg, 0.168 mmol) were added, and the resulting mixture was stirred at room temperature for 2 h. The reaction mixture was concentrated, and the residue was purified by silica gel column chromatography (0-5% MeOH/EtOAc) to yield compound 444 (77.0 mg, quant.) as a yellow oil; $^1$H-NMR (400 MHz, $CDCl_3$) δ 7.99 (dd, J=7.4, 0.8 Hz, 1H), 7.59 (dd, J=6.3, 1.0 Hz, 1H), 7.49-7.44 (m, 2H), 7.41-7.33 (m, 3H), 7.30 (s, 1H), 7.18-6.47 (m, 4H), 5.90-5.80 (m, 2H), 4.82-4.61 (m, 2H), 4.39-4.29 (m, 2H), 4.23-4.09 (m, 2H), 3.84 (s, 3H), 1.89-1.77 (m, 1H), 1.74-1.64 (m, 1H), 1.16-1.07 (m, 1H); MS ($ESI^+$): 628 $[M+H]^+$.

The following compounds were synthesized from the corresponding starting materials and reagents using conditions analogous to compound 444.

| Compound No. | Chemical structural formula | Spectrum data |
|---|---|---|
| 445 | 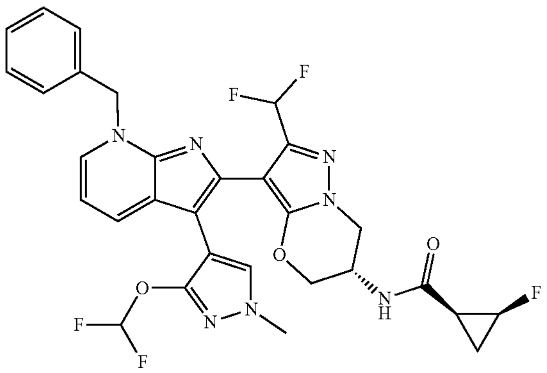 [SMILES: Cn1cc(-c2c3cccn(Cc4ccccc4)c-3nc2-c2c(C(F)F)nn3c2OC[C@@H](NC(=O)[C@@H]2C[C@@H]2F)C3)c(OC(F)F)n1] | $^1$H-NMR (400 MHz, $CDCl_3$) δ 1.06-1.15 (m, 1H), 1.69-1.87 (m, 2H), 3.83 (s, 3H), 4.09-4.40 (m, 4H), 4.58-4.80 (m, 2H), 5.80-5.90 (m, 2H), 6.48-7.17 (m, 4H), 7.30 (s, 1H), 7.33-7.42 (m, 3H), 7.43-7.48 (m, 2H), 7.58 (dd, J = 6.3, 0.9 Hz, 1H), 7.99 (dd, J = 7.4, 0.8 Hz, 1H); MS (ESI$^+$): 628 [M + H]$^+$. |
| 446 | 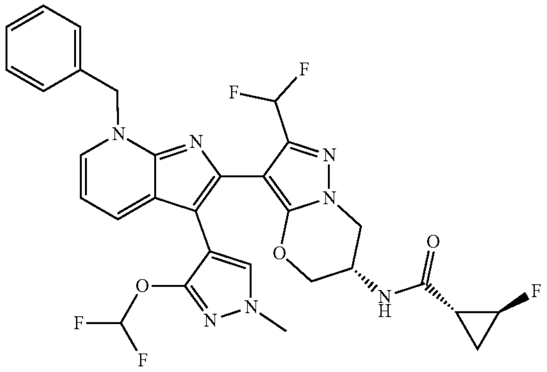 [SMILES: Cn1cc(-c2c3cccn(Cc4ccccc4)c-3nc2-c2c(C(F)F)nn3c2OC[C@@H](NC(=O)[C@H]2C[C@@H]2F)C3)c(OC(F)F)n1] | $^1$H-NMR (400 MHz, $CDCl_3$) δ 1.24-1.46 (2H, m), 1.92-2.02 (1H, m), 3.83 (3H, s), 4.11-4.35 (4H, m), 4.65-4.68 (1H, m), 4.71-4.89 (1H, m), 5.83 (1H, d, J = 14.5 Hz), 5.87 (1H, d, J = 14.4 Hz), 6.53-7.12 (4H, m), 7.30 (1H, s), 7.35-7.41 (3H, m), 7.44-7.46 (2H, m), 7.59 (1H, d, J = 6.1 Hz), 8.00 (1H, d, J = 6.6 Hz); MS (ESI$^+$): 628 [M + H]$^+$. |
| 447 | 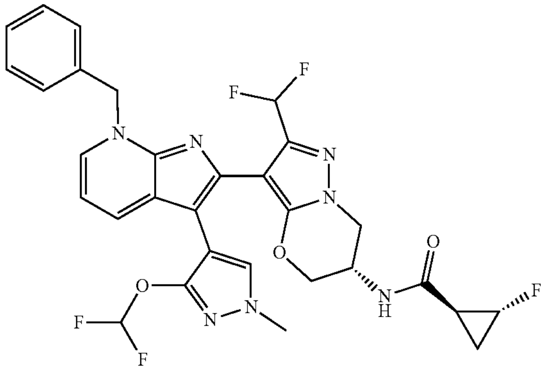 [SMILES: Cn1cc(-c2c3cccn(Cc4ccccc4)c-3nc2-c2c(C(F)F)nn3c2OC[C@@H](NC(=O)[C@@H]2C[C@H]2F)C3)c(OC(F)F)n1] | $^1$H-NMR (400 MHz, $CDCl_3$) δ 1.30-1.45 (2H, m), 1.88-1.96 (1H, m), 3.83 (3H, s), 4.11-4.20 (2H, m), 4.27-4.37 (2H, m), 4.64-4.67 (1H, m), 4.68-4.87 (1H, m), 5.79 (1H, d, J = 14.4 Hz), 5.87 (1H, d, J = 14.4 Hz), 6.55-7.11 (4H, m), 7.28 (1H, s), 7.35-7.40 (3H, m), 7.43-7.46 (2H, m), 7.57 (1H, dd, J = 6.3, 0.8 Hz), 8.00 (1H, dd, J = 7.4, 0.7 Hz); MS (ESI$^+$): 628 [M + H]$^+$. |
| 448 | 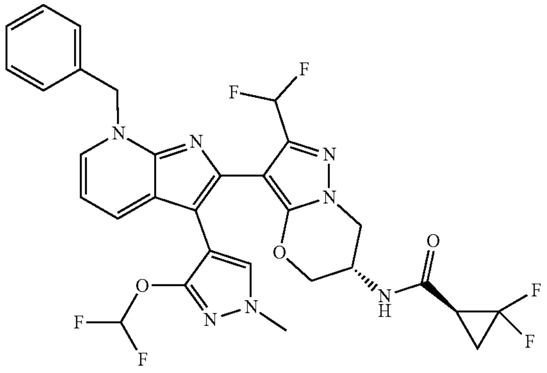 [SMILES: Cn1cc(-c2c3cccn(Cc4ccccc4)c-3nc2-c2c(C(F)F)nn3c2OC[C@@H](NC(=O)[C@@H]2CC2(F)F)C3)c(OC(F)F)n1] | $^1$H-NMR (400 MHz, $CDCl_3$) δ 1.63-1.73 (1H, m), 2.07-2.15 (1H, m), 2.34-2.42 (1H, m), 3.82 (3H, s), 4.12 (1H, dd, J = 11.3, 1.5 Hz), 4.19 (1H, dt, J = 11.4, 2.2 Hz), 4.27 (1H, d, J = 13.2 Hz), 4.37 (1H, dd, J = 13.2, 4.3 Hz), 4.72-4.75 (1H, m), 5.81 (1H, d, J = 14.4 Hz), 5.86 (1H, d, J = 14.3 Hz), 6.49-7.15 (4H, m), 7.28 (1H, s), 7.34-7.39 (3H, m), 7.42-7.45 (2H, m), 7.57 (1H, dd, J = 6.2, 0.9 Hz), 7.99 (1H, dd, J = 7.4, 0.8 Hz); MS (ESI$^+$): 646 [M + H]$^+$. |

-continued
| Compound No. | Chemical structural formula | Spectrum data |
|---|---|---|
| 449 | 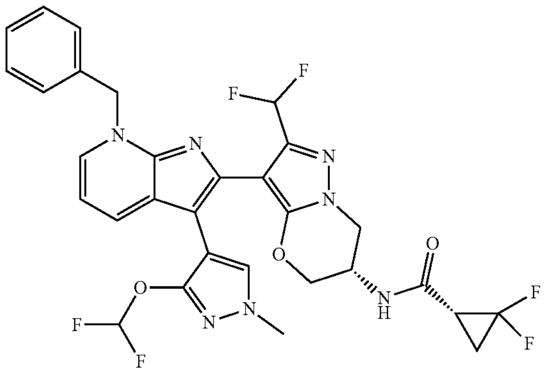 [SMILES: Cn1cc(-c2c3cccn(Cc4ccccc4)c-3nc2-c2c(C(F)F)nn3c2OC[C@@H](NC(=O)[C@H]2CC2(F)F)C3)c(OC(F)F)n1] | $^1$H-NMR (400 MHz, $CDCl_3$) δ 1.65-1.75 (m, 1H), 2.07-2.17 (m, 1H), 2.33-2.42 (m, 1H), 3.84 (s, 3H), 4.12-4.23 (m, 2H), 4.25-4.37 (m, 2H), 4.70-4.75 (m, 1H), 5.84 (s, 2H), 6.49-7.11 (m, 4H), 7.31 (s, 1H), 7.34-7.41 (m, 3H), 7.41-7.47 (m, 2H), 7.59 (dd, J = 6.3, 0.9 Hz, 1H), 7.98-8.03 (m, 1H); MS (ESI$^+$): 646 [M + H]$^+$. |
| 450 | 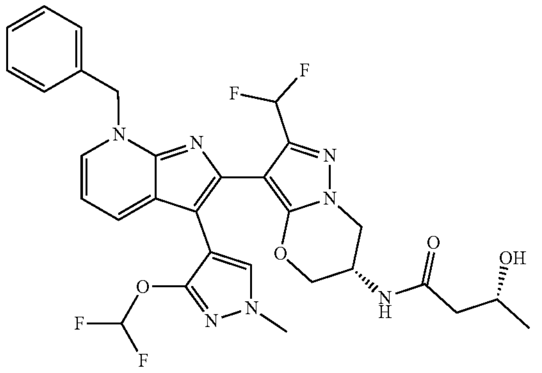 [SMILES: C[C@@H](O)CC(=O)N[C@@H]1COc2c(-c3nc4n(Cc5ccccc5)cccc-4c3-c3cn(C)nc3OC(F)F)c(C(F)F)nn2C1] | $^1$H-NMR (400 MHz, $CDCl_3$) δ 1.18-1.24 (m, 3H), 2.27-2.39 (m, 2H), 3.83 (s, 3H), 4.05-4.42 (m, 6H), 4.66 (s, 1H), 5.79-5.90 (m, 2H), 6.47-7.04 (m, 3H), 7.29-7.59 (m, 6H), 8.01-8.03 (m, 1H); MS (ESI$^+$): 628 [M + H]$^+$. |
| 451 | 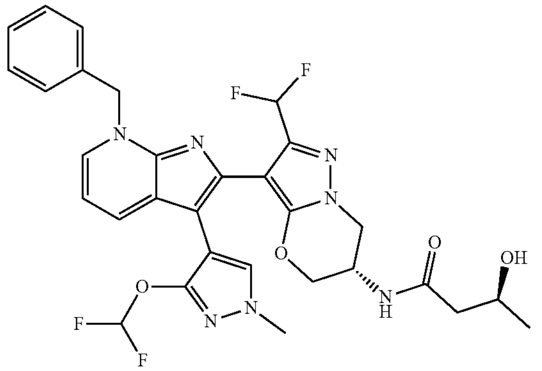 [SMILES: C[C@H](O)CC(=O)N[C@@H]1COc2c(-c3nc4n(Cc5ccccc5)cccc-4c3-c3cn(C)nc3OC(F)F)c(C(F)F)nn2C1] | $^1$H-NMR (400 MHz, $CDCl_3$) δ 8.10-8.00 (m, 1H), 7.78-7.23 (m, 6H), 7.17-6.46 (m, 3H), 5.83 (s, 2H), 4.77-4.65 (m, 1H), 4.51-4.10 (m, 6H), 3.83 (s, 3H), 2.50-2.21 (m, 2H), 1.17 (d, J = 6.3 Hz, 3H); MS (ESI$^+$): 628 [M + H]$^+$. |
| 452 | 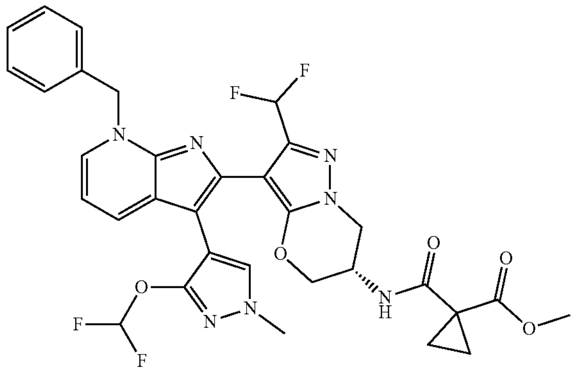 [SMILES: COC(=O)C1(C(=O)N[C@@H]2COc3c(-c4nc5n(Cc6ccccc6)cccc-5c4-c4cn(C)nc4OC(F)F)c(C(F)F)nn3C2)CC1] | $^1$H-NMR (400 MHz, $CDCl_3$) δ 1.56-1.79 (m, 4H), 3.63 (s, 3H), 3.80 (s, 3H), 4.16-4.23 (m, 2H), 4.27-4.41 (m, 2H), 4.61-4.67 (m, 1H), 5.80-5.92 (m, 2H), 6.62-7.11 (m, 3H), 7.19-7.25 (m, 1H), 7.33-7.60 (m, 6H), 7.99-8.03 (m, 1H), 9.25 (d, J = 7.3 Hz, 1H); MS (ESI$^+$): 668 [M + H]$^+$. |

-continued

| Compound No. | Chemical structural formula | Spectrum data |
|---|---|---|
| 453 | 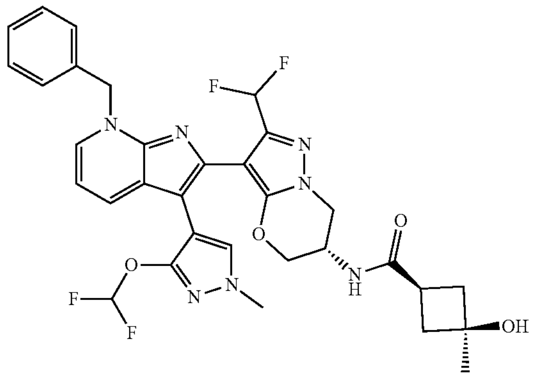 [SMILES: Cn1cc(-c2c3cccn(Cc4ccccc4)c-3nc2-c2c(C(F)F)nn3c2OC[C@@H](NC(=O)[C@H]2C[C@@](C)(O)C2)C3)c(OC(F)F)n1] | $^1$H-NMR (400 MHz, $CDCl_3$) δ 1.34 (3H, s), 2.19-2.27 (2H, m), 2.30-2.41 (2H, m), 2.60-2.71 (1H, m), 3.78-3.97 (4H, m), 4.08-4.25 (2H, m), 4.27-4.40 (2H, m), 4.65-4.73 (1H, m), 5.30 (OH, s), 5.82 (1H, d, J = 14.4 Hz), 5.86 (1H, d, J = 14.3 Hz), 6.40-7.13 (4H, m), 7.32 (1H, s), 7.35-7.42 (3H, m), 7.43-7.49 (2H, m), 7.58 (1H, dd, J = 6.3, 1.0 Hz), 8.00 (1H, dd, J = 7.5, 1.1 Hz); MS (ESI$^+$): 654 [M + H]$^+$. |
| 454 | 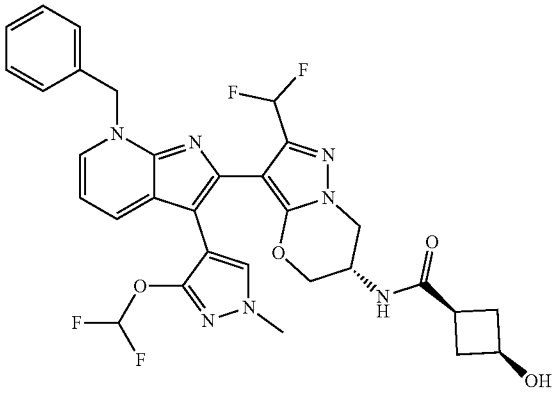 [SMILES: Cn1cc(-c2c3cccn(Cc4ccccc4)c-3nc2-c2c(C(F)F)nn3c2OC[C@@H](NC(=O)[C@H]2C[C@@H](O)C2)C3)c(OC(F)F)n1] | $^1$H-NMR (400 MHz, $CDCl_3$) δ 2.06-2.19 (2H, m), 2.50-2.66 (3H, m), 3.38 (1H, s), 3.84 (3H, s), 4.09-4.26 (3H, m), 4.27-4.41 (2H, m), 4.66-4.74 (1H, m), 5.81 (1H, d, J = 14.4 Hz), 5.86 (1H, d, J = 14.4 Hz), 6.40-7.12 (4H, m), 7.32 (1H, s), 7.35-7.42 (3H, m), 7.42-7.48 (2H, m), 7.59 (1H, dd, J = 6.3, 1.1 Hz), 8.01 (1H, dd, J = 7.5, 0.9 Hz); MS (ESI$^+$): 640[M + H]$^+$. |
| 455 | 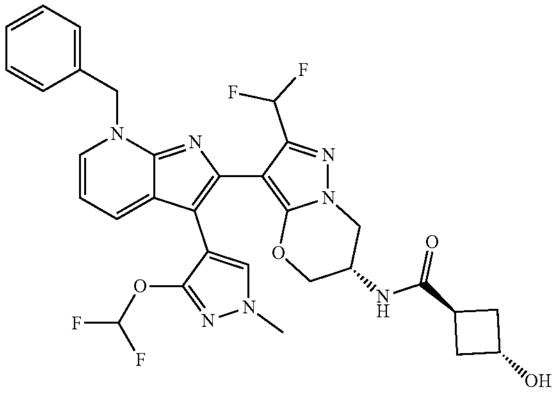 [SMILES: Cn1cc(-c2c3cccn(Cc4ccccc4)c-3nc2-c2c(C(F)F)nn3c2OC[C@@H](NC(=O)[C@H]2C[C@H](O)C2)C3)c(OC(F)F)n1] | $^1$H-NMR (400 MHz, $CDCl_3$) δ 2.08-2.25 (3H, m), 2.45-2.61 (2H, m), 2.85-2.98 (1H, m), 3.82 (3H, s), 4.08-4.40 (4H, m), 4.51-4.62 (1H, m), 4.66-4.75 (1H, m), 5.81 (1H, d, J = 14.3 Hz), 5.88 (1H, d, J = 14.3 Hz), 6.40-7.11 (4H, m), 7.23-7.31 (1H, m), 7.33-7.48 (5H, m), 7.58 (1H, dd, J = 6.3, 0.9 Hz), 8.00 (1H, dd, J = 7.4, 0.9 Hz); MS (ESI$^+$): 640[M + H]$^+$. |

(209) Reference Procedure of (S)-2-((3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl)amino)ethan-1-ol (457)

(457)

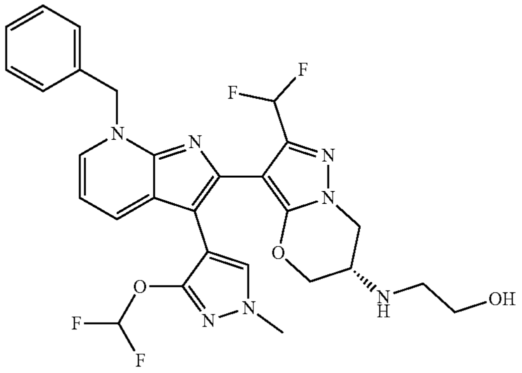

A mixture of compound 438 (62.0 mg, 0.0886 mmol) and TFA (0.45 mL) in $CH_2Cl_2$ (0.45 ml) was stirred at room temperature for 2 h. The reaction mixture was concentrated, and the residue was purified by silica gel column chromatography (10-100% EtOAc/hexane) to yield compound 457 (42.0 mg, 81%) as a yellow amorphous; $^1$H-NMR (400 MHz, $CDCl_3$) δ 2.83-2.90 (m, 2H), 3.32-3.35 (m, 1H), 3.65-3.88 (m, 5H), 4.06-4.37 (m, 4H), 5.85 (s, 2H), 6.57-7.09 (m, 3H), 7.18-7.64 (m, 7H), 7.99 (d, J=7.4 Hz, 1H); MS ($ESI^+$): 586 $[M+H]^+$.

The following compounds were synthesized from the corresponding starting materials and reagents using conditions analogous to compound 457.

| Compound No. | Chemical structural formula | Spectrum data |
|---|---|---|
| 458 | 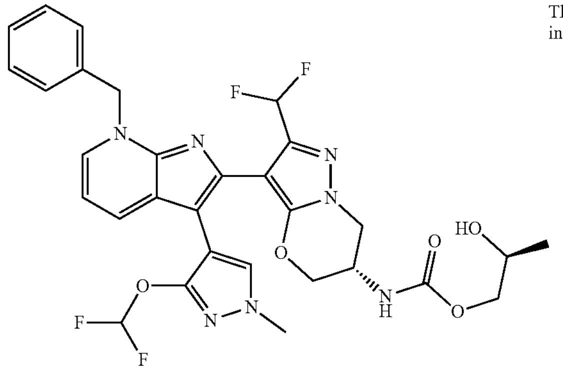 | The crude product was used directly in the next step without purification. |

-continued

| Compound No. | Chemical structural formula | Spectrum data |
|---|---|---|
| 459 | 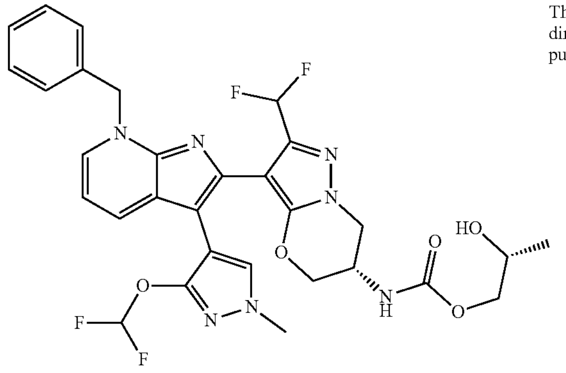 | The crude product was used directly in the next step without purification. |

(210) Reference Procedure of (R)—N—((S)-3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl)-2-hydroxypropanamide (460)

(460)

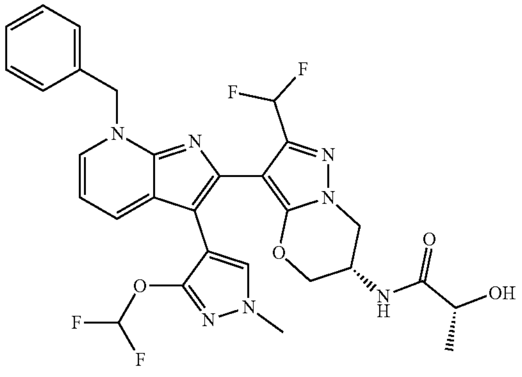

A mixture of compound 441 (65.0 mg, 0.0991 mmol) and 5 mol/L sodium methoxide in MeOH (0.060 mL, 0.30 mmol) in MeOH (1 ml) was stirred at room temperature for 1 h. The reaction mixture was concentrated, and the residue was purified by silica gel column chromatography (0-8% MeOH/EtOAc) to yield compound 460 (55.0 mg, 91%) as a yellow amorphous; $^1$H-NMR (400 MHz, DMSO-$d_6$) δ 1.42 (d, J=6.9 Hz, 3H), 3.81-3.88 (m, 3H), 3.99-4.40 (m, 6H), 4.60-4.65 (m, 1H), 5.80-5.89 (m, 2H), 6.43-7.16 (m, 3H), 7.30-7.62 (m, 8H), 8.02 (d, J=7.3 Hz, 1H); MS (ESI$^+$): 614 [M+H]$^+$.

(211) Reference Procedure of (S)—N—((S)-3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl)-2-hydroxypropanamide (461)

(461)

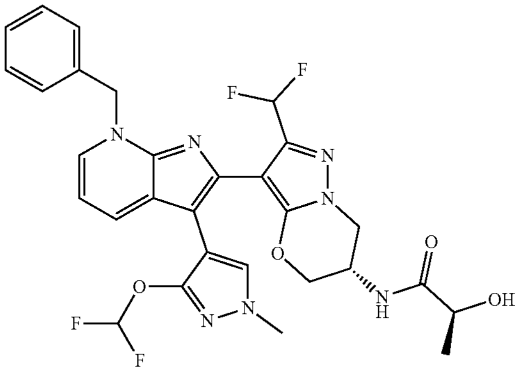

The compound 461 was synthesized from compound 442 using conditions analogous to compound 460; $^1$H-NMR (400 MHz, $CDCl_3$) δ 1.41 (d, J=6.9 Hz, 3H), 3.83 (s, 3H), 4.00-4.59 (m, 6H), 5.80-5.90 (m, 2H), 6.51 (t, J=73.9 Hz, 1H), 6.85-7.14 (m, 2H), 7.31-7.61 (m, 8H), 8.00 (d, J=6.9 Hz, 1H); MS (ESI$^+$): 614 [M+H]$^+$.

(212) Reference Procedure of 2-hydroxyethyl(S)-(3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl) carbamate (462)

(462)

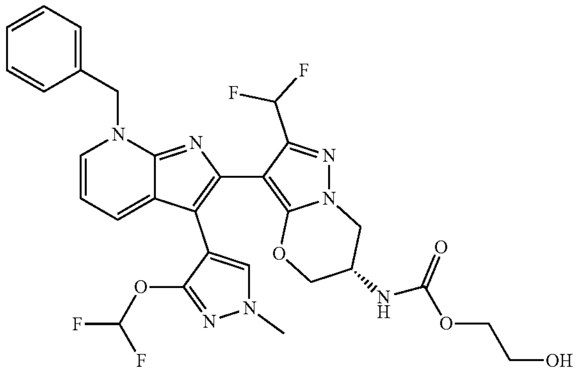

To a stirred solution of compound 411 (11.0 mg, 0.0153 mmol) in $CH_2Cl_2$ (0.3 mL) at room temperature, anisole (0.033 mL, 0.306 mmol) and aluminium chloride (33.0 mg, 0.245 mmol) were added, and the resulting mixture was stirred at room temperature for 2 h. The reaction was quenched with water and the resulting mixture was extracted with EtOAc. The organic layer was washed with brine, dried over $Na_2SO_4$, and concentrated. The residue was purified by silica gel column chromatography (0-10% MeOH/EtOAc) to yield compound 462 (5.5 mg, 57%) as a yellow oil; $^1$H-NMR (400 MHz, $CDCl_3$) δ 3.66-3.85 (m, 5H), 4.07-4.16 (m, 3H), 4.19-4.43 (m, 4H), 4.81-4.93 (m, 2H), 5.80-5.92 (m, 2H), 6.62-7.00 (m, 3H), 7.23-7.61 (m, 6H), 7.98-8.02 (m, 1H); MS (ESI$^+$): 630 [M+H]$^+$.

(213) Reference Procedure of (S)-3-(3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl) oxazolidin-2-one (463)

(463)

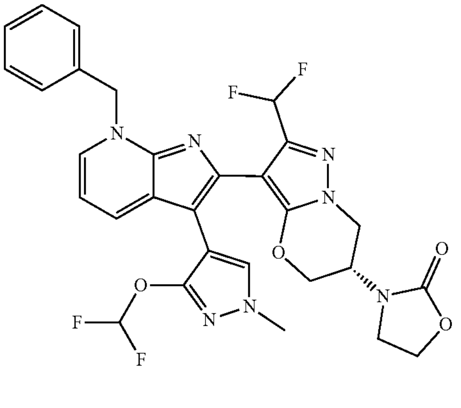

To a stirred solution of compound 462 (19.0 mg, 0.0302 mmol) and triphenylphosphine (12.0 mg, 0.0454 mmol) in THF (1 mL) at room temperature, diisopropyl azodicarboxylate (0.0071 mL, 0.0362 mmol) was added, and the resulting mixture was stirred at room temperature for 1 h. The reaction mixture was concentrated and the residue was purified by silica gel column chromatography (0-10% MeOH/EtOAc) to yield compound 463 (4.5 mg, 24%) as a yellow oil; MS (ESI$^+$): 612 [M+H]$^+$.

(214) Reference Procedure of (S)-2-(3-(7-benzyl-3-(3-(difluoromethoxy)-1-methyl-1H-pyrazol-4-yl)-7H-pyrrolo[2,3-b]pyridin-2-yl)-2-(difluoromethyl)-6,7-dihydro-5H-pyrazolo[5,1-b][1,3]oxazin-6-yl) isothiazolidine 1,1-dioxide (464)

(464)

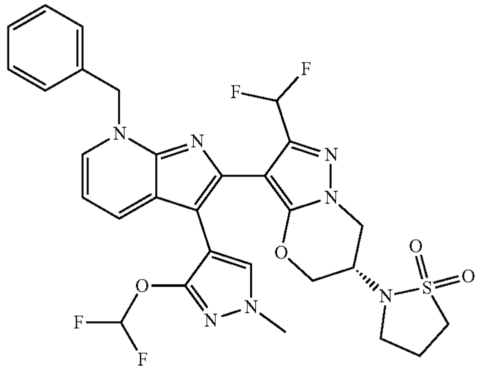

The compound 464 was synthesized from compound 429 using conditions analogous to compound 463; $^1$H-NMR (400 MHz, $CDCl_3$) δ 2.30-2.39 (m, 2H), 3.09-3.22 (m, 3H), 3.27-3.32 (m, 1H), 3.83 (s, 3H), 4.17-4.26 (m, 2H), 4.35-4.52 (m, 3H), 5.81-5.91 (m, 2H), 6.54-7.13 (m, 3H), 7.23 (s, 1H), 7.33-7.42 (m, 3H), 7.45-7.50 (m, 2H), 7.59 (d, J=6.3 Hz, 1H), 7.95 (d, J=7.4 Hz, 1H); MS (ESI$^+$): 646 [M+H]$^+$.

(215) Experimental procedure of (S)—N-(3-(3-(3-(difluoromethoxy)-1-methyl-1H-pyrazol-4-yl)-1H-pyrrolo[2,3-b]pyridin-2-yl)-2-(difluoromethyl)-6,7-dihydro-5H-pyrazolo[5,1-b][1,3]oxazin-6-yl) methanesulfonamide (EX.526)

EX. 526

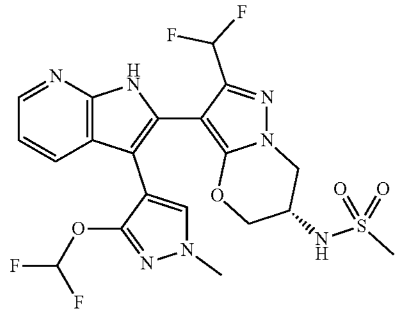

To a stirred solution of compound 406 (28.0 mg, 0.0517 mmol) in $CH_2Cl_2$ (0.5 mL) at 0° C., triethylamine (0.022 mL, 0.159 mmol) and methanesulfonyl chloride (0.0060 mL, 0.0775 mmol) were added, and the resulting mixture was stirred at room temperature for 3 h. The reaction was quenched with brine and the resulting mixture was extracted with EtOAc. The organic layer was dried over $Na_2SO_4$, and concentrated.

The residue was dissolved in EtOH (5 mL), and 10% Pd—C (5.0 mg) was added. The resulting mixture was stirred at room temperature for 2 h under hydrogen atmosphere (1 atm). The reaction mixture was purged and backfilled with Ar, and filtered off through a pad of Celite. The filtrate was concentrated, and the residue was purified by silica gel column chromatography (5-100% EtOAc/hexane then 0-10% MeOH/EtOAc) to yield: EX.526 (19 mg, 69%) as a white solid; $^1$H-NMR (400 MHz, $CDCl_3$) δ 3.06 (s, 3H), 3.77 (s, 3H), 4.20 (dd, J=11.3, 1.3 Hz, 1H), 4.32 (d, J=4.7 Hz, 1H), 4.36-4.42 (m, 3H), 6.28 (t, J=54.0 Hz, 1H), 6.46-6.61 (m, 1H), 6.55-6.92 (m, 1H), 7.07-7.13 (m, 2H), 7.85-7.88 (m, 1H), 8.22 (dd, J=4.9, 1.5 Hz, 1H), 9.59 (s, 1H); MS (ESI$^+$): 530 [M+H]$^+$.

(216) Experimental procedure of (S)-3-(3-(3-(difluoromethoxy)-1-methyl-1H-pyrazol-4-yl)-1H-pyrrolo[2,3-b]pyridin-2-yl)-2-(difluoromethyl)-6,7-dihydro-5H-pyrazolo[5,1-b][1,3]oxazin-6-ol (EX.527)

EX. 527

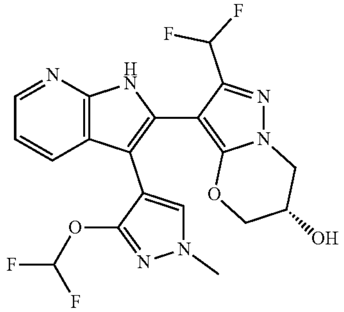

A mixture of compound 396 (100 mg, 0.184 mmol) and 10% Pd—C (25 mg) in EtOH (5 mL) was stirred at room temperature for 2 h under hydrogen atmosphere (1 atm). The reaction mixture was purged and backfilled with Ar, and filtered off through a pad of Celite. The filtrate was concentrated, and the residue was purified by silica gel column chromatography (0-40% MeOH/$CHCl_3$) to yield EX.527 (81.0 mg, 97%) as a white solid; $^1$H-NMR (400 MHz, DMSO-$d_6$) δ 3.69 (3H, s), 3.99 (1H, d, J=11.6 Hz), 4.15 (2H, s), 4.29 (2H, d, J=11.6 Hz), 5.66 (1H, d, J=3.1 Hz), 6.66 (1H, t, J=54.1 Hz), 7.05 (1H, dd, J=7.9, 4.9 Hz), 7.09 (1H, t, J=74.0 Hz), 7.49 (1H, s), 7.79 (1H, d, J=6.7 Hz), 8.19 (1H, dd, J=4.6, 1.5 Hz), 11.72 (1H, s); MS (ESI$^+$): 453 [M+H]$^+$.

The following compounds were synthesized from the corresponding starting materials and reagents using conditions analogous to EX.527.

| Compound No. | Chemical structural formula | Spectrum data |
|---|---|---|
| EX.528 | 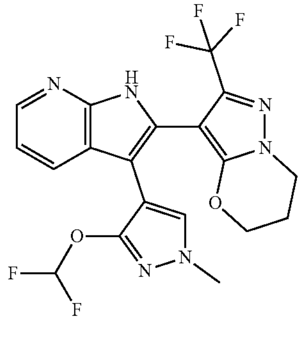 [SMILES: Cn1cc(-c2c(-c3c(C(F)(F)F)nn4c3OCCC4)[nH]c3ncccc23)c(OC(F)F)n1] | $^1$H-NMR (400 MHz, DMSO-$d_6$) δ 2.19-2.29 (m, 2H), 3.76 (s, 3H), 4.22 (t, J = 6.0 Hz, 2H), 4.27-4.35 (m, 2H), 6.93-7.32 (m, 2H), 7.60 (s, 1H), 7.85 (dd, J = 7.9, 1.5 Hz, 1H), 8.25 (dd, J = 4.7, 1.6 Hz, 1H), 11.81 (s, 1H); MS (ESI$^+$): 455 [M + H]$^+$. |

-continued

| Compound No. | Chemical structural formula | Spectrum data |
|---|---|---|
| EX.529 | 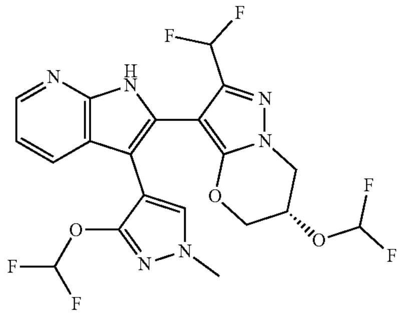 [SMILES: Cn1cc(-c2c(-c3c(C(F)F)nn4c3OC[C@@H](OC(F)F)C4)[nH]c3ncccc23)c(OC(F)F)n1] | $^1$H-NMR (400 MHz, DMSO-$d_6$) δ 3.74 (s, 3H), 4.26-4.36 (m, 2H), 4.42-4.54 (m, 2H), 5.03-5.09 (m, 1H), 6.60-7.30 (m, 4H), 7.51 (s, 1H), 7.83 (dd, J = 8.0, 1.3 Hz, 1H), 8.24 (dd, J - 4.7, 1.6 Hz, 1H), 11.80 (s, 1H); MS (ESI$^+$): 503 [M + H]$^+$. |
| EX.530 | 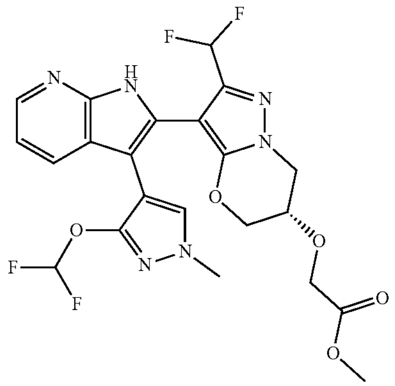 [SMILES: COC(=O)CO[C@@H]1COc2c(-c3[nH]c4ncccc4c3-c3cn(C)nc3OC(F)F)c(C(F)F)nn2C1] | $^1$H-NMR (400 MHz, DMSO-$d_6$) δ 3.67 (s, 3H), 3.73 (s, 3H), 4.21 (d, J = 11.7 Hz, 1H), 4.27-4.40 (m, 5H), 4.49 (d, J = 12.2 Hz, 1H), 6.55-7.29 (m, 3H), 7.51 (s, 1H), 7.82 (d, J = 7.9 Hz, 1H), 8.23 (dd, J = 4.6, 1.3 Hz, 1H), 11.77 (s, 1H); MS (ESI$^+$): 525 [M + H]$^+$. |
| EX.531 | 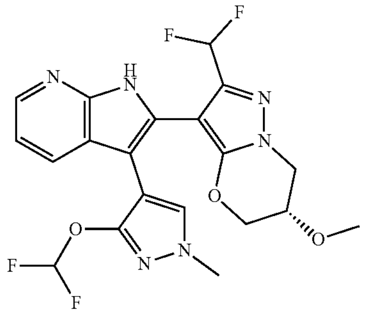 [SMILES: CO[C@@H]1COc2c(-c3[nH]c4ncccc4c3-c3cn(C)nc3OC(F)F)c(C(F)F)nn2C1] | $^1$H-NMR (400 MHz, DMSO-$d_6$) δ 3.37 (s, 3H), 3.75 (s, 3H), 4.04-4.09 (m, 1H), 4.15-4.21 (m, 1H), 4.23-4.36 (m, 2H), 4.45-4.52 (m, 1H), 6.72 (t, J = 54.1 Hz, 1H), 6.92-7.29 (m, 2H), 7.50 (s, 1H), 7.82 (dd, J = 7.8, 1.2 Hz, 1H), 8.23 (dd, J = 4.7, 1.6 Hz, 1H), 11.76 (s, 1H); MS (ESI$^+$): 467 [M + H]$^+$. |
| EX.532 | 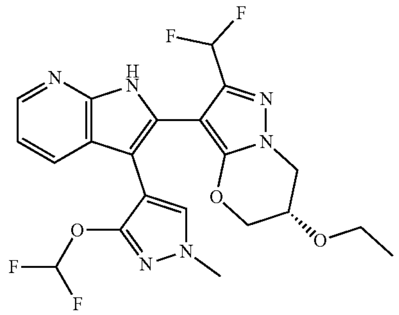 [SMILES: CCO[C@@H]1COc2c(-c3[nH]c4ncccc4c3-c3cn(C)nc3OC(F)F)c(C(F)F)nn2C1] | $^1$H-NMR (400 MHz, DMSO-$d_6$) δ 1.13 (t, J = 7.0 Hz, 3H), 3.60 (q, J = 7.0 Hz, 2H), 3.75 (s, 3H), 4.12-4.25 (m, 3H), 4.29-4.45 (m, 2H), 6.72 (t, J = 54.1 Hz, 1H), 6.90-7.29 (m, 2H), 7.53 (s, 1H), 7.81 (dd, J = 7.9, 1.4 Hz, 1H), 8.23 (dd, J = 4.7, 1.6 Hz, 1H), 11.76 (s, 1H); MS (ESI$^+$): 481 [M + H]$^+$. |

-continued

| Compound No. | Chemical structural formula | Spectrum data |
|---|---|---|
| EX.533 | 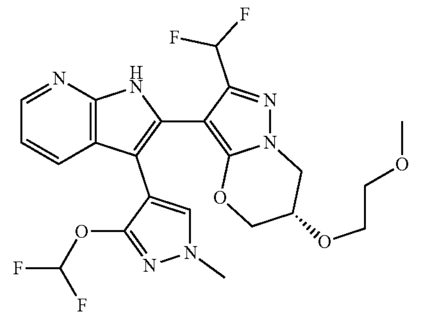 [SMILES: COCCO[C@@H]1COc2c(-c3[nH]c4ncccc4c3-c3cn(C)nc3OC(F)F)c(C(F)F)nn2C1] | $^1$H-NMR (400 MHz, DMSO-$d_6$) δ 3.24 (s, 3H), 3.43-3.49 (m, 2H), 3.67-3.72 (m, 2H), 3.75 (s, 3H), 4.14-4.46 (m, 5H), 6.72 (t, J = 54.1 Hz, 1H), 6.91-7.28 (m, 2H), 7.52 (s, 1H), 7.82 (dd, J = 7.9, 1.5 Hz, 1H), 8.23 (dd, J = 4.7, 1.6 Hz, 1H), 11.76 (s, 1H); MS (ESI$^+$): 511 [M + H]$^+$. |
| EX.534 | 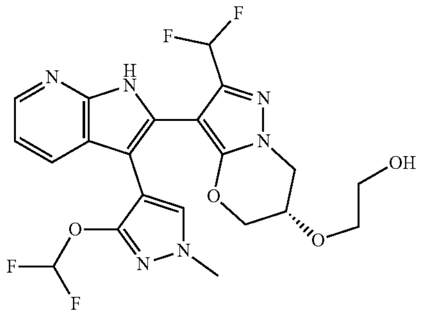 [SMILES: Cn1cc(-c2c(-c3c(C(F)F)nn4c3OC[C@@H](OCCO)C4)[nH]c3ncccc23)c(OC(F)F)n1] | $^1$H-NMR (400 MHz, DMSO-$d_6$) δ 3.49-3.63 (m, 4H), 3.75 (s, 3H), 4.13-4.38 (m, 4H), 4.42-4.49 (m, 1H), 4.71 (t, J = 5.4 Hz, 1H), 6.71 (t, J = 54.1 Hz, 1H), 6.92-7.29 (m, 2H), 7.52 (s, 1H), 7.82 (dd, J = 7.9, 1.1 Hz, 1H), 8.23 (dd, J = 4.7, 1.5 Hz, 1H), 11.76 (s, 1H); MS (ESI$^+$): 497 [M + H]$^+$. |
| EX.535 | 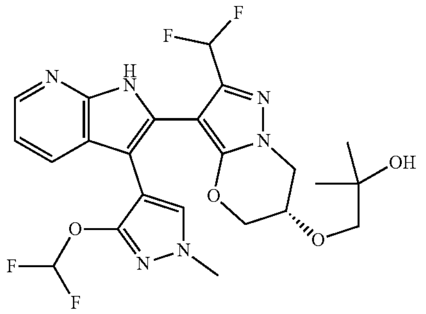 [SMILES: Cn1cc(-c2c(-c3c(C(F)F)nn4c3OC[C@@H](OCC(C)(C)O)C4)[nH]c3ncccc23)c(OC(F)F)n1] | $^1$H-NMR (400 MHz, DMSO-$d_6$) δ 1.05 (s, 6H), 3.30-3.37 (m, 2H), 3.75 (s, 3H), 4.13-4.47 (m, 6H), 6.70 (t, J = 54.1 Hz, 1H), 6.91-7.29 (m, 2H), 7.49 (s, 1H), 7.81 (dd, J = 7.9, 1.4 Hz, 1H), 8.23 (dd, J = 4.7, 1.6 Hz, 1H), 11.76 (s, 1H); MS (ESI$^+$): 525 [M + H]$^+$. |
| EX.536 | 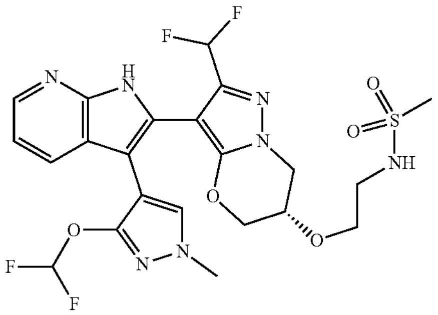 [SMILES: Cn1cc(-c2c(-c3c(C(F)F)nn4c3OC[C@@H](OCCNS(C)(=O)=O)C4)[nH]c3ncccc23)c(OC(F)F)n1] | $^1$H-NMR (400 MHz, DMSO-$d_6$) δ 2.85 (s, 3H), 3.10-3.16 (m, 2H), 3.58-3.67 (m, 2H), 3.76 (s, 3H), 4.14-4.37 (m, 4H), 4.43-4.49 (m, 1H), 6.71 (t, J = 54.1 Hz, 1H), 6.91-7.29 (m, 3H), 7.52 (s, 1H), 7.81 (dd, J = 7.8, 1.5 Hz, 1H), 8.23 (dd, J = 4.7, 1.6 Hz, 1H), 11.75 (s, 1H); MS (ESI$^+$): 574 [M + H]$^+$. |
| EX.537 | 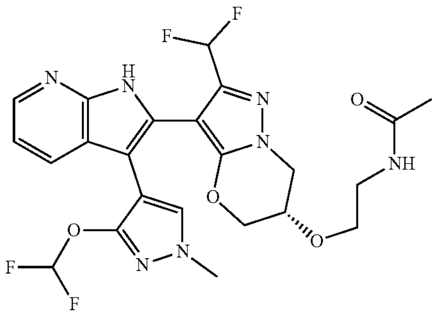 [SMILES: CC(=O)NCCO[C@@H]1COc2c(-c3[nH]c4ncccc4c3-c3cn(C)nc3OC(F)F)c(C(F)F)nn2C1] | $^1$H-NMR (400 MHz, DMSO-$d_6$) δ 1.79 (s, 3H), 3.15-3.26 (m, 2H), 3.50-3.60 (m, 2H), 3.75 (s, 3H), 4.13-4.47 (m, 5H), 6.70 (t, J = 54.1 Hz, 1H), 6.91-7.29 (m, 2H), 7.53 (s, 1H), 7.82 (dd, J = 7.9, 1.5 Hz, 1H), 7.92 (t, J = 5.5 Hz, 1H), 8.23 (dd, J = 4.7, 1.5 Hz, 1H), 11.76 (s, 1H); MS (ESI$^+$): 538 [M + H]$^+$. |

-continued

| Compound No. | Chemical structural formula | Spectrum data |
|---|---|---|
| EX.538 | 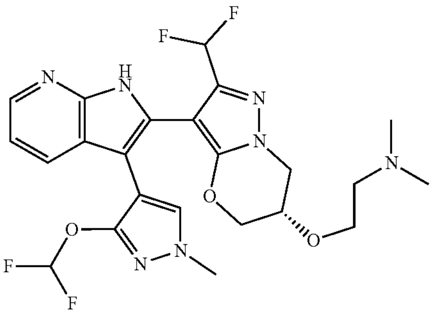 [SMILES: CN(C)CCO[C@@H]1COc2c(-c3[nH]c4ncccc4c3-c3cn(C)nc3OC(F)F)c(C(F)F)nn2C1] | $^1$H-NMR (400 MHz, DMSO-$d_6$) δ 2.13 (s, 6H), 2.40 (t, J = 6.0 Hz, 2H), 3.58-3.65 (m, 2H), 3.76 (s, 3H), 4.13-4.46 (m, 5H), 6.72 (t, J = 54.1 Hz, 1H), 6.91-7.29 (m, 2H), 7.52 (s, 1H), 7.82 (dd, J = 7.9, 1.1 Hz, 1H), 8.23 (dd, J = 4.7, 1.5 Hz, 1H), 11.75 (s, 1H); MS (ESI$^-$): 522 [M − H]$^-$. |
| EX.539 | 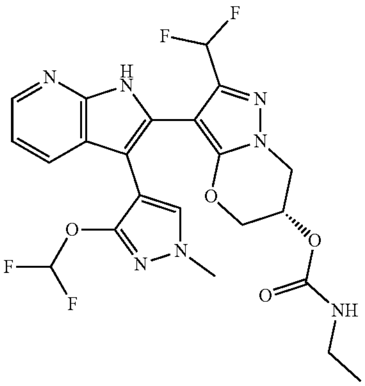 [SMILES: CCNC(=O)O[C@@H]1COc2c(-c3[nH]c4ncccc4c3-c3cn(C)nc3OC(F)F)c(C(F)F)nn2C1] | $^1$H-NMR (400 MHz, DMSO-$d_6$) δ 1.01 (t, J = 7.2 Hz, 3H), 2.98-3.08 (m, 2H), 3.76 (s, 3H), 4.16-4.30 (m, 2H), 4.37-4.54 (m, 2H), 5.25-5.30 (m, 1H), 6.75 (t, J = 54.1 Hz, 1H), 6.92-7.29 (m, 2H), 7.39 (t, J = 5.5 Hz, 1H), 7.52 (s, 1H), 7.81 (dd, J = 7.8, 1.3 Hz, 1H), 8.24 (dd, J = 4.7, 1.6 Hz, 1H), 11.72 (s, 1H); MS (ESI$^+$): 524 [M + H]$^+$. |
| EX.540 | 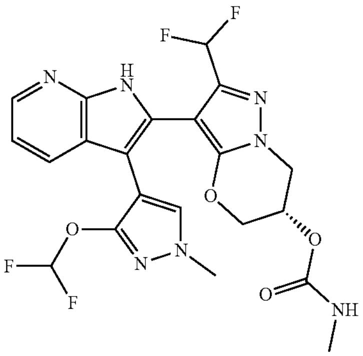 [SMILES: CNC(=O)O[C@@H]1COc2c(-c3[nH]c4ncccc4c3-c3cn(C)nc3OC(F)F)c(C(F)F)nn2C1] | $^1$H-NMR (400 MHz, DMSO-$d_6$) δ 2.58 (d, J = 4.6 Hz, 3H), 3.76 (s, 3H), 4.18-4.30 (m, 2H), 4.39-4.53 (m, 2H), 5.26-5.30 (m, 1H), 6.54-7.37 (m, 4H), 7.53 (s, 1H), 7.81 (dd, J = 7.9, 1.2 Hz, 1H), 8.24 (dd, J = 4.7, 1.5 Hz, 1H), 11.77 (s, 1H); MS (ESI$^+$): 510 [M + H]$^+$. |
| EX.541 | 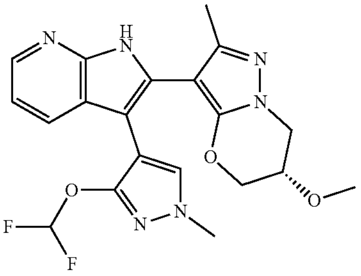 [SMILES: CO[C@@H]1COc2c(-c3[nH]c4ncccc4c3-c3cn(C)nc3OC(F)F)c(C)nn2C1] | $^1$H-NMR (400 MHz, DMSO-$d_6$) δ 1.94 (s, 3H), 3.35 (s, 3H), 3.75 (s, 3H), 3.95-4.00 (m, 1H), 4.06-4.22 (m, 3H), 4.35-4.42 (m, 1H), 6.93-7.32 (m, 2H), 7.53 (s, 1H), 7.77 (dd, J = 7.8, 1.2 Hz, 1H), 8.19 (dd, J = 4.7, 1.5 Hz, 1H), 11.64 (s, 1H); MS (ESI$^+$): 431 [M + H]$^+$. |

-continued

| Compound No. | Chemical structural formula | Spectrum data |
|---|---|---|
| EX.542 | 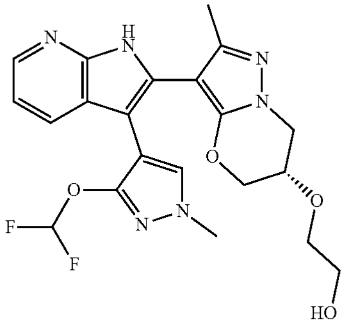 [SMILES: Cc1nn2c(c1-c1[nH]c3ncccc3c1-c1cn(C)nc1OC(F)F)OC[C@@H](OCCO)C2] | $^1$H-NMR (400 MHz, DMSO-$d_6$) δ 1.93 (s, 3H), 3.48-3.62 (m, 4H), 3.76 (s, 3H), 4.05-4.23 (m, 4H), 4.32-4.39 (m, 1H), 4.70 (t, J = 5.0 Hz, 1H), 6.93-7.32 (m, 2H), 7.54 (s, 1H), 7.77 (dd, J = 7.9, 1.3 Hz, 1H), 8.19 (dd, J = 4.7, 1.5 Hz, 1H), 11.63 (s, 1H); MS (ESI$^+$): 461 [M + H]$^+$. |
| EX.543 | 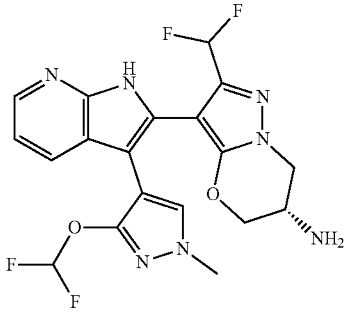 [SMILES: Cn1cc(-c2c(-c3c(C(F)F)nn4c3OC[C@@H](N)C4)[nH]c3ncccc23)c(OC(F)F)n1] | $^1$H-NMR (400 MHz, $CDCl_3$) δ 1.69 (s, 4H), 3.55-3.67 (m, 1H), 3.79-3.83 (m, 3H), 3.92-3.99 (m, 2H), 4.13 (dd, J = 11.1, 2.3 Hz, 1H), 4.36 (dd, J = 12.5, 4.6 Hz, 1H), 6.34-6.61 (m, 1H), 6.57-6.94 (m, 1H), 7.09 (dd, J = 7.9, 4.8 Hz, 1H), 7.29 (s, 1H), 7.87 (dd, J = 7.9, 1.4 Hz, 1H), 8.28 (d, J = 3.5 Hz, 1H), 9.20 (s, 1H); MS (ESI$^+$): 452 [M + H]$^+$. |
| EX.544 | 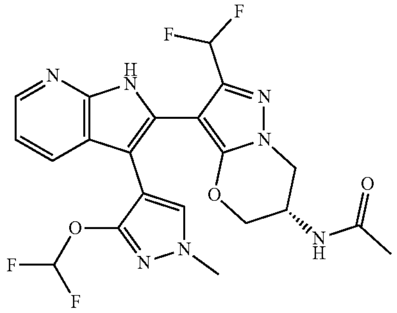 [SMILES: CC(=O)N[C@@H]1COc2c(-c3[nH]c4ncccc4c3-c3cn(C)nc3OC(F)F)c(C(F)F)nn2C1] | $^1$H-NMR (400 MHz, $CDCl_3$) δ 2.02 (3H, s), 3.85 (3H, s), 4.15 (1H, dd, J = 11.5, 1.5 Hz), 4.23-4.34 (3H, m), 4.70 (1H, dq, J = 7.9, 2.1 Hz), 6.44 (1H, t, J = 74.0 Hz), 6.49-6.86 (2H, m), 7.18 (1H, dd, J = 7.8, 5.1 Hz), 7.41 (1H, s), 8.01 (1H, d, J = 7.7 Hz), 8.25 (1H, d, J = 4.6 Hz), 10.18 (1H, s); MS (ESI$^+$): 494 [M + H]$^+$. |
| EX.545 | 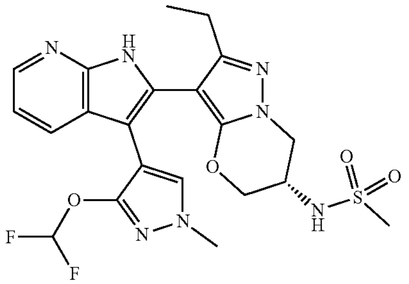 [SMILES: CCc1nn2c(c1-c1[nH]c3ncccc3c1-c1cn(C)nc1OC(F)F)OC[C@@H](NS(C)(=O)=O)C2] | $^1$H-NMR (400 MHz, DMSO-$d_6$) δ 0.92 (t, J = 7.6 Hz, 3H), 3.09 (s, 3H), 3.79 (s, 3H), 4.00-4.39 (m, 7H), 7.01-7.38 (m, 2H), 7.55-7.64 (m, 2H), 7.80-7.82 (m, 1H), 8.20-8.24 (m, 1H), 11.63 (s, 1H); MS (ESI$^+$): 508 [M + H]$^+$. |
| EX.546 | 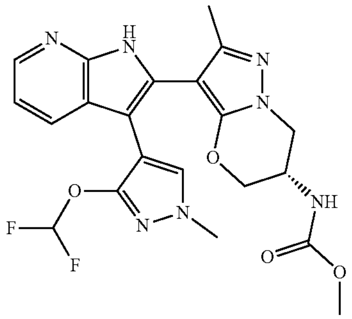 [SMILES: COC(=O)N[C@@H]1COc2c(-c3[nH]c4ncccc4c3-c3cn(C)nc3OC(F)F)c(C)nn2C1] | $^1$H-NMR (400 MHz, DMSO-$d_6$) δ 1.83 (s, 3H), 3.61 (s, 3H), 3.76 (s, 3H), 3.92-3.98 (m, 1H), 4.10-4.27 (m, 4H), 6.97-7.34 (m, 2H), 7.55-7.63 (m, 2H), 7.78 (dd, J = 7.8, 1.0 Hz, 1H), 8.18 (dd, J = 4.7, 1.6 Hz, 1H), 11.53 (s, 1H); MS (ESI$^+$): 474 [M + H]$^+$. |

-continued

| Compound No. | Chemical structural formula | Spectrum data |
|---|---|---|
| EX.547 | 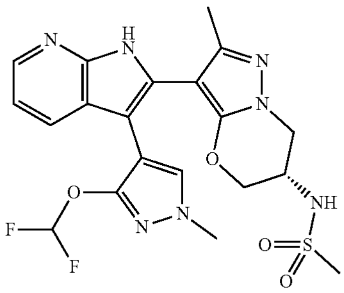 [SMILES: Cc1nn2c(c1-c1[nH]c3ncccc3c1-c1cn(C)nc1OC(F)F)OC[C@@H](NS(C)(=O)=O)C2] | $^1$H-NMR (400 MHz, DMSO-d$_6$) δ 1.87 (s, 3H), 3.05 (s, 3H), 3.76 (s, 3H), 3.96-4.32 (m, 5H), 6.97-7.34 (m, 2H), 7.54 (s, 1H), 7.58 (s, 1H), 7.78 (d, J = 7.9 Hz, 1H), 8.18 (dd, J = 4.6, 1.4 Hz, 1H), 11.56 (s, 1H); MS (ESI$^+$): 494 [M + H]$^+$. |
| EX.548 | 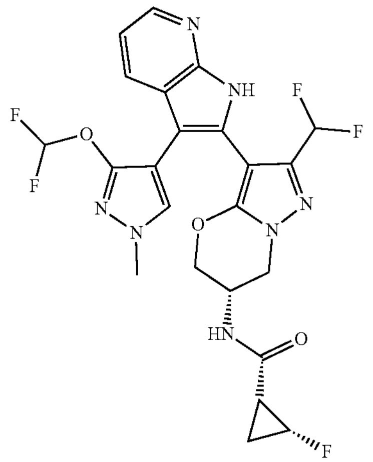 | $^1$H-NMR (400 MHz, CDCl$_3$) δ 1.09-1.21 (m, 1H), 1.71-1.89 (m, 2H), 3.88 (s, 3H), 4.07-4.14 (m, 1H), 4.14-4.21 (m, 1H), 4.25-4.38 (m, 2H), 4.64-4.86 (m, 2H), 6.38-6.77 (m, 3H), 7.12 (dd, J = 7.9, 4.8 Hz, 1H), 7.46 (s, 1H), 7.88 (dd, J = 7.9, 1.5 Hz, 1H), 8.32 (dd, J = 4.8, 1.5 Hz, 1H), 9.18 (s, 1H); MS (ESI$^+$): 538 [M + H]$^+$. |
| EX.549 | 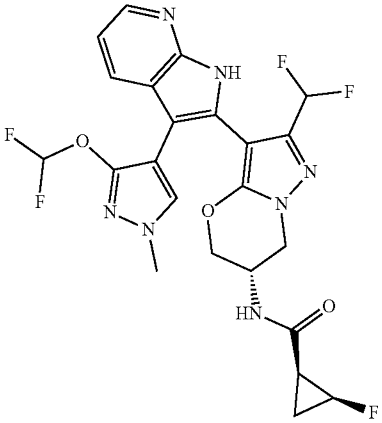 [SMILES: Cn1cc(-c2c(-c3c(C(F)F)nn4c3OC[C@@H](NC(=O)[C@@H]3C[C@@H]3F)C4)[nH]c3ncccc23)c(OC(F)F)n1] | $^1$H-NMR (400 MHz, CDCl$_3$) δ 1.09-1.18 (m, 1H), 1.75-1.89 (m, 2H), 3.86 (s, 3H), 4.05-4.10 (m, 1H), 4.16-4.38 (m, 3H), 4.59-4.80 (m, 2H), 6.39-6.78 (m, 3H), 7.12 (dd, J = 7.9, 4.7 Hz, 1H), 7.47 (s, 1H), 7.89 (dd, J = 7.9, 1.5 Hz, 1H), 8.33 (dd, J = 4.7, 1.5 Hz, 1H), 9.24 (s, 1H); MS (ESI$^+$): 538 [M + H]$^+$. |
| EX.550 | 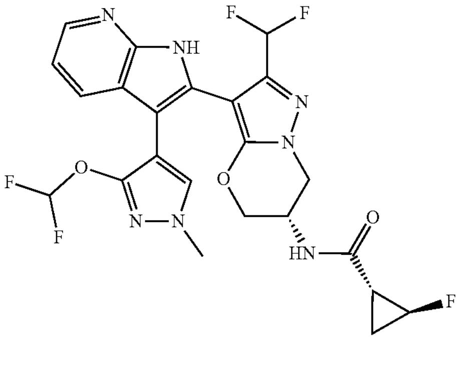 [SMILES: Cn1cc(-c2c(-c3c(C(F)F)nn4c3OC[C@@H](NC(=O)[C@H]3C[C@@H]3F)C4)[nH]c3ncccc23)c(OC(F)F)n1] | $^1$H-NMR (400 MHz, CDCl$_3$) δ 1.30-1.50 (m, 2H), 2.02-2.12 (m, 1H), 3.87 (s, 3H), 4.04-4.09 (m, 1H), 4.14-4.25 (m, 2H), 4.28-4.36 (m, 1H), 4.66-4.91 (m, 2H), 6.40-6.84 (m, 3H), 7.13 (dd, J = 7.8, 4.7 Hz, 1H), 7.48 (s, 1H), 7.89 (dd, J = 7.9, 1.5 Hz, 1H), 8.33 (dd, J = 4.7, 1.5 Hz, 1H), 9.23 (s, 1H); MS (ESI$^+$): 538 [M + H]$^+$. |

-continued

| Compound No. | Chemical structural formula | Spectrum data |
|---|---|---|
| EX.551 | 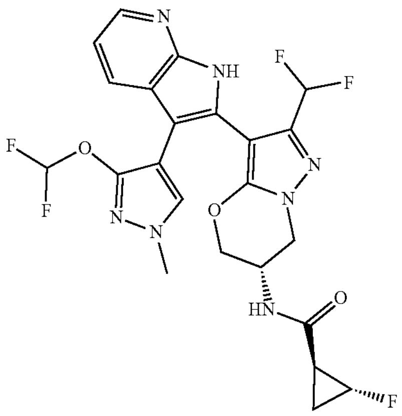 [SMILES: Cn1cc(-c2c(-c3c(C(F)F)nn4c3OC[C@@H](NC(=O)[C@@H]3C[C@H]3F)C4)[nH]c3ncccc23)c(OC(F)F)n1] | $^1$H-NMR (400 MHz, $CDCl_3$) δ 1.31-1.49 (m, 2H), 1.93-2.04 (m, 1H), 3.86 (s, 3H), 4.01-4.09 (m, 1H), 4.13-4.20 (m, 1H), 4.22-4.29 (m, 1H), 4.29-4.36 (m, 1H), 4.63-4.88 (m, 2H), 6.38-6.88 (m, 3H), 7.13 (dd, J - 7.9, 4.7 Hz, 1H), 7.44 (s, 1H), 7.89 (dd, J = 7.9, 1.4 Hz, 1H), 8.34 (dd, J = 4.7, 1.4 Hz, 1H), 9.30 (s, 1H); MS (ESI$^+$): 538 [M + H]$^+$. |
| EX.552 | 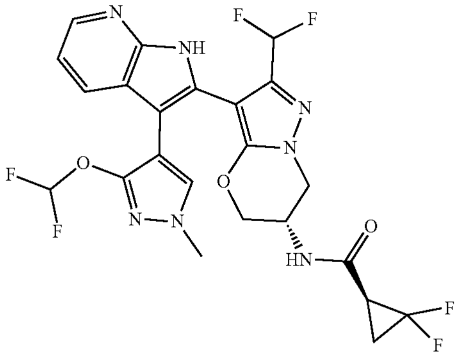 [SMILES: Cn1cc(-c2c(-c3c(C(F)F)nn4c3OC[C@@H](NC(=O)[C@@H]3CC3(F)F)C4)[nH]c3ncccc23)c(OC(F)F)n1] | $^1$H-NMR (400 MHz, $CDCl_3$) δ 1.57-1.75 (m, 1H), 2.09-2.18 (m, 1H), 2.37-2.47 (m, 1H), 3.86 (s, 3H), 3.96-4.03 (m, 1H), 4.13-4.26 (m, 2H), 4.29-4.37 (m, 1H), 4.71-4.76 (m, 1H), 6.37-6.85 (m, 3H), 7.13 (dd, J = 7.9, 4.8 Hz, 1H), 7.45 (s, 1H), 7.89 (dd, J = 7.9, 1.4 Hz, 1H), 8.35 (dd, J = 4.7, 1.4 Hz, 1H), 9.32 (s, 1H); MS (ESI$^+$): 556 [M + H]$^+$. |
| EX.553 | 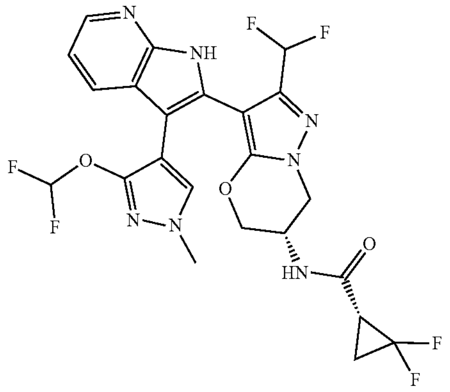 [SMILES: Cn1cc(-c2c(-c3c(C(F)F)nn4c3OC[C@@H](NC(=O)[C@H]3CC3(F)F)C4)[nH]c3ncccc23)c(OC(F)F)n1] | $^1$H-NMR (400 MHz, DMSO-$d_6$) δ 1.84-1.99 (m, 2H), 2.58-2.69 (m, 1H), 3.76 (s, 3H), 4.12-4.17 (m, 1H), 4.19-4.30 (m, 2H), 4.40-4.51 (m, 2H), 6.56-7.33 (m, 3H), 7.57 (s, 1H), 7.83 (dd, J = 7.9, 1.0 Hz, 1H), 8.24 (dd, J = 4.7, 1.5 Hz, 1H), 8.93 (d, J = 5.9 Hz, 1H), 11.74 (s, 1H); MS (ESI$^+$): 556 [M + H]$^+$. |
| EX.554 | 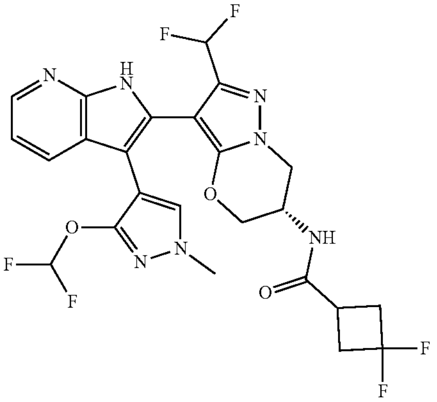 [SMILES: Cn1cc(-c2c(-c3c(C(F)F)nn4c3OC[C@@H](NC(=O)C3CC(F)(F)C3)C4)[nH]c3ncccc23)c(OC(F)F)n1] | $^1$H-NMR (400 MHz, DMSO-$d_6$) δ 2.63-2.80 (4H, m), 2.86-2.98 (1H, m), 3.76 (3H, s), 4.05-4.14 (1H, m), 4.16-4.27 (2H, m), 4.38-4.49 (2H, m), 6.70 (1H, t, J = 54.0 Hz), 6.92-7.33 (2H, m), 7.56 (1H, s), 7.83 (1H, dd, J = 7.9, 1.3 Hz), 8.24 (1H, dd, J = 4.7, 1.5 Hz), 8.59 (1H, d, J = 6.1 Hz), 11.72 (1H, s); MS (ESI$^+$): 570 [M + H]$^+$. |

-continued

| Compound No. | Chemical structural formula | Spectrum data |
|---|---|---|
| EX.555 | 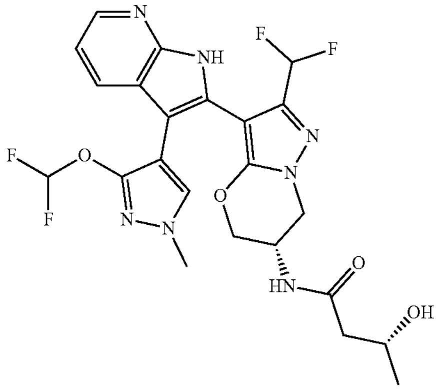 [SMILES: C[C@@H](O)CC(=O)N[C@@H]1COc2c(-c3[nH]c4ncccc4c3-c3cn(C)nc3OC(F)F)c(C(F)F)nn2C1] | $^1$H-NMR (400 MHz, DMSO-$d_6$) δ 1.04 (d, J = 6.2 Hz, 3H), 2.12-2.28 (m, 2H), 3.75 (s, 3H), 3.94-4.22 (m, 4H), 4.37-4.46 (m, 2H), 4.65 (d, J = 4.6 Hz, 1H), 6.67 (t, J = 54.0 Hz, 1H), 6.93-7.30 (m, 2H), 7.54 (s, 1H), 7.82 (dd, J = 7.9, 1.3 Hz, 1H), 8.23 (dd, J = 4.6, 1.5 Hz, 1H), 8.31 (d, J = 6.3 Hz, 1H), 11.69 (s, 1H); MS (ESI$^+$): 538 [M + H]$^+$. |
| EX.556 | 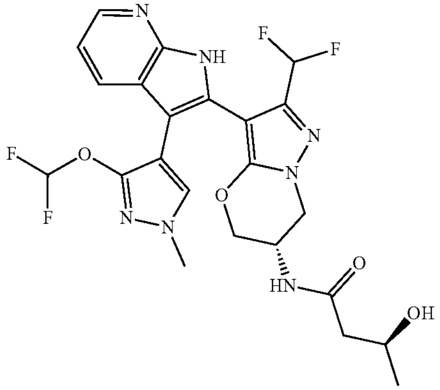 [SMILES: C[C@H](O)CC(=O)N[C@@H]1COc2c(-c3[nH]c4ncccc4c3-c3cn(C)nc3OC(F)F)c(C(F)F)nn2C1] | $^1$H-NMR (400 MHz, DMSO-$d_6$) δ 1.01-1.06 (m, 3H), 2.13-2.28 (m, 2H), 3.75 (s, 3H), 3.94-4.23 (m, 4H), 4.37-4.44 (m, 2H), 4.66 (d, J = 4.6 Hz, 1H), 6.66 (t, J = 54.0 Hz, 1H), 6.93-7.30 (m, 2H), 7.55 (s, 1H), 7.81-7.83 (m, 1H), 8.23 (dd, J = 4.7, 1.5 Hz, 1H), 8.30 (d, J = 6.2 Hz, 1H), 11.70 (s, 1H); MS (ESI$^+$): 538 [M + H]$^+$. |
| EX.557 | 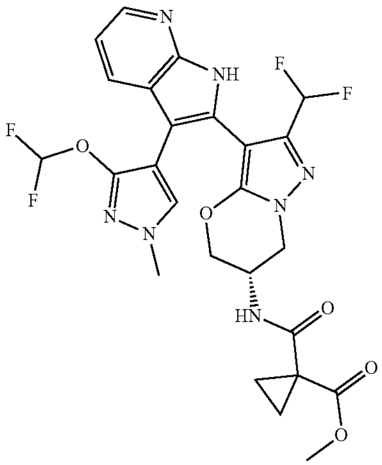 [SMILES: COC(=O)C1(C(=O)N[C@@H]2COc3c(-c4[nH]c5ncccc5c4-c4cn(C)nc4OC(F)F)c(C(F)F)nn3C2)CC1] | $^1$H-NMR (400 MHz, $CDCl_3$) δ 1.56-1.77 (m, 4H), 3.66 (s, 3H), 3.83 (s, 3H), 4.18-4.40 (m, 4H), 4.64-4.69 (m, 1H), 6.33-7.00 (m, 2H), 7.11 (dd, J = 7.6, 4.7 Hz, 1H), 7.33 (s, 1H), 7.89 (dd, J = 7.9, 1.4 Hz, 1H), 8.31 (dd, J = 4.8, 1.6 Hz, 1H), 8.95-9.08 (m, 1H), 9.38 (d, J = 7.2 Hz, 1H); MS (ESI$^+$): 578 [M + H]$^+$. |
| EX.558 | 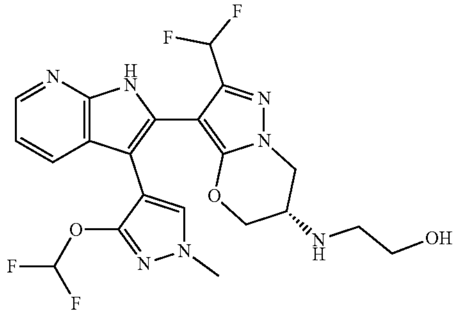 [SMILES: Cn1cc(-c2c(-c3c(C(F)F)nn4c3OC[C@@H](NCCO)C4)[nH]c3ncccc23)c(OC(F)F)n1] | $^1$H-NMR (400 MHz, DMSO-$d_6$) δ 2.04-2.12 (m, 1H), 2.65-2.72 (m, 2H), 3.43-3.49 (m, 2H), 3.74 (s, 3H), 3.97-4.03 (m, 1H), 4.11-4.17 (m, 1H), 4.22-4.32 (m, 2H), 4.57 (t, J = 5.3 Hz, 1H), 6.67 (t, J = 54.1 Hz, 1H), 6.92-7.30 (m, 2H), 7.54 (s, 1H), 7.79-7.83 (m, 1H), 8.22 (dd, J = 4.6, 1.4 Hz, 1H), 11.72 (s, 1H); MS (ESI$^+$): 496 [M + H]$^+$. |

-continued

| Compound No. | Chemical structural formula | Spectrum data |
|---|---|---|
| EX.559 | 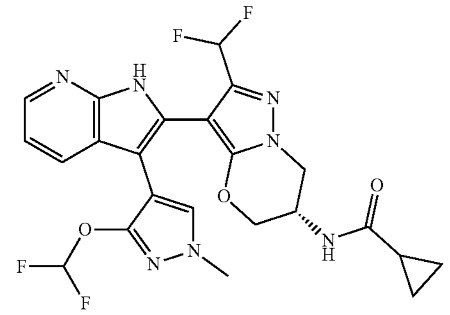 [SMILES: Cn1cc(-c2c(-c3c(C(F)F)nn4c3OC[C@@H](NC(=O)C3CC3)C4)[nH]c3ncccc23)c(OC(F)F)n1] | $^1$H-NMR (400 MHz, DMSO-$d_6$) δ 0.66-0.75 (m, 4H), 1.59-1.65 (m, 1H), 3.75 (s, 3H), 4.06-4.25 (m, 3H), 4.37-4.44 (m, 2H), 6.69 (t, J = 54.1 Hz, 1H), 6.93-7.31 (m, 2H), 7.56 (s, 1H), 7.81-7.83 (m, 1H), 8.23 (dd, J = 4.7, 1.5 Hz, 1H), 8.60 (d, J = 5.7 Hz, 1H), 11.71 (s, 1H); MS (ESI$^+$): 520 [M + H]$^+$. |
| EX.560 | 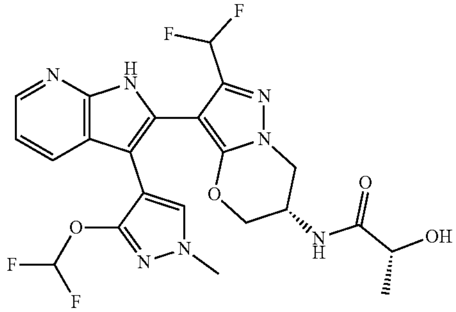 [SMILES: C[C@@H](O)C(=O)N[C@@H]1COc2c(-c3[nH]c4ncccc4c3-c3cn(C)nc3OC(F)F)c(C(F)F)nn2C1] | $^1$H-NMR (400 MHz, DMSO-$d_6$) δ 1.18-1.24 (m, 3H), 3.75 (s, 3H), 3.98-4.05 (m, 1H), 4.12-4.24 (m, 3H), 4.31-4.51 (m, 2H), 5.61-5.65 (m, 1H), 6.64 (t, J = 54.1 Hz, 1H), 6.91-7.29 (m, 2H), 7.55-7.58 (m, 1H), 7.79-7.83 (m, 1H), 8.02-8.07 (m, 1H), 8.20-8.24 (m, 1H), 11.75 (s, 1H); MS (ESI$^+$): 524 [M + H]$^+$. |
| EX.561 | 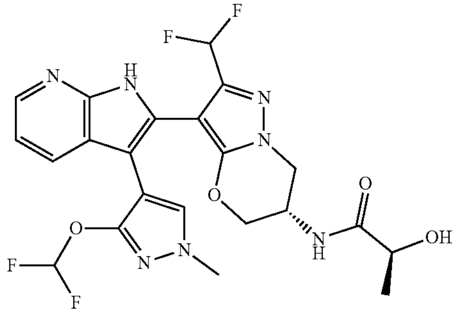 [SMILES: C[C@H](O)C(=O)N[C@@H]1COc2c(-c3[nH]c4ncccc4c3-c3cn(C)nc3OC(F)F)c(C(F)F)nn2C1] | $^1$H-NMR (400 MHz, DMSO-$d_6$) δ 1.22 (d, J = 6.7 Hz, 3H), 3.75 (s, 3H), 3.99-4.23 (m, 5H), 4.34-4.51 (m, 2H), 5.61 (d, J = 5.2 Hz, 1H), 6.64 (t, J = 54.1 Hz, 1H), 6.91-7.29 (m, 2H), 7.57 (s, 1H), 7.82 (dd, J = 7.8, 1.2 Hz, 1H), 8.06 (d, J = 7.5 Hz, 1H), 8.22 (dd, J = 4.7, 1.6 Hz, 1H), 11.74 (s, 1H); MS (ESI$^+$): 524 [M + H]$^+$. |
| EX.562 | 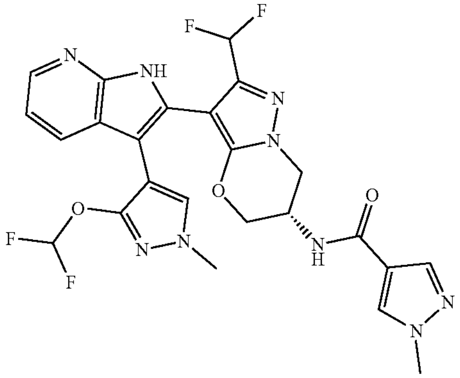 [SMILES: Cn1cc(C(=O)N[C@@H]2COc3c(-c4[nH]c5ncccc5c4-c4cn(C)nc4OC(F)F)c(C(F)F)nn3C2)cn1] | $^1$H-NMR (400 MHz, DMSO-$d_6$) δ 3.70 (s, 3H), 3.85 (s, 3H), 4.16-4.34 (m, 3H), 4.43-4.52 (m, 1H), 4.53-4.63 (m, 1H), 6.69 (t, J = 54.0 Hz, 1H), 7.09 (dd, J = 7.9, 4.7 Hz, 1H), 7.12 (t, J = 74.0 Hz, 1H), 7.57 (s, 1H), 7.83 (dd, J = 7.9, 1.3 Hz, 1H), 7.89 (s, 1H), 8.20 (s, 1H), 8.24 (dd, J = 4.6, 1.5 Hz, 1H), 8.36 (d, J = 6.2 Hz, 1H), 11.74 (s, 1H); MS (ESI$^+$): 560 [M + H]$^+$. |

-continued

| Compound No. | Chemical structural formula | Spectrum data |
|---|---|---|
| EX.563 | 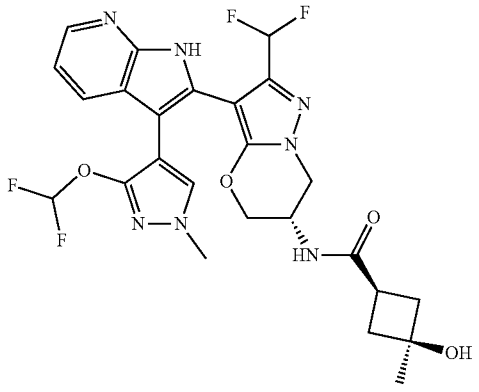 [SMILES: Cn1cc(-c2c(-c3c(C(F)F)nn4c3OC[C@@H](NC(=O)[C@H]3C[C@@](C)(O)C3)C4)[nH]c3ncccc23)c(OC(F)F)n1] | $^1$H-NMR (400 MHz, DMSO-$d_6$) δ 1.21 (3H, s), 1.92-2.04 (2H, m), 2.08-2.20 (2H, m), 2.48-2.60 (1H, m), 3.76 (3H, s), 3.99-4.11 (1H, m), 4.12-4.27 (2H, m), 4.35-4.47 (2H, m), 5.05 (1H, s), 6.67 (1H, t, J = 54.0 Hz), 6.92-7.32 (2H, m), 7.56 (1H, s), 7.83 (1H, dd, J = 8.1, 1.3 Hz), 8.24 (2H, dd, J = 4.7, 1.6 Hz), 11.71 (1H, s); MS (ESI$^+$): 564 [M + H]$^+$. |
| EX.564 | 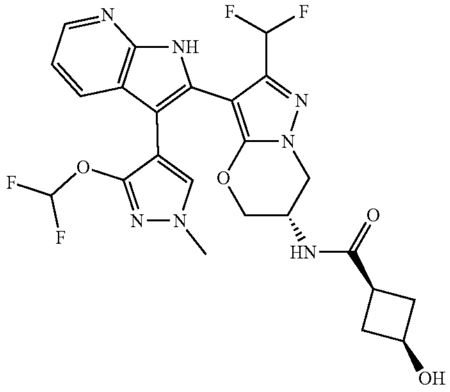 [SMILES: Cn1cc(-c2c(-c3c(C(F)F)nn4c3OC[C@@H](NC(=O)[C@H]3C[C@@H](O)C3)C4)[nH]c3ncccc23)c(OC(F)F)n1] | $^1$H-NMR (400 MHz, DMSO-$d_6$) δ 1.89-2.01 (2H, m), 2.20-2.30 (2H, m), 2.37-2.47 (1H, m), 3.76 (3H, s), 3.86-3.97 (1H, m), 3.99-4.11 (1H, m), 4.12-4.26 (2H, m), 4.35-4.47 (2H, m), 5.12 (1H, d, J = 7.0 Hz), 6.68 (1H, t, J = 54.1 Hz), 6.91-7.33 (2H, m), 7.56 (1H, s), 7.83 (1H, dd, J = 7.8, 1.2 Hz), 8.20-8.30 (2H, m), 11.72 (1H, s); MS (ESI$^+$): 550 [M + H]$^+$. |
| EX.565 | 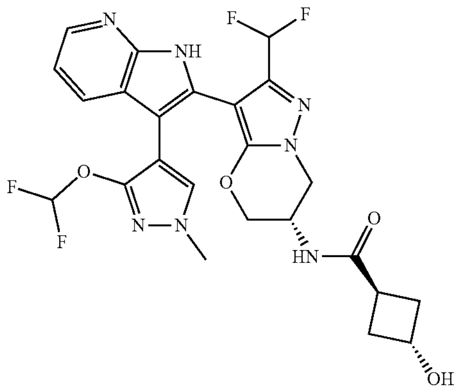 [SMILES: Cn1cc(-c2c(-c3c(C(F)F)nn4c3OC[C@@H](NC(=O)[C@H]3C[C@H](O)C3)C4)[nH]c3ncccc23)c(OC(F)F)n1] | $^1$H-NMR (400 MHz, DMSO-$d_6$) δ 1.90-2.05 (2H, m), 2.23-2.36 (2H, m), 2.81-2.93 (1H, m), 3.76 (3H, s), 3.99-4.11 (1H, m), 4.12-4.32 (3H, m), 4.36-4.48 (2H, m), 5.05 (1H, d, J = 6.3 Hz), 6.67 (1H, t, J = 54.0 Hz), 6.90-7.34 (2H, m), 7.56 (1H, s), 7.83 (1H, dd, J = 7.9, 1.0 Hz), 8.24 (2H, dd, J = 4.7, 1.6 Hz), 11.71 (1H, s); MS (ESI$^+$): 550 [M + H]$^+$. |
| EX.566 | 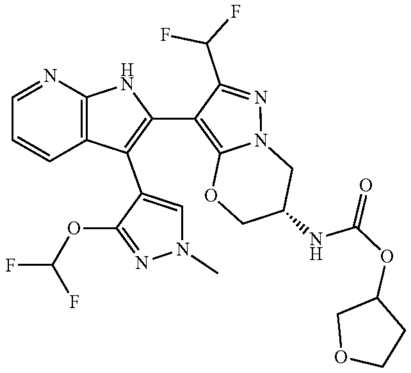 [SMILES: Cn1cc(-c2c(-c3c(C(F)F)nn4c3OC[C@@H](NC(=O)OC3CCOC3)C4)[nH]c3ncccc23)c(OC(F)F)n1] | $^1$H-NMR (400 MHz, DMSO-$d_6$) δ 1.85-1.92 (m, 1H), 2.07-2.15 (m, 1H), 3.67-3.81 (m, 7H), 4.07-4.43 (m, 5H), 5.14-5.18 (m, 1H), 6.62 (t, J = 54.0 Hz, 1H), 6.93-7.31 (m, 2H), 7.56-7.59 (m, 1H), 7.73-7.78 (m, 1H), 7.81-7.85 (m, 1H), 8.23 (dd, J = 4.7, 1.5 Hz, 1H), 11.67 (s, 1H); MS (ESI$^+$): 566 [M + H]$^+$. |

-continued

| Compound No. | Chemical structural formula | Spectrum data |
|---|---|---|
| EX.567 | 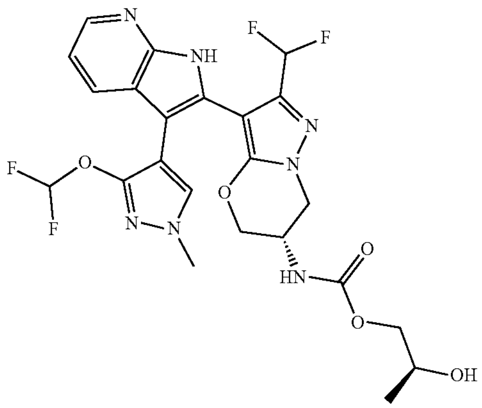 [SMILES: C[C@H](O)COC(=O)N[C@@H]1COc2c(-c3[nH]c4ncccc4c3-c3cn(C)nc3OC(F)F)c(C(F)F)nn2C1] | $^1$H-NMR (400 MHz, DMSO-$d_6$) δ 1.02-1.07 (m, 3H), 3.73-3.89 (m, 6H), 4.09-4.42 (m, 5H), 4.74 (d, J = 4.3 Hz, 1H), 6.48-7.30 (m, 3H), 7.56 (s, 1H), 7.68 (d, J = 4.7 Hz, 1H), 7.82 (dd, J = 7.9, 1.3 Hz, 1H), 8.22 (dd, J = 4.6, 1.5 Hz, 1H), 11.67 (s, 1H); MS (ESI$^+$): 554 [M + H]$^+$. |
| EX.568 | 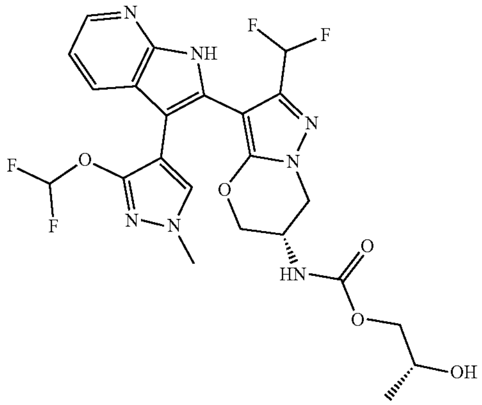 [SMILES: C[C@@H](O)COC(=O)N[C@@H]1COc2c(-c3[nH]c4ncccc4c3-c3cn(C)nc3OC(F)F)c(C(F)F)nn2C1] | $^1$H-NMR (400 MHz, DMSO-$d_6$) δ 1.04 (d, J = 6.1 Hz, 3H), 3.75-3.88 (m, 6H), 4.09-4.42 (m, 5H), 4.74 (d, J = 4.2 Hz, 1H), 6.48-7.30 (m, 3H), 7.57 (s, 1H), 7.68 (d, J = 5.5 Hz, 1H), 7.82 (d, J = 7.2 Hz, 1H), 8.22 (dd, J = 4.7, 1.0 Hz, 1H), 11.67 (s, 1H); MS (ESI$^+$): 554 [M + H]$^+$. |
| EX.569 | 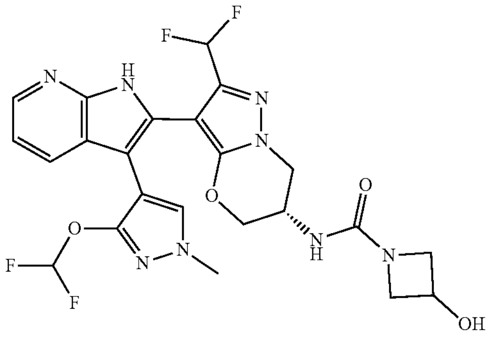 [SMILES: Cn1cc(-c2c(-c3c(C(F)F)nn4c3OC[C@@H](NC(=O)N3CC(O)C3)C4)[nH]c3ncccc23)c(OC(F)F)n1] | $^1$H-NMR (400 MHz, DMSO-$d_6$) δ 3.55-3.59 (m, 2H), 3.75 (s, 3H), 3.96-4.11 (m, 4H), 4.18-4.39 (m, 4H), 5.59 (d, J = 6.4 Hz, 1H), 6.50-6.77 (m, 2H), 6.91-7.28 (m, 2H), 7.57 (s, 1H), 7.82 (dd, J = 7.9, 1.3 Hz, 1H), 8.22 (dd, J = 4.7, 1.6 Hz, 1H), 11.72 (s, 1H); MS (ESI$^+$): 551 [M + H]$^+$. |
| EX.570 | 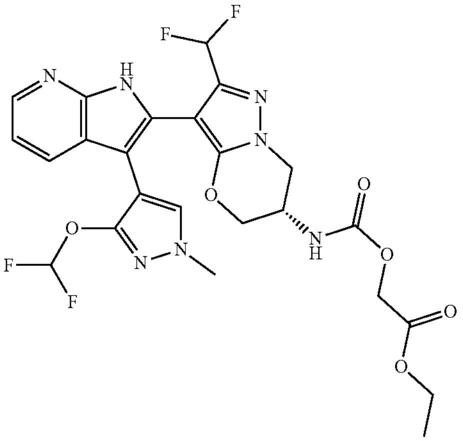 [SMILES: CCOC(=O)COC(=O)N[C@@H]1COc2c(-c3[nH]c4ncccc4c3-c3cn(C)nc3OC(F)F)c(C(F)F)nn2C1] | $^1$H-NMR (400 MHz, $CDCl_3$) δ 1.20-1.37 (m, 3H), 3.80-3.86 (m, 3H), 4.10-4.82 (m, 7H), 6.35-7.31 (m, 6H), 7.86-7.92 (m, 1H), 8.30 (dd, J = 4.7, 1.4 Hz, 1H), 9.02-9.15 (m, 1H). |

-continued

| Compound No. | Chemical structural formula | Spectrum data |
|---|---|---|
| EX.571 | 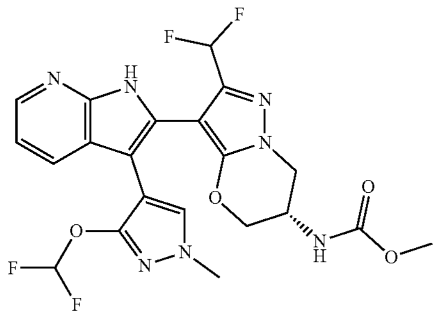 [SMILES: COC(=O)N[C@@H]1COc2c(-c3[nH]c4ncccc4c3-c3cn(C)nc3OC(F)F)c(C(F)F)nn2C1] | $^1$H-NMR (400 MHz, DMSO-$d_6$) δ 3.58 (s, 3H), 3.75 (s, 3H), 4.09-4.43 (m, 5H), 6.62 (t, J = 54.0 Hz, 1H), 6.93-7.31 (m, 2H), 7.56 (s, 1H), 7.66-7.69 (m, 1H), 7.81-7.84 (m, 1H), 8.22-8.24 (m, 1H), 11.68 (s, 1H); MS (ESI$^+$): 510 [M + H]$^+$. |
| EX.572 | 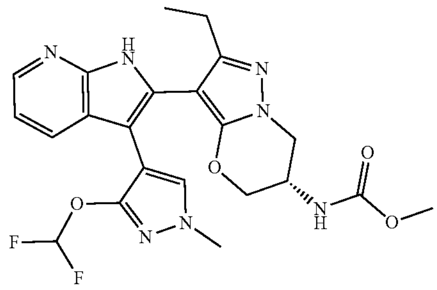 [SMILES: CCc1nn2c(c1-c1[nH]c3ncccc3c1-c1cn(C)nc1OC(F)F)OC[C@@H](NC(=O)OC)C2] | $^1$H-NMR (400 MHz, DMSO-$d_6$) δ 0.88 (t, J = 7.5 Hz, 3H), 2.25 (q, J = 7.5 Hz, 2H), 3.59 (s, 3H), 3.76 (s, 3H), 3.96-4.00 (m, 1H), 4.11-4.29 (m, 4H), 7.06 (dd, J = 7.9, 4.7 Hz, 1H), 7.17 (t, J = 73.9 Hz, 1H), 7.55 (s, 1H), 7.62 (d, J = 5.3 Hz, 1H), 7.78 (dd, J = 7.8, 1.1 Hz, 1H), 8.19 (dd, J = 4.7, 1.6 Hz, 1H), 11.56 (s, 1H); MS (ESI$^+$): 488 [M + H]$^+$. |
| EX.573 | 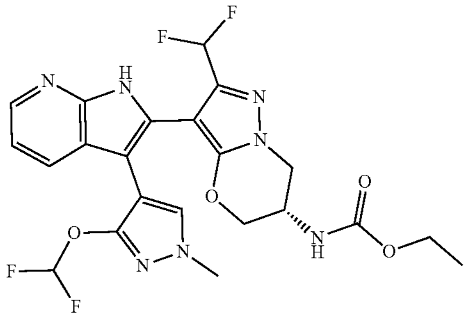 [SMILES: CCOC(=O)N[C@@H]1COc2c(-c3[nH]c4ncccc4c3-c3cn(C)nc3OC(F)F)c(C(F)F)nn2C1] | $^1$H-NMR (400 MHz, DMSO-$d_6$) δ 1.17 (t, J = 7.1 Hz, 3H), 3.75 (s, 3H), 4.01-4.12 (m, 3H), 4.21-4.41 (m, 4H), 6.61 (t, J = 53.8 Hz, 1H), 6.93-7.30 (m, 2H), 7.56 (s, 1H), 7.63 (s, 1H), 7.81-7.83 (m, 1H), 8.22 (dd, J = 4.6, 1.5 Hz, 1H), 11.67 (s, 1H); MS (ESI$^+$): 524 [M + H]$^+$. |
| EX.574 | 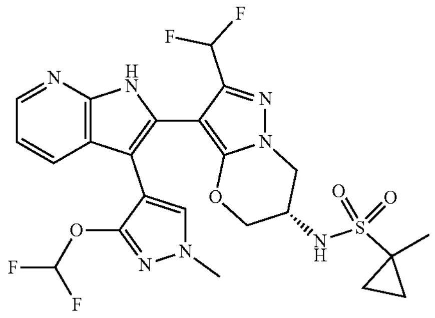 [SMILES: Cn1cc(-c2c(-c3c(C(F)F)nn4c3OC[C@@H](NS(=O)(=O)C3(C)CC3)C4)[nH]c3ncccc23)c(OC(F)F)n1] | $^1$H-NMR (400 MHz, DMSO-$d_6$) δ 0.85-0.90 (m, 2H), 1.17-1.24 (m, 2H), 1.43 (s, 3H), 3.75 (s, 3H), 4.11-4.30 (m, 4H), 4.41-4.47 (m, 1H), 6.66 (t, J = 54.0 Hz, 1H), 6.94-7.32 (m, 2H), 7.57 (s, 1H), 7.81-7.85 (m, 2H), 8.23 (dd, J = 4.6, 1.5 Hz, 1H), 11.68 (s, 1H); MS (ESI$^+$): 570 [M + H]$^+$. |

-continued

| Compound No. | Chemical structural formula | Spectrum data |
|---|---|---|
| EX.575 | 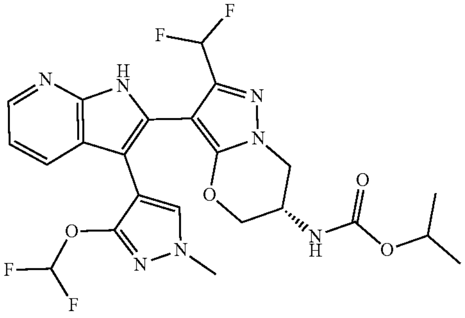 [SMILES: CC(C)OC(=O)N[C@@H]1COc2c(-c3[nH]c4ncccc4c3-c3cn(C)nc3OC(F)F)c(C(F)F)nn2C1] | $^1$H-NMR (400 MHz, DMSO-d$_6$) δ 1.14-1.30 (m, 6H), 3.61-3.95 (m, 3H), 4.04-4.45 (m, 5H), 4.76-4.84 (m, 1H), 6.60 (t, J = 54.0 Hz, 1H), 6.92-7.29 (m, 2H), 7.53-7.61 (m, 2H), 7.81-7.85 (m, 1H), 8.22 (dd, J = 4.7, 1.6 Hz, 1H), 11.66 (s, 1H); MS (ESI$^+$): 538 [M + H]$^+$. |
| EX.576 | 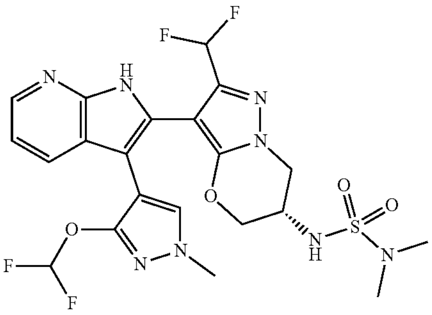 [SMILES: CN(C)S(=O)(=O)N[C@@H]1COc2c(-c3[nH]c4ncccc4c3-c3cn(C)nc3OC(F)F)c(C(F)F)nn2C1] | $^1$H-NMR (400 MHz, DMSO-d$_6$) δ 2.68 (s, 6H), 3.74 (s, 3H), 3.98-4.04 (m, 1H), 4.16-4.29 (m, 3H), 4.41 (dd, J = 12.6, 4.8 Hz, 1H), 6.66 (t, J = 54.0 Hz, 1H), 6.94-7.31 (m, 2H), 7.55 (s, 1H), 7.77-7.84 (m, 2H), 8.23 (dd, J = 4.7, 1.6 Hz, 1H), 11.68 (s, 1H); MS (ESI$^+$): 559 [M + H]$^+$. |
| EX.577 | 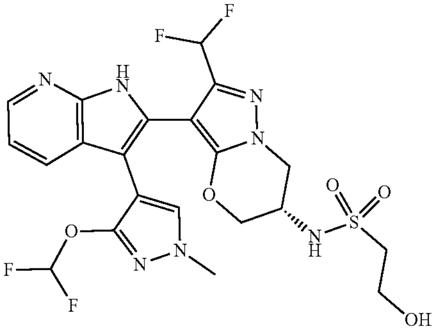 [SMILES: Cn1cc(-c2c(-c3c(C(F)F)nn4c3OC[C@@H](NS(=O)(=O)CCO)C4)[nH]c3ncccc23)c(OC(F)F)n1] | $^1$H-NMR (400 MHz, DMSO-d$_6$) δ 3.28-3.38 (m, 2H), 3.73-3.80 (m, 5H), 4.08-4.45 (m, 5H), 5.01-5.05 (m, 1H), 6.66 (t, J = 54.0 Hz, 1H), 6.94-7.31 (m, 2H), 7.53 (s, 1H), 7.60-7.65 (m, 1H), 7.80-7.83 (m, 1H), 8.22 (dd, J = 4.7, 1.5 Hz, 1H), 11.70 (s, 1H); MS (ESI$^+$): 560 [M + H]$^+$. |
| EX.578 | 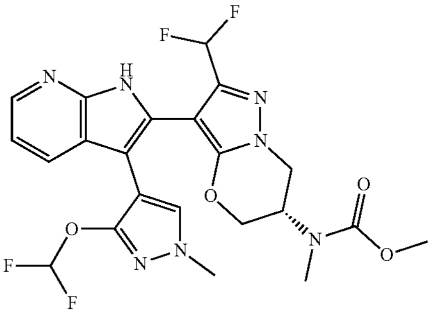 [SMILES: COC(=O)N(C)[C@@H]1COc2c(-c3[nH]c4ncccc4c3-c3cn(C)nc3OC(F)F)c(C(F)F)nn2C1] | $^1$H-NMR (400 MHz, DMSO-d$_6$) δ 2.72 (s, 3H), 3.63 (s, 3H), 3.73 (s, 3H), 4.31-4.64 (m, 5H), 6.54-7.28 (m, 3H), 7.54 (s, 1H), 7.78-7.81 (m, 1H), 8.22 (dd, J = 4.7, 1.5 Hz, 1H), 11.77 (s, 1H); MS (ESI$^+$): 524 [M + H]$^+$. |

-continued
| Compound No. | Chemical structural formula | Spectrum data |
|---|---|---|
| EX.579 | 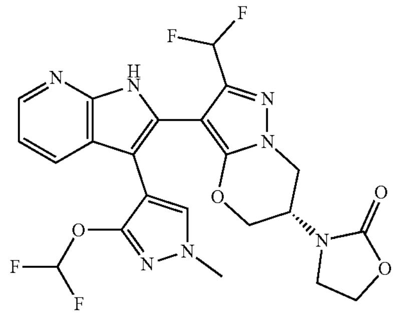 [SMILES: Cn1cc(-c2c(-c3c(C(F)F)nn4c3OC[C@@H](N3CCOC3=O)C4)[nH]c3ncccc23)c(OC(F)F)n1] | $^1$H-NMR (400 MHz, DMSO-$d_6$) δ 3.29-3.47 (m, 2H), 3.74 (s, 3H), 4.24 (t, J = 8.0 Hz, 2H), 4.34-4.51 (m, 5H), 6.54-7.28 (m, 3H), 7.58 (s, 1H), 7.79-7.81 (m, 1H), 8.23 (dd, J = 4.6, 1.6 Hz, 1H), 11.78 (s, 1H); MS (ESI$^+$): 522 [M + H]$^+$. |
| EX.580 | 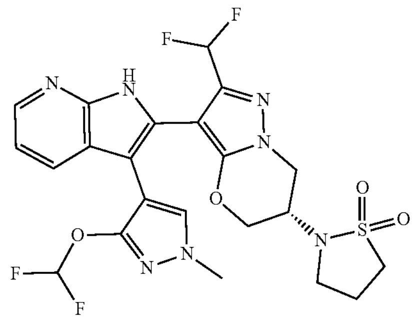 [SMILES: Cn1cc(-c2c(-c3c(C(F)F)nn4c3OC[C@@H](N3CCCS3(=O)=O)C4)[nH]c3ncccc23)c(OC(F)F)n1] | $^1$H-NMR (400 MHz, DMSO-$d_6$) δ 2.17-2.24 (m, 2H), 3.09-3.29 (m, 4H), 3.74 (s, 3H), 4.14 (s, 1H), 4.32-4.50 (m, 4H), 6.69 (t, J = 54.0 Hz, 1H), 6.86-7.23 (m, 2H), 7.58 (s, 1H), 7.80 (dd, J = 8.0, 1.3 Hz, 1H), 8.22 (dd, J = 4.6, 1.5 Hz, 1H), 11.78 (s, 1H); MS (ESI$^+$): 556 [M + H]$^+$. |
| EX.581 | 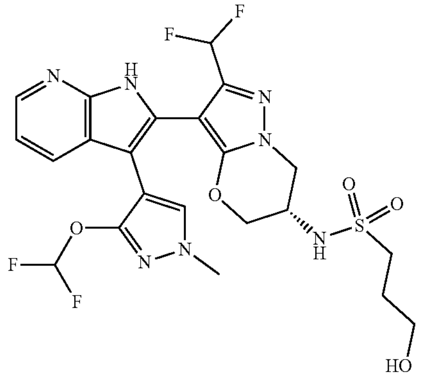 [SMILES: Cn1cc(-c2c(-c3c(C(F)F)nn4c3OC[C@@H](NS(=O)(=O)CCCO)C4)[nH]c3ncccc23)c(OC(F)F)n1] | $^1$H-NMR (400 MHz, DMSO-$d_6$) δ 1.76-1.84 (m, 2H), 3.15-3.21 (m, 2H), 3.43-3.52 (m, 2H), 3.75 (s, 3H), 4.07-4.30 (m, 4H), 4.41-4.47 (m, 1H), 4.65-4.71 (m, 1H), 6.66 (t, J = 53.9 Hz, 1H), 6.94-7.32 (m, 2H), 7.54 (s, 1H), 7.69-7.84 (m, 2H), 8.23 (d, J = 4.6 Hz, 1H), 11.69 (s, 1H); MS (ESI$^+$): 574 [M + H]$^+$. |

(217) Experimental procedure of (S)-3-(3-(3-(difluoromethoxy)-1-methyl-1H-pyrazol-4-yl)-1H-pyrrolo[2,3-b]pyridin-2-yl)-2-(difluoromethyl)-N-methyl-6,7-dihydro-5H-pyrazolo[5,1-b][1,3]oxazin-6-amine (EX.582)

EX. 582

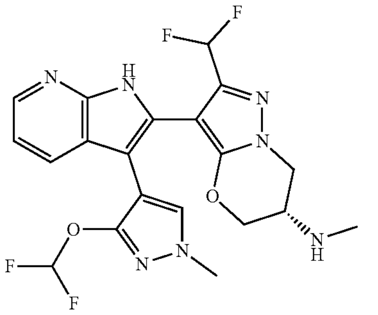

EX.582 was synthesized from compound 405 using conditions analogous to EX.527 and compound 457; $^{1}$H-NMR (400 MHz, DMSO-$d_6$) § 2.32 (3H, s), 3.15 (1H, s), 3.71 (3H, s), 3.96-4.00 (1H, m), 4.14-4.27 (3H, m), 6.64 (1H, t, J=54.1 Hz), 7.05 (1H, dd, J=7.9, 4.7 Hz), 7.09 (1H, t, J=74.0 Hz), 7.52 (1H, s), 7.79 (1H, dd, J=7.9, 1.1 Hz), 8.19 (1H, dd, J=4.7, 1.6 Hz), 11.70 (1H, s); MS (ESI$^{+}$): 466 $[M+H]^{+}$.

(218) Reference Procedure of (S)-2-((3-(3-(3-(difluoromethoxy)-1-methyl-1H-pyrazol-4-yl)-1H-pyrrolo[2,3-b]pyridin-2-yl)-2-(difluoromethyl)-6,7-dihydro-5H-pyrazolo[5,1-b][1,3]oxazin-6-yl)oxy) acetic acid (465)

(465)

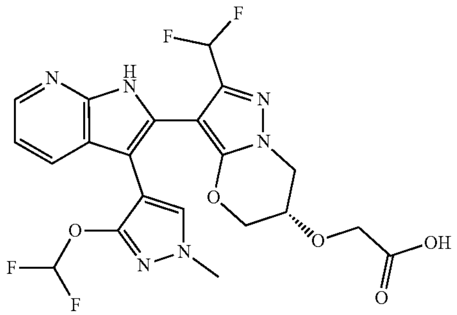

The compound 465 was synthesized from EX.530 using conditions analogous to compound 214; $^{1}$H-NMR (400 MHz, DMSO-$d_6$) δ 3.74 (s, 3H), 4.17-4.24 (m, 3H), 4.27-4.38 (m, 3H), 4.46-4.53 (m, 1H), 6.71 (t, J=54.1 Hz, 1H), 7.09 (dd, J=7.9, 4.7 Hz, 1H), 7.12 (t, J=73.9 Hz, 1H), 7.51 (s, 1H), 7.82 (dd, J=7.9, 1.0 Hz, 1H), 8.23 (dd, J=4.7, 1.6 Hz, 1H), 11.77 (s, 1H), 12.84 (s, 1H); MS (ESI$^{+}$): 511 $[M+H]^{+}$.

The following compounds were also synthesized from the corresponding starting materials and reagents using conditions analogous to compound 214.

| Compound No. | Chemical structural formula | Spectrum data |
|---|---|---|
| 466 | 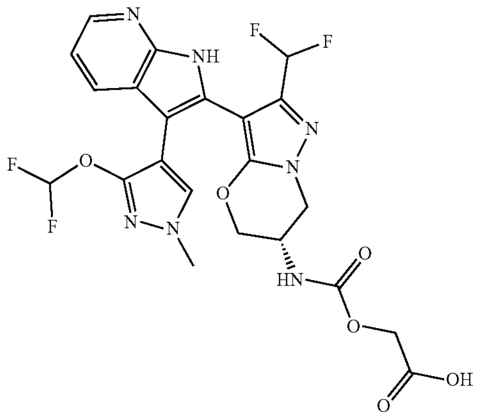 [SMILES: Cn1cc(-c2c(-c3c(C(F)F)nn4c3OC[C@@H](NC(=O)OCC(=O)O)C4)[nH]c3ncccc23)c(OC(F)F)n1] | $^{1}$H-NMR (400 MHz, DMSO-$d_6$) δ 3.15 (s, 2H), 3.75 (s, 3H), 4.00-4.39 (m, 5H), 6.58 (t, J = 54.1 Hz, 1H), 6.94-7.31 (m, 2H), 7.58 (s, 2H), 7.82 (dd, J = 7.8, 1.4 Hz, 1H), 8.22 (dd, J = 4.7, 1.5 Hz, 1H), 11.69 (s, 1H); MS (ESI$^{+}$): 554 $[M + H]^{+}$. |

-continued

| Compound No. | Chemical structural formula | Spectrum data |
|---|---|---|
| 467 | 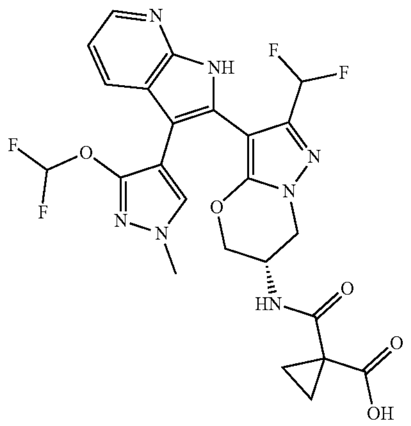 [SMILES: Cn1cc(-c2c(-c3c(C(F)F)nn4c3OC[C@@H](NC(=O)C3(C(=O)O)CC3)C4)[nH]c3ncccc23)c(OC(F)F)n1] | $^1$H-NMR (400 MHz, DMSO-$d_6$) δ 1.39 (s, 4H), 3.74 (s, 3H), 4.14-4.50 (m, 5H), 6.64 (t, J = 54.1 Hz, 1H), 6.93-7.30 (m, 2H), 7.52 (s, 1H), 7.82 (d, J = 7.8 Hz, 1H), 8.23 (dd, J = 4.6, 1.4 Hz, 1H), 9.27 (s, 1H), 11.76 (s, 1H), 13.11 (s, 1H); MS ($ESI^+$): 564 $[M + H]^+$. |

(219) Experimental procedure of (S)-2-((3-(3-(3-(difluoromethoxy)-1-methyl-1H-pyrazol-4-yl)-1H-pyrrolo[2,3-b]pyridin-2-yl)-2-(difluoromethyl)-6,7-dihydro-5H-pyrazolo[5,1-b][1,3]oxazin-6-yl)oxy)acetamide (EX.583)

EX. 583

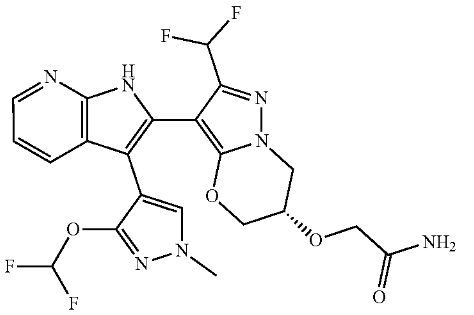

EX.583 was synthesized from compound 465 using conditions analogous to compound 130; $^1$H-NMR (400 MHz, DMSO-$d_6$) δ 3.74 (s, 3H), 4.14-4.47 (m, 4H), 4.54-4.62 (m, 1H), 5.72-5.81 (m, 2H), 6.70 (t, J=54.1 Hz, 1H), 6.92-7.35 (m, 4H), 7.53 (s, 1H), 7.82 (dd, J=7.9, 1.2 Hz, 1H), 8.23 (dd, J=4.6, 1.5 Hz, 1H), 11.77 (s, 1H); MS ($ESI^+$): 510 $[M+H]^+$.

The following compounds were also synthesized from the corresponding starting materials and reagents using conditions analogous to 130.

| Compound No. | Chemical structural formula | Spectrum data |
|---|---|---|
| EX.584 | 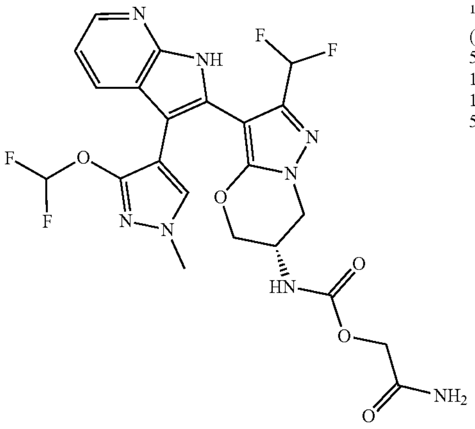 | $^{1}$H-NMR (400 MHz, DMSO-$d_6$) δ 3.74 (s, 3H), 4.09-4.44 (m, 7H), 6.63 (t, J = 54.0 Hz, 1H), 6.93-7.37 (m, 4H), 7.56 (s, 1H), 7.79-7.84 (m, 2H), 8.22 (dd, J = 4.7, 1.5 Hz, 1H), 11.69 (s, 1H); MS (ESI$^+$): 553 [M + H]$^+$. |
| EX.585 | 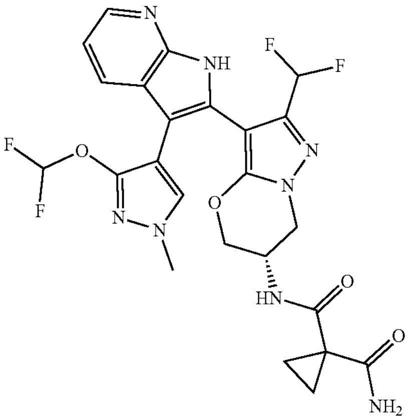 [SMILES: Cn1cc(-c2c(-c3c(C(F)F)nn4c3OC[C@@H](NC(=O)C3(C(N)=O)CC3)C4)[nH]c3ncccc23)c(OC(F)F)n1] | $^{1}$H-NMR (400 MHz, DMSO-$d_6$) δ 1.29-1.36 (m, 4H), 3.73 (s, 3H), 4.11-4.17 (m, 1H), 4.26 (s, 2H), 4.38-4.53 (m, 2H), 6.63 (t, J = 53.9 Hz, 1H), 6.93-7.32 (m, 4H), 7.50 (s, 1H), 7.82 (d, J = 7.9 Hz, 1H), 8.21-8.25 (m, 1H), 9.49-9.52 (m, 1H), 11.76 (s, 1H); MS (ESI$^+$): 563 [M + H]$^+$. |

(220) Experimental procedure of (S)—N-(3-(3-(3-(difluoromethoxy)-1-methyl-1H-pyrazol-4-yl)-1H-pyrrolo[2,3-b]pyridin-2-yl)-2-(difluoromethyl)-6,7-dihydro-5H-pyrazolo[5,1-b][1,3]oxazin-6-yl)-3-hydroxy-3-methylbutanamide (EX.586)

EX. 586

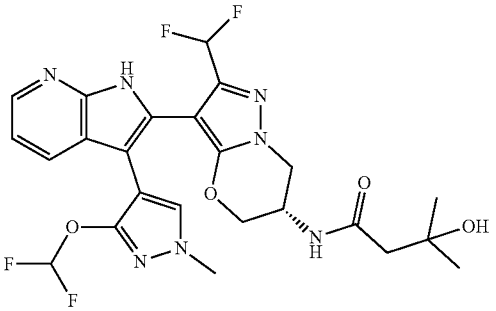

EX.586 was synthesized from EX.543 using conditions analogous to compound 444; LH-NMR (400 MHz, DMSO-$d_6$) δ 1.10-1.17 (m, 6H), 2.24 (s, 2H), 3.75 (s, 3H), 4.06-4.47 (m, 5H), 4.67 (s, 1H), 6.65 (t, J=54.1 Hz, 1H), 6.93-7.31 (m, 2H), 7.53 (s, 1H), 7.81-7.84 (m, 1H), 8.23 (dd, J=4.7, 1.6 Hz, 1H), 8.30 (d, J=6.4 Hz, 1H), 11.71 (s, 1H); MS ($ESI^+$): 552 $[M+H]^+$.

The following compounds were also synthesized from the corresponding starting materials and reagents using conditions analogous to compound 444.

| Compound No. | Chemical structural formula | Spectrum data |
|---|---|---|
| EX.587 | 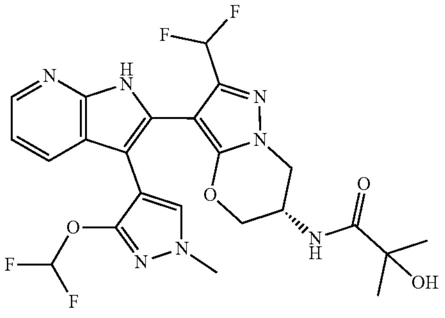 [SMILES: Cn1cc(-c2c(-c3c(C(F)F)nn4c3OC[C@@H](NC(=O)C(C)(C)O)C4)[nH]c3ncccc23)c(OC(F)F)n1] | $^1$H-NMR (400 MHz, DMSO-$d_6$) δ 1.26 (s, 6H), 3.75 (s, 3H), 4.11-4.50 (m, 5H), 5.57 (dd, J = 5.7, 3.7 Hz, 1H), 6.64 (t, J = 54.0 Hz, 1H), 6.91-7.29 (m, 2H), 7.58 (s, 1H), 7.80-7.84 (m, 1H), 7.99 (d, J = 7.9 Hz, 1H), 8.23 (dd, J = 4.7, 1.6 Hz, 1H), 11.77 (s, 1H); MS ($ESI^+$): 538 $[M + H]^+$. |
| EX.588 | 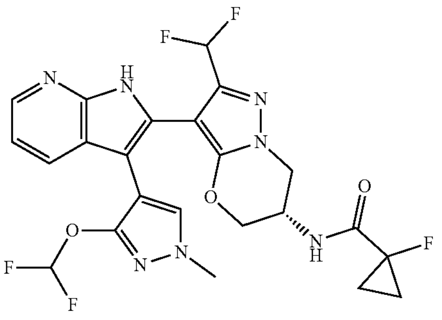 [SMILES: Cn1cc(-c2c(-c3c(C(F)F)nn4c3OC[C@@H](NC(=O)C3(F)CC3)C4)[nH]c3ncccc23)c(OC(F)F)n1] | $^1$H-NMR (400 MHz, DMSO-$d_6$) δ 1.20-1.29 (2H, m), 1.30-1.41 (2H, m), 3.76 (3H, s), 4.16-4.33 (3H, m), 4.39-4.49 (1H, m), 4.52-4.61 (1H, m), 6.66 (1H, t, J = 54.0 Hz), 6.91-7.31 (2H, m), 7.60 (1H, s), 7.84 (1H, dd, J = 7.9, 1.3 Hz), 8.24 (1H, dd, J = 4.7, 1.6 Hz), 8.78 (1H, d, J = 7.0 Hz), 11.75 (1H, s); MS ($ESI^+$): 538 $[M + H]^+$. |

-continued

| Compound No. | Chemical structural formula | Spectrum data |
|---|---|---|
| EX.589 | 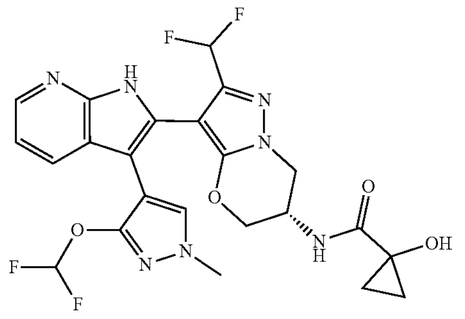 [SMILES: Cn1cc(-c2c(-c3c(C(F)F)nn4c3OC[C@@H](NC(=O)C3(O)CC3)C4)[nH]c3ncccc23)c(OC(F)F)n1] | $^1$H-NMR (400 MHz, DMSO-$d_6$) δ 0.83-0.97 (2H, m), 1.01-1.12 (2H, m), 3.76 (3H, s), 4.14-4.30 (3H, m), 4.33-4.43 (1H, m), 4.50-4.61 (1H, m), 6.40 (1H, s), 6.64 (1H, t, J = 54.0 Hz), 6.91-7.32 (2H, m), 7.60 (1H, s), 7.83 (1H, dd, J = 7.9, 1.3 Hz), 8.20-8.29 (2H, m), 11.78 (1H, s); MS (ESI$^+$): 536 [M + H]$^+$. |
| EX.590 | 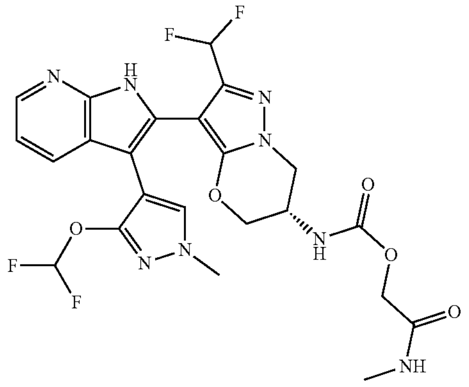 [SMILES: CNC(=O)COC(=O)N[C@@H]1COc2c(-c3[nH]c4ncccc4c3-c3cn(C)nc3OC(F)F)c(C(F)F)nn2C1] | $^1$H-NMR (400 MHz, DMSO-$d_6$) δ 2.59 (d, J = 4.5 Hz, 3H), 3.74 (s, 3H), 4.10-4.44 (m, 7H), 6.63 (t, J = 54.0 Hz, 1H), 6.93-7.31 (m, 2H), 7.57 (s, 1H), 7.80-7.88 (m, 3H), 8.23 (dd, J = 4.7, 1.5 Hz, 1H), 11.68 (s, 1H); MS (ESI$^+$): 567 [M + H]$^+$. |
| EX.591 | 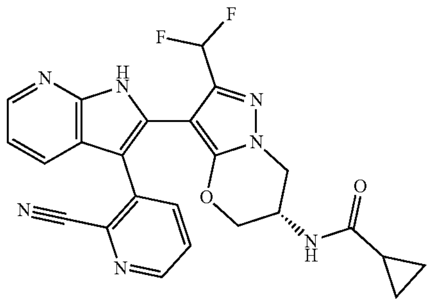 [SMILES: N#Cc1ncccc1-c1c(-c2c(C(F)F)nn3c2OC[C@@H](NC(=O)C2CC2)C3)[nH]c2ncccc12] | $^1$H-NMR (400 MHz, DMSO-$d_6$) δ 0.64-0.75 (m, 4H), 1.53-1.60 (m, 1H), 3.98-4.14 (m, 3H), 4.30-4.41 (m, 2H), 6.77 (t, J = 54.0 Hz, 1H), 7.17 (dd, J = 8.0, 4.7 Hz, 1H), 7.69 (dd, J = 8.0, 4.7 Hz, 1H), 7.82-7.88 (m, 2H), 8.29-8.46 (m, 2H), 8.66 (dd, J = 4.7, 1.5 Hz, 1H), 12.16 (s, 1H); MS (ESI$^+$): 476 [M + H]$^+$. |
| EX.592 | 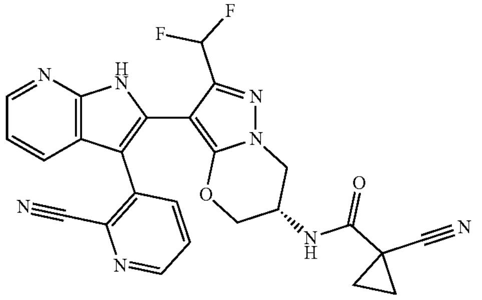 [SMILES: N#Cc1ncccc1-c1c(-c2c(C(F)F)nn3c2OC[C@@H](NC(=O)C2(C#N)CC2)C3)[nH]c2ncccc12] | $^1$H-NMR (400 MHz, DMSO-$d_6$) δ 1.51-1.70 (4H, m), 3.76 (3H, s), 4.14-4.30 (3H, m), 4.35-4.54 (2H, m), 6.66 (1H, t, J = 54.0 Hz), 6.90-7.32 (2H, m), 7.58 (1H, s), 7.83 (1H, dd, J = 7.9, 1.5 Hz), 8.24 (1H, dd, J = 4.7, 1.6 Hz), 8.58 (1H, s), 11.77 (1H, s); MS (ESI$^+$): 545 [M + H]$^+$. |

(221) Experimental procedure of (S)—N-(3-(3-(3-cyano-1-methyl-1H-pyrazol-4-yl)-1H-pyrrolo[2,3-b]pyridin-2-yl)-2-(difluoromethyl)-6,7-dihydro-5H-pyrazolo[5,1-b][1,3]oxazin-6-yl)cyclopropanecarboxamide (EX.593)

EX. 593

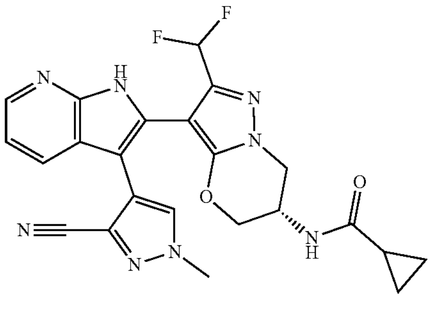

EX.593 was synthesized from EX.511 using conditions analogous to compound 381; $^1$H-NMR (400 MHz, DMSO-$d_6$) δ 0.65-0.77 (m, 4H), 1.55-1.64 (m, 1H), 3.97 (s, 3H), 4.05-4.15 (m, 1H), 4.17-4.28 (m, 2H), 4.38-4.50 (m, 2H), 6.68 (t, J=54.0 Hz, 1H), 7.15 (dd, J=7.9, 4.7 Hz, 1H), 7.92 (dd, J=7.9, 1.1 Hz, 1H), 8.00 (s, 1H), 8.29 (dd, J=4.7, 1.5 Hz, 1H), 8.48-8.49 (m, 1H), 11.98 (s, 1H); MS (ESI$^+$): 479 $[M+H]^+$.

(222) Experimental procedure of (S)—N-(3-(3-(2-(difluoromethoxy)pyridin-3-yl)-1H-pyrrolo[2,3-b]pyridin-2-yl)-2-methyl-6,7-dihydro-5H-pyrazolo[5,1-b][1,3]oxazin-6-yl)cyclopropanecarboxamide (EX.594)

EX. 594

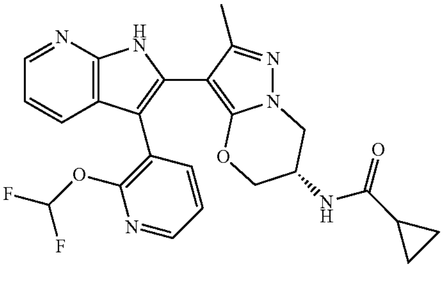

EX.594 was synthesized from EX.510 using conditions analogous to compound 381; $^1$H-NMR (400 MHz, DMSO-$d_6$) δ0.63-0.88 (m, 4H), 1.56-1.68 (m, 1H), 1.86-2.09 (m, 3H), 3.55-3.77 (m, 2H), 3.85-4.07 (m, 2H), 4.17-4.33 (m, 1H), 6.85-7.29 (m, 3H), 7.54-7.93 (m, 3H), 8.16-8.27 (m, 1H), 8.44-8.50 (m, 1H), 11.82 (s, 1H); MS (ESI$^+$): 481 $[M+H]^+$.

(223) Experimental procedure of 3-((S)-3-(3-(3-(difluoromethoxy)-1-methyl-1H-pyrazol-4-yl)-1H-pyrrolo[2,3-b]pyridin-2-yl)-2-(difluoromethyl)-6,7-dihydro-5H-pyrazolo[5,1-b][1,3]oxazin-6-yl)-1-((S)-2-hydroxypropyl)-1-methylurea (EX.595)

EX. 595

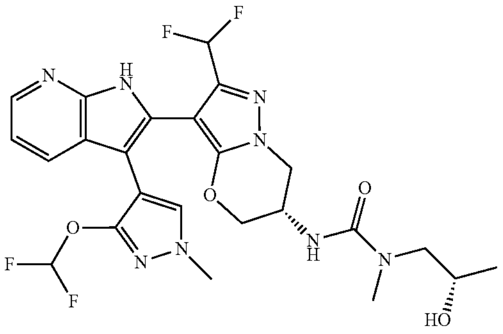

To a stirred suspension of EX.543 (50.0 mg, 0.111 mmol) in THF (0.8 mL) at room temperature under Ar atmosphere, 4-nitrophenyl chloroformate (25.0 mg, 0.124 mmol) and pyridine (0.011 mL, 0.136 mmol) were added. After stirring at room temperature for 1 h, a solution of (2S)-1-(methylamino)propan-2-ol (30.0 mg, 0.337 mmol) in THF (0.2 mL) and N,N-diisopropylethylamine (0.029 mL, 0.168 mmol) were added, and the reaction mixture was stirred at room temperature for 1 h. Water was added, and the resulting mixture was extracted with EtOAc. The organic layer was concentrated, and the residue was purified by silica gel column chromatography (0-20% MeOH/$CHCl_3$) to yield EX.595 (27.0 mg, 43%) as a white solid; $^1$H-NMR (400 MHz, DMSO-$d_6$) δ 1.00 (d, J=6.3 Hz, 3H), 2.86 (s, 3H), 3.06 (dd, J=14.4, 7.4 Hz, 1H), 3.19 (dd, J=14.4, 4.2 Hz, 1H), 3.73-3.84 (m, 4H), 4.08-4.17 (m, 2H), 4.20-4.27 (m, 1H), 4.29-4.40 (m, 2H), 4.79-4.86 (m, 1H), 6.43-6.49 (m, 1H), 6.63 (t, J=54 Hz, 1H), 6.91-7.30 (m, 2H), 7.59 (s, 1H), 7.83 (dd, J=8.0, 1.3 Hz, 1H), 8.24 (dd, J=4.6, 1.5 Hz, 1H), 11.73 (s, 1H); MS (ESI$^+$): 567 $[M+H]^+$.

(224) Experimental procedure of 2-cyclopropyl-3-(3-(3-(difluoromethoxy)-1-methyl-1H-pyrazol-4-yl)-1H-pyrrolo[2,3-b]pyridin-2-yl)-6,7-dihydro-5H-pyrazolo[5,1-b][1,3]oxazine hydrochloride (EX.596)

EX. 596

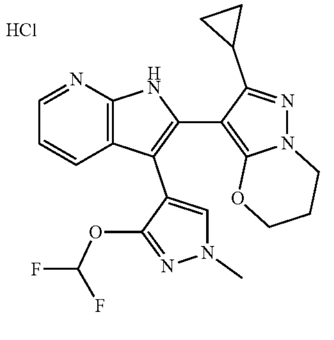

To a stirred solution of EX.420 (5.6 mg, 0.0131 mmol) in acetone (0.17 mL) at room temperature, 6 mol/L HCl (0.003 mL) was added. After stirring at 40° C. for 0.5 h, followed by stirring at room temperature for 1 h, the resulting precipitate was collected by filtration. The solid was then washed with acetone to yield EX.596 (4.5 mg, 74%) as a pale yellow solid; $^1$H-NMR (400 MHz, $CD_3OD$) δ 0.67-0.82 (4H, m), 1.51-1.64 (1H, m), 2.29-2.40 (2H, m), 3.81-3.89 (3H, m), 4.13-4.25 (2H, m), 4.38-4.49 (2H, m), 6.82-7.23 (1H, m), 7.60-7.79 (2H, m), 8.38-8.46 (1H, m), 8.60-8.69 (1H, m).

The following compounds were synthesized from the corresponding starting materials and reagents using conditions analogous to EX.596.

| Compound No. | Chemical structural formula | Spectrum data |
|---|---|---|
| EX.597 | 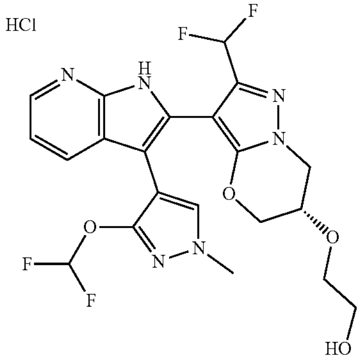 [SMILES: Cl ; Cn1cc(-c2c(-c3c(C(F)F)nn4c3OC[C@@H](OCCO)C4)[nH]c3ncccc23)c(OC(F)F)n1] | $^1$H-NMR (400 MHz, DMSO-$d_6$) δ 3.49-3.62 (4H, m), 3.70-4.04 (4H, m), 4.14-4.50 (5H, m), 6.72 (1H, t, J = 54.0 Hz), 6.91-7.33 (2H, m), 7.54 (1H, s), 7.91-7.96 (1H, m), 8.28 (1H, d, J = 4.7 Hz), 12.00 (1H, s). |
| EX.598 | 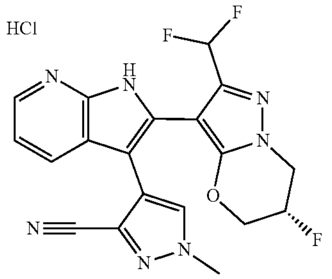 [SMILES: Cl ; Cn1cc(-c2c(-c3c(C(F)F)nn4c3OC[C@@H](F)C4)[nH]c3ncccc23)c(C#N)n1] | $^1$H-NMR (400 MHz, $CD_3OD$) δ 4.02 (3H, s), 4.28-4.62 (4H, m), 5.35-5.48 (1H, m), 6.52 (1H, t, J = 54.0 Hz), 7.66 (1H, dd, J - 7.9, 5.9 Hz), 7.98 (1H, s), 8.47 (1H, dd, J = 5.9, 1.1 Hz), 8.67 (1H, dd, J = 7.9, 1.2 Hz). |
| EX.599 | 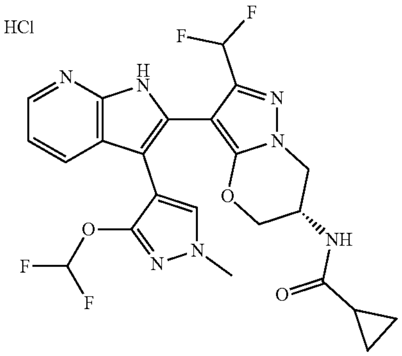 [SMILES: Cl ; Cn1cc(-c2c(-c3c(C(F)F)nn4c3OC[C@@H](NC(=O)C3CC3)C4)[nH]c3ncccc23)c(OC(F)F)n1] | $^1$H-NMR (400 MHz, $CD_3OD$) δ 0.76-0.82 (2H, m), 0.86-0.91 (2H, m), 1.59-1.66 (1H, m), 3.83 (3H, s), 4.18-4.32 (3H, m), 4.45 (1H, dd, J = 12.7, 5.1 Hz), 4.52-4.57 (1H, m), 6.52 (1H, t, J = 54.0 Hz), 6.94 (1H, t, J = 73.6 Hz), 7.55 (1H, dd, J = 7.9, 5.8 Hz), 7.61 (1H, s), 8.39 (1H, d, J = 5.6 Hz), 8.50-8.59 (2H, m). |
| EX.600 | 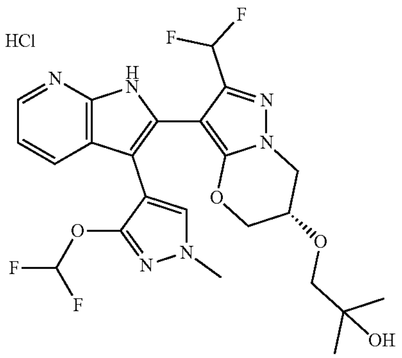 [SMILES: Cl ; Cn1cc(-c2c(-c3c(C(F)F)nn4c3OC[C@@H](OCC(C)(C)O)C4)[nH]c3ncccc23)c(OC(F)F)n1] | $^1$H-NMR (400 MHz, $CD_3OD$) δ 1.16 (6H, s), 3.40-3.47 (2H, m), 3.81 (3H, s), 4.19-4.39 (4H, m), 4.48-4.53 (1H, m), 6.38-7.10 (2H, m), 7.46-7.52 (1H, m), 7.54 (1H, s), 8.34-8.46 (2H, m). |

-continued
| Compound No. | Chemical structural formula | Spectrum data |
|---|---|---|
| EX.601 | 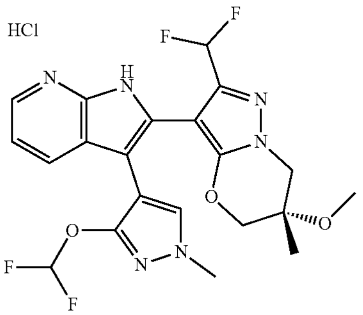 [SMILES: CO[C@]1(C)COc2c(-c3[nH]c4ncccc4c3-c3cn(C)nc3OC(F)F)c(C(F)F)nn2C1 ; Cl] | $^1$H-NMR (400 MHz, $CD_3OD$) δ 1.34 (3H, s), 3.25 (3H, s), 3.81 (3H, s), 4.03-4.10 (2H, m), 4.24-4.29 (1H, m), 4.36 (1H, dd, J = 11.9, 2.5 Hz), 6.41-7.06 (2H, m), 7.38-7.42 (1H, m), 7.50 (1H, s), 8.30-8.34 (2H, m). |
| EX.602 | 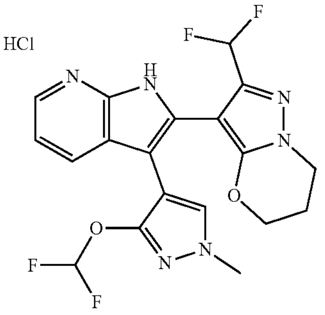 [SMILES: Cl ; Cn1cc(-c2c(-c3c(C(F)F)nn4c3OCCC4)[nH]c3ncccc23)c(OC(F)F)n1] | $^1$H-NMR (400 MHz, DMSO-$d_6$) δ 2.16-2.24 (2H, m), 3.76 (3H, s), 4.17 (2H, t, J = 5.9 Hz), 4.23-4.30 (2H, m), 6.51-6.82 (1H, m), 6.92-7.68 (3H, m), 8.09-8.25 (1H, m), 8.31-8.39 (1H, m), 12.38-12.73 (1H, m). |
| EX.603 | 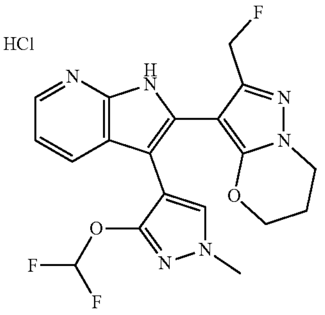 [SMILES: Cl ; Cn1cc(-c2c(-c3c(CF)nn4c3OCCC4)[nH]c3ncccc23)c(OC(F)F)n1] | $^1$H-NMR (400 MHz, $CD_3OD$) δ 2.27-2.33 (2H, m), 3.81 (3H, s), 4.19 (2H, td, J = 6.2, 2.1 Hz), 4.32 (2H, t, J = 5.1 Hz), 5.01 (2H, d, J = 48.4 Hz), 6.91 (1H, t, J = 73.6 Hz), 7.57 (1H, ddd, J = 7.9, 6.0, 0.9 Hz), 7.64 (1H, s), 8.36 (1H, d, J = 5.9 Hz), 8.55 (1H, dt, J = 7.9, 1.1 Hz). |
| EX.604 | 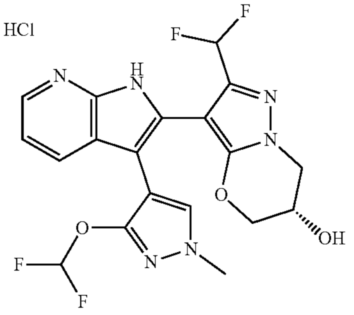 [SMILES: Cl ; Cn1cc(-c2c(-c3c(C(F)F)nn4c3OC[C@@H](O)C4)[nH]c3ncccc23)c(OC(F)F)n1] | $^1$H-NMR (400 MHz, DMSO-$d_6$) δ 3.74 (3H, s), 3.82-4.46 (6H, m), 6.71 (1H, t, J = 54.0 Hz), 6.94-7.34 (2H, m), 7.56 (1H, s), 7.98 (1H, d, J = 7.7 Hz), 8.29 (1H, dd, J = 4.9, 1.5 Hz), 12.07 (1H, s). |

-continued

| Compound No. | Chemical structural formula | Spectrum data |
|---|---|---|
| EX.605 | 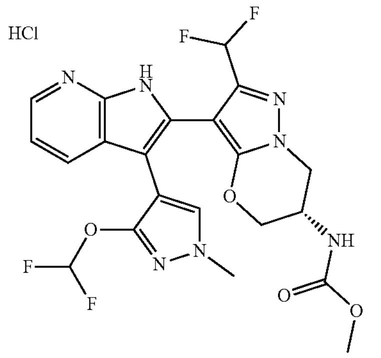 [SMILES: Cl ; COC(=O)N[C@@H]1COc2c(-c3[nH]c4ncccc4c3-c3cn(C)nc3OC(F)F)c(C(F)F)nn2C1] | $^1$H-NMR (400 MHz, DMSO-$d_6$) δ 3.59 (3H, s), 3.76 (3H, s), 4.04-4.44 (5H, m), 6.65 (1H, t, J = 54.0 Hz), 6.93-7.34 (2H, m), 7.59 (1H, s), 7.66-7.72 (1H, m), 7.91-7.97 (1H, m), 8.28 (1H, dd, J = 4.8, 1.5 Hz), 11.91 (1H, s). |
| EX.606 | 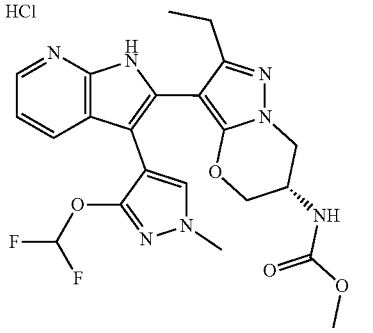 [SMILES: Cl ; CCc1nn2c(c1-c1[nH]c3ncccc3c1-c1cn(C)nc1OC(F)F)OC[C@@H](NC(=O)OC)C2] | $^1$H-NMR (400 MHz, DMSO-$d_6$) δ 0.88 (3H, t, J = 7.5 Hz), 2.25 (2H, q, J = 7.6 Hz), 3.59 (3H, s), 3.76 (3H, s), 3.94-4.33 (5H, m), 6.96-7.37 (2H, m), 7.58 (1H, s), 7.61-7.65 (1H, m), 7.85-7.91 (1H, m), 8.23 (1H, dd, J = 4.9, 1.5 Hz), 11.77 (1H, s). |

(225) Reference Procedure of 3-(2-((S)-6-amino-2-methyl-6,7-dihydro-5H-pyrazolo[5,1-b][1,3]oxazin-3-yl)-1-((2-(trimethylsilyl)ethoxy)methyl)-1H-pyrrolo[2,3-b]pyridin-3-yl)-5-methylthiophene-2-carbonitrile (468)

(468)

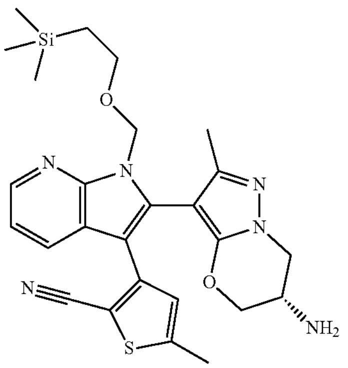

The compound 468 was synthesized from compound 332 using conditions analogous to compound 217. The crude product obtained was used directly in the next step without purification.

Reference Procedure of Compound 137

137

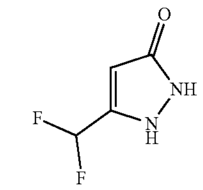

To a stirred solution of ethyl 4,4-difluoroacetoacetate (30.1 g, 181 mmol) in EtOH (30 mL) and iPrOAc (151 mL) at 0° C. under an Ar atmosphere, hydrazine hydrate (17.7 mL, 364 mmol) and AcOH (20.8 mL, 364 mmol) were added. After stirring at 60° C. for 2 h, water was added, and the resulting mixture was extracted with EtOAc. The organic layer was washed with brine, dried over $Na_2SO_4$, and concentrated to yield compound 137 (22.3 g, 94%) lid; $^1$H-NMR (400 MHz, DMSO-$d_6$) δ 5.51 (s, 1H), 6.72 (t, J=56.3 Hz, 1H), 10.84 (s, 1H), 12.46 (s, 1H); MS ($ESI^-$): 133 $[M-H]^-$.

Reference Procedure of Compound 469

469

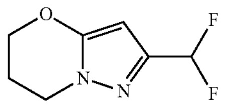

To a stirred suspension of $K_2CO_3$ (16.5 g, 119 mmol) in DMA (32 mL) at 70° C. under an Ar atmosphere, a solution of compound 137 (8.00 g, 59.7 mmol) and 1,3-dibromopropane (6.70 mL, 65.7 mmol) in DMA (16 mL) was slowly added. After stirring at the same temperature for 2.5 h, water was added, and the resulting mixture was extracted with EtOAc. The organic layer was washed with brine, dried over $Na_2SO_4$, and concentrated to yield compound 469 (10.3 g). The crude compound obtained was used directly in the next step without purification.

Reference Procedure of Compound 10wwwi

10wwwi

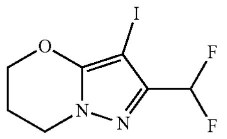

To a stirred solution of compound 469 (10.3 g) in acetonitrile (40 mL) at room temperature, NIS (14.8 g, 65.8 mmol) was added. After stirring at the same temperature for 1 h, saturated aqueous $NaHSO_3$ was added, and the resulting mixture was stirred at 0° C. for 0.5 h. The resulting precipitate was collected by filtration. The precipitated material was triturated with cold MeOH, and subsequently collected by filtration to yield compound 10wwwi (11.1 g, 62%); MS ($ESI^+$): 301 $[M+H]^+$.

Reference Procedure of Compound 10tt

10tt

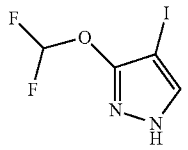

To a stirred solution of compound 51a (0.14 mL, 1.49 mmol) in DMF (3 mL), NIS (336 mg, 1.49 mmol) was added. After stirring at room temperature for 80 min. The reaction was quenched with water and extracted thrice with EtOAc. The combined organic layers were dried over $Na_2SO_4$, and concentrated to afford a light-yellow color compound (261 mg, 67%) as a crude product which was used for the next step without further purification.

Reference Procedure of Compound 10jj

10jj

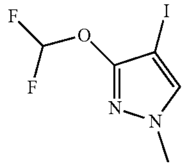

Compound 10tt (84.4 mg, 0.32 mmol) was dissolved in DMSO (0.19 mL), cooled to 0° C., added $K_2CO_3$ (68.5 mg, 0.5 mmol) and iodomethane (0.02 mL, 0.39 mmol). The reaction was stirred from 0° C. to room temperature. After 1 h additional iodomethane (0.02 mL) was added and reacted at room temperature for 1.2 h. Further addition of iodomethane (0.0099 mL) and reacted at room temperature for another 1.5 h. The reaction was partitioned between water and extracted with EtOAc. The combined organic layers were dried over $Na_2SO_4$ and concentrated in vacuo. The crude residue was purified by silica gel column chromatography (0-1% EtOAc/DCM) to afford compound 10jj (52.6 mg, 59%) as a yellow oil; MS ($ESI^+$): 275 $[M+H]^+$ Reference Procedure of Compound 470

470

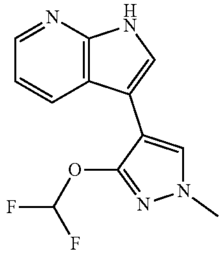

A mixture of compound 10jj (263 mg, 0.959 mmol), tert-butyl 3-(4,4,5,5-tetramethyl-1,3,2-dioxaborolan-2-yl)pyrrolo[2,3-b]pyridine-1-carboxylate (330 mg, 0.959 mmol), $PdCl_2(dppf)-CH_2Cl_2$ (157 mg, 0.192 mmol), and $Cs_2CO_3$ (937 mg, 2.88 mmol) in dioxane (6 mL) and water (2 mL) was stirred at 90° C. for 2 h under a nitrogen atmosphere. The reaction mixture was cooled to room temperature, and the aqueous phase was removed using a glass pipette. The organic layer was concentrated and then purified by silica gel column chromatography (0-60% EtOAc/n-hexane) to afford compound 470 (72 mg, 28%) as a brown oil; MS ($ESI^+$): 265 $[M+H]^+$.

Reference Procedure of Compound 471

471

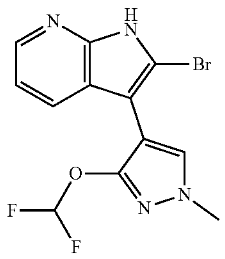

A mixture of compound 470 (72.0 mg, 0.272 mmol) and NBS (47.9 mg, 0.300 mmol) in $CH_2Cl_2$ (2 mL) was stirred at room temperature for 1 h. The reaction mixture was concentrated and the residue was purified by silica gel column chromatography (0-70% EtOAc/n-hexane) to afford compound 471 (65 mg, 69%); MS (ESI$^+$): 343, 345 $[M+H]^+$.

Reference Procedure of Compound 472

472

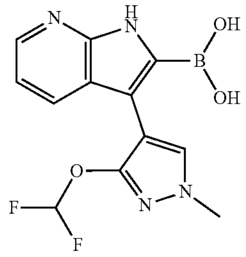

A mixture of compound 471 (80 mg, 0.26 mmol), bis (pinacolato)diboron (66.6 mg, 0.262 mmol), $PdCl_2$(dppf)-$CH_2Cl_2$ (28.6 mg, 0.0350 mmol), and AcOK (51.5 mg, 0.525 mmol) in dioxane (2 mL) was stirred at 90° C. for 3.5 h under a nitrogen atmosphere. After cooling to room temperature, the reaction mixture was diluted with $CH_2Cl_2$ and then extracted twice with 2N aqueous NaOH solution. The aqueous solution was then acidified with 12N HCl solution to pH ~5, and extracted with DCM. Finally, EtOAc was used to extract more products from the aqueous layer. The combined organic layers were dried over $Na_2SO_4$, then filtered and concentrated to provide compound 472 (47 mg) as a brown oil. The crude compound obtained was used directly in the next step without purification.

Experimental Procedure of EX.272

EX. 272

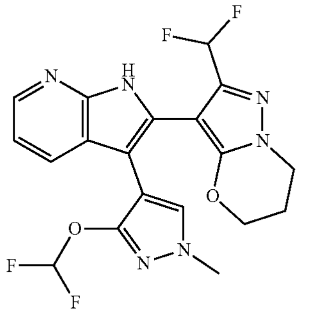

A mixture of compound 472 (60 mg, 0.26 mmol), compound 10wwwi (93.5 mg, 0.312 mmol), $PdCl_2$(dppf)-$CH_2Cl_2$ (42.4 mg, 0.0520 mmol), and $Cs_2CO_3$ (254 mg, 0.779 mmol) in dioxane (2.4 mL) and water (0.8 mL) was stirred at 90° C. for 1.5 h under a nitrogen atmosphere. After cooling to room temperature, the reaction mixture was concentrated and the residue was purified by silica gel column chromatography (0-2.5% MeOH/$CH_2Cl_2$) to afford EX.272 (26 mg, 22%); $^1$H-NMR (400 MHz, $CD_3OD$) δ 2.28-2.34 (2H, m), 3.81 (3H, s), 4.22 (2H, apparent t, J=6.2 Hz), 4.30-4.33 (2H, m), 6.44 (1H, t, $J_{H-F}$=54.1 Hz), 6.82 (1H, t, $J_{H-F}$=74.0 Hz), 7.15 (1H, dd, J=7.9, 4.8 Hz), 7.52 (1H, s), 7.97 (1H, dd, J=7.9, 1.5 Hz), 8.21 (1H, dd, J=4.8, 1.5 Hz); MS (ESI$^+$): 437 $[M+H]^+$.

Experimental Procedure of EX.602

EX. 602

HCl

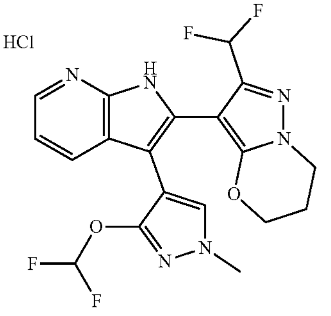

To a stirred suspension of EX.272 (3.00 g, 6.88 mmol) in THF (90 mL) at room temperature, 6 mol/L HCl (1.5 mL) was added. After stirring at 50° C. for 0.5 h, the reaction mixture was cooled to 0° C. The resulting precipitate was collected by filtration. The filtered material was then washed with THE to yield EX.602 (3.17 g, 97%); $^1$H-NMR (400 MHz, DMSO-$d_6$) δ 2.16-2.24 (2H, m), 3.76 (3H, s), 4.17 (2H, t, J=5.9 Hz), 4.23-4.30 (2H, m), 6.51-6.82 (1H, m), 6.92-7.68 (3H, m), 8.09-8.25 (1H, m), 8.31-8.39 (1H, m), 12.38-12.73 (1H, m).

Reference Procedure of Compound 10zzzz

10zzzz

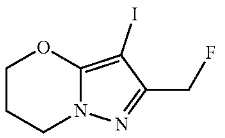

To a stirred solution of compound 10nnnna (100 g, 357 mmol, WO2020151738) in $CH_2Cl_2$ (1 L) at −10° C. under an Ar atmosphere, DAST (93.6 mL, 714 mmol) was slowly added. The reaction mixture was poured into saturated aqueous $NaHCO_3$, and the resulting insoluble material was removed by filtration. The organic layer was separated from the filtrate, and dried over $Na_2SO_4$ and concentrated in vacuo. The residue was purified by silica gel column chromatography (16-100% EtOAc/n-hexane), followed by recrystallization from EtOH to yield compound 10zzzz (32 g, 32%); $^1$H-NMR (500 MHz, $CDCl_3$) δ 2.26-2.32 (m, 2H), 4.17-4.22 (m, 2H), 4.36-4.39 (m, 2H), 5.24 (t, J=48.5 Hz, 2H).

Reference Procedure of compound 233

233

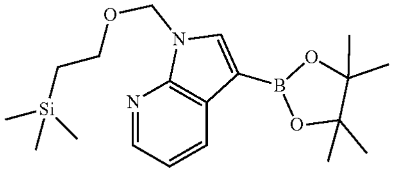

To a stirred solution of 3-bromo-1-((2-(trimethylsilyl)ethoxy)methyl)-1H-pyrrolo[2,3-b]pyridine (Journal of Organic Chemistry (2020), 85(17), 11519-11530) (157 mg, 0.480 mmol) and 2-isopropoxy-4,4,5,5-tetramethyl-1,3,2-dioxaborolane (0.15 mL, 0.722 mmol) in THF (2.4 mL) at −78° C. under an Ar atmosphere, 1.6 mol/L n-butyllithium in hexane (0.48 mL, 0.767 mmol) was slowly added. After stirring at −78° C. for 2 h, the reaction was quenched with sat. aq. $NH_4Cl$, and the resulting mixture was extracted with EtOAc. The organic layer was washed with brine, dried over $Na_2SO_4$, and concentrated. The residue was purified by silica gel column chromatography (0-20% EtOAc/hexane) to yield compound 233 (65.0 mg, 41%) as a colorless oil; $^1$H-NMR (400 MHz, $CDCl_3$) δ −0.07 (s, 9H), 0.87-0.94 (m, 2H), 1.37 (s, 12H), 3.51-3.56 (m, 2H), 5.67 (s, 2H), 7.14 (dd, J=7.8, 4.7 Hz, 1H), 7.80 (s, 1H), 8.27 (dd, J=7.8, 1.6 Hz, 1H), 8.33 (dd, J=4.7, 1.6 Hz, 1H); MS ($ESI^+$): 375 $[M+H]^+$.

Reference Procedure of Compound 473'

473'

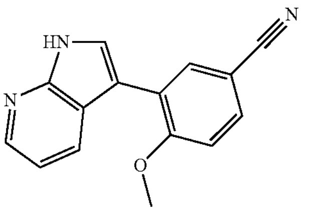

A mixture of 2-bromo-4-methoxy-benzonitrile (739 mg, 3.49 mmol), tert-butyl 3-(4,4,5,5-tetramethyl-1,3,2-dioxaborolan-2-yl)pyrrolo[2,3-b]pyridine-1-carboxylate (1.00 g, 2.91 mmol), $PdCl_2$(dppf)-$CH_2Cl_2$ (475 mg, 0.581 mmol), and $Cs_2CO_3$ (2.84 g, 2.88 mmol) in dioxane (3 mL) and water (1 mL) was stirred at 80° C. for 45 min under a nitrogen atmosphere. The reaction mixture was filtered through a pad of Celite, and the filtrate was concentrated. The residue was purified by silica gel column chromatography (30% EtOAc/n-hexane) to afford compound 473' (637 mg, 62%) as a brown oil; MS ($ESI^+$): 250 $[M+H]^+$.

Reference Procedure of Compound 473

473

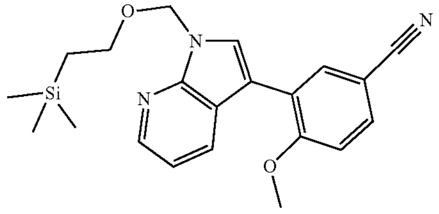

To a stirred solution of compound 473' (44.0 mg, 0.177 mmol) in DMF (1 mL) at 0° C. was added NaH (4.66 g, 0.190 mmol), and the reaction mixture was stirred at 0° C. for 1 h. After the addition of 2-(trimethylsilyl)ethoxymethyl chloride (35.3 mg, 0.212 mmol) dropwise over 10 min, the reaction mixture was stirred at room temperature for 2 h. After dilution with $CH_2Cl_2$, the mixture was washed with water. The organic layer was dried over $Na_2SO_4$, and concentrated. The residue was purified by silica gel column chromatography (0-30% EtOAc/hexane) to yield compound 473 (29 mg, 43%) as a colorless oil; MS ($ESI^+$): 380 $[M+H]^+$.

Reference Procedure of Compound 474

474

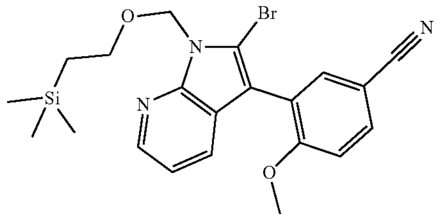

To a stirred solution of compound 473 (1.29 g, 3.39 mmol) in $CH_2Cl_2$ (20 ml) was added NBS (664 mg, 3.73 mmol) at room temperature. After stirring at the same temperature for 1 h, the reaction mixture was concentrated and the residue was purified by silica gel column chromatography (0-20% EtOAc/n-hexane) to afford compound 474 (1.39 g, 89%) as a yellow oil; MS ($ESI^+$): 458, 460 $[M+H]^+$.

Reference Procedure of Compound 475

475

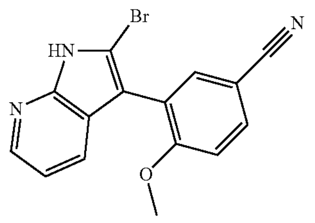

A mixture of compound 474 (857 mg, 1.87 mmol) and TFA (4.29 mL) was stirred at room temperature for 1 h. After concentration, the residue was dissolved in MeOH (4.2 mL), and ethylenediamine (3.7 mL) was added. After stirring for 1.5 h, the resulting precipitate was collected by filtration to afford compound 475 (121 mg, 71%); MS ($ESI^+$): 328, 330 $[M+H]^+$ Reference Procedure of Compound 476

476

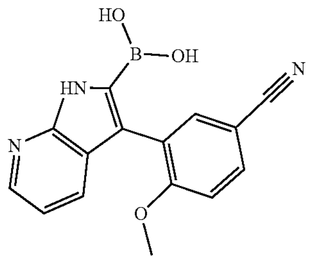

A mixture of compound 475 (167 mg, 0.509 mmol), bis(pinacolato)diboron (194 mg, 0.763 mmol), $PdCl_2$(dppf)-$CH_2Cl_2$ (41.6 mg, 0.0510 mmol), and AcOK (150 mg, 1.53 mmol) in dioxane (3 mL) was heated under reflux in a nitrogen atmosphere. After cooling to room temperature, the reaction mixture was filtered through a pad of Celite and then extracted twice with 2N aqueous NaOH solution. The aqueous solution was then acidified with 12N aqueous HCl solution to pH 6-7, and the resulting precipitate was collected by filtration to provide compound 476 (90 mg). The crude compound obtained was used directly in the next step without purification.

Experimental Procedure of EX.234

EX. 234

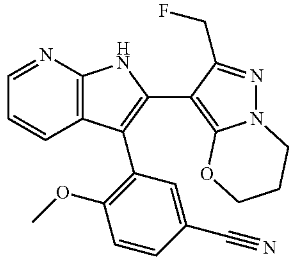

A mixture of compound 476 (44.9 mg, 0.153 mmol), compound 10zzzz (36.0 mg, 0.128 mmol), $PdCl_2$(dppf)-$CH_2Cl_2$ (20.9 mg, 0.0260 mmol), and $Cs_2CO_3$ (125 mg, 0.383 mmol) in dioxane (2 mL) and water (0.6 mL) was stirred at 90° C. for 1.5 h under a nitrogen atmosphere. The reaction mixture was cooled to room temperature, and the aqueous phase was removed using a glass pipette. The organic layer was concentrated and then purified by silica gel column chromatography (0-6% MeOH/$CH_2Cl_2$), followed by preparative HPLC to afford EX.234 (5.3 mg, 10%); $^1$H-NMR (400 MHz, DMSO-$d_6$) δ 2.12 (2H, bs), 3.79 (3H, s), 4.12 (4H, apparent t, J=5.6 Hz), 4.81-5.11 (2H, m), 6.89 (1H, d, J=2.6 Hz), 7.04 (1H, dd, J=8.7, 2.6 Hz), 7.13 (1H, dd, J=7.9, 4.7 Hz), 7.79 (1H, d, J=8.7 Hz) 7.82 (1H, dd, J=7.9, 1.6 Hz), 8.28 (1H, dd, J=4.7, 1.5 Hz), 12.00 (1H, brs); MS ($ESI^+$): 404 $[M+H]^+$.

Reference Procedure of Compound 140

140

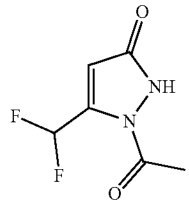

A mixture of compound 137 (15.3 g, 114 mmol) and acetic anhydride (11.0 mL, 114 mmol) in AcOH (92 mL) was stirred at room temperature for 2 h. Toluene was added, and the resulting mixture was concentrated. $CHCl_3$ was added to the residue at 0° C., and the resulting precipitate was collected by filtration to yield compound 140 (5.00 g). The filtrate was concentrated, and the residue was purified by silica gel column chromatography (10-50% EtOAc/hexane) to yield compound 140 (3.74). The combined yield of compound 140 was 8.74 g (44%); $^1$H-NMR (400 MHz, $CDCl_3$) δ 2.58 (3H, s), 6.34 (1H, s), 7.19 (1H, t, J=53.9 Hz), 9.55 (1H, s); MS ($ESI^-$): 175 $[M-H]^-$.

Reference Procedure of Compound 153

153

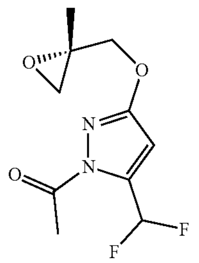

[(2R)-2-methyloxiran-2-yl]methanol (0.35 mL, 5.29 mmol), 1,1'-(azodicarbonyl)dipiperidine (2.14 g, 8.48 mmol), and then triphenylphosphine (2.23 g, 8.50 mmol) were successively added to a stirred solution of compound 140 (829 mg, 4.71 mmol) in THF (23.5 mL) at room temperature under an Ar atmosphere. After stirring at the same temperature for 14 h. Water was added, and the resulting mixture was extracted with EtOAc. The organic layer was washed with brine, dried over $Na_2SO_4$, and concentrated. The residue was purified by silica gel column chromatography (5-40% EtOAc/hexane) to yield compound 153 (731 mg, 63%) as a colorless oil; $^1$H-NMR (400 MHz, $CDCl_3$) δ 1.48 (s, 3H), 2.60 (s, 3H), 2.74 (d, J=4.7 Hz, 1H), 2.89 (d, J=4.7 Hz, 1H), 4.20 (d, J=11.3 Hz, 1H), 4.34 (d, J=11.3 Hz, 1H), 6.34 (d, J=0.6 Hz, 1H), 7.21 (td, J=54.0, 0.5 Hz, 1H); MS (ESI$^+$): 247 [M+H]$^+$.

Reference Procedure of Compound 162

162

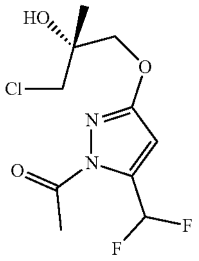

A mixture of 153 (731 mg, 2.97 mmol), AcOH (0.510 mL, 8.92 mmol), and LiCl (378 mg, 8.92 mmol) in THF (15 mL) was stirred at 60° C. for 2 h. The reaction was quenched by saturated aqueous $NaHCO_3$, and the resulting mixture was extracted with EtOAc. The organic layer was washed with brine, dried over $Na_2SO_4$, and concentrated. The residue was purified by silica gel column chromatography (5-40% EtOAc/hexane) to yield compound 162 (794 mg, 95%) as a colorless oil; $^1$H-NMR (400 MHz, $CDCl_3$) δ 1.41 (s, 3H), 2.58 (s, 1H), 2.62 (s, 3H), 3.64 (d, J=11.1 Hz, 1H), 3.68 (d, J=11.2 Hz, 1H), 4.23 (d, J=10.5 Hz, 1H), 4.29 (d, J=10.5 Hz, 1H), 6.35 (d, J=0.6 Hz, 1H), 7.21 (t, J=54.0 Hz, 1H); MS (ESI$^+$): 283 [M+H]$^+$.

Reference Procedure of Compound 169

169

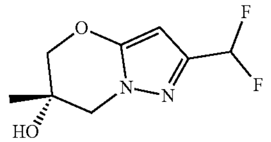

A mixture of 162 (794 mg, 2.81 mmol) and $K_2CO_3$ (1.17 g, 8.47 mmol) in DMF (14 mL) was stirred at 135° C. for 1 h. The reaction mixture was cooled to room temperature, and MeOH (14 mL) was added. After stirring at 50° C. for 1 h, the reaction mixture was filtered through a pad of Celite, and the filtrate was concentrated. The residue was purified by silica gel column chromatography (25-100% EtOAc/n-hexane) to yield compound 169 (211 mg, 37%) as a colorless oil; $^1$H-NMR (400 MHz, $CDCl_3$) δ 0.64-0.68 (2H, m), 0.84-0.89 (2H, m), 1.77-1.84 (1H, m), 2.28 (1H, s), 4.08-4.26 (4H, m), 4.35 (1H, ddd, J=7.0, 4.0, 1.8 Hz), 5.19 (1H, s); MS (ESI$^+$): 181 [M+H]$^+$.

Reference Procedure of Compound 202

202

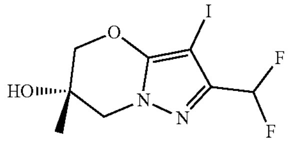

To a stirred solution of compound 169 (211 mg, 1.03 mmol) in MeCN (5.2 mL) at room temperature, NIS (698 mg, 3.10 mmol) was added. After stirring at room temperature for 2 h, the reaction was quenched with saturated aqueous $NaHCO_3$ and saturated aqueous $Na_2S_2O_3$, and the resulting mixture was extracted with EtOAc. The organic layer was washed with water, followed by brine, dried over $Na_2SO_4$, and concentrated. The residue was purified by silica gel column chromatography (25-100% EtOAc/hexane) to yield compound 202 (268 mg, 79%); $^1$H-NMR (400 MHz, $CDCl_3$) δ 1.46 (s, 3H), 2.27 (s, 1H), 4.02-4.25 (m, 4H), 6.53 (t, J=53.7 Hz, 1H); MS (ESI$^+$): 331 [M+H]$^+$.

Reference Procedure of Compound 212

212

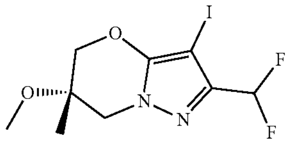

To a stirred solution of compound 202 (100 mg, 0.303 mmol) in THF (1.52 mL) at 0° C. under an Ar atmosphere, 60% sodium hydride (15.0 mg, 0.332 mmol) was added.

After stirring at 0° C. for 0.5 h, iodomethane (0.025 mL, 0.402 mmol) was added to the reaction mixture, which was stirred at room temperature for 2 h, followed by stirring at 40° C. for an additional 2 h. The reaction was quenched with saturated aqueous $NH_4Cl$, and the resulting mixture was extracted with EtOAc. The organic layer was washed with brine, dried over $Na_2SO_4$, and concentrated. The residue was purified by silica gel column chromatography (8-66% EtOAc/hexane) to yield compound 212 (86.0 mg, 83%); $^1$H-NMR (400 MHz, $CDCl_3$) δ 1.35 (s, 3H), 3.30 (s, 3H), 3.94 (dt, J=12.9, 1.4 Hz, 1H), 3.98 (d, J=11.8 Hz, 1H), 4.28 (dd, J=12.9, 2.1 Hz, 1H), 4.40 (dd, J=11.8, 2.4 Hz, 1H), 6.52 (t, J=53.9 Hz, 1H); MS (ESI$^+$): 345 [M+H]$^+$.

Reference Procedure of Compound 266

266

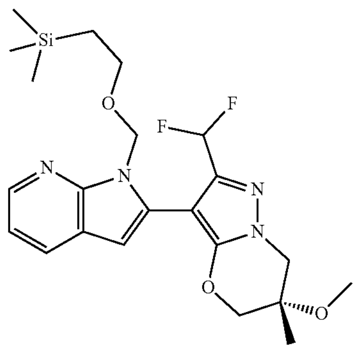

A mixture of compound 212 (89.5 mg, 0.239 mmol), 2-(4,4,5,5-tetramethyl-1,3,2-dioxaborolan-2-yl)-1-((2-(trimethylsilyl)ethoxy)methyl)-1H-pyrrolo[2,3-b]pyridine (Chemical Science (2021), 12 (4), 1528-1534) (86.4 mg, 0.251 mmol), SPhos Pd G4 (19.0 mg, 0.0239 mmol), and $K_3PO_4$ (206 mg, 0.718 mmol) in toluene (1.2 mL) was stirred at 90° C. for 14 h. The reaction mixture was cooled to room temperature and filtered through a pad of Celite. The filtrate was purified by silica gel column chromatography (12-100% EtOAc/hexane) to yield compound 266 (109 mg, 98%) as a yellow oil; $^1$H-NMR (400 MHz, $CDCl_3$) δ −0.14 (s, 9H), 0.75-0.82 (m, 2H), 1.38 (s, 3H), 3.31-3.41 (m, 5H), 3.97-4.05 (m, 2H), 4.32-4.40 (m, 2H), 5.59 (d, J=11.0 Hz, 1H), 5.74 (d, J=11.0 Hz, 1H), 6.55 (s, 1H), 6.60 (t, J=54.1 Hz, 1H), 7.09 (dd, J=7.8, 4.8 Hz, 1H), 7.88 (dd, J=7.8, 1.5 Hz, 1H), 8.33 (dd, J=4.8, 1.6 Hz, 1H); MS (ESI$^+$): 465 [M+H]$^+$.

Reference Procedure of Compound 280

280

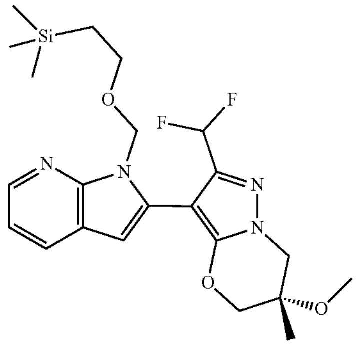

To a stirred solution of compound 266 (109 g, 0.235 mmol) in MeCN (1.2 ml) was added NBS (43.9 mg, 0.247 mmol) at room temperature. After stirring at the same temperature for 2 h, the reaction was quenched with saturated aqueous $NaHCO_3$ and saturated aqueous $Na_2S_2O_3$, and the resulting mixture was extracted with EtOAc. The organic layer was washed with brine, dried over $Na_2SO_4$, and concentrated. The residue was purified by silica gel column chromatography (8-66% EtOAc/n-hexane) to afford compound 280 (115 mg, 90%) as a yellow oil; $^1$H-NMR (400 MHz, $CDCl_3$) δ −0.11 (s, 9H), 0.77-0.90 (m, 2H), 1.38 (d, J=2.5 Hz, 3H), 3.33 (dd, J=15.9, 5.7 Hz, 3H), 3.38-3.48 (m, 2H), 3.95-4.08 (m, 2H), 4.30-4.41 (m, 2H), 5.41-5.76 (m, 2H), 6.50-6.83 (m, 1H), 7.15-7.20 (m, 1H), 7.84-7.89 (m, 1H), 8.35-8.42 (m, 1H); MS (ESI$^+$): 543 [M+H]$^+$.

Reference Procedure of Compound 232

232

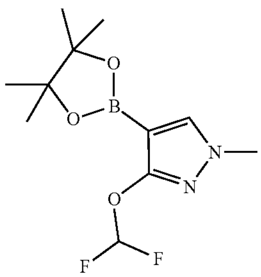

To a stirred solution of compound 10jj (44.5 g, 162 mmol) and 2-isopropoxy-4,4,5,5-tetramethyl-1,3,2-dioxaborolane (24.6 mL, 122 mmol) in THF (145 mL) at 0° C. under an Ar atmosphere, 2 mol/L isopropylmagnesium chloride in THF (52.7 mL, 105 mmol) was slowly added. After stirring at 0° C. for 0.5 h, the reaction was quenched with saturated aqueous $NH_4Cl$, and the resulting mixture was extracted with EtOAc. The organic layer was with brine, dried over $Na_2SO_4$, and concentrated under reduced pressure to approximately 110 mL. Toluene (180 mL) was added to the residue, and the mixture was concentrated under reduced pressure to approximately 110 mL. This process was repeated once more with toluene (180 mL). Toluene (73 mL) was then added to the residue, and the mixture was stirred at an external temperature of 40° C. The solvent was concentrated under reduced pressure to approximately 110 mL. IPA (180 mL) was added to the residue, and the mixture was concentrated under reduced pressure to approximately 110 mL. This process was repeated once more with IPA (180 mL). Hexane (145 mL) was added to the mixture at room temperature, followed by stirring under ice-cooling for 30 minutes. The resulting precipitate was collected by filtration to yield compound 232 (15.0 g, 34%); $^1$H-NMR (500 MHz, $CDCl_3$) § 1.30 (s, 12H), 3.77 (s, 3H), 6.96 (t, J=73.8 Hz, 1H), 7.49 (s, 1H); MS (ESI$^+$): 275 [M+H]$^+$.

Reference Procedure of Compound 292

292

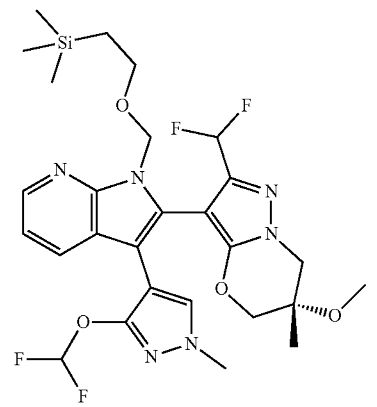

A mixture of compound 280 (115 mg, 0.212 mmol), compound 232 (116 mg, 0.423 mmol), SPhos Pd G4 (16.8 mg, 0.0212 mmol), and $K_3PO_4$ (180 mg, 0.636 mmol) in toluene (2.1 mL) was stirred at 100° C. for 14 h. The reaction mixture was cooled to room temperature and purified by silica gel column chromatography (25-100% EtOAc/hexane) to yield compound 292 (119 mg, 92%) as a colorless oil; $^1$H-NMR (400 MHz, $CDCl_3$) δ −0.11–−0.08 (m, 9H), 0.79-0.91 (m, 2H), 1.34-1.36 (m, 3H), 3.23-3.32 (m, 3H), 3.41-3.53 (m, 2H), 3.76-3.80 (m, 3H), 3.92-4.02 (m, 2H), 4.26-4.34 (m, 2H), 5.38-5.83 (m, 2H), 6.26-7.16 (m, 4H), 7.86-7.99 (m, 1H), 8.36-8.39 (m, 1H); MS (ESI$^+$): 611 [M+H]$^+$.

Experimental Procedure of EX.435

EX. 435

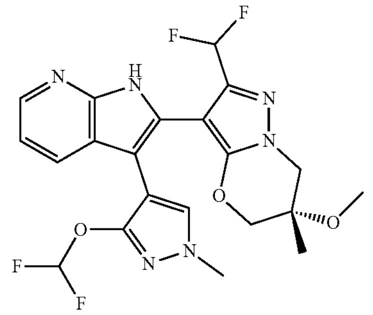

To a stirred solution of compound 292 (119 mg, 0.195 mmol) in $CH_2Cl_2$ (2 mL) at room temperature, TFA (2 mL) was added. After stirring at room temperature for 6 h, the reaction mixture was concentrated. The residue was dissolved in MeOH (2 mL) and then 5 mol/L aqueous NaOH solution was added to the resulting solution. After stirring at room temperature for 14 h, the resulting mixture was concentrated. The residue was purified by silica gel column chromatography (25-100% EtAOc/n-hexane then 0-20% MeOH/EtOAc) to yield EX.435 (78 mg, 83%); $^1$H-NMR (400 MHz, DMSO-$d_6$) § 1.26 (s, 3H), 3.17 (s, 3H), 3.75 (s, 3H), 3.99-4.05 (m, 1H), 4.07-4.14 (m, 1H), 4.16-4.23 (m, 1H), 4.35 (dd, J=11.9, 2.3 Hz, 1H), 6.75 (t, J=54.1 Hz, 1H), 6.91-7.28 (m, 2H), 7.49 (s, 1H), 7.81 (dd, J=8.0, 1.3 Hz, 1H), 8.23 (dd, J=4.7, 1.6 Hz, 1H), 11.77 (s, 1H); MS (ESI$^+$): 481 [M+H]$^+$.

Experimental Procedure of EX.601

EX. 601

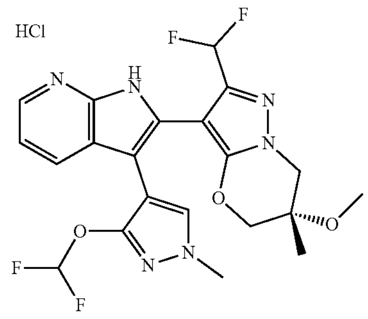

To a stirred solution of EX.435 (10 mg, 0.021 mmol) in acetone (0.3 mL) at room temperature, 6 mol/L HCl (0.005 mL) was added. After stirring at 45° C. for 0.5 h, followed by stirring at room temperature for 1 h, the resulting precipitate was collected by filtration. The filtered material was then washed with acetone to yield EX.601 (4.1 mg, 38%); $^1$H-NMR (400 MHz, $CD_3OD$) δ 1.34 (3H, s), 3.25 (3H, s), 3.81 (3H, s), 4.03-4.10 (2H, m), 4.24-4.29 (1H, m), 4.36 (1H, dd, J=11.9, 2.5 Hz), 6.41-7.06 (2H, m), 7.38-7.42 (1H, m), 7.50 (1H, s), 8.30-8.34 (2H, m).

Reference Procedure of Compound 151

151

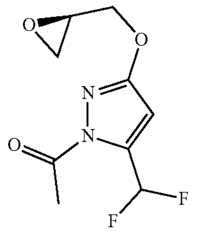

[(2S)-Oxiran-2-yl]methanol (2.0 mL, 30 mmol) was added to a stirred solution of compound 140 (4.30 g, 24.4 mmol) in THF (50 mL) at 0° C., followed by 2.2 mol/L diethyl azodicarboxylate in toluene (16.6 mL, 36.6 mmol). After stirring at the same temperature for 1 h, triphenylphosphine (9.70 g, 37.0 mmol) was added, and the reaction mixture was stirred at room temperature for 4 h. The reaction mixture was concentrated to approximately 20 mL and purified by silica gel column chromatography (5-70% EtOAc/hexane) to yield compound 151 (4.4 g, 78%) as a light brown oil; $^1$H-NMR (400 MHz, $CDCl_3$) δ 2.59 (3H, s), 2.73-2.75 (1H, m), 2.90 (1H, dd, J=4.9, 4.2 Hz), 3.34-3.38 (1H, m), 4.16 (1H, dd, J=11.8, 6.1 Hz), 4.52 (1H, dd, J=11.8, 3.1 Hz), 6.32 (1H, d, J=0.6 Hz), 7.19 (1H, td, J=54.0, 0.5 Hz).

Reference Procedure of Compound 158

158

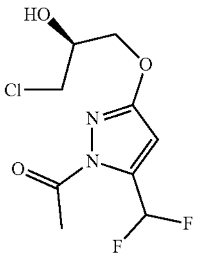

A mixture of 151 (4.70 g, 19.0 mmol), AcOH (3.32 mL, 58.1 mmol), and LiCl (1.47 g, 34.7 mmol) in THF (66 mL) was stirred at 50° C. for 2 h. Then, LiCl (733 mg, 17.3 mmol) was added and the reaction mixture was stirred at 50° C. for 1 h. The reaction was quenched by brine, and the resulting mixture was extracted with EtOAc. The organic layer was washed with sat. aq. $NaHCO_3$, brine, dried over $Na_2SO_4$, and concentrated to yield compound 158 (5.1 g, 94%) as a colorless oil; $^1$H-NMR (400 MHz, $CDCl_3$) δ 2.60 (3H, s), 2.66 (1H, s), 3.71 (2H, dq, J=19.9, 5.6 Hz), 4.20-4.27 (1H, m), 4.38 (2H, d, J=4.9 Hz), 6.32 (1H, s), 7.19 (1H, t, J=54.1 Hz); MS (EI$^+$): 268 [M$^+$].

Reference Procedure of Compound 164

164

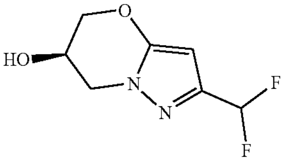

A mixture of 158 (1.70 g, 6.33 mmol) and $K_2CO_3$ (2.64 g, 19.1 mmol) in DMF (40 mL) was stirred at 135° C. for 1 h. The reaction mixture was cooled to room temperature, and MeOH (40 mL) was added. After stirring at 50° C. for 3 h, saturated aqueous $NH_4Cl$ was added, and the resulting mixture was concentrated. Brine was added to the residue, and the resulting mixture was extracted with EtOAc. The organic layer was dried over $Na_2SO_4$ and concentrated. The residue was purified by silica gel column chromatography (0-30% MeOH/EtOAc) to yield compound 164 (1.1 g, 91%); $^1$H-NMR (400 MHz, $CDCl_3$) δ 1.91 (1H, s), 4.18-4.34 (4H, m), 4.44 (1H, qd, J=3.6, 1.5 Hz), 5.76 (1H, s), 6.52 (1H, t, J=55.0 Hz); MS (ESI$^+$): 191 [M+H]$^+$.

Reference Procedure of Compound 170

170

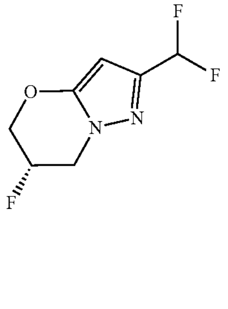

Diethylaminosulfur trifluoride (DAST) (0.413 mL, 3.15 mmol) was added to a stirred suspension of compound 164 (300 mg, 1.58 mmol) in $CH_2Cl_2$ (6 mL) at 0° C. under an Ar atmosphere. After stirring at room temperature for 46.5 h. The reaction mixture was poured into saturated aqueous $NaHCO_3$. The resulting mixture was then extracted with $CH_2Cl_2$. The organic layer was washed with brine, dried over $Na_2SO_4$, and concentrated. The residue was purified by silica gel column chromatography (10-100% EtOAc/hexane) to yield compound 170 (100 mg, 33%); $^1$H-NMR (400 MHz, $CDCl_3$) δ 4.21 (1H, ddd, J=36.7, 12.7, 0.8 Hz), 4.28-4.42 (1H, m), 4.47-4.55 (1H, m), 4.58-4.65 (1H, m), 5.16-5.30 (1H, m), 5.79 (1H, s), 6.54 (1H, t, J=55.0 Hz); MS (ESI$^+$): 193 [M+H]$^+$.

Reference Procedure of Compound 209

209

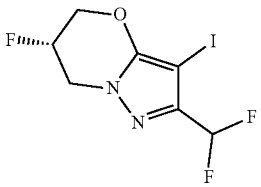

To a stirred solution of compound 170 (242 mg, 1.26 mmol) in MeCN (6.3 mL) at room temperature, NIS (850 mg, 3.78 mmol) was added. After stirring at room temperature for 2 h, the reaction was quenched with saturated aqueous $NaHCO_3$ and saturated aqueous $Na_2S_2O_3$, and the resulting mixture was extracted with EtOAc. The organic layer was washed with water, followed by brine, dried over $Na_2SO_4$, and concentrated. The residue was purified by silica gel column chromatography (5-50% EtOAc/hexane) to yield compound 209 (382 mg, 96%) as a colorless oil; $^1$H-NMR (400 MHz, $CDCl_3$) δ 4.21-4.44 (2H, m), 4.54 (1H, t, J=15.7 Hz), 4.69-4.76 (1H, m), 5.19-5.33 (1H, m), 6.54 (1H, t, J=53.7 Hz); MS (ESI$^+$): 319 [M+H]$^+$.

Reference Procedure of Compound 259

259

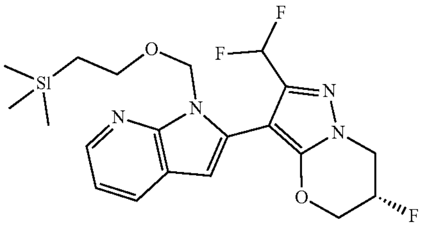

A mixture of compound 209 (432 mg, 1.15 mmol), 2-(4,4,5,5-tetramethyl-1,3,2-dioxaborolan-2-yl)-1-((2-(trimethylsilyl)ethoxy)methyl)-1H-pyrrolo[2,3-b]pyridine (Chemical Science (2021), 12(4), 1528-1534) (350 mg, 1.10 mmol), SPhos Pd G4 (88.0 mg, 0.110 mmol), and $K_3PO_4$ (935 mg, 3.30 mmol) in dioxane (5.5 mL) was stirred at 90° C. for 18 h under an Ar atmosphere. The reaction mixture was cooled to room temperature, filtered through a pad of Celite, and the filtrate was concentrated. The residue was purified by silica gel column chromatography (5-65%

EtOAc/hexane) to yield compound 259 (468 mg, 97%) as a brown oil; $^{1}$H-NMR (400 MHz, $CDCl_3$) δ −0.14 (9H, s), 0.73-0.85 (2H, m), 3.33-3.42 (2H, m), 4.21-4.33 (1H, m), 4.38-4.51 (1H, m), 4.58-4.69 (2H, m), 5.24-5.36 (1H, m), 5.60 (1H, d, J=11.0 Hz), 5.72 (1H, d, J=11.0 Hz), 6.47-6.74 (2H, m), 7.10 (1H, dd, J=7.8, 4.9 Hz), 7.89 (1H, dd, J=7.8, 1.5 Hz), 8.34 (1H, dd, J=4.7, 1.7 Hz); MS (ESI$^+$): 439 $[M+H]^+$.

Reference Procedure of Compound 273

273

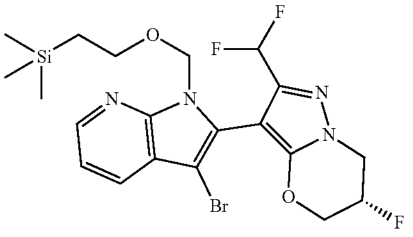

To a stirred solution of compound 259 (465 mg, 1.06 mmol) in MeCN (5.3 mL) at room temperature, NBS (198 mg, 1.11 mmol) was added portionwise. After stirring at room temperature for 2 h, the reaction was quenched with saturated aqueous $NaHCO_3$ and saturated aqueous $Na_2S_2O_3$, and the resulting mixture was extracted with EtOAc. The organic layer was washed with water, followed by brine, dried over $Na_2SO_4$, and concentrated. The residue was purified by silica gel column chromatography (10-75% EtOAc/hexane) to yield compound 273 (488 mg, 89%) as a slightly brown oil; $^{1}$H-NMR (400 MHz, $CDCl_3$) δ −0.10 (9H, s), 0.76-0.90 (2H, m), 3.38-3.48 (2H, m), 4.20-4.68 (4H, m), 5.25-5.36 (1H, m), 5.53-5.57 (1H, m), 5.62-5.65 (1H, m), 6.51-6.80 (1H, m), 7.17-7.20 (1H, m), 7.86-7.89 (1H, m), 8.37-8.41 (1H, m); MS (ESI$^+$): 517 $[M+H]^+$.

Reference Procedure of Compound 307

307

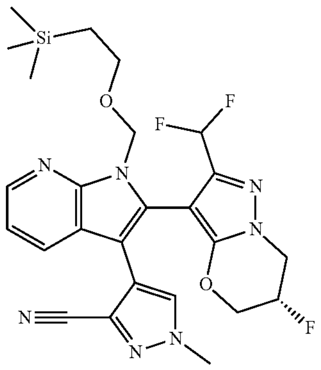

A mixture of compound 273 (143 mg, 0.232 mmol), 1-methyl-4-(4,4,5,5-tetramethyl-1,3,2-dioxaborolan-2-yl) pyrazole-3-carbonitrile (105 mg, 0.451 mmol), SPhos Pd G4 (19.0 mg, 0.0239 mmol), and $K_3PO_4$ (200 mg, 0.697 mmol) in dioxane (2.5 mL) and water (0.042 ml) was stirred at 100° C. for 1.5 h under an Ar atmosphere. The reaction mixture was cooled to room temperature, filtered through a pad of Celite, and the filtrate was concentrated. The residue was purified by silica gel column chromatography (5-65% EtOAc/hexane) to yield compound 307 (182 mg) along with some impurities. This compound was used in the next step without further purification; $^{1}$H-NMR (400 MHz, $CDCl_3$) δ −0.10-−0.06 (m, 9H), 0.74-0.94 (m, 2H), 3.36-3.57 (m, 2H), 3.91-4.04 (m, 3H), 4.09-4.64 (m, 4H), 5.19-5.36 (m, 1H), 5.46-5.88 (m, 2H), 6.11-6.58 (m, 1H), 7.14-7.22 (m, 1H), 7.24-7.65 (m, 1H), 7.84-8.03 (m, 1H), 8.40-8.44 (m, 1H); MS (ESI$^+$): 544 $[M+H]^+$.

Experimental Procedure of EX.449

EX. 449

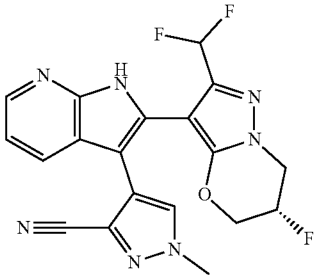

To a stirred solution of compound 307 (182 mg) in $CH_2Cl_2$ (1 mL) at room temperature, TFA (2 mL) was added. After stirring at room temperature for 2 h, the reaction mixture was concentrated. The residue was dissolved in MeOH (2 mL) and then 5 mol/L aqueous NaOH solution was added to the resulting solution. After stirring at room temperature for 2 h, the resulting mixture was concentrated. The residue was purified by silica gel column chromatography (0-5% MeOH/EtOAc) to yield EX.449 (62 mg, 65%); $^{1}$H-NMR (400 MHz, DMSO-$d_6$) δ 3.95 (s, 3H), 4.20-4.38 (m, 1H), 4.39-4.61 (m, 3H), 5.42-5.58 (m, 1H), 6.70 (t, J=53.9 Hz, 1H), 7.15 (dd, J=7.9, 4.7 Hz, 1H), 7.90 (dd, J=7.9, 1.5 Hz, 1H), 7.95 (s, 1H), 8.29 (dd, J=4.7, 1.6 Hz, 1H), 12.05 (s, 1H); MS (ESI$^+$): 414 $[M+H]^+$.

Experimental Procedure of EX.598

EX. 598

HCl

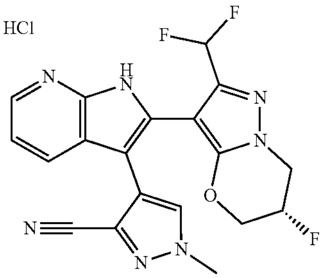

EX.598

To a stirred solution of EX.449 (15.0 mg, 0.0363 mmol) in acetone (0.45 mL) at room temperature, 6 mol/L HCl (0.008 mL) was added. After stirring at 40° C. for 0.5 h, followed by stirring at room temperature for 1 h, the resulting precipitate was collected by filtration. The filtered material was then washed with acetone to yield EX.598 (14 mg, 84%); $^{1}$H-NMR (400 MHz, $CD_3OD$) δ 4.02 (3H, s), 4.28-4.62 (4H, m), 5.35-5.48 (1H, m), 6.52 (1H, t, J=54.0 Hz), 7.66 (1H, dd, J=7.9, 5.9 Hz), 7.98 (1H, s), 8.47 (1H, dd, J=5.9, 1.1 Hz), 8.67 (1H, dd, J=7.9, 1.2 Hz).

Reference Procedure of compound 234

234

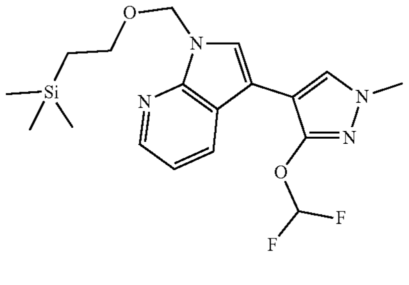

A mixture of compound 233 (2.43 g, 6.49 mmol), compound 10jj (1.94 g, 7.08 mmol), 2-dicyclohexylphosphino-2',6'-dimethoxybiphenyl (SPhos) (136 mg, 0.331 mmol), $Pd_2(dba)_3$ (198 mg, 0.162 mmol), $K_3PO_4$ (4.14 g, 19.5 mmol), and water (1.2 mL, 67.7 mmol) in toluene (25 mL) was stirred at 80° C. for 4 h. The reaction mixture was cooled to room temperature and purified directly by silica gel column chromatography (5-80% EtOAc/hexane) to yield compound 234 (708 mg, 28%); $^1$H-NMR (400 MHz, $CDCl_3$) δ −0.08 (9H, s), 0.85-0.94 (2H, m), 3.54-3.58 (2H, m), 3.86 (3H, s), 5.70 (2H, s), 7.01 (1H, t, J=74.0 Hz), 7.13 (1H, q, J=4.3 Hz), 7.57 (1H, s), 7.60 (1H, s), 7.99 (1H, dd, J=7.9, 1.8 Hz), 8.36 (1H, dd, J=4.6, 1.5 Hz).

Reference Procedure of Compound 235

235

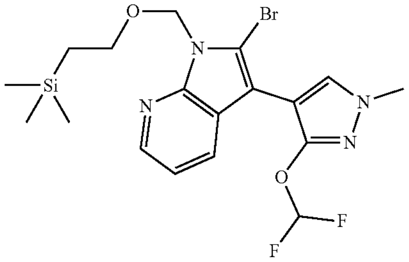

To a stirred solution of compound 234 (650 mg, 1.65 mmol) in MeCN (6.5 mL) at room temperature, NBS (294 mg, 1.65 mmol) was added portionwise. After stirring at room temperature for 0.5 h, the reaction was quenched with saturated aqueous $NaHCO_3$ and saturate aqueous $Na_2S_2O_3$, and the resulting mixture was extracted with EtOAc. The organic layer was washed with water, followed by brine, dried over $Na_2SO_4$, and concentrated. The residue was purified by silica gel column chromatography (5-70% EtOAc/hexane) to yield compound 235 (720 mg, 92%) as a slightly yellow oil; $^1$H-NMR (400 MHz, $CDCl_3$) δ −0.09 (9H, s), 0.90-0.95 (2H, m), 3.61-3.65 (2H, m), 3.88 (3H, s), 5.79 (2H, s), 6.97 (1H, t), 7.11 (1H, q, J=4.3 Hz), 7.52 (1H, s), 7.88 (1H, dd, J=7.9, 1.2 Hz), 8.32 (1H, dd, J=4.9, 1.2 Hz).

Reference Procedure of Compound 136

136

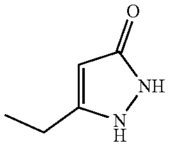

To a stirred solution of ethyl 3-oxopentanoate (27.4 g, 190 mmol) in EtOH (32 mL) and iPrOAc (158 mL) at room temperature, hydrazine hydrate (18.5 mL, 381 mmol) and AcOH (21.8 mL, 381 mmol) were slowly added. After stirring at 60° C. for 2 h, the resulting mixture was cooled to 0° C., and the resulting material was collected by filtration to yield compound 136 (20 g, 94%); $^1$H-NMR (400 MHz, DMSO-$d_6$) δ 1.12 (3H, t, J=7.6 Hz), 2.44 (2H, q, J=7.6 Hz), 5.22 (1H, s); MS (ESI$^+$): 113 $[M+H]^+$.

Reference Procedure of Compound 145

145

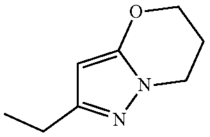

A mixture of compound 136 (500 mg, 4.46 mmol), 1,3-dibromopropane (0.507 mL, 4.98 mmol), and $K_2CO_3$ (1.85 g, 13.4 mmol) in DMA (30 mL) was stirred at 70° C. for 2 h under an Ar atmosphere. The reaction was quenched with saturated aqueous $NH_4Cl$, and the resulting mixture was extracted with EtOAc/MeOH (9/1). The organic layer was dried over $Na_2SO_4$, and concentrated. The residue was purified by silica gel column chromatography (5-100% EtOAc/hexane then 0-30% MeOH/EtOAc) to yield compound 145 (424 mg, 62%) as a colorless oil; $^1$H-NMR (400 MHz, $CDCl_3$) δ 1.19 (3H, t, J=7.6 Hz), 2.18-2.24 (2H, m), 2.53 (2H, q, J=7.5 Hz), 4.09 (2H, t, J=6.1 Hz), 4.23 (2H, t, J=5.2 Hz), 5.30 (1H, s).

Reference Procedure of Compound 195

195

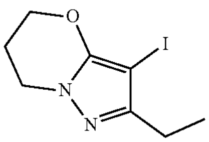

To a stirred solution of compound 145 (417 mg, 2.74 mmol) in acetonitrile (15 mL) at room temperature, NIS (1.85 g, 8.22 mmol) was added. After stirring at the same temperature for 2 h, saturated aqueous $NaHSO_3$ was added, and the resulting mixture was extracted with EtOAc. The organic layer was washed with water, followed by brine, dried over $Na_2SO_4$, and concentrated. The residue was purified by silica gel column chromatography (5-100% EtOAc/hexane) to yield compound 195 (590 mg, 77%);

$^1$H-NMR (400 MHz, $CDCl_3$) δ 1.21 (3H, t, J=7.6 Hz), 2.24 (2H, dt, J=11.6, 5.2 Hz), 2.52 (2H, q, J=7.5 Hz), 4.12 (2H, t, J=6.1 Hz), 4.32 (2H, dd, J=6.1, 4.9 Hz); MS (ESI$^+$): 279 $[M+H]^+$.

Reference Procedure of Compound 223

223

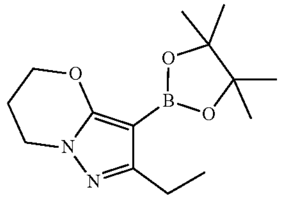

To a stirred solution of compound 195 (550 mg, 1.98 mmol) and 2-isopropoxy-4,4,5,5-tetramethyl-1,3,2-dioxaborolane (0.720 mL, 3.56 mmol) in THF (5 mL) at 0° C. under an Ar atmosphere, 2 mol/L isopropylmagnesium chloride in THF (1.5 mL, 1.5 mmol) was slowly added. After stirring at 0° C. for 2 h, the reaction was quenched with saturated aqueous $NH_4Cl$, and the resulting mixture was extracted with EtOAc. The organic layer was dried over $Na_2SO_4$, and concentrated. The residue was purified by silica gel column chromatography (0-30% MeOH/EtOAc) to yield compound 223 (267 mg, 49%); $^1$H-NMR (400 MHz, $CDCl_3$) δ 1.20 (3H, t, J=7.6 Hz), 1.28 (12H, s), 2.19 (2H, dt, J=11.8, 5.5 Hz), 2.69 (2H, q, J=7.5 Hz), 4.08 (2H, t, J=6.4 Hz), 4.32 (2H, t, J=5.2 Hz); MS (ESI$^+$): 279 $[M+H]^+$.

Reference Procedure of Compound 242

242

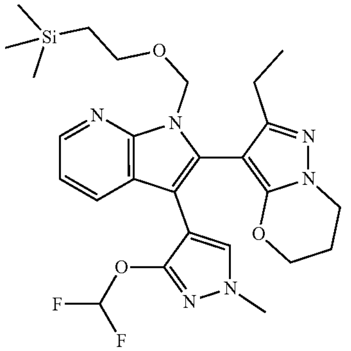

A mixture of compound 235 (130 mg, 0.275 mmol), compound 223 (92.0 mg, 0.331 mmol), SPhos Pd G4 (23.0 mg, 0.0290 mmol), and $K_3PO_4$ (180 mg, 0.848 mmol) in toluene (3 mL) was stirred at 100° C. for 1 h under microwave irradiation. The reaction mixture was cooled to room temperature, brine was added, and the resulting mixture was extracted with EtOAc. The organic layer was dried over $Na_2SO_4$, and concentrated. The residue was purified by silica gel column chromatography (0-30% MeOH/EtOAc) to yield compound 242 (29 mg, 19%) as a light yellow oil; $^1$H-NMR (400 MHz, $CDCl_3$) δ −0.11 (9H, s), 0.73-0.89 (2H, m), 0.93 (3H, t, J=7.6 Hz), 1.20 (3H, t, J=7.6 Hz), 2.19-2.27 (2H, m), 2.54 (2H, q, J=7.7 Hz), 3.39-3.51 (2H, m), 3.78 (3H, s), 4.11 (2H, t, J=6.1 Hz), 4.17 (2H, t, J=6.7 Hz), 4.24 (2H, t, J=5.2 Hz), 5.48 (1H, d, J=10.4 Hz), 5.71 (1H, d, J=11.0 Hz), 6.79 (1H, t, J=74.0 Hz), 7.10 (1H, q, J=4.3 Hz), 7.16 (1H, s), 7.89 (1H, dd, J=7.9, 1.8 Hz), 8.34 (1H, dd, J=4.9, 1.8 Hz); MS (ESI$^+$): 545 $[M+H]^+$.

Experimental Procedure of EX.422

EX. 422

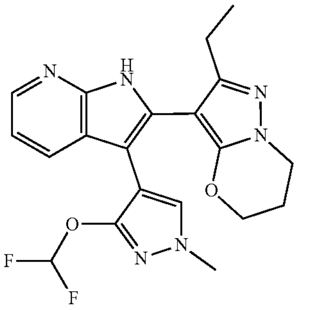

To a stirred solution of compound 242 (25.0 mg, 0.0459 mmol) in $CH_2Cl_2$ (1 mL) at room temperature, TFA (2 mL) was added. After stirring at room temperature for 1 h, the reaction mixture was concentrated. The residue was dissolved in MeOH (3 mL) and then 5 mol/L aqueous NaOH solution was added to the resulting solution. After stirring at 50° C. for 0.5 h, the resulting mixture was concentrated to approximately 0.5 mL. Saturated aqueous $NH_4Cl$ was added, and the resulting mixture was extracted with $CHCl_3$/MeOH (9/1). The organic layer was dried over $Na_2SO_4$, and concentrated. The residue was purified by silica gel column chromatography (0-20% MeOH/$CHCl_3$) to yield EX.422 (12 mg, 63%); $^1$H-NMR (400 MHz, DMSO-$d_6$) δ 0.84 (3H, t, J=7.6 Hz), 2.09-2.15 (2H, m), 2.23 (2H, q, J=7.5 Hz), 3.72 (3H, s), 4.00 (2H, t, J=6.1 Hz), 4.16 (2H, t, J=4.9 Hz), 7.01 (1H, dd, J=7.9, 4.9 Hz), 7.10 (1H, t, J=74.0 Hz), 7.50 (1H, s), 7.73 (1H, dd, J=7.9, 1.2 Hz), 8.14 (1H, dd, J=4.6, 1.5 Hz), 11.56 (1H, s); MS (ESI$^+$): 415 $[M+H]^+$.

Reference Procedure of Compound 387

387

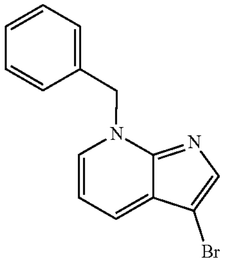

To a stirred suspension of 3-bromo-7-azaindole (10.0 g, 50.8 mmol) in MeCN (40 mL) at room temperature under an Ar atmosphere, benzyl bromide (6.4 mL, 53.5 mmol) was added. After stirring at 80° C. for 9.5 h, diisopropyl ether was added, and the resulting mixture was stirred at 0° C. for 0.5 h. The precipitate was collected by filtration, and the filtered material was washed with MeCN. The material was dissolved in EtOH-$H_2O$ (2.5/1) at 50° C., and activated charcoal was added. The resulting mixture was stirred at the same temperature for 40 min. The activated charcoal was filtered off through a pad of Celite, and aqueous NaOH solution was added to the filtrate. The resulting mixture was stirred at 0° C. for 1 h. The resulting precipitate was collected by filtration to yield compound 387 (12.9 g, 89%); $^1$H-NMR (400 MHz, $CDCl_3$) δ 5.88 (2H, s), 6.93 (1H, dd, J=7.4, 6.3 Hz), 7.34-7.37 (5H, m), 7.64 (1H, d, J=5.5 Hz), 7.85 (1H, s), 8.06 (1H, dd, J=7.5, 1.1 Hz).

Reference Procedure of Compound 388

388

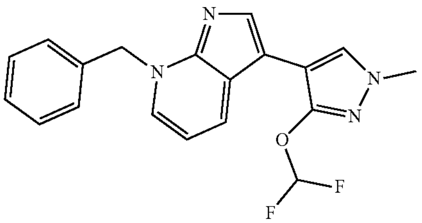

A mixture of compound 387 (600 g, 2.09 mol), compound 232 (687 g, 2.51 mol), Pd(amphos)$Cl_2$ (14.8 g, 20.9 mmol), and $K_3PO_4$ (1.73 kg, 6.27 mol) in DMF (5.4 L) was stirred at 70° C. for 1 hour under a nitrogen atmosphere. The reaction mixture was cooled to room temperature, and EtOAc (3 L) was added. The resulting mixture was stirred, and the insoluble material was removed by filtration. Brine was added to the filtrate, and the organic layer was separated. Maleic acid (255 g, 2.20 mol) was then added, and the resulting precipitate was collected by filtration. The obtained material was suspended in EtOH (6.1 L), followed by the addition of NaOH (262 g) and water (3.5 L). The resulting solution was cooled to 0° C., and water (6.1 L) was added. The precipitate thus formed was collected by filtration to afford compound 388 (637 g, 86%); $^1$H-NMR (500 MHz, $CDCl_3$) δ 3.85 (s, 3H), 5.90 (s, 2H), 6.89 (dd, J=6.5 Hz, 7.6 Hz, 1H), 6.97 (t, J=73.8 Hz, 1H), 7.33-7.40 (m, 5H), 7.46 (s, 1H), 7.59 (dd, J=0.8 Hz, 6.1 Hz, 1H), 8.04 (s, 1H), 8.25 (dd, J=0.8 Hz, 7.3 Hz, 1H); MS (ESI$^+$): 355 [M+H]$^+$.

Reference Procedure of Compound 389

389

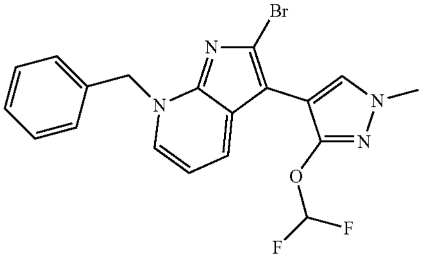

To a stirred suspension of compound 388 (600 g, 1.69 mol) and LiBr—$H_2O$ (710 g, 6.77 mol) in DMA (6 L) at 60° C., $CuBr_2$ (1.13 kg, 5.06 mol) was added. After stirring at the same temperature for 1 h, $NaHCO_3$ (213 g, 2.54 mol) was added, and the resulting mixture was stirred at 60° C. for 3 h. The reaction mixture was cooled to room temperature, and EtOAc (9 L), 28% aqueous ammonia solution (3 L), and water (6 L) were added. The organic layer was separated, washed with brine, and treated with activated charcoal (60 g). The activated charcoal was then removed by filtration, and the filtrate and washings were concentrated under reduced pressure at a set temperature of 40° C. to obtain approximately 2.4 L of concentrated residue. The concentrated residue was then subjected to vacuum concentration at a set temperature of 40° C. with 3.00 L of EtOH, yielding approximately 2.4 L of concentrated residue. This process was repeated twice more under the same conditions, each time yielding approximately 2.4 L of concentrated residue. The concentrated residue was heated to dissolve at an internal temperature of 57° C. The solution was then cooled, and 3.60 L of water was added dropwise at an internal temperature of 48-55° C. to induce crystallization. The resulting mixture was stirred for 30 min under cooling at an internal temperature of 13-15° C. The resulting precipitate was collected by filtration to yield compound 389 (616 g, 84%); $^1$H-NMR (500 MHz, $CDCl_3$) δ 3.87 (s, 3H), 5.86 (s, 2H), 6.88 (dd, J=6.5 Hz, 7.6 Hz, 1H), 6.97 (t, J=73.8 Hz, 1H), 7.35-7.41 (m, 5H), 7.51 (d, J=6.5 Hz, 1H), 7.62 (s, 1H), 8.12 (d, J=7.6 Hz, 1H); MS (ESI$^+$): 433 [M+H]$^+$.

Reference Procedure of Compound 150

150

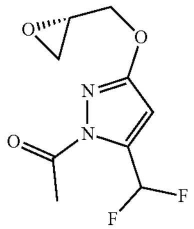

[(2R)-Oxiran-2-yl]methanol (0.060 mL, 0.91 mmol) was added to a stirred solution of compound 140 (132 mg, 0.750 mmol) in THF (2 mL) at 0° C., followed by 2.2 mol/L diethyl azodicarboxylate in toluene (0.510 mL, 1.12 mmol). After stirring at the same temperature for 1 h, triphenylphosphine (295 mg, 1.13 mmol) was added, and the reaction mixture was stirred at room temperature for 3 h. The reaction mixture was purified directly by silica gel column chromatography (5-70% EtOAc/hexane) to yield compound 150 (128 mg, 74%); $^1$H-NMR (400 MHz, $CDCl_3$) δ 2.59 (3H, s), 2.74 (1H, q, J=2.5 Hz), 2.90 (1H, dd, J=4.8, 4.2 Hz), 3.34-3.38 (1H, m), 4.16 (1H, dd, J=11.8, 6.1 Hz), 4.52 (1H, dd, J=11.8, 3.1 Hz), 6.32 (1H, d, J=0.7 Hz), 7.19 (1H, td, J=54.0, 0.6 Hz); MS (ESI$^+$): 233 [M+H]$^+$.

Reference Procedure of Compound 157

157

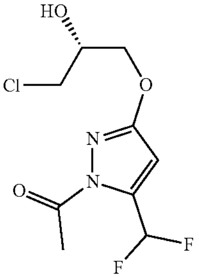

A mixture of 150 (120 mg, 0.517 mmol), AcOH (0.090 mL, 1.57 mmol), and LiCl (18.0 mg, 0.425 mmol) in THF (1 mL) was stirred at 50° C. for 2 h. Then, LiCl (129 mg, 3.04 mmol) was added and the reaction mixture was stirred at 50° C. for 1 h. The reaction was quenched by brine, and the resulting mixture was extracted with EtOAc. The organic layer was washed with saturated aqueous $NaHCO_3$, brine, dried over $Na_2SO_4$, and concentrated to yield compound 157 (137 mg, 99%) as a colorless oil; $^1$H-NMR (400 MHz, $CDCl_3$) δ 2.60 (3H, s), 2.66 (1H, s), 3.66-3.76 (2H, m), 4.19-4.26 (1H, m), 4.38 (2H, d, J=5.1 Hz), 6.32 (1H, s), 7.19 (1H, t, J=54.0 Hz); MS (ESI$^-$): 267 [M−H]$^-$.

Reference Procedure of Compound 58u

189

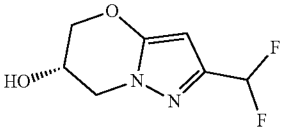

A mixture of 157 (75 mg, 0.279 mmol) and $K_2CO_3$ (116 mg, 0.839 mmol) in DMF (3 mL) was stirred at 135° C. for 4 h. The reaction mixture was cooled to room temperature, and Brine was added. The resulting mixture was extracted with EtOAc. The organic layer was washed with brine, dried over $Na_2SO_4$, and concentrated. The residue was purified by silica gel column chromatography (5-100% EtOAc/n-hexane then 0-40% MeOH/EtOAc) to yield compound 58u (22 mg, 41%); MS (ESI$^+$): 191 [M+H]$^+$.

Reference Procedure of Compound 189

189

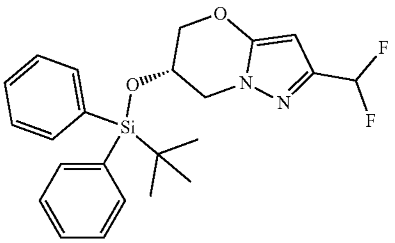

A mixture of compound 58u (420 mg, 2.21 mmol), TBDPSCl (0.85 mL, 3.32 mmol), imidazole (331 mg, 4.86 mmol), and 4-dimethylaminopyridine (80.0 mg, 0.655 mmol) in $CH_2Cl_2$ (6 mL) was stirred at room temperature for 1 h. Water was added, and the resulting mixture was extracted with $CH_2Cl_2$. The organic layer was dried over $Na_2SO_4$, and concentrated. The residue was purified by silica gel column chromatography (5-60% EtOAc/hexane) to yield compound 189 (915 mg, 97%) as a colorless oil; $^1$H-NMR (400 MHz, $CDCl_3$) δ 1.03 (9H, s), 4.00-4.12 (4H, m), 4.29 (1H, qd, J=4.5, 2.4 Hz), 5.73 (1H, s), 6.51 (1H, t, J=55.3 Hz), 7.36-7.49 (6H, m), 7.56-7.58 (2H, m), 7.64-7.67 (2H, m); MS (ESI$^+$): 429 [M+H]$^+$.

Reference Procedure of Compound 197

197

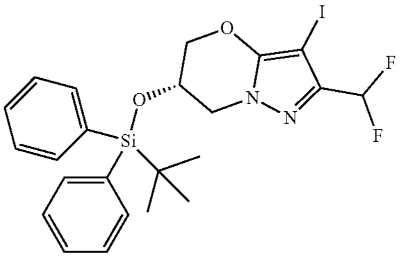

To a stirred solution of compound 189 (910 mg, 2.12 mmol) in MeCN (5 mL) at room temperature, NIS (1.43 mg, 6.36 mmol) was added. After stirring at room temperature for 2 h, the reaction was quenched with saturated aqueous $NaHCO_3$ and saturated aqueous $Na_2S_2O_3$, and the resulting mixture was extracted with EtOAc. The organic layer was washed with water, followed by brine, dried over $Na_2SO_4$, and concentrated. The residue was purified by silica gel column chromatography (5-50% EtOAc/hexane) to yield compound 197 (1.13 mg, 96%); $^1$H-NMR (400 MHz, $CDCl_3$) δ 1.03 (9H, s), 4.09-4.18 (4H, m), 4.29-4.33 (1H, m), 6.51 (1H, t, J=53.8 Hz), 7.37-7.51 (6H, m), 7.55-7.57 (2H, m), 7.64 (2H, dd, J=7.9, 1.2 Hz); MS (ESI$^+$): 555 [M+H]$^+$.

Reference Procedure of Compound 226

226

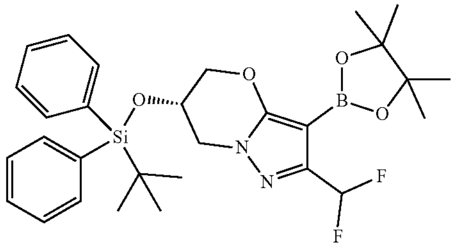

To a stirred solution of compound 197 (600 mg, 1.08 mmol) and 2-isopropoxy-4,4,5,5-tetramethyl-1,3,2-dioxaborolane (0.340 mL, 1.68 mmol) in THF (5.5 mL) at 0° C. under an Ar atmosphere, 2 mol/L isopropylmagnesium chloride in THF (0.670 mL, 1.34 mmol) was slowly added. After stirring at 0° C. for 2 h, the reaction was quenched with saturated aqueous $NH_4Cl$, and the resulting mixture was extracted with EtOAc. The organic layer was dried over $Na_2SO_4$, and concentrated. The residue was purified by silica gel column chromatography (5-70% EtOAc/n-hexane) to yield compound 226 (550 mg, 92%); $^1$H-NMR (400 MHz, $CDCl_3$) δ 1.03 (9H, s), 1.28 (12H, s), 4.02-4.17 (4H, m), 4.25-4.30 (1H, m), 6.88 (1H, t, J=54.3 Hz), 7.35-7.48 (6H, m), 7.56-7.64 (4H, m); MS (ESI$^+$): 555 [M+H]$^+$.

Reference Procedure of Compound 390

390

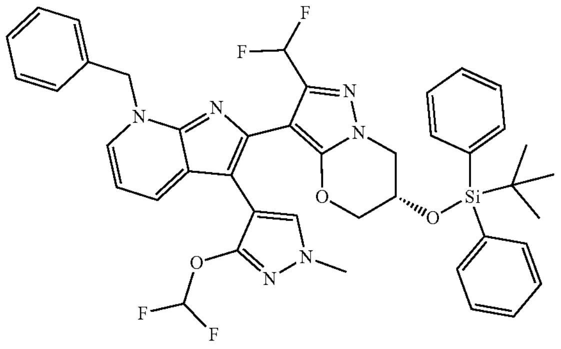

A mixture of compound 389 (70.0 mg, 0.162 mmol), compound 226 (99.0 mg, 0.179 mmol), Pd(amphos)$Cl_2$ (12.0 mg, 0.0169 mmol), and $K_3PO_4$ (103 mg, 0.485 mmol) in DMA (2 mL) was stirred at 60° C. for 2 h under an Ar atmosphere. Water was added, and the resulting precipitate was collected by filtration. The material was dissolved in EtOAc, the resulting solution was dried over $Na_2SO_4$, and concentrated. The residue was purified by silica gel column chromatography (5-100% EtOAc/hexane) to yield compound 390 (56.0 mg, 44%) as a yellow oil; MS (ESI$^+$): 781 [M+H]$^+$.

Reference Procedure of Compound 396

396

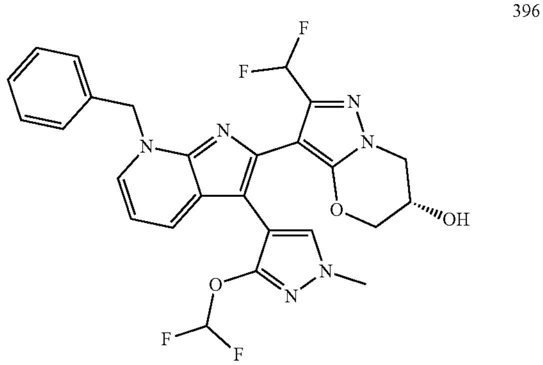 [SMILES: Cn1cc(-c2c3cccn(Cc4ccccc4)c-3nc2-c2c(C(F)F)nn3c2OC[C@@H](O)C3)c(OC(F)F)n1]

To a stirred solution of compound 390 (45.0 mg, 0.0576 mmol) in THF (0.5 mL) at room temperature, 1 mol/L TBAF in THF (0.17 mL, 0.17 mmol) was added. After stirring at the same temperature for 0.5 h, the reaction was quenched with saturated aqueous $NH_4Cl$ and brine. The resulting mixture was extracted with EtOAc, the organic layer was dried over $Na_2SO_4$, and concentrated. The residue was purified by silica gel column chromatography (0-50% MeOH/EtOAc) to yield compound 396 (26.0 mg, 83%) as a yellow amorphous; $^1$H-NMR (400 MHz, $CDCl_3$) δ 1.80 (1H, s), 3.74 (3H, s), 4.00-4.24 (5H, m), 5.81 (2H, s), 6.60-7.03 (3H, m), 7.16 (1H, s), 7.32-7.42 (6H, m), 7.56 (1H, d, J=5.5 Hz), 8.03 (1H, d, J=7.3 Hz); MS (ESI$^+$): 543 [M+H]$^+$.

Experimental Procedure of EX.527

EX. 527

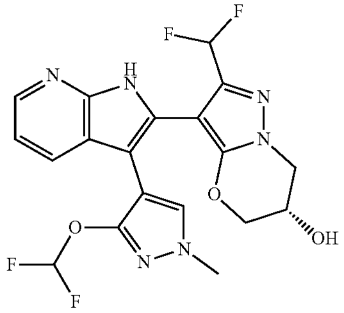

A mixture of compound 396 (100 mg, 0.184 mmol) and 10% Pd—C (25 mg) in EtOH (5 mL) was stirred at room temperature for 2 h under a a hydrogen atmosphere (1 atm). The reaction mixture was purged and backfilled with Ar, and filtered off through a pad of Celite. The filtrate was concentrated, and the residue was purified by silica gel column chromatography (0-40% MeOH/$CHCl_3$) to yield EX.527 (81.0 mg, 97%); $^1$H-NMR (400 MHz, DMSO-$d_6$) δ 3.69 (3H, s), 3.99 (1H, d, J=11.6 Hz), 4.15 (2H, s), 4.29 (2H, d, J=11.6 Hz), 5.66 (1H, d, J=3.1 Hz), 6.66 (1H, t, J=54.1 Hz), 7.05 (1H, dd, J=7.9, 4.9 Hz), 7.09 (1H, t, J=74.0 Hz), 7.49 (1H, s), 7.79 (1H, d, J=6.7 Hz), 8.19 (1H, dd, J=4.6, 1.5 Hz), 11.72 (1H, s); MS (ESI$^+$): 453 [M+H]$^+$.

Experimental Procedure of EX.604

EX. 604

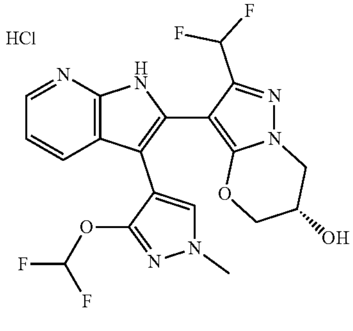

To a stirred solution of EX.527 (23.0 mg, 0.0508 mmol) in acetone (0.5 mL) at room temperature, 6 mol/L HCl (0.0011 mL) was added. After stirring at the same temperature for 1.5 h, the reaction mixture was concentrated. The residue was dissolved in $CH_2Cl_2$, and then diisopropyl ether was added. The resulting precipitate was collected by filtration to yield EX.604 (18 mg, 73%); $^1$H-NMR (400 MHz, DMSO-$d_6$) δ 3.74 (3H, s), 3.82-4.46 (6H, m), 6.71 (1H, t, J=54.0 Hz), 6.94-7.34 (2H, m), 7.56 (1H, s), 7.98 (1H, d, J=7.7 Hz), 8.29 (1H, dd, J=4.9, 1.5 Hz), 12.07 (1H, s).

Reference Procedure of Compound 399

(399)

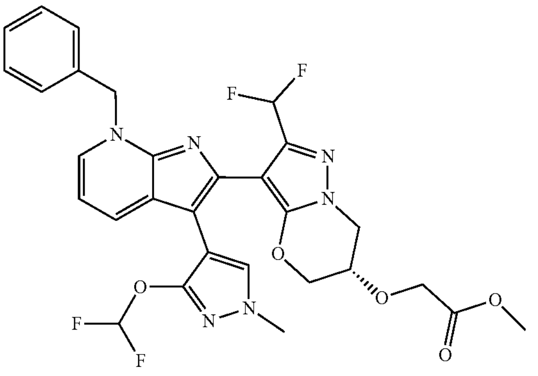

To a stirred solution of compound 396 (50.0 mg, 0.0922 mmol) in THF (0.46 mL) at 0° C. under Ar atmosphere, 60% sodium hydride (4.4 mg, 0.10 mmol) was added. After stirring at 0° C. for 0.5 h, methyl bromoacetate (0.011 mL, 0.12 mmol) was added to the reaction mixture, which was stirred at room temperature for 1 h. The reaction was quenched with sat. aq. $NH_4Cl$, and the resulting mixture was extracted with EtOAc. The organic layer was washed with brine, dried over $Na_2SO_4$, and concentrated. The residue was purified by silica gel column chromatography (25-100% EtOAc/hexane) to yield compound 399 (35 mg, 62%) as a yellow oil; $^1$H-NMR (400 MHz, $CDCl_3$) δ 3.77 (s, 3H), 3.78 (s, 3H), 4.08-4.11 (m, 2H), 4.20 (s, 2H), 4.22-4.42 (m, 3H), 5.80 (d, J=14.2 Hz, 1H), 5.89 (d, J=14.2 Hz, 1H), 6.81 (t, J=74.0 Hz, 1H), 6.85 (dd, J=7.4, 6.3 Hz, 1H), 7.00 (t, J=54.5 Hz, 1H), 7.17 (s, 1H), 7.32-7.42 (m, 3H), 7.44-7.49 (m, 2H), 7.57 (dd, J=6.3, 1.0 Hz, 1H), 8.02 (dd, J=7.5, 1.1 Hz, 1H); MS (ESI$^+$): 615 [M+H]$^+$.

Reference Procedure of Compound 417

(417)

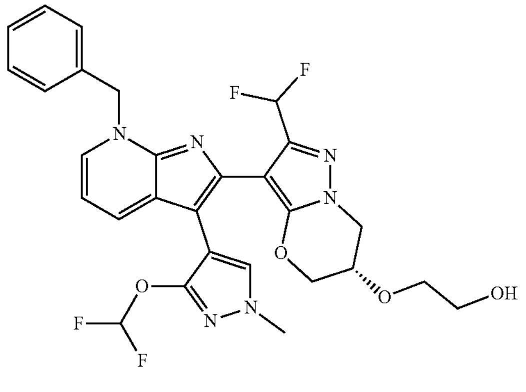

To a stirred solution of compound 399 (29.8 mg, 0.0485 mmol) in THF (0.24 mL) at 0° C. under Ar atmosphere, 4 mol/L lithium borohydride in THF (0.061 mL, 0.24 mmol) was added. After stirring at room temperature for 1 h, the reaction was quenched with sat. aq. $NH_4Cl$, and the resulting mixture was extracted with EtOAc. The organic layer was washed with brine, dried over $Na_2SO_4$, and concentrated. The residue was purified by silica gel column chromatography (25-100% EtOAc/hexane) to yield compound 417 (19 mg, 65%) as a yellow oil; $^1$H-NMR (400 MHz, $CDCl_3$) δ 3.60-3.76 (m, 4H), 3.81 (s, 3H), 4.00-4.08 (m, 2H), 4.23-4.42 (m, 3H), 5.82 (d, J=14.2 Hz, 1H), 5.88 (d, J=14.2 Hz, 1H), 6.57-7.12 (m, 3H), 7.19 (s, 1H), 7.33-7.42 (m, 3H), 7.45-7.51 (m, 2H), 7.57 (d, J=6.2 Hz, 1H), 7.98 (d, J=7.4 Hz, 1H); MS (ESI$^+$): 587 [M+H]$^+$.

Experimental Procedure of EX.534

EX. 534

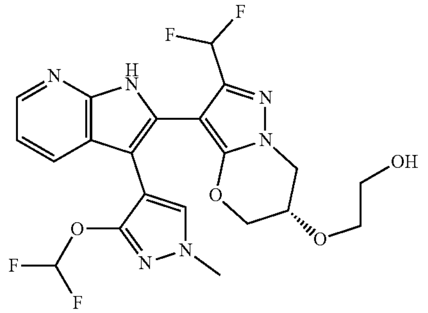

A mixture of compound 417 (19 mg, 0.032 mmol) and 5% Pd on barium carbonate powder (3.7 mg) in EtOH (0.16 mL) was stirred at 50° C. for 3 h under a hydrogen atmosphere (1 atm). The reaction mixture was purged and backfilled with Ar, and filtered off through a pad of Celite. The filtrate was concentrated, and the residue was purified by silica gel column chromatography (25-100% EtOAc/n-hexane then 0-20% MeOH/EtOAc) to yield EX.534 (8.6 mg, 55%); $^1$H-NMR (400 MHz, DMSO-$d_6$) δ 3.49-3.63 (m, 4H), 3.75 (s, 3H), 4.13-4.38 (m, 4H), 4.42-4.49 (m, 1H), 4.71 (t, J=5.4 Hz, 1H), 6.71 (t, J=54.1 Hz, 1H), 6.92-7.29 (m, 2H), 7.52 (s, 1H), 7.82 (dd, J=7.9, 1.1 Hz, 1H), 8.23 (dd, J=4.7, 1.5 Hz, 1H), 11.76 (s, 1H); MS (ESI$^+$): 497 [M+H]$^+$.

Experimental Procedure of EX.597

EX. 597

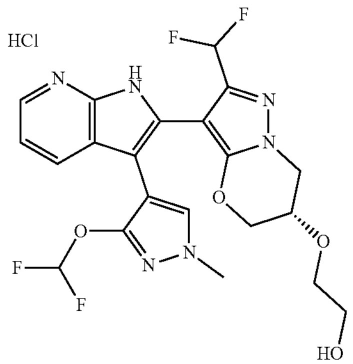

To a stirred solution of EX.534 (20.0 mg, 0.0403 mmol) in acetone (0.5 mL) at room temperature, 6 mol/L HCl (0.0085 mL) was added. After stirring at the same temperature for 1.5 h, the reaction mixture was concentrated. The residue was dissolved in $CH_2Cl_2$, and then diisopropyl ether was added. The resulting precipitate was collected by filtration to yield EX.597 (16 mg, 74%); $^1$H-NMR (400 MHz, DMSO-$d_6$) δ 3.49-3.62 (4H, m), 3.70-4.04 (4H, m), 4.14-4.50 (5H, m), 6.72 (1H, t, J=54.0 Hz), 6.91-7.33 (2H, m), 7.54 (1H, s), 7.91-7.96 (1H, m), 8.28 (1H, d, J=4.7 Hz), 12.00 (1H, s).

Reference Procedure of Compound 171

171

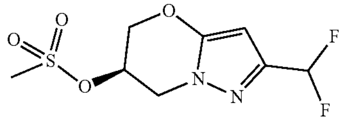

To a stirred solution of compound 164 (1.00 g, 5.26 mmol) in THF (40 mL) at 0° C. under an Ar atmosphere, triethylamine (0.88 mL, 6.35 mmol) was added, followed by the addition of methanesulfonyl chloride (0.45 mL, 5.81 mmol). After stirring at room temperature for 1 h, ice-water was added. The resulting mixture was extracted with EtOAc. The organic layer was dried over $Na_2SO_4$, and concentrated to yield compound 171 (1.41 g); $^1$H-NMR (400 MHz, $CDCl_3$) δ 3.13 (3H, s), 4.27 (1H, d, J=12.6 Hz), 4.40-4.51 (2H, m), 4.63 (1H, ddd, J=12.5, 3.0, 2.2 Hz), 5.35-5.37 (1H, m), 5.80 (1H, s), 6.52 (1H, t, J=55.0 Hz); MS (ESI$^+$): 269 [M+H]$^+$.

Reference Procedure of Compound 175

175

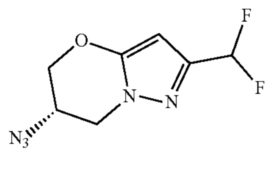

A mixture of compound 171 (1.41 g) and sodium azide (700 mg, 10.8 mmol) in DMF (20 mL) was stirred at 120° C. for 3 h. The reaction mixture was cooled to room temperature, and brine was added. The resulting mixture was extracted with EtOAc. The organic layer was dried over $Na_2SO_4$, and concentrated. The residue was purified by silica gel column chromatography (5-100% EtOAc/hexane) to yield compound 175 (960 mg, 84%) as a slightly yellow oil; $^1$H-NMR (400 MHz, $CDCl_3$) δ 4.18-4.24 (2H, m), 4.28-4.40 (3H, m), 5.77 (1H, s), 6.52 (1H, t, J=55.1 Hz); MS (ESI$^+$): 216 [M+H]$^+$.

Reference Procedure of Compound 179

179

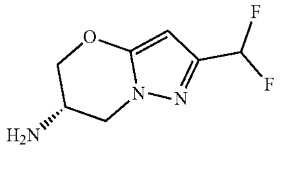

A mixture of compound 175 (950 mg, 4.42 mmol) and 10% Pd—C (95 mg) in EtOH (30 mL) was stirred at room temperature for 2 h under a hydrogen atmosphere (1 atm). The reaction mixture was purged and backfilled with Ar, and filtered off through a pad of Celite. The filtrate was concentrated to yield compound 179 (835 mg, quant.) as a slightly brown oil; $^1$H-NMR (400 MHz, $CDCl_3$) δ 1.51 (2H, s), 3.60-3.63 (1H, m), 3.90 (1H, dd, J=12.3, 5.5 Hz), 4.03 (1H, dd, J=10.9, 6.2 Hz), 4.25 (1H, d, J=11.0 Hz), 4.34 (1H, dd, J=12.3, 4.7 Hz), 5.73 (1H, s), 6.51 (1H, t, J=55.1 Hz); MS (ESI$^+$): 190 [M+H]$^+$.

Reference Procedure of Compounds 183 and 183'

183

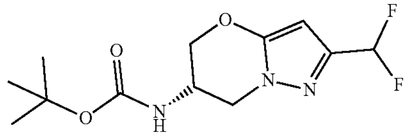

183'

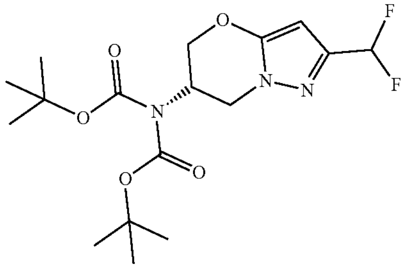

A mixture of compound 179 (730 mg, 3.86 mmol), (Boc) 2O (2.11 g, 9.67 mmol), triethylamine (1.60 mL, 11.6 mmol), and 4-dimethylaminopyridine (95.0 mg, 0.778 mmol) in THF (40 mL) was stirred at room temperature for 2 h. The reaction mixture was purified directly by silica gel column chromatography (5-100% EtOAc/hexane) to yield compound 183 (155 mg, 14%) as a slightly yellow oil and compound 183' (747 mg, 50%); 183: $^1$H-NMR (400 MHz, $CDCl_3$) δ 1.45 (s, 9H), 4.17-4.43 (m, 5H), 5.06 (s, 1H), 5.78 (s, 1H), 6.53 (t, J=55.1 Hz, 1H); MS$^-$ (ESI$^-$): 288 [M−H]. 183': $^1$H-NMR (400 MHz, $CDCl_3$) δ 1.49 (18H, s), 4.30 (2H, dd, J=10.6, 6.9 Hz), 4.48 (1H, t, J=10.7 Hz), 4.61-4.66 (1H, m), 4.83-4.91 (1H, m), 5.72 (1H, s), 6.50 (1H, t, J=55.1 Hz); MS (ESI$^+$): 390 [M+H]$^+$.

Reference Procedure of Compound 210

210

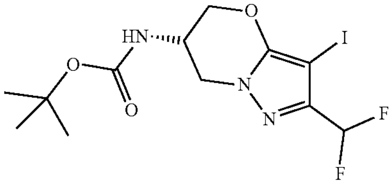

To a stirred solution of compound 183 (2.11 g, 7.29 mmol) in MeCN (36 mL) at room temperature, NIS (4.92 mg, 21.9 mmol) was added. After stirring at room temperature for 2 h, the reaction was quenched with saturated aqueous $NaHCO_3$ and saturated aqueous $Na_2S_2O_3$, and the resulting mixture was extracted with EtOAc. The organic layer was washed with water, followed by brine, dried over $Na_2SO_4$, and concentrated. The residue was purified by silica gel column chromatography (10-60% EtOAc/hexane) to yield compound 210 (2.76 g, 91%); $^1$H-NMR (400 MHz, $CDCl_3$) δ 1.45 (s, 9H), 4.22-4.47 (m, 5H), 5.02-5.08 (m, 1H), 6.53 (t, J=53.7 Hz, 1H); MS (ESI$^+$): 416 [M+H]$^+$.

Reference Procedure of Compound 229

229

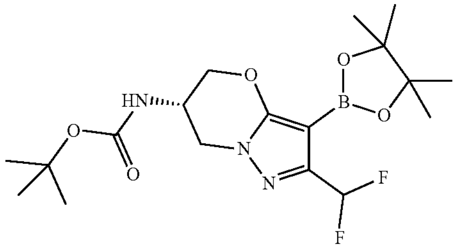

To a stirred solution of compound 210 (600 mg, 1.16 mmol) and 2-isopropoxy-4,4,5,5-tetramethyl-1,3,2-dioxaborolane (0.360 mL, 1.78 mmol) in THF (10 mL) at 0° C. under an Ar atmosphere, 2 mol/L isopropylmagnesium chloride in THF (0.70 mL, 1.4 mmol) was slowly added. After stirring at 0° C. for 1 h, the reaction was quenched with saturated aqueous $NH_4Cl$, and the resulting mixture was extracted with EtOAc. The organic layer was dried over $Na_2SO_4$, and concentrated. The residue was purified by silica gel column chromatography (5-100% EtOAc/n-hexane) to yield compound 229 (305 mg, 51%); $^1$H-NMR (400 MHz, $CDCl_3$) δ 1.29 (12H, s), 1.42 (9H, s), 4.08-4.45 (5H, m), 5.10 (1H, s), 6.89 (1H, t, J=54.2 Hz); MS (ESI$^+$): 416 [M+H]$^+$.

Reference Procedure of Compound 391

391

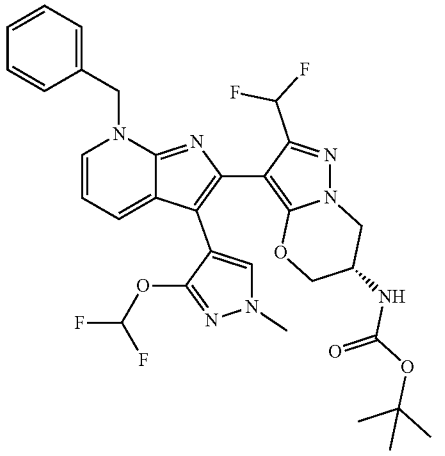

A mixture of compound 389 (140 mg, 0.323 mmol), compound 229 (140 mg, 0.337 mmol), Pd(amphos)$Cl_2$ (56.0 mg, 0.0791 mmol), and $K_3PO_4$ (210 mg, 0.989 mol) in DMF (3 mL) was stirred at 60° C. for 3 h under a nitrogen atmosphere. The reaction mixture was cooled to room temperature, and purified directly by silica gel column chromatography (5-100% EtOAc/n-hexane then 0-30% MeOH/EtOAc) to yield compound 391 (102 mg, 49%) as a yellow oil; $^1$H-NMR (400 MHz, $CDCl_3$) δ 1.43 (9H, s), 3.80 (3H, s), 4.06-4.15 (2H, m), 4.30-4.33 (3H, m), 5.05 (1H, d, J=7.3 Hz), 5.83 (2H, s), 6.79 (1H, t, J=74.4 Hz), 6.85 (1H, t, J=6.8 Hz), 7.09 (1H, t, J=54.4 Hz), 7.17 (1H, s), 7.31-7.39 (3H, m), 7.43-7.46 (2H, m), 7.57 (1H, d, J=6.1 Hz), 7.99 (1H, d, J=7.3 Hz); MS (ESI$^+$): 642 [M+H]$^+$.

Reference Procedure of Compound 406

406

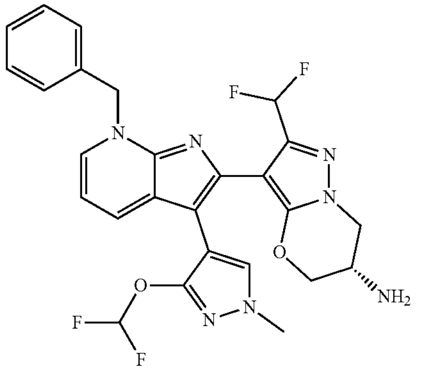

To a stirred solution of compound 391 (60.0 mg, 0.0935 mmol) in $CH_2Cl_2$ (1 mL) at room temperature was added TFA (1 mL). After stirring for 1 h at the same temperature, the reaction mixture was concentrated. Saturated aqueous $NaHCO_3$ and brine were added to the residue, and the resulting mixture was extracted with $CHCl_3$. The organic layer was dried over $Na_2SO_4$, and concentrated. The residue was purified by silica gel column chromatography (0-50% MeOH/EtOAc) to yield compound 406 (49 mg, 97%) as a yellow oil; $^1$H-NMR (400 MHz, $CDCl_3$) δ 1.62 (2H, s), 3.55 (1H, qd, J=5.3, 2.8 Hz), 3.78 (3H, s), 3.89 (1H, dd, J=10.7, 5.8 Hz), 3.97 (1H, dd, J=12.5, 5.2 Hz), 4.08-4.13 (2H, m), 4.37 (1H, dd, J=12.2, 4.9 Hz), 5.85 (2H, s), 6.77 (1H, t, J=74.0 Hz), 6.85 (1H, t, J=6.7 Hz), 7.06 (1H, t, J=54.4 Hz), 7.17 (1H, s), 7.31-7.40 (3H, m), 7.46 (2H, dd, J=7.9, 1.8 Hz), 7.56 (1H, d, J=6.7 Hz), 7.99 (1H, d, J=7.9 Hz); MS (ESI$^+$): 542 [M+H]$^+$.

Reference Procedure of Compound 409

409

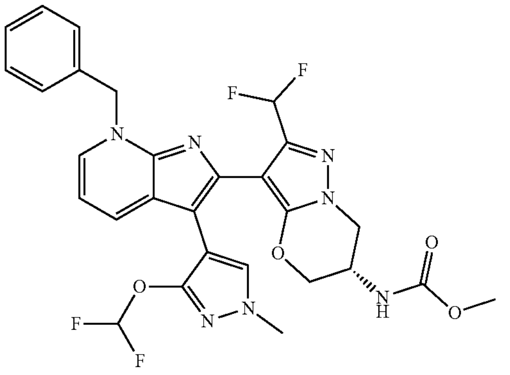

To a stirred solution of compound 406 (40.0 mg, 0.0739 mmol) in $CH_2Cl_2$ (0.7 mL) at room temperature, N,N-diisopropylethylamine (0.0251 mL, 0.148 mmol) and methyl chloroformate (0.0068 mL, 0.089 mmol) were added. After stirring at room temperature for 1 h, the reaction mixture was concentrated, and the residue was purified by silica gel column chromatography (20-100% EtOAc/n-hexane) to yield compound 409 (43 mg, 98%) as a yellow oil; $^1$H-NMR (400 MHz, $CDCl_3$) δ 3.71 (s, 3H), 3.83 (s, 3H), 4.11-4.42 (m, 5H), 5.32 (s, 1H), 5.87 (s, 2H), 6.63-7.19 (m, 4H), 7.36-7.61 (m, 6H), 8.02 (d, J=7.3 Hz, 1H); MS (ESI$^+$): 600 $[M+H]^+$.

Experimental Procedure of EX.571

EX. 571

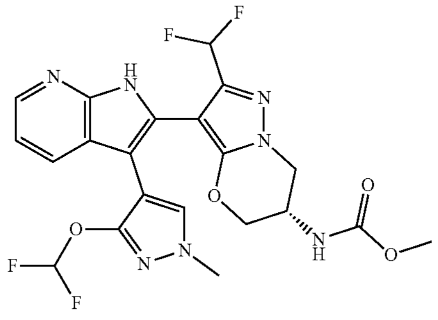

A mixture of compound 409 (43.2 mg, 0.0721 mmol) and 10% Pd—C (8.6 mg) in EtOH (0.7 mL) was stirred at room temperature for 3 h under a hydrogen atmosphere (1 atm). The reaction mixture was purged and backfilled with Ar, and filtered off through a pad of Celite. The filtrate was concentrated, and the residue was purified by silica gel column chromatography (20-100% EtOAc/n-hexane) to yield EX.571 (2.3 mg, 6.3%); $^1$H-NMR (400 MHz, DMSO-$d_6$) δ 3.58 (s, 3H), 3.75 (s, 3H), 4.09-4.43 (m, 5H), 6.62 (t, J=54.0 Hz, 1H), 6.93-7.31 (m, 2H), 7.56 (s, 1H), 7.66-7.69 (m, 1H), 7.81-7.84 (m, 1H), 8.22-8.24 (m, 1H), 11.68 (s, 1H); MS (ESI$^+$): 510 $[M+H]^+$.

Experimental Procedure of EX.605

EX. 605

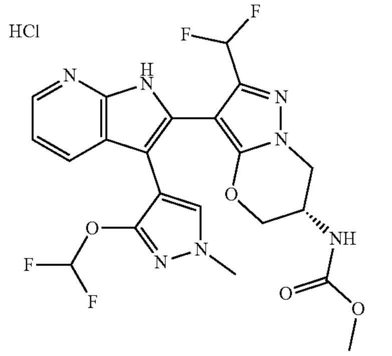

To a stirred solution of EX.571 (20.0 mg, 0.0393 mmol) in acetone (0.5 mL) at room temperature, 6 mol/L HCl (0.0075 mL) was added. After stirring at the same temperature for 1 h, the reaction mixture was concentrated. The residue was dissolved in $CH_2Cl_2$, and then diisopropyl ether was added. The resulting precipitate was collected by filtration to yield EX.605 (21 mg, 99%); $^1$H-NMR (400 MHz, DMSO-$d_6$) δ 3.59 (3H, s), 3.76 (3H, s), 4.04-4.44 (5H, m), 6.65 (1H, t, J=54.0 Hz), 6.93-7.34 (2H, m), 7.59 (1H, s), 7.66-7.72 (1H, m), 7.91-7.97 (1H, m), 8.28 (1H, dd, J=4.8, 1.5 Hz), 11.91 (1H, s).

Reference Procedure of Compound 440

440

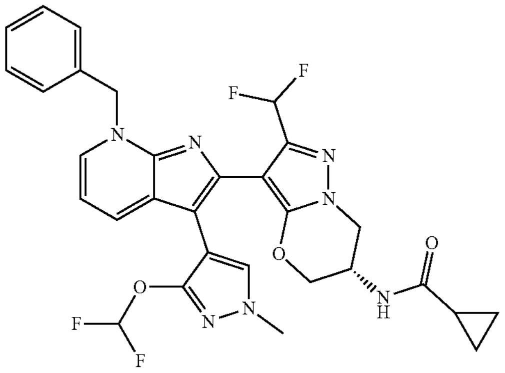

To a stirred solution of compound 406 (40.0 mg, 0.0739 mmol) in $CH_2Cl_2$ (0.7 mL) at room temperature, N,N-diisopropylethylamine (0.0251 mL, 0.148 mmol) and cyclopropanecarbonyl chloride (0.0081 mL, 0.089 mmol) were added. After stirring at room temperature for 1 h, the reaction mixture was concentrated, and the residue was purified by silica gel column chromatography (20-100% EtOAc/n-hexane) to yield compound 440 (44 mg, 97%) as a yellow oil; $^1$H-NMR (400 MHz, $CDCl_3$) δ 0.76-0.81 (m, 2H), 0.90-1.00 (m, 2H), 1.39-1.44 (m, 1H), 3.83 (s, 3H), 4.10-4.37 (m, 5H), 4.70-4.75 (m, 1H), 5.82-5.91 (m, 2H), 6.48-6.53 (m, 1H), 6.70-7.02 (m, 2H), 7.29-7.61 (m, 7H), 7.98-8.02 (m, 1H); MS (ESI$^+$): 610 $[M+H]^+$.

Experimental Procedure of EX.559

EX. 559

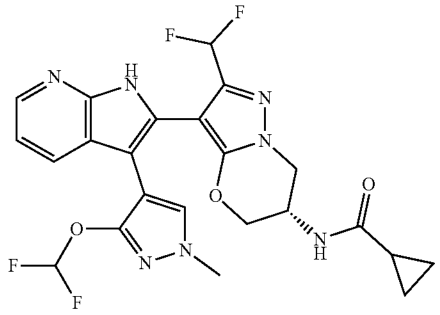 [SMILES: Cn1cc(-c2c(-c3c(C(F)F)nn4c3OC[C@@H](NC(=O)C3CC3)C4)[nH]c3ncccc23)c(OC(F)F)n1]

A mixture of compound 440 (43.0 mg, 0.0735 mmol) and 10% Pd—C (8.5 mg) in EtOH (0.7 mL) was stirred at room temperature for 3 h under a hydrogen atmosphere (1 atm). The reaction mixture was purged and backfilled with Ar, and filtered off through a pad of Celite. The filtrate was concentrated, and the residue was purified by silica gel column chromatography (20-100% EtOAc/n-hexane) to yield EX.559 (26 mg, 72%); $^1$H-NMR (400 MHz, DMSO-$d_6$) δ 0.66-0.75 (m, 4H), 1.59-1.65 (m, 1H), 3.75 (s, 3H), 4.06-4.25 (m, 3H), 4.37-4.44 (m, 2H), 6.69 (t, J=54.1 Hz, 1H), 6.93-7.31 (m, 2H), 7.56 (s, 1H), 7.81-7.83 (m, 1H), 8.23 (dd, J=4.7, 1.5 Hz, 1H), 8.60 (d, J=5.7 Hz, 1H), 11.71 (s, 1H); MS (ESI$^+$): 520 $[M+H]^+$.

Experimental Procedure of EX.599

EX. 599

HCl

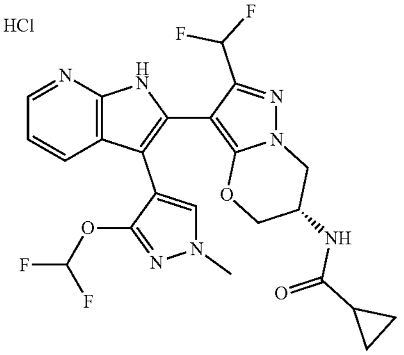

To a stirred solution of EX.559 (5.0 mg, 0.0096 mmol) in acetone (0.15 mL) at room temperature, 6 mol/L HCl (0.002 mL) was added. After stirring at 40° C. for 0.5 h, followed by stirring at room temperature for 1 h, the reaction mixture was concentrated. The residue was dissolved in $CH_2Cl_2$, and then diisopropyl ether was added. The resulting precipitate was collected by filtration. The collected material was then washed with acetone to yield EX.599 (1.0 mg, 19%); $^1$H-NMR (400 MHz, $CD_3OD$) δ 0.76-0.82 (2H, m), 0.86-0.91 (2H, m), 1.59-1.66 (1H, m), 3.83 (3H, s), 4.18-4.32 (3H, m), 4.45 (1H, dd, J=12.7, 5.1 Hz), 4.52-4.57 (1H, m), 6.52 (1H, t, J=54.0 Hz), 6.94 (1H, t, J=73.6 Hz), 7.55 (1H, dd, J=7.9, 5.8 Hz), 7.61 (1H, s), 8.39 (1H, d, J=5.6 Hz), 8.50-8.59 (2H, m).

Reference Procedure of Compound 139

139

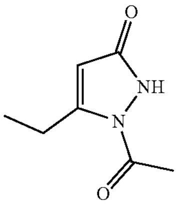

A mixture of compound 136 (20.1 g, 179 mmol) and acetic anhydride (18 mL, 188 mmol) in pyridine (120 mL) was stirred at 100° C. for 2 h. The resulting mixture was concentrated. The residue was purified by silica gel column chromatography (5-100% EtOAc/hexane) to yield compound 139 (13.5 g, 49%); $^1$H-NMR (400 MHz, DMSO-$d_6$) δ 1.14 (t, J=7.4 Hz, 3H), 2.46 (s, 3H), 2.86 (qd, J=7.4, 1.0 Hz, 2H), 5.79 (t, J=1.0 Hz, 1H), 10.75 (s, 1H); MS (ESI$^+$): 155 $[M+H]^+$.

Reference Procedure of Compound 155

155

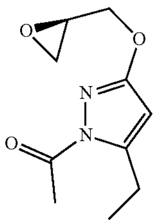

[(2S)-oxiran-2-yl]methanol (3.47 mL, 52.5 mmol), 1,1'-(azodicarbonyl)dipiperidine (19.9 g, 78.8 mmol), and then triphenylphosphine (20.7 g, 78.8 mmol) were successively added to a stirred solution of compound 139 (6.75 g, 43.8 mmol) in THF (220 mL) at 0° C. under an Ar atmosphere. After stirring at room temperature for 6 h. Water was added, and the resulting mixture was extracted with EtOAc. The organic layer was washed with brine, dried over $Na_2SO_4$, and concentrated. The residue was purified by silica gel column chromatography (5-30% EtOAc/hexane) to yield compound 155 (5.23 g, 57%); $^1$H-NMR (400 MHz, DMSO-$d_6$) δ 1.16 (3H, t, J=7.4 Hz), 2.48-2.53 (3H, m), 2.71 (1H, dd, J=5.0, 2.6 Hz), 2.83 (1H, t, J=4.6 Hz), 2.89 (2H, qd, J=7.4, 0.8 Hz), 3.31-3.38 (1H, m), 3.96 (1H, dd, J=11.8, 6.8 Hz), 4.51 (1H, dd, J=11.8, 2.7 Hz), 6.05 (1H, s); MS (ESI$^+$): 211 $[M+H]^+$.

Reference Procedure of Compound 160

160

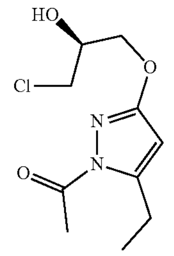

A mixture of 155 (5.23 g, 24.9 mmol), AcOH (4.3 mL, 75 mmol), and LiCl (3.17 g, 74.8 mmol) in THF (124 mL) was stirred at 60° C. for 6 h. The reaction was quenched by saturated aqueous $NaHCO_3$, and the resulting mixture was extracted with EtOAc. The organic layer was washed with brine, dried over $Na_2SO_4$, and concentrated. The residue was purified by silica gel column chromatography (5-35% EtOAc/hexane) to yield compound 160 (6.08 g, 99%) as a colorless oil; $^1$H-NMR (400 MHz, $CDCl_3$) δ 1.16 (3H, t, J=7.3 Hz), 2.46-2.53 (3H, m), 2.88 (2H, q, J=7.4 Hz), 3.64 (1H, dd, J=11.2, 5.3 Hz), 3.70 (1H, dd, J=11.2, 5.0 Hz), 3.99-4.08 (1H, m), 4.11-4.23 (2H, m), 5.58 (1H, d, J=5.3 Hz), 6.02 (1H, s); MS (ESI$^+$): 247 [M+H]$^+$.

Reference Procedure of Compound 166

166

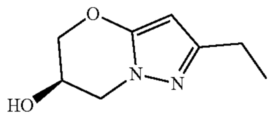

A mixture of 160 (6.08 g, 24.7 mmol) and $K_2CO_3$ (10.2 g, 74.0 mmol) in DMF (123 mL) was stirred at 135° C. for 1.5 h. The reaction mixture was cooled to room temperature, and MeOH (123 mL) was added. After stirring at 50° C. for 1 h, the reaction mixture was filtered through a pad of Celite, and the filtrate was concentrated. The residue was purified by silica gel column chromatography (20-100% EtOAc/n-hexane then 0-10% MeOH/EtOAc) to yield compound 166 (2.77 g, 67%); $^1$H-NMR (400 MHz, DMSO-$d_6$) δ 1.10 (3H, t, J=7.6 Hz), 2.39 (2H, q, J=7.6 Hz), 3.78-3.85 (1H, m), 4.02-4.16 (3H, m), 4.17-4.23 (1H, m), 5.28 (1H, s), 5.48 (1H, d, J=3.5 Hz); MS (ESI$^+$): 169 [M+H]$^+$.

Reference Procedure of Compound 173

173

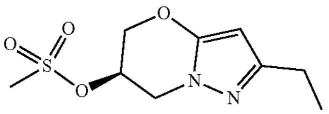

To a stirred solution of compound 166 (1.55 g, 9.23 mmol) in $CH_2Cl_2$ (46 mL) at room temperature, triethylamine (1.80 mL, 13.0 mmol) and methanesulfonyl chloride (0.930 mL, 12.0 mmol) were added. After stirring at room temperature for 1.5 h, the reaction mixture was concentrated to yield compound 173 (4.31 g). The crude compound obtained was used directly in the next step without purification.

Reference Procedure of Compound 177

177

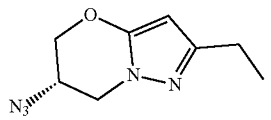

A mixture of compound 173 (4.31 g) and sodium azide (1.20 mg, 18.5 mmol) in DMF (31 mL) was stirred at 120° C. for 3 h. The reaction mixture was cooled to room temperature, and the insoluble material was removed by filtration. The filtrate was concentrated and the residue was purified by silica gel column chromatography (25-100% EtOAc/hexane) to yield compound 177 (1.35 g, 76%) as a brown oil; $^1$H-NMR (400 MHz, $CDCl_3$) δ 1.21 (3H, t, J=7.6 Hz), 2.55 (2H, q, J=7.6 Hz), 4.12-4.19 (2H, m), 4.23-4.38 (3H, m), 5.39 (1H, s); MS (ESI$^+$): 194 [M+H]$^+$.

Reference Procedure of Compound 181

181

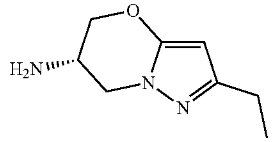

A mixture of compound 177 (1.35 g, 6.99 mmol) and 10% Pd—C (270 mg) in EtOH (35 mL) was stirred at room temperature for 3 h under a hydrogen atmosphere (1 atm). The reaction mixture was purged and backfilled with Ar, and filtered off through a pad of Celite. The filtrate was concentrated to yield compound 181 (1.08 g, 93%); $^1$H-NMR (400 MHz, $CDCl_3$) δ 1.21 (3H, t, J=7.6 Hz), 1.41 (2H, s), 2.55 (2H, q, J=7.6 Hz), 3.50-3.61 (1H, m), 3.81-3.88 (1H, m), 3.96-4.02 (1H, m), 4.17-4.23 (1H, m), 4.26-4.33 (1H, m), 5.35 (1H, s); MS (ESI$^+$): 168 [M+H]$^+$.

Reference Procedure of Compound 185

185

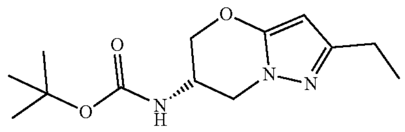

To a stirred solution of compound 181 (1.08 g, 6.48 mmol) and triethylamine (0.950 mL, 6.85 mmol) in THF (22 ml) at room temperature, (Boc) 20 (1.49 g, 6.83 mmol) was added. After stirring for 0.5 h and allowing the mixture to stand for 14 h at the same temperature, the reaction mixture was concentrated and the residue was purified by silica gel column chromatography (10-65% EtOAc/hexane) to yield compound 185 (1.55 g, 90%); $^1$H-NMR (400 MHz, $CDCl_3$) δ 1.22 (3H, t, J=7.6 Hz), 1.45 (9H, s), 2.56 (2H, q, J=7.6 Hz), 4.04-4.41 (5H, m), 5.09 (1H, d, J=7.8 Hz), 5.38 (1H, s); MS ($ESI^+$): 268 $[M+H]^+$.

Reference Procedure of Compound 204

204

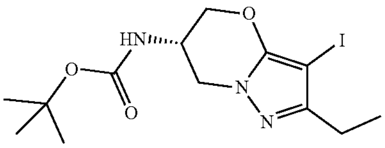

To a stirred solution of compound 185 (1.55 g, 5.81) in acetonitrile (29 mL) at room temperature, NIS (3.92 g, 17.4 mmol) was added. After stirring at the same temperature for 1.5 h, the reaction was quenched by saturated aqueous $NaHCO_3$ and saturated aqueous $Na_2S_2O_3$, and the resulting mixture was extracted with EtOAc. The organic layer was washed with brine, dried over $Na_2SO_4$, and concentrated. The residue was purified by silica gel column chromatography (5-50% EtOAc/hexane) to yield compound 204 (2.11 g, 93%); $^1$H-NMR (400 MHz, $CDCl_3$) δ 1.23 (3H, t, J=7.6 Hz), 1.45 (9H, s), 2.54 (2H, q, J=7.6 Hz), 4.06-4.49 (5H, m), 5.08 (1H, d, J=6.6 Hz); MS ($ESI^+$): 394 $[M+H]^+$.

Reference Procedure of Compound 231

231

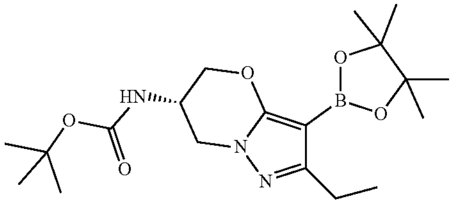

To a stirred solution of compound 204 (500 mg, 1.27 mmol) and 2-isopropoxy-4,4,5,5-tetramethyl-1,3,2-dioxaborolane (0.390 mL, 1.93 mmol) in THF (6.4 mL) at 0° C. under an Ar atmosphere, 2 mol/L isopropylmagnesium chloride in THF (1.4 mL, 2.8 mmol) was slowly added. After stirring at 0° C. for 1 h, the reaction was quenched with saturated aqueous $NH_4Cl$, and the resulting mixture was extracted with EtOAc. The organic layer was dried over $Na_2SO_4$, and concentrated. The residue was purified by silica gel column chromatography (8-66% EtOAc/n-hexane) to yield compound 231 (311 mg, 62%); $^1$H-NMR (400 MHz, $CDCl_3$) δ 1.21 (t, J=7.5 Hz, 3H), 1.30 (s, 6H), 1.31 (s, 6H), 1.44 (s, 9H), 2.71 (q, J=7.4 Hz, 2H), 4.07-4.10 (m, 1H), 4.18-4.25 (m, 2H), 4.30-4.43 (m, 2H), 5.14 (d, J=5.1 Hz, 1H); MS ($ESI^+$): 394 $[M+H]^+$.

Reference Procedure of Compound 393

393

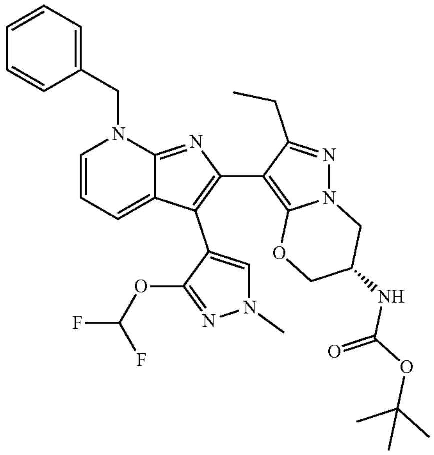

A mixture of compound 231 (311 mg, 0.791 mmol), compound 389 (311 mg, 0.718 mmol), Pd(amphos)$Cl_2$ (50.9 mg, 0.0719 mmol), and $K_3PO_4$ (618 mg, 2.15 mmol) in DMA (7.2 mL) was stirred at 75° C. for 14 h under an Ar atmosphere. The reaction mixture was purified directly by silica gel column chromatography (25-100% EtOAc/hexane) to yield compound 393 (286 mg, 64%); $^1$H-NMR (400 MHz, $CDCl_3$) δ1.09-1.17 (m, 3H), 1.44 (s, 9H), 2.62-2.72 (m, 2H), 3.77-3.84 (m, 3H), 4.08-4.33 (m, 4H), 5.17 (d, J=8.0 Hz, 1H), 5.90 (d, J=9.4 Hz, 2H), 6.64-7.02 (m, 2H), 7.15 (d, J=4.3 Hz, 1H), 7.30-7.41 (m, 4H), 7.45-7.48 (m, 2H), 7.52 (dd, J=6.3, 1.0 Hz, 1H), 8.00-8.04 (m, 1H); MS ($ESI^+$): 620 $[M+H]^+$.

Reference Procedure of Compound 408

408

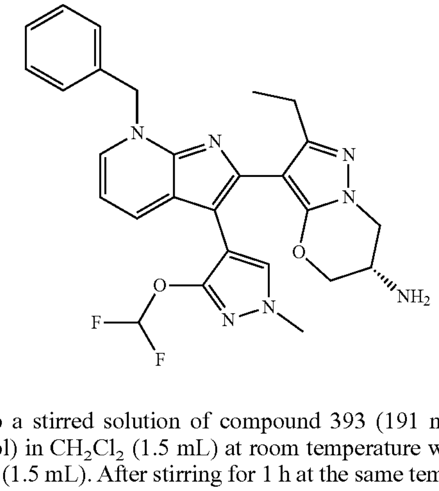

To a stirred solution of compound 393 (191 mg, 0.308 mmol) in $CH_2Cl_2$ (1.5 mL) at room temperature was added TFA (1.5 mL). After stirring for 1 h at the same temperature, the reaction mixture was concentrated. The residue was purified by silica gel column chromatography (25-100% EtOAc/n-hexane then 0-20% MeOH/EtOAc) to yield compound 408 (131 mg, 82%) as a yellow oil;

$^1$H-NMR (400 MHz, $CDCl_3$) δ 1.10 (t, J=7.5 Hz, 3H), 2.64 (q, J=7.6 Hz, 2H), 3.52-3.60 (m, 1H), 3.78 (s, 3H), 3.88-3.95 (m, 2H), 4.13-4.17 (m, 1H), 4.33 (dd, J=12.2, 5.1 Hz, 1H), 5.89 (s, 2H), 6.62-7.00 (m, 2H), 7.15 (s, 1H), 7.32-7.41 (m, 3H), 7.45-7.52 (m, 3H), 8.01 (dd, J=7.4, 1.1 Hz, 1H); MS (ESI$^+$): 520 $[M+H]^+$.

Reference Procedure of Compound 413

413

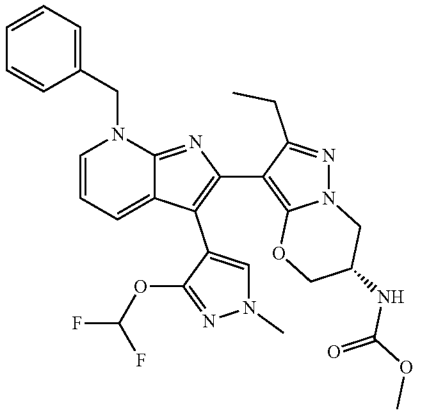

To a stirred solution of compound 408 (131 mg, 0.252 mmol) in $CH_2Cl_2$ (2.5 mL) at room temperature, N,N-diisopropylethylamine (0.0860 mL, 0.506 mmol) and methyl chloroformate (0.0230 mL, 0.299 mmol) were added. After stirring at room temperature for 1 h, the reaction mixture was concentrated, and the residue was purified by silica gel column chromatography (25-100% EtOAc/n-hexane then 0-20% MeOH/EtOAc) to yield compound 413 (137 mg, 94%) as a yellow oil; $^1$H-NMR (400 MHz, $CDCl_3$) δ 1.06-1.13 (m, 3H), 2.64 (q, J=7.6 Hz, 2H), 3.67-3.72 (m, 3H), 3.76-3.84 (m, 3H), 4.18-4.40 (m, 5H), 5.45-5.47 (m, 1H), 5.89 (s, 2H), 6.81-6.86 (m, 1H), 7.15 (s, 1H), 7.35-7.54 (m, 7H), 8.00-8.02 (m, 1H); MS (ESI$^+$): 578 $[M+H]^+$.

Experimental Procedure of EX.572

EX. 572

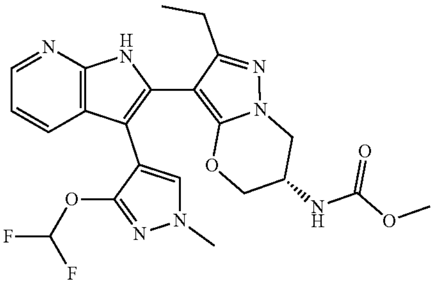

A mixture of compound 413 (57.0 mg, 0.0987 mmol) and 10% Pd—C (11.4 mg) in EtOH (1 mL) was stirred at 50° C. for 3 h under a hydrogen atmosphere (1 atm). The reaction mixture was purged and backfilled with Ar, and filtered off through a pad of Celite. The filtrate was concentrated and the residue was purified by silica gel column chromatography (0-8% MeOH/EtOAc) to yield EX.572 (35 mg, 73%); $^1$H-NMR (400 MHz, DMSO-$d_6$) δ 0.88 (t, J=7.5 Hz, 3H), 2.25 (q, J=7.5 Hz, 2H), 3.59 (s, 3H), 3.76 (s, 3H), 3.96-4.00 (m, 1H), 4.11-4.29 (m, 4H), 7.06 (dd, J=7.9, 4.7 Hz, 1H), 7.17 (t, J=73.9 Hz, 1H), 7.55 (s, 1H), 7.62 (d, J=5.3 Hz, 1H), 7.78 (dd, J=7.8, 1.1 Hz, 1H), 8.19 (dd, J=4.7, 1.6 Hz, 1H), 11.56 (s, 1H); MS (ESI$^+$): 488 $[M+H]^+$.

Experimental Procedure of EX.606

EX. 606

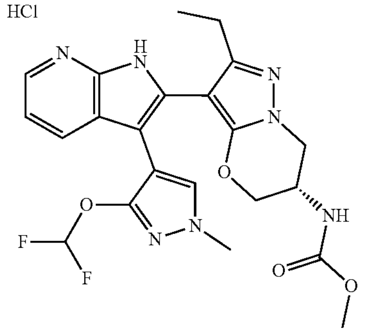

To a stirred solution of EX.572 (20.0 mg, 0.0410 mmol) in acetone (0.5 mL) at room temperature, 6 mol/L HCl (0.0075 mL) was added. After stirring at room temperature for 1 h, the reaction mixture was concentrated. The residue was dissolved in $CH_2Cl_2$, and then diisopropyl ether was added. The resulting precipitate was collected by filtration. The collected material was then washed with acetone to yield EX.606 (18 mg, 83%); $^1$H-NMR (400 MHz, DMSO-$d_6$) δ 0.88 (3H, t, J=7.5 Hz), 2.25 (2H, q, J=7.6 Hz), 3.59 (3H, s), 3.76 (3H, s), 3.94-4.33 (5H, m), 6.96-7.37 (2H, m), 7.58 (1H, s), 7.61-7.65 (1H, m), 7.85-7.91 (1H, m), 8.23 (1H, dd, J=4.9, 1.5 Hz), 11.77 (1H, s).

Reference Procedure of Compound 141

141

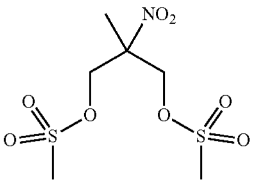

Triethyl amine (3.1 mL, 22.2 mmol) and methanesulfonyl chloride (1.2 mL, 15.6 mmol) were added to a solution of 2-methyl-2-nitropropane-1,3-diol (1.00 g, 7.40 mmol) in $CH_2Cl_2$ (18.5 mL) at 0° C. After stirring at room temperature for 3 h, water was added, and the resulting mixture was extracted with EtOAc. The organic layer was washed with brine, dried over $Na_2SO_4$, and concentrated to yield compound 141 (1.92 g, 89%); $^1$H-NMR (400 MHz, $CDCl_3$) δ 1.74 (s, 3H), 3.10 (s, 6H), 4.60 (d, J=11.0 Hz, 2H), 4.64 (d, J=11.0 Hz, 2H).

Reference Procedure of Compound 142

142

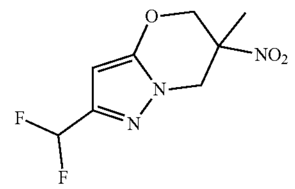

A mixture of compound 141 (1.92 g, 6.59 mmol), compound 137 (803 mg, 5.99 mmol), and $K_2CO_3$ (3.31 g, 23.9 mmol) in DMF (29.9 mL) was stirred at 80° C. for 14 h under an Ar atmosphere. The reaction mixture was filtered off through a pad of Celite, and the filtrate was concentrated. The residue was purified by silica gel column chromatography (25-100% EtOAc/hexane) to yield compound 142 (1.19 mg, 85%) as a colorless oil; MS ($ESI^+$): 234 $[M+H]^+$.

Reference Procedure of Compound 200

200

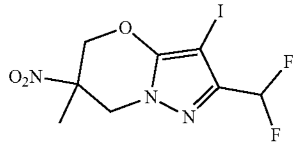

To a stirred solution of compound 142 (1.19 g, 5.10 mmol) in MeCN (25.5 mL) at room temperature, NIS (3.44 g, 15.3 mmol) was added. After stirring at room temperature for 3 h, the reaction was quenched with saturated aqueous $NaHCO_3$ and saturated aqueous $Na_2S_2O_3$, and the resulting mixture was extracted with EtOAc. The organic layer was washed with water, followed by brine, dried over $Na_2SO_4$, and concentrated. The residue was purified by silica gel column chromatography (8-66% EtOAc/hexane) to yield compound 200 (1.17 g, 64%) as a colorless oil; $^1$H-NMR (400 MHz, $CDCl_3$) δ 1.81 (s, 3H), 4.27 (d, J=12.1 Hz, 2H), 5.05 (dd, J=12.3, 2.2 Hz, 1H), 5.18 (dd, J=14.0, 2.0 Hz, 1H), 6.52 (t, J=53.7 Hz, 1H); MS ($ESI^+$): 360 $[M+H]^+$.

Reference Procedure of Compound 216

216

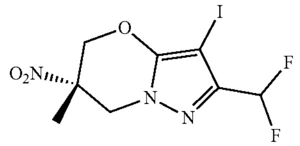

Compound 216 was prepared by optical resolution of compound 200 using chiral HPLC (DAICEL CHIRALPAK IG column; eluent: EtOH/hexane=50/50; flow rate: 1 mL/min; retention time: 8.92 min); $^1$H-NMR (400 MHz, $CDCl_3$) δ 1.79 (s, 3H), 4.22-4.30 (m, 2H), 5.03 (dd, J=12.2, 2.3 Hz, 1H), 5.16 (dd, J=14.0, 2.0 Hz, 1H), 6.51 (t, J=53.7 Hz, 1H); MS ($ESI^+$): 360 $[M+H]^+$.

Reference Procedure of Compound 267

267

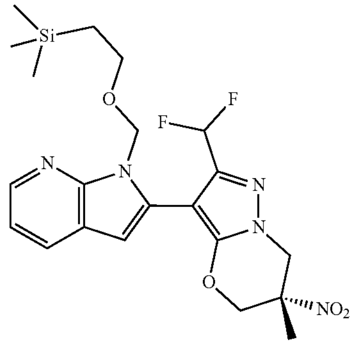

A mixture of compound 216 (473 mg, 1.32 mmol), 2-(4,4,5,5-tetramethyl-1,3,2-dioxaborolan-2-yl)-1-((2-(trimethylsilyl)ethoxy)methyl)-1H-pyrrolo[2,3-b]pyridine (Chemical Science (2021), 12(4), 1528-1534) (469 mg, 1.25 mmol), SPhos Pd G4 (99.8 mg, 0.123 mmol), and $K_3PO_4$ (798 mg, 3.76 mmol) in dioxane (6.3 mL) was stirred at 90° C. for 14 h. The reaction mixture was cooled to room temperature, filtered through a pad of Celite, and the filtrate was concentrated. The residue was purified by silica gel column chromatography (8-66% EtOAc/hexane) to yield compound 267 (222 mg, 37%) as yellow oil; $^1$H-NMR (400 MHz, $CDCl_3$) δ −0.13 (s, 9H), 0.74-0.92 (m, 2H), 1.83 (s, 3H), 3.30-3.40 (m, 2H), 4.29 (d, J=12.2 Hz, 1H), 4.35 (d, J=14.2 Hz, 1H), 4.98 (dd, J=12.1, 2.3 Hz, 1H), 5.25 (d, J=14.0 Hz, 1H), 5.47 (d, J=11.0 Hz, 1H), 5.66 (d, J=10.9 Hz, 1H), 6.54 (s, 1H), 6.59 (t, J=53.9 Hz, 1H), 7.10 (dd, J=7.8, 4.7 Hz, 1H), 7.89 (dd, J=7.8, 1.6 Hz, 1H), 8.34 (dd, J=4.7, 1.5 Hz, 1H); MS ($ESI^+$): 480 $[M+H]^+$.

Reference Procedure of Compound 281

281

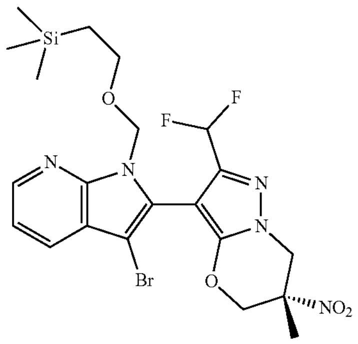

To a stirred solution of compound 267 (222 mg, 0.463 mmol) in MeCN (2.3 ml) was added NBS (86.5 mg, 0.486 mmol) at room temperature. After stirring at the same temperature for 2 h, the reaction was quenched with saturated aqueous $NaHCO_3$ and saturated aqueous $Na_2S_2O_3$, and the resulting mixture was extracted with EtOAc. The organic layer was washed with brine, dried over $Na_2SO_4$, and concentrated. The residue was purified by silica gel column chromatography (8-66% EtOAc/n-hexane) to afford compound 281 (202 mg, 78%) as a yellow oil; $^1$H-NMR (400

MHz, $CDCl_3$) δ −0.11-−0.08 (m, 9H), 0.78-0.89 (m, 2H), 1.84 (d, J=2.9 Hz, 3H), 3.34-3.47 (m, 2H), 4.27-4.42 (m, 2H), 4.96 (dt, J=12.2, 2.1 Hz, 1H), 5.25 (d, J=14.1 Hz, 1H), 5.41-5.68 (m, 2H), 6.65 (td, J=54.2, 10.7 Hz, 1H), 7.18 (dd, J=7.9, 4.7 Hz, 1H), 7.86 (dt, J=7.9, 2.0 Hz, 1H), 8.39 (ddd, J=8.3, 4.8, 1.6 Hz, 1H); MS ($ESI^+$): 558 $[M+H]^+$.

Reference Procedure of Compound 297

297

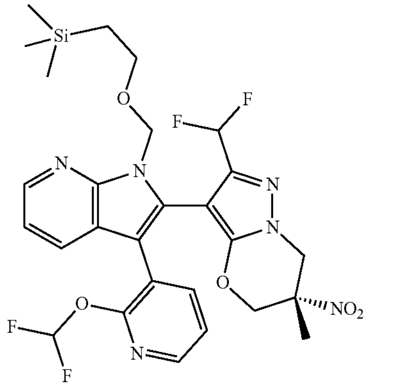

A mixture of compound 281 (342 mg, 0.612 mmol), [2-(difluoromethoxy)-3-pyridyl]boronic acid (232 mg, 1.23 mmol), SPhos Pd G4 (48.6 mg, 0.0612 mmol), and $K_3PO_4$ (391 mg, 1.84 mmol) in dioxane (6 mL) and water (0.11 mL) was stirred at 100° C. for 14 h. The reaction mixture was cooled to room temperature and purified by silica gel column chromatography (25-100% EtOAc/hexane) to yield compound 297 (335 mg) along with some impurities. This compound was used in the next step without further purification.

Reference Procedure of Compound 337

337

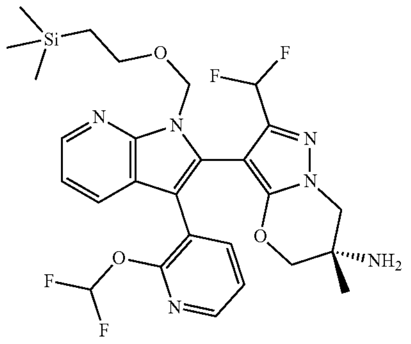

A mixture of compound 297 (335 mg, 0.538 mmol) and iron powder (150 mg, 2.69 mmol) in EtOH and AcOH (1/1, 2.7 mL) was stirred at 80° C. for 5 h under an Ar atmosphere. The reaction mixture was filtered off through a pad of Celite, and the filtrate was concentrated. The residue was purified by silica gel column chromatography (25-100% EtOAc/hexane) to yield compound 337 (225 mg, 71%) as a colorless oil; $^1H$-NMR (400 MHz, $CDCl_3$) δ −0.12-−0.07 (m, 9H), 0.80-0.93 (m, 2H), 1.22-1.31 (m, 3H), 3.47-3.56 (m, 2H), 3.79-4.06 (m, 4H), 5.59 (dd, J=16.8, 11.0 Hz, 1H), 5.75 (dd, J=12.6, 10.9 Hz, 1H), 6.30-6.66 (m, 1H), 7.09 (td, J=7.5, 4.9 Hz, 1H), 7.15 (ddd, J=7.9, 4.7, 1.8 Hz, 1H), 7.29-7.70 (m, 2H), 7.80 (dd, J=7.9, 1.6 Hz, 1H), 8.12 (dd, J=4.9, 1.4 Hz, 1H), 8.41 (dt, J=4.7, 1.8 Hz, 1H); MS ($ESI^+$): 593 $[M+H]^+$.

Reference Procedure of Compound 352

352

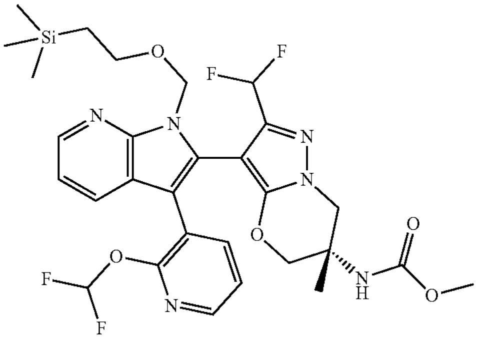

To a stirred solution of compound 337 (144 mg, 0.243 mmol) in $CH_2Cl_2$ (1.2 mL) at room temperature, N,N-diisopropylethylamine (0.0620 mL, 0.365 mmol) and methyl chloroformate (0.0210 mL, 0.273 mmol) were added. After stirring at room temperature for 3 h, the reaction mixture was concentrated, and the residue was purified by silica gel column chromatography (20-100% EtOAc/n-hexane) to yield compound 352 (153 mg, 97%); $^1H$-NMR (400 MHz, $CDCl_3$) δ −0.09-−0.06 (m, 9H), 0.85-0.92 (m, 2H), 1.53 (s, 3H), 3.53-3.59 (m, 2H), 3.67 (d, J=9.9 Hz, 3H), 3.86-3.95 (m, 2H), 4.29-4.38 (m, 1H), 4.65-4.71 (m, 1H), 5.35-6.72 (m, 4H), 7.00-7.23 (m, 2H), 7.29-7.52 (m, 1H), 7.55-7.74 (m, 1H), 7.80 (ddd, J=7.9, 5.1, 1.6 Hz, 1H), 8.13 (dd, J=4.9, 1.9 Hz, 1H), 8.40 (dd, J=4.7, 1.4 Hz, 1H); MS ($ESI^+$): 651 $[M+H]^+$.

Experimental Procedure of EX.492

EX. 492

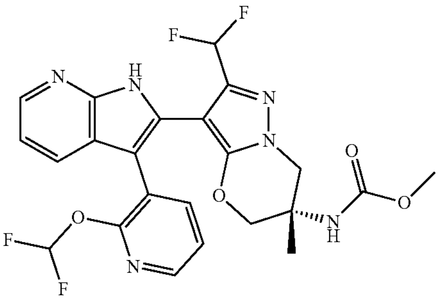

To a stirred solution of compound 352 (153 mg, 0.235 mmol) in $CH_2Cl_2$ (2.4 mL) at room temperature, TFA (2.4 mL) was added. After stirring at room temperature for 6 h, the reaction mixture was concentrated. The residue was dissolved in MeOH (2.4 mL) and then 5 mol/L aqueous NaOH solution was added to the resulting solution. After stirring at room temperature for 14 h, the resulting mixture was concentrated. The residue was purified by silica gel column chromatography (25-100% EtAOc/n-hexan) to yield EX.492 (79 mg, 65%); $^1$H-NMR (400 MHz, DMSO-d$_6$) δ 1.27 (s, 3H), 3.53 (s, 3H), 3.81 (d, J=11.0 Hz, 1H), 4.04 (d, J=12.7 Hz, 1H), 4.44-4.48 (m, 2H), 6.78 (t, J=54.0 Hz, 1H), 7.11 (dd, J=7.9, 4.7 Hz, 1H), 7.19 (dd, J=7.4, 4.9 Hz, 1H), 7.42 (s, 1H), 7.51-7.87 (m, 3H), 8.18 (dd, J=4.9, 1.9 Hz, 1H), 8.27 (dd, J=4.7, 1.6 Hz, 1H), 11.98 (s, 1H); MS (ESI$^+$): 521 [M+H]$^+$.

Reference Procedure of Compound 401

401

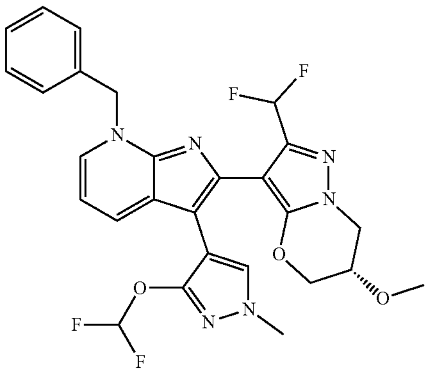

To a stirred solution of compound 396 (103 mg, 0.190 mmol) in THF (0.95 mL) at 0° C. under an Ar atmosphere, 60% sodium hydride (7.90 mg, 0.211 mmol) was added. After stirring at 0° C. for 0.5 h, iodomethane (0.0150 mL, 0.241 mmol) was added to the reaction mixture, which was stirred at room temperature for 1 h. The reaction was quenched with saturated aqueous $NH_4Cl$, and the resulting mixture was extracted with EtOAc. The organic layer was washed with brine, dried over $Na_2SO_4$, and concentrated. The residue was purified by silica gel column chromatography (25-100% EtOAc/hexane then 0-20% MeOH/EtOAc) to yield compound 401 (85 mg, 80%) as a yellow oil; $^1$H-NMR (400 MHz, $CDCl_3$) δ 3.43 (s, 3H), 3.79 (s, 3H), 3.85-3.91 (m, 1H), 4.01-4.07 (m, 1H), 4.20-4.32 (m, 2H), 4.33-4.40 (m, 1H), 5.78 (d, J=14.2 Hz, 1H), 5.90 (d, J=14.2 Hz, 1H), 6.63-7.23 (m, 4H), 7.32-7.41 (m, 3H), 7.45-7.50 (m, 2H), 7.57 (dd, J=6.3, 1.1 Hz, 1H), 8.03 (dd, J=7.5, 1.1 Hz, 1H); MS (ESI$^+$): 557 [M+H]$^+$.

Experimental Procedure of EX.531

EX. 531

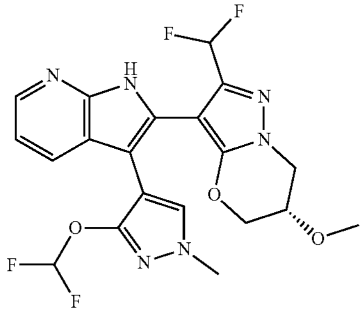

A mixture of compound 401 (84.7 mg, 0.152 mmol) and 5% Pd on barium carbonate powder (16.9 mg) in EtOH (1.5 mL) was stirred at 50° C. for 3 h under a hydrogen atmosphere (1 atm). The reaction mixture was purged and backfilled with Ar, and filtered off through a pad of Celite. The filtrate was concentrated, and the residue was purified by silica gel column chromatography (25-100% EtOAc/n-hexane then 0-20% MeOH/EtOAc) to yield EX.531 (54 mg, 76%); $^1$H-NMR (400 MHz, DMSO-d$_6$) δ 3.37 (s, 3H), 3.75 (s, 3H), 4.04-4.09 (m, 1H), 4.15-4.21 (m, 1H), 4.23-4.36 (m, 2H), 4.45-4.52 (m, 1H), 6.72 (t, J=54.1 Hz, 1H), 6.92-7.29 (m, 2H), 7.50 (s, 1H), 7.82 (dd, J=7.8, 1.2 Hz, 1H), 8.23 (dd, J=4.7, 1.6 Hz, 1H), 11.76 (s, 1H); MS (ESI$^+$): 467 [M+H]$^+$.

Reference Procedure of Compound 399

399

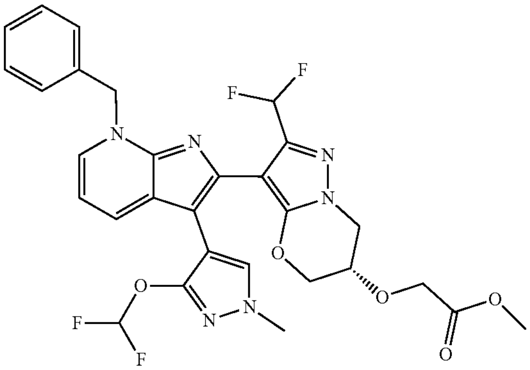

To a stirred solution of compound 396 (50.0 mg, 0.0922 mmol) in THF (0.46 mL) at 0° C. under Ar atmosphere, 60% sodium hydride (4.40 mg, 0.101 mmol) was added. After stirring at 0° C. for 0.5 h, methyl bromoacetate (0.011 mL, 0.12 mmol) was added to the reaction mixture, which was stirred at room temperature for 1 h. The reaction was quenched with saturated aqueous $NH_4Cl$, and the resulting mixture was extracted with EtOAc. The organic layer was washed with brine, dried over $Na_2SO_4$, and concentrated. The residue was purified by silica gel column chromatography (25-100% EtOAc/hexane then 0-20% MeOH/EtOAc) to yield compound 399 (35 mg, 62%) as a colorless oil; $^1$H-NMR (400 MHz, $CDCl_3$) δ 3.77 (s, 3H), 3.78 (s, 3H), 4.08-4.11 (m, 2H), 4.20 (s, 2H), 4.22-4.42 (m, 3H), 5.80 (d, J=14.2 Hz, 1H), 5.89 (d, J=14.2 Hz, 1H), 6.81 (t, J=74.0 Hz, 1H), 6.85 (dd, J=7.4, 6.3 Hz, 1H), 7.00 (t, J=54.5 Hz, 1H), 7.17 (s, 1H), 7.32-7.42 (m, 3H), 7.44-7.49 (m, 2H), 7.57 (dd, J=6.3, 1.0 Hz, 1H), 8.02 (dd, J=7.5, 1.1 Hz, 1H); MS (ESI$^+$): 615 [M+H]$^+$.

Reference Procedure of Compound 419

419

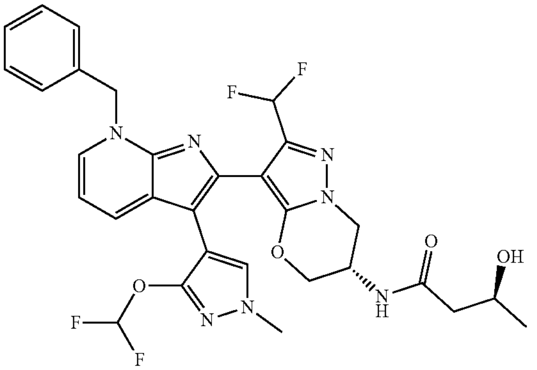

To a stirred solution of compound 399 (123 mg, 0.200 mmol) in THF (2 mL) at 0° C. under Ar atmosphere, 3 mol/L methylmagnesium bromide in diethyl ether (0.20 mL, 0.60 mmol) was slowly added. After stirring at the same temperature for 1 h, the reaction was quenched with sat. aq. $NH_4Cl$, and the resulting mixture was extracted with EtOAc. The organic layer was washed with brine, dried over $Na_2SO_4$, and concentrated. The residue was purified by silica gel column chromatography (20-100% EtOAc/hexane then 0-20% MeOH/EtOAc) to yield compound 419 (119 mg, 97%); $^1$H-NMR (400 MHz, DMSO-$d_6$) δ 1.03 (s, 6H), 3.29 (s, 2H), 3.76 (s, 3H), 3.98-4.06 (m, 1H), 4.11-4.32 (m, 4H), 4.40 (s, 1H), 5.83 (s, 2H), 6.91-7.57 (m, 9H), 7.93 (dd, J=7.5, 0.9 Hz, 1H), 8.26 (dd, J=6.2, 1.0 Hz, 1H); MS (ESI$^+$): 615 $[M+H]^+$.

Experimental Procedure of EX.535

EX. 535

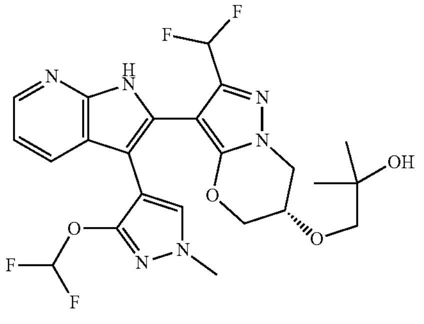

A mixture of compound 419 (110 mg, 0.179 mmol) and 5% Pd on barium carbonate powder (22 mg) in EtOH (2 mL) was stirred at 50° C. for 3 h under a hydrogen atmosphere (1 atm). The reaction mixture was purged and backfilled with Ar, and filtered off through a pad of Celite. The filtrate was concentrated, and the residue was purified by silica gel column chromatography (0-10% MeOH/EtOAc) to yield EX.535 (61 mg, 65%); $^1$H-NMR (400 MHz, DMSO-$d_6$) § 1.05 (s, 6H), 3.30-3.37 (m, 2H), 3.75 (s, 3H), 4.13-4.47 (m, 6H), 6.70 (t, J=54.1 Hz, 1H), 6.91-7.29 (m, 2H), 7.49 (s, 1H), 7.81 (dd, J=7.9, 1.4 Hz, 1H), 8.23 (dd, J=4.7, 1.6 Hz, 1H), 11.76 (s, 1H); MS (ESI$^+$): 525 $[M+H]^+$.

Reference Procedure of Compound 349

349

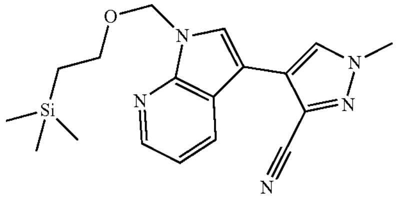

A mixture of compound 233 (1.00 g, 2.67 mmol), 4-bromo-1-methyl-1H-pyrazole-3-carbonitrile (547 mg, 2.94 mmol), $PdCl_2$(dppf)-$CH_2Cl_2$ (218 mg, 0.267 mmol), and $K_3PO_4$ (1.70 g, 8.01 mmol) in dioxane (12 mL) and water (1.2 mL) was stirred at 90° C. for 1 h under an Ar atmosphere. The reaction mixture was cooled to room temperature, and water was added. The resulting mixture was extracted with EtOAc. The organic layer was washed with brine, dried over $Na_2SO_4$, and concentrated. The residue was purified by silica gel column chromatography (10-50% EtOAc/n-hexane) to afford compound 349 (873 mg) along with some impurities. This compound was used in the next step without further purification; $^1$H-NMR (400 MHz, $CDCl_3$) δ −0.06 (s, 9H), 0.90-0.98 (m, 2H), 3.56-3.64 (m, 2H), 4.06 (s, 3H), 5.73 (s, 2H), 7.19 (dd, J=7.9, 4.7 Hz, 1H), 7.74 (s, 1H), 7.81 (s, 1H), 8.00 (dd, J=7.9, 1.5 Hz, 1H), 8.41 (dd, J=4.7, 1.5 Hz, 1H).

Reference Procedure of Compound 350

350

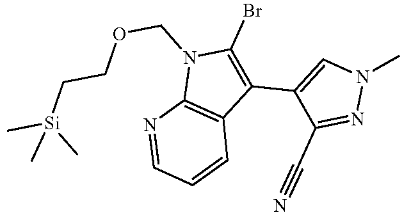

To a stirred solution of compound 349 (873 mg, 2.47 mmol) in MeCN (12 mL) was added NBS (460 mg, 2.59 mmol) at room temperature. After stirring at the same temperature for 1 h, the reaction was quenched with saturated aqueous $NaHCO_3$ and saturated aqueous $Na_2S_2O_3$, and the resulting mixture was extracted with EtOAc. The organic layer was washed with brine, dried over $Na_2SO_4$, and concentrated. The residue was purified by silica gel column chromatography (10-50% EtOAc/n-hexane) to afford compound 350 (604 mg, 57%) as a yellow oil; $^1$H-NMR (400 MHz, $CDCl_3$) δ −0.05 (s, 9H), 0.92-0.99 (m, 2H), 3.63-3.70 (m, 2H), 4.08 (s, 3H), 5.83 (s, 2H), 7.17 (dd, J=7.9, 4.7 Hz, 1H), 7.69 (s, 1H), 7.89 (dd, J=7.9, 1.5 Hz, 1H), 8.37 (dd, J=4.7, 1.5 Hz, 1H); MS (ESI$^+$): 432 $[M+H]^+$.

Reference Procedure of Compound 383

383

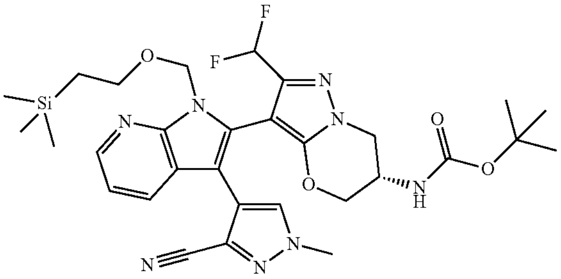

A mixture of compound 350 (125 mg, 0.289 mmol), compound 229 (100 mg, 0.241 mmol), $PdCl_2(dppf)-CH_2Cl_2$ (20.0 mg, 0.0245 mmol), and $K_3PO_4$ (155 mg, 0.730 mmol) in dioxane (1.2 mL) was stirred at 90° C. for 1 h under an Ar atmosphere. The reaction mixture was cooled to room temperature, and water was added. The resulting mixture was extracted with EtOAc. The organic layer was washed with brine, dried over $Na_2SO_4$, and concentrated. The residue was purified by silica gel column chromatography (20-70% EtOAc/hexane) to yield compound 383 (109 mg, 98%); 1H-NMR (400 MHz, $CDCl_3$) δ −0.14-−0.11 (m, 9H), 0.75-0.94 (m, 2H), 1.03-1.12 (m, 9H), 3.34-3.52 (m, 2H), 3.74-4.01 (m, 3H), 4.03-4.37 (m, 5H), 5.42-6.04 (m, 2H), 6.17-6.59 (m, 1H), 7.14-7.20 (m, 1H), 7.35-7.72 (m, 11H), 7.84-7.98 (m, 1H), 8.38-8.44 (m, 1H) MS ($ESI^+$): 780 $[M+H]^+$.

Experimental Procedure of EX.511

EX. 511

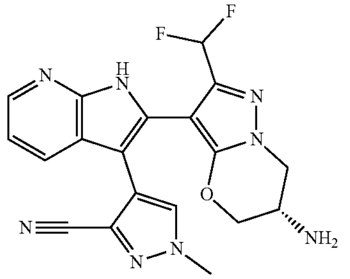

To a stirred solution of compound 383 (98.0 mg, 0.153 mmol) in $CH_2Cl_2$ (1 mL) at room temperature, TFA (2 mL) was added. After stirring at room temperature for 5 h, the reaction mixture was concentrated. The residue was dissolved in MeOH (2 mL) and then 5 mol/L aqueous NaOH solution was added to the resulting solution. After stirring at room temperature for 1.5 h, the resulting mixture was acidified with 2N HCl at 0° C. The resulting mixture was extracted thrice with EtOAc. The organic layer was washed with brine, dried over $Na_2SO_4$, and concentrated. The residue was purified by silica gel column chromatography (0-10% MeOH/EtOAc) to yield EX.511 (15 mg, 24%); $^1H$-NMR (400 MHz, DMSO-$d_6$) δ 1.78-2.07 (m, 2H), 3.42-3.52 (m, 1H), 3.81-3.90 (m, 1H), 3.91-4.00 (m, 4H), 4.20 (dd, J=10.7, 2.7 Hz, 1H), 4.28 (dd, J=12.1, 4.7 Hz, 1H), 6.60 (t, J=54.0 Hz, 1H), 7.14 (dd, J=8.0, 4.7 Hz, 1H), 7.91 (dd, J=7.9, 1.4 Hz, 1H), 8.02 (s, 1H), 8.28 (dd, J=4.7, 1.5 Hz, 1H), 11.97 (s, 1H); MS ($ESI^+$): 411 $[M+H]^+$.

Experimental Procedure of EX.517

EX. 517

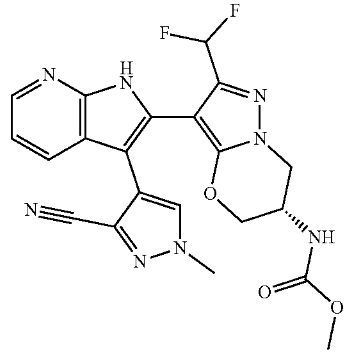

To a stirred solution of EX.511 (52.0 mg, 0.127 mmol) in THF (1.3 mL) at room temperature, N,N-diisopropylethylamine (0.043 mL, 0.25 mmol) and methyl chloroformate (0.0117 mL, 0.152 mmol) were added. After stirring at room temperature for 1 h, the reaction mixture was concentrated, and the residue was purified by silica gel column chromatography (0-10% MeOH/$CHCl_3$) to yield EX.517 (43 mg, 98%); $^1H$-NMR (400 MHz, DMSO-$d_6$) § 3.59 (s, 3H), 3.96 (s, 3H), 4.07-4.15 (m, 1H), 4.17-4.31 (m, 3H), 4.38-4.47 (m, 1H), 6.62 (t, J=53.9 Hz, 1H), 7.15 (dd, J=7.9, 4.7 Hz, 1H), 7.51-7.62 (m, 1H), 7.92 (dd, J=7.9, 1.5 Hz, 1H), 8.00 (s, 1H), 8.29 (dd, J=4.7, 1.5 Hz, 1H), 11.93 (s, 1H); MS ($ESI^+$): 469 $[M+H]^+$.

Experimental Example 1: MRGPRX2 Reporter Cell Assays

U2OS cells (ATCC, Manassas, VA) were stably transfected with MRGPRX2 expression clones (GeneCopoeia, Rockville, MD) and the pGL4.30[luc2P/NFAT-RE/Hygro] reporter plasmid (Promega, Madison, WI). Clonal cells were maintained in Growth Media (McCoy's 5A, 10% FBS, 495 μg/ml hygromycin, 2 μg/ml puromycin, 100 units/ml penicillin, and 100 μg/ml streptomycin). The day before assay, cells were plated to white 384-well microplates at 3000 (MRGPRX2) cells/well in 10 ul Assay Media (McCoy's 5A, 2% charcoal dextran stripped FBS, 100 units/ml penicillin, and 100 μg/ml streptomycin) (Gibco, Thermo Fisher) and allowed to adhere overnight. The following day, serially diluted compound stocks were added directly to the cells (final DMSO concentration of 0.5%) and pre-incubated for 30 minutes at 37° C., 5% $CO_2$. The final concentration of Substance P (Tocris, Minneapolis, MN, or PEPTIDE INSTITUTE, Osaka, Japan) corresponding to EC80 was added to stimulate the (MRGPRX2) cells. Cells were returned to the incubator for 6 hrs, after which 5 ul of ONE-GLO substrate (Promega) was added. Luminescence was read within 15 minutes (BioTek, Winooski, VT or infinite M1000Pro, Tecan Japan, Kanagawa, Japan).

$IC_{50}$ for each test compound is shown in Table below.

Percent inhibition for each test compound was calculated using the formula:

$$\text{Percent inhibition}=100*(1-((A-B)/(C-B)))$$

where:

A=the luminescence count of the "test compound" well

B=the median luminescence count of the "Vehicle (0.5% DMSO)" wells

C=the median luminescence count of the "Vehicle (0.5% DMSO)+5 uM of substance P" wells The mean percent inhibition of each concentration of "test compound" was used to generate dose-response curves. IC50 values were calculated using a four-parameter logistic fit to the data using GraphPad Prism software.

+++: IC50 values <10 nM

++: 10 nM=<IC50 values <100 nM

+: 100 nM=<IC50 values <1000 nM

| Test compound | IC50 |
|---|---|
| EX.21 | +++ |
| EX.27 | +++ |
| EX.45 | +++ |
| EX.50 | +++ |
| EX.53 | +++ |
| EX.54 | +++ |
| EX.67 | +++ |
| EX.71 | +++ |
| EX.75 | +++ |
| EX.77 | +++ |
| EX.78 | +++ |
| EX.80 | +++ |
| EX.81 | +++ |
| EX.89 | +++ |
| EX.90 | +++ |
| EX.94 | +++ |
| EX.96 | +++ |
| EX.99 | +++ |
| EX.100 | +++ |
| EX.101 | +++ |
| EX.107 | +++ |
| EX.109 | +++ |
| EX.113 | +++ |
| EX.116 | +++ |
| EX.122 | +++ |
| EX.128 | +++ |
| EX.133 | +++ |
| EX.137 | +++ |
| EX.141 | +++ |
| EX.146 | +++ |
| EX.147 | +++ |
| EX.153 | +++ |
| EX.157 | +++ |
| EX.158 | +++ |
| EX.167 | +++ |
| EX.168 | +++ |
| EX.169 | +++ |
| EX.170 | +++ |
| EX.175 | +++ |
| EX.176 | +++ |
| EX.177 | +++ |
| EX.178 | +++ |
| EX.179 | +++ |
| EX.181 | +++ |
| EX.182 | +++ |
| EX.183 | +++ |
| EX.199 | +++ |
| EX.200 | +++ |
| EX.201 | +++ |
| EX.202 | +++ |
| EX.203 | +++ |
| EX.216 | +++ |

-continued

| Test compound | IC50 |
|---|---|
| EX.218 | +++ |
| EX.225 | +++ |
| EX.227 | +++ |
| EX.230 | +++ |
| EX.234 | +++ |
| EX.235 | +++ |
| EX.236 | +++ |
| EX.238 | +++ |
| EX.239 | +++ |
| EX.241 | +++ |
| EX.242 | +++ |
| EX.243 | +++ |
| EX.245 | +++ |
| EX.247 | +++ |
| EX254 | +++ |
| EX.256 | +++ |
| EX.257 | +++ |
| EX.264 | +++ |
| EX.266 | +++ |
| EX.270 | +++ |
| EX.271 | +++ |
| EX.272 | +++ |
| EX.281 | +++ |
| EX.287 | +++ |
| EX.288 | +++ |
| EX.291 | ++ |
| EX.292 | + |
| EX.299 | +++ |
| EX.300 | +++ |
| EX.301 | + |
| EX,307 | +++ |
| EX.314 | +++ |
| EX.316 | +++ |
| EX.322 | + |
| EX.323 | +++ |
| EX.324 | + |
| EX.326 | +++ |
| EX.328 | +++ |
| EX.329 | +++ |
| EX.330 | + |
| EX.336 | +++ |
| EX.344 | +++ |
| EX.345 | +++ |
| EX.346 | +++ |
| EX.351 | + |
| EX.354 | +++ |
| EX.355 | +++ |
| EX.356 | +++ |
| EX.357 | +++ |
| EX.358 | +++ |
| EX.359 | +++ |
| EX.361 | +++ |
| EX.362 | +++ |
| EX.363 | +++ |
| EX.364 | +++ |
| EX.366 | +++ |
| EX.367 | +++ |
| EX.368 | +++ |
| EX.369 | +++ |
| EX.370 | +++ |
| EX.371 | +++ |
| EX.375 | +++ |
| EX.377 | +++ |
| EX.380 | ++ |
| EX.381 | +++ |
| EX.388 | ++ |
| EX.389 | ++ |
| EX.400 | ++ |
| EX.401 | +++ |
| EX.402 | +++ |
| EX.403 | +++ |
| EX.404 | ++ |
| EX.405 | ++ |
| EX.406 | + |
| EX.407 | ++ |
| EX.408 | +++ |
| EX.409 | + |

-continued

| Test compound | IC50 |
|---|---|
| EX.410 | +++ |
| EX.411 | ++ |
| EX.412 | ++ |
| EX.413 | + |
| EX.416 | ++ |
| EX.420 | +++ |
| EX.421 | +++ |
| EX.422 | +++ |
| EX.423 | +++ |
| EX.424 | +++ |
| EX.425 | +++ |
| EX.426 | +++ |
| EX.427 | +++ |
| EX.428 | +++ |
| EX.429 | +++ |
| EX.430 | +++ |
| EX.431 | +++ |
| EX.432 | +++ |
| EX.433 | +++ |
| EX.434 | +++ |
| EX.435 | +++ |
| EX.436 | +++ |
| EX.437 | +++ |
| EX.438 | +++ |
| EX.439 | +++ |
| EX.440 | +++ |
| EX.441 | +++ |
| EX.442 | +++ |
| EX.444 | +++ |
| EX.445 | +++ |
| EX.446 | +++ |
| EX.447 | +++ |
| EX.448 | +++ |
| EX.449 | +++ |
| EX.450 | +++ |
| EX.451 | +++ |
| EX.452 | +++ |
| EX.453 | +++ |
| EX.454 | +++ |
| EX.455 | +++ |
| EX.456 | +++ |
| EX.457 | +++ |
| EX.458 | +++ |
| EX.459 | +++ |
| EX.460 | +++ |
| EX.461 | +++ |
| EX.462 | +++ |
| EX.463 | +++ |
| EX.464 | +++ |
| EX.465 | +++ |
| EX.466 | +++ |
| EX.467 | +++ |
| EX.468 | +++ |
| EX.469 | +++ |
| EX.470 | +++ |
| EX.471 | +++ |
| EX.476 | +++ |
| EX.477 | +++ |
| EX.478 | +++ |
| EX.479 | +++ |
| EX.480 | +++ |
| EX.481 | +++ |
| EX.482 | +++ |
| EX.483 | +++ |
| EX.484 | +++ |
| EX.485 | +++ |
| EX.486 | +++ |
| EX.488 | +++ |
| EX.489 | +++ |
| EX.490 | +++ |
| EX.491 | +++ |
| EX.492 | +++ |
| EX.493 | +++ |
| EX.494 | +++ |
| EX.495 | +++ |
| EX.496 | +++ |
| EX.497 | +++ |

-continued

| Test compound | IC50 |
|---|---|
| EX.498 | +++ |
| EX.499 | +++ |
| EX.500 | +++ |
| EX.501 | +++ |
| EX.502 | +++ |
| EX.503 | +++ |
| EX.504 | +++ |
| EX.505 | +++ |
| EX.506 | +++ |
| EX.507 | +++ |
| EX.508 | +++ |
| EX.509 | +++ |
| EX.512 | +++ |
| EX.513 | +++ |
| EX.514 | +++ |
| EX.515 | +++ |
| EX.516 | +++ |
| EX.517 | +++ |
| EX.518 | +++ |
| EX.519 | +++ |
| EX.520 | +++ |
| EX.521 | +++ |
| EX.522 | +++ |
| EX.523 | +++ |
| EX.524 | +++ |
| EX.525 | +++ |
| EX.526 | +++ |
| EX.527 | +++ |
| EX.528 | +++ |
| EX.529 | +++ |
| EX.530 | +++ |
| EX.531 | +++ |
| EX.532 | +++ |
| EX.533 | +++ |
| EX.534 | +++ |
| EX.535 | +++ |
| EX.536 | +++ |
| EX.537 | +++ |
| EX.538 | +++ |
| EX.539 | +++ |
| EX.540 | +++ |
| EX.541 | +++ |
| EX.542 | +++ |
| EX.543 | +++ |
| EX.544 | +++ |
| EX.545 | +++ |
| EX.546 | +++ |
| EX.547 | +++ |
| EX.548 | +++ |
| EX.549 | +++ |
| EX.550 | +++ |
| EX.551 | +++ |
| EX.552 | +++ |
| EX.553 | +++ |
| EX.554 | +++ |
| EX.555 | +++ |
| EX.556 | +++ |
| EX.558 | +++ |
| EX.559 | +++ |
| EX.560 | +++ |
| EX.561 | +++ |
| EX.562 | +++ |
| EX.563 | +++ |
| EX.564 | +++ |
| EX.565 | +++ |
| EX.566 | +++ |
| EX.567 | +++ |
| EX.568 | +++ |
| EX.569 | +++ |
| EX.571 | +++ |
| EX.572 | +++ |
| EX.573 | +++ |
| EX.574 | +++ |
| EX.575 | +++ |
| EX.576 | +++ |
| EX.577 | +++ |
| EX.578 | +++ |

-continued

| Test compound | IC50 |
|---|---|
| EX.579 | +++ |
| EX.580 | +++ |
| EX.581 | +++ |
| EX.582 | +++ |
| EX.583 | +++ |
| EX.584 | +++ |
| EX.585 | +++ |
| EX.586 | +++ |
| EX.587 | +++ |
| EX.588 | +++ |
| EX.589 | +++ |
| EX.590 | +++ |
| EX.591 | +++ |
| EX.592 | +++ |
| EX.593 | +++ |
| EX.594 | +++ |
| EX.595 | +++ |

| Test Compounds | IC50(nM) |
|---|---|
| EX.272 | 2.9 |
| EX.234 | 1.8 |
| Ex.572 | 3.6 |
| Ex.422 | 5.8 |
| EX.534 | 2.1 |
| EX.435 | 4.1 |
| EX.449 | 2.6 |
| EX.492 | 1.9 |
| EX.517 | 3.2 |
| EX.527 | 4.4 |
| EX.531 | 2.3 |
| EX.535 | 2.0 |
| EX.559 | 3.0 |
| EX.571 | 1.2 |

Experimental Example 2: Evans Blue Vascular Permeability Assay

Twenty-five to twenty-six-week-old humanized mice (NOG-hGM-CSF/hIL-3 Tg mice at 17-18 weeks after transplantation of human umbilical cord blood-derived CD34+ cells; Central Institute for Experimental Animals) were anesthetized with isoflurane and injected intravenously with 200 μL of 0.5% Evans blue (cat. no. 056-04061; FUJIFILM Wako Pure Chemical Corporation). Subsequently, vehicle (0.5w/v % Methyl Cellulose) or mg/kg of EX.381 were orally administered. After 30 minutes, animals were anesthetized with isoflurane and injected intradermally with 10 μL of (R)-Zinc3573 ((R)-Zinc; 3 μM, cat. no. SML1699; Sigma-Aldrich) into the right ear or with saline (0.1% DMSO) into the left ear as a control. Fifteen minutes after intradermal injection, animals were sacrificed and the ears were collected in 1.5 mL tubes. Evans blue dye was extracted from the tissue by adding 150 μL of N, N-dimethyl formamide (cat. no. 04096-34; nacalai tesque) for 12 hours at 55° C. Fifty μL of extracted dye in N, N-dimethyl formamide was then placed into a 96 well plate along with a standard curve of known Evans blue concentration standards. The plate was read at 620 nm and 740 nm on a plate reader and the Evans blue dye concentration in each sample was determined by a standard curve using corrected absorbance (corrected absorbance=A620−A740). Statistical analysis was performed with the software GraphPad Prism 6 (GraphPad Software). Data is expressed as mean and standard error of mean.

Unpaired t-tests were used to compare the statistical difference between groups.

| compound | Inhibition % | p |
|---|---|---|
| EX.381 | 76.1 + 12.1 | <0.05 |

Mast cells are involved in a variety of inflammatory diseases, and antigen-dependent activation of tissue mast cells with IgE bound to their surface is a major event in acute allergic reactions. In addition to the case where mast cells are activated by the combination of IgE-allergen, there is the case where the ligand directly stimulates and activates the Mas-related G protein-coupled receptor (MRGPR) on the mast cells. In particular, many new studies on MRGPRX2-mediated IgE-independent mast cell activation have been reported in recent years.

Suppressing mast cell activation using an antagonist targeting MRGPRX2 is considered to be effective in treating a pseudo-allergic reaction, an itch-associated condition, a pain-associated condition, or an inflammatory or autoimmune disorder. and the development of drugs containing MRGPRX2 antagonist as an active ingredient is expected.

Experimental example 3: SEB/HDM-Induced Dermatitis Model Assay hMRGPRX2 knock-in mice were generated using CRISPR-Cas9 gene editing technology to replace the Mrgprb2 locus with hMRGPRX2 (BioSafety Research Center Inc., Sizuoka, Japan). Mice were bred and maintained under controlled environmental conditions; temperature (standard range: 20-26° C.), relative humidity (standard range: 30-70%) and a 12-hr light/dark cycle (lighting from 7:00 a.m. to 7:00 p.m.). All animal procedures used in this study were conducted according to guidelines established by the Institutional Animal Care and Use Committee of Kyorin Pharmaceutical Co., Ltd. To evaluate the efficacy of the compound, we used the hMRGPRX2 knock-in mice with house dust mite/*Staphylococcus aureus* enterotoxin B (HDM/SEB) model of atopic dermatitis. On day 0, the dorsal skin was shaved and a solution of 10 μg/mL SEB (Sigma-Aldrich, Rehovot, Israel) diluted in 0.5% Tween 20/D-PBS was applied to the dorsal skin and both auricles. After the skin was dried, 100 mg of HDM ointment (Biostir AD, Biostir Inc., Kobe, Japan) was applied to the same area. From the second induction (on day 2) and thereafter, 150 μL of 4% sodium dodecyl sulfate was applied to the same area, followed by the application of SEB and HDM. The application was performed every 2 to 3 days. The administration of the test compound was started from day 0. The disease scores and skin thickness were measured every 2 to 3 days, up to 21 days, and the efficacy of the test compound was evaluated based on these indications. The test compound significantly prevented the increase in both the disease score and skin thickness.

Obviously, numerous modifications and variations of the present invention are possible in light of the above teachings. It is therefore to be understood that within the scope of the appended claims, the invention may be practiced otherwise than as specifically described herein.

The invention claimed is:

1. A compound represented by structural formula (Ih*):

(Ih*)

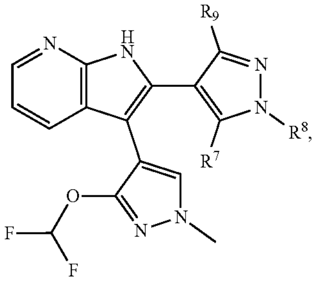

or a pharmaceutically acceptable salt thereof, wherein $R^7$ and $R^8$ together with the atoms to which they are attached form 4- to 12-membered heterocyclyl or 5- to 12-membered heteroaryl, wherein the 4- to 12-membered heterocyclyl or 5- to 12-membered heteroaryl is optionally substituted with one or more substituents independently selected from group Q; or $R^7$ is selected from H, deuterium, F, Cl, Br, OH, CN, $NO_2$, $NR^{10c}R^{10d}$, $C(=O)NR^{11c}R^{11d}$, $C_1$-$C_6$ alkyl, $C_1$-$C_6$ alkoxy, $C_2$-$C_6$ alkenyl, $C_2$-$C_6$ alkynyl, $C_3$-$C_{12}$ cycloalkyl, $C_6$-$C_{12}$ aryl, 5- to 12-membered heteroaryl, and 4- to 12-membered heterocyclyl, wherein each $C_1$-$C_6$ alkyl, $C_1$-$C_6$ alkoxy, $C_2$-$C_6$ alkenyl, $C_2$-$C_6$ alkynyl, $C_3$-$C_{12}$ cycloalkyl, $C_6$-$C_{12}$ aryl, 5- to 12-membered heteroaryl, or 4- to 12-membered heterocyclyl is optionally substituted with one or more substituents independently selected from a group Q;

$R^8$ is selected from H and $C_{1-6}$ alkyl optionally substituted with one or more substituents independently selected from a group Q;

$R^9$ is selected from F, Cl, Br, OH, CN, $NO_2$, $NR^{10e}R^{10f}$, $C(=O)NR^{11e}R^{11f}$, $C_1$-$C_6$ alkyl, $C_1$-$C_6$ alkoxy, $C_2$-$C_6$ alkenyl, $C_2$-$C_6$ alkynyl, $C_3$-$C_{12}$ cycloalkyl, $C_6$-$C_{12}$ aryl, 5- to 12-membered heteroaryl, and 4- to 12-membered heterocyclyl, wherein each $C_1$-$C_6$ alkyl, $C_1$-$C_6$ alkoxy, $C_2$-$C_6$ alkenyl, $C_2$-$C_6$ alkynyl, $C_3$-$C_{12}$ cycloalkyl, $C_6$-$C_{12}$ aryl, 5- to 12-membered heteroaryl, and 4- to 12-membered heterocyclyl is optionally substituted with one or more substituents independently selected from a group Q; and $R^{10c}$, $R^{10d}$, $R^{10e}$, $R^{10f}$, $R^{11c}$, $R^{11d}$, $R^{11e}$, and $R^{11f}$ are each independently selected from H and $C_1$-$C_6$ alkyl optionally substituted with one or more substituents independently selected from a group Q, or one or more of the pairs of variables selected from $R^{10c}$ and $R^{10d}$, $R^{10e}$ and $R^{10f}$, $R^{11c}$ and $R^{11d}$, and $R^{11e}$ and $R^{11f}$, together with the nitrogen to which they are attached, form 5- to 12-membered heteroaryl or 4- to 12-membered heterocyclyl, wherein each 5- to 12-membered heteroaryl or 4- to 12-membered heterocyclyl is optionally substituted with one or more substituents independently selected from a group Q;

wherein each of the one or more substituents of group Q is independently selected from deuterium, F, Cl, Br, OH, $NH_2$, $NH(C=O)(C_1$-$C_6$ alkyl), $NH(C=O)(C_3$-$C_8$ cycloalkyl), $NH(C=O)(O-C_1$-$C_6$ alkyl), $C_1$-$C_6$ alkyl optionally substituted with one or more deuterium, $C_1$-$C_6$ haloalkyl, $C_1$-$C_6$ alkoxy optionally substituted with one or more deuterium, $C_1$-$C_6$ haloalkoxy, $C_2$-$C_6$ alkenyl, $C_1$-$C_6$ hydroxyalkyl, $C_1$-$C_6$ hydroxyalkoxy, carboxy-$C_1$-$C_6$ alkyl, amino optionally having at least one $C_1$-$C_3$alkyl, $NO_2$, CN, $CONH_2$, aminocarbonyl substituted with at least one $C_1$-$C_6$ alkyl, oxo, $C_1$-$C_6$ alkyl-carbonyl, $C_1$-$C_6$ alkoxy-carbonyl, $C_1$-$C_6$ alkyl-carbonylamino, $C_1$-$C_6$ alkoxy-carbonylamino, $C_1$-$C_6$ alkyl-carbonyl-N-methylamino, $C_1$-$C_6$ alkoxy-carbonyl-N-methylamino, $C_1$-$C_6$ alkylsulfanyl, $C_1$-$C_6$ alkylsulfinyl, $C_1$-$C_6$ alkylsulfonyl, $C_1$-$C_6$ alkylamino-sulfonyl, $C_1$-$C_6$ alkylsulfinyl-$C_1$-$C_6$ alkyl, $C_1$-$C_6$ alkylsulfonyl-$C_1$-$C_6$ alkyl, $C_3$-$C_8$ cycloalkyl, $C_3$-$C_8$ cycloalkyl-$C_1$-$C_6$alkoxy, $C_1$-$C_3$ alkoxy-$C_1$-$C_3$ alkyl, $C_1$-$C_3$ alkoxy-$C_1$-$C_3$alkoxy-$C_1$-$C_3$ alkyl, $C_1$-$C_3$ alkoxy-carbonyl-$C_1$-$C_3$ alkyl, phenyl-$C_1$-$C_6$ alkoxy, N-methyl-amino-carbonyl-$C_1$-$C_6$ alkyl, N,N-dimethylaminocarbonyl-$C_1$-$C_6$ alkyl, heterocyclyl, heterocyclyl-$C_1$-$C_3$ alkyl or a spiro ring.

2. The compound of claim 1, wherein $R^9$ is selected from F, Cl, Br, OH, CN, $NO_2$, $C_1$-$C_6$ alkyl, $C_1$-$C_6$ alkoxy, $C_1$-$C_6$ haloalkyl, and $C_1$-$C_6$ haloalkoxy.

3. The compound of claim 1, wherein $R^9$ is $C_1$-$C_8$ haloalkyl.

4. The compound of claim 1, wherein $R^9$ is $CHF_2$.

5. The compound of claim 1, wherein $R^9$ is $C_1$-$C_3$ alkyl.

6. The compound of claim 5, wherein $R^9$ is ethyl.

7. The compound of claim 1, wherein $R^7$ is selected from H, F, Cl, Br, OH, CN, $NO_2$, $C_1$-$C_6$ alkyl, $C_1$-$C_6$ alkoxy, $C_1$-$C_6$ haloalkyl, and $C_1$-$C_6$ haloalkoxy.

8. The compound of claim 1, wherein $R^7$ and $R^8$ together with the atoms to which they are attached form 5- to 12-membered heteroaryl.

9. The compound of claim 1, wherein $R^7$ and $R^8$ together with the atoms to which they are attached form 4- to 12-membered heterocyclyl.

10. The compound of claim 1, wherein the compound is represented by structural formula (Ij*):

(Ij*)

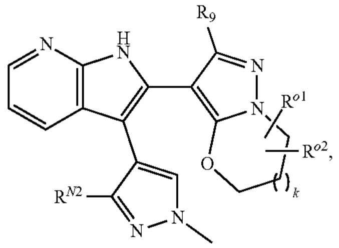

or a pharmaceutically acceptable salt thereof, wherein k is 1 or 2;

$R^9$ is selected from $C_1$-$C_8$alkyl and $C_1$-$C_8$ haloalkyl;

$R^{N2}$ is $OCHF_2$; and $R^{o1}$ and $R^{o2}$ are each independently selected from H, OH, F, Cl, Br, $C_1$-$C_3$ alkyl, $C_1$-$C_3$ alkoxy, $NR^{x1}R^{x2}$, $NR^{x3}C(=O)R^{x5}$, and $NR^{x6}C(=O)OR^{x7}$, wherein $R^{x1}$, $R^{x2}$, $R^{x3}$, $R^{x5}$, $R^{x6}$, and $R^{x7}$ is each independently selected from H, $C_1$-$C_3$ alkyl, and $C_3$-$C_6$ cycloalkyl, and wherein each $C_1$-$C_3$ alkyl, $C_1$-$C_3$ alkoxy, or $C_3$-$C_6$ cycloalkyl is substituted with one or more substituents independently selected from group Q.

11. The compound of claim 10, wherein the compound is represented by structural formula (Ik*):

(Ik*)

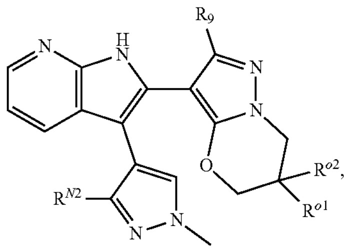

or a pharmaceutically acceptable salt thereof, wherein $R^{o1}$ is selected from H and $C_1$-$C_2$ alkyl; and $R^{o2}$ is selected from H, OH, F, NHC(═O)O($C_1$-$C_2$ alkyl), NHC(═O)O($C_3$-$C_6$ cycloalkyl), $C_1$-$C_3$ alkoxy, and —O($C_1$-$C_3$ hydroxyalkyl).

12. The compound of claim 11, wherein $R^{o1}$ is H.

13. The compound of claim 11, wherein $R^{o1}$ is methyl.

14. The compound of claim 11, wherein $R^{o1}$ and $R^{o2}$ are each H.

15. The compound of claim 11, wherein $R^{o2}$ is selected from OH, F, methoxy, —$OCH_2CH_2OH$, —$OCH_2C(Me)_2OH$, NHC(═O)$OCH_3$, and NHC(═O)O($C_3$ cycloalkyl).

16. The compound of claim 11, wherein $R^9$ is $CHF_2$ or ethyl.

17. The compound of claim 1, wherein the compound is selected from

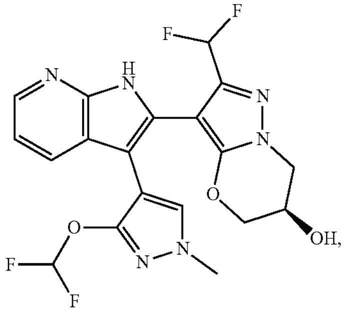

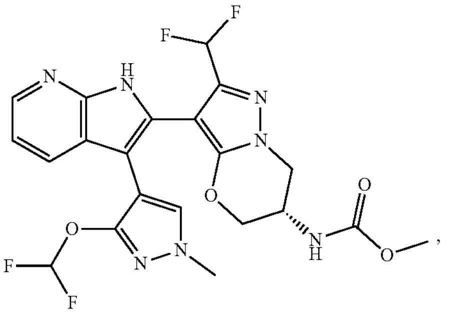

-continued

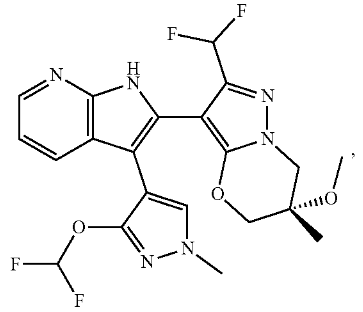

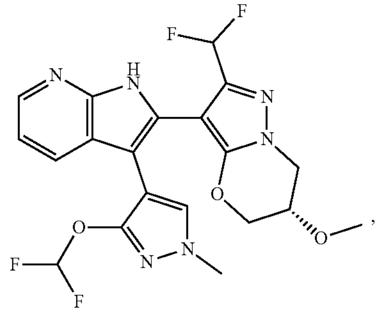

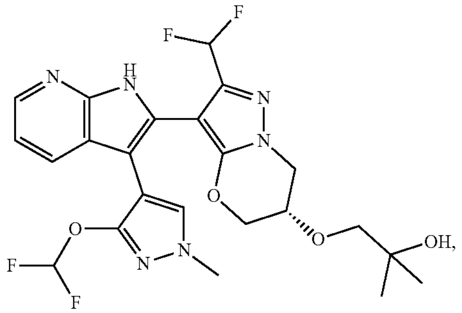

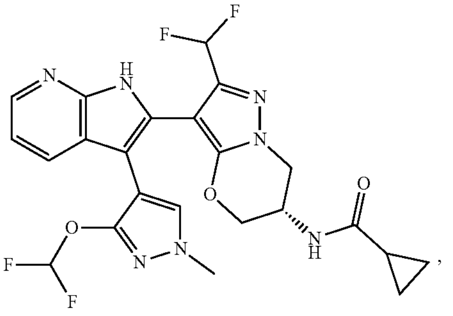

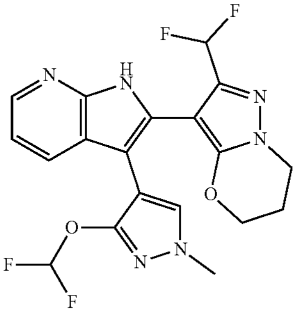 [SMILES: Cn1cc(-c2c(-c3c(C(F)F)nn4c3OCCC4)[nH]c3ncccc23)c(OC(F)F)n1]

-continued

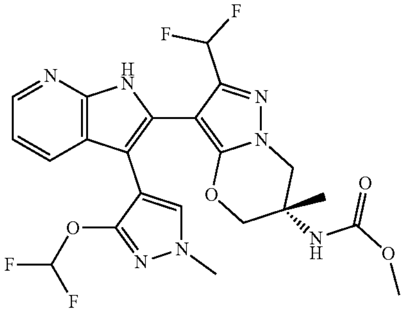

,

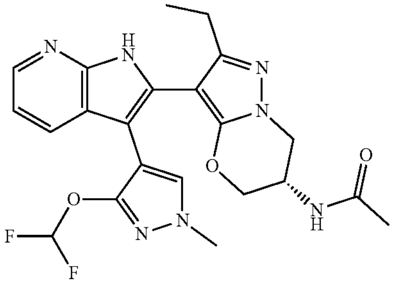

,

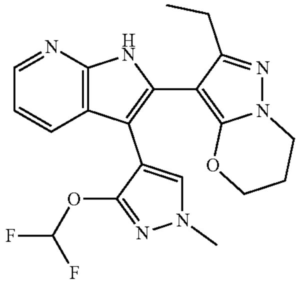

, and

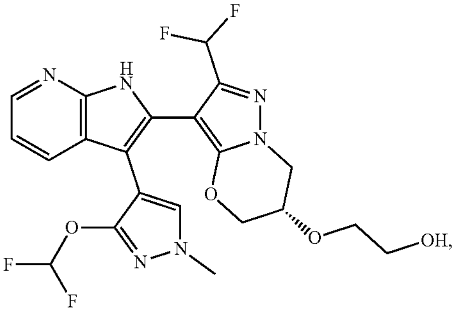

or a pharmaceutically acceptable salt thereof.

18. A compound represented by structural formula

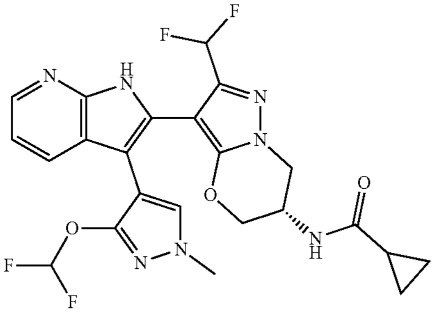

or a pharmaceutically acceptable salt thereof.

19. A compound represented by structural formula

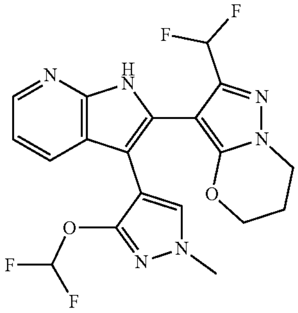

or a pharmaceutically acceptable salt thereof.

20. A compound represented by structural formula

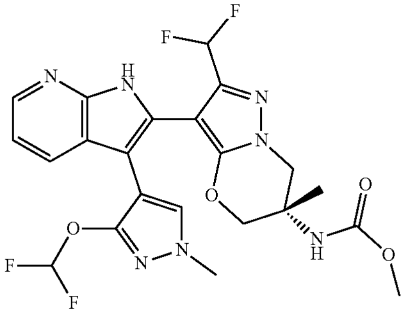 [SMILES: COC(=O)N[C@]1(C)COc2c(-c3[nH]c4ncccc4c3-c3cn(C)nc3OC(F)F)c(C(F)F)nn2C1]

or a pharmaceutically acceptable salt thereof.

21. A pharmaceutical composition, comprising a compound of claim 1 and a pharmaceutically acceptable carrier.

22. A method of treating an MRGPRX2-mediated disease or disorder, comprising administering to a patient in need thereof a therapeutically effective amount of a compound of claim 1, wherein the MRGPRX2-mediated disease or disorder is selected from the group consisting of chronic spontaneous urticaria, chronic inducible urticaria, mastocytosis, atopic dermatitis, rosacea, Crohn's disease, ulcerative colitis, irritable bowel syndrome, rheumatoid arthritis, fibromyalgia, nasal polyps, neuropathic pain, inflammatory pain, chronic itch, drug-induced anaphylactoid reactions, metabolic syndrome, oesophagus reflux, asthma, cough, migraine, chronic pruritus, acute pruritus, prurigo nodularis, osteoarthritis, and pseudo anaphylaxis.

23. The method of claim 22, wherein the MRGPRX2-mediated disease or disorder is chronic spontaneous urticaria or chronic inducible urticaria.

24. The method of claim 23, wherein the chronic inducible urticaria is cold urticaria, cholinergic urticaria, heat urticaria, solar urticaria, symptomatic demographism urticaria, pressure urticaria, or contact urticaria.

25. The method of claim 22, wherein the chronic pruritus is chronic pruritus of unknown origin.

26. The method of claim 22, wherein the rosacea is papulopustular rosacea.

27. The compound of claim 1, wherein the compound is represented by one of the following structural formulas:
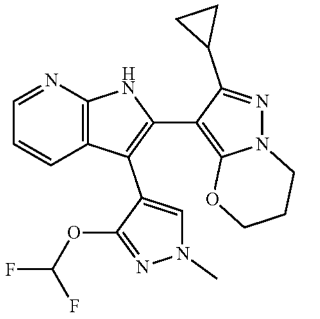
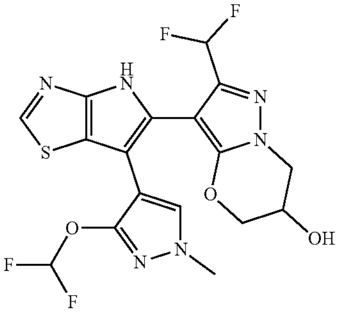
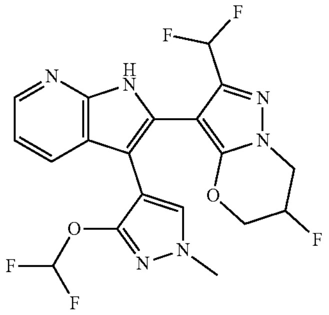
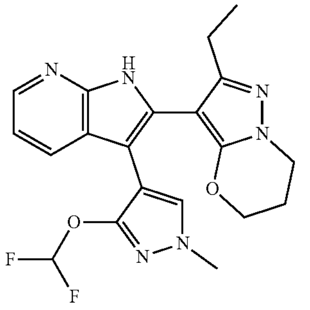
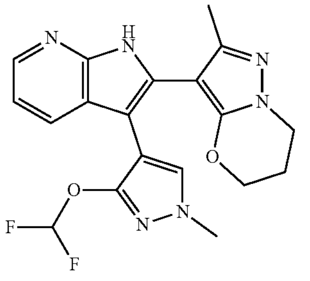
-continued
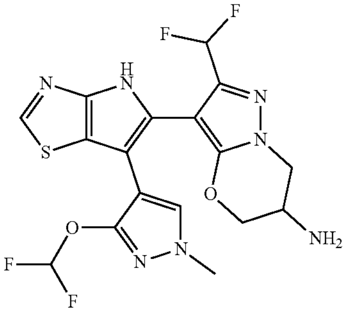
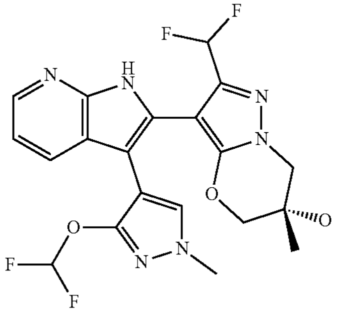
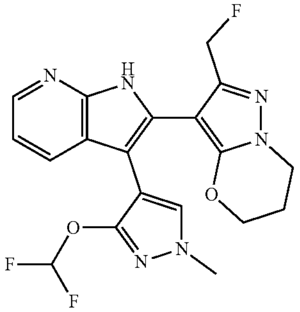
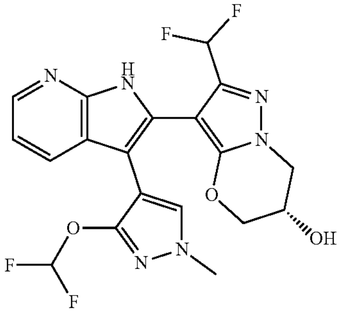
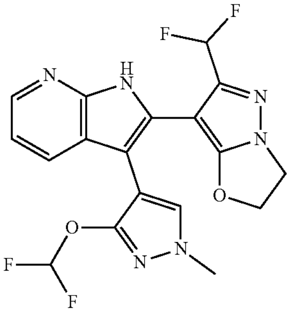

-continued
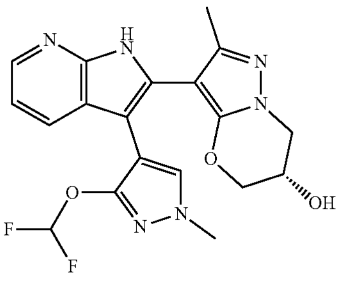
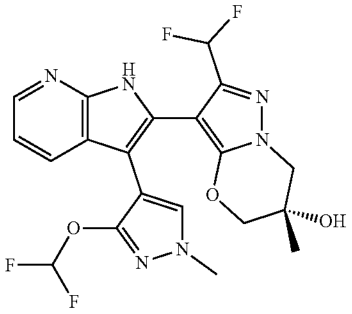
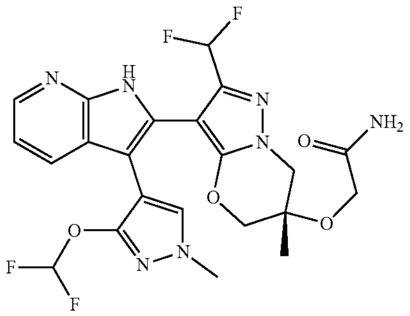
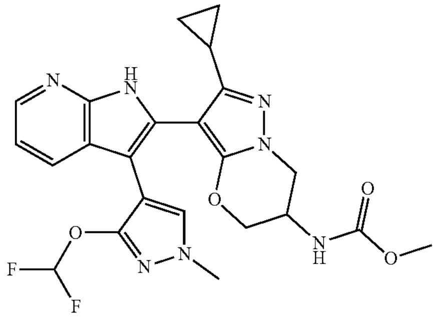
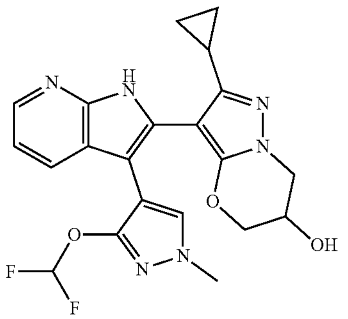
-continued
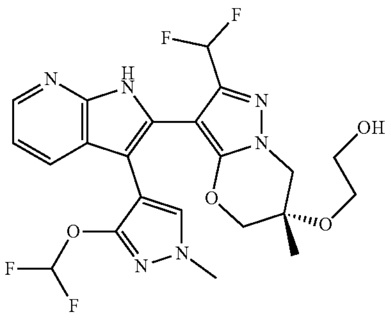
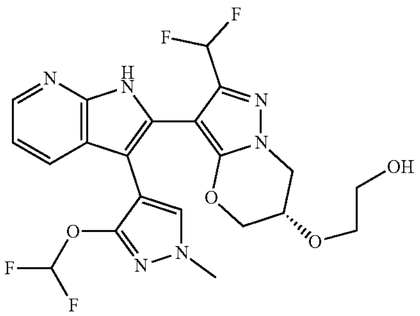
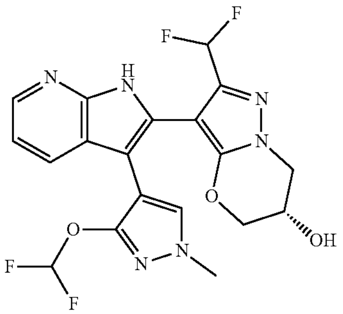
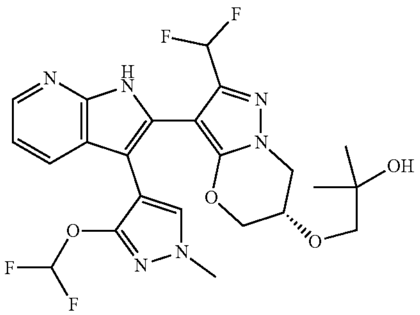
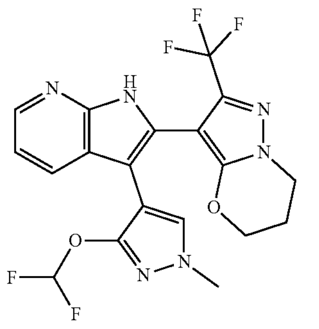

-continued
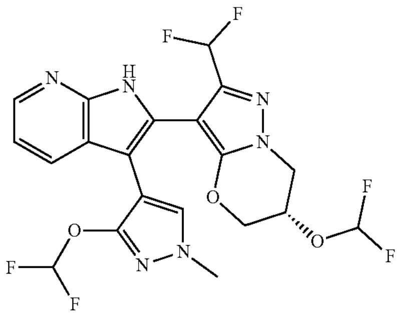
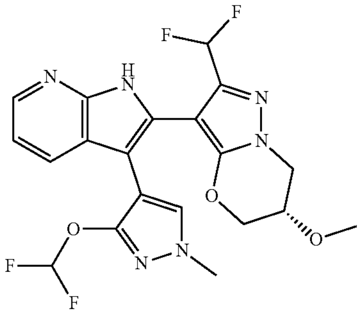
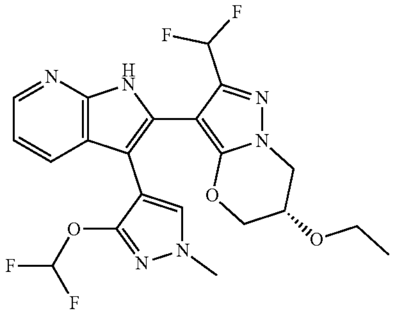
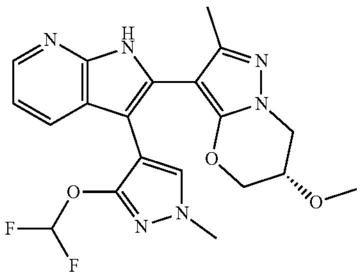
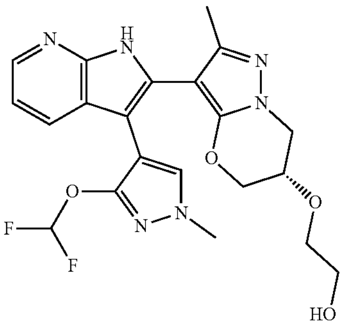
-continued
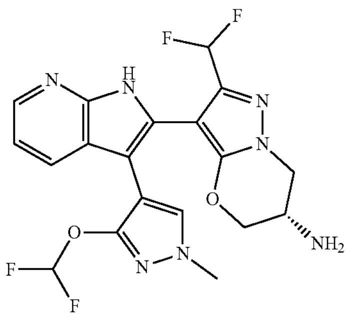
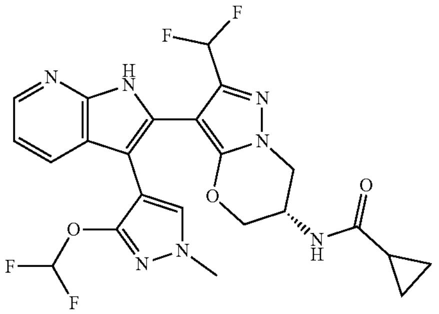
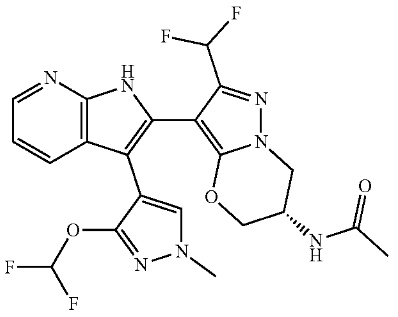
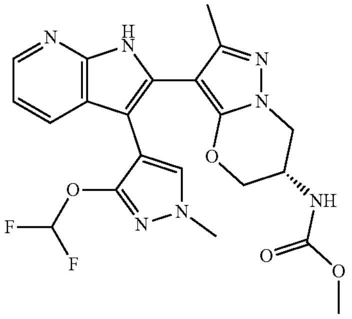
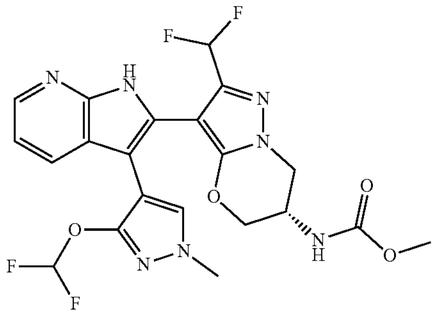

-continued
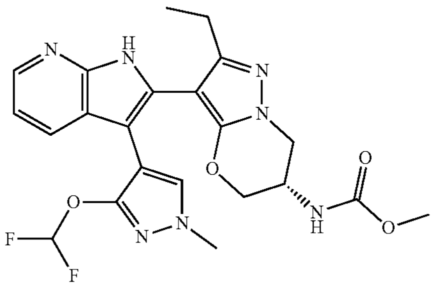
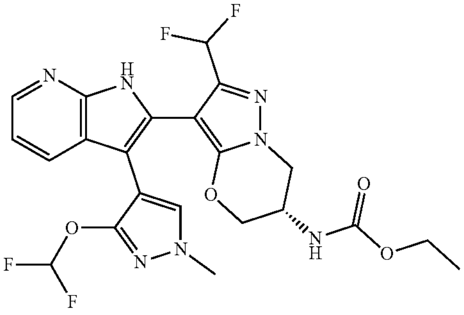
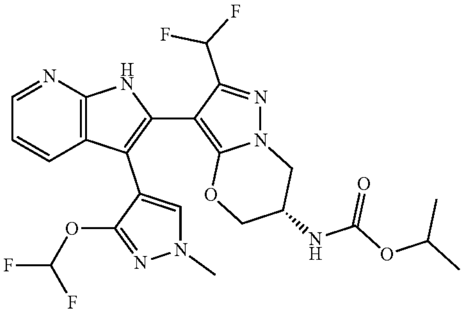
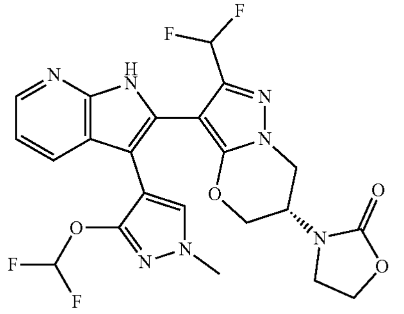
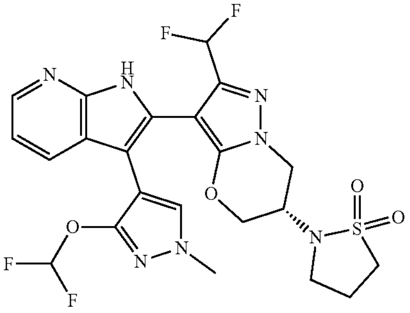
-continued
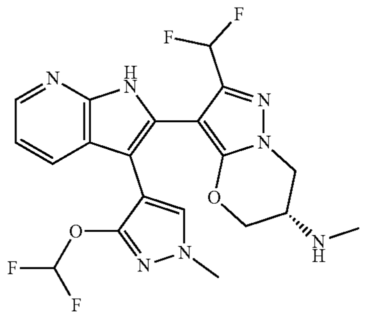
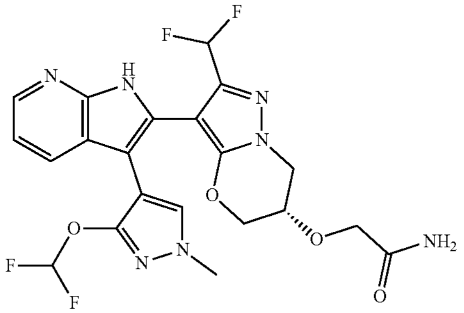
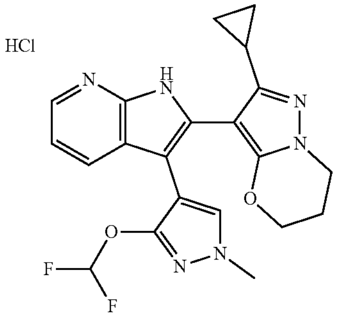
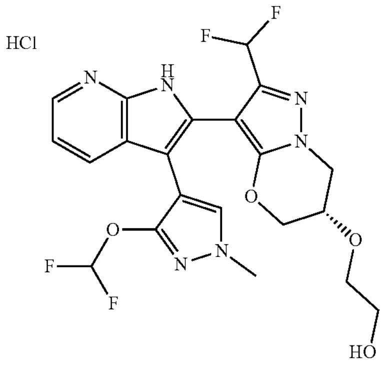
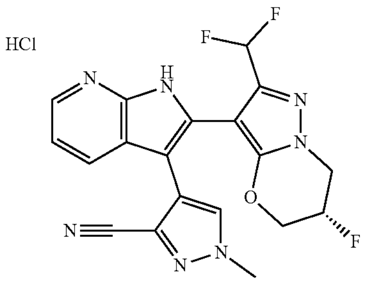

-continued
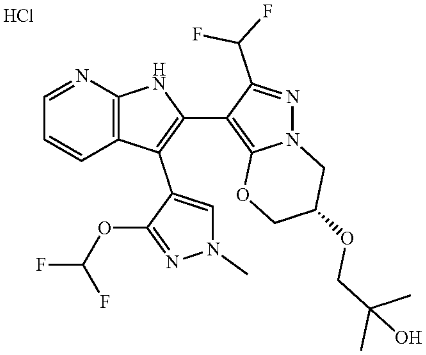
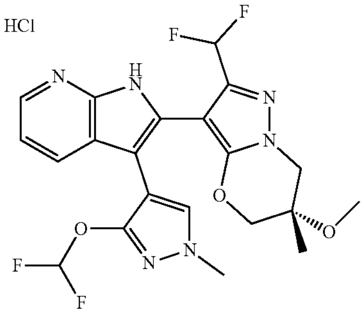
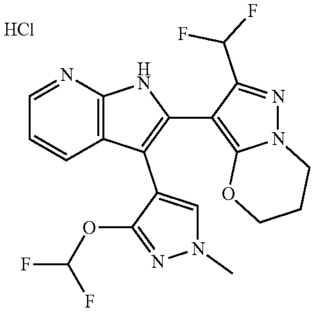
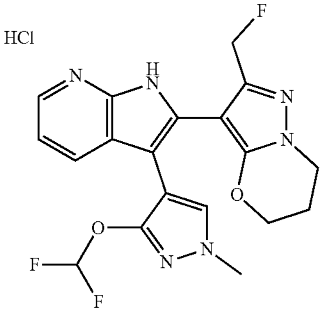
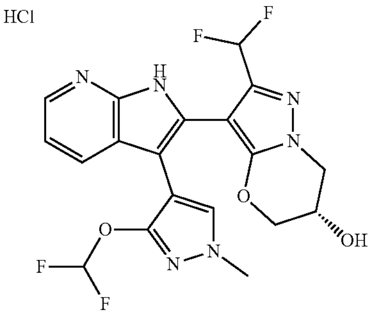
-continued
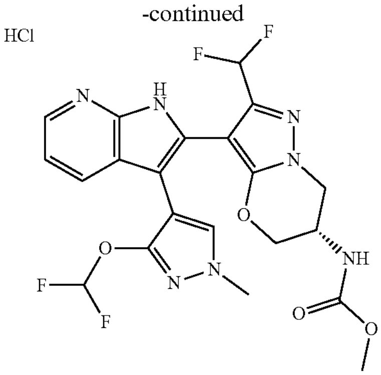
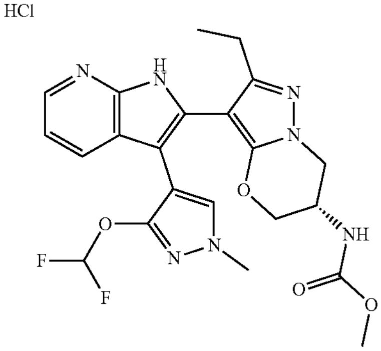
28. The compound of claim 19, wherein the compound is represented by structural formula
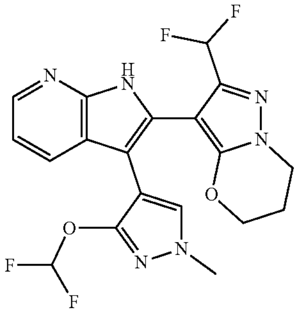 [SMILES: Cn1cc(-c2c(-c3c(C(F)F)nn4c3OCCC4)[nH]c3ncccc23)c(OC(F)F)n1]
or a hydrochloride salt thereof.
29. The compound of claim 28, wherein the compound is represented by structural formula
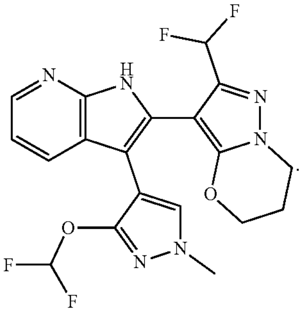 [SMILES: Cn1cc(-c2c(-c3c(C(F)F)nn4c3OCCC4)[nH]c3ncccc23)c(OC(F)F)n1]

30. A method of treating an MRGPRX2-mediated disease or disorder, comprising administering to a patient in need thereof a therapeutically effective amount of a compound of claim 29, wherein the MRGPRX2-mediated disease or disorder is selected from the group consisting of chronic spontaneous urticaria, chronic inducible urticaria, mastocytosis, atopic dermatitis, rosacea, Crohn's disease, ulcerative colitis, irritable bowel syndrome, rheumatoid arthritis, fibromyalgia, nasal polyps, neuropathic pain, inflammatory pain, chronic itch, drug-induced anaphylactoid reactions, metabolic syndrome, oesophagus reflux, asthma, cough, migraine, chronic pruritus, acute pruritus, prurigo nodularis, osteoarthritis, and pseudo anaphylaxis.

* * * * *